US012799125B2

(12) United States Patent
Nishimura et al.

(10) Patent No.: US 12,799,125 B2
(45) Date of Patent: Nov. 17, 2026

(54) ORGANIC ELECTROLUMINESCENT ELEMENT AND ELECTRONIC DEVICE

(71) Applicant: IDEMITSU KOSAN CO., LTD., Tokyo (JP)

(72) Inventors: Kazuki Nishimura, Tokyo (JP); Satomi Tasaki, Tokyo (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 1198 days.

(21) Appl. No.: 17/642,652

(22) PCT Filed: Sep. 11, 2020

(86) PCT No.: PCT/JP2020/034604
§ 371 (c)(1),
(2) Date: Mar. 11, 2022

(87) PCT Pub. No.: WO2021/049661
PCT Pub. Date: Mar. 18, 2021

(65) Prior Publication Data

US 2022/0356133 A1 Nov. 10, 2022

(30) Foreign Application Priority Data

Sep. 13, 2019 (JP) ................................ 2019-167636
Nov. 26, 2019 (JP) ................................ 2019-213374
Dec. 27, 2019 (JP) ................................ 2019-239821

(51) Int. Cl.
*C07D 487/06* (2006.01)
*C07C 15/28* (2006.01)
(Continued)

(52) U.S. Cl.
CPC ............ *C07D 487/06* (2013.01); *C07C 15/28* (2013.01); *C07C 15/30* (2013.01); *C07C 15/38* (2013.01);
(Continued)

(58) Field of Classification Search
CPC .. C07D 487/06; C07D 209/82; C07D 307/91; C07D 311/82; C07D 333/76;
(Continued)

(56) References Cited

U.S. PATENT DOCUMENTS 6,929,870 B2 * 8/2005 Ishida .................. C07C 211/61
313/506
11,094,886 B2 8/2021 Tasaki et al.
(Continued)

FOREIGN PATENT DOCUMENTS

CN 106565705 A 4/2017
JP 2006-176494 A 7/2006
(Continued)

OTHER PUBLICATIONS

Bin, J. K., & Hong, J. I. (2011). Efficient blue organic light-emitting diode using anthracene-derived emitters based on polycyclic aromatic hydrocarbons. Organic Electronics, 12(5), 802-808. (Year: 2011).*

(Continued)

*Primary Examiner* — Dawn L Garrett
(74) *Attorney, Agent, or Firm* — Foley & Lardner LLP

(57) ABSTRACT

An organic electroluminescence device includes an anode, a cathode, a first emitting layer, and a second emitting layer provided between the first emitting layer and the cathode, in which the first emitting layer contains, as a first host material, a first compound represented by a formula (1) below and having a group represented by a formula (11) below, the second emitting layer contains a second compound represented by one of formulae (2-1D) to (2-4D) below as a second host material, and the first emitting layer is in direct contact with the second emitting layer.

(1)

(11)

$$*-(L_{101})_{mx}-Ar_{101}$$

(2-1D)

(Continued)

-continued (2-2D)

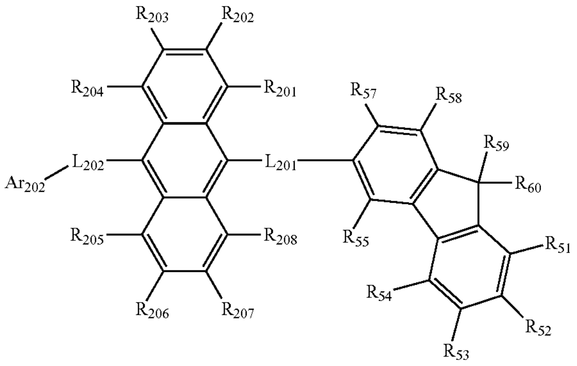

(2-3D)

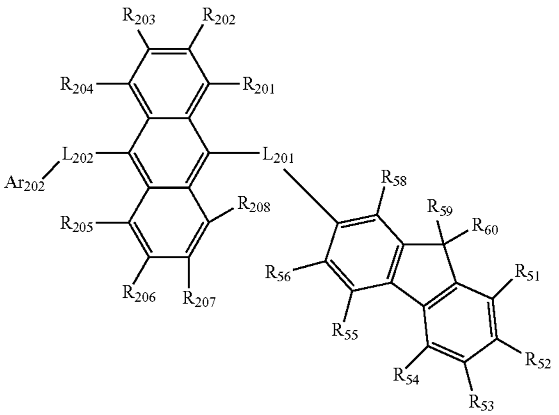

(2-4D)

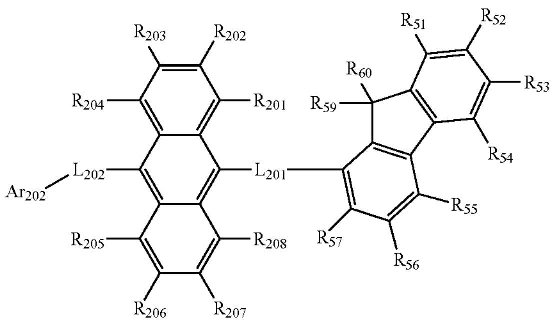

4 Claims, 1 Drawing Sheet

(51) Int. Cl.

| | |
|---|---|
| ***C07C 15/30*** | (2006.01) |
| ***C07C 15/38*** | (2006.01) |
| ***C07C 251/24*** | (2006.01) |
| ***C07C 255/51*** | (2006.01) |
| ***C07D 209/82*** | (2006.01) |
| ***C07D 307/91*** | (2006.01) |
| ***C07D 311/82*** | (2006.01) |
| ***C07D 333/76*** | (2006.01) |
| ***C07D 405/10*** | (2006.01) |
| ***C07D 407/10*** | (2006.01) |
| ***C07D 487/16*** | (2006.01) |
| ***C07D 491/16*** | (2006.01) |
| ***C07D 491/22*** | (2006.01) |
| ***C07D 493/04*** | (2006.01) |
| ***C07D 495/04*** | (2006.01) |
| ***C07D 495/22*** | (2006.01) |
| ***C07D 519/00*** | (2006.01) |
| ***C07F 5/02*** | (2006.01) |
| ***C07F 7/08*** | (2006.01) |
| ***H10K 85/40*** | (2023.01) |
| ***H10K 85/60*** | (2023.01) |
| *H10K 50/125* | (2023.01) |

(52) U.S. Cl.

CPC .......... *C07C 251/24* (2013.01); *C07C 255/51* (2013.01); *C07D 209/82* (2013.01); *C07D 307/91* (2013.01); *C07D 311/82* (2013.01); *C07D 333/76* (2013.01); *C07D 405/10* (2013.01); *C07D 407/10* (2013.01); *C07D 487/16* (2013.01); *C07D 491/16* (2013.01); *C07D 491/22* (2013.01); *C07D 493/04* (2013.01); *C07D 495/04* (2013.01); *C07D 495/22* (2013.01); *C07D 519/00* (2013.01); *C07F 5/027* (2013.01); *C07F 7/081* (2013.01); *C07F 7/0827* (2013.01); *H10K 85/40* (2023.02); *H10K 85/615* (2023.02); *H10K 85/622* (2023.02); *H10K 85/623* (2023.02); *H10K 85/624* (2023.02); *H10K 85/631* (2023.02); *H10K 85/636* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 85/658* (2023.02); *C07B 2200/05* (2013.01); *H10K 50/125* (2023.02)

(58) Field of Classification Search

CPC .. C07D 405/10; C07D 407/10; C07D 487/16; C07D 491/16; C07D 491/22; C07D 493/04; C07D 495/04; C07D 495/22; C07D 519/00; C07C 15/28; C07C 15/30; C07C 15/38; C07C 251/24; C07C 255/51; H10K 85/322; H10K 85/40; H10K 85/615; H10K 85/622; H10K 85/623; H10K 85/624; H10K 85/631; H10K 85/636; H10K 85/654; H10K 85/657; H10K 85/6572; H10K 85/6574; H10K 85/6576; H10K 85/658; H10K 50/125; H10K 85/626; C07F 5/027; C07F 7/081; C07F 7/0827; C07B 2200/05; C09K 11/06; H05B 33/12

See application file for complete search history.

(56) References Cited

U.S. PATENT DOCUMENTS

| | | | |
|---|---|---|---|
| 2006/0043858 | A1 | 3/2006 | Ikeda et al. |
| 2006/0154107 | A1 | 7/2006 | Kubota et al. |
| 2007/0013296 | A1 | 1/2007 | Kubota et al. |
| 2008/0012475 | A1 | 1/2008 | Oyamada et al. |
| 2008/0193796 | A1 | 8/2008 | Arakane et al. |
| 2009/0200919 | A1 | 8/2009 | Kamatani et al. |
| 2009/0278446 | A1 | 11/2009 | Igawa et al. |
| 2010/0308718 | A1 | 12/2010 | Kubota et al. |
| 2011/0034744 | A1 | 2/2011 | Ikeda et al. |
| 2011/0133632 | A1 | 6/2011 | Lecloux et al. |
| 2012/0168739 | A1 | 7/2012 | Kamatani et al. |
| 2012/0187826 | A1 | 7/2012 | Kawamura et al. |
| 2012/0235561 | A1 | 9/2012 | Ikeda et al. |
| 2014/0183500 | A1 | 7/2014 | Ikeda et al. |
| 2014/0291653 | A1 | 10/2014 | Ikeda et al. |

(56) References Cited

U.S. PATENT DOCUMENTS

| | | | |
|---|---|---|---|
| 2016/0351818 A1 | 12/2016 | Kim et al. | |
| 2017/0069864 A1 | 3/2017 | Lee et al. | |
| 2017/0110667 A1 | 4/2017 | Nishimura et al. | |
| 2017/0125687 A1 | 5/2017 | Ikeda et al. | |
| 2017/0324043 A1 | 11/2017 | Ikeda et al. | |
| 2017/0338432 A1 | 11/2017 | Adamovich et al. | |
| 2017/0342318 A1 | 11/2017 | Kim et al. | |
| 2018/0261791 A1 | 9/2018 | Yoo et al. | |
| 2019/0221747 A1* | 7/2019 | Takahashi ............ | H10K 85/633 |
| 2019/0280209 A1 | 9/2019 | Fujita | |
| 2019/0305227 A1 | 10/2019 | Yoon et al. | |

FOREIGN PATENT DOCUMENTS

| | | | |
|---|---|---|---|
| JP | 2007-302650 | A | 11/2007 |
| JP | 2010-161356 | A | 7/2010 |
| JP | 2011-173973 | A | 9/2011 |
| JP | 2013-513690 | A | 4/2013 |
| JP | 2013-157552 | A | 8/2013 |
| JP | 2015-041775 | A | 3/2015 |
| JP | 2017-123352 | A | 7/2017 |
| JP | 2018-125504 | A | 8/2018 |
| KR | 10-0967355 | B1 | 7/2010 |
| KR | 2011-0034981 | A | 4/2011 |
| KR | 2018-0077887 | A | 7/2018 |
| WO | WO-2004/018587 | A1 | 3/2004 |
| WO | WO-2005/115950 | A1 | 12/2005 |
| WO | WO-2007/007553 | A1 | 1/2007 |
| WO | WO-2008/062773 | A1 | 5/2008 |
| WO | WO-2011/077691 | A1 | 6/2011 |
| WO | WO-2014/104144 | A1 | 7/2014 |
| WO | WO-2019/124550 | A1 | 6/2019 |
| WO | WO-2020/080417 | A1 | 4/2020 |

OTHER PUBLICATIONS

International Searching Authority, "International Search Report," issued in connection with International Patent Application No. PCT/JP2020/034604, dated Dec. 8, 2020.

International Searching Authority, "Written Opinion," issued in connection with International Patent Application No. PCT/JP2020/034604, dated Dec. 8, 2020.

International Preliminary Report on Patentability, "Written Opinion," issued in connection with International Patent Application No. PCT/JP2020/044062, dated May 17, 2022, English translation (7 pages).

International Preliminary Report on Patentability, "Written Opinion," issued in connection with International Patent Application No. PCT/JP2021/009835, dated Oct. 13, 2022, English translation (7 pages).

International Preliminary Report on Patentability issued in corresponding International Patent Application No. PCT/JP2020/034604 dated Mar. 15, 2022.

* cited by examiner

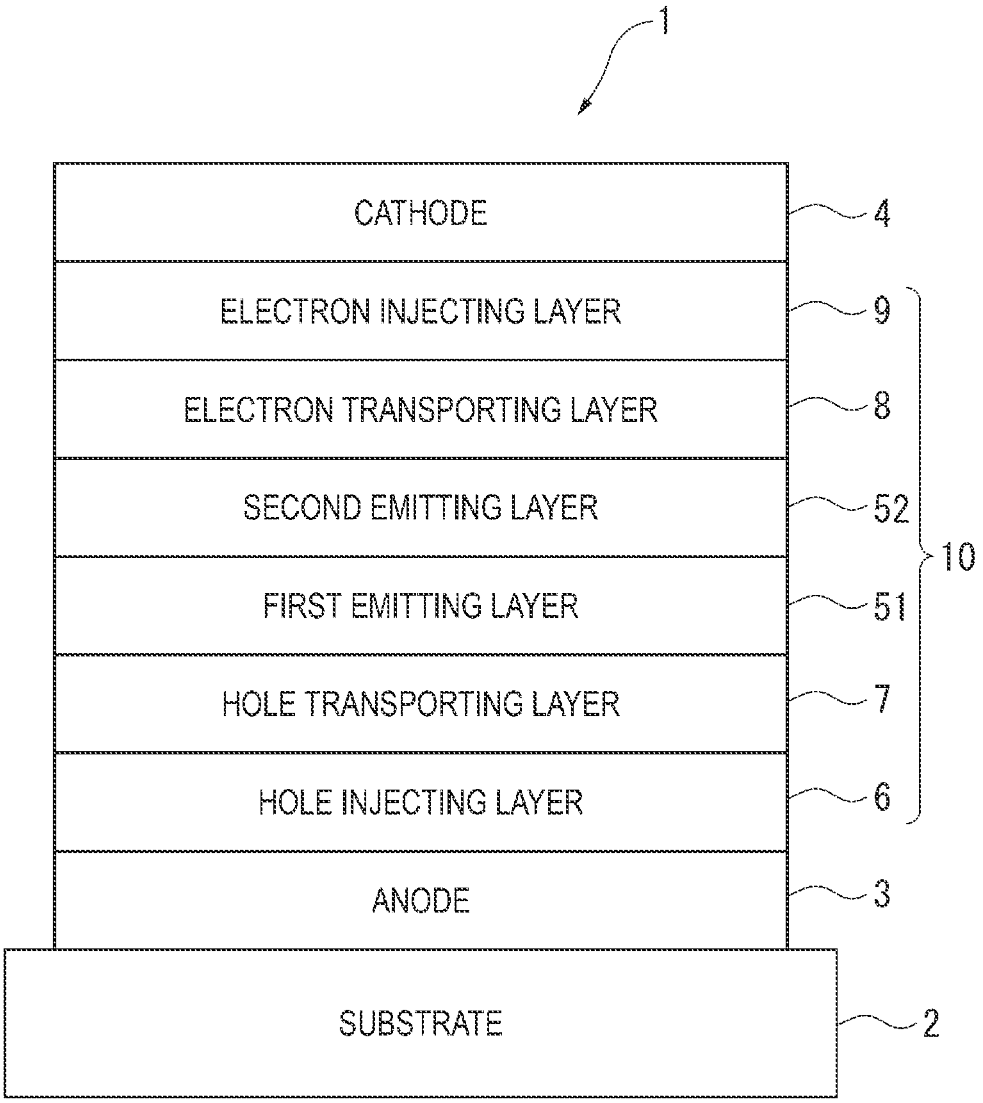
1
CATHODE
4
ELECTRON INJECTING LAYER
9
ELECTRON TRANSPORTING LAYER
8
SECOND EMITTING LAYER
52
10
FIRST EMITTING LAYER
51
HOLE TRANSPORTING LAYER
7
HOLE INJECTING LAYER
6
ANODE
3
SUBSTRATE
2

ORGANIC ELECTROLUMINESCENT ELEMENT AND ELECTRONIC DEVICE

CROSS-REFERENCE TO RELATED APPLICATIONS

The present application claims priority under 37 U.S.C. § 371 to International Patent Application No. PCT/JP2020/034604, filed Sep. 11, 2020, which claims priority to and the benefit of Japanese Patent Application Nos. 2019-167636, filed on Sep. 13, 2019, 2019-213374, filed on Nov. 26, 2019, and 2019-239821, filed on Dec. 27, 2019. The contents of these applications are hereby incorporated by reference in their entireties.

TECHNICAL FIELD

The present invention relates to an organic electroluminescence device and an electronic device.

BACKGROUND ART

An organic electroluminescence device (hereinafter, occasionally referred to as "organic EL device") has found its application in a full-color display for mobile phones, televisions and the like. When a voltage is applied to an organic EL device, holes and electrons are injected from an anode and a cathode, respectively, into an emitting layer. The injected holes and electrons are recombined in the emitting layer to form excitons. Specifically, according to the electron spin statistics theory, singlet excitons and triplet excitons are generated at a ratio of 25%:75%.

Various studies have been made for compounds to be used for the organic EL device in order to enhance the performance of the organic EL device (e.g., see Patent Literatures 1 to 6). The performance of the organic EL device is evaluable in terms of, for instance, luminance, emission wavelength, chromaticity, emission efficiency, drive voltage, and lifetime.

CITATION LIST

Patent Literature(s)

Patent Literature 1: JP 2013-157552 A
Patent Literature 2: International Publication No. WO2004/018587
Patent Literature 3: International Publication No. WO2005/115950
Patent Literature 4: International Publication No. WO2011/077691
Patent Literature 5: JP 2018-125504 A
Patent Literature 6: US Patent Application Publication No. 2019/280209

SUMMARY OF THE INVENTION

Problem(s) to be Solved by the Invention

An object of the invention is to provide an organic electroluminescence device with enhanced performance. Another object of the invention is to provide an organic electroluminescence device with an improved lifetime and an electronic device including the organic electroluminescence device.

Means for Solving the Problem(s)

According to an aspect of the invention, there is provided an organic electroluminescence device including: an anode; a cathode; a first emitting layer provided between the anode and the cathode; and a second emitting layer provided between the first emitting layer and the cathode, in which the first emitting layer contains a first compound represented by a formula (1) below as a first host material, the first compound containing at least one group represented by a formula (11) below, the second emitting layer contains a second compound represented by a formula (2) below as a second host material, and the first emitting layer is in direct contact with the second emitting layer.

[Formula 1]

(1)

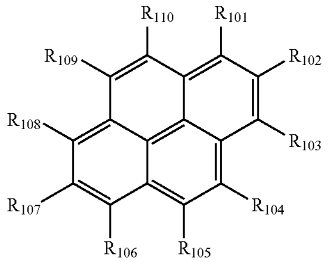

(11)

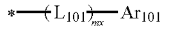

In the formula (1):

$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of $R_{101}$ to $R_{110}$ is a group represented by the formula (11);

when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a pyrene ring in the formula (1).

[Formula 2]

(2)

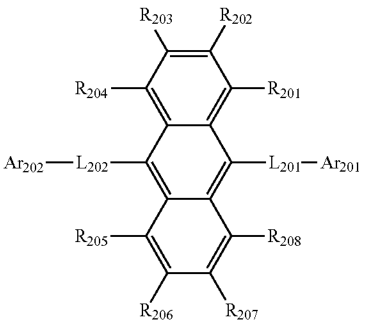

In the formula (2):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the first compound represented by the formula (1) and the second compound represented by the formula (2), $R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of Rom are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{807}$ are present, the plurality of $R_{807}$ are mutually the same or different;

when a plurality of $R_{501}$ are present, the plurality of $R_{501}$ are mutually the same or different; and when a plurality of $R_{502}$ are present, the plurality of $R_{502}$ are mutually the same or different.

According to another aspect of the invention, there is provided an organic electroluminescence device including: an anode; a cathode; a first emitting layer provided between the anode and the cathode; and a second emitting layer provided between the first emitting layer and the cathode, in which the first emitting layer contains a first compound represented by a formula (1) below as a first host material, the first compound containing at least one group represented by a formula (11) below, the second emitting layer contains a second compound represented by one of formulae (2-1 D) to (2-4D) below as a second host material, and the first emitting layer is in direct contact with the second emitting layer.

[Formula 3]

(1)

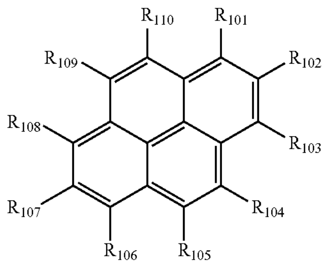

(11)

$$*-(L_{101})_{mx}-Ar_{101}$$

In the formula (1):

$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of $R_{101}$ to $R_{110}$ is a group represented by the formula (11), when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a pyrene ring in the formula (1).

[Formula 4]

(2-1D)

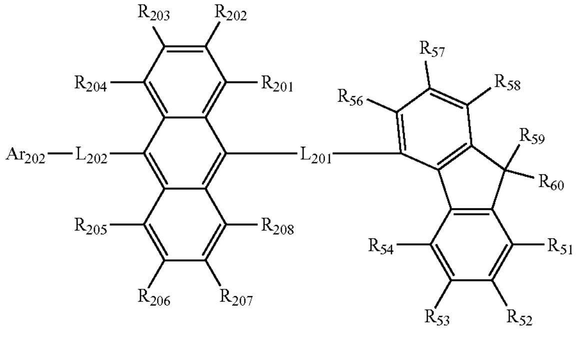

(2-2D)

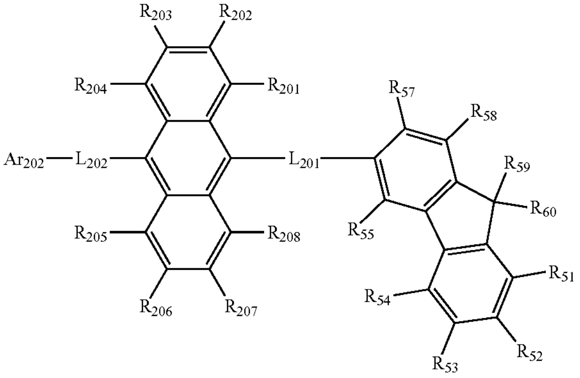

[Formula 5]

(2-3D)

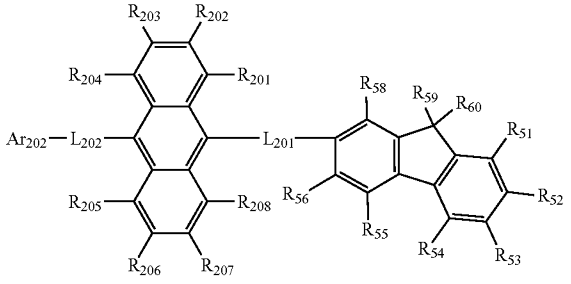

-continued (2-4D)

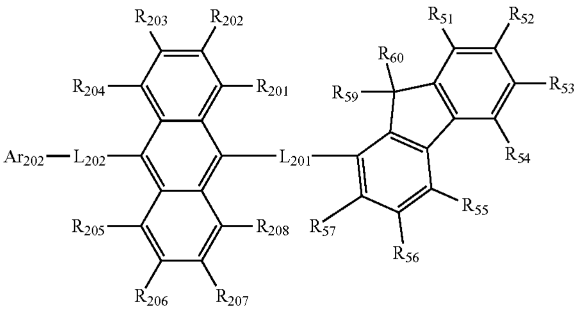

In the formulae (2-1 D) to (2-4D):

$R_{201}$ to $R_{205}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$R_{51}$ to $R_{60}$ are each independently a hydrogen atom or a substituent, or at least one combination of a combination of $R_{51}$ and $R_{52}$, a combination of $R_{52}$ and $R_{53}$, a combination of $R_{53}$ and $R_{54}$, a combination of $R_{55}$ and $R_{56}$, a combination of $R_{56}$ and $R_{57}$, a combination of $R_{57}$ and $R_{58}$, or a combination of $R_{59}$ and $R_{60}$ are mutually bonded to form a monocyclic ring or a fused ring;

$R_{51}$ to $R_{60}$ as a substituent are each independently a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a substituted or unsubstituted aralkyl group having 7 to 50 carbon atoms, a group represented by $—C(=O)R_{801}$, a group represented by $—COOR_{802}$, a halogen atom, a cyano group, a nitro group, or a substituted or unsubstituted aryl group having 6 to 50 ring carbon atoms;

$L_{201}$ and $L_{202}$ are each independently a single bond, or a substituted or unsubstituted arylene group having 6 to 50 ring carbon atoms;

a substituent, if present, for $L_{201}$ and $L_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by —S—($R_{905}$), a group represented by —N($R_{906}$)($R_{907}$), a substituted or unsubstituted aralkyl group having 7 to 50 carbon atoms, a group represented by —C(═O)$R_{801}$, a group represented by —COO$R_{802}$, a halogen atom, a cyano group, a nitro group, and an unsubstituted aryl group having 6 to 50 ring carbon atoms;

$Ar_{202}$ is a substituted or unsubstituted aryl group having 6 to 50 ring carbon atoms; and a substituent, if present, for $Ar_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by —S—($R_{905}$), a group represented by —N($R_{906}$)($R_{907}$), a substituted or unsubstituted aralkyl group having 7 to 50 carbon atoms, a group represented by —C(═O)$R_{801}$, a group represented by —COO$R_{802}$, a halogen atom, a cyano group, a nitro group, and an unsubstituted aryl group having 6 to 50 ring carbon atoms.

In the first compound represented by the formula (1) and the second compound represented by the formulae (2-1 D) to (2-4D):

$R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

According to a still another aspect of the invention, there is provided an organic electroluminescence device including: an anode; a cathode; a first emitting layer provided between the anode and the cathode; and a second emitting layer provided between the first emitting layer and the cathode, in which the first emitting layer contains a first compound represented by a formula (1) below as a first host material, the first compound containing at least one group represented by a formula (11) below, the second emitting layer contains a second compound represented by a formula (2-1E) below as a second host material, and the first emitting layer is in direct contact with the second emitting layer.

[Formula 6]

(1)

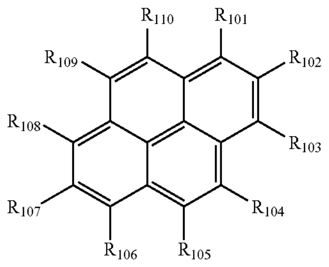

(11)

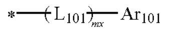

In the formula (1):

$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of $R_{101}$ to $R_{110}$ is a group represented by the formula (11);

when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a pyrene ring in the formula (1).

[Formula 7]

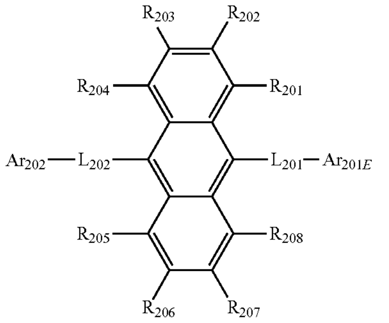

(2-1E)

In the formula (2-1E):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, or a substituted or unsubstituted arylene group having 6 to 50 ring carbon atoms;

a substituent, if present, for $L_{201}$ and $L_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(=O)R_{801}$, a group represented by $—COOR_{802}$, a halogen atom, a cyano group, a nitro group, and an unsubstituted aryl group having 6 to 50 ring carbon atoms;

$Ar_{201E}$ and $Ar_{202}$ are each independently a substituted or unsubstituted aryl group having 6 to 50 ring carbon atoms;

a substituent, if present, for $Ar_{201E}$ and $Ar_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(=O)R_{801}$, a group represented by $—COOR_{802}$, a halogen atom, a cyano group, a nitro group, and an unsubstituted aryl group having 6 to 50 ring carbon atoms;

(i) when $L_{201}$ and $L_{202}$ are each independently a substituted or unsubstituted arylene group having 6 to 50 ring carbon atoms, the arylene group is not a substituted or unsubstituted phenylene group; and (ii) at least one of $Ar_{201E}$, $Ar_{202}$, $L_{201}$ or $L_{202}$ is a substituted or unsubstituted anthryl group, a substituted or unsubstituted benzanthryl group, a substituted or unsubstituted phenanthryl group, a substituted or unsubstituted benzophenanthryl group, a substituted or unsubstituted phenalenyl group, a substituted or unsubstituted pyrenyl group, a substituted or unsubstituted chrysenyl group, a substituted or unsubstituted benzochrysenyl group, a substituted or unsubstituted triphenylenyl group, a substituted or unsubstituted benzotriphenylenyl group, a substituted or unsubstituted tetracenyl group, a substituted or unsubstituted pentacenyl group, a substituted or unsubstituted dibenzofluorenyl group, a substituted or unsubstituted fluoranthenyl group, or a substituted or unsubstituted benzofluoranthenyl group.

In the first compound represented by the formula (1) and the second compound represented by the formula (2-1E):

$R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

According to a further aspect of the invention, there is provided an organic electroluminescence device including: an anode; a cathode; a first emitting layer provided between the anode and the cathode; and a second emitting layer provided between the first emitting layer and the cathode, in which the first emitting layer contains a first compound represented by a formula (1) below as a first host material, the first compound containing at least one group represented by a formula (11) below, the second emitting layer contains a second compound represented by a formula (2-1E) below as a second host material, and the first emitting layer is in direct contact with the second emitting layer.

[Formula 8]

(1)

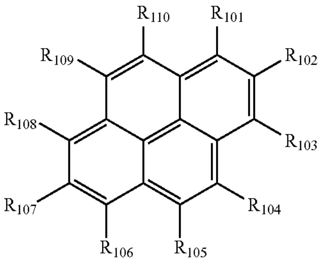

(11)

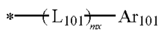

In the formula (1):

$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of $R_{101}$ to $R_{110}$ is a group represented by the formula (11);

when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a pyrene ring in the formula (1).

[Formula 9]

(2-1E)

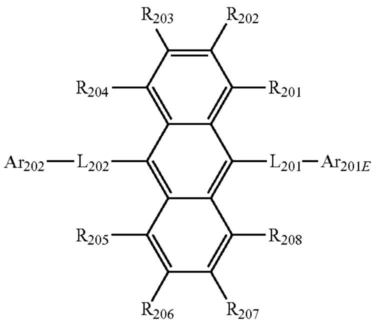

In the formula (2-1E):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, or a substituted or unsubstituted arylene group having 6 to 50 ring carbon atoms;

a substituent, if present, for $L_{201}$ and $L_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(=O)R_{801}$, a group represented by $—COOR_{802}$, a halogen atom, a cyano group, a nitro group, and an unsubstituted aryl group having 6 to 50 ring carbon atoms;

$Ar_{201E}$ and $Ar_{202}$ are each independently a substituted or unsubstituted aryl group having 6 to 50 ring carbon atoms;

a substituent, if present, for $Ar_{201E}$ and $Ar_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(=O)R_{801}$, a group represented by $—COOR_{802}$, a halogen atom, a cyano group, a nitro group, and an unsubstituted aryl group having 6 to 50 ring carbon atoms;

(i) when $L_{201}$ and $L_{202}$ are each independently a substituted or unsubstituted arylene group having 6 to 50 ring carbon atoms, the arylene group is not a substituted or unsubstituted phenylene group; and (ii) at least one of $Ar_{201E}$, $Ar_{202}$, $L_{201}$ or $L_{202}$ is a substituted or unsubstituted naphthyl group, a substituted or unsubstituted anthryl group, a substituted or unsubstituted benzanthryl group, a substituted or unsubstituted phenanthryl group, a substituted or unsubstituted benzophenanthryl group, a substituted or unsubstituted phenalenyl group, a substituted or unsubstituted pyrenyl group, a substituted or unsubstituted chrysenyl group, a substituted or unsubstituted benzochrysenyl group, a substituted or unsubstituted triphenylenyl group, a substituted or unsubstituted benzotriphenylenyl group, a substituted or unsubstituted tetracenyl group, a substituted or unsubstituted pentacenyl group, a substituted or unsubstituted dibenzofluorenyl group, a substituted or unsubstituted fluoranthenyl group, or a substituted or unsubstituted benzofluoranthenyl group, and when a group represented by $-L_{202}-Ar_{202}$ is an unsubstituted phenyl group, at least one of $Ar_{201E}$ or $L_{201}$ is a substituted or unsubstituted anthryl group, a substituted or unsubstituted benzanthryl group, a substituted or unsubstituted phenanthryl group, a substituted or unsubstituted benzophenanthryl group, a substituted or unsubstituted phenalenyl group, a substituted or unsubstituted pyrenyl group, a substituted or unsubstituted chrysenyl group, a substituted or unsubstituted benzochrysenyl group, a substituted or unsubstituted triphenylenyl group, a substituted or unsubstituted benzotriphenylenyl group, a substituted or unsubstituted tetracenyl group, a substituted or unsubstituted pentacenyl group, a substituted or unsubstituted dibenzofluorenyl group, a substituted or unsubstituted fluoranthenyl group, or a substituted or unsubstituted benzofluoranthenyl group.

In the first compound represented by the formula (1) and the second compound represented by the formula (2-1E):

$R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{501}$ are present, the plurality of $R_{501}$ are mutually the same or different; and when a plurality of $R_{502}$ are present, the plurality of $R_{502}$ are mutually the same or different.

According to a still further aspect of the invention, there is provided an organic electroluminescence device including: an anode; a cathode; a first emitting layer provided between the anode and the cathode; and a second emitting layer provided between the first emitting layer and the cathode, in which the first emitting layer contains a first compound represented by a formula (1) below as a first host material, the first compound containing at least one group represented by a formula (11) below, the second emitting layer contains a second compound represented by a formula (2-1F) below as a second host material, and the first emitting layer is in direct contact with the second emitting layer.

[Formula 10]

(1)

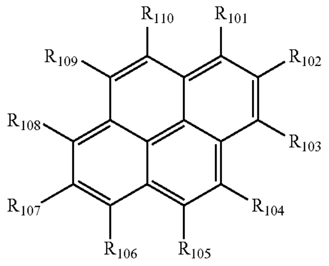

(11)

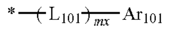

In the formula (1):

$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of $R_{101}$ to $R_{110}$ is a group represented by the formula (11);

when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a pyrene ring in the formula (1).

[Formula 11]

(2-1F)

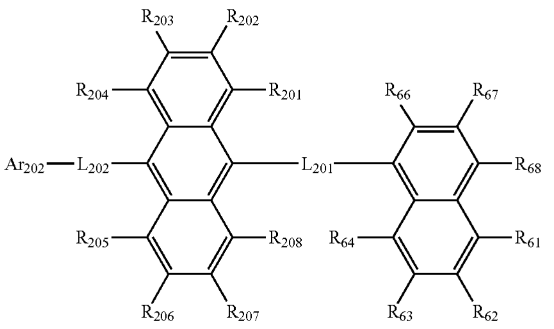

In the formula (2-1F):

$R_{201}$ to $R_{208}$, $R_{61}$ to $R_{64}$, $R_{66}$ and $R_{68}$ are each independently a hydrogen atom or a substituent, and $R_{67}$ is a substituent;

$R_{201}$ to $R_{208}$ as a substituent are each independently a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$R_{61}$ to $R_{64}$ and $R_{66}$ to $R_{68}$ as a substituent are each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, and an unsubstituted aryl group having 6 to 50 ring carbon atoms;

$L_{201}$ and $L_{202}$ are each independently a single bond, or a substituted or unsubstituted arylene group having 6 to 50 ring carbon atoms;

a substituent, if present, for $L_{201}$ and $L_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, and an unsubstituted aryl group having 6 to 50 ring carbon atoms;

$Ar_{202}$ is a substituted or unsubstituted aryl group having 6 to 50 ring carbon atoms; and a substituent, if present, for $Ar_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, and an unsubstituted aryl group having 6 to 50 ring carbon atoms.

In the first compound represented by the formula (1) and the second compound represented by the formula (2-1F):

$R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{501}$ are present, the plurality of $R_{501}$ are mutually the same or different; and when a plurality of $R_{802}$ are present, the plurality of $R_{802}$ are mutually the same or different.

According to a still further aspect of the invention, there is provided an electronic device including the organic electroluminescence device according to the above aspect of the invention.

According to a still further aspect of the invention, there is provided an organic electroluminescence device with enhanced performance. According to a still further aspect of the invention, there is provided an organic electroluminescence device with an improved lifetime. According to a still further aspect of the invention, there is provided an electronic device including the organic electroluminescence device.

BRIEF DESCRIPTION OF DRAWING(S)

The FIGURE schematically shows an exemplary arrangement of an organic electroluminescence device according to an exemplary embodiment of the invention.

DESCRIPTION OF EMBODIMENT(S)

Definitions

Herein, a hydrogen atom includes isotope having different numbers of neutrons, specifically, protium, deuterium and tritium.

In chemical formulae herein, it is assumed that a hydrogen atom (i.e. protium, deuterium and tritium) is bonded to each of bondable positions that are not annexed with signs "R" or the like or "D" representing a deuterium.

Herein, the ring carbon atoms refer to the number of carbon atoms among atoms forming a ring of a compound (e.g., a monocyclic compound, fused-ring compound, cross-linking compound, carbon ring compound, and heterocyclic compound) in which the atoms are bonded to each other to form the ring. When the ring is substituted by a substituent(s), carbon atom(s) contained in the substituent(s) is not counted in the ring carbon atoms. Unless otherwise specified, the same applies to the "ring carbon atoms" described later. For instance, a benzene ring has 6 ring carbon atoms, a naphthalene ring has 10 ring carbon atoms, a pyridine ring has 5 ring carbon atoms, and a furan ring has 4 ring carbon atoms. Further, for instance, 9,9-diphenylfluorenyl group has 13 ring carbon atoms and 9,9'-spirobifluorenyl group has 25 ring carbon atoms.

When a benzene ring is substituted by a substituent in a form of, for instance, an alkyl group, the number of carbon atoms of the alkyl group is not counted in the number of the ring carbon atoms of the benzene ring. Accordingly, the benzene ring substituted by an alkyl group has 6 ring carbon atoms. When a naphthalene ring is substituted by a substituent in a form of, for instance, an alkyl group, the number of carbon atoms of the alkyl group is not counted in the number of the ring carbon atoms of the naphthalene ring. Accordingly, the naphthalene ring substituted by an alkyl group has 10 ring carbon atoms.

Herein, the ring atoms refer to the number of atoms forming a ring of a compound (e.g., a monocyclic compound, fused-ring compound, cross-linking compound, carbon ring compound, and heterocyclic compound) in which the atoms are bonded to each other to form the ring (e.g., monocyclic ring, fused ring, and ring assembly). Atom(s) not forming the ring (e.g., hydrogen atom(s) for saturating the valence of the atom which forms the ring) and atom(s) in a substituent by which the ring is substituted are not counted as the ring atoms. Unless otherwise specified, the same applies to the "ring atoms" described later. For instance, a pyridine ring has 6 ring atoms, a quinazoline ring has 10 ring atoms, and a furan ring has 5 ring atoms. For instance, the number of hydrogen atom(s) bonded to a pyridine ring or the number of atoms forming a substituent are not counted as the pyridine ring atoms. Accordingly, a pyridine ring bonded to a hydrogen atom(s) or a substituent(s) has 6 ring atoms. For instance, the hydrogen atom(s) bonded to carbon atom(s) of a quinazoline ring or the atoms forming a substituent are not counted as the quinazoline ring atoms. Accordingly, a quinazoline ring bonded to hydrogen atom(s) or a substituent(s) has 10 ring atoms.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX," "XX" representing an integer of 1 or more and "YY" representing an integer of 2 or more.

Herein, "XX to YY atoms" in the description of "substituted or unsubstituted ZZ group having XX to YY atoms" represent atoms of an unsubstituted ZZ group and do not include atoms of a substituent(s) of the substituted ZZ group. Herein, "YY" is larger than "XX," "XX" representing an integer of 1 or more and "YY" representing an integer of 2 or more.

Herein, an unsubstituted ZZ group refers to an "unsubstituted ZZ group" in a "substituted or unsubstituted ZZ group," and a substituted ZZ group refers to a "substituted ZZ group" in a "substituted or unsubstituted ZZ group."

Herein, the term "unsubstituted" used in a "substituted or unsubstituted ZZ group" means that a hydrogen atom(s) in the ZZ group is not substituted with a substituent(s). The hydrogen atom(s) in the "unsubstituted ZZ group" is protium, deuterium, or tritium.

Herein, the term "substituted" used in a "substituted or unsubstituted ZZ group" means that at least one hydrogen atom in the ZZ group is substituted with a substituent. Similarly, the term "substituted" used in a "BB group substituted by AA group" means that at least one hydrogen atom in the BB group is substituted with the AA group.

Substituents Mentioned Herein

Substituents mentioned herein will be described below.

An "unsubstituted aryl group" mentioned herein has, unless otherwise specified herein, 6 to 50, preferably 6 to 30, more preferably 6 to 18 ring carbon atoms.

An "unsubstituted heterocyclic group" mentioned herein has, unless otherwise specified herein, 5 to 50, preferably 5 to 30, more preferably 5 to 18 ring atoms.

An "unsubstituted alkyl group" mentioned herein has, unless otherwise specified herein, 1 to 50, preferably 1 to 20, more preferably 1 to 6 carbon atoms.

An "unsubstituted alkenyl group" mentioned herein has, unless otherwise specified herein, 2 to 50, preferably 2 to 20, more preferably 2 to 6 carbon atoms.

An "unsubstituted alkynyl group" mentioned herein has, unless otherwise specified herein, 2 to 50, preferably 2 to 20, more preferably 2 to 6 carbon atoms.

An "unsubstituted cycloalkyl group" mentioned herein has, unless otherwise specified herein, 3 to 50, preferably 3 to 20, more preferably 3 to 6 ring carbon atoms.

An "unsubstituted arylene group" mentioned herein has, unless otherwise specified herein, 6 to 50, preferably 6 to 30, more preferably 6 to 18 ring carbon atoms.

An "unsubstituted divalent heterocyclic group" mentioned herein has, unless otherwise specified herein, 5 to 50, preferably 5 to 30, more preferably 5 to 18 ring atoms.

An "unsubstituted alkylene group" mentioned herein has, unless otherwise specified herein, 1 to 50, preferably 1 to 20, more preferably 1 to 6 carbon atoms.

Substituted or Unsubstituted Aryl Group

Specific examples (specific example group G1) of the "substituted or unsubstituted aryl group" mentioned herein include unsubstituted aryl groups (specific example group G1A) below and substituted aryl groups (specific example group G1B). (Herein, an unsubstituted aryl group refers to an "unsubstituted aryl group" in a "substituted or unsubstituted aryl group", and a substituted aryl group refers to a "substituted aryl group" in a "substituted or unsubstituted aryl group.") A simply termed "aryl group" herein includes both of an "unsubstituted aryl group" and a "substituted aryl group."

The "substituted aryl group" refers to a group derived by substituting at least one hydrogen atom in an "unsubstituted aryl group" with a substituent. Examples of the "substituted aryl group" include a group derived by substituting at least one hydrogen atom in the "unsubstituted aryl group" in the specific example group G1A below with a substituent, and examples of the substituted aryl group in the specific example group G1B below. It should be noted that the examples of the "unsubstituted aryl group" and the "substituted aryl group" mentioned herein are merely exemplary, and the "substituted aryl group" mentioned herein includes a group derived by further substituting a hydrogen atom bonded to a carbon atom of a skeleton of a "substituted aryl group" in the specific example group G1B below, and a group derived by further substituting a hydrogen atom of a substituent of the "substituted aryl group" in the specific example group G1B below.

Unsubstituted Aryl Group (Specific Example Group G1A):

a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, benzanthryl group, phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluorenyl group, 9,9'-spirobifluorenyl group, benzofluorenyl group, dibenzofluorenyl group, fluoranthenyl group, benzofluoranthenyl group, perylenyl group, and a monovalent aryl group derived by removing one hydrogen atom from cyclic structures represented by formulae (TEMP-1) to (TEMP-15) below.

[Formula 12]

(TEMP-1)

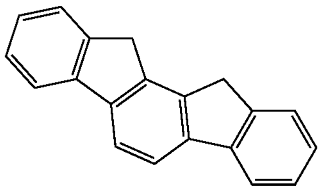

(TEMP-2)

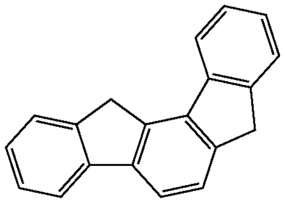

-continued (TEMP-3)

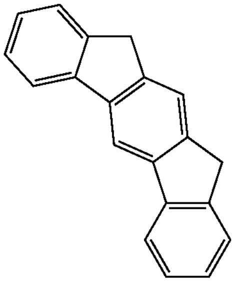

(TEMP-4)

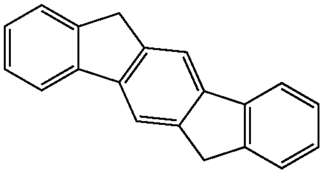

(TEMP-5)

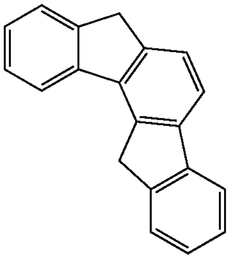

(TEMP-6)

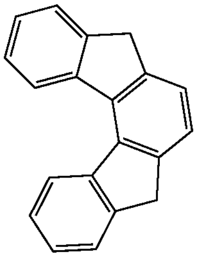

(TEMP-7)

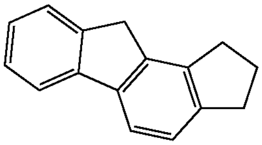

(TEMP-8)

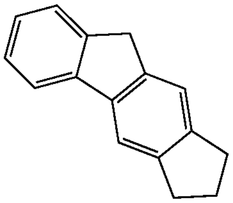

(TEMP-9)

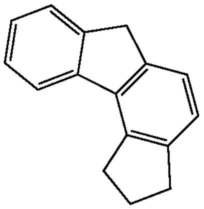

-continued

[Formula 13]

(TEMP-10)

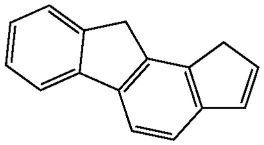

(TEMP-11)

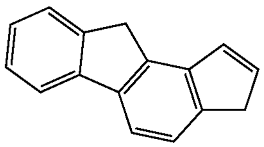

(TEMP-12)

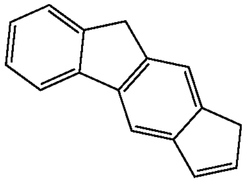

(TEMP-13)

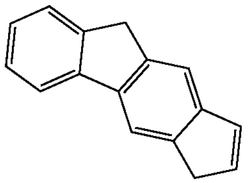

(TEMP-14)

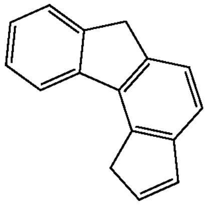

(TEMP-15)

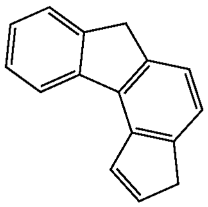

Substituted Aryl Group (Specific Example Group G1B):

o-tolyl group, m-tolyl group, p-tolyl group, para-xylyl group, meta-xylyl group, ortho-xylyl group, para-isopropylphenyl group, meta-isopropylphenyl group, ortho-isopropylphenyl group, para-t-butylphenyl group, meta-t-butylphenyl group, ortho-t-butylphenyl group, 3,4,5-trimethylphenyl group, 9,9-dimethylfluorenyl group, 9,9-diphenylfluorenyl group, 9,9-bis(4-methylphenyl)fluorenyl group, 9,9-bis(4-isopropylphenyl)fluorenyl group, 9,9-bis(4-t-butylphenyl)fluorenyl group, cyanophenyl group, triphenylsilylphenyl group, trimethylsilylphenyl group, phenylnaphthyl group, naphthylphenyl group, and a group derived by substituting at least one hydrogen atom of a monovalent group derived from one of the cyclic structures represented by the formulae (TEMP-1) to (TEMP-15) with a substituent.

Substituted or Unsubstituted Heterocyclic Group

The "heterocyclic group" mentioned herein refers to a cyclic group having at least one hetero atom in the ring atoms. Specific examples of the hetero atom include a nitrogen atom, oxygen atom, sulfur atom, silicon atom, phosphorus atom, and boron atom.

The "heterocyclic group" mentioned herein is a monocyclic group or a fused-ring group.

The "heterocyclic group" mentioned herein is an aromatic heterocyclic group or a non-aromatic heterocyclic group.

Specific examples (specific example group G2) of the "substituted or unsubstituted heterocyclic group" mentioned herein include unsubstituted heterocyclic groups (specific example group G2A) and substituted heterocyclic groups (specific example group G2B). (Herein, an unsubstituted heterocyclic group refers to an "unsubstituted heterocyclic group" in a "substituted or unsubstituted heterocyclic group," and a substituted heterocyclic group refers to a "substituted heterocyclic group" in a "substituted or unsubstituted heterocyclic group.") A simply termed "heterocyclic group" herein includes both of "unsubstituted heterocyclic group" and "substituted heterocyclic group."

The "substituted heterocyclic group" refers to a group derived by substituting at least one hydrogen atom in an "unsubstituted heterocyclic group" with a substituent. Specific examples of the "substituted heterocyclic group" include a group derived by substituting at least one hydrogen atom in the "unsubstituted heterocyclic group" in the specific example group G2A below with a substituent, and examples of the substituted heterocyclic group in the specific example group G2B below. It should be noted that the examples of the "unsubstituted heterocyclic group" and the "substituted heterocyclic group" mentioned herein are merely exemplary, and the "substituted heterocyclic group" mentioned herein includes a group derived by further substituting a hydrogen atom bonded to a ring atom of a skeleton of a "substituted heterocyclic group" in the specific example group G2B below, and a group derived by further substituting a hydrogen atom of a substituent of the "substituted heterocyclic group" in the specific example group G2B below.

The specific example group G2A includes, for instance, unsubstituted heterocyclic groups including a nitrogen atom (specific example group G2A1) below, unsubstituted heterocyclic groups including an oxygen atom (specific example group G2A2) below, unsubstituted heterocyclic groups including a sulfur atom (specific example group G2A3) below, and monovalent heterocyclic groups (specific example group G2A4) derived by removing a hydrogen atom from cyclic structures represented by formulae (TEMP-16) to (TEMP-33) below.

The specific example group G2B includes, for instance, substituted heterocyclic groups including a nitrogen atom (specific example group G2B1) below, substituted heterocyclic groups including an oxygen atom (specific example group G2B2) below, substituted heterocyclic groups including a sulfur atom (specific example group G2B3) below, and groups derived by substituting at least one hydrogen atom of the monovalent heterocyclic groups (specific example group G2B4) derived from the cyclic structures represented by formulae (TEMP-16) to (TEMP-33) below.

Unsubstituted Heterocyclic Groups Including Nitrogen Atom (Specific Example Group G2A1):

pyrrolyl group, imidazolyl group, pyrazolyl group, triazolyl group, tetrazolyl group, oxazolyl group, isoxazolyl group, oxadiazolyl group, thiazolyl group, isothiazolyl group, thiadiazolyl group, pyridyl group, pyridazynyl group, pyrimidinyl group, pyrazinyl group, triazinyl group, indolyl group, isoindolyl group, indolizinyl group, quinolizinyl group, quinolyl group, isoquinolyl group, cinnolyl group, phthalazinyl group, quinazolinyl group, quinoxalinyl group, benzimidazolyl group, indazolyl group, phenanthrolinyl group, phenanthridinyl group, acridinyl group, phenazinyl group, carbazolyl group, benzocarbazolyl group, morpholino group, phenoxazinyl group, phenothiazinyl group, azacarbazolyl group, and diazacarbazolyl group.

Unsubstituted Heterocyclic Groups Including Oxygen Atom (Specific Example Group G2A2):

furyl group, oxazolyl group, isoxazolyl group, oxadiazolyl group, xanthenyl group, benzofuranyl group, isobenzofuranyl group, dibenzofuranyl group, naphthobenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

Unsubstituted Heterocyclic Groups Including Sulfur Atom (Specific Example Group G2A3):

thienyl group, thiazolyl group, isothiazolyl group, thiadiazolyl group, benzothiophenyl group (benzothienyl group), isobenzothiophenyl group (isobenzothienyl group), dibenzothiophenyl group (dibenzothienyl group), naphthobenzothiophenyl group (nahthobenzothienyl group), benzothiazolyl group, benzisothiazolyl group, phenothiazinyl group, dinaphthothiophenyl group (dinaphthothienyl group), azadibenzothiophenyl group (azadibenzothienyl group), diazadibenzothiophenyl group (diazadibenzothienyl group), azanaphthobenzothiophenyl group (azanaphthobenzothienyl group), and diazanaphthobenzothiophenyl group (diazanaphthobenzothienyl group).

Monovalent Heterocyclic Groups Derived by Removing One Hydrogen Atom from Cyclic Structures Represented by Formulae (TEMP-16) to (TEMP-33) (Specific Example Group G2A4):

[Formula 14]

(TEMP-16)

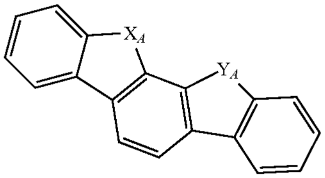

(TEMP-17)

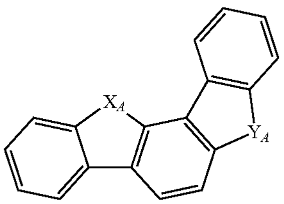

(TEMP-18)

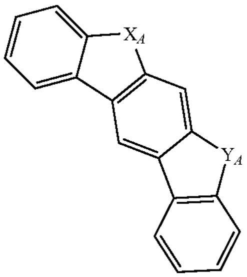

-continued (TEMP-19)

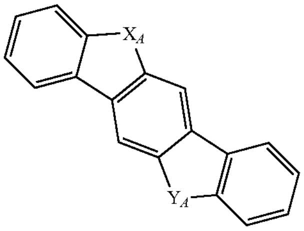

(TEMP-20)

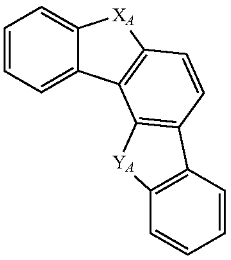

(TEMP-21)

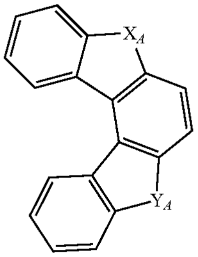

(TEMP-22)

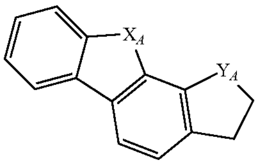

(TEMP-23)

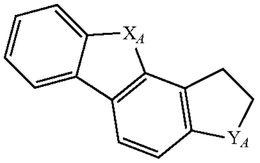

(TEMP-24)

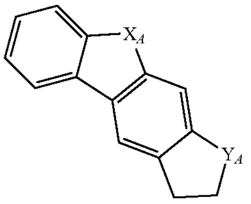

[Formula 15]

(TEMP-25)

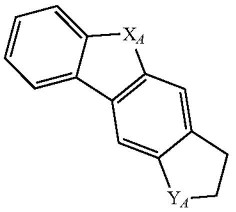

-continued (TEMP-26)

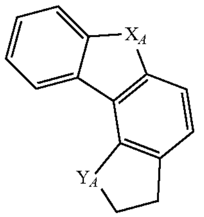

(TEMP-27)

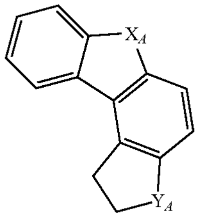

(TEMP-28)

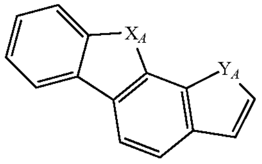

(TEMP-29)

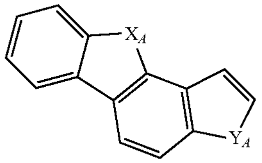

(TEMP-30)

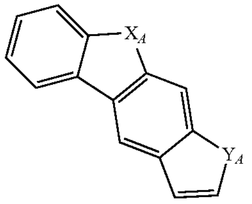

(TEMP-31)

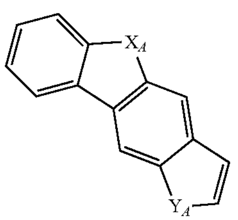

(TEMP-32)

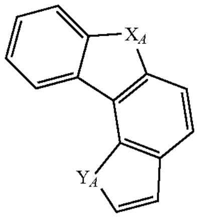

-continued (TEMP-33)

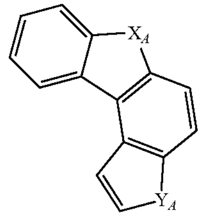

In the formulae (TEMP-16) to (TEMP-33), $X_A$ and $Y_A$ are each independently an oxygen atom, a sulfur atom, NH or $CH_2$, with a proviso that at least one of $X_A$ or $Y_A$ is an oxygen atom, a sulfur atom, or NH.

When at least one of $X_A$ or $Y_A$ in the formulae (TEMP-16) to (TEMP-33) is NH or $CH_2$, the monovalent heterocyclic groups derived from the cyclic structures represented by the formulae (TEMP-16) to (TEMP-33) include a monovalent group derived by removing one hydrogen atom from NH or $CH_2$.

Substituted Heterocyclic Groups Including Nitrogen Atom (Specific Example Group G2B1):

(9-phenyl)carbazolyl group, (9-biphenylyl)carbazolyl group, (9-phenyl)phenylcarbazolyl group, (9-naphthyl)carbazolyl group, diphenylcarbazole-9-yl group, phenylcarbazole-9-yl group, methylbenzimidazolyl group, ethylbenzimidazolyl group, phenyltriazinyl group, biphenylyltriazinyl group, diphenyltriazinyl group, phenylquinazolinyl group, and biphenylquinazolinyl group.

Substituted Heterocyclic Groups Including Oxygen Atom (Specific Example Group G2B2):

phenyldibenzofuranyl group, methyldibenzofuranyl group, t-butyldibenzofuranyl group, and monovalent residue of spiro[9H-xanthene-9,9'-[9H]fluorene].

Substituted Heterocyclic Groups Including Sulfur Atom (Specific Example Group G2B3):

phenyldibenzothiophenyl group, methyldibenzothiophenyl group, t-butyldibenzothiophenyl group, and monovalent residue of spiro[9H-thioxanthene-9,9'-[9H]fluorene].

Groups Obtained by Substituting at Least One Hydrogen Atom of Monovalent Heterocyclic Group Derived from Cyclic Structures Represented by Formulae: (TEMP-16) to (TEMP-33) with Substituent (Specific Example Group G2B4)

The "at least one hydrogen atom of a monovalent heterocyclic group" means at least one hydrogen atom selected from a hydrogen atom bonded to a ring carbon atom of the monovalent heterocyclic group, a hydrogen atom bonded to a nitrogen atom of at least one of XA or YA in a form of NH, and a hydrogen atom of one of XA and YA in a form of a methylene group (CH2).

Substituted or Unsubstituted Alkyl Group:

Specific examples (specific example group G3) of the "substituted or unsubstituted alkyl group" mentioned herein include unsubstituted alkyl groups (specific example group G3A) and substituted alkyl groups (specific example group G3B) below. (Herein, an unsubstituted alkyl group refers to an "unsubstituted alkyl group" in a "substituted or unsubstituted alkyl group," and a substituted alkyl group refers to a "substituted alkyl group" in a "substituted or unsubstituted alkyl group.") A simply termed "alkyl group" herein includes both of "unsubstituted alkyl group" and "substituted alkyl group."

The "substituted alkyl group" refers to a group derived by substituting at least one hydrogen atom in an "unsubstituted alkyl group" with a substituent. Specific examples of the "substituted alkyl group" include a group derived by substituting at least one hydrogen atom of an "unsubstituted alkyl group" (specific example group G3A) below with a substituent, and examples of the substituted alkyl group (specific example group G3B) below. Herein, the alkyl group for the "unsubstituted alkyl group" refers to a chain alkyl group. Accordingly, the "unsubstituted alkyl group" include linear "unsubstituted alkyl group" and branched "unsubstituted alkyl group." It should be noted that the examples of the "unsubstituted alkyl group" and the "substituted alkyl group" mentioned herein are merely exemplary, and the "substituted alkyl group" mentioned herein includes a group derived by further substituting a hydrogen atom of a skeleton of the "substituted alkyl group" in the specific example group G3B, and a group derived by further substituting a hydrogen atom of a substituent of the "substituted alkyl group" in the specific example group G3B.

Unsubstituted Alkyl Group (Specific Example Group G3A):

methyl group, ethyl group, n-propyl group, isopropyl group, n-butyl group, isobutyl group, s-butyl group, and t-butyl group.

Substituted Alkyl Group (Specific Example Group G3B):

heptafluoropropyl group (including isomer thereof), pentafluoroethyl group, 2,2,2-trifluoroethyl group, and trifluoromethyl group.

Substituted or Unsubstituted Alkenyl Group

Specific examples (specific example group G4) of the "substituted or unsubstituted alkenyl group" mentioned herein include unsubstituted alkenyl groups (specific example group G4A) and substituted alkenyl groups (specific example group G4B). (Herein, an unsubstituted alkenyl group refers to an "unsubstituted alkenyl group" in a "substituted or unsubstituted alkenyl group," and a substituted alkenyl group refers to a "substituted alkenyl group" in a "substituted or unsubstituted alkenyl group.") A simply termed "alkenyl group" herein includes both of "unsubstituted alkenyl group" and "substituted alkenyl group."

The "substituted alkenyl group" refers to a group derived by substituting at least one hydrogen atom in an "unsubstituted alkenyl group" with a substituent. Specific examples of the "substituted alkenyl group" include an "unsubstituted alkenyl group" (specific example group G4A) substituted by a substituent, and examples of the substituted alkenyl group (specific example group G4B) below. It should be noted that the examples of the "unsubstituted alkenyl group" and the "substituted alkenyl group" mentioned herein are merely exemplary, and the "substituted alkenyl group" mentioned herein includes a group derived by further substituting a hydrogen atom of a skeleton of the "substituted alkenyl group" in the specific example group G4B with a substituent, and a group derived by further substituting a hydrogen atom of a substituent of the "substituted alkenyl group" in the specific example group G4B with a substituent.

Unsubstituted Alkenyl Group (Specific Example Group G4A):

vinyl group, allyl group, 1-butenyl group, 2-butenyl group, and 3-butenyl group.

Substituted Alkenyl Group (Specific Example Group G4B):

1,3-butanedienyl group, 1-methylvinyl group, 1-methylallyl group, 1,1-dimethylallyl group, 2-methylallyl group, and 1,2-dimethylallyl group.

Substituted or Unsubstituted Alkynyl Group

Specific examples (specific example group G5) of the "substituted or unsubstituted alkynyl group" mentioned herein include unsubstituted alkynyl groups (specific example group G5A) below. (Herein, an unsubstituted alkynyl group refers to an "unsubstituted alkynyl group" in a "substituted or unsubstituted alkynyl group.") A simply termed "alkynyl group" herein includes both of "unsubstituted alkynyl group" and "substituted alkynyl group."

The "substituted alkynyl group" refers to a group derived by substituting at least one hydrogen atom in an "unsubstituted alkynyl group" with a substituent. Specific examples of the "substituted alkynyl group" include a group derived by substituting at least one hydrogen atom of the "unsubstituted alkynyl group" (specific example group G5A) below with a substituent.

Unsubstituted Alkynyl Group (Specific Example Group G5A): Ethynyl Group.

Substituted or Unsubstituted Cycloalkyl Group

Specific examples (specific example group G6) of the "substituted or unsubstituted cycloalkyl group" mentioned herein include unsubstituted cycloalkyl groups (specific example group G6A) and substituted cycloalkyl groups (specific example group G6B). (Herein, an unsubstituted cycloalkyl group refers to an "unsubstituted cycloalkyl group" in a "substituted or unsubstituted cycloalkyl group," and a substituted cycloalkyl group refers to a "substituted cycloalkyl group" in a "substituted or unsubstituted cycloalkyl group.") A simply termed "cycloalkyl group" herein includes both of "unsubstituted cycloalkyl group" and "substituted cycloalkyl group."

The "substituted cycloalkyl group" refers to a group derived by substituting at least one hydrogen atom of an "unsubstituted cycloalkyl group" with a substituent. Specific examples of the "substituted cycloalkyl group" include a group derived by substituting at least one hydrogen atom of the "unsubstituted cycloalkyl group" (specific example group G6A) below with a substituent, and examples of the substituted cycloalkyl group (specific example group G6B) below. It should be noted that the examples of the "unsubstituted cycloalkyl group" and the "substituted cycloalkyl group" mentioned herein are merely exemplary, and the "substituted cycloalkyl group" mentioned herein includes a group derived by substituting at least one hydrogen atom bonded to a carbon atom of a skeleton of the "substituted cycloalkyl group" in the specific example group G6B with a substituent, and a group derived by further substituting a hydrogen atom of a substituent of the "substituted cycloalkyl group" in the specific example group G6B with a substituent.

Unsubstituted Cycloalkyl Group (Specific Example Group G6A):

cyclopropyl group, cyclobutyl group, cyclopentyl group, cyclohexyl group, 1-adamantyl group, 2-adamantyl group, 1-norbornyl group, and 2-norbornyl group.

Substituted Cycloalkyl Group (Specific Example Group G6B): 4-methylcyclohexyl Group Group Represented by $—Si(R_{901})(R_{902})(R_{903})$ Specific examples (specific example group G7) of the group represented herein by $—Si(R_{901})(R_{902})(R_{903})$ include: —Si(G1)(G1)(G1); —Si(G1)(G2)(G2); Si(G1)(G1)(G2); —Si(G2)(G2)(G2); —Si(G3)(G3)(G3); and —Si(G6)(G6)(G6), where:

- G1 represents a "substituted or unsubstituted aryl group" in the specific example group G1;
- G2 represents a "substituted or unsubstituted heterocyclic group" in the specific example group G2;
- G3 represents a "substituted or unsubstituted alkyl group" in the specific example group G3;
- G6 represents a "substituted or unsubstituted cycloalkyl group" in the specific example group G6;

- a plurality of G1 in —Si(G1)(G1)(G1) are mutually the same or different;
- a plurality of G2 in —Si(G1)(G2)(G2) are mutually the same or different;
- a plurality of G1 in —Si(G1)(G1)(G2) are mutually the same or different;
- a plurality of G2 in —Si(G2)(G2)(G2) are mutually the same or different;
- a plurality of G3 in —Si(G3)(G3)(G3) are mutually the same or different; and
- a plurality of G6 in —Si(G6)(G6)(G6) are mutually the same or different.

Group Represented by —O—($R_{904}$)

Specific examples (specific example group G8) of a group represented by —O—($R_{904}$) herein include: —O(G1); —O(G2); —O(G3); and —O(G6), where:

- G1 represents a "substituted or unsubstituted aryl group" in the specific example group G1;
- G2 represents a "substituted or unsubstituted heterocyclic group" in the specific example group G2;
- G3 represents a "substituted or unsubstituted alkyl group" in the specific example group G3; and
- G6 represents a "substituted or unsubstituted cycloalkyl group" in the specific example group G6.

Group Represented by —S—($R_{905}$)

Specific examples (specific example group G9) of a group represented herein by —S—($R_{905}$) include: —S(G1); —S(G2); —S(G3); and —S(G6), where:

- G1 represents a "substituted or unsubstituted aryl group" in the specific example group G1;
- G2 represents a "substituted or unsubstituted heterocyclic group" in the specific example group G2;
- G3 represents a "substituted or unsubstituted alkyl group" in the specific example group G3; and
- G6 represents a "substituted or unsubstituted cycloalkyl group" in the specific example group G6.

Group Represented by —N($R_{906}$)($R_{907}$)

Specific examples (specific example group G10) of a group represented herein by —N($R_{906}$)($R_{907}$) include: —N(G1)(G1); —N(G2)(G2); —N(G1)(G2); —N(G3)(G3); and —N(G6)(G6), where:

- G1 represents a "substituted or unsubstituted aryl group" in the specific example group G1;
- G2 represents a "substituted or unsubstituted heterocyclic group" in the specific example group G2;
- G3 represents a "substituted or unsubstituted alkyl group" in the specific example group G3;
- G6 represents a "substituted or unsubstituted cycloalkyl group" in the specific example group G6;
- a plurality of G1 in —N(G1)(G1) are mutually the same or different;
- a plurality of G2 in —N(G2)(G2) are mutually the same or different;
- a plurality of G3 in —N(G3)(G3) are mutually the same or different; and
- a plurality of G6 in —N(G6)(G6) are mutually the same or different.

Halogen Atom

Specific examples (specific example group G11) of "halogen atom" mentioned herein include a fluorine atom, chlorine atom, bromine atom, and iodine atom.

Substituted or Unsubstituted Fluoroalkyl Group

The "substituted or unsubstituted fluoroalkyl group" mentioned herein refers to a group derived by substituting at least one hydrogen atom bonded to at least one of carbon atoms forming an alkyl group in the "substituted or unsubstituted alkyl group" with a fluorine atom, and also includes a group (perfluoro group) derived by substituting all of hydrogen atoms bonded to carbon atoms forming the alkyl group in the "substituted or unsubstituted alkyl group" with fluorine atoms. An "unsubstituted fluoroalkyl group" has, unless otherwise specified herein, 1 to 50, preferably 1 to 30, more preferably 1 to 18 carbon atoms. The "substituted fluoroalkyl group" refers to a group derived by substituting at least one hydrogen atom in a "fluoroalkyl group" with a substituent. It should be noted that the examples of the "substituted fluoroalkyl group" mentioned herein include a group derived by further substituting at least one hydrogen atom bonded to a carbon atom of an alkyl chain of a "substituted fluoroalkyl group" with a substituent, and a group derived by further substituting at least one hydrogen atom of a substituent of the "substituted fluoroalkyl group" with a substituent. Specific examples of the "substituted fluoroalkyl group" include a group derived by substituting at least one hydrogen atom of the "alkyl group" (specific example group G3) with a fluorine atom.

Substituted or Unsubstituted Haloalkyl Group

The "substituted or unsubstituted haloalkyl group" mentioned herein refers to a group derived by substituting at least one hydrogen atom bonded to carbon atoms forming the alkyl group in the "substituted or unsubstituted alkyl group" with a halogen atom, and also includes a group derived by substituting all hydrogen atoms bonded to carbon atoms forming the alkyl group in the "substituted or unsubstituted alkyl group" with halogen atoms. An "unsubstituted haloalkyl group" has, unless otherwise specified herein, 1 to 50, preferably 1 to 30, more preferably 1 to 18 carbon atoms. The "substituted haloalkyl group" refers to a group derived by substituting at least one hydrogen atom in a "haloalkyl group" with a substituent. It should be noted that the examples of the "substituted haloalkyl group" mentioned herein include a group derived by further substituting at least one hydrogen atom bonded to a carbon atom of an alkyl chain of a "substituted haloalkyl group" with a substituent, and a group derived by further substituting at least one hydrogen atom of a substituent of the "substituted haloalkyl group" with a substituent. Specific examples of the "substituted haloalkyl group" include a group derived by substituting at least one hydrogen atom of the "alkyl group" (specific example group G3) with a halogen atom. The haloalkyl group is sometimes referred to as a halogenated alkyl group.

Substituted or Unsubstituted Alkoxy Group

Specific examples of a "substituted or unsubstituted alkoxy group" mentioned herein include a group represented by —O(G3), G3 being the "substituted or unsubstituted alkyl group" in the specific example group G3. An "unsubstituted alkoxy group" has, unless otherwise specified herein, 1 to 50, preferably 1 to 30, more preferably 1 to 18 carbon atoms.

Substituted or Unsubstituted Alkylthio Group

Specific examples of a "substituted or unsubstituted alkylthio group" mentioned herein include a group represented by —S(G3), G3 being the "substituted or unsubstituted alkyl group" in the specific example group G3. An "unsubstituted alkylthio group" has, unless otherwise specified herein, 1 to 50, preferably 1 to 30, more preferably 1 to 18 carbon atoms.

Substituted or Unsubstituted Aryloxy Group

Specific examples of a "substituted or unsubstituted aryloxy group" mentioned herein include a group represented by —O(G1), G1 being the "substituted or unsubstituted aryl group" in the specific example group G1. An "unsubstituted aryloxy group" has, unless otherwise specified herein, 6 to 50, preferably 6 to 30, more preferably 6 to 18 ring carbon atoms.

Substituted or Unsubstituted Arylthio Group

Specific examples of a "substituted or unsubstituted arylthio group" mentioned herein include a group represented by —S(G1), G1 being the "substituted or unsubstituted aryl group" in the specific example group G1. An "unsubstituted arylthio group" has, unless otherwise specified herein, 6 to 50, preferably 6 to 30, more preferably 6 to 18 ring carbon atoms.

Substituted or Unsubstituted Trialkylsilyl Group

Specific examples of a "trialkylsilyl group" mentioned herein include a group represented by —Si(G3)(G3)(G3), G3 being the "substituted or unsubstituted alkyl group" in the specific example group G3. The plurality of G3 in —Si(G3)(G3)(G3) are mutually the same or different. Each of the alkyl groups in the "trialkylsilyl group" has, unless otherwise specified herein, 1 to 50, preferably 1 to 20, more preferably 1 to 6 carbon atoms.

Substituted or Unsubstituted Aralkyl Group

Specific examples of a "substituted or unsubstituted aralkyl group" mentioned herein include a group represented by (G3)-(G1), G3 being the "substituted or unsubstituted alkyl group" in the specific example group G3, G1 being the "substituted or unsubstituted aryl group" in the specific example group G1. Accordingly, the "aralkyl group" is a group derived by substituting a hydrogen atom of the "alkyl group" with a substituent in a form of the "aryl group," which is an example of the "substituted alkyl group." An "unsubstituted aralkyl group," which is an "unsubstituted alkyl group" substituted by an "unsubstituted aryl group," has, unless otherwise specified herein, 7 to 50 carbon atoms, preferably 7 to 30 carbon atoms, more preferably 7 to 18 carbon atoms.

Specific examples of the "substituted or unsubstituted aralkyl group" include a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Preferable examples of the substituted or unsubstituted aryl group mentioned herein include, unless otherwise specified herein, a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, phenanthryl group, pyrenyl group, chrysenyl group, triphenylenyl group, fluorenyl group, 9,9'-spirobifluorenyl group, 9,9-dimethylfluorenyl group, and 9,9-diphenylfluorenyl group.

Preferable examples of the substituted or unsubstituted heterocyclic group mentioned herein include, unless otherwise specified herein, a pyridyl group, pyrimidinyl group, triazinyl group, quinolyl group, isoquinolyl group, quinazolinyl group, benzimidazolyl group, phenanthrolinyl group, carbazolyl group (1-carbazolyl group, 2-carbazolyl group, 3-carbazolyl group, 4-carbazolyl group, or 9-carbazolyl group), benzocarbazolyl group, azacarbazolyl group, diazacarbazolyl group, dibenzofuranyl group, naphthobenzofuranyl group, azadibenzofuranyl group, diazadibenzofuranyl group, dibenzothiophenyl group, naphthobenzothiophenyl group, azadibenzothiophenyl group, diazadibenzothiophenyl group, (9-phenyl)carbazolyl group ((9-phenyl)carbazole-1-yl group, (9-phenyl)carbazole-2-yl group, (9-phenyl)carbazole-3-yl group, or (9-phenyl)carbazole-4-yl group), (9-biphenylyl)carbazolyl group, (9-phenyl)phenylcarbazolyl group, diphenylcarbazole-9-yl group, phenylcarbazole-9-yl group, phenyltriazinyl group, biphenylyltriazinyl group, diphenyltriazinyl group, phenyldibenzofuranyl group, and phenyldibenzothiophenyl group.

The carbazolyl group mentioned herein is, unless otherwise specified herein, specifically a group represented by one of formulae below.

[Formula 16]

(TEMP-Cz1)

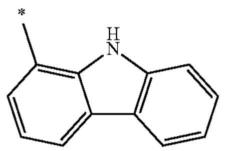

(TEMP-Cz2)

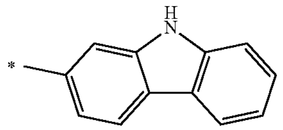

(TEMP-Cz3)

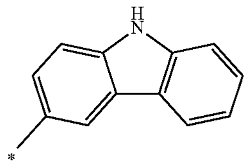

(TEMP-Cz4)

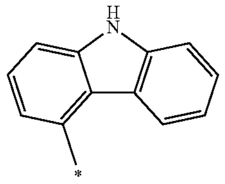

(TEMP-Cz5)

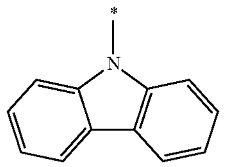

The (9-phenyl)carbazolyl group mentioned herein is, unless otherwise specified herein, specifically a group represented by one of formulae below.

[Formula 17]

(TEMP-Cz6)

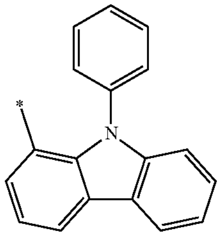

(TEMP-Cz7)

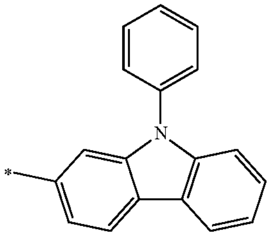

(TEMP-Cz8)

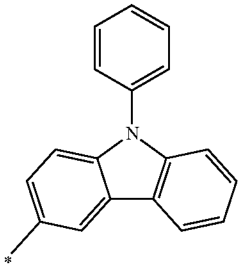

(TEMP-Cz9)

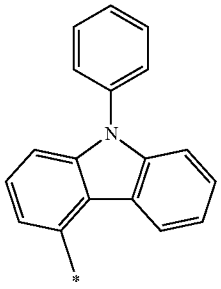

In the formulae (TEMP-Cz1) to (TEMP-Cz9), * represents a bonding position.

The dibenzofuranyl group and dibenzothiophenyl group mentioned herein are, unless otherwise specified herein, each specifically represented by one of formulae below.

[Formula 18]

(TEMP-34)

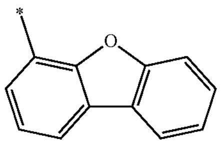

(TEMP-35)

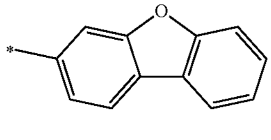

-continued (TEMP-36)

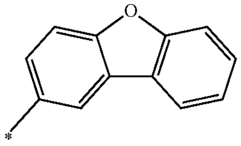

(TEMP-37)

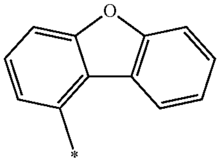

(TEMP-38)

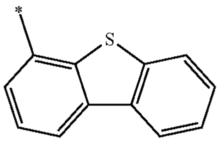

(TEMP-39)

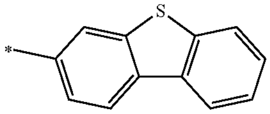

(TEMP-40)

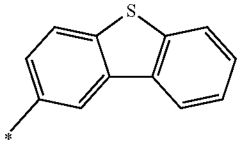

(TEMP-41)

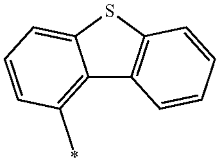

In the formulae (TEMP-34) to (TEMP-41), * represents a bonding position.

Preferable examples of the substituted or unsubstituted alkyl group mentioned herein include, unless otherwise specified herein, a methyl group, ethyl group, propyl group, isopropyl group, n-butyl group, isobutyl group, and t-butyl group.

Substituted or Unsubstituted Arylene Group

The "substituted or unsubstituted arylene group" mentioned herein is, unless otherwise specified herein, a divalent group derived by removing one hydrogen atom on an aryl ring of the "substituted or unsubstituted aryl group." Specific examples of the "substituted or unsubstituted arylene group" (specific example group G12) include a divalent group derived by removing one hydrogen atom on an aryl ring of the "substituted or unsubstituted aryl group" in the specific example group G1.

Substituted or Unsubstituted Divalent Heterocyclic Group

The "substituted or unsubstituted divalent heterocyclic group" mentioned herein is, unless otherwise specified herein, a divalent group derived by removing one hydrogen atom on a heterocycle of the "substituted or unsubstituted heterocyclic group." Specific examples of the "substituted or unsubstituted divalent heterocyclic group" (specific example group G13) include a divalent group derived by removing one hydrogen atom on a heterocyclic ring of the "substituted or unsubstituted heterocyclic group" in the specific example group G2.

Substituted or Unsubstituted Alkylene Group

The "substituted or unsubstituted alkylene group" mentioned herein is, unless otherwise specified herein, a divalent group derived by removing one hydrogen atom on an alkyl chain of the "substituted or unsubstituted alkyl group." Specific examples of the "substituted or unsubstituted alkylene group" (specific example group G14) include a divalent group derived by removing one hydrogen atom on an alkyl chain of the "substituted or unsubstituted alkyl group" in the specific example group G3.

The substituted or unsubstituted arylene group mentioned herein is, unless otherwise specified herein, preferably any one of groups represented by formulae (TEMP-42) to (TEMP-68) below.

[Formula 19]

(TEMP-42)

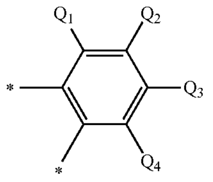

(TEMP-43)

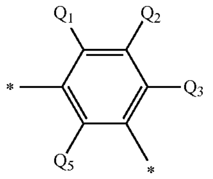

(TEMP-44)

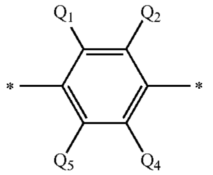

(TEMP-45)

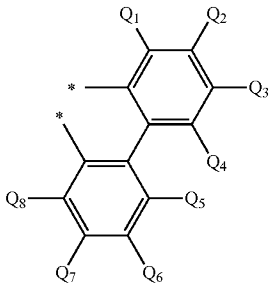

(TEMP-46)

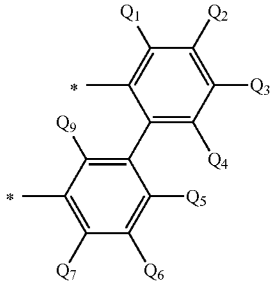

-continued (TEMP-47)

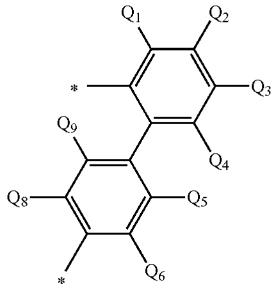

[Formula 20]

(TEMP-48)

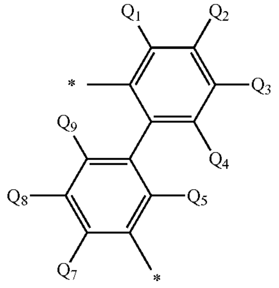

(TEMP-49)

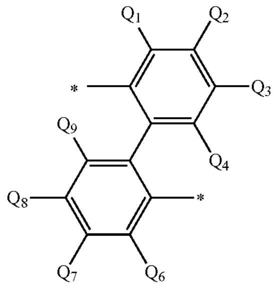

(TEMP-50)

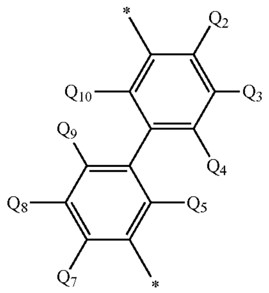

(TEMP-51)

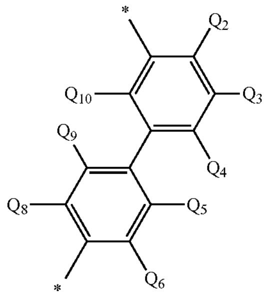

-continued (TEMP-52)

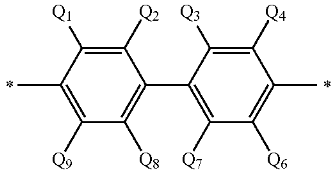

In the formulae (TEMP-42) to (TEMP-52), $Q_1$ to $Q_{10}$ each independently are a hydrogen atom or a substituent.

In the formulae (TEMP-42) to (TEMP-52), * represents a bonding position.

[Formula 21]

(TEMP-53)

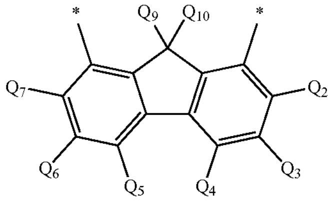

(TEMP-54)

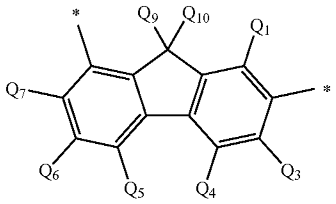

(TEMP-55)

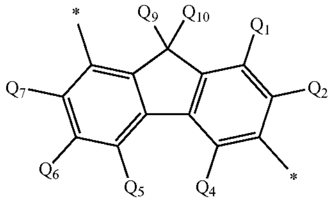

(TEMP-56)

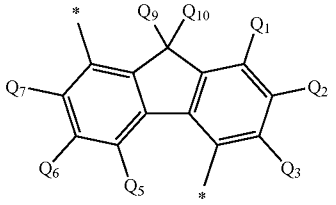

(TEMP-57)

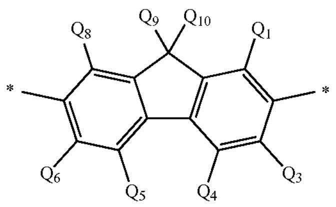

-continued (TEMP-58)

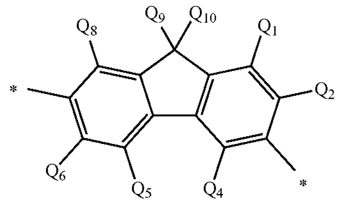

(TEMP-59)

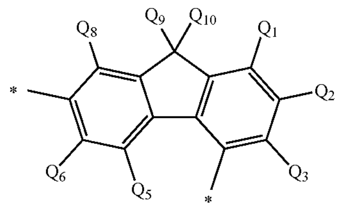

(TEMP-60)

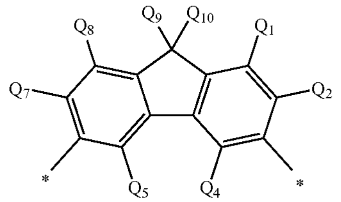

(TEMP-61)

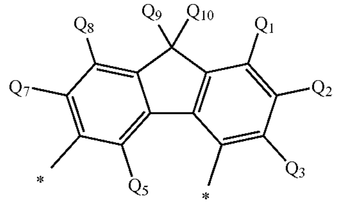

(TEMP-62)

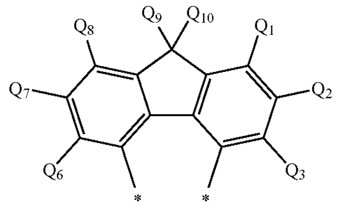

In the formulae (TEMP-53) to (TEMP-62), $Q_1$ to $Q_{10}$ each independently are a hydrogen atom or a substituent.

In the formulae, $Q_9$ and $Q_{10}$ may be mutually bonded through a single bond form a ring.

In the formulae (TEMP-53) to (TEMP-62), * represents a bonding position.

[Formula 22]

(TEMP-63)

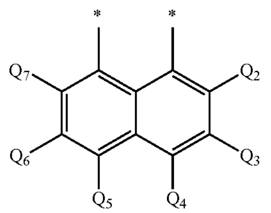

-continued (TEMP-64)

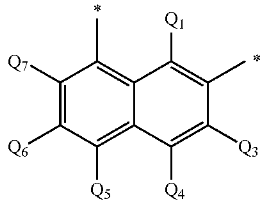

(TEMP-65)

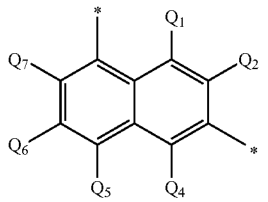

(TEMP-66)

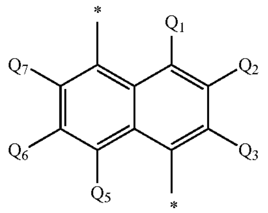

(TEMP-67)

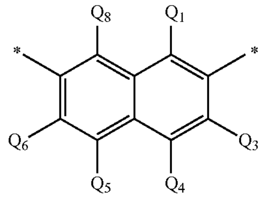

(TEMP-68)

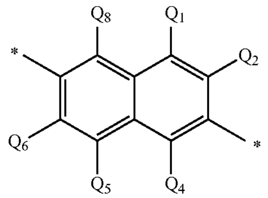

In the formulae (TEMP-63) to (TEMP-68), $Q_1$ to $Q_8$ each independently are a hydrogen atom or a substituent.

In the formulae (TEMP-63) to (TEMP-68), * represents a bonding position.

The substituted or unsubstituted divalent heterocyclic group mentioned herein is, unless otherwise specified herein, preferably a group represented by any one of formulae (TEMP-69) to (TEMP-102) below.

[Formula 23]

(TEMP-69)

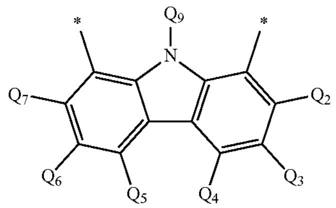

-continued (TEMP-70)

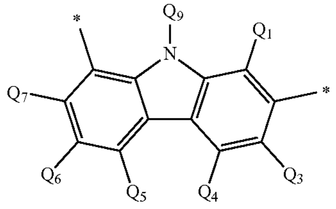

(TEMP-71)

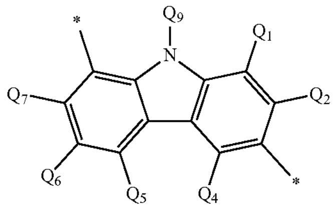

(TEMP-72)

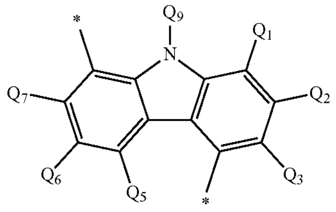

(TEMP-73)

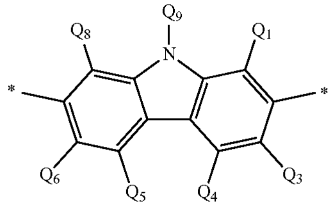

(TEMP-74)

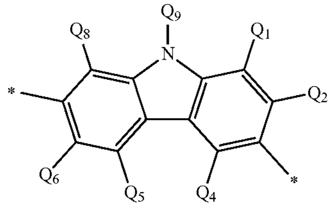

[Formula 24]

(TEMP-75)

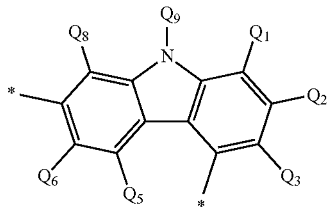

(TEMP-76)

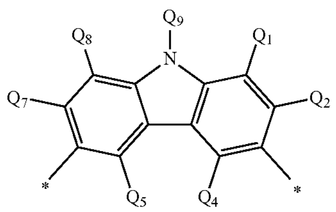

-continued
(TEMP-77)
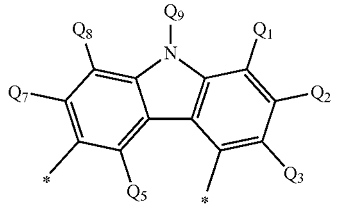
(TEMP-78)
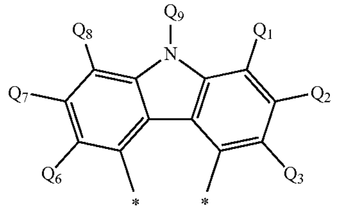
(TEMP-79)
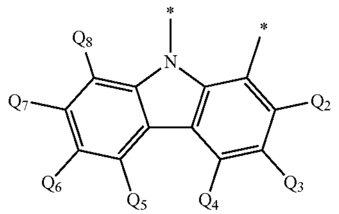
(TEMP-80)
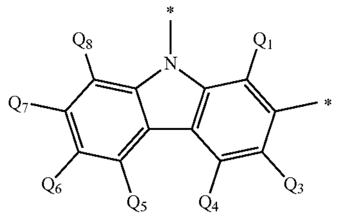
[Formula 25]
(TEMP-81)
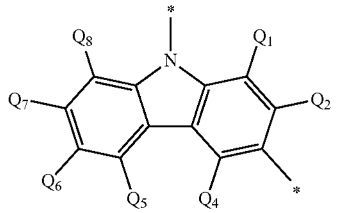
(TEMP-82)
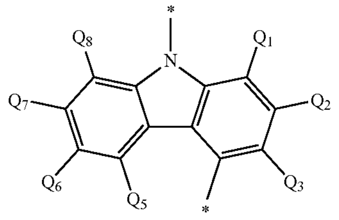
In the formulae (TEMP-69) to (TEMP-82), $Q_1$ to $Q_9$ each independently are a hydrogen atom or a substituent.
[Formula 26]
(TEMP-83)
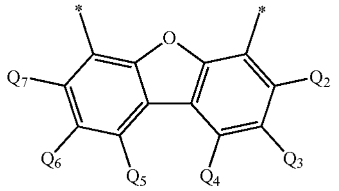
(TEMP-84)
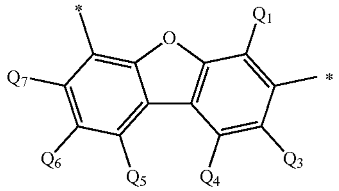
(TEMP-85)
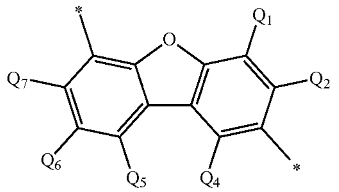
(TEMP-86)
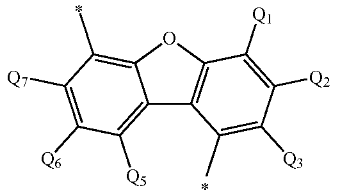
(TEMP-87)
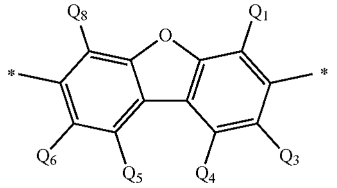
(TEMP-88)
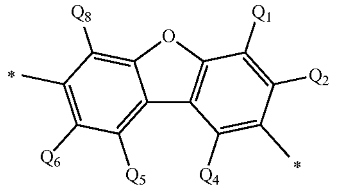
[Formula 27]
(TEMP-89)
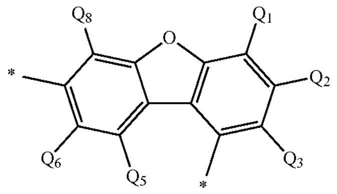

-continued (TEMP-90)

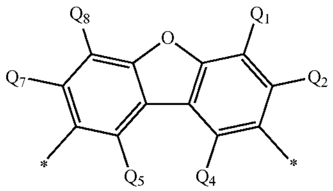

(TEMP-91)

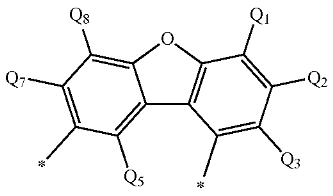

(TEMP-92)

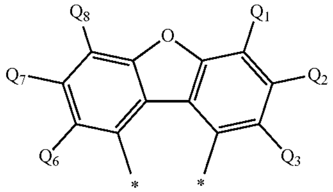

[Formula 28]

(TEMP-93)

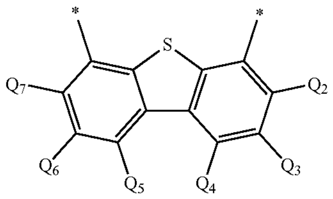

(TEMP-94)

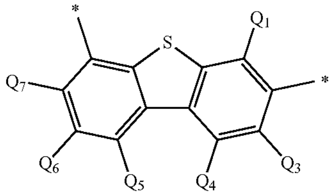

(TEMP-95)

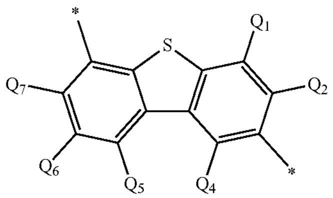

(TEMP-96)

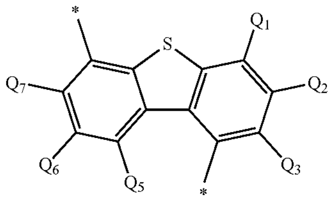

-continued (TEMP-97)

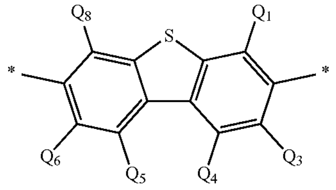

(TEMP-98)

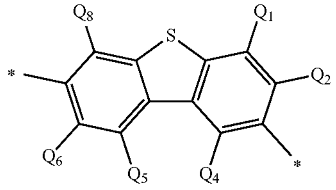

[Formula 29]

(TEMP-99)

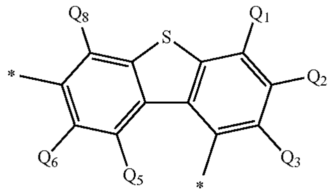

(TEMP-100)

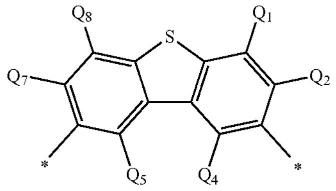

(TEMP-101)

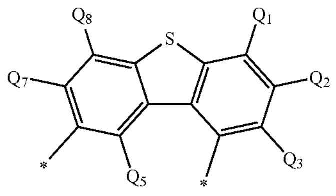

(TEMP-102)

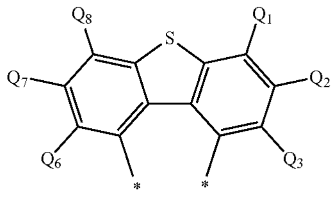

In the formulae (TEMP-83) to (TEMP-102), $Q_1$ to $Q_8$ each independently are a hydrogen atom or a substituent.

The substituent mentioned herein has been described above.

Instance of "Bonded to Form Ring"

Instances where "at least one combination of adjacent two or more (of . . . ) are mutually bonded to form a substituted or unsubstituted monocyclic ring, mutually bonded to form a substituted or unsubstituted fused ring, or not mutually bonded" mentioned herein refer to instances where "at least one combination of adjacent two or more (of . . . ) are mutually bonded to form a substituted or unsubstituted monocyclic ring, "at least one combination of adjacent two or more (of . . . ) are mutually bonded to form a substituted or unsubstituted fused ring," and "at least one combination of adjacent two or more (of . . . ) are not mutually bonded."

Instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (these instances will be sometimes collectively referred to as an instance of "bonded to form a ring" hereinafter) will be described below. An anthracene compound having a basic skeleton in a form of an anthracene ring and represented by a formula (TEMP-103) below will be used as an example for the description.

[Formula 30]

(TEMP-103)

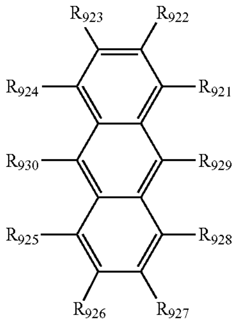

For instance, when "at least one combination of adjacent two or more of $R_{921}$ to $R_{930}$ are mutually bonded to form a ring," the combination of adjacent ones of $R_{921}$ to $R_{930}$ (i.e. the combination at issue) is a combination of $R_{921}$ and $R_{922}$, a combination of $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, or a combination of $R_{929}$ and $R_{921}$.

The term "at least one combination" means that two or more of the above combinations of adjacent two or more of $R_{921}$ to $R_{930}$ may simultaneously form rings. For instance, when $R_{921}$ and $R_{922}$ are mutually bonded to form a ring $Q_A$ and $R_{925}$ and $R_{926}$ are simultaneously mutually bonded to form a ring $Q_B$, the anthracene compound represented by the formula (TEMP-103) is represented by a formula (TEMP-104) below.

[Formula 31]

(TEMP-104)

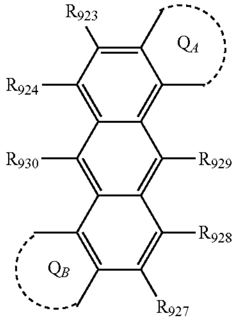

The instance where the "combination of adjacent two or more" form a ring means not only an instance where the "two" adjacent components are bonded but also an instance where adjacent "three or more" are bonded. For instance, $R_{921}$ and $R_{922}$ are mutually bonded to form a ring $Q_A$ and $R_{922}$ and $R_{923}$ are mutually bonded to form a ring $Q_C$, and mutually adjacent three components ($R_{921}$, $R_{922}$ and $R_{923}$) are mutually bonded to form a ring fused to the anthracene basic skeleton. In this case, the anthracene compound represented by the formula (TEMP-103) is represented by a formula (TEMP-105) below. In the formula (TEMP-105) below, the ring $Q_A$ and the ring $Q_C$ share $R_{922}$.

[Formula 32]

(TEMP-105)

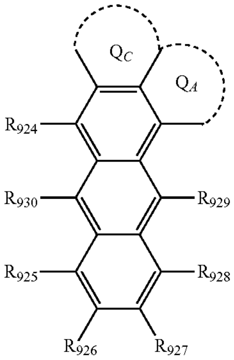

The formed "monocyclic ring" or "fused ring" may be, in terms of the formed ring in itself, a saturated ring or an unsaturated ring. When the "combination of adjacent two" form a "monocyclic ring" or a "fused ring," the "monocyclic ring" or "fused ring" may be a saturated ring or an unsaturated ring. For instance, the ring $Q_A$ and the ring $Q_B$ formed in the formula (TEMP-104) are each independently a "monocyclic ring" or a "fused ring." Further, the ring $Q_A$ and the ring $Q_C$ formed in the formula (TEMP-105) are each a "fused ring." The ring $Q_A$ and the ring $Q_C$ in the formula (TEMP-105) are fused to form a fused ring. When the ring $Q_A$ in the formula (TMEP-104) is a benzene ring, the ring $Q_A$ is a monocyclic ring. When the ring $Q_A$ in the formula (TMEP-104) is a naphthalene ring, the ring $Q_A$ is a fused ring.

The "unsaturated ring" represents an aromatic hydrocarbon ring or an aromatic heterocycle. The "saturated ring" represents an aliphatic hydrocarbon ring or a non-aromatic heterocycle.

Specific examples of the aromatic hydrocarbon ring include a ring formed by terminating a bond of a group in the specific example of the specific example group G1 with a hydrogen atom.

Specific examples of the aromatic heterocycle include a ring formed by terminating a bond of an aromatic heterocyclic group in the specific example of the specific example group G2 with a hydrogen atom.

Specific examples of the aliphatic hydrocarbon ring include a ring formed by terminating a bond of a group in the specific example of the specific example group G6 with a hydrogen atom.

The phrase "to form a ring" herein means that a ring is formed only by a plurality of atoms of a basic skeleton, or by a combination of a plurality of atoms of the basic skeleton and one or more optional atoms. For instance, the ring $Q_A$ formed by mutually bonding $R_{921}$ and $R_{922}$ shown in the formula (TEMP-104) is a ring formed by a carbon atom of the anthracene skeleton bonded to $R_{921}$, a carbon atom of the anthracene skeleton bonded to $R_{922}$, and one or more optional atoms. Specifically, when the ring $Q_A$ is a monocyclic unsaturated ring formed by $R_{921}$ and $R_{922}$, the ring formed by a carbon atom of the anthracene skeleton bonded to $R_{921}$, a carbon atom of the anthracene skeleton bonded to $R_{922}$, and four carbon atoms is a benzene ring.

The "optional atom" is, unless otherwise specified herein, preferably at least one atom selected from the group consisting of a carbon atom, nitrogen atom, oxygen atom, and sulfur atom. A bond of the optional atom (e.g. a carbon atom and a nitrogen atom) not forming a ring may be terminated by a hydrogen atom or the like or may be substituted by an "optional substituent" described later. When the ring includes an optional element other than carbon atom, the resultant ring is a heterocycle.

The number of "one or more optional atoms" forming the monocyclic ring or fused ring is, unless otherwise specified herein, preferably in a range from 2 to 15, more preferably in a range from 3 to 12, further preferably in a range from 3 to 5.

Unless otherwise specified herein, the ring, which may be a "monocyclic ring" or "fused ring," is preferably a "monocyclic ring."

Unless otherwise specified herein, the ring, which may be a "saturated ring" or "unsaturated ring," is preferably an "unsaturated ring."

Unless otherwise specified herein, the "monocyclic ring" is preferably a benzene ring.

Unless otherwise specified herein, the "unsaturated ring" is preferably a benzene ring.

When "at least one combination of adjacent two or more" (of . . . ) are "mutually bonded to form a substituted or unsubstituted monocyclic ring" or "mutually bonded to form a substituted or unsubstituted fused ring," unless otherwise specified herein, at least one combination of adjacent two or more of components are preferably mutually bonded to form a substituted or unsubstituted "unsaturated ring" formed of a plurality of atoms of the basic skeleton, and 1 to 15 atoms of at least one element selected from the group consisting of carbon, nitrogen, oxygen and sulfur.

When the "monocyclic ring" or the "fused ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

When the "saturated ring" or the "unsaturated ring" has a substituent, the substituent is the substituent described in later-described "optional substituent." When the "monocyclic ring" or the "fused ring" has a substituent, specific examples of the substituent are the substituents described in the above under the subtitle "Substituent Mentioned Herein."

The above is the description for the instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (sometimes referred to as an instance of "bonded to form a ring").

Substituent for Substituted or Unsubstituted Group

In an exemplary embodiment herein, a substituent for the substituted or unsubstituted group (sometimes referred to as an "optional substituent" hereinafter) is, for instance, a group selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901}$)($R_{902}$)($R_{903}$), —O—($R_{904}$), —S—($R_{905}$), —N($R_{906}$)($R_{907}$), a halogen atom, a cyano group, a nitro group, an unsubstituted aryl group having 6 to 50 ring carbon atoms, and an unsubstituted heterocyclic group having 5 to 50 ring atoms; $R_{901}$ to $R_{907}$ each independently are a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when two or more $R_{901}$ are present, the two or more $R_{901}$ are mutually the same or different;

when two or more $R_{902}$ are present, the two or more $R_{902}$ are mutually the same or different;

when two or more $R_{903}$ are present, the two or more $R_{903}$ are mutually the same or different;

when two or more $R_{904}$ are present, the two or more $R_{904}$ are mutually the same or different;

when two or more $R_{905}$ are present, the two or more $R_{905}$ are mutually the same or different;

when two or more $R_{906}$ are present, the two or more $R_{906}$ are mutually the same or different; and when two or more $R_{907}$ are present, the two or more $R_{907}$ are mutually the same or different.

In an exemplary embodiment, a substituent for the substituted or unsubstituted group is selected from the group consisting of an alkyl group having 1 to 50 carbon atoms, an aryl group having 6 to 50 ring carbon atoms, and a heterocyclic group having 5 to 50 ring atoms.

In an exemplary embodiment, a substituent for the substituted or unsubstituted group is selected from the group consisting of an alkyl group having 1 to 18 carbon atoms, an aryl group having 6 to 18 ring carbon atoms, and a heterocyclic group having 5 to 18 ring atoms.

Specific examples of the above optional substituent are the same as the specific examples of the substituent described in the above under the subtitle "Substituent Mentioned Herein."

Unless otherwise specified herein, adjacent ones of the optional substituents may form a "saturated ring" or an "unsaturated ring," preferably a substituted or unsubstituted saturated five-membered ring, a substituted or unsubstituted saturated six-membered ring, a substituted or unsubstituted unsaturated five-membered ring, or a substituted or unsubstituted unsaturated six-membered ring, more preferably a benzene ring.

Unless otherwise specified herein, the optional substituent may further include a substituent. Examples of the substituent for the optional substituent are the same as the examples of the optional substituent.

Herein, numerical ranges represented by "AA to BB" represent a range whose lower limit is the value (AA) recited before "to" and whose upper limit is the value (BB) recited after "to."

First Exemplary Embodiment

Organic Electroluminescence Device

An organic electroluminescence device according to a first exemplary embodiment includes an anode, a cathode, a first emitting layer provided between the anode and the cathode, and a second emitting layer provided between the first emitting layer and the cathode. The first emitting layer contains a first compound represented by a formula (1) below as a first host material, the first compound containing at least one group represented by a formula (11) below. The second emitting layer contains a second compound represented by a formula (2) below as a second host material. In the organic EL device according to the exemplary embodiment, the first emitting layer is in direct contact with the second emitting layer.

The organic electroluminescence device according to the exemplary embodiment includes the anode, the first emitting layer, the second emitting layer, and the cathode in this order.

Herein, the "host material" refers to, for instance, a material that accounts for "50 mass % or more of the layer." Accordingly, for instance, the first emitting layer contains 50 mass % or more of the first compound represented by the formula (1) below with respect to a total mass of the first emitting layer. The second emitting layer contains 50 mass % or more of the second compound represented by the formula (2) below with respect to a total mass of the second emitting layer.

Herein, a layer arrangement in which the first emitting layer and the second emitting layer are in direct contact with each other can include one of embodiments (LS1), (LS2) and (LS3) below.

(LS1) An embodiment in which a region containing both the first compound and the second compound is generated in a process of vapor-depositing the compound of the first emitting layer and vapor-depositing the compound of the second emitting layer, and is present on the interface between the first emitting layer and the second emitting layer.

(LS2) An embodiment in which in a case of containing an emitting compound in the first emitting layer and the second emitting layer, a region containing all of the first compound, the second compound and the emitting compound is generated in a process of vapor-depositing the compound of the first emitting layer and vapor-depositing the compound of the second emitting layer, and is present on the interface between the first emitting layer and the second emitting layer.

(LS3) An embodiment in which in a case of containing an emitting compound in the first emitting layer and the second emitting layer, a region containing the emitting compound, a region containing the first compound or a region containing the second compound is generated in a process of vapor-depositing the compound of the first emitting layer and vapor-depositing the compound of the second emitting layer, and is present on the interface between the first emitting layer and the second emitting layer.

Emission Wavelength of Organic EL Device

The organic electroluminescence device according to the exemplary embodiment preferably emits light having a main peak wavelength in a range from 430 nm to 480 nm when the organic electroluminescence device is driven.

The main peak wavelength of the light emitted from the organic EL device when being driven is measured as follows. Voltage is applied on the organic EL devices such that a current density becomes 10 $mA/cm^2$, where spectral radiance spectrum is measured by a spectroradiometer CS-2000 (manufactured by Konica Minolta, Inc.). A peak wavelength of an emission spectrum, at which the luminous intensity of the resultant spectral radiance spectrum is at the maximum, is measured and defined as the main peak wavelength (unit:nm).

The organic EL device according to the exemplary embodiment may include one or more organic layer(s) in addition to the first emitting layer and the second emitting layer. Examples of the organic layer include, for instance, at least one layer selected from the group consisting of a hole injecting layer, a hole transporting layer, an emitting layer, an electron injecting layer, an electron transporting layer, a hole blocking layer, and an electron blocking layer.

In the organic EL device according to the exemplary embodiment, the organic layer may consist of the first emitting layer and the second emitting layer. Alternatively, the organic layer may further include, for instance, at least one layer selected from the group consisting of the hole injecting layer, the hole transporting layer, the electron injecting layer, the electron transporting layer, the hole blocking layer, and the electron blocking layer.

Hole Transporting Layer

The organic EL device according to the exemplary embodiment preferably includes a hole transporting layer between the anode and the first emitting layer.

The organic EL device according to the exemplary embodiment preferably includes an electron transporting layer between the cathode and the second emitting layer.

The FIGURE schematically shows an exemplary arrangement of the organic EL device according to the exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, a first emitting layer 51, a second emitting layer 52, an electron transporting layer 8, and an electron injecting layer 9, which are sequentially laminated on the anode 3.

First Compound

In the organic EL device according to the exemplary embodiment, the first compound is a compound represented by the formula (1).

[Formula 33]

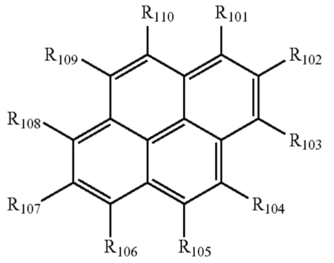

(1)

$$*-(L_{101})_{mx}-Ar_{101} \quad (11)$$

In the formula (1):

$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (11);

at least one of $R_{101}$ to $R_{110}$ is a group represented by the formula (11);

when a plurality of groups represented by the formula (11) are present, the plurality of groups represented by the formula (11) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (11) represents a bonding position to a pyrene ring in the formula (1).

In the first compound according to the exemplary embodiment:

$R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In the organic EL device according to the exemplary embodiment, the group represented by the formula (11) is preferably a group represented by a formula (111) below.

[Formula 34]

(111)

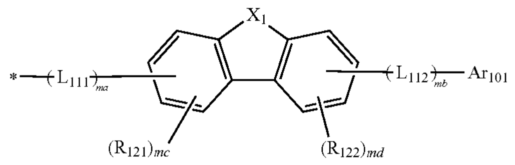

In the formula (111):

$X_1$ is $CR_{123}R_{124}$, an oxygen atom, a sulfur atom, or $NR_{125}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 0, 1, 2, 3, or 4;

mb is 0, 1, 2, 3, or 4;

ma+mb is 0, 1, 2, 3, or 4;

$Ar_{101}$ represents the same as $Ar_{101}$ in the formula (11);

$R_{121}$, $R_{122}$, $R_{123}$, $R_{124}$ and $R_{125}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{121}$ are mutually the same or different;

and is 3; and three $R_{122}$ are mutually the same or different.

Among positions *1 to *8 of carbon atoms in a cyclic structure represented by a formula (111a) below in the group represented by the formula (111), $L_{111}$ is bonded to one of the positions *1 to *4, $R_{121}$ is bonded to each of three positions of the rest of *1 to *4, $L_{112}$ is bonded to one of the positions *5 to *8, and $R_{122}$ is bonded to each of three positions of the rest of *5 to *8.

[Formula 35]

(111a)

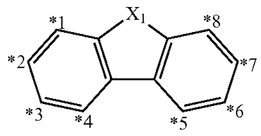

For instance, in the group represented by the formula (111), when $L_{111}$ is bonded to a carbon atom at the position *2 in the cyclic structure represented by the formula (111a) and $L_{112}$ is bonded to a carbon atom at the position *7 in the cyclic structure represented by the formula (111a), the group represented by the formula (111) is represented by a formula (111b) below.

[Formula 36]

(111b)

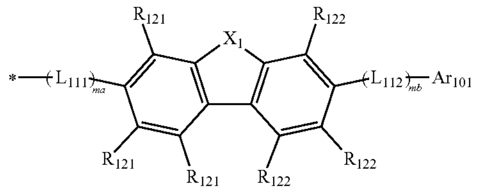

In the formula (111b):

$X_1$, $L_{111}$, $L_{112}$, ma, mb, $Ar_{101}$, $R_{121}$, $R_{122}$, $R_{123}$, $R_{124}$ and $R_{125}$ each independently represent the same as $X_1$, $L_{111}$, $L_{112}$, ma, mb, $Ar_{101}$, $R_{121}$, $R_{122}$, $R_{123}$, $R_{124}$ and $R_{125}$ in the formula (111);

a plurality of $R_{121}$ are mutually the same or different; and a plurality of $R_{122}$ are mutually the same or different.

In the organic EL device according to the exemplary embodiment, the group represented by the formula (111) is preferably a group represented by the formula (111b).

In the organic EL device according to the exemplary embodiment, it is preferable that: ma is 0, 1, or 2; and mb is 0, 1, or 2.

In the organic EL device according to the exemplary embodiment, it is preferable that: ma is 0 or 1; and mb is 0 or 1.

In the organic EL device according to the exemplary embodiment, $Ar_{101}$ is preferably a substituted or unsubstituted aryl group having 6 to 50 ring carbon atoms.

In the organic EL device according to the exemplary embodiment, $Ar_{101}$ is preferably a substituted or unsubstituted phenyl group, a substituted or unsubstituted naphthyl group, a substituted or unsubstituted biphenyl group, a substituted or unsubstituted terphenyl group, a substituted or unsubstituted pyrenyl group, a substituted or unsubstituted phenanthryl group, or a substituted or unsubstituted fluorenyl group.

In the organic EL device according to the exemplary embodiment, $Ar_{101}$ is also preferably a group represented by a formula (12), (13) or (14) below.

[Formula 37]

(12)

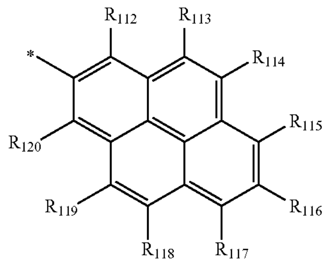

-continued (13)

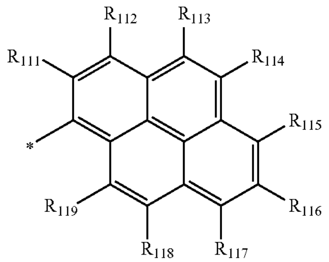

(14)

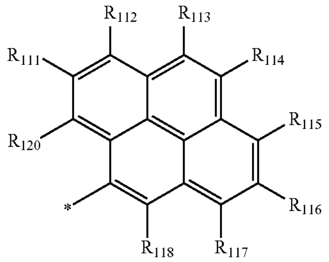

In the formulae (12), (13) and (14):

$R_{111}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aralkyl group having 7 to 50 carbon atoms, a group represented by $-C(=O)R_{124}$, a group represented by $-COOR_{125}$, a halogen atom, a cyano group, a nitro group, a substituted or unsubstituted aryl group having 6 to 50 ring carbon atoms, or a substituted or unsubstituted heterocyclic group having 5 to 50 ring atoms; and

* in the formulae (12), (13) and (14) represents a bonding position to $L_{101}$ in the formula (11), or a bonding position to $L_{112}$ in the formula (111) or (111b).

In the organic EL device according to the exemplary embodiment, the first compound is preferably represented by a formula (101) below.

[Formula 38]

(101)

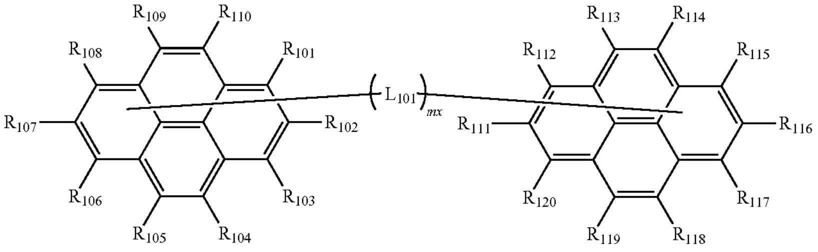

In the formula (101):

$R_{101}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a substituted or unsubstituted aralkyl group having 7 to 50 carbon atoms, a group represented by —$C(=O)R_{801}$, a group represented by —$COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

one of $R_{101}$ to $R_{110}$ represents a bonding position to $L_{101}$, and one of $R_{111}$ to $R_{120}$ represents a bonding position to $L_{101}$;

$L_{101}$ is a single bond, a substituted or unsubstituted arylene group having 6 to 50 ring carbon atoms, or a substituted or unsubstituted divalent heterocyclic group having 5 to 50 ring atoms;

mx is 0, 1, 2, 3, 4, or 5; and when two or more $L_{101}$ are present, the two or more $L_{101}$ are mutually the same or different.

In the organic EL device according to the exemplary embodiment, $L_{101}$ is preferably a single bond, or a substituted or unsubstituted arylene group having 6 to 50 ring carbon atoms.

In the organic EL device according to the exemplary embodiment, the first compound is preferably represented by a formula (102) below.

In the formula (102):

$R_{101}$ to 8120 each independently represent the same as $R_{101}$ to 8120 in the formula (101);

one of $R_{101}$ to $R_{110}$ represents a bonding position to Li, and one of $R_{111}$ to $R_{120}$ represents a bonding position to $L_{112}$;

$X_1$ is $CR_{123}R_{124}$, an oxygen atom, a sulfur atom, or $NR_{125}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 0, 1, 2, 3, or 4;

mb is 0, 1, 2, 3, or 4;

ma+mb is 0, 1, 2, 3, or 4;

$R_{121}$, $R_{122}$, $R_{123}$, $R_{124}$ and $R_{125}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si$(R_{901})(R_{902})(R_{903})$, a group represented by —O—$(R_{904})$, a group represented by —S—$(R_{905})$, a substituted or unsubstituted aralkyl group having 7 to 50 carbon atoms, a group represented by —$C(=O)R_{801}$, a group represented by —$COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

[Formula 39]

(102)

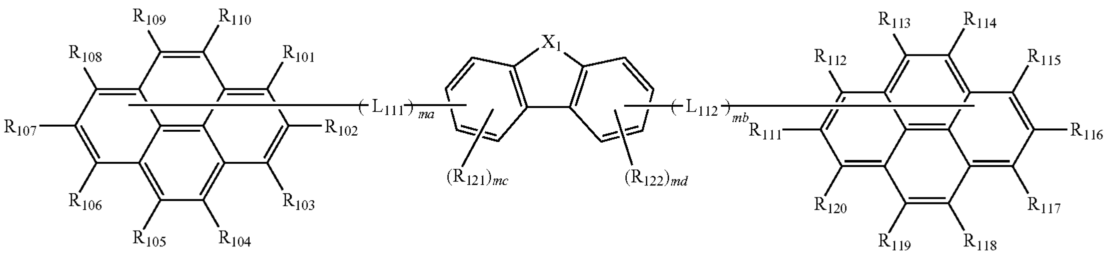

mc is 3;

three $R_{121}$ are mutually the same or different;

and is 3; and three $R_{122}$ are mutually the same or different.

In the formula (102), it is preferable that $X_1$ is $CR_{123}R_{124}$, and $R_{123}$ and $R_{124}$ are each independently a substituted or unsubstituted phenyl group.

That is, in a compound represented by the formula (102), a cyclic structure containing $X_1$ is preferably a diphenylfluorene ring.

Further, in a compound represented by the formula (102), the cyclic structure containing $X_1$ is preferably not a spirofluorene ring.

The diphenylfluorene ring exhibits higher hole transportability than the spirofluorene ring.

Thus, when a compound represented by the formula (102) in which the cyclic structure containing $X_1$ is a diphenylfluorene ring is used as the first host material, an emitting region becomes closer to the second emitting layer than when a compound represented by the formula (102) in which the diphenylfluorene ring is replaced by a spirofluorene ring is used. This allows triplet excitons to transfer easily to the second host material contained in the second emitting layer, and thus further improvement in luminous efficiency is expected.

Specifically, the compound represented by the formula (102) is preferably a compound represented by a formula (102A) below.

In the compounds represented by the formulae (102) and (102A), it is preferable that: ma is 0, 1, or 2; and mb is 0, 1, or 2.

In the compounds represented by the formulae (102) and (102A), it is preferable that: ma is 0 or 1; and mb is 0 or 1.

In the formulae (102) and (102A), $R_{101}$ to $R_{120}$ not being a bonding position to $L_{111}$ and $L_{112}$ are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the formulae (102) and (102A), $R_{101}$ to $R_{120}$ not being a bonding position to $L_{111}$ and $L_{112}$ are preferably each independently a hydrogen atom, a substituted or unsubstituted alkyl group having 1 to 50 carbon atoms, or a substituted or unsubstituted cycloalkyl group having 3 to 50 ring carbon atoms.

In the formulae (102) and (102A), $R_{101}$ to $R_{120}$ not being a bonding position to $L_{111}$ and $L_{112}$ are preferably a hydrogen atom.

In the organic EL device according to the exemplary embodiment, two or more of $R_{101}$ to $R_{110}$ are preferably a group represented by the formula (11).

In the organic EL device according to the exemplary embodiment, it is preferable that two or more of $R_{101}$ to $R_{110}$

[Formula 40]

(102A)

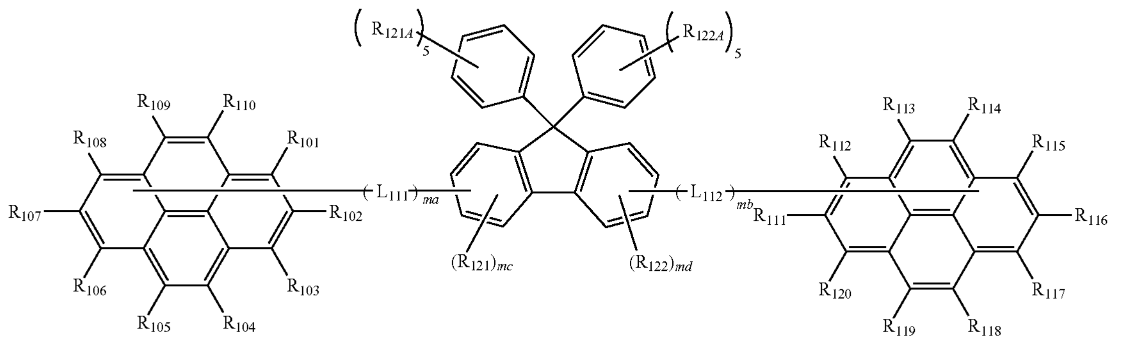

In the formula (102A): $R_{101}$ to $R_{120}$, $L_{111}$, $L_{112}$, ma, mb, ma+mb, $R_{121}$, $R_{122}$, mc and md each independently represent the same as $R_{101}$ to $R_{120}$, $L_{111}$, $L_{112}$, ma, mb, ma+mb, $R_{121}$, $R_{122}$, mc and md in the formula (102); $R_{121A}$ and $R_{122A}$ each independently represent the same as $R_{121}$ and $R_{122}$ in the formula (102); five $R_{121A}$ are mutually the same or different; and five $R_{122A}$ are mutually the same or different.

In the formula (102), it is preferable that a substituent for $R_{123}$ and $R_{124}$ when $R_{123}$ and $R_{124}$ are each a substituted phenyl group, or $R_{121A}$ and $R_{122A}$ in the formula (102A) are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the formula (102), $R_{123}$ and $R_{124}$ are preferably an unsubstituted phenyl group. In the formula (102A), $R_{121A}$ and $R_{122A}$ are preferably a hydrogen atom.

are a group represented by the formula (11) and $Ar_{101}$ is a substituted or unsubstituted aryl group having 6 to 50 ring carbon atoms.

In the organic EL device according to the exemplary embodiment, it is preferable that: $Ar_{101}$ is not a substituted or unsubstituted pyrenyl group; $L_{101}$ is not a substituted or unsubstituted pyrenylene group; and the substituted or unsubstituted aryl group having 6 to 50 ring carbon atoms for $R_{101}$ to $R_{110}$ not being the group represented by the formula (11) is not a substituted or unsubstituted pyrenyl group.

In the organic EL device according to the exemplary embodiment, $R_{101}$ to $R_{110}$ not being the group represented by the formula (11) are preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, $R_{101}$ to $R_{110}$ not being the group represented by the formula (11) are preferably each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, $R_{101}$ to $R_{110}$ not being the group represented by the formula (11) are preferably a hydrogen atom.

In the first compound and the second compound, it is preferable that all groups described as "substituted or unsubstituted" groups are "unsubstituted" groups.

In the organic EL device according to the exemplary embodiment, for instance, two of $R_{101}$ to $R_{110}$ in the first compound represented by the formula (1) are groups represented by the formula (11).

In the organic EL device according to the exemplary embodiment, for instance, three of $R_{101}$ to $R_{110}$ in the first compound represented by the formula (1) are groups represented by the formula (11).

In the organic EL device according to the exemplary embodiment, for instance, four of $R_{101}$ to $R_{110}$ in the first compound represented by the formula (1) are groups represented by the formula (11).

In the organic EL device according to the exemplary embodiment, for instance, one of $R_{101}$ to $R_{110}$ in the first compound represented by the formula (1) is a group represented by the formula (11) and mx is 1 or more.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted aryl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted heterocyclic group containing a nitrogen atom.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted heterocyclic group containing a sulfur atom.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted furyl group, oxazolyl group, isoxazolyl group, oxadiazolyl group, xanthenyl group, benzofuranyl group, isobenzofuranyl group, dibenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is at least one group selected from the group consisting of unsubstituted furyl group, oxazolyl group, isoxazolyl group, oxadiazolyl group, xanthenyl group, benzofuranyl group, isobenzofuranyl group, dibenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is a substituted or unsubstituted dibenzofuranyl group.

In the organic EL device according to the exemplary embodiment, for instance, one of $R_{101}$ to $R_{110}$ in the first compound represented by the formula (1) is a group represented by the formula (11), mx is 0, and $Ar_{101}$ is an unsubstituted dibenzofuranyl group.

In the organic EL device according to the exemplary embodiment, for instance, mx in the first compound represented by the formula (101) is 2 or more.

In the organic EL device according to the exemplary embodiment, for instance, mx in the first compound represented by the formula (101) is 1 or more, and $L_{101}$ is an arylene group having 6 to 24 ring carbon atoms or a divalent heterocyclic group having 5 to 24 ring atoms.

In the organic EL device according to the exemplary embodiment, for instance, mx in the first compound represented by the formula (101) is 1 or more, and $L_{101}$ is an arylene group having 6 to 18 ring carbon atoms or a divalent heterocyclic group having 5 to 18 ring atoms.

Manufacturing Method of First Compound

The first compound can be manufactured by a known method. The first compound can also be manufactured based on a known method through a known alternative reaction using a known material(s) tailored for the target compound.

Specific examples of the first compound include the following compounds. It should however be noted that the invention is not limited to the specific examples of the first compound.

[Formula 41]

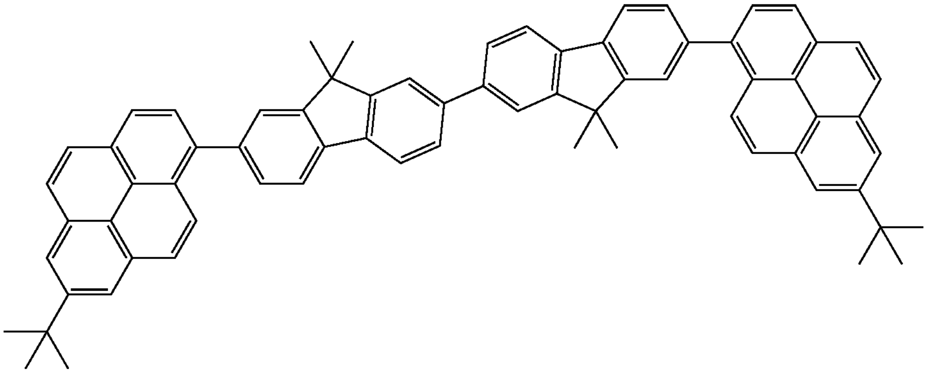

-continued
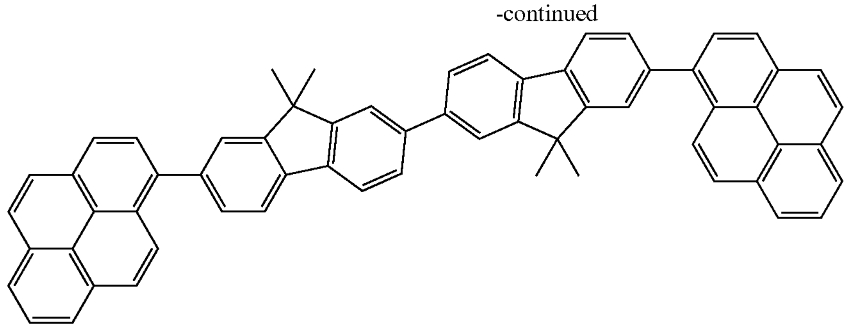
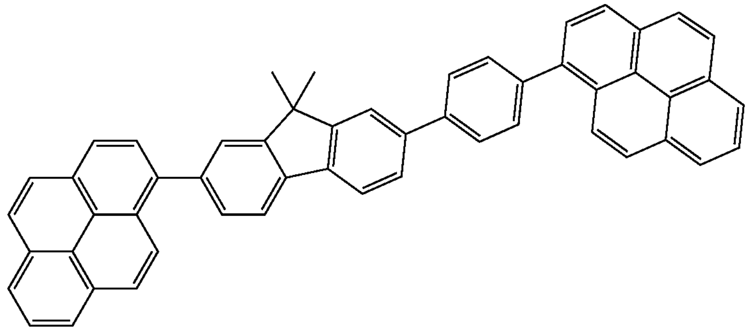
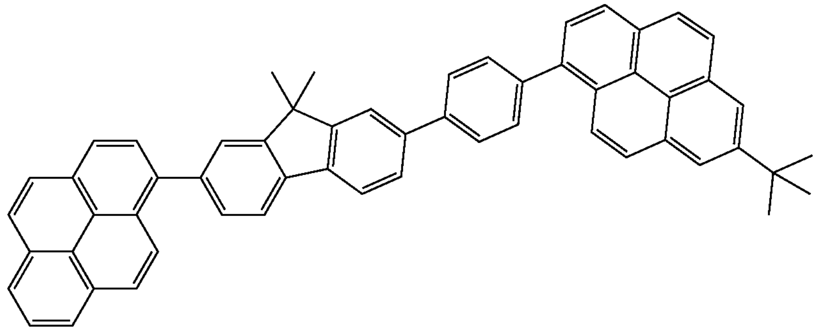
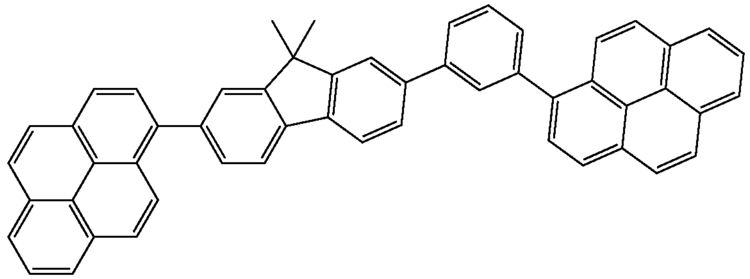
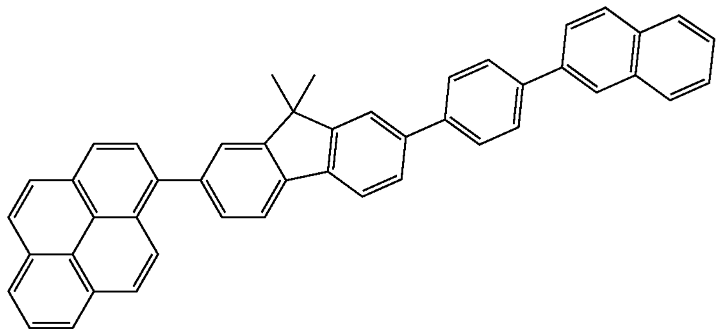

-continued
[Formula 42]
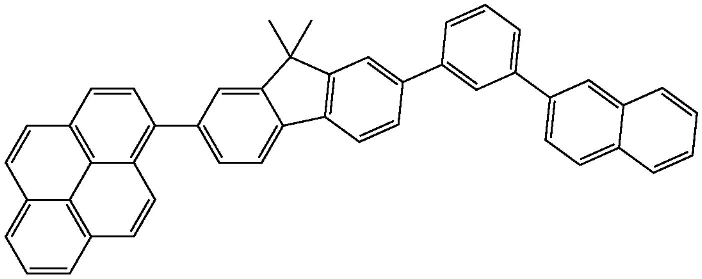
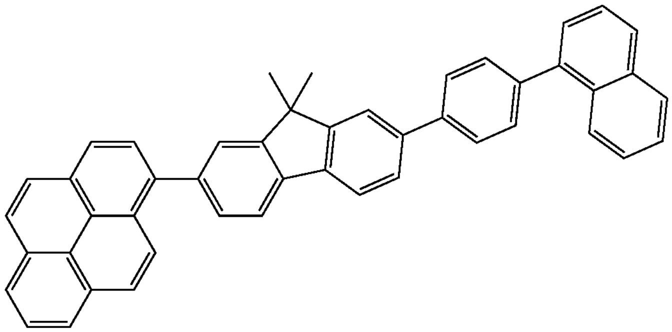
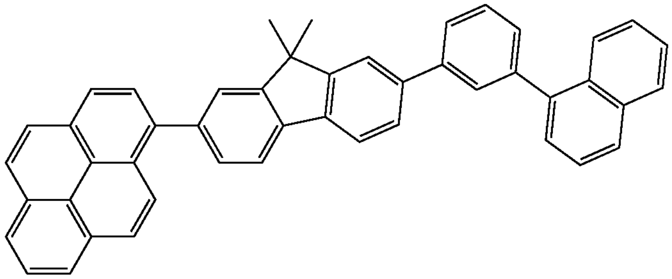
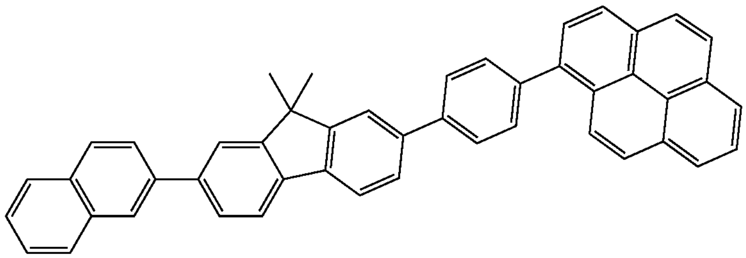
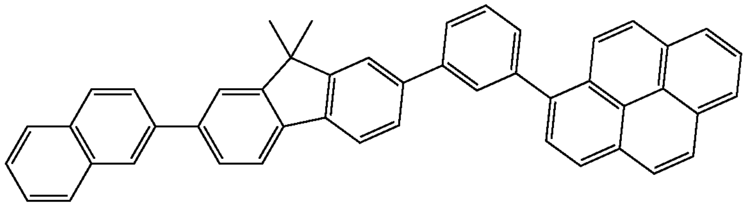
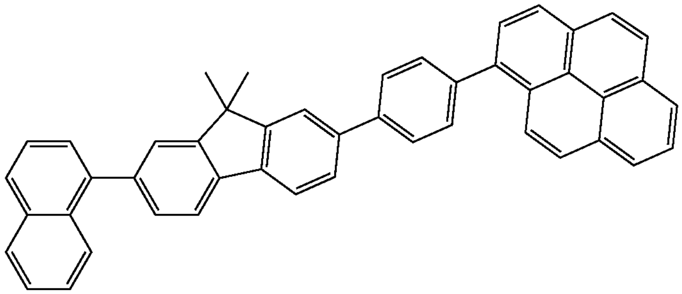

-continued
[Formula 43]
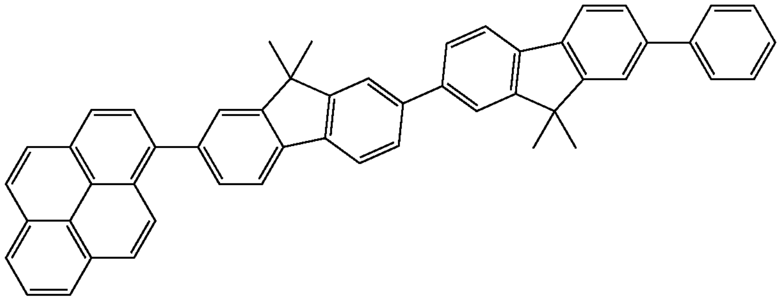
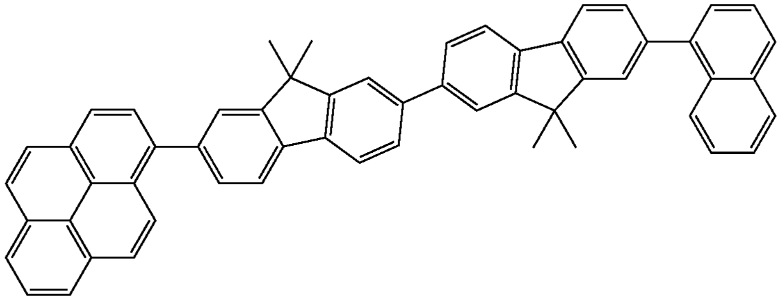
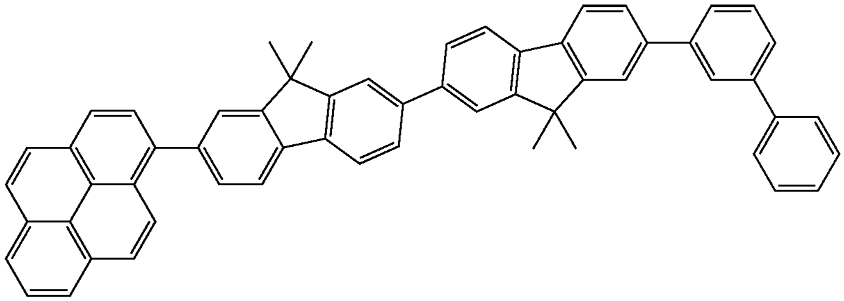
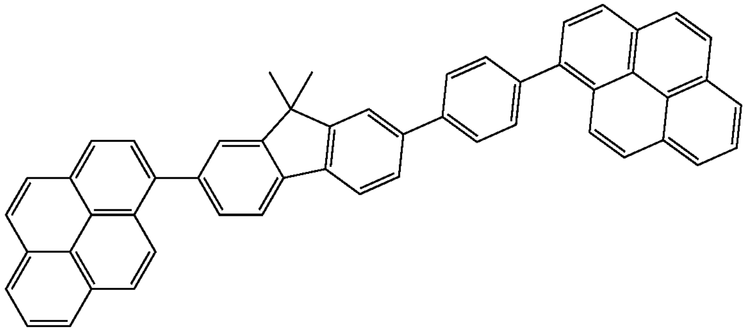
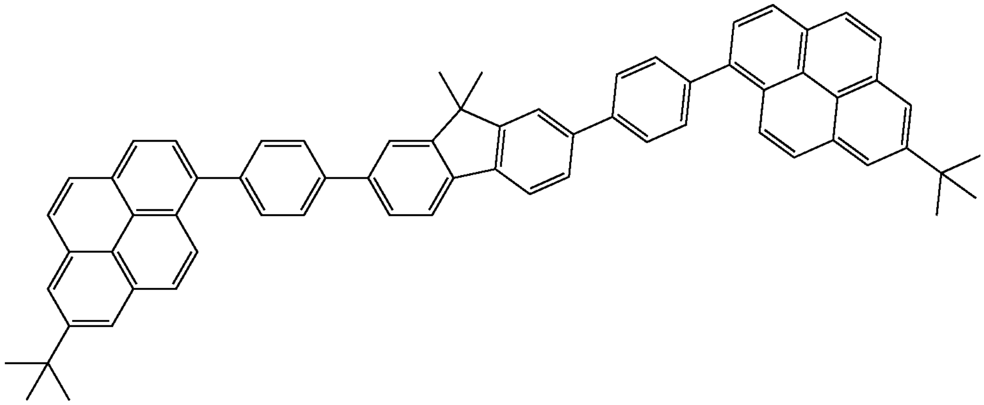

-continued
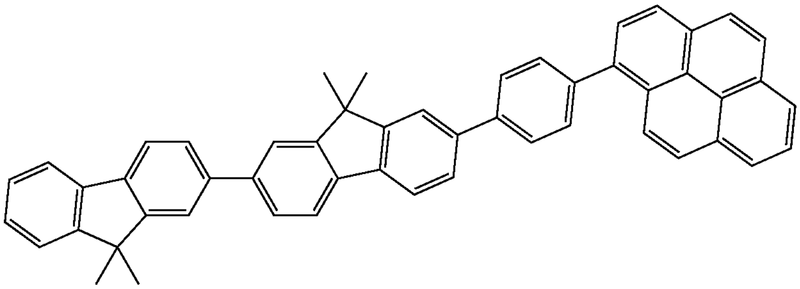
[Formula 44]
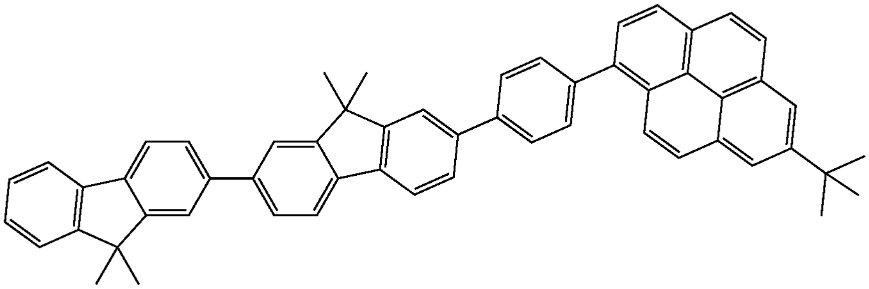
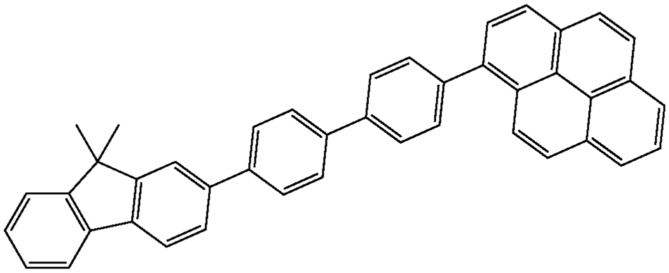
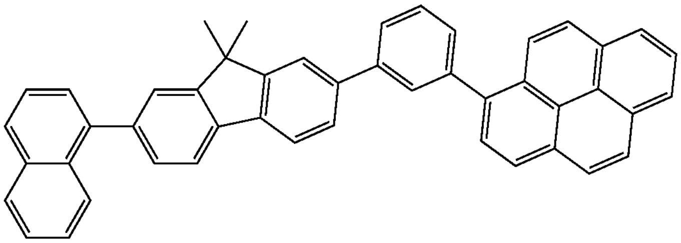
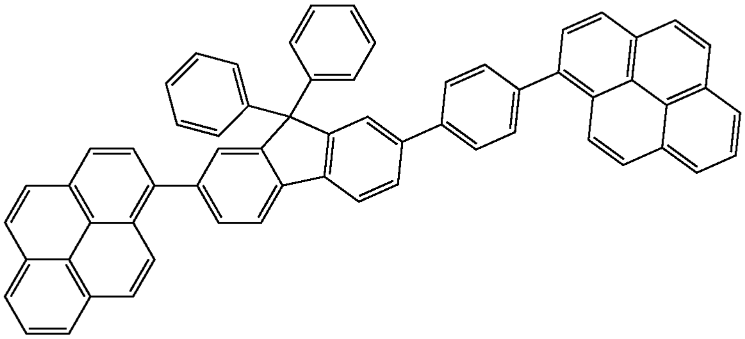

-continued
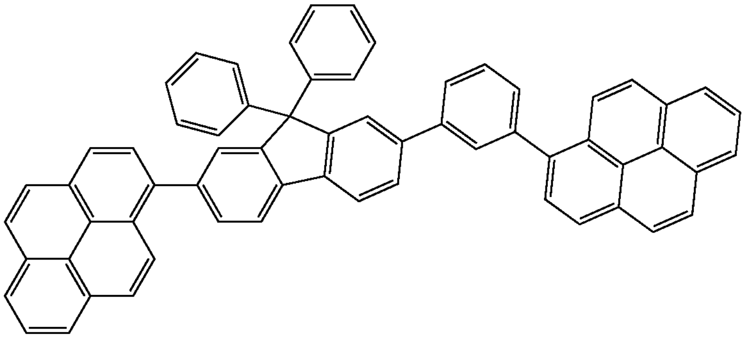
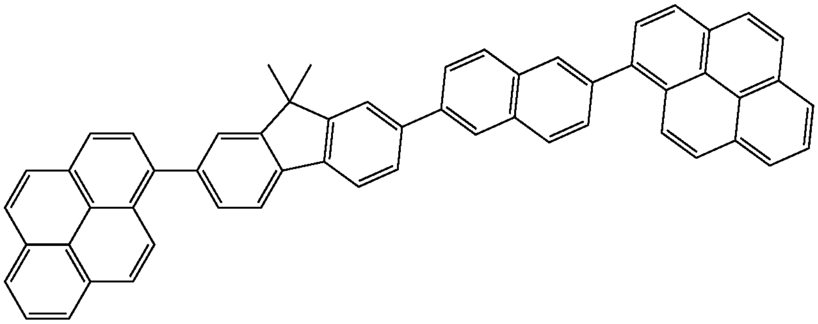
[Formula 45]
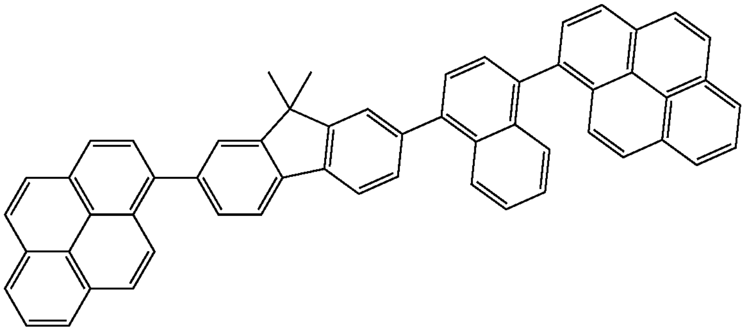
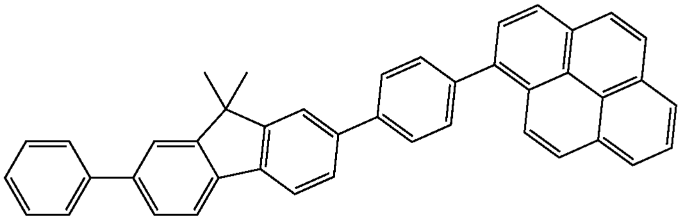
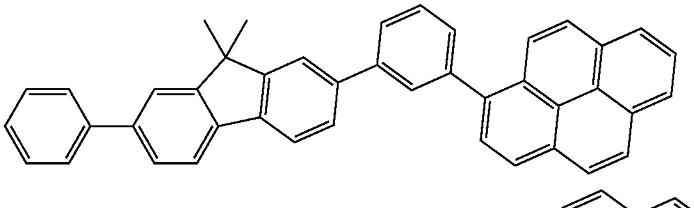
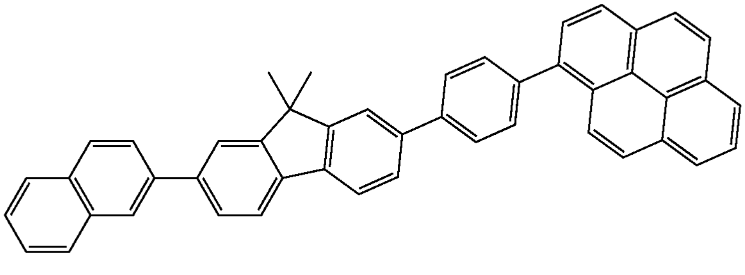

-continued
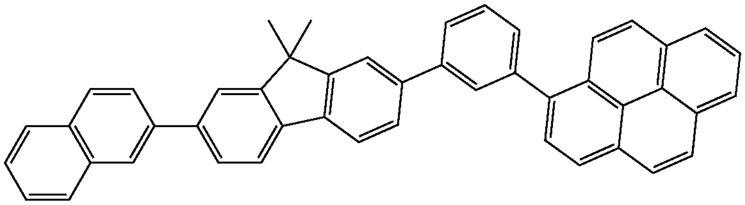
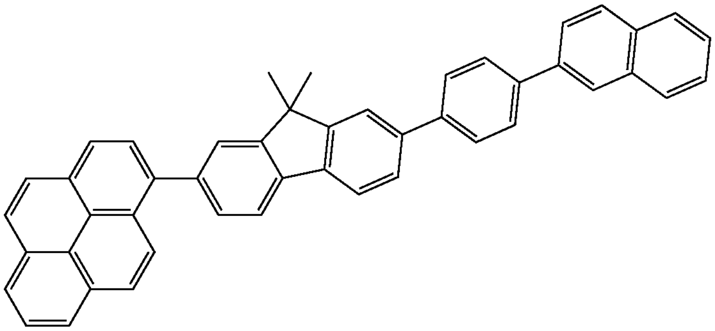
[Formula 46]
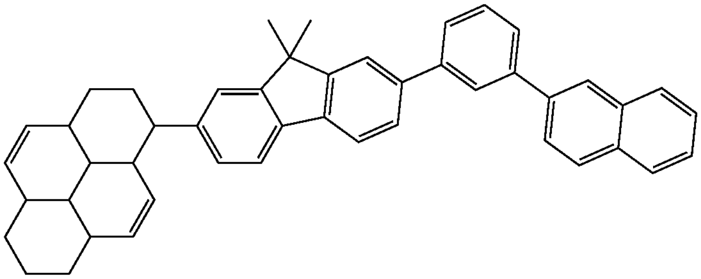
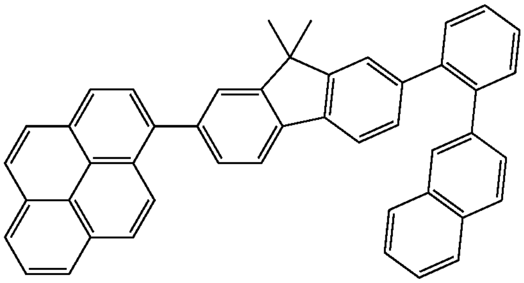
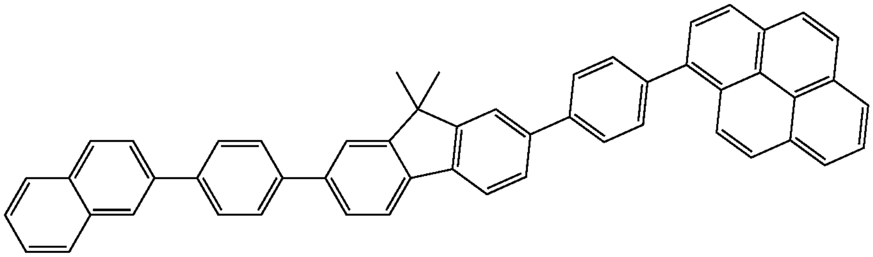
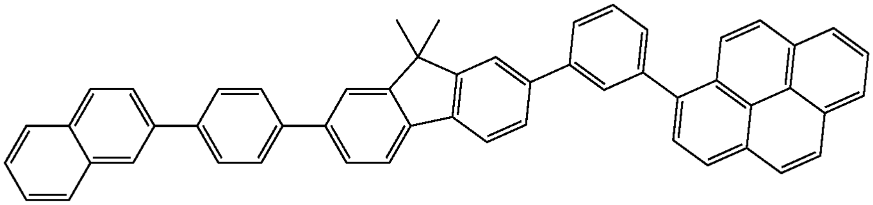

-continued
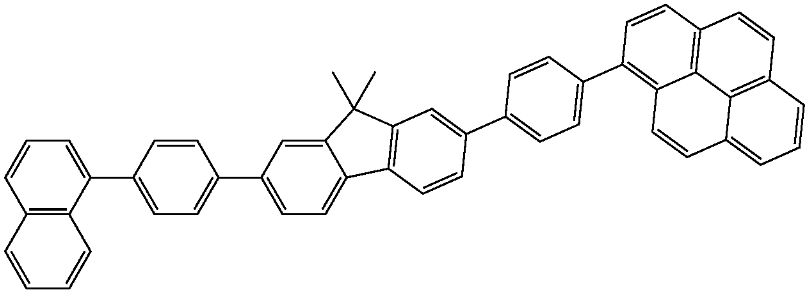
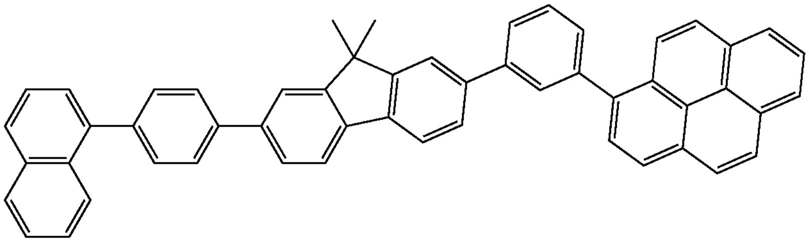
[Formula 47]
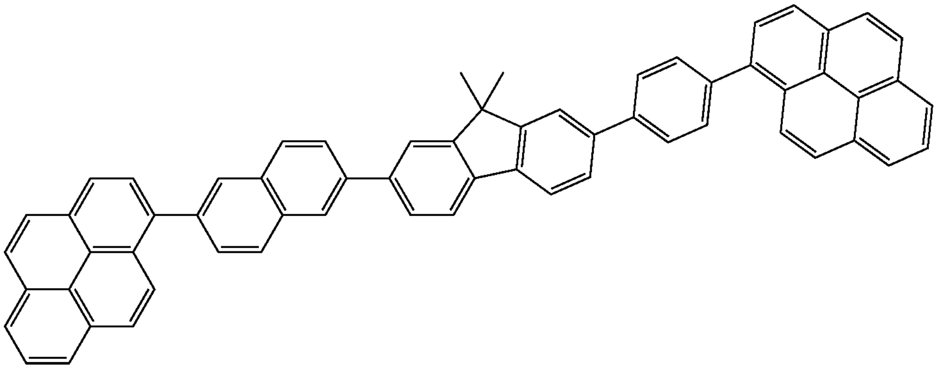
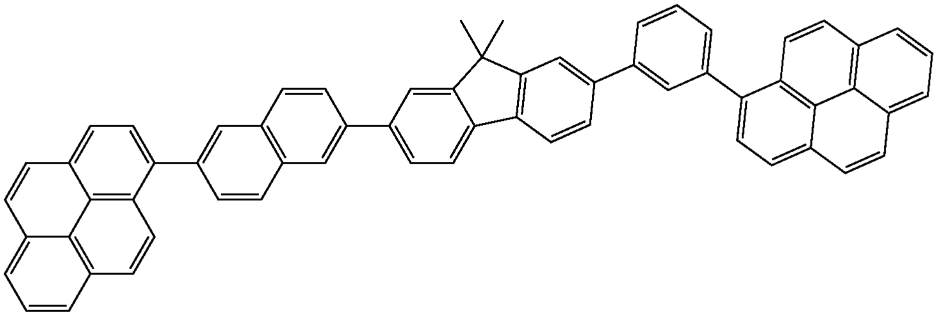
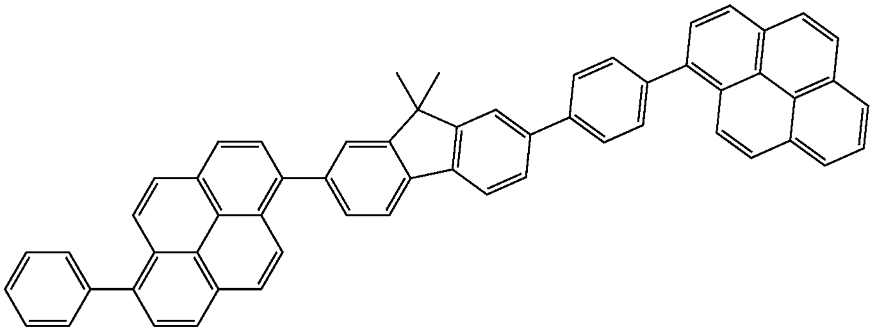

-continued
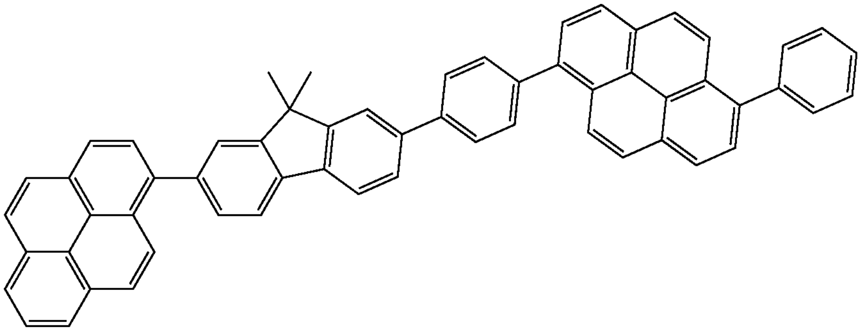
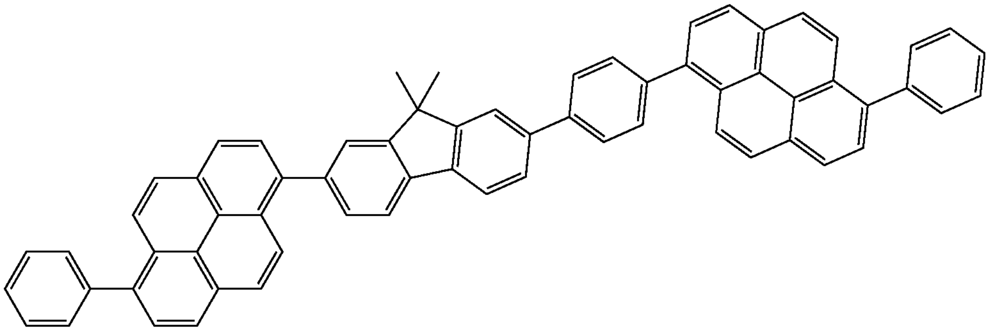
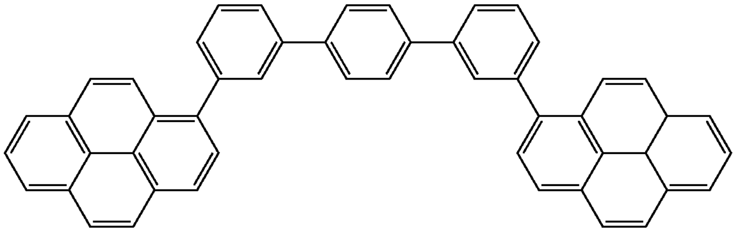
[Formula 48]
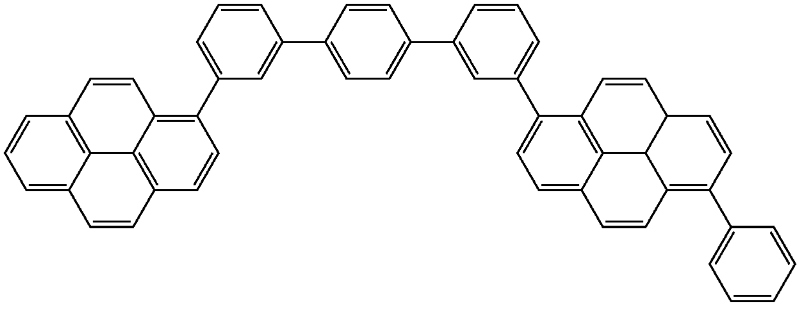
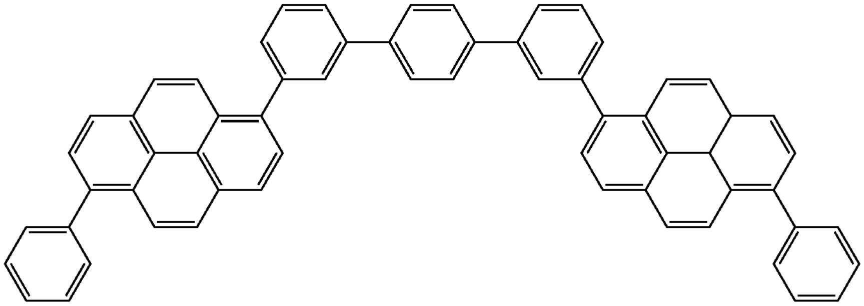

-continued
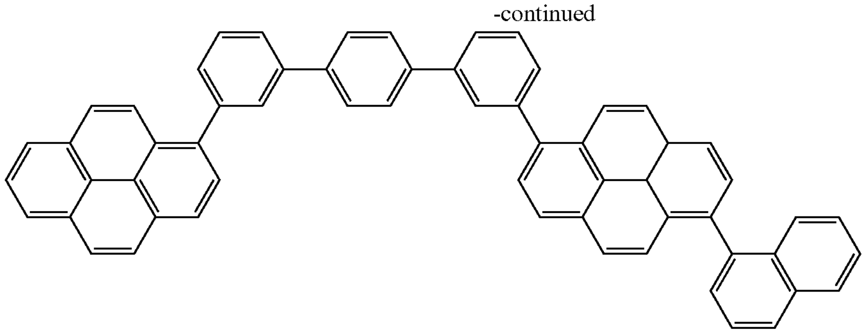
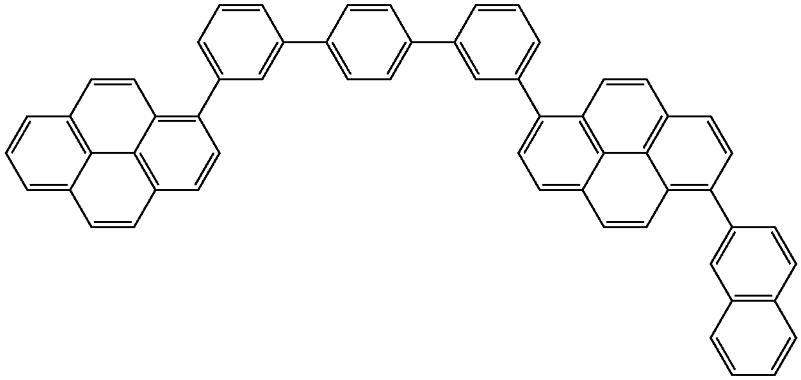
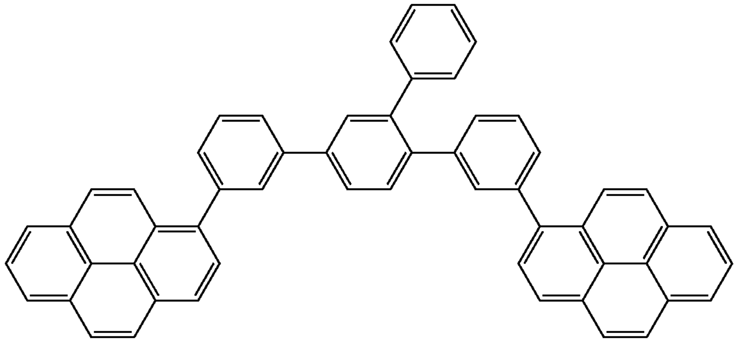
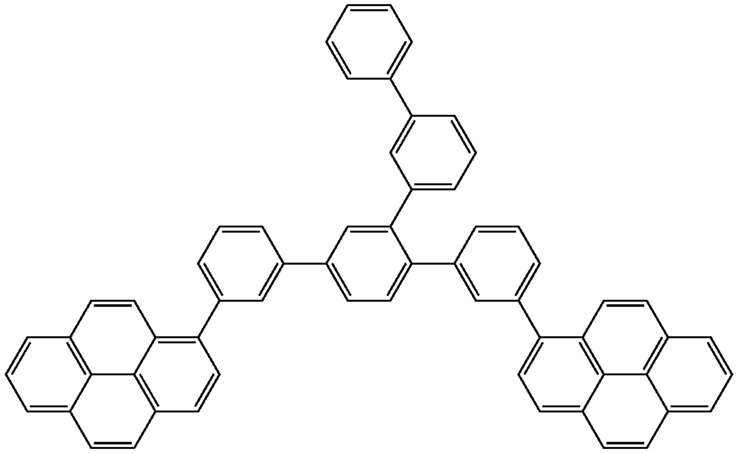

-continued
[Formula 49]
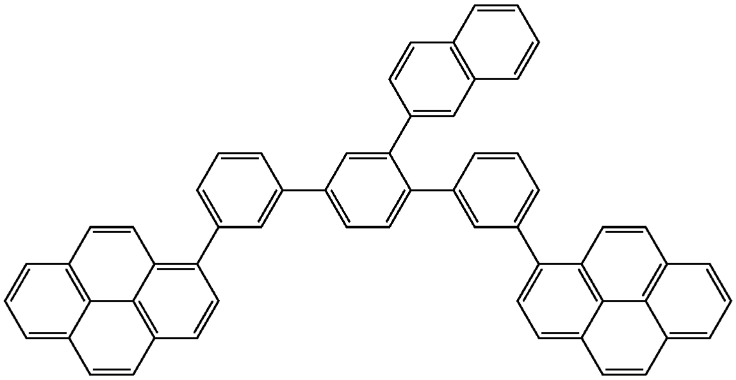
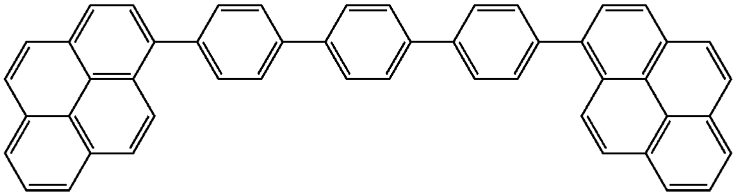
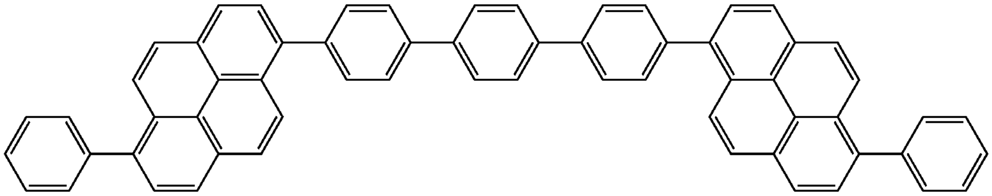
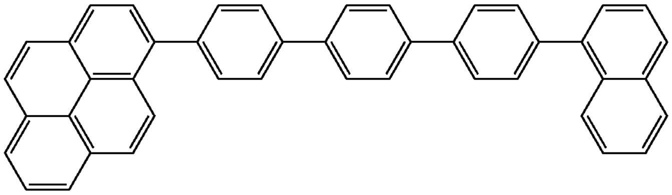
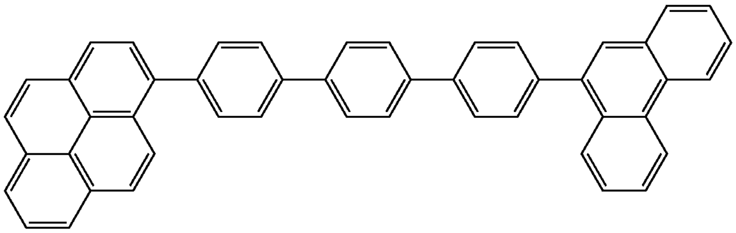
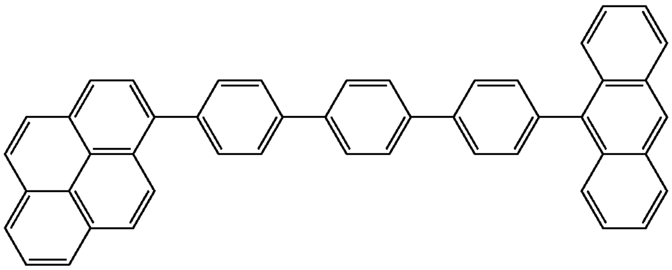

-continued
[Formula 50]
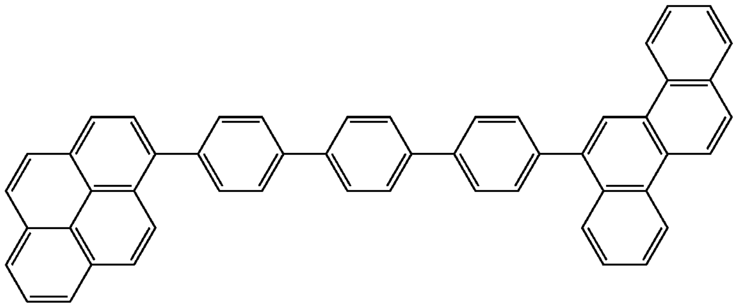
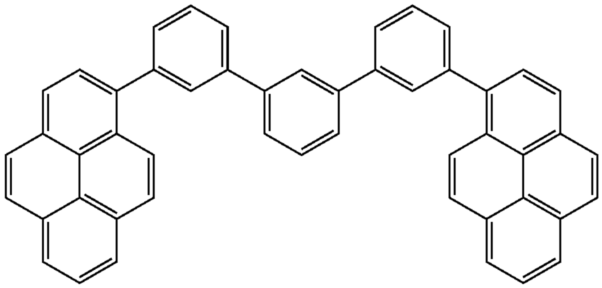
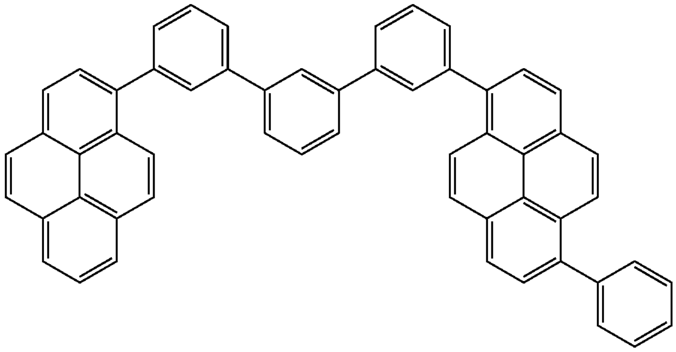
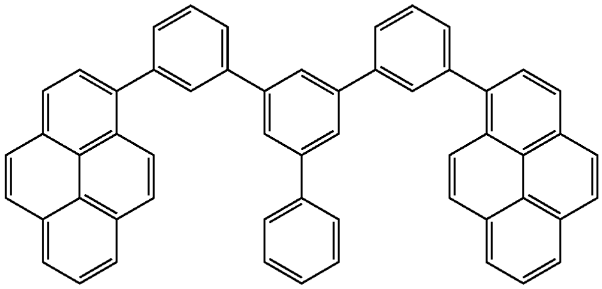
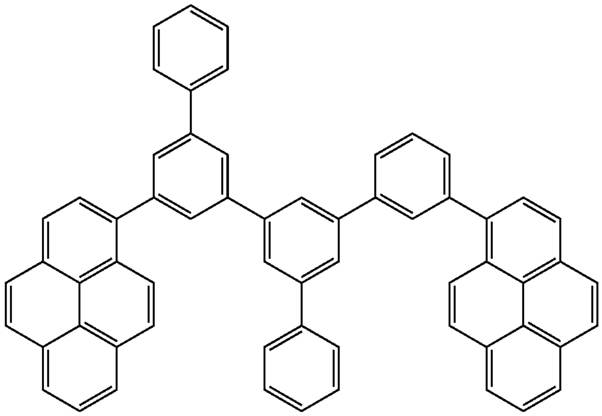

-continued
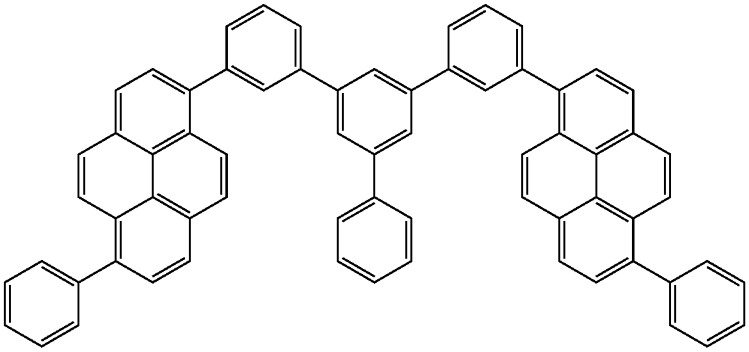
[Formula 51]
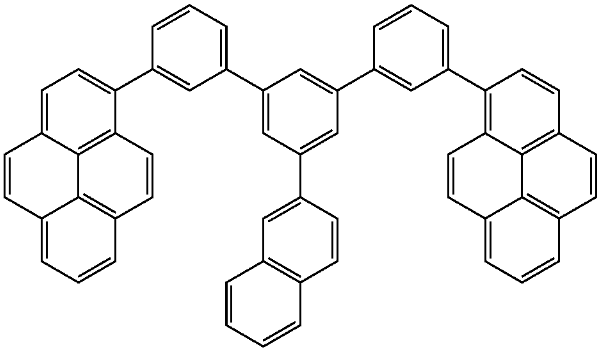
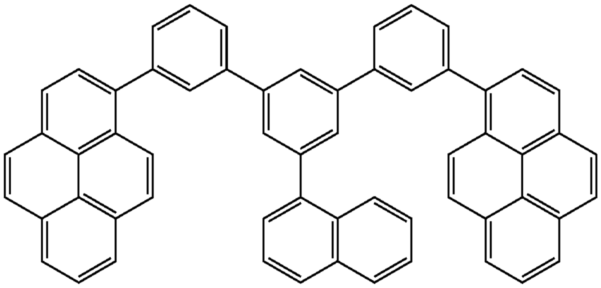
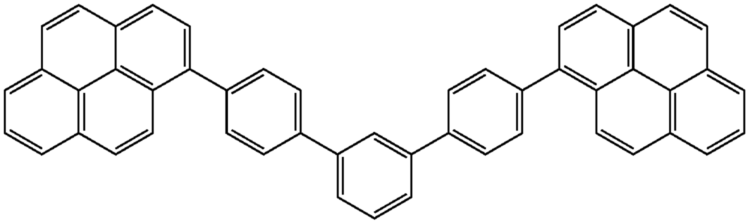
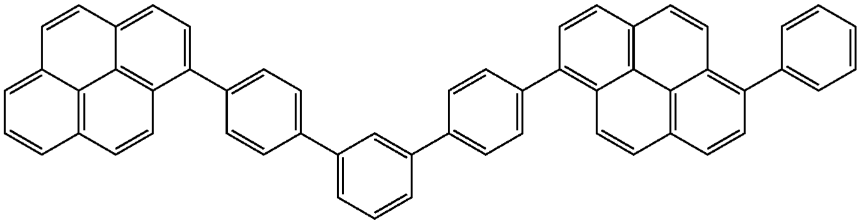
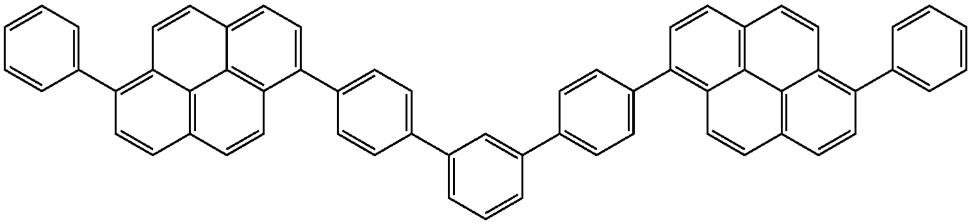

-continued
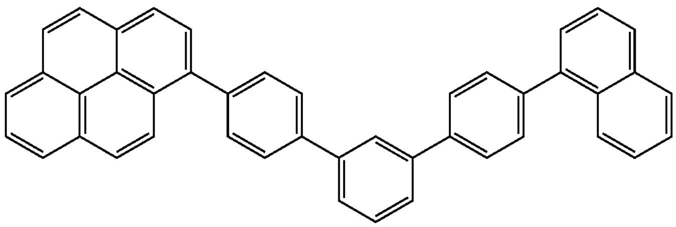
[Formula 52]
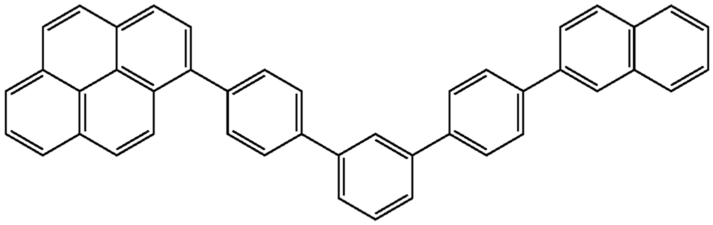
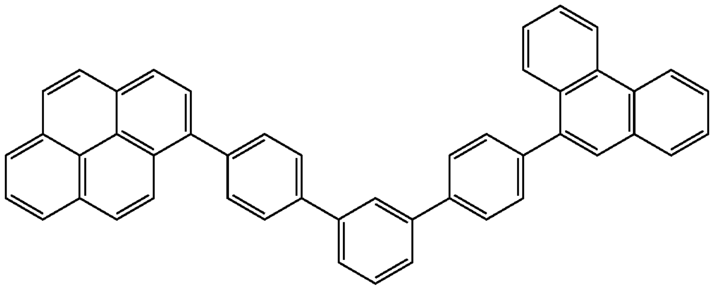
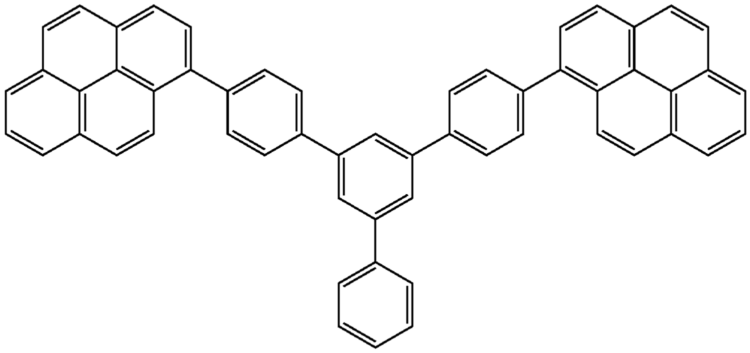
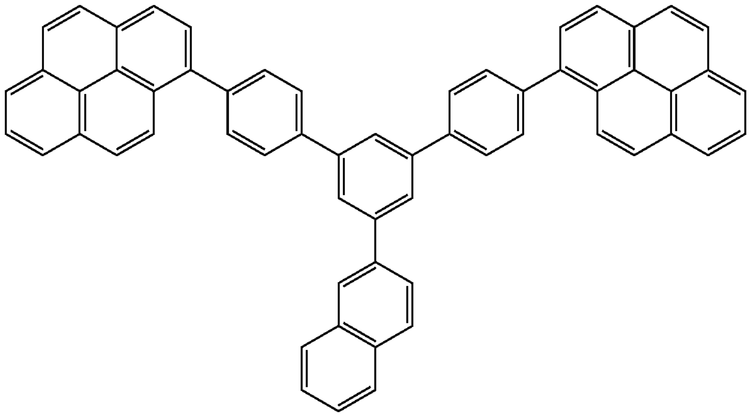

-continued
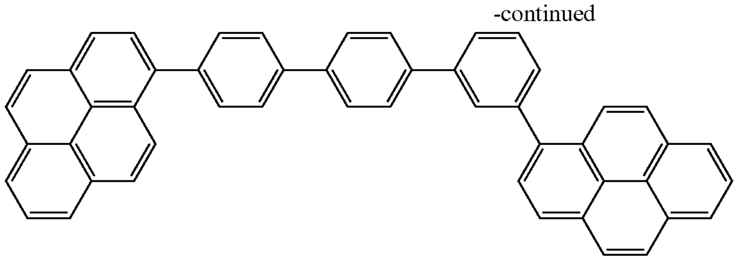
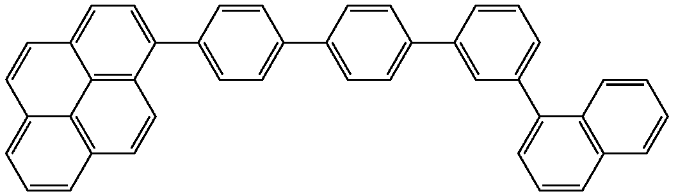
[Formula 53]
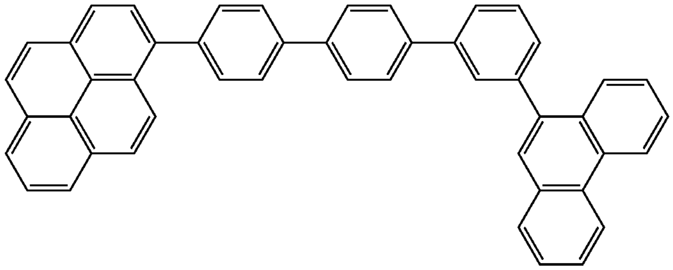
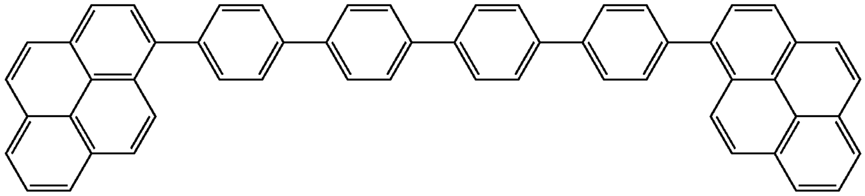
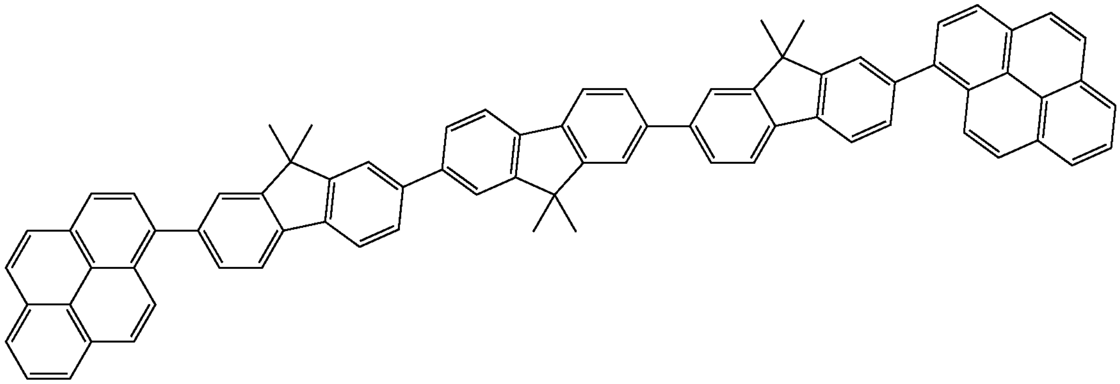

-continued
[Formula 54]
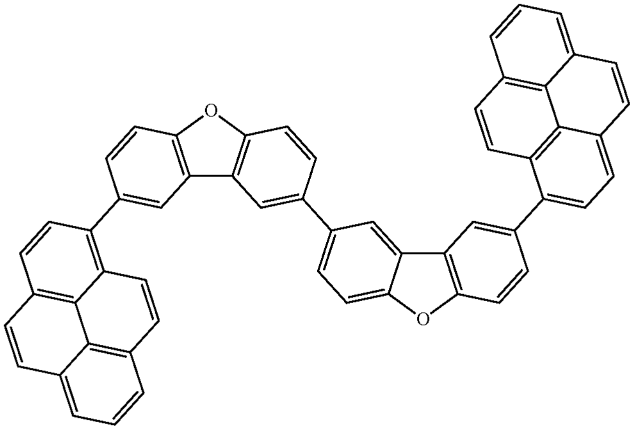
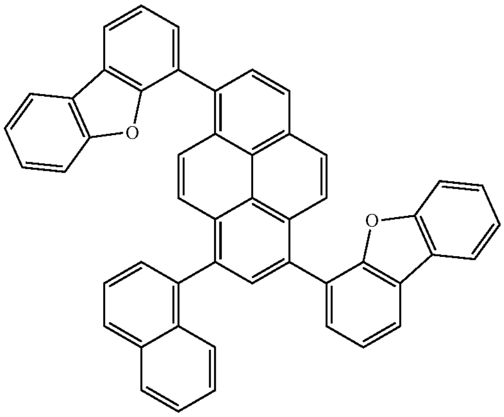
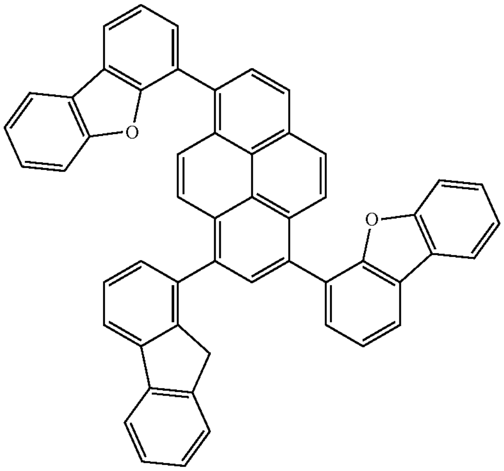
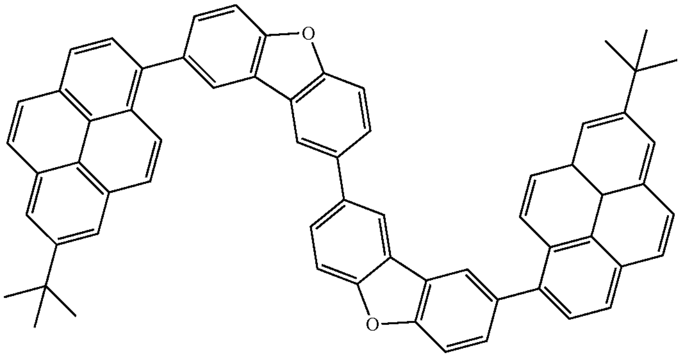
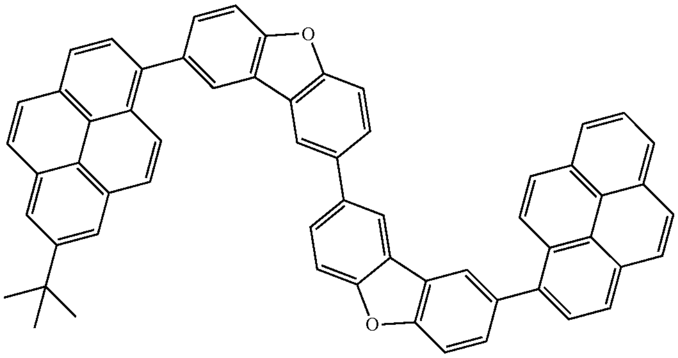

-continued
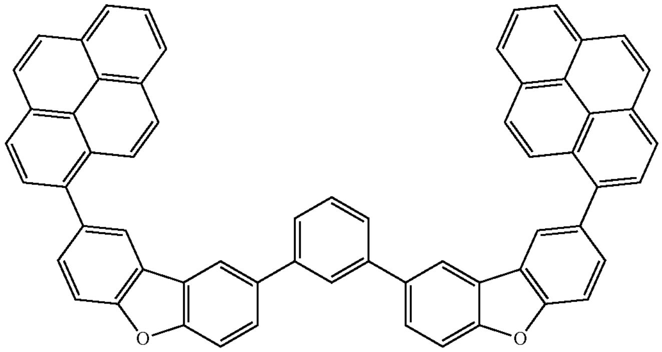
[Formula 55]
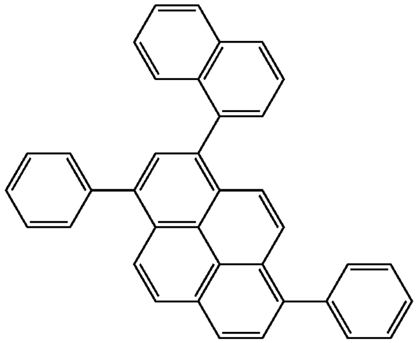
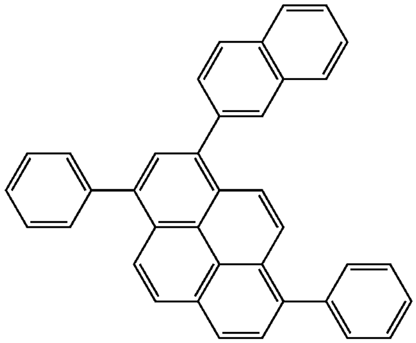
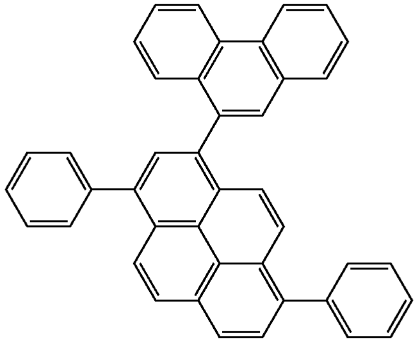
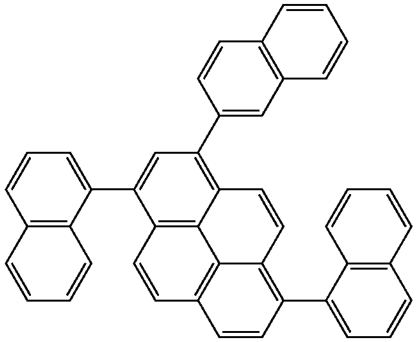
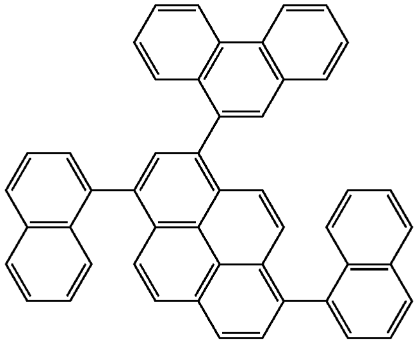
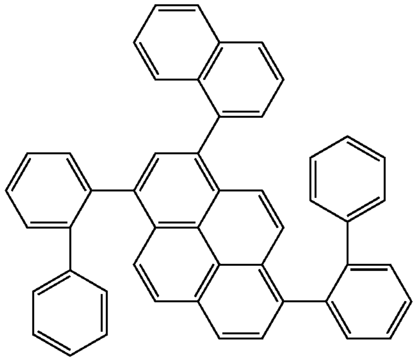

-continued
[Formula 56]
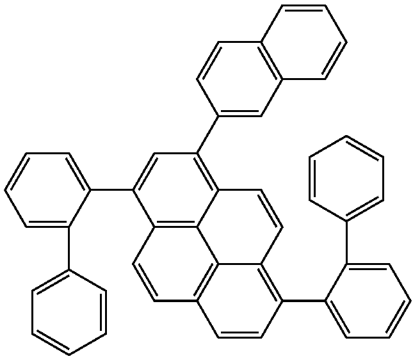
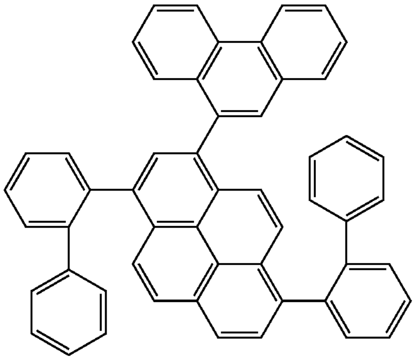
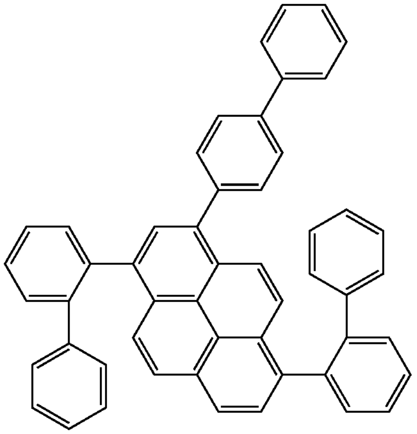
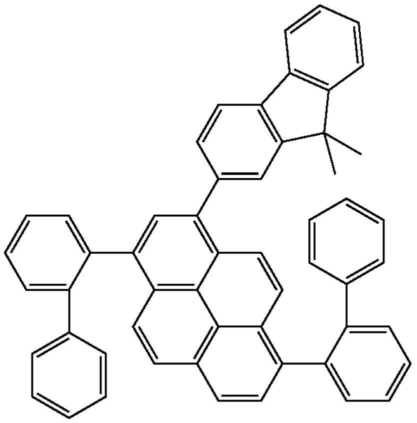
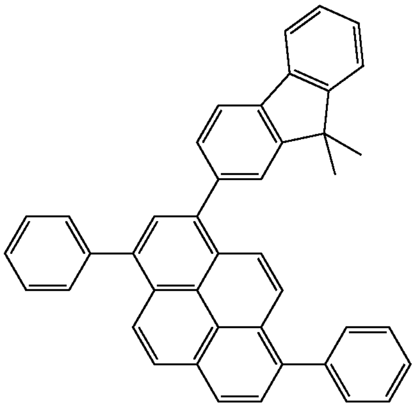
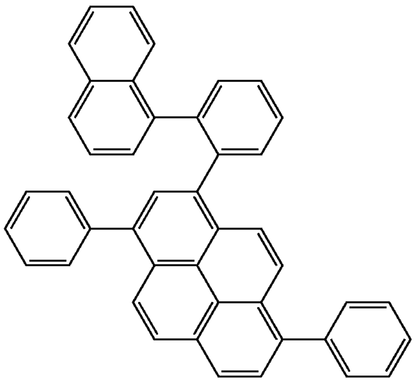
[Formula 57]
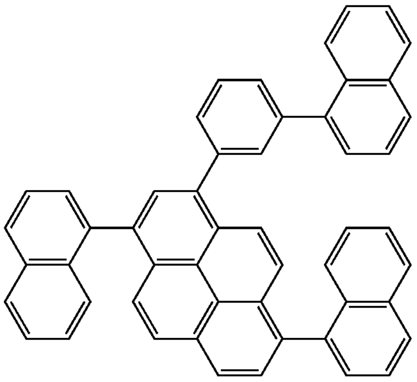
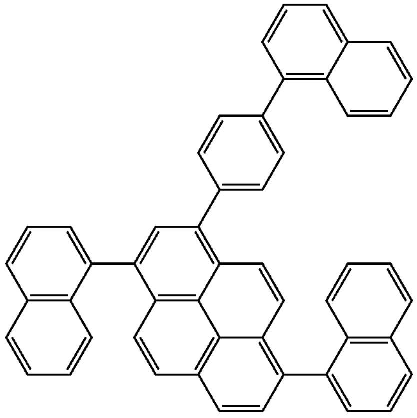

-continued
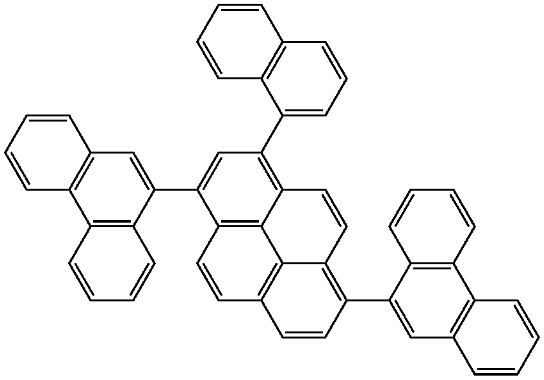
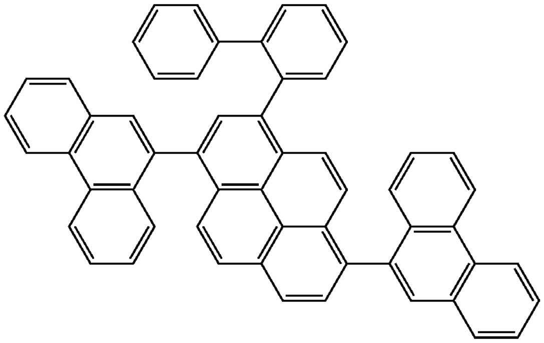
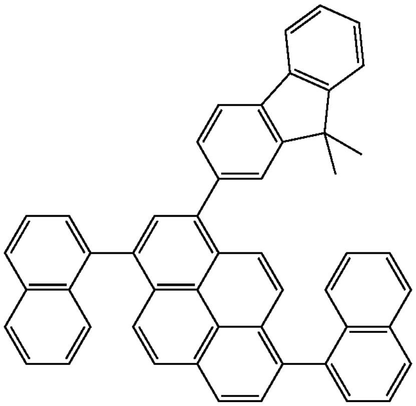
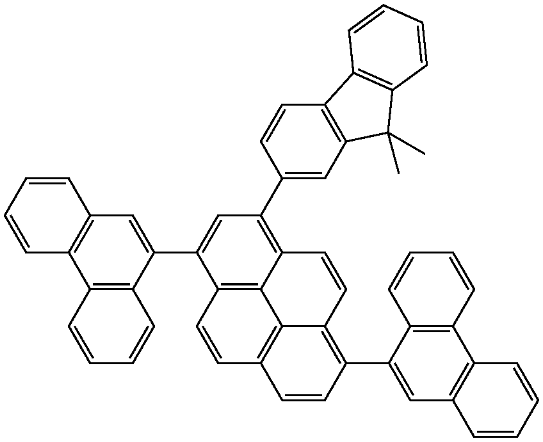
[Formula 58]
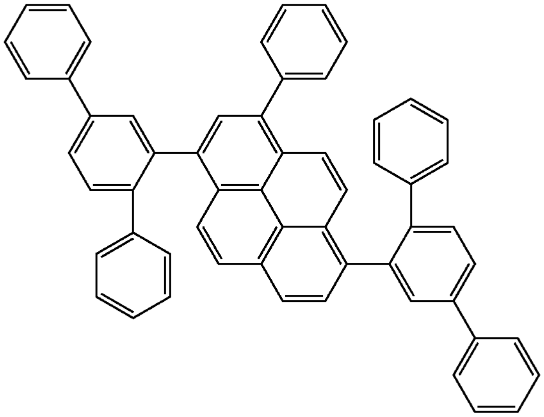
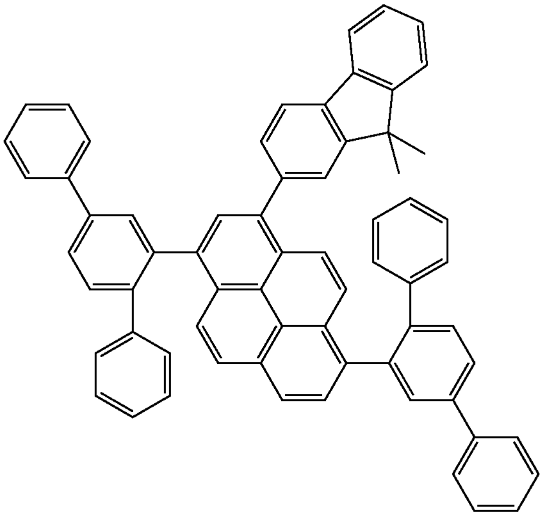

-continued

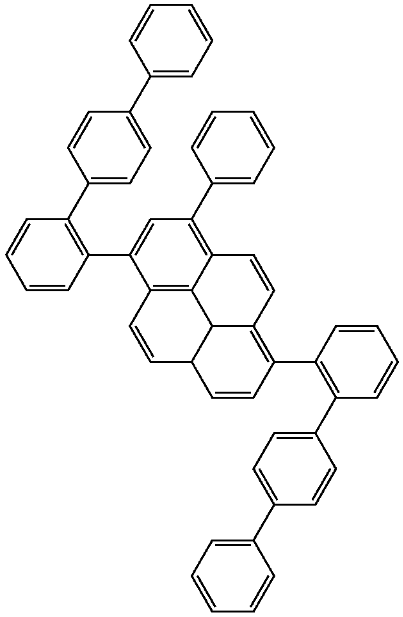

Second Compound

In the organic EL device according to the exemplary embodiment, the second compound is a compound represented by the formula (2).

Compound Represented by Formula (2)

[Formula 59]

(2)

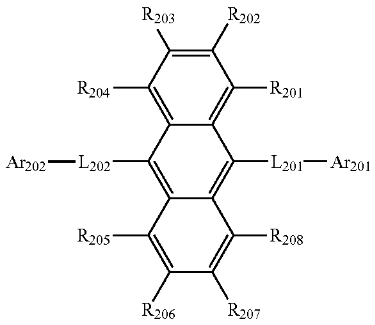

In the formula (2):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the second compound according to the exemplary embodiment:

$R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In the organic EL device according to the exemplary embodiment, it is preferable that: $R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aralkyl group having 7 to 50 carbon atoms, a group represented by $-C(=O)R_{801}$, a group represented by $-COOR_{802}$, a halogen atom, a cyano group, or a nitro group; $L_{201}$ and $L_{202}$ are each independently a single bond, a substituted or unsubstituted arylene group having 6 to 50 ring carbon atoms, or a substituted or unsubstituted divalent heterocyclic group having 5 to 50 ring atoms; and $Ar_{201}$ and $Ar_{202}$ are each independently a substituted or unsubstituted aryl group having 6 to 50 ring carbon atoms, or a substituted or unsubstituted heterocyclic group having 5 to 50 ring atoms.

In the organic EL device according to the exemplary embodiment, it is preferable that: $L_{201}$ and $L_{202}$ are each independently a single bond, or a substituted or unsubstituted arylene group having 6 to 50 ring carbon atoms; and $Ar_{201}$ and $Ar_{202}$ are each independently a substituted or unsubstituted aryl group having 6 to 50 ring carbon atoms.

In the organic EL device according to the exemplary embodiment, Arm and $Ar_{202}$ are preferably each independently a phenyl group, a naphthyl group, a phenanthryl group, a biphenyl group, a terphenyl group, a diphenylfluorenyl group, a dimethylfluorenyl group, a benzodiphenylfluorenyl group, a benzodimethylfluorenyl group, a dibenzofuranyl group, a dibenzothienyl group, a naphthobenzofuranyl group, or a naphthobenzothienyl group.

In the organic EL device according to the exemplary embodiment, the second compound represented by the formula (2) is preferably a compound represented by a formula (201), (202), (203), (204), (205), (206), (207), (208) or (209) below.

[Formula 60]

(201)

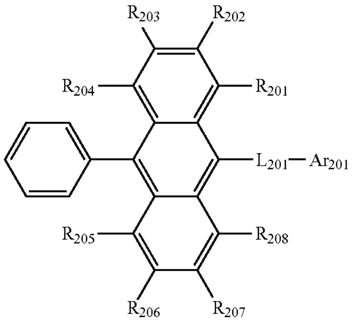

-continued

[Formula 61]

(202)

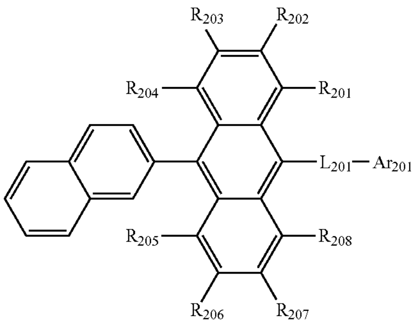

[Formula 62]

(203)

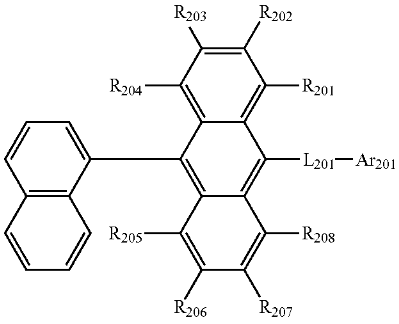

[Formula 63]

(204)

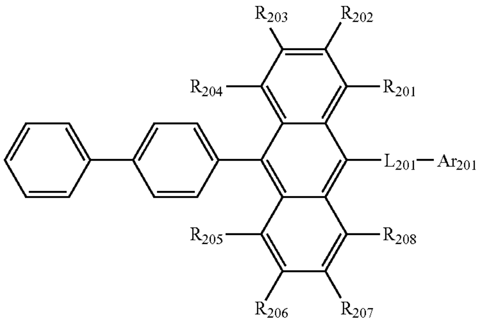

[Formula 64]

(205)

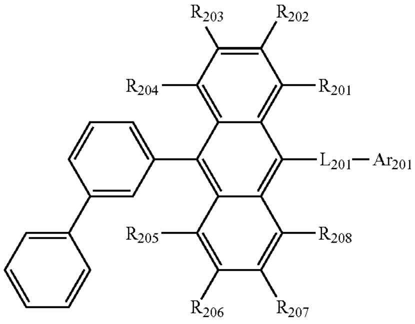

-continued
[Formula 65]
(206)
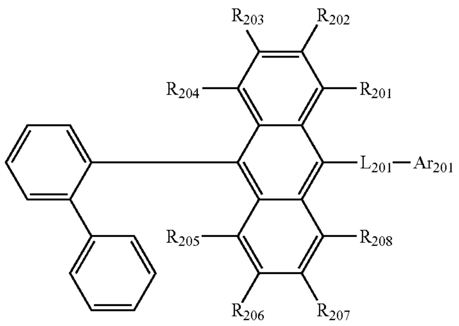
[Formula 66]
(207)
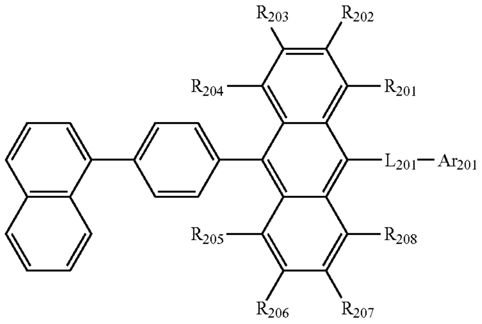
[Formula 67]
(208)
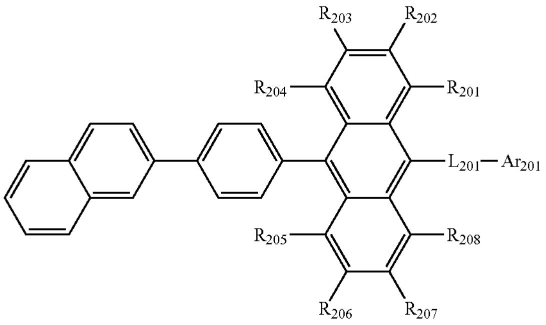
[Formula 68]
(209)
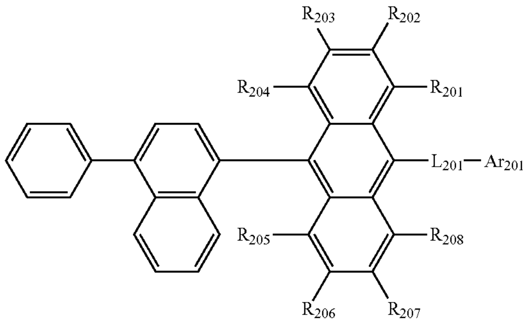
In the formulae (201) to (209):
$L_{201}$ and $Ar_{201}$ represent the same as $L_{201}$ and $Ar_{201}$ in the formula (2); and
$R_{201}$ to $R_{208}$ each independently represent the same as $R_{201}$ to $R_{208}$ in the formula (2).
The second compound represented by the formula (2) is also preferably a compound represented by a formula (221), (222), (223), (224), (225), (226), (227), (228) or (229) below.
[Formula 69]
(221)
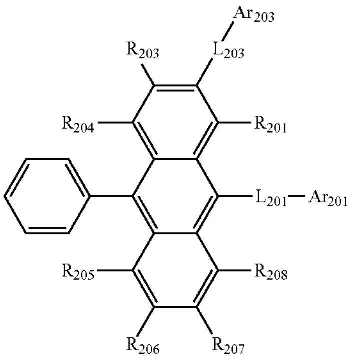
[Formula 70]
(222)
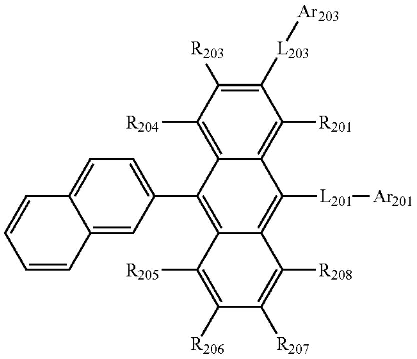
[Formula 71]
(223)
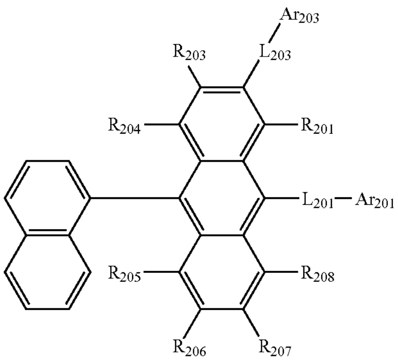

-continued

[Formula 72]

(224)

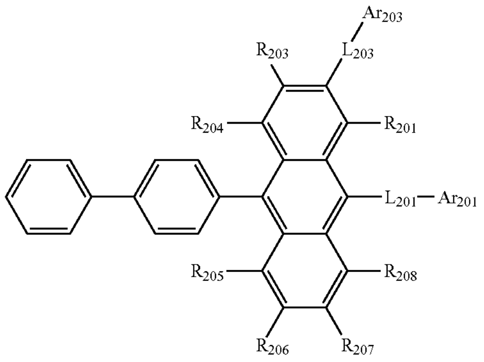

[Formula 73]

(225)

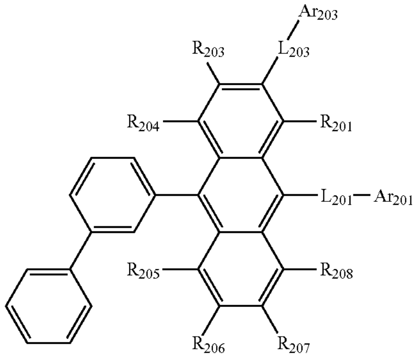

[Formula 74]

(226)

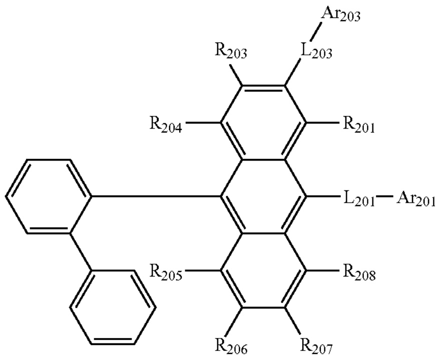

-continued

[Formula 75]

(227)

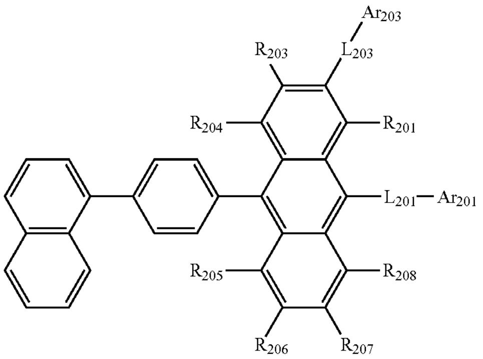

[Formula 76]

(228)

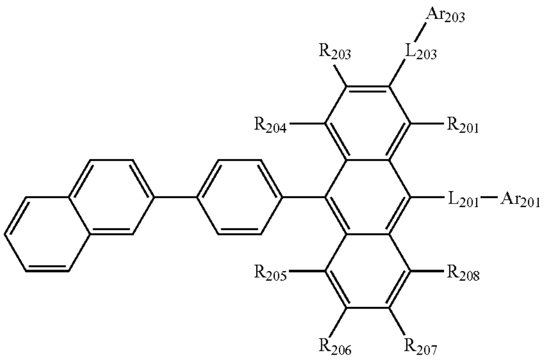

[Formula 77]

(229)

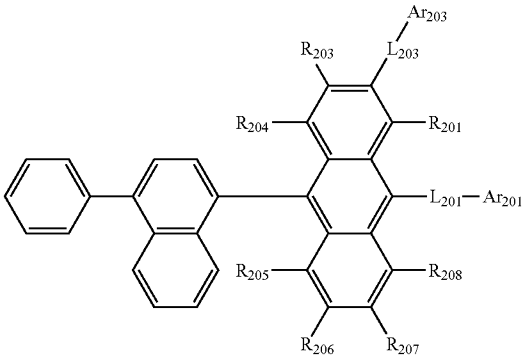

In the formulae (221), (222), (223), (224), (225), (226), (227), (228) and (229):

$R_{201}$ and $R_{203}$ to $R_{208}$ each independently represent the same as $R_{201}$ and $R_{203}$ to $R_{208}$ in the formula (2);

$L_{201}$ and $Ar_{201}$ respectively represent the same as $L_{201}$ and $Ar_{201}$ in the formula (2);

$L_{203}$ represents the same as $L_{201}$ in the formula (2);

$L_{203}$ and $L_{201}$ are mutually the same or different;

$Ar_{203}$ represents the same as $Ar_{201}$ in the formula (2); and $Ar_{203}$ and $Ar_{201}$ are mutually the same or different.

The second compound represented by the formula (2) is also preferably a compound represented by a formula (241), (242), (243), (244), (245), (246), (247), (248) or (249) below.

[Formula 78]
(241)
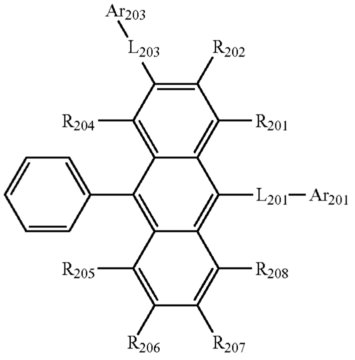
[Formula 79]
(242)
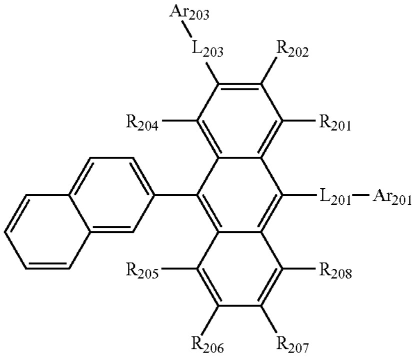
[Formula 80]
(243)
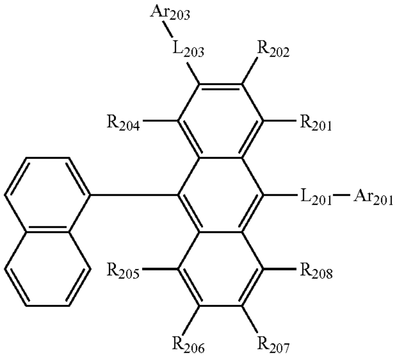
[Formula 81]
(244)
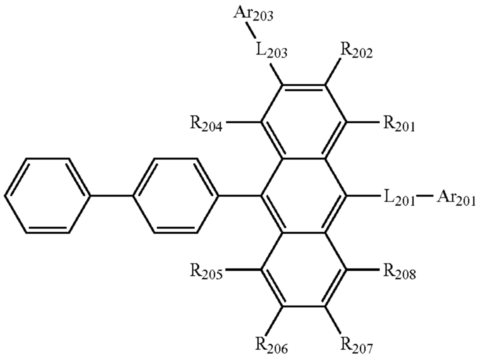
-continued
[Formula 82]
(245)
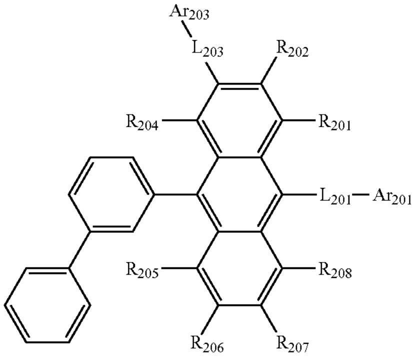
[Formula 83]
(246)
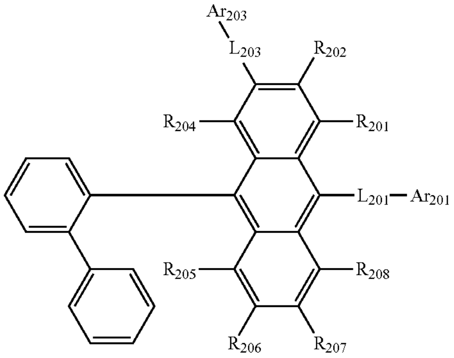
[Formula 84]
(247)
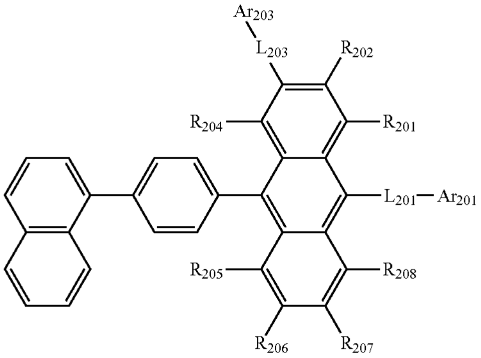

-continued

[Formula 85]

(248)

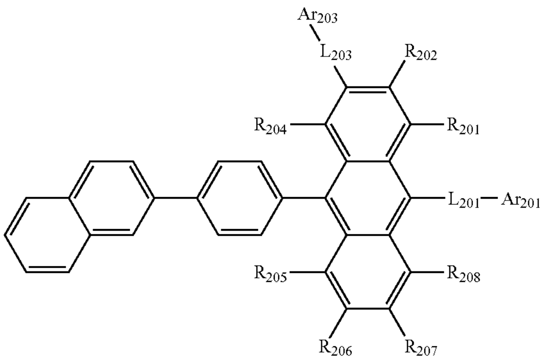

[Formula 86]

(249)

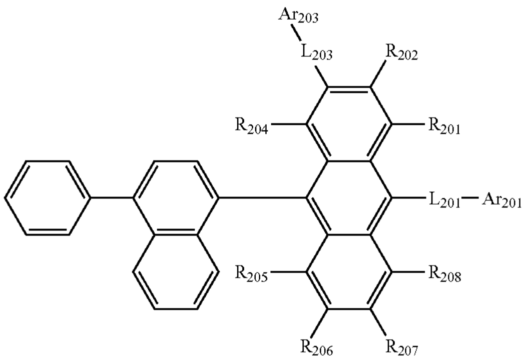

In the formulae (241), (242), (243), (244), (245), (246), (247), (248) and (249):

$R_{201}$, $R_{202}$ and $R_{204}$ to $R_{208}$ each independently represent the same as $R_{201}$, $R_{202}$ and $R_{204}$ to $R_{208}$ in the formula (2);

$L_{203}$ represents the same as $L_{201}$ in the formula (2);

$L_{203}$ and $L_{201}$ are mutually the same or different;

$Ar_{203}$ represents the same as $Ar_{201}$ in the formula (2); and $Ar_{203}$ and $Ar_{201}$ are mutually the same or different.

In the second compound represented by the formula (2), $R_{201}$ to $R_{208}$ not being a group represented by a formula (21) are preferably each independently a hydrogen atom, a substituted or unsubstituted alkyl group having 1 to 50 carbon atoms, a substituted or unsubstituted cycloalkyl group having 3 to 50 ring carbon atoms, or a group represented by $-Si(R_{901})(R_{902})(R_{903})$.

It is preferable that: $L_{101}$ is a single bond, or an unsubstituted arylene group having 6 to 22 ring carbon atoms; and $Ar_{101}$ is a substituted or unsubstituted aryl group having 6 to 22 ring carbon atoms.

In the organic EL device according to the exemplary embodiment, $R_{201}$ to $R_{208}$ in the second compound represented by the formula (2) are preferably each independently a hydrogen atom, a substituted or unsubstituted alkyl group having 1 to 50 carbon atoms, a substituted or unsubstituted cycloalkyl group having 3 to 50 ring carbon atoms, or a group represented by $-Si(R_{901})(R_{902})(R_{903})$.

In the organic EL device according to the exemplary embodiment, $R_{201}$ to $R_{208}$ in the second compound represented by the formula (2) are preferably a hydrogen atom.

In the second compound, all groups described as "substituted or unsubstituted" groups are preferably "unsubstituted" groups.

In the organic EL device according to the exemplary embodiment, for instance, $Ar_{201}$ in the second compound represented by the formula (2) is a substituted or unsubstituted dibenzofuranyl group.

In the organic EL device according to the exemplary embodiment, for instance, $Ar_{201}$ in the second compound represented by the formula (2) is an unsubstituted dibenzofuranyl group.

In the organic EL device according to the exemplary embodiment, for instance, the second compound represented by the formula (2) has at least one hydrogen atom, the hydrogen atom including at least one deuterium atom.

In the organic EL device according to the exemplary embodiment, for instance, $L_{201}$ in the second compound represented by the formula (2) is one of TEMP-63 to TEMP-68.

[Formula 87]

(TEMP-63)

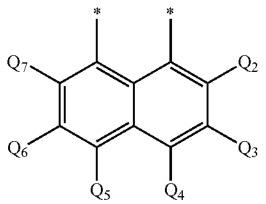

(TEMP-64)

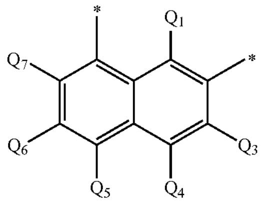

(TEMP-65)

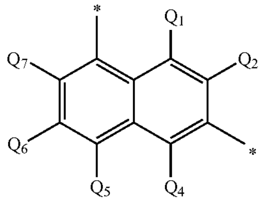

(TEMP-66)

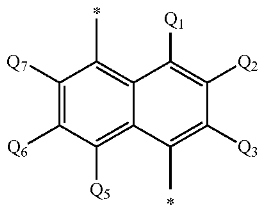

(TEMP-67)

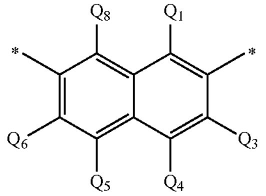

-continued (TEMP-68)

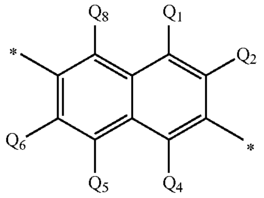

In the organic EL device according to the exemplary embodiment, for instance, $Ar_{201}$ in the second compound represented by the formula (2) is at least one group selected from the group consisting of substituted or unsubstituted anthryl group, benzanthryl group, phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluoranthenyl group, benzofluoranthenyl group, and perylenyl group.

In the organic EL device according to the exemplary embodiment, for instance, $Ar_{201}$ in the second compound represented by the formula (2) is a substituted or unsubstituted fluorenyl group.

In the organic EL device according to the exemplary embodiment, for instance, $Ar_{201}$ in the second compound represented by the formula (2) is a substituted or unsubstituted xanthenyl group.

In the organic EL device according to the exemplary embodiment, for instance, $Ar_{201}$ in the second compound represented by the formula (2) is a benzoxanthenyl group.

In an organic EL device according to an exemplary embodiment, the second compound represented by the formula (2) is a compound represented by one of formulae (2-1 D) to (2-4D) below.

Compound Represented by One of Formulae (2-1 D) to (2-4D)

[Formula 88]

(2-1D)

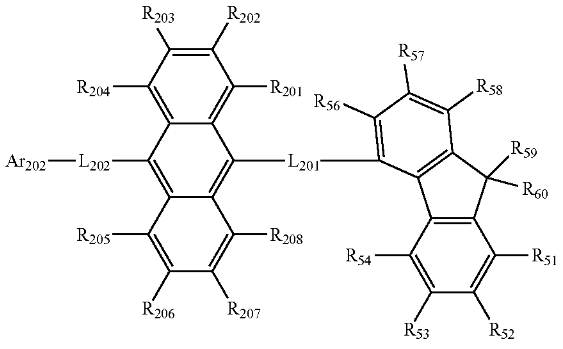

-continued (2-2D)

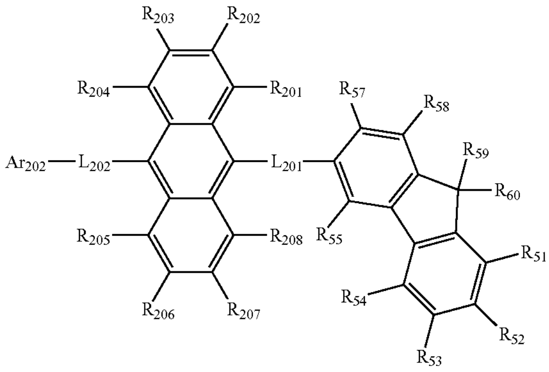

[Formula 89]

(2-3D)

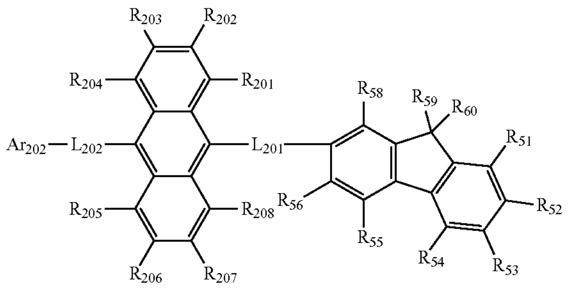

(2-4D)

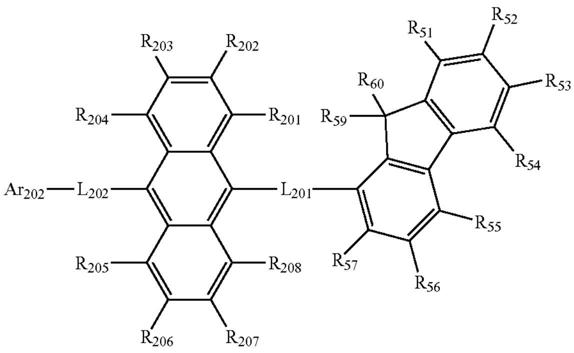

In the formulae (2-1 D) to (2-4D):

$R_{201}$ to $R_{205}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$R_{51}$ to $R_{60}$ are each independently a hydrogen atom or a substituent, or at least one combination of a combination of $R_{51}$ and $R_{52}$, a combination of $R_{52}$ and $R_{53}$, a combination of $R_{53}$ and $R_{54}$, a combination of $R_{55}$ and $R_{56}$, a combination of $R_{56}$ and $R_{57}$, a combination of $R_{57}$ and $R_{58}$, or a combination of $R_{59}$ and $R_{60}$ are mutually bonded to form a monocyclic ring or a fused ring;

$R_{51}$ to $R_{60}$ as a substituent are each independently a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a substituted or unsubstituted aralkyl group having 7 to 50 carbon atoms, a group represented by $—C(═O)R_{801}$, a group represented by $—COOR_{802}$, a halogen atom, a cyano group, a nitro group, or a substituted or unsubstituted aryl group having 6 to 50 ring carbon atoms;

$L_{201}$ and $L_{202}$ are each independently a single bond, or a substituted or unsubstituted arylene group having 6 to 50 ring carbon atoms; and a substituent, if present, for $L_{201}$ and $L_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $—S—(R_{905})$, a group represented by $—N(R_{906})(R_{907})$, a substituted or unsubstituted aralkyl group having 7 to 50 carbon atoms, a group represented by $—C(═O)R_{801}$, a group represented by $—COOR_{802}$, a halogen atom, a cyano group, a nitro group, and an unsubstituted aryl group having 6 to 50 ring carbon atoms;

$Ar_{202}$ is a substituted or unsubstituted aryl group having 6 to 50 ring carbon atoms; and a substituent, if present, for $Ar_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $—S—(R_{905})$, a group represented by $N(R_{906})(R_{907})$, a substituted or unsubstituted aralkyl group having 7 to 50 carbon atoms, a group represented by $—C(═O)R_{801}$, a group represented by $—COOR_{802}$, a halogen atom, a cyano group, a nitro group, and an unsubstituted aryl group having 6 to 50 ring carbon atoms.

In the second compound represented by the formulae (2-1 D) to (2-4D), $R_{901}$, $R_{902}$, $R_{903}$, $R_{904}$, $R_{905}$, $R_{906}$, $R_{907}$, $R_{801}$ and $R_{802}$ each independently represent the same as $R_{901}$, $R_{902}$, $R_{903}$, $R_{904}$, $R_{905}$, $R_{906}$, $R_{907}$, $R_{801}$ and $R_{802}$ in the second compound represented by the formula (2).

In an organic EL device according to an exemplary embodiment, the second compound is preferably a compound represented by one of formulae (21 D) to (24D) below.

[Formula 90]

(21D)

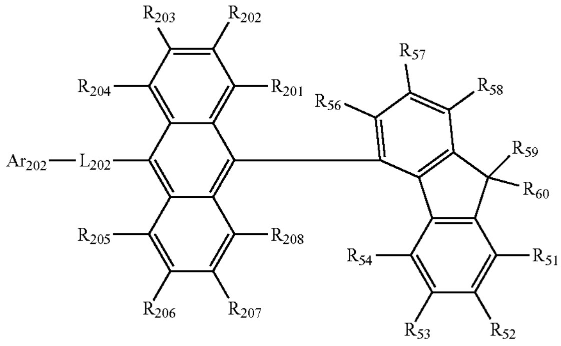

(22D)

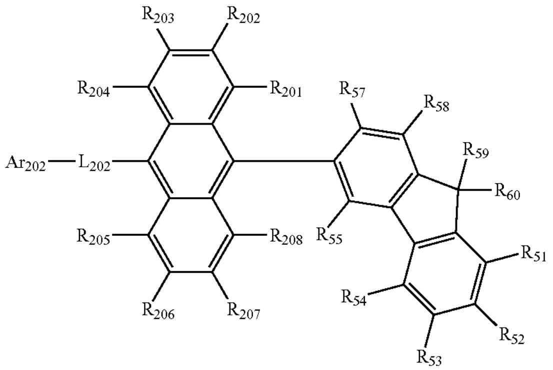

[Formula 91]

(23D)

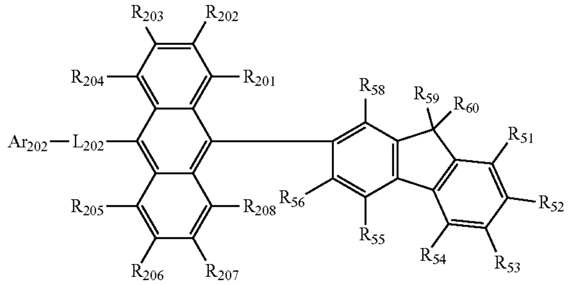

(24D)

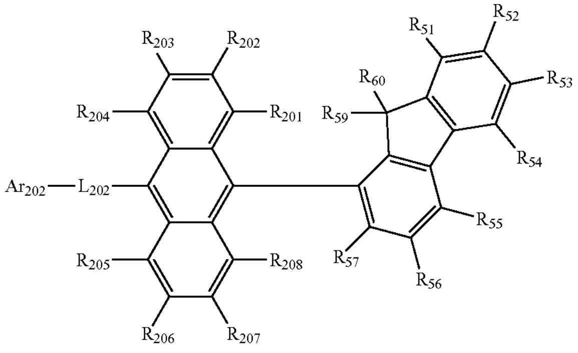

In the formulae (21 D) to (24D):

$L_{202}$, $Ar_{202}$, $R_{201}$ to $R_{208}$ and $R_{51}$ to $R_{60}$ each independently represent the same as $L_{202}$, $Ar_{202}$, $R_{201}$ to $R_{208}$ and $R_{51}$ to $R_{60}$ in the formulae (2-1 D) to (2-4D).

In an organic EL device according to an exemplary embodiment, it is preferable that the combination of $R_{51}$ and $R_{52}$, the combination of $R_{52}$ and $R_{53}$, the combination of $R_{53}$ and $R_{54}$, the combination of $R_{55}$ and $R_{56}$, the combination of $R_{56}$ and $R_{57}$, and the combination of $R_{57}$ and $R_{58}$ are not mutually bonded.

In an organic EL device according to an exemplary embodiment, the combination of $R_{59}$ and $R_{60}$ are preferably not mutually bonded.

In an organic EL device according to an exemplary embodiment, it is preferable that: the combination of $R_{59}$ and $R_{60}$ are mutually bonded to form a monocyclic ring or a fused ring when the second compound is a compound represented by the formula (2-1 D), (2-2D) or (2-4D); and the combination of $R_{59}$ and $R_{60}$ are not mutually bonded when the second compound is a compound represented by the formula (2-3D).

In an organic EL device according to an exemplary embodiment, it is preferable that: $R_{51}$ to $R_{58}$ are each independently a hydrogen atom, a substituted or unsubstituted alkyl group having 1 to 30 carbon atoms, a substituted or unsubstituted haloalkyl group having 1 to 30 carbon atoms, or a substituted or unsubstituted aryl group having 6 to 30 ring carbon atoms; $R_{59}$ to $R_{60}$ are a substituent, or the combination of $R_{59}$ and $R_{60}$ are mutually bonded to form a monocyclic ring or a fused ring; and $R_{59}$ to $R_{60}$ as a substituent are each independently a substituted or unsubstituted alkyl group having 1 to 30 carbon atoms, or a substituted or unsubstituted aryl group having 6 to 30 ring carbon atoms.

In an organic EL device according to an exemplary embodiment, it is preferable that: $R_{51}$ to $R_{58}$ are a hydrogen atom; and $R_{59}$ to $R_{60}$ are each independently a substituted or unsubstituted alkyl group having 1 to 30 carbon atoms, or a substituted or unsubstituted aryl group having 6 to 30 ring carbon atoms.

In an organic EL device according to an exemplary embodiment, the second compound represented by the formula (2) is a compound represented by a formula (2-1E) below.

Compound Represented by Formula (2-1E)

[Formula 92]

(2-1E)

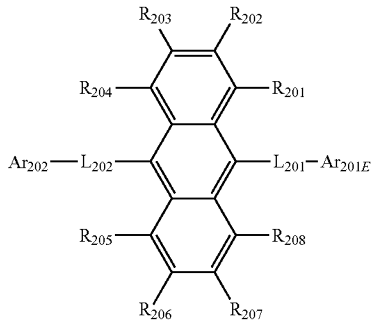

In the formula (2-1E):

$R_{201}$ to $R_{208}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{201}$ and $L_{202}$ are each independently a single bond, or a substituted or unsubstituted arylene group having 6 to 50 ring carbon atoms;

a substituent, if present, for $L_{201}$ and $L_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, and an unsubstituted aryl group having 6 to 50 ring carbon atoms;

$Ar_{201E}$ and $Ar_{202}$ are each independently a substituted or unsubstituted aryl group having 6 to 50 ring carbon atoms;

a substituent, if present, for $Ar_{201E}$ and $Ar_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, and an unsubstituted aryl group having 6 to 50 ring carbon atoms;

(i) when $L_{201}$ and $L_{202}$ are each independently a substituted or unsubstituted arylene group having 6 to 50 ring carbon atoms, the arylene group is not a substituted or unsubstituted phenylene group; and (ii) at least one of $Ar_{201E}$, $Ar_{202}$, $L_{201}$ or $L_{202}$ is a substituted or unsubstituted naphthyl group, a substituted or unsubstituted anthryl group, a substituted or unsubstituted benzanthryl group, a substituted or unsubstituted phenanthryl group, a substituted or unsubstituted benzophenanthryl group, a substituted or unsubstituted phenalenyl group, a substituted or unsubstituted pyrenyl group, a substituted or unsubstituted chrysenyl group, a substituted or unsubstituted benzochrysenyl group, a substituted or unsubstituted triphenylenyl group, a substituted or unsubstituted benzotriphenylenyl group, a substituted or unsubstituted tetracenyl group, a substituted or unsubstituted pentacenyl group, a substituted or unsubstituted dibenzofluorenyl group, a substituted or unsubstituted fluoranthenyl group, or a substituted or unsubstituted benzofluoranthenyl group, and when a group represented by $-L_{202}-Ar_{202}$ is an unsubstituted phenyl group, at least one of $Ar_{201E}$ or $L_{201}$ is a substituted or unsubstituted anthryl group, a substituted or unsubstituted benzanthryl group, a substituted or unsubstituted phenanthryl group, a substituted or unsubstituted benzophenanthryl group, a substituted or unsubstituted phenalenyl group, a substituted or unsubstituted pyrenyl group, a substituted or unsubstituted chrysenyl group, a substituted or unsubstituted benzochrysenyl group, a substituted or unsubstituted triphenylenyl group, a substituted or unsubstituted benzotriphenylenyl group, a substituted or unsubstituted tetracenyl group, a substituted or unsubstituted pentacenyl group, a substituted or unsubstituted dibenzofluorenyl group, a substituted or unsubstituted fluoranthenyl group, or a substituted or unsubstituted benzofluoranthenyl group.

In the second compound represented by the formula (2-1E), $R_{901}$, $R_{902}$, $R_{903}$, $R_{904}$, $R_{905}$, $R_{906}$, $R_{907}$, $R_{801}$ and $R_{802}$ each independently represent the same as $R_{901}$, $R_{902}$, $R_{903}$, $R_{904}$, $R_{905}$, $R_{906}$, $R_{907}$, $R_{801}$ and $R_{802}$ in the second compound represented by the formula (2).

In the second compound represented by the formula (2-1E), none of $Ar_{201E}$, $Ar_{202}$, $L_{201}$ and $L_{202}$ is a heterocyclic group, and the substituent, if present, for $Ar_{201E}$, $Ar_{202}$, $L_{201}$ and $L_{202}$ is not a heterocyclic group. That is, in the second compound represented by the formula (2-1E), none of groups bonded to positions 9 and 10 of an anthracene skeleton has a heterocyclic group.

Further, in the second compound represented by the formula (2-1E): at least one of $Ar_{201E}$, $Ar_{202}$, $L_{201}$ or $L_{202}$ is a substituted or unsubstituted aromatic hydrocarbon ring having 10 or more ring carbon atoms (i.e., having at least the same number of ring carbon atoms as that of a naphthalene ring); and when a group represented by $*-L_{202}-Ar_{202}$ is an unsubstituted phenyl group, at least one of $Ar_{201E}$ or $L_{201}$ is a substituted or unsubstituted aromatic hydrocarbon ring having 11 or more ring carbon atoms (i.e., having more ring carbon atoms than a naphthalene ring). It should be noted that * represents a bonding position to the position 9 or 10 of an anthracene ring in the formula (2-1E). The same applies to the description below.

The second compound represented by the formula (2-1E) having the above structure (hereinafter, also referred to as the "second host material having the (2-1E) structure") is suitable as a host material for the second emitting layer of an organic EL device according to an exemplary embodiment.

Specifically, in an organic EL device according to an exemplary embodiment, when the second emitting layer in a laminate arrangement of the first emitting layer and the second emitting layer contains the second host material having the (2-1E) structure, holes are easily injected from the anode into the first emitting layer, and further, hole injectability into the second emitting layer close to the cathode is likely to decrease. As a result of hole blocking properties in the second emitting layer being favorable, a recombination probability in the first emitting layer increases.

Thus, use of the second host material having the (2-1E) structure can be expected to improve luminous efficiency.

Further, when the group represented by $*-L_{202}-Ar_{202}$ in (2-1E) is an unsubstituted phenyl group, the second host material having the (2-1E) structure is specifically the second host material represented by a formula (2-10E) below (hereinafter, also referred to as the "second host material having the (2-10E) structure").

The second host material having the (2-10E) structure can be expected to have higher electron transportability than a compound represented by a formula (20C) or (21C) below in which $Ar_{201E}$ and $L_{201}$ are each formed by an aromatic hydrocarbon ring having 10 or less ring carbon atoms. Thus, use of the second host material having the (2-10E) structure in an organic EL device according to an exemplary embodiment can be expected to improve luminous efficiency.

[Formula 93]

(2-10E)

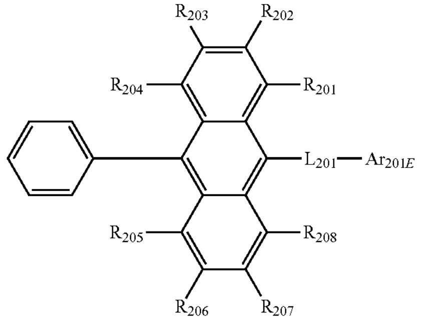

In the formula (2-10E), $R_{201}$ to $R_{208}$, $L_{201}$ and $Ar_{202E}$ each independently represent the same as $R_{201}$ to $R_{208}$, $L_{201}$ and $Ar_{202E}$ in the formula (2-1E).

[Formula 94]

(20C)

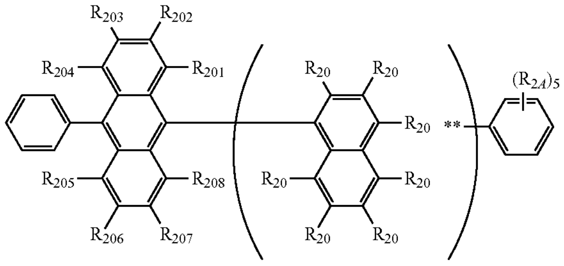

(21C)

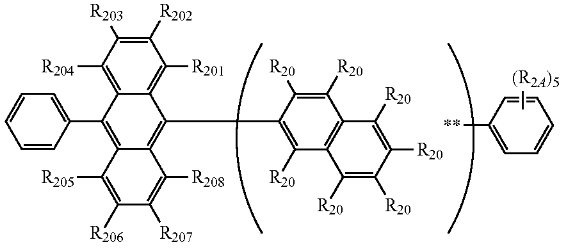

In the formulae (20C) to (21C): $R_{20}$ to $R_{208}$ each independently represent the same as $R_{20}$ to $R_{208}$ in the formula (2-1E); $R_{20}$ each independently represents the same as the substituent, if present, for $L_{201}$ in the formula (2-1E); a plurality of $R_{20}$ are mutually the same or different; $R_{2A}$ each independently represents the same as the substituent, if present, for $Ar_{201E}$ in the formula (2-1E); a plurality of $R_{2A}$ are mutually the same or different; and one $R_{20}$ is a bonding position ** to a benzene ring having $R_{2A}$.

Further, it is expected that the second host material having the (2-10E) structure is less likely to cause crucible blocking than a compound represented by a formula (22C) or (23C) below in which $Ar_{201E}$ and $L_{201}$ are each formed by an aromatic hydrocarbon ring having 10 or less ring carbon atoms.

The crucible blocking refers to the following phenomenon.

When an emitting layer is formed through vapor deposition using a crucible containing a target compound for film formation, a sublimated material may adhere to an opening of the crucible in a manner to block the opening. When the opening of the crucible becomes narrow, the target compound for film formation does not easily go out of the crucible to increase a time required for allowing the target compound to adhere to a substrate or the like to form a film having a predetermined thickness, resulting in a decrease in production efficiency.

[Formula 95]

(22C)

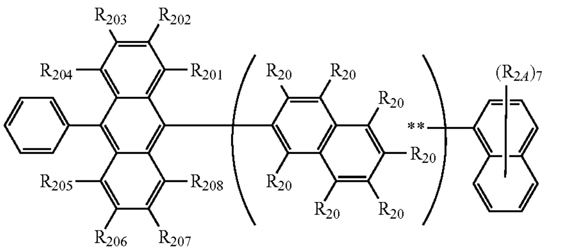

(23C)

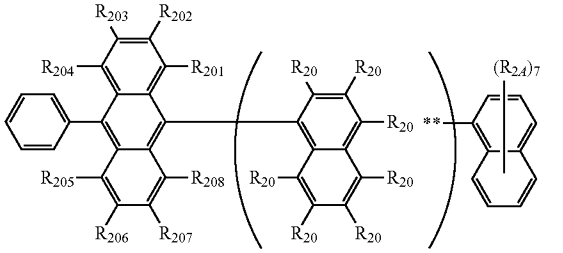

In the formulae (22C) to (23C): $R_{201}$ to $R_{208}$ each independently represent the same as $R_{201}$ to $R_{208}$ in the formula (2-1E); $R_{20}$ each independently represents the same as the substituent, if present, for $L_{201}$ in the formula (2-1E); a plurality of $R_{20}$ are mutually the same or different; $R_{2A}$ each independently represents the same as the substituent, if present, for $Ar_{201E}$ in the formula (2-1E); a plurality of $R_{2A}$ are mutually the same or different; and one $R_{20}$ is a bonding position ** to a naphthalene ring having $R_{2A}$.

An organic EL device according to an exemplary embodiment includes the first emitting layer containing the first compound represented by the formula (1) and the second emitting layer containing the second compound represented by the formula (2-1E) in this order from the anode.

An organic EL device according to an exemplary embodiment, when the first emitting layer and the second emitting layer are laminated in this order (i.e., laminated in normal order), exhibits an effect of relatively improving electron transportability to enhance luminous efficiency.

In contrast, the first emitting layer and the second emitting layer may be reversely laminated (i.e., laminated in reverse order), specifically, the first emitting layer close to the anode may contain the second host material having the (2-1E) structure that decreases hole injectability as described above. In this arrangement, holes are unlikely to be injected into not only the first emitting layer but also the second emitting layer. Consequently, recombination of holes and electrons decreases, making it unlikely to obtain the effect of improving luminous efficiency.

In the second compound according to an exemplary embodiment:

$R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, or a substituted or unsubstituted aryl group having 6 to 50 ring carbon atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In an organic EL device according to an exemplary embodiment, $Ar_{201E}$ and $Ar_{202}$ are preferably each independently a substituted or unsubstituted naphthyl group, a substituted or unsubstituted anthryl group, a substituted or unsubstituted benzanthryl group, a substituted or unsubstituted phenanthryl group, a substituted or unsubstituted benzophenanthryl group, a substituted or unsubstituted phenalenyl group, a substituted or unsubstituted chrysenyl group, a substituted or unsubstituted benzochrysenyl group, a substituted or unsubstituted triphenylenyl group, a substituted or unsubstituted benzotriphenylenyl group, a substituted or unsubstituted tetracenyl group, a substituted or unsubstituted pentacenyl group, a substituted or unsubstituted fluorenyl group, a substituted or unsubstituted 9,9'-spirobifluorenyl group, a substituted or unsubstituted benzofluorenyl group, a substituted or unsubstituted dibenzofluorenyl group, a substituted or unsubstituted fluoranthenyl group, a substituted or unsubstituted benzofluoranthenyl group, or a substituted or unsubstituted perylenyl group.

In an organic EL device according to an exemplary embodiment, $Ar_{201E}$ is preferably each independently a monovalent group represented by one of formulae (2-1e) to (2-9e) below.

[Formula 96]

(2-1e)

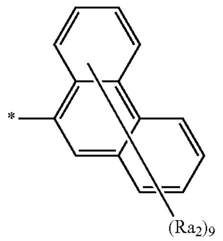

-continued (2-2e)

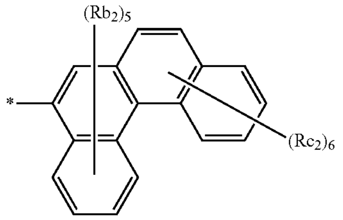

(2-3e)

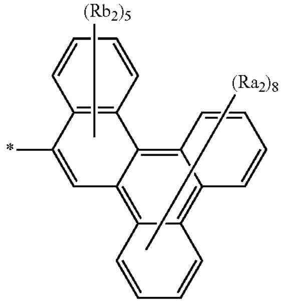

(2-4e)

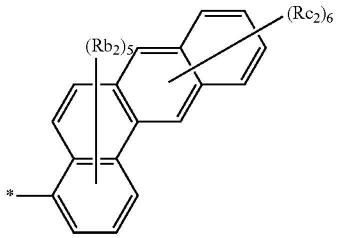

(2-5e)

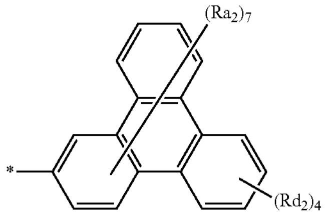

(2-6e)

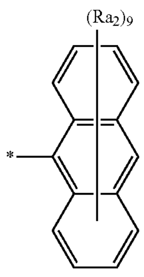

(2-7e)

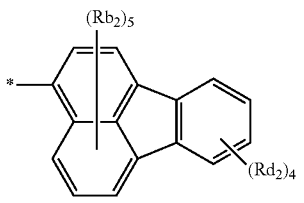

-continued (2-8e)

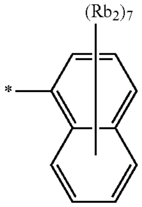

(2-9e)

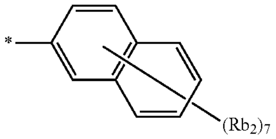

In the formulae (2-1e) to (2-9e): $Ra_2$ to $Rd_2$ each independently represent the same as the substituent, if present, for $Ar_{201E}$ in the formula (2-1E); and * represents a bonding position.

In an organic EL device according to an exemplary embodiment, the compound represented by the formula (2-1E) is preferably a compound represented by one of formulae (21E) to (24E) below.

[Formula 97]

(21E)

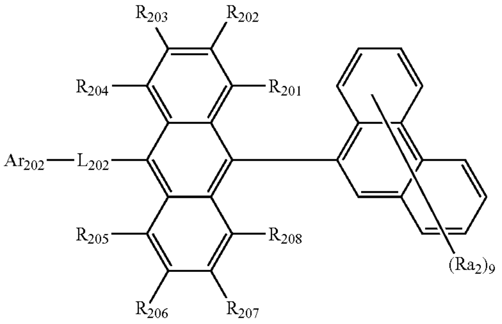

(22E)

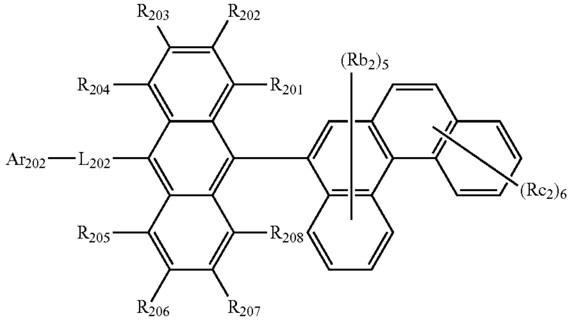

-continued

[Formula 98]

(23E)

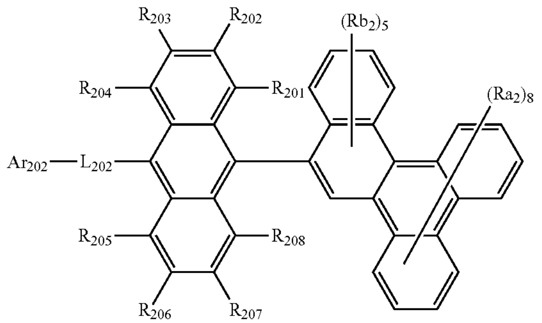

(24E)

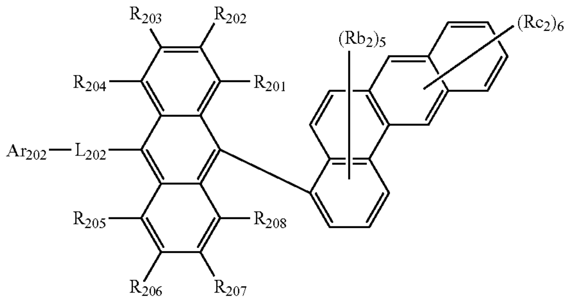

In the formulae (21E) to (24E): $R_{201}$ to $R_{208}$, $L_{202}$ and $Ar_{202}$ each independently represent the same as $R_{201}$ to $R_{208}$, $L_{202}$ and $Ar_{202}$ in the formula (2-1E); and $Ra_2$ to $Rc_2$ each independently represent the same as the substituent, if present, for $Ar_{201E}$ in the formula (2-1E).

In an organic EL device according to an exemplary embodiment, $Ra_2$ to $Rd_2$ are preferably a hydrogen atom, a substituted or unsubstituted alkyl group having 1 to 30 carbon atoms, a substituted or unsubstituted haloalkyl group having 1 to 30 carbon atoms, or a substituted or unsubstituted aryl group having 6 to 30 ring carbon atoms.

In an organic EL device according to an exemplary embodiment, $Ra_2$ to $Rd_2$ are preferably a hydrogen atom.

In an organic EL device according to an exemplary embodiment, the second compound represented by the formula (2) is a compound represented by a formula (2-1F) below.

Compound Represented by Formula (2-1F)

[Formula 99]

(2-1F)

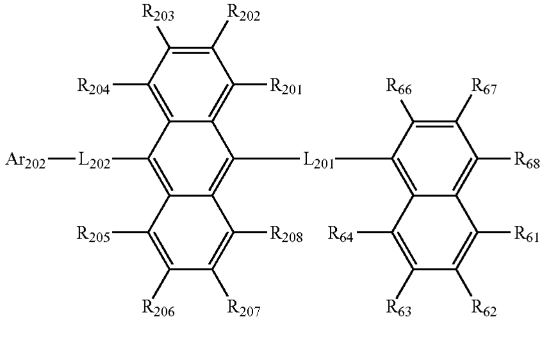

In the formula (2-1F):

$R_{201}$ to $R_{208}$, $R_{61}$ to $R_{64}$, $R_{66}$ and $R_{68}$ are each independently a hydrogen atom or a substituent, and $R_{67}$ is a substituent;

$R_{201}$ to $R_{208}$ as a substituent are each independently a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a substituted or unsubstituted aralkyl group having 7 to 50 carbon atoms, a group represented by $—C(═O)R_{801}$, a group represented by $—COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$R_{61}$ to $R_{64}$ and $R_{66}$ to $R_{68}$ as a substituent are each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(═O)R_{801}$, a group represented by $—COOR_{802}$, a halogen atom, a cyano group, a nitro group, and an unsubstituted aryl group having 6 to 50 ring carbon atoms;

$L_{201}$ and $L_{202}$ are each independently a single bond, or a substituted or unsubstituted arylene group having 6 to 50 ring carbon atoms;

a substituent, if present, for $L_{201}$ and $L_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(═O)R_{801}$, a group represented by $—COOR_{802}$, a halogen atom, a cyano group, a nitro group, and an unsubstituted aryl group having 6 to 50 ring carbon atoms;

$Ar_{202}$ is a substituted or unsubstituted aryl group having 6 to 50 ring carbon atoms; and a substituent, if present, for $Ar_{202}$ is each independently selected from the group consisting of an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(═O)R_{801}$, a group represented by $—COOR_{802}$, a halogen atom, a cyano group, a nitro group, and an unsubstituted aryl group having 6 to 50 ring carbon atoms.

In the second compound represented by the formula (2-1F), $R_{901}$, $R_{902}$, $R_{903}$, $R_{904}$, $R_{905}$, $R_{906}$, $R_{907}$, $R_{801}$ and $R_{802}$ each independently represent the same as $R_{901}$, $R_{902}$, $R_{903}$, $R_{904}$, $R_{905}$, $R_{906}$, $R_{907}$, $R_{801}$ and $R_{802}$ in the second compound represented by the formula (2).

In an organic EL device according to an exemplary embodiment, the second compound is preferably a compound represented by a formula (21F) or (22F) below.

[Formula 100]

(21F)

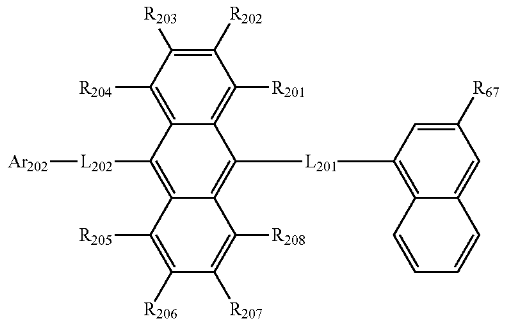

(22F)

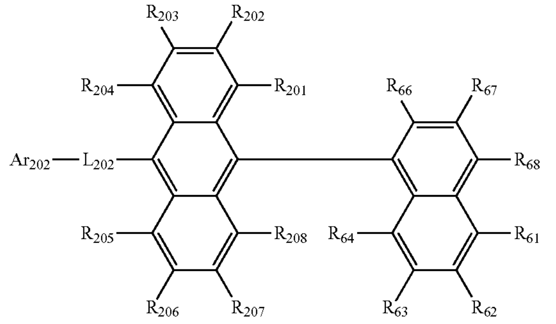

In the formula (21F), $L_{201}$, $L_{202}$, $Ar_{202}$, $R_{201}$ to $R_{208}$ and $R_{67}$ each independently represent the same as $L_{201}$, $L_{202}$, $Ar_{202}$, $R_{201}$ to $R_{208}$ and $R_{67}$ in the formula (2-1F). In the formula (22F), $L_{202}$, $Ar_{202}$, $R_{201}$ to $R_{208}$, $R_{61}$ to $R_{64}$ and $R_{66}$ to $R_{68}$ each independently represent the same as $L_{202}$, $Ar_{202}$, $R_{201}$ to $R_{208}$, $R_{61}$ to $R_{64}$ and $R_{66}$ to $R_{68}$ in the formula (2-1F).

In an organic EL device according to an exemplary embodiment, it is preferable that: $R_{61}$ to $R_{64}$, $R_{66}$ and $R_{68}$ are each independently a hydrogen atom, a substituted or unsubstituted alkyl group having 1 to 30 carbon atoms, a substituted or unsubstituted haloalkyl group having 1 to 30 carbon atoms, or a substituted or unsubstituted aryl group having 6 to 30 ring carbon atoms; and $R_{67}$ is a substituted or unsubstituted alkyl group having 1 to 30 carbon atoms, or a substituted or unsubstituted aryl group having 6 to 30 ring carbon atoms.

In an organic EL device according to an exemplary embodiment, it is preferable that: $R_{61}$ to $R_{64}$, $R_{66}$ and $R_{68}$ are a hydrogen atom; and $R_{67}$ is a substituted or unsubstituted aryl group having 6 to 30 ring carbon atoms.

In the formulae (2-1 D) to (2-4D), (2-1E) and (2-1F), $L_{201}$ and $L_{202}$ are preferably each independently a single bond, or a substituted or unsubstituted arylene group having 6 to 18 ring carbon atoms.

In the formulae (2-1 D) to (2-4D), (2-1E) and (2-1F), $L_{201}$ and $L_{202}$ are preferably each independently a single bond, or a group represented by one of formulae (2-1a) to (2-4a) below.

[Formula 101]

(2-1a)

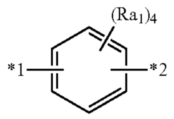

(2-2a)

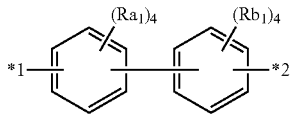

(2-3a)

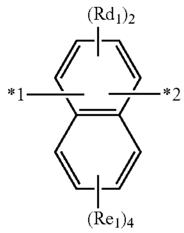

(2-4a)

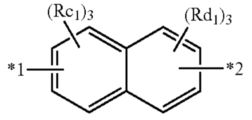

In the formulae (2-1a) to (2-4a): $Ra_1$ to $Re_1$ each independently represent the same as the substituent, if present, for $L_{201}$ and $L_{202}$ in the formulae (2-1 D) to (2-4D), (2-1E) and (2-1F); and *1 and *2 each represent a bonding position.

In the formulae (2-1 D) to (2-4D), (2-1E) and (2-1F), one or both of $L_{201}$ and $L_{202}$ are preferably a single bond.

In the formulae (2-1D) to (2-4D), (2-1E) and (2-1F), $Ar_{202}$ is preferably a substituted or unsubstituted phenyl group, a substituted or unsubstituted naphthyl group, a substituted or unsubstituted phenanthryl group, a substituted or unsubstituted biphenyl group, a substituted or unsubstituted terphenyl group, a substituted or unsubstituted diphenylfluorenyl group, a substituted or unsubstituted dimethylfluorenyl group, a substituted or unsubstituted benzodiphenylfluorenyl group, a substituted or unsubstituted benzodimethylfluorenyl group, a substituted or unsubstituted dibenzofuranyl group, a substituted or unsubstituted dibenzothienyl group, a substituted or unsubstituted naphthobenzofuranyl group, or a substituted or unsubstituted naphthobenzothienyl group.

In the formulae (2-1 D) to (2-4D), (2-1E) and (2-1F), the group represented by $-L_{202}-Ar_{202}$ is preferably a group represented by one of formulae (2-11a) to (2-30a) below.

[Formula 102]

(2-11a)

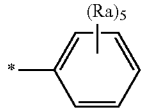

-continued
(2-12a)
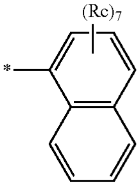
(2-13a)
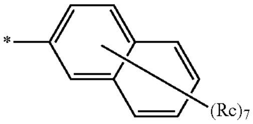
(2-14a)
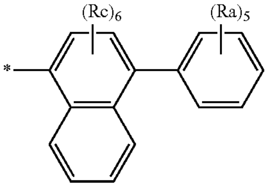
(2-15a)
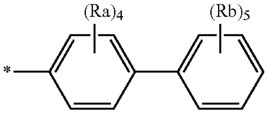
(2-16a)
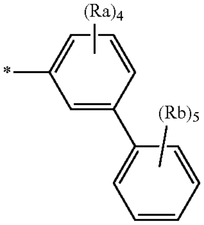
(2-17a)
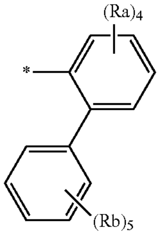
(2-18a)
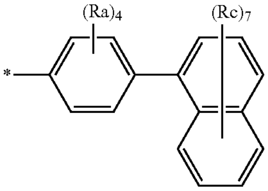
(2-19a)
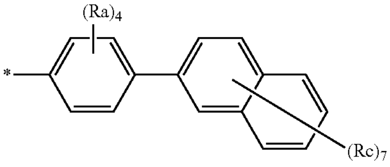
-continued
(2-20a)
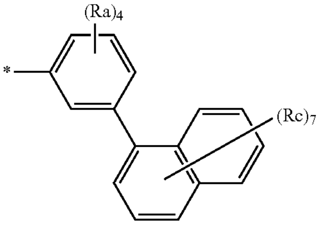
[Formula 103]
(2-21a)
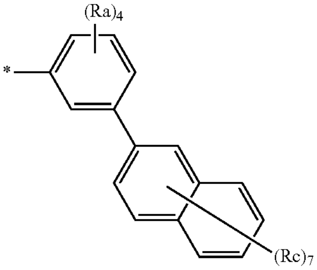
(2-22a)
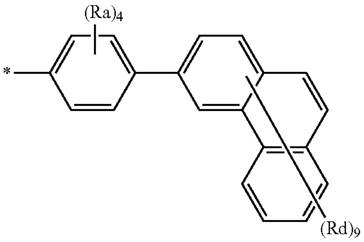
(2-23a)
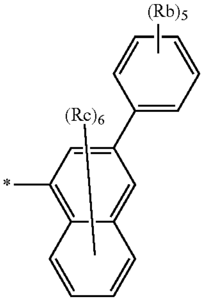
(2-24a)
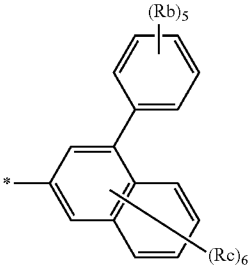
(2-25a)
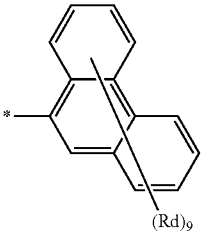

-continued (2-26a)

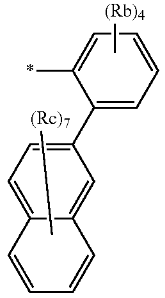

(2-27a)

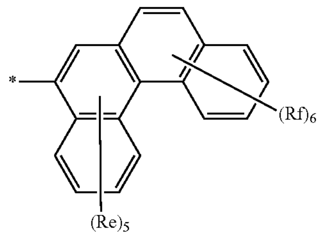

(2-28a)

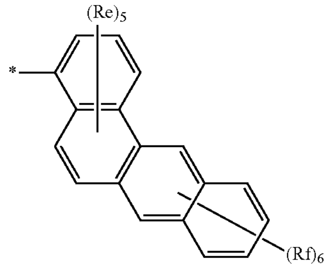

(2-29a)

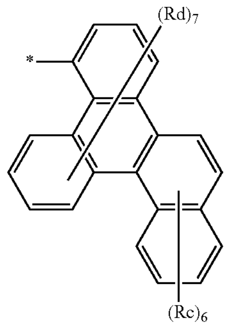

(2-30a)

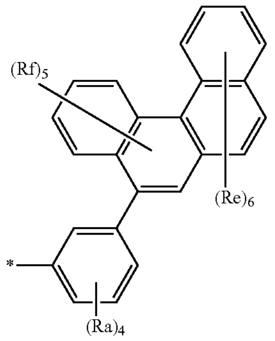

In the formulae (2-11a) to (2-30a): Ra to Rf each independently represent the same as the substituent, if present, for $Ar_{202}$ in the formulae (2-1 D) to (2-4D), (2-1E) and (2-1F); and * represents a bonding position.

In an organic EL device according to an exemplary embodiment, $R_{201}$ to $R_{208}$ that are substituents on an anthracene skeleton in the second compound are preferably hydrogen atoms in terms of preventing inhibition of intermolecular interaction to inhibit a decrease in electron mobility. However, $R_{201}$ to $R_{208}$ may be a substituted or unsubstituted aryl group having 6 to 50 ring carbon atoms or a substituted or unsubstituted heterocyclic group having 5 to 50 ring atoms.

Assuming that $R_{201}$ to $R_{208}$ each are a bulky substituent such as an alkyl group and a cycloalkyl group, intermolecular interaction may be inhibited to decrease the electron mobility of the second compound relative to that of the first compound, so that a relationship of μH2>μH1 shown by a numerical formula below (Numerical Formula 3) may not be satisfied. When the second compound is used in the second emitting layer, it can be expected that satisfying the relationship of μH2>μH1 inhibits a decrease in a recombination ability between holes and electrons in the first emitting layer and a decrease in a luminous efficiency. It should be noted that substituents, namely, a haloalkyl group, alkenyl group, alkynyl group, group represented by —Si($R_{901}$)($R_{902}$)($R_{903}$), group represented by —O—($R_{904}$), group represented by —S—($R_{905}$), group represented by —N($R_{906}$)($R_{907}$), aralkyl group, group represented by —C(=O)$R_{801}$, group represented by —COO$R_{802}$, halogen atom, cyano group, and nitro group are likely to be bulky, and an alkyl group and cycloalkyl group are likely to be further bulky.

In the second compound, $R_{201}$ to $R_{208}$, which are the substituents on the anthracene skeleton, are each preferably not a bulky substituent and preferably not an alkyl group and cycloalkyl group. More preferably, $R_{201}$ to $R_{208}$ are not an alkyl group, cycloalkyl group, haloalkyl group, alkenyl group, alkynyl group, group represented by —Si($R_{901}$)($R_{902}$)($R_{903}$), group represented by —O—($R_{904}$), group represented by —S—($R_{905}$), group represented by —N($R_{906}$)($R_{907}$), aralkyl group, group represented by —C(=O)$R_{801}$, group represented by —COO$R_{802}$, halogen atom, cyano group, and nitro group.

In the formulae (2-1D) to (2-4D), (2-1E) and (2-1F), $R_{201}$ to $R_{208}$ are also preferably each independently a hydrogen atom, a substituted or unsubstituted alkyl group having 1 to 50 carbon atoms, a substituted or unsubstituted cycloalkyl group having 3 to 50 ring carbon atoms, a group represented by —Si($R_{901}$)($R_{902}$)($R_{903}$), a cyano group, a substituted or unsubstituted aryl group having 6 to 50 ring carbon atoms, or a substituted or unsubstituted heterocyclic group having 5 to 50 ring atoms.

In the formulae (2-1D) to (2-4D), (2-1E) and (2-1F), $R_{201}$ to $R_{208}$ are also preferably each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In an organic EL device according to an exemplary embodiment, examples of the substituent for a "substituted or unsubstituted" group on $R_{201}$ to $R_{208}$ in the second compound also preferably do not include the above-described substituent that is likely to be bulky, especially a substituted or unsubstituted alkyl group and a substituted or unsubstituted cycloalkyl group. Since the examples of the substituent for the "substituted or unsubstituted" group on $R_{201}$ to $R_{208}$ do not include a substituted or unsubstituted alkyl group and a substituted or unsubstituted cycloalkyl group, inhibition of intermolecular interaction to be caused by presence of a bulky substituent such as an alkyl group and a cycloalkyl group can be prevented, thereby preventing a decrease in the electron mobility. Moreover, when the second compound described above is used in the second emitting layer, a decrease in a recombination ability between holes and electrons in the first emitting layer and a decrease in the luminous efficiency can be inhibited.

It is more preferable that $R_{201}$ to $R_{208}$, which are the substituents on the anthracene skeleton, are not bulky substituents, and $R_{201}$ to $R_{208}$ as substituents are unsubstituted. Assuming that $R_{201}$ to $R_{208}$, which are the substituents on the anthracene skeleton, are not bulky substituents and substituents are bonded to $R_{201}$ to $R_{208}$ which are the not-bulky substituents, the substituents bonded to $R_{201}$ to $R_{208}$ are preferably not the bulky substituents; the substituents bonded to $R_{201}$ to $R_{208}$ serving as substituents are preferably not an alkyl group and cycloalkyl group, more preferably not an alkyl group, cycloalkyl group, haloalkyl group, alkenyl group, alkynyl group, group represented by $-Si(R_{901})(R_{902})(R_{903})$, group represented by $-O-(R_{904})$, group represented by $-S-(R_{905})$, group represented by $-N(R_{906})(R_{907})$, aralkyl group, group represented by $-C(=O)R_{801}$, group represented by $-COOR_{802}$, halogen atom, cyano group, and nitro group.

In the formulae (2-1 D) to (2-4D), (2-1E) and (2-1F), it is preferable that: $R_{202}$ or $R_{203}$ in the second compound is a group represented by $-L_{203}-Ar_{203}$; $L_{203}$ is a single bond, or a substituted or unsubstituted phenylene group; $Ar_{203}$ is a substituted or unsubstituted phenyl group, a substituted or unsubstituted naphthyl group, a substituted or unsubstituted phenanthryl group, a substituted or unsubstituted biphenyl group, a substituted or unsubstituted terphenyl group, a substituted or unsubstituted diphenylfluorenyl group, a substituted or unsubstituted dimethylfluorenyl group, a substituted or unsubstituted benzodiphenylfluorenyl group, a substituted or unsubstituted benzodimethylfluorenyl group, a substituted or unsubstituted dibenzofuranyl group, a substituted or unsubstituted dibenzothienyl group, a substituted or unsubstituted naphthobenzofuranyl group, or a substituted or unsubstituted naphthobenzothienyl group.

In the formulae (2-1 D) to (2-4D), (2-1E) and (2-1F), all groups described as "substituted or unsubstituted" groups are preferably "unsubstituted" groups.

Manufacturing Method of Second Compound

The second compound can be manufactured by a known method. The second compound can also be manufactured based on a known method through a known alternative reaction using a known material(s) tailored for the target compound.

Specific examples of the second compound include the following compounds. It should however be noted that the invention is not limited to the specific examples of the second compound.

[Formula 104]

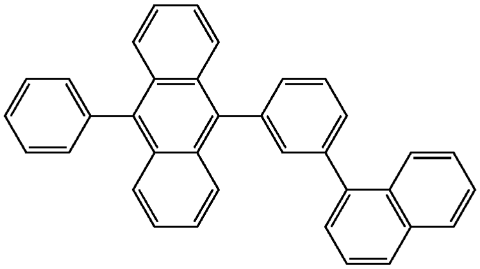

-continued

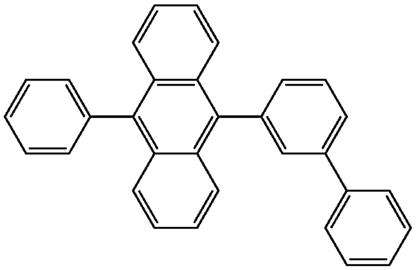

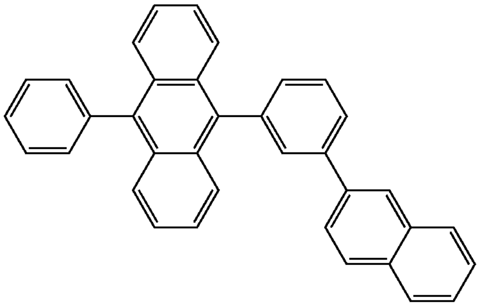

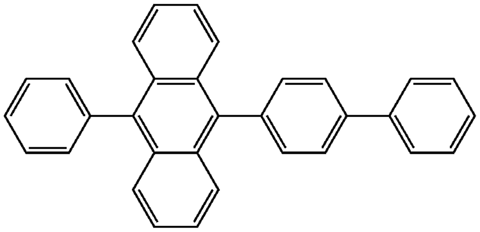

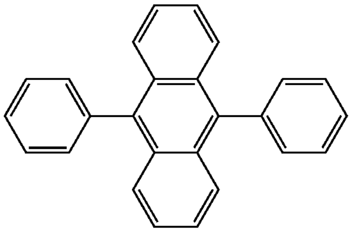

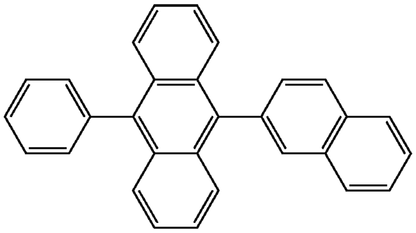

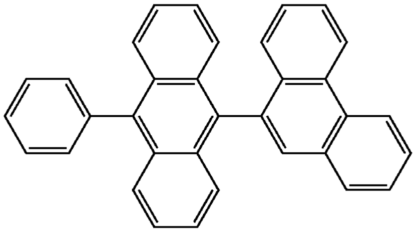

-continued
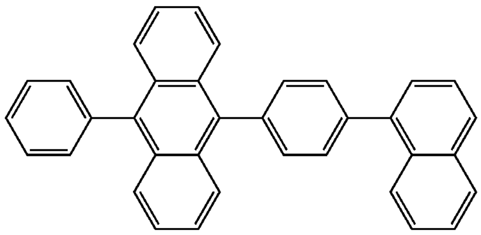
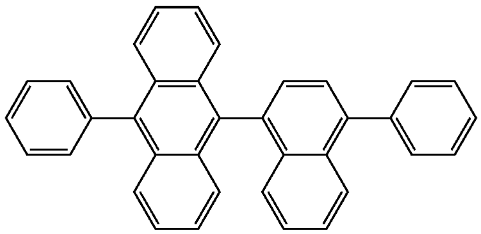
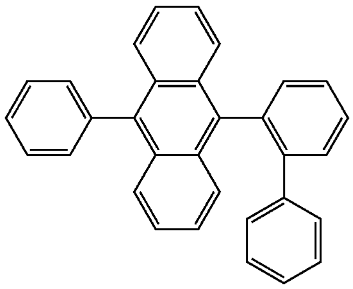
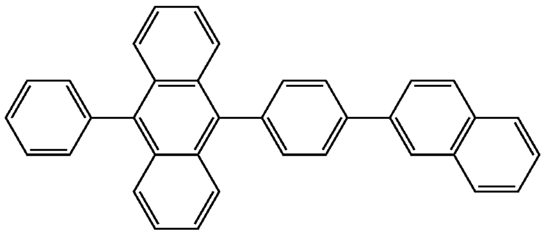
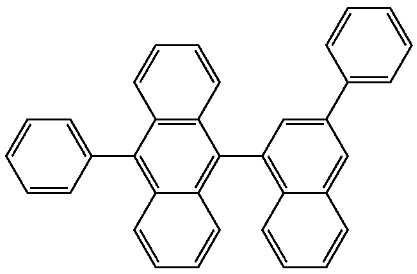
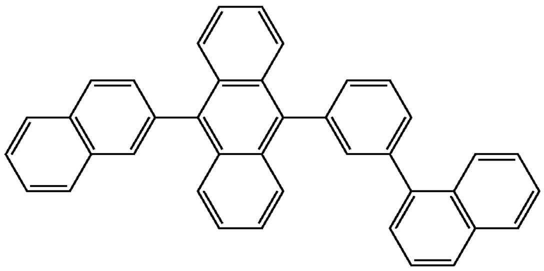
-continued
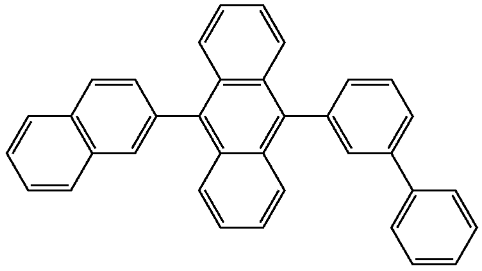
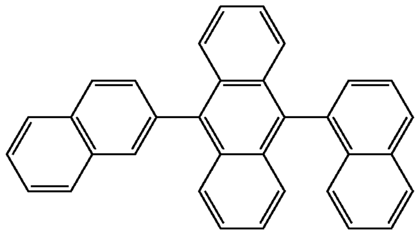
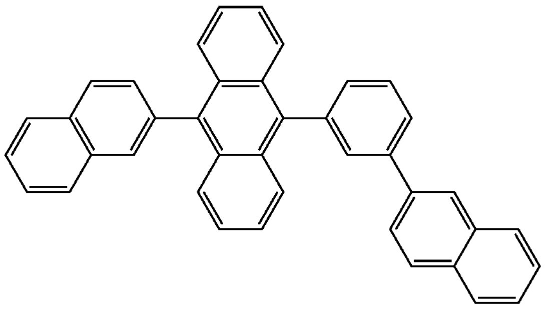
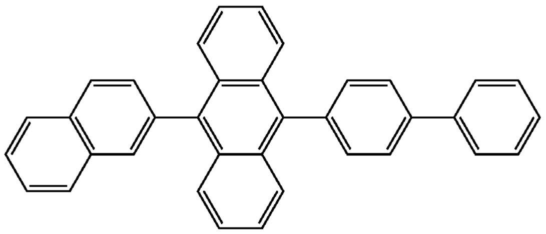
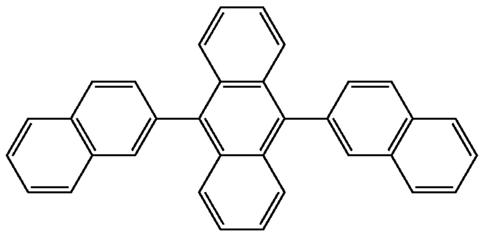
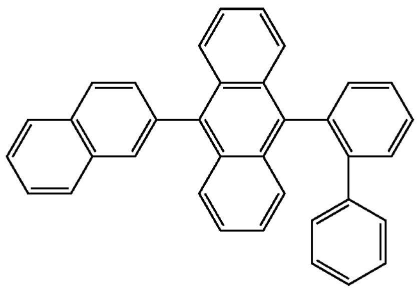

-continued
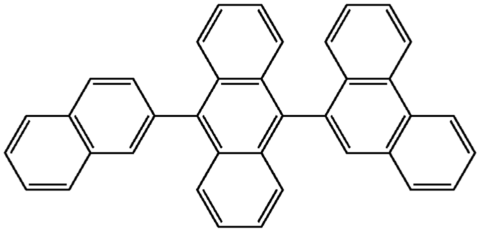
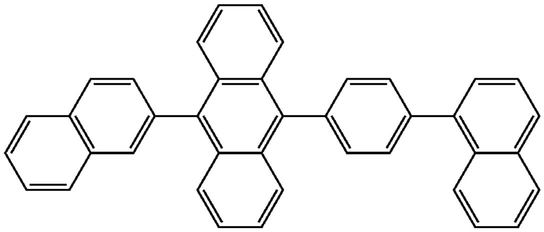
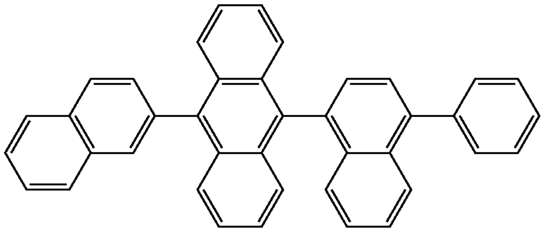
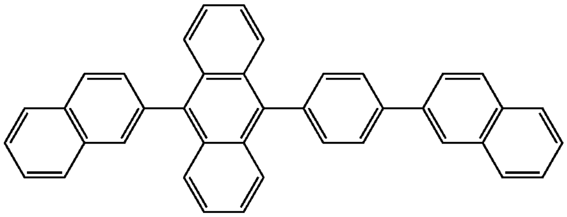
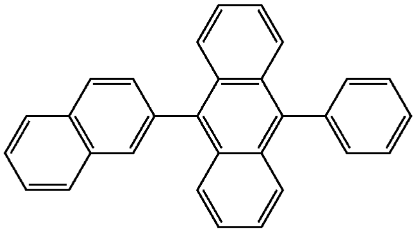
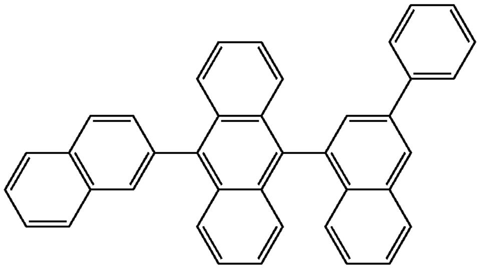
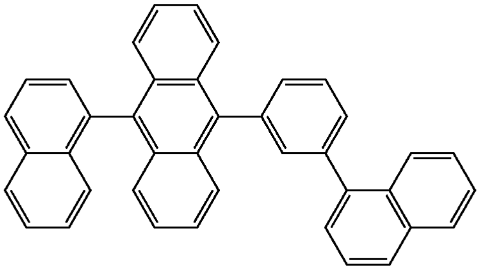
-continued
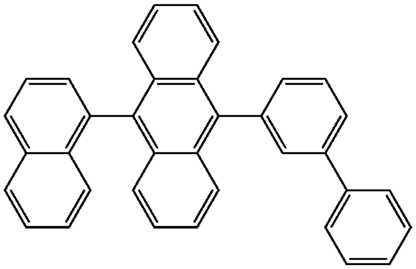
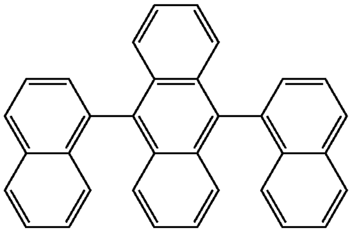
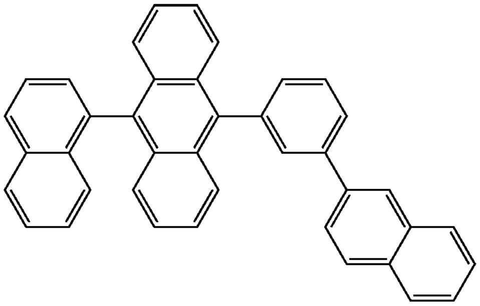
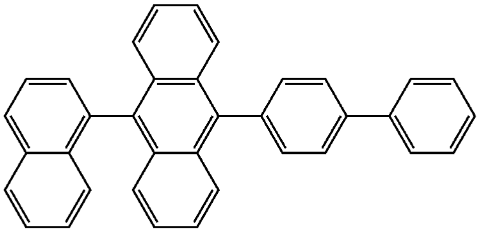
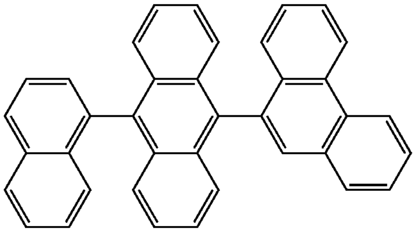
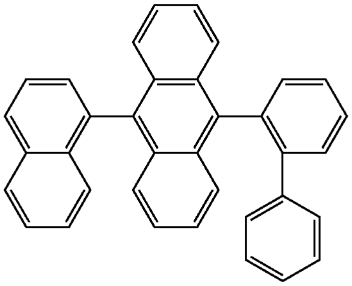

-continued
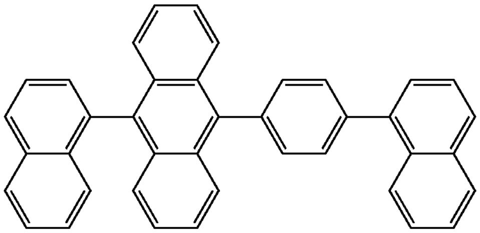
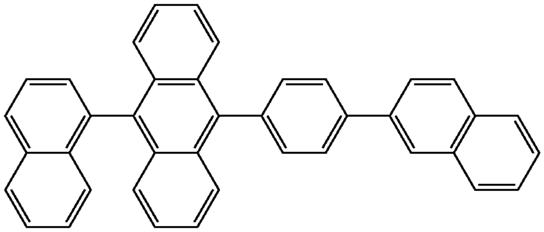
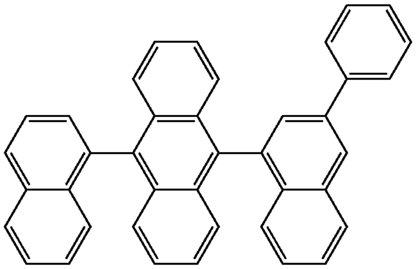
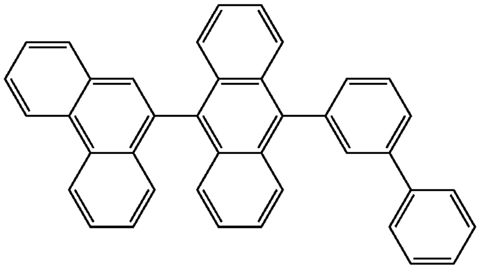
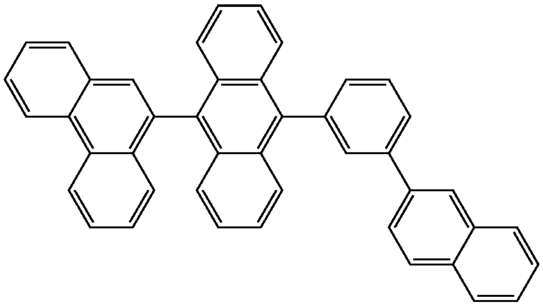
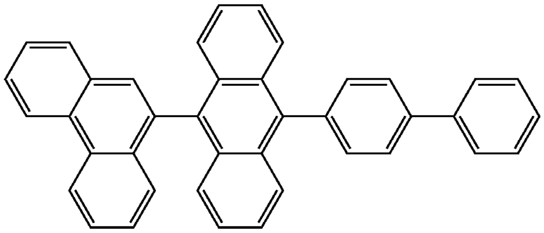
-continued
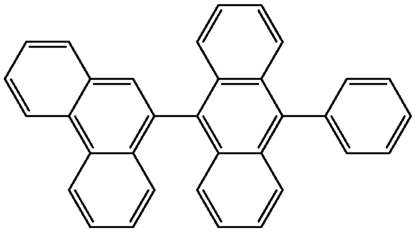
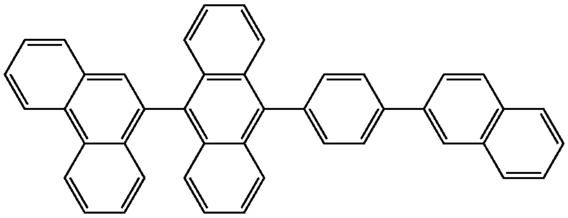
[Formula 105]
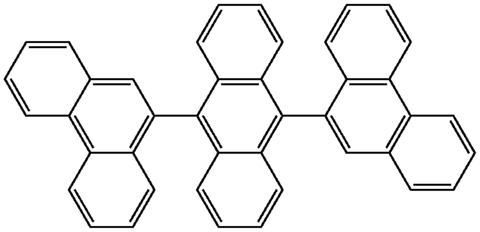
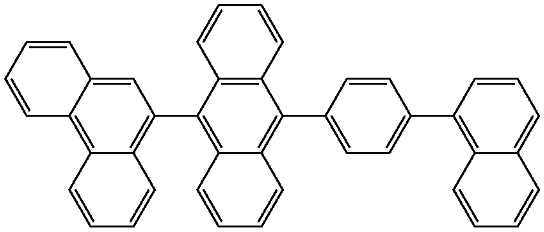
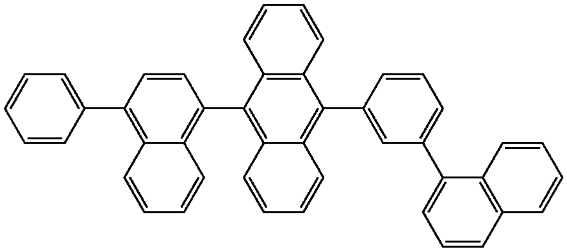
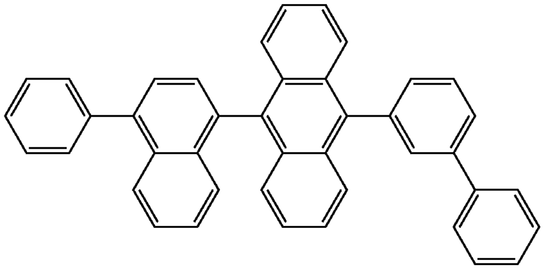

-continued
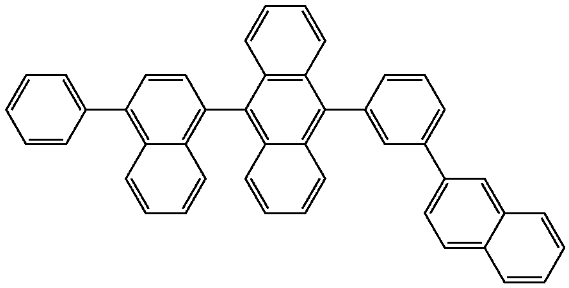
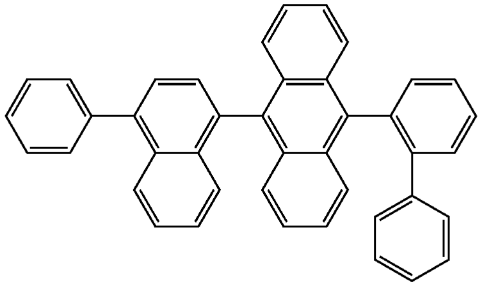
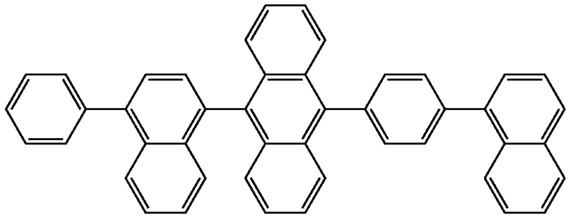
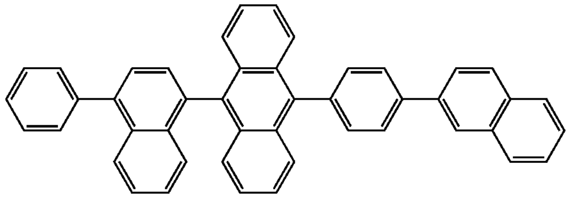
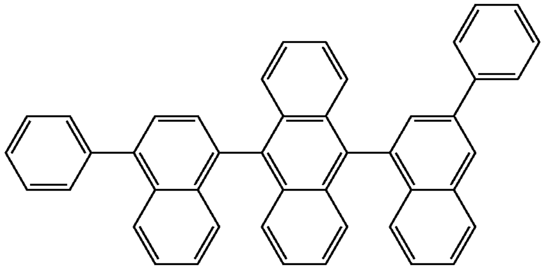
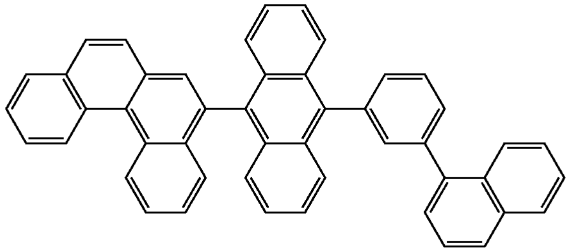
-continued
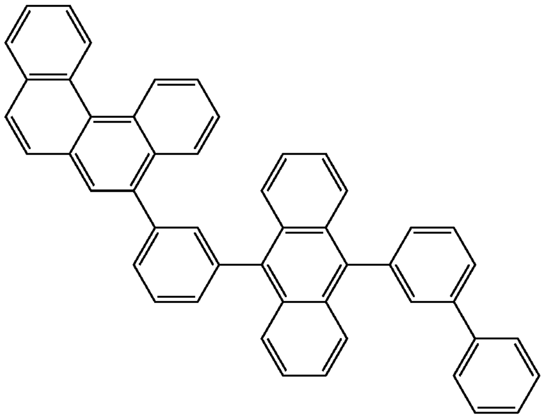
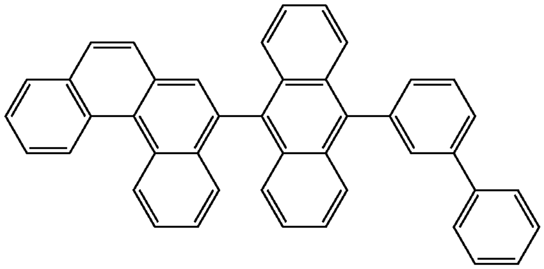
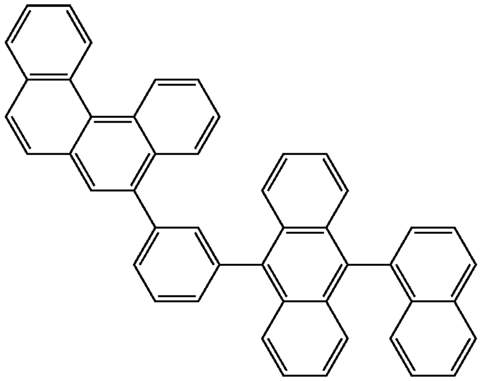
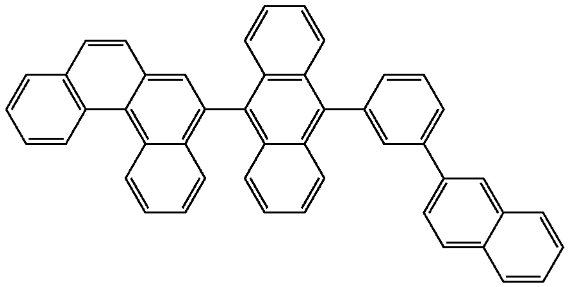
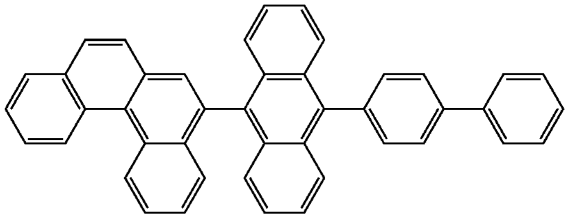

-continued
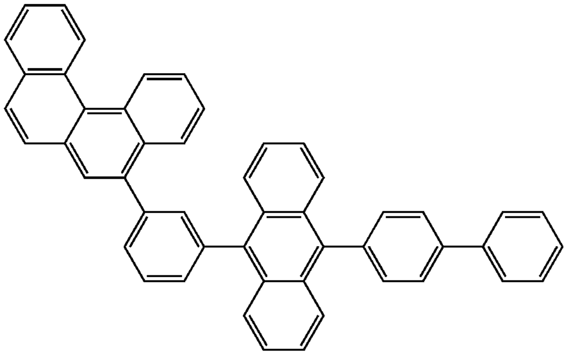
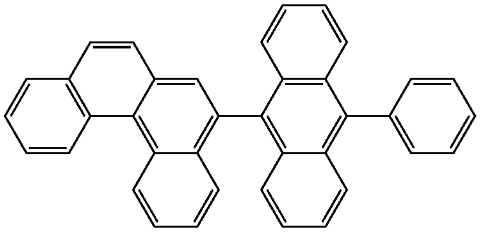
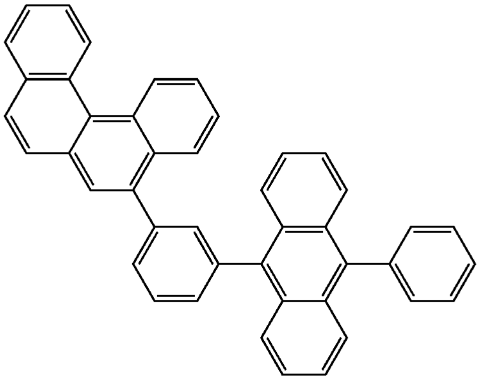
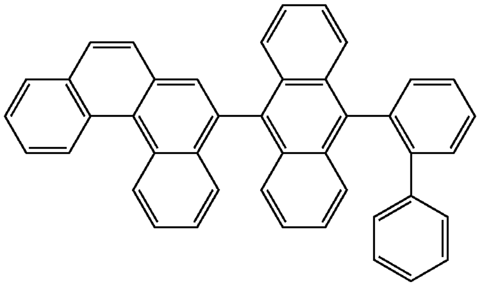
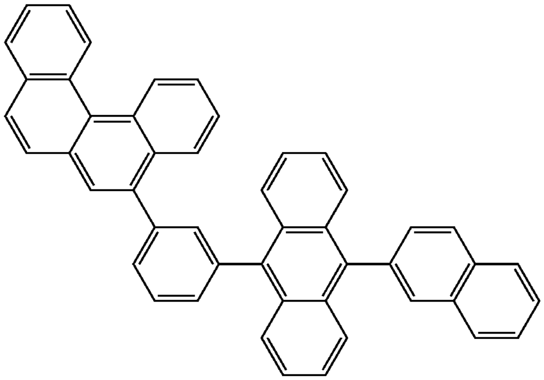
-continued
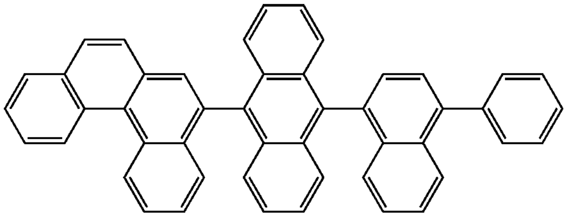
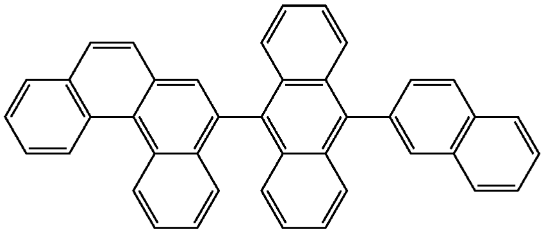
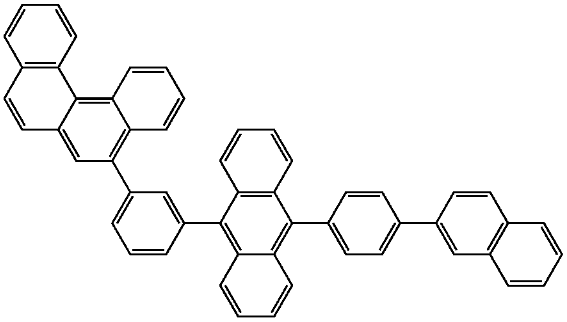
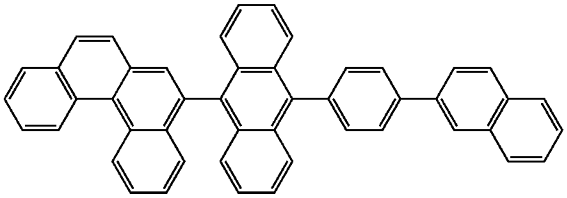
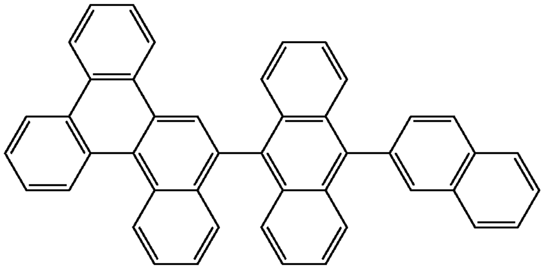
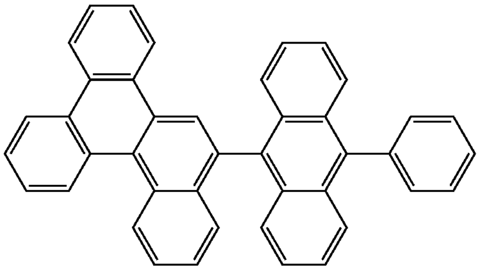

-continued
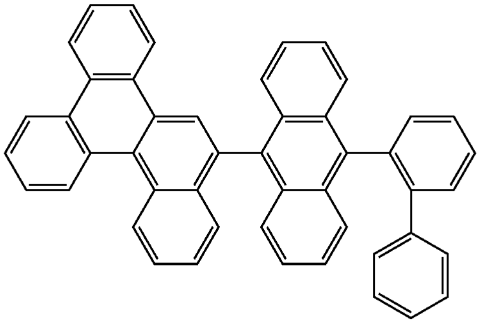
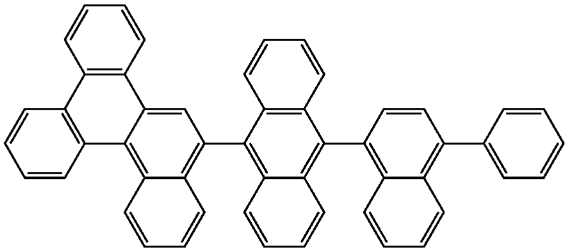
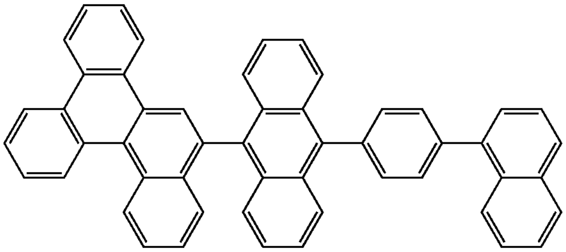
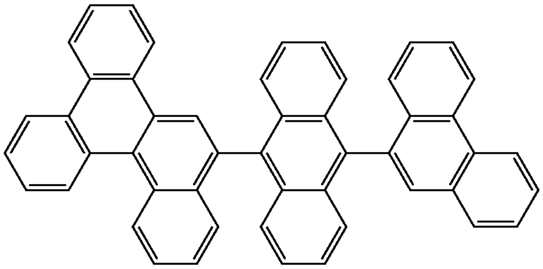
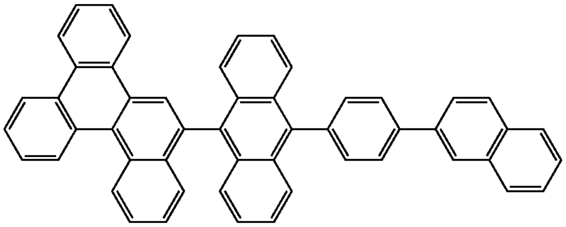
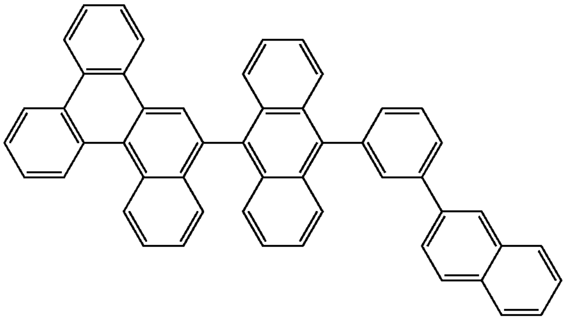
-continued
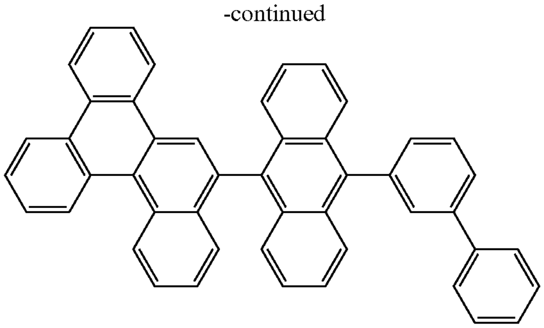
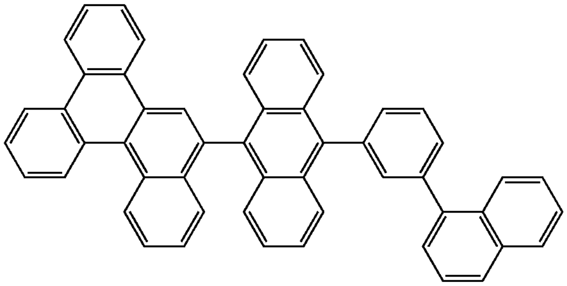
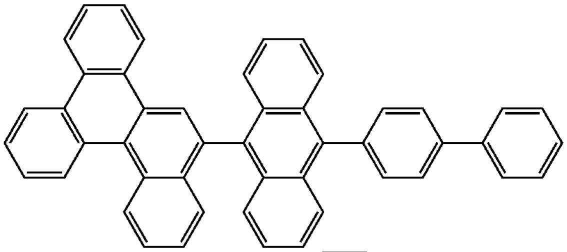
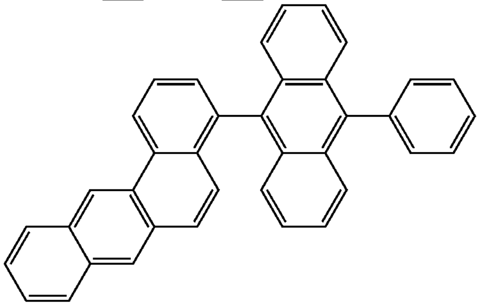
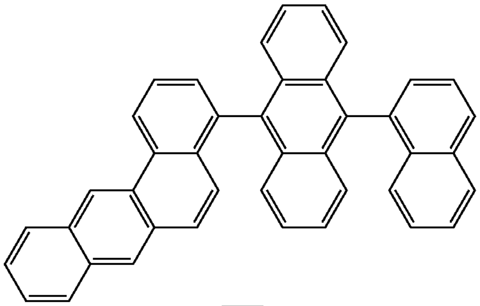
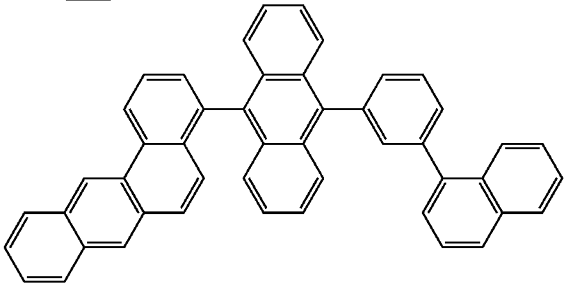

-continued
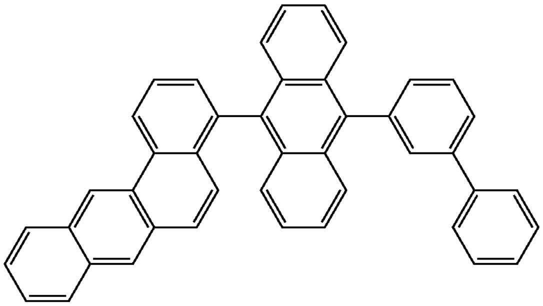
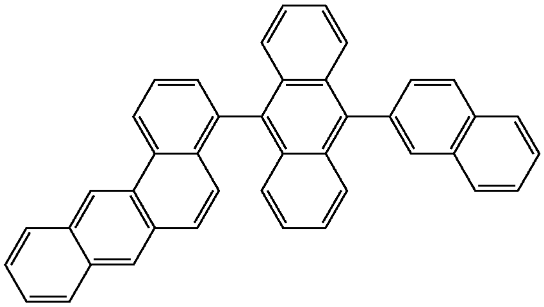
[Formula 106]
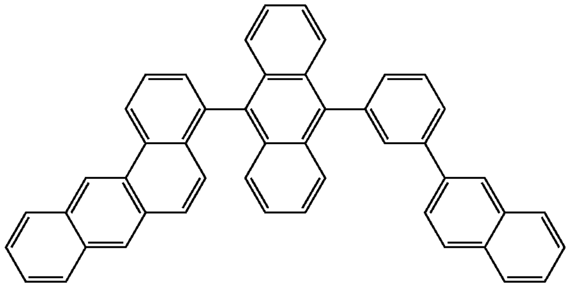
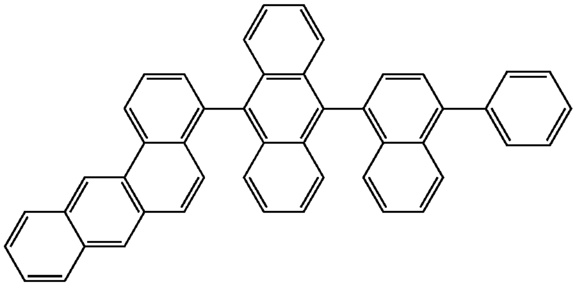
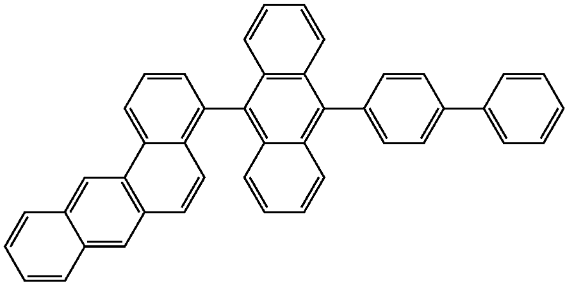
-continued
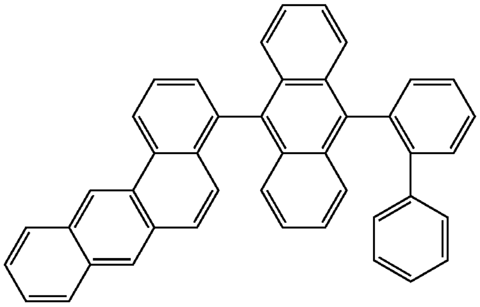
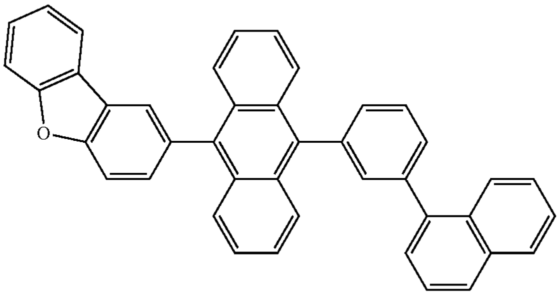
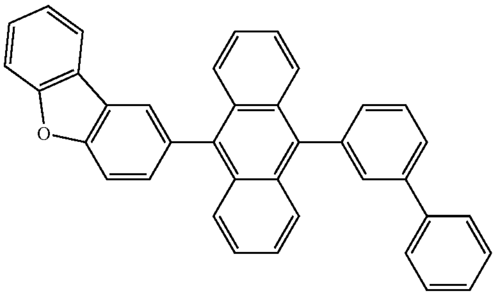
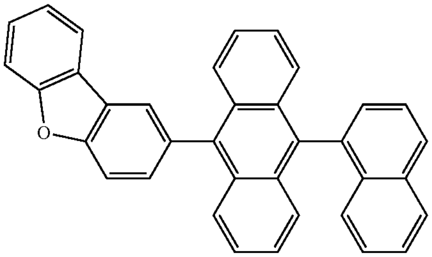
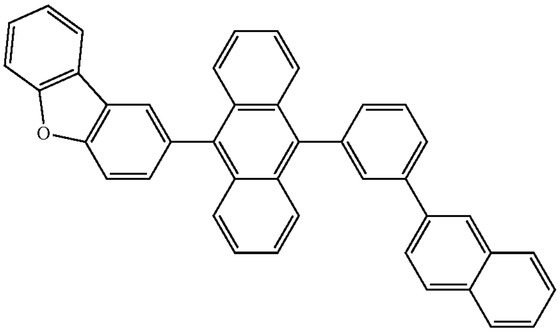

-continued
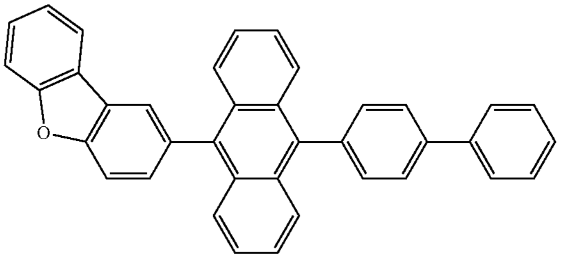
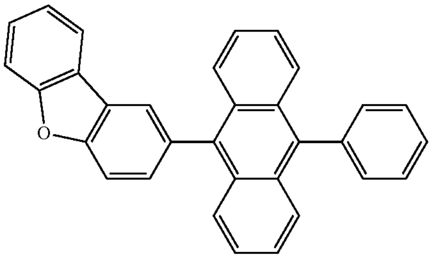
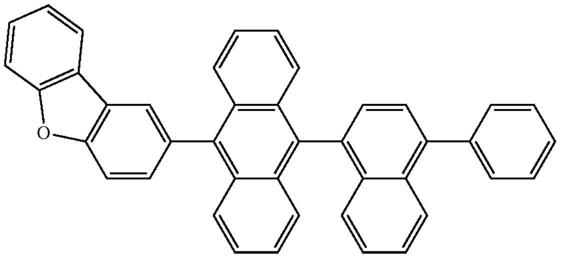
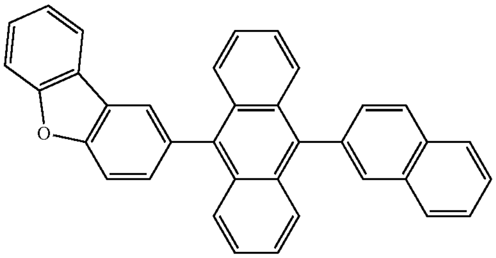
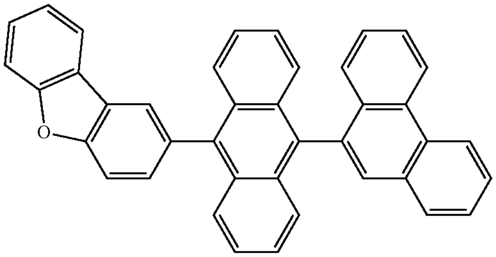
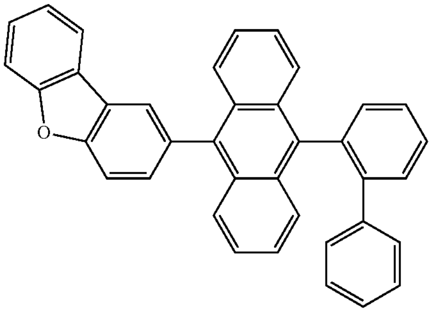
-continued
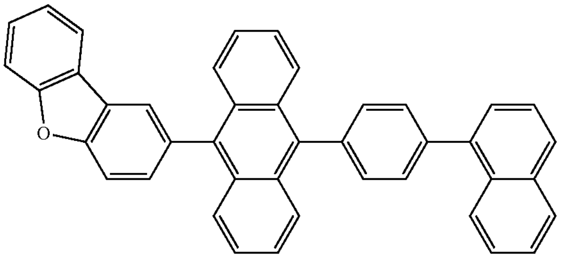
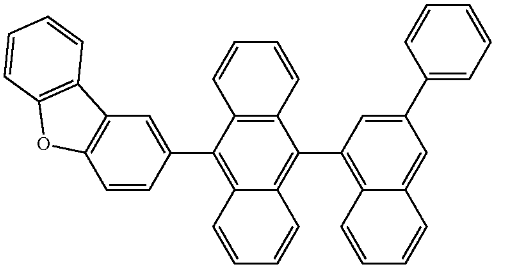
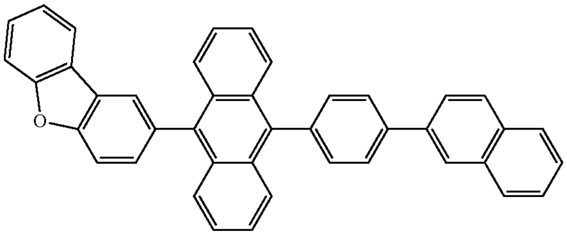
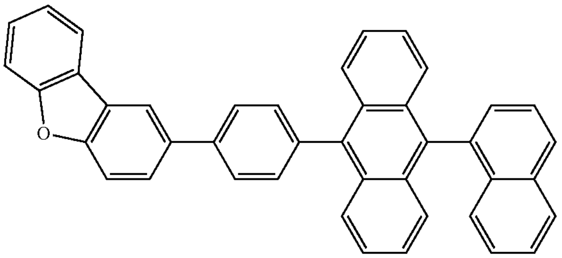
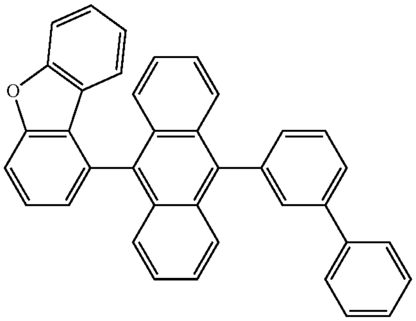
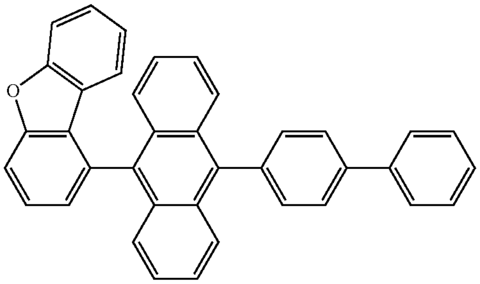

-continued
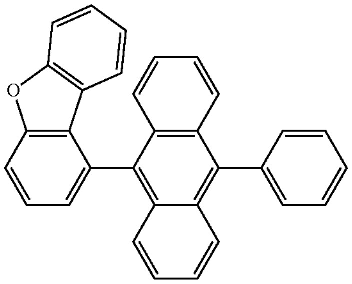
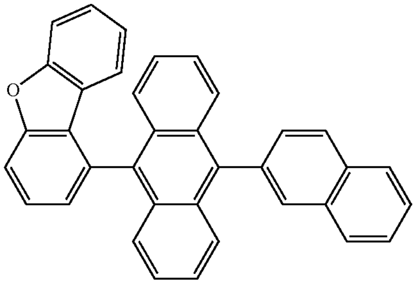
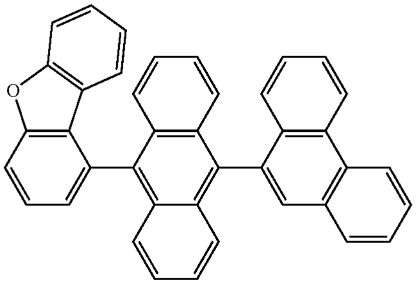
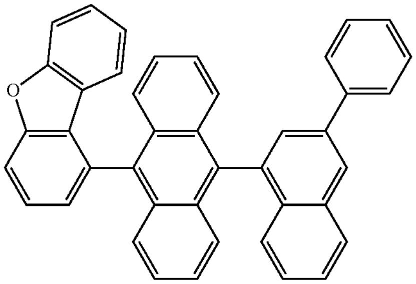
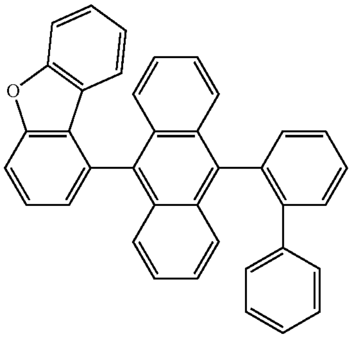
-continued
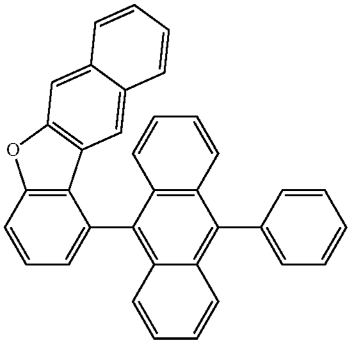
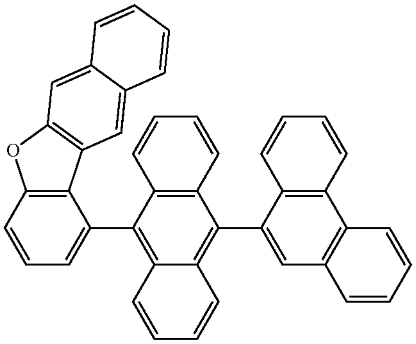
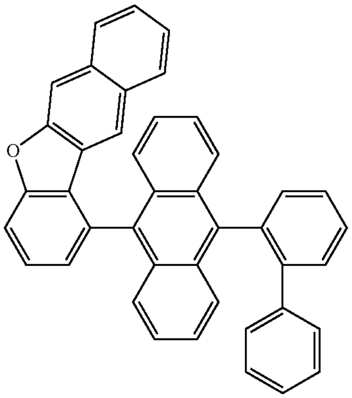
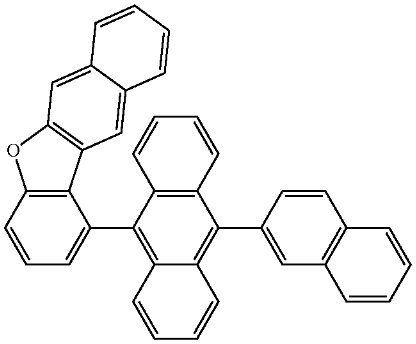

-continued
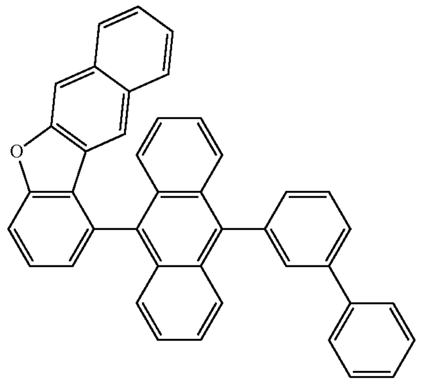
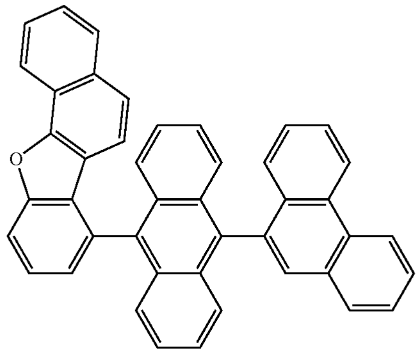
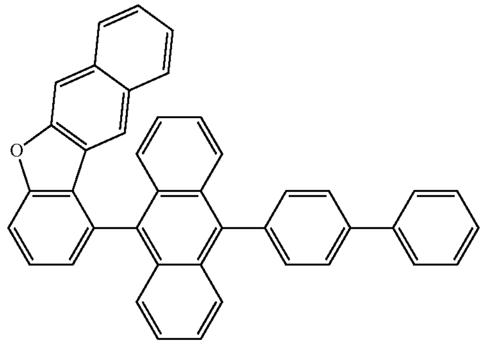
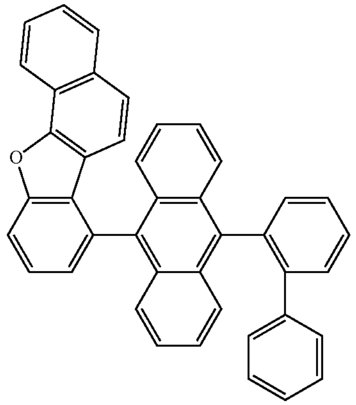
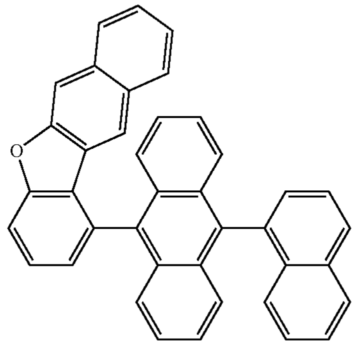
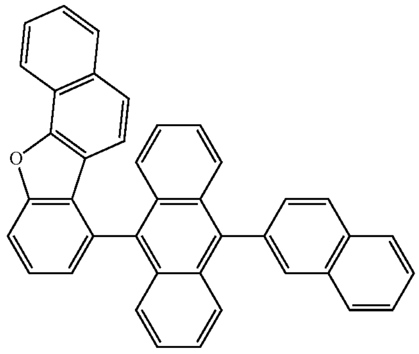
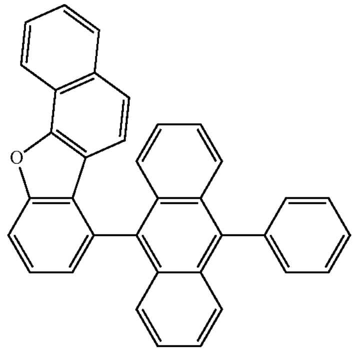
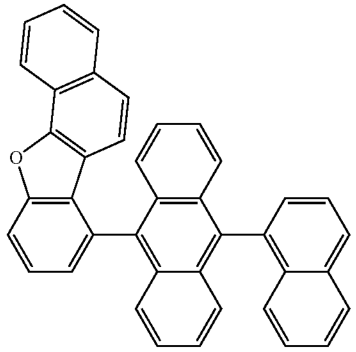

-continued
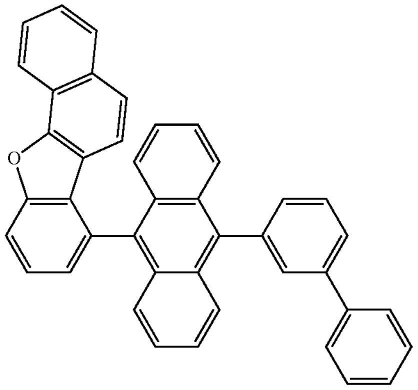
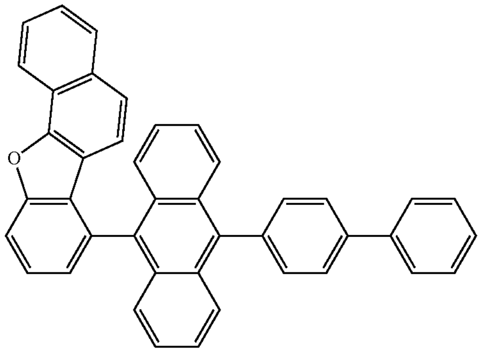
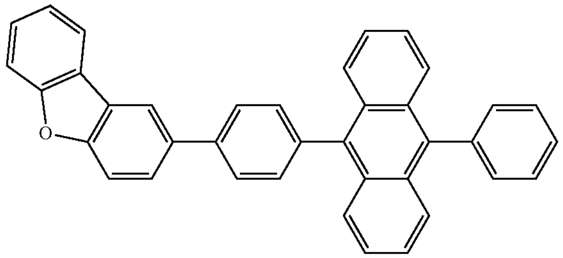
[Formula 107]
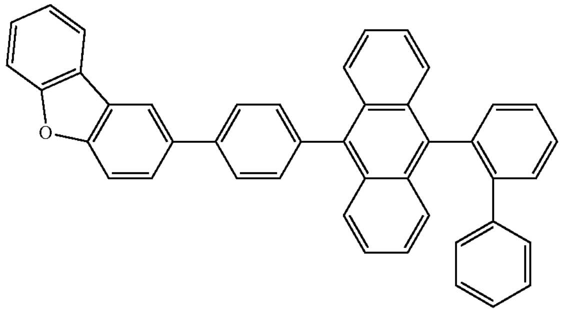
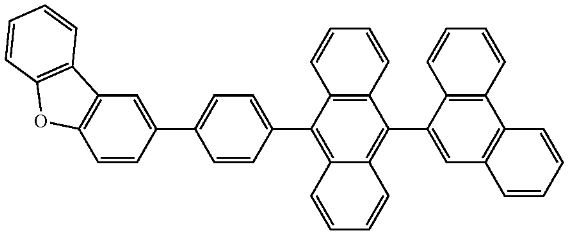
-continued
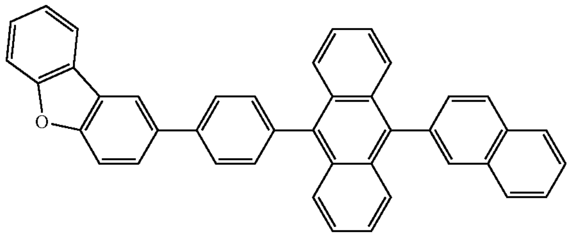
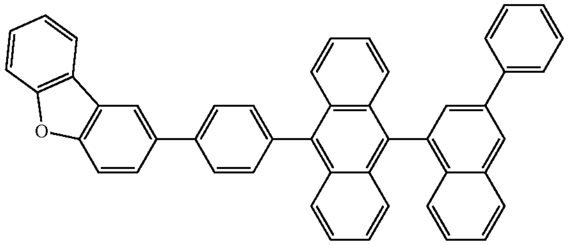
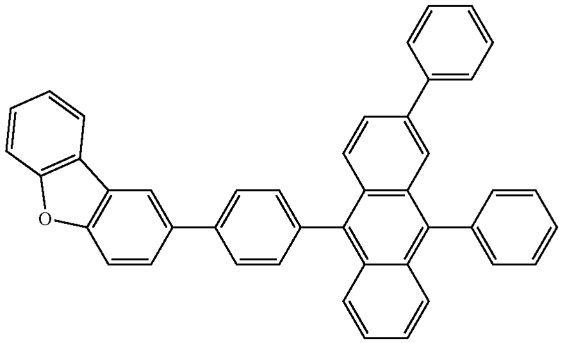
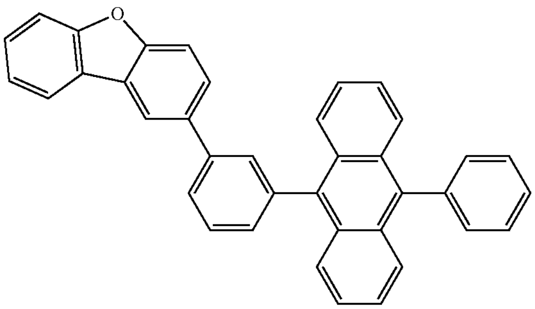
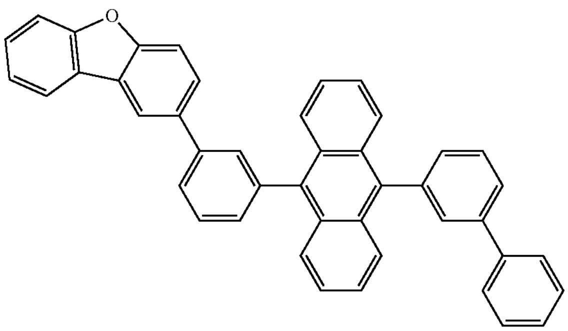

-continued
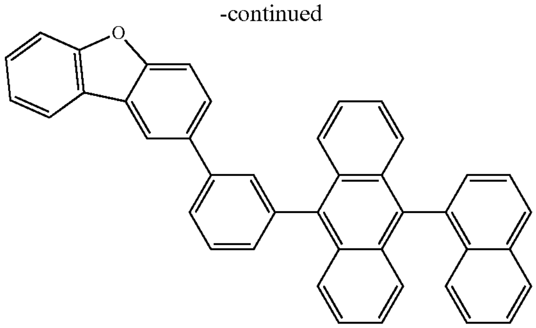
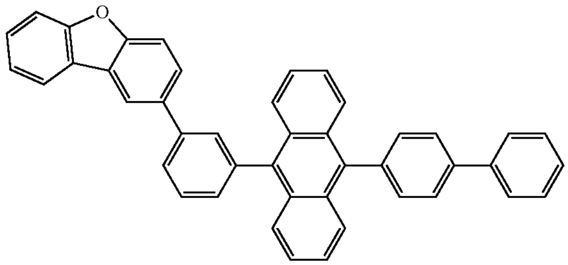
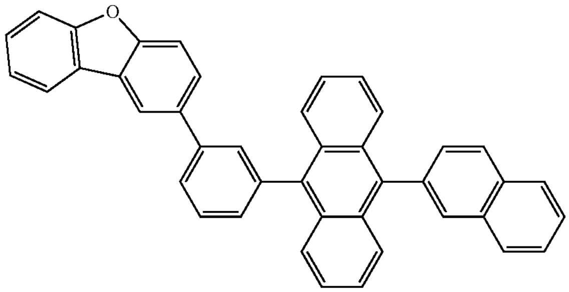
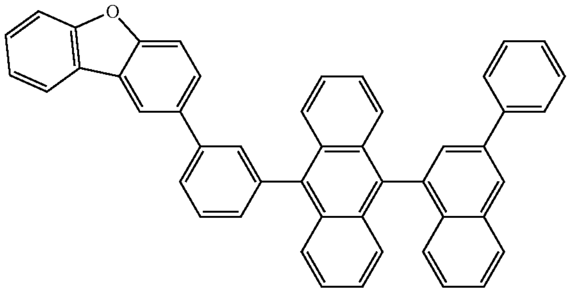
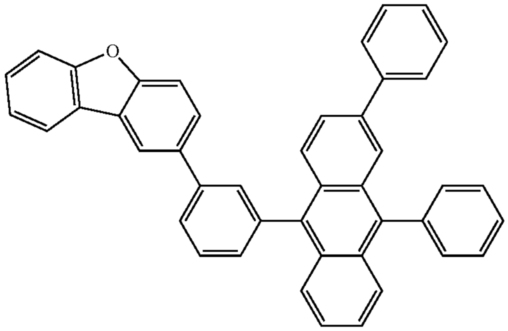
-continued
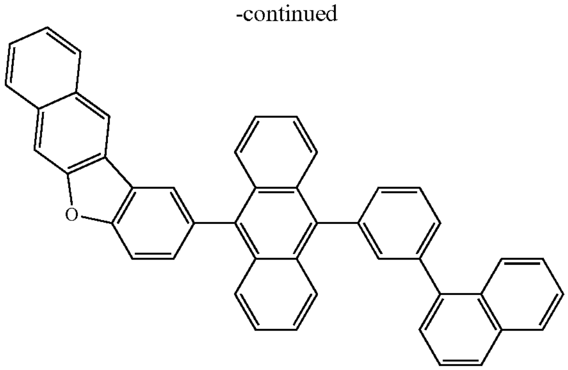
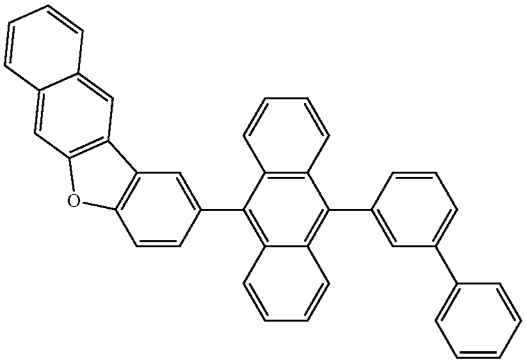
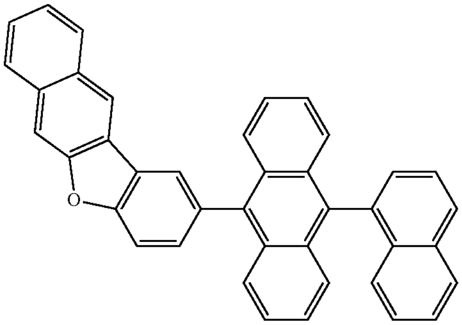
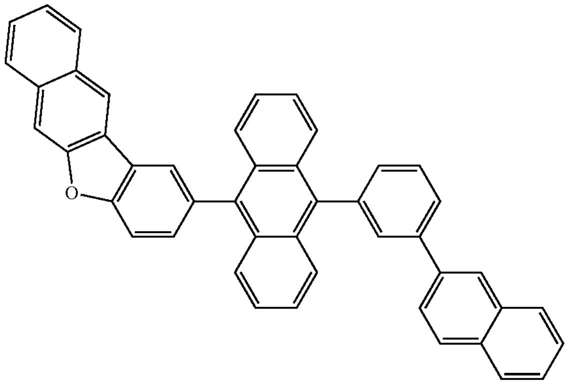
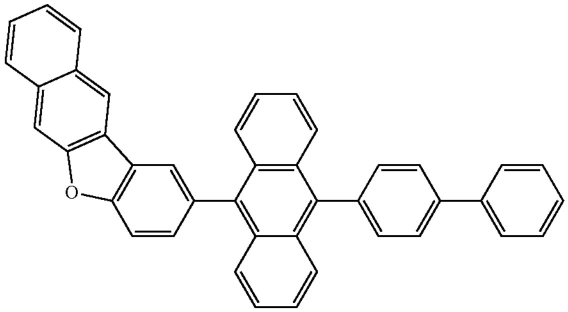

-continued
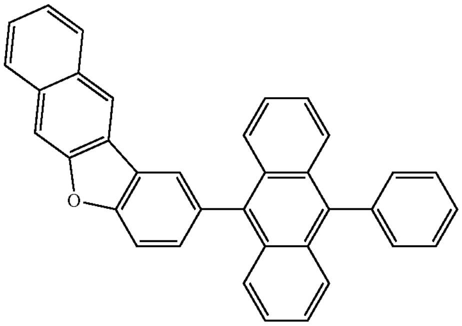
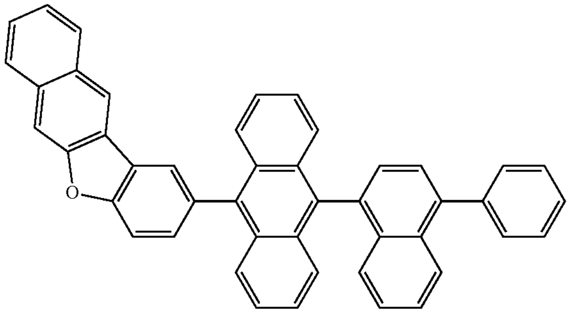
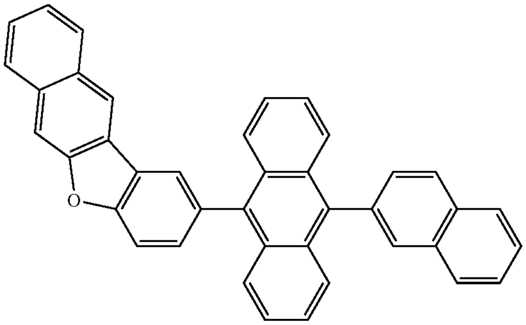
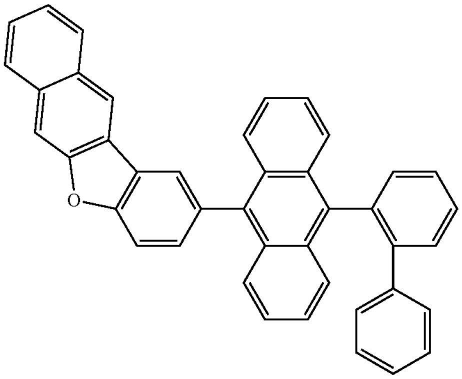
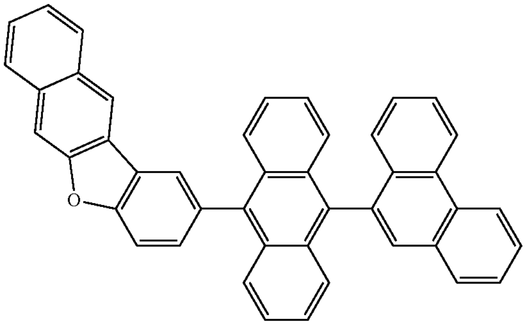
-continued
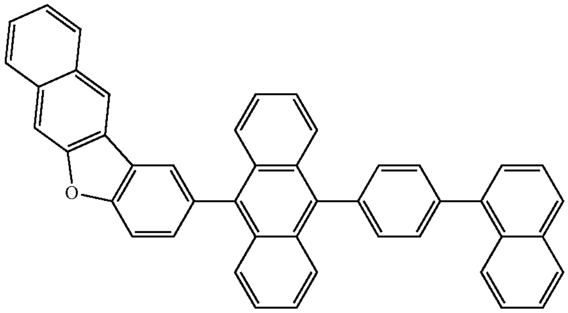
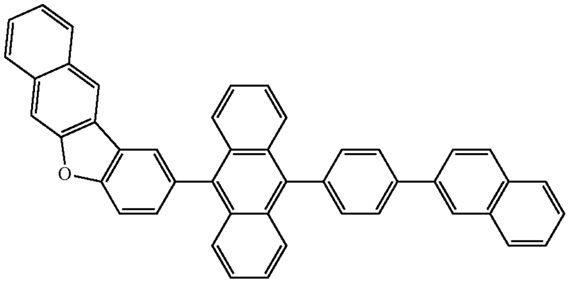
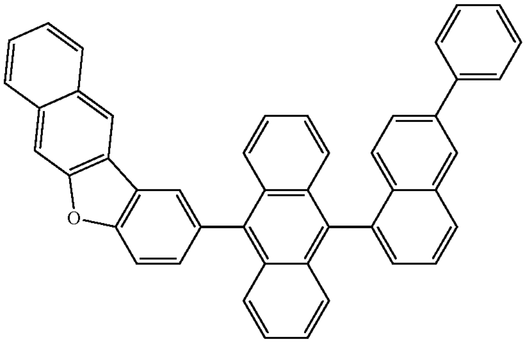
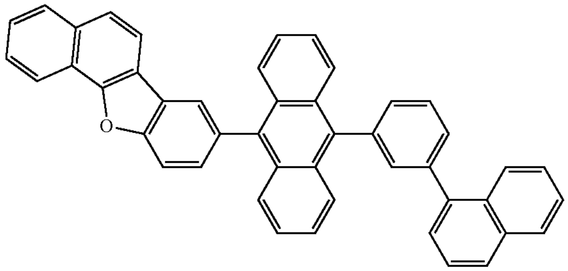
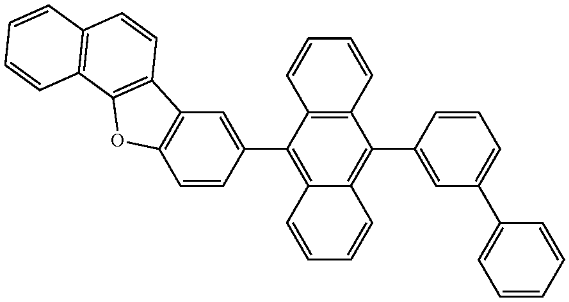

-continued
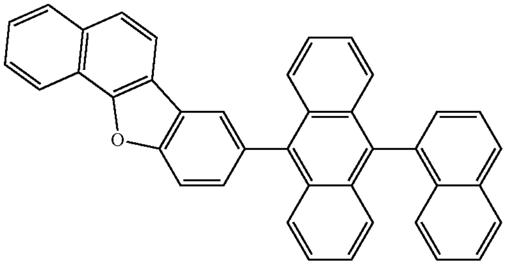
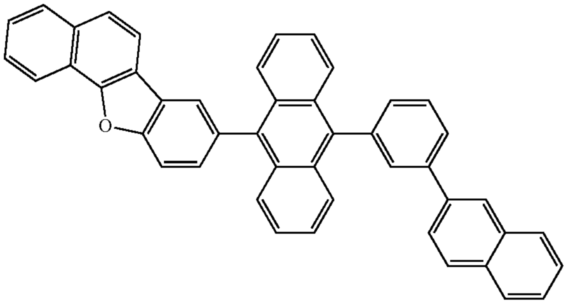
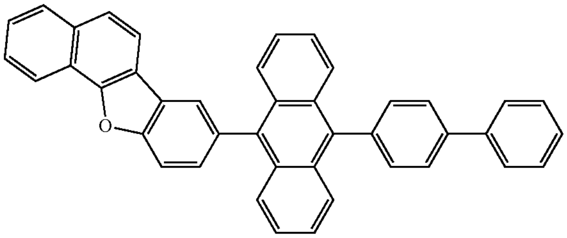
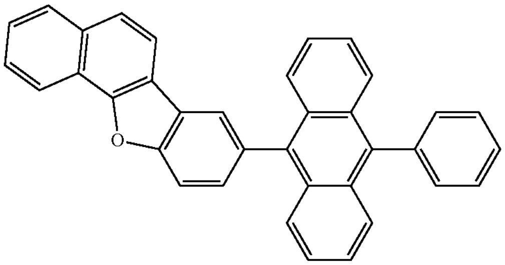
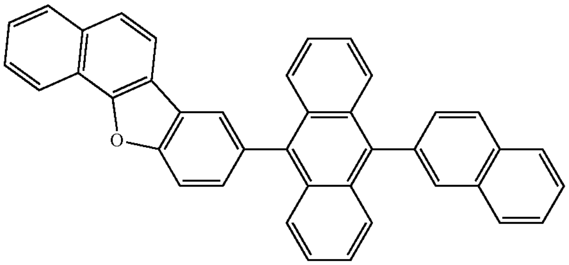
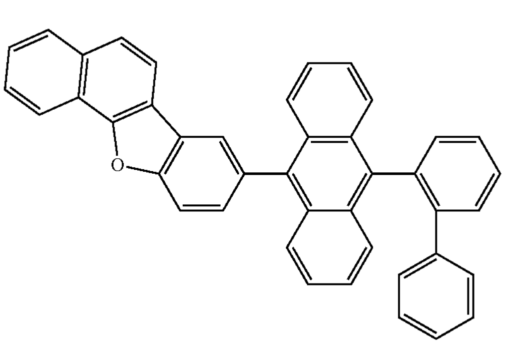
-continued
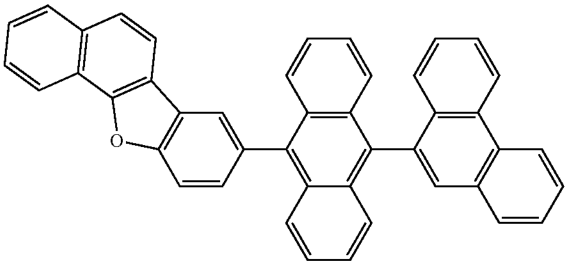
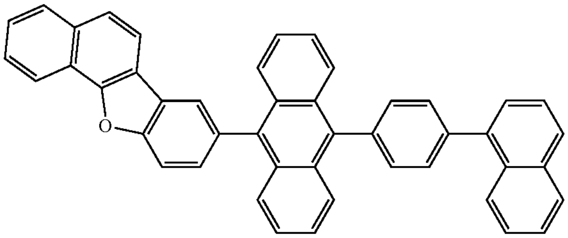
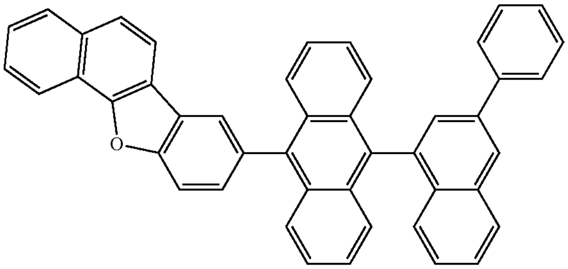
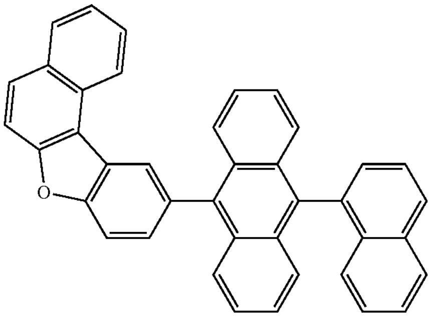
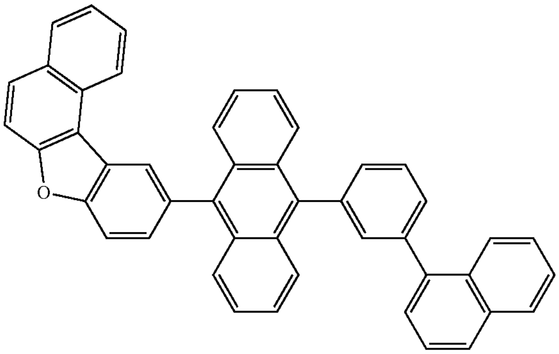

-continued
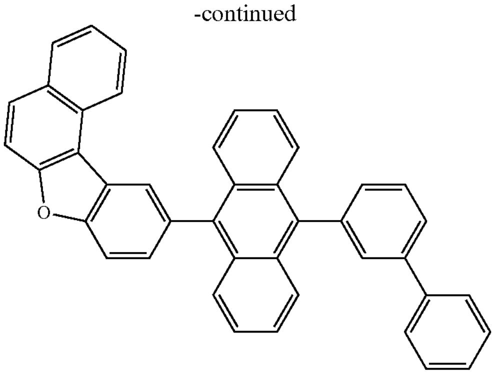
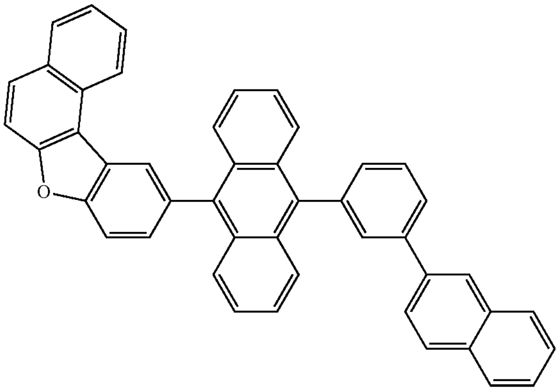
[Formula 108
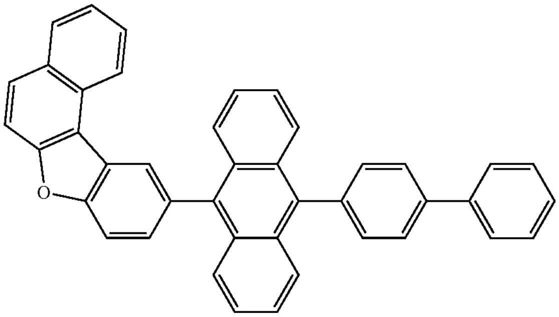
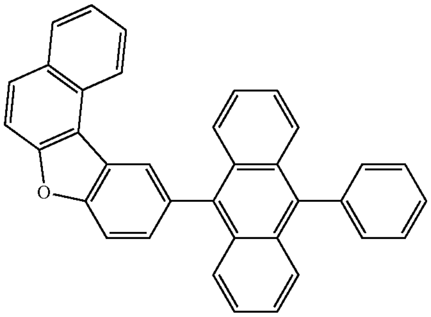
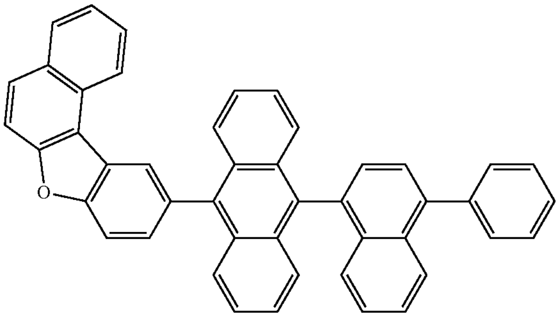
-continued
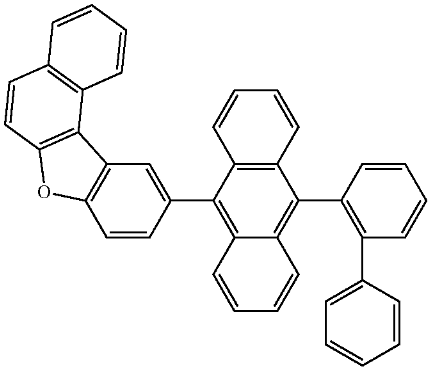
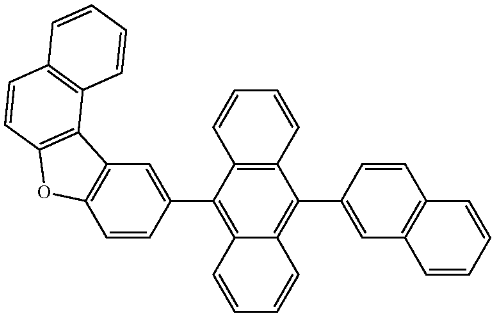
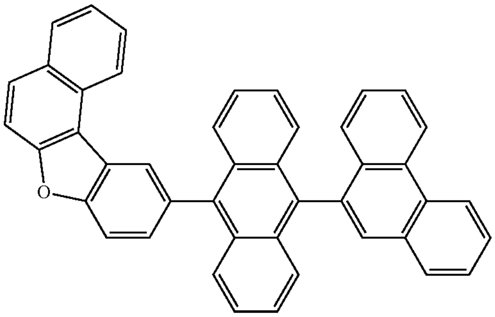
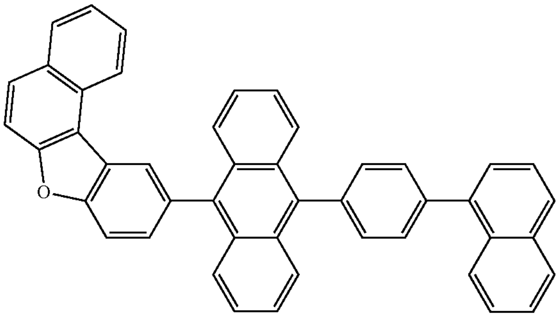
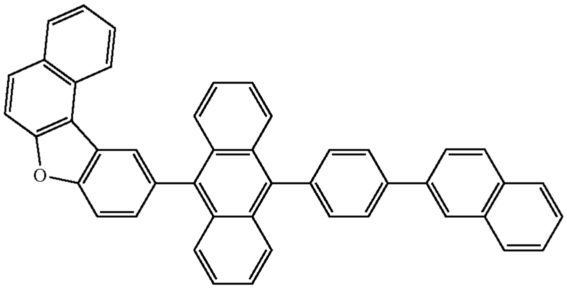

-continued
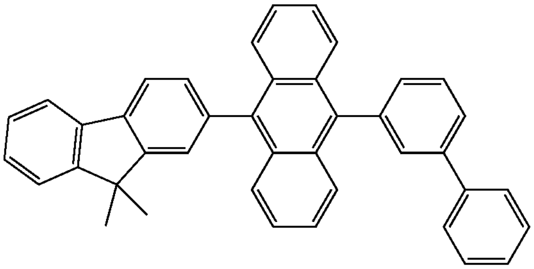
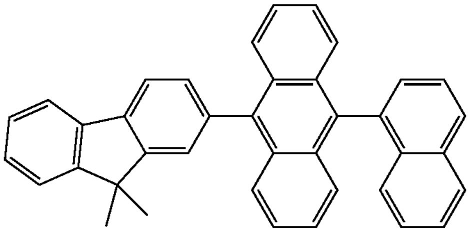
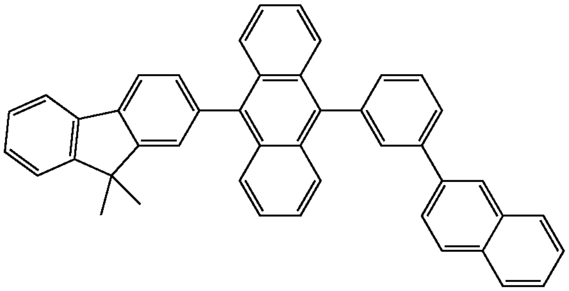
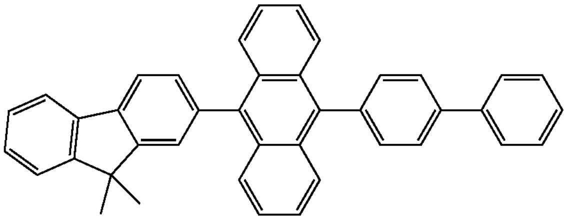
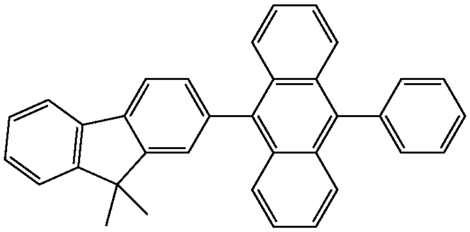
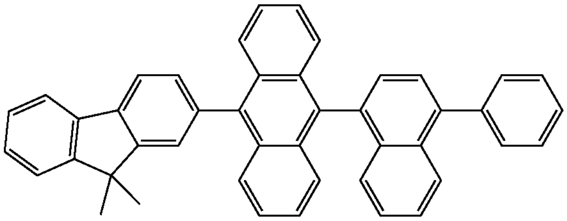
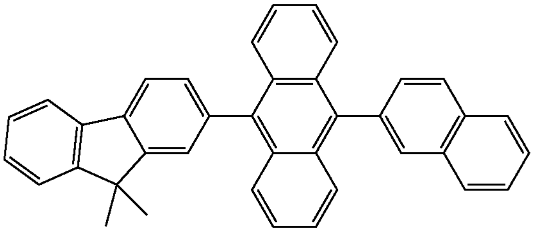
-continued
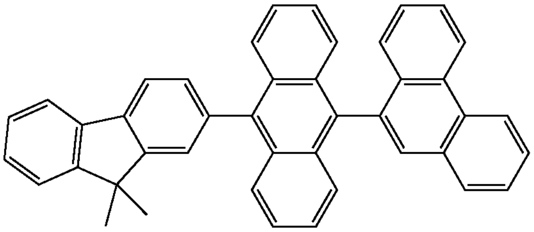
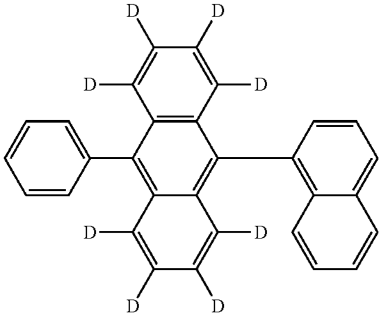
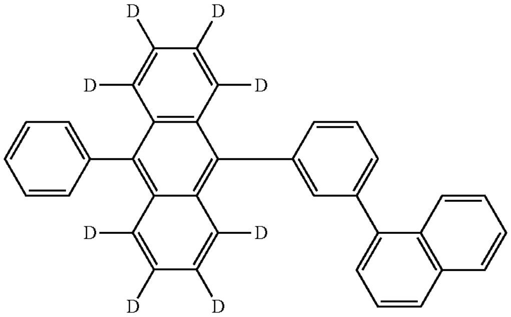
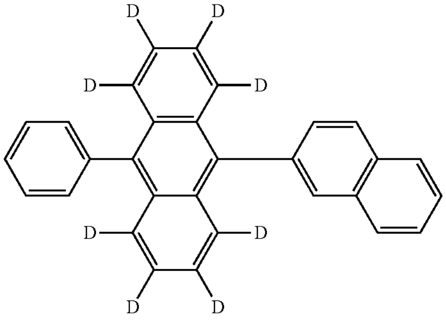
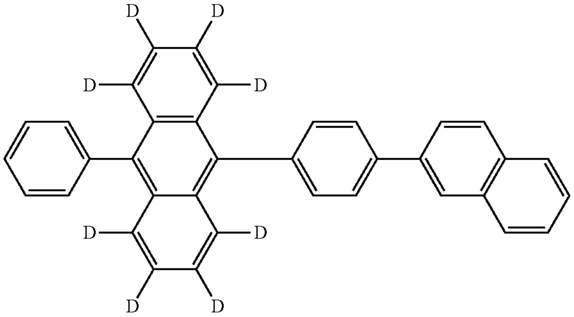

-continued
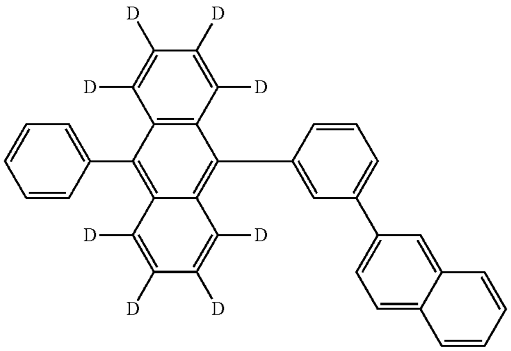
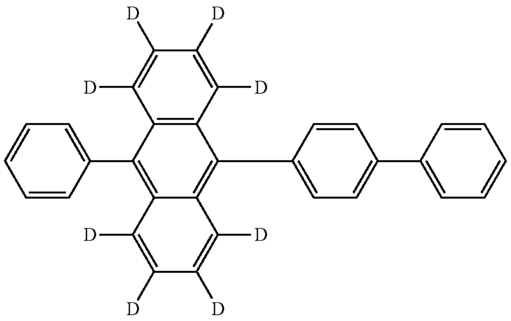
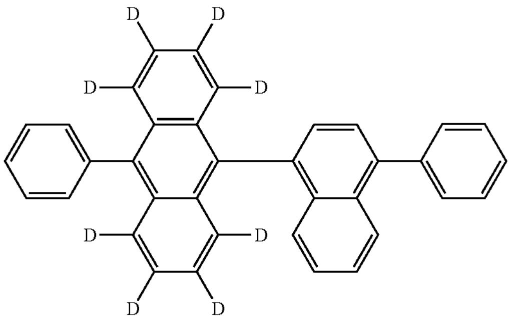
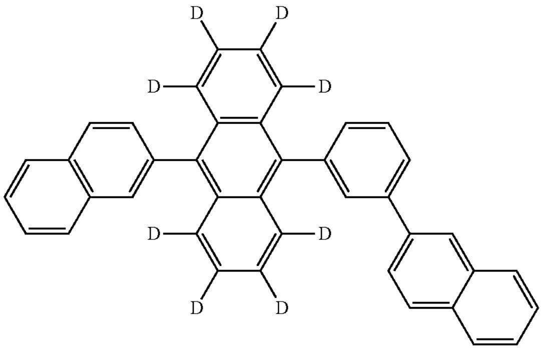
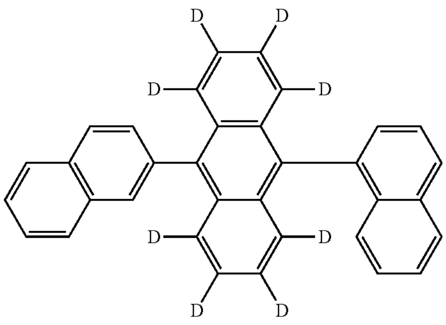
-continued
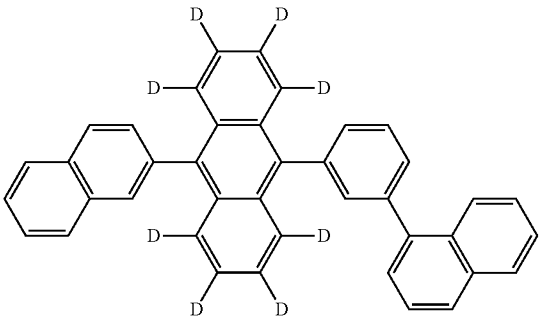
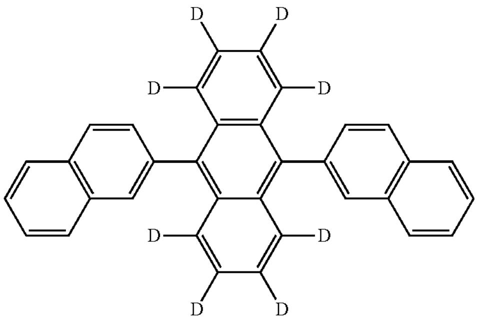
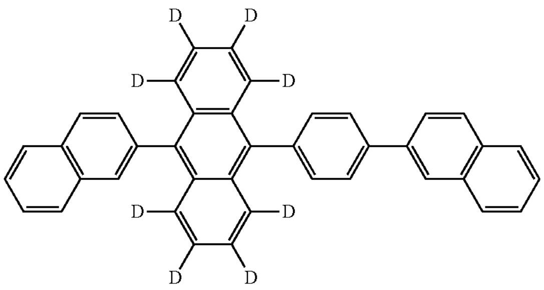
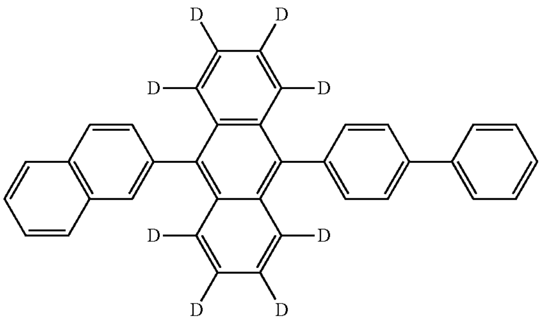
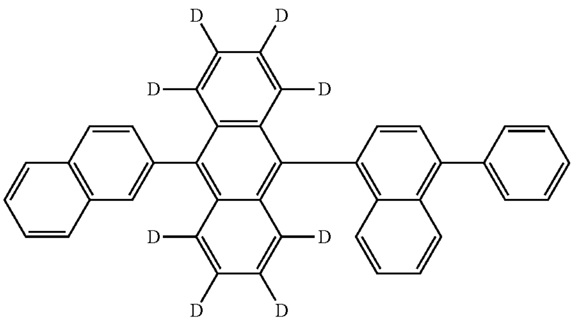

-continued
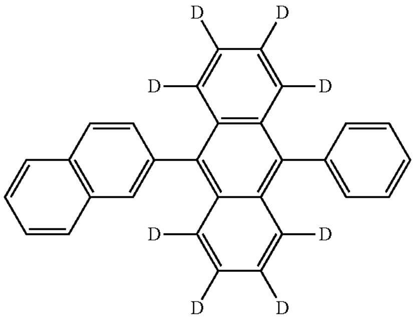
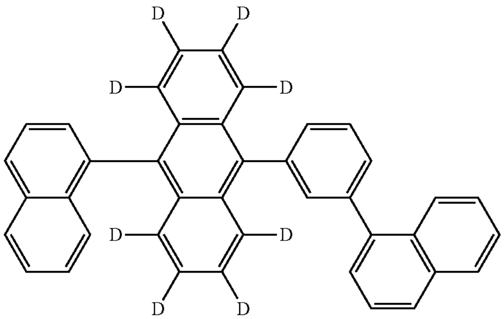
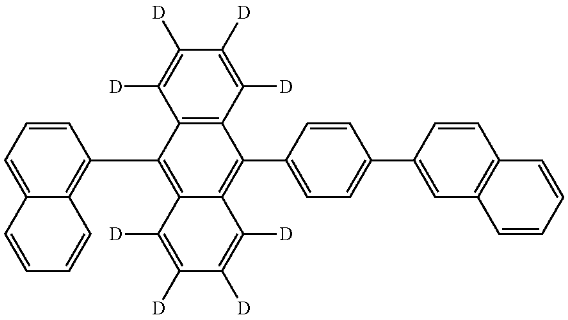
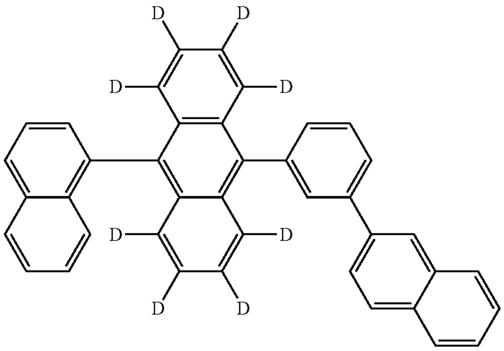
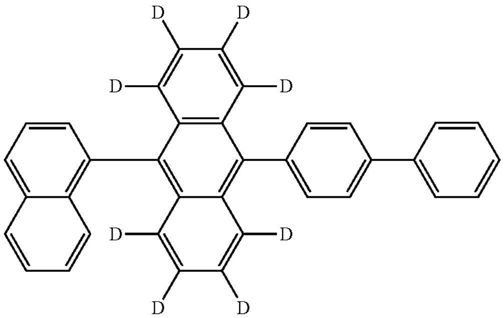
-continued
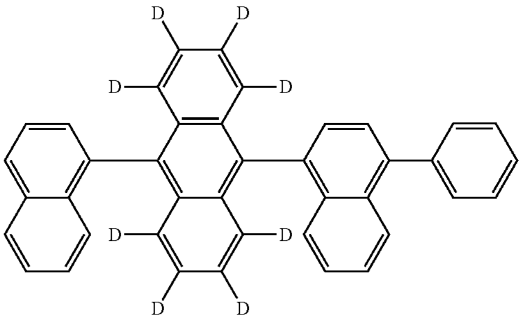
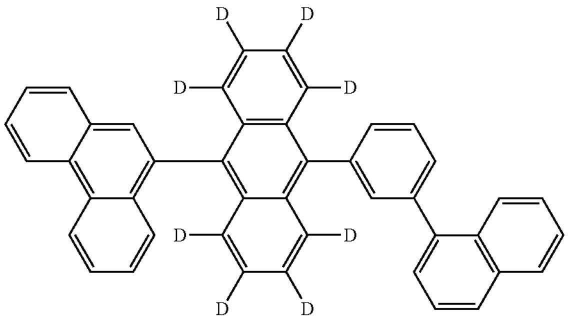
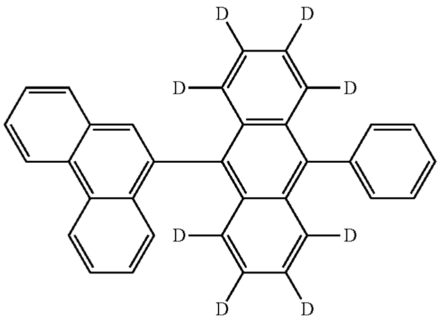
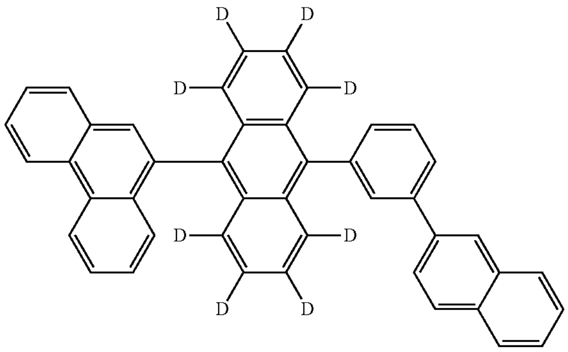
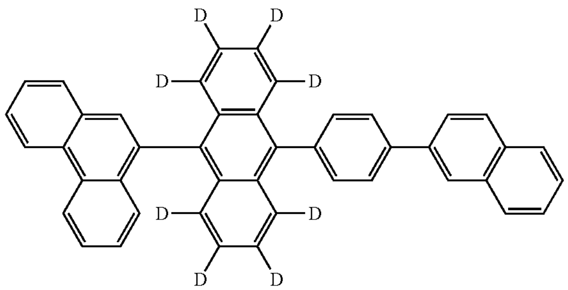

-continued
[Formula 109]
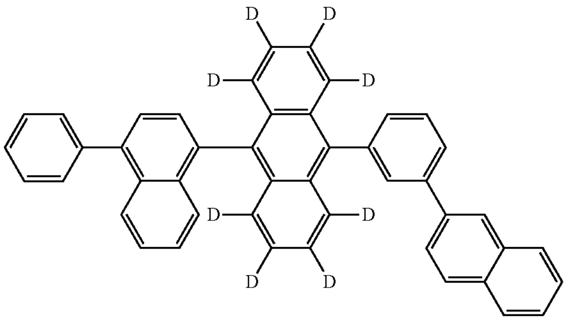
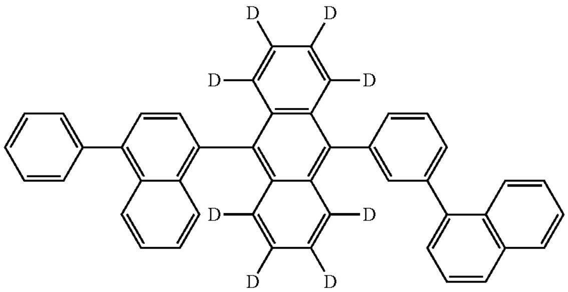
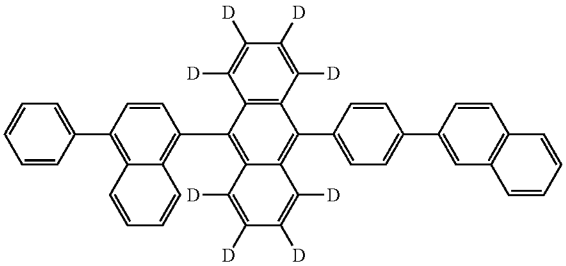
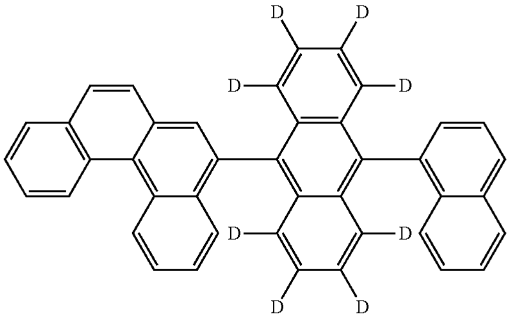
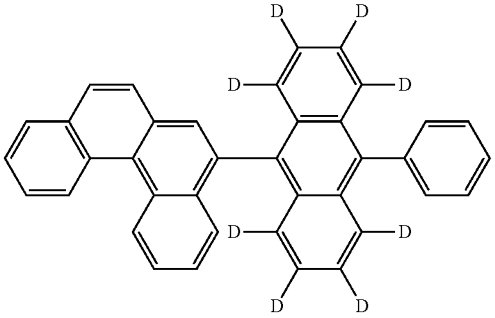
-continued
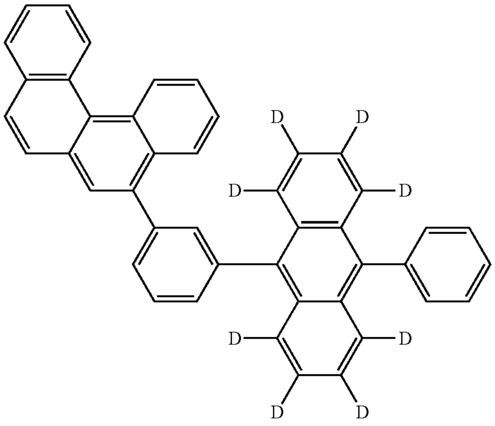
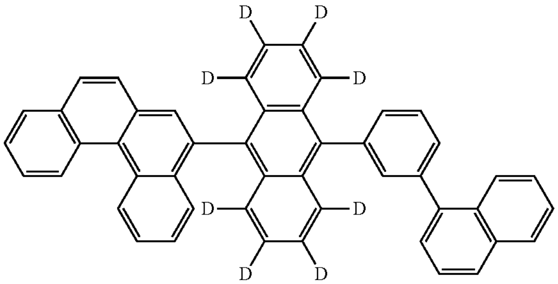
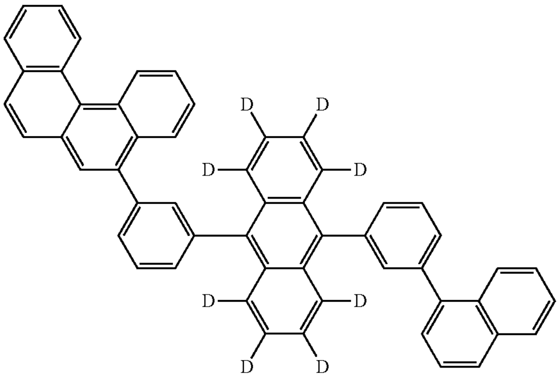
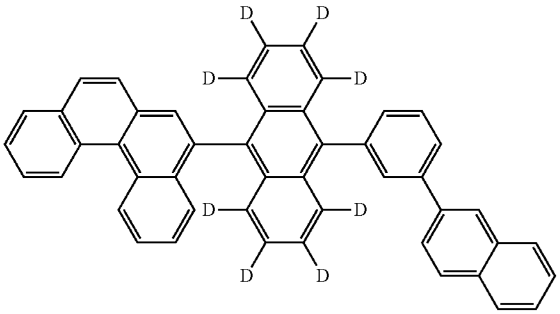

-continued
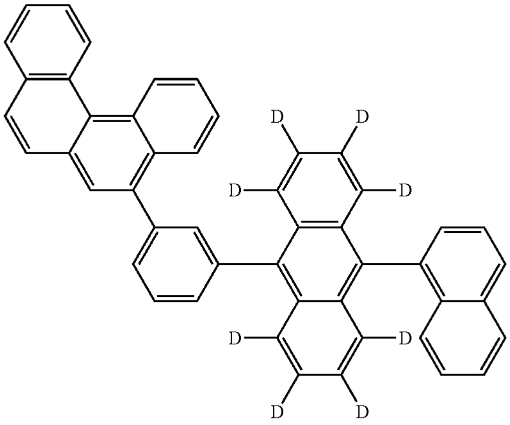
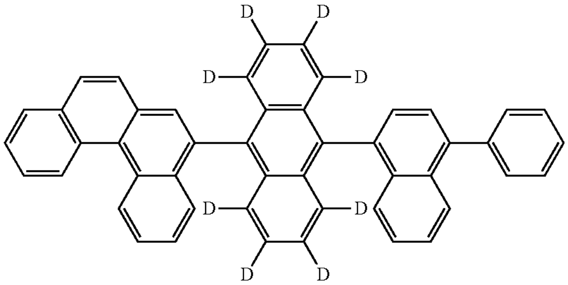
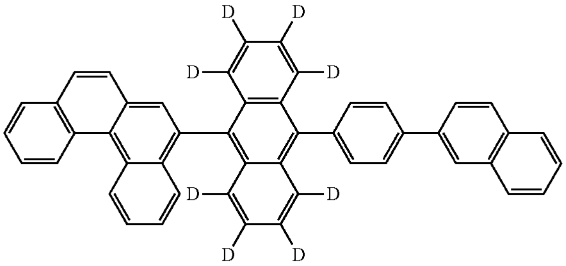
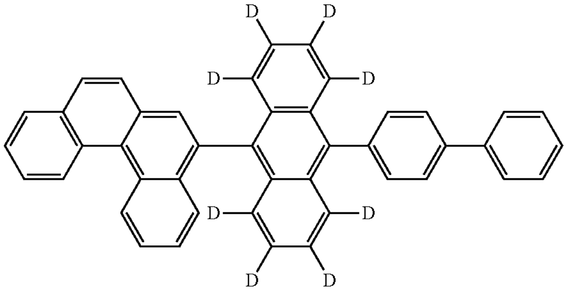
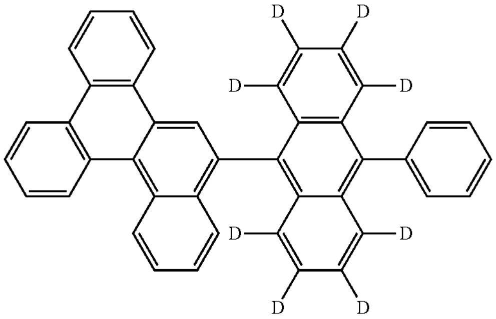
-continued
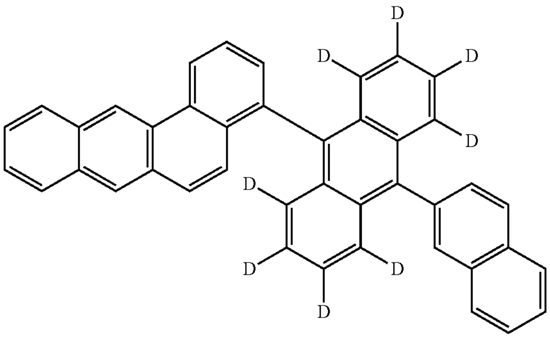
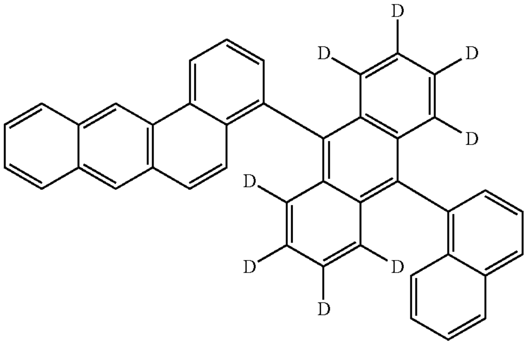
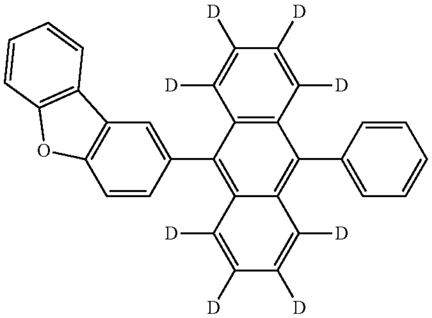
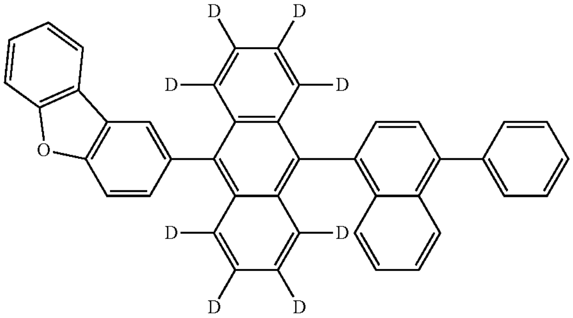
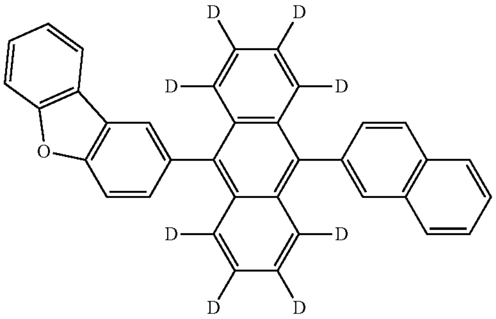

-continued
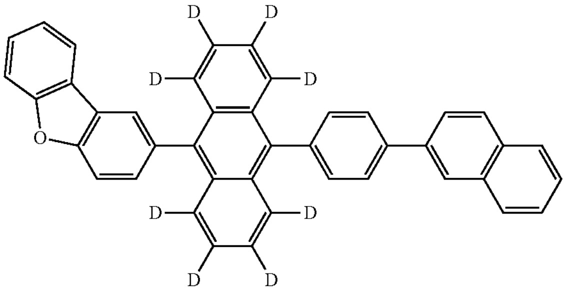
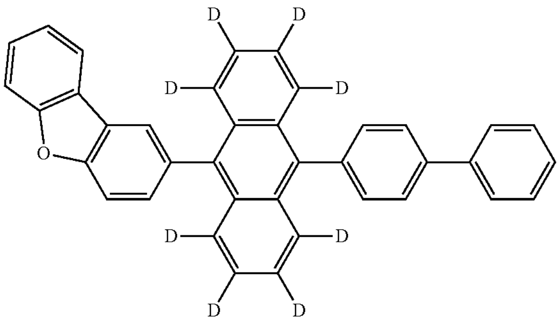
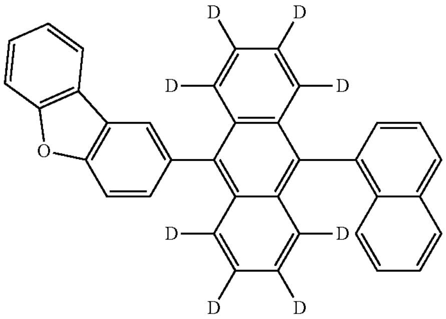
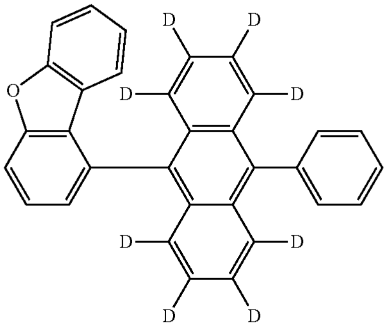
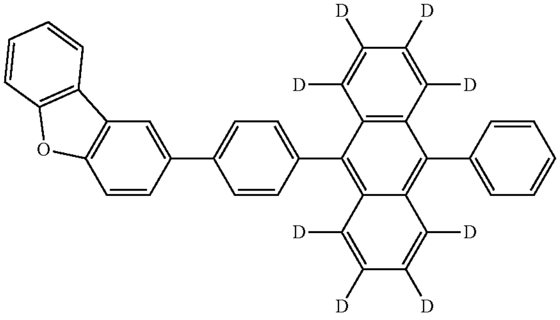
-continued
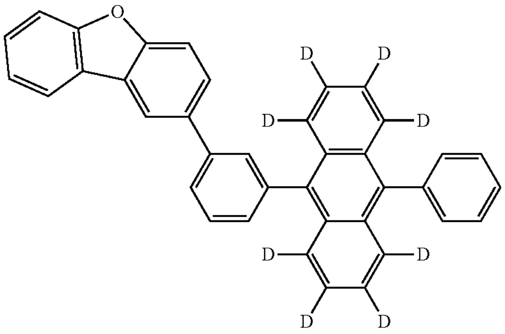
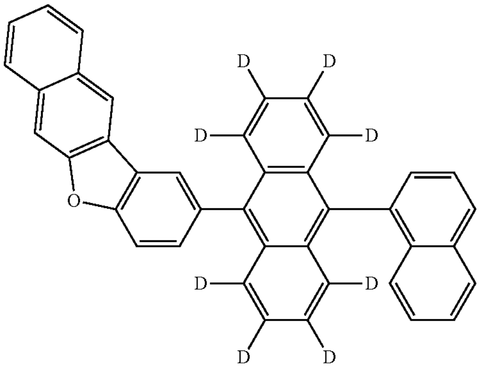
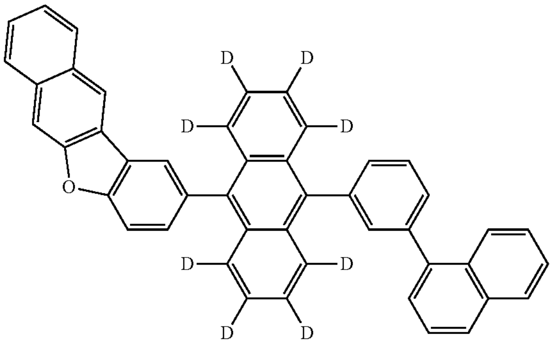
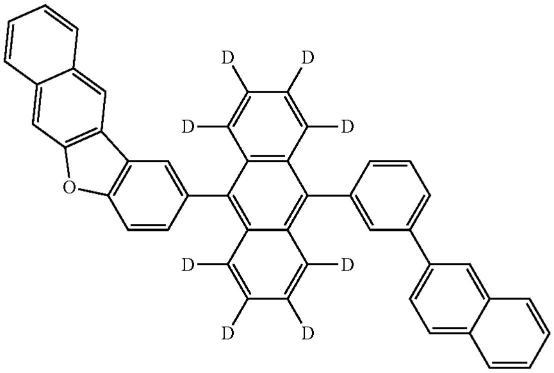

-continued
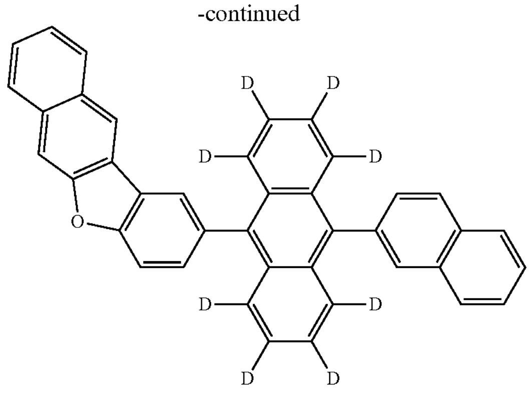
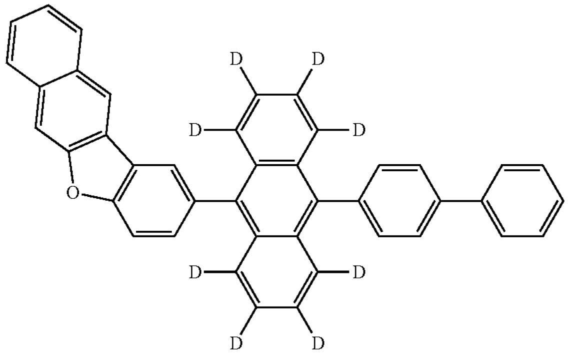
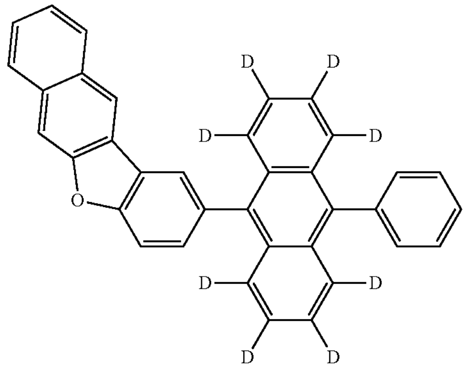
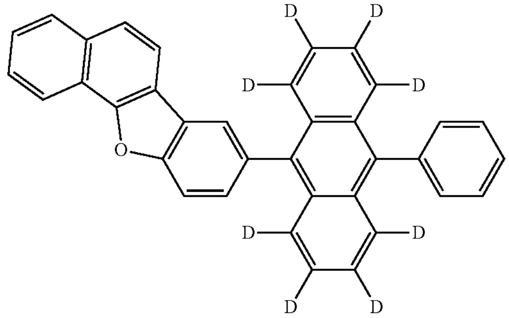
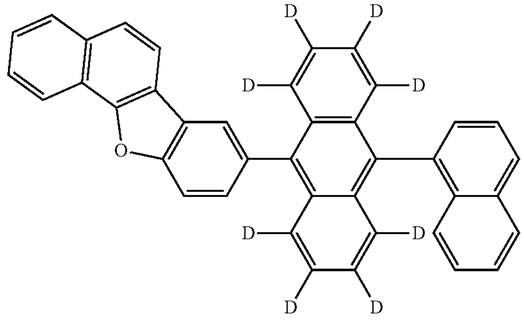
-continued
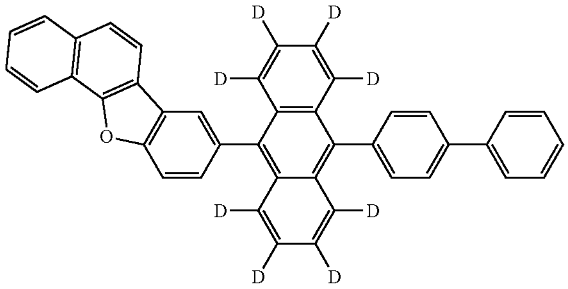
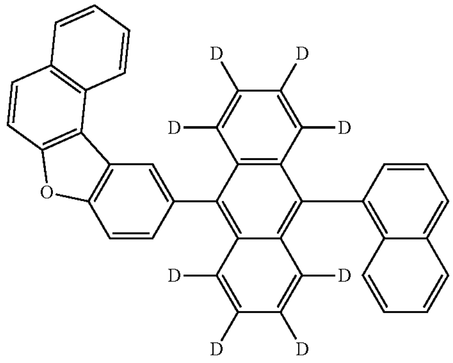
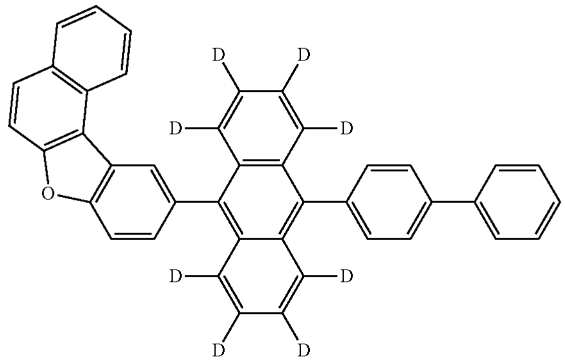
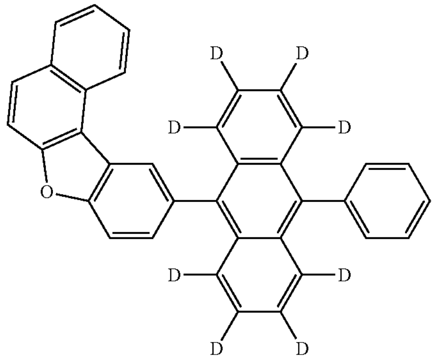
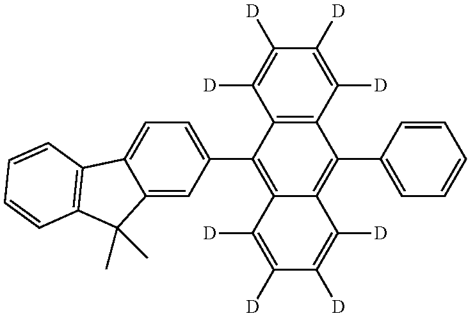

-continued
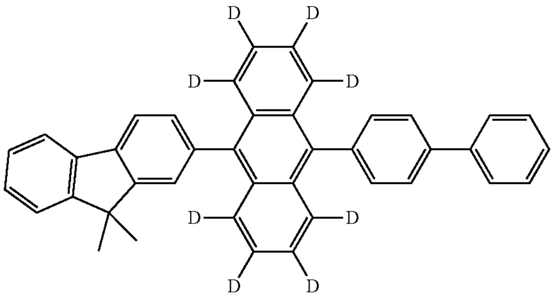
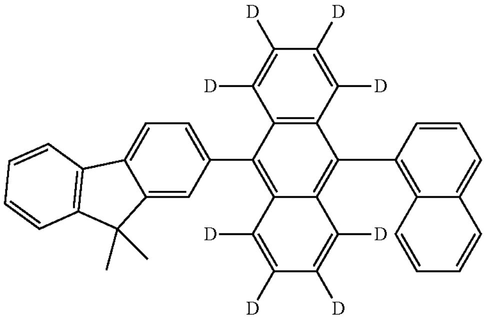 [SMILES: [2H]c1c([2H])c([2H])c2c(-c3cccc4ccccc34)c3c([2H])c([2H])c([2H])c([2H])c3c(-c3ccc4c(c3)C(C)(C)c3ccccc3-4)c2c1[2H]]
[Formula 110]
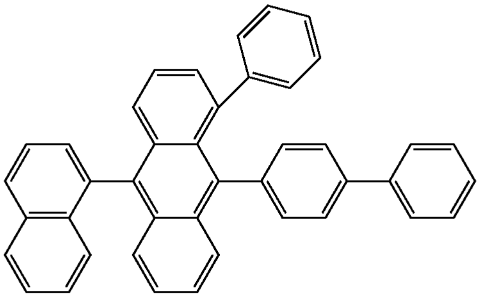
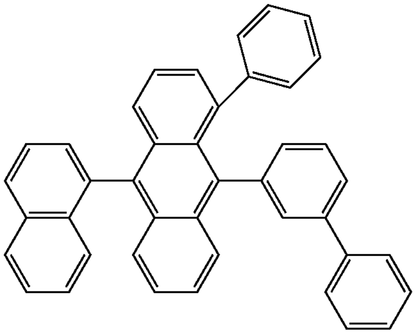
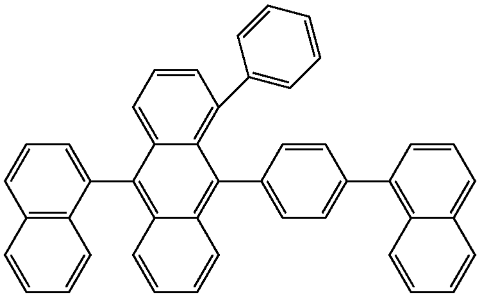
-continued
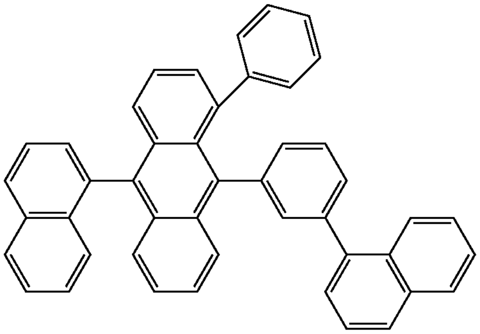
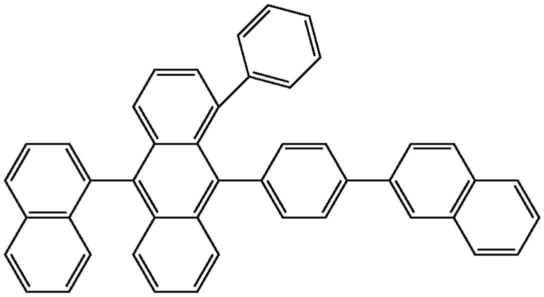
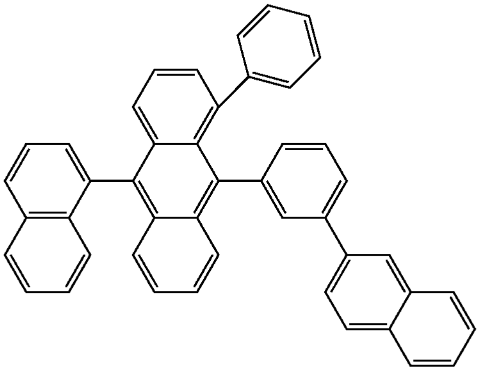
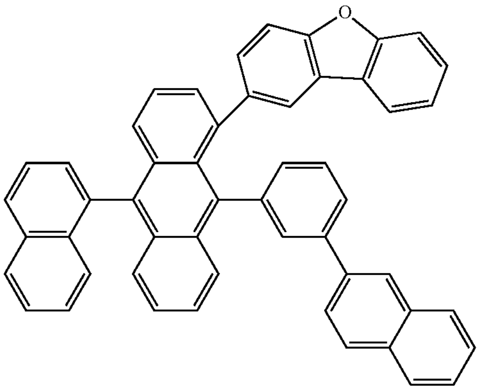

-continued
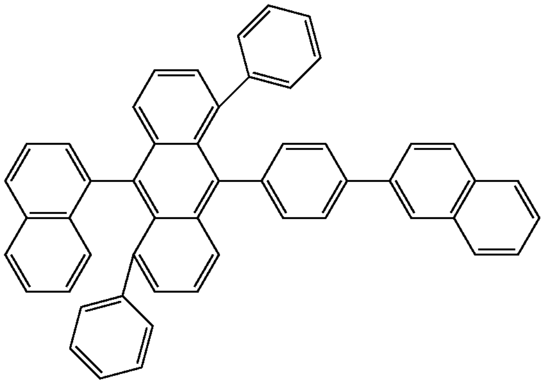
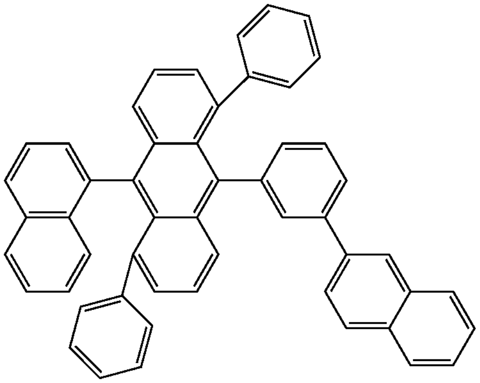
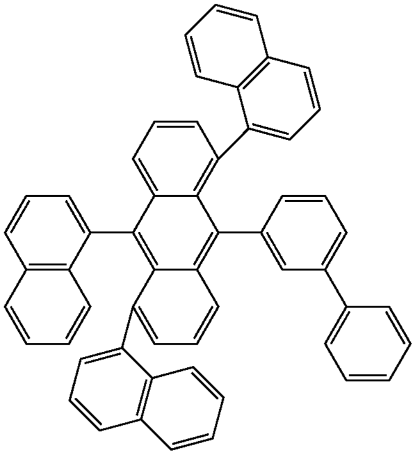
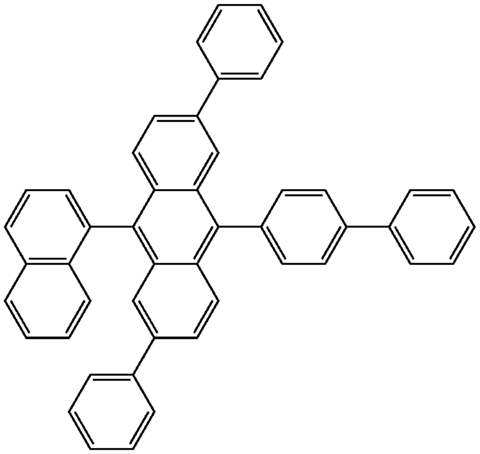
-continued
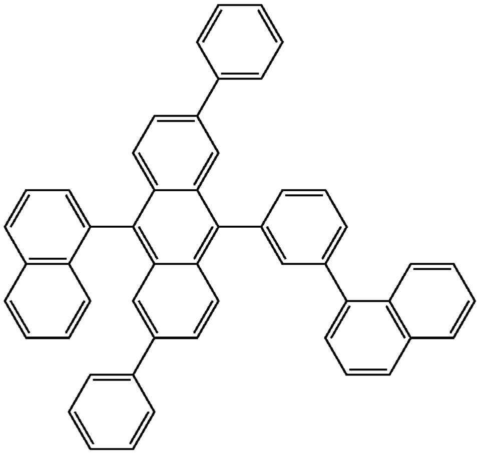
[Formula 111]
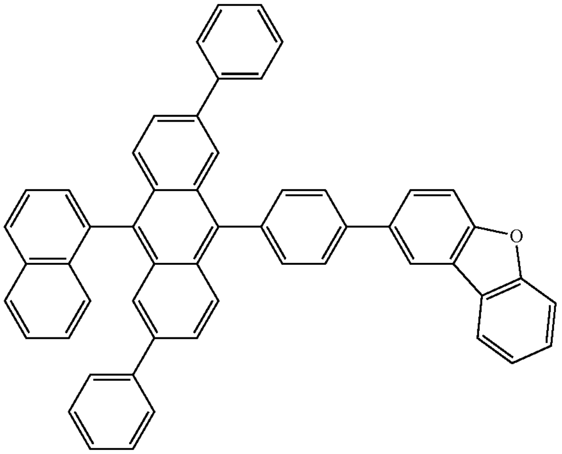
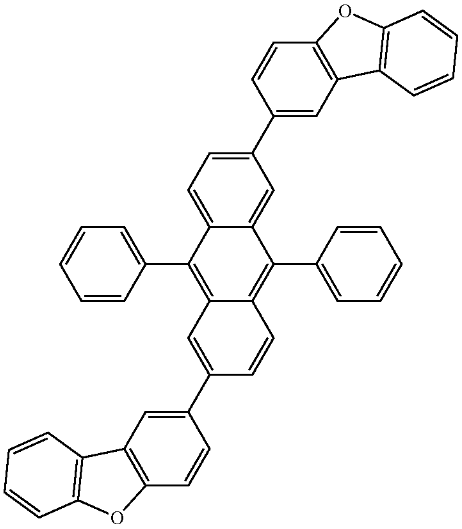

-continued
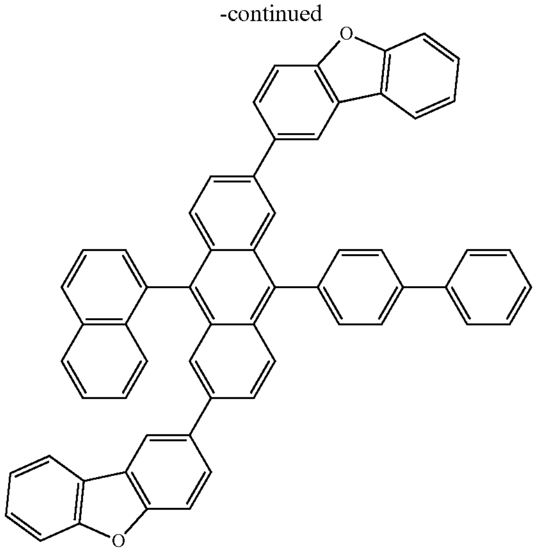
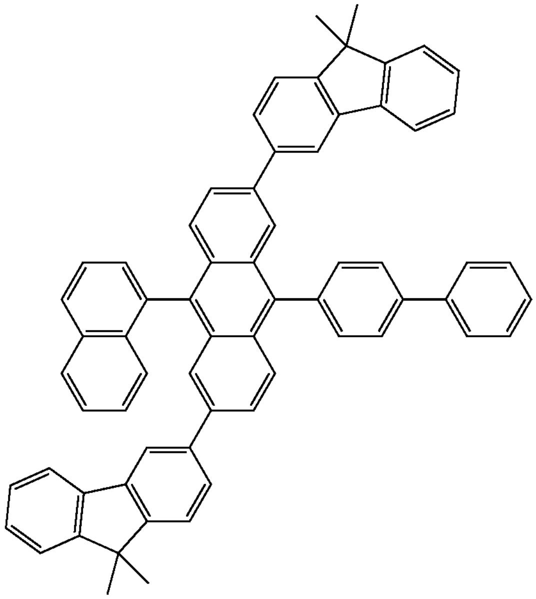
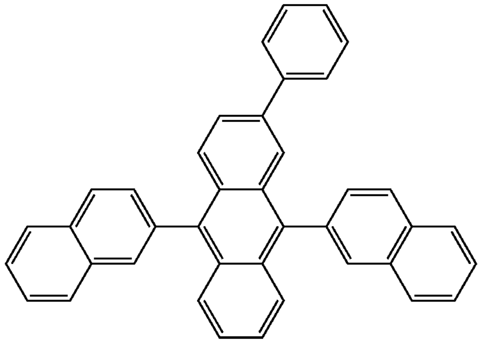
-continued
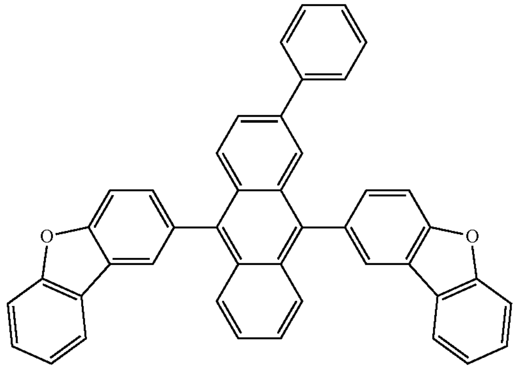
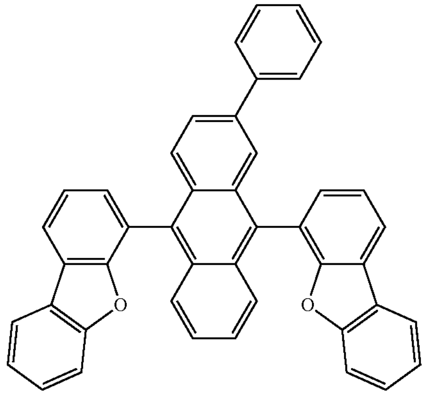
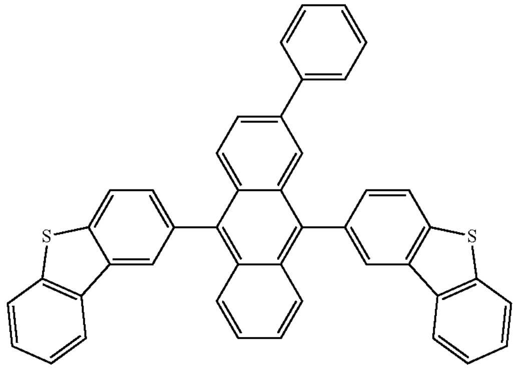 [SMILES: c1ccc(-c2ccc3c(-c4ccc5sc6ccccc6c5c4)c4ccccc4c(-c4ccc5sc6ccccc6c5c4)c3c2)cc1]

[Formula 112]
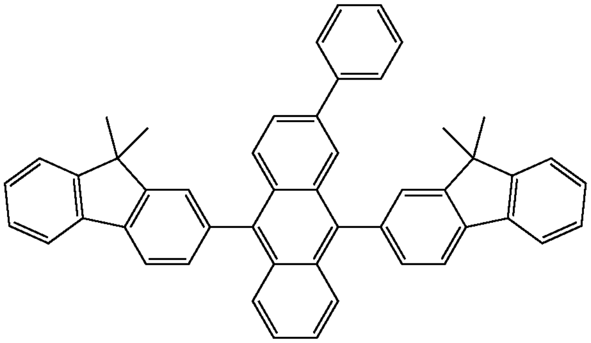
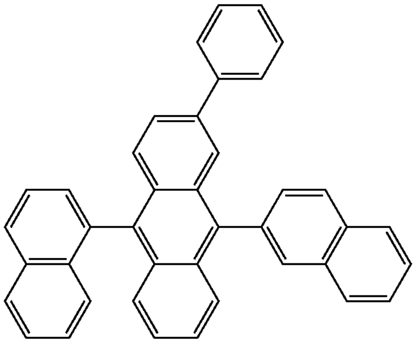
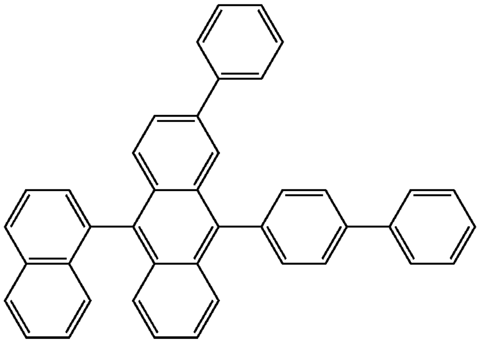
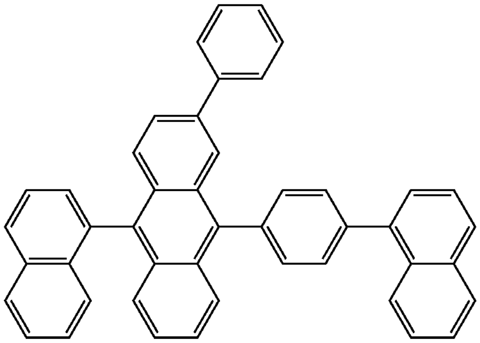
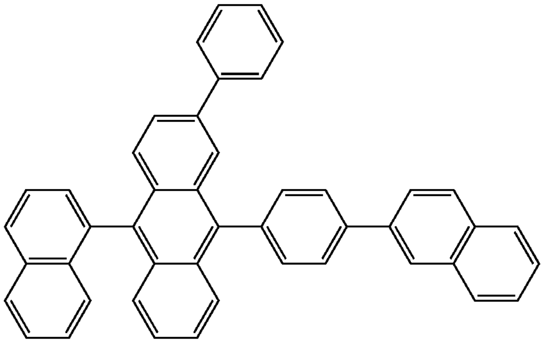
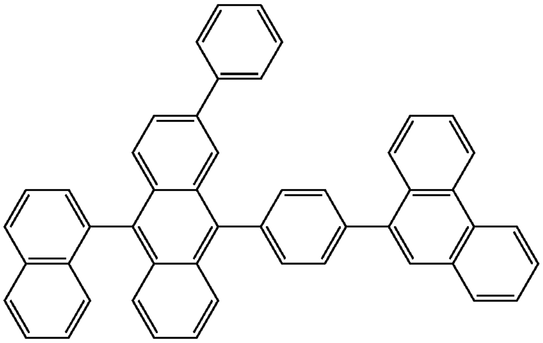
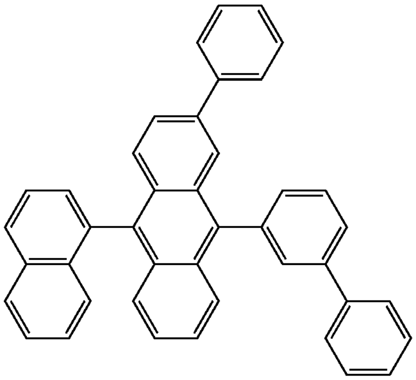
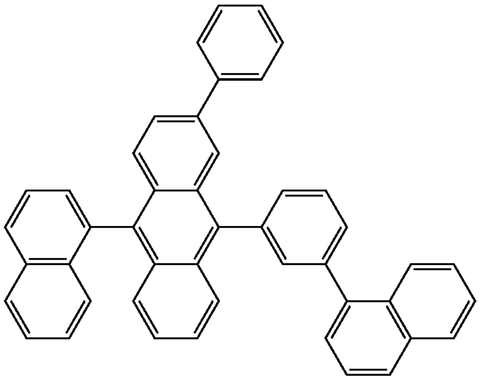

-continued
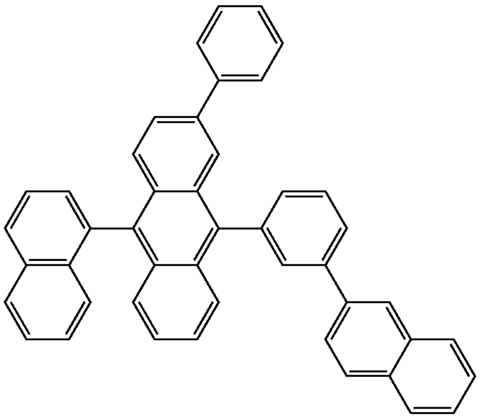
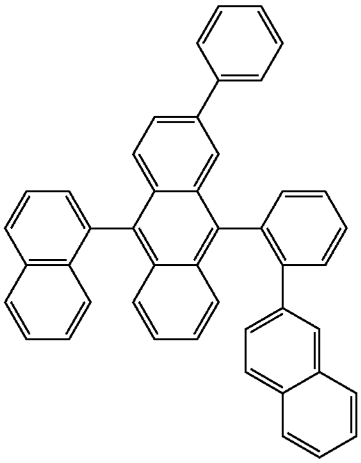
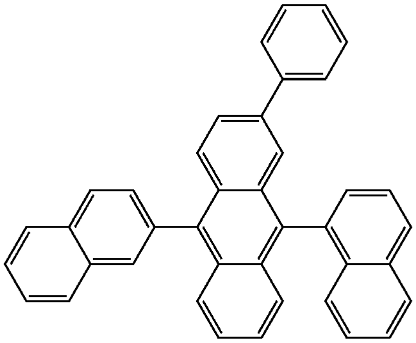
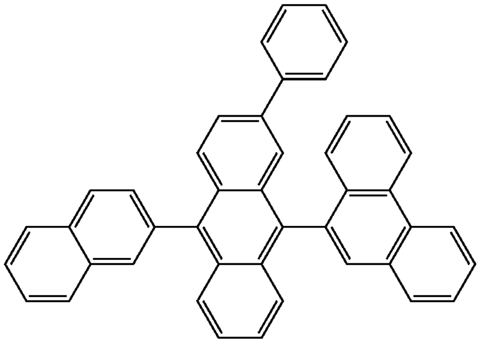
[Formula 113]
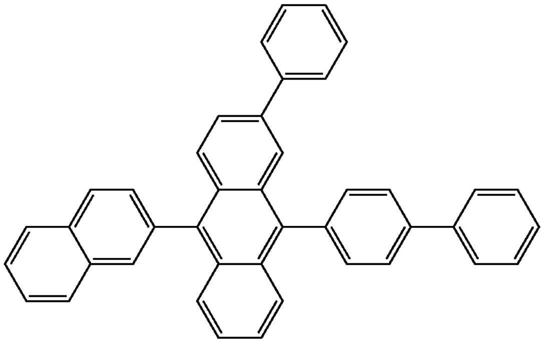
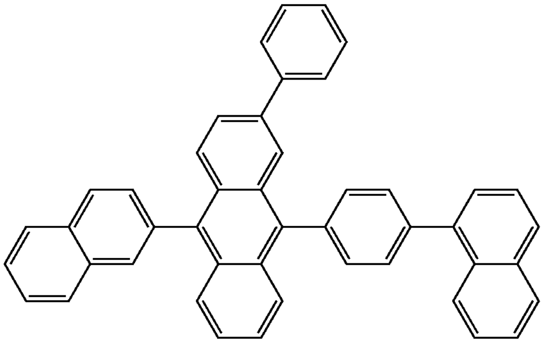
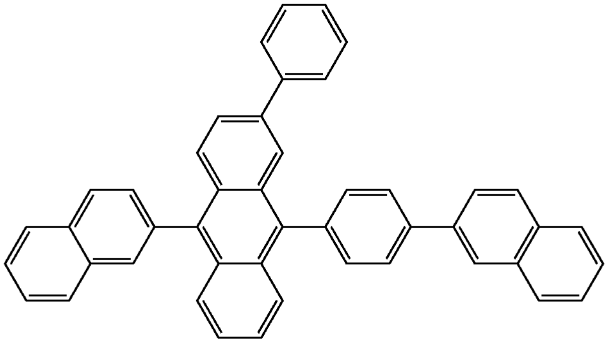
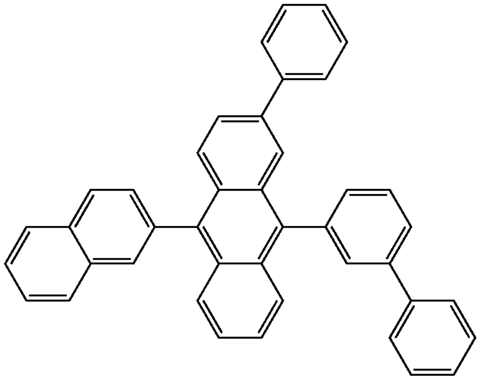

-continued
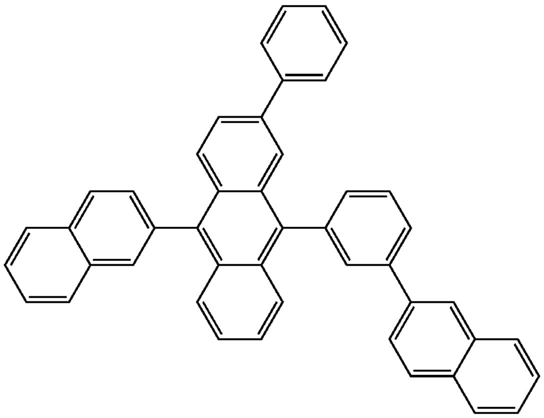
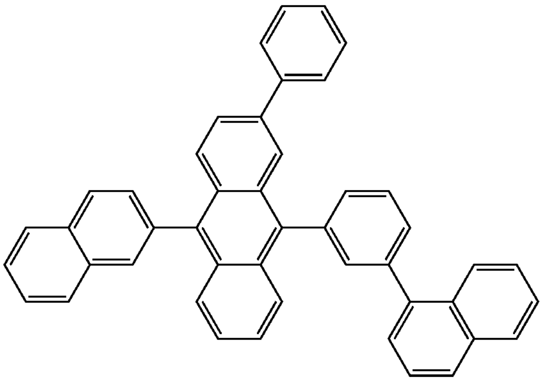
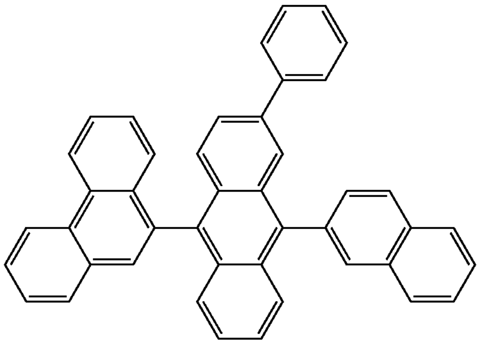
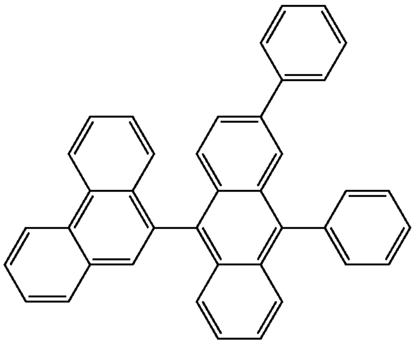
[Formula 114]
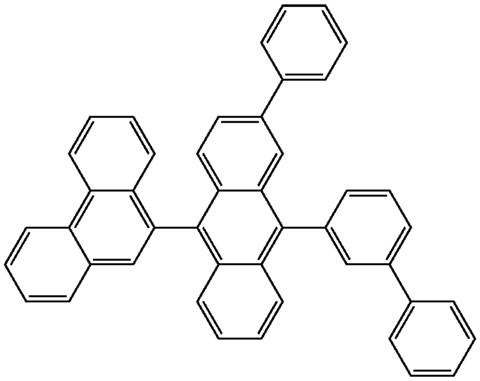
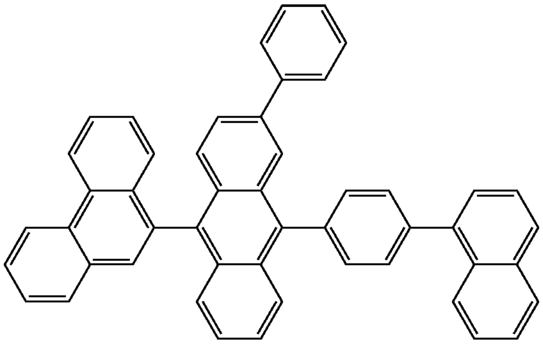
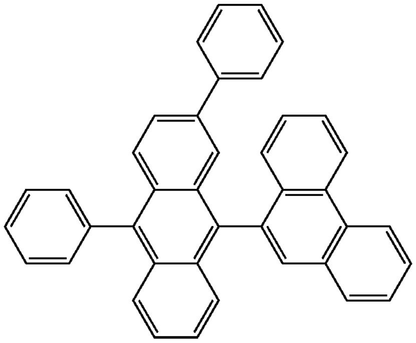
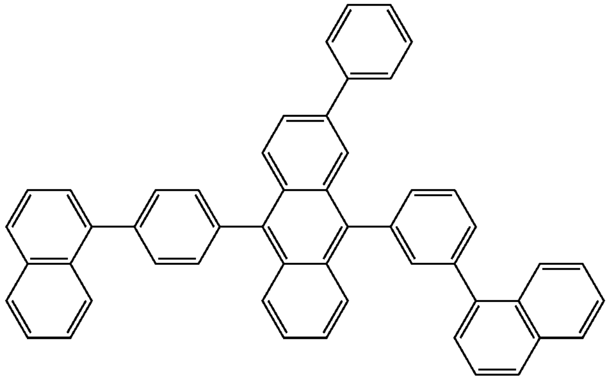

-continued
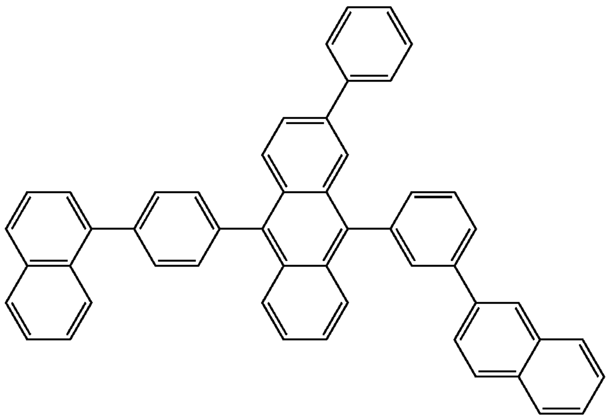
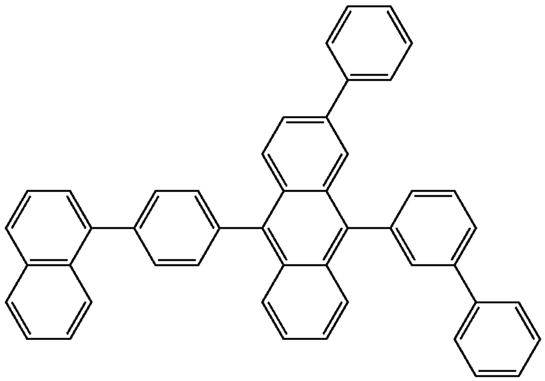
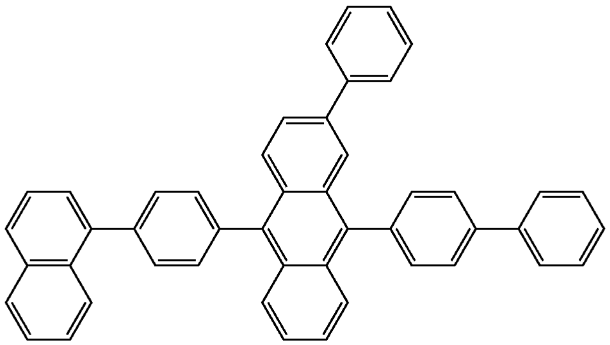
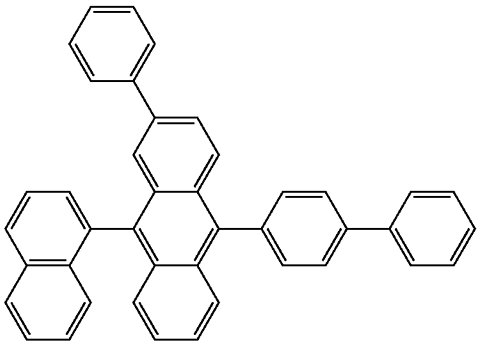
[Formula 115]
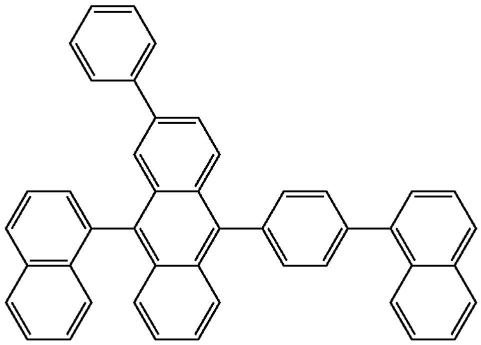
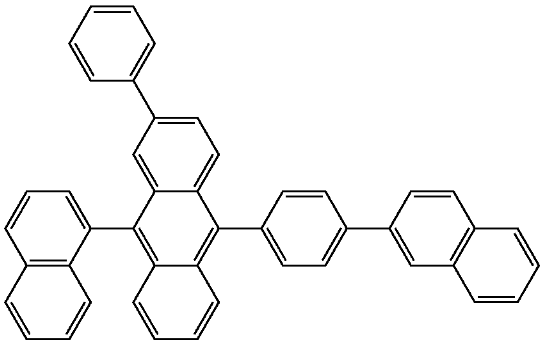

-continued
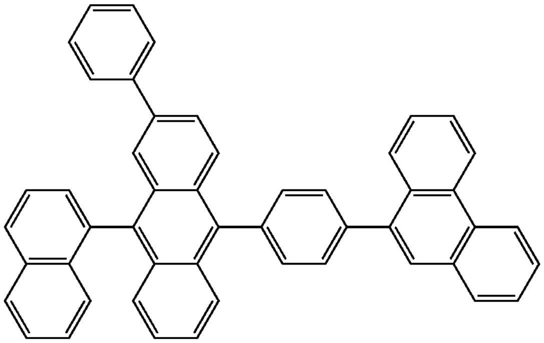
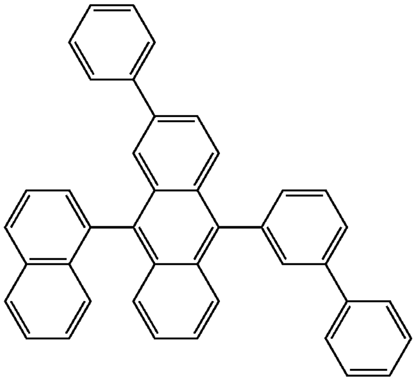
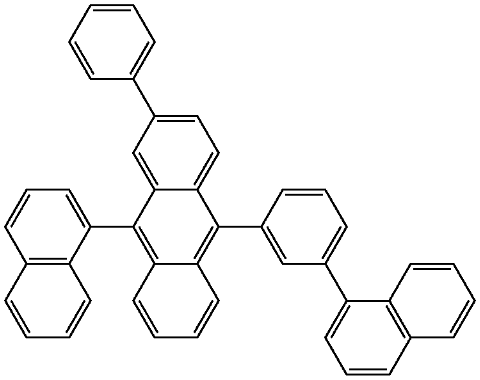
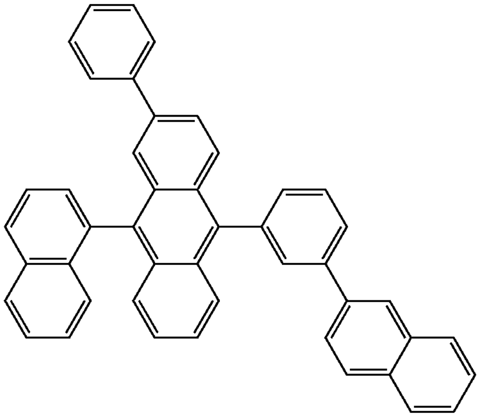
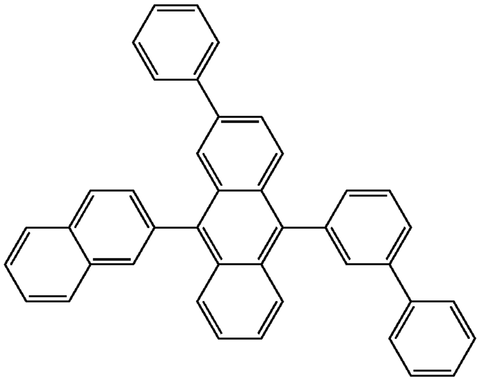
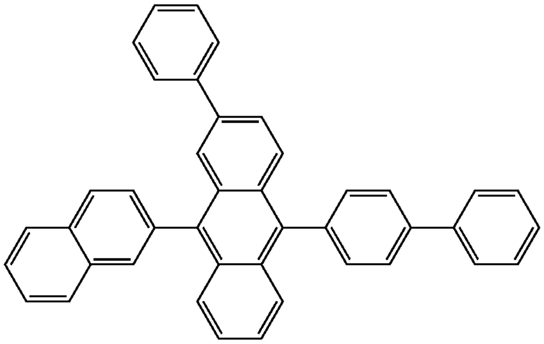
[Formula 116]
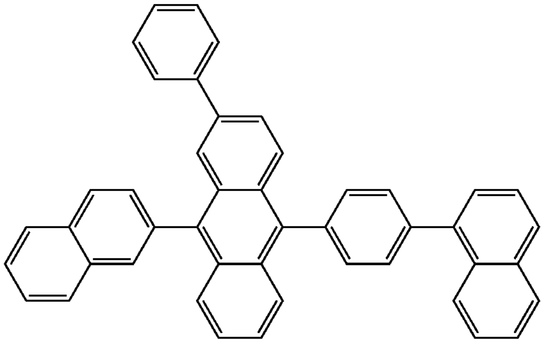

-continued
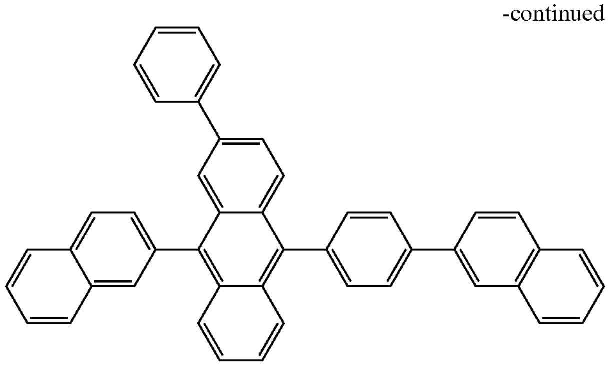
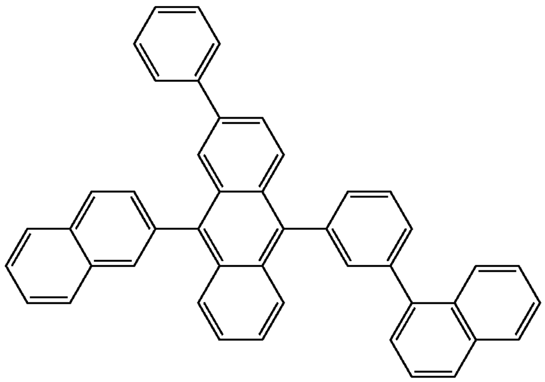
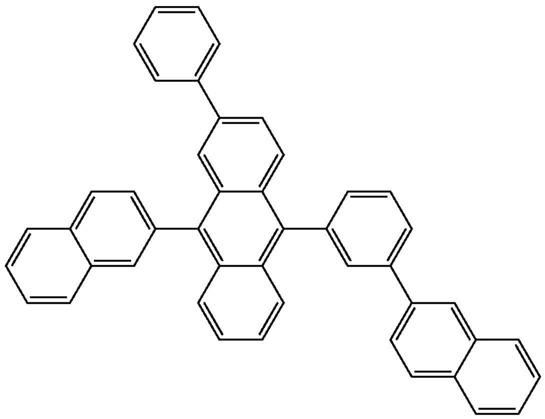
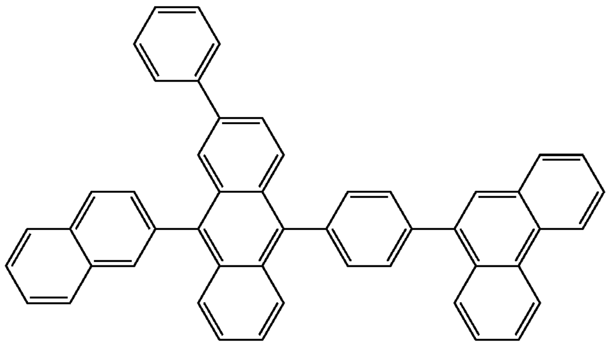
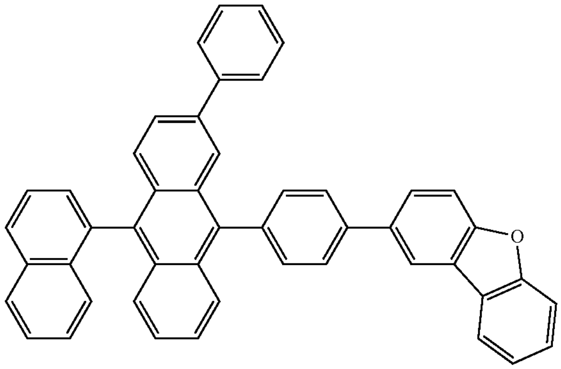
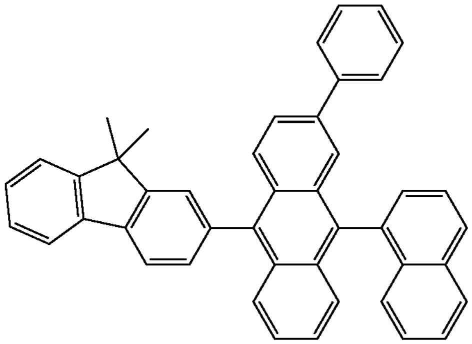

-continued
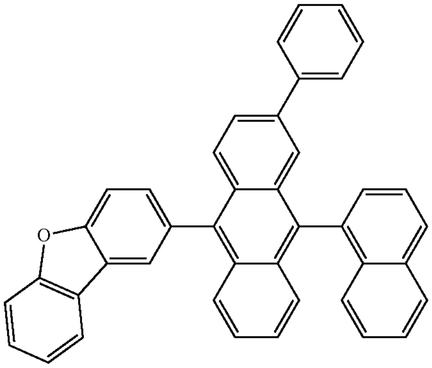
[Formula 117]
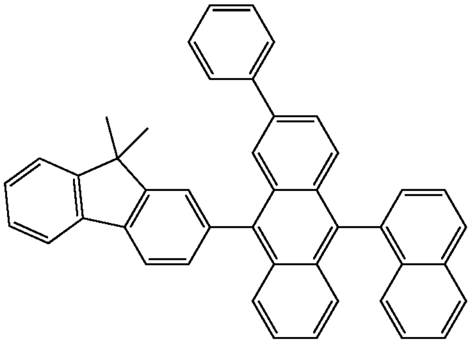
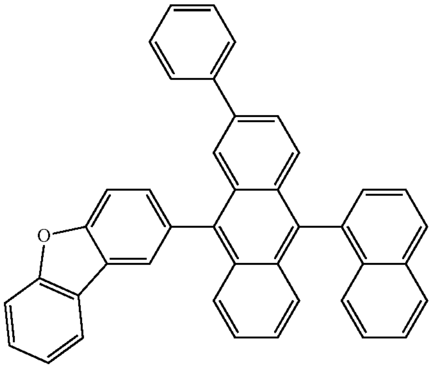
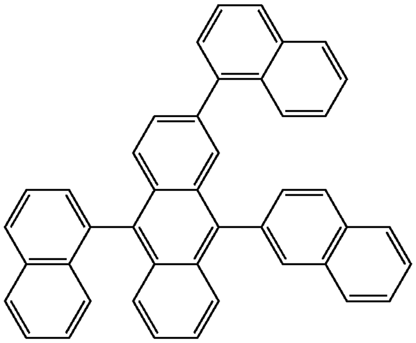
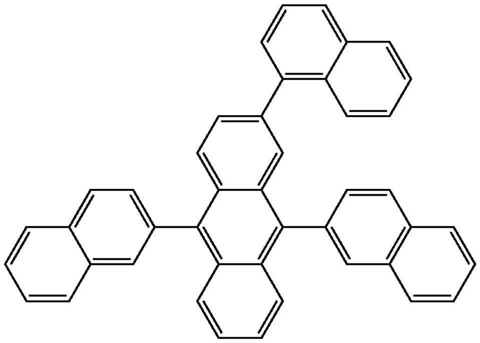
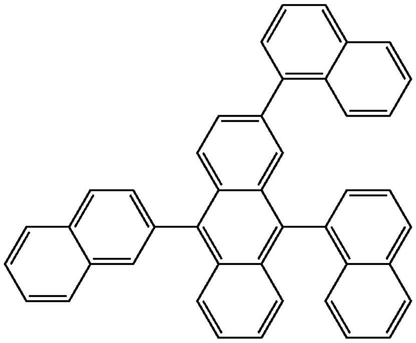
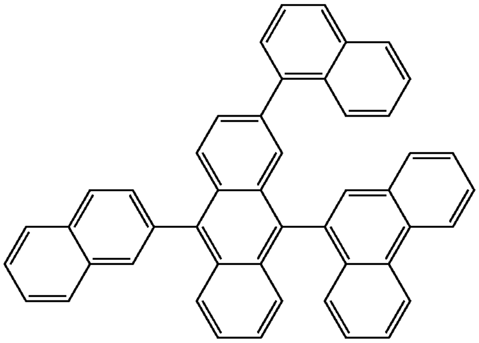

-continued
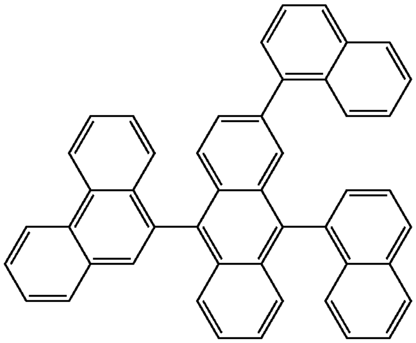
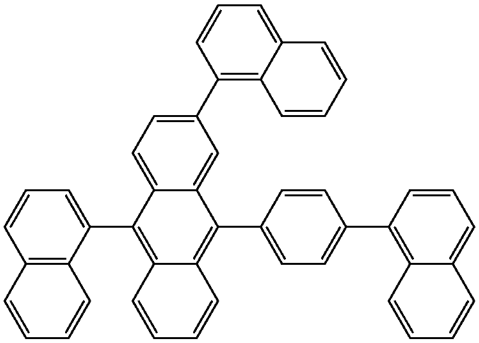
[Formula 118]
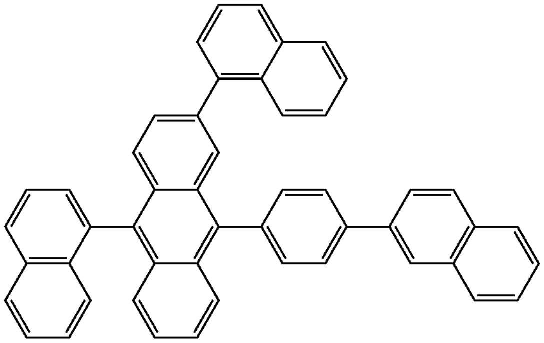
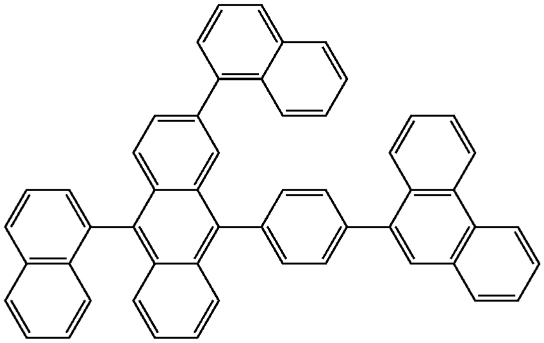
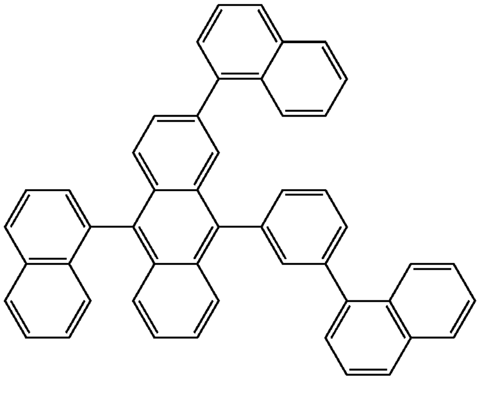
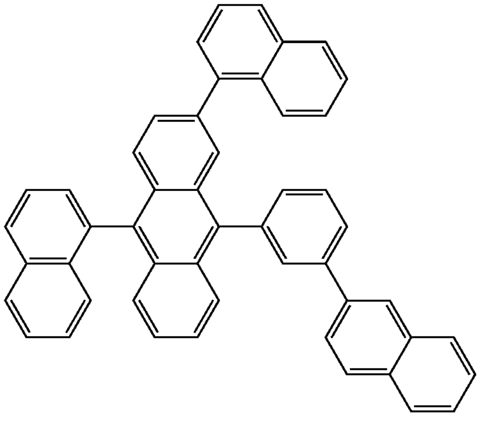
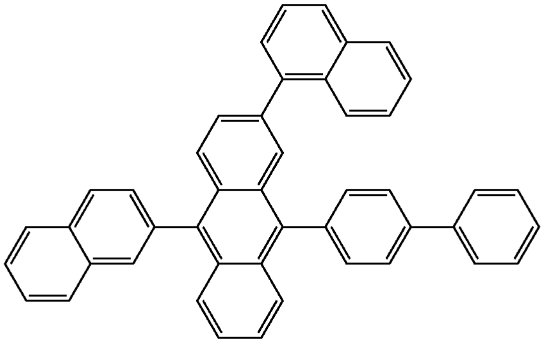
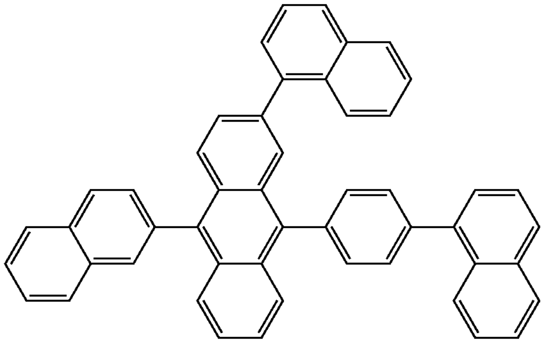

-continued
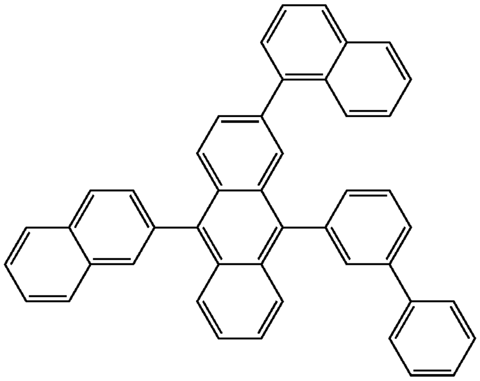
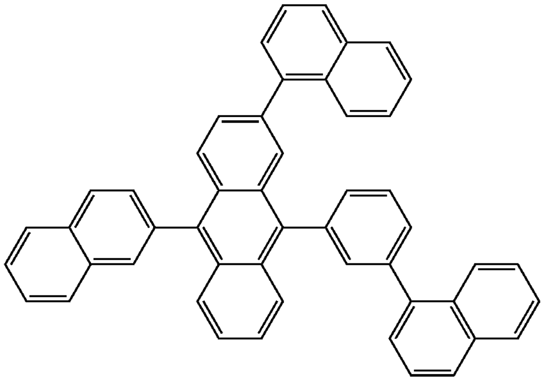
[Formula 119]
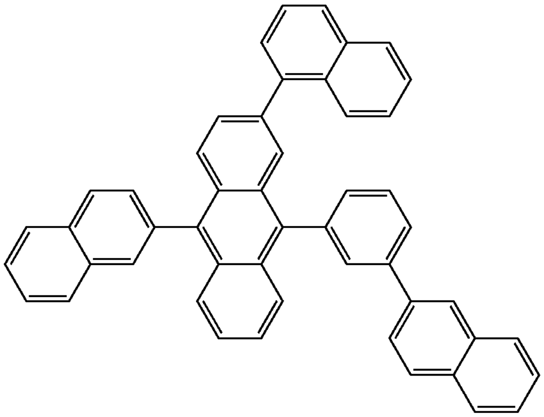
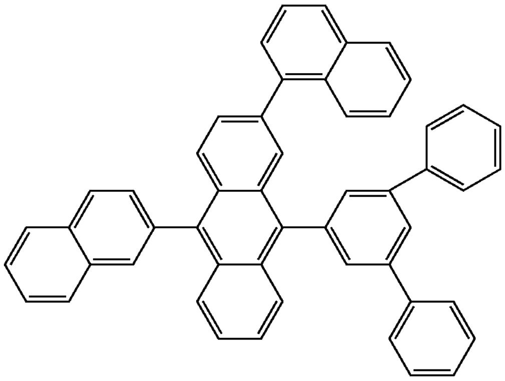
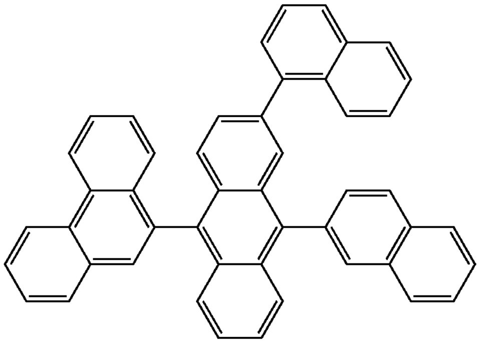
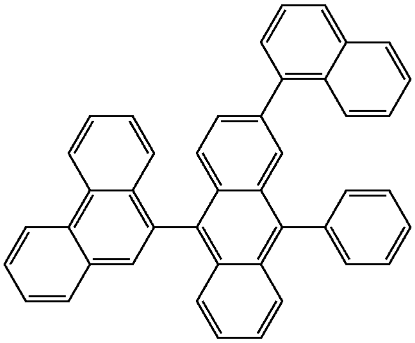
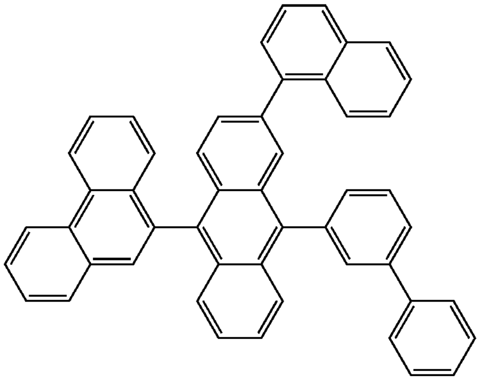
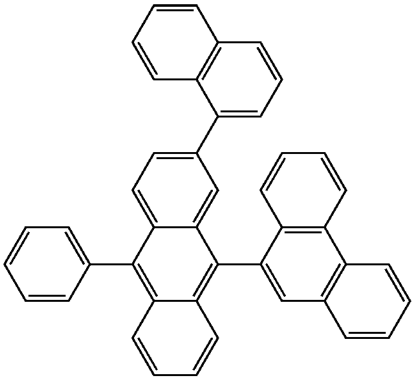

-continued
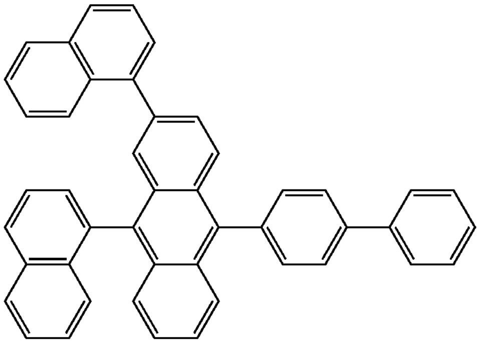 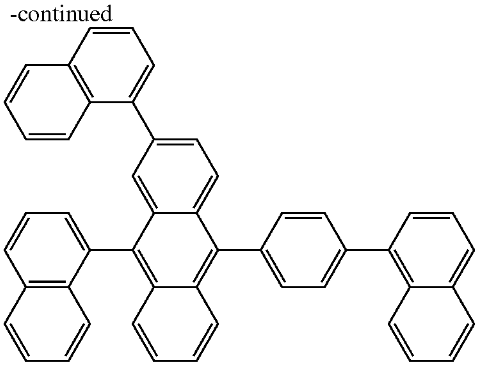
[Formula 120]
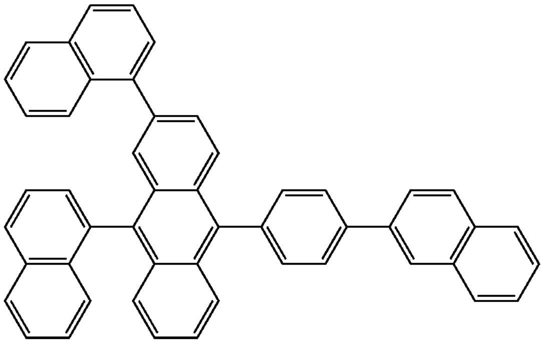 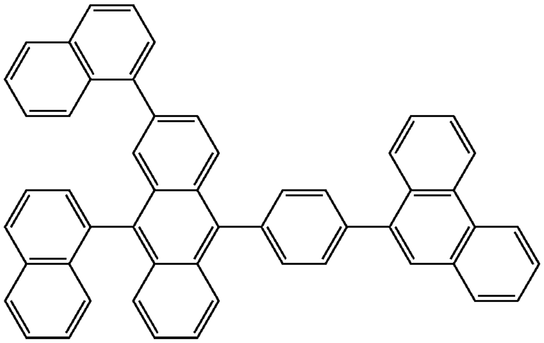
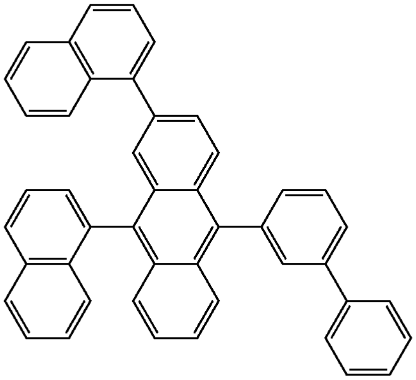 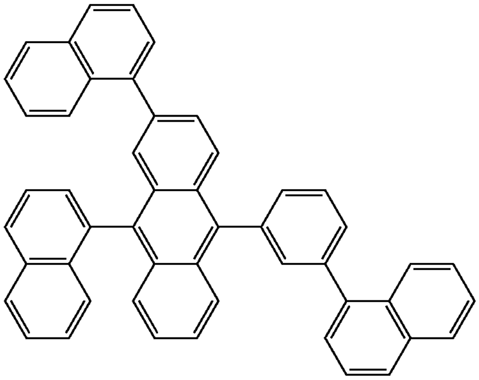
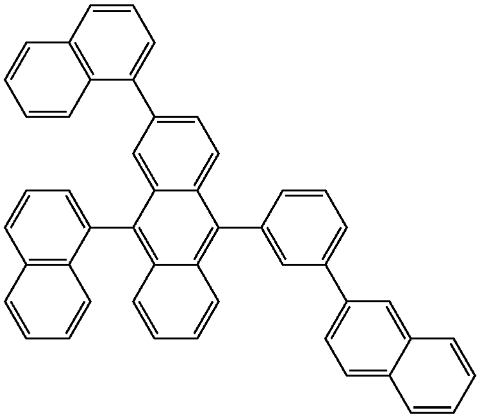 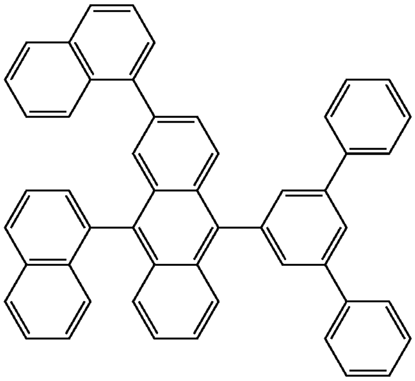

-continued
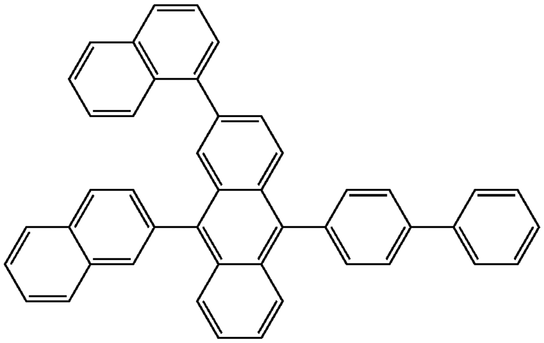
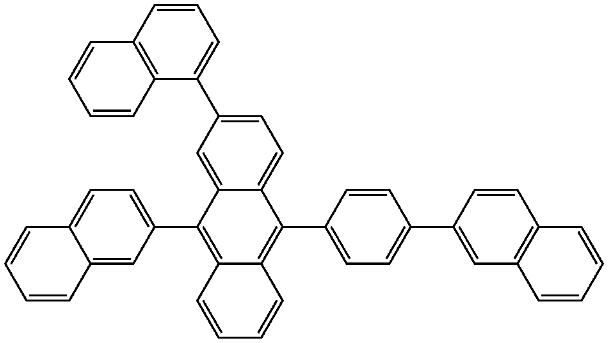
[Formula 121]
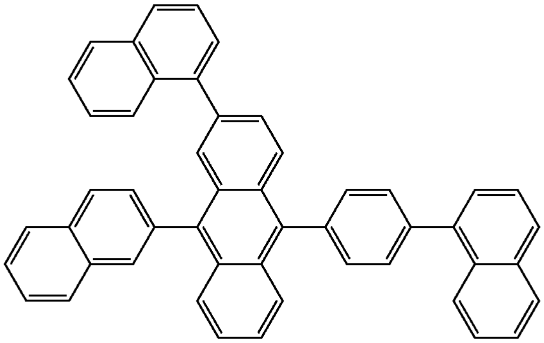
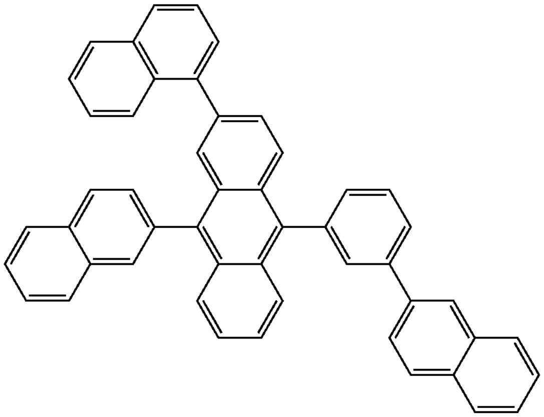
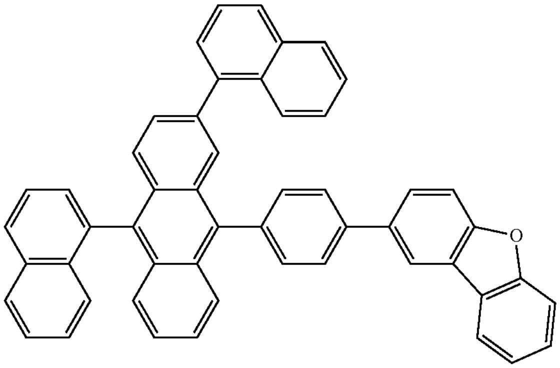
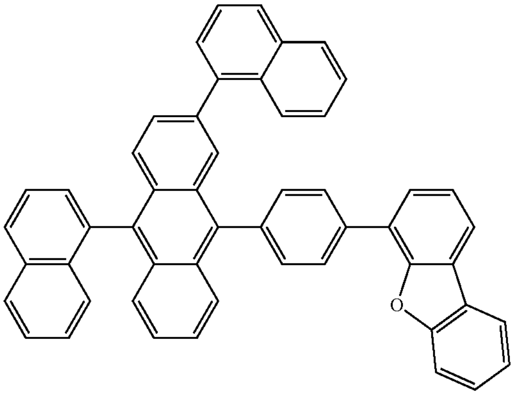

-continued
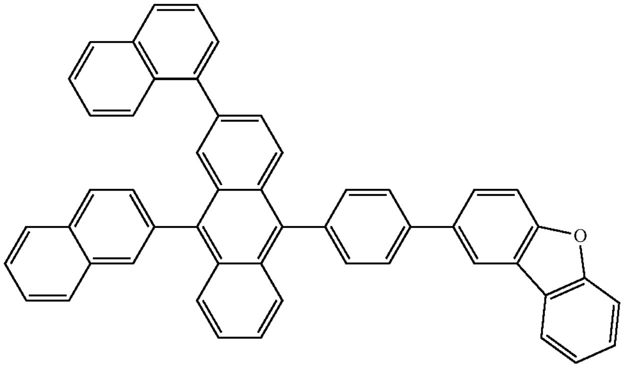
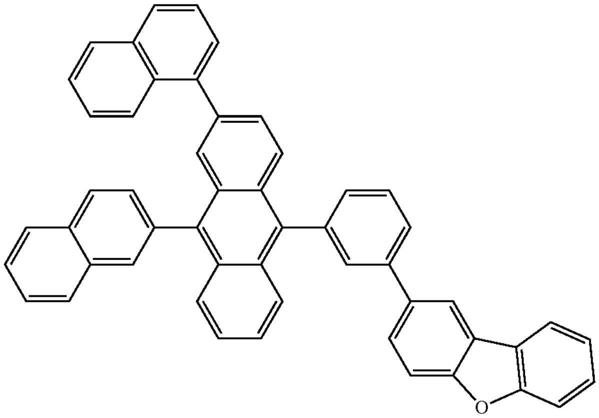
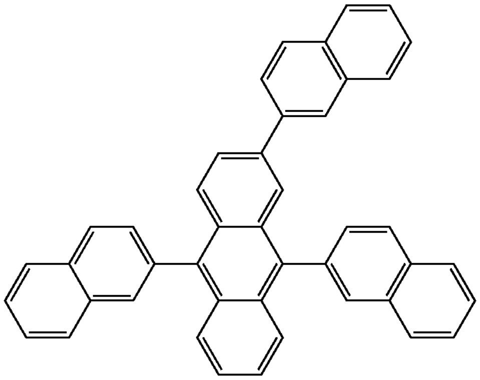
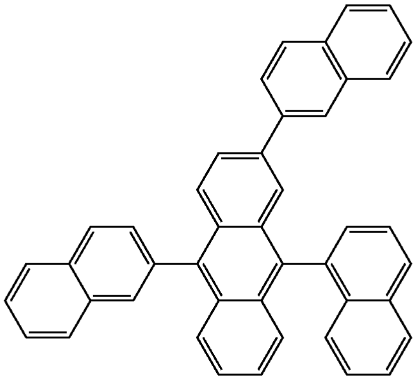
[Formula 122]
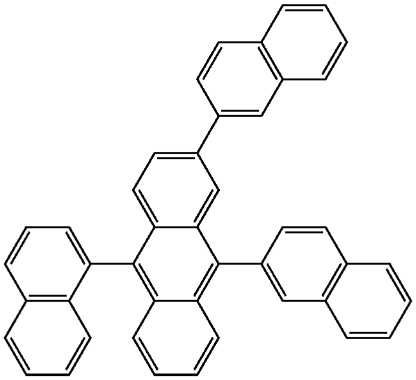
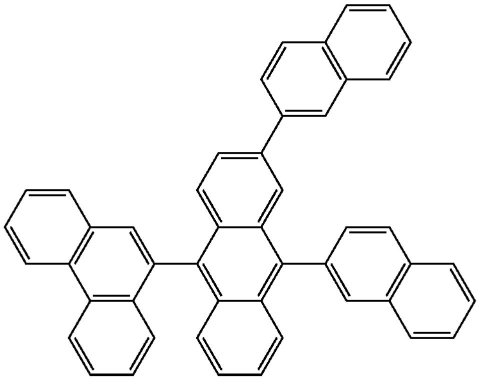

-continued
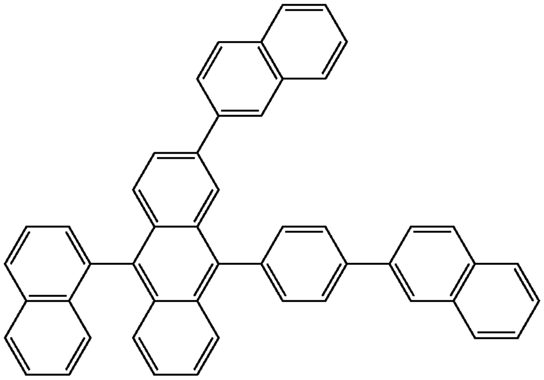
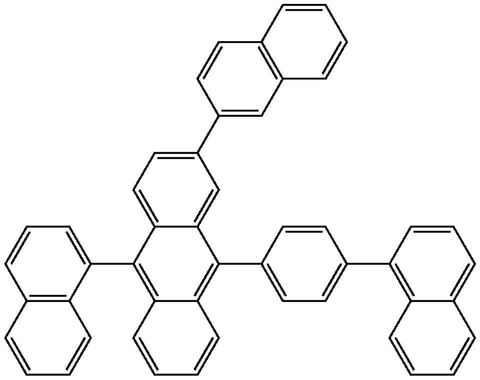
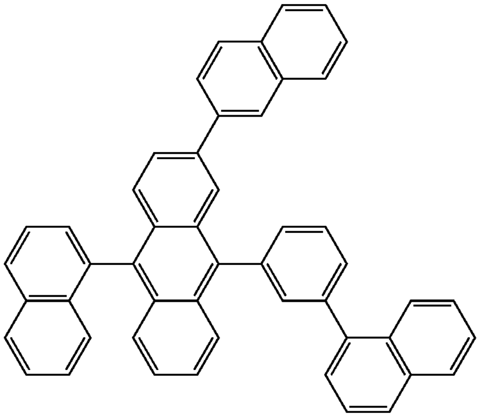
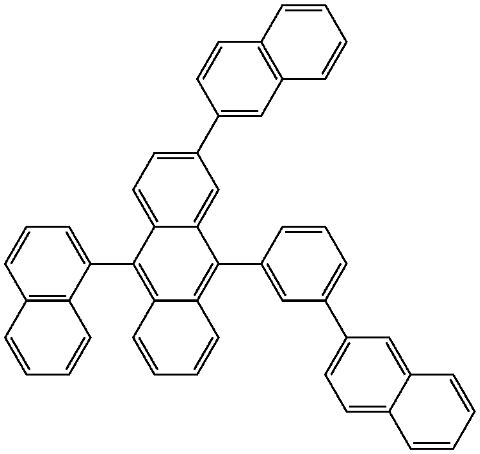
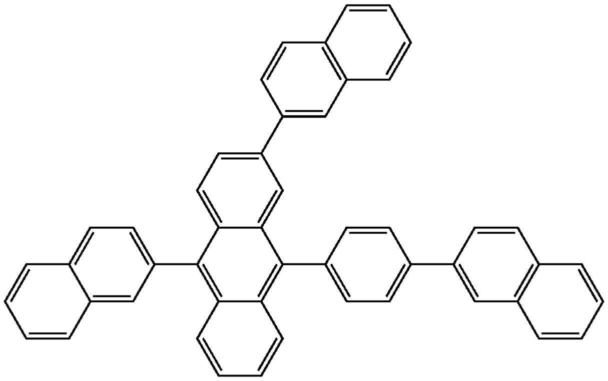
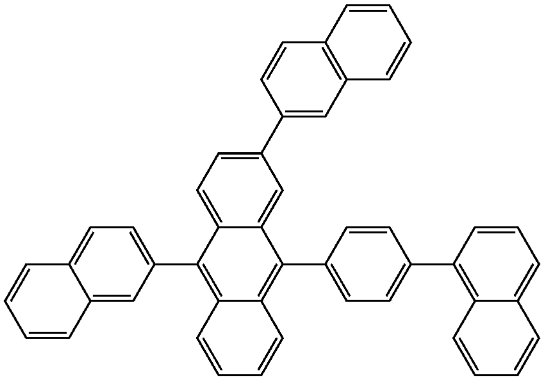

-continued
[Formula 123]
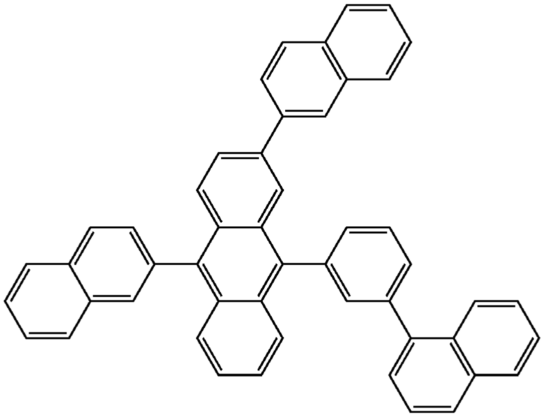
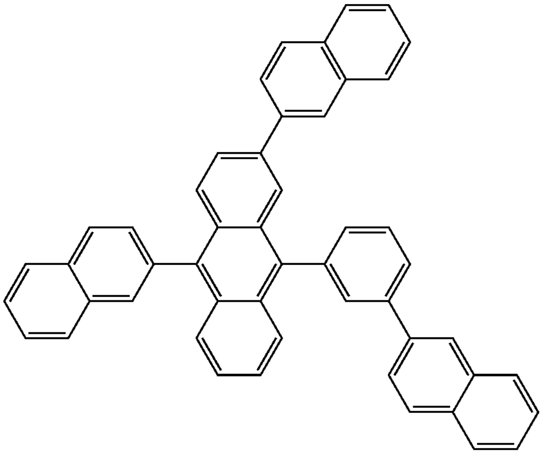
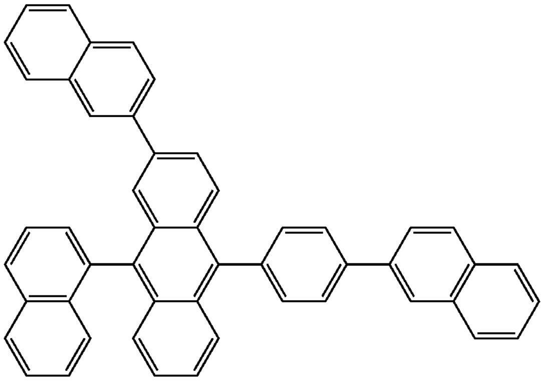
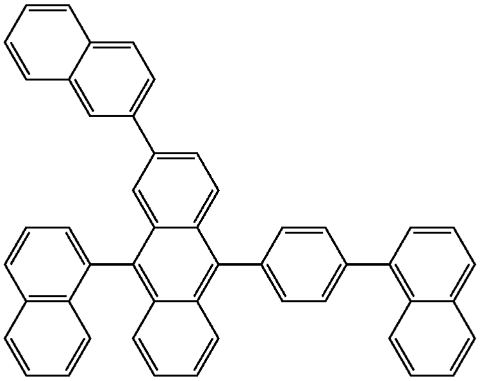
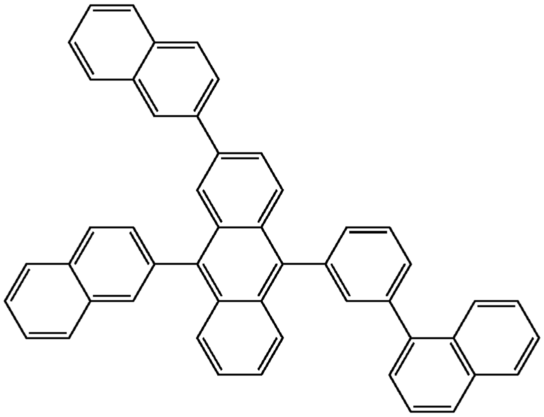
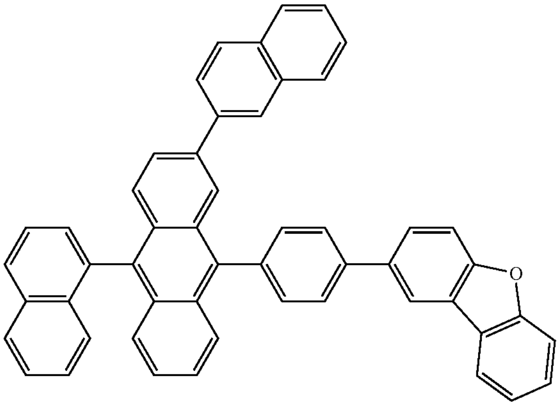

-continued
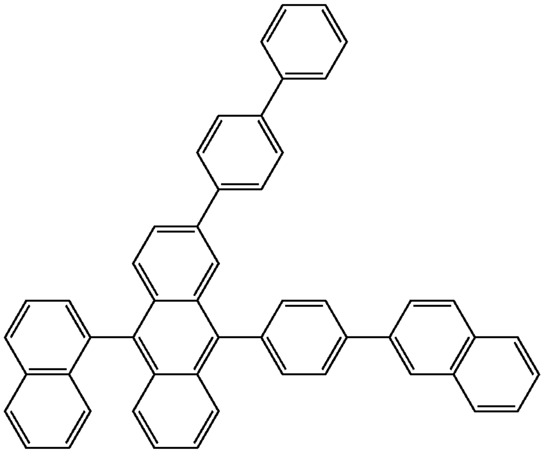
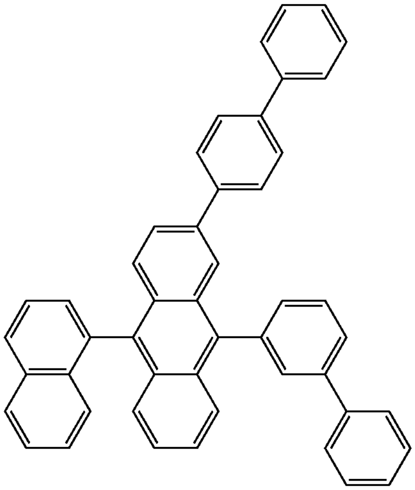
[Formula 124]
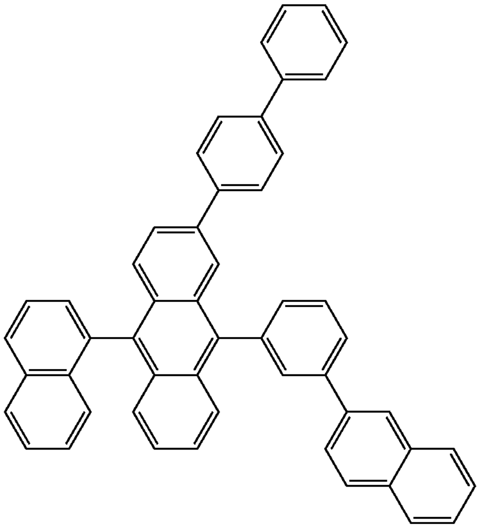
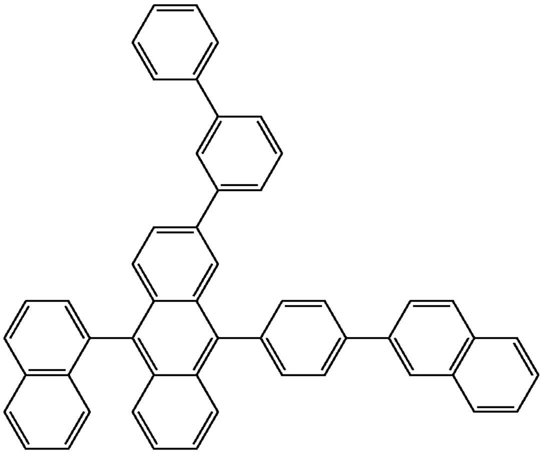
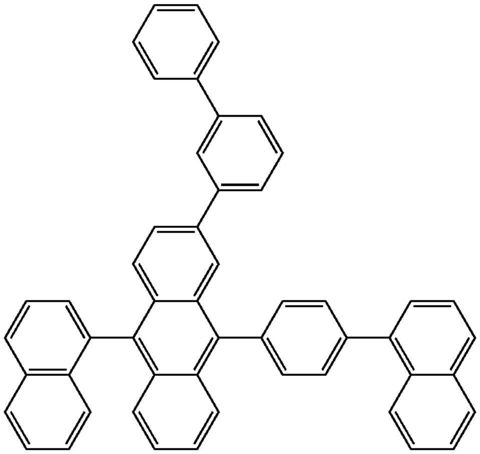
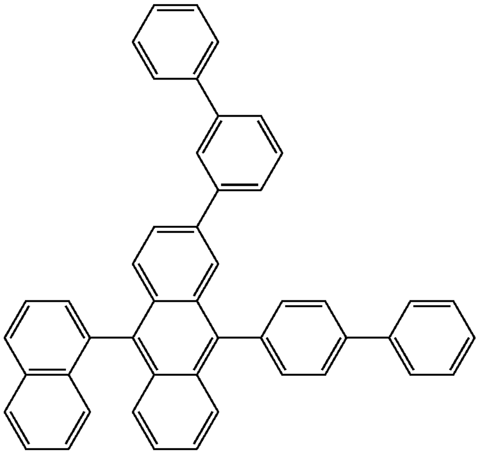

-continued
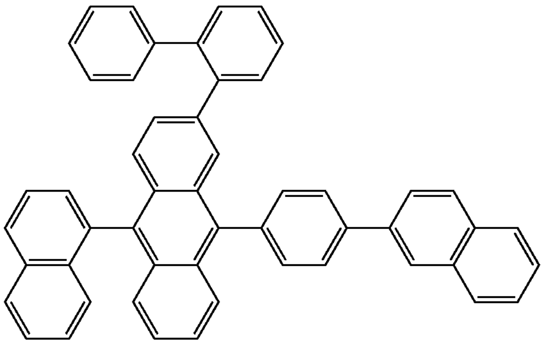
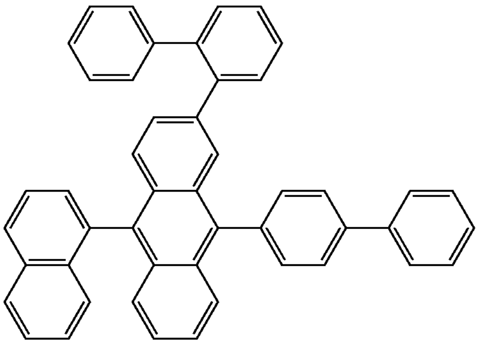
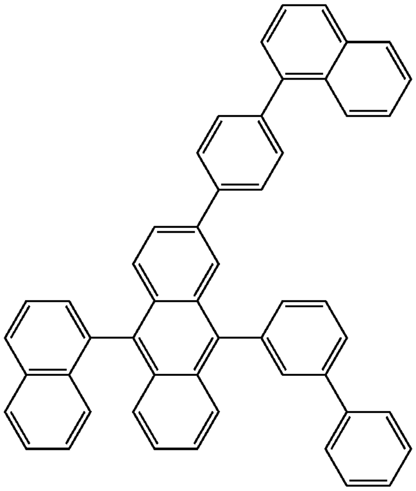
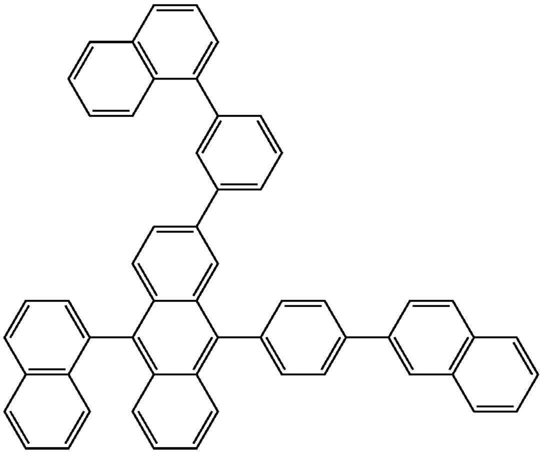
[Formula 125]
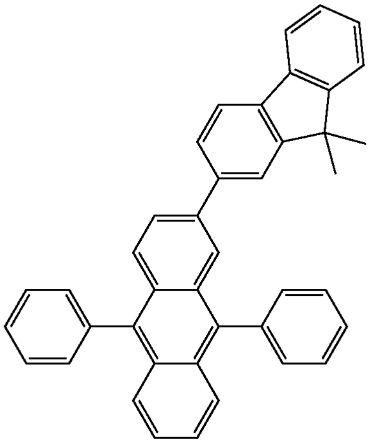
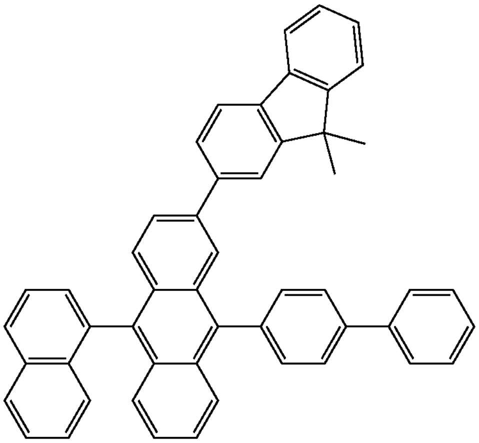

-continued
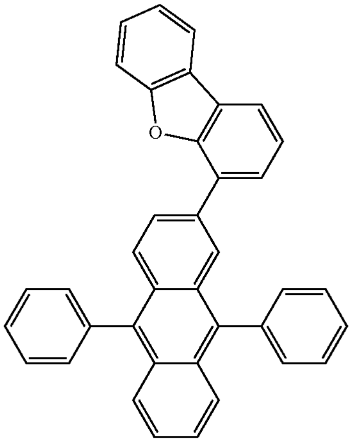
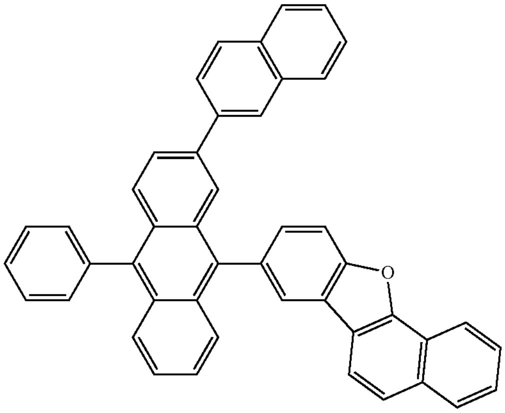
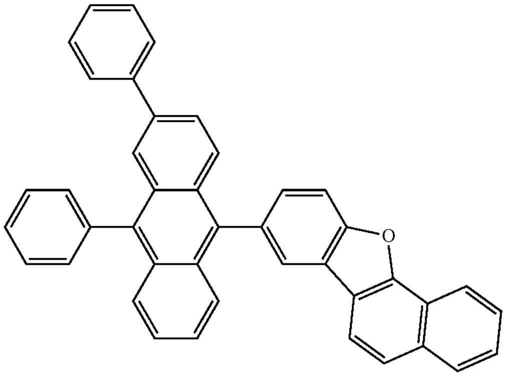
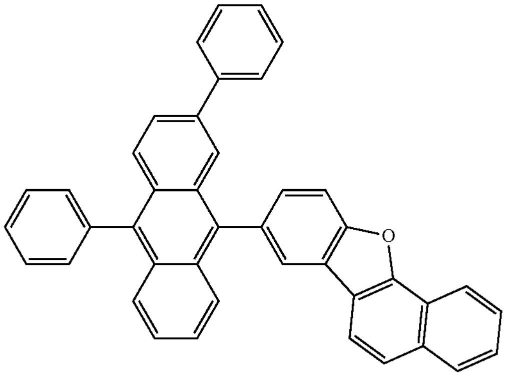
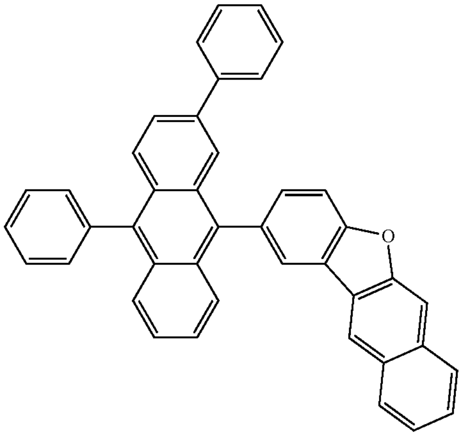
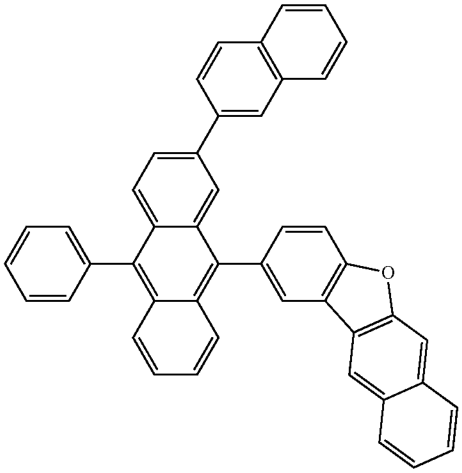

-continued
[Formula 126]
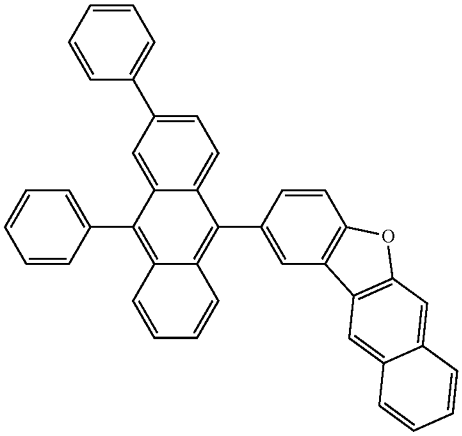
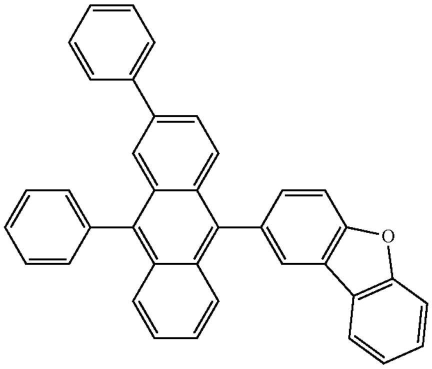
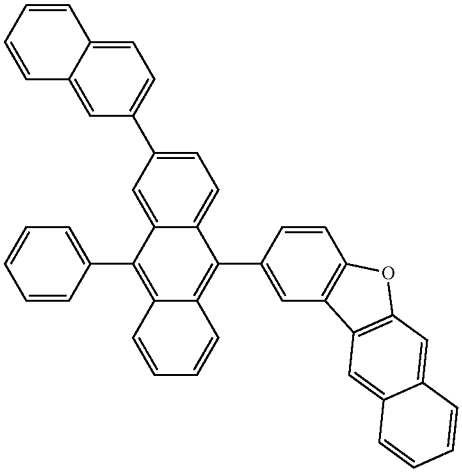
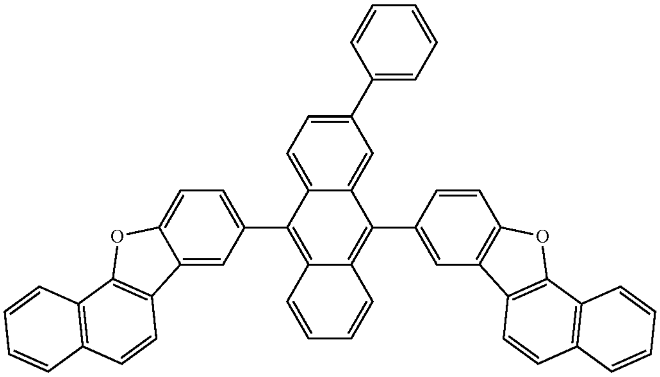
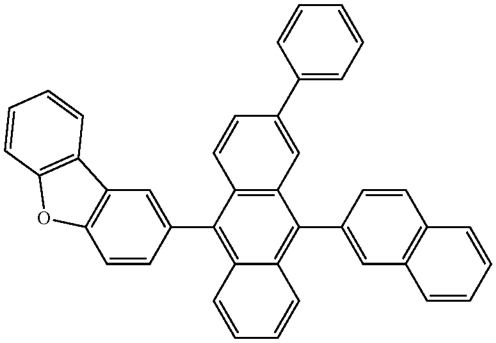
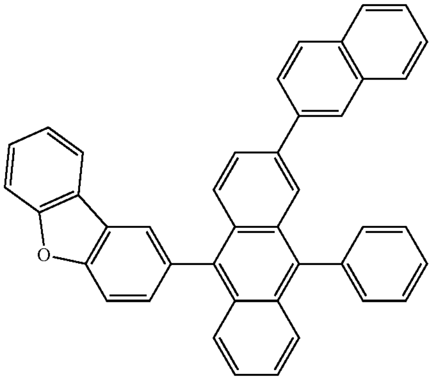
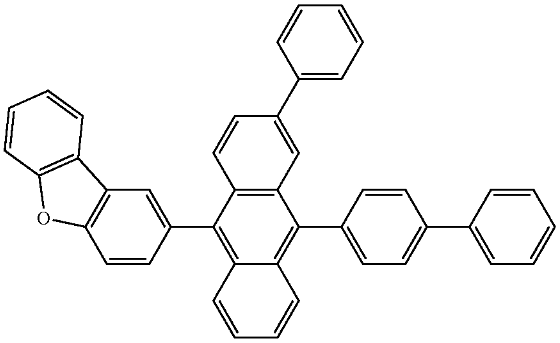
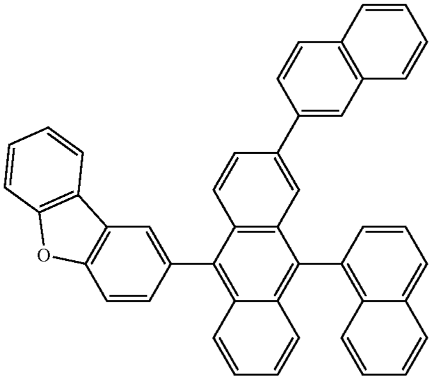

-continued
[Formula 127]
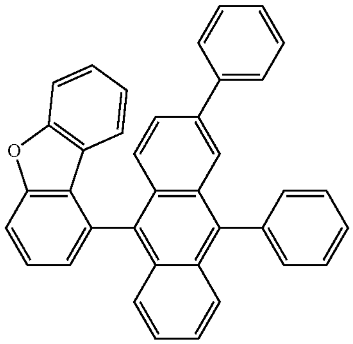
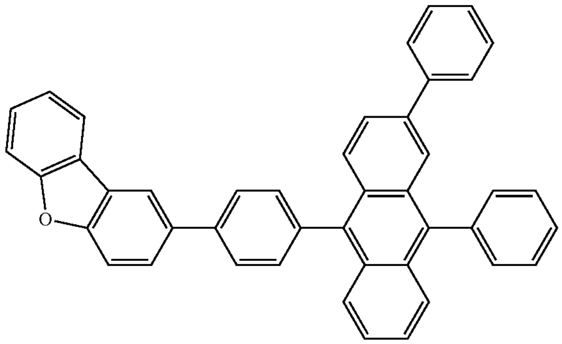
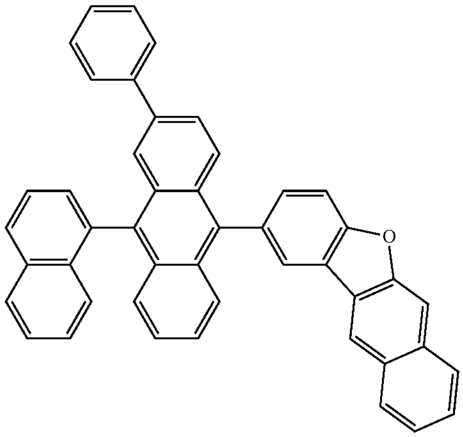
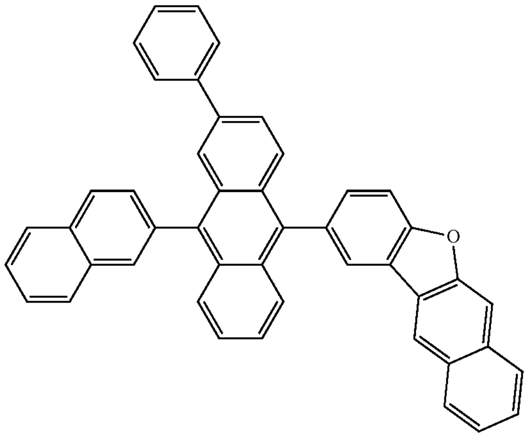
[Formula 128]
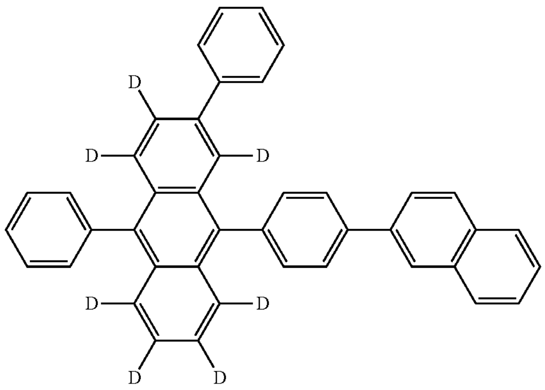
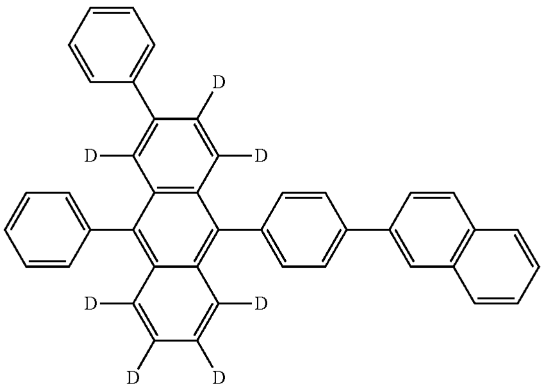
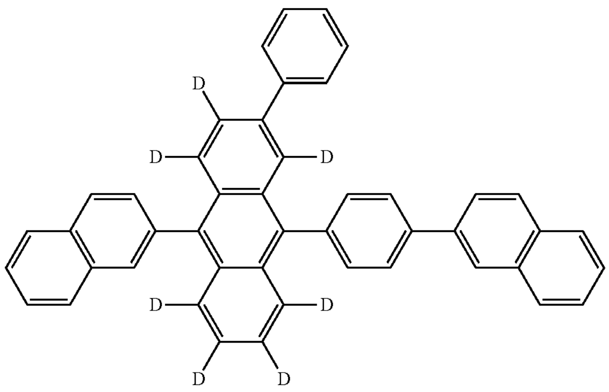

-continued
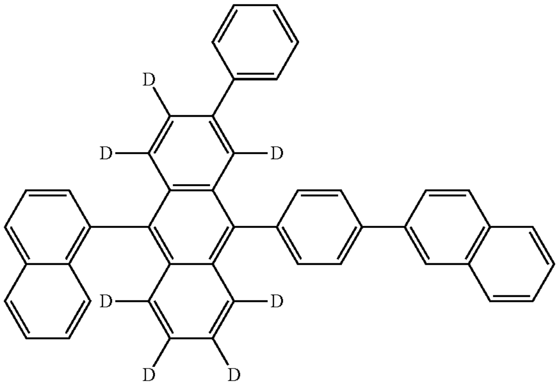
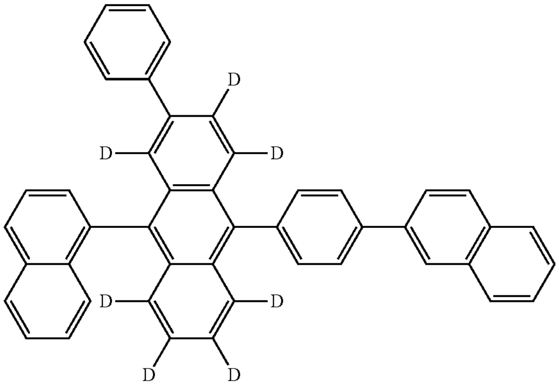
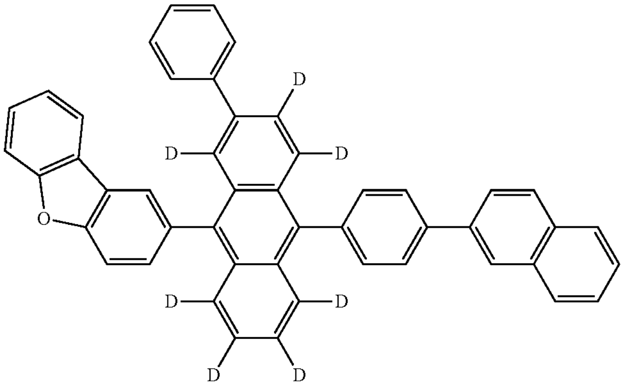
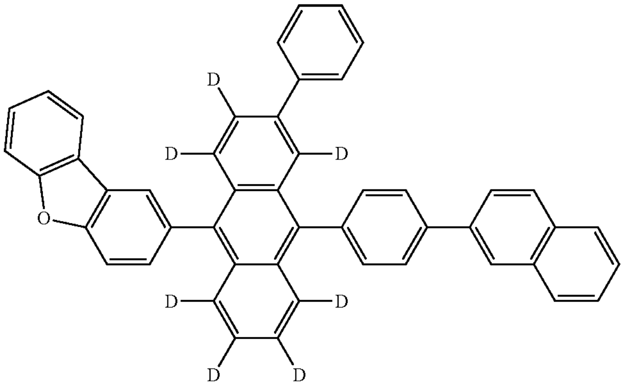
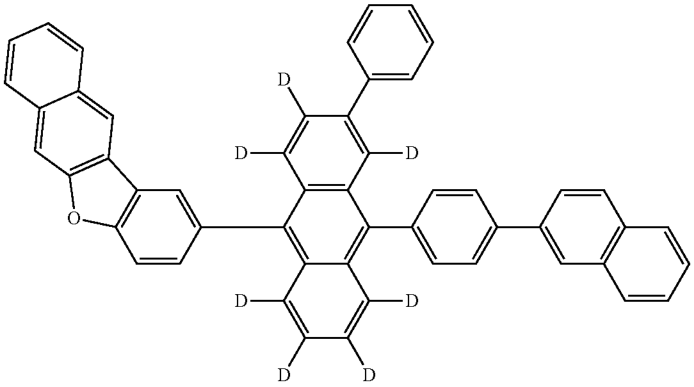

-continued
[Formula 129]
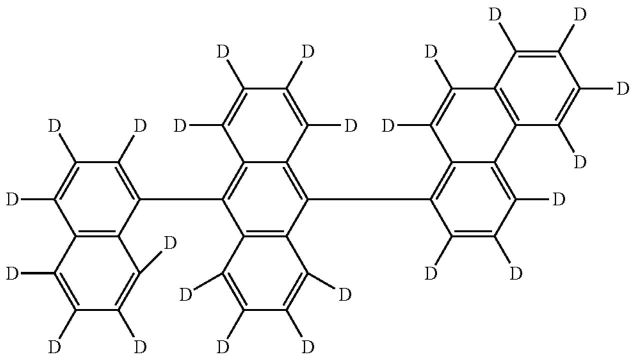
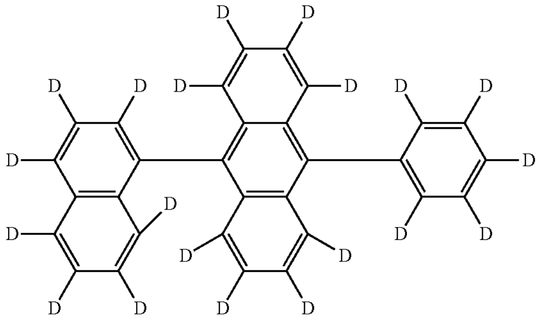
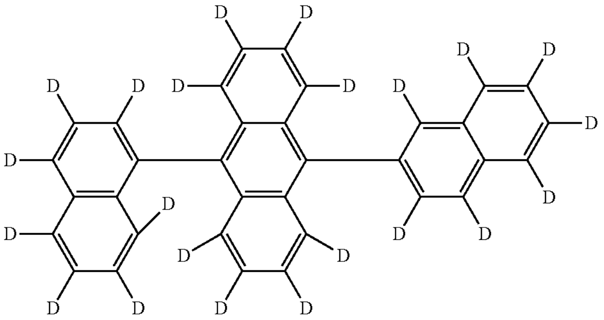
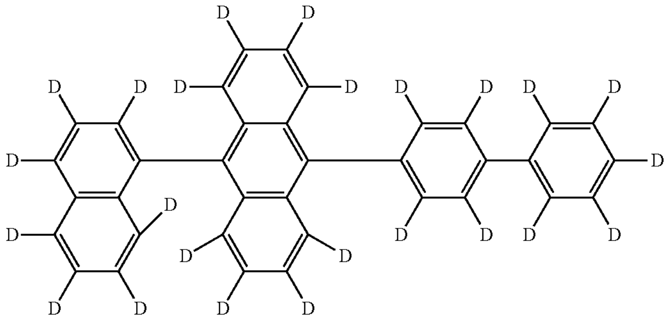
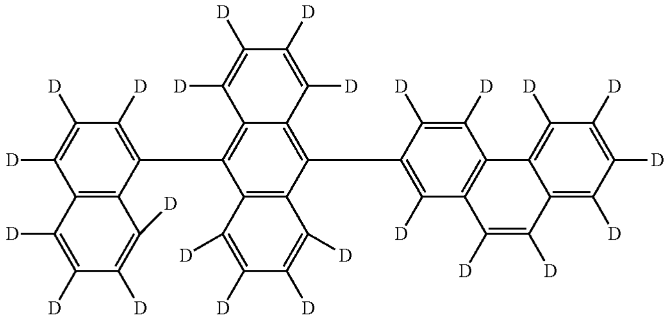
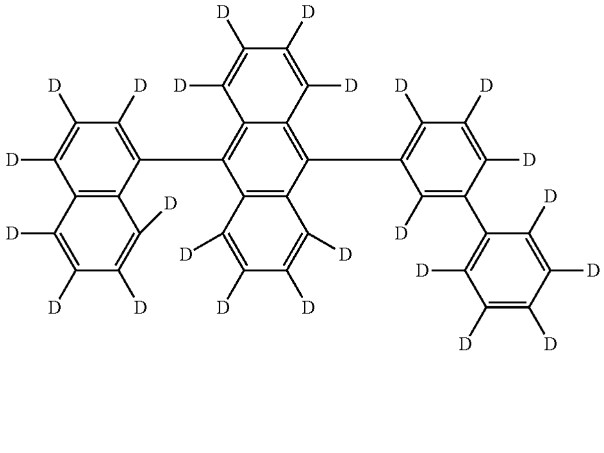

-continued
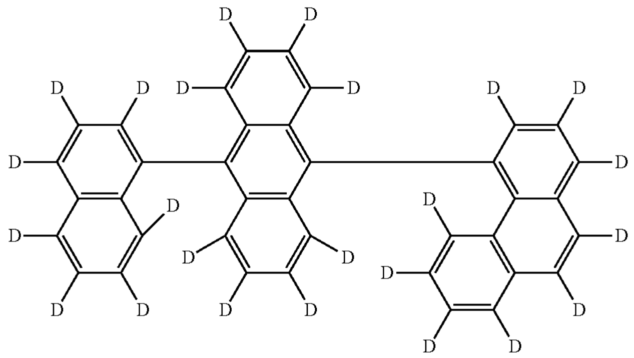
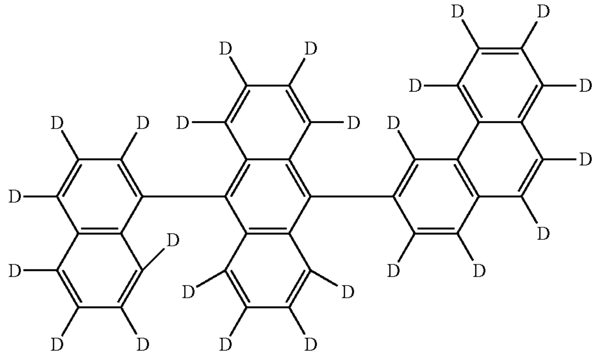
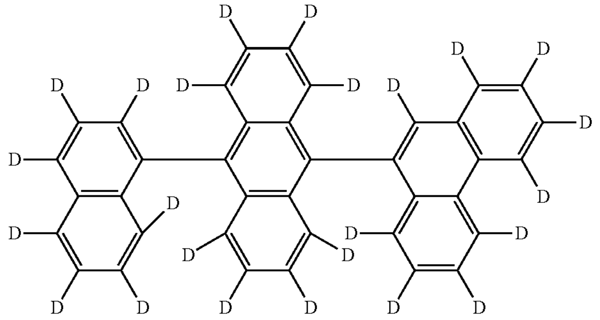
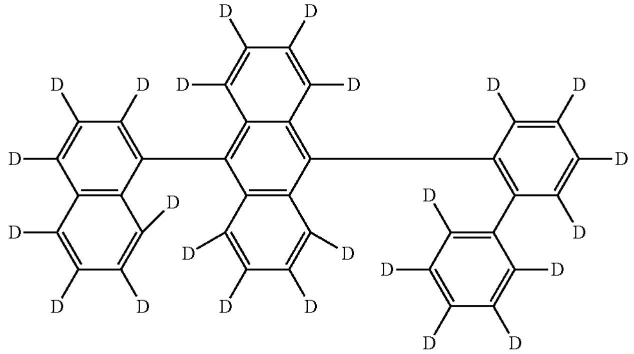
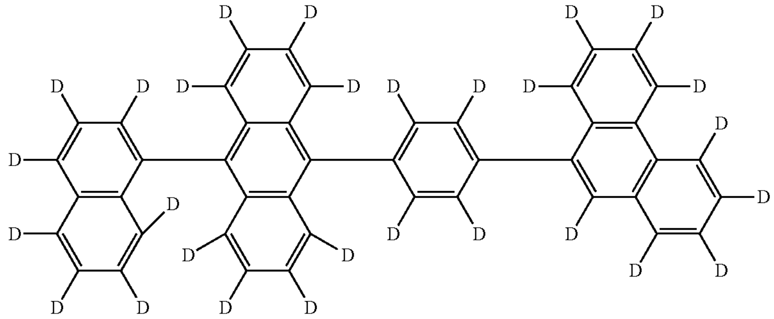

-continued
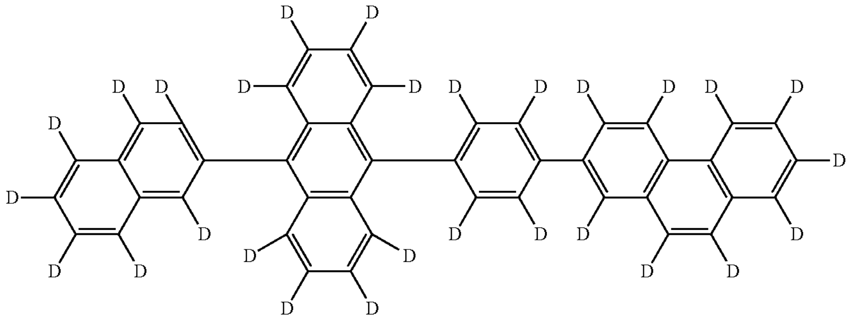
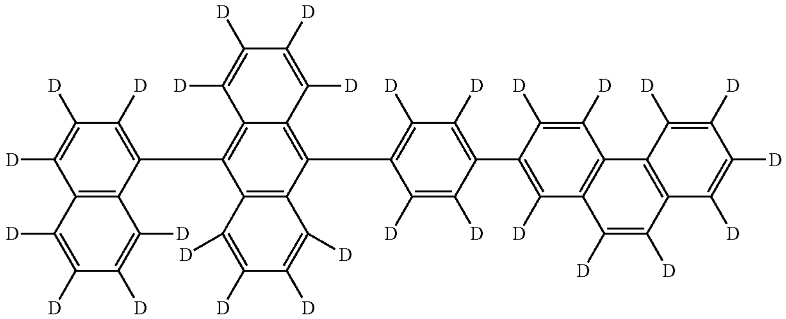
[Formula 130]
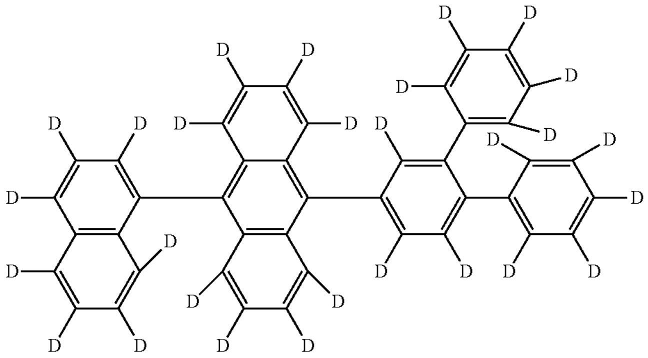
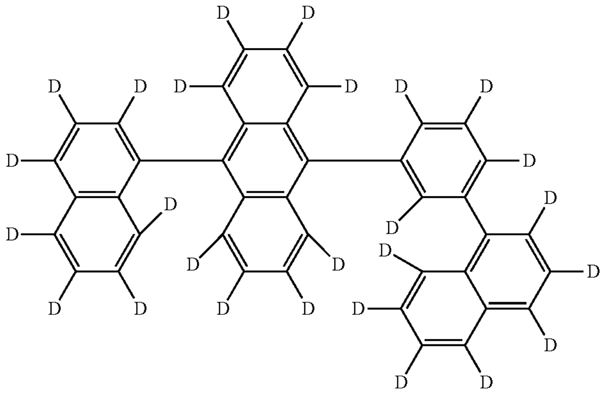

-continued
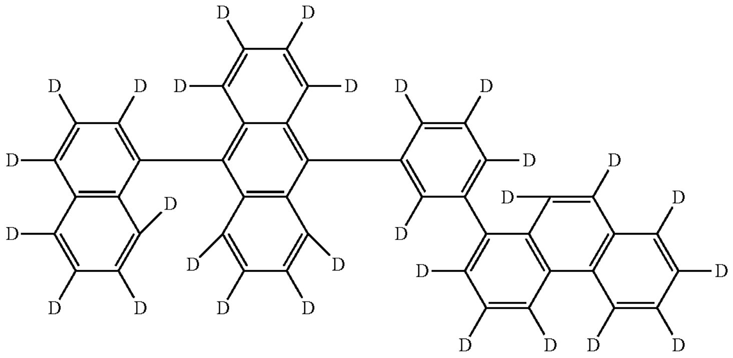
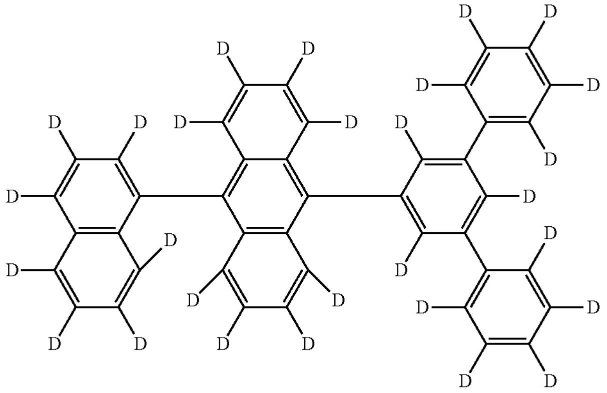
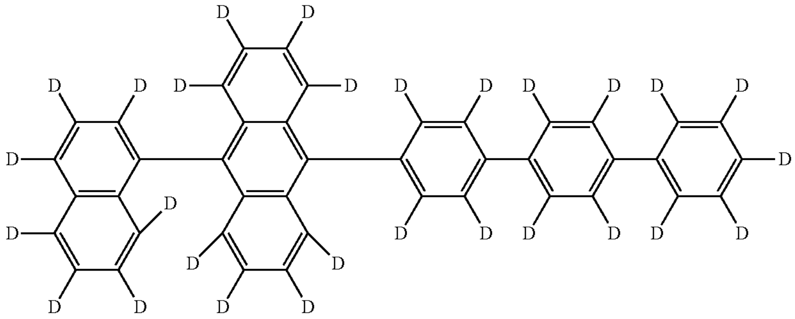
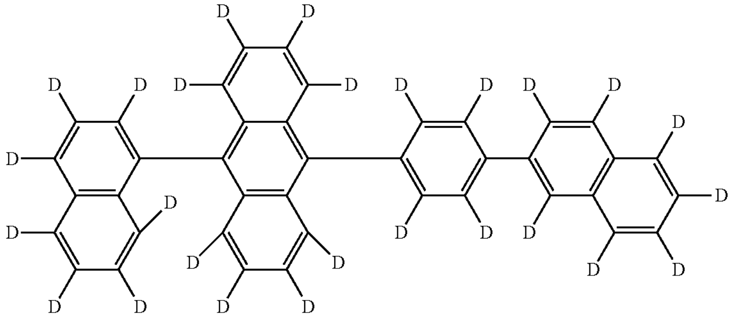
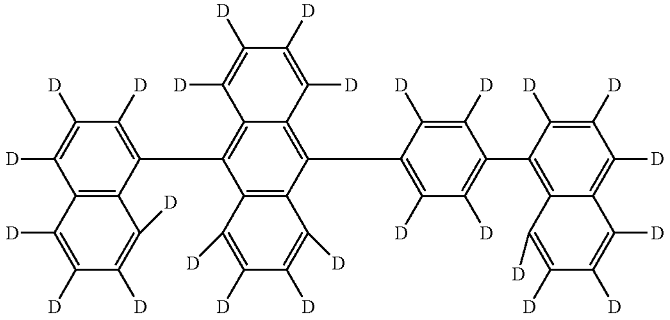

-continued
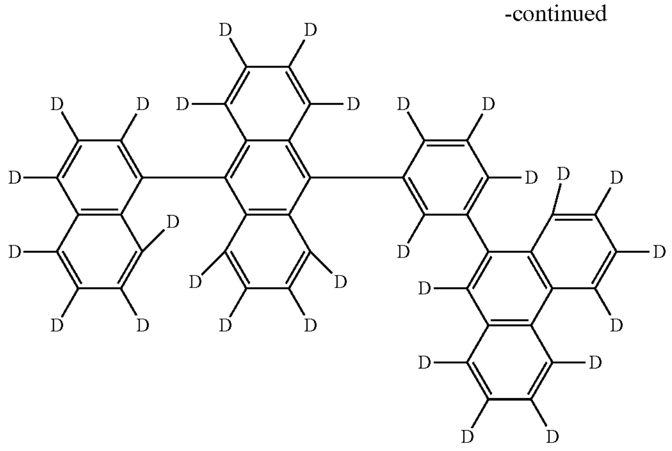
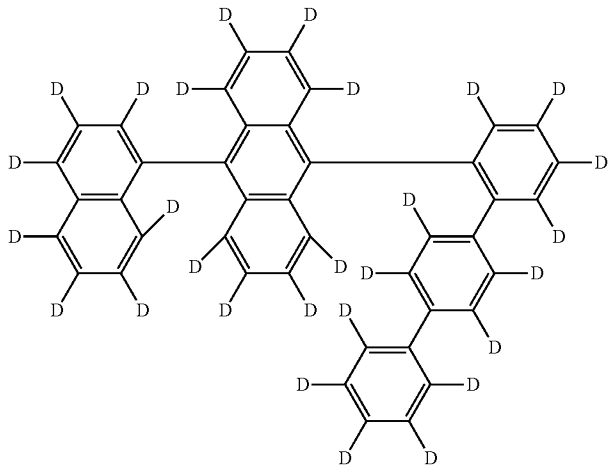
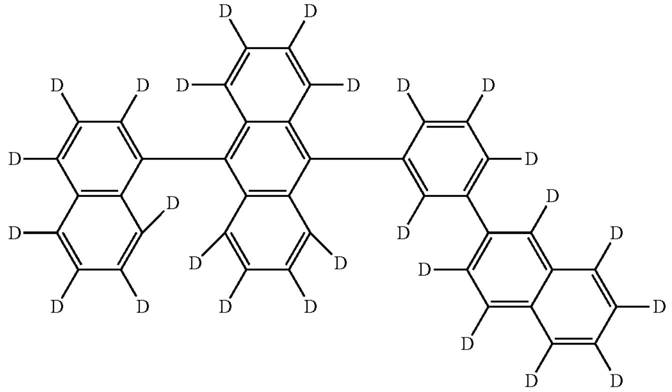

-continued
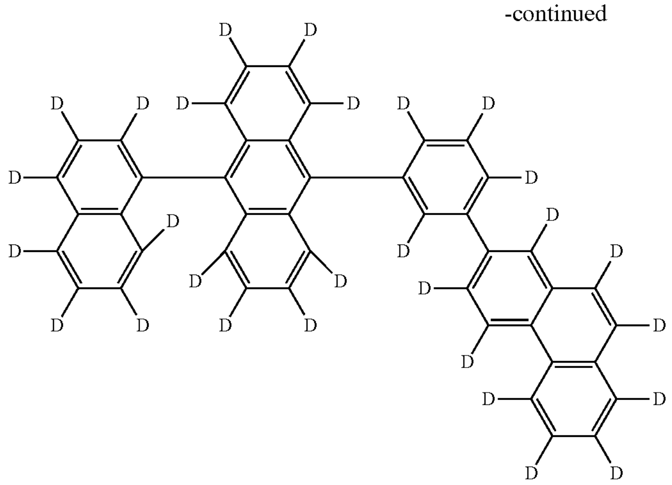
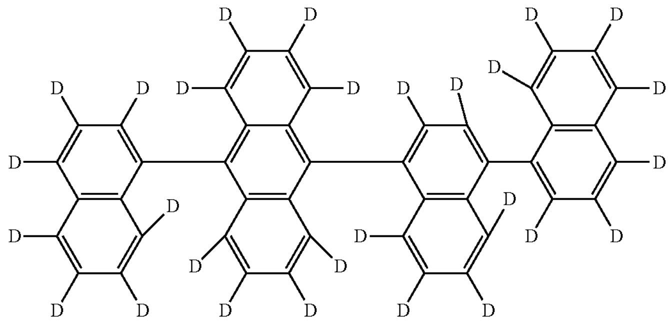
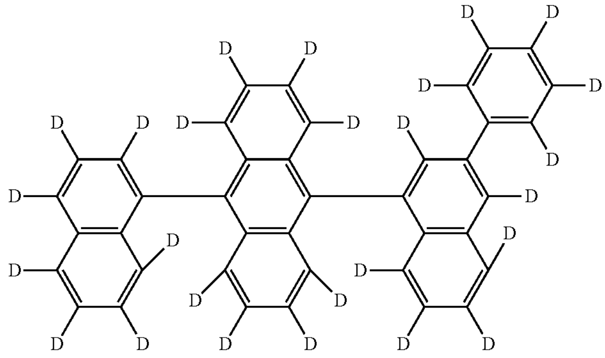
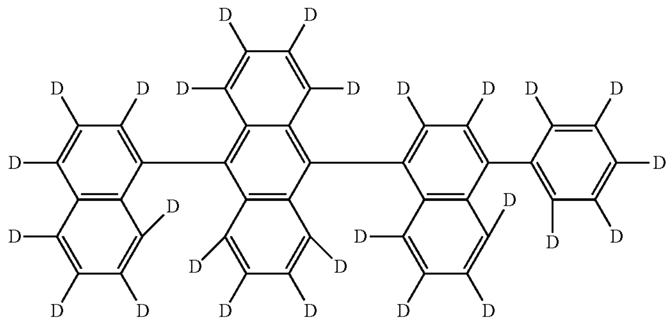

-continued
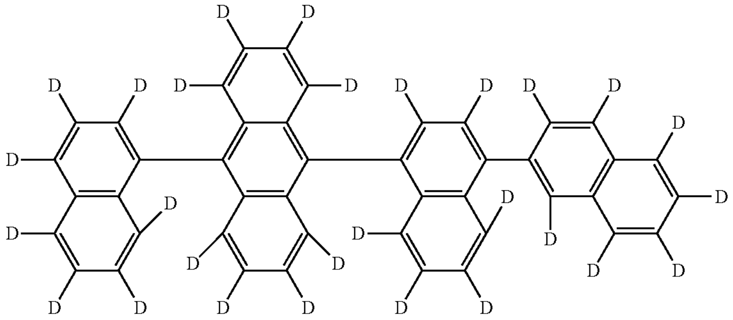
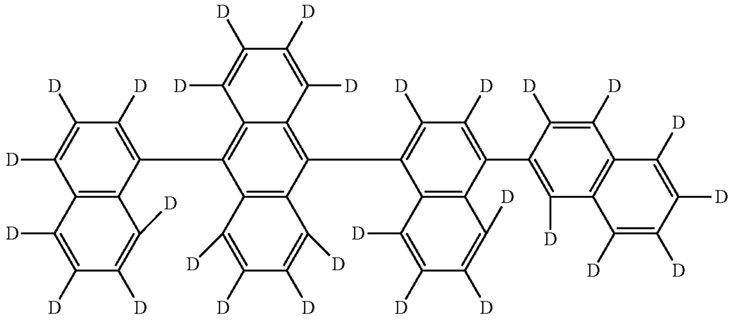
[Formula 131]
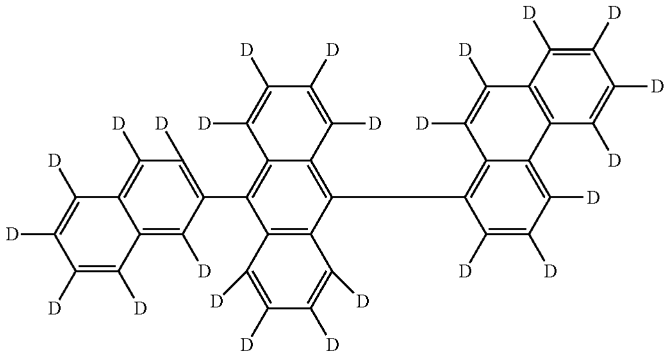
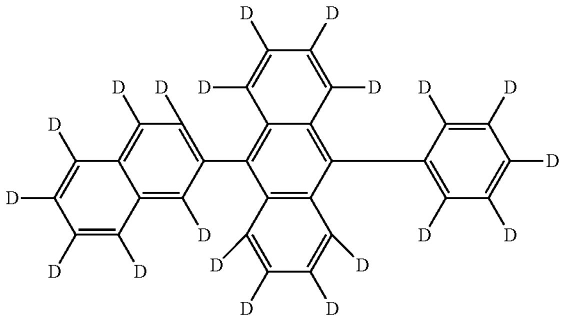
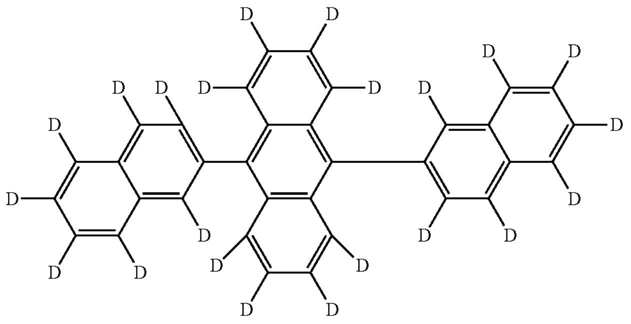

-continued
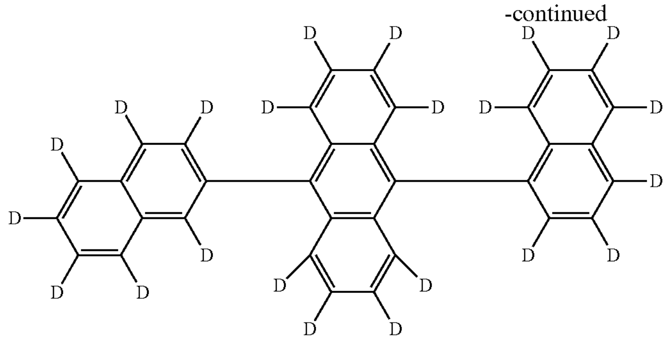
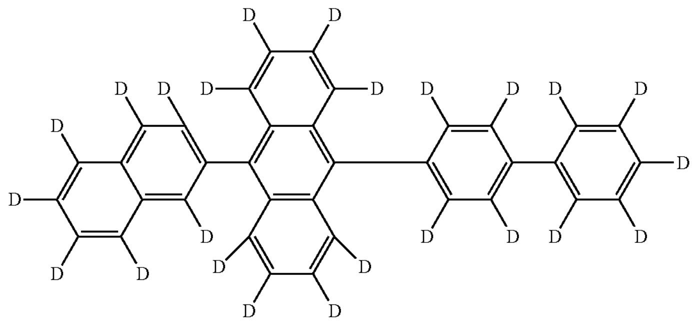
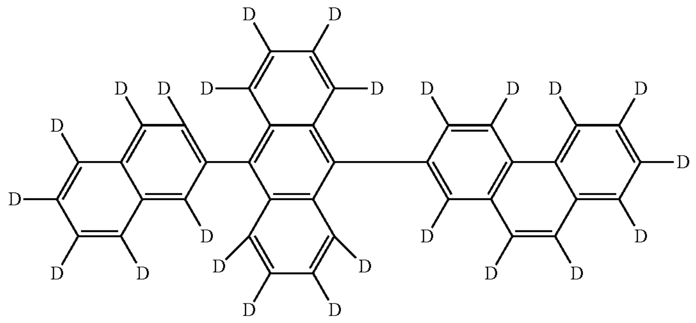
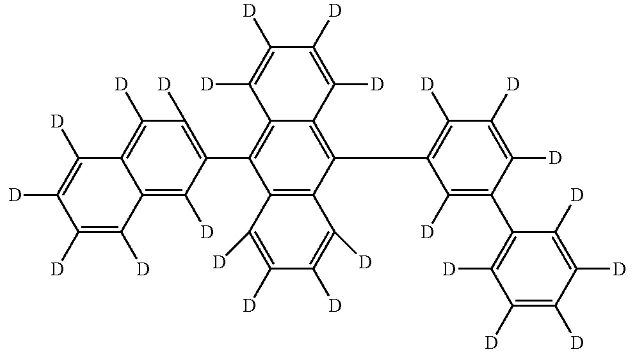
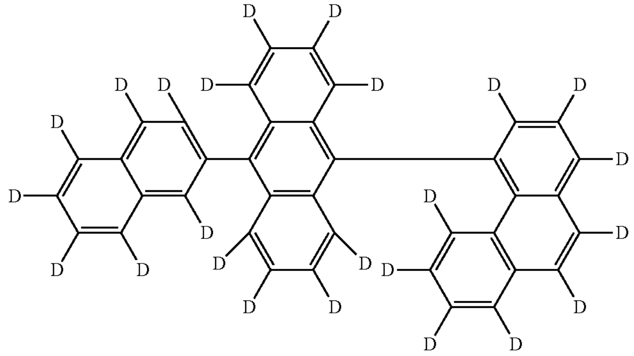

-continued
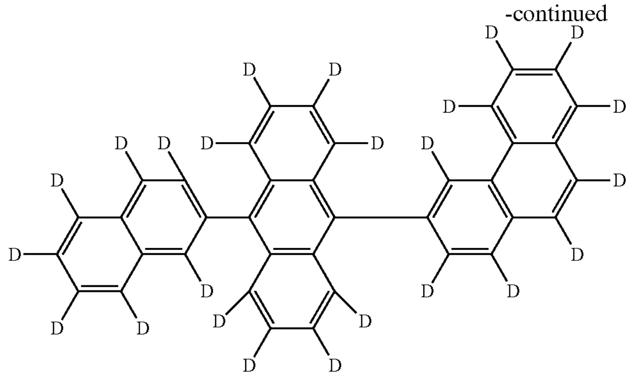
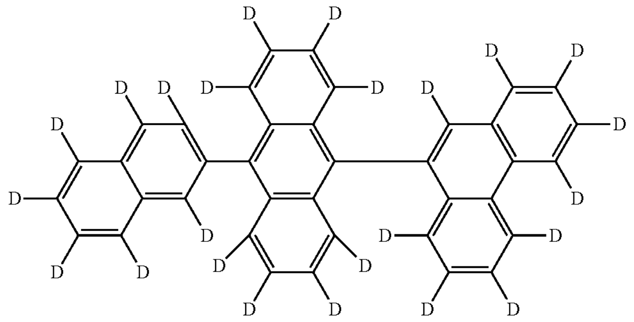
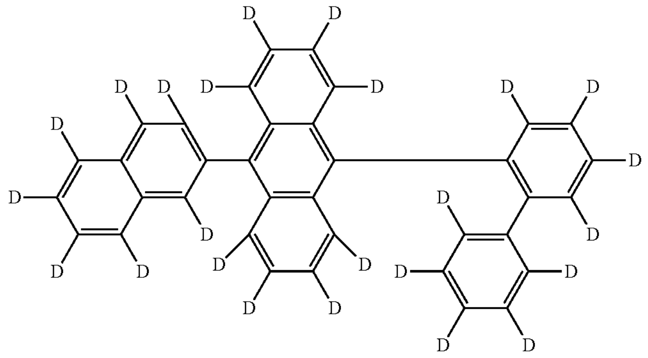
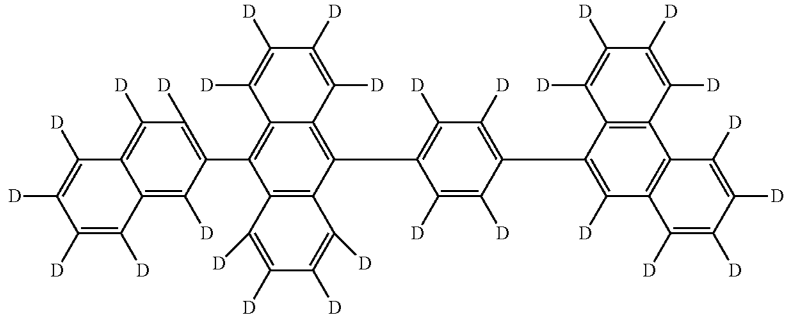

-continued
[Formula 132]
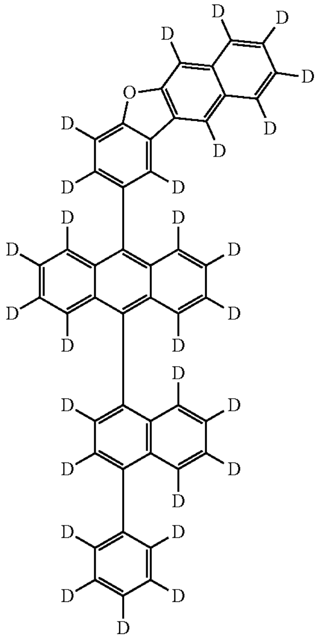
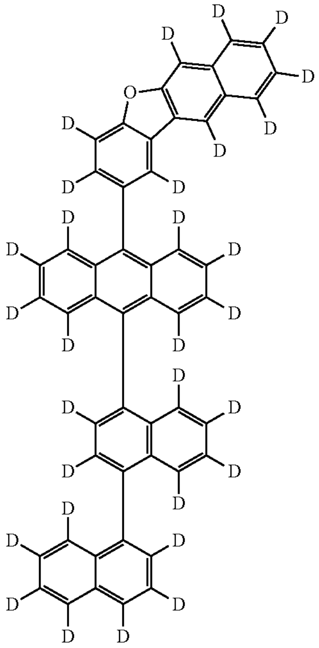
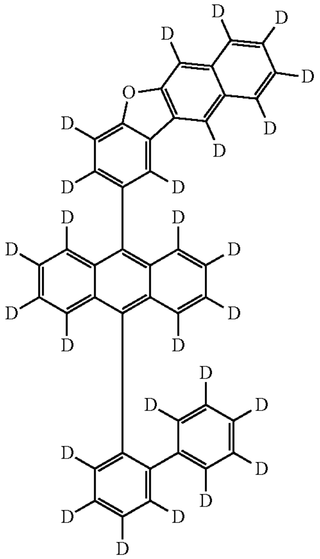
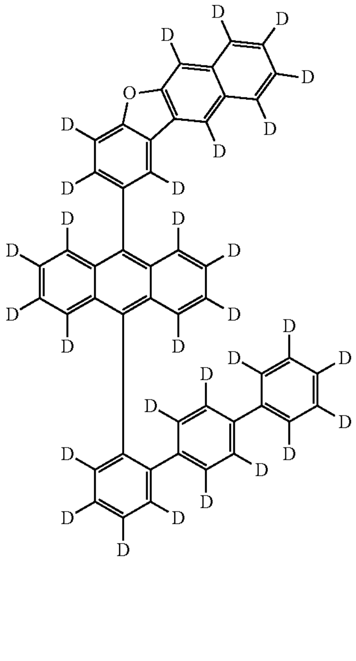
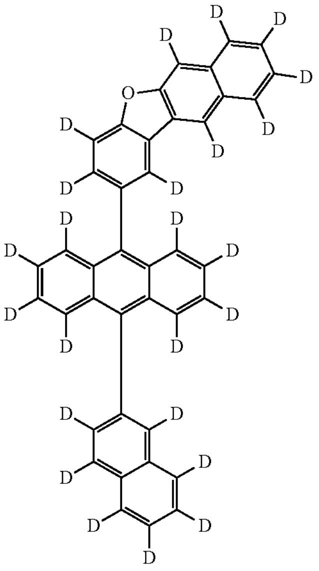
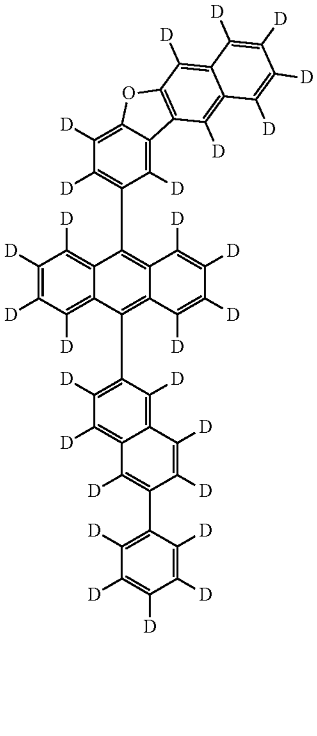

-continued
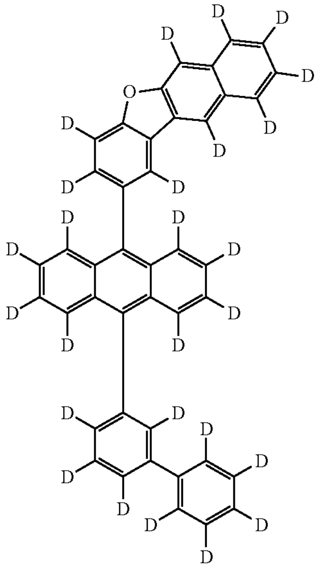
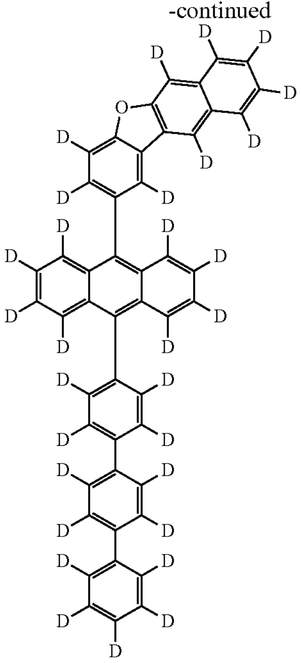
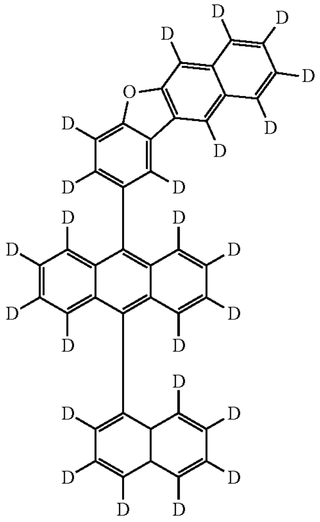
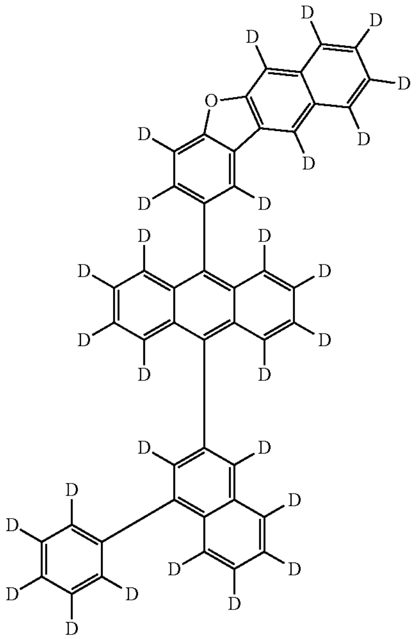
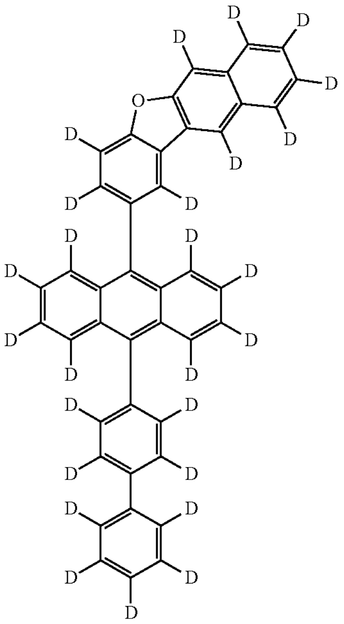

-continued
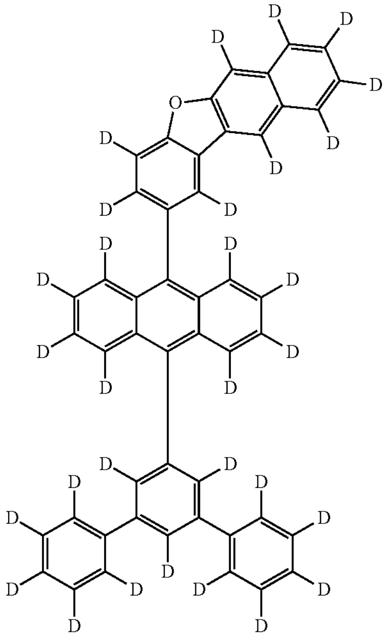
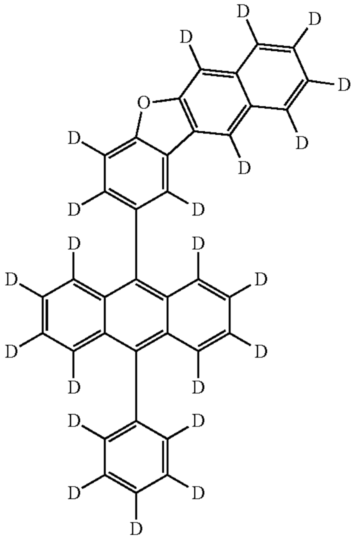
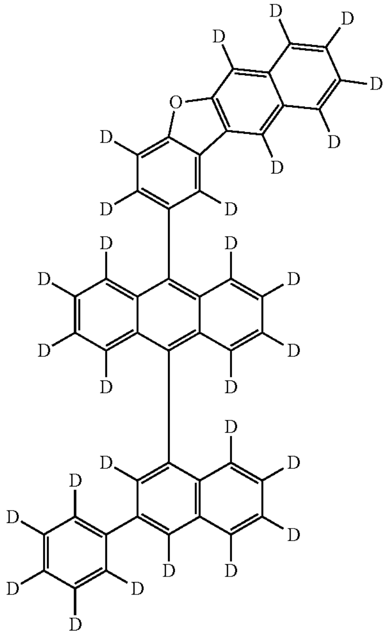
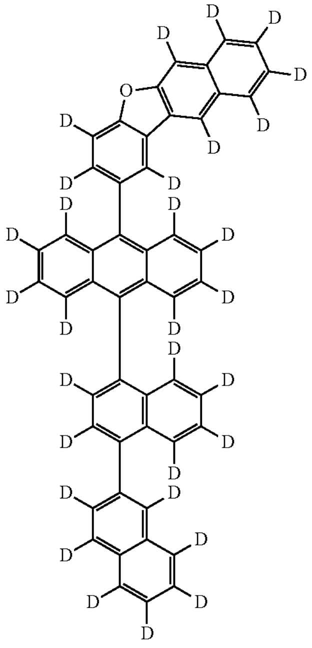
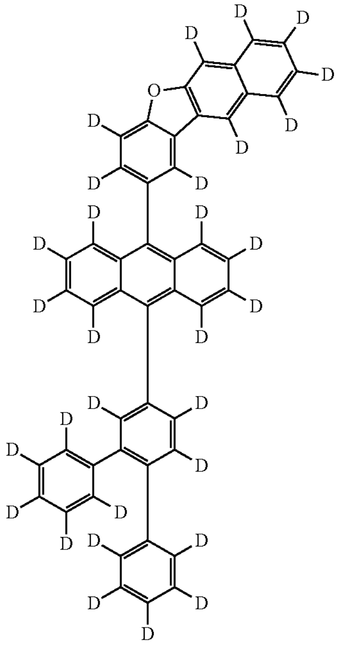

-continued
[Formula 133]
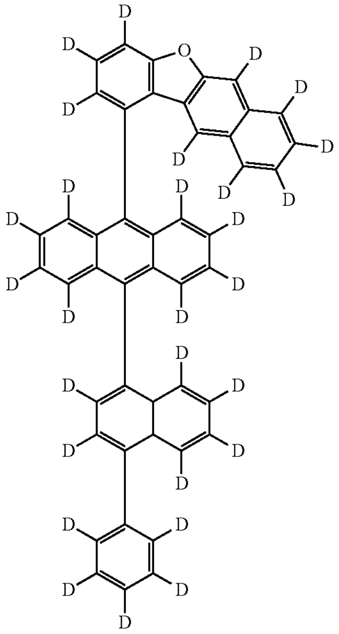
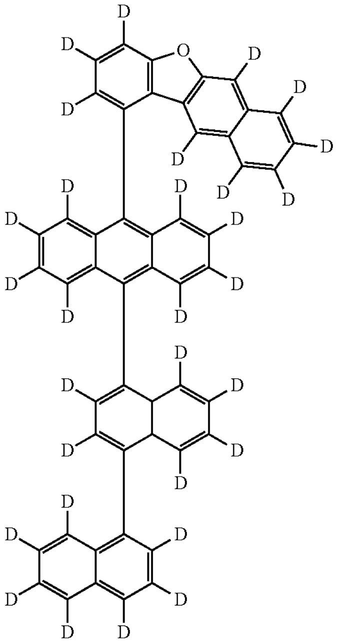
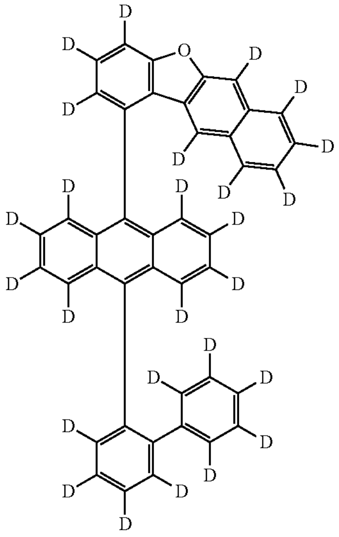
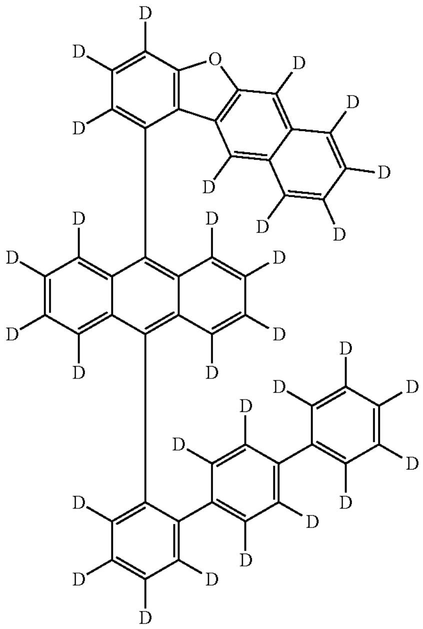
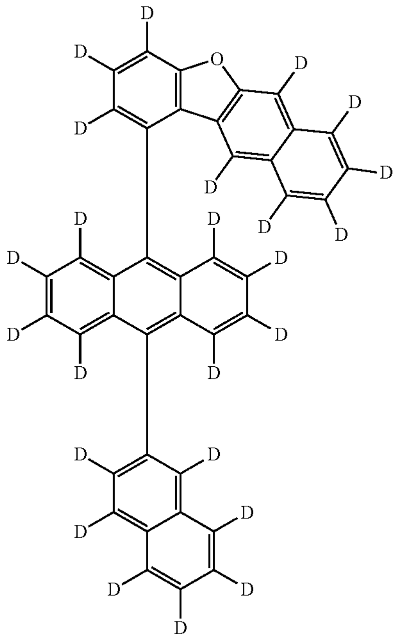

-continued
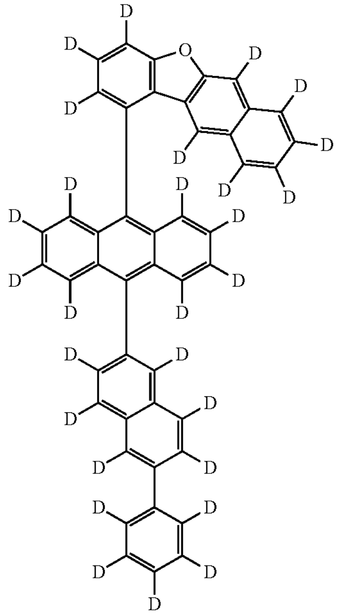
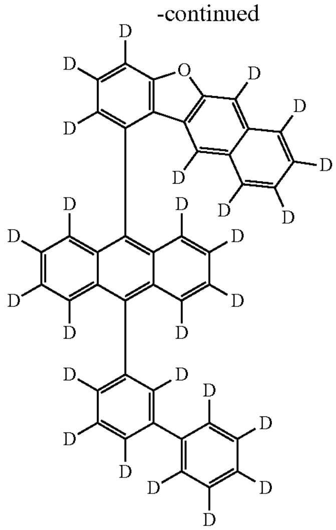
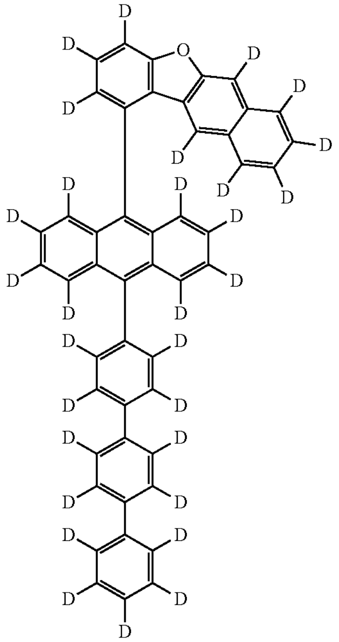
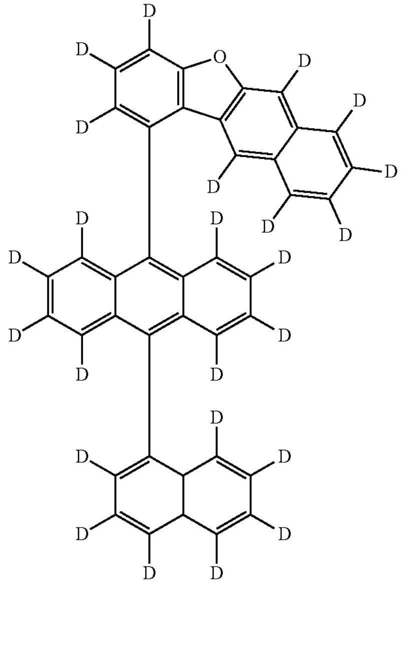
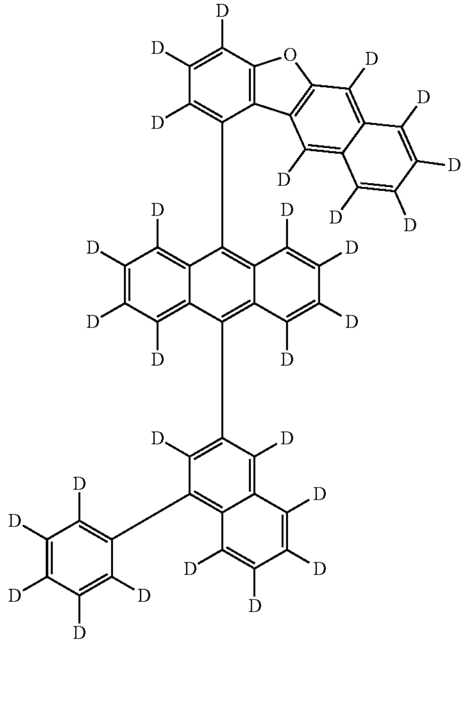

-continued
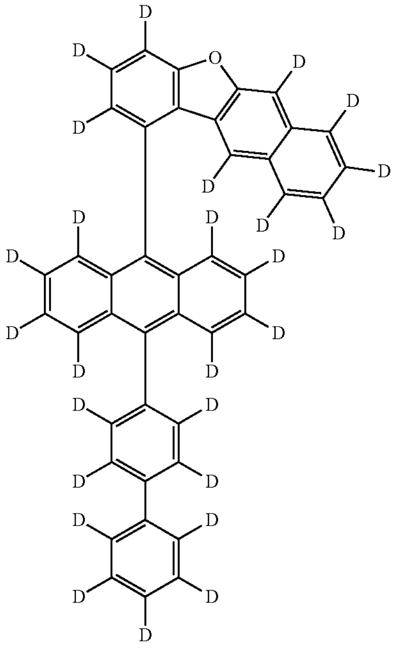
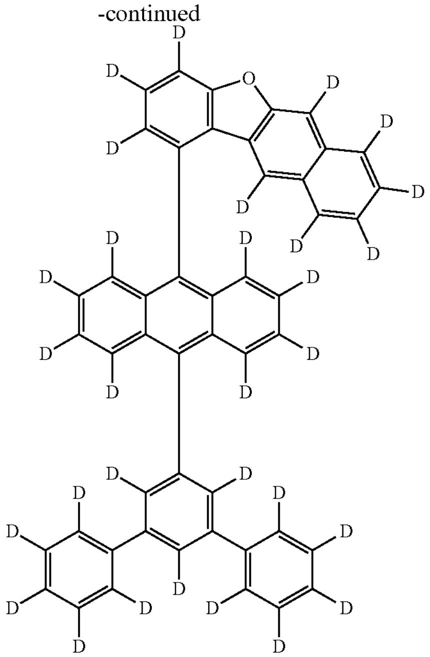
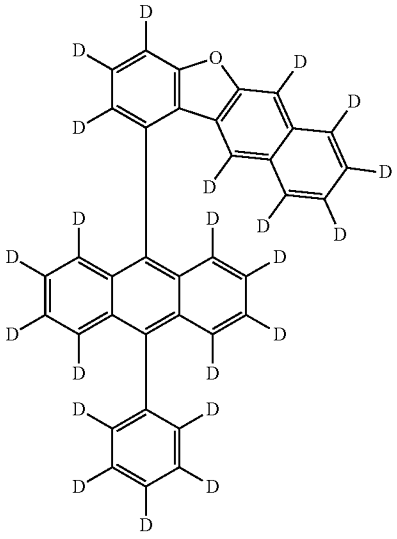
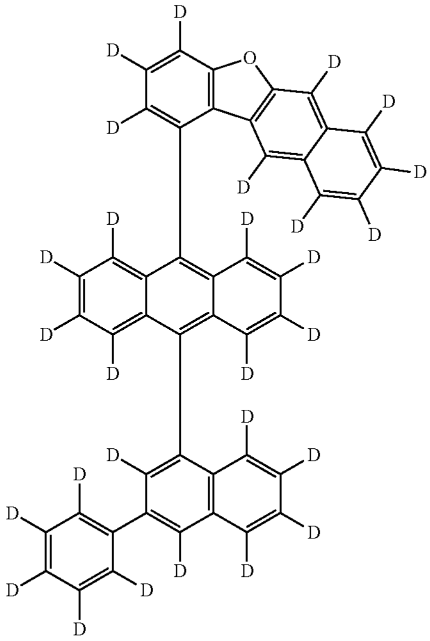

-continued
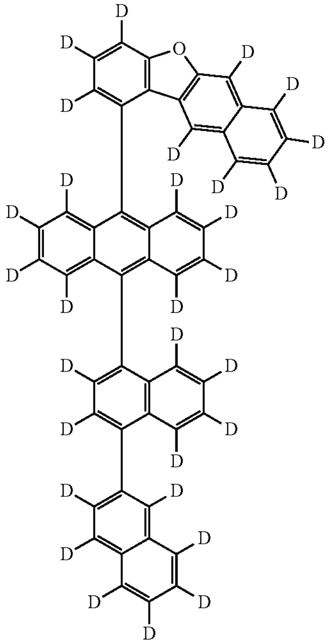
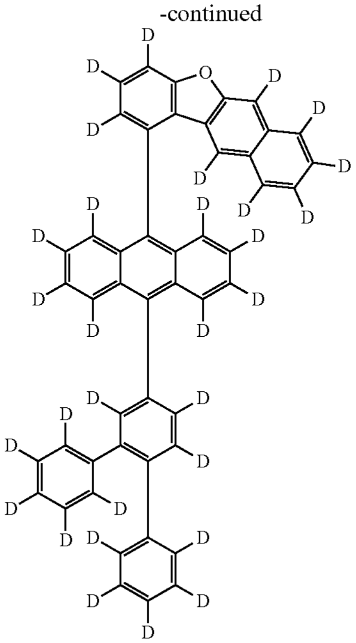
[Formula 134]
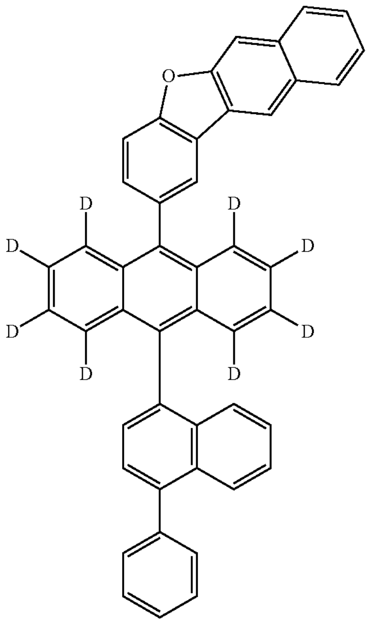
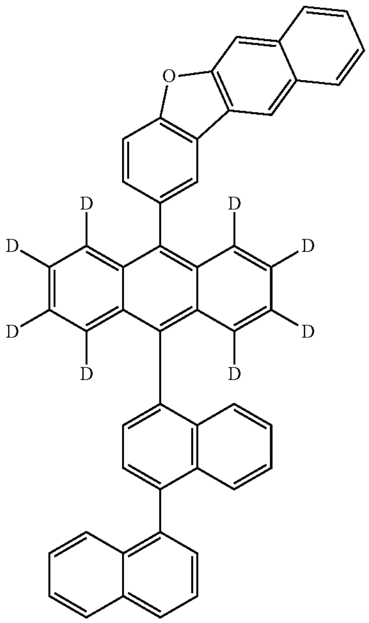

-continued
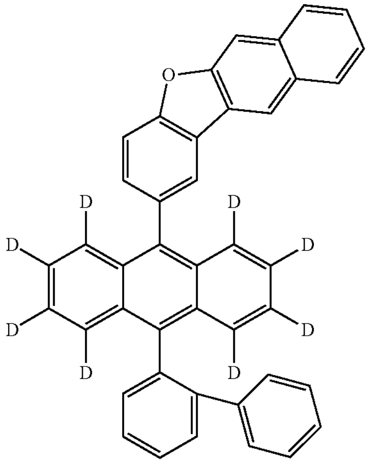
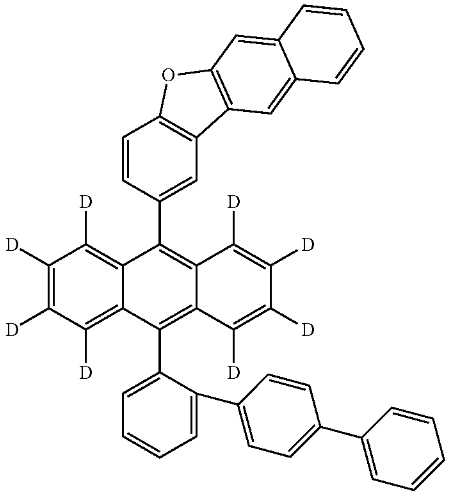
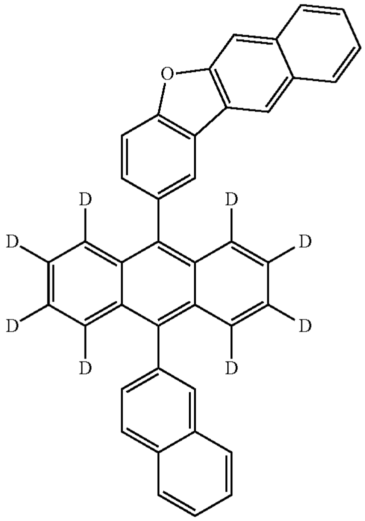
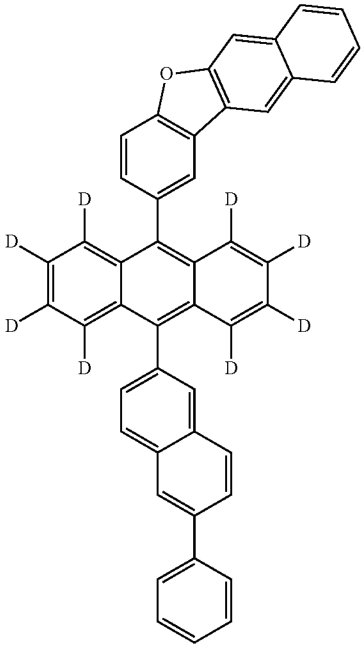
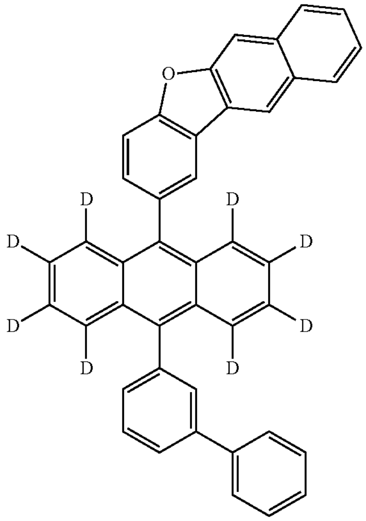

-continued
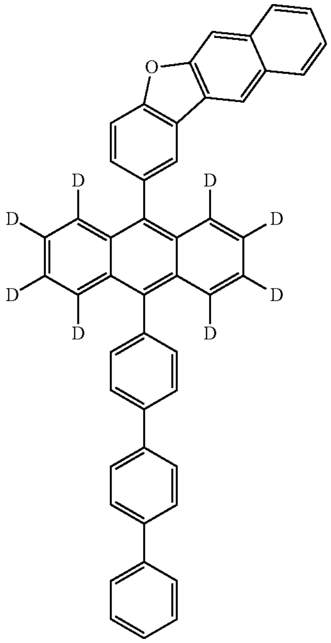
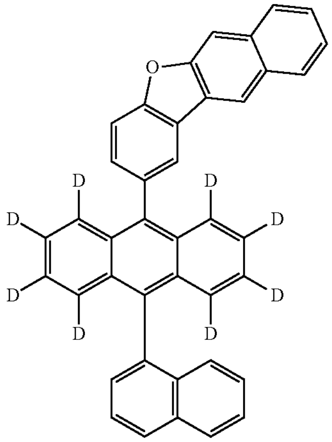
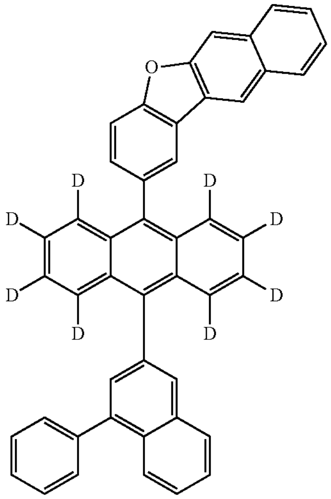
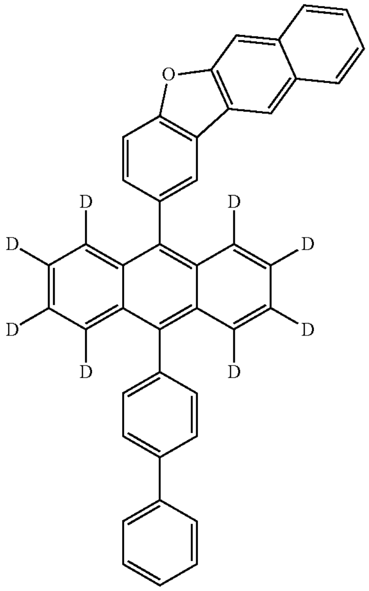
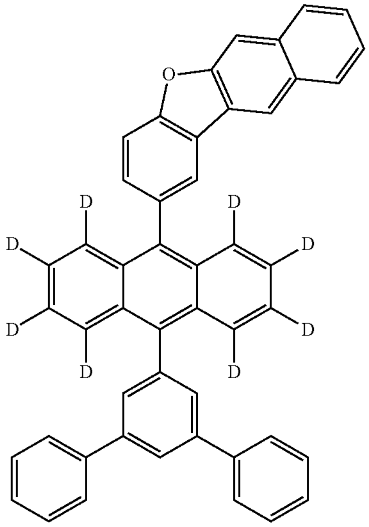
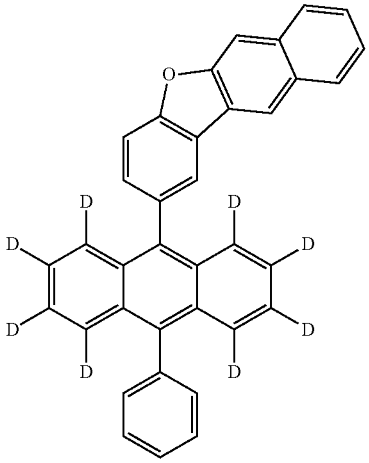

-continued
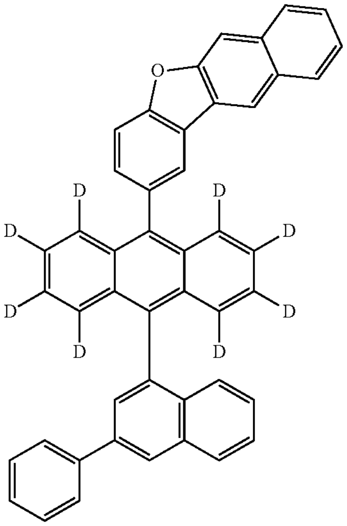
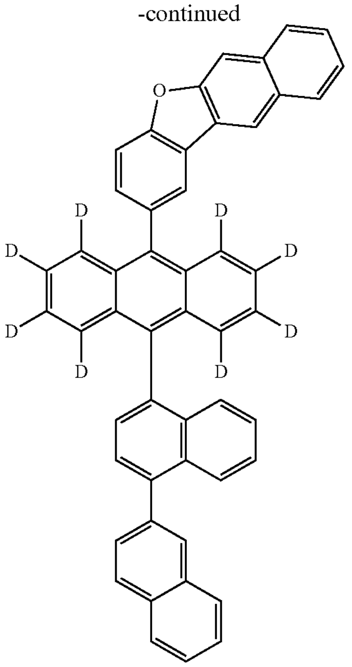
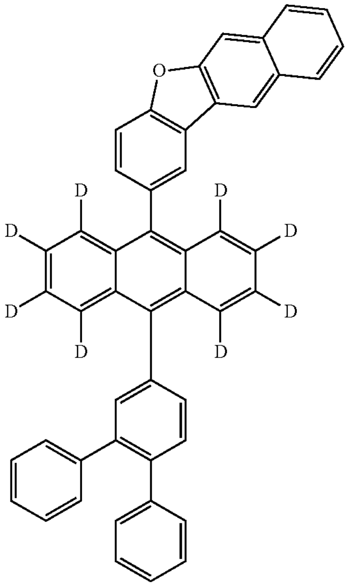
[Formula 135]
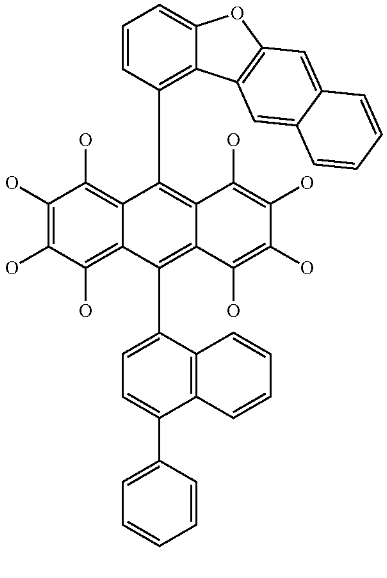
-continued
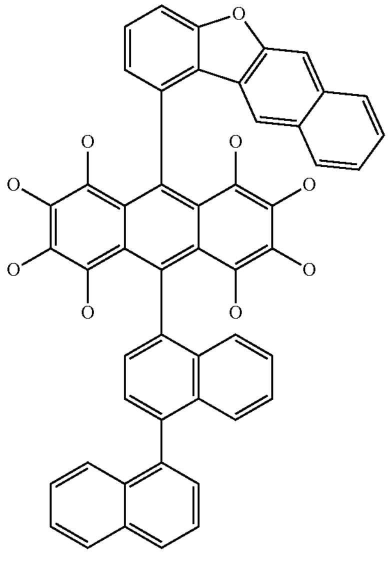

-continued
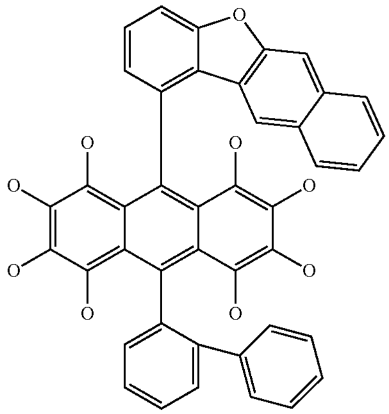
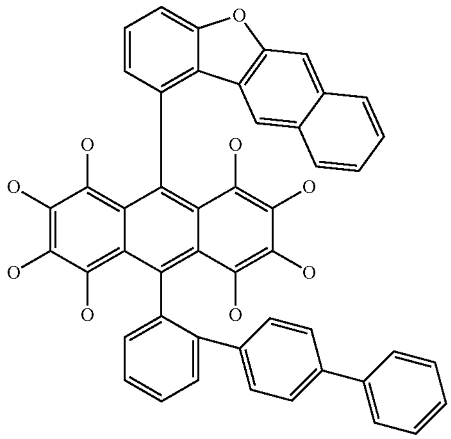
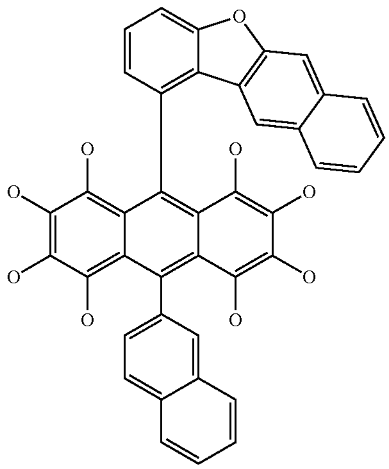
-continued
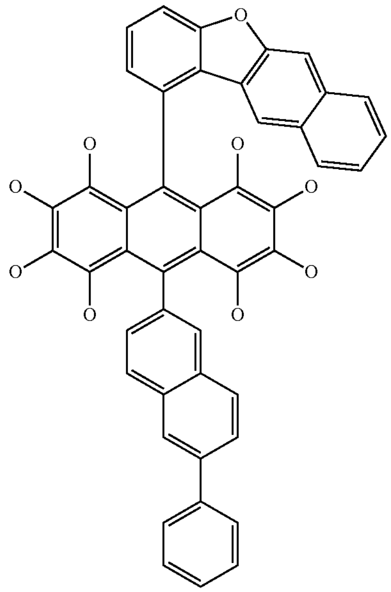
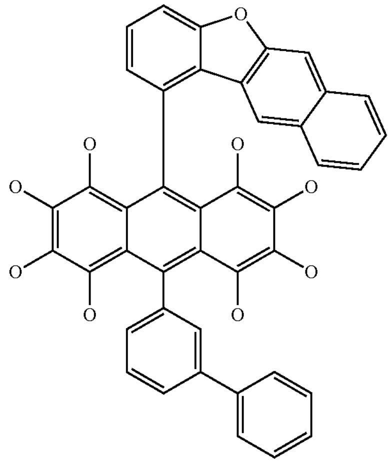
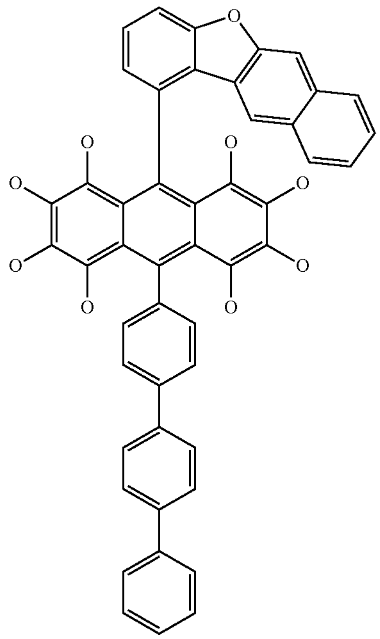

-continued
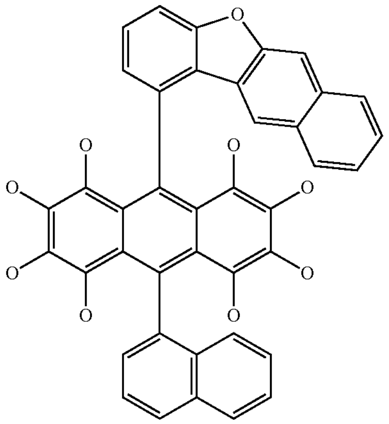
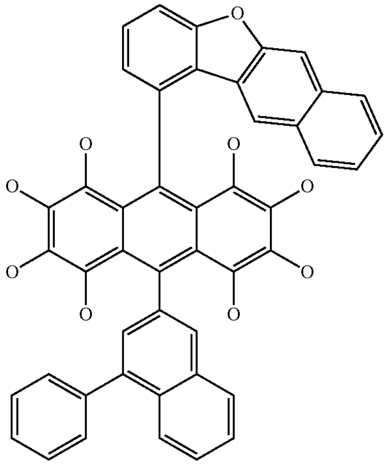
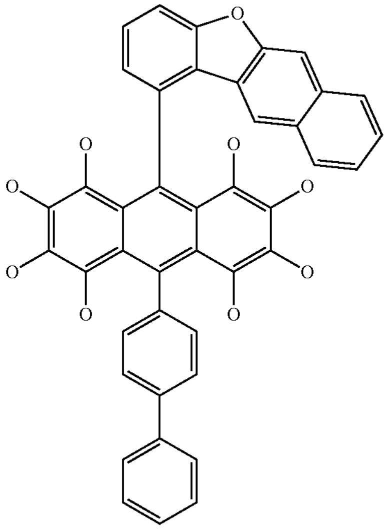
-continued
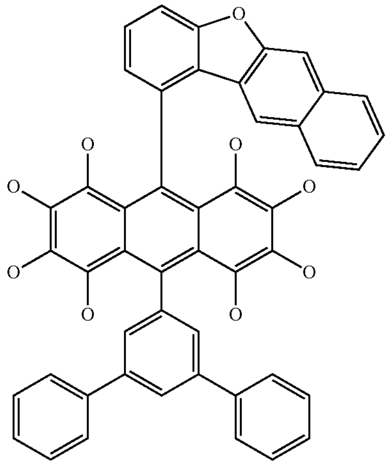
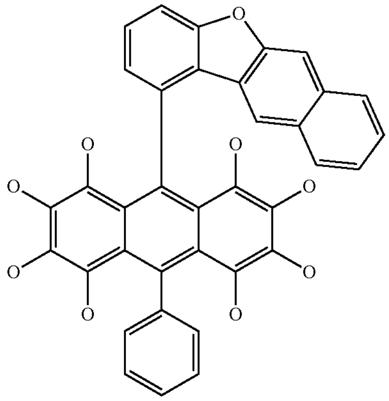
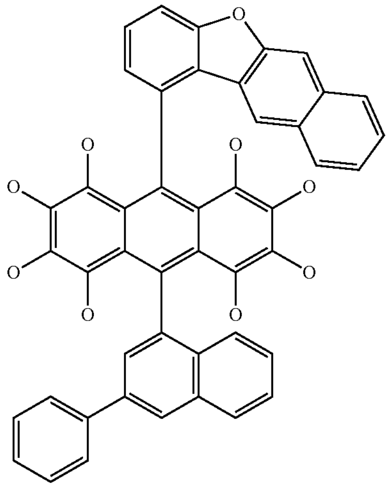

-continued
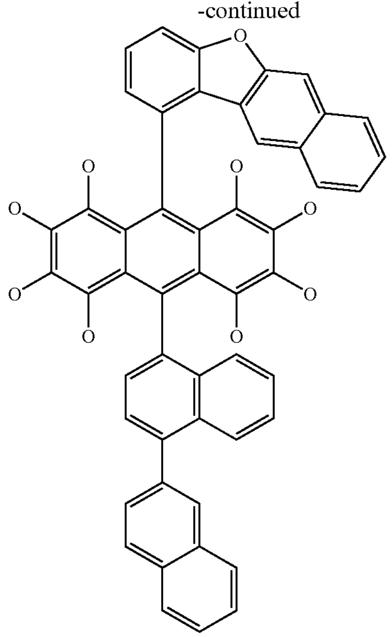
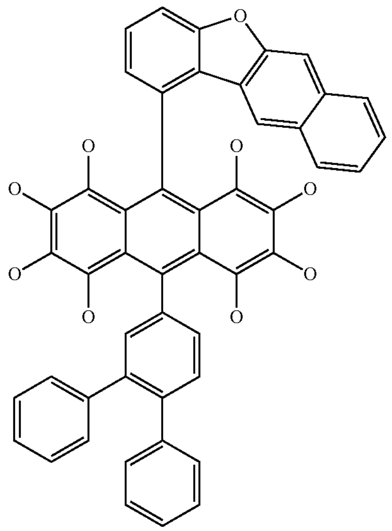
-continued
[Formula 136]
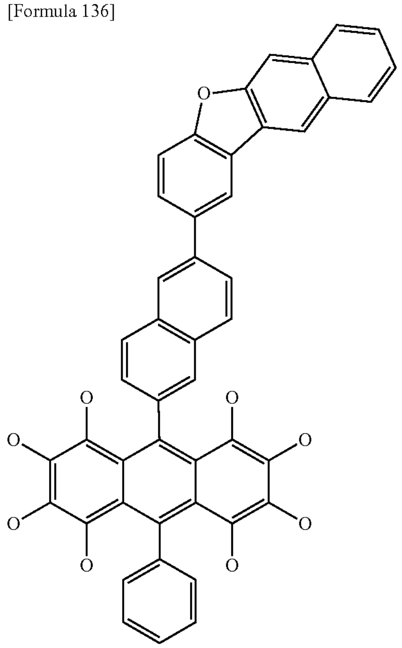
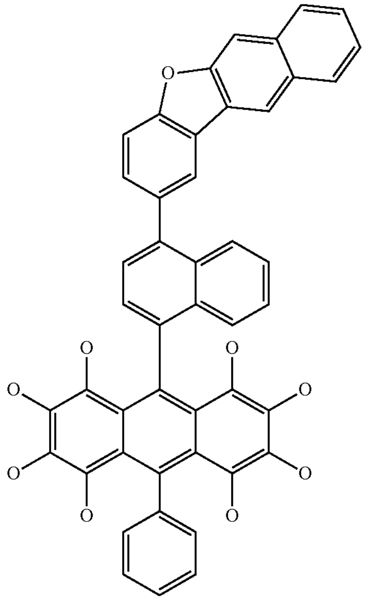
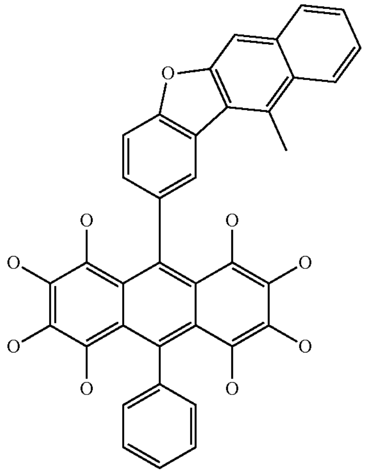

-continued
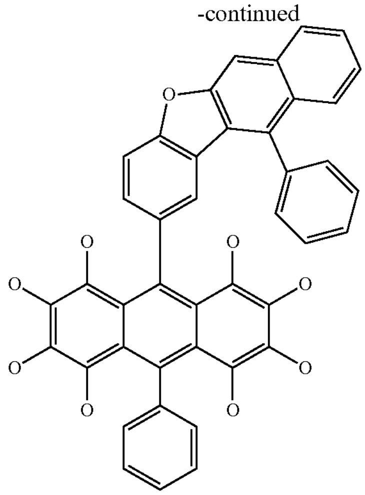
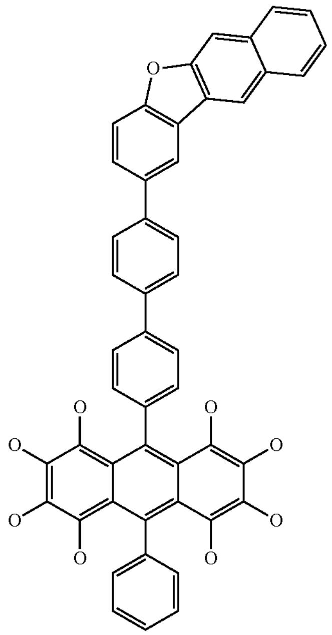
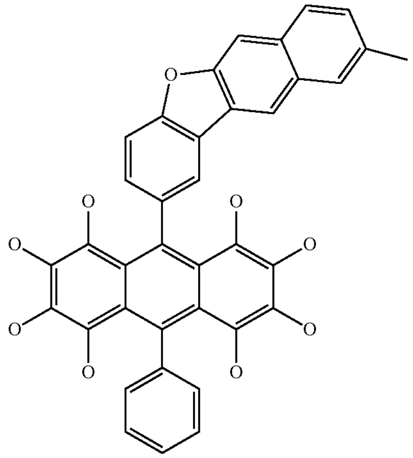
-continued
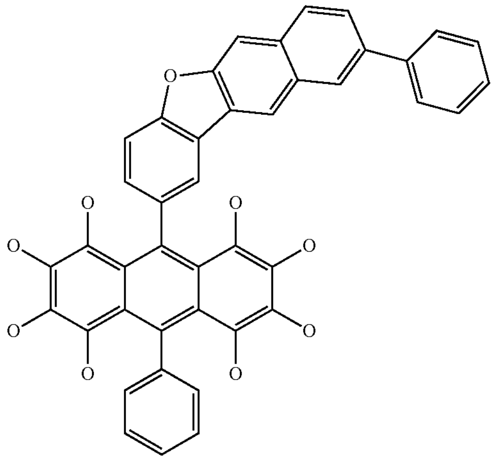
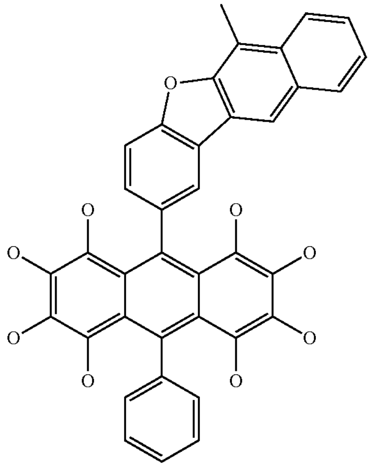
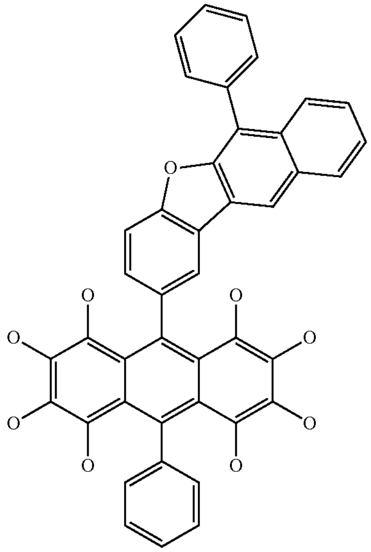

-continued
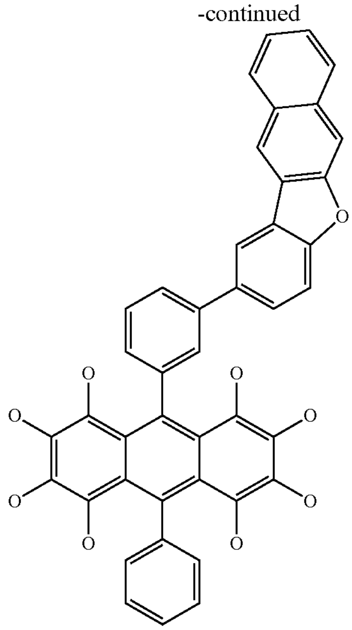
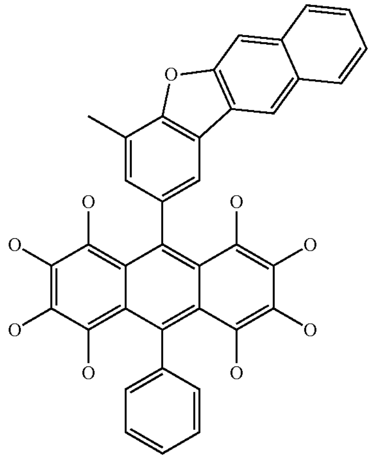
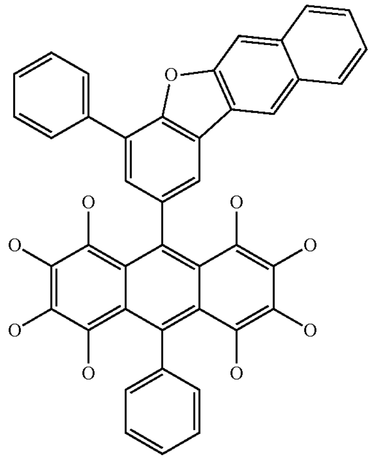
-continued
[Formula 137]
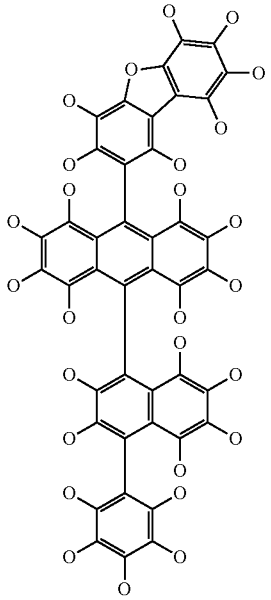
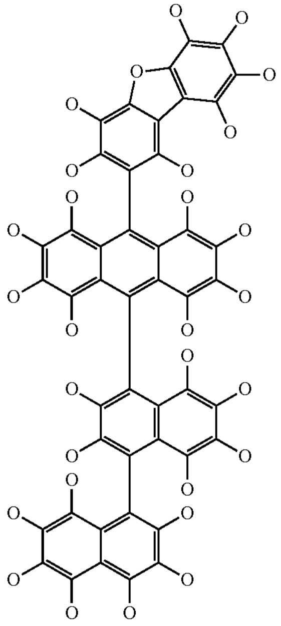

-continued
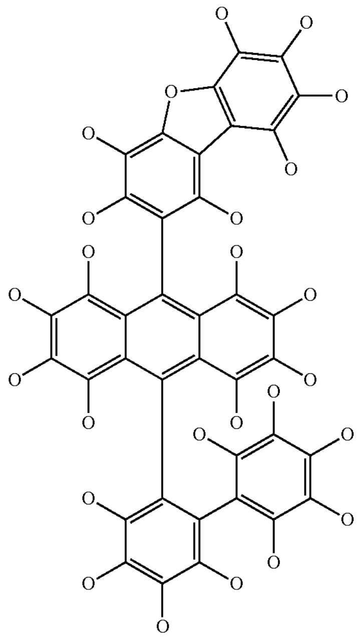
-continued
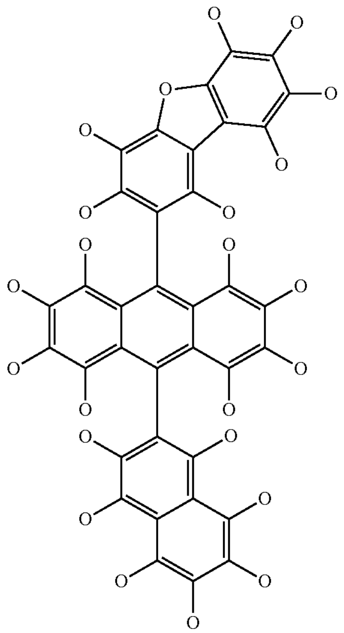
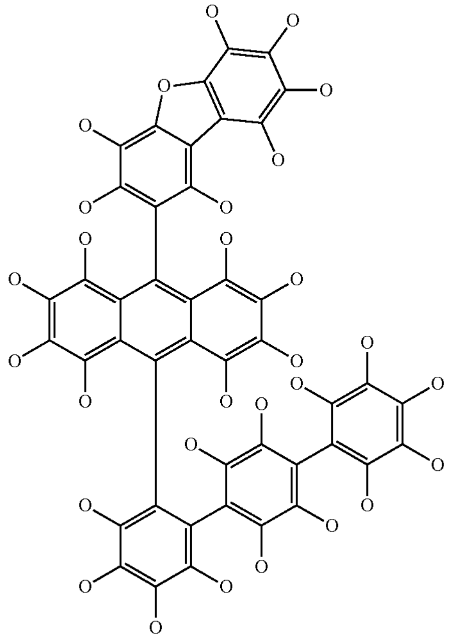
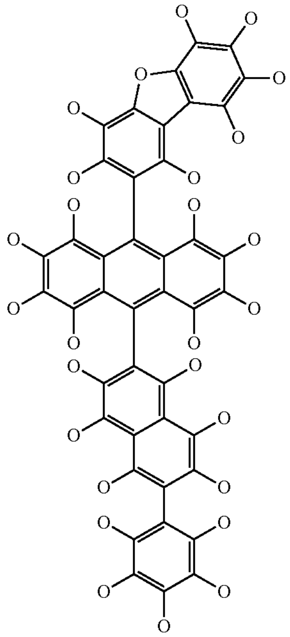

-continued
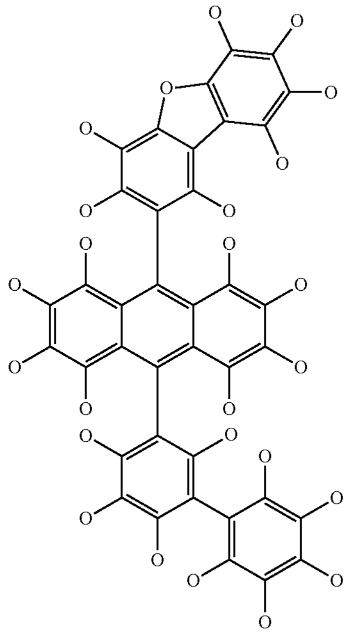
-continued
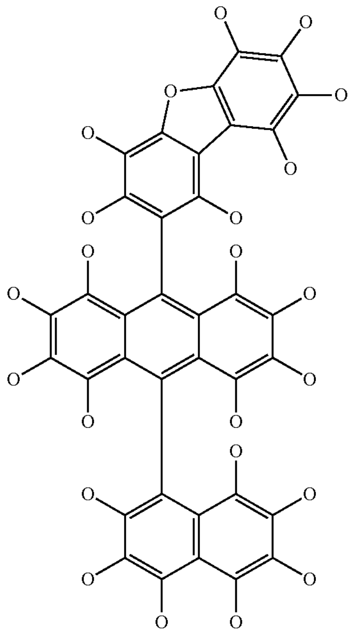
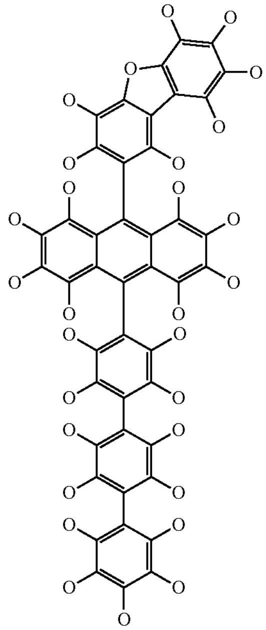
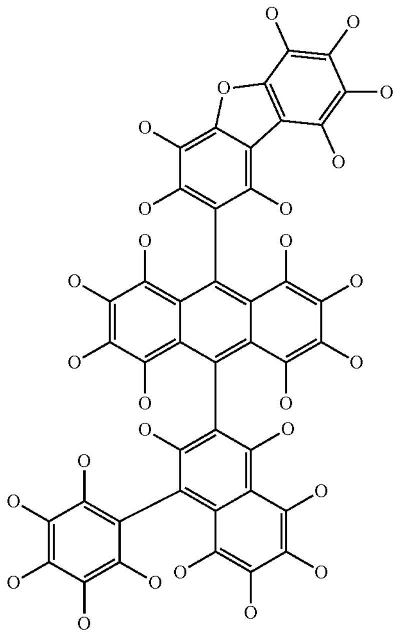

-continued
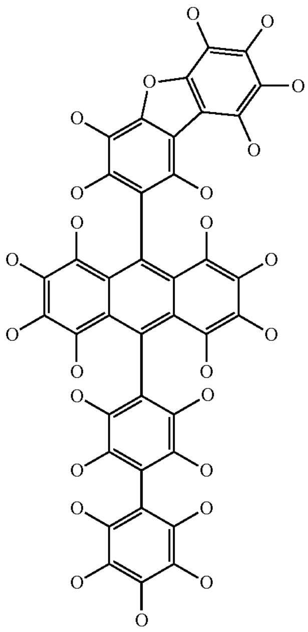
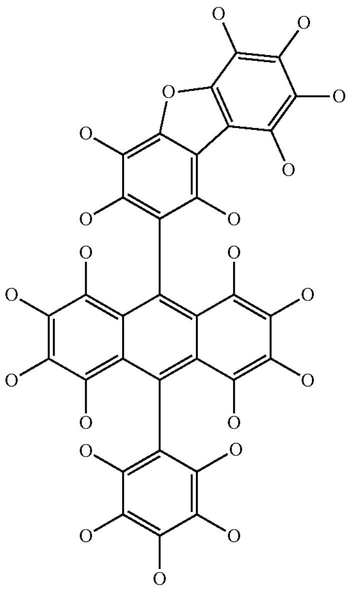
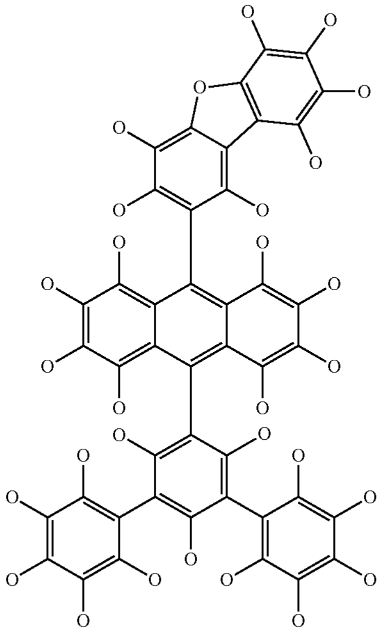
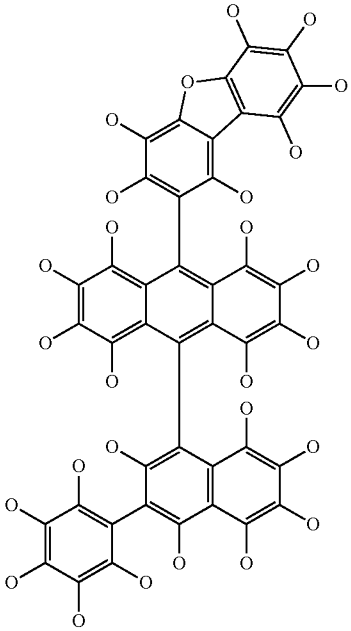

-continued
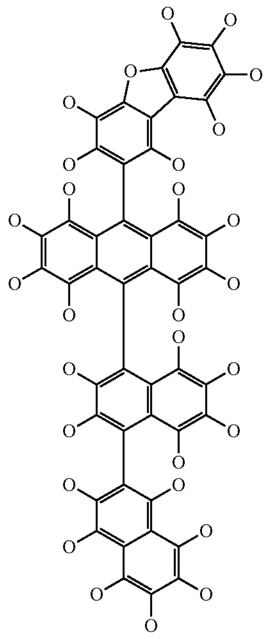
-continued
[Formula 138]
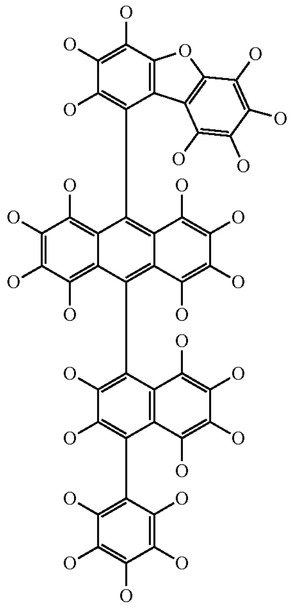
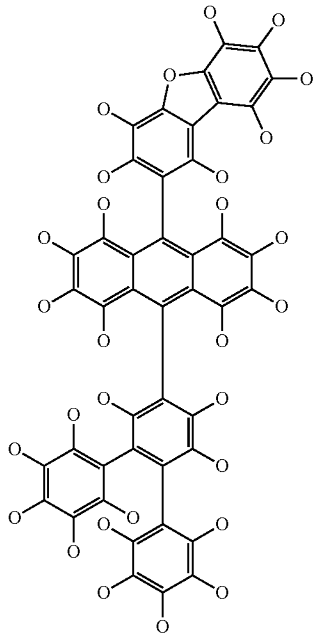
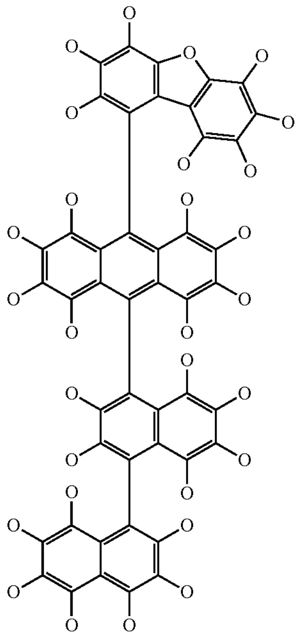

-continued
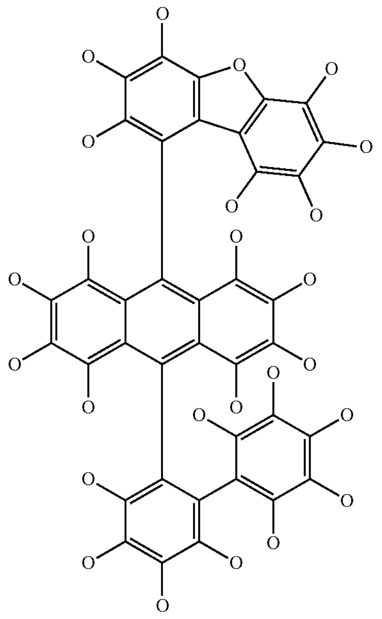
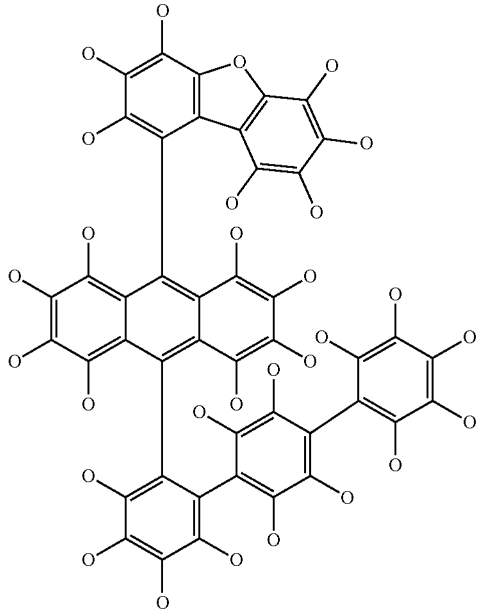
-continued
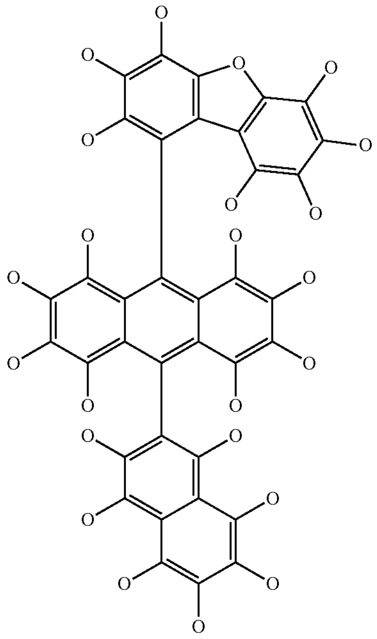
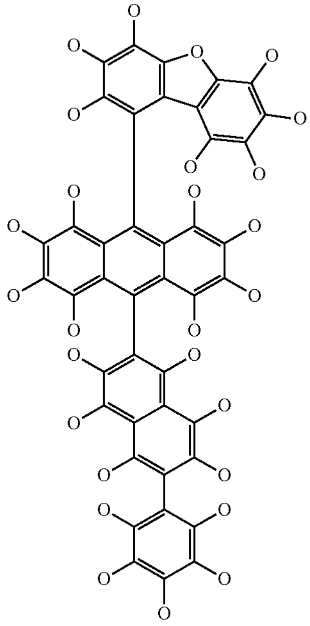

-continued
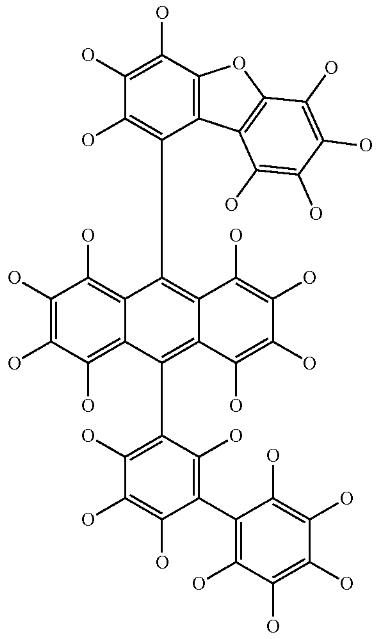
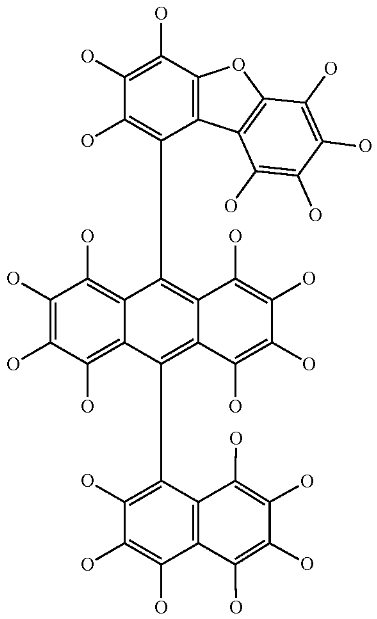
-continued
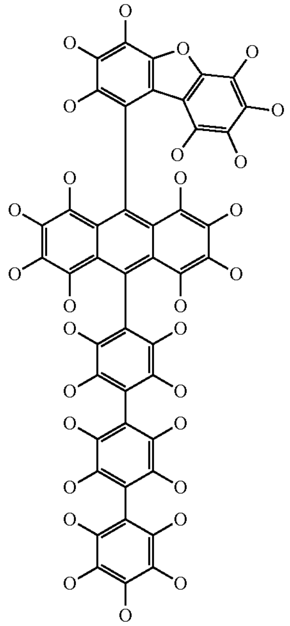
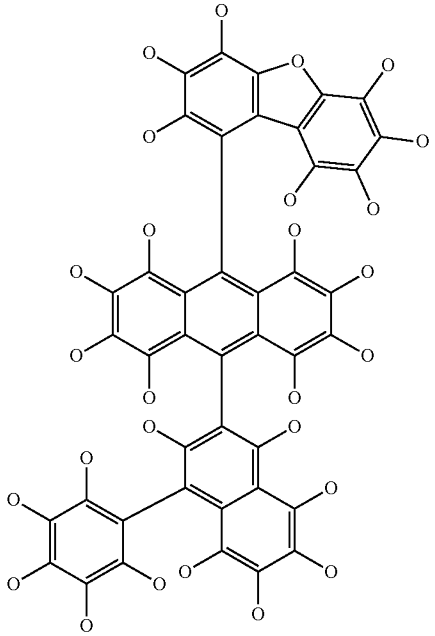

-continued
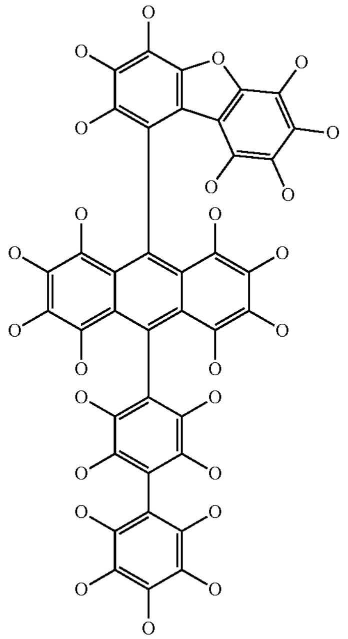
-continued
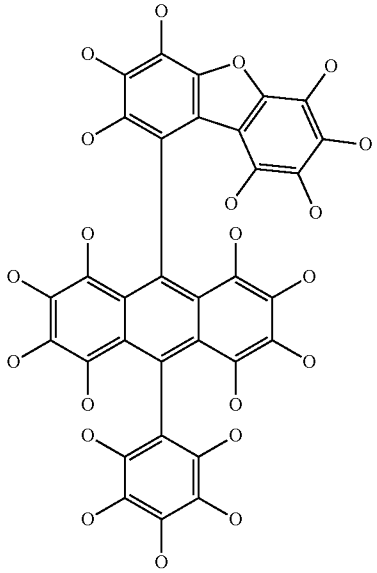
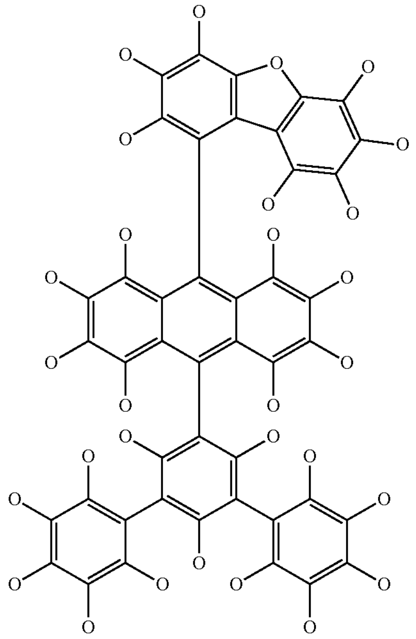
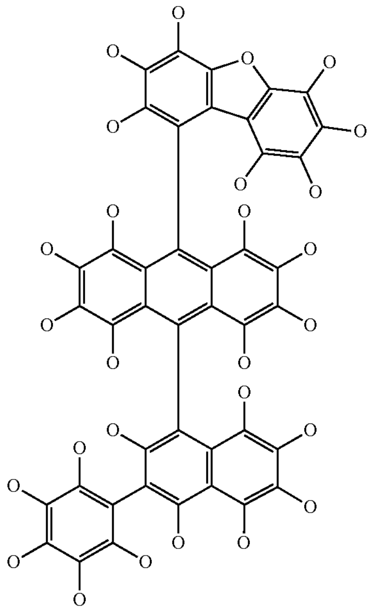

-continued
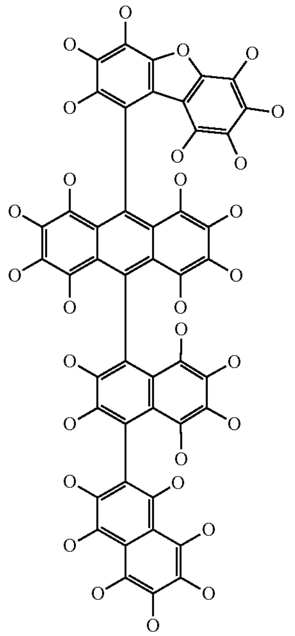
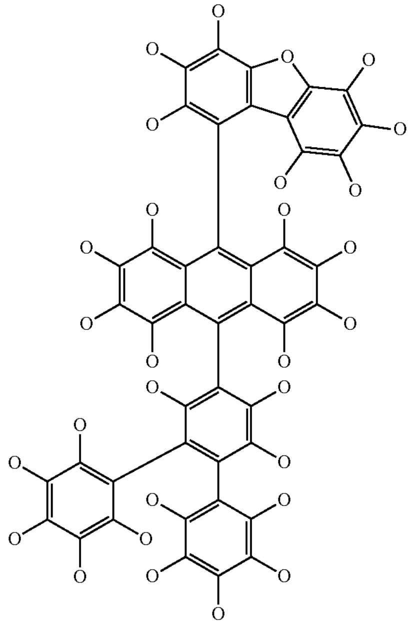
-continued
[Formula 139]
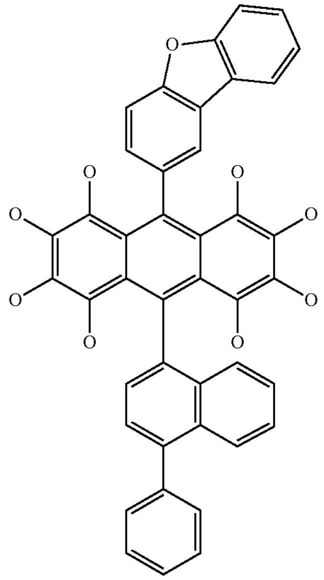
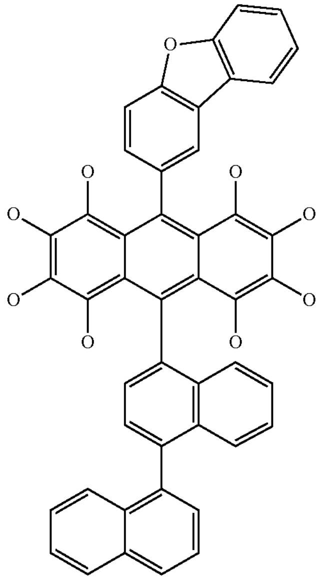
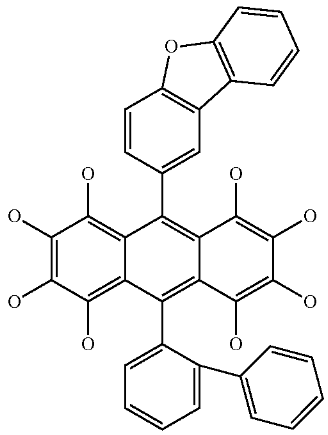

-continued
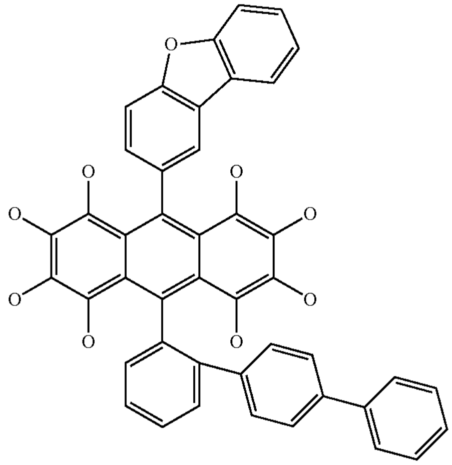
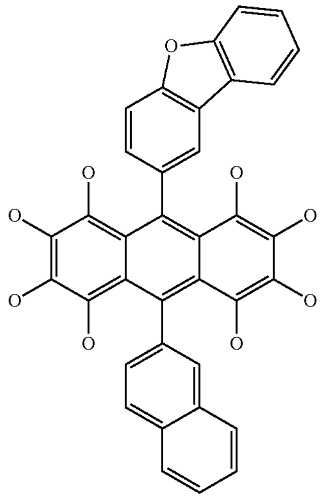
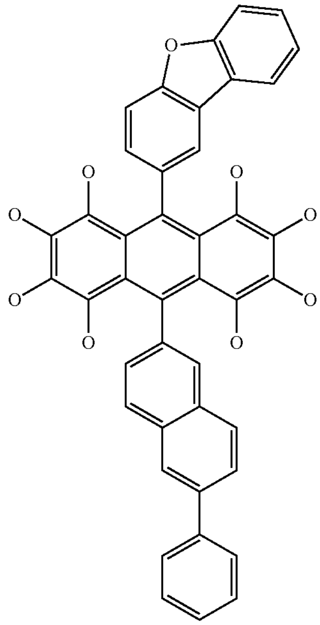
-continued
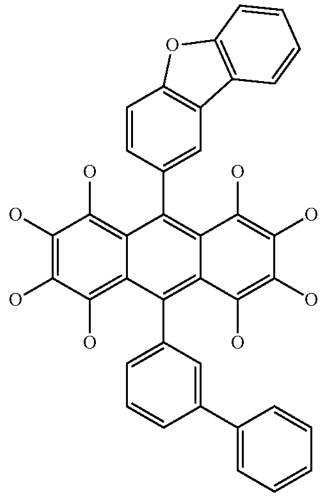
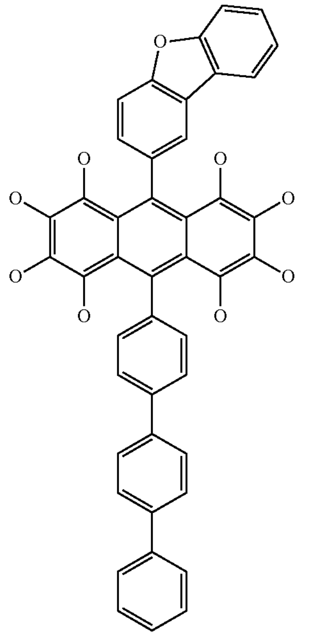
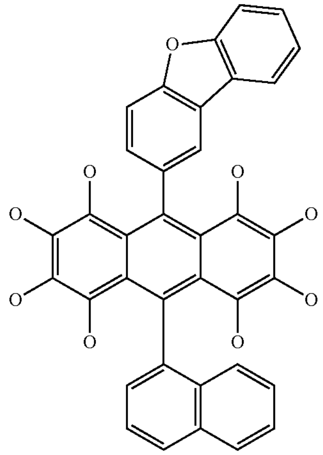

-continued
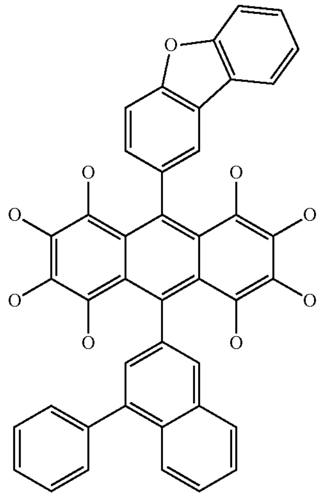
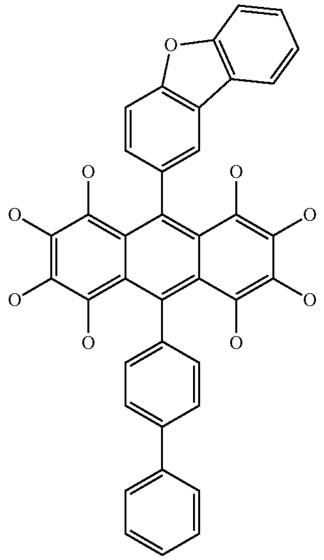
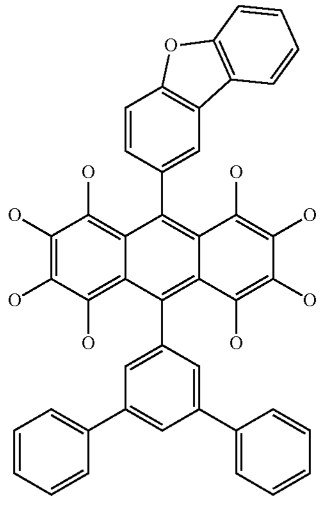
-continued
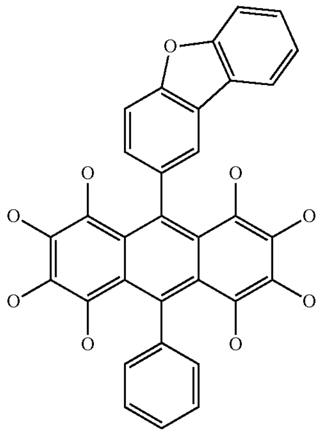
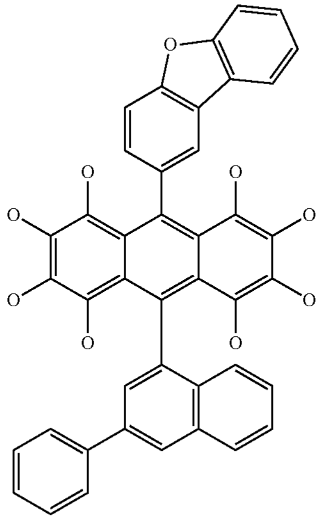
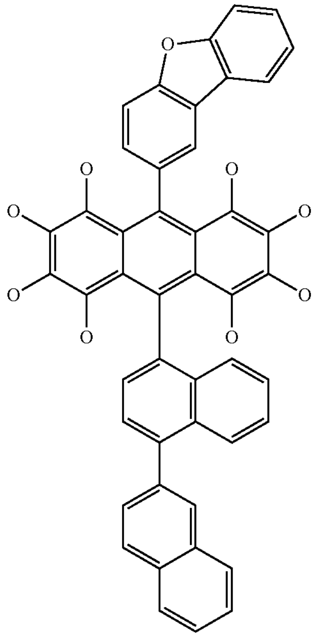

-continued
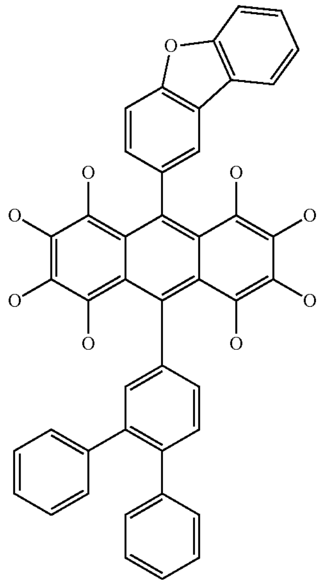
[Formula 140]
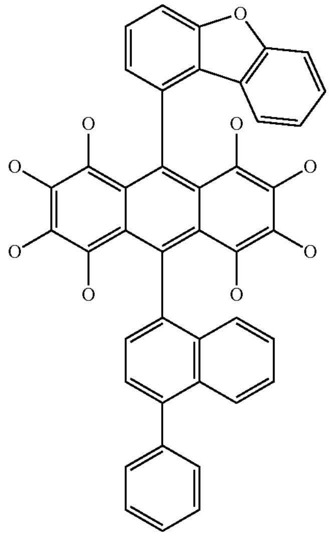
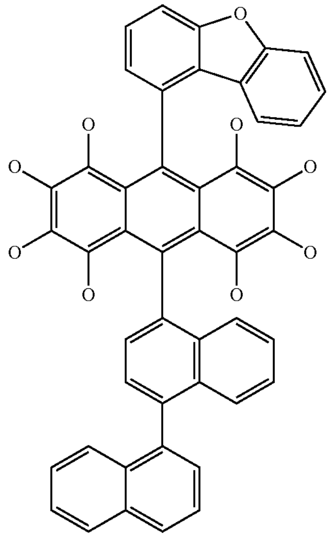
-continued
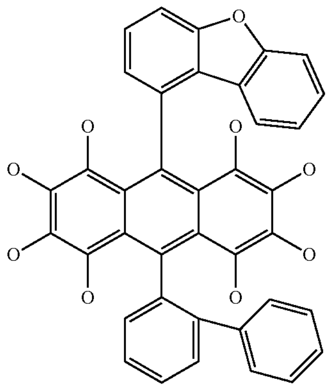
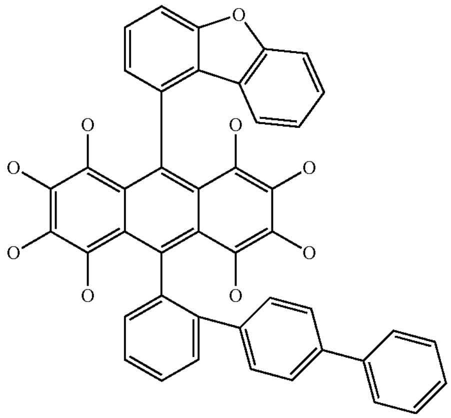
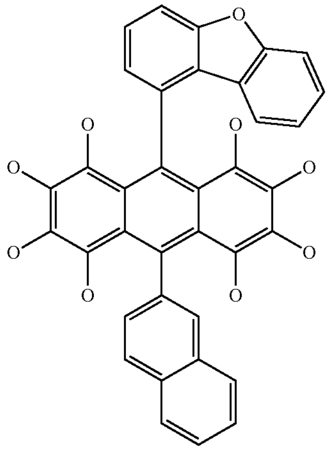

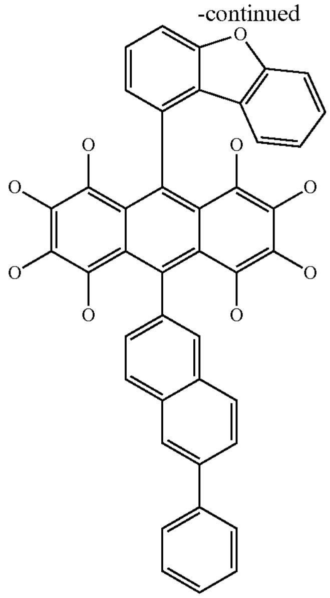
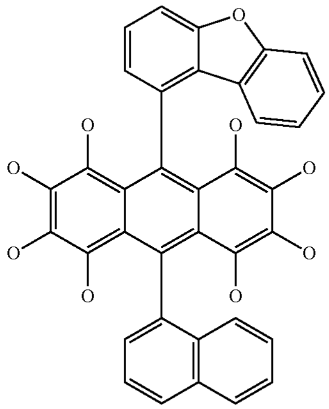
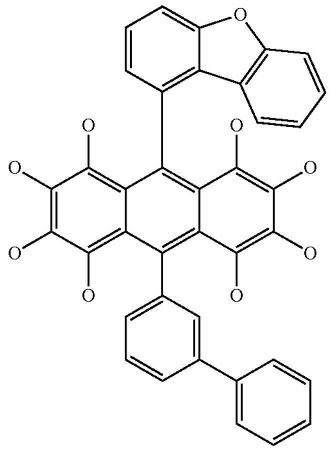
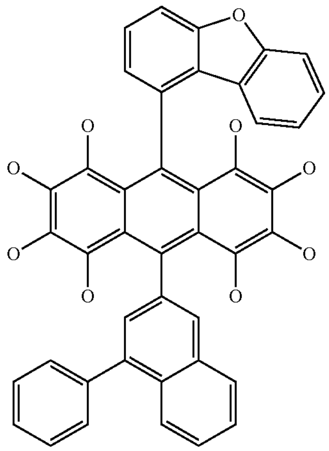
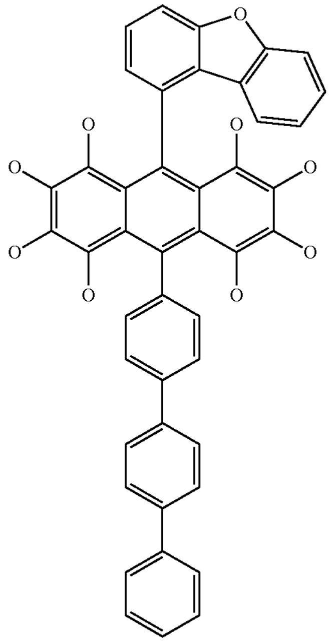
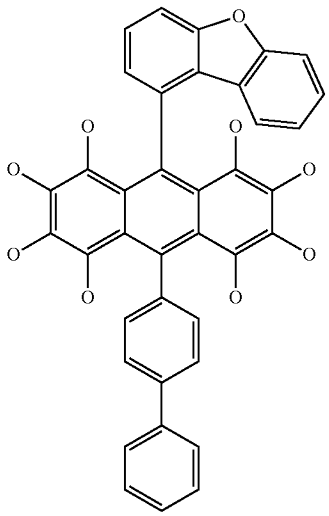

-continued
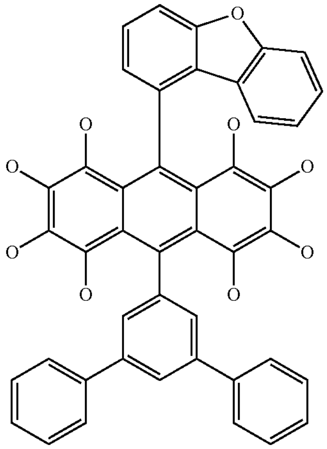
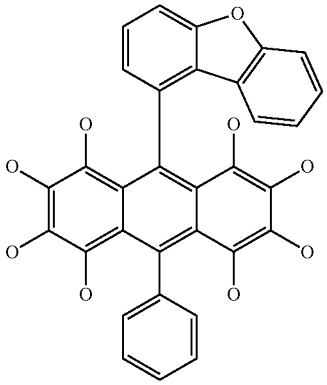
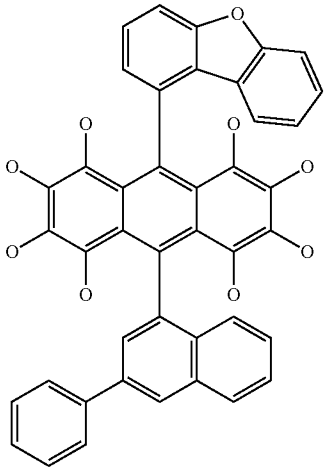
-continued
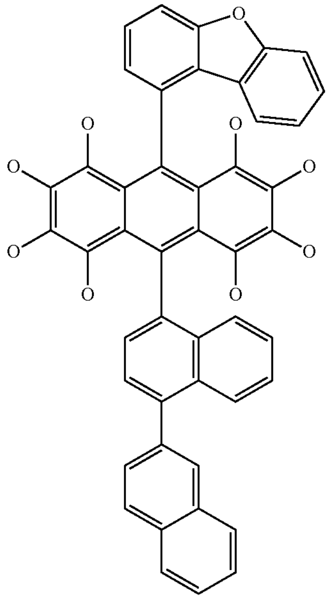
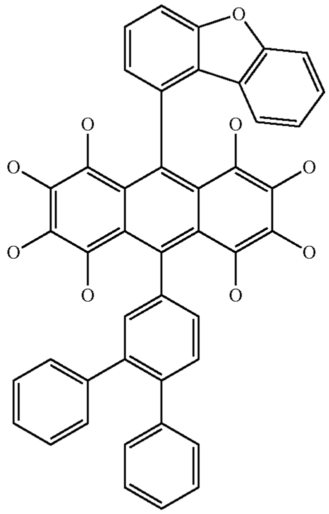
[Formula 141]
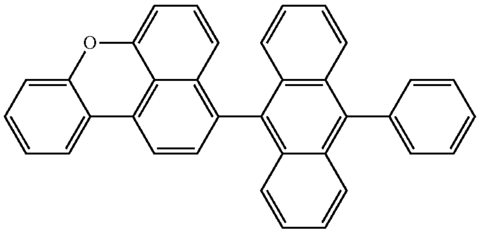
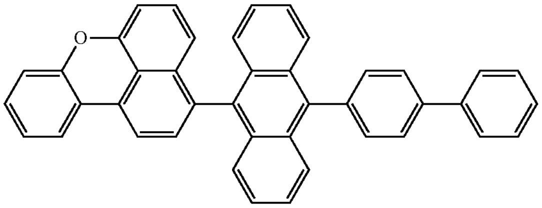

-continued
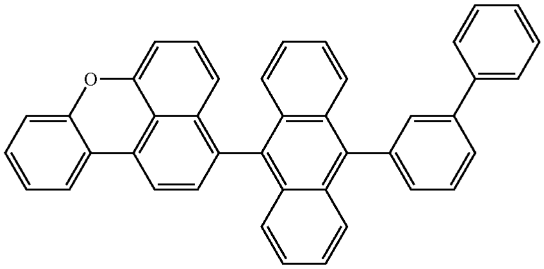
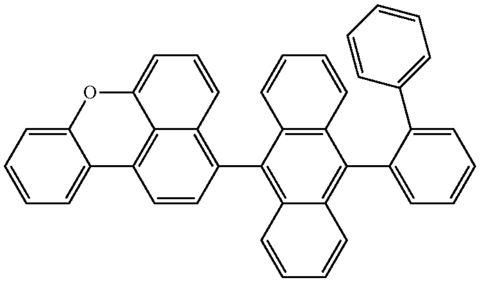
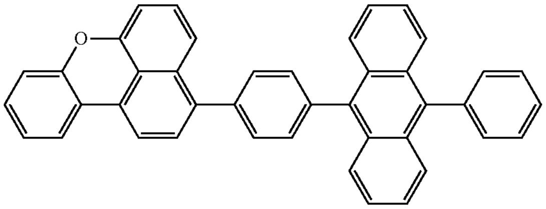
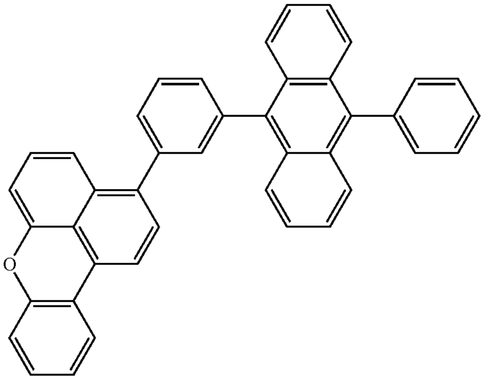
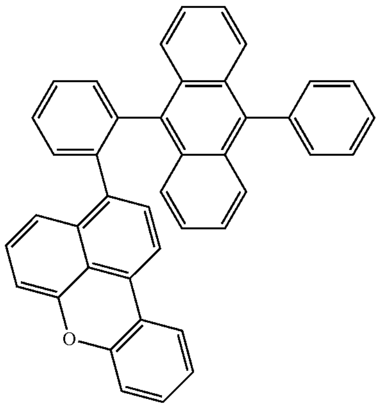
-continued
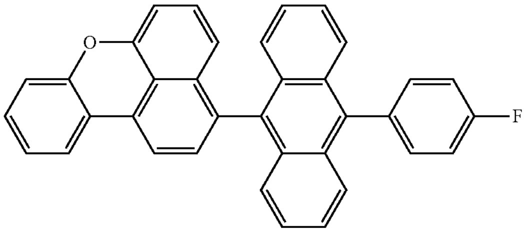
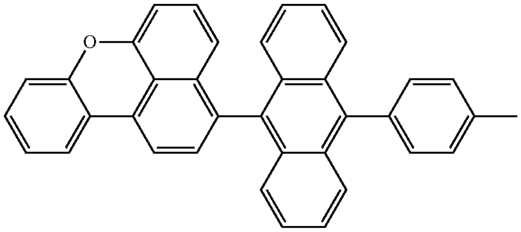
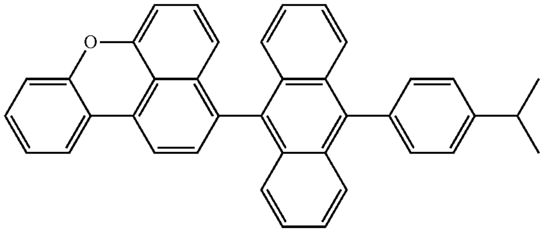
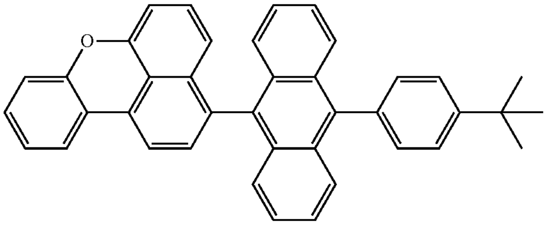
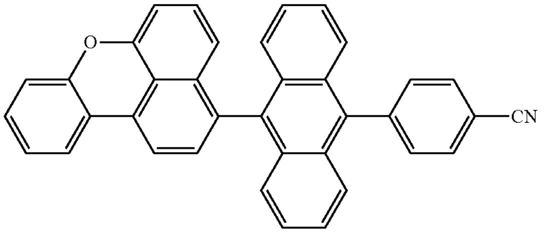
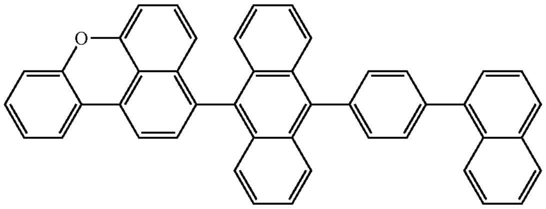
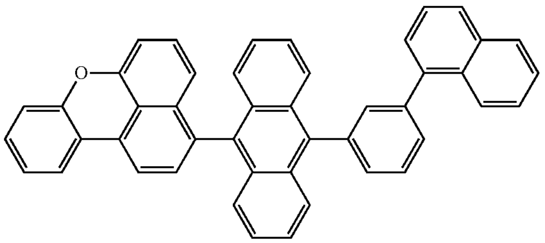

-continued
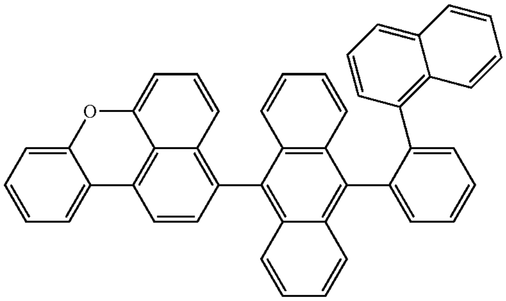
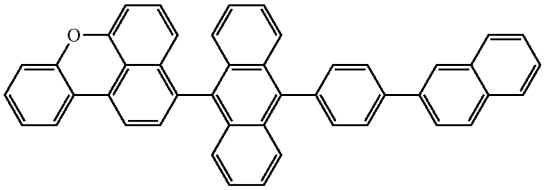
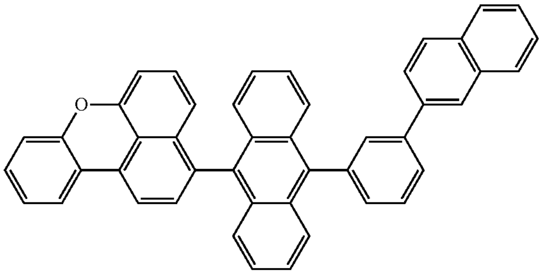
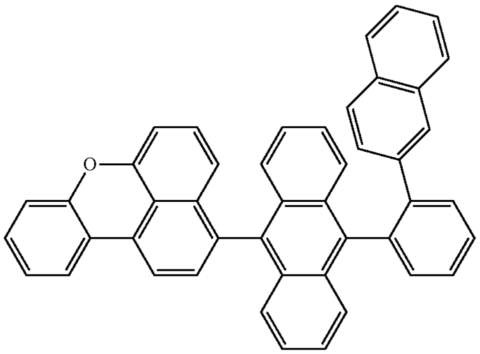
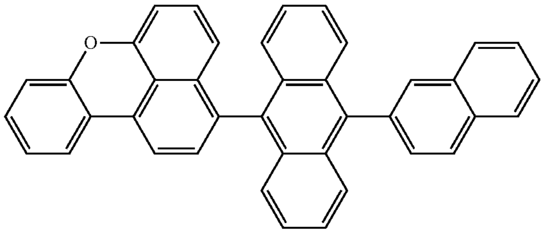
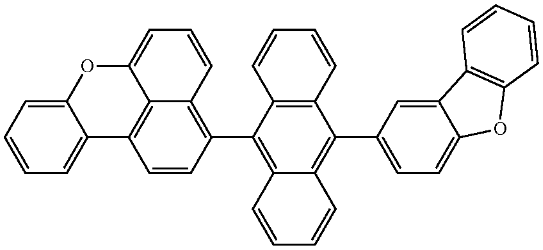
-continued
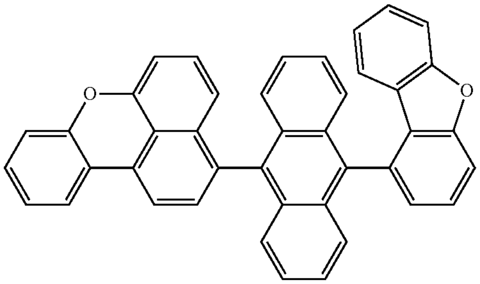
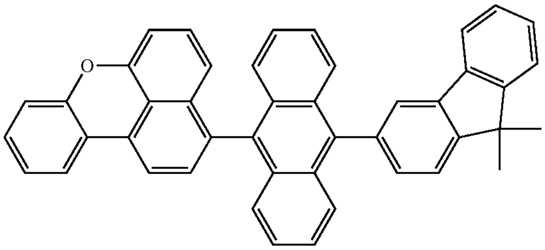
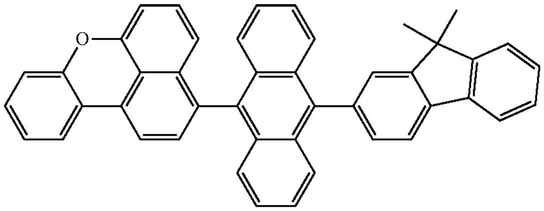
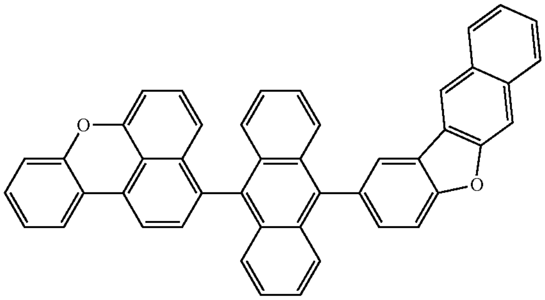
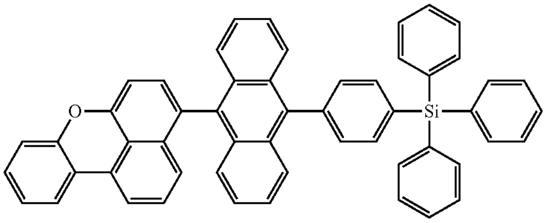
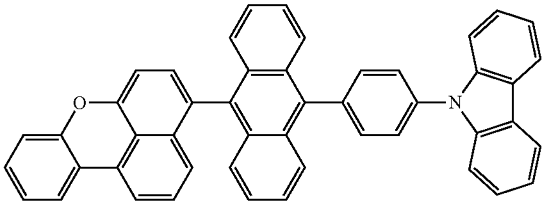
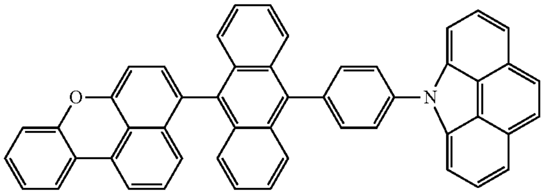

-continued
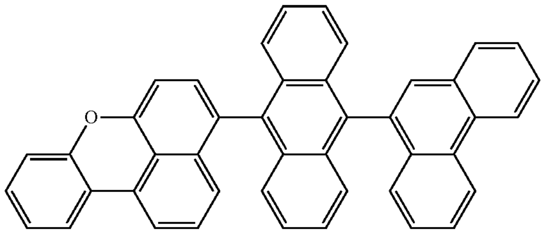
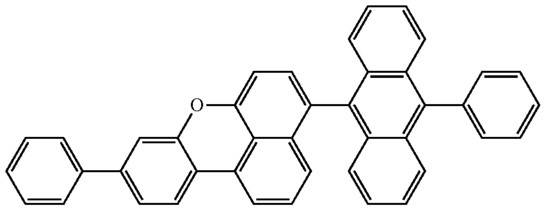
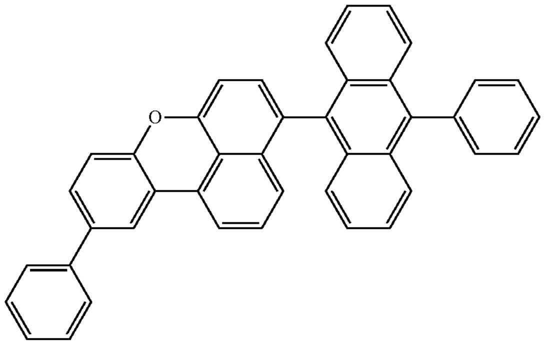
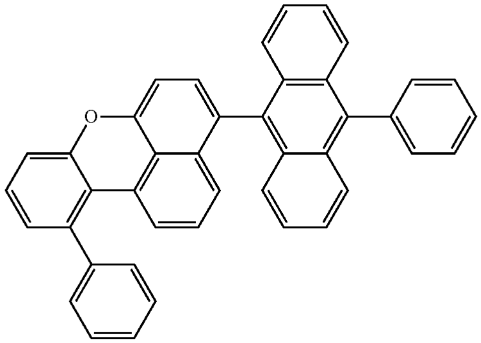
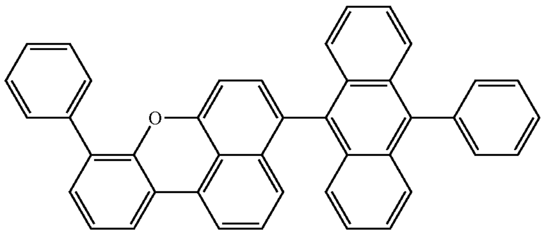
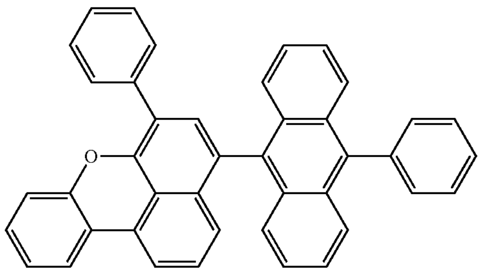
-continued
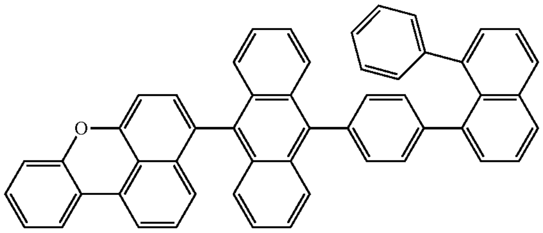
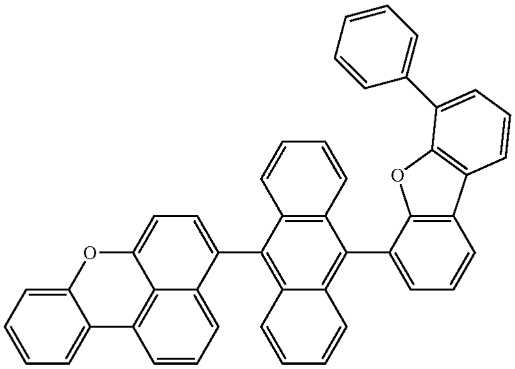
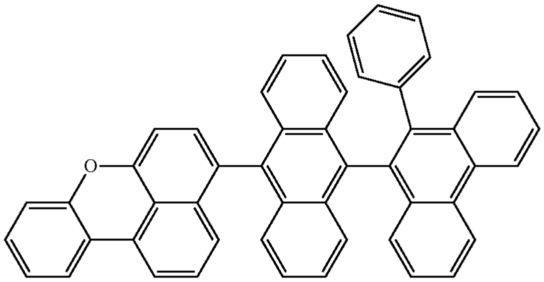
[Formula 142]
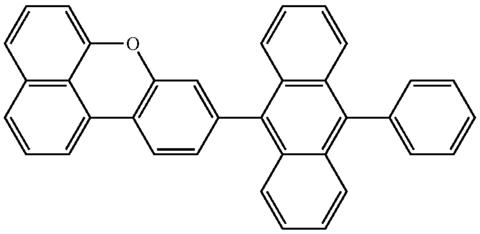
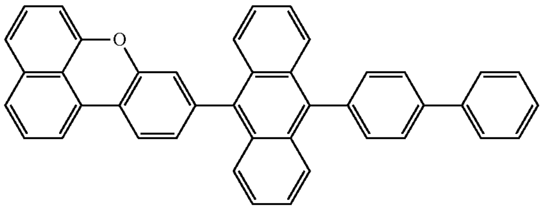
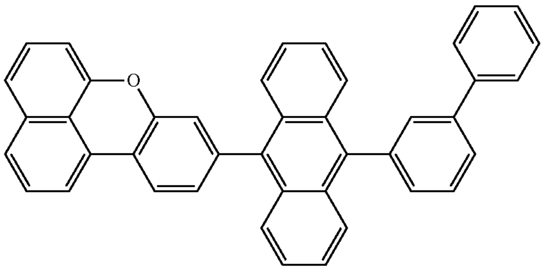

-continued
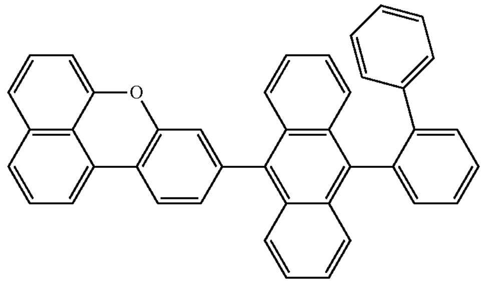
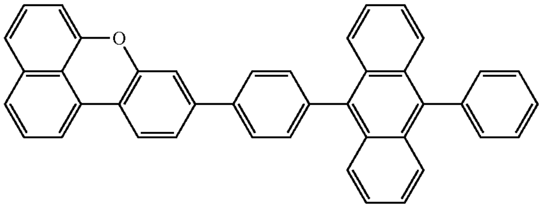
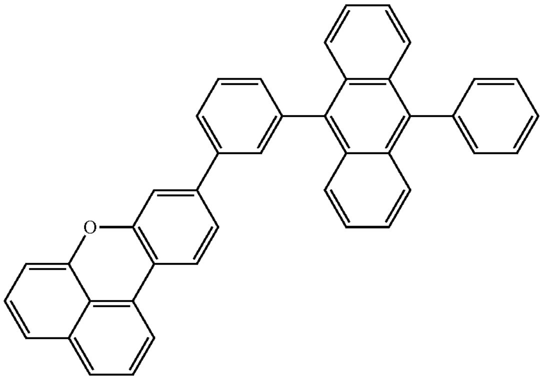
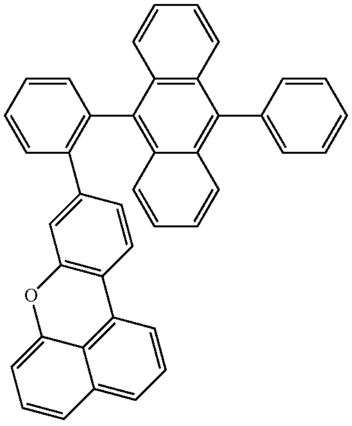
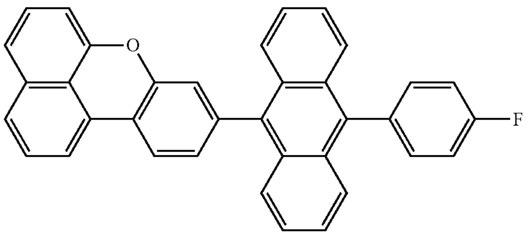
-continued
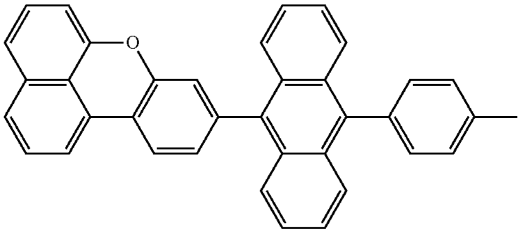
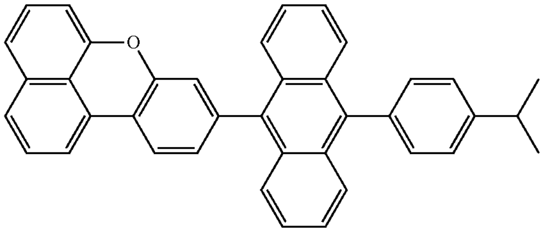
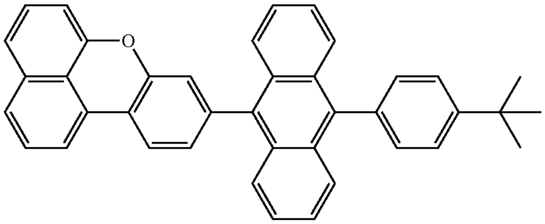
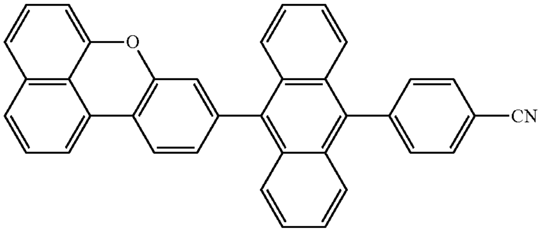
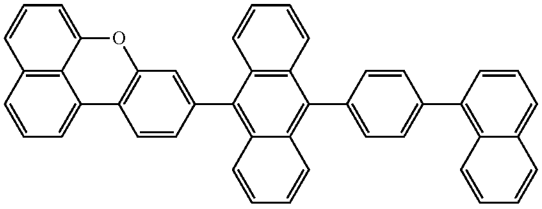
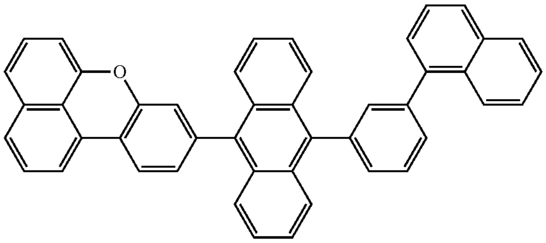
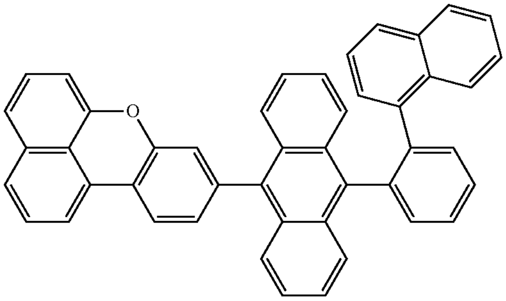

-continued
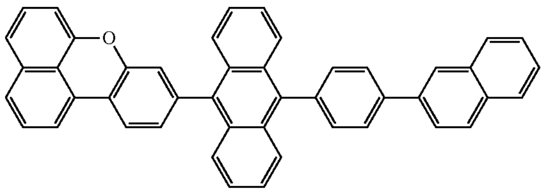
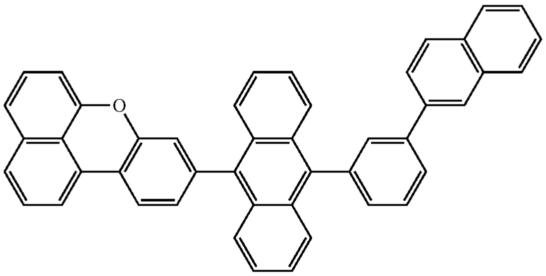
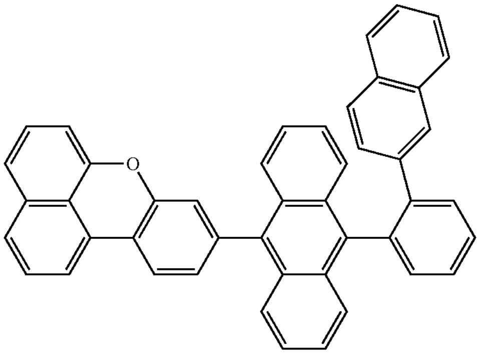
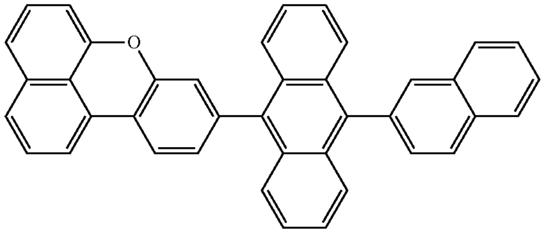
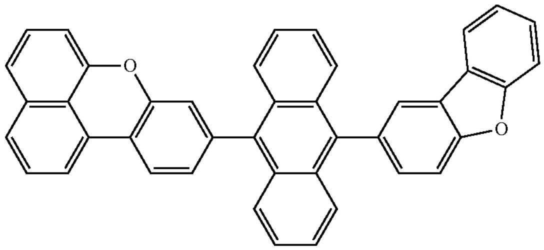
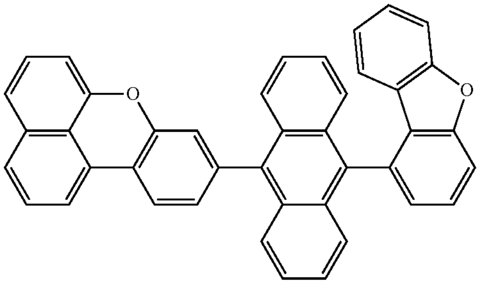
-continued
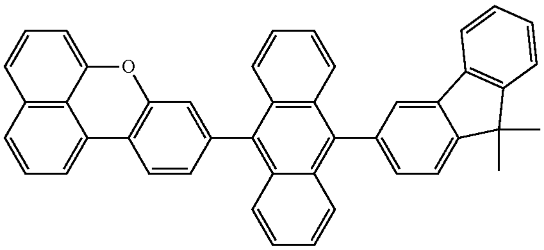
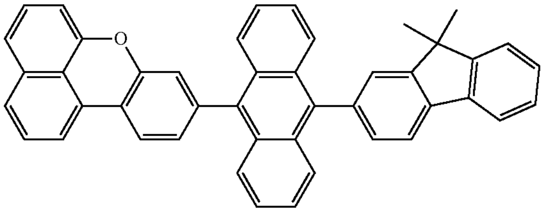
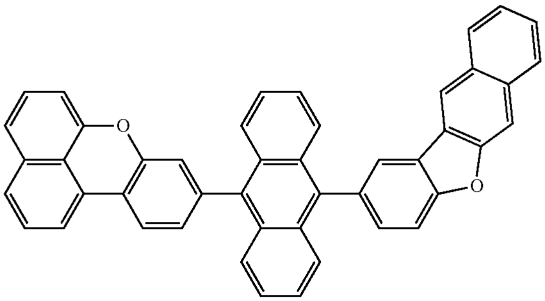
[Formula 143]
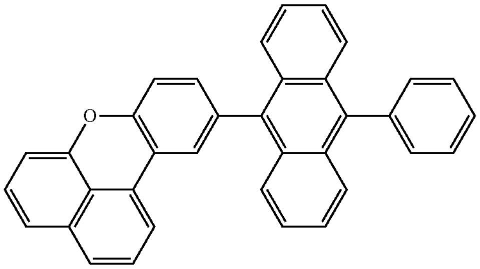
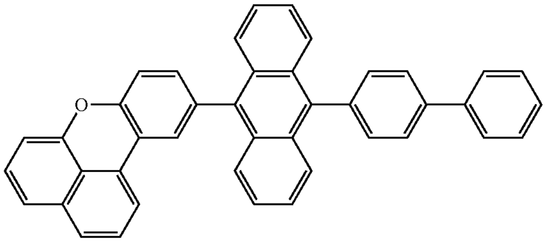
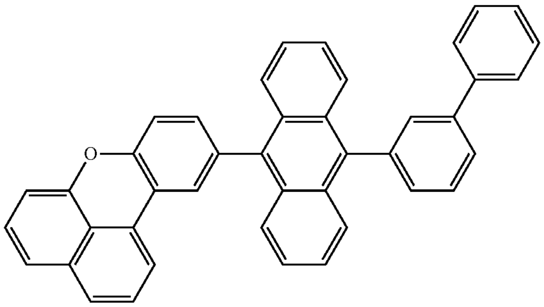

-continued
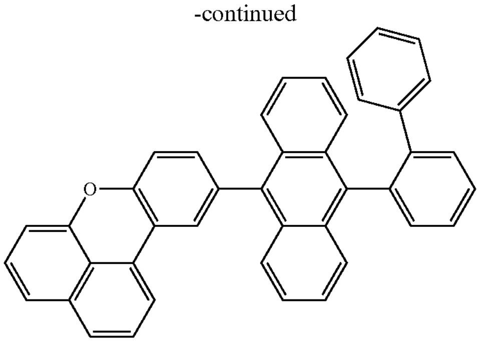
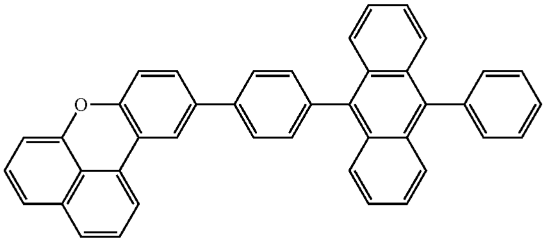
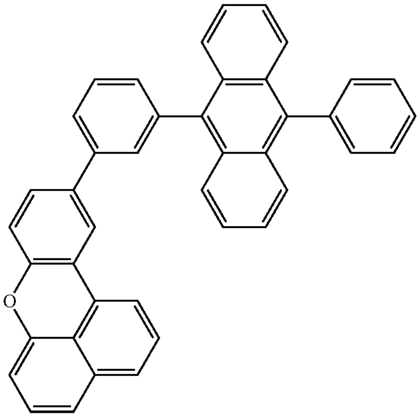
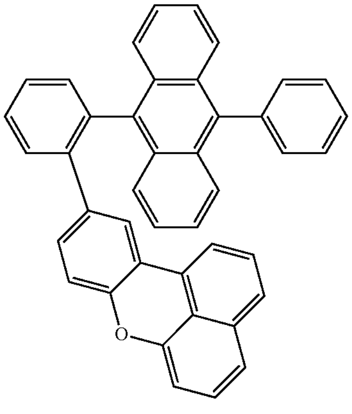
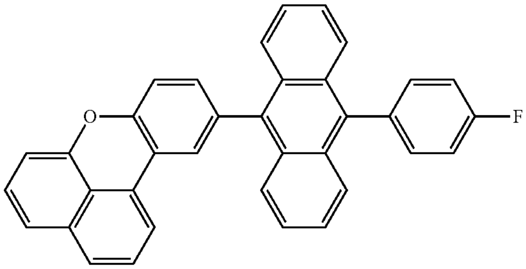
-continued
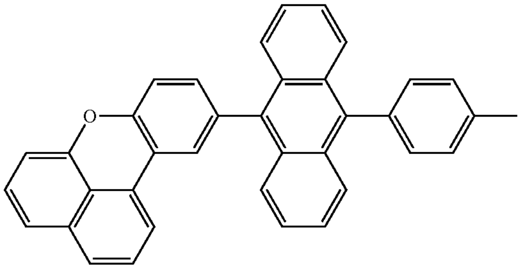
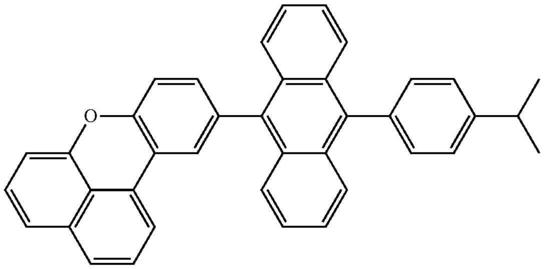
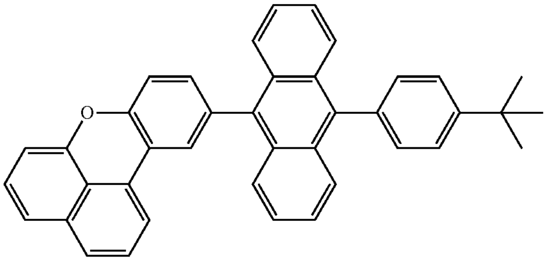
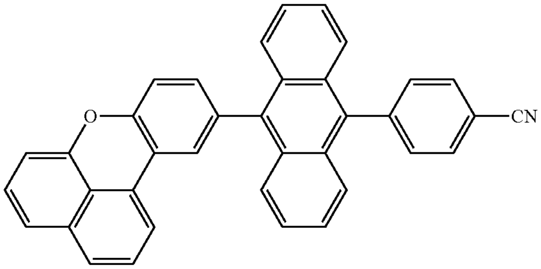
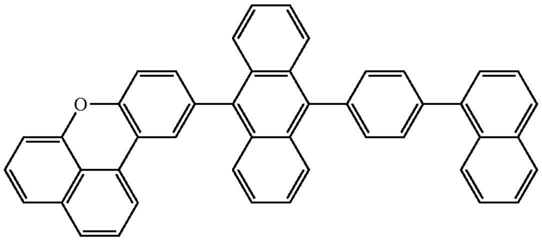
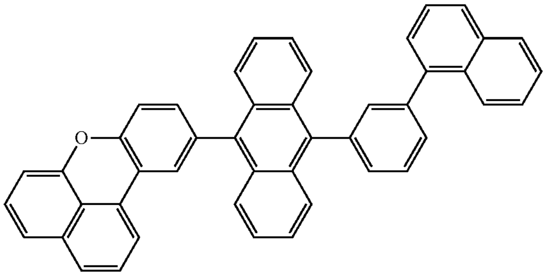

-continued
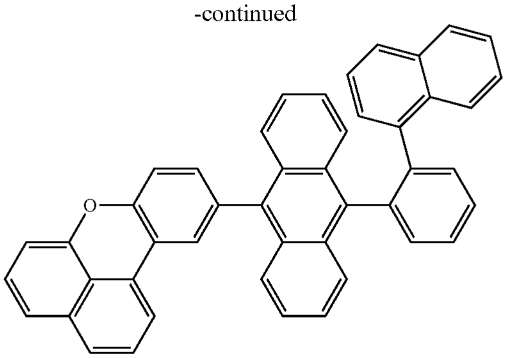
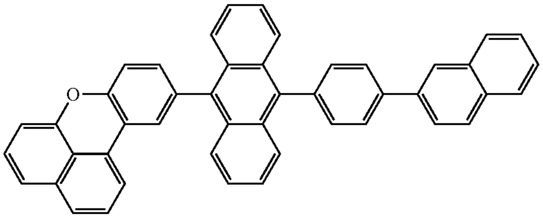
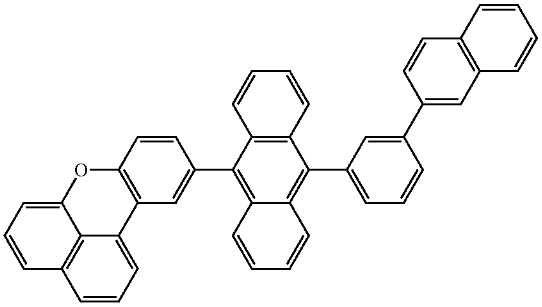
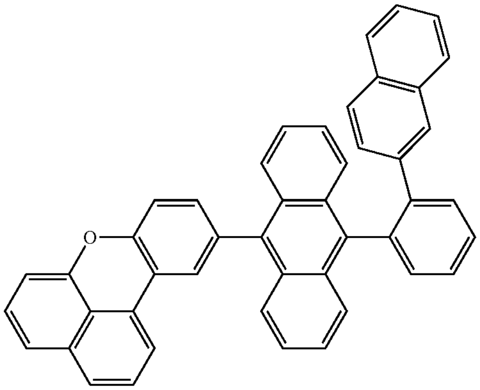
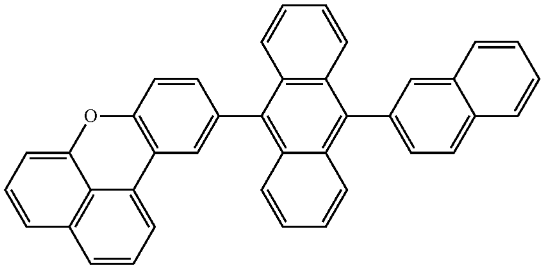
-continued
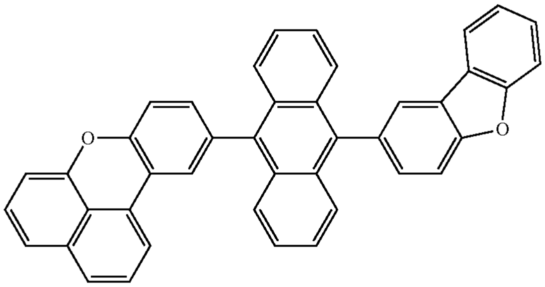
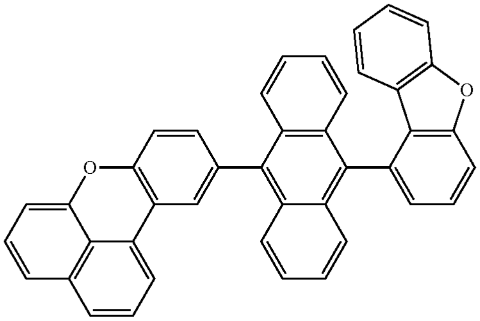
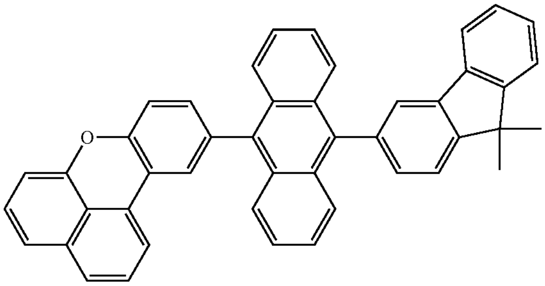
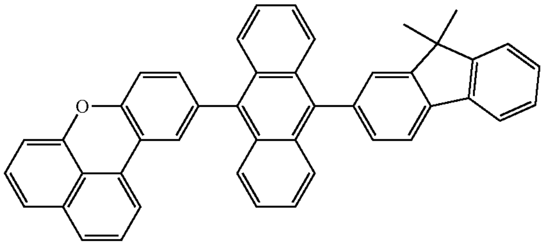
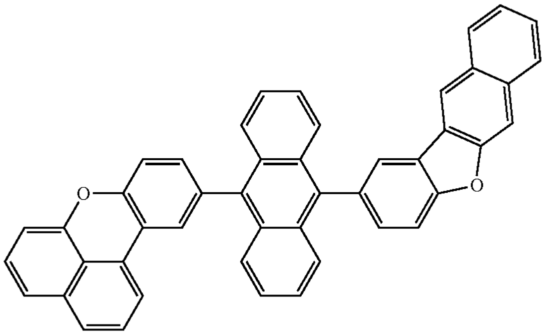

-continued
[Formula 144]
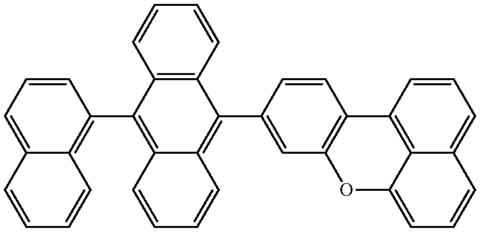
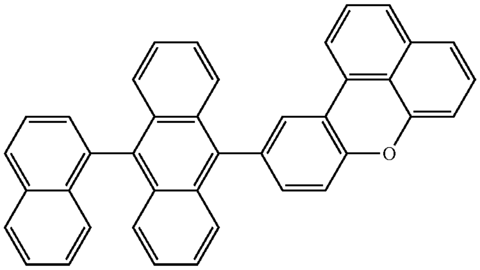
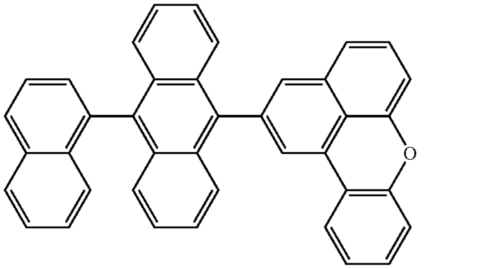
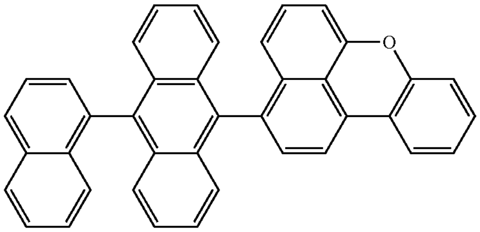
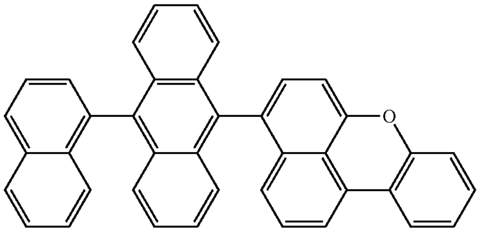
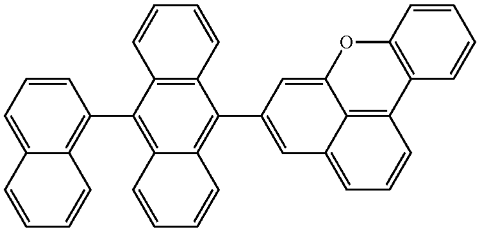
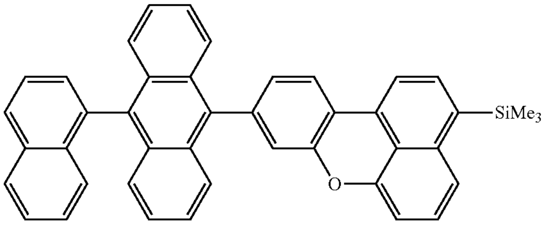
-continued
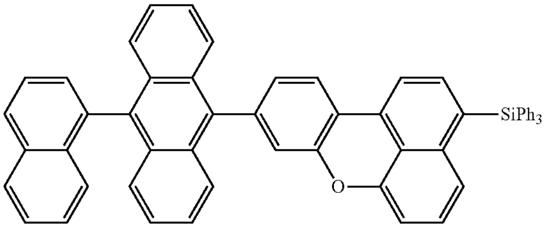
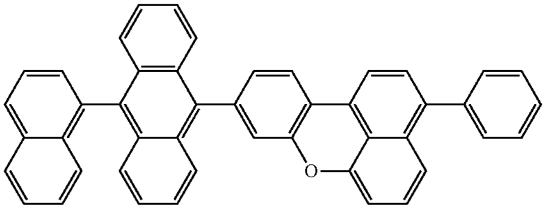
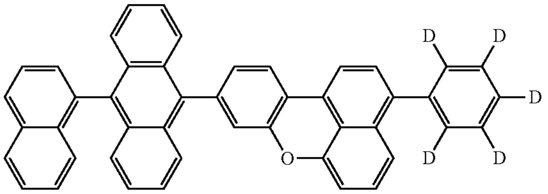
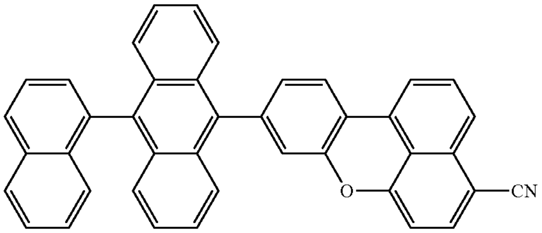
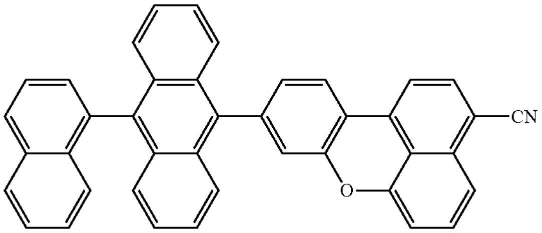
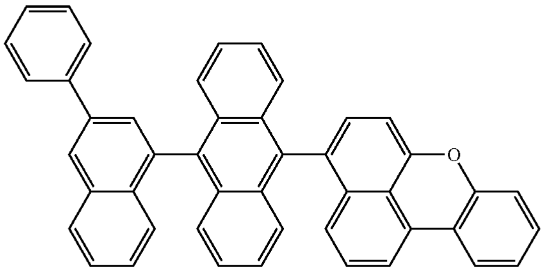
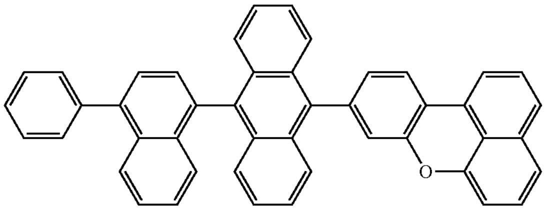

-continued
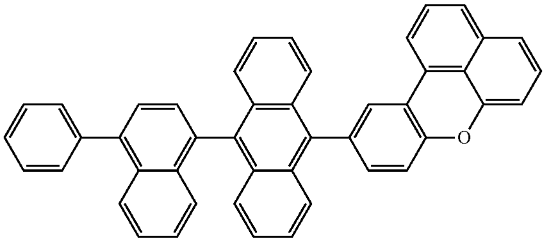
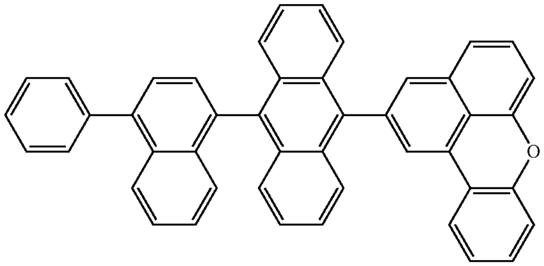
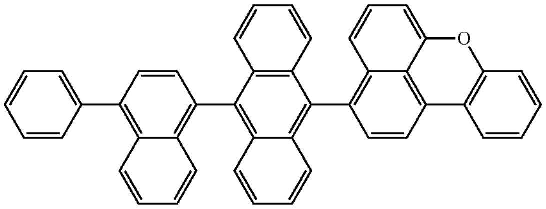
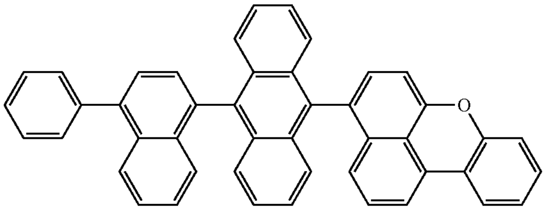
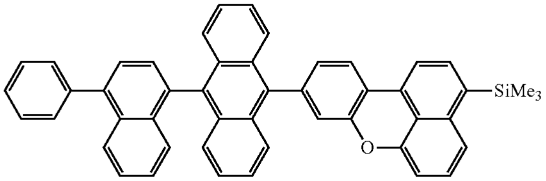
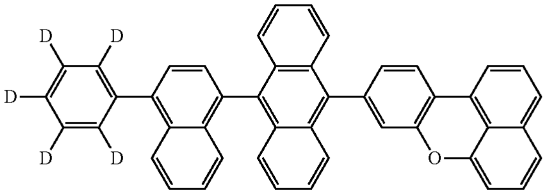
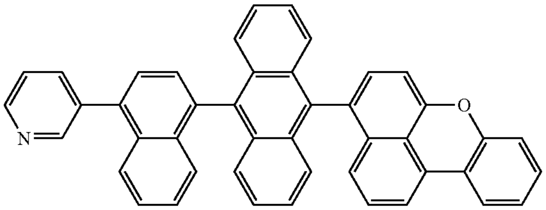
-continued
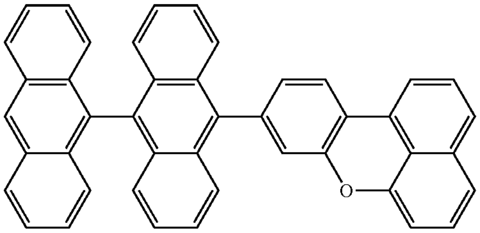
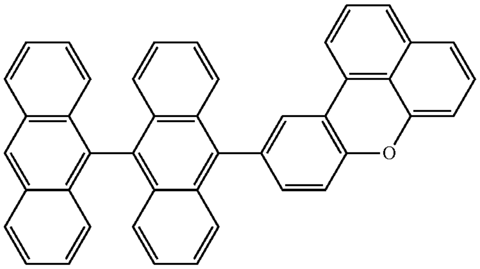
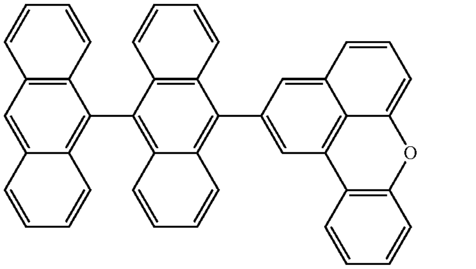
[Formula 145]
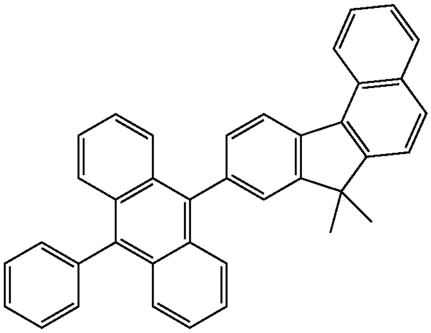
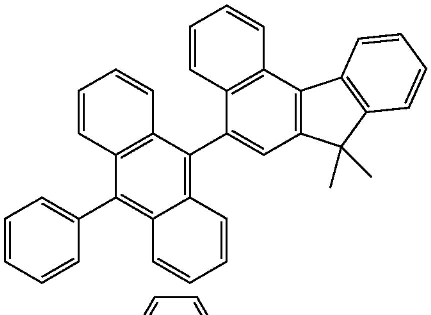
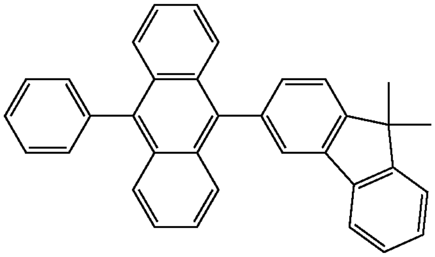

-continued

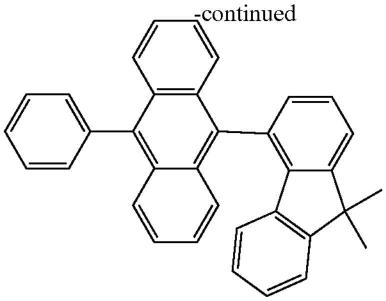

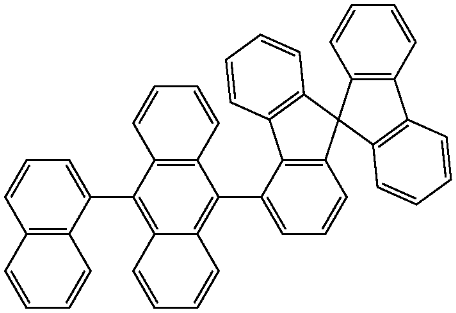

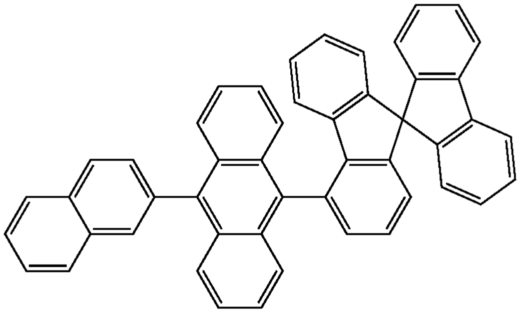

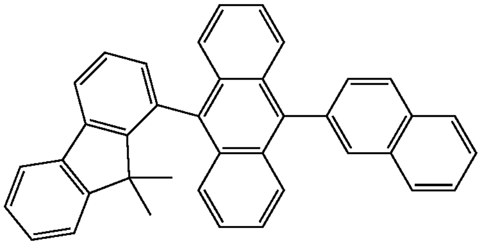

Third Compound and Fourth Compound

In the organic EL device according to the exemplary embodiment, the first emitting layer also preferably contains a third compound that fluoresces.

In the organic EL device according to the exemplary embodiment, the second emitting layer also preferably contains a fourth compound that fluoresces.

When the first emitting layer contains the third compound and the second emitting layer contains the fourth compound, the third compound and the fourth compound are mutually the same or different.

The third compound and the fourth compound are each independently at least one compound selected from the group consisting of a compound represented by a formula (3) below, a compound represented by a formula (4) below, a compound represented by a formula (5) below, a compound represented by a formula (6) below, a compound represented by a formula (7) below, a compound represented by a formula (8) below, a compound represented by a formula (9) below, and a compound represented by a formula (10) below.

Compound Represented by Formula (3)

The compound represented by the formula (3) will be described.

[Formula 146]

(3)

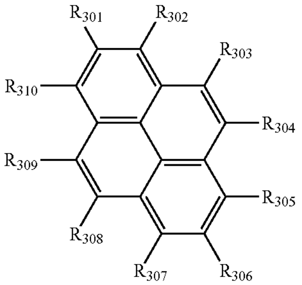

In the formula (3):

at least one combination of adjacent two or more of $R_{301}$ to $R_{310}$ are mutually bonded to form a substituted or unsubstituted monocyclic ring, mutually bonded to form a substituted or unsubstituted fused ring, or not mutually bonded;

at least one of $R_{301}$ to $R_{310}$ is a monovalent group represented by a formula (31) below; and $R_{301}$ to $R_{310}$ not forming the monocyclic ring, not forming the fused ring and not being the monovalent group represented by the formula (31) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

[Formula 147]

(31)

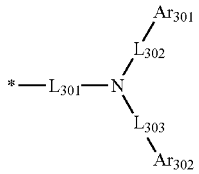

In the formula (31):

$Ar_{301}$ and $Ar_{302}$ are each independently a substituted or unsubstituted aryl group having 6 to 50 ring carbon atoms, or a substituted or unsubstituted heterocyclic group having 5 to 50 ring atoms;

$L_{301}$ to $L_{303}$ are each independently a single bond, a substituted or unsubstituted arylene group having 6 to 30 ring carbon atoms, or a substituted or unsubstituted divalent heterocyclic group having 5 to 30 ring atoms; and represents a bonding position to a pyrene ring in the formula (3).

In the third and fourth compounds:

$R_{901}$, $R_{902}$, $R_{903}$, $R_{904}$, $R_{905}$, $R_{906}$ and $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different; and when a plurality of $R_{907}$ are present, the plurality of $R_{907}$ are mutually the same or different.

In the formula (3), two of $R_{301}$ to $R_{310}$ are preferably groups represented by the formula (31).

In an exemplary embodiment, the compound represented by the formula (3) is a compound represented by a formula (33) below.

[Formula 148]

(33)

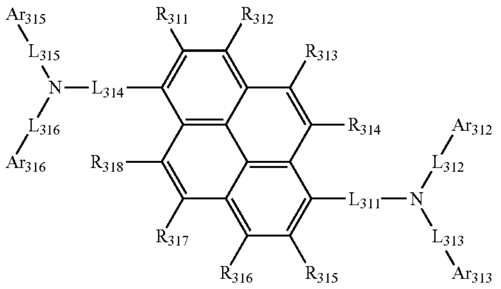

In the formula (33):

$R_{311}$ to $R_{318}$ each independently represent the same as $R_{301}$ to $R_{310}$ in the formula (3) that are not a monovalent group represented by the formula (31);

$L_{311}$ to $L_{316}$ are each independently a single bond, a substituted or unsubstituted arylene group having 6 to 30 ring carbon atoms, or a substituted or unsubstituted divalent heterocyclic group having 5 to 30 ring atoms; and $Ar_{312}$, $Ar_{313}$, $Ar_{315}$ and $Ar_{316}$ are each independently a substituted or unsubstituted aryl group having 6 to 50 ring carbon atoms, or a substituted or unsubstituted heterocyclic group having 5 to 50 ring atoms.

In the formula (31), $L_{301}$ is preferably a single bond, and $L_{302}$ and $L_{303}$ are preferably a single bond.

In an exemplary embodiment, the compound represented by the formula (3) is represented by a formula (34) or (35) below.

[Formula 149]

(34)

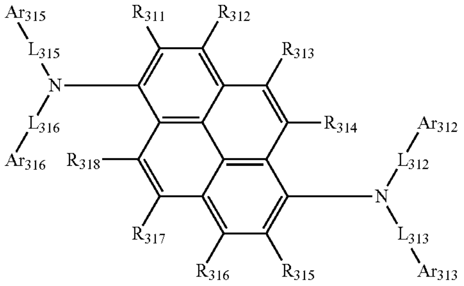

In the formula (34):

$R_{311}$ to $R_{318}$ each independently represent the same as $R_{301}$ to $R_{310}$ in the formula (3) that are not a monovalent group represented by the formula (31);

$L_{312}$, $L_{313}$, $L_{315}$ and $L_{316}$ each independently represent the same as $L_{312}$, $L_{313}$, $L_{315}$ and $L_{316}$ in the formula (33); and $Ar_{312}$, $Ar_{313}$, $Ar_{315}$ and $Ar_{316}$ each independently represent the same as $Ar_{312}$, $Ar_{313}$, $Ar_{315}$ and $Ar_{316}$ in the formula (33).

[Formula 150]

(35)

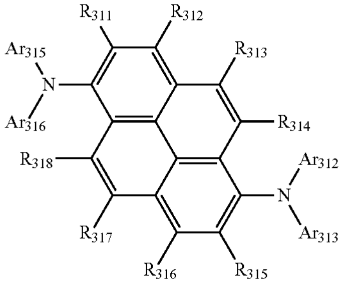

In the formula (35):

$R_{311}$ to $R_{318}$ each independently represent the same as $R_{301}$ to $R_{310}$ in the formula (3) that are not a monovalent group represented by the formula (31); and $Ar_{312}$, $Ar_{313}$, $Ar_{315}$ and $Ar_{316}$ each independently represent the same as $Ar_{312}$, $Ar_{313}$, $Ar_{315}$ and $Ar_{316}$ in the formula (33).

In the formula (31), at least one of $Ar_{301}$ or $Ar_{302}$ is preferably a group represented by a formula (36) below.

In the formulae (33) to (35), at least one of $Ar_{312}$ or $Ar_{313}$ is preferably a group represented by the formula (36).

In the formulae (33) to (35), at least one of $Ar_{315}$ or $Ar_{316}$ is preferably a group represented by the formula (36).

[Formula 151]

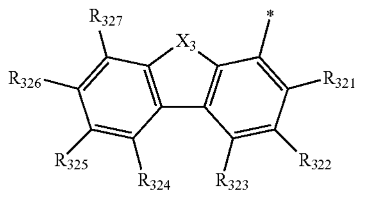

(36)

In the formula (36):

$X_3$ represents an oxygen atom or a sulfur atom;

at least one combination of adjacent two or more of $R_{321}$ to $R_{327}$ are mutually bonded to form a substituted or unsubstituted monocyclic ring, mutually bonded to form a substituted or unsubstituted fused ring, or not mutually bonded;

$R_{321}$ to $R_{327}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and represents a bonding position to $L_{302}$, $L_{303}$, $L_{312}$, $L_{313}$, $L_{315}$ or $L_{316}$.

$X_3$ is preferably an oxygen atom.

At least one of $R_{321}$ to $R_{327}$ is preferably a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the formula (31), it is preferable that: $Ar_{301}$ is a group represented by the formula (36); and $Ar_{302}$ is a substituted or unsubstituted aryl group having 6 to 50 ring carbon atoms.

In the formulae (33) to (35), it is preferable that: $Ar_{312}$ is a group represented by the formula (36); and $Ar_{313}$ is a substituted or unsubstituted aryl group having 6 to 50 ring carbon atoms.

In the formulae (33) to (35), it is preferable that: $Ar_{315}$ is a group represented by the formula (36); and $Ar_{316}$ is a substituted or unsubstituted aryl group having 6 to 50 ring carbon atoms.

In an exemplary embodiment, the compound represented by the formula (3) is represented by a formula (37) below.

[Formula 152]

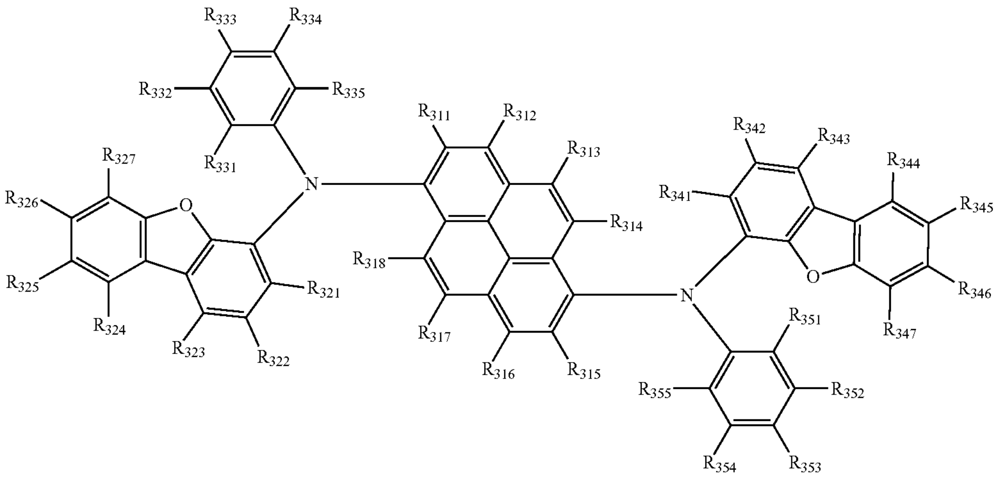

(37)

In the formula (37):

$R_{311}$ to $R_{318}$ each independently represent the same as $R_{301}$ to $R_{310}$ in the formula (3) that are not a monovalent group represented by the formula (31);

at least one combination of adjacent two or more of $R_{321}$ to $R_{327}$ are mutually bonded to form a substituted or unsubstituted monocyclic ring, mutually bonded to form a substituted or unsubstituted fused ring, or not mutually bonded;

at least one combination of adjacent two or more of $R_{341}$ to $R_{347}$ are mutually bonded to form a substituted or unsubstituted monocyclic ring, mutually bonded to form a substituted or unsubstituted fused ring, or not mutually bonded;

$R_{321}$ to $R_{327}$ and $R_{341}$ to $R_{347}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and $R_{331}$ to $R_{335}$ and $R_{351}$ to $R_{355}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

Specific examples of the compound represented by the formula (3) include compounds shown below.

[Formula 153]

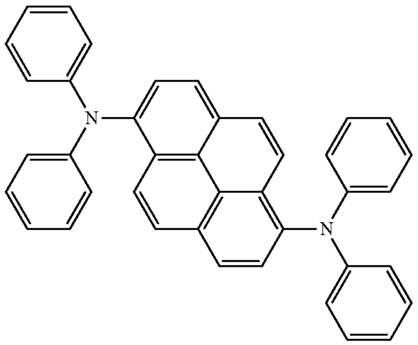

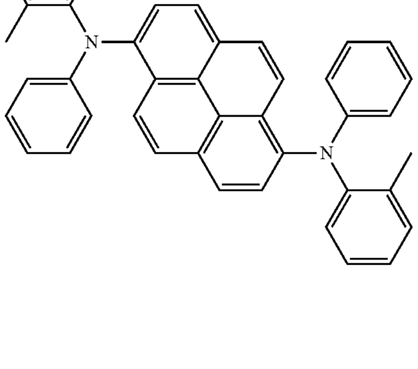

-continued

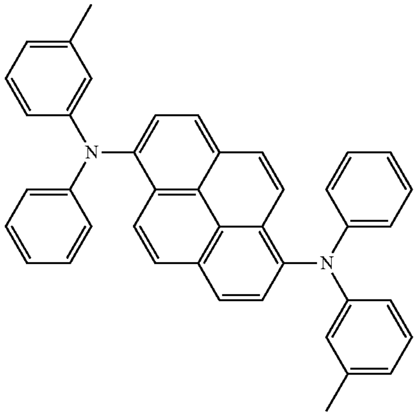

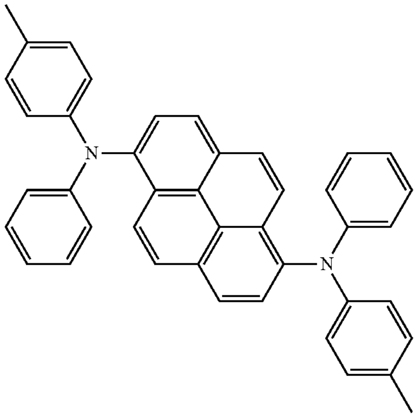

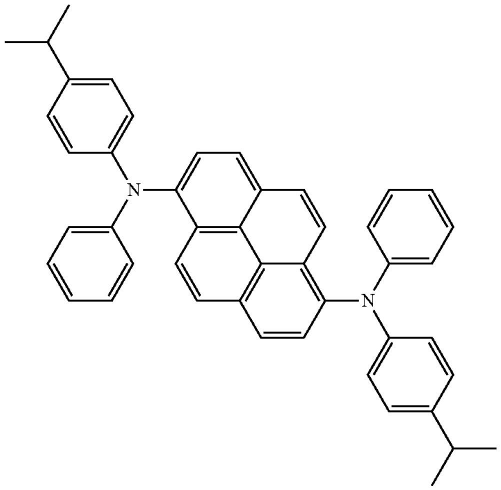

-continued
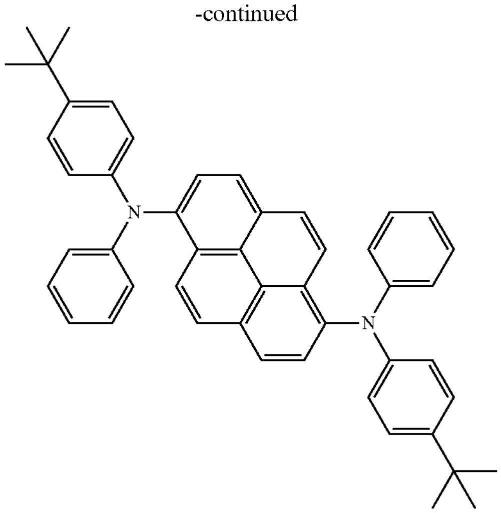
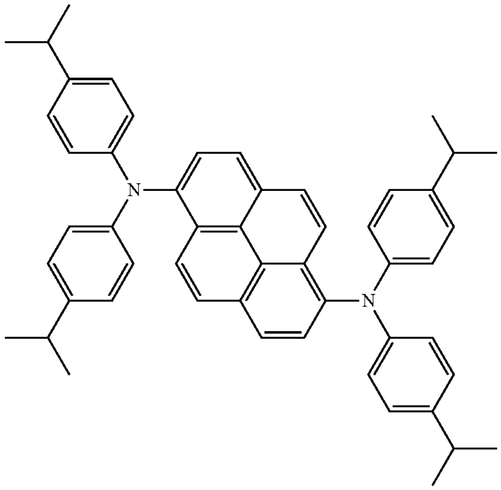
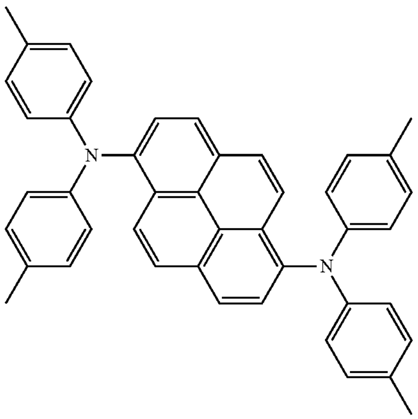
-continued
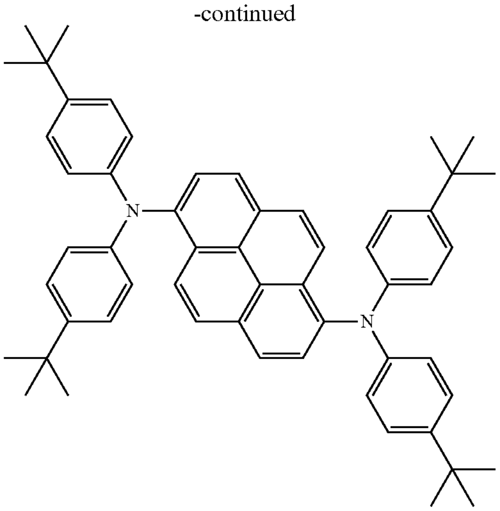
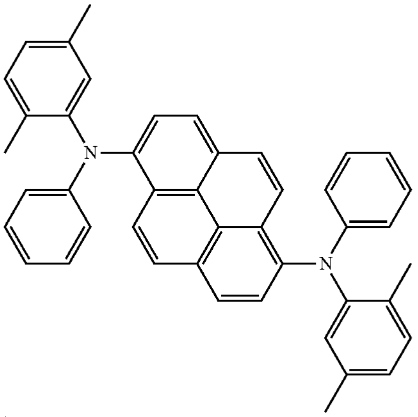
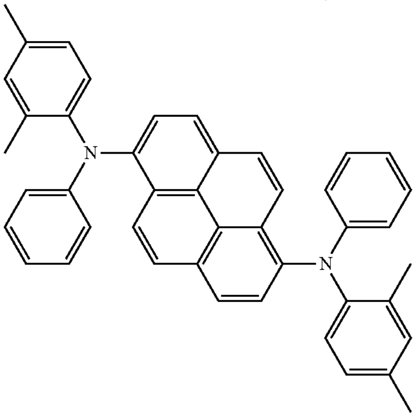
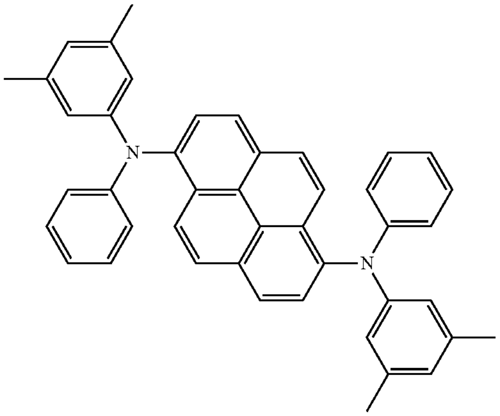

-continued
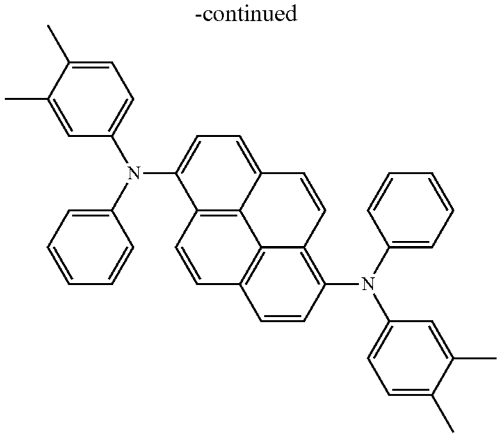
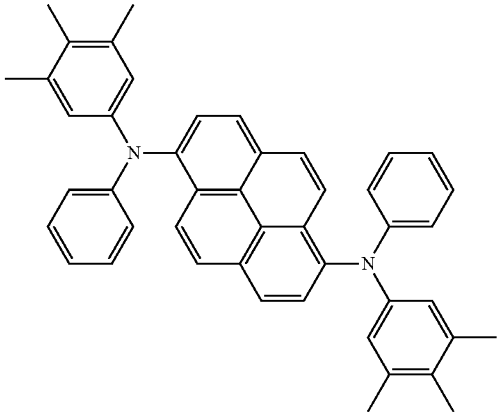
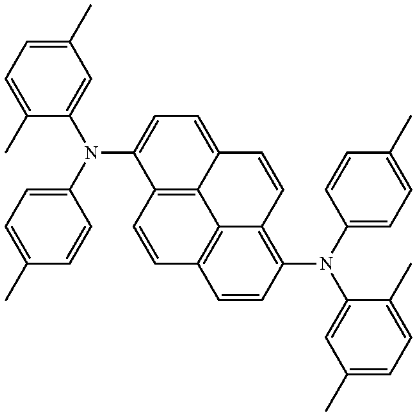
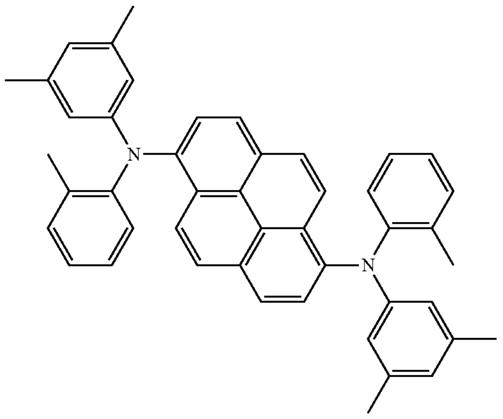
-continued
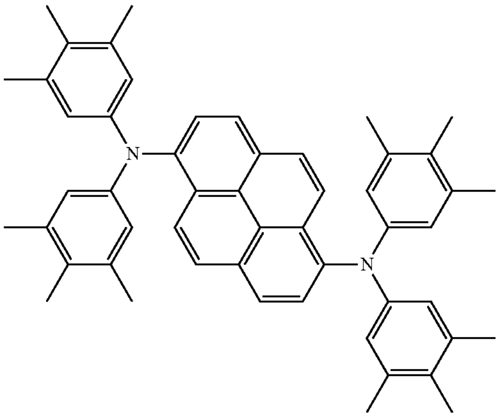
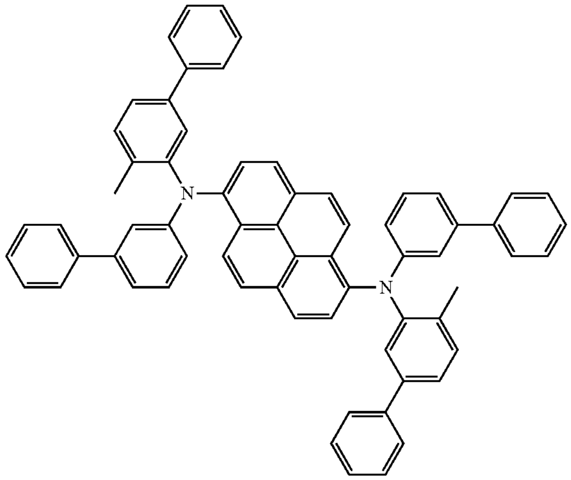
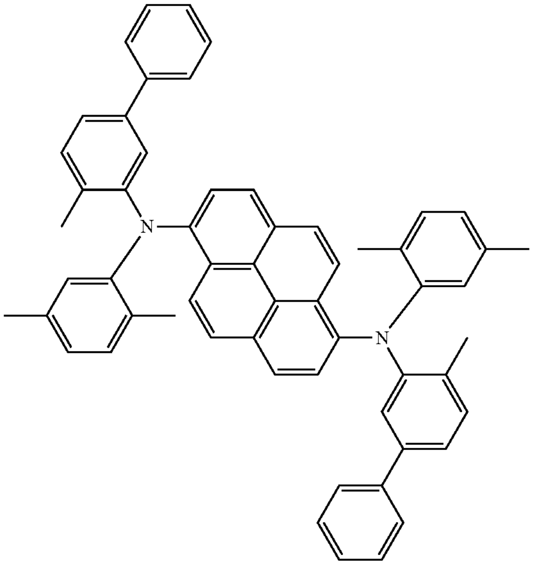

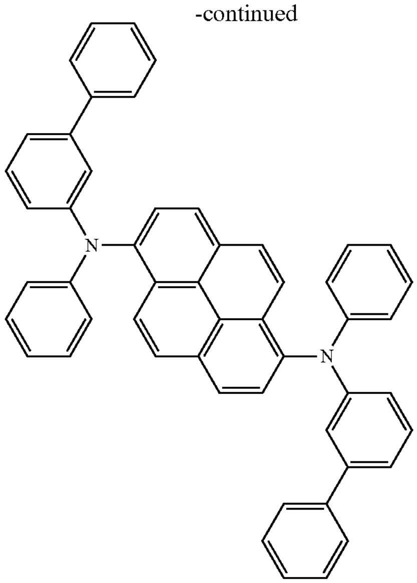
[Formula 154]
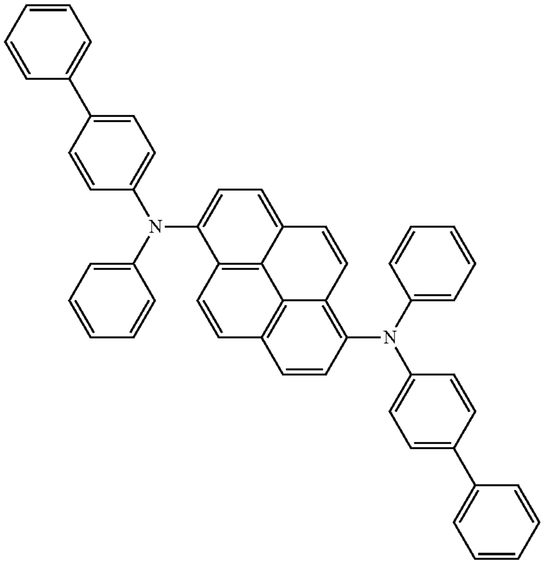
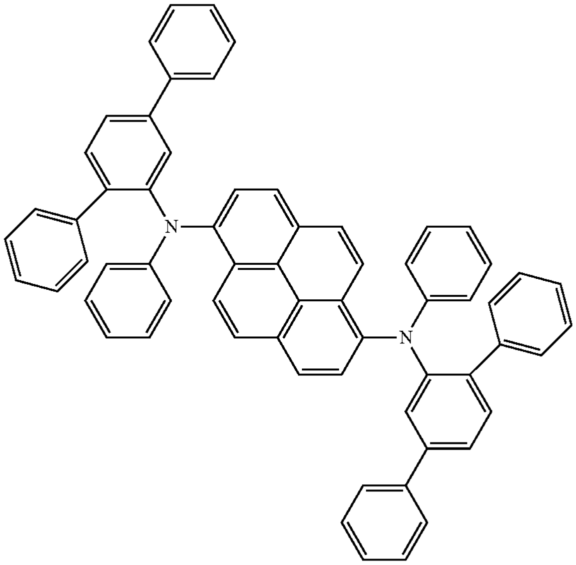
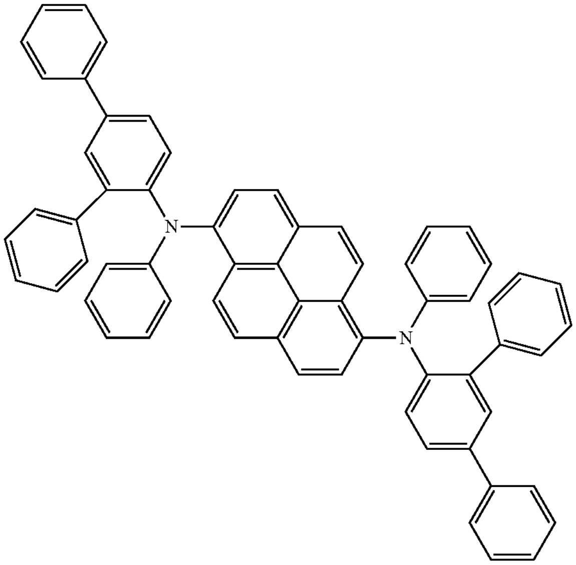
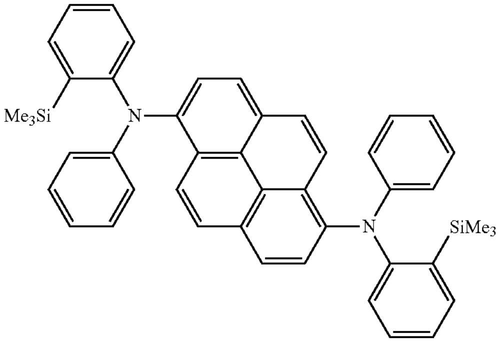
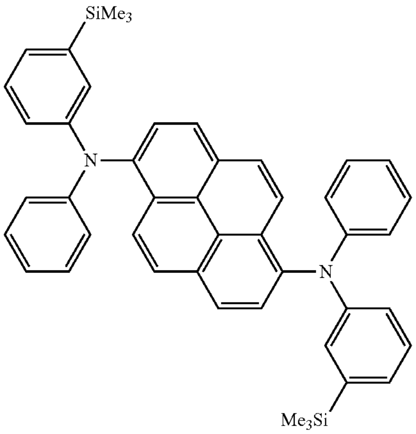

-continued
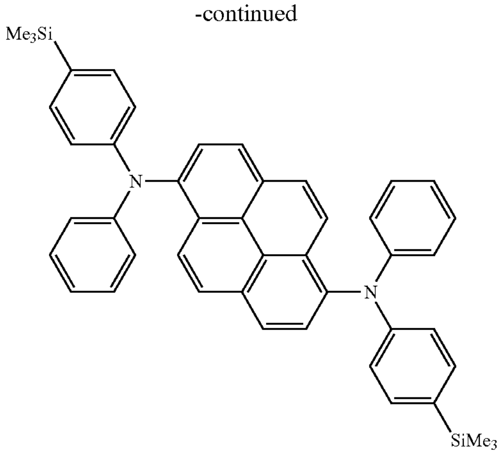
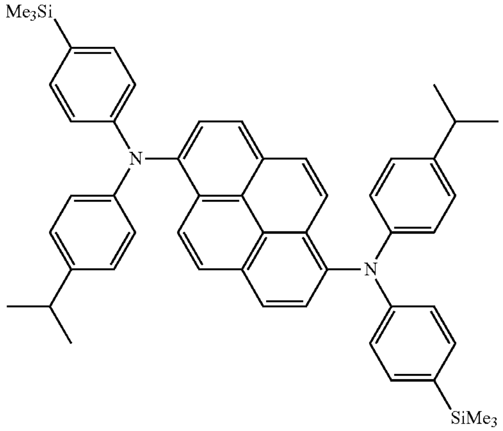
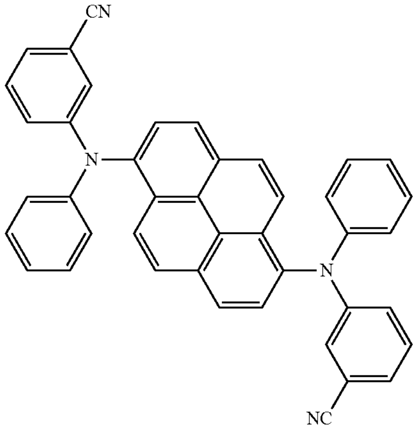
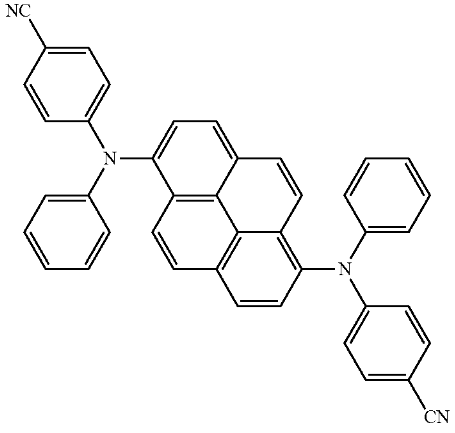
-continued
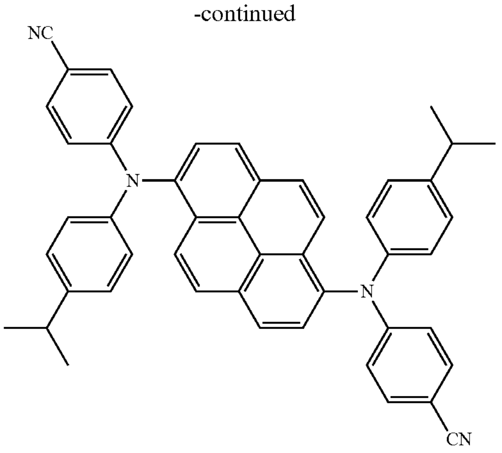
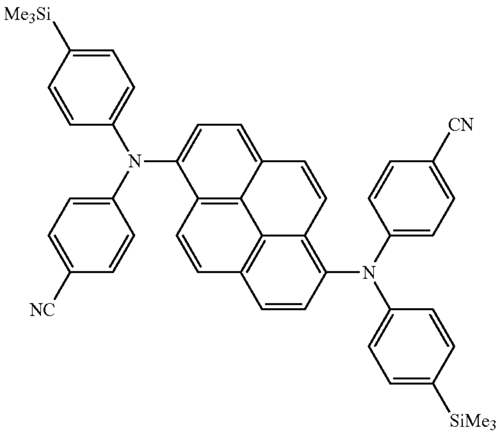
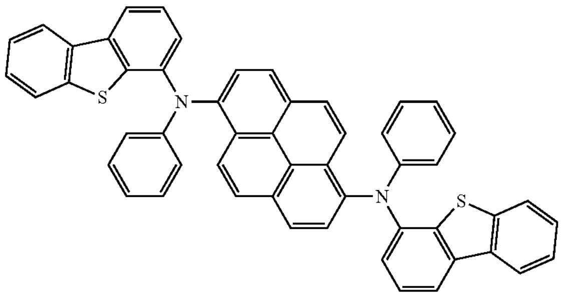
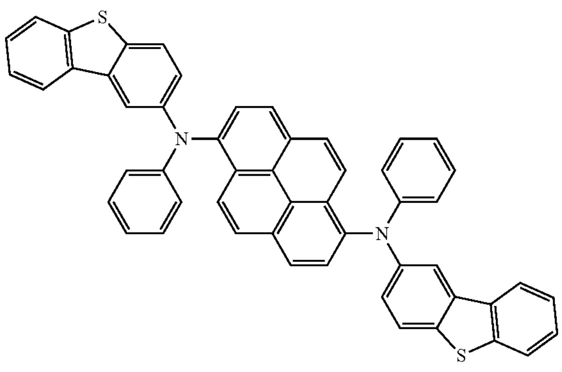

-continued
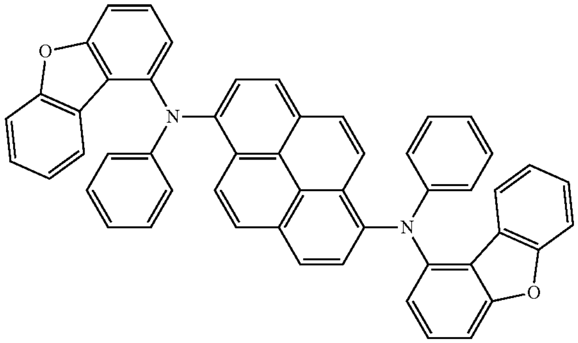
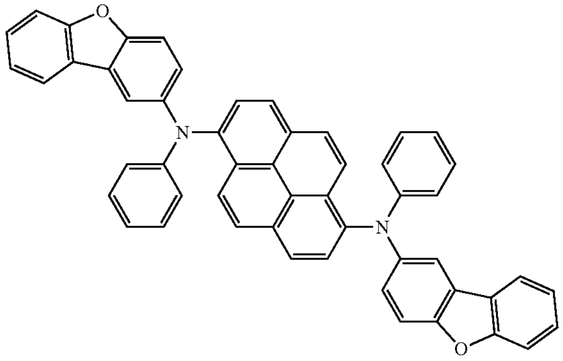
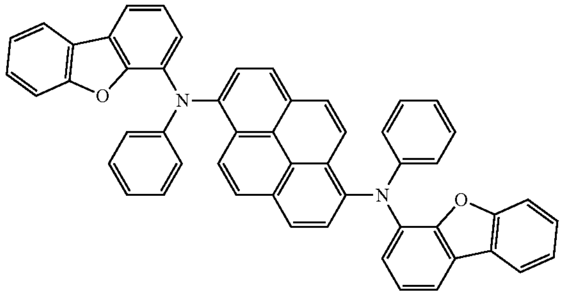
[Formula 155]
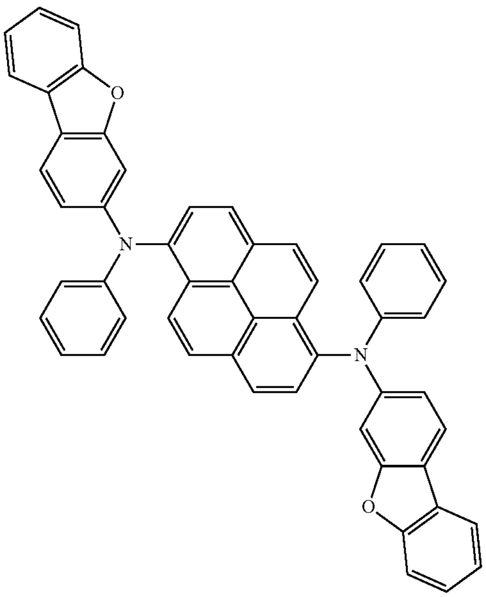
-continued
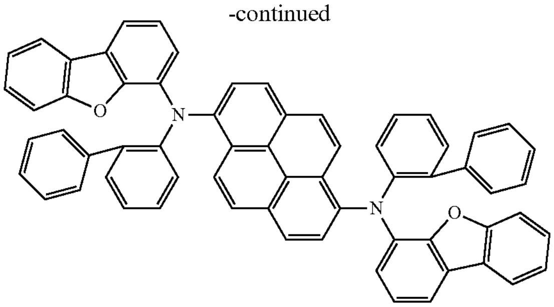
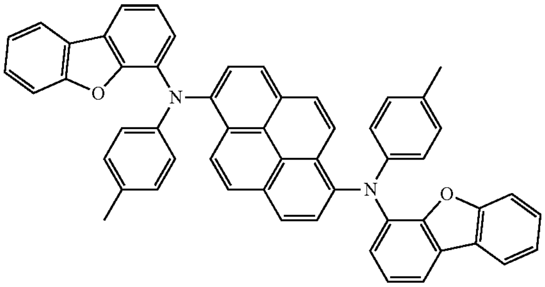
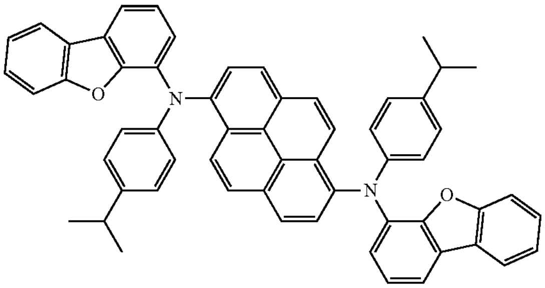
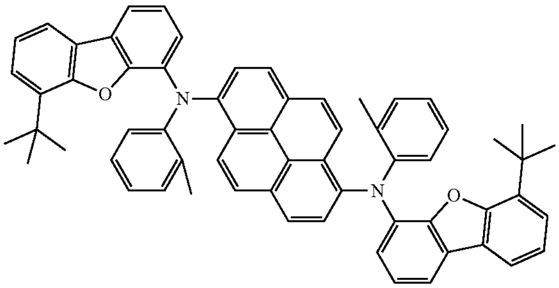
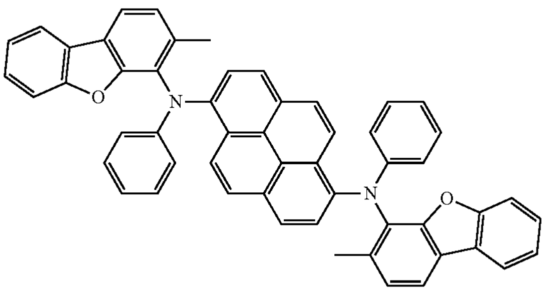
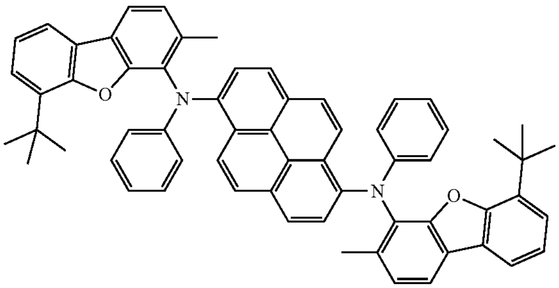

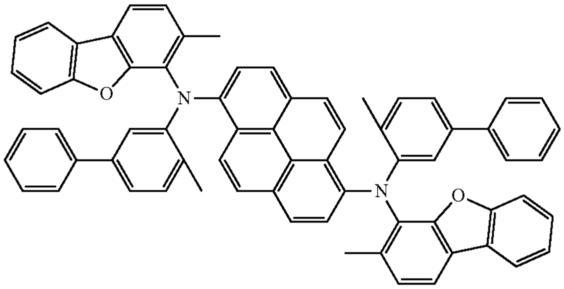
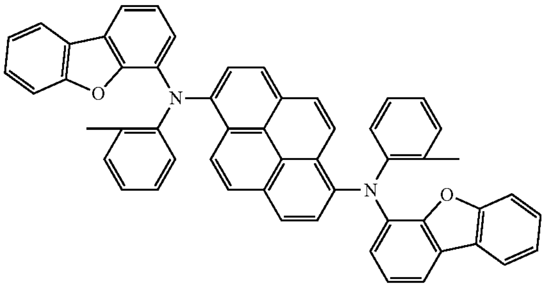
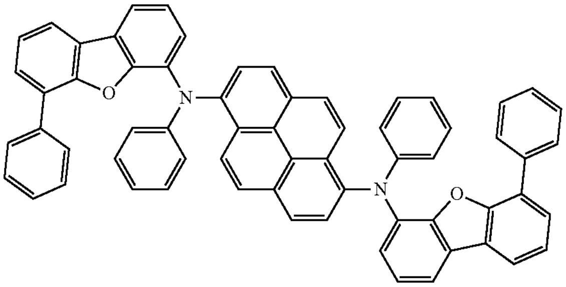
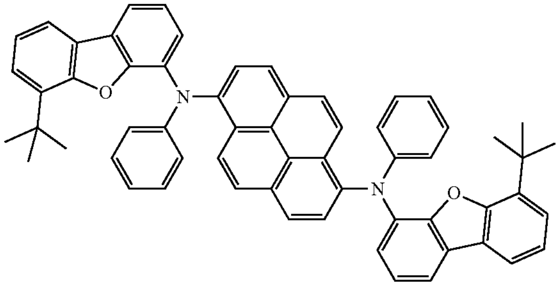
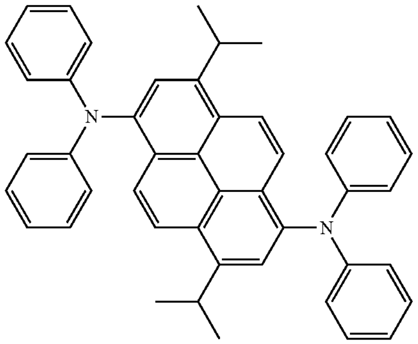
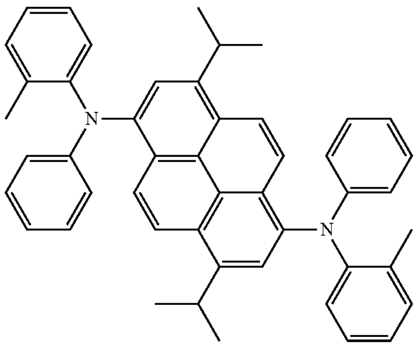
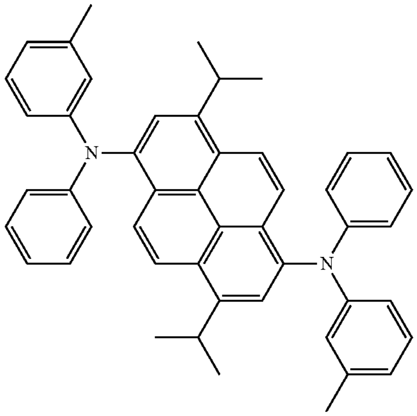
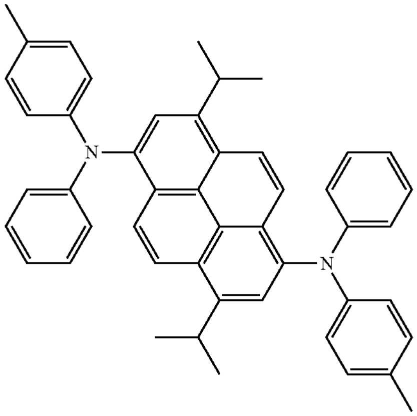
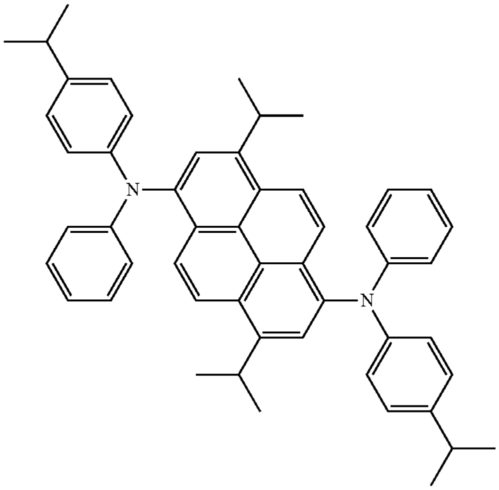

-continued
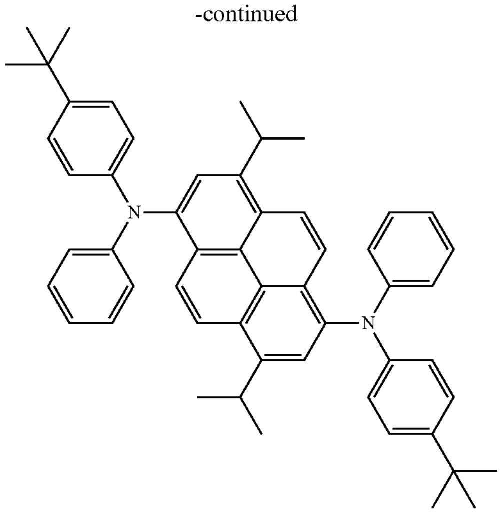
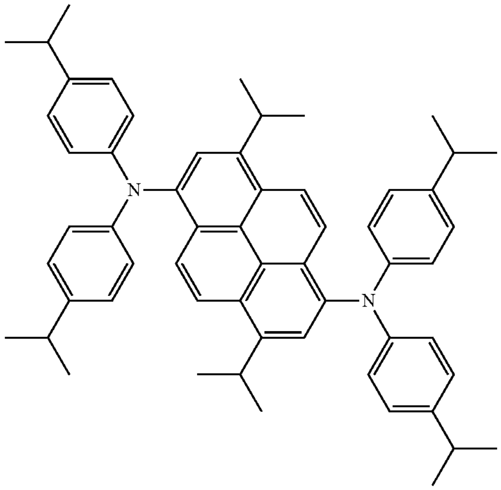
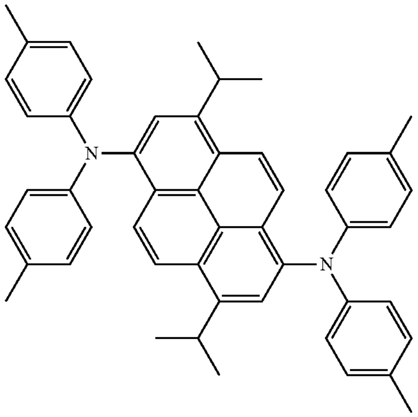
-continued
[Formula 156]
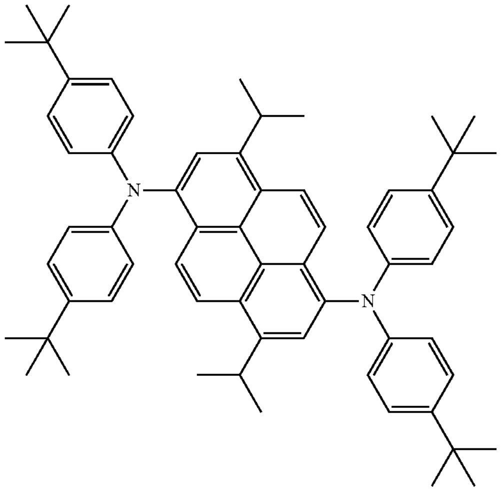
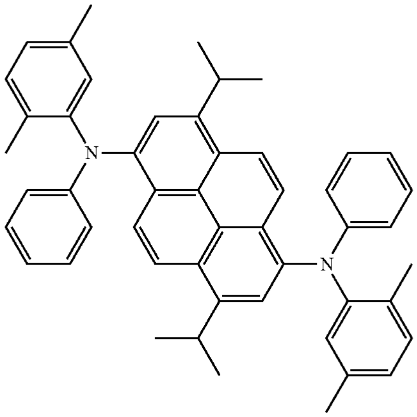
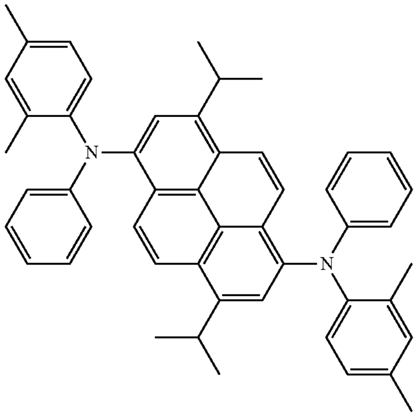

-continued
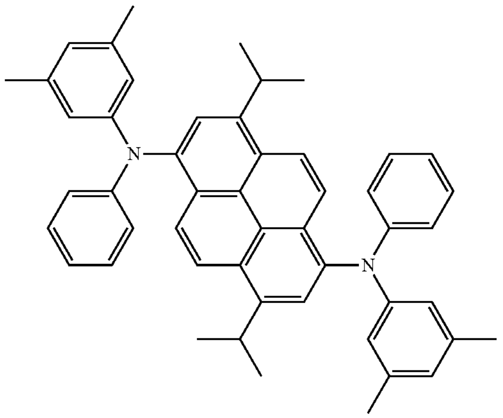
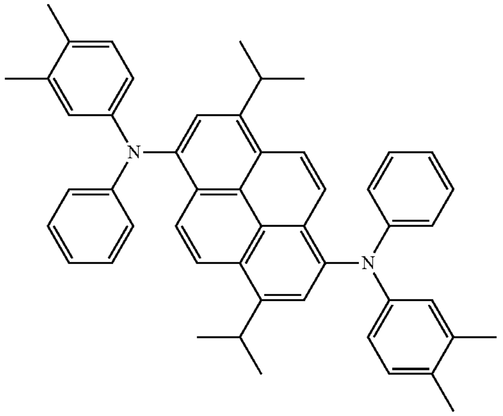
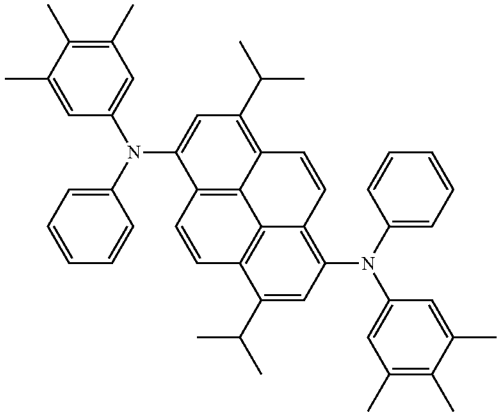
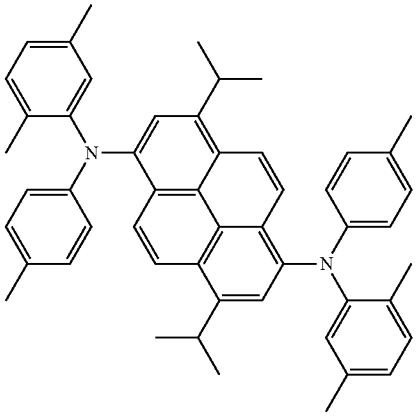
-continued
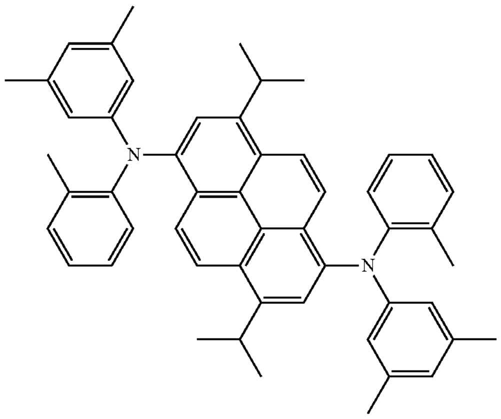
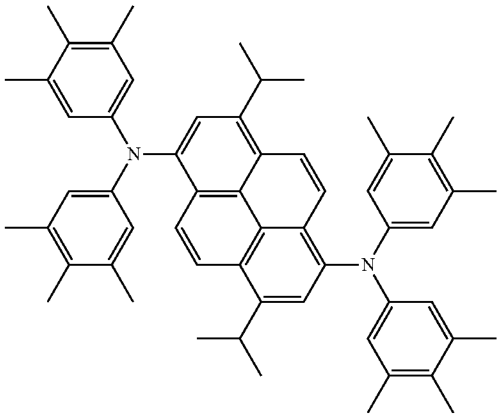
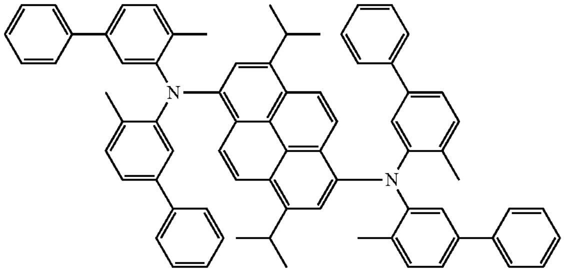
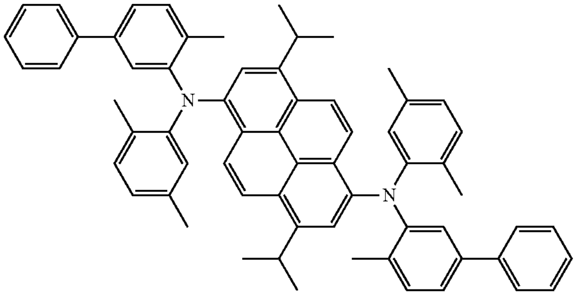

-continued
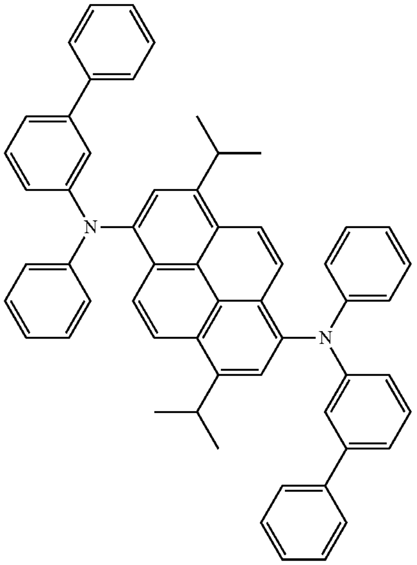
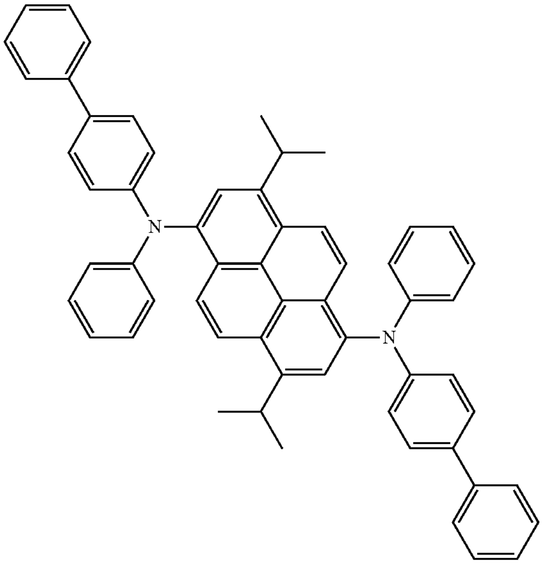
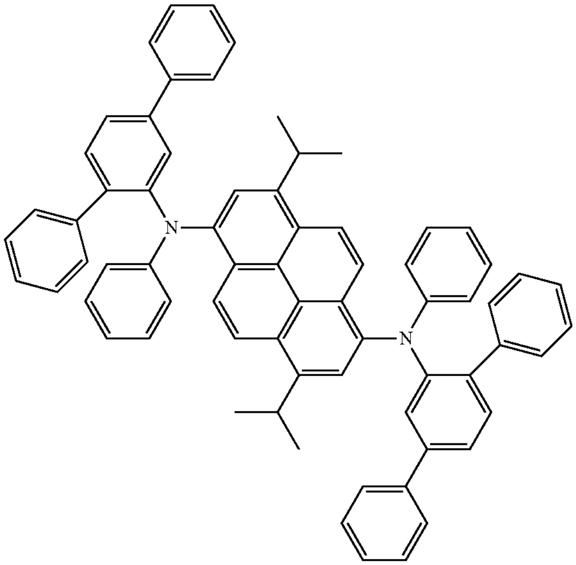
-continued
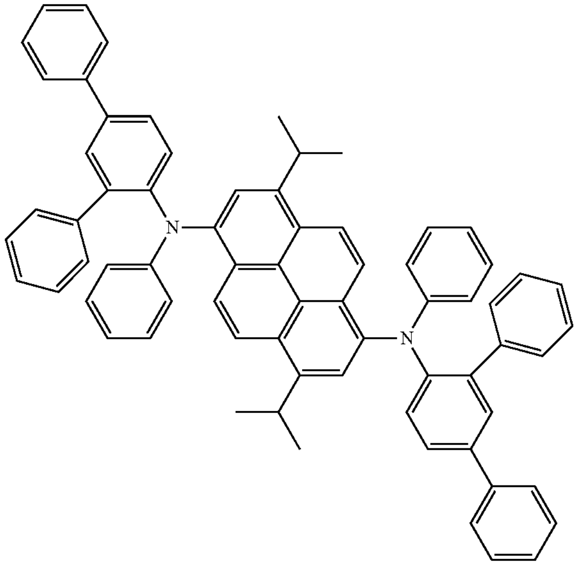
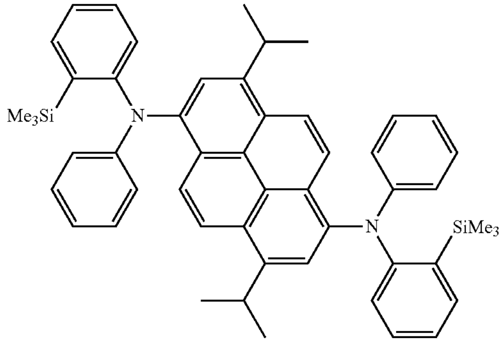
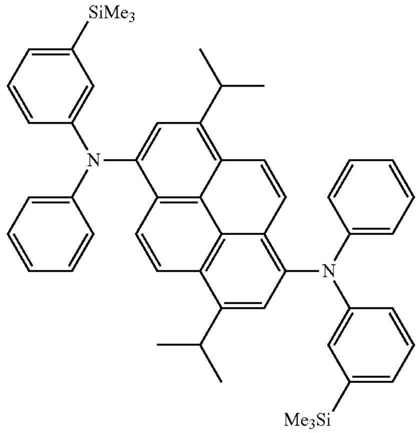

-continued
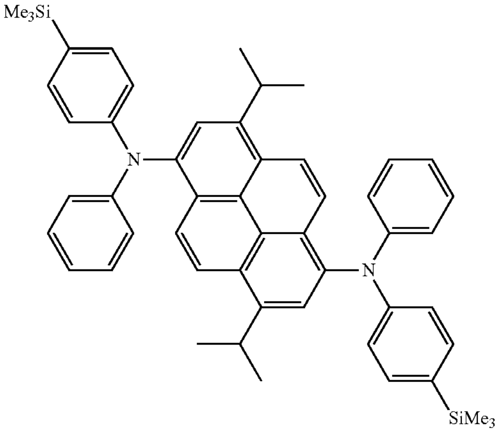
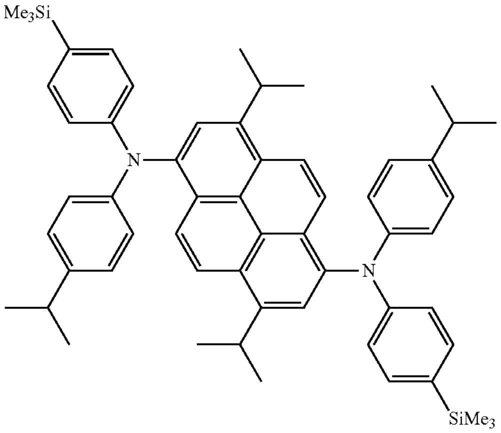
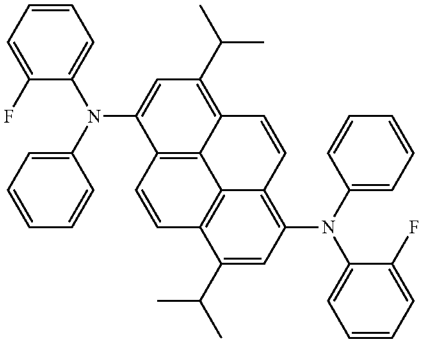
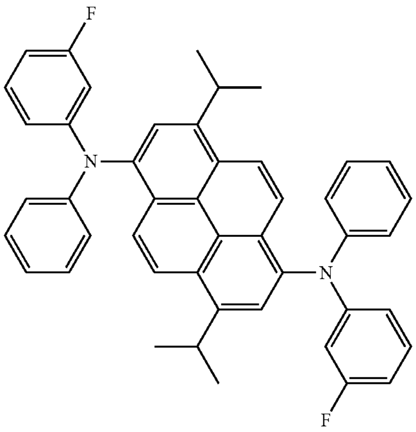
-continued
[Formula 157]
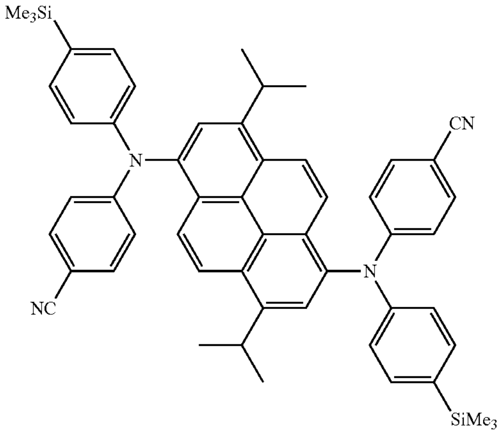
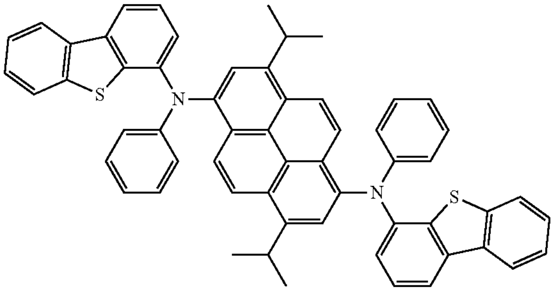
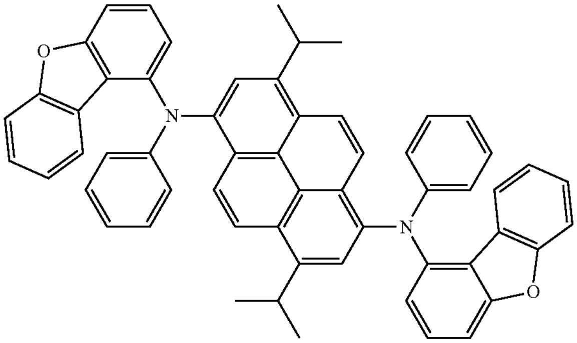
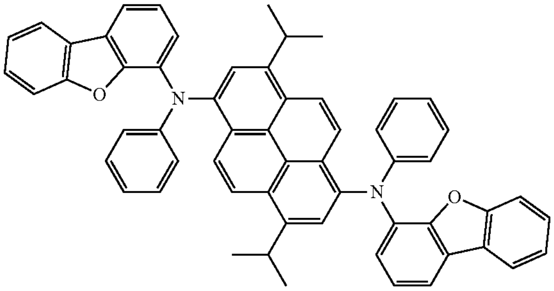
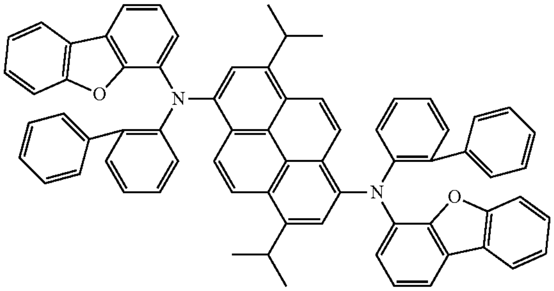

-continued
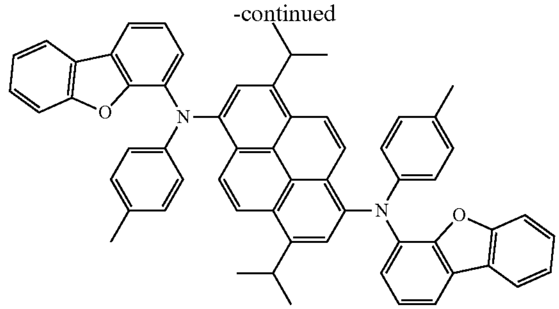
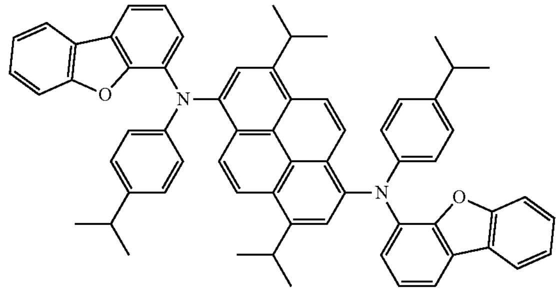
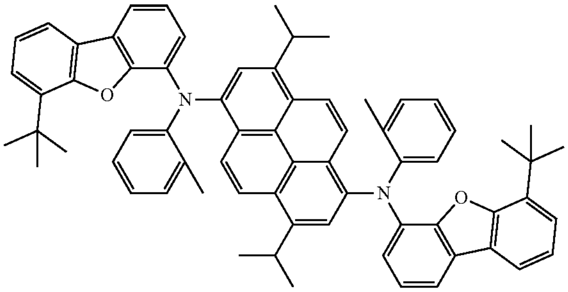
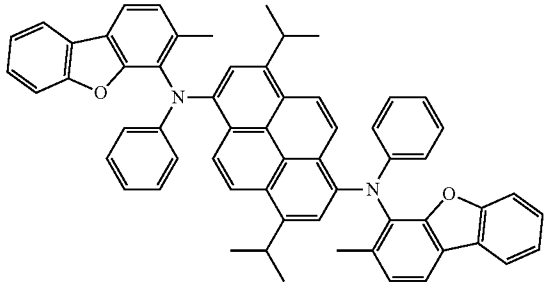
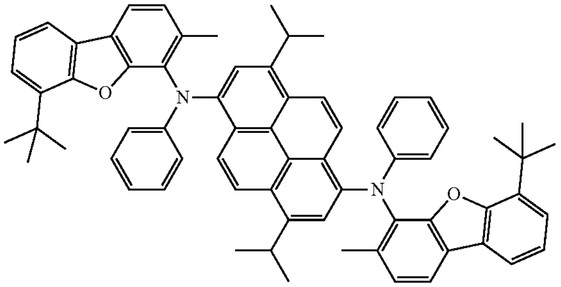
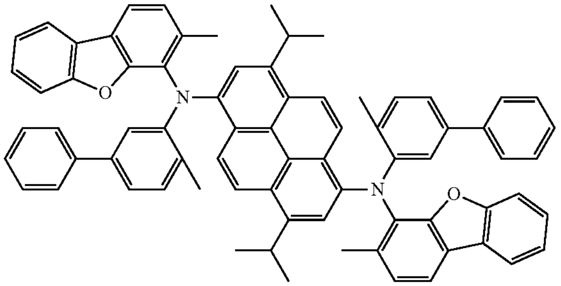
-continued
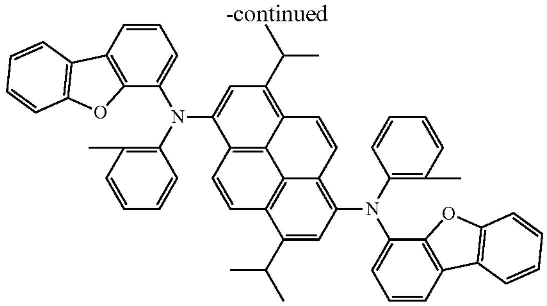
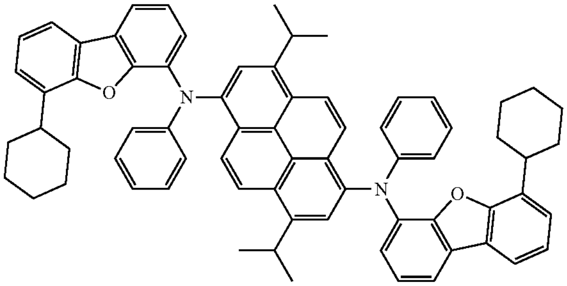
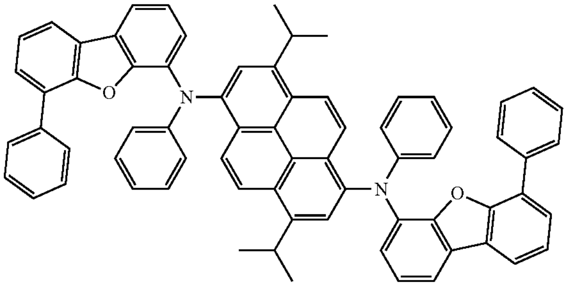
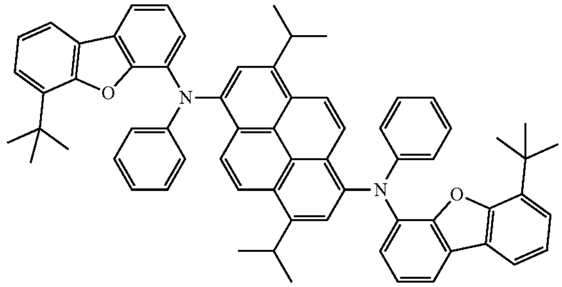
Compound Represented by Formula (4)
The compound represented by the formula (4) will be described.
[Formula 158]
(4)
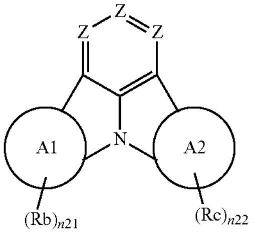
In the formula (4):
Z is each independently CRa or a nitrogen atom;
A1 ring and A2 ring are each independently a substituted or unsubstituted aromatic hydrocarbon ring having 6 to 50 ring carbon atoms, or a substituted or unsubstituted heterocycle having 5 to 50 ring atoms;

when a plurality of Ra are present, at least one combination of adjacent two or more of the plurality of Ra are mutually bonded to form a substituted or unsubstituted monocyclic ring, mutually bonded to form a substituted or unsubstituted fused ring, or not mutually bonded;

n21 and n22 are each independently 0, 1, 2, 3, or 4;

when a plurality of Rb are present, at least one combination of adjacent two or more of the plurality of Rb are mutually bonded to form a substituted or unsubstituted monocyclic ring, mutually bonded to form a substituted or unsubstituted fused ring, or not mutually bonded;

when a plurality of Rc are present, at least one combination of adjacent two or more of the plurality of Rc are mutually bonded to form a substituted or unsubstituted monocyclic ring, mutually bonded to form a substituted or unsubstituted fused ring, or not mutually bonded; and Ra, Rb and Rc not forming the monocyclic ring and not forming the fused ring are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

The "aromatic hydrocarbon ring" for the A1 ring and A2 ring has the same structure as the compound formed by introducing a hydrogen atom to the "aryl group" described above.

Ring atoms of the "aromatic hydrocarbon ring" for the A1 ring and the A2 ring include two carbon atoms on a fused bicyclic structure at the center of the formula (4).

Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the A1 ring and A2 ring has the same structure as the compound formed by introducing a hydrogen atom to the "heterocyclic group" described above.

Ring atoms of the "heterocycle" for the A1 ring and the A2 ring include two carbon atoms on a fused bicyclic structure at the center of the formula (4).

Specific examples of the "substituted or unsubstituted heterocycle having 5 to 50 ring atoms" include a compound formed by introducing a hydrogen atom to the "heterocyclic group" described in the specific example group G2.

Rb is bonded to any one of carbon atoms forming the aromatic hydrocarbon ring as the A1 ring or any one of the atoms forming the heterocycle as the A1 ring.

Rc is bonded to any one of carbon atoms forming the aromatic hydrocarbon ring as the A2 ring or any one of the atoms forming the heterocycle as the A2 ring.

At least one of Ra, Rb, or Rc is preferably a group represented by a formula (4a) below. More preferably, at least two of Ra, Rb, and Rc are groups represented by the formula (4a).

$*-L_{401}-Ar_{401}$[Formula 159]

In the formula (4a):

$L_{401}$ is a single bond, a substituted or unsubstituted arylene group having 6 to 30 ring carbon atoms, or a substituted or unsubstituted divalent heterocyclic group having 5 to 30 ring atoms; and $Ar_{401}$ is a substituted or unsubstituted aryl group having 6 to 50 ring carbon atoms, a substituted or unsubstituted heterocyclic group having 5 to 50 ring atoms, or a group represented by a formula (4b) below.

[Formula 160]

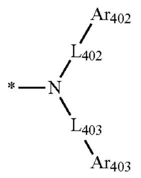

(4b)

In the formula (4b):

$L_{402}$ and $L_{403}$ are each independently a single bond, a substituted or unsubstituted arylene group having 6 to 30 ring carbon atoms, or a substituted or unsubstituted divalent heterocyclic group having 5 to 30 ring atoms;

a combination of $Ar_{402}$ and $Ar_{403}$ are mutually bonded to form a substituted or unsubstituted monocyclic ring, mutually bonded to form a substituted or unsubstituted fused ring, or not mutually bonded; and $Ar_{402}$ and $Ar_{403}$ not forming the monocyclic ring and not forming the fused ring are each independently a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is represented by a formula (42) below.

[Formula 161]

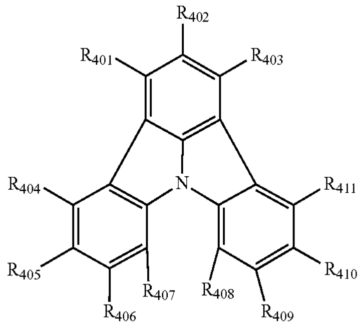

(42)

In the formula (42):

at least one combination of adjacent two or more of $R_{401}$ to $R_{411}$ are mutually bonded to form a substituted or unsubstituted monocyclic ring, mutually bonded to form a substituted or unsubstituted fused ring, or not mutually bonded; and $R_{401}$ to $R_{411}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

At least one of $R_{401}$ to $R_{411}$ is preferably a group represented by the formula (4a). More preferably, at least two of $R_{401}$ to $R_{411}$ are groups represented by the formula (4a).

$R_{404}$ and $R_{411}$ are preferably groups represented by the formula (4a).

In an exemplary embodiment, the compound represented by the formula (4) is a compound formed by bonding a structure represented by a formula (4-1) or a formula (4-2) below to the A1 ring.

Further, in an exemplary embodiment, the compound represented by the formula (42) is a compound formed by bonding the structure represented by the formula (4-1) or the formula (4-2) to the ring bonded with $R_{404}$ to $R_{407}$.

[Formula 162]

(4-1)

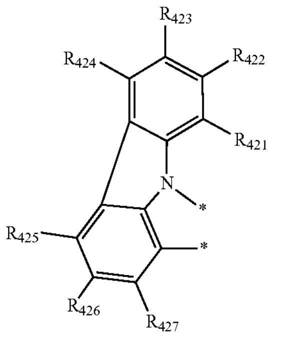

(4-2)

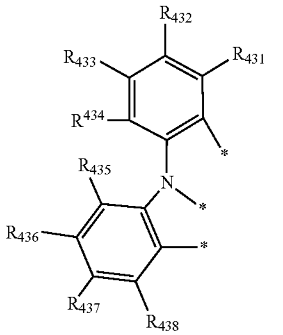

In the formula (4-1), two bonds * are each independently bonded to the ring-forming carbon atom of the aromatic hydrocarbon ring or the ring atom of the heterocycle as the A1 ring in the formula (4) or bonded to one of $R_{404}$ to $R_{407}$ in the formula (42);

* in the formula (4-2), three bonds * are each independently bonded to the ring-forming carbon atom of the aromatic hydrocarbon ring or the ring atom of the heterocycle as the A1 ring in the formula (4) or bonded to one of $R_{404}$ to $R_{407}$ in the formula (42);

at least one combination of adjacent two or more of $R_{421}$ to $R_{427}$ are mutually bonded to form a substituted or unsubstituted monocyclic ring, mutually bonded to form a substituted or unsubstituted fused ring, or not mutually bonded;

at least one combination of adjacent two or more of $R_{431}$ to $R_{438}$ are mutually bonded to form a substituted or unsubstituted monocyclic ring, mutually bonded to form a substituted or unsubstituted fused ring, or not mutually bonded; and $R_{421}$ to $R_{427}$ and $R_{431}$ to $R_{438}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is a compound represented by a formula (41-3), (41-4) or (41-5) below.

[Formula 163]

(41-3)

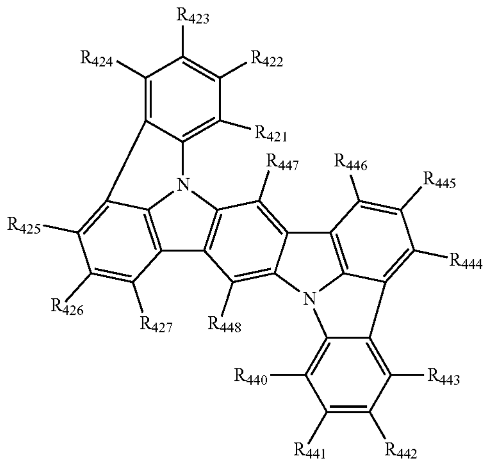

[Formula 164]

(41-4)

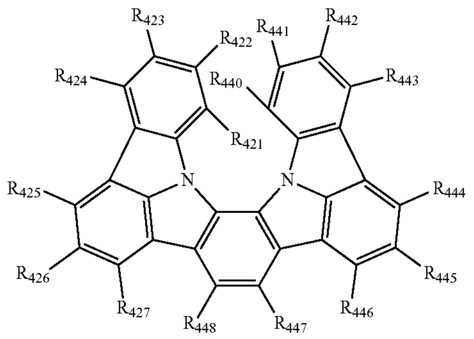

-continued

[Formula 165]

(41-5)

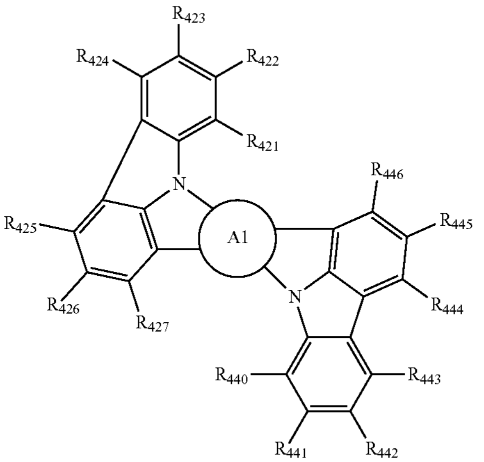

In the formulae (41-3), (41-4) and (41-5):

A1 ring is as defined for the formula (4);

$R_{421}$ to $R_{427}$ each independently represent the same as $R_{421}$ to $R_{427}$ in the formula (4-1); and $R_{440}$ to $R_{448}$ each independently represent the same as $R_{401}$ to $R_{411}$ in the formula (42).

In an exemplary embodiment, a substituted or unsubstituted aromatic hydrocarbon ring having 6 to 50 ring carbon atoms for the A1 ring in the formula (41-5) is a substituted or unsubstituted naphthalene ring, or a substituted or unsubstituted fluorene ring.

In an exemplary embodiment, a substituted or unsubstituted heterocycle having 5 to 50 ring atoms for the A1 ring in the formula (41-5) is a substituted or unsubstituted dibenzofuran ring, a substituted or unsubstituted carbazole ring, or a substituted or unsubstituted dibenzothiophene ring.

In an exemplary embodiment, the compound represented by the formula (4) or (42) is selected from the group consisting of compounds represented by formulae (461) to (467) below.

[Formula 166]

(461)

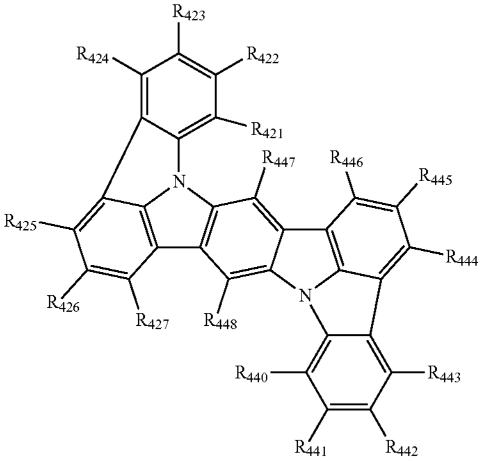

-continued (462)

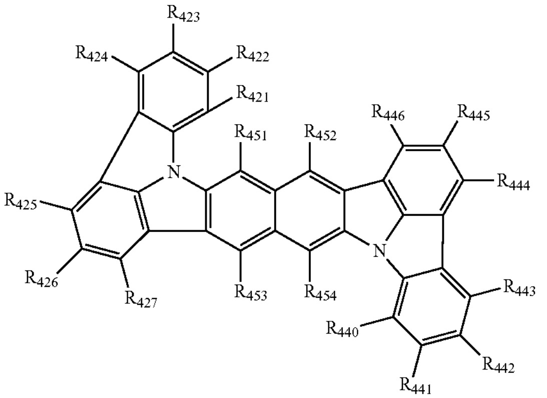

[Formula 167]

(463)

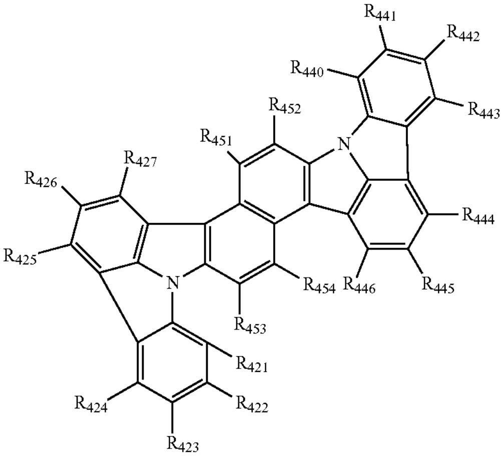

(464)

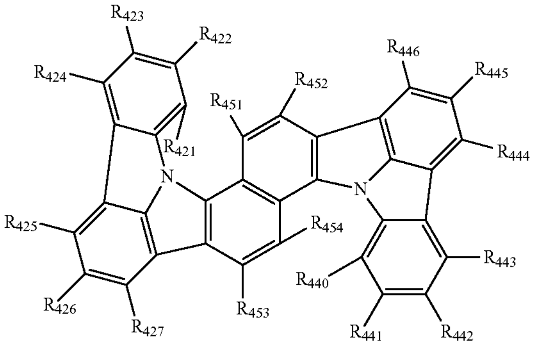

[Formula 168]

(465)

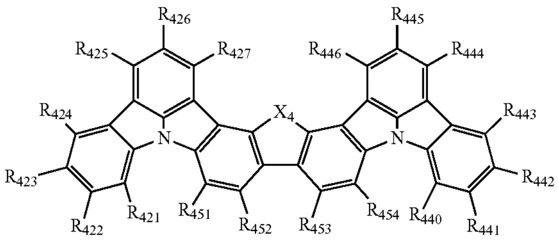

-continued

[Formula 169]

(466)

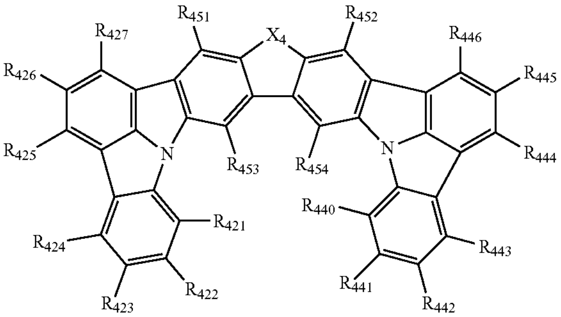

[Formula 170]

(467)

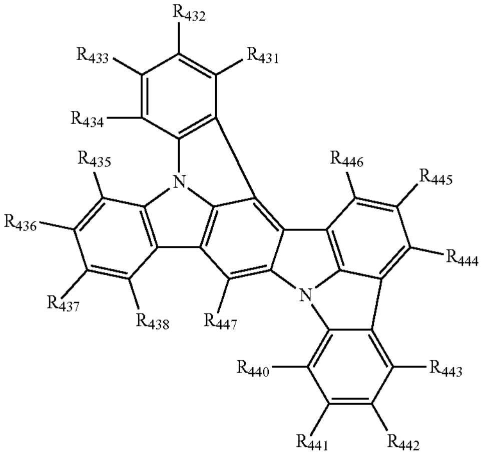

In the formulae (461), (462), (463), (464), (465), (466) and (467):

$R_{421}$ to $R_{427}$ each independently represent the same as $R_{421}$ to $R_{427}$ in the formula (4-1);

$R_{431}$ to $R_{438}$ each independently represent the same as $R_{431}$ to $R_{438}$ in the formula (4-2);

$R_{440}$ to $R_{448}$ and $R_{451}$ to $R_{454}$ each independently represent the same as $R_{401}$ to $R_{411}$ in the formula (42);

$X_4$ is an oxygen atom, $NR_{801}$, or $C(R_{802})(R_{803})$;

$R_{801}$, $R_{802}$ and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, in the compound represented by the formula (42), at least one combination of adjacent two or more of $R_{401}$ to $R_{411}$ are mutually bonded to form a substituted or unsubstituted monocyclic ring or a substituted or unsubstituted fused ring. The compound represented by the formula (42) in the exemplary embodiment is described in detail as a compound represented by a formula (45).

Compound Represented by Formula (45)

The compound represented by the formula (45) will be described.

[Formula 171]

(45)

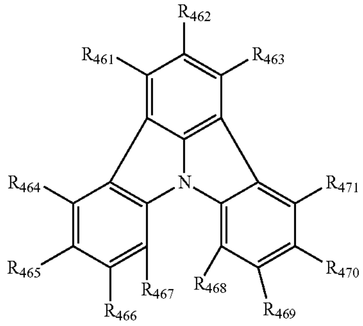

In the formula (45):

two or more of combinations selected from the group consisting of a combination of $R_{461}$ and $R_{462}$, a combination of $R_{462}$ and $R_{463}$, a combination of $R_{464}$ and $R_{465}$, a combination of $R_{465}$ and $R_{466}$, a combination of $R_{466}$ and $R_{467}$, a combination of $R_{468}$ and $R_{469}$, a combination of $R_{469}$ and $R_{470}$, and a combination of $R_{470}$ and $R_{471}$ are mutually bonded to form a substituted or unsubstituted monocyclic ring or a substituted or unsubstituted fused ring;

the combination of $R_{461}$ and $R_{462}$ and the combination of $R_{462}$ and $R_{463}$, the combination of $R_{464}$ and $R_{465}$ and the combination of $R_{465}$ and $R_{466}$, the combination of $R_{465}$ and $R_{466}$ and the combination of $R_{466}$ and $R_{467}$, the combination of $R_{468}$ and $R_{469}$ and the combination of $R_{469}$ and $R_{470}$, and the combination of $R_{469}$ and $R_{470}$ and the combination of $R_{470}$ and $R_{471}$ do not simultaneously form a ring;

at least two rings formed by $R_{461}$ to $R_{471}$ are mutually the same or different; and $R_{461}$ to $R_{471}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

In the formula (45), $R_n$ and $R_{n+1}$ (n being an integer selected from 461, 462, 464 to 466, and 468 to 470) are mutually bonded to form a substituted or unsubstituted monocyclic ring or fused ring together with two ring-forming carbon atoms bonded with $R_n$ and $R_{n+1}$. The ring is preferably formed of atoms selected from the group consisting of a carbon atom, an oxygen atom, a sulfur atom, and a nitrogen atom, and is preferably made of 3 to 7, more preferably 5 or 6 atoms.

The number of the above cyclic structures in the compound represented by the formula (45) is, for instance, 2, 3, or 4. The two or more of the cyclic structures may be present on the same benzene ring on the basic skeleton represented by the formula (45) or may be present on different benzene rings. For instance, when three cyclic structures are present, each of the cyclic structures may be present on corresponding one of the three benzene rings of the formula (45).

Examples of the above cyclic structures in the compound represented by the formula (45) include structures represented by formulae (451) to (460) below.

[Formula 172]

(451)

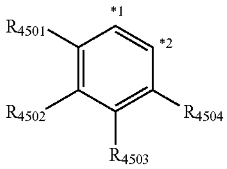

(452)

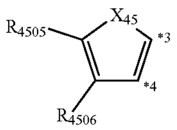

(453)

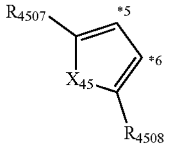

(454)

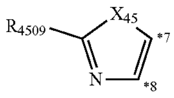

(455)

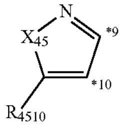

(456)

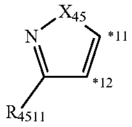

(457)

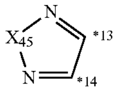

In the formulae (451) to (457):

each combination of *1 and *2, *3 and *4, *5 and *6, *7 and *8, *9 and *10, *11 and *12, and *13 and *14 represent the two ring-forming carbon atoms bonded with $R_n$ and $R_{n+1}$;

the ring-forming carbon atom bonded with $R_n$ may be any one of the two ring-forming carbon atoms represented by *1 and *2, *3 and *4, *5 and *6, *7 and *8, *9 and *10, *11 and *12, and *13 and *14;

$X_{45}$ is $C(R_{4512})(R_{4513})$, $NR_{4514}$, an oxygen atom, or a sulfur atom;

at least one combination of adjacent two or more of $R_{4501}$ to $R_{4506}$ and $R_{4512}$ to $R_{4513}$ are mutually bonded to form a substituted or unsubstituted monocyclic ring, mutually bonded to form a substituted or unsubstituted fused ring, or not mutually bonded; and $R_{4501}$ to $R_{4514}$ not forming the monocyclic ring and not forming the fused ring each independently represent the same as $R_{461}$ to $R_{471}$ in the formula (45).

[Formula 173]

(458)

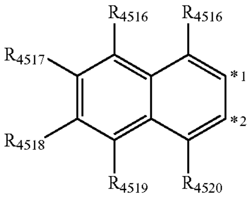

(459)

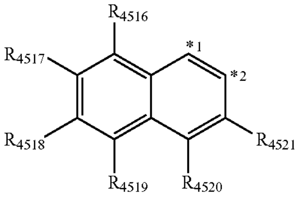

(460)

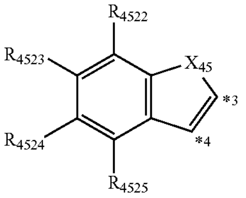

In the formulae (458) to (460):

each combination of *1 and *2, and *3 and *4 represent the two ring-forming carbon atoms bonded with $R_n$ and $R_n$+1;

the ring-forming carbon atom bonded with $R_n$ may be any one of the two ring-forming carbon atoms represented by *1 and *2, or *3 and *4;

$X_{45}$ is $C(R_{4512})(R_{4513})$, $NR_{4514}$, an oxygen atom, or a sulfur atom;

at least one combination of adjacent two or more of $R_{4512}$ to $R_{4513}$ and $R_{4515}$ to $R_{4525}$ are mutually bonded to form a substituted or unsubstituted monocyclic ring, mutually bonded to form a substituted or unsubstituted fused ring, or not mutually bonded; and $R_{4512}$ to $R_{4513}$, $R_{4515}$ to $R_{4521}$ and $R_{4522}$ to $R_{4525}$ not forming the monocyclic ring and not forming the fused ring, and $R_{4514}$ each independently represent the same as $R_{461}$ to $R_{471}$ in the formula (45).

In the formula (45), it is preferable that at least one of $R_{462}$, $R_{464}$, $R_{465}$, $R_{470}$ or $R_{471}$ (preferably, at least one of $R_{462}$, $R_{465}$ or $R_{470}$, more preferably $R_{462}$) is a group not forming the cyclic structure.

(i) A substituent, if present, of the cyclic structure formed by $R_n$ and $R_{n+1}$ of the formula (45), (ii) $R_{461}$ to $R_{471}$ not forming the cyclic structure in the formula (45), and (iii) $R_{4501}$ to $R_{4514}$, $R_{4515}$ to $R_{4525}$ in the formulae (451) to (460) are preferably each independently any one of groups selected from the group consisting of a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), a substituted or unsubstituted aryl group having 6 to 50 ring carbon atoms, a substituted or unsubstituted heterocyclic group having 5 to 50 ring atoms, and groups represented by formulae (461) to (464).

[Formula 174]

(461)

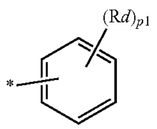

(462)

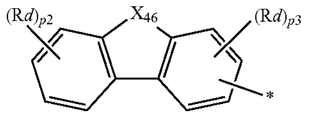

(463)

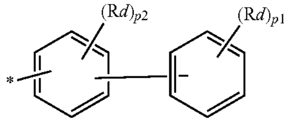

(464)

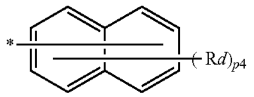

In the formulae (461) to (464):

$R_d$ is each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms;

$X_{46}$is C($R_{801}$)($R_{802}$), $NR_{803}$, an oxygen atom, or a sulfur atom;

$R_{801}$, $R_{802}$ and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different;

when a plurality of $R_{803}$ are present, the plurality of $R_{803}$ are mutually the same or different;

p1 is 5;

p2 is 4;

p3 is 3;

p4 is 7; and

* in the formulae (461) to (464) each independently represent a bonding position to a cyclic structure.

In the third and fourth compounds, $R_{901}$ to $R_{907}$ represent the same as those as described above.

In an exemplary embodiment, the compound represented by the formula (45) is represented by one of formulae (45-1) to (45-6) below.

[Formula 175]

(45-1)

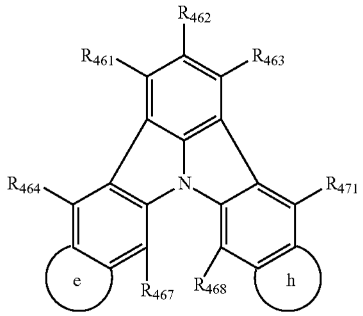

(45-2)

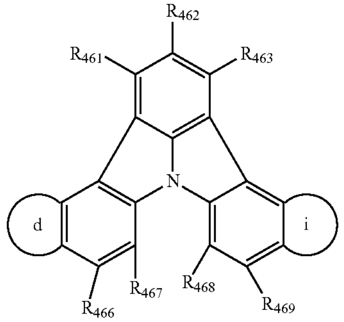

(45-3)

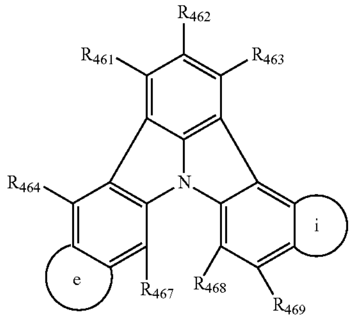

-continued

[Formula 176]

(45-4)

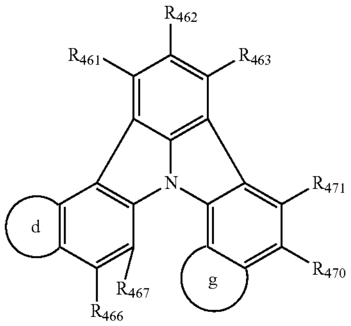

(45-5)

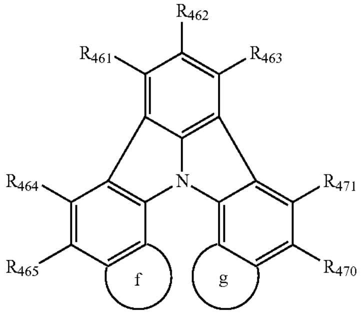

(45-6)

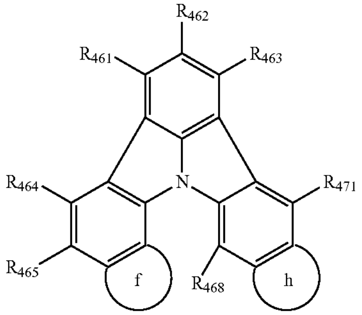

In the formulae (45-1) to (45-6):

rings d to i are each independently a substituted or unsubstituted monocyclic ring or a substituted or unsubstituted fused ring; and $R_{461}$ to $R_{471}$ each independently represent the same as $R_{461}$ to $R_{471}$ in the formula (45).

In an exemplary embodiment, the compound represented by the formula (45) is represented by one of formulae (45-7) to (45-12) below.

[Formula 177]

(45-7)

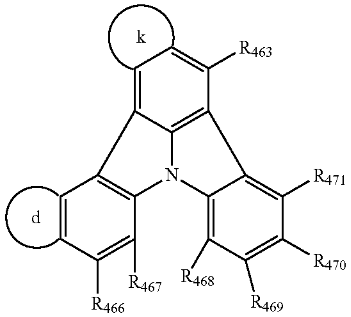

-continued (45-8)

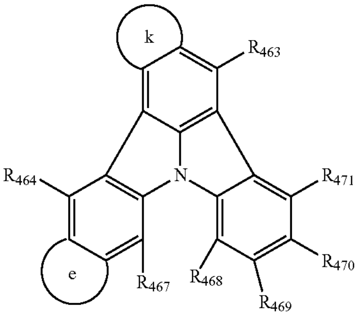

(45-9)

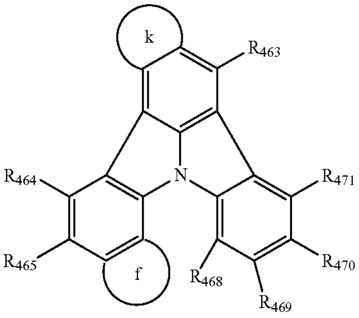

[Formula 178]

(45-10)

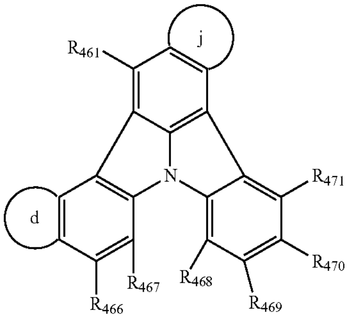

(45-11)

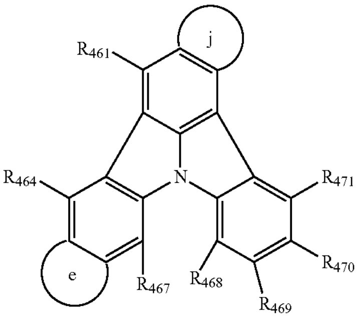

-continued (45-12)

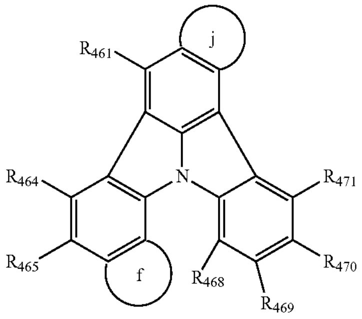

In the formulae (45-7) to (45-12):

rings d to f, k and j are each independently a substituted or unsubstituted monocyclic ring or a substituted or unsubstituted fused ring; and $R_{461}$ to $R_{471}$ each independently represent the same as $R_{461}$ to $R_{471}$ in the formula (45).

In an exemplary embodiment, the compound represented by the formula (45) is represented by one of formulae (45-13) to (45-21) below.

[Formula 179]

(45-13)

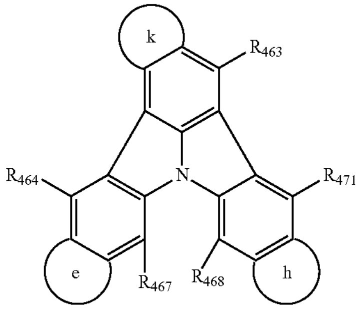

(45-14)

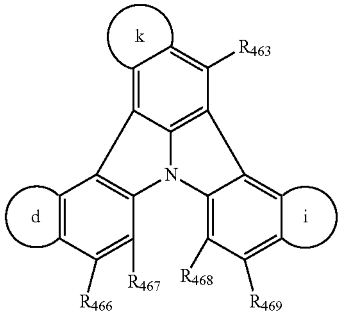

(45-15)

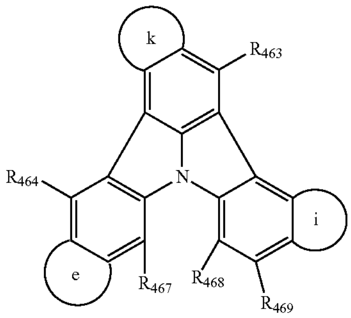

-continued

[Formula 180]

(45-16)

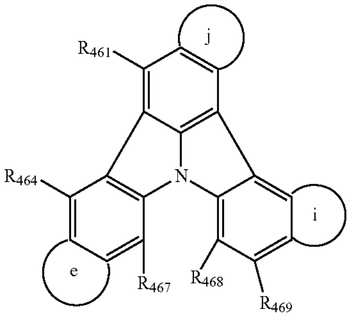

(45-17)

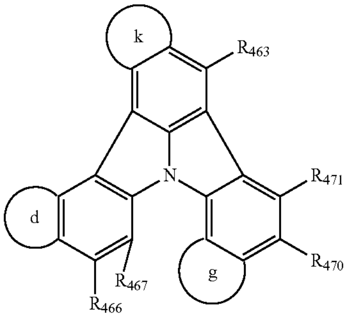

(45-18)

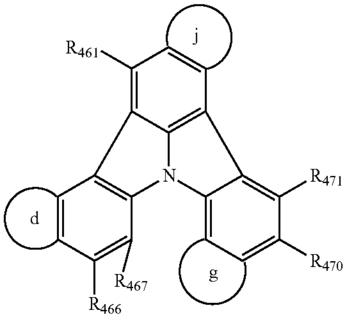

[Formula 181]

(45-19)

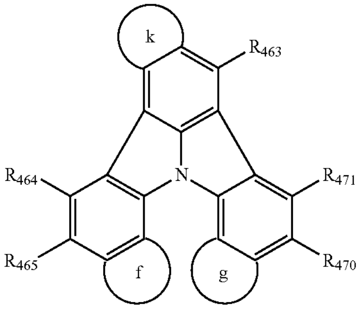

-continued (45-20)

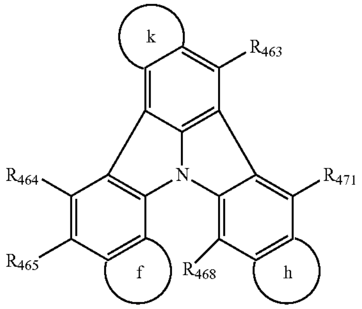

(45-21)

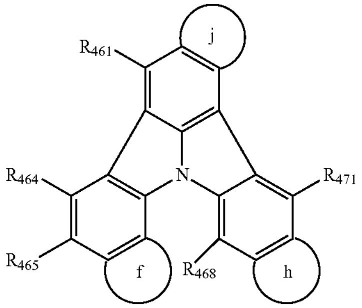

In the formulae (45-13) to (45-21):

rings d to k are each independently a substituted or unsubstituted monocyclic ring or a substituted or unsubstituted fused ring; and $R_{461}$ to $R_{471}$ each independently represent the same as $R_{461}$ to $R_{471}$ in the formula (45).

When the ring g or the ring h further has a substituent, examples of the substituent include a substituted or unsubstituted alkyl group having 1 to 50 carbon atoms, a substituted or unsubstituted aryl group having 6 to 50 ring carbon atoms, a group represented by the formula (461), a group represented by the formula (463), or a group represented by the formula (464).

In an exemplary embodiment, the compound represented by the formula (45) is represented by one of formulae (45-22) to (45-25) below.

[Formula 182]

(45-22)

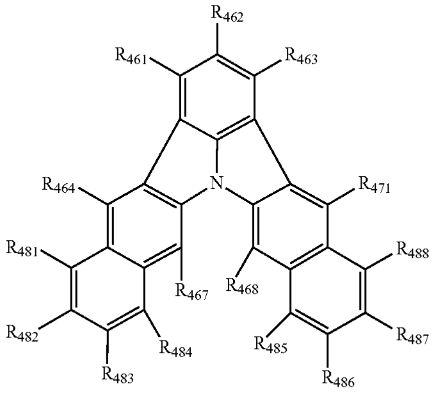

-continued (45-23)

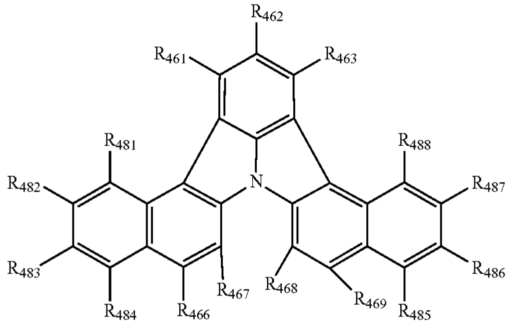

(45-24)

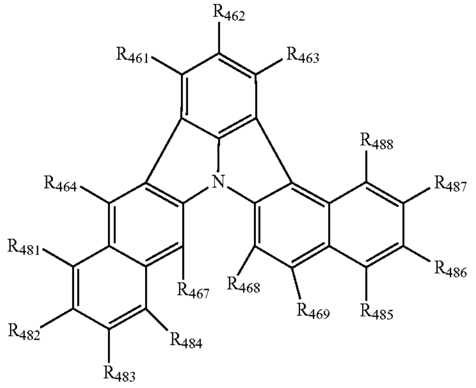

(45-25)

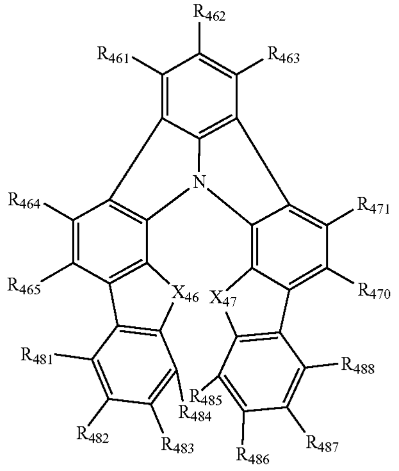

$X_{46}$ and $X_{47}$ are each independently $C(R_{801})(R_{802})$, $NR_{803}$, an oxygen atom, or a sulfur atom;

$R_{461}$ to $R_{471}$ and $R_{481}$ to $R_{488}$ each independently represent the same as $R_{461}$ to $R_{471}$ in the formula (45);

$R_{801}$, $R_{802}$ and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, the compound represented by the formula (45) is represented by a formula (45-26) below.

[Formula 183]

(45-26)

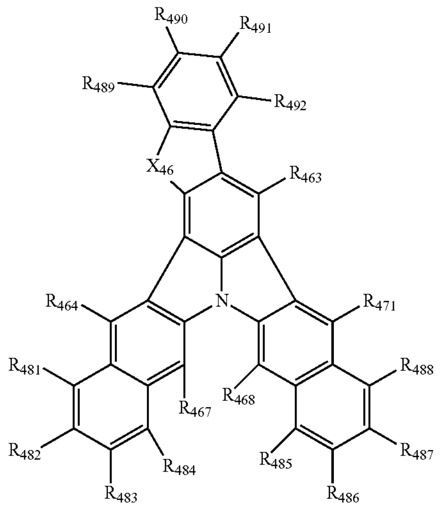

In the formula (45-26):

$X_{46}$ is $C(R_{801})(R_{802})$, $NR_{803}$, an oxygen atom, or a sulfur atom;

$R_{463}$, $R_{464}$, $R_{467}$, $R_{468}$, $R_{471}$ and $R_{481}$ to $R_{492}$ each independently represent the same as $R_{461}$ to $R_{471}$ in the formula (45);

$R_{801}$, $R_{802}$ and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

Specific examples of the compound represented by the formula (4) include compounds shown below. In the specific examples below, Ph represents a phenyl group, and D represents a deuterium atom.

[Formula 184]

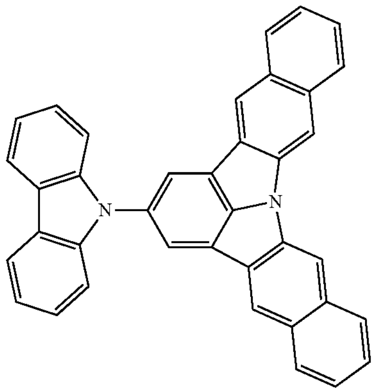

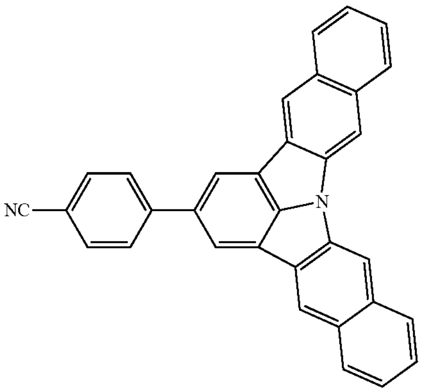

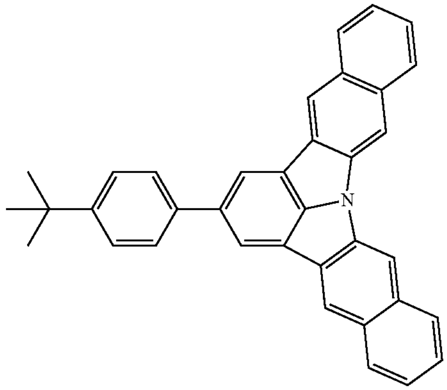

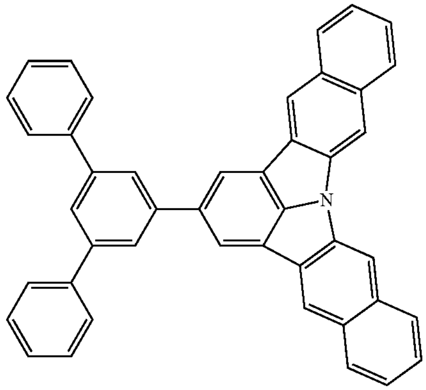

-continued
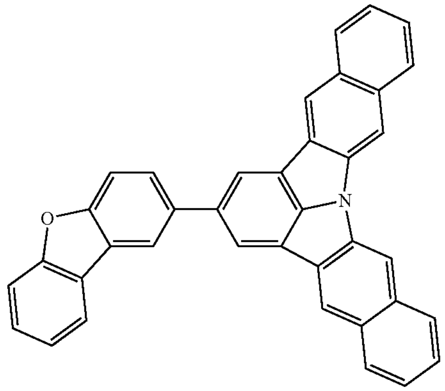
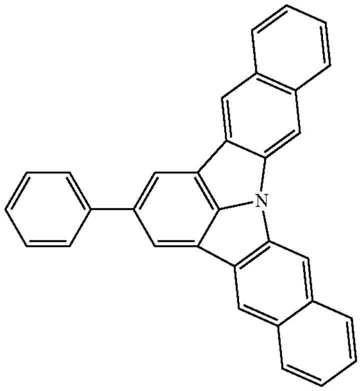
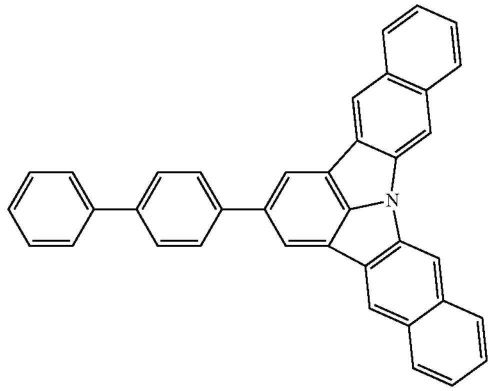
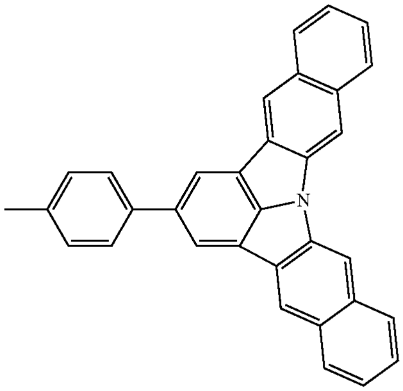
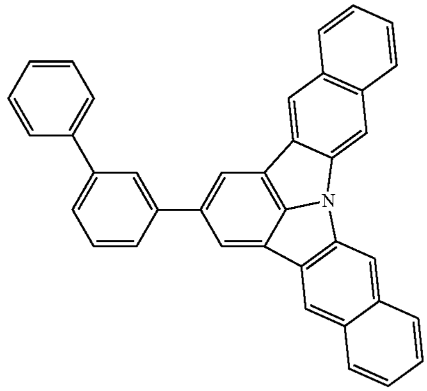
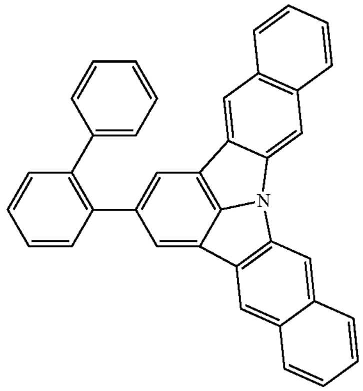
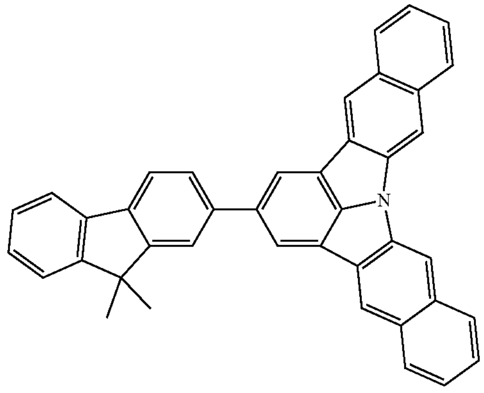
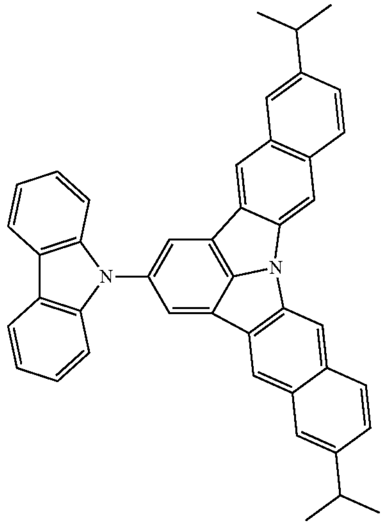

-continued
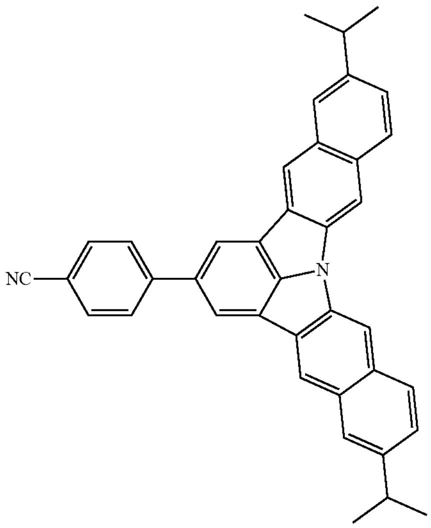
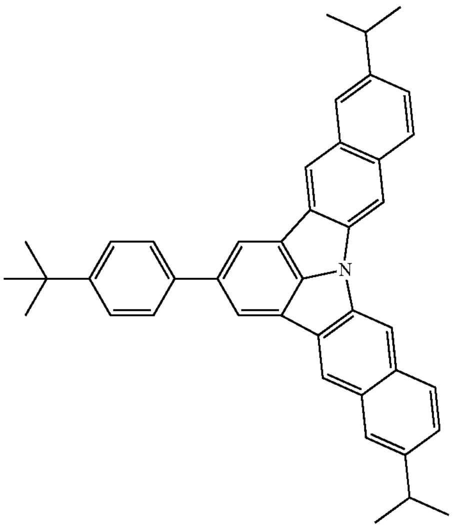
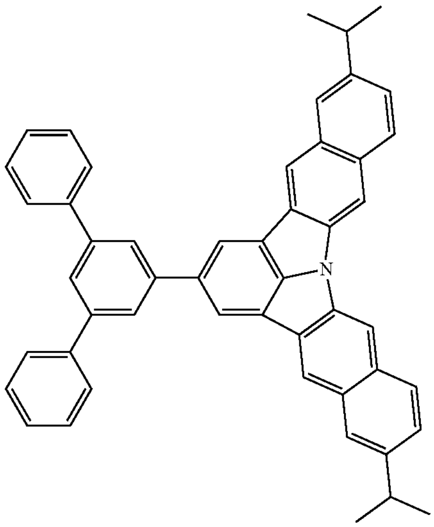
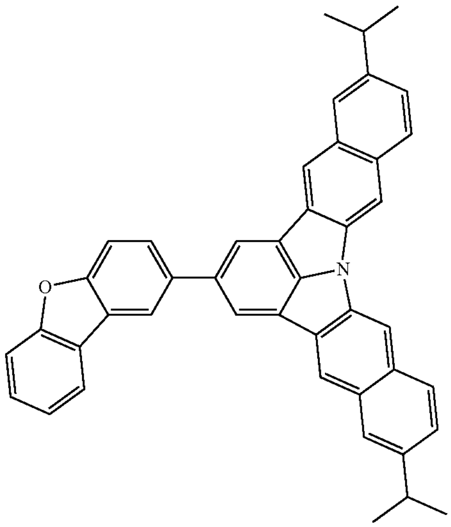
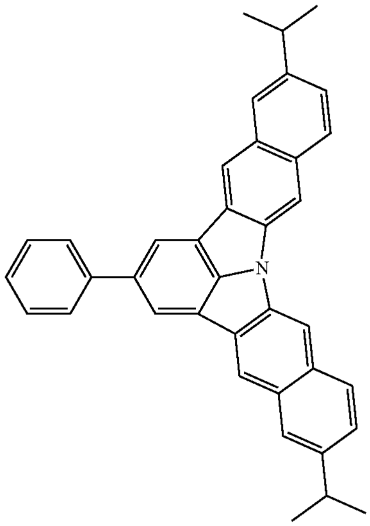
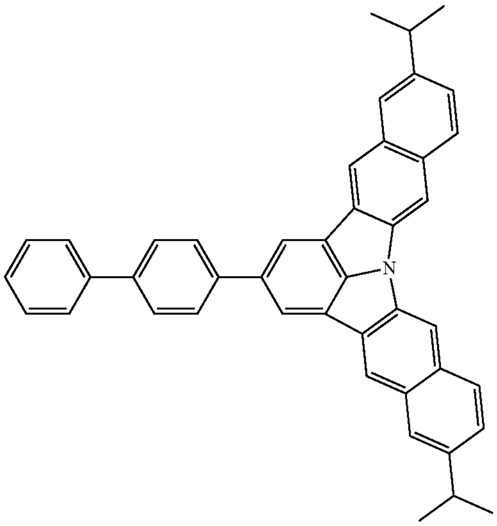

-continued
[Formula 185]
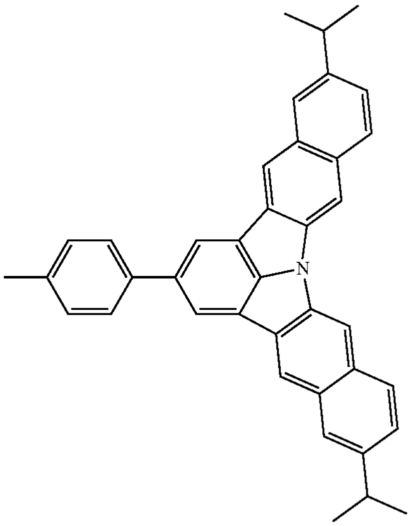
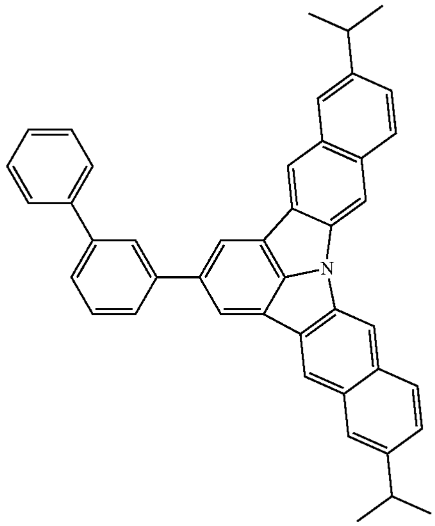
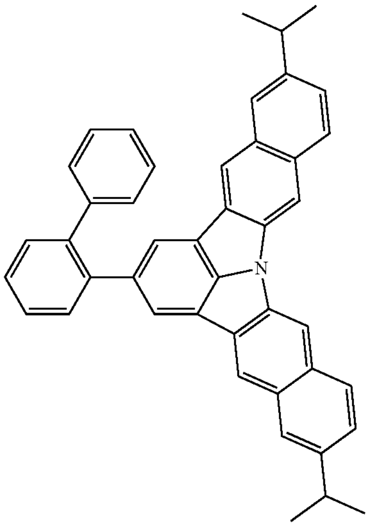
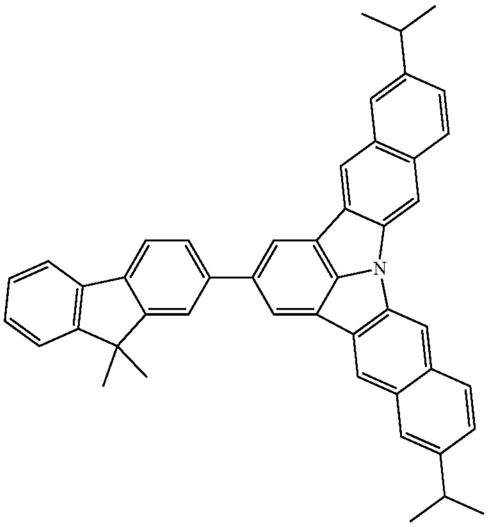
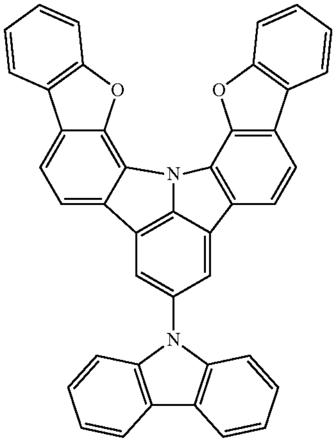
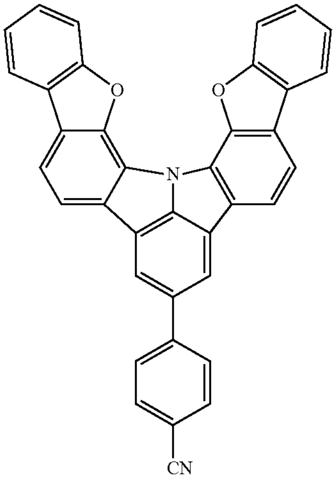
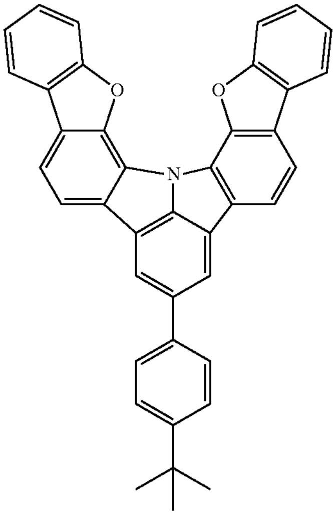

-continued
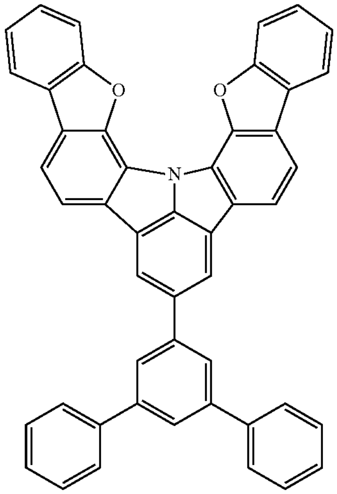
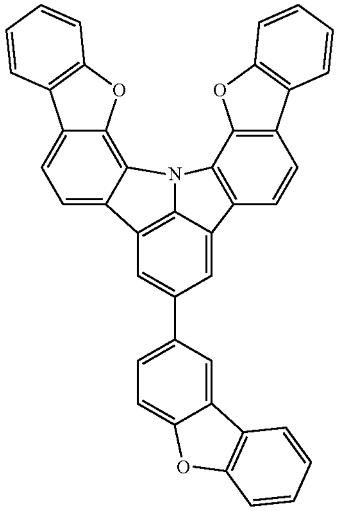
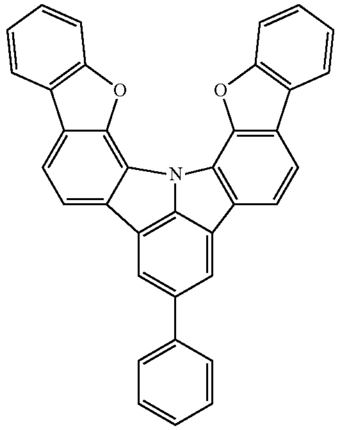
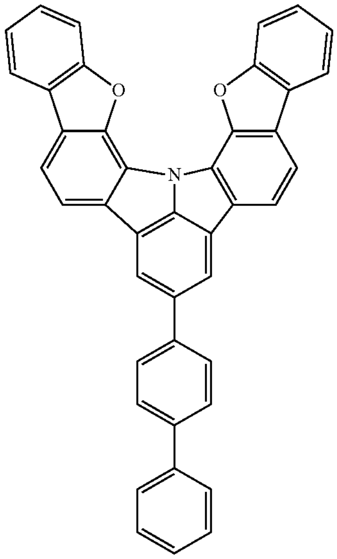
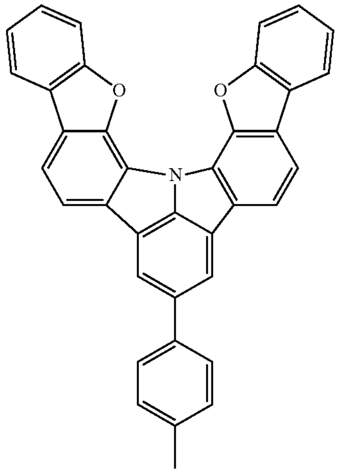
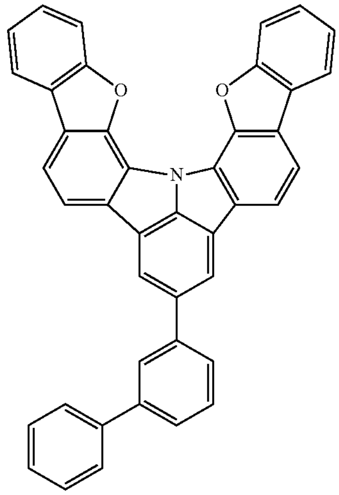
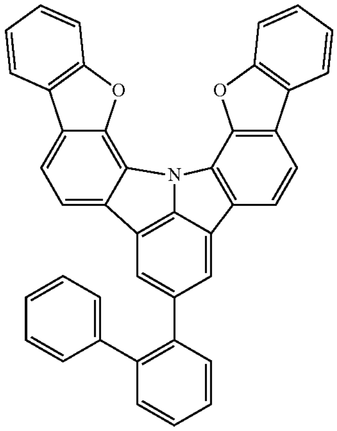
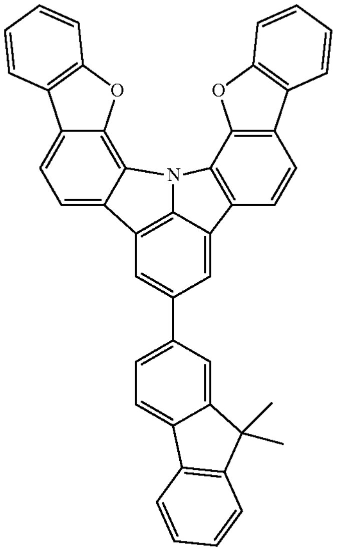

-continued
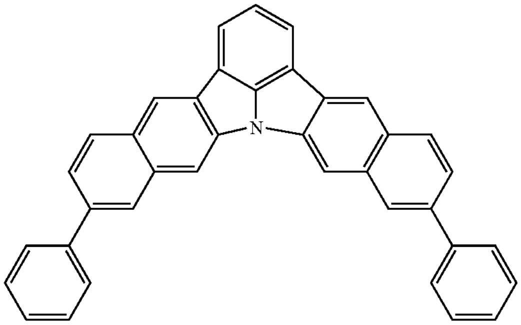
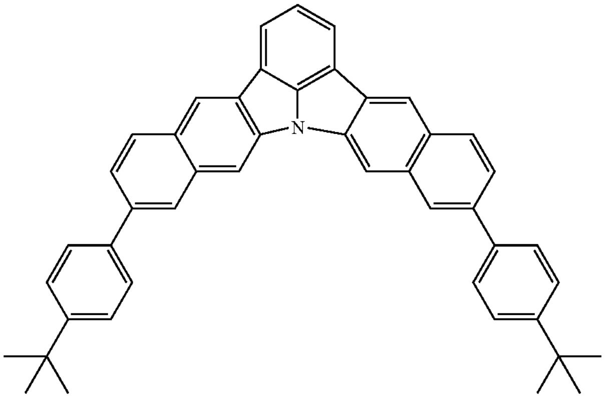
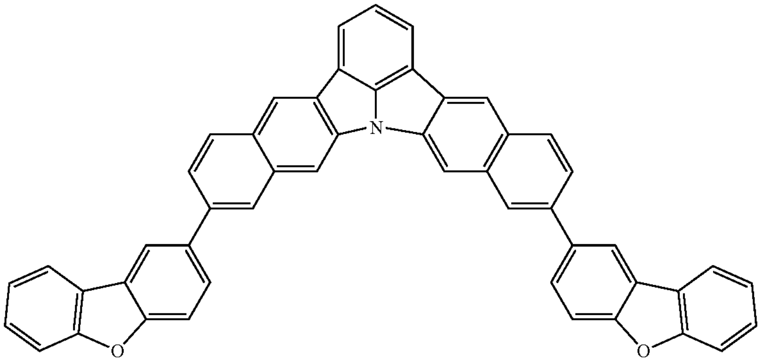
[Formula 186]
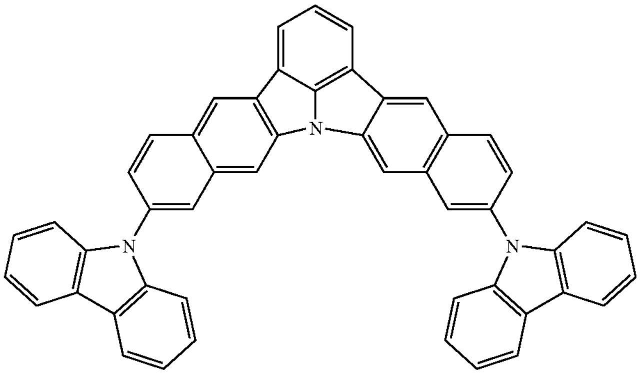
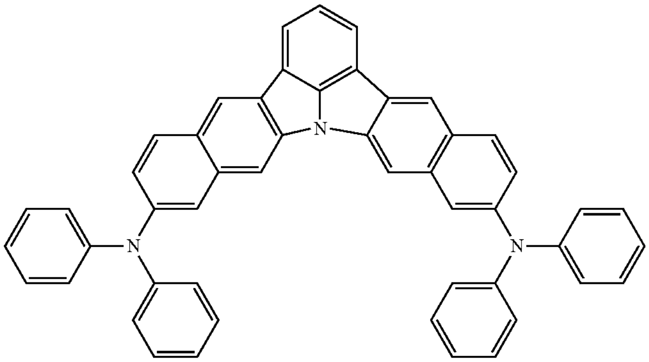

-continued
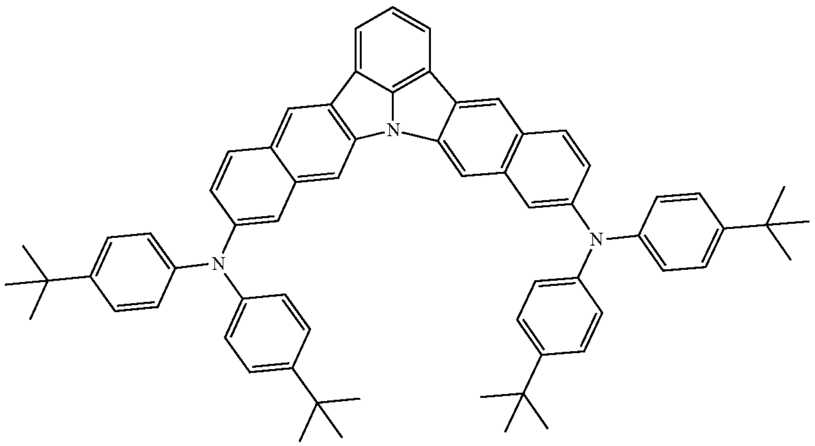
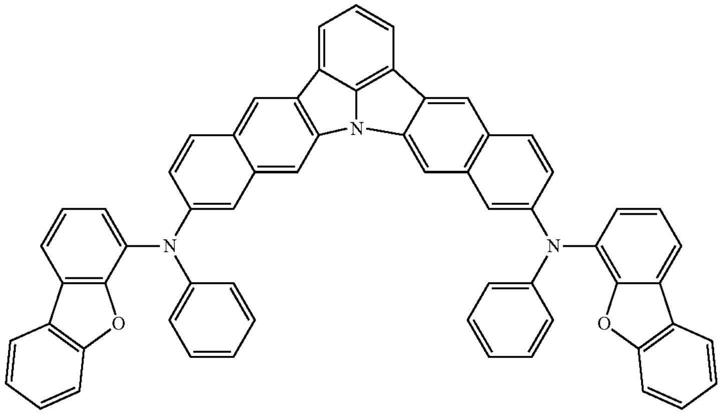
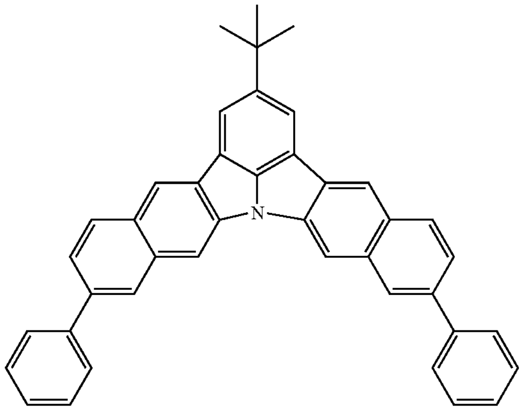
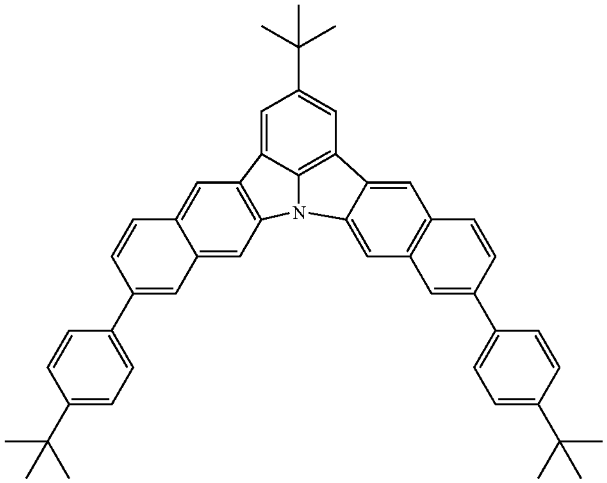

-continued
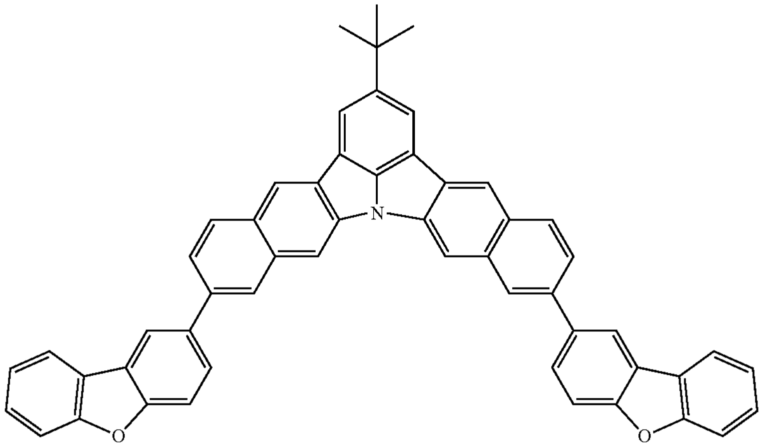
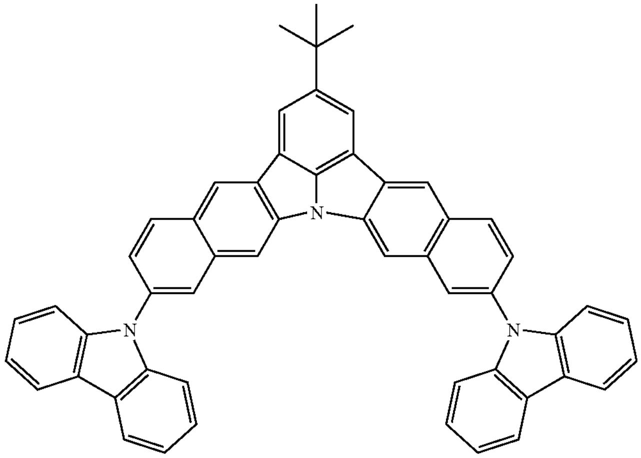
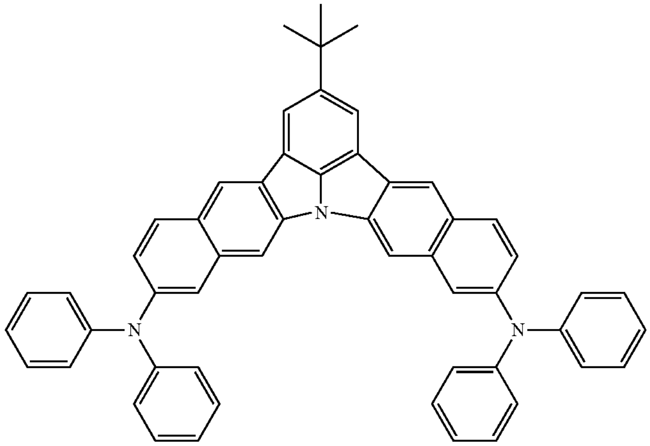

-continued
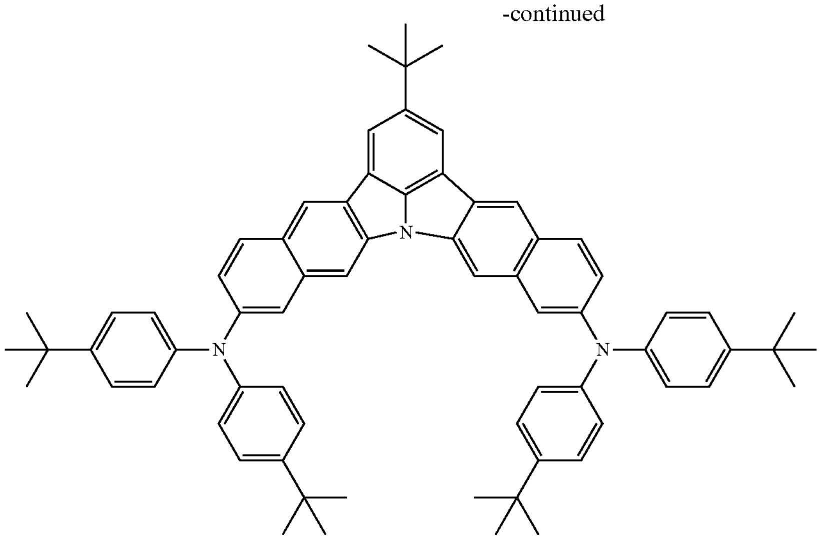
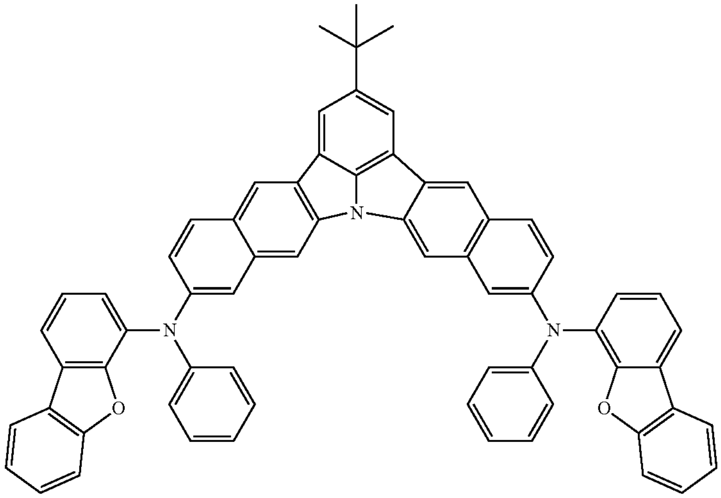
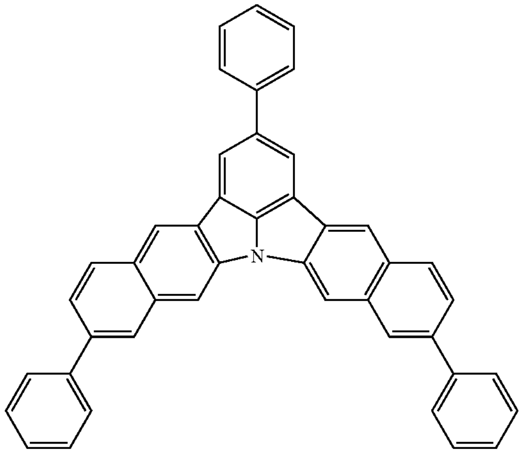
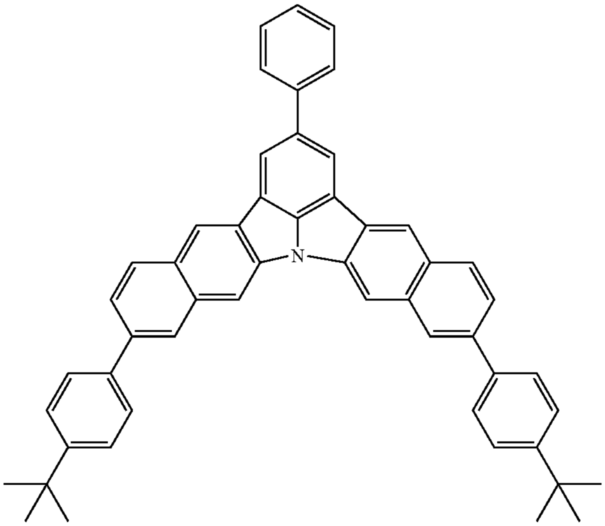

-continued
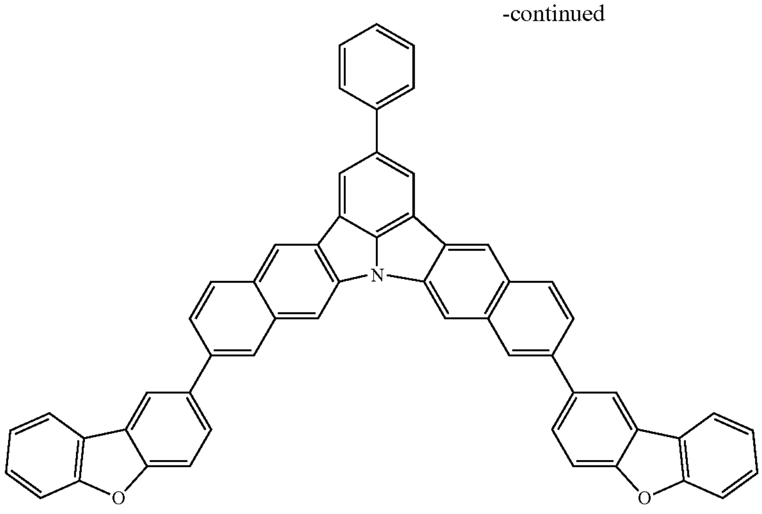
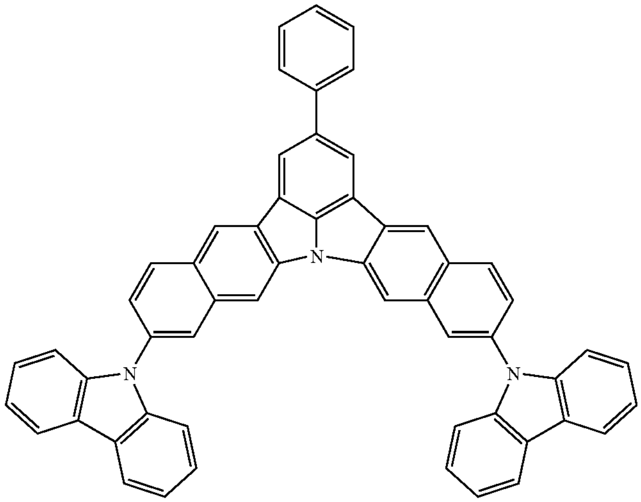
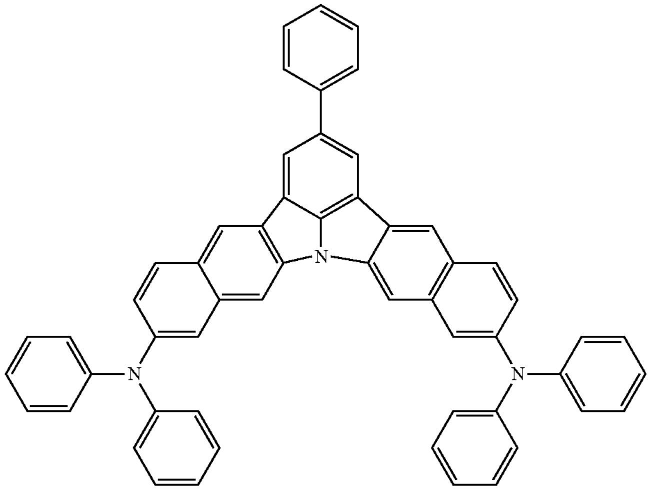

-continued
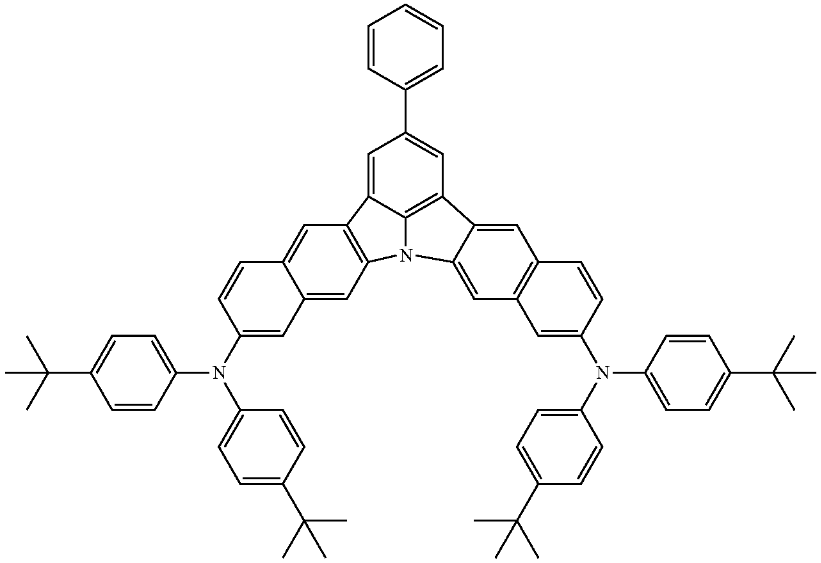
[Formula 187]
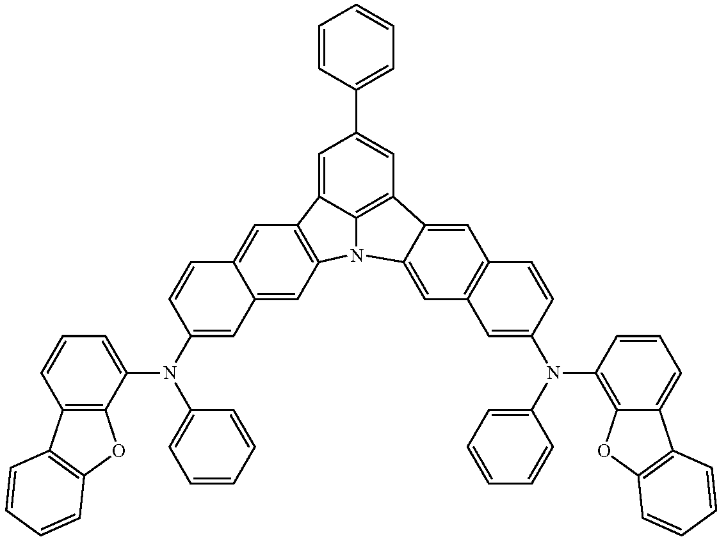

-continued
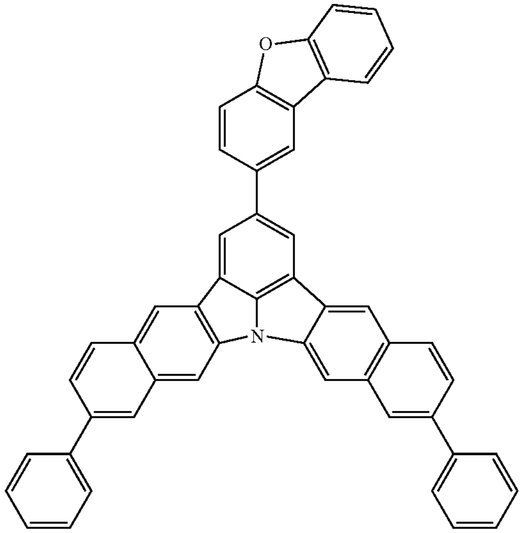
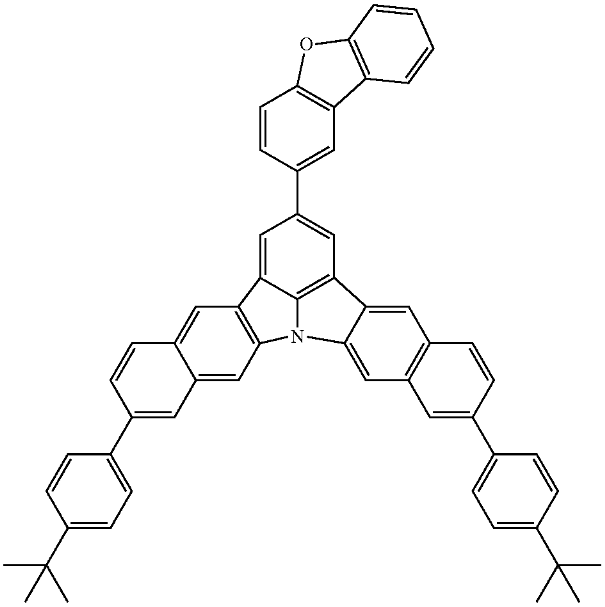
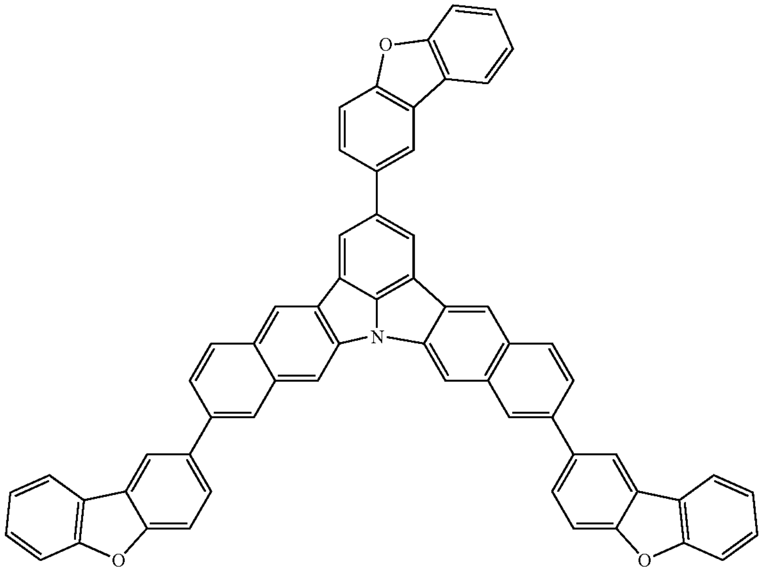

-continued
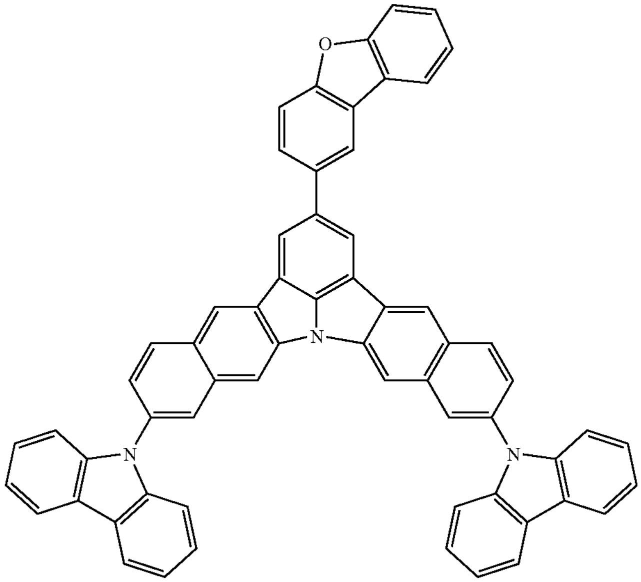
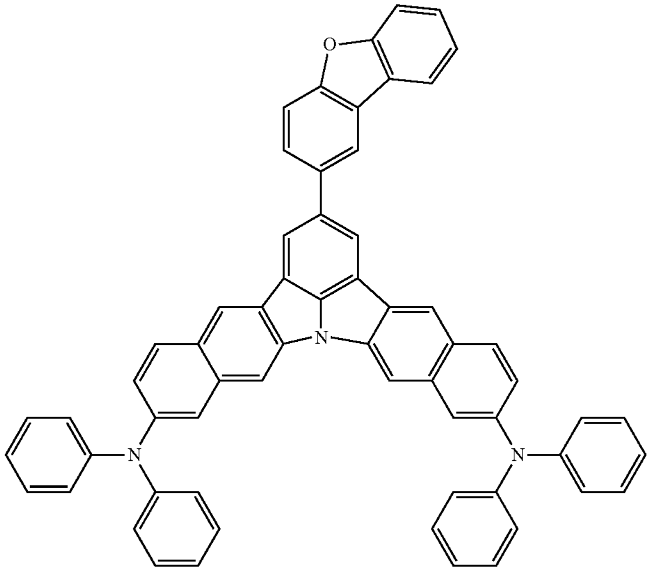

-continued
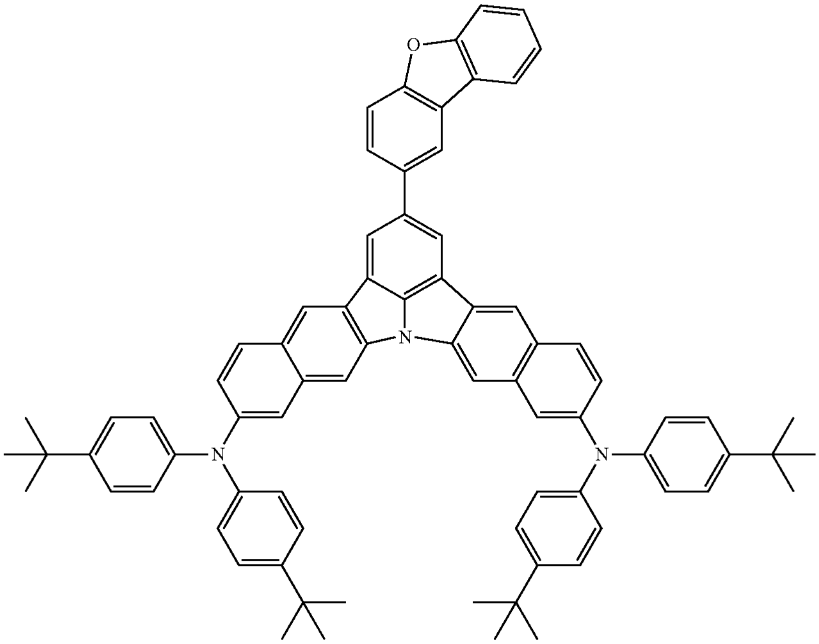
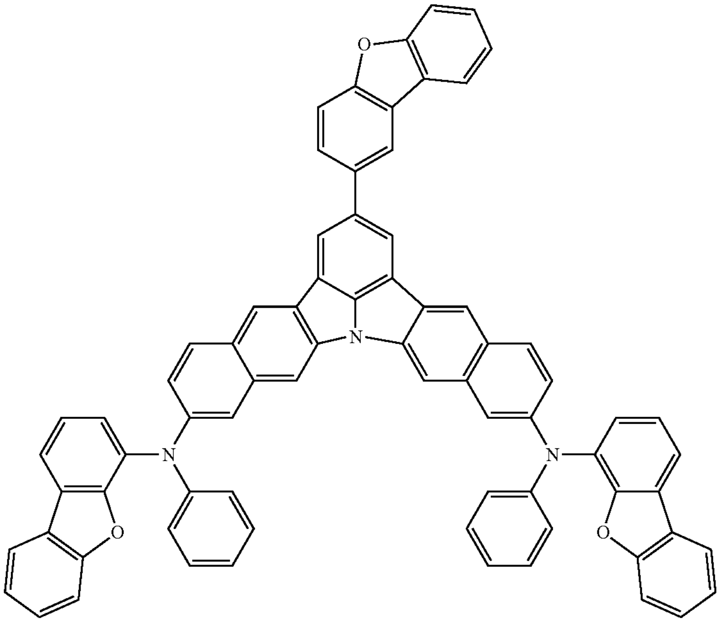

-continued
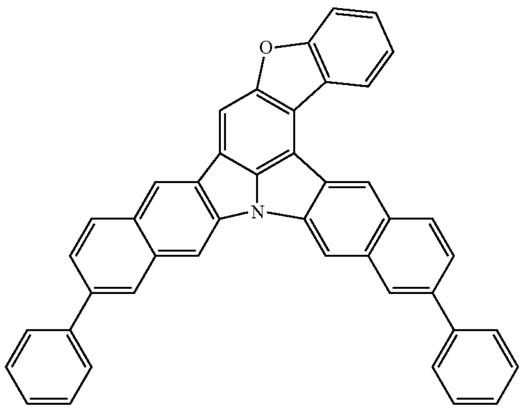
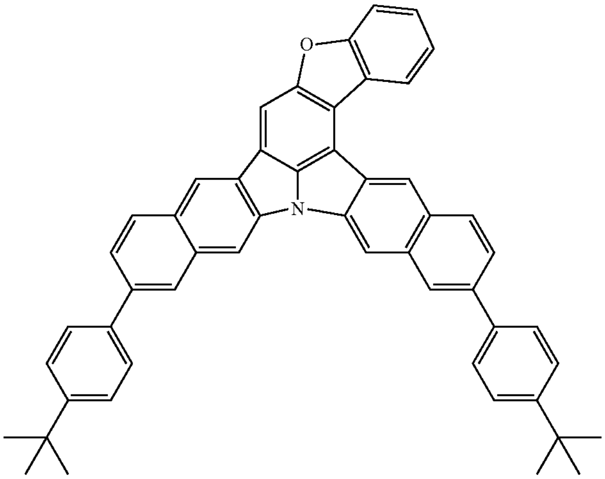
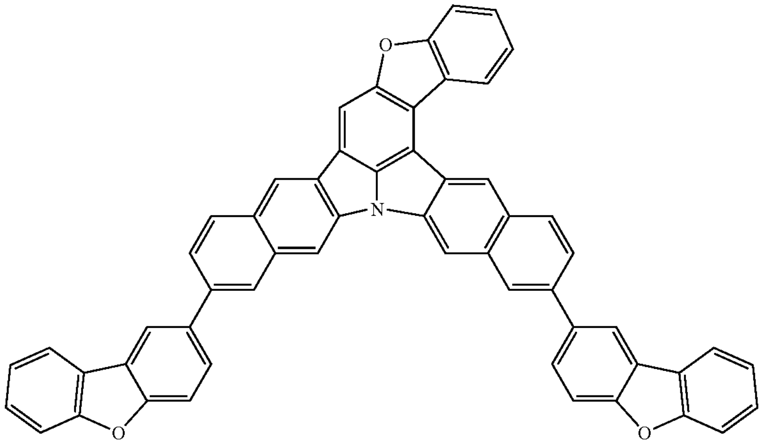
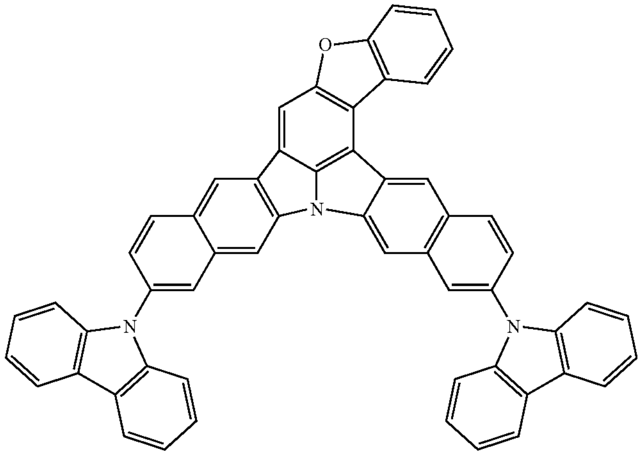

-continued
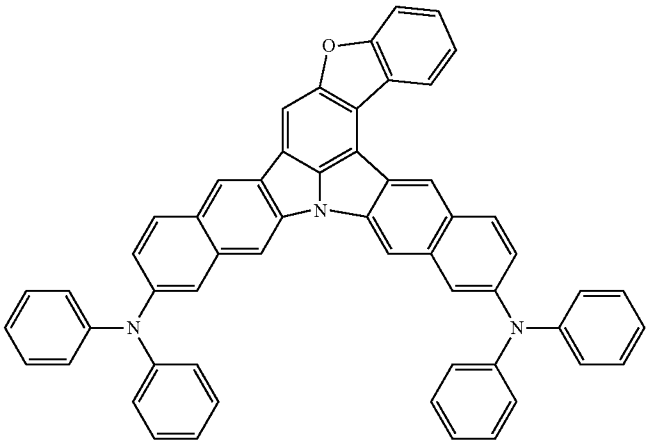
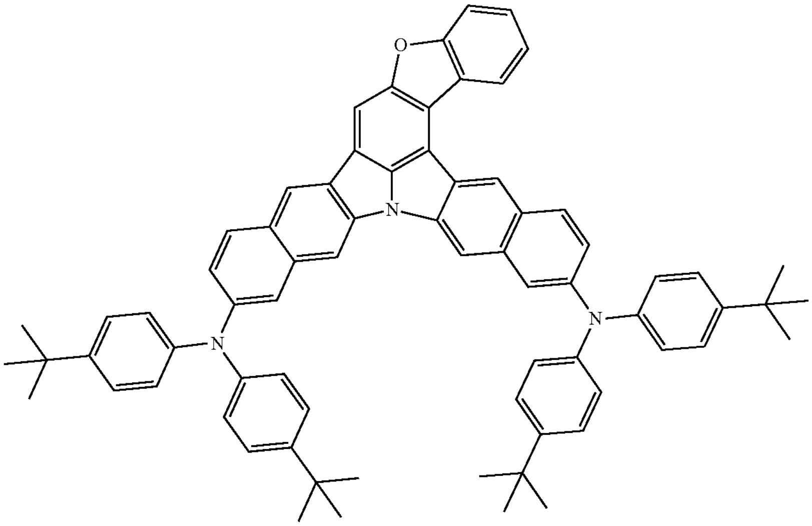
[Formula 188]
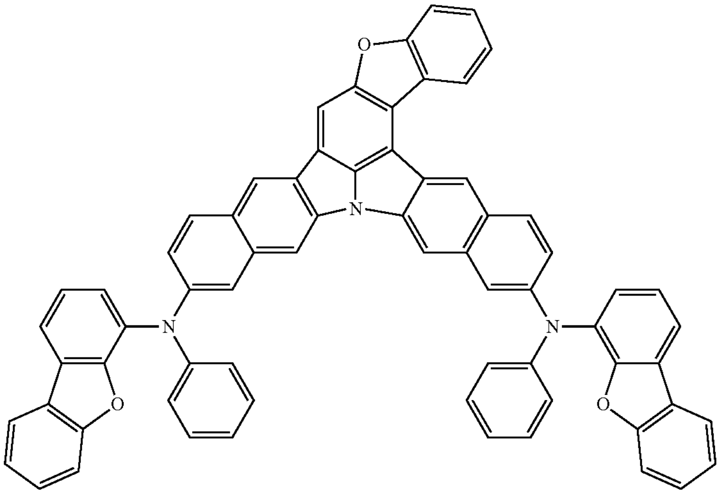

-continued
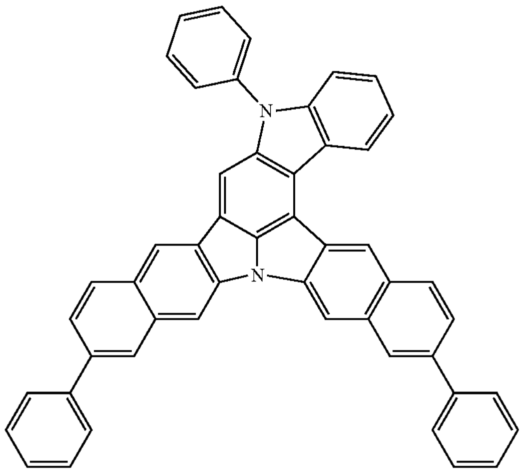
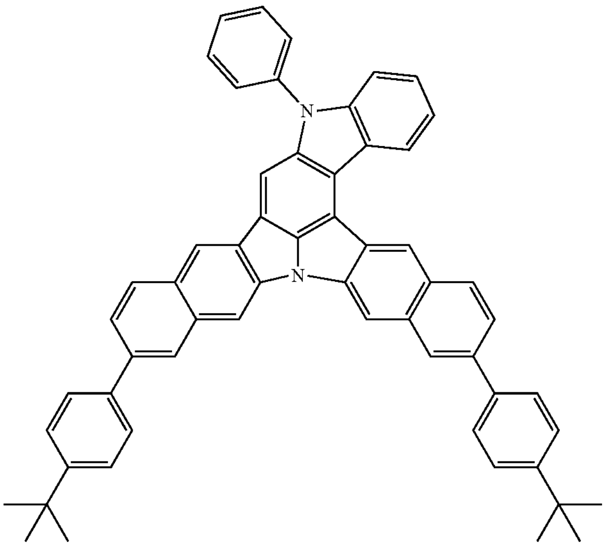
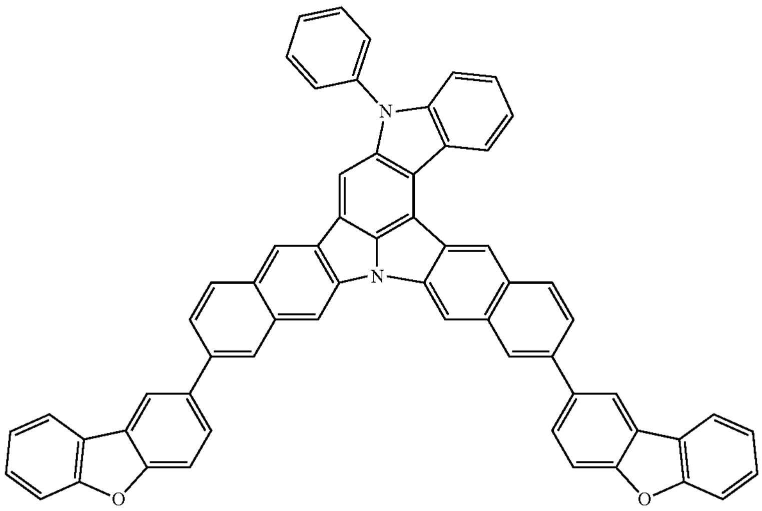
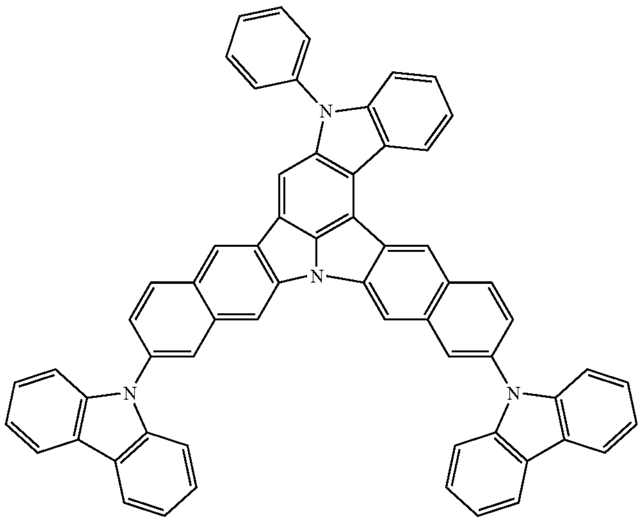

-continued
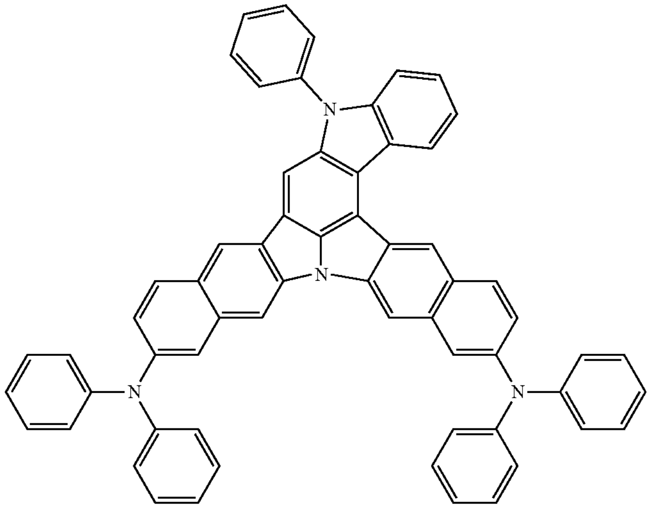
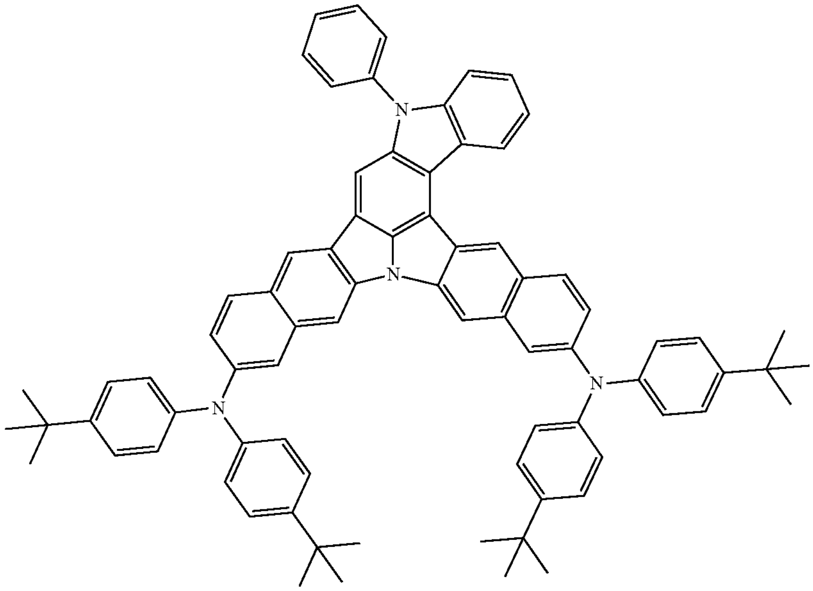
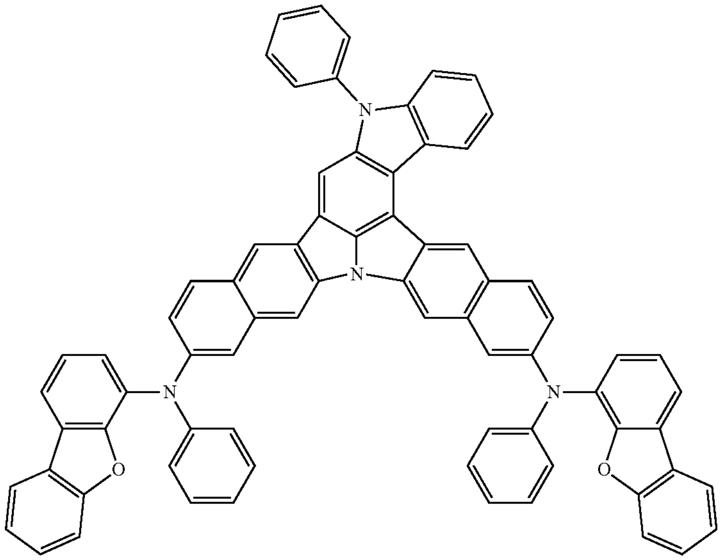

-continued
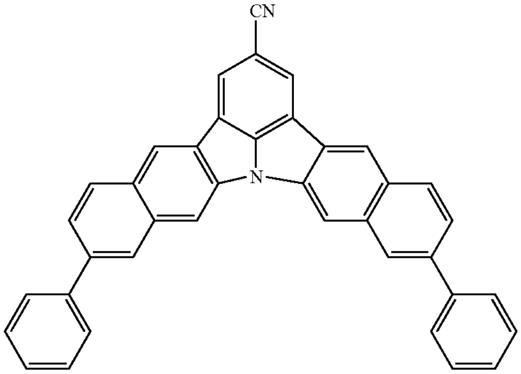
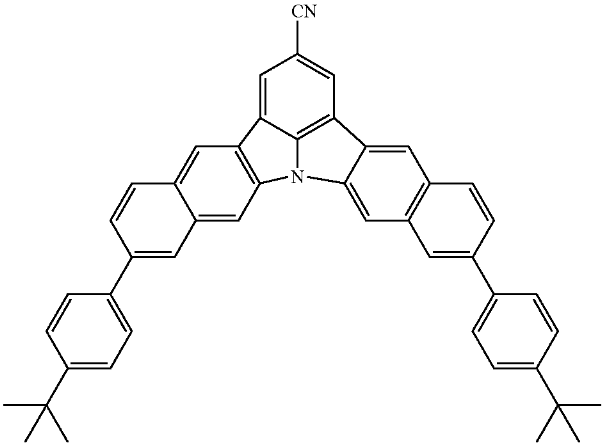
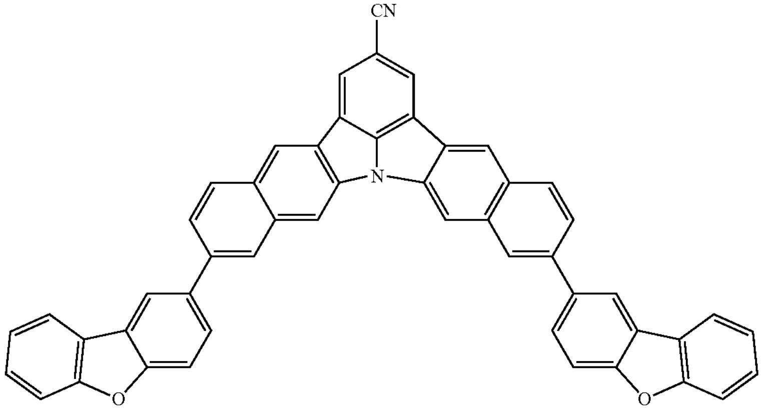
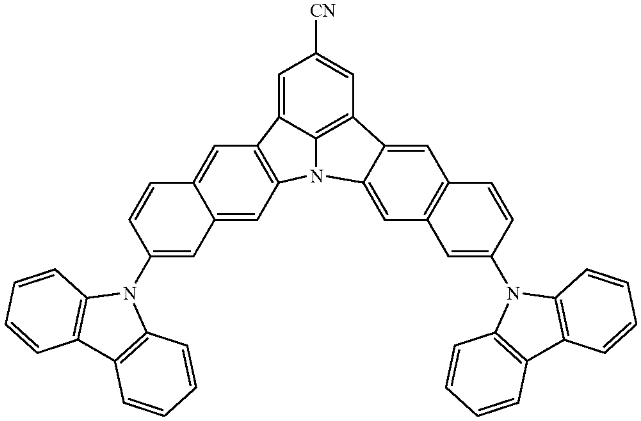
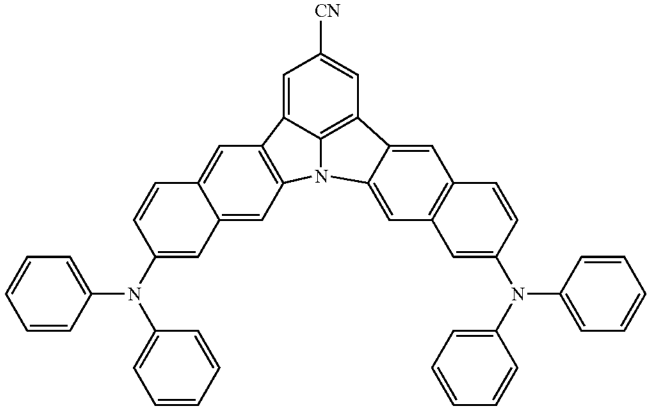

-continued
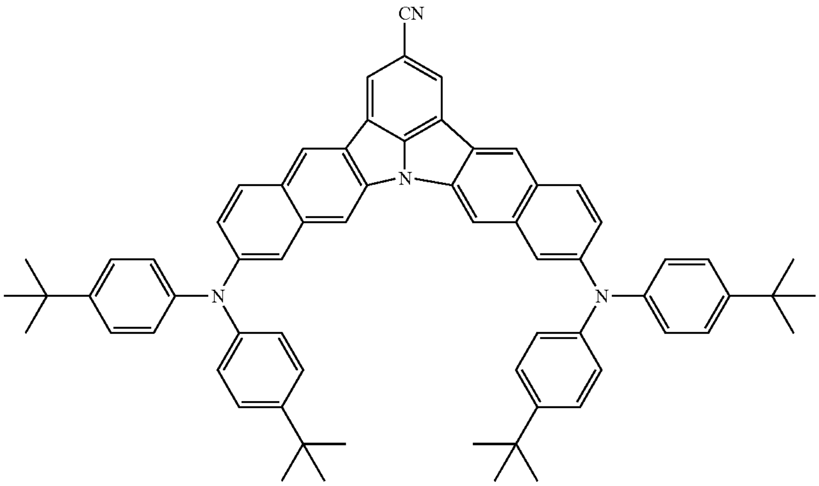
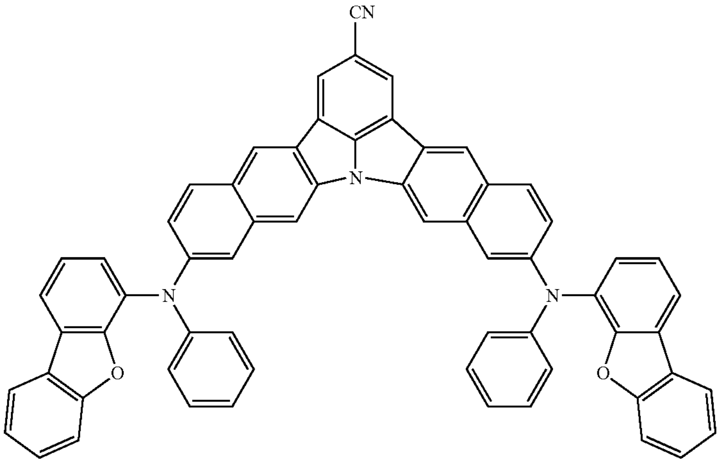
[Formula 189]
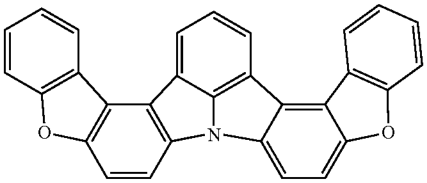
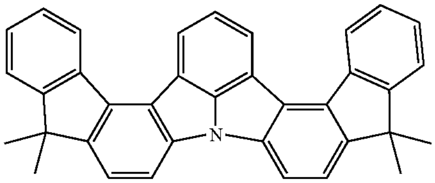
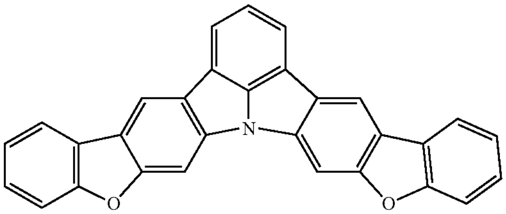
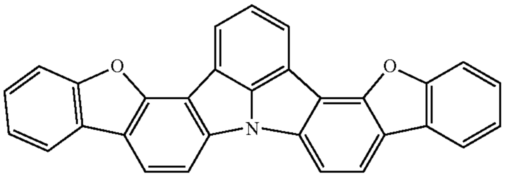
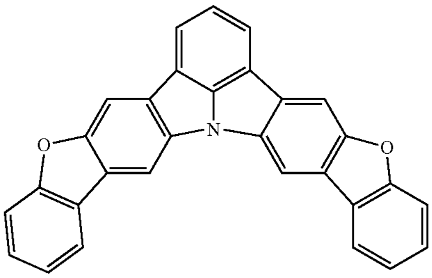
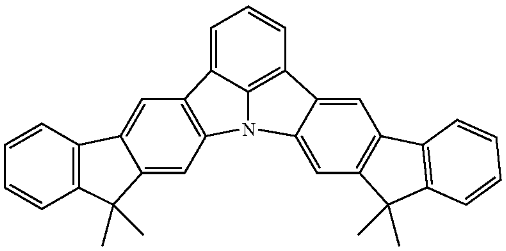

-continued
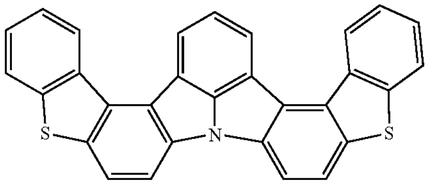
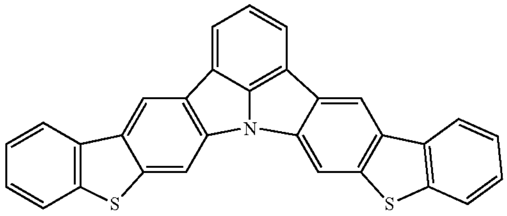
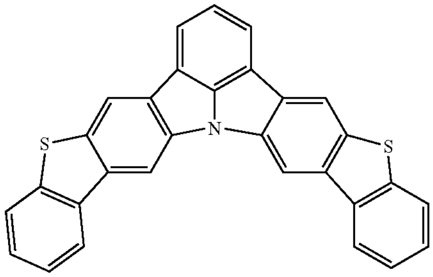
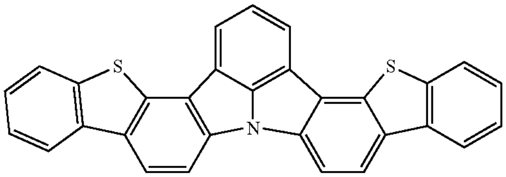
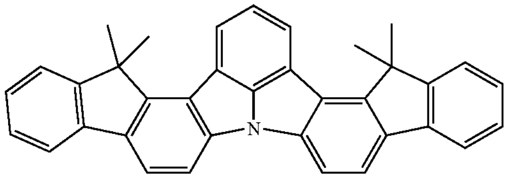
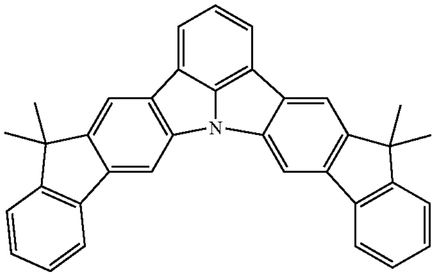
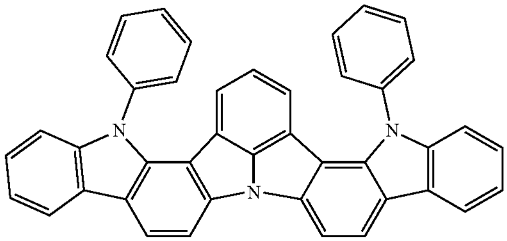
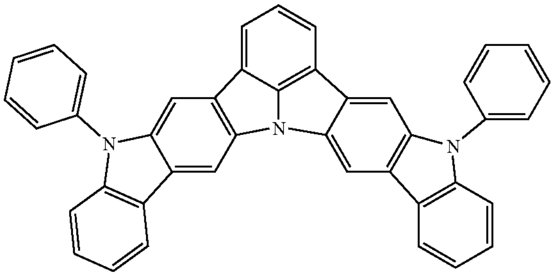
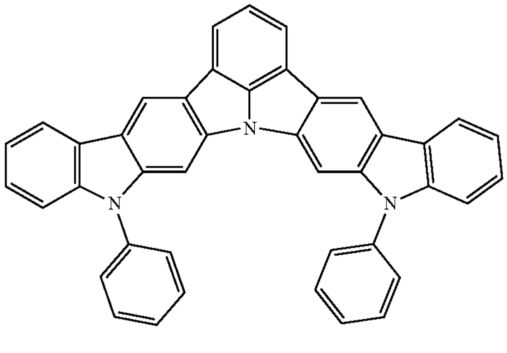
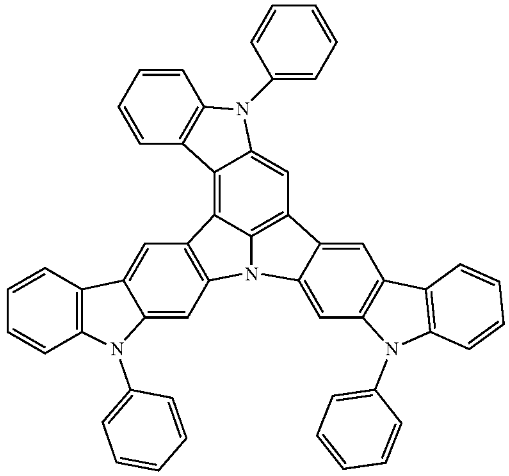

-continued
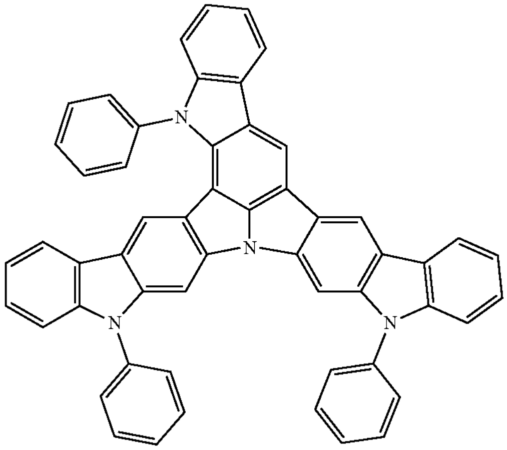
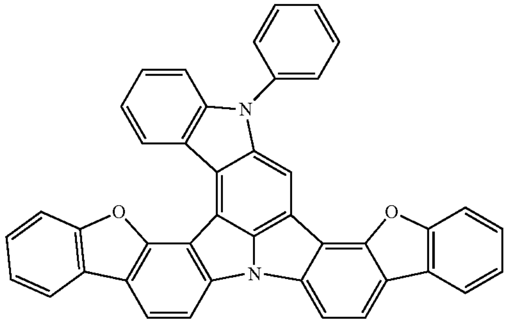
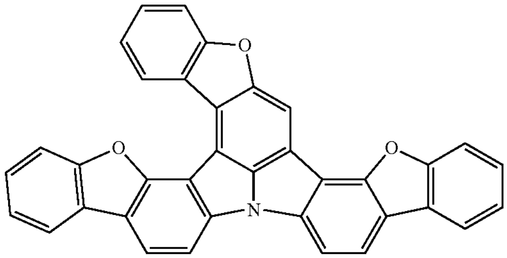
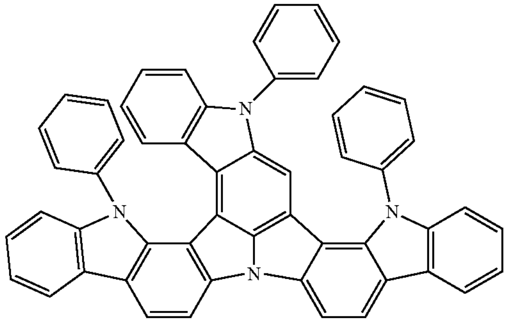
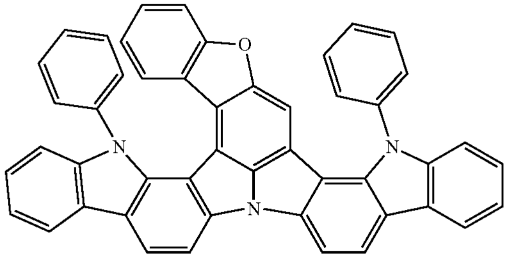
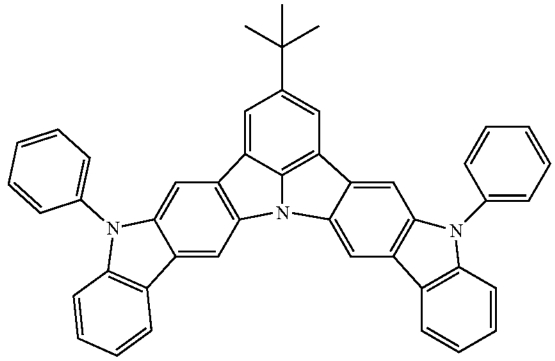
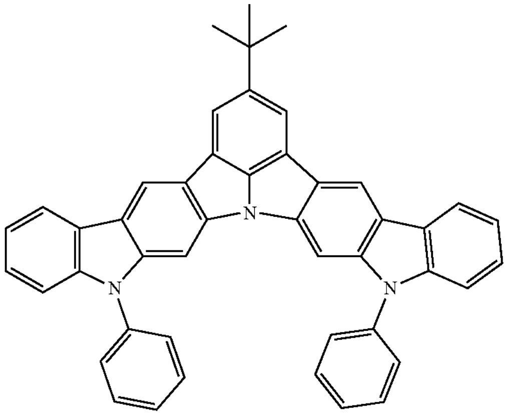

-continued
[Formula 190]
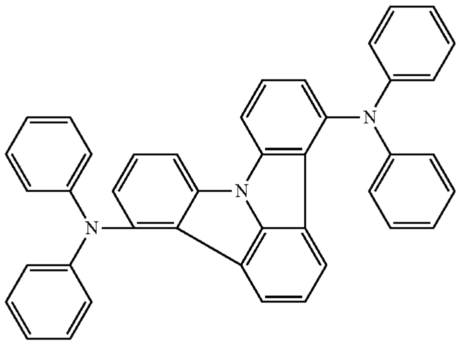
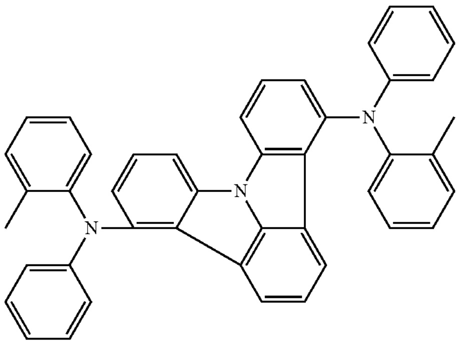
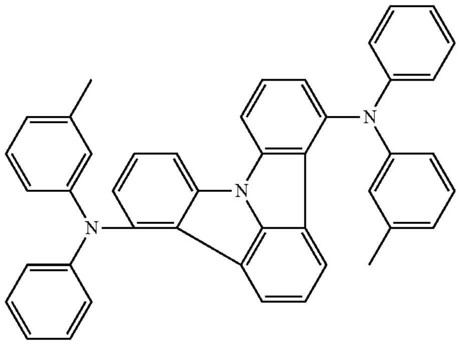
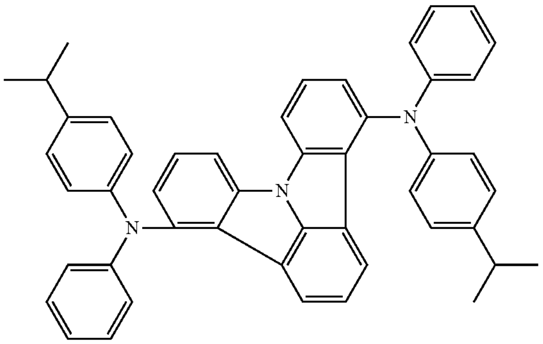
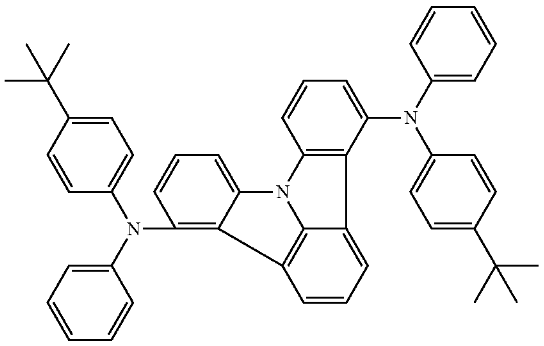
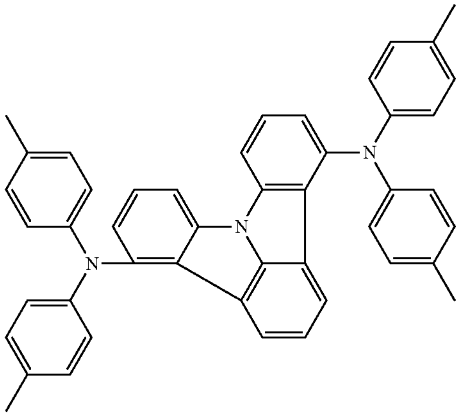
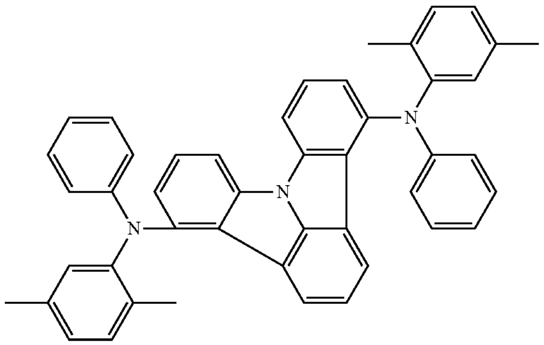
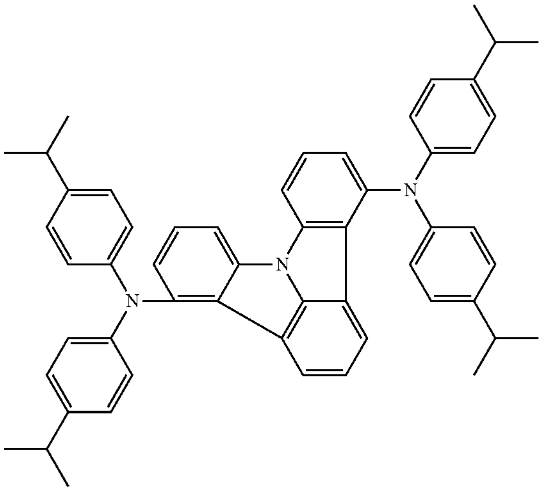

-continued
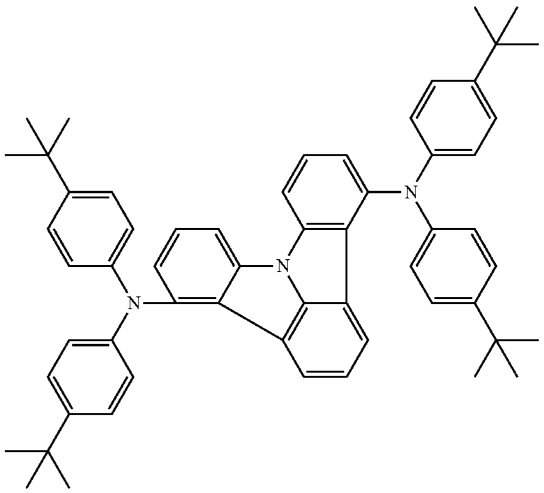
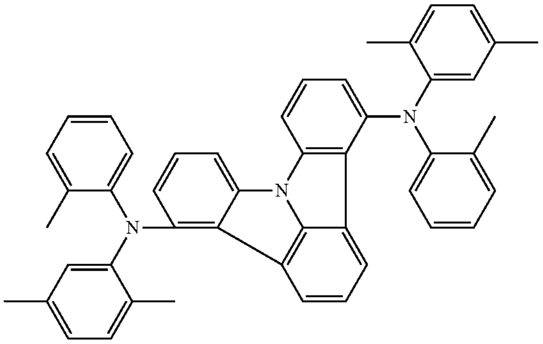
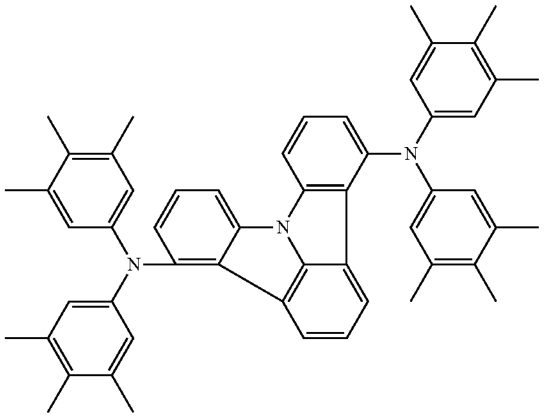
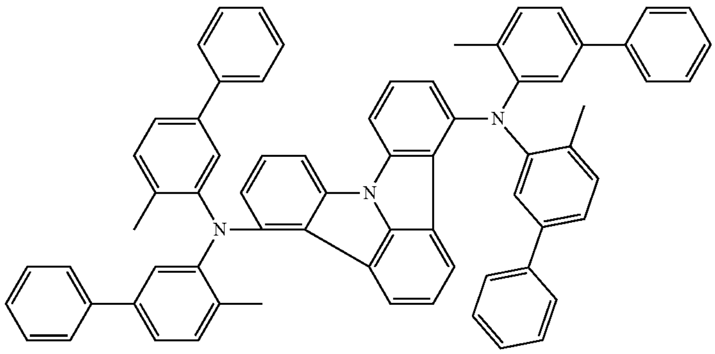
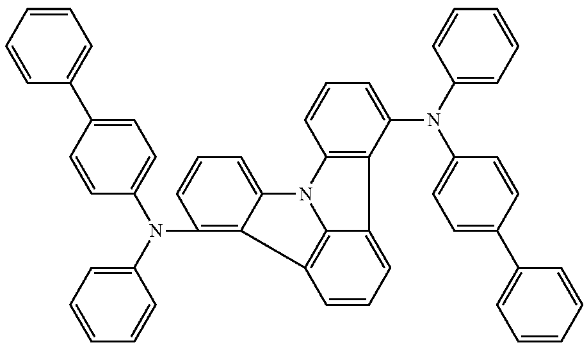
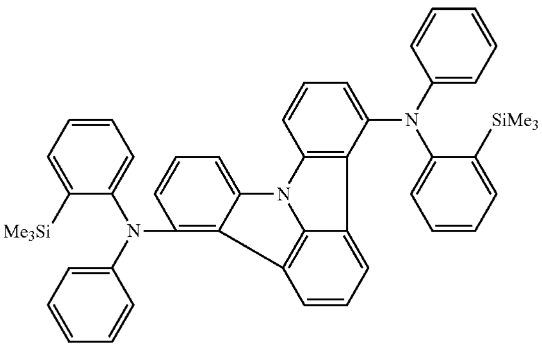

-continued
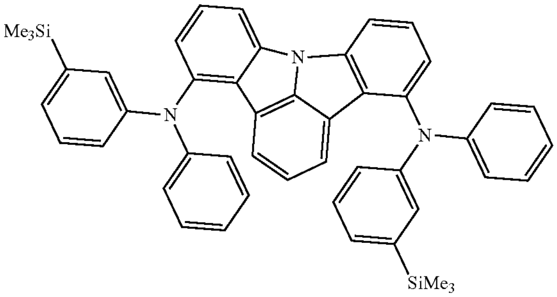
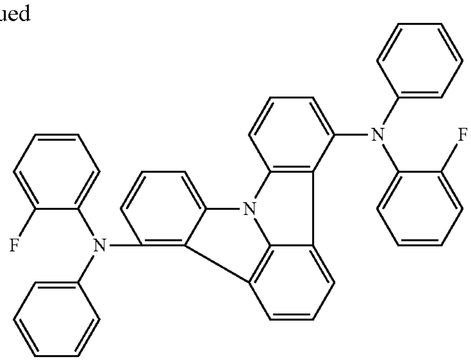
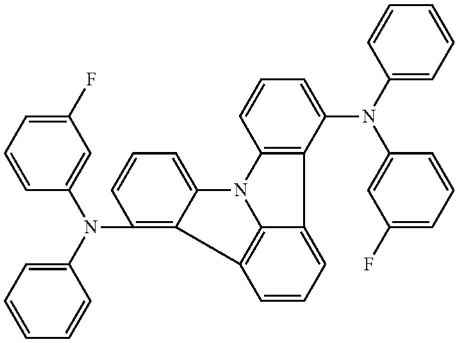
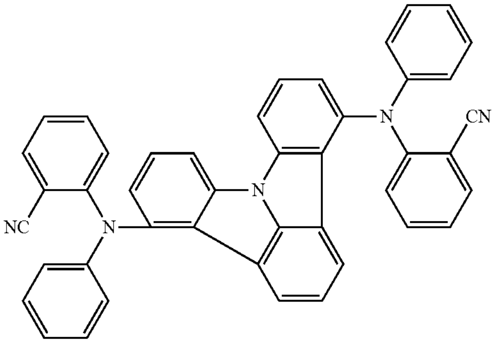
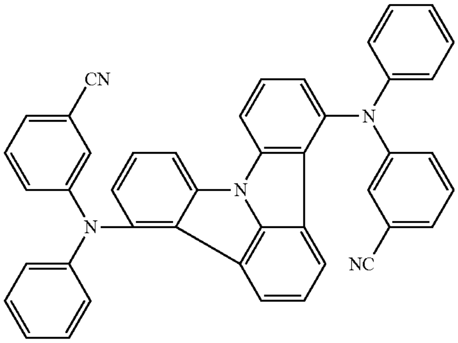
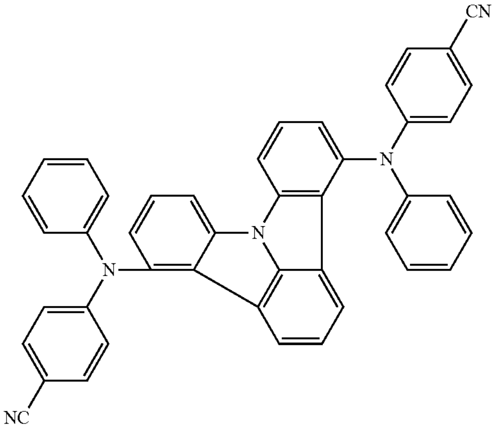
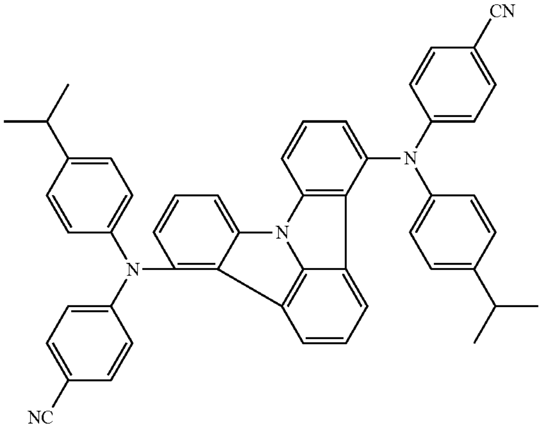

-continued
[Formula 191]
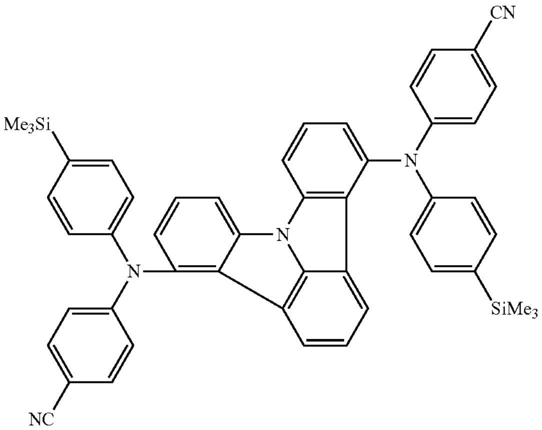
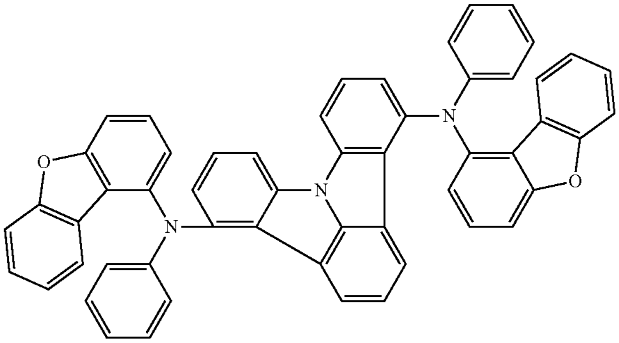
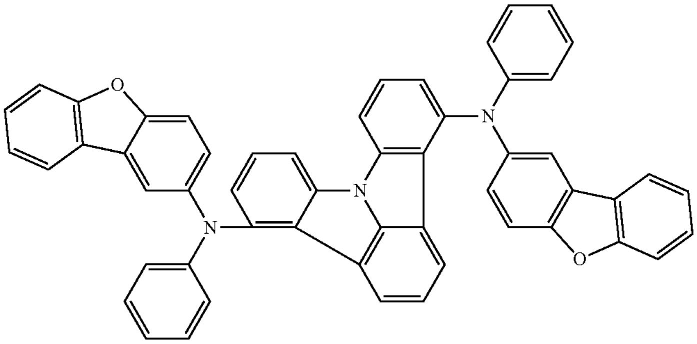
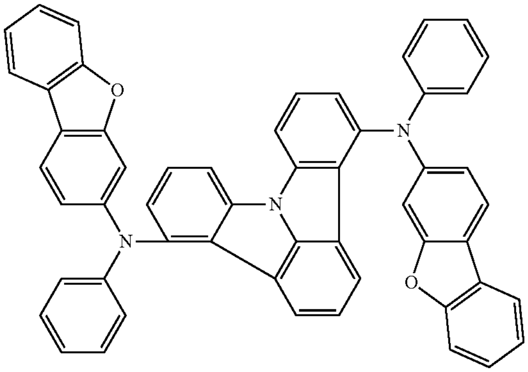

-continued
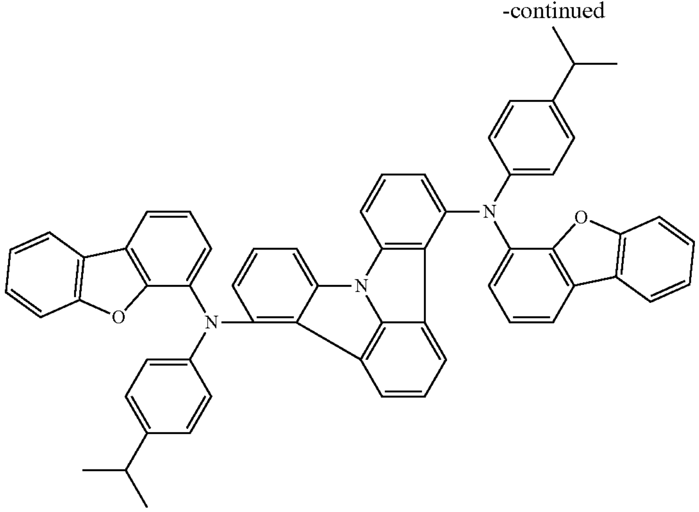
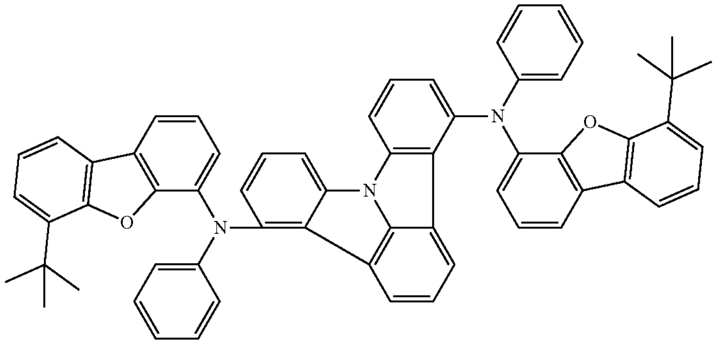
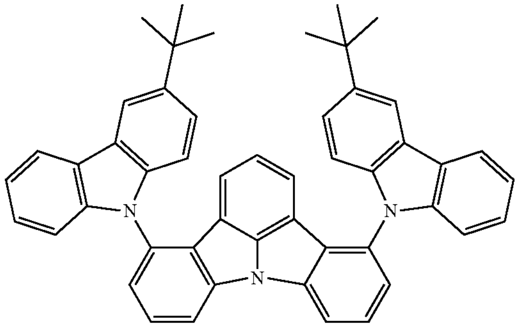
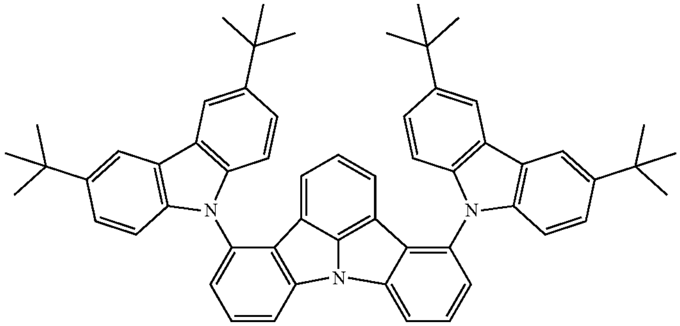

-continued
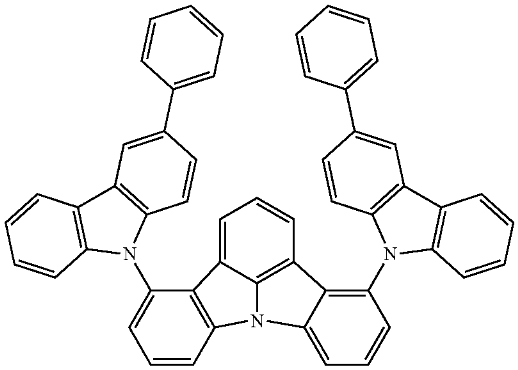
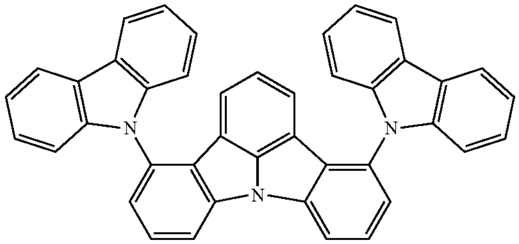
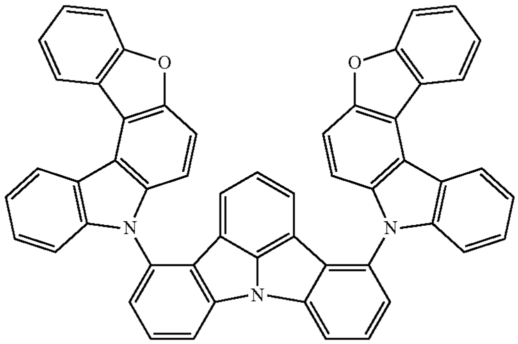
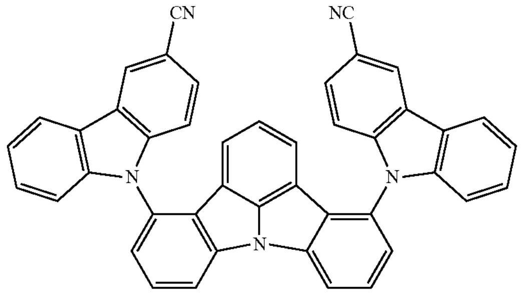
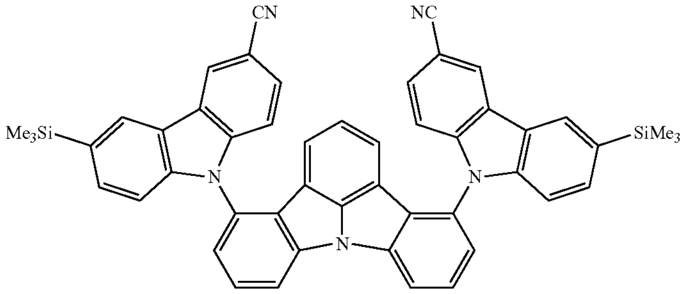
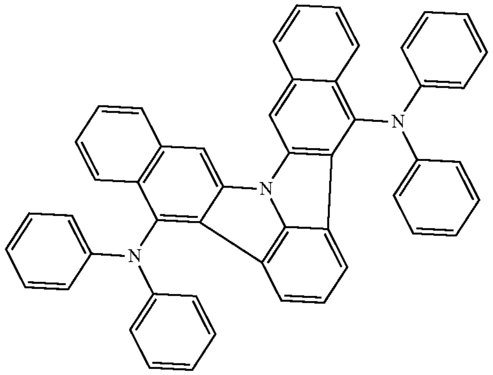
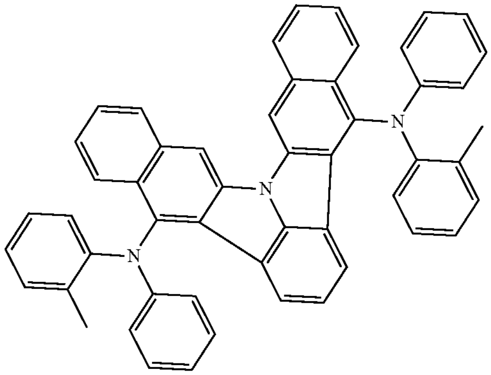

-continued
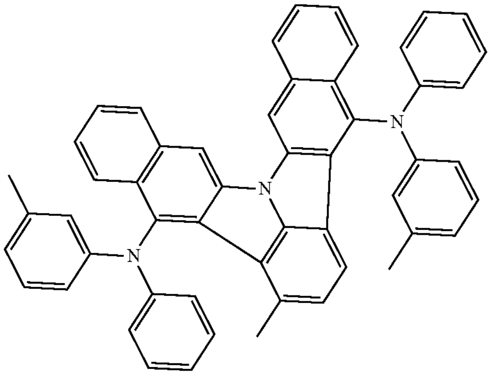
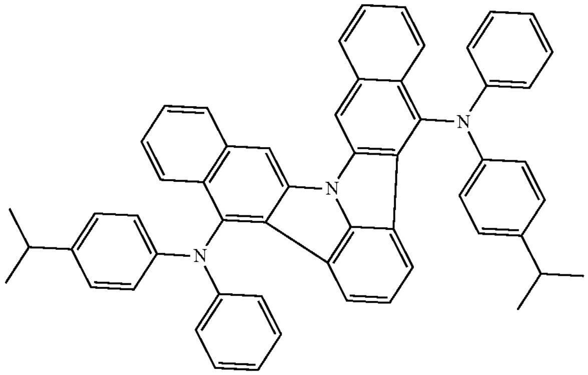
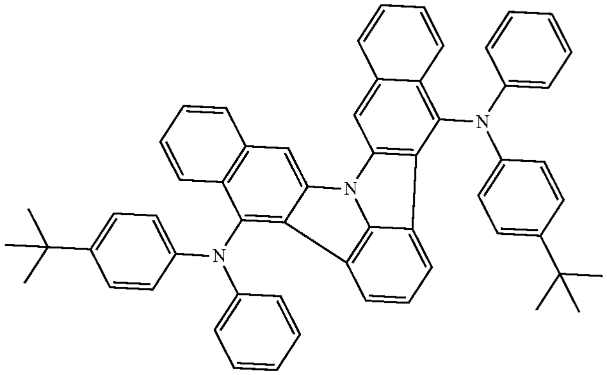
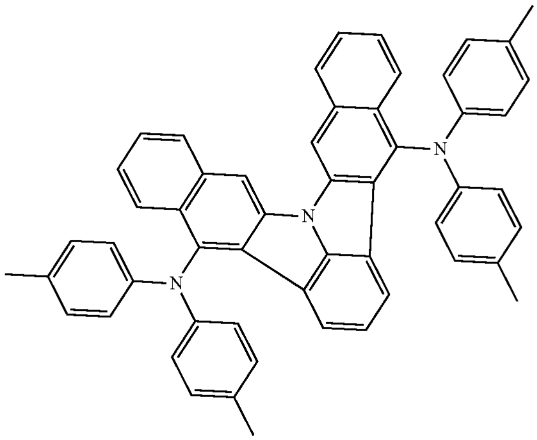
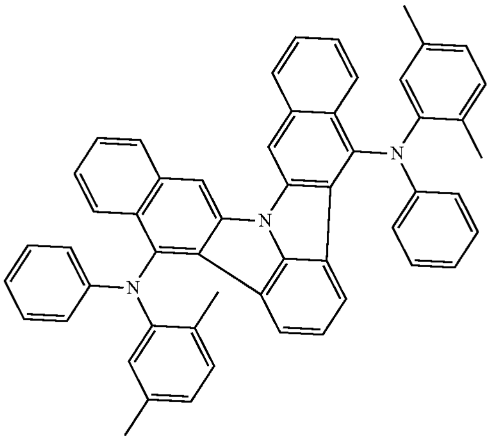
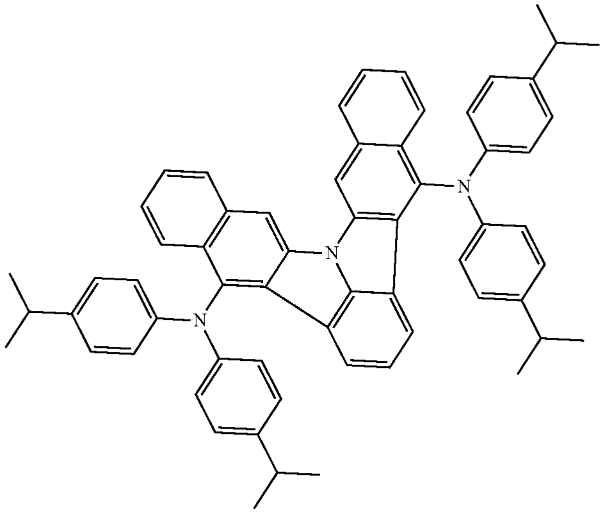

-continued
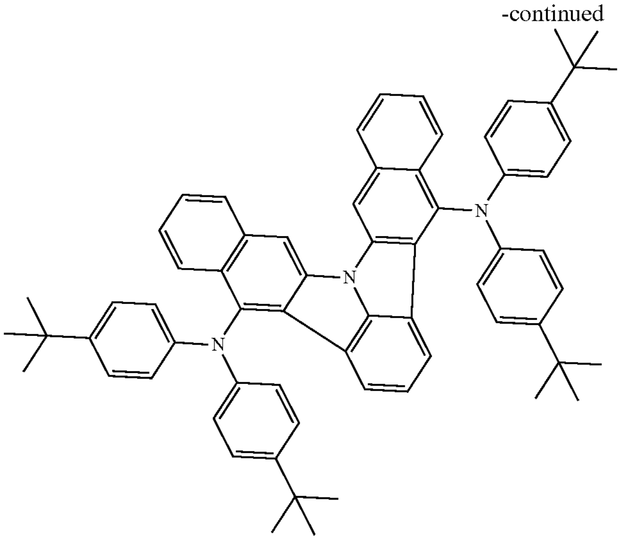
[Formula 192]
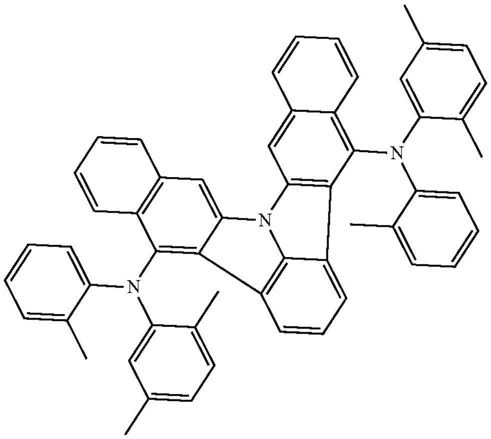
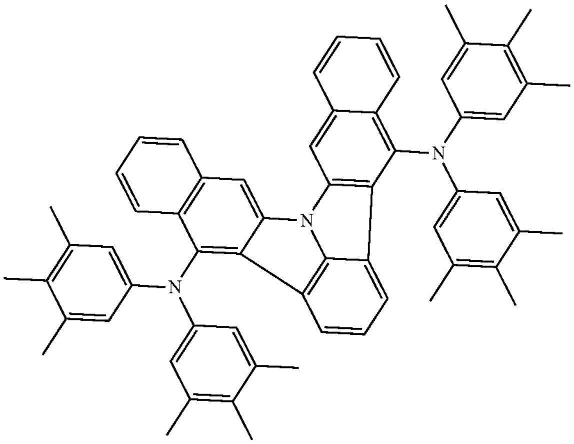
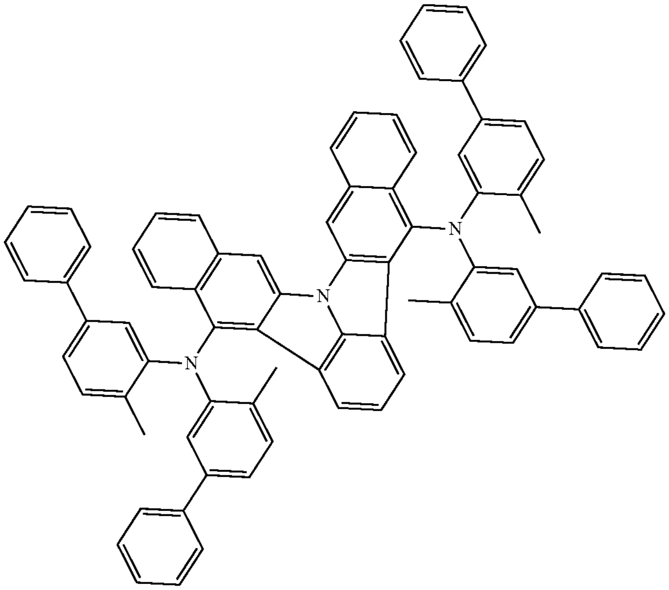

-continued
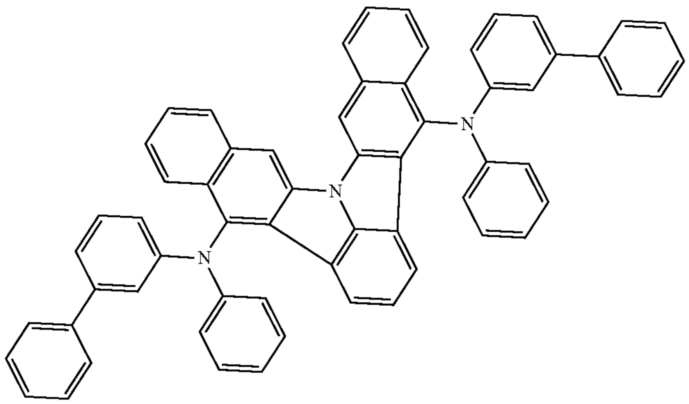
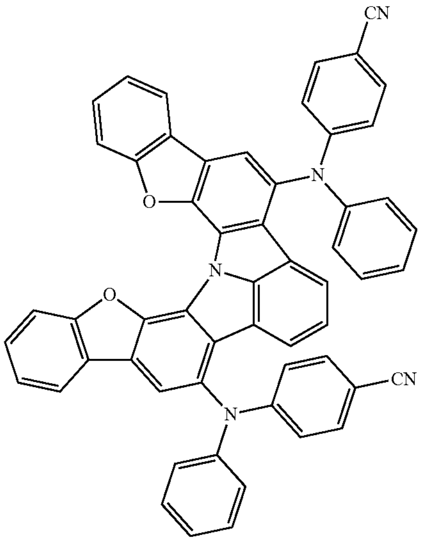
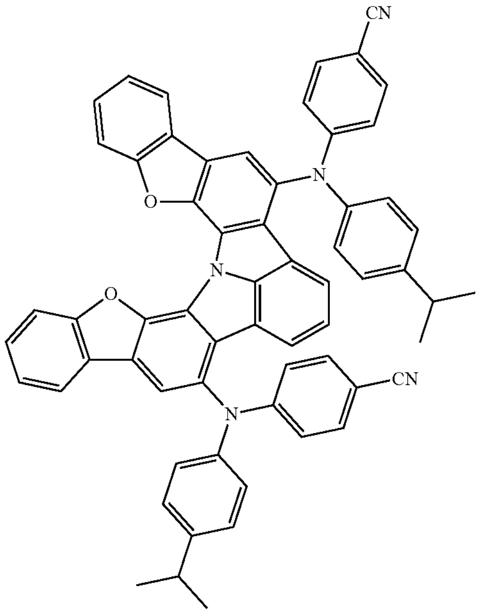
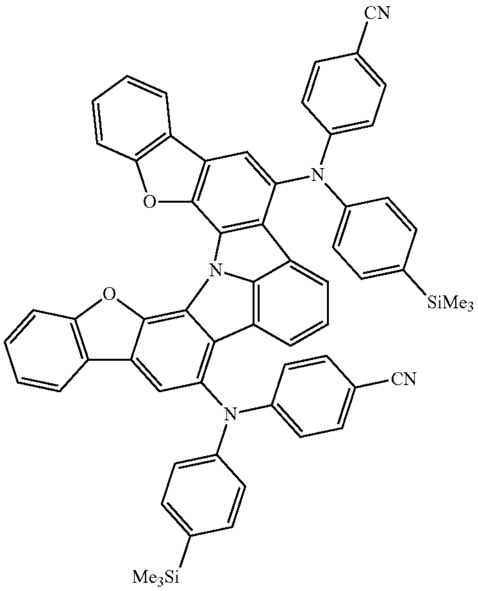

-continued
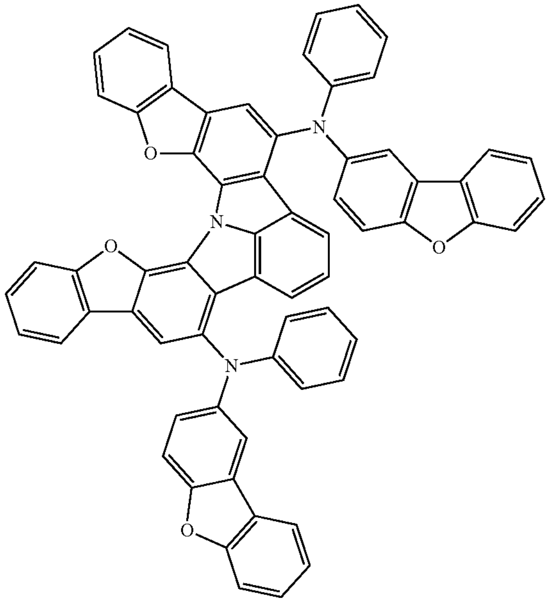
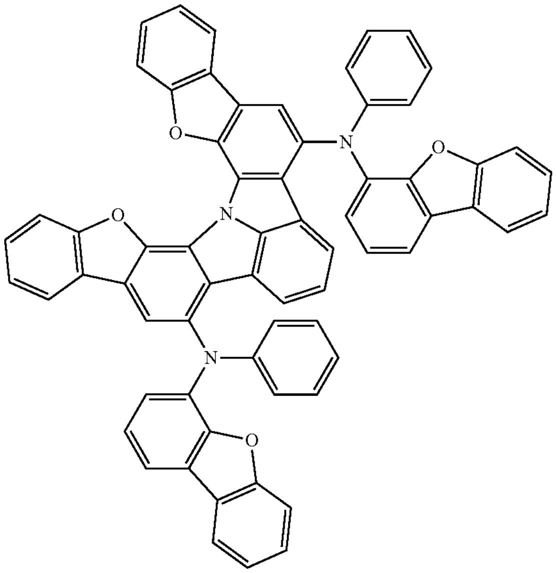
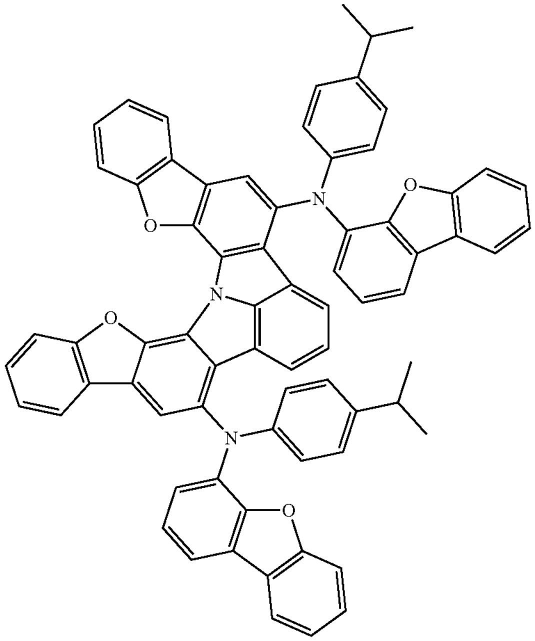
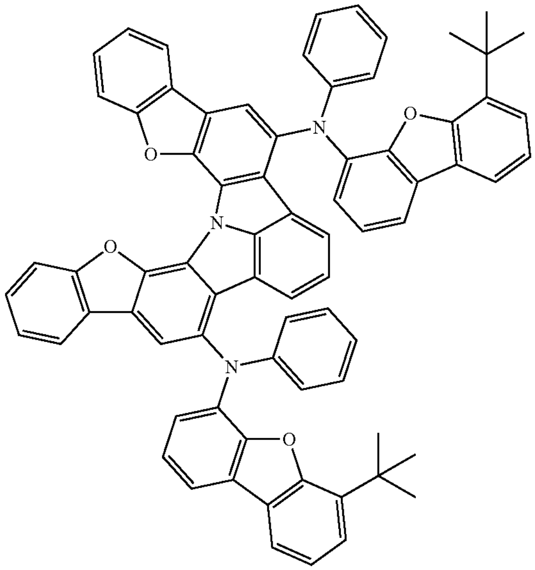

-continued
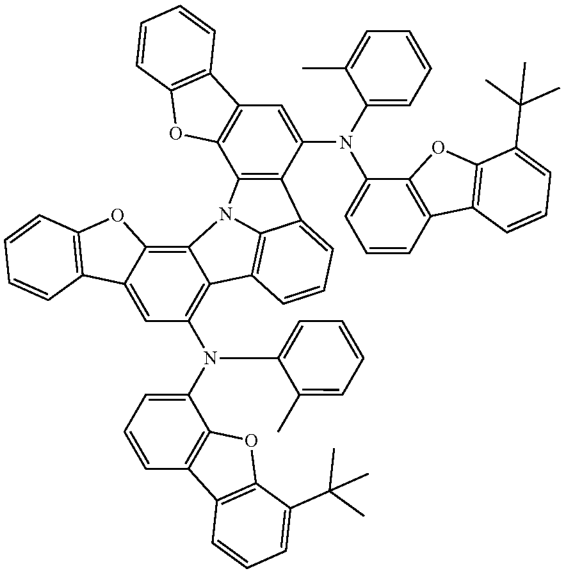
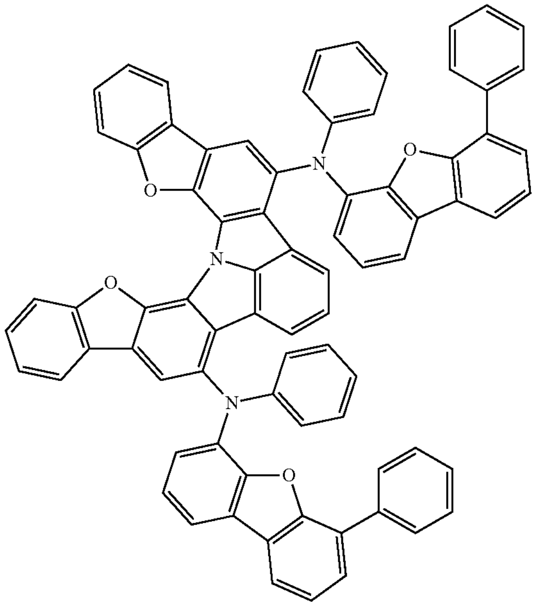
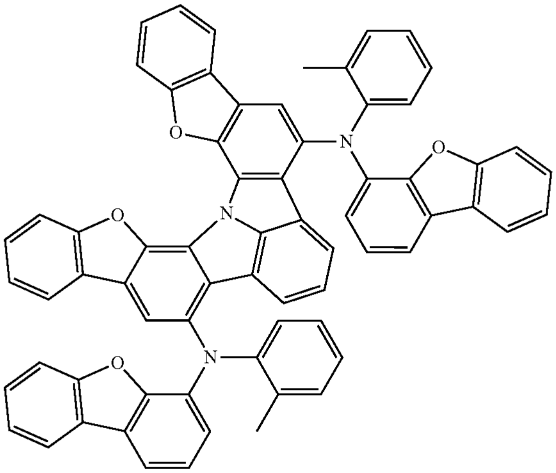
[Formula 193]
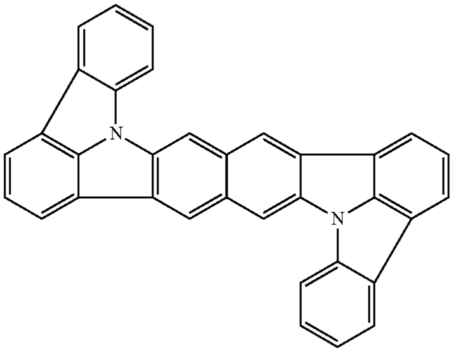
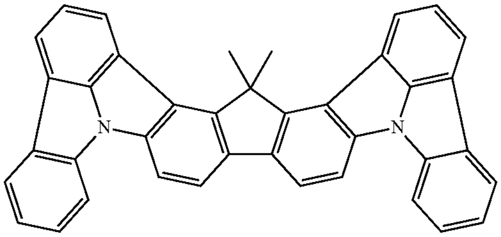

-continued
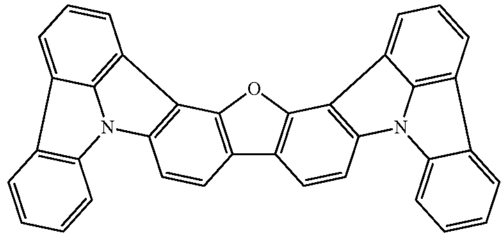
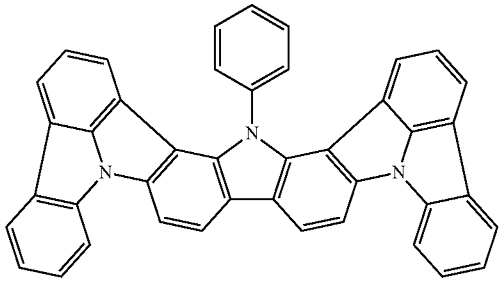
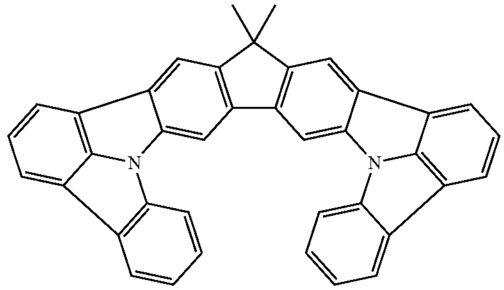
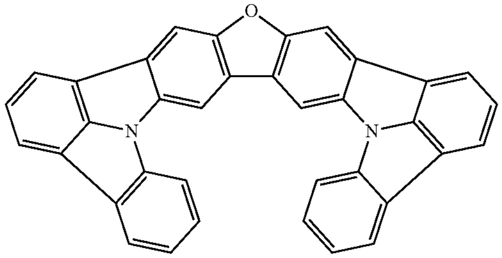
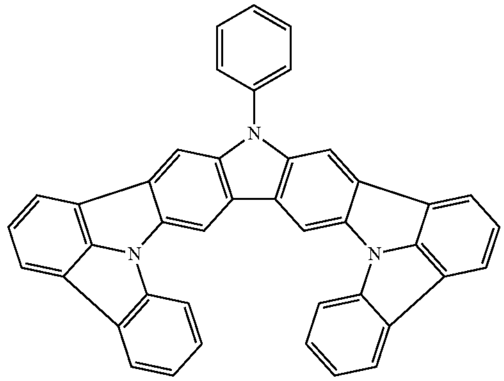
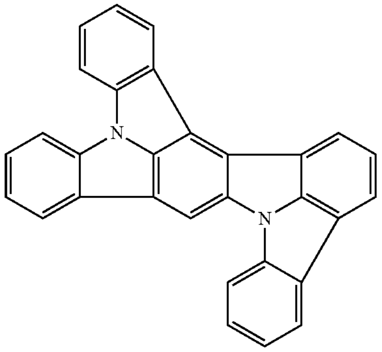

-continued

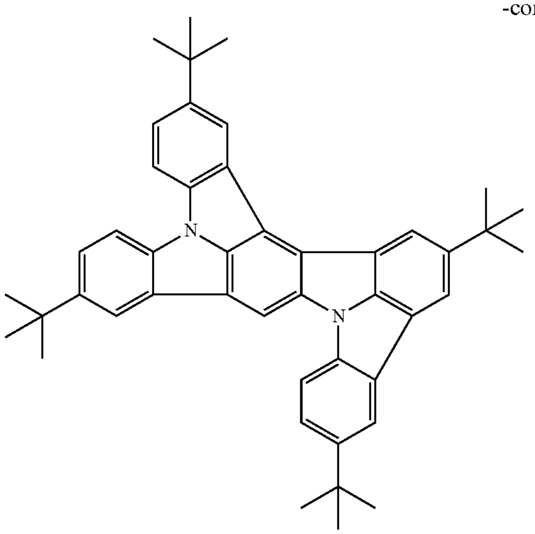

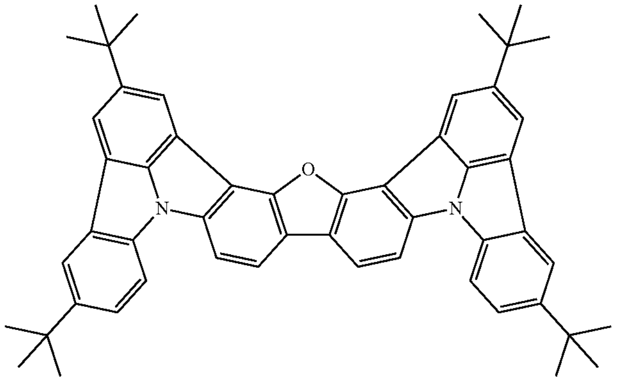

.

Compound Represented by Formula (5)

The compound represented by the formula (5) will be described. The compound represented by the formula (5) corresponds to the compound represented by the above-described formula (41-3).

[Formula 194]

(5)

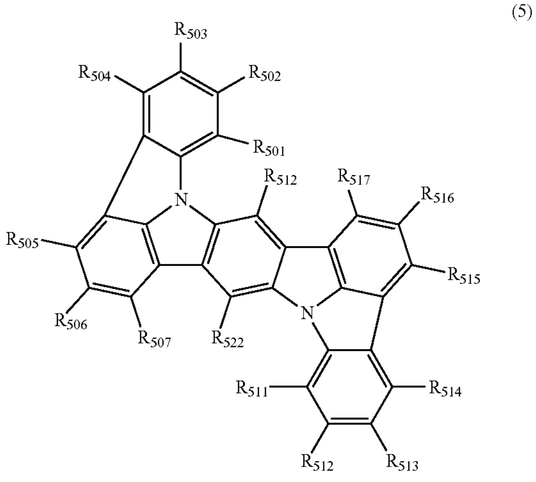

In the formula (5):

at least one combination of adjacent two or more of $R_{501}$ to $R_{507}$ and $R_{511}$ to $R_{517}$ are mutually bonded to form a substituted or unsubstituted monocyclic ring, mutually bonded to form a substituted or unsubstituted fused ring, or not mutually bonded;

$R_{501}$ to $R_{507}$ and $R_{511}$ to $R_{517}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and $R_{521}$ and $R_{522}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

"A combination of adjacent two or more of $R_{501}$ to $R_{507}$ and $R_{511}$ to $R_{517}$" refers to, for instance, a combination of $R_{501}$ and $R_{502}$, a combination of $R_{502}$ and $R_{503}$, a combination of $R_{503}$ and $R_{504}$, a combination of $R_{505}$ and $R_{506}$, a combination of $R_{506}$ and $R_{507}$, and a combination of $R_{501}$, $R_{502}$ and $R_{503}$.

In an exemplary embodiment, at least one, preferably two of $R_{501}$ to $R_{507}$ and $R_{511}$ to $R_{517}$ are groups represented by —N($R_{906}$)($R_{907}$).

In an exemplary embodiment, $R_{501}$ to $R_{507}$ and $R_{511}$ to $R_{517}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is a compound represented by a formula (52) below.

[Formula 195]

(52)

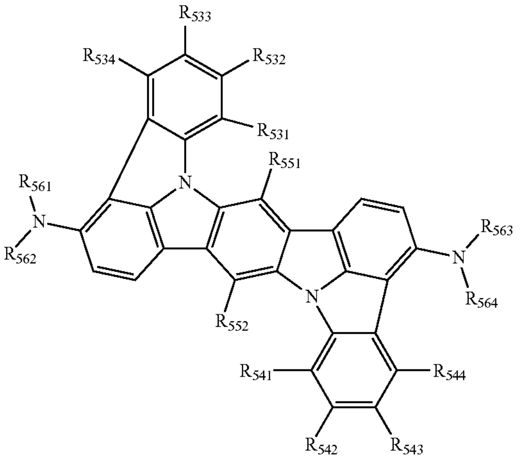

In the formula (52):

at least one combination of adjacent two or more of $R_{531}$ to $R_{534}$ and $R_{541}$ to $R_{544}$ are mutually bonded to form a substituted or unsubstituted monocyclic ring, mutually bonded to form a substituted or unsubstituted fused ring, or not mutually bonded;

$R_{531}$ to $R_{534}$ and $R_{541}$ to $R_{544}$ not forming the monocyclic ring and not forming the fused ring, and $R_{551}$ to $R_{552}$ are each independently a hydrogen atom, a substituted or unsubstituted aryl group having 6 to 50 ring carbon atoms, or a substituted or unsubstituted heterocyclic group having 5 to 50 ring atoms; and $R_{561}$ to $R_{564}$ are each independently a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is a compound represented by a formula (53) below.

[Formula 196]

(53)

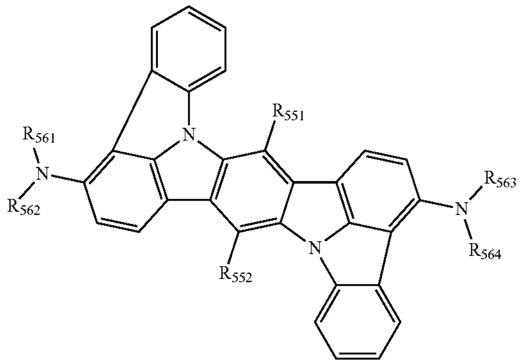

In the formula (53), $R_{551}$, $R_{552}$ and $R_{561}$ to $R_{564}$ each independently represent the same as $R_{551}$, $R_{552}$ and $R_{561}$ to $R_{564}$ in the formula (52).

In an exemplary embodiment, $R_{561}$ to $R_{564}$ in the formulae (52) and (53) are each independently a substituted or unsubstituted aryl group having 6 to 50 ring carbon atoms (preferably a phenyl group).

In an exemplary embodiment, $R_{521}$ and $R_{522}$ in the formula (5), and $R_{551}$ and $R_{552}$ in the formulae (52) and (53) are each a hydrogen atom.

In an exemplary embodiment, a substituent for the "substituted or unsubstituted" group in the formulae (5), (52) and (53) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

Specific examples of the compound represented by the formula (5) include compounds shown below.

[Formula 197]
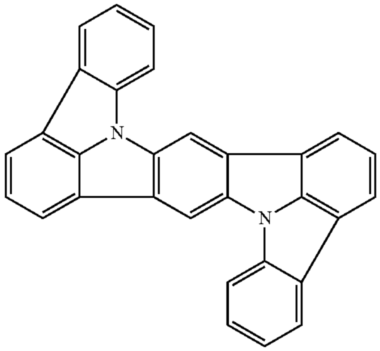
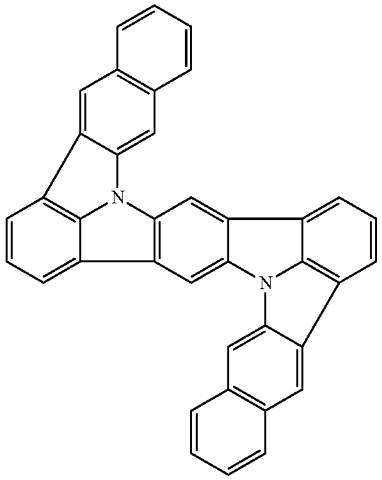
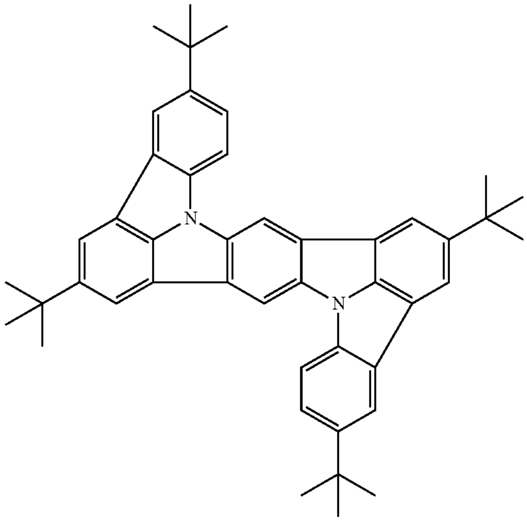
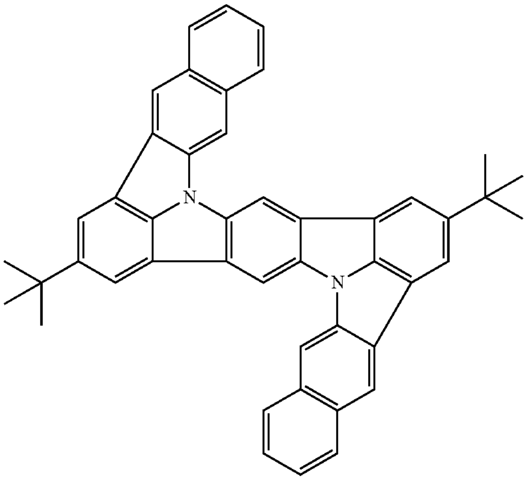
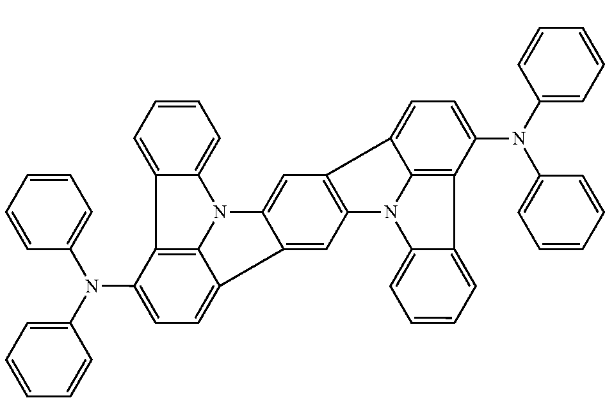

-continued
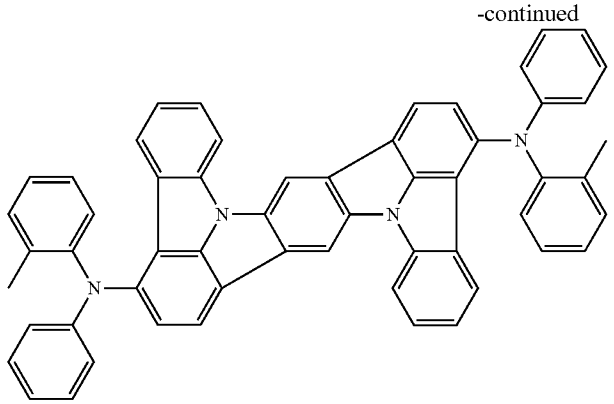
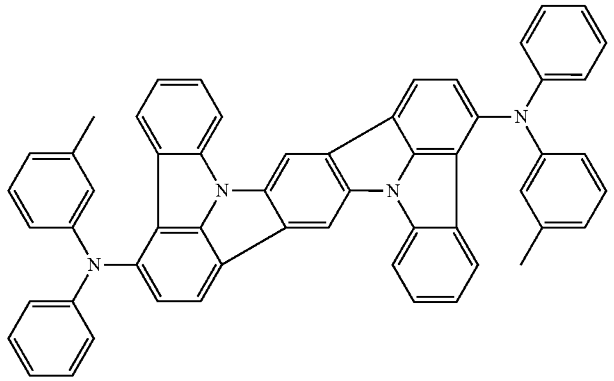
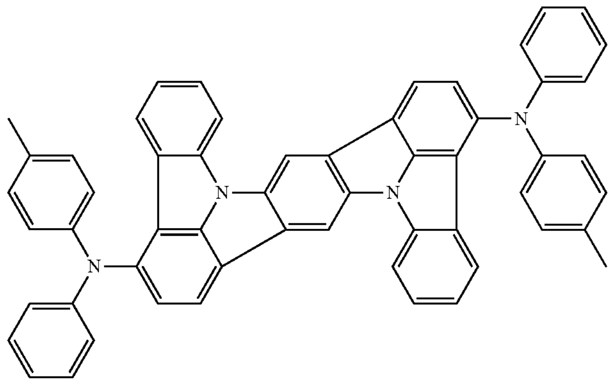
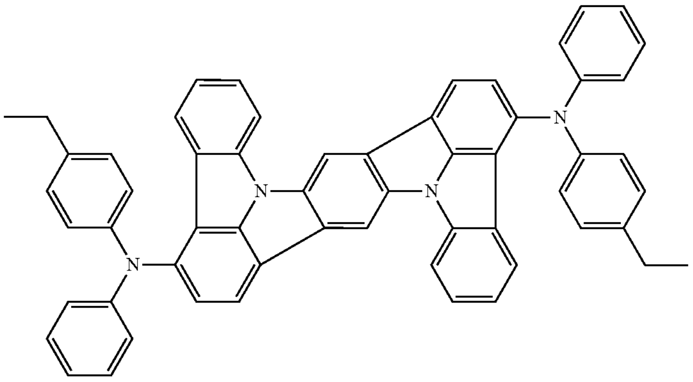

-continued
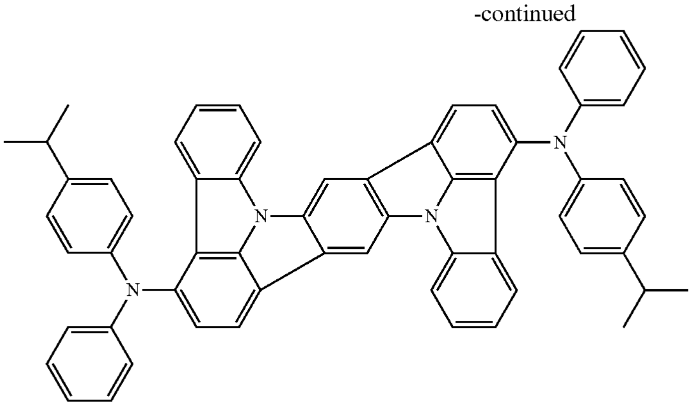
[Formula 198]
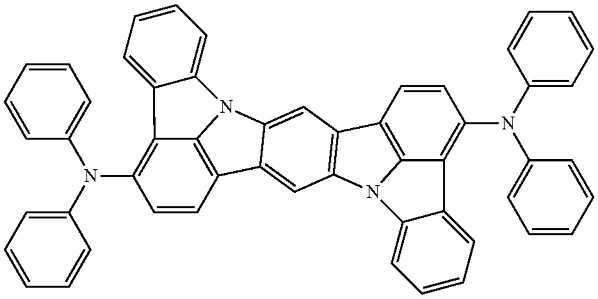
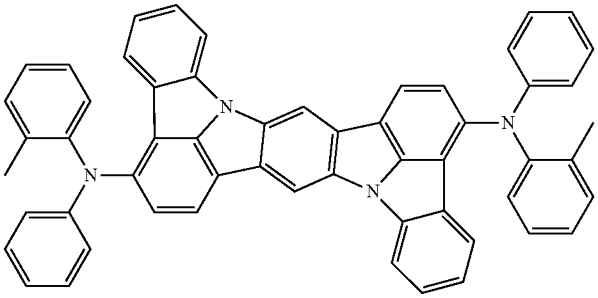
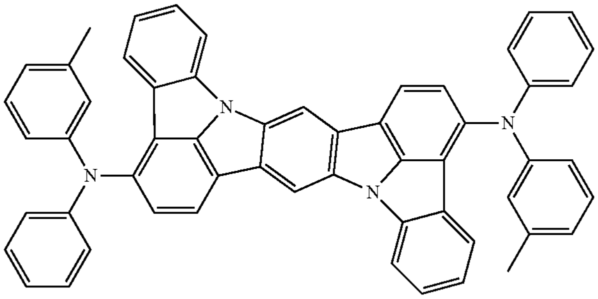
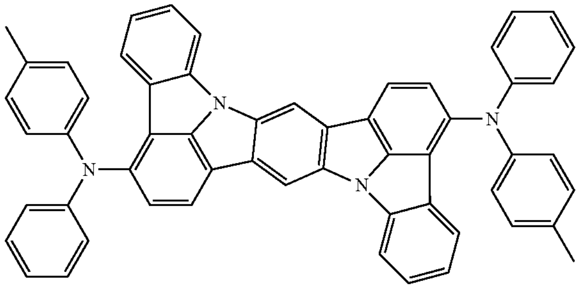

-continued
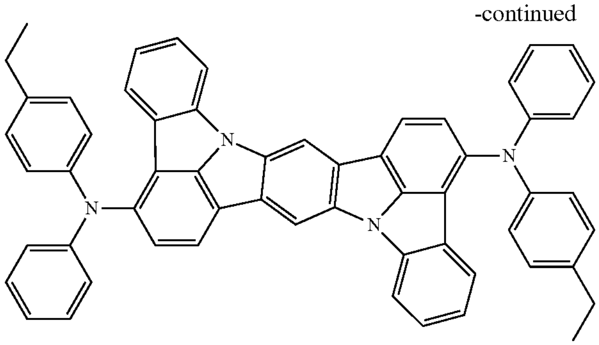
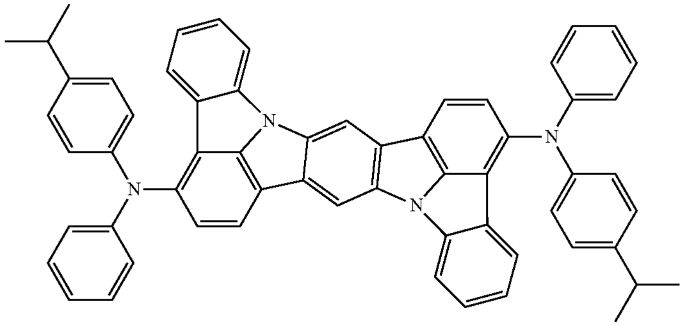
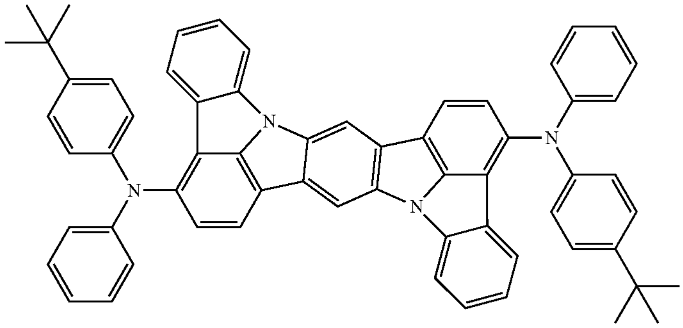
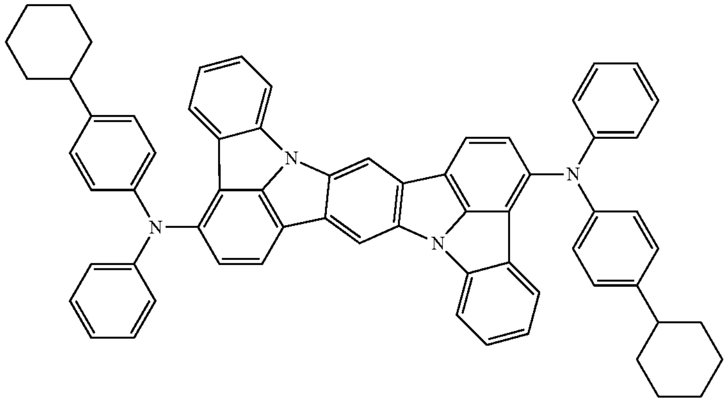

-continued
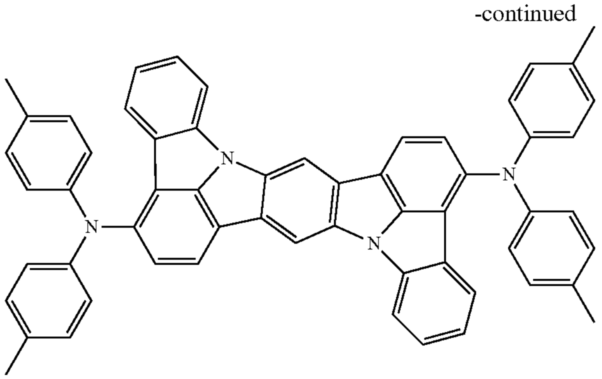
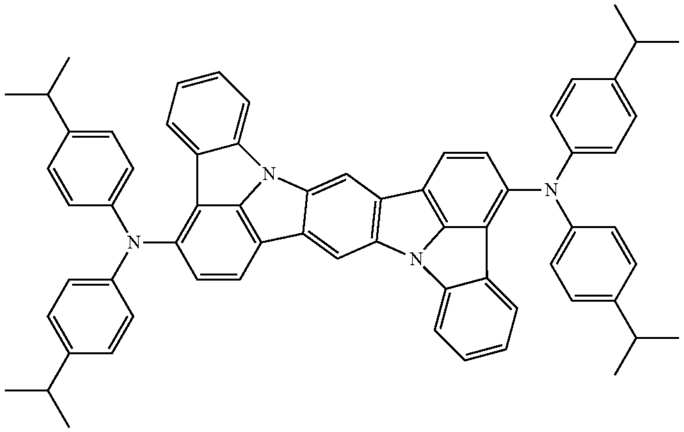
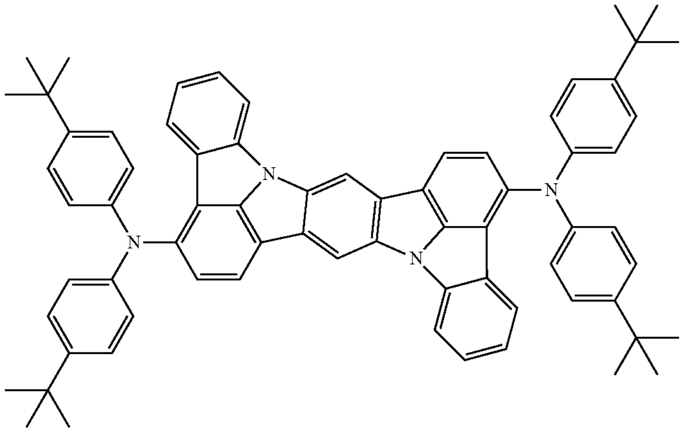
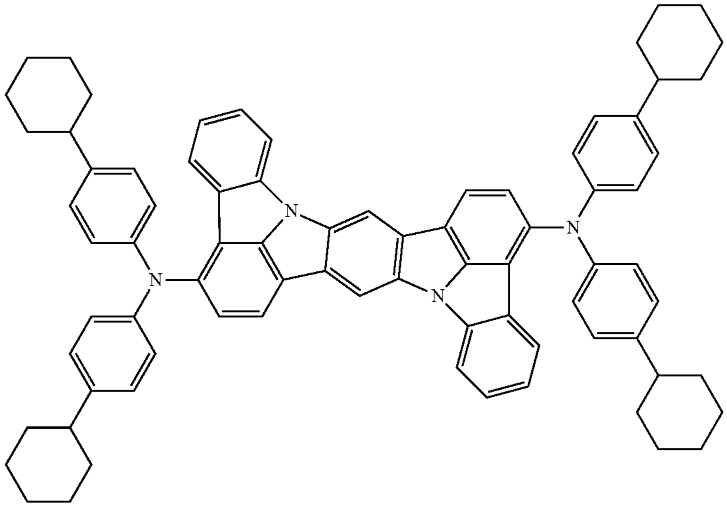

-continued
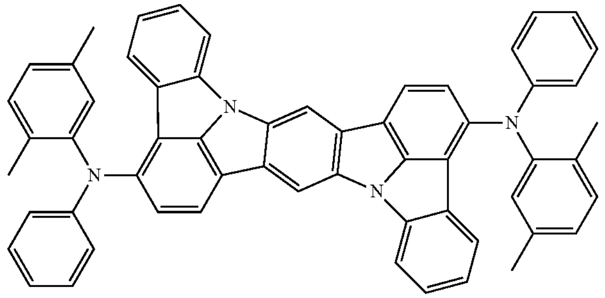
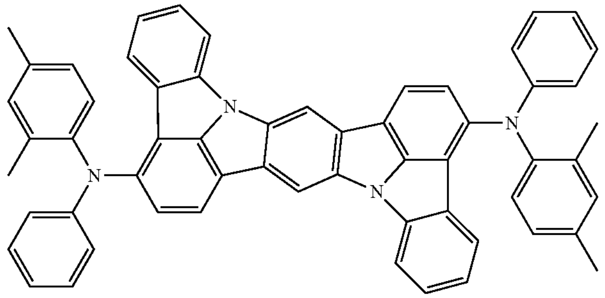
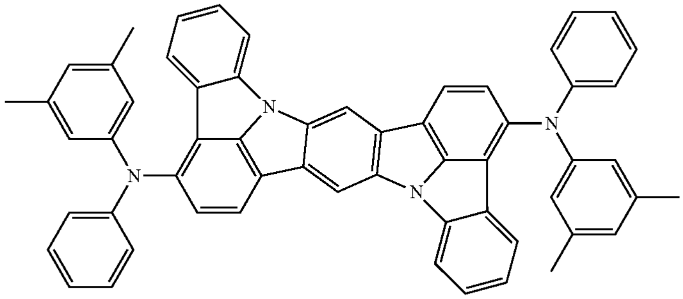
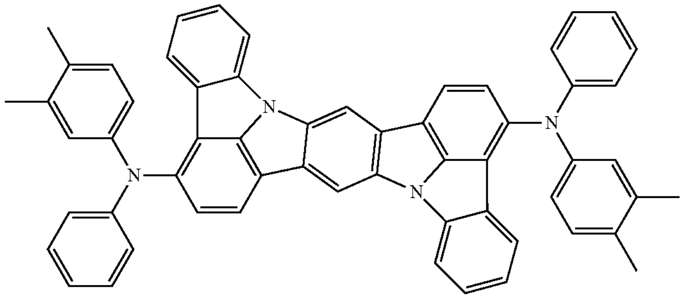
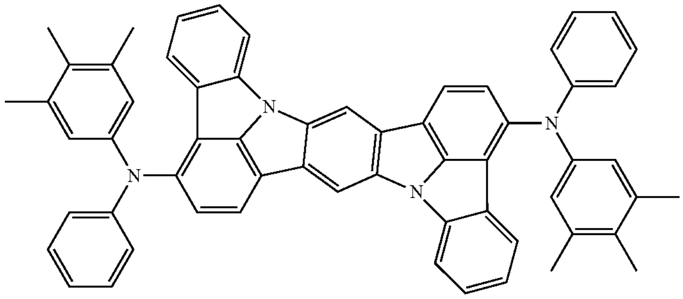

-continued
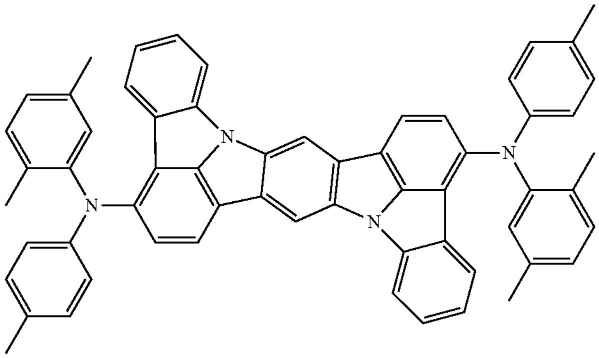
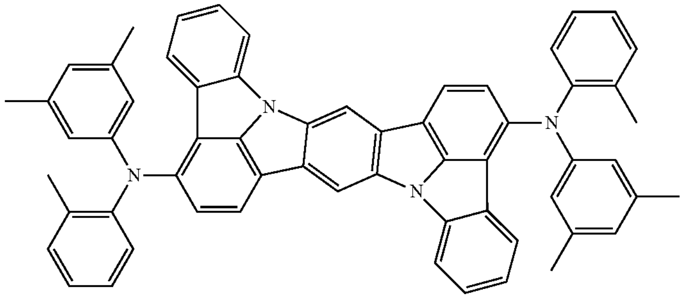
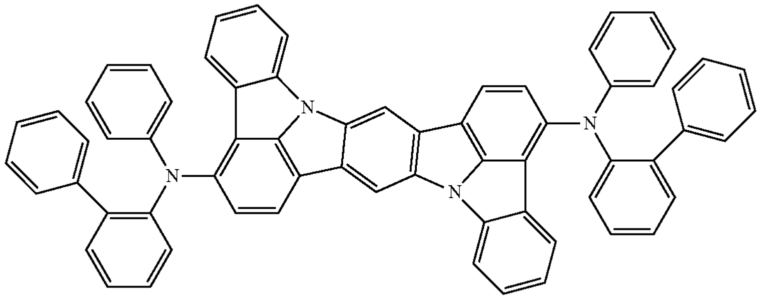
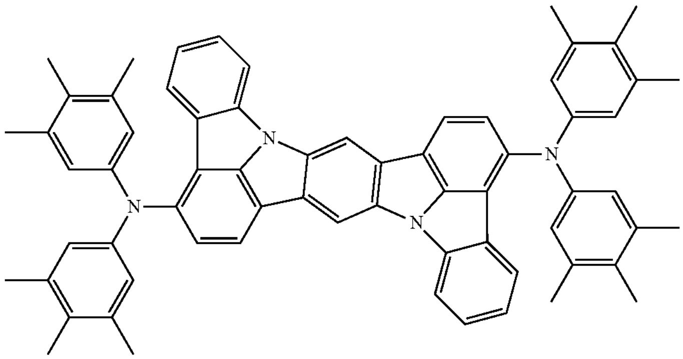

-continued
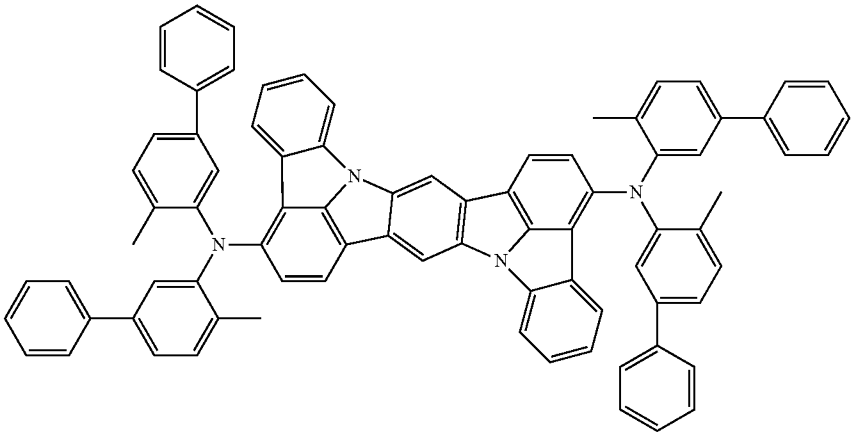
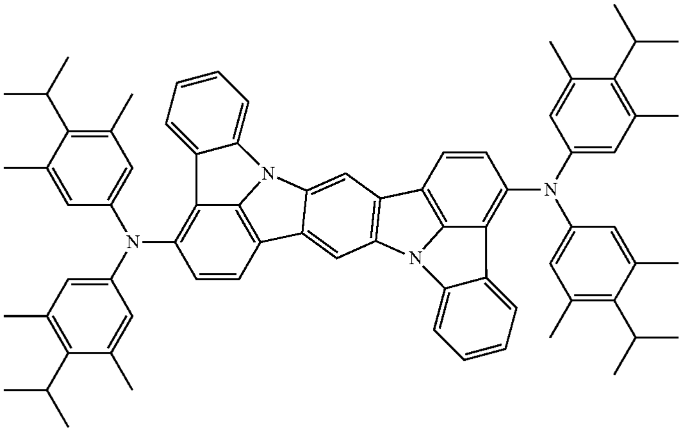
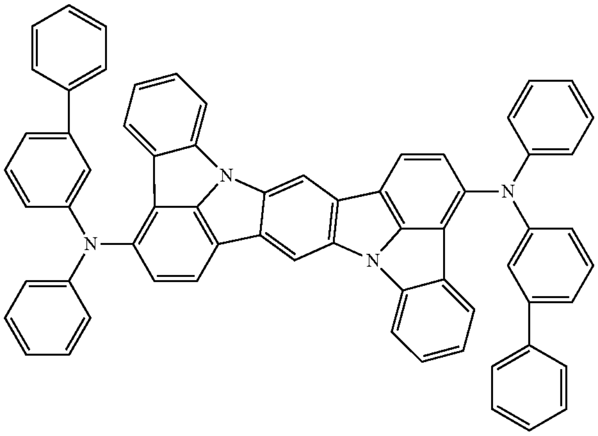
[Formula 199]
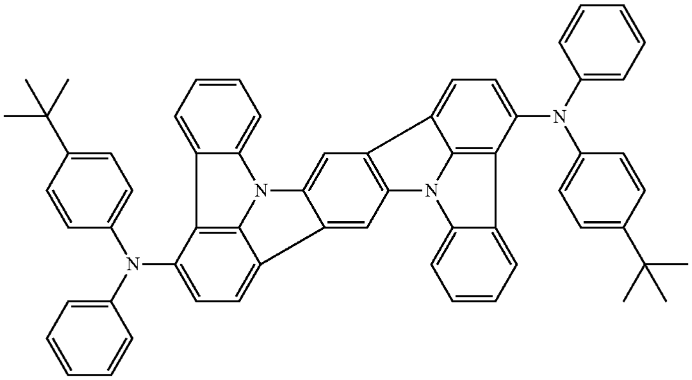

-continued
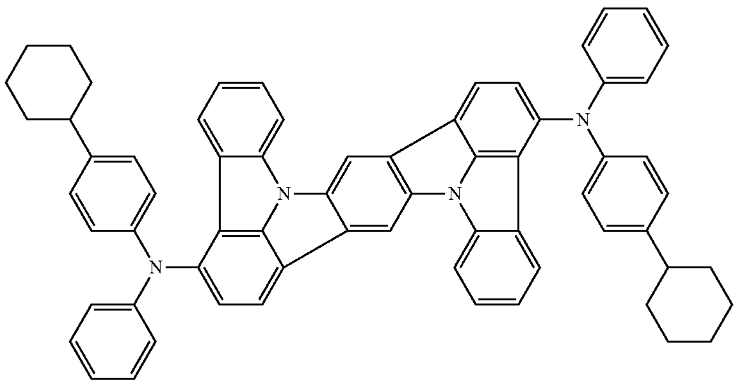
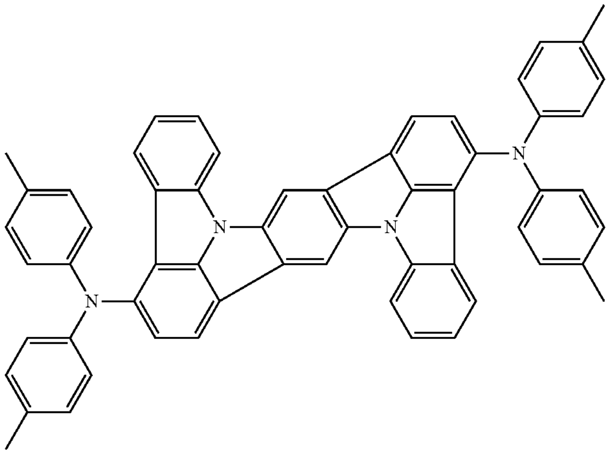
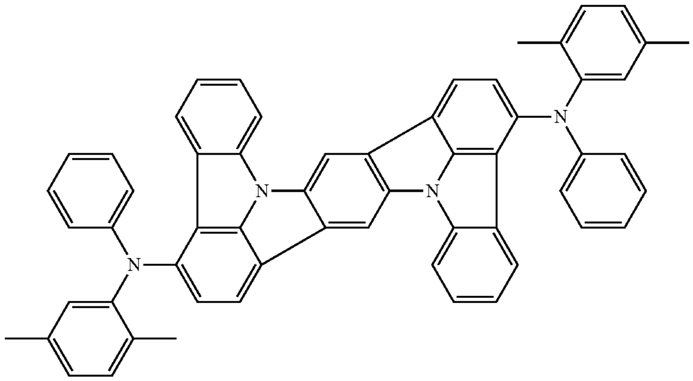
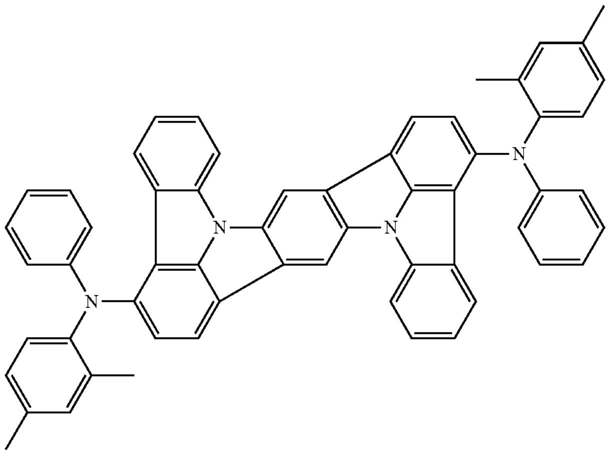

-continued
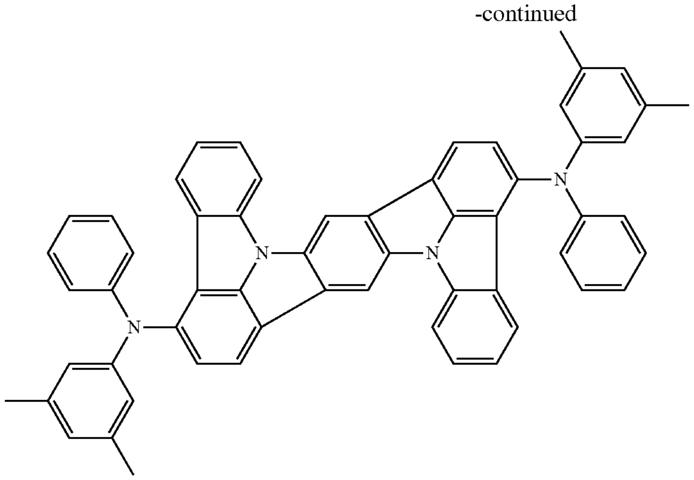
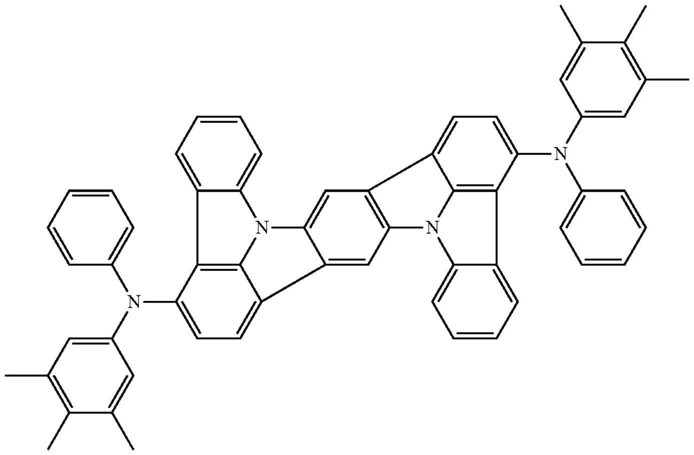
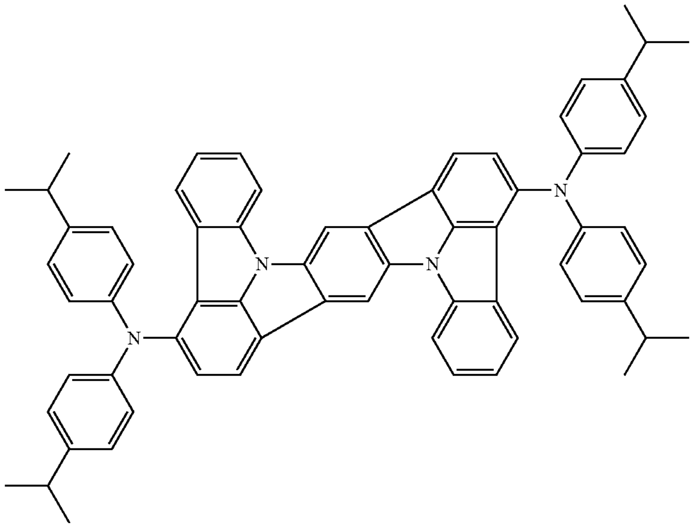

-continued
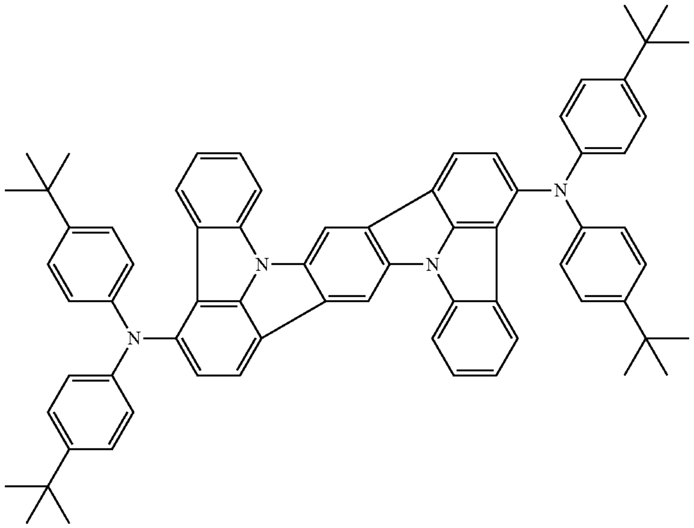
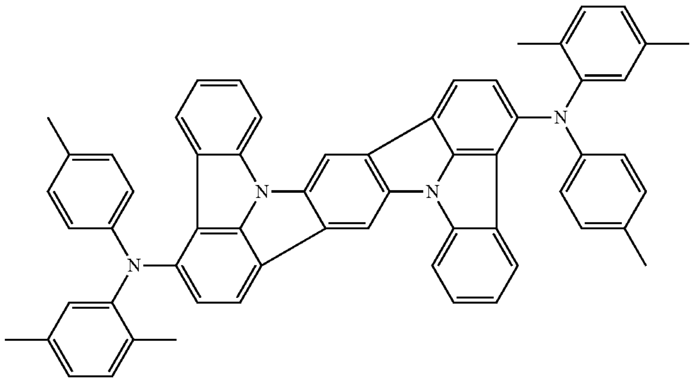
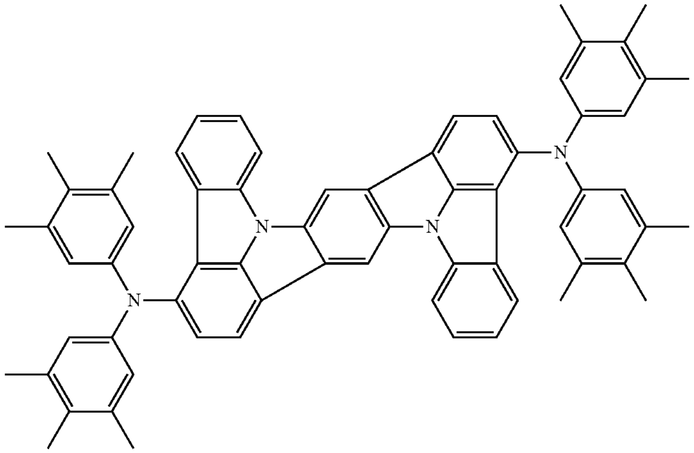

-continued
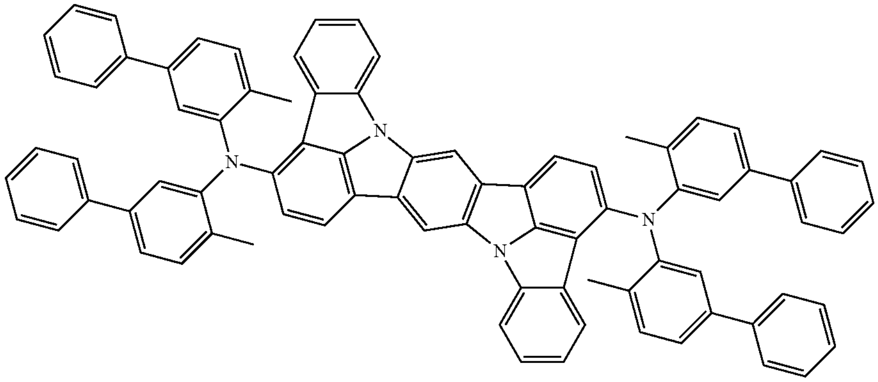
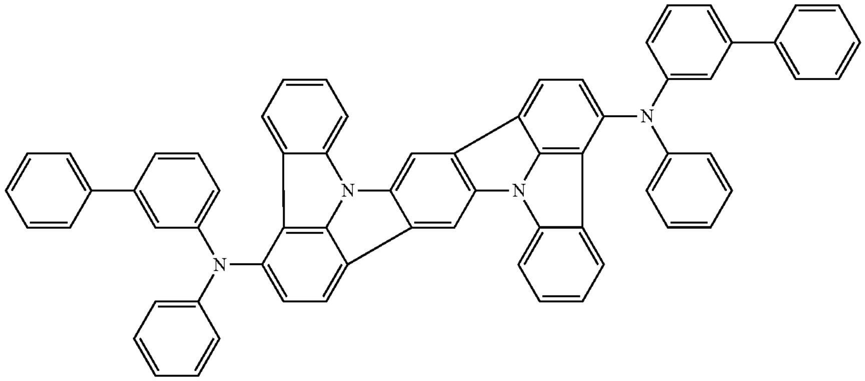
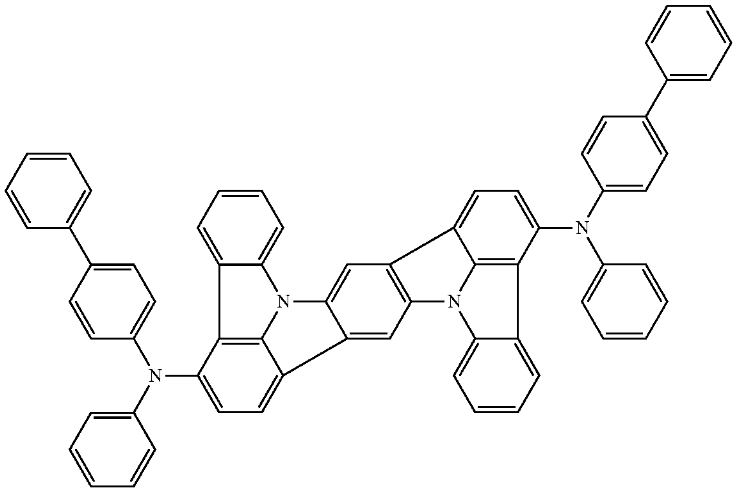
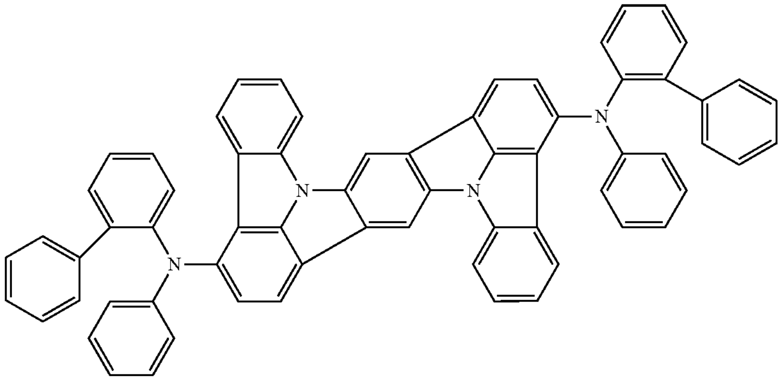

-continued
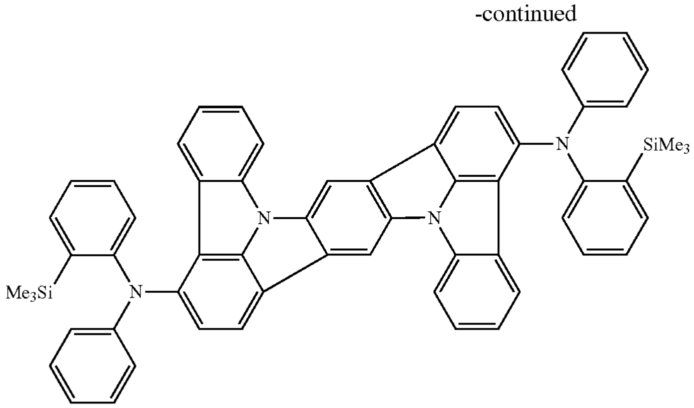
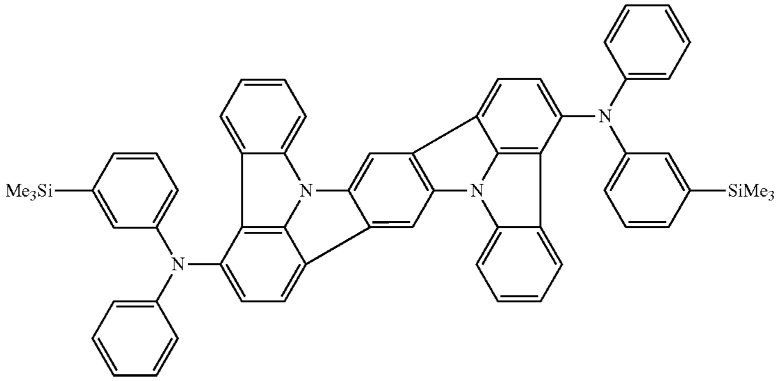
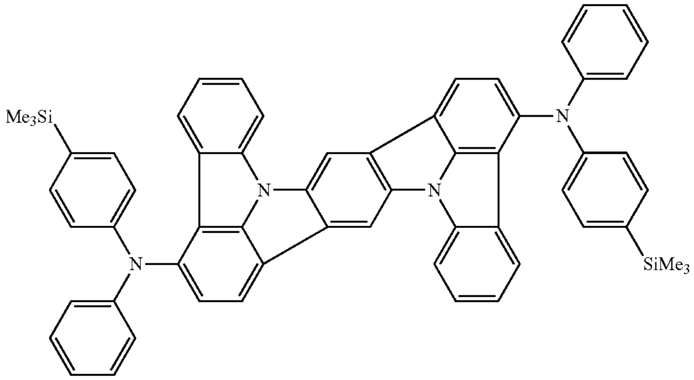
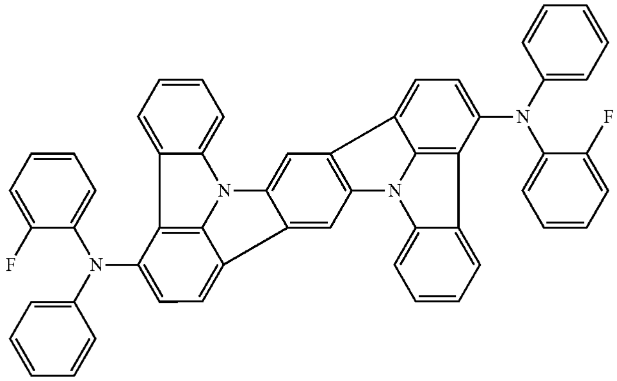

-continued
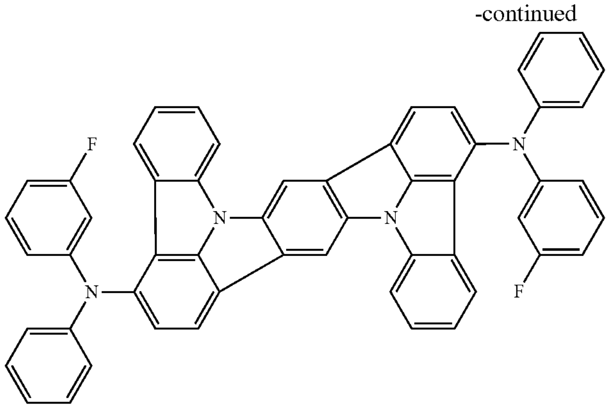
[Formula 200]
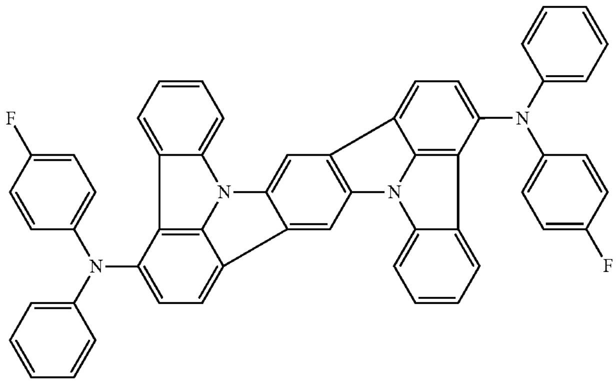
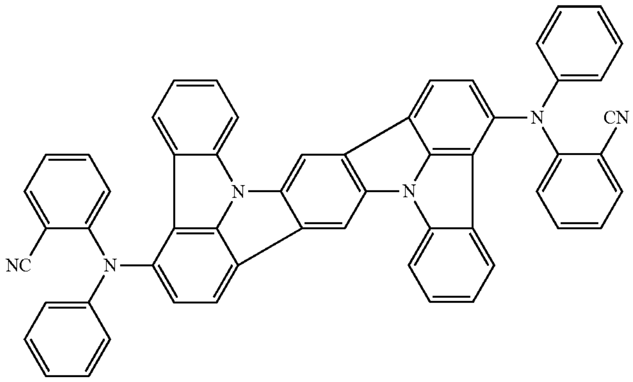
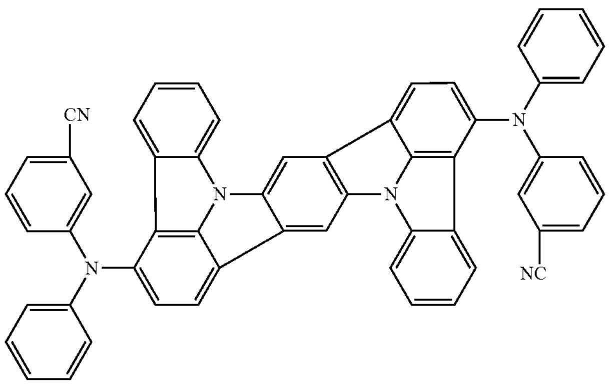

-continued
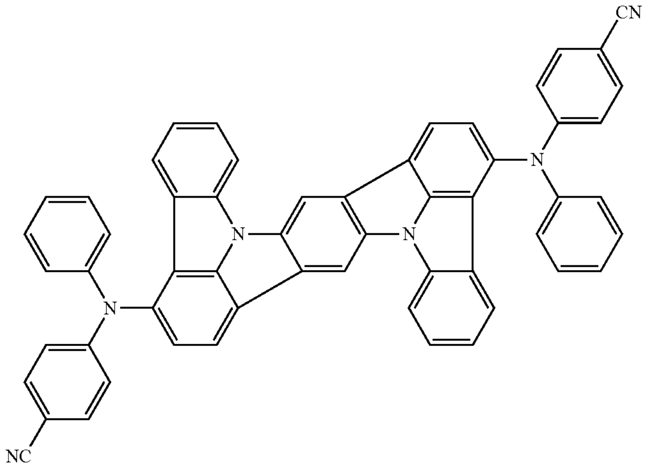
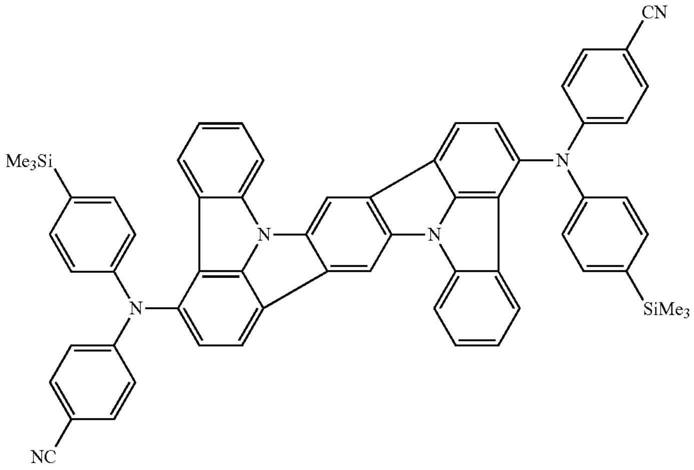
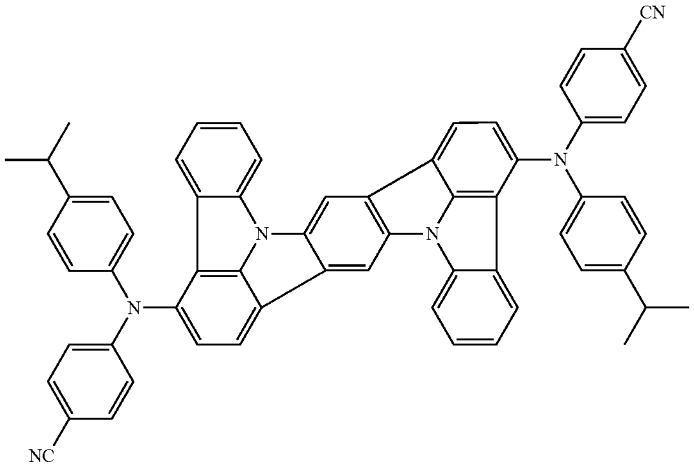

-continued
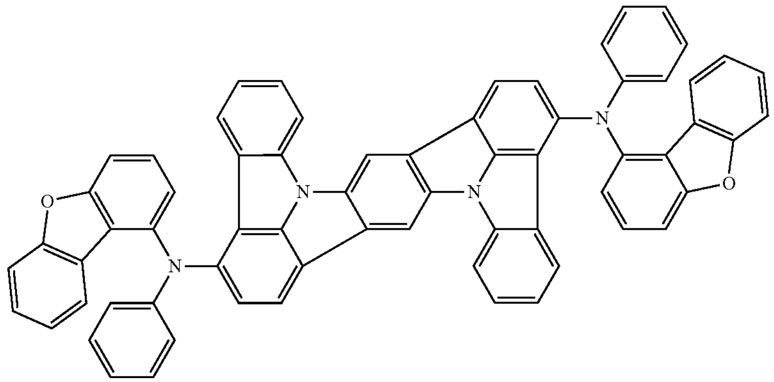
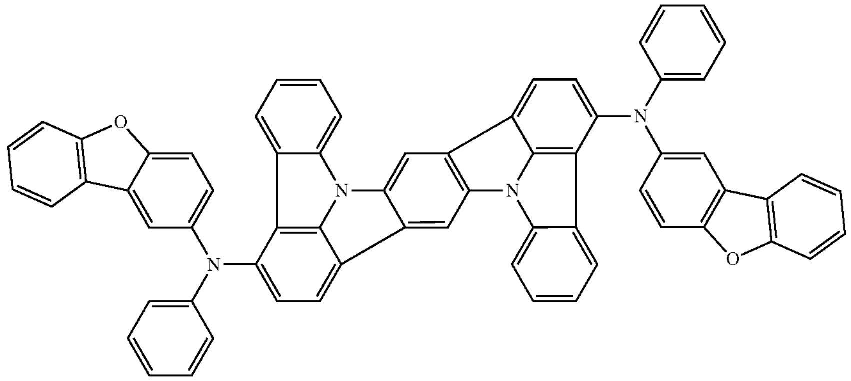
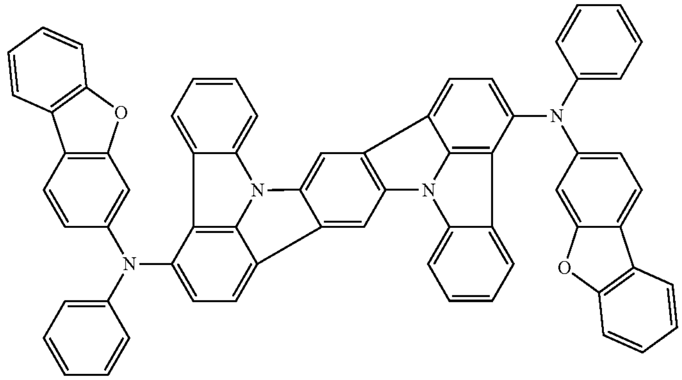
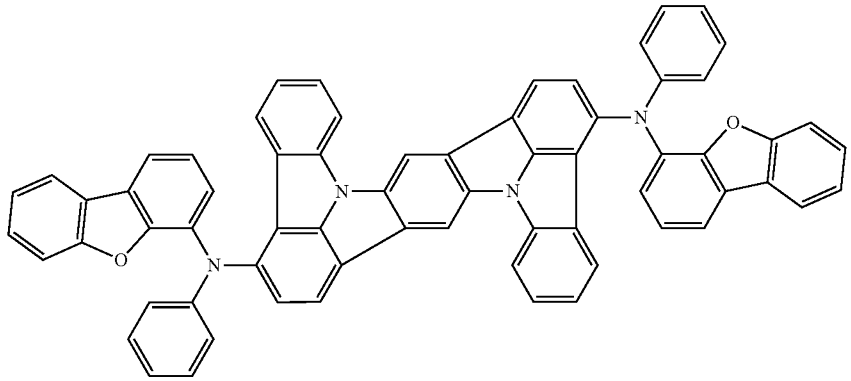

-continued
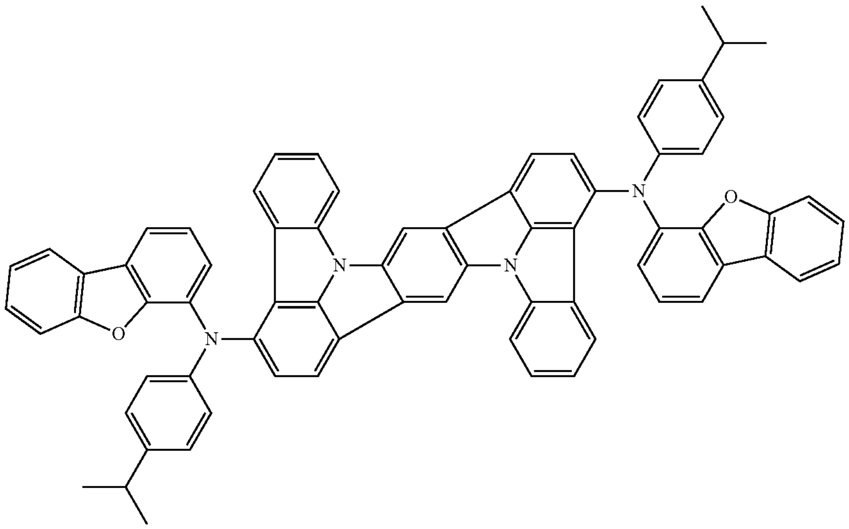
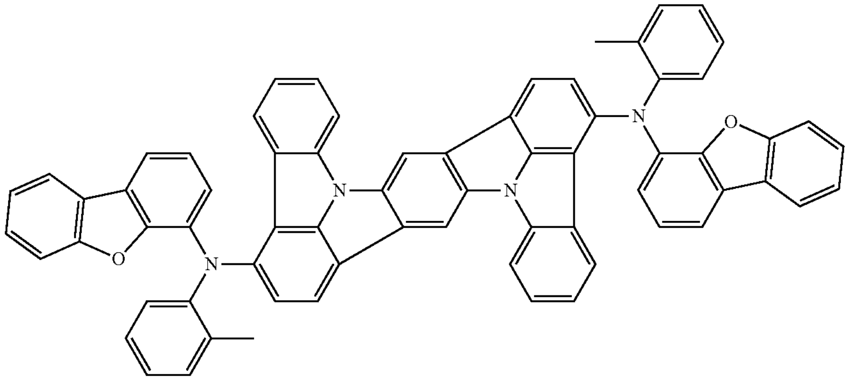
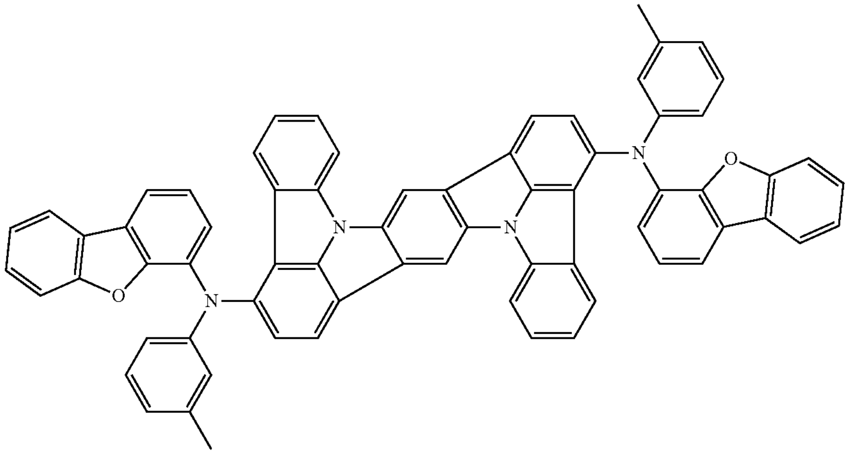

-continued
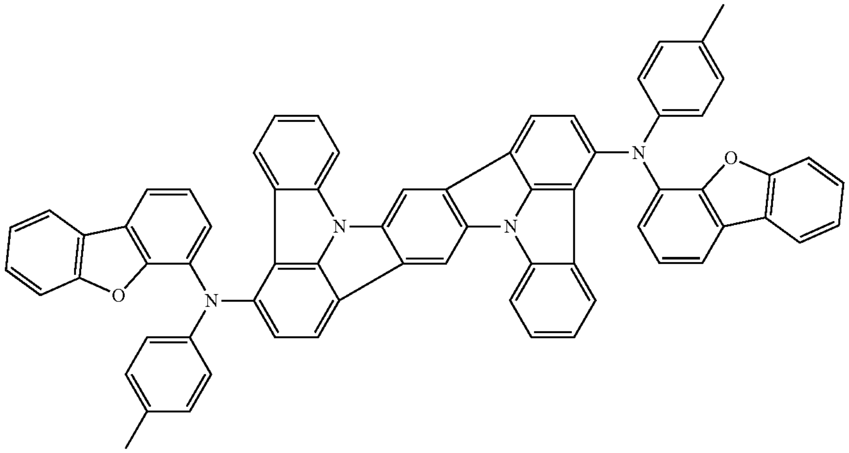
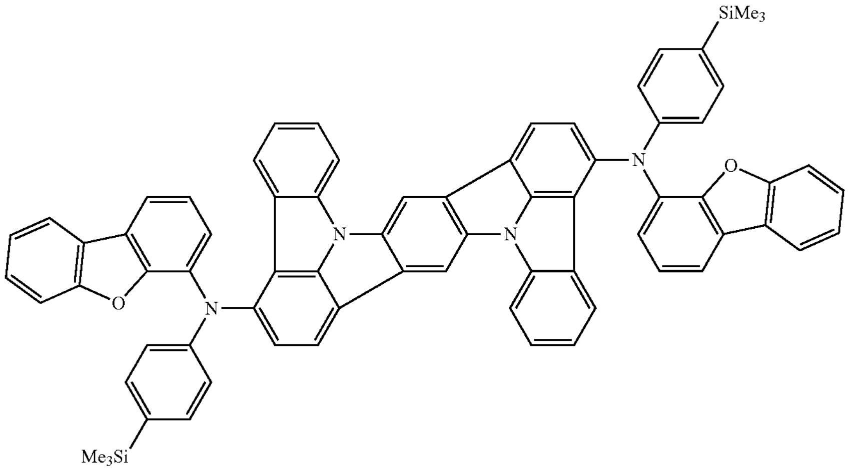
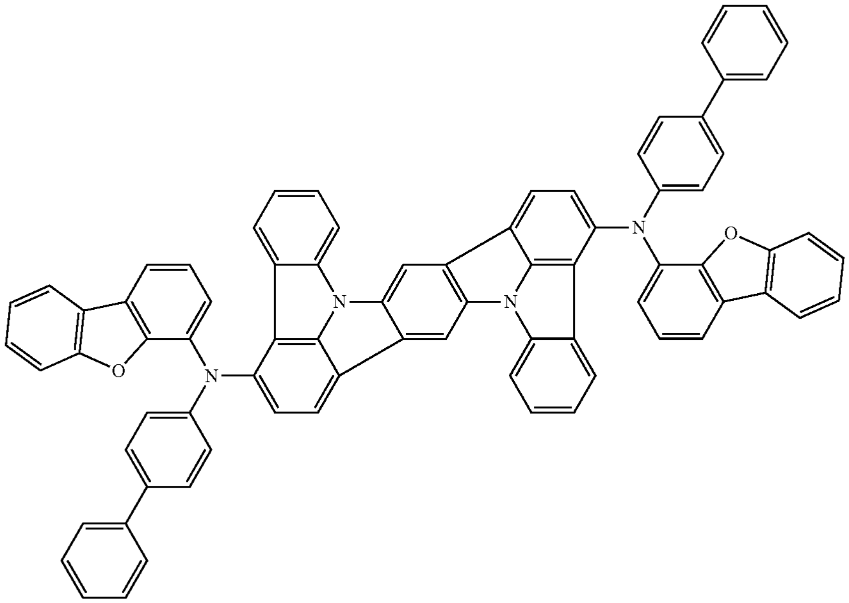

-continued
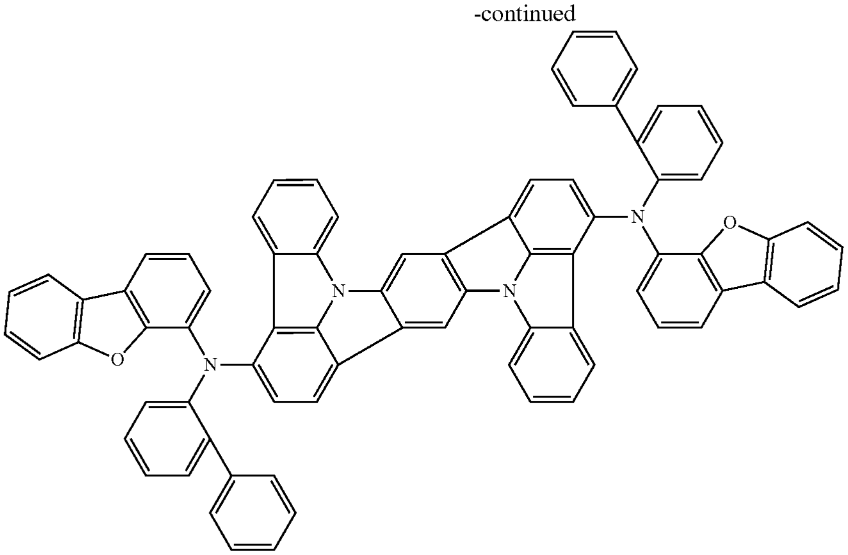
[Formula 201]
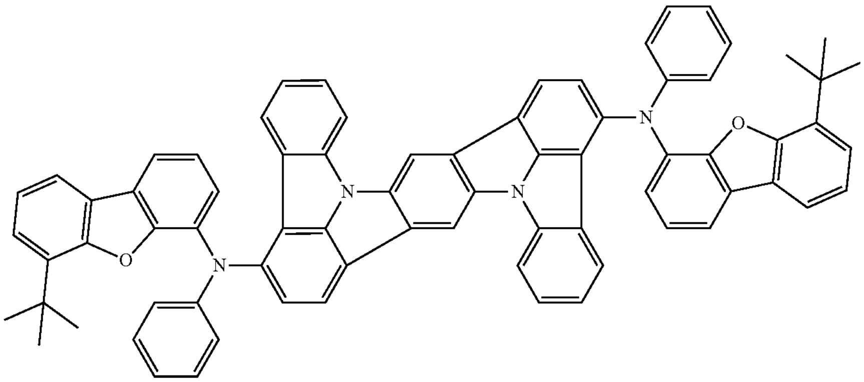
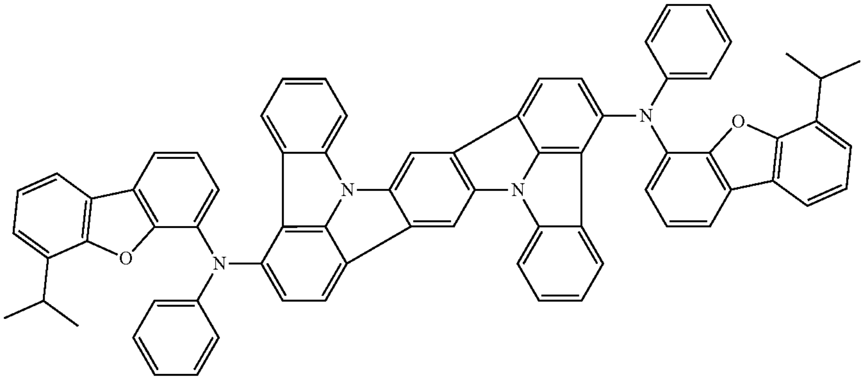
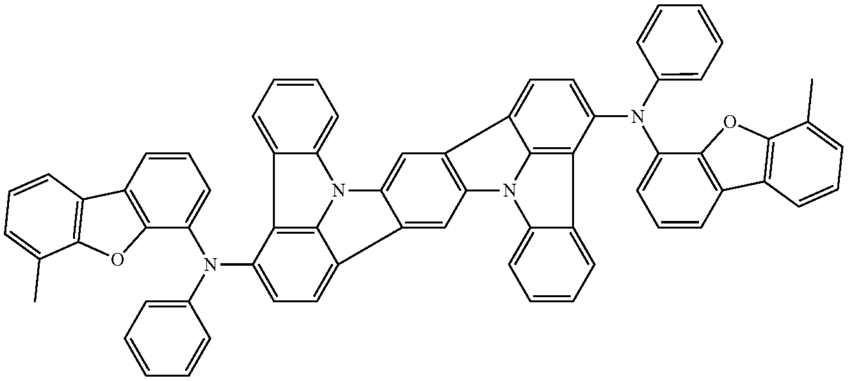

-continued
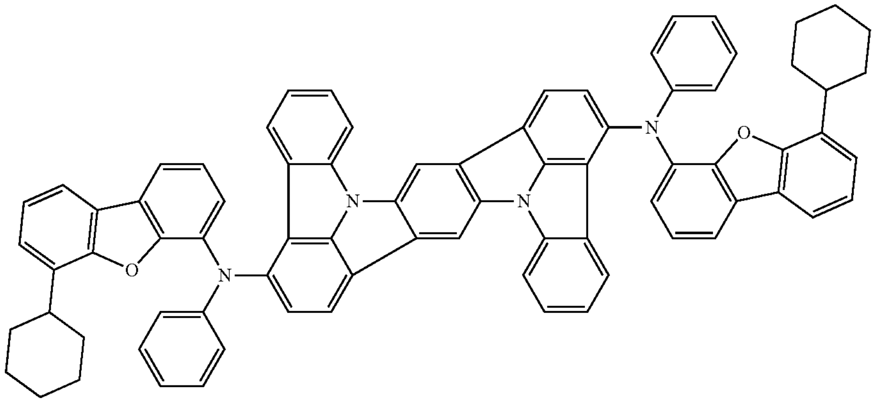
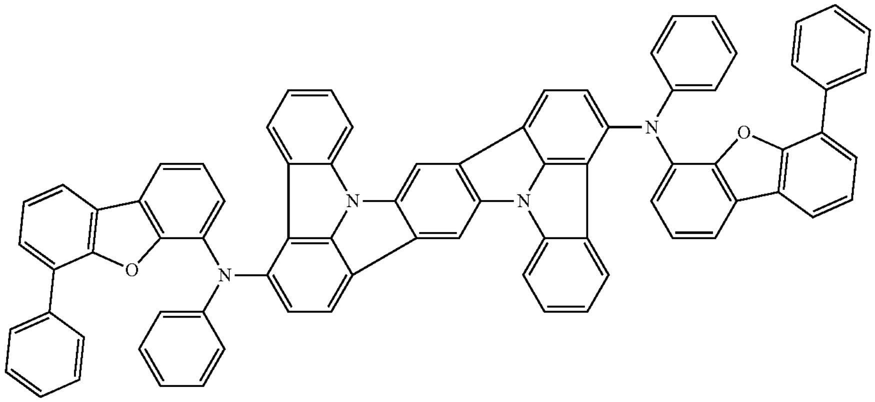
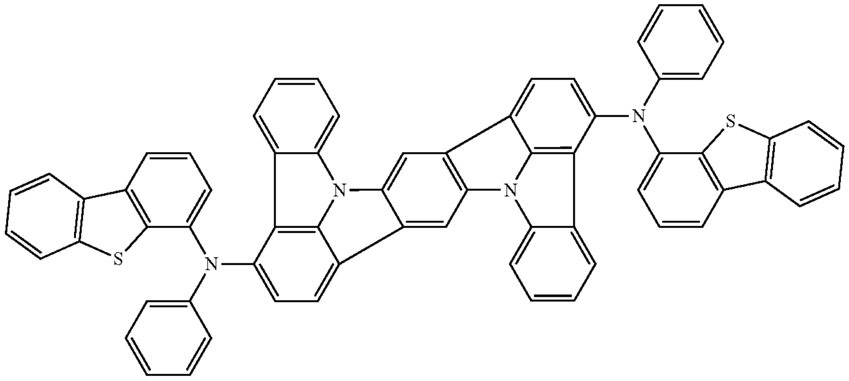

-continued
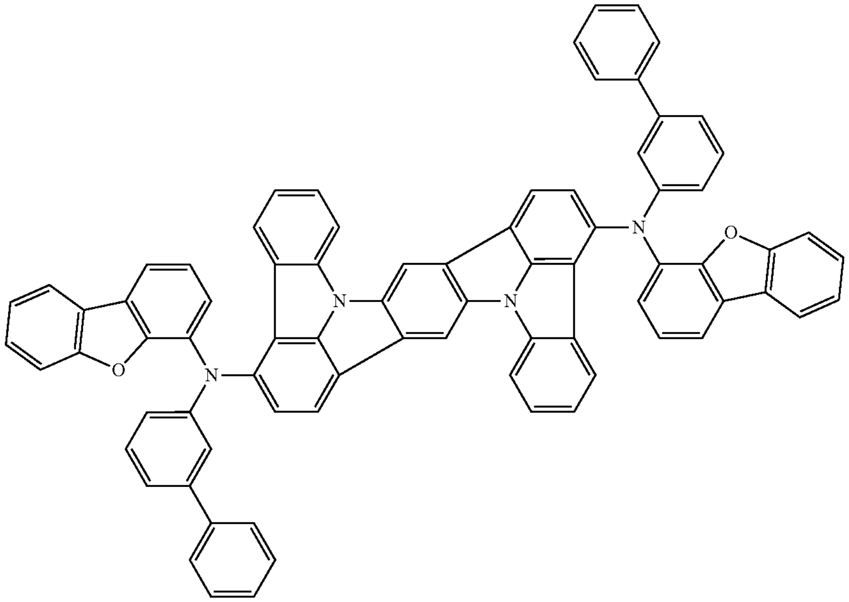
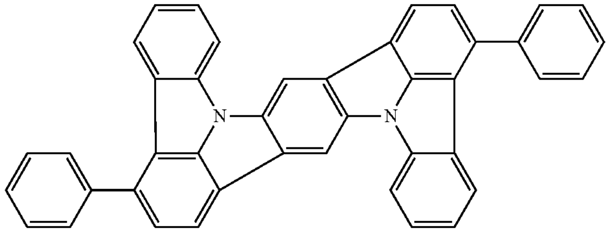
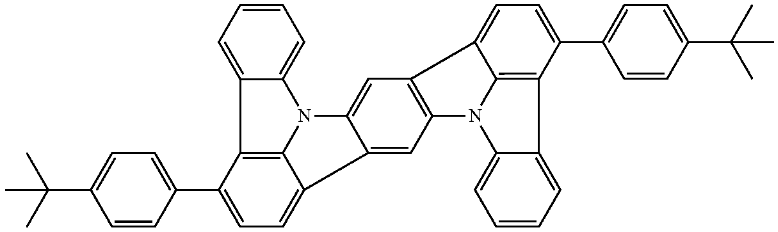
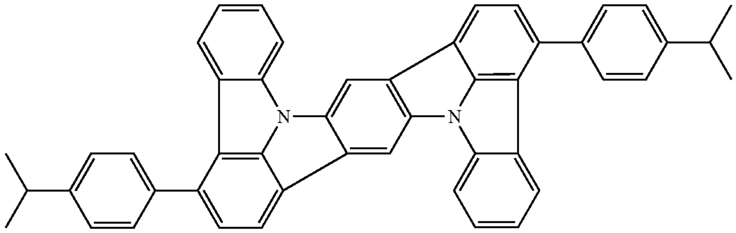
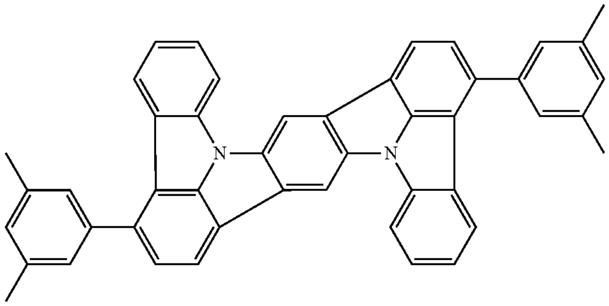

-continued
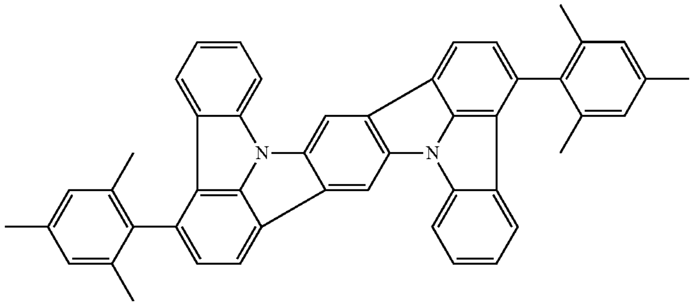
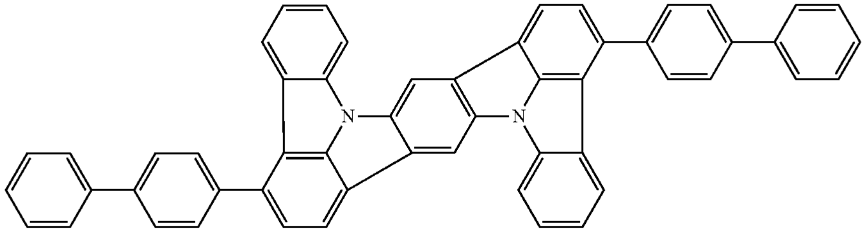
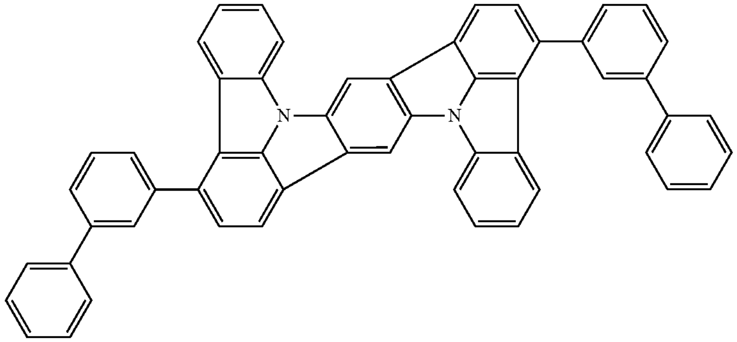
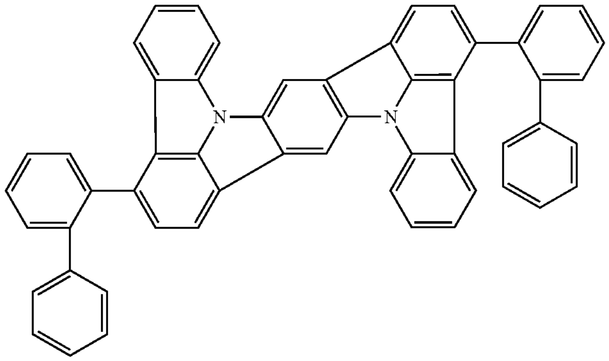
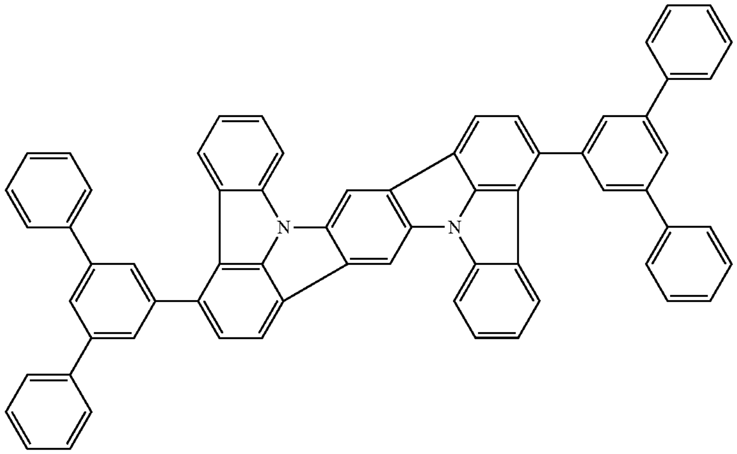

-continued
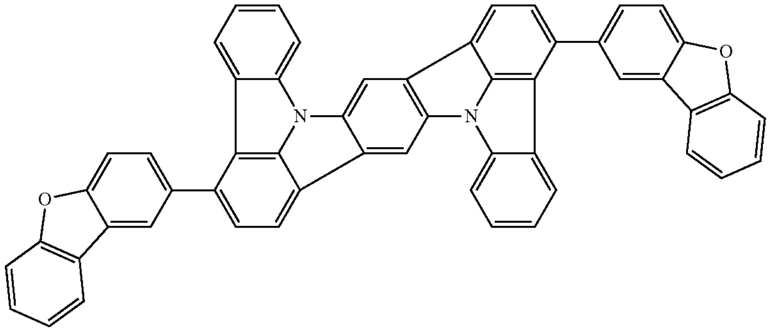
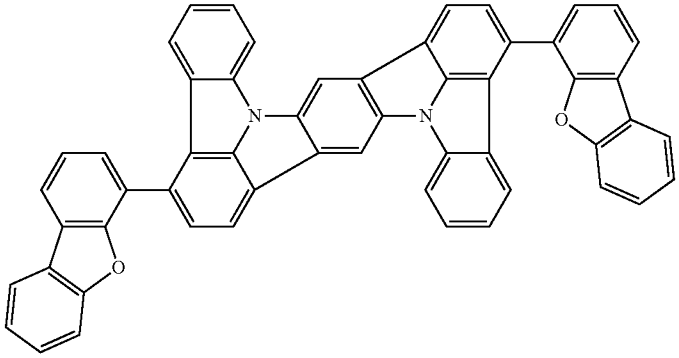
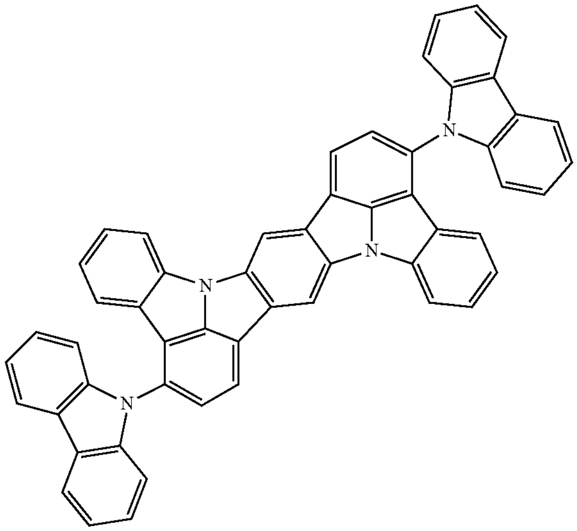
[Formula 202]
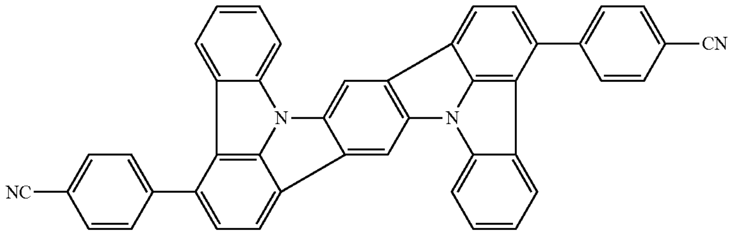

-continued
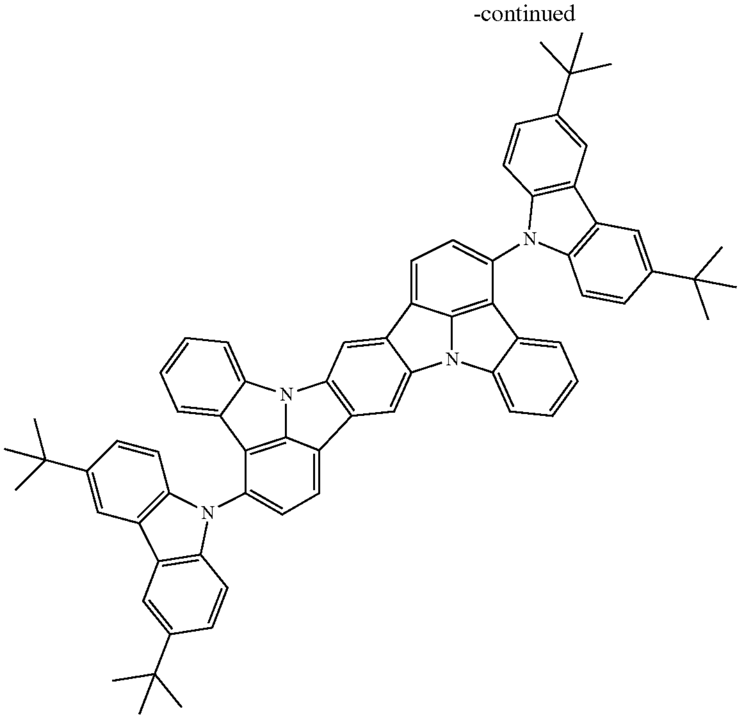
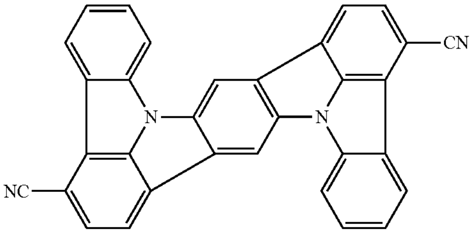
[Formula 203]
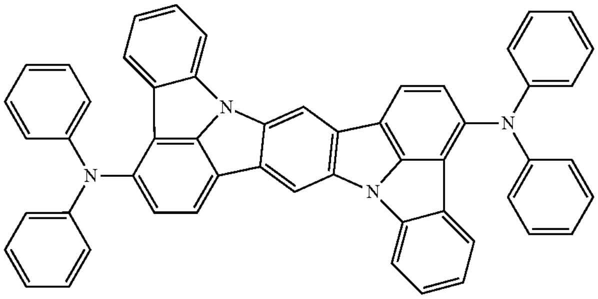
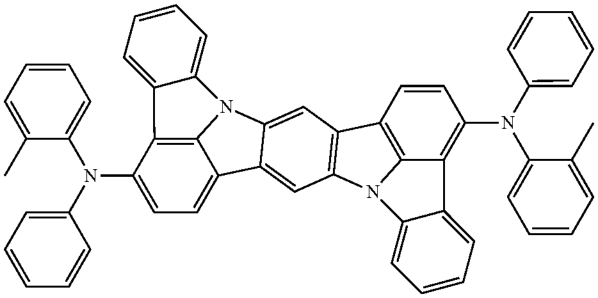

-continued
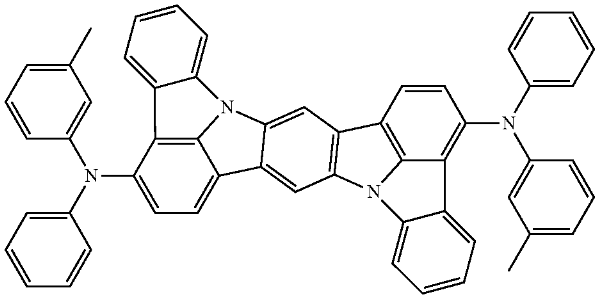
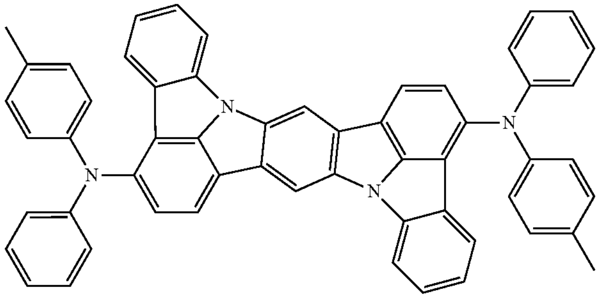
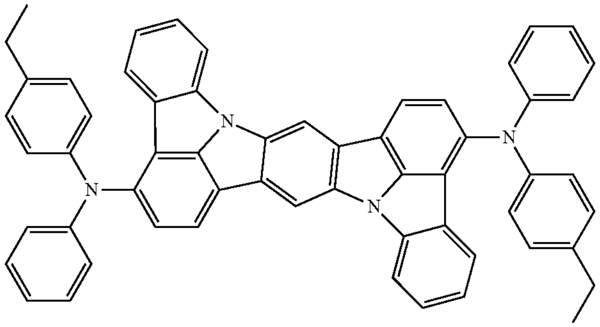
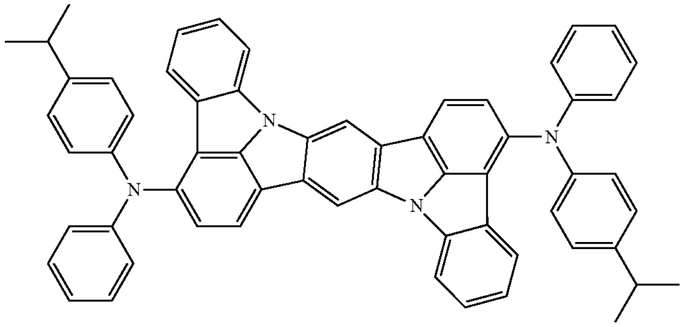
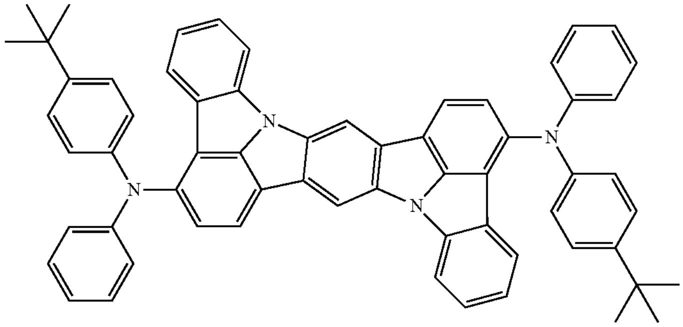

-continued
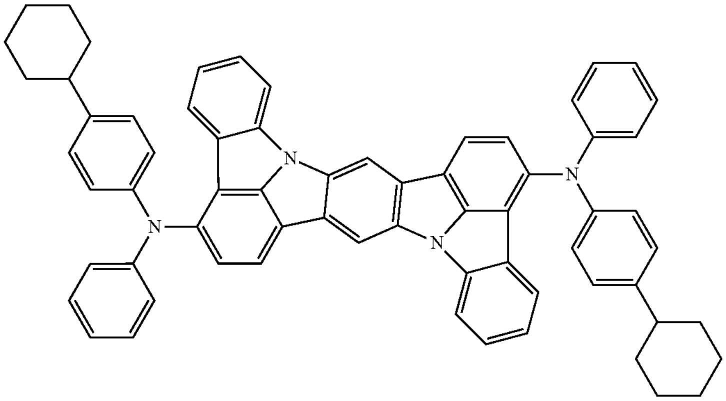
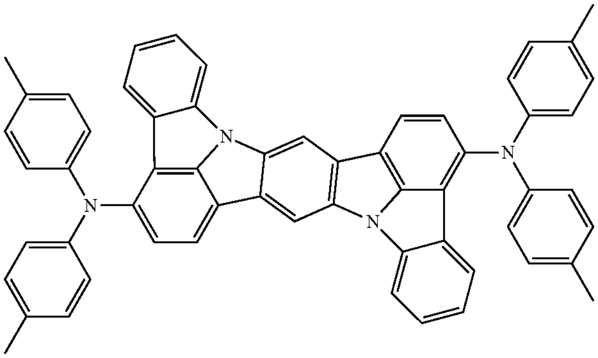
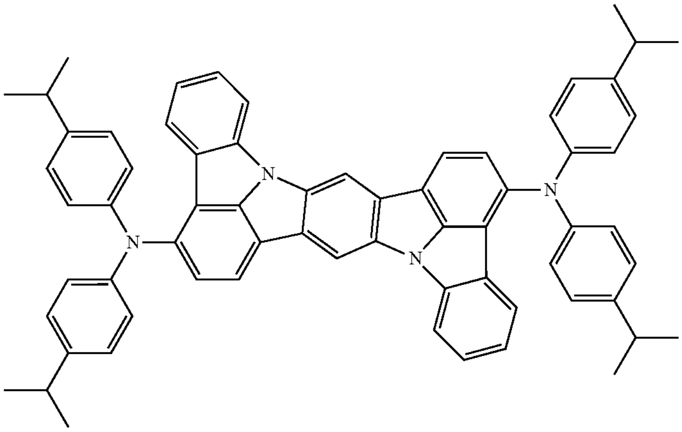
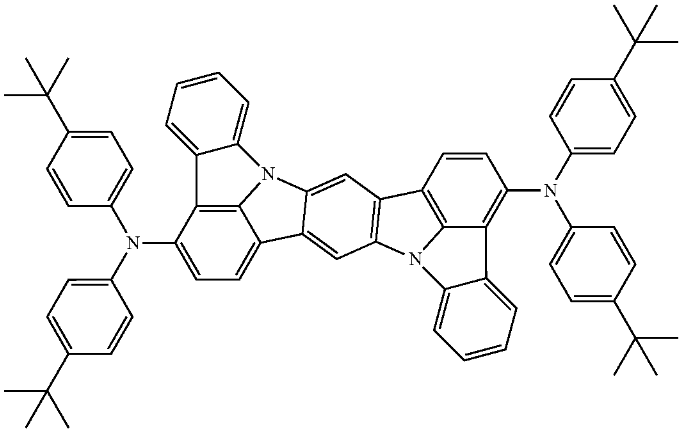

-continued
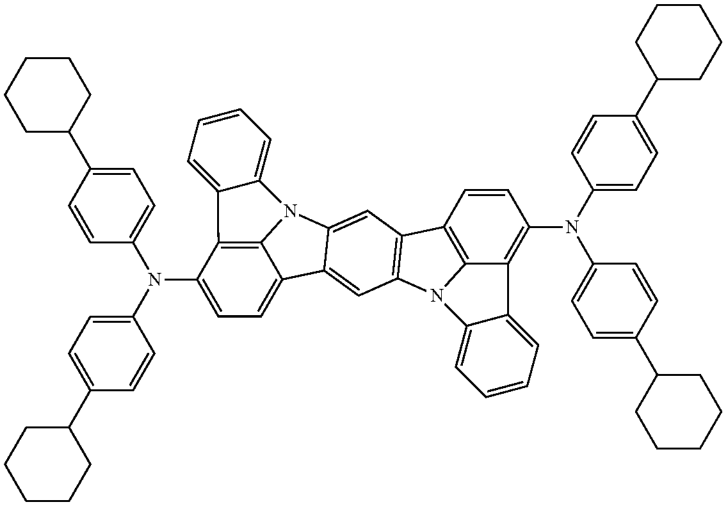
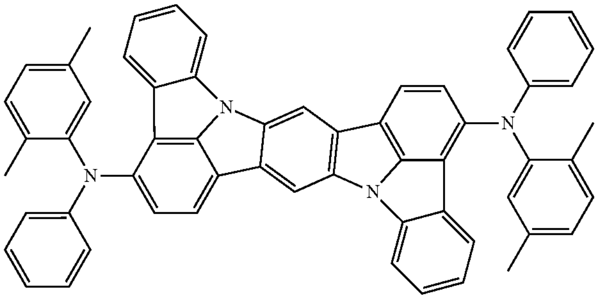
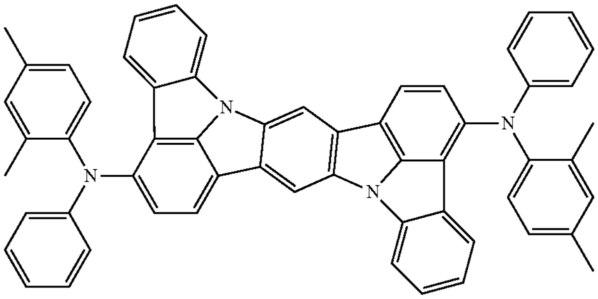
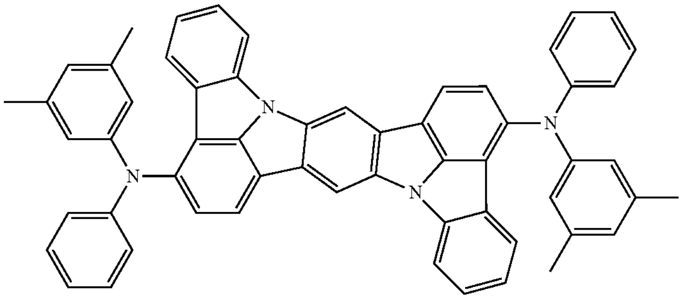
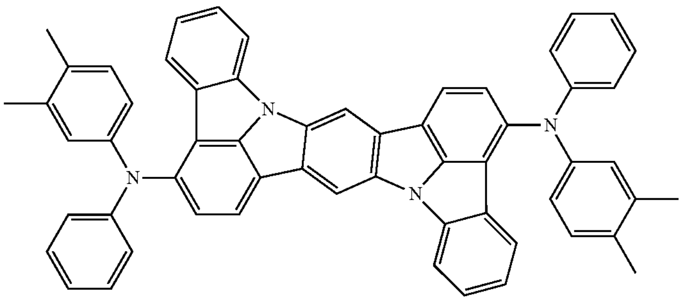

-continued
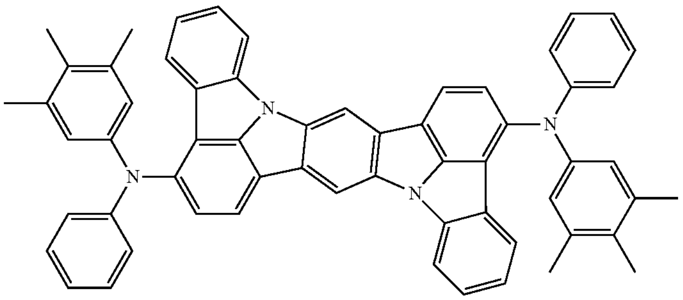
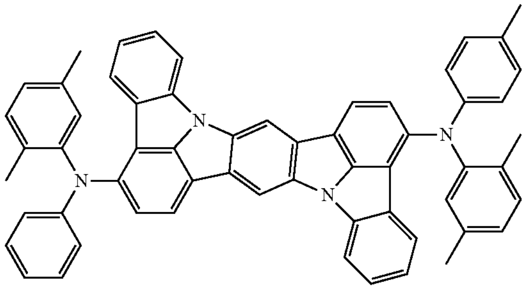
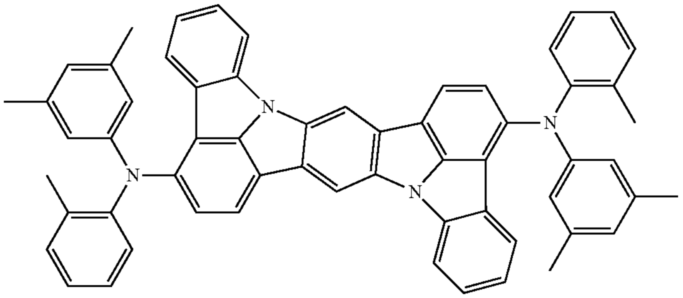
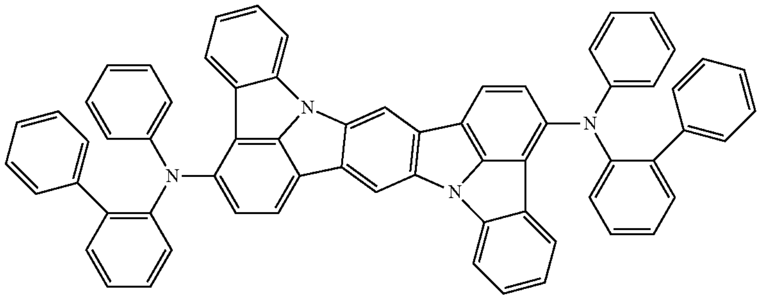
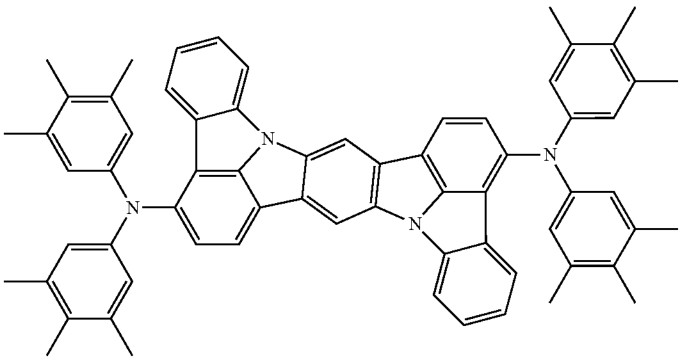

-continued
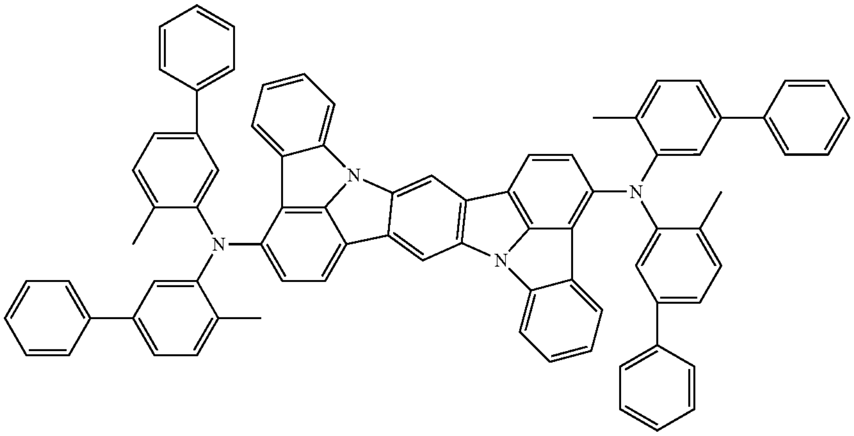
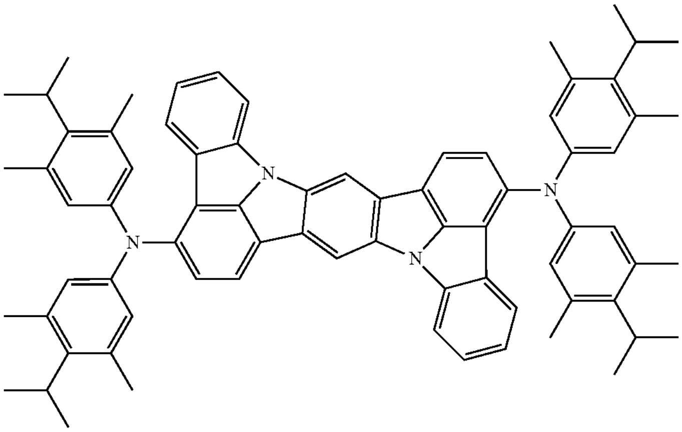
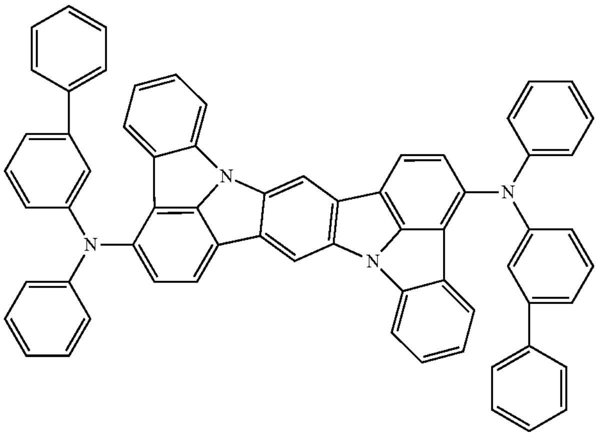
[Formula 204]
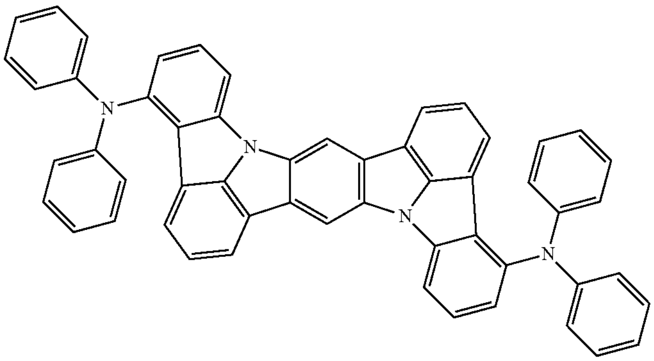

-continued
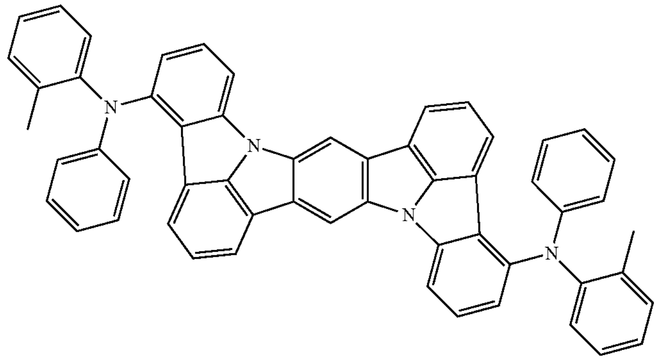
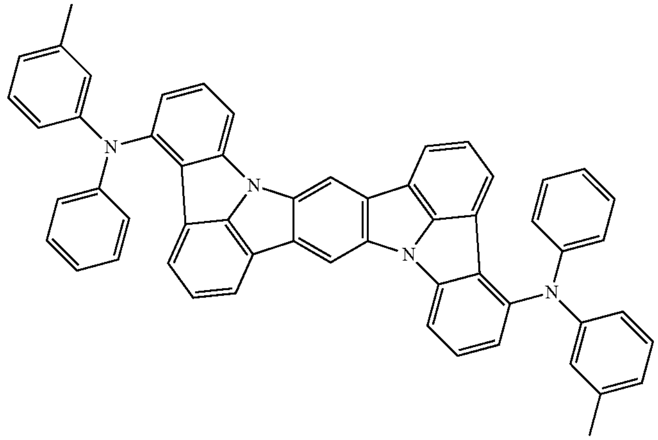
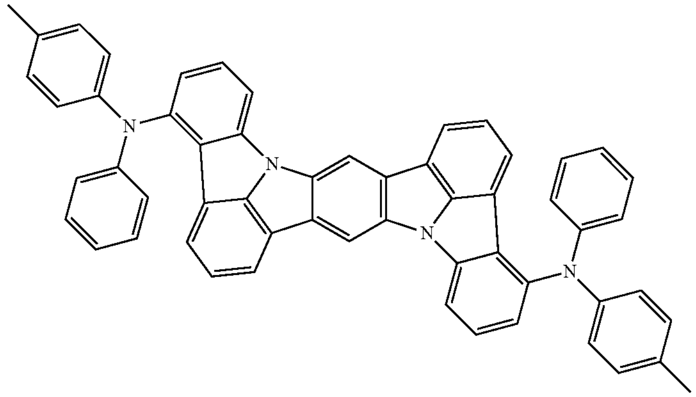
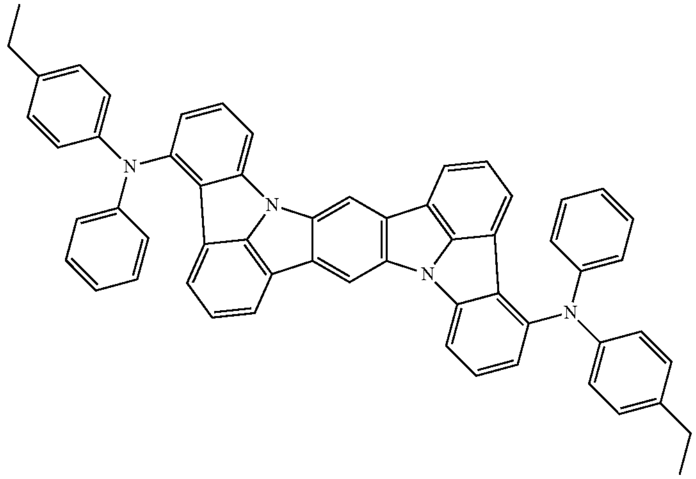

-continued
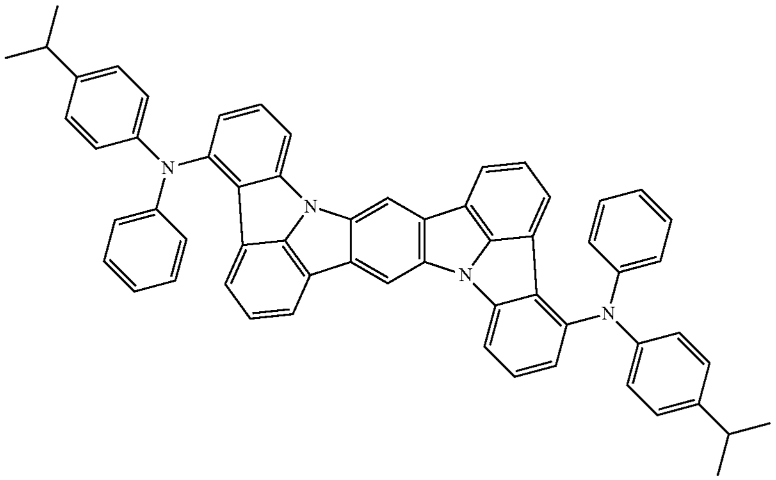
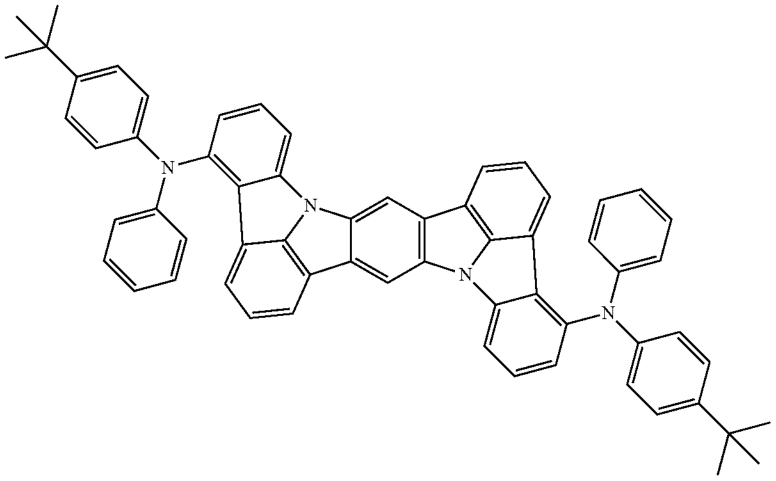
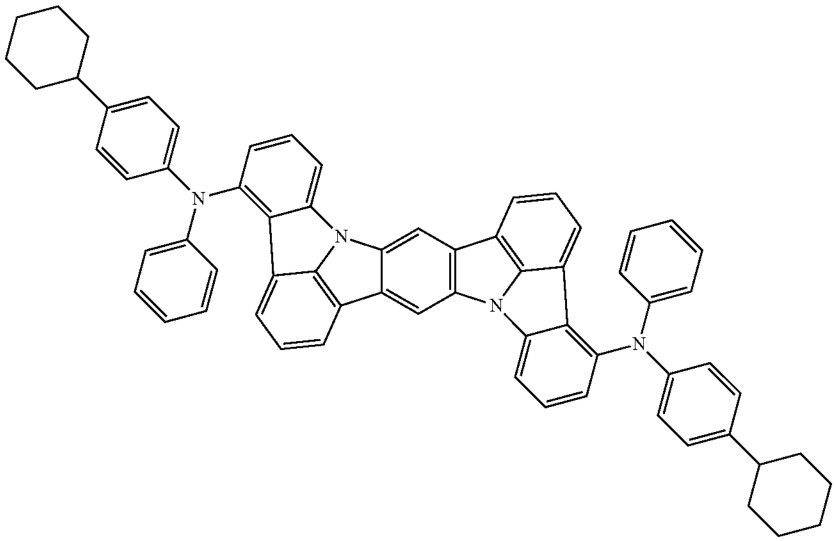

-continued
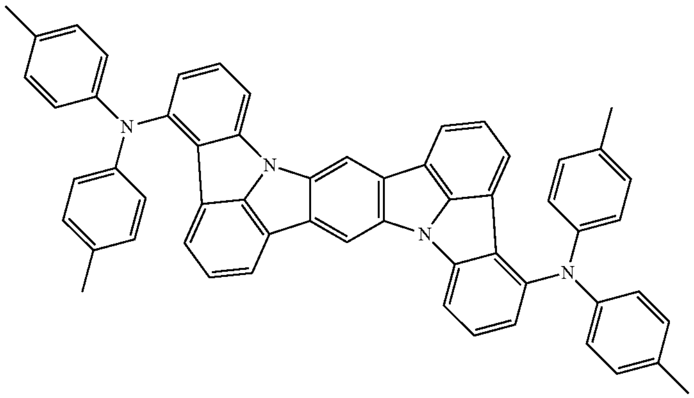
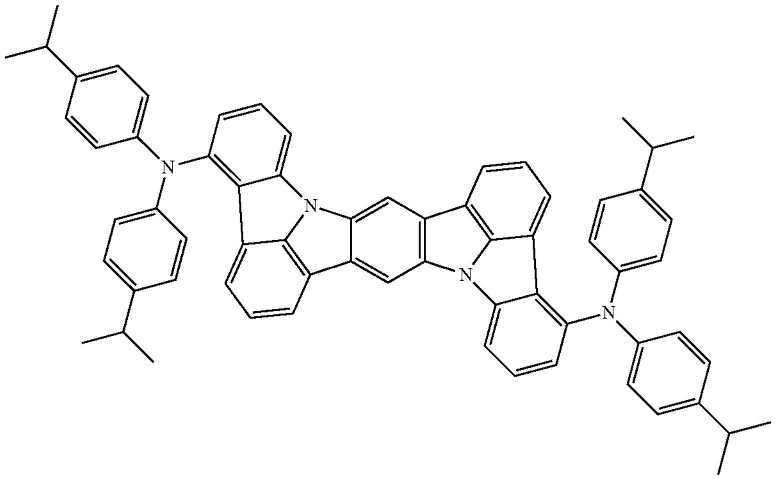
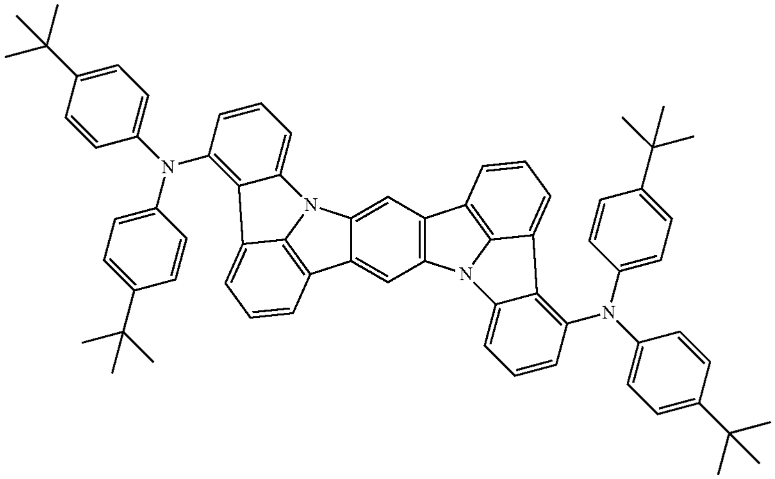

-continued
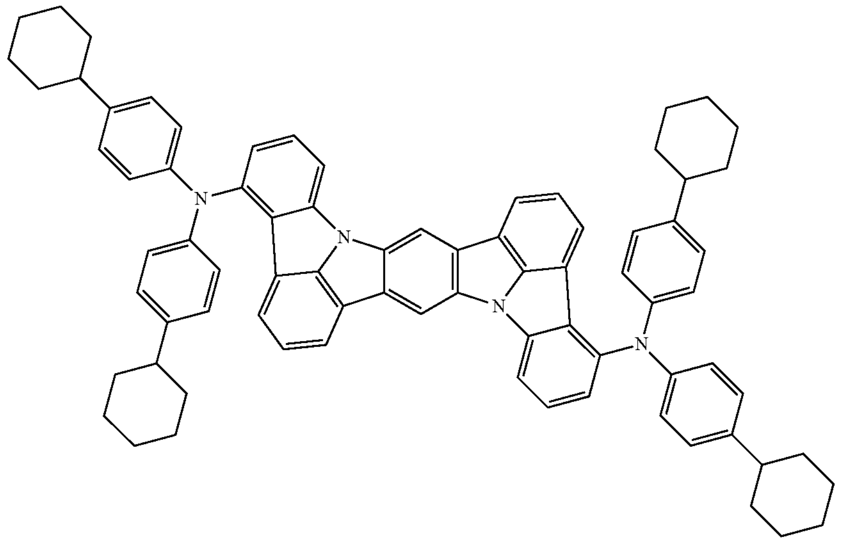
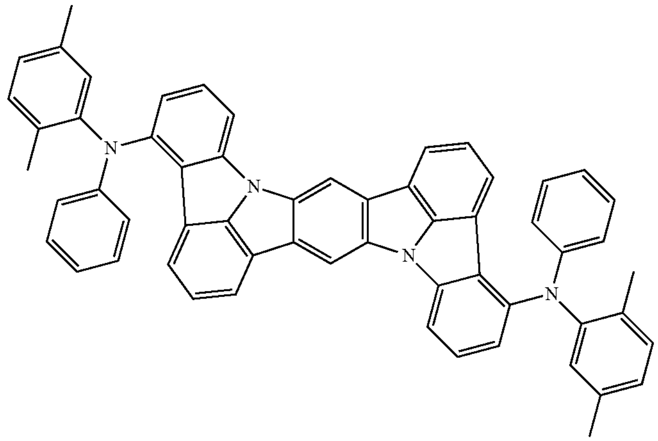
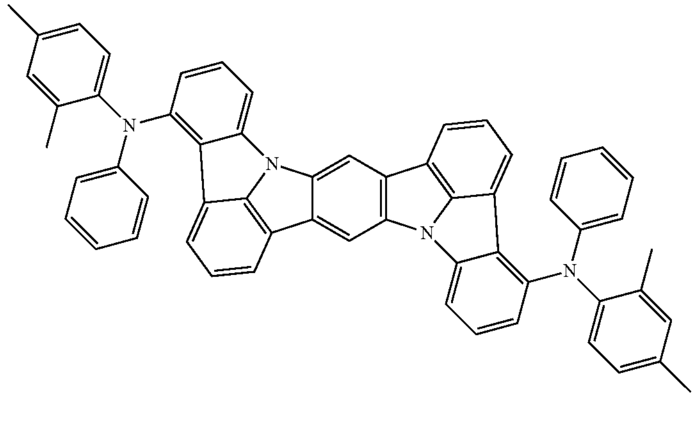

-continued
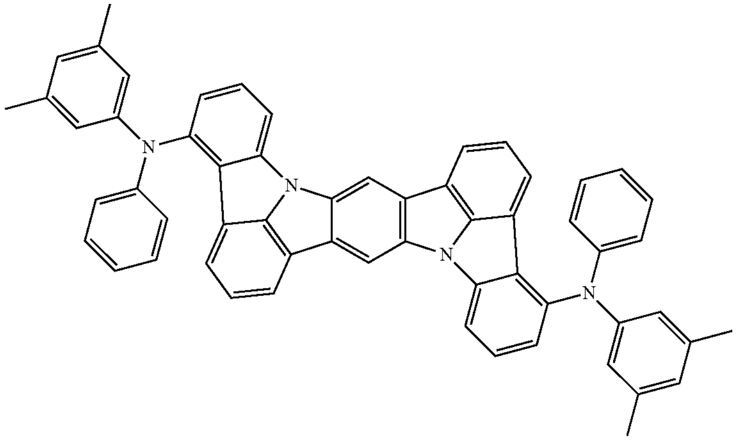
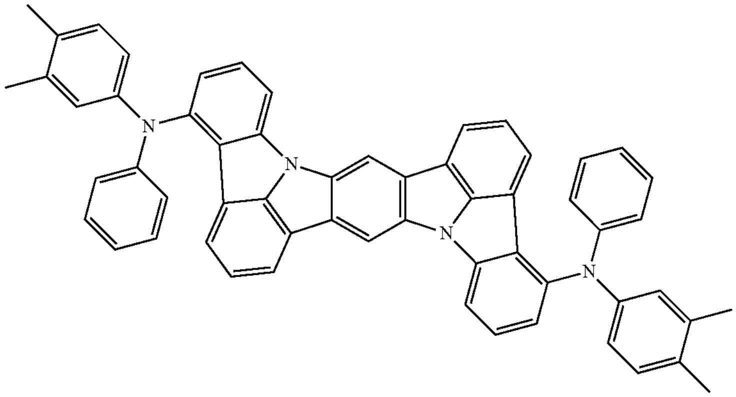
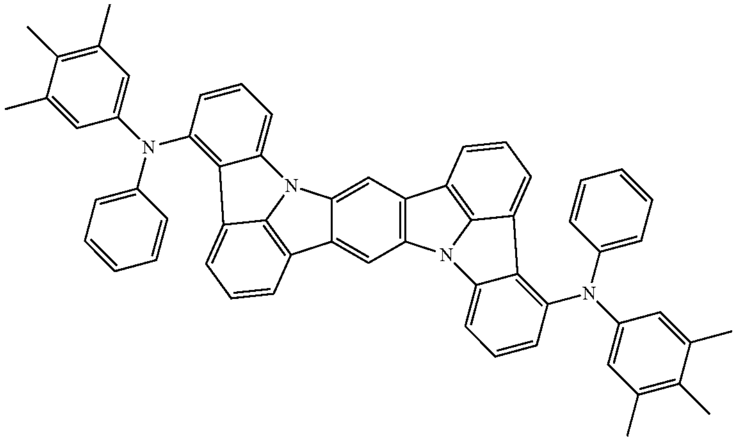
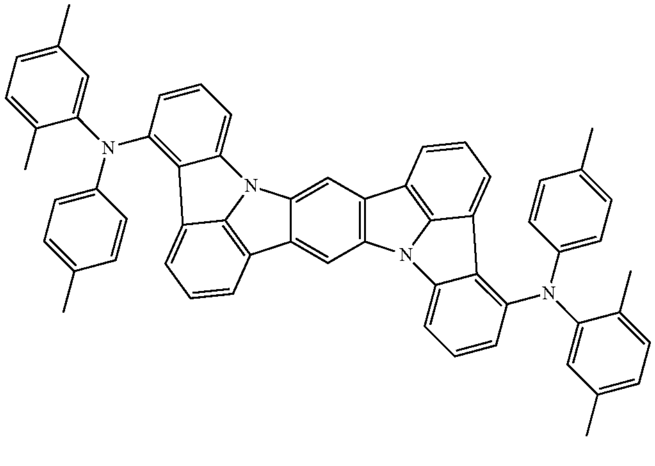

-continued
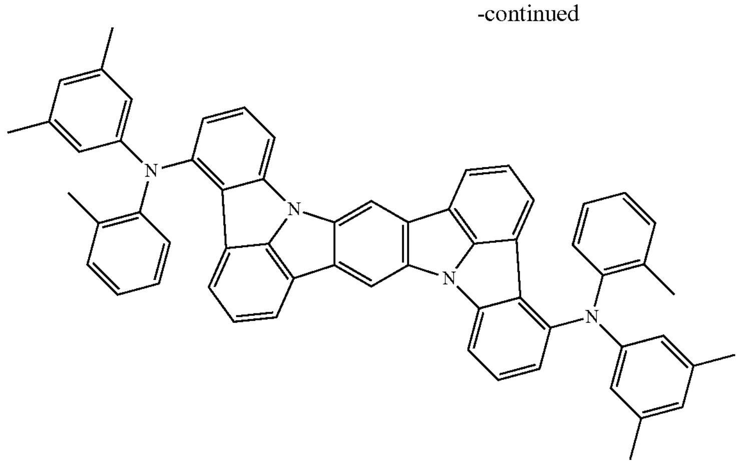
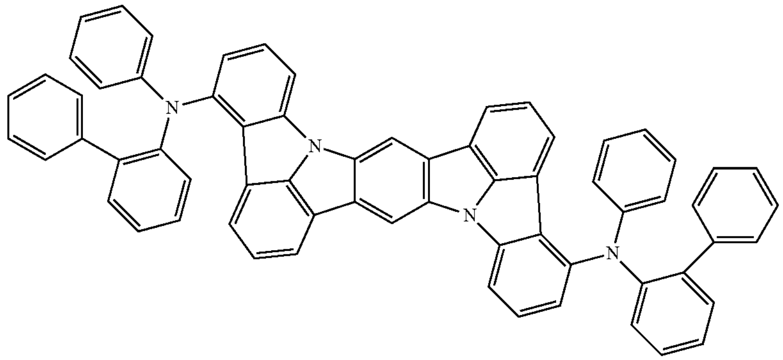
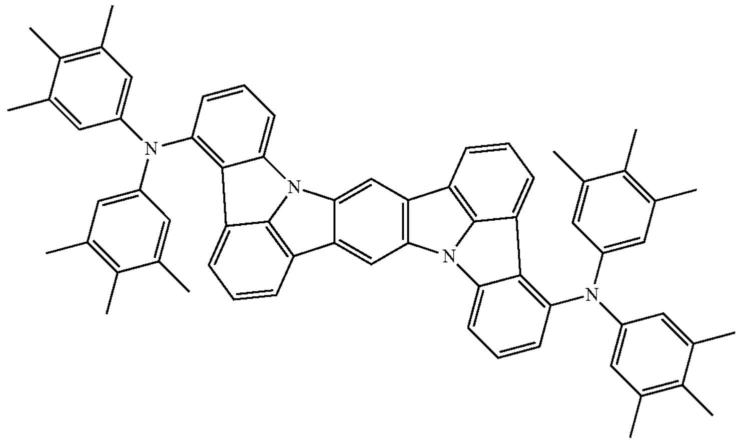

-continued
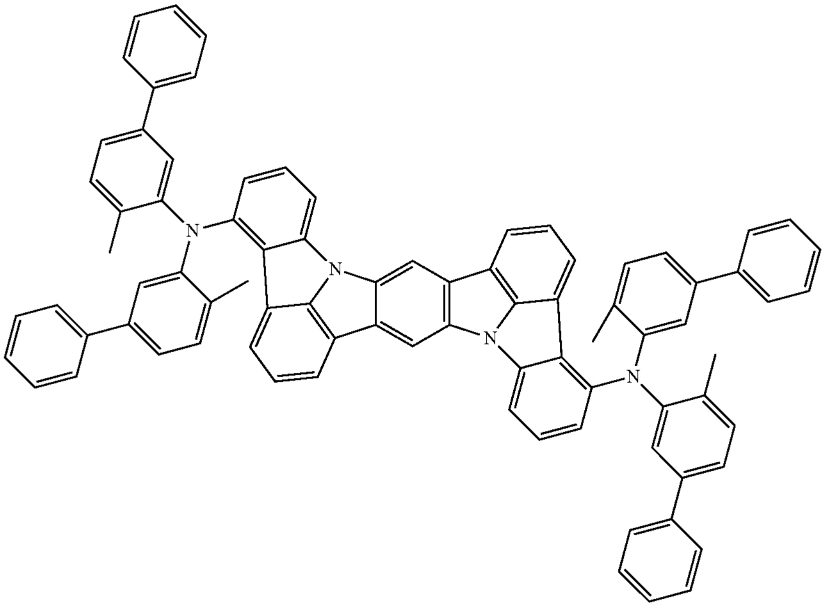
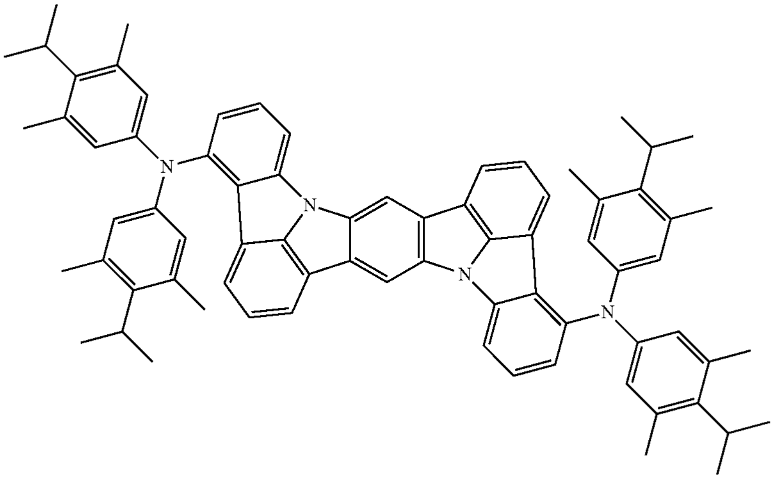
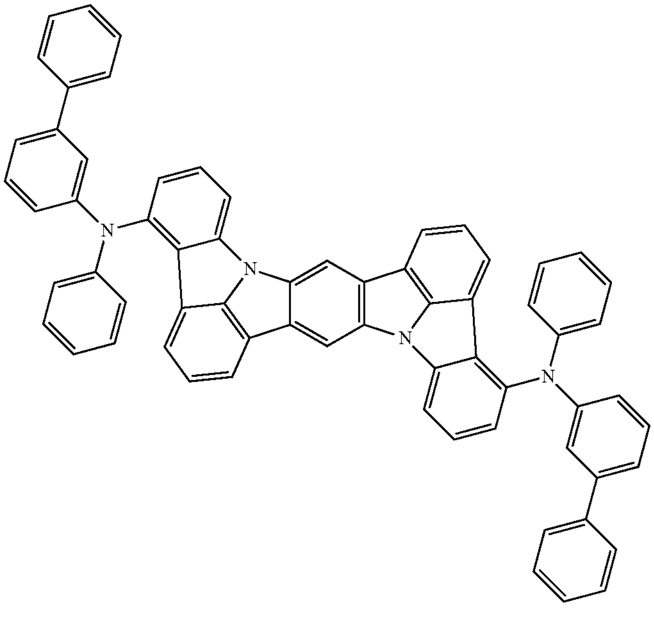

[Formula 205]
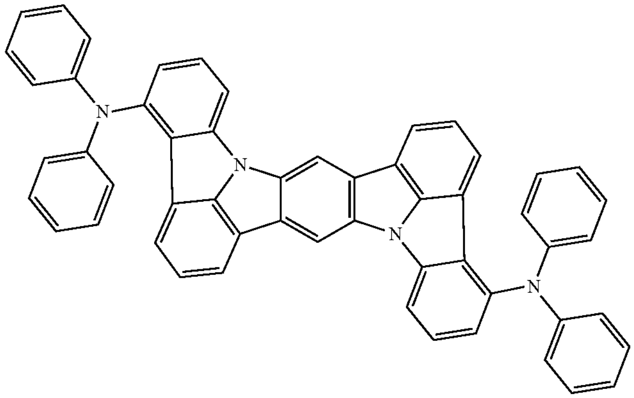
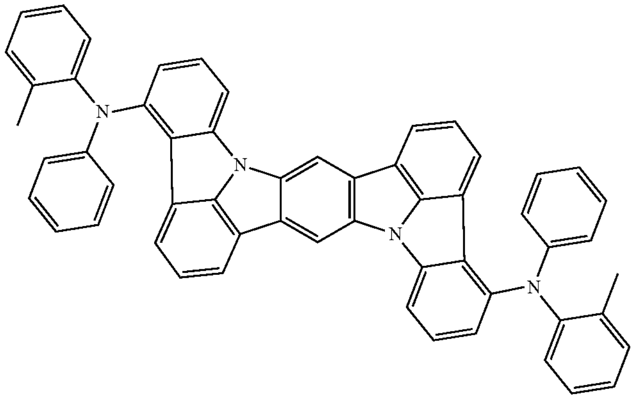
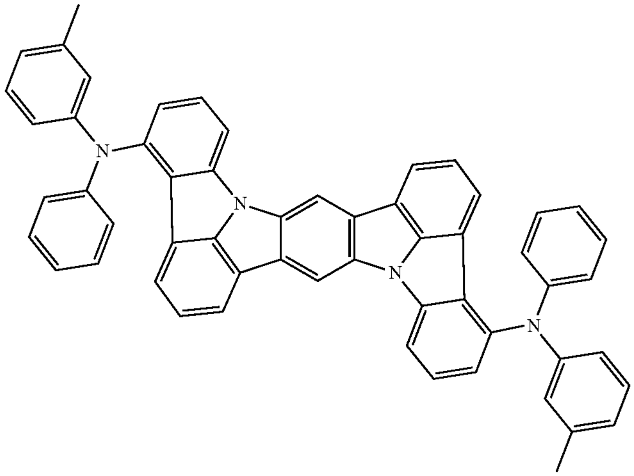

-continued
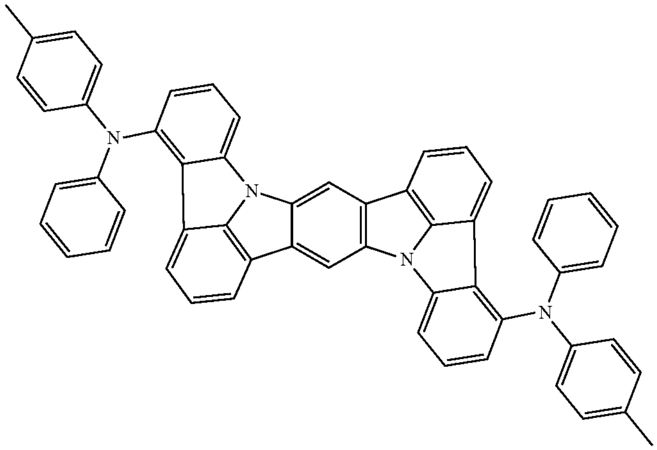
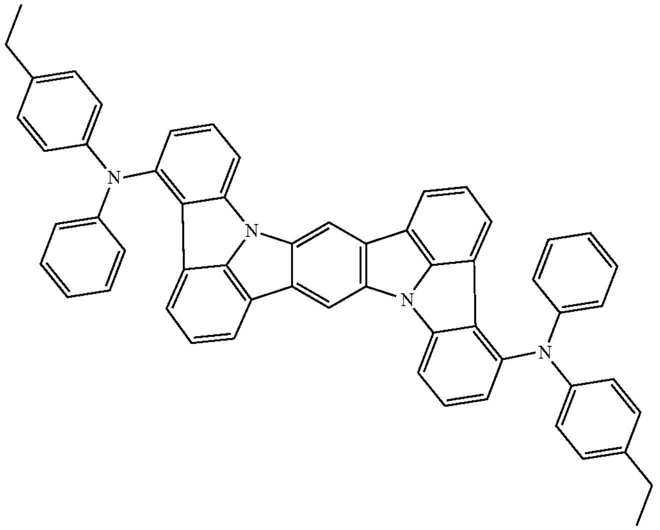
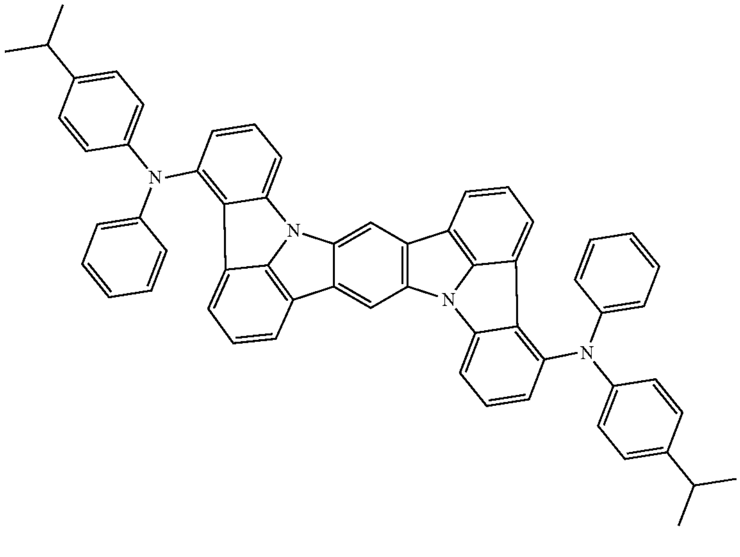

-continued
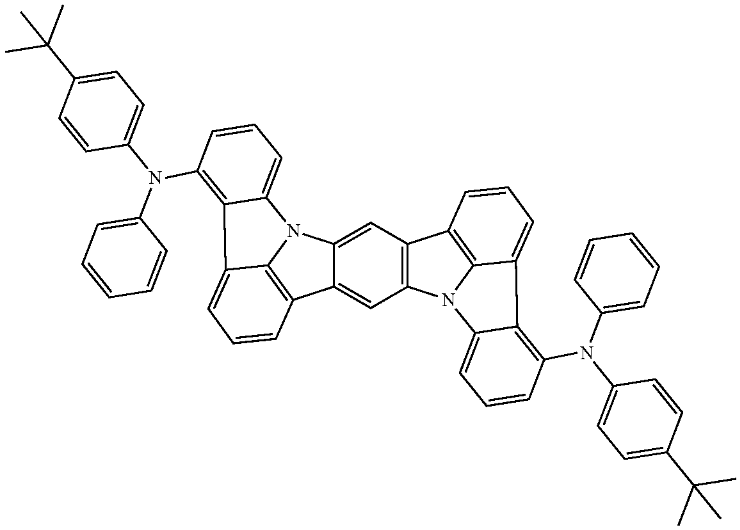
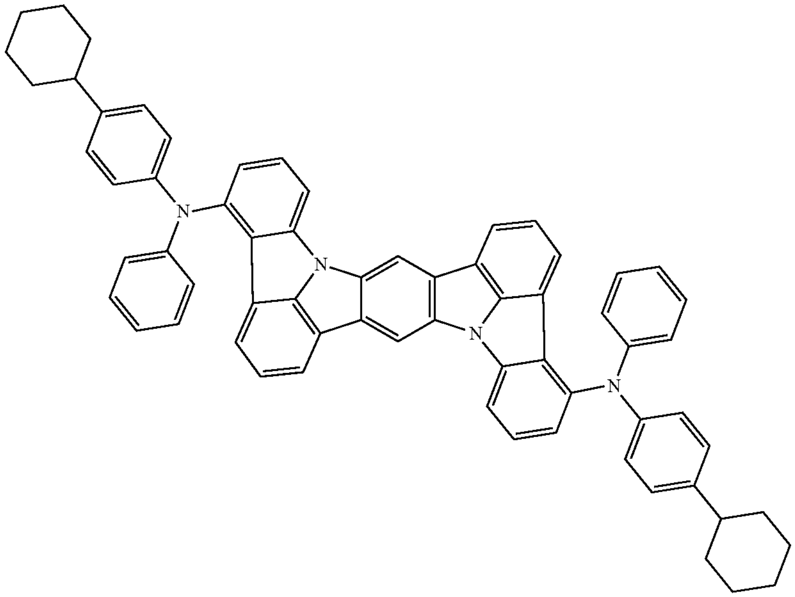
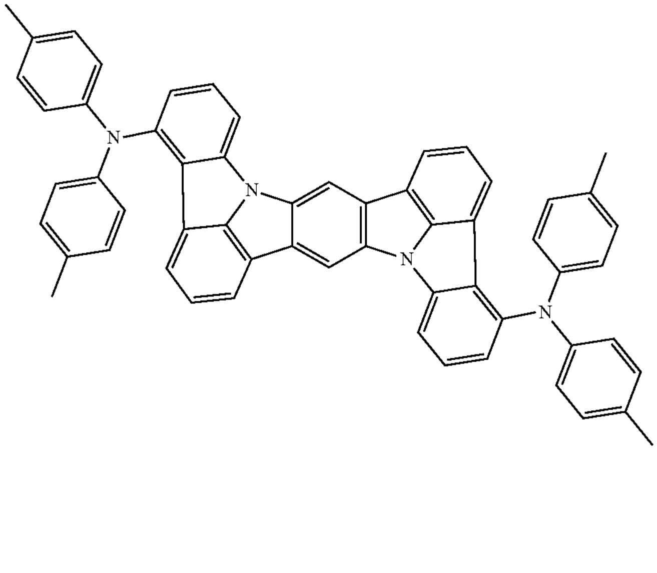

-continued
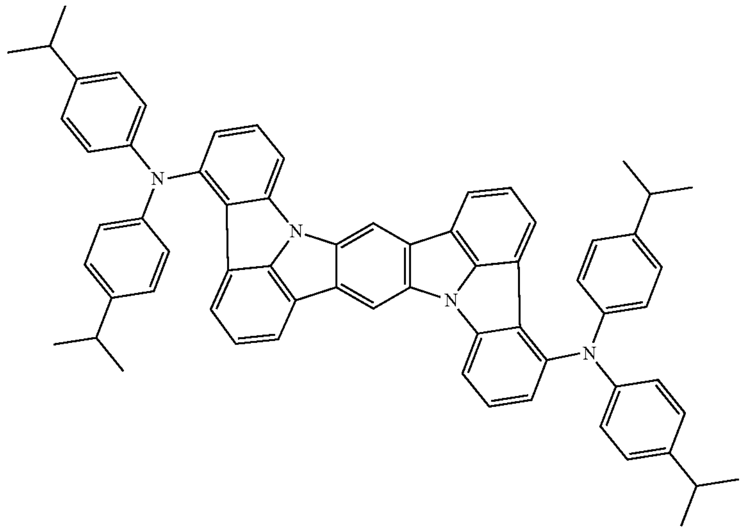
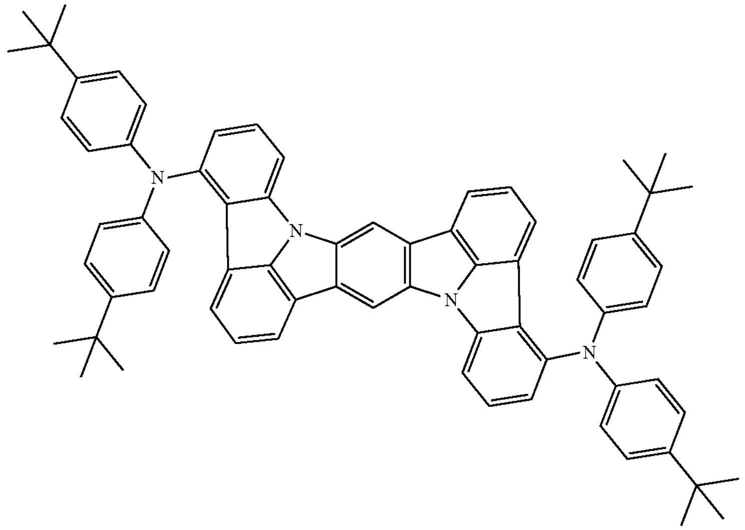
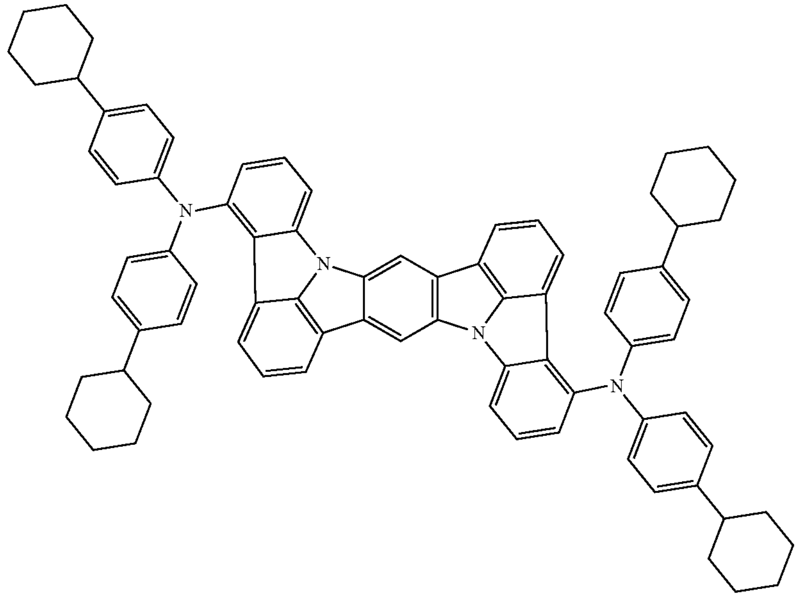

-continued
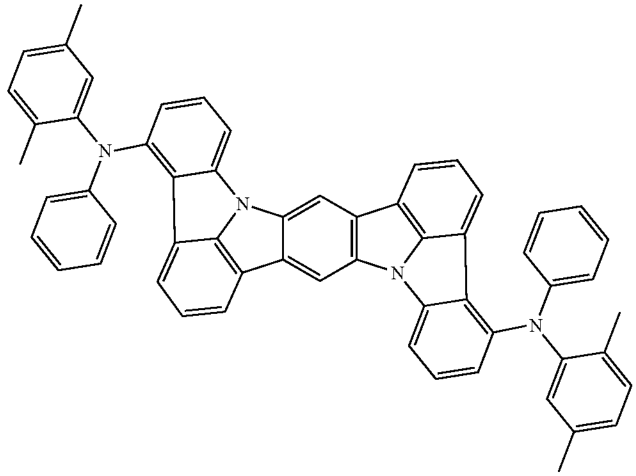
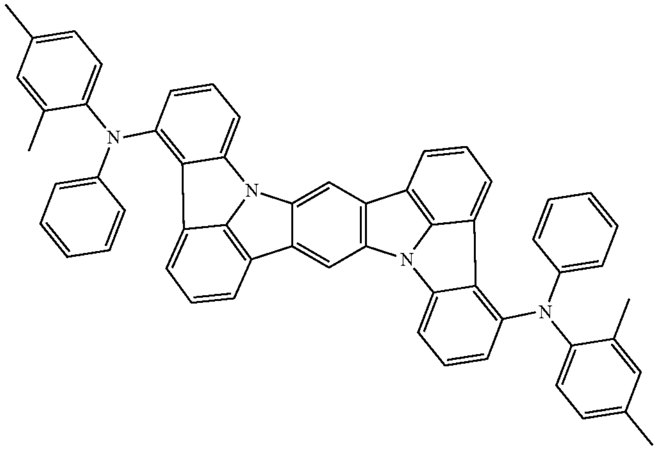
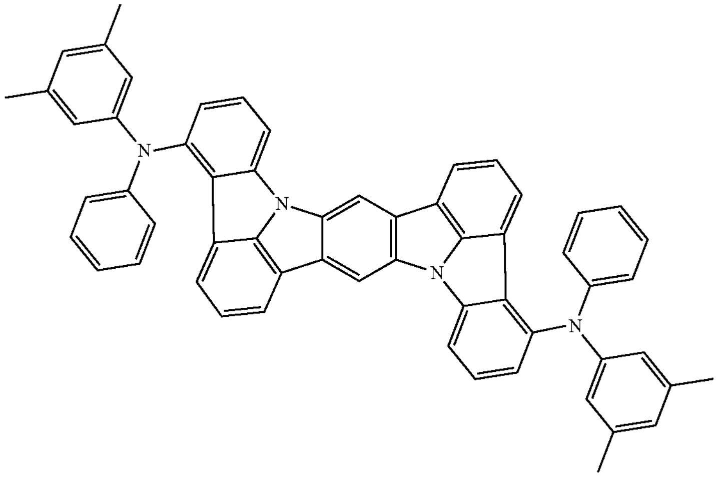

-continued
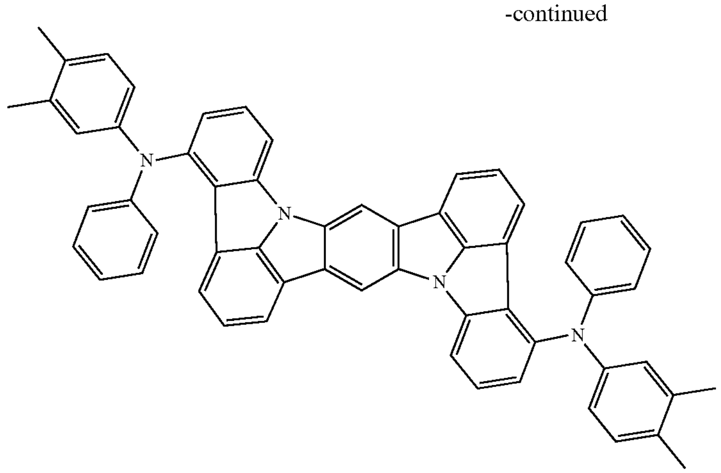
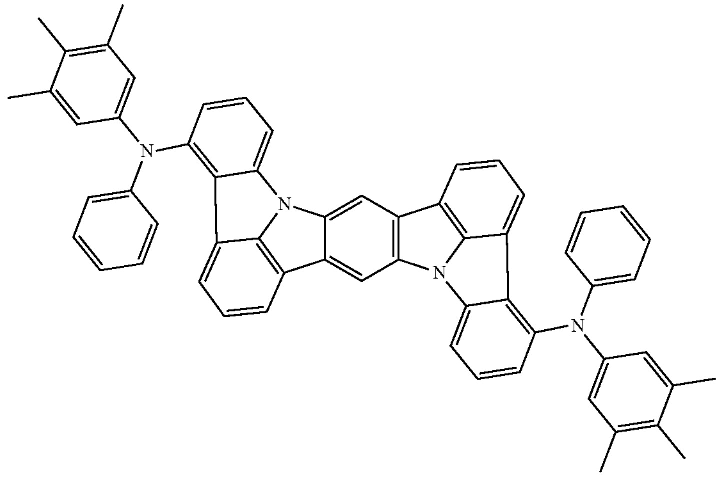
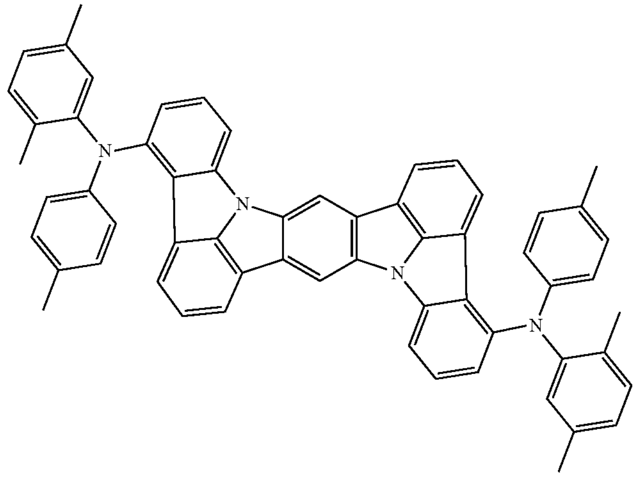

-continued
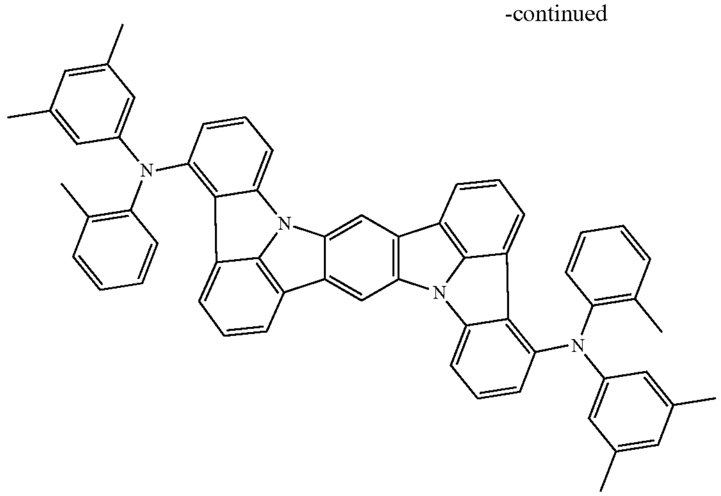
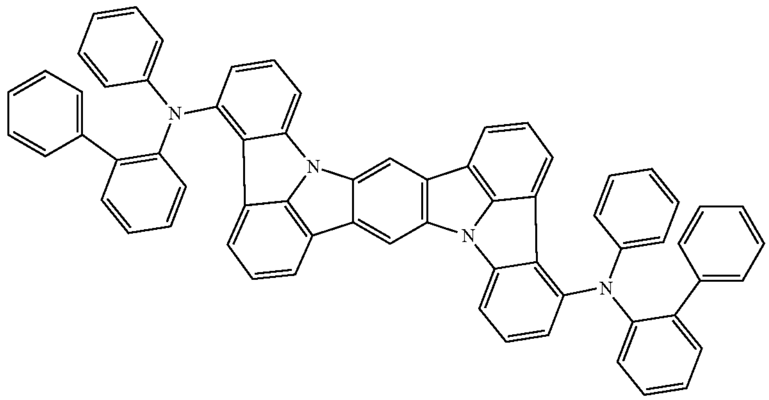
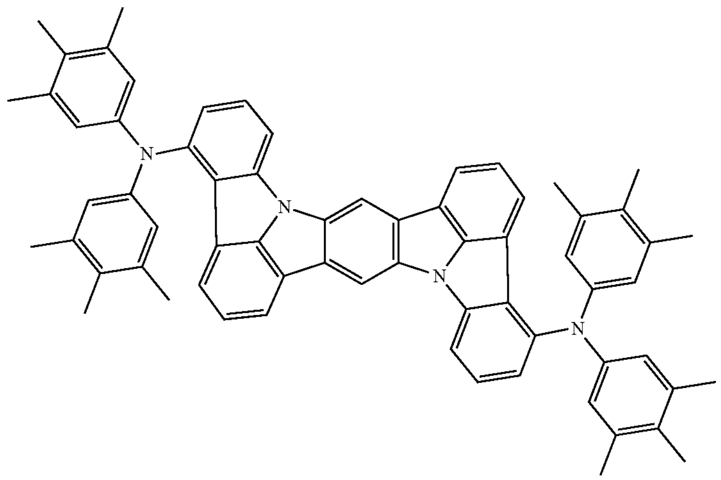

-continued
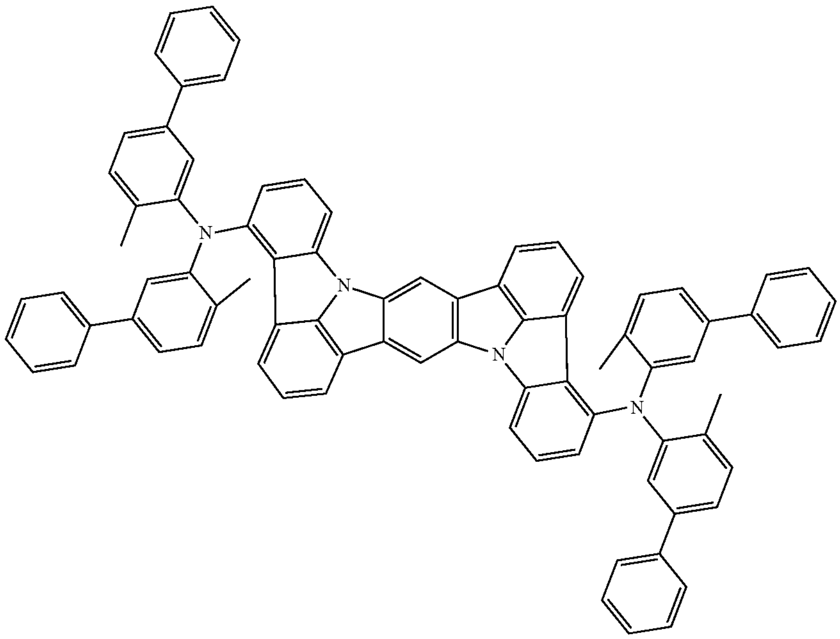
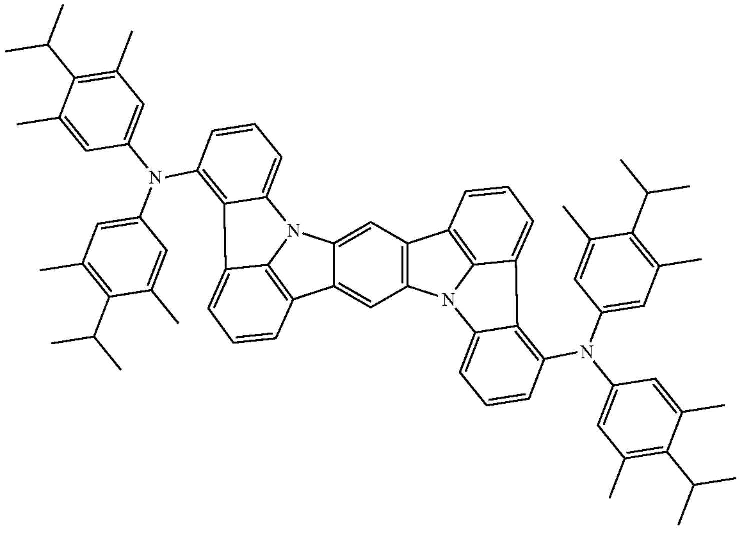

-continued
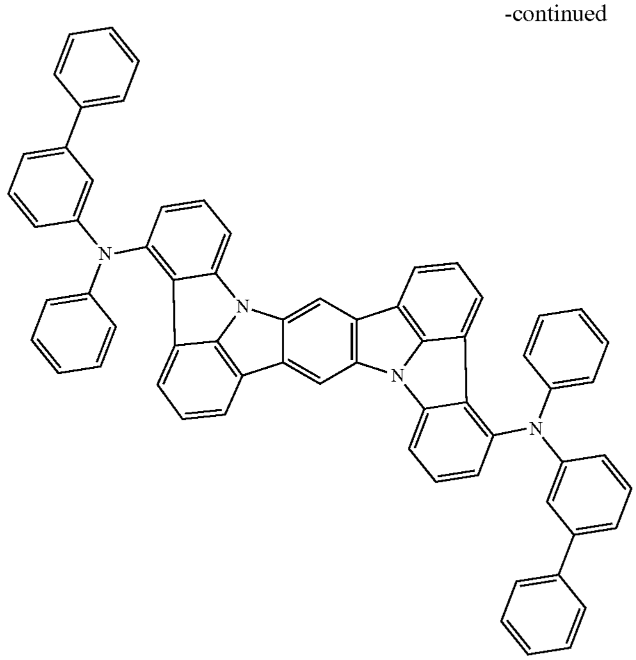
[Formula 206]
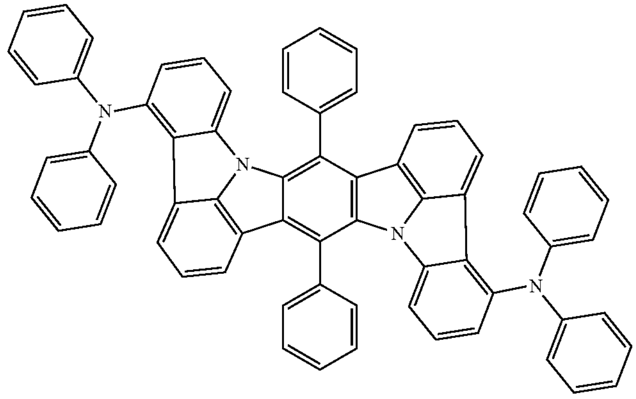
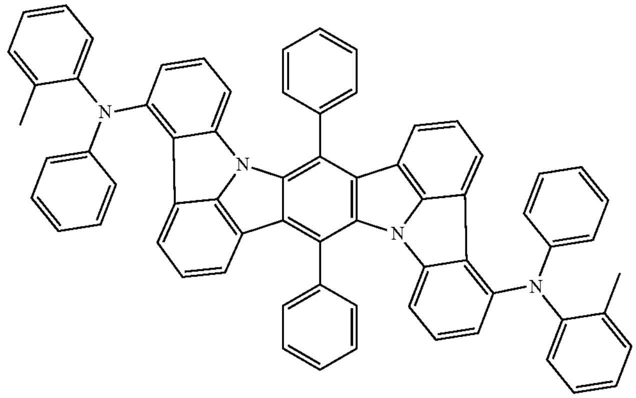

-continued
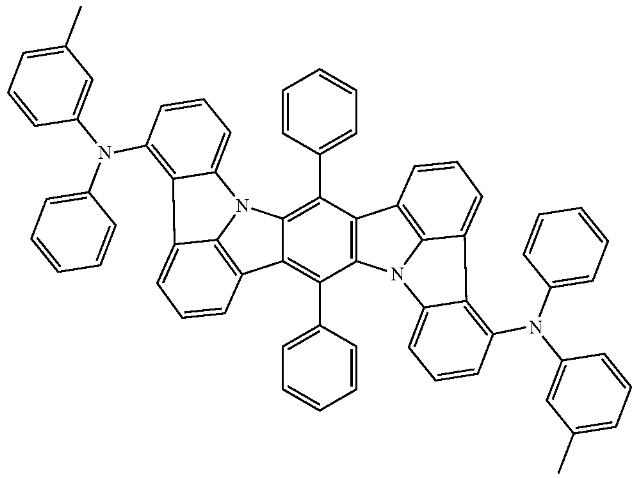
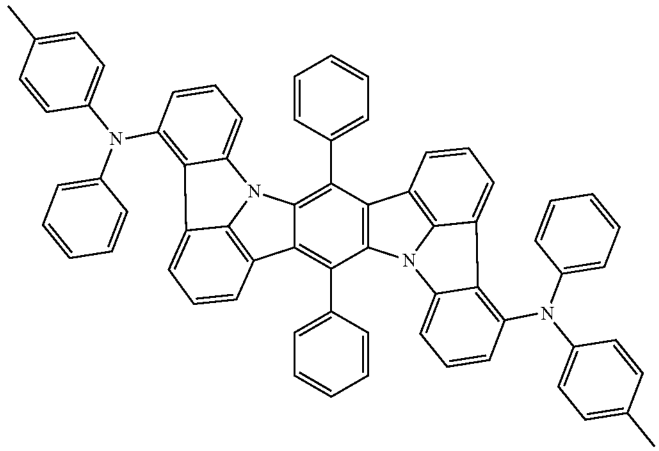
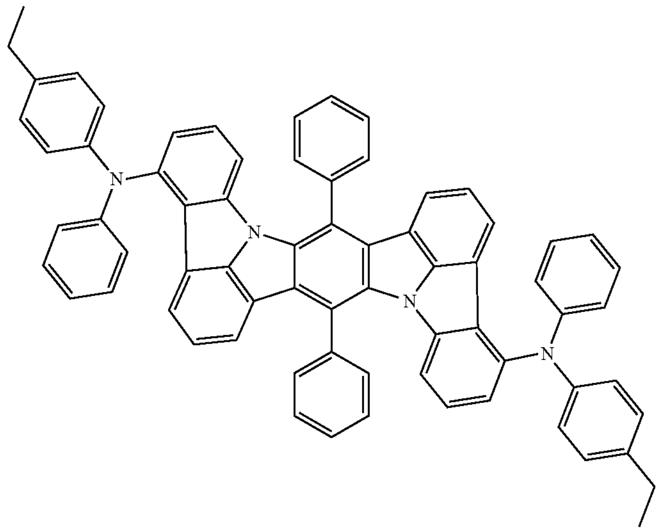

-continued
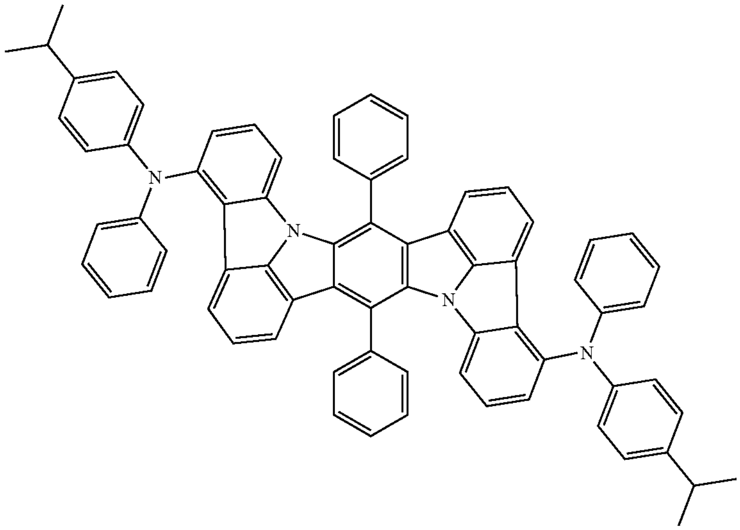
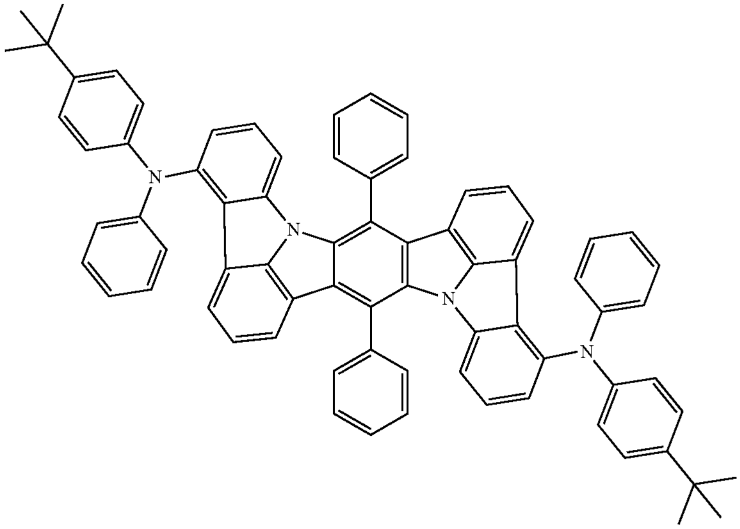
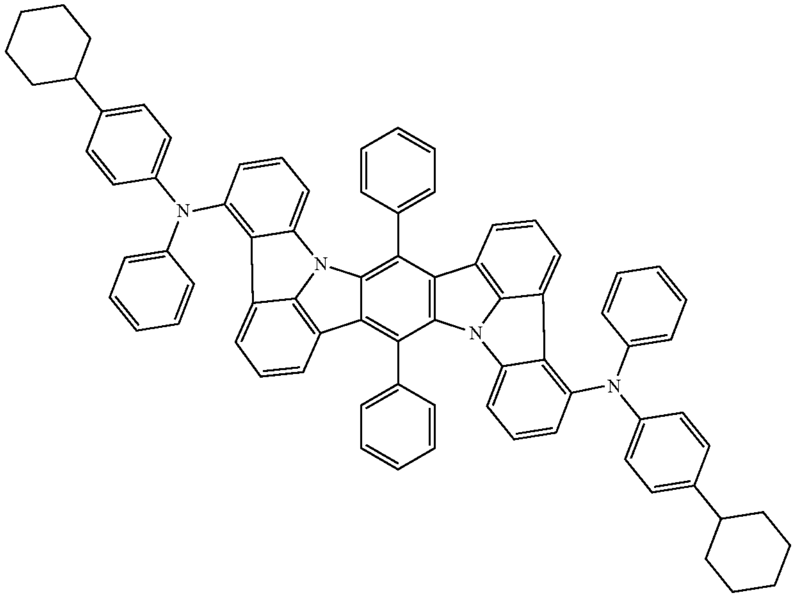

-continued
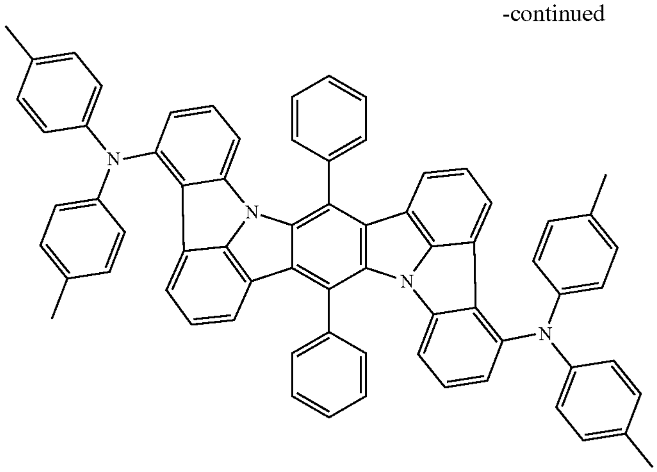
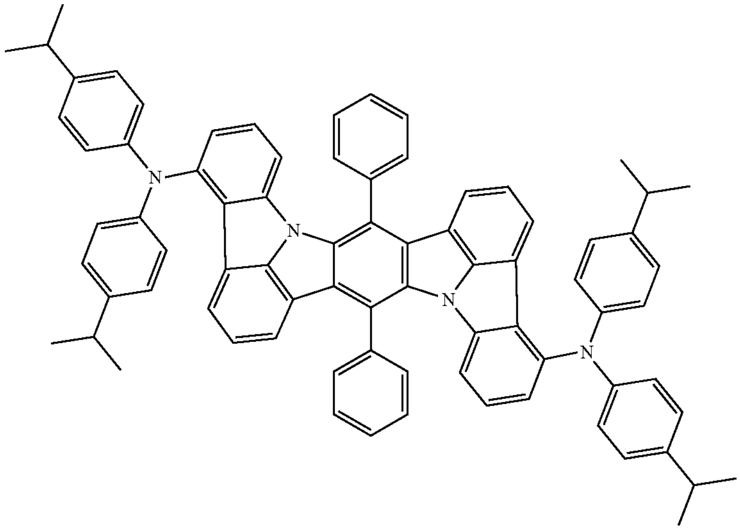
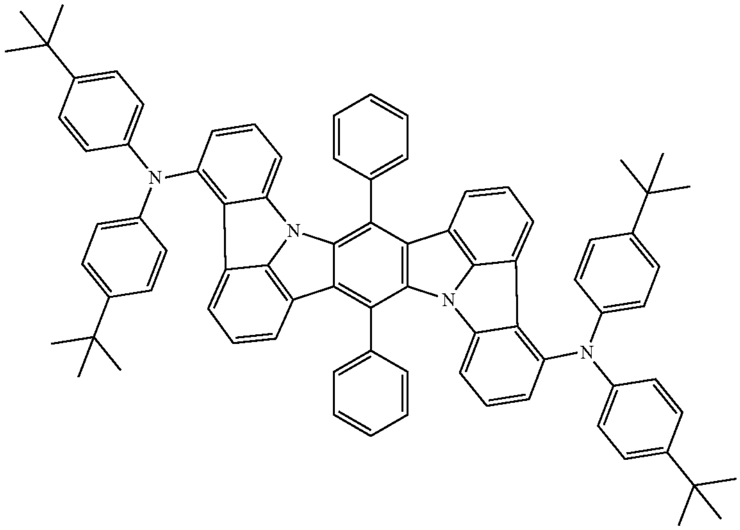

-continued
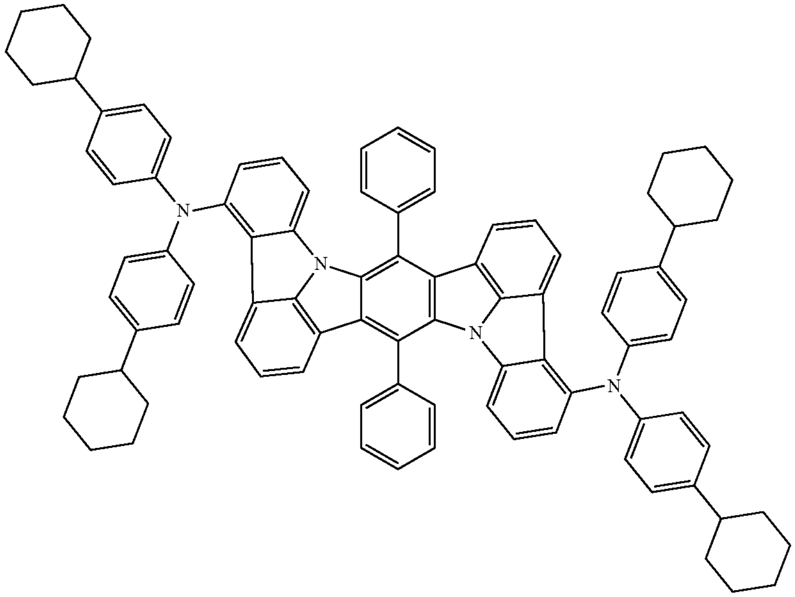
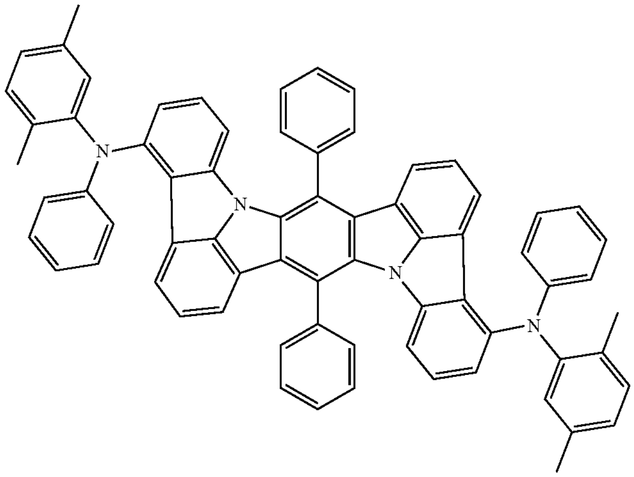
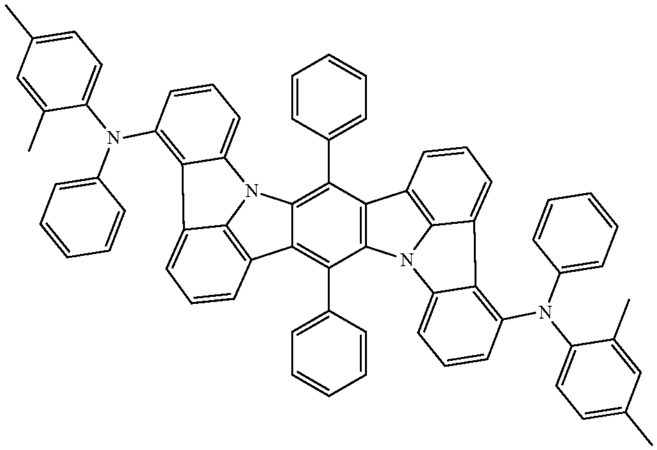

-continued
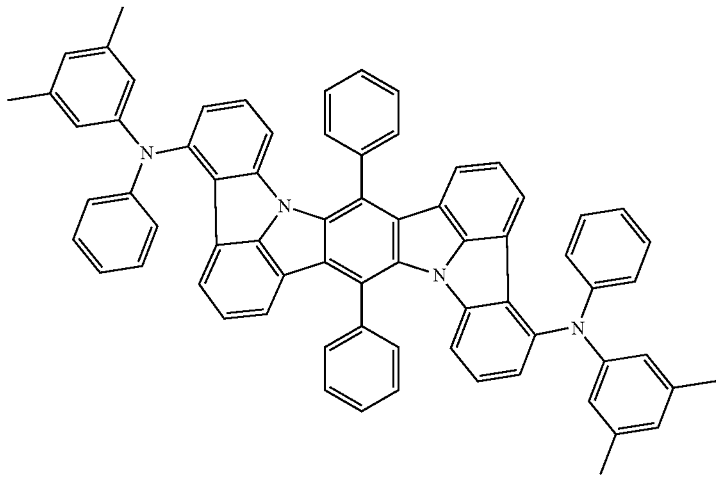
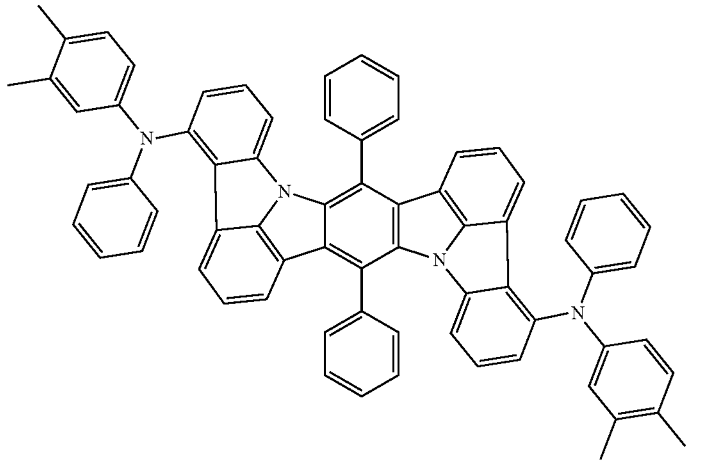
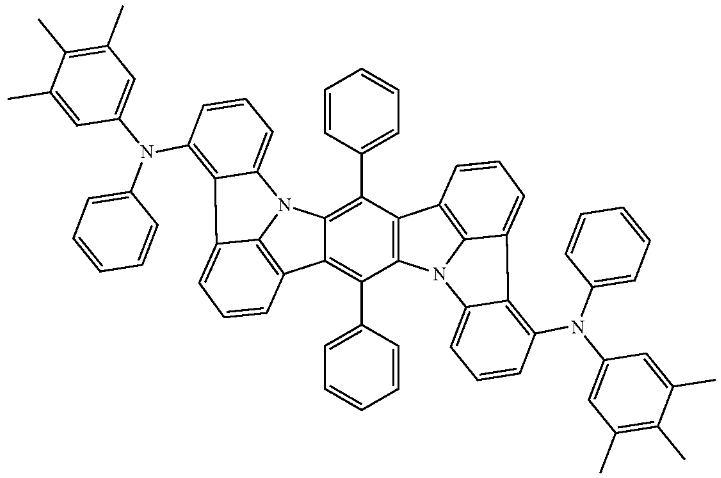

-continued
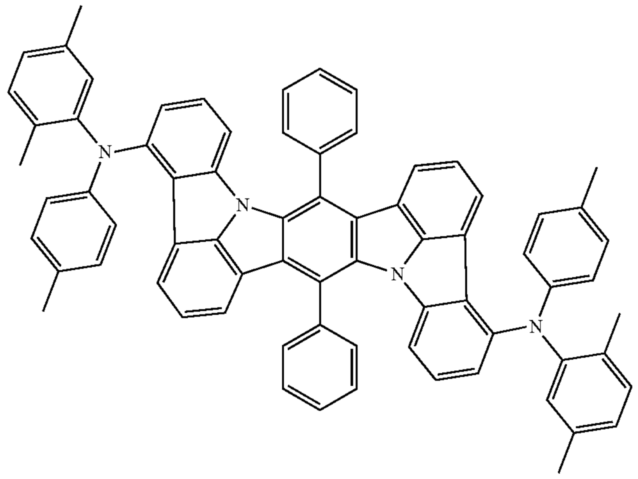
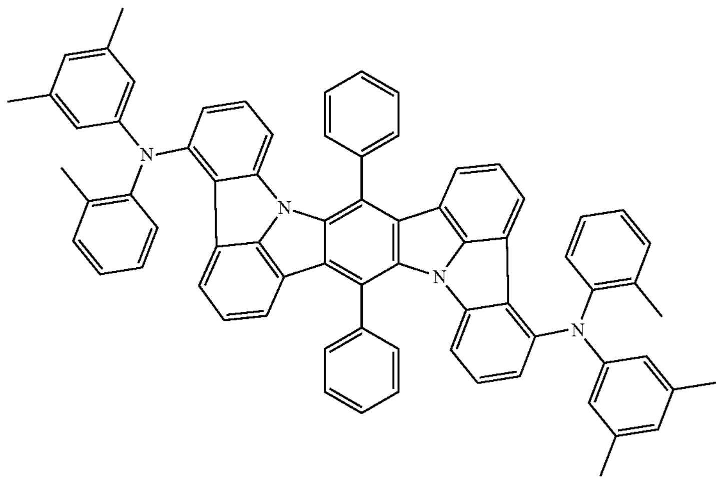
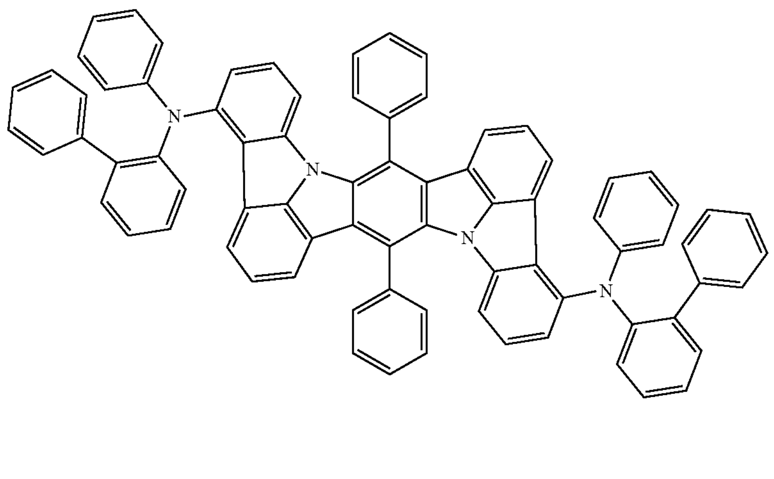

-continued
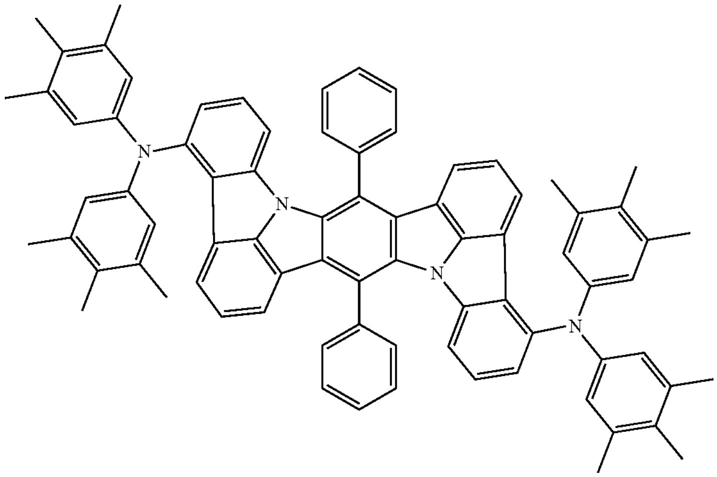
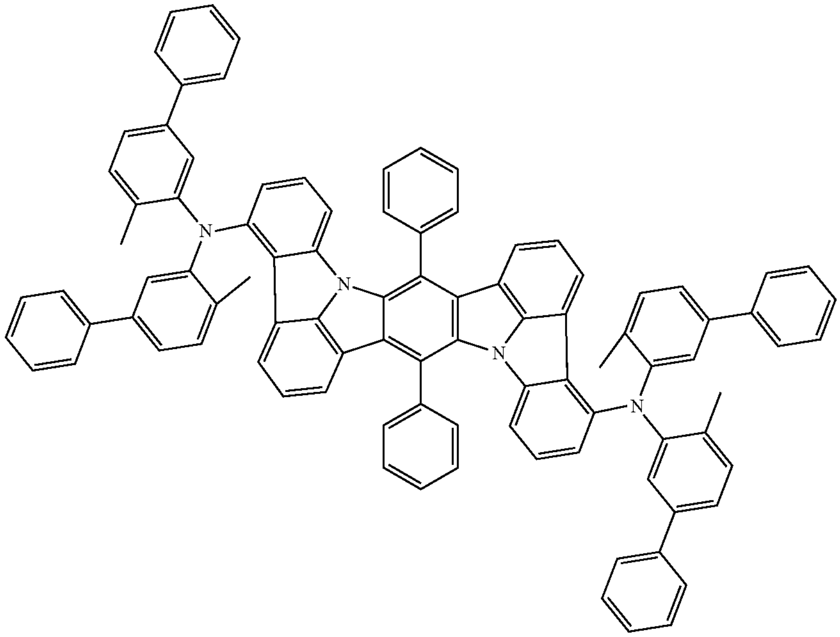
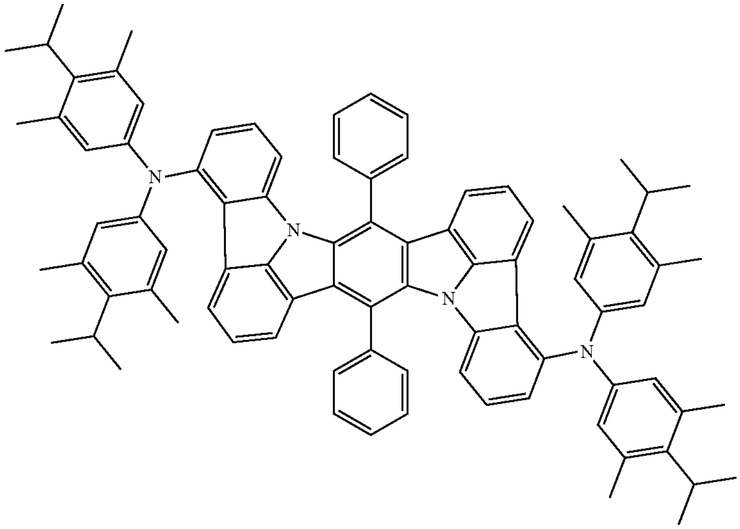

-continued
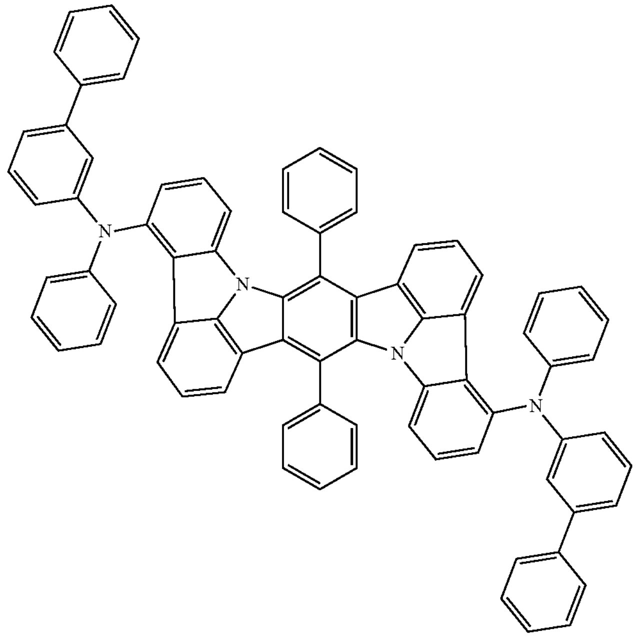 [SMILES: c1ccc(-c2cccc(N(c3ccccc3)c3cccc4c3c3cccc5c6c(-c7ccccc7)c7c(c(-c8ccccc8)c6n4c35)c3cccc4c5c(N(c6ccccc6)c6cccc(-c8ccccc8)c6)cccc5n7c43)c2)cc1]
[Formula 207]
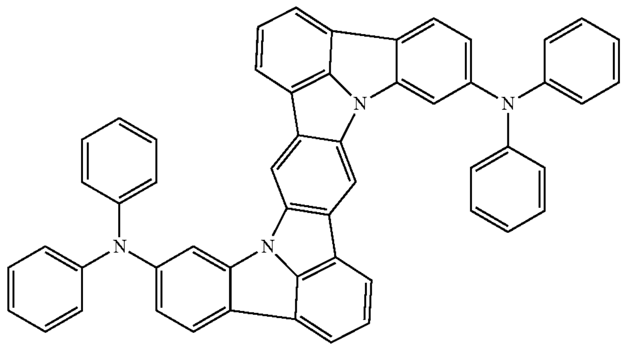
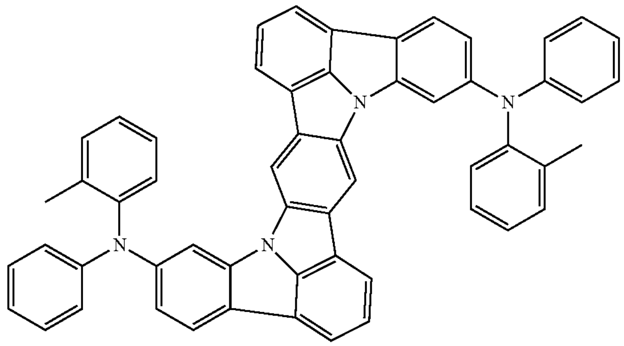
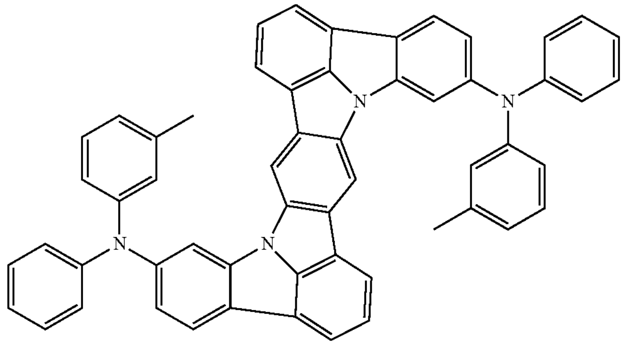

-continued
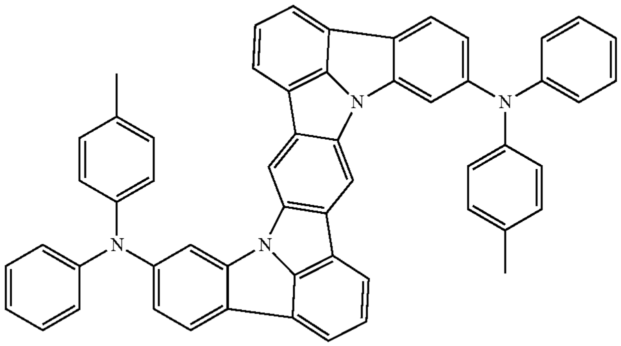
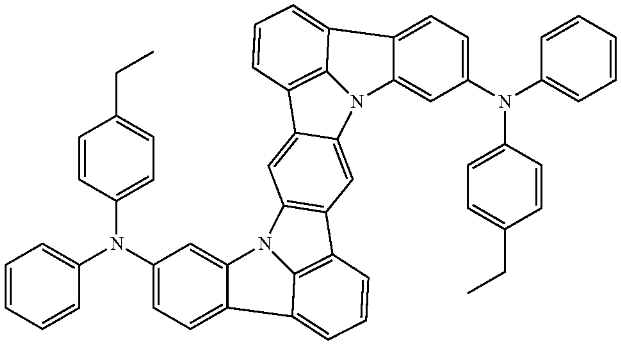
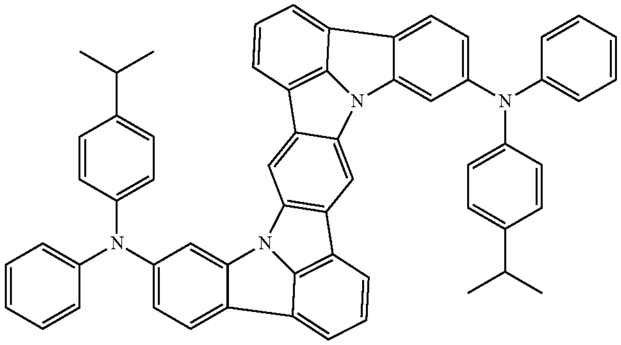
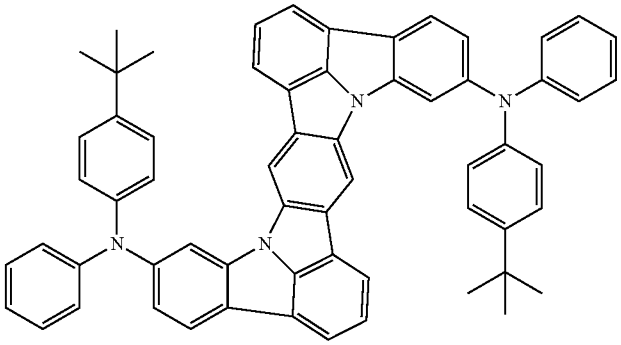

-continued
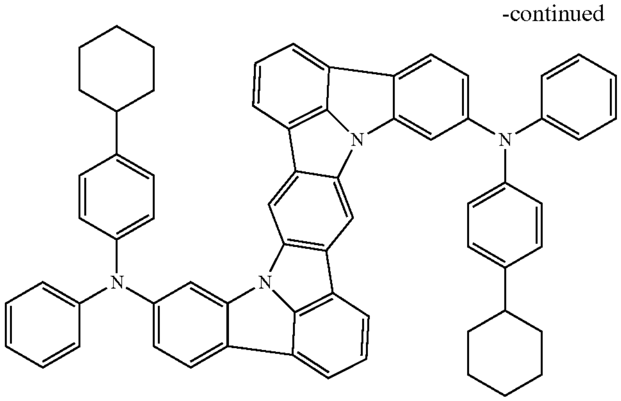
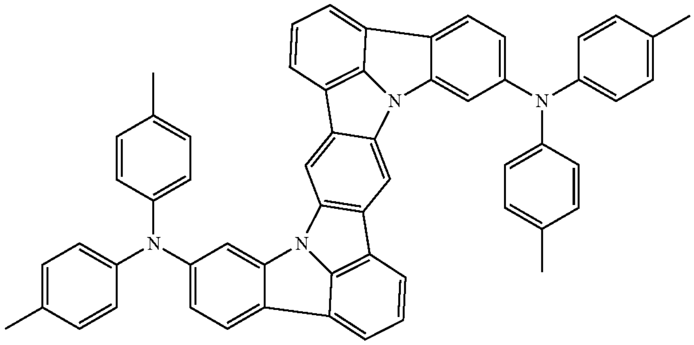
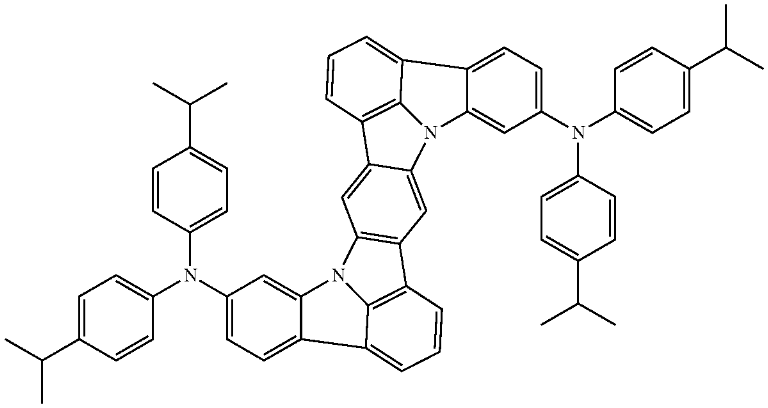
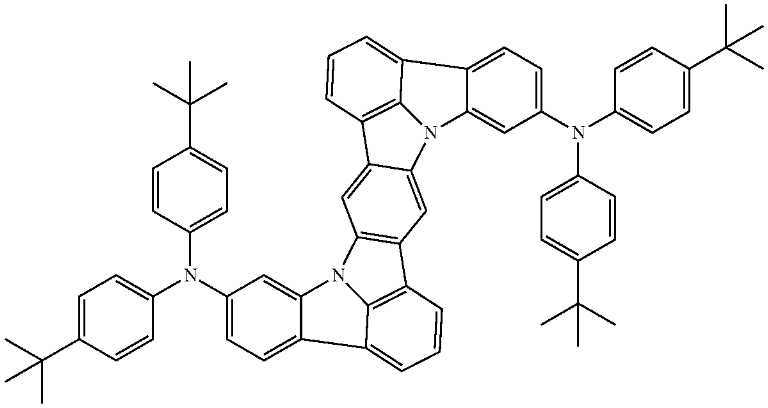 [SMILES: CC(C)(C)c1ccc(N(c2ccc(C(C)(C)C)cc2)c2ccc3c4cccc5c6cc7c(cc6n(c3c2)c45)c2cccc3c4ccc(N(c5ccc(C(C)(C)C)cc5)c5ccc(C(C)(C)C)cc5)cc4n7c32)cc1]

-continued
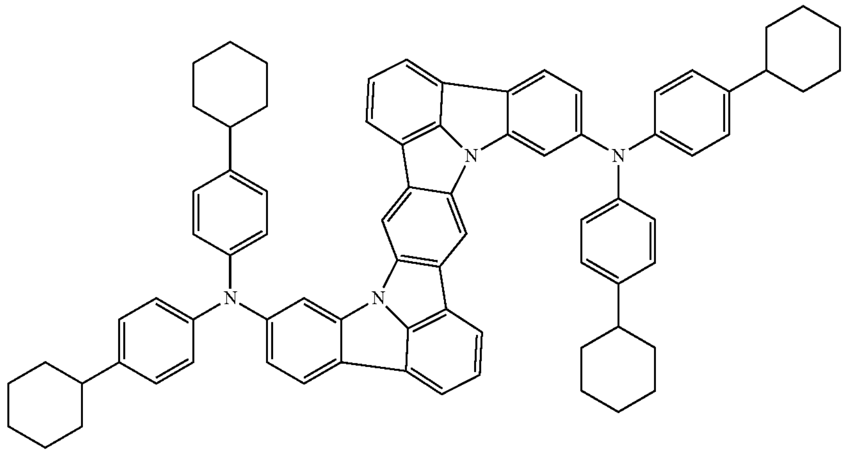
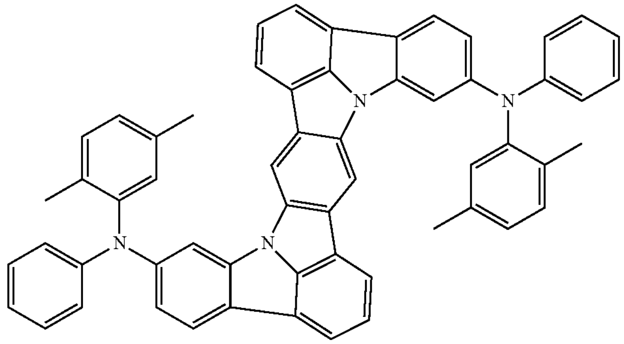
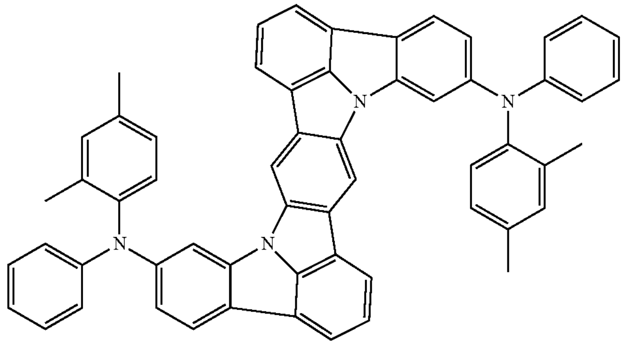
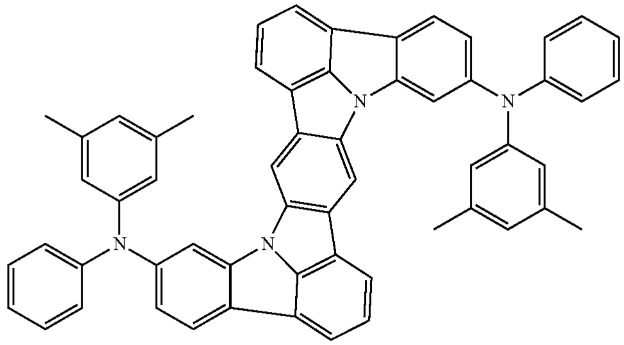

-continued
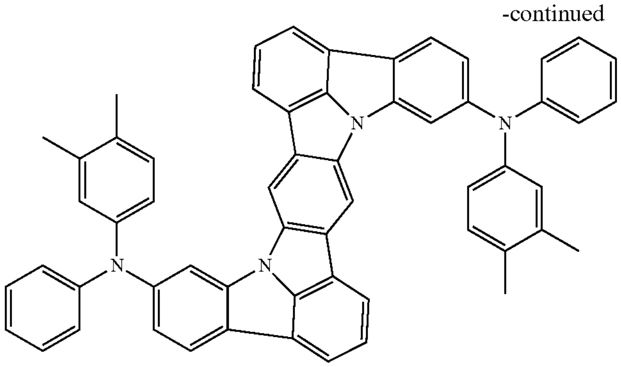
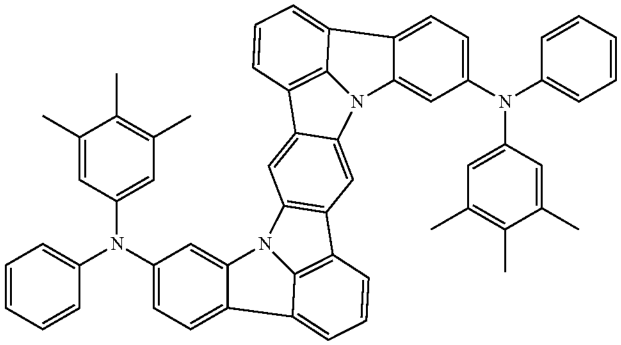
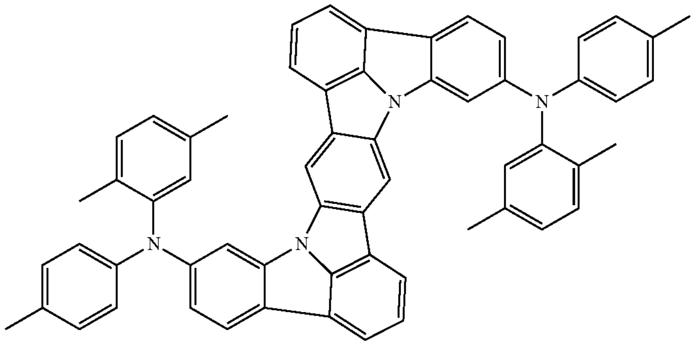
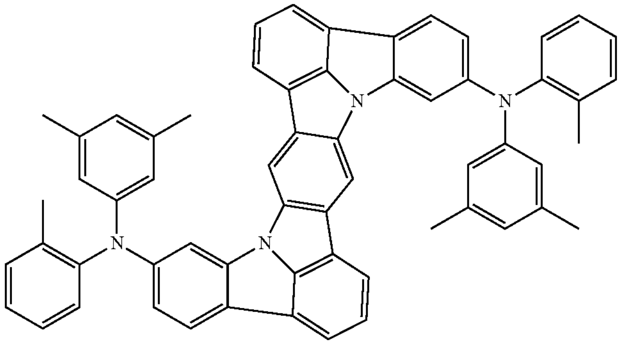
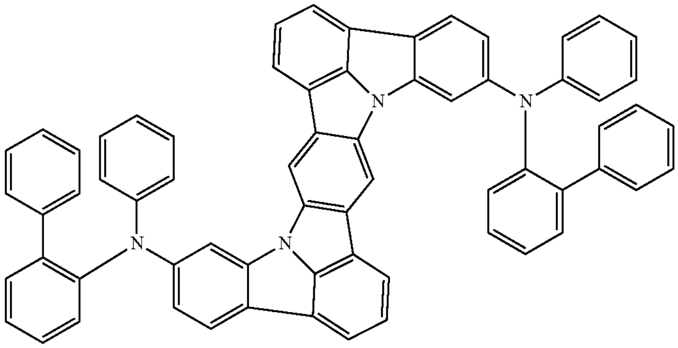

-continued
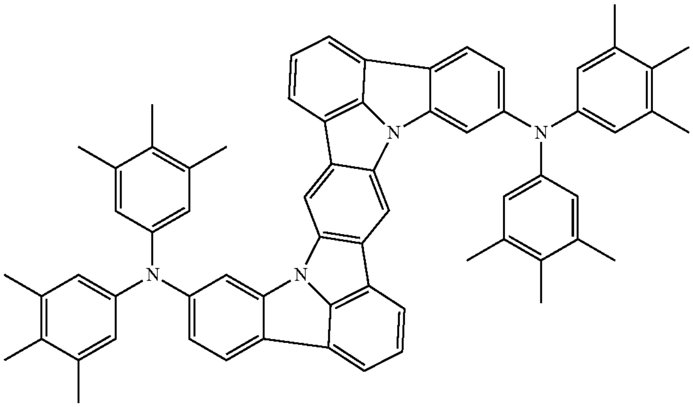
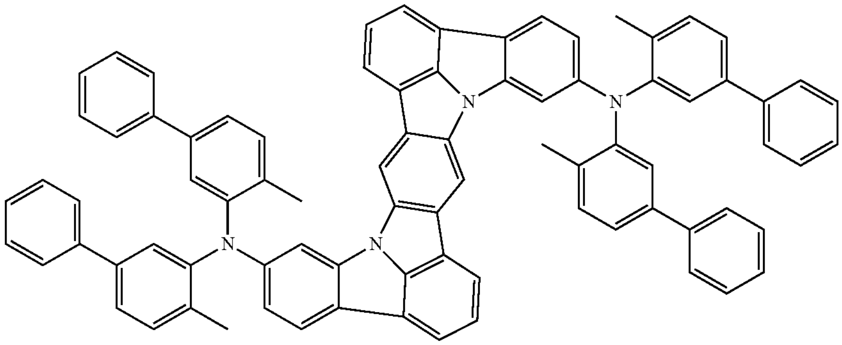
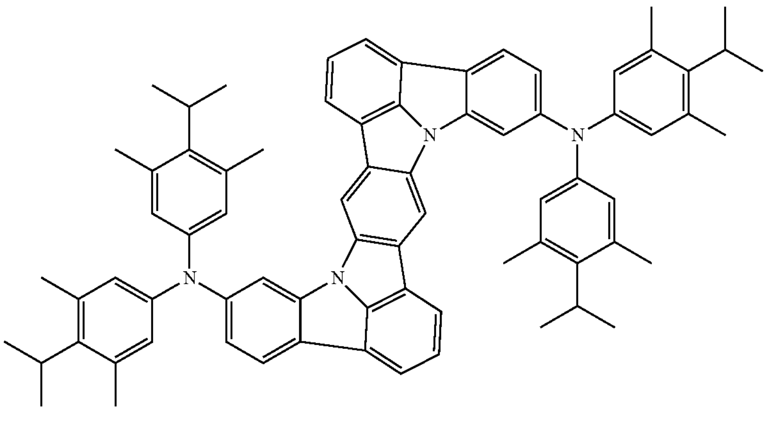

-continued
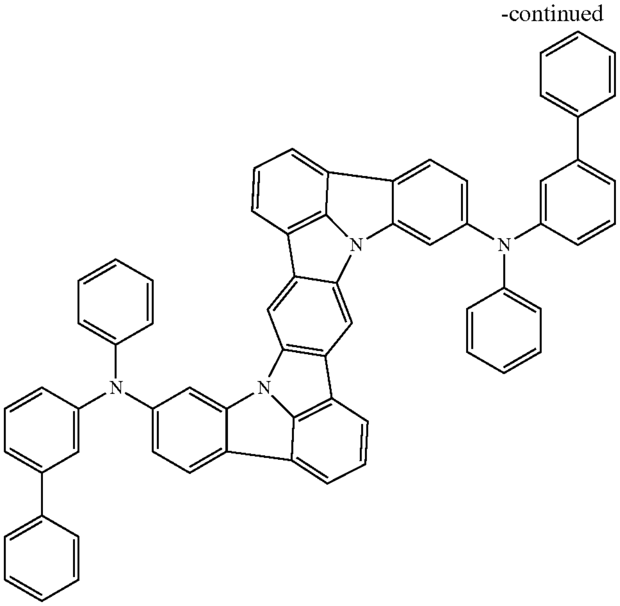
[Formula 208]
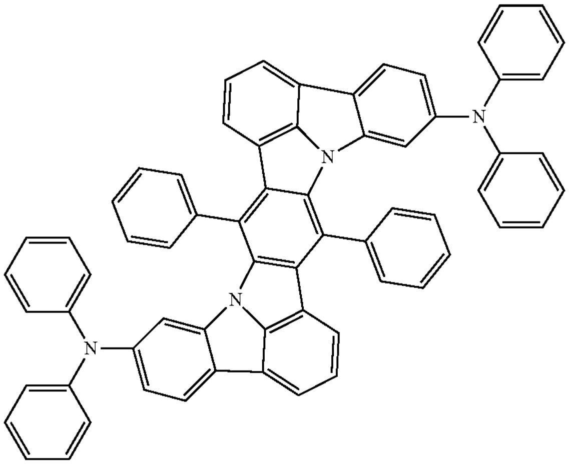
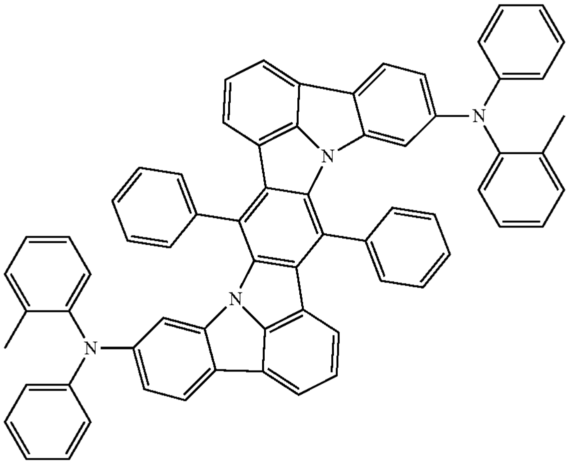

-continued
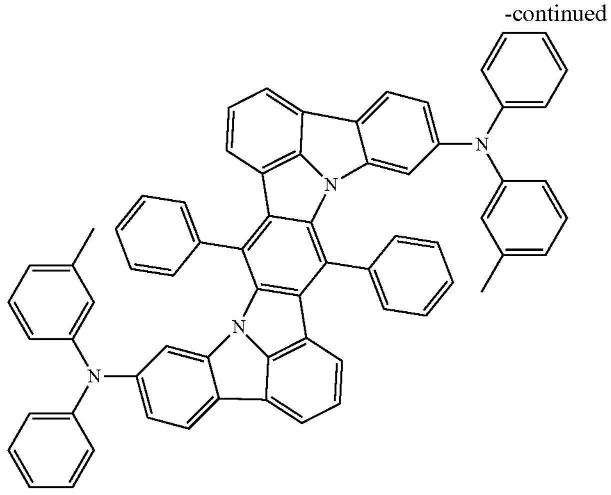
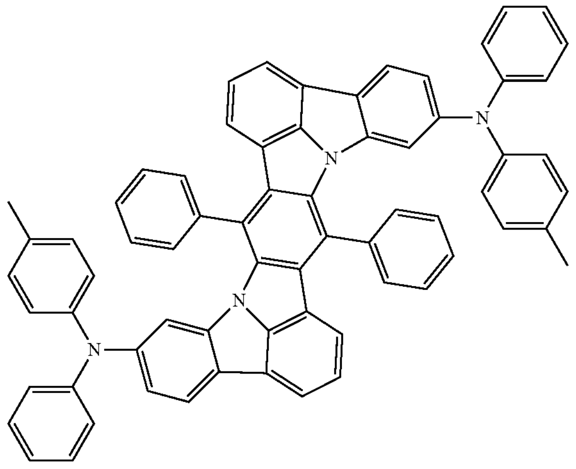
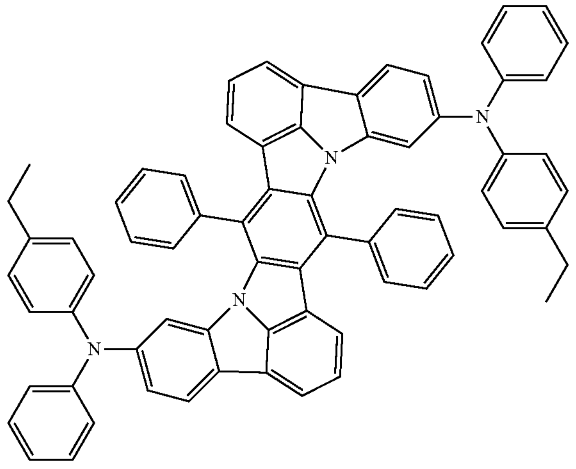

-continued
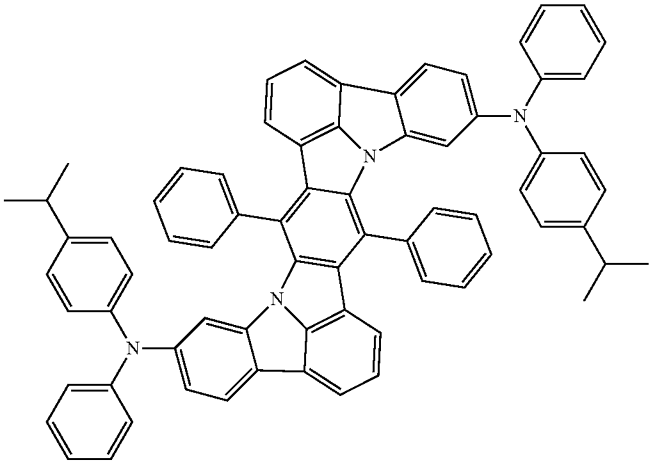
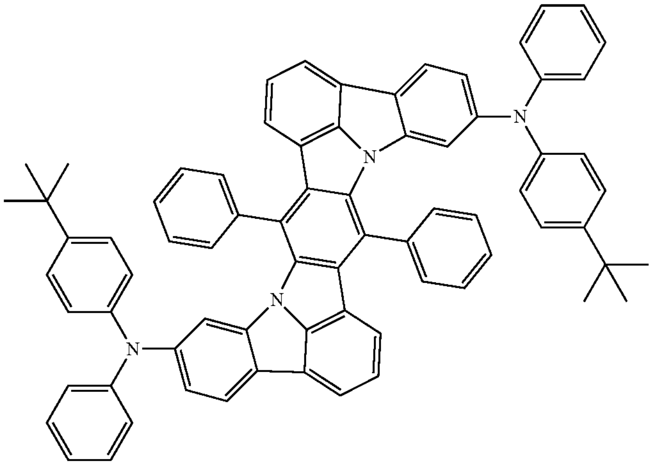
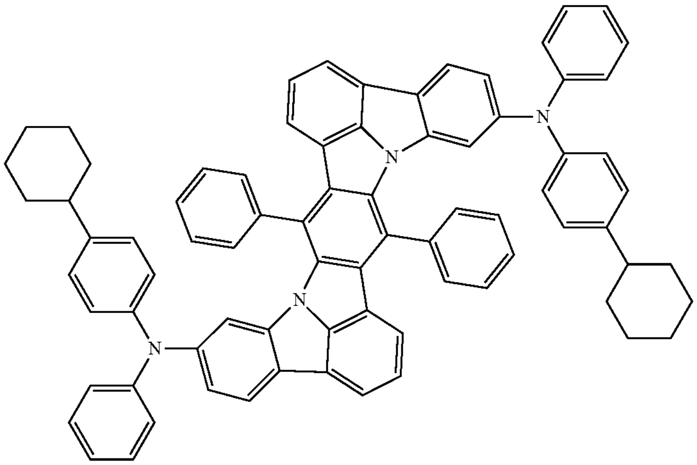

-continued
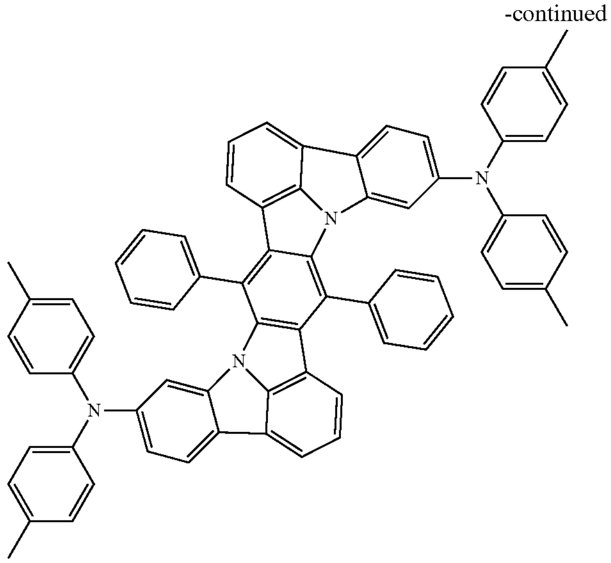
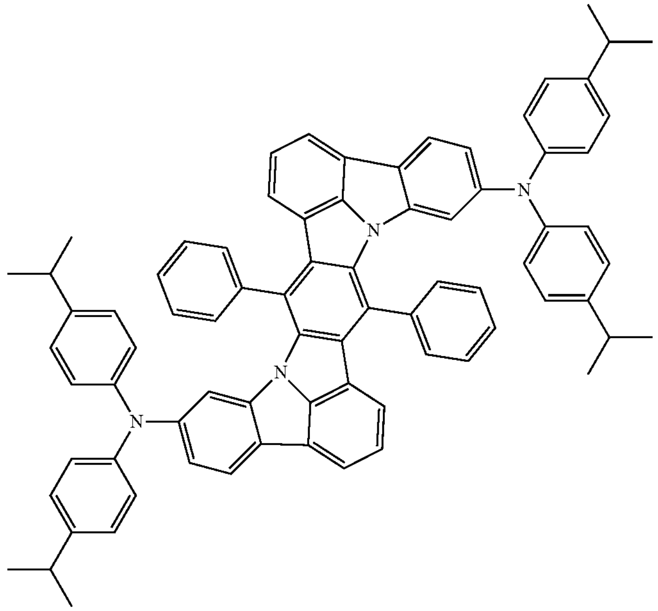

-continued
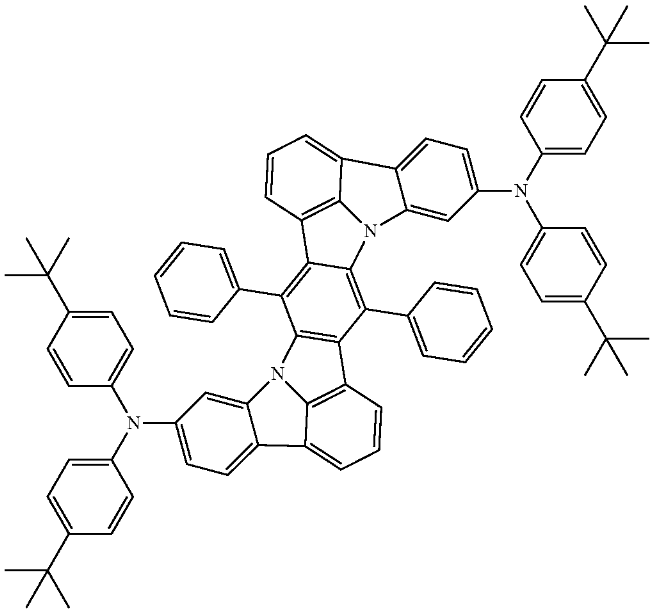
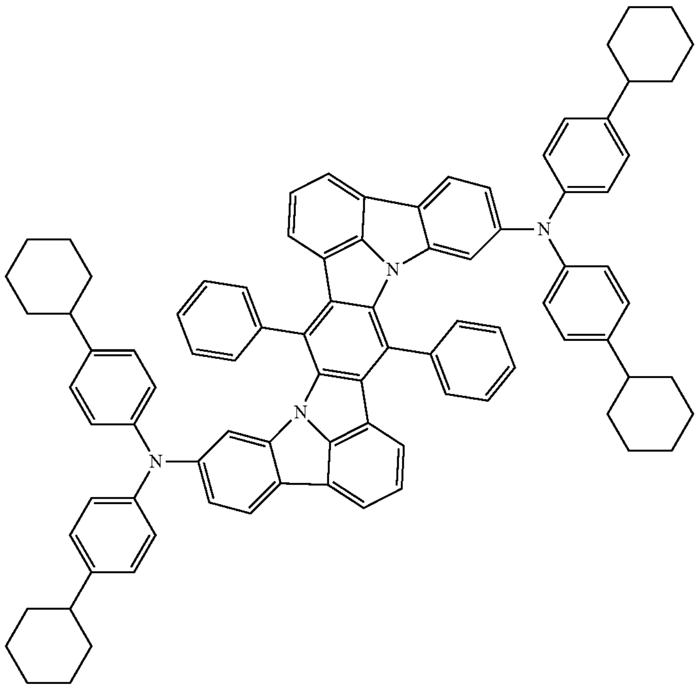

-continued
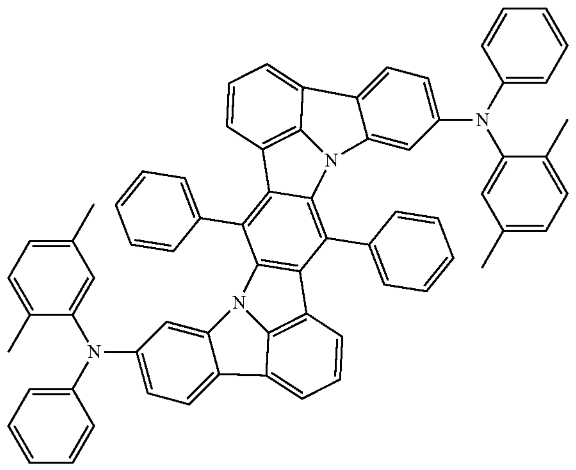
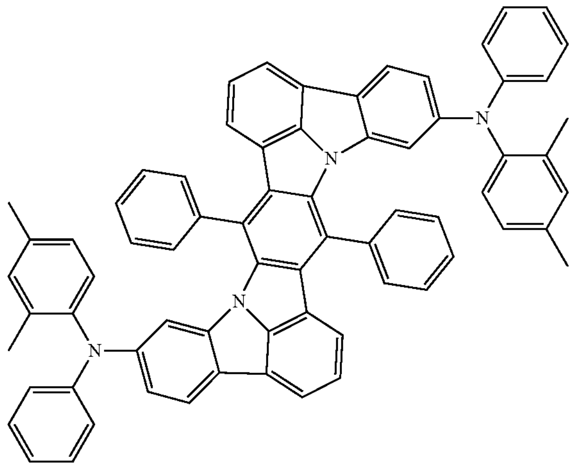
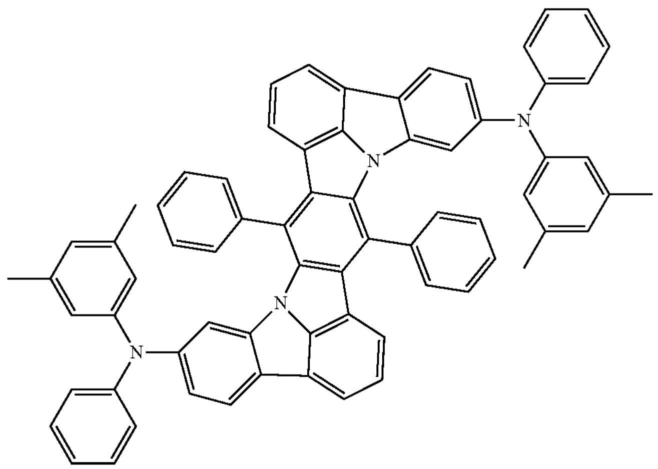
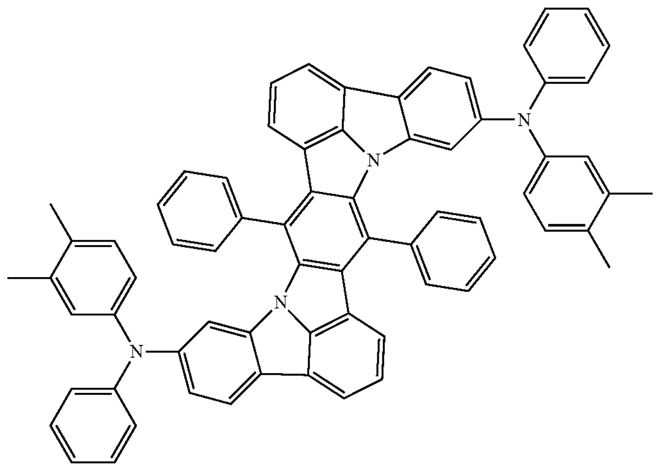

-continued
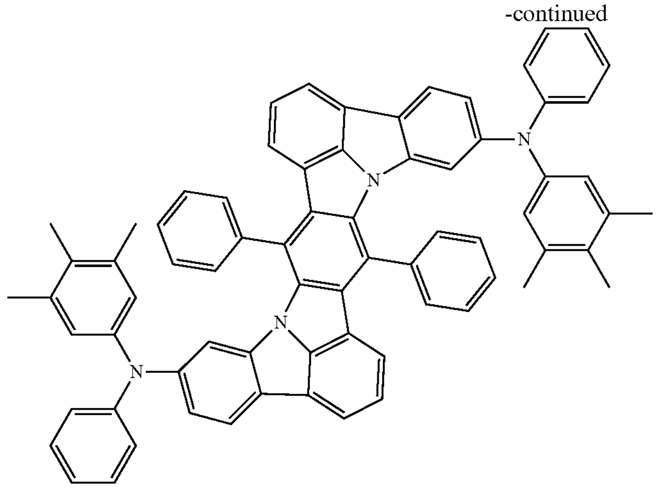
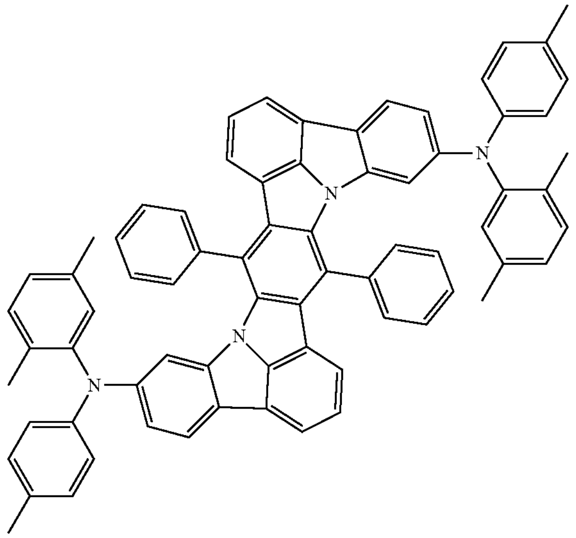
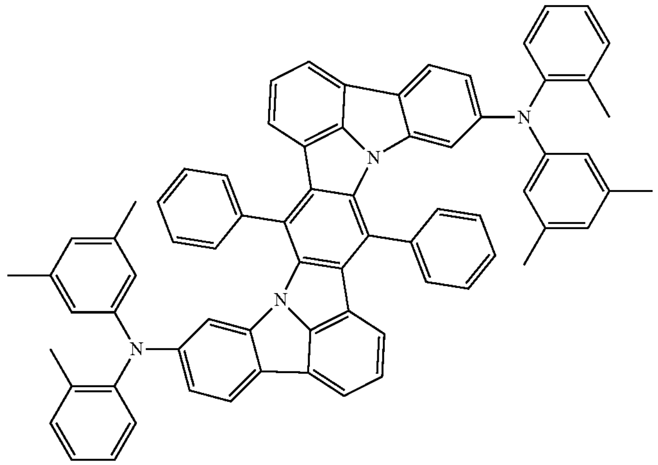

-continued
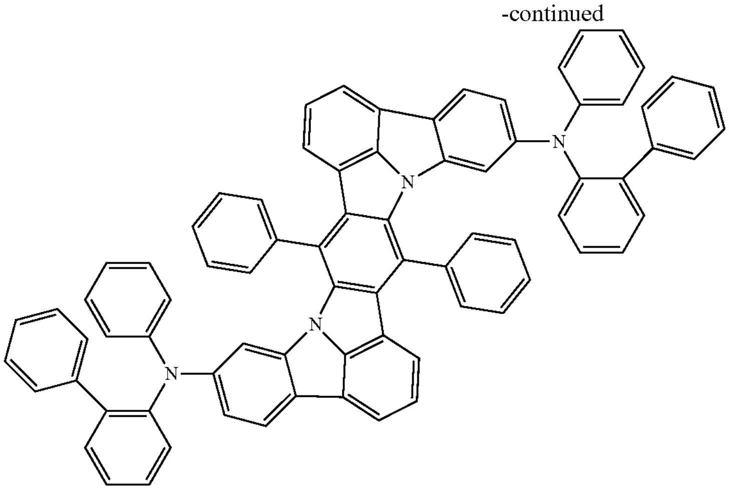
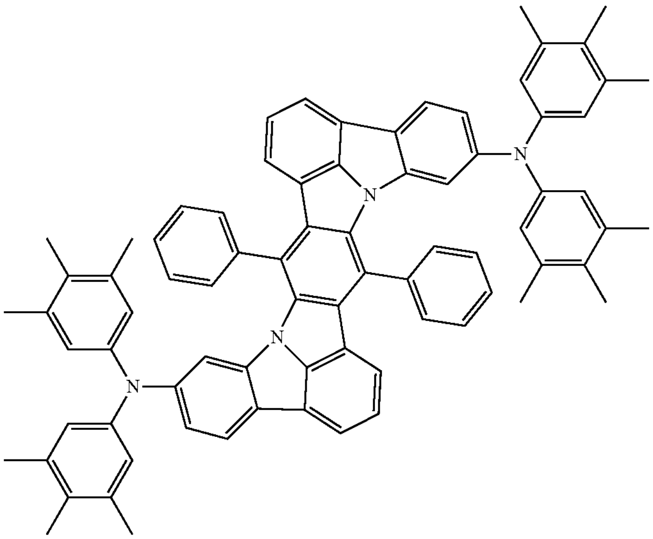
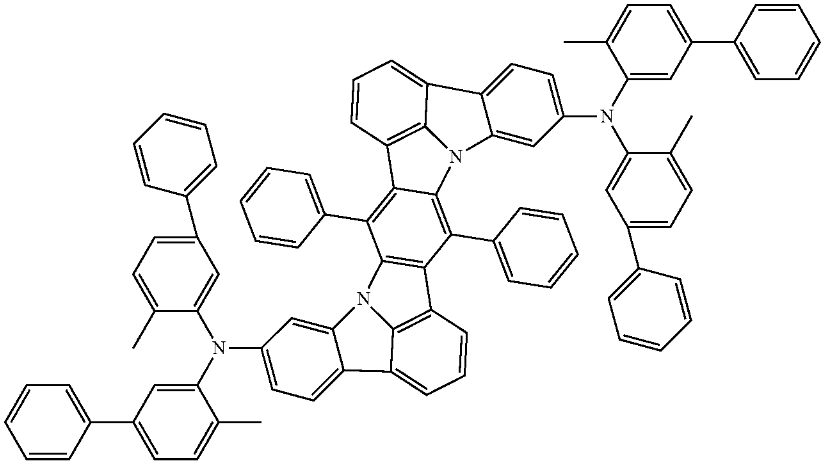

-continued
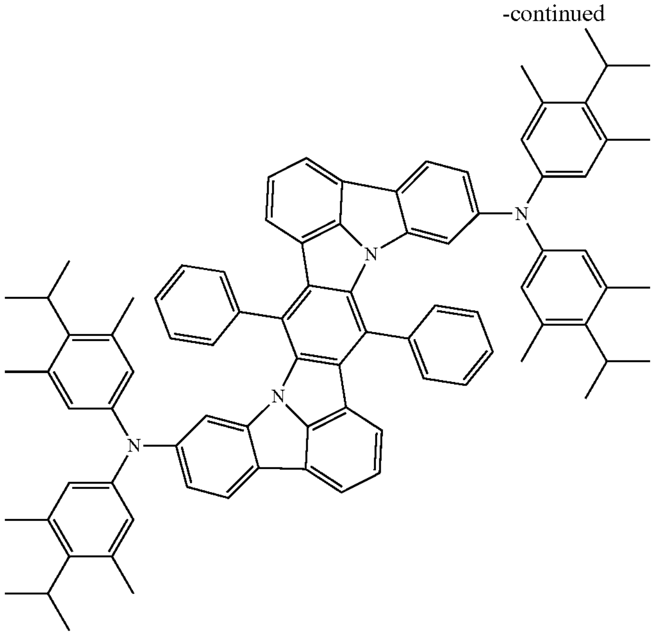
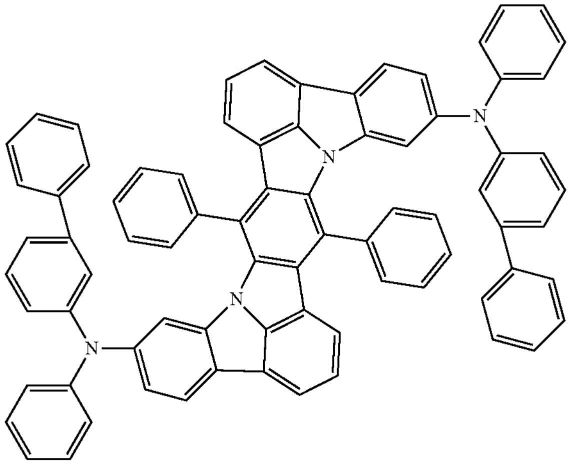
[Formula 209]
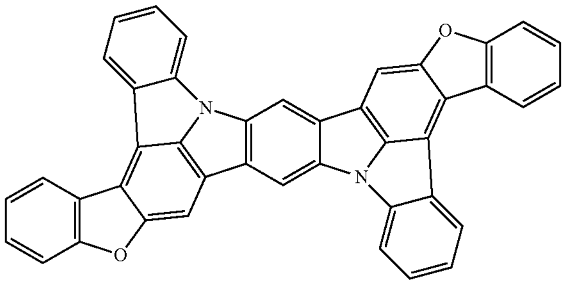
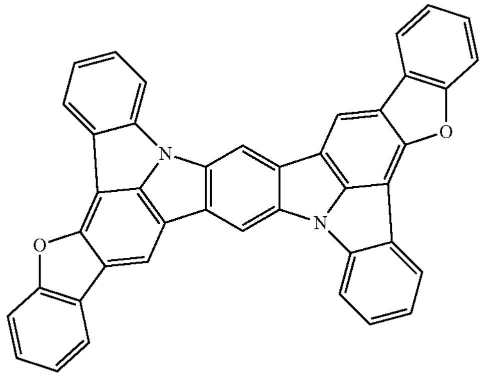

-continued
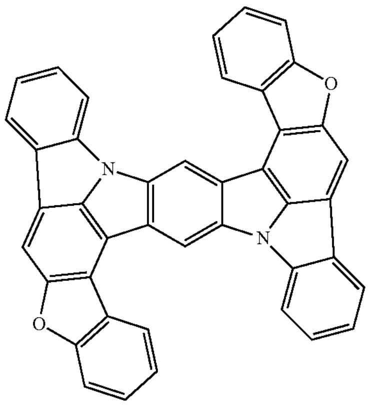
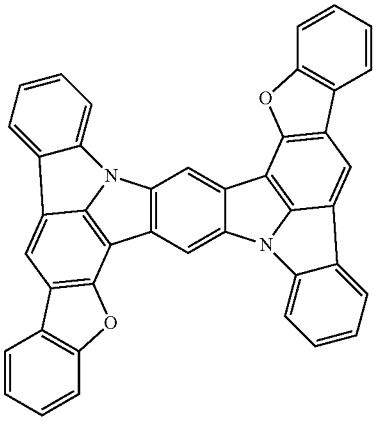
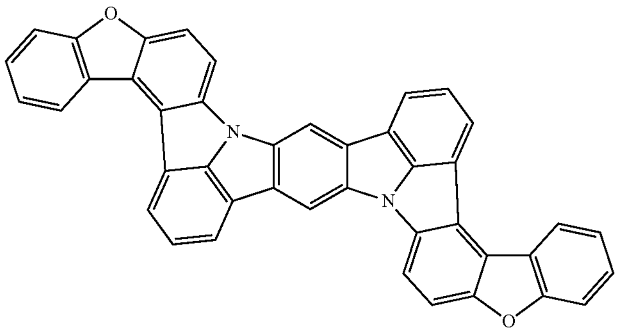
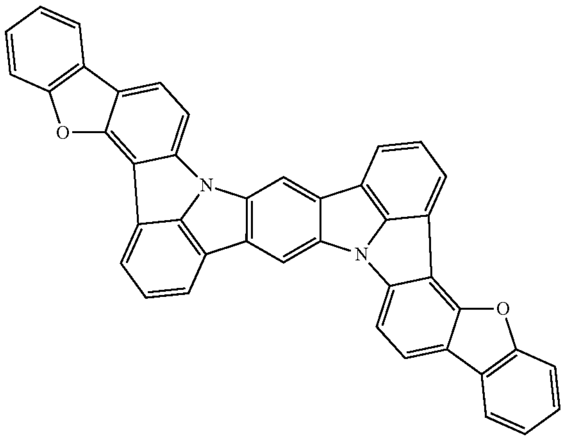
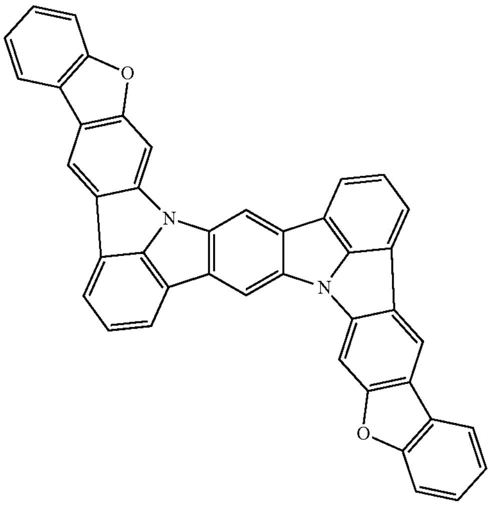

-continued
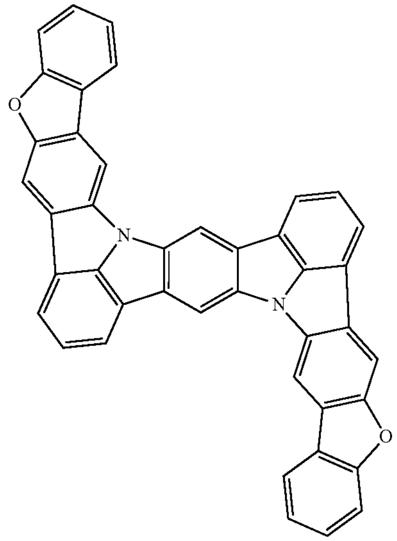
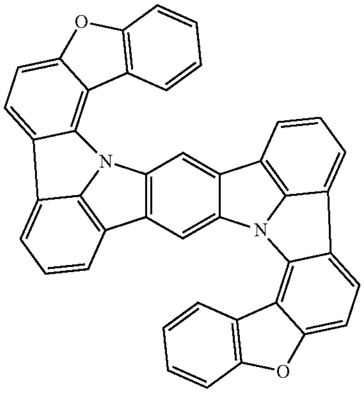
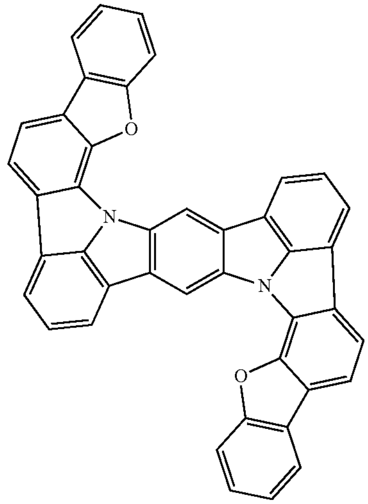
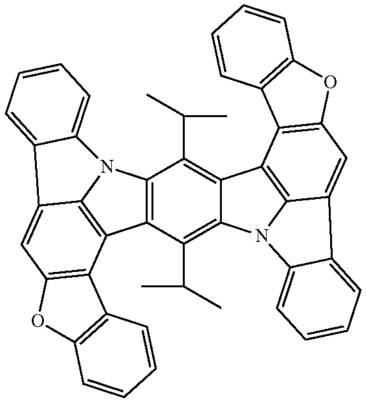
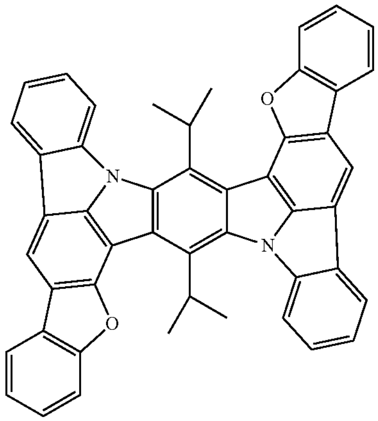
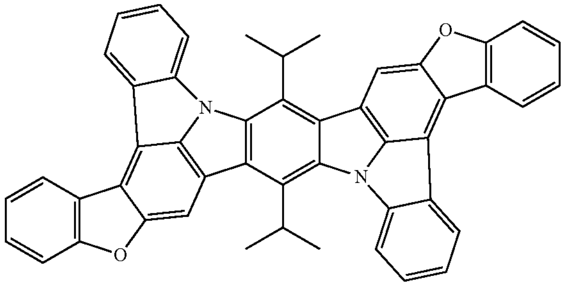
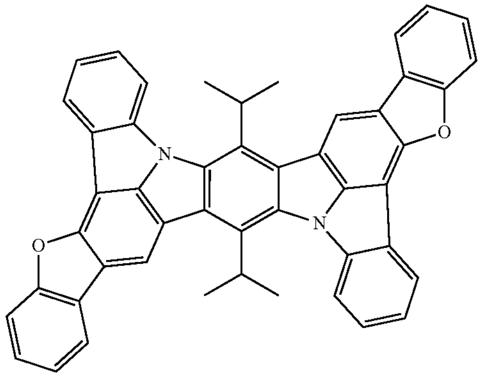

-continued
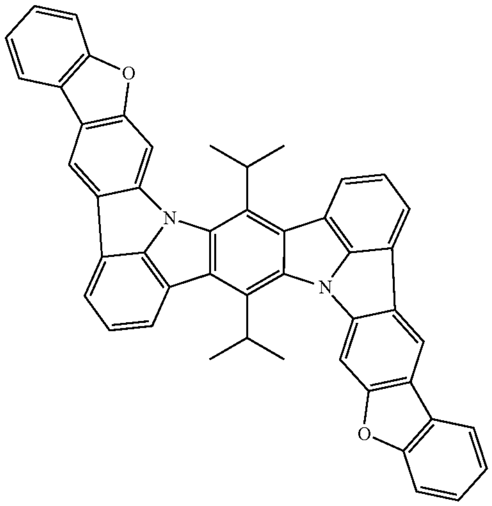
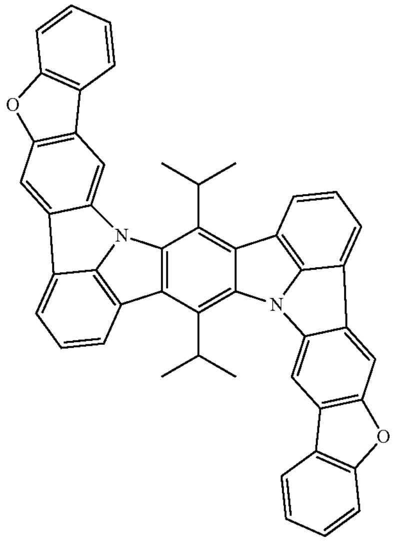
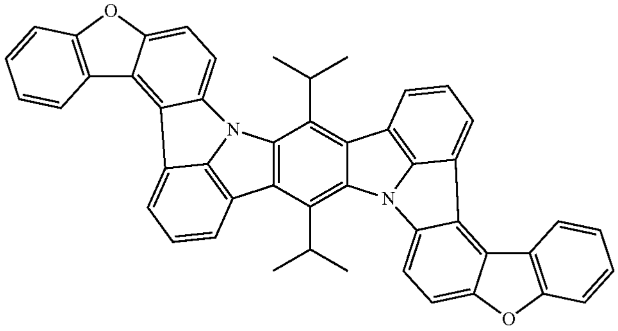
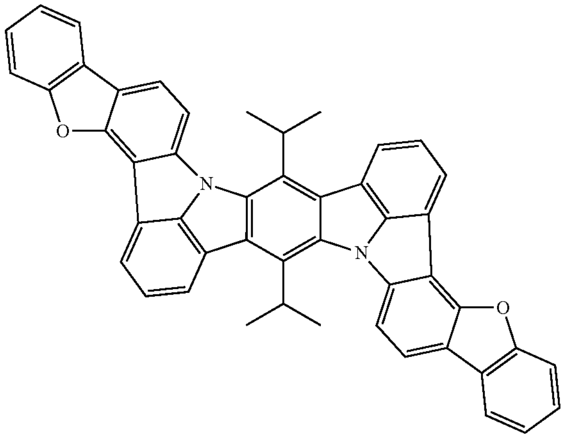
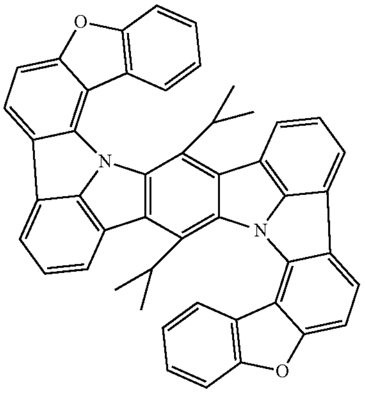

-continued
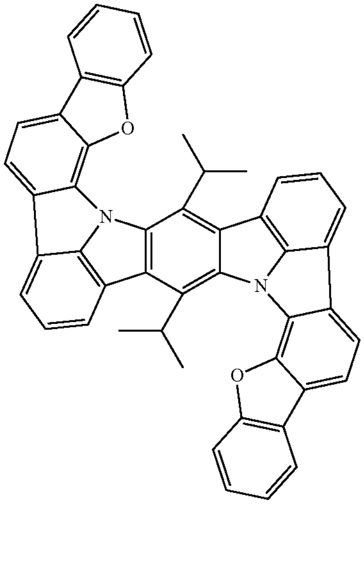
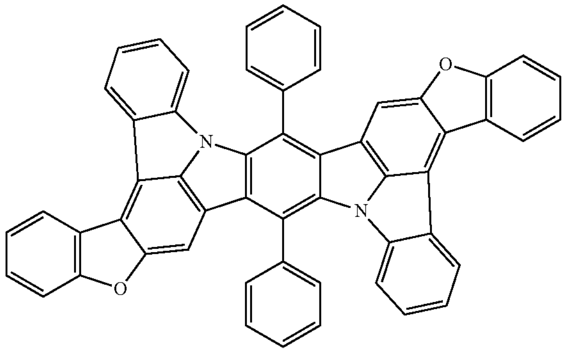
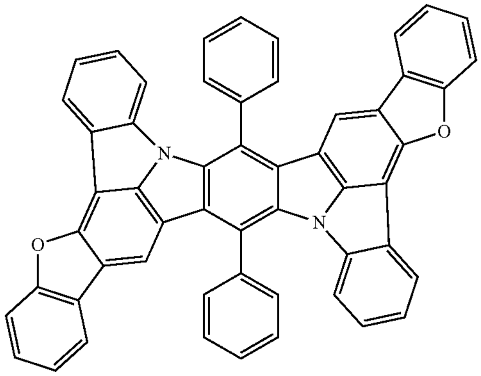
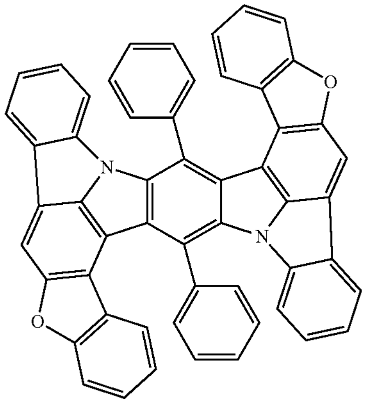
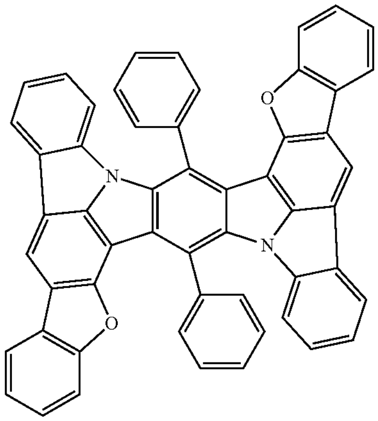
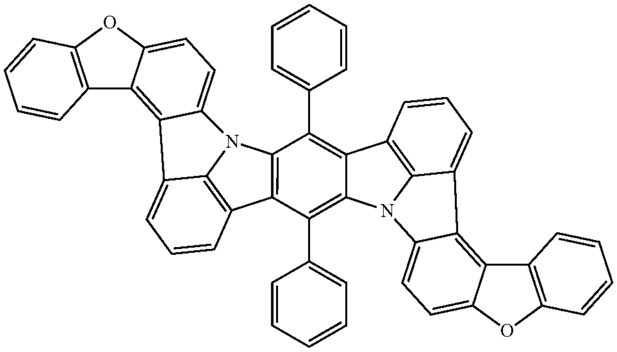

-continued
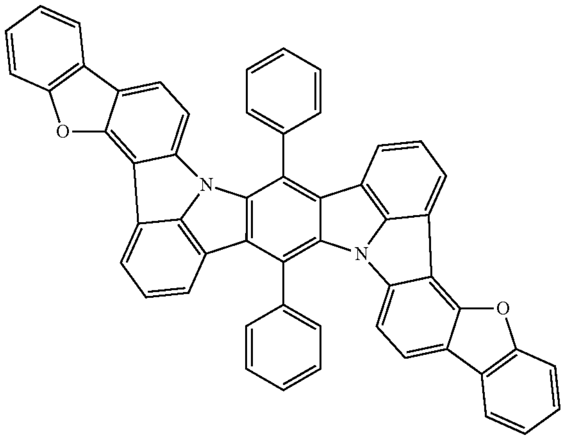
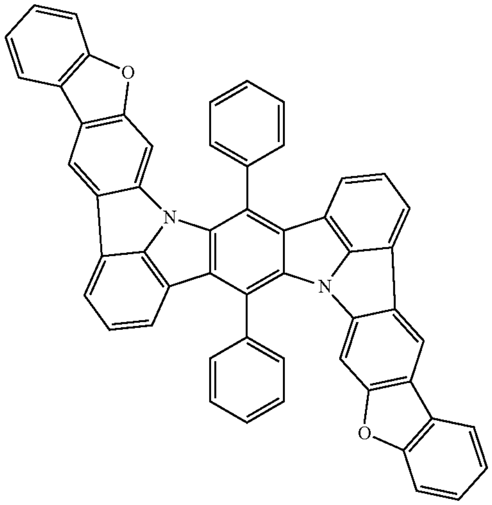
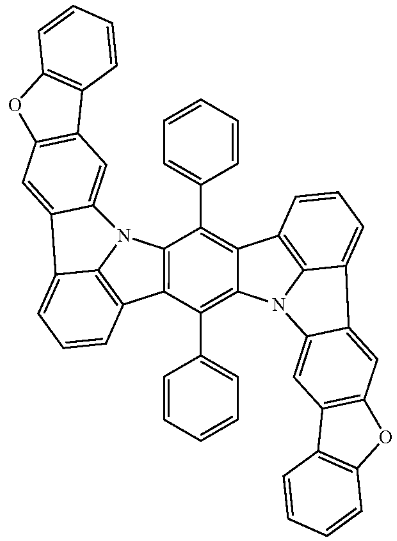
[Formula 210]
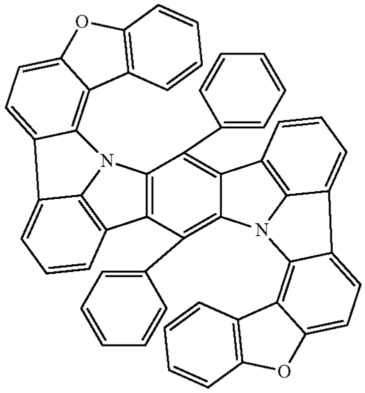
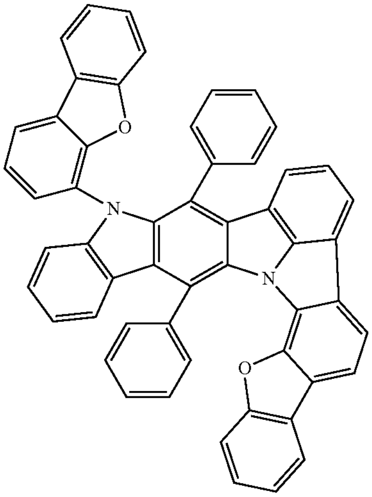

-continued
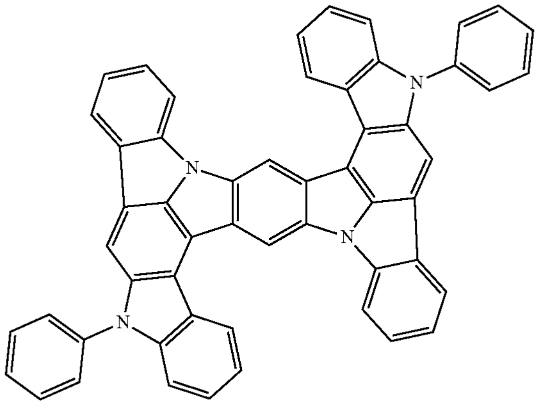
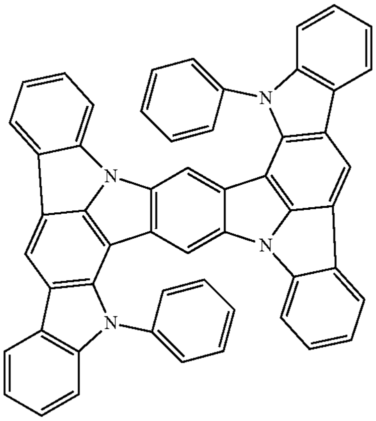
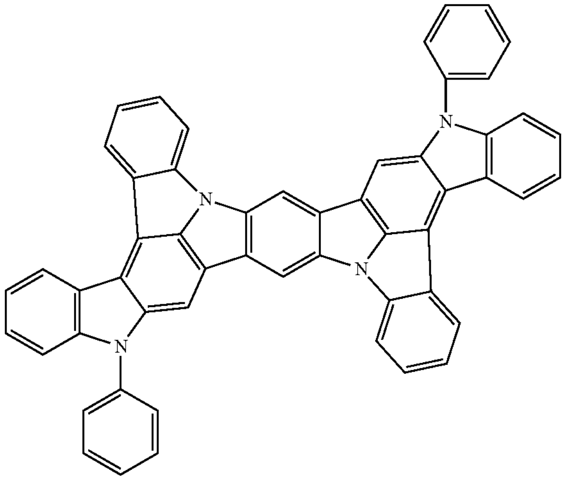
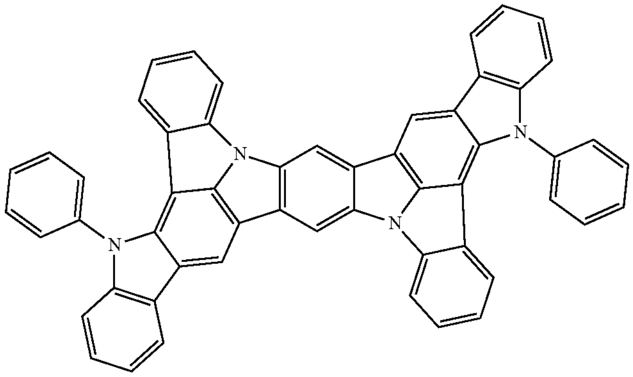
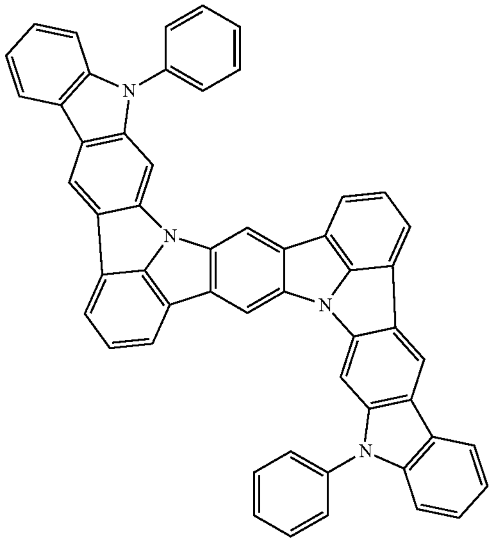

-continued
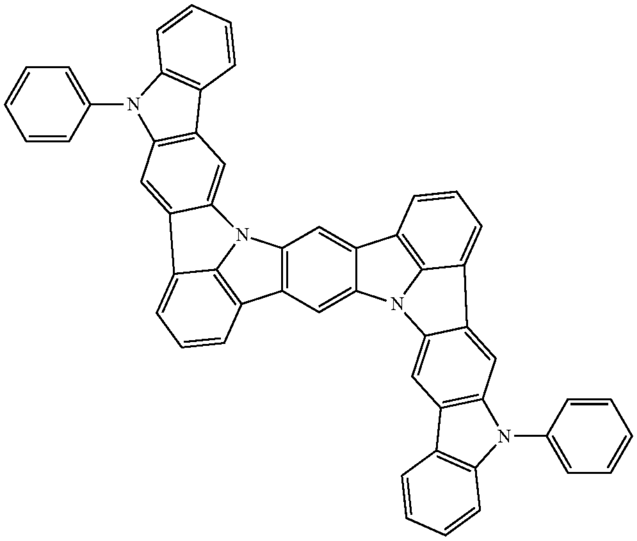
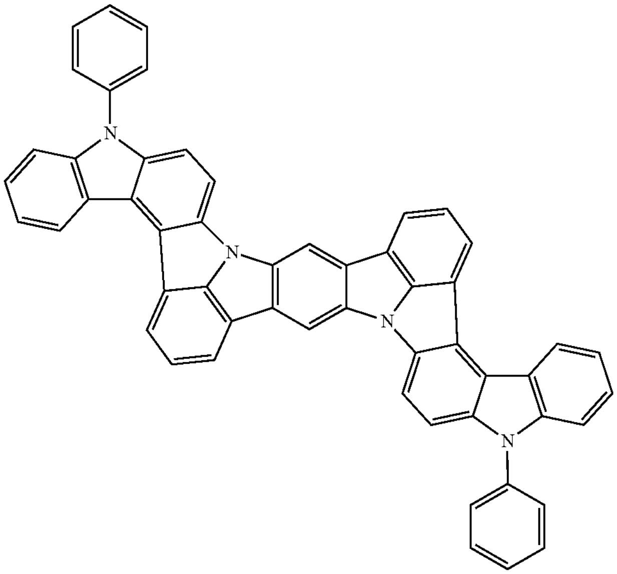
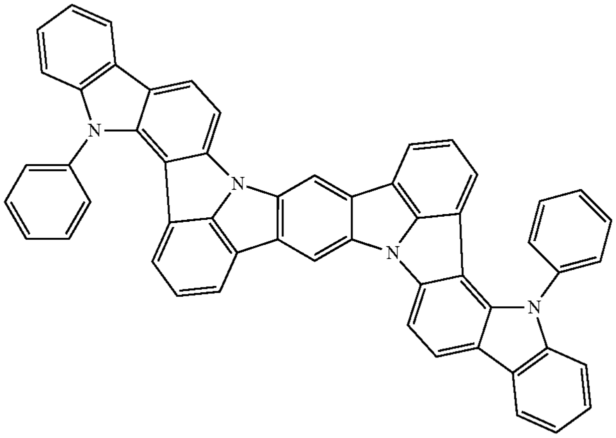
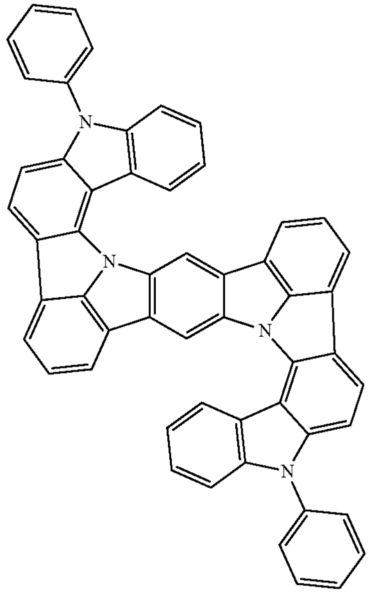

-continued
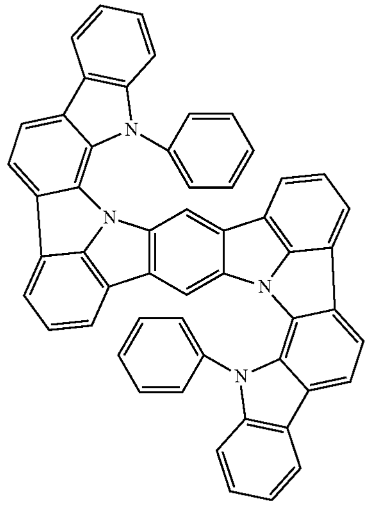
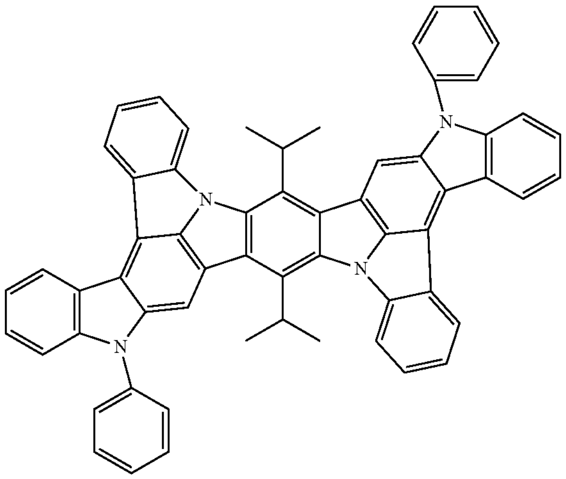
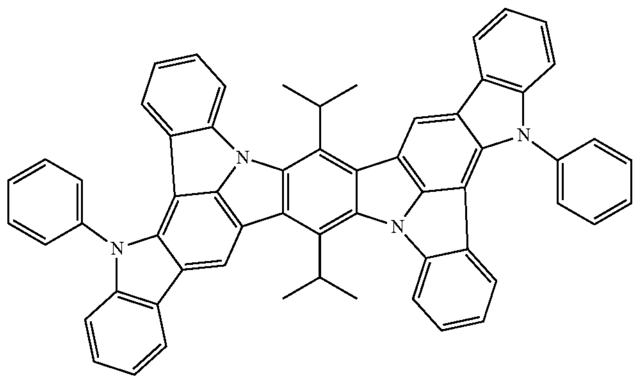
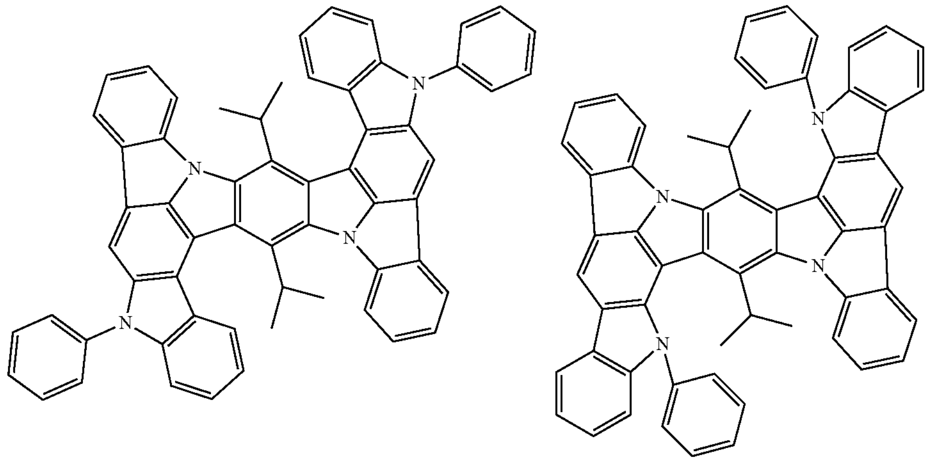

-continued
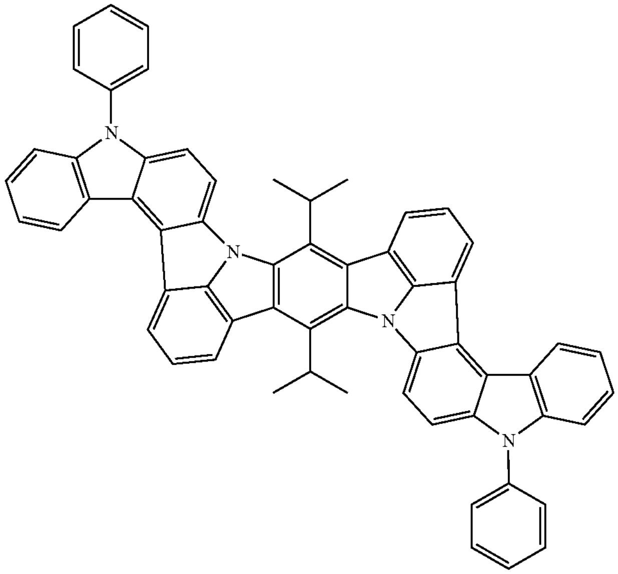
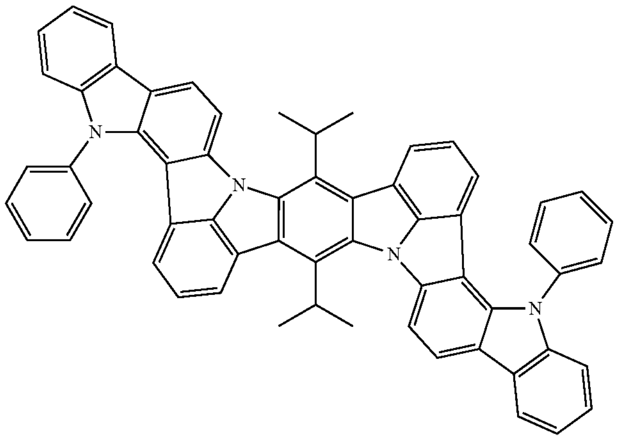
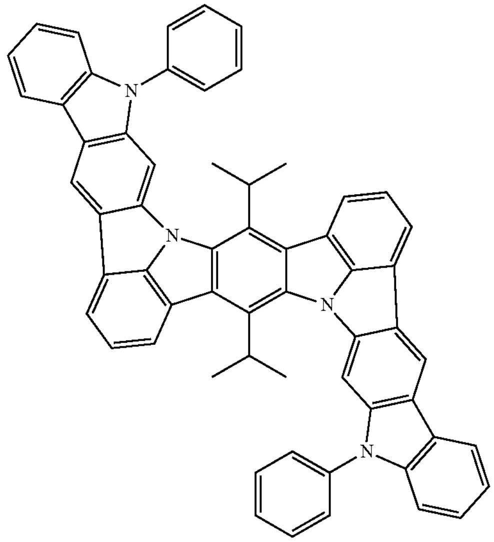
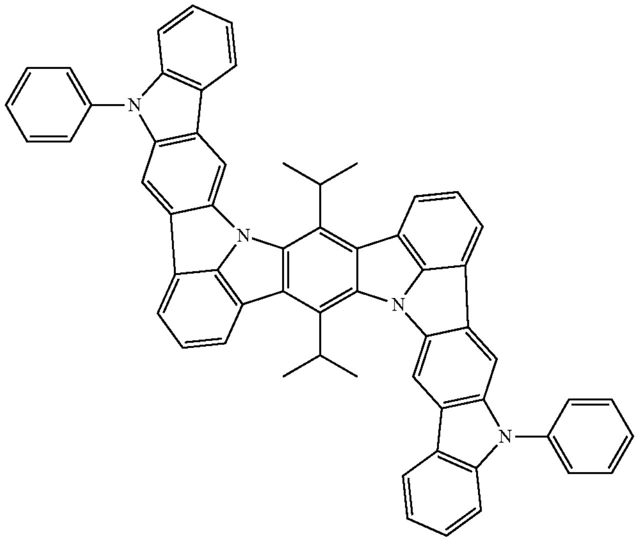
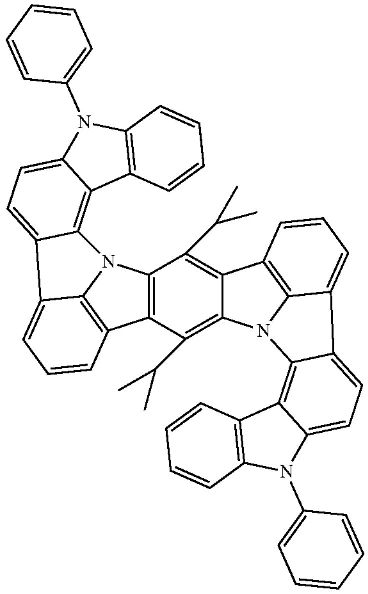

-continued
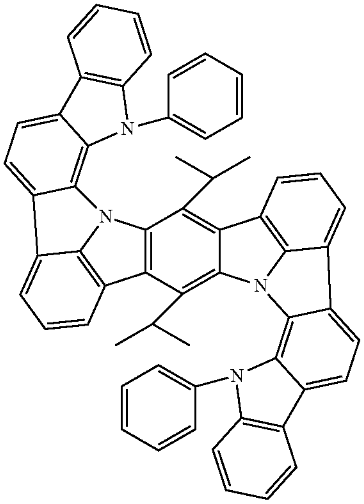
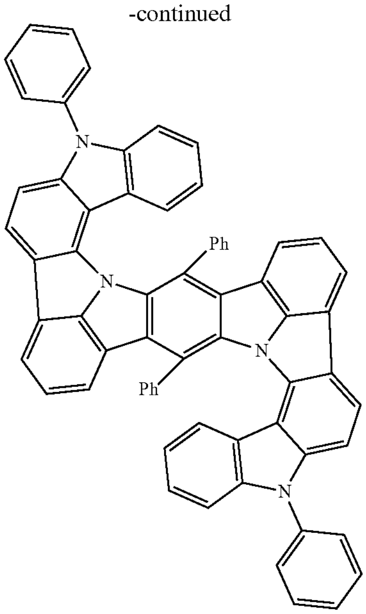
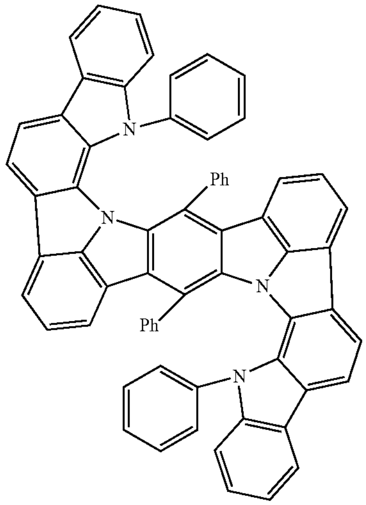
(In the formulae, Ph is a phenyl group.)
[Formula 211]
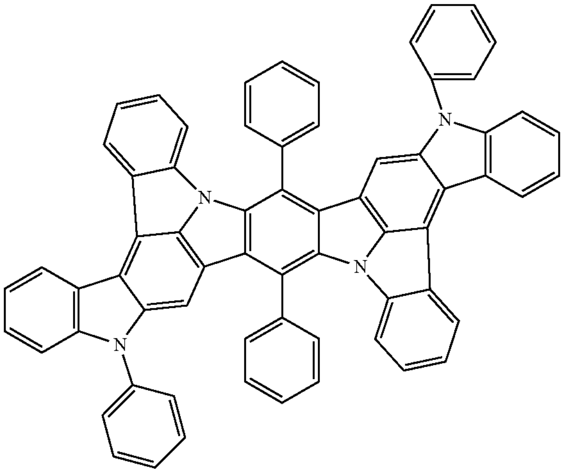
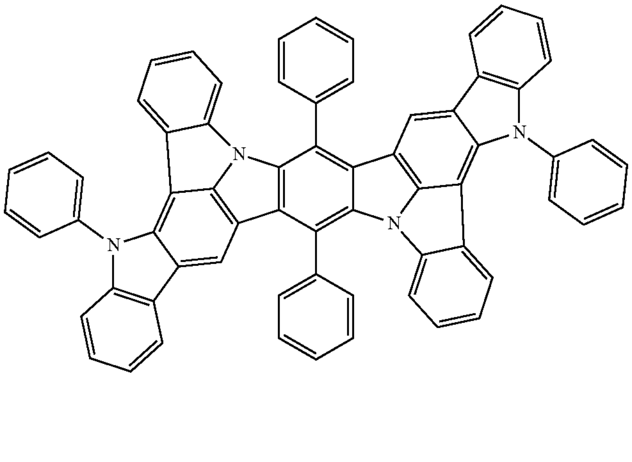

-continued
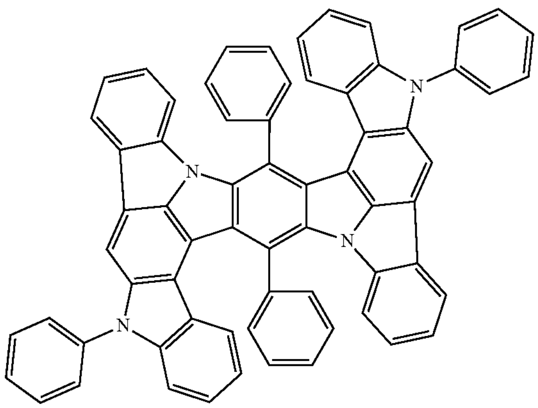
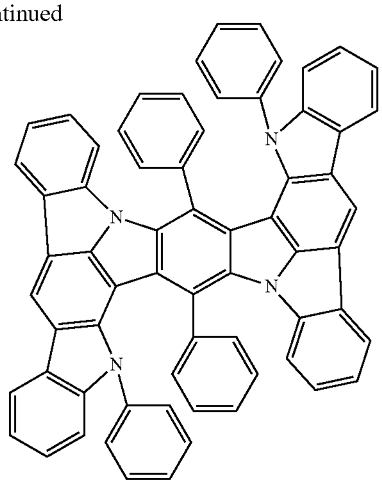
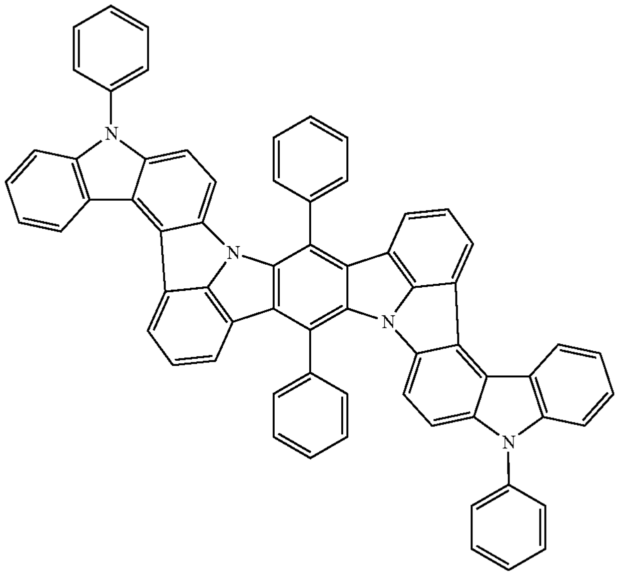
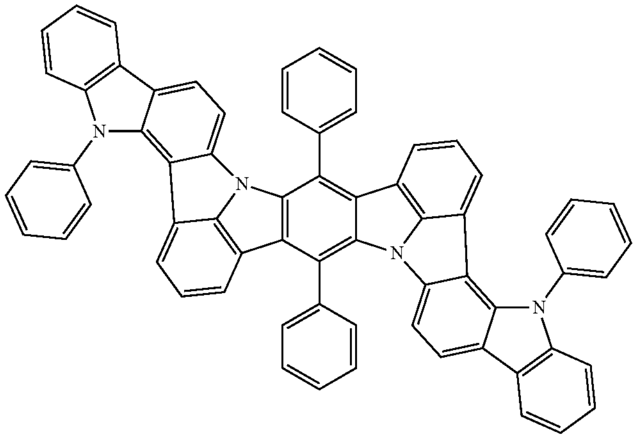

-continued
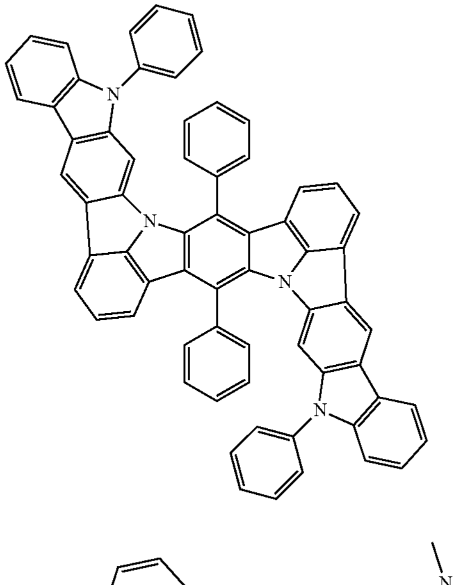
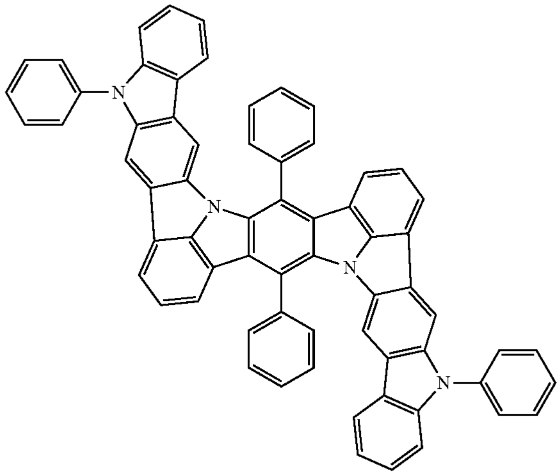
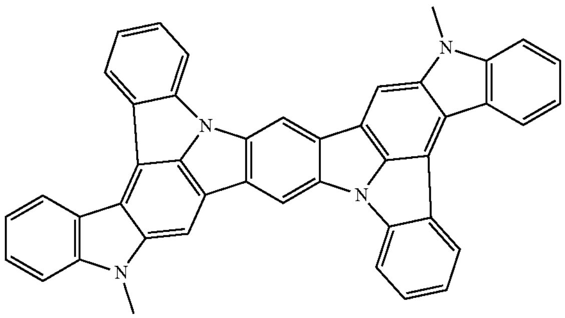
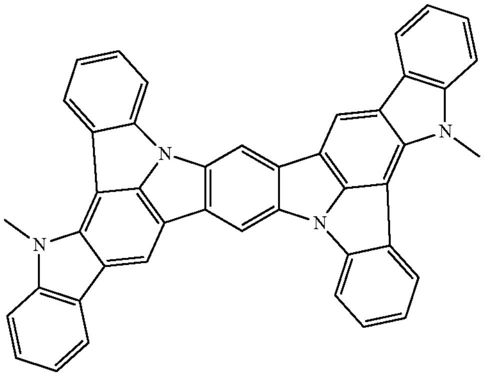
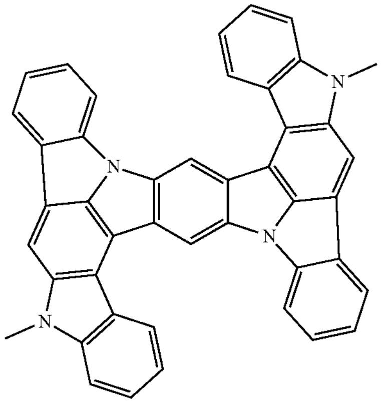
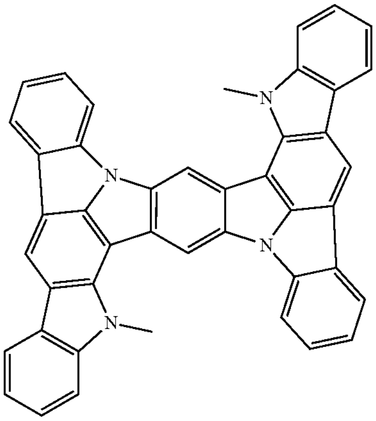
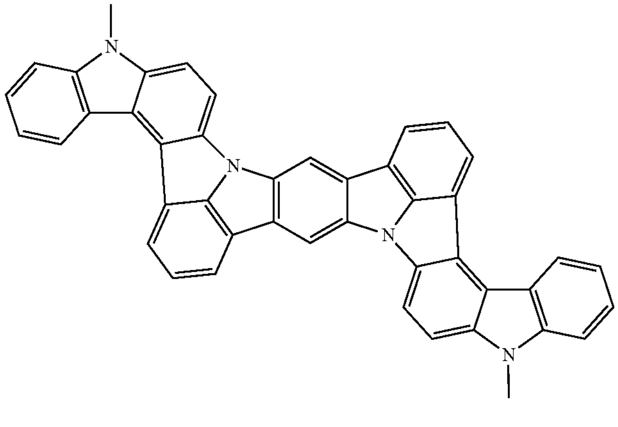

-continued
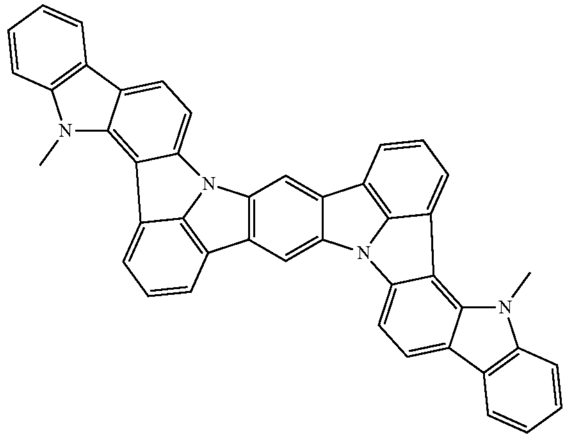
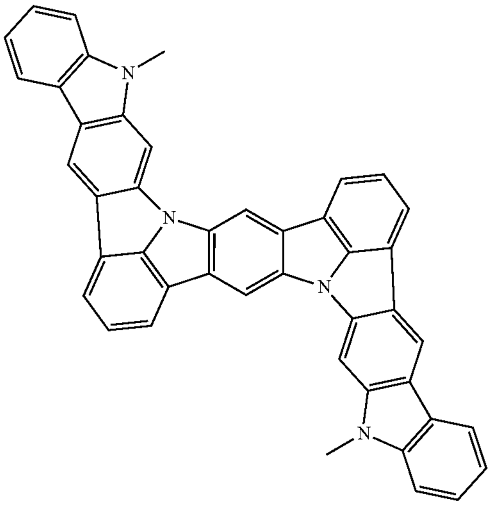
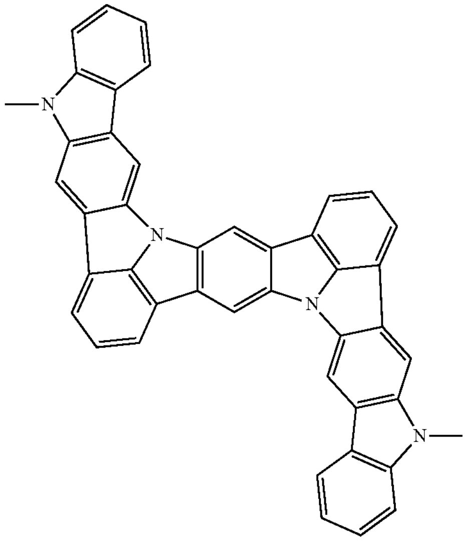
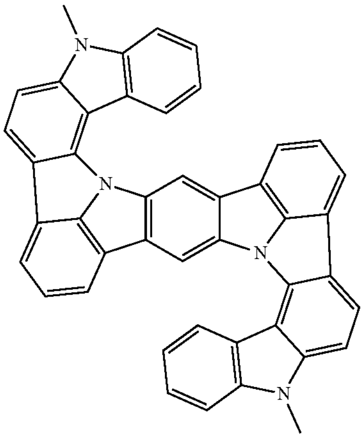
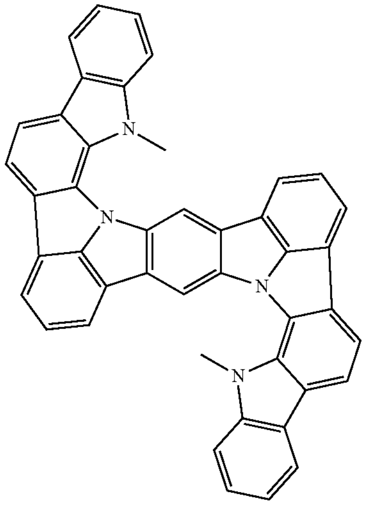
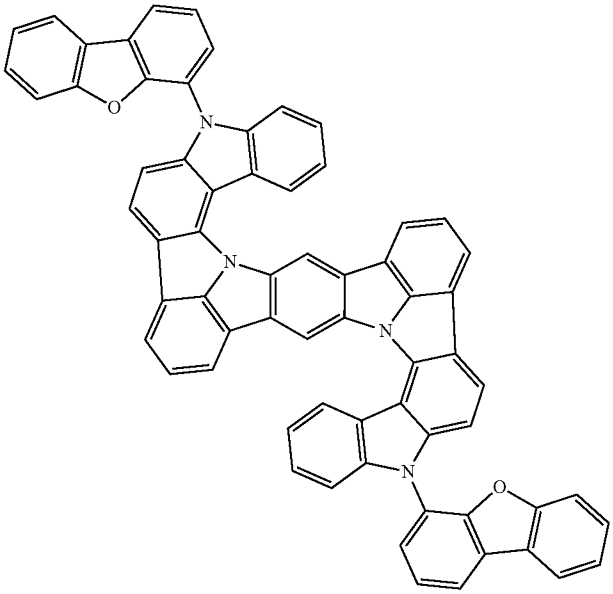

-continued
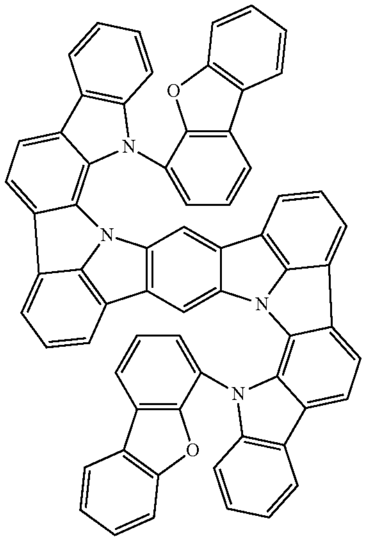
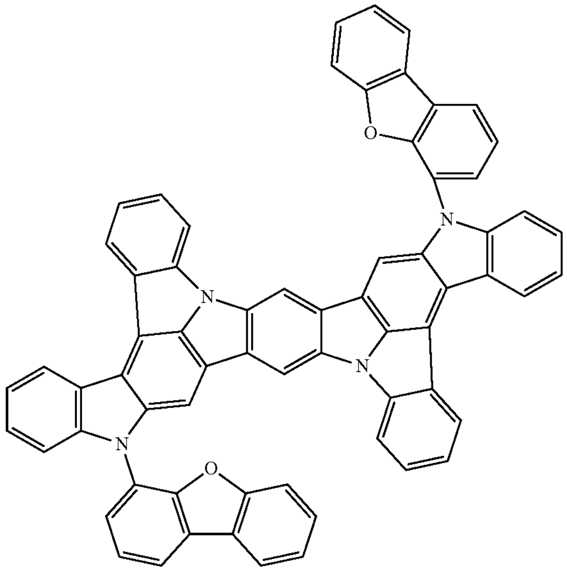
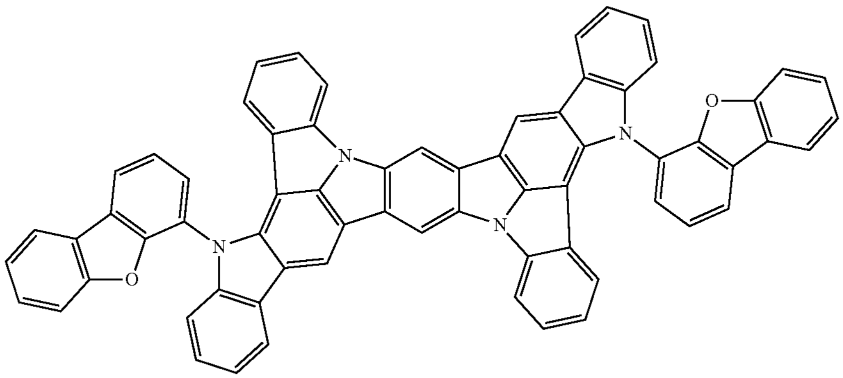
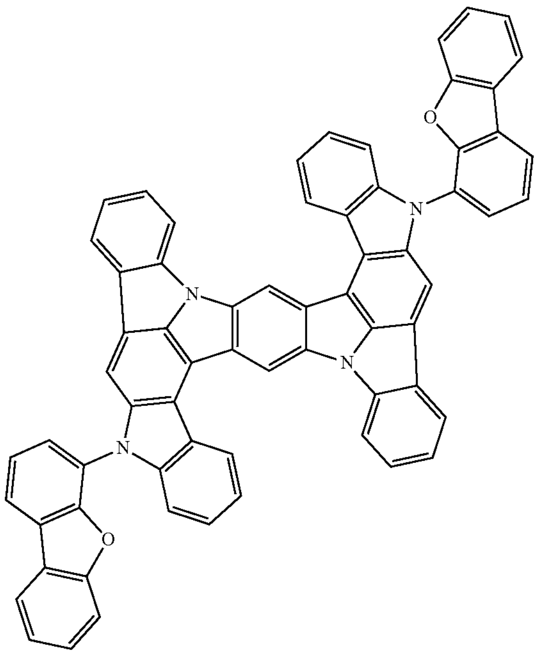
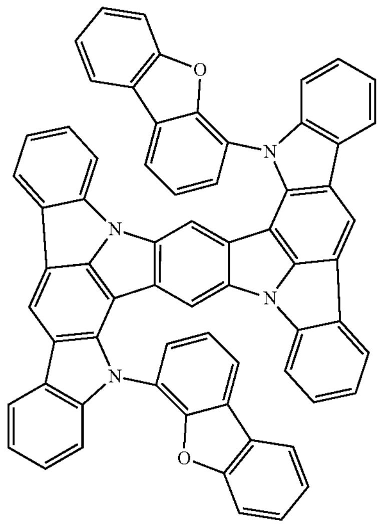

-continued
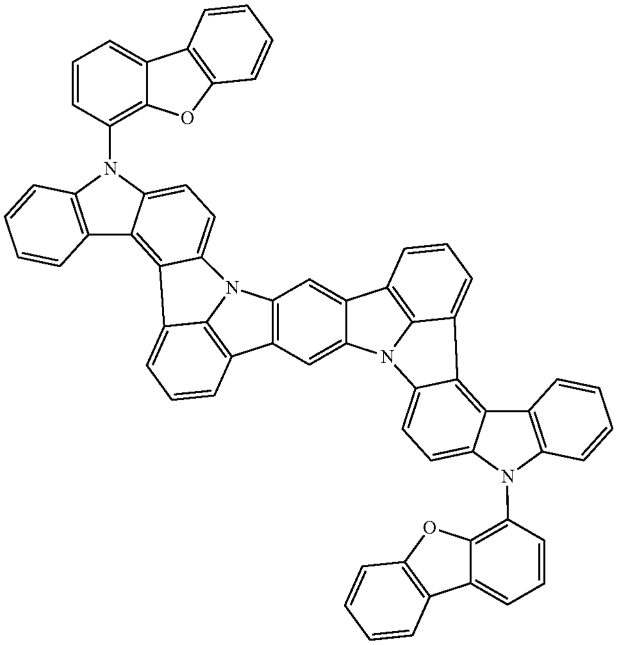
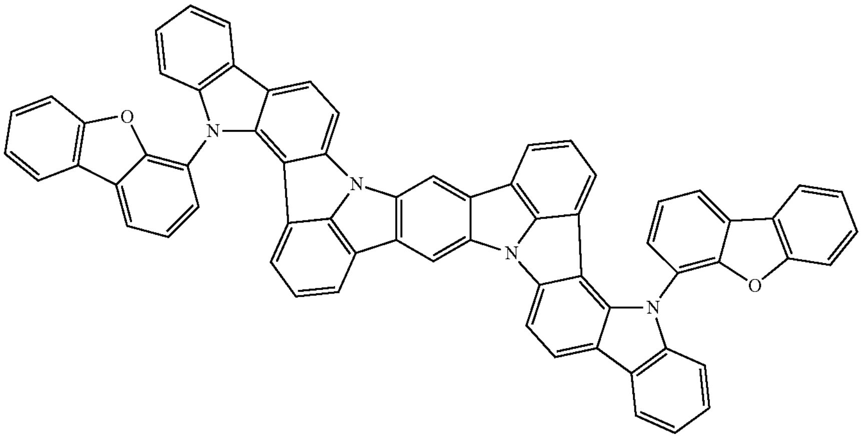
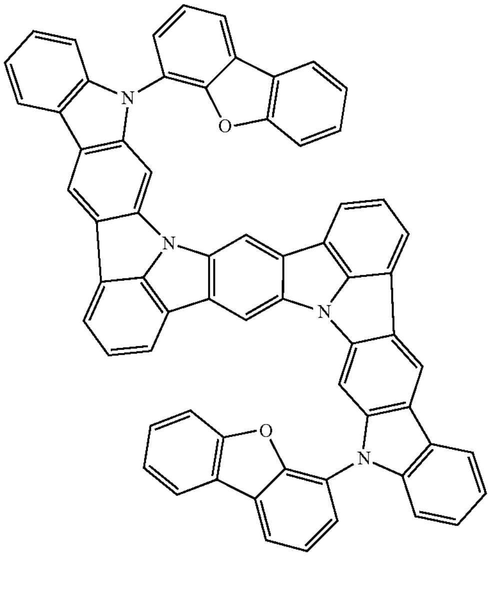

-continued
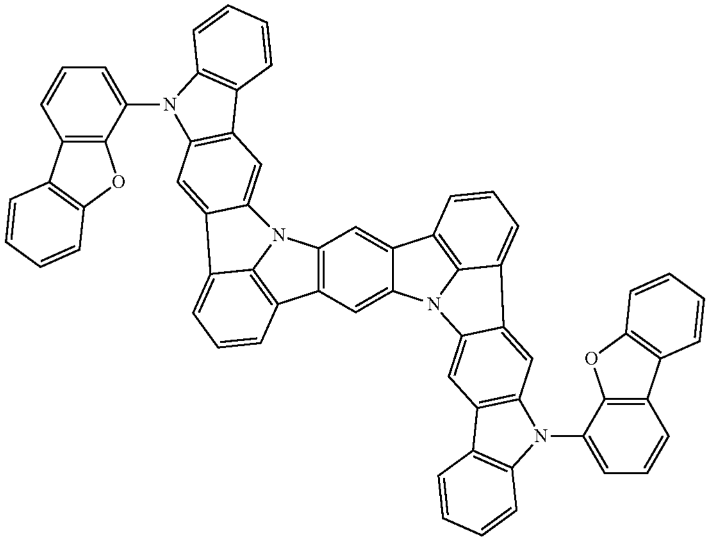
[Formula 212]
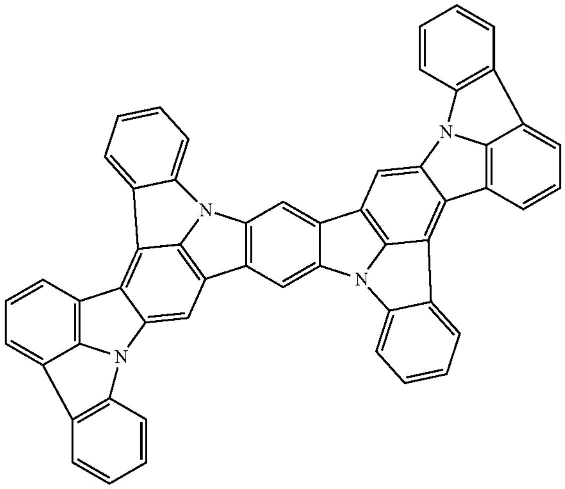
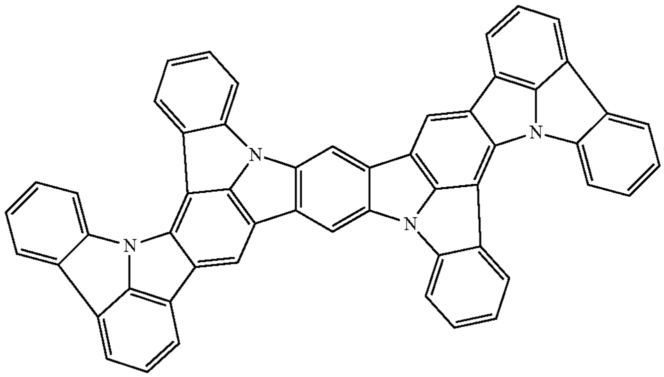

-continued
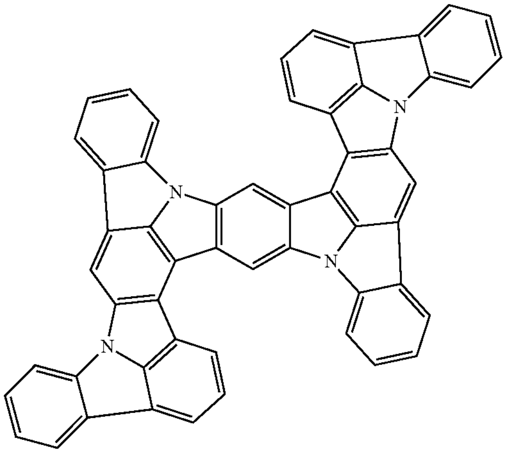
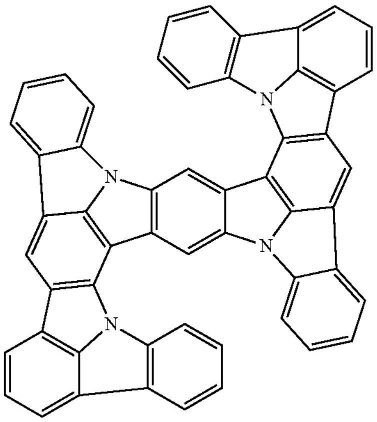
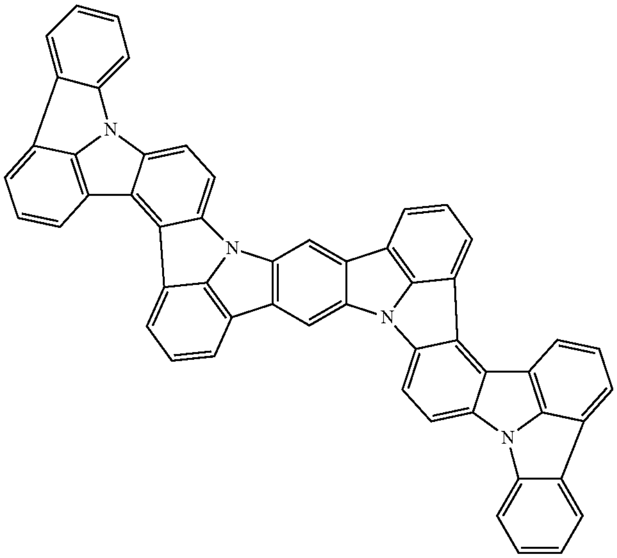
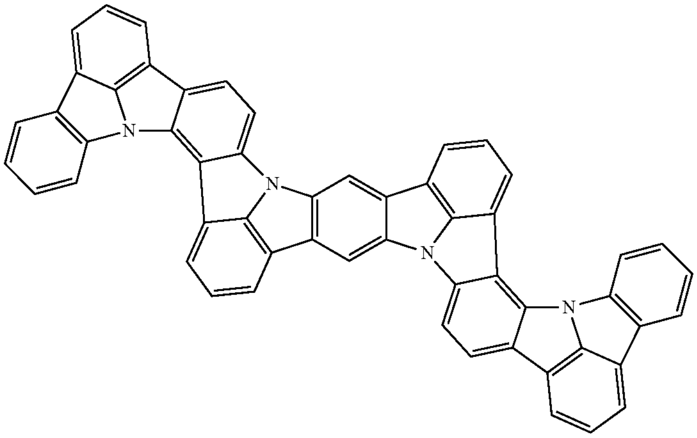

-continued
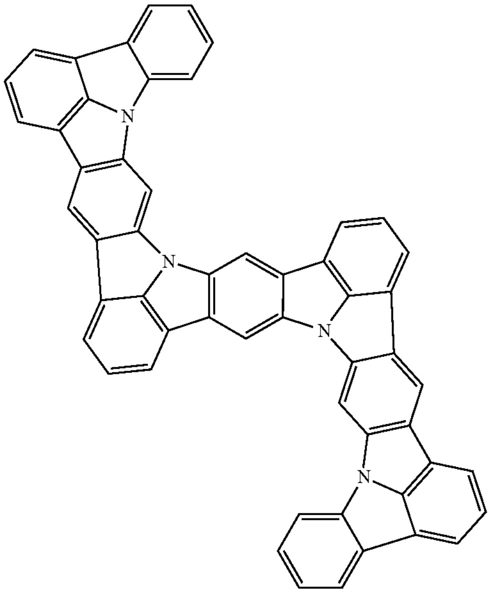
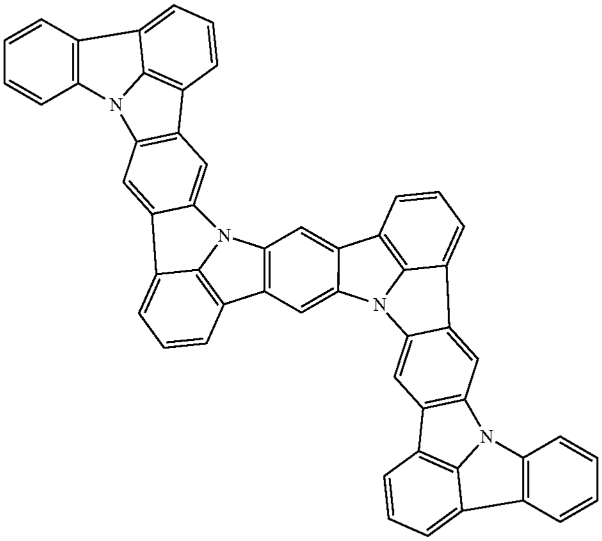
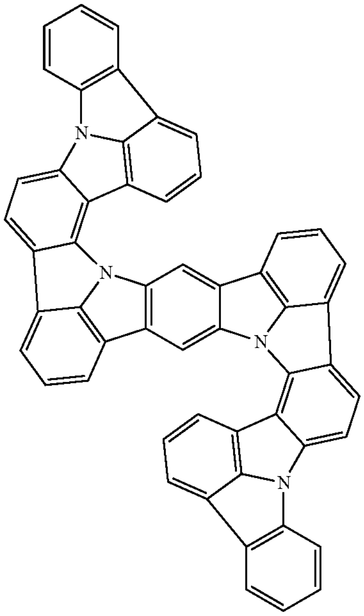
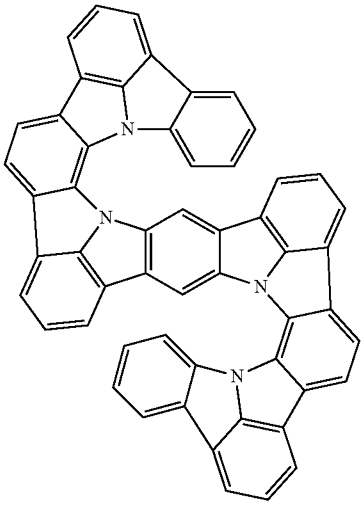
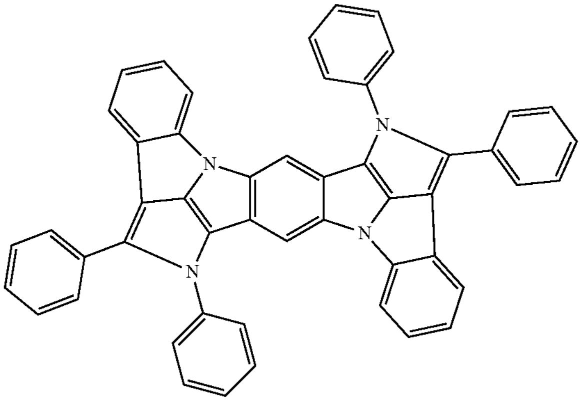
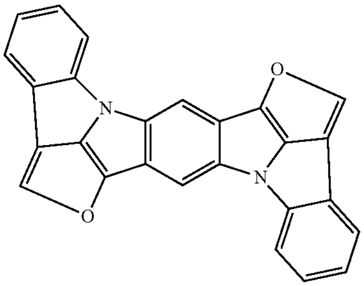

-continued
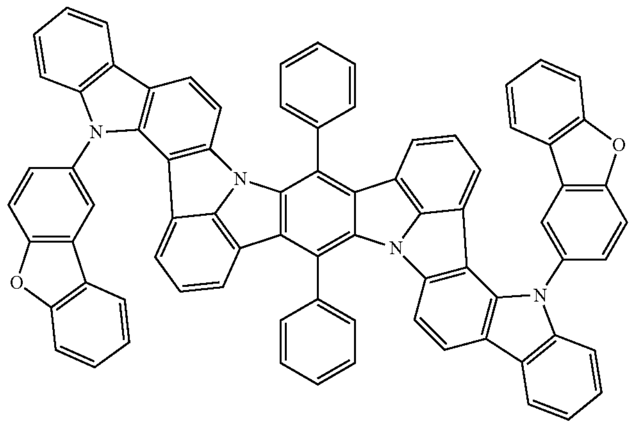
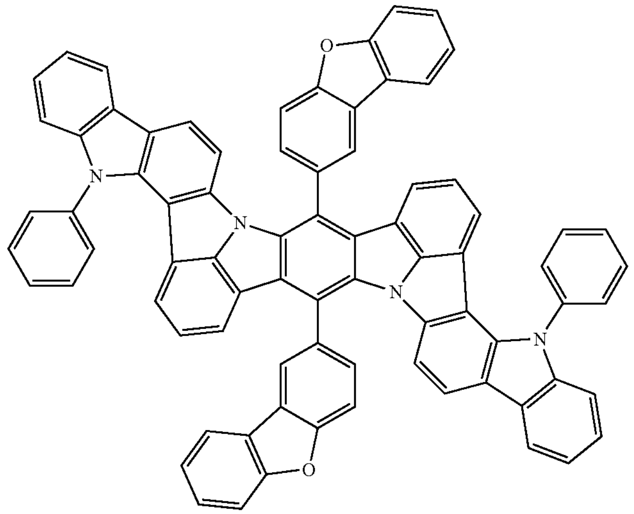
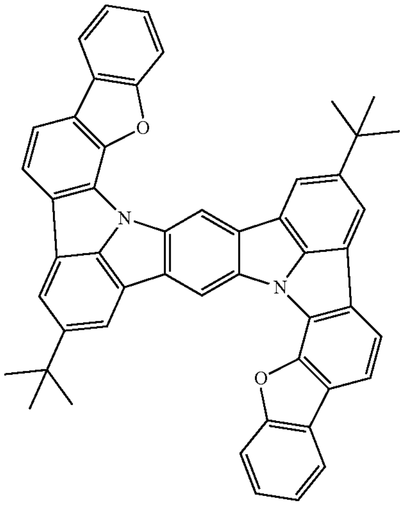
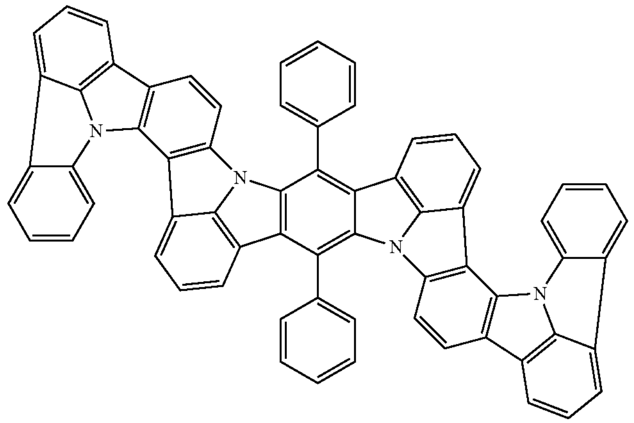

-continued

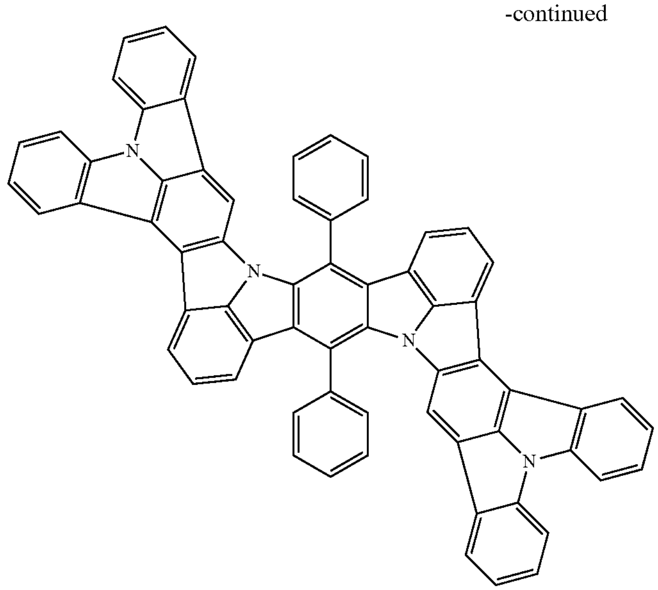

Compound Represented by Formula (6)

The compound represented by the formula (6) will be described.

[Formula 213]

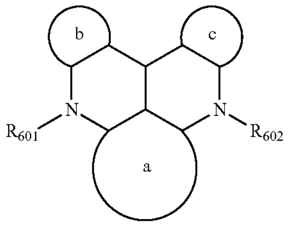

(6)

In the formula (6):

a ring, b ring and c ring are each independently a substituted or unsubstituted aromatic hydrocarbon ring having 6 to 50 ring carbon atoms, or a substituted or unsubstituted heterocycle having 5 to 50 ring atoms;

$R_{601}$ and $R_{602}$ are each independently bonded to the a ring, the b ring or the c ring to form a substituted or unsubstituted heterocycle, or not bonded to form no substituted or unsubstituted heterocycle; and $R_{601}$ and $R_{602}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The a ring, b ring and c ring are each a ring (a substituted or unsubstituted aromatic hydrocarbon ring having 6 to 50 ring carbon atoms, or a substituted or unsubstituted heterocycle having 5 to 50 ring atoms) fused with the fused bicyclic structure formed of a boron atom and two nitrogen atoms at the center of the formula (6).

The "aromatic hydrocarbon ring" for the a, b, and c rings has the same structure as the compound formed by introducing a hydrogen atom to the "aryl group" described above.

Ring atoms of the "aromatic hydrocarbon ring" for the a ring include three carbon atoms on the fused bicyclic structure at the center of the formula (6).

Ring atoms of the "aromatic hydrocarbon ring" for the b ring and the c ring include two carbon atoms on a fused bicyclic structure at the center of the formula (6).

Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the a, b, and c rings has the same structure as the compound formed by introducing a hydrogen atom to the "heterocyclic group" described above.

Ring atoms of the "heterocycle" for the a ring include three carbon atoms on the fused bicyclic structure at the center of the formula (6). Ring atoms of the "heterocycle" for the b ring and the c ring include two carbon atoms on a fused bicyclic structure at the center of the formula (6). Specific examples of the "substituted or unsubstituted heterocycle having 5 to 50 ring atoms" include a compound formed by introducing a hydrogen atom to the "heterocyclic group" described in the specific example group G2.

$R_{601}$ and $R_{602}$ are optionally each independently bonded with the a ring, b ring, or c ring to form a substituted or unsubstituted heterocycle. The "heterocycle" in this arrangement includes the nitrogen atom on the fused bicyclic structure at the center of the formula (6). The heterocycle in the above arrangement optionally includes a hetero atom other than the nitrogen atom. $R_{601}$ and $R_{602}$ bonded with the a ring, b ring, or c ring specifically means that atoms forming $R_{601}$ and $R_{602}$ are bonded with atoms forming the a ring, b ring, or c ring. For instance, $R_{601}$ may be bonded to the a ring to form a bicyclic (or tri-or-more cyclic) fused nitrogen-containing heterocycle, in which the ring including $R_{601}$ and the a ring are fused. Specific examples of the nitrogen-containing heterocycle include a compound corresponding to the nitrogen-containing bi(or-more)cyclic fused heterocyclic group in the specific example group G2.

The same applies to $R_{601}$ bonded with the b ring, $R_{602}$ bonded with the a ring, and $R_{602}$ bonded with the c ring.

In an exemplary embodiment, the a ring, b ring and c ring in the formula (6) are each independently a substituted or unsubstituted aromatic hydrocarbon ring having 6 to 50 ring carbon atoms.

In an exemplary embodiment, the a ring, b ring and c ring in the formula (6) are each independently a substituted or unsubstituted benzene ring or a substituted or unsubstituted naphthalene ring.

In an exemplary embodiment, $R_{601}$ and $R_{602}$ in the formula (6) are each independently a substituted or unsubstituted aryl group having 6 to 50 ring carbon atoms, or a substituted or unsubstituted heterocyclic group having 5 to 50 ring atoms, preferably a substituted or unsubstituted aryl group having 6 to 50 ring carbon atoms.

In an exemplary embodiment, the compound represented by the formula (6) is a compound represented by a formula (62) below.

[Formula 214]

(62)

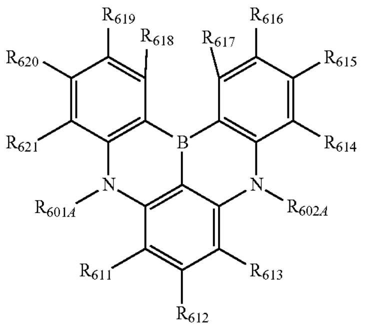

In the formula (62):

$R_{601A}$ is bonded with at least one of $R_{611}$ or $R_{621}$ to form a substituted or unsubstituted heterocycle or not bonded to form no substituted or unsubstituted heterocycle;

$R_{602A}$ is bonded with at least one of $R_{613}$ or $R_{614}$ to form a substituted or unsubstituted heterocycle or not bonded to form no substituted or unsubstituted heterocycle;

$R_{601A}$ and $R_{602A}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

at least one combination of adjacent two or more of $R_{611}$ to $R_{621}$ are mutually bonded to form a substituted or unsubstituted monocyclic ring, mutually bonded to form a substituted or unsubstituted fused ring, or not mutually bonded; and $R_{611}$ to $R_{621}$ not forming the substituted or unsubstituted heterocycle, not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

$R_{601A}$ and $R_{602A}$ in the formula (62) are groups corresponding to $R_{601}$ and $R_{602}$ in the formula (6), respectively.

For instance, $R_{601A}$ and $R_{611}$ are optionally bonded with each other to form a bicyclic (or tri-or-more cyclic) fused nitrogen-containing heterocycle, in which the ring including $R_{601A}$ and $R_{611}$ and a benzene ring corresponding to the a ring are fused. Specific examples of the nitrogen-containing heterocycle include a compound corresponding to the nitrogen-containing bi(or-more)cyclic fused heterocyclic group in the specific example group G2. The same applies to $R_{601A}$ bonded with $R_{621}$, $R_{602A}$ bonded with $R_{613}$, and $R_{602A}$ bonded with $R_{614}$.

At least one combination of adjacent two or more of $R_{611}$ to $R_{621}$ are optionally mutually bonded to form a substituted or unsubstituted monocyclic ring, or mutually bonded to form a substituted or unsubstituted fused ring.

For instance, $R_{611}$ and $R_{612}$ are optionally mutually bonded to form a structure in which a benzene ring, indole ring, pyrrole ring, benzofuran ring, benzothiophene ring or the like is fused to the six-membered ring bonded with $R_{611}$ and $R_{612}$, the resultant fused ring forming a naphthalene ring, carbazole ring, indole ring, dibenzofuran ring, or dibenzothiophene ring, respectively.

In an exemplary embodiment, $R_{611}$ to $R_{621}$ not contributing to ring formation are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$ not contributing to ring formation are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$ not contributing to ring formation are each independently a hydrogen atom, or a substituted or unsubstituted alkyl group having 1 to 50 carbon atoms.

In an exemplary embodiment, $R_{611}$ to $R_{621}$ not contributing to ring formation are each independently a hydrogen atom, or a substituted or unsubstituted alkyl group having 1 to 50 carbon atoms, and at least one of $R_{611}$ to $R_{621}$ is a substituted or unsubstituted alkyl group having 1 to 50 carbon atoms.

In an exemplary embodiment, the compound represented by the formula (62) is a compound represented by a formula (63) below.

[Formula 215]

(63)

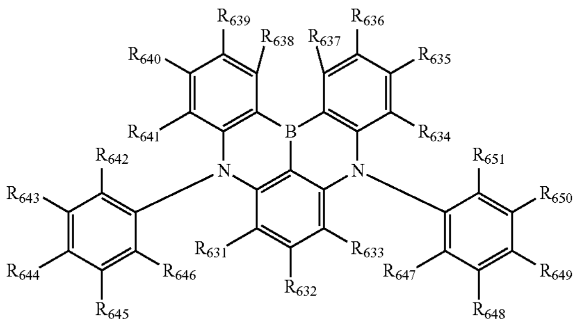

In the formula (63):

$R_{631}$ is bonded with $R_{646}$ to form a substituted or unsubstituted heterocycle or not bonded to form no substituted or unsubstituted heterocycle;

$R_{633}$ is bonded with $R_{647}$ to form a substituted or unsubstituted heterocycle or not bonded to form no substituted or unsubstituted heterocycle;

$R_{634}$ is bonded with $R_{651}$ to form a substituted or unsubstituted heterocycle or not bonded to form no substituted or unsubstituted heterocycle;

$R_{641}$ is bonded with $R_{642}$ to form a substituted or unsubstituted heterocycle or not bonded to form no substituted or unsubstituted heterocycle;

at least one combination of adjacent two or more of $R_{631}$ to $R_{651}$ are mutually bonded to form a substituted or unsubstituted monocyclic ring, mutually bonded to form a substituted or unsubstituted fused ring, or not mutually bonded; and $R_{631}$ to $R_{651}$ not forming the substituted or unsubstituted heterocycle, not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

$R_{631}$ are optionally mutually bonded with $R_{646}$ to form a substituted or unsubstituted heterocycle. For instance, $R_{631}$ and $R_{646}$ are optionally bonded with each other to form a tri-or-more cyclic fused nitrogen-containing heterocycle, in which a benzene ring bonded with $R_{646}$, a ring including a nitrogen atom, and a benzene ring corresponding to the a ring are fused. Specific examples of the nitrogen-containing heterocycle include a compound corresponding to the nitrogen-containing tri(-or-more)cyclic fused heterocyclic group in the specific example group G2. The same applies to $R_{633}$ bonded with $R_{647}$, $R_{634}$ bonded with $R_{651}$, and $R_{641}$ bonded with $R_{642}$.

In an exemplary embodiment, $R_{631}$ to $R_{651}$ not contributing to ring formation are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$ not contributing to ring formation are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$ not contributing to ring formation are each independently a hydrogen atom, or a substituted or unsubstituted alkyl group having 1 to 50 carbon atoms.

In an exemplary embodiment, $R_{631}$ to $R_{651}$ not contributing to ring formation are each independently a hydrogen atom, or a substituted or unsubstituted alkyl group having 1 to 50 carbon atoms, and at least one of $R_{631}$ to $R_{651}$ is a substituted or unsubstituted alkyl group having 1 to 50 carbon atoms.

In an exemplary embodiment, the compound represented by the formula (63) is a compound represented by a formula (63A) below.

[Formula 216]

(63A)

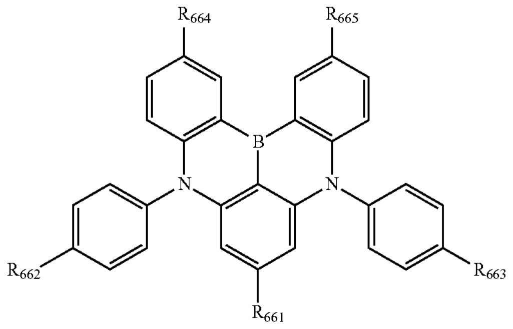

In the formula (63A):

$R_{661}$ is a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{662}$ to $R_{665}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, $R_{661}$ to $R_{665}$ are each independently a substituted or unsubstituted alkyl group having 1 to 50 carbon atoms, or a substituted or unsubstituted aryl group having 6 to 50 ring carbon atoms.

In an exemplary embodiment, $R_{661}$ to $R_{665}$ are each independently a substituted or unsubstituted alkyl group having 1 to 50 carbon atoms.

In an exemplary embodiment, the compound represented by the formula (63) is a compound represented by a formula (63B) below.

[Formula 217]

(63B)

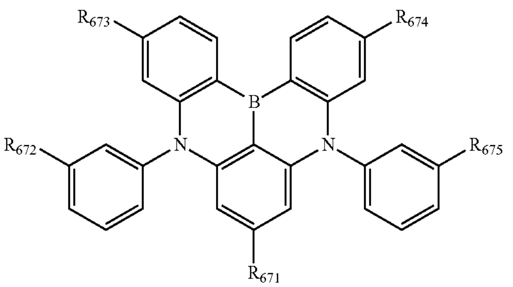

In the formula (63B):

$R_{671}$ and $R_{672}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms; and $R_{673}$ to $R_{675}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms.

In an exemplary embodiment, the compound represented by the formula (63) is a compound represented by a formula (63B') below.

[Formula 218]

(63B')

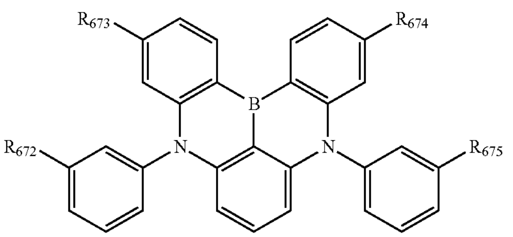

In the formula (63B'), $R_{672}$ to $R_{675}$ each independently represent the same as $R_{672}$ to $R_{675}$ in the formula (63B).

In an exemplary embodiment, at least one of $R_{671}$ to $R_{675}$ is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —N($R_{906}$)($R_{907}$), or a substituted or unsubstituted aryl group having 6 to 50 ring carbon atoms.

In an exemplary embodiment: $R_{672}$ is a hydrogen atom, a substituted or unsubstituted alkyl group having 1 to 50 carbon atoms, a group represented by —N($R_{906}$)($R_{907}$), or a substituted or unsubstituted aryl group having 6 to 50 ring carbon atoms; and $R_{671}$ and $R_{673}$ to $R_{675}$ are each independently a substituted or unsubstituted alkyl group having 1 to 50 carbon atoms, a group represented by —N($R_{906}$)($R_{907}$), or a substituted or unsubstituted aryl group having 6 to 50 ring carbon atoms.

In an exemplary embodiment, the compound represented by the formula (63) is a compound represented by a formula (63C) below.

[Formula 219]

(63C)

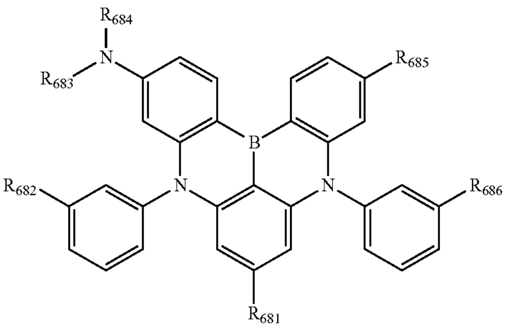

In the formula (63C):

$R_{681}$ and $R_{682}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{683}$ to $R_{686}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, the compound represented by the formula (63) is a compound represented by a formula (63C') below.

[Formula 220]

(63C')

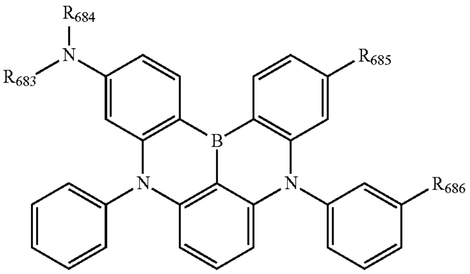

In the formula (63C'), $R_{683}$ to $R_{686}$ each independently represent the same as $R_{683}$ to $R_{686}$ in the formula (63C).

In an exemplary embodiment, $R_{681}$ to $R_{686}$ are each independently a substituted or unsubstituted alkyl group having 1 to 50 carbon atoms, or a substituted or unsubstituted aryl group having 6 to 50 ring carbon atoms.

In an exemplary embodiment, $R_{681}$ to $R_{686}$ are each independently a substituted or unsubstituted aryl group having 6 to 50 ring carbon atoms.

The compound represented by the formula (6) is producible by initially bonding the a ring, b ring and c ring with linking groups (a group including N—$R_{601}$ and a group including N—$R_{602}$) to form an intermediate (first reaction), and bonding the a ring, b ring and c ring with a linking group (a group including a boron atom) to form a final product (second reaction). In the first reaction, an amination reaction (e.g. Buchwald-Hartwig reaction) is applicable. In the second reaction, Tandem Hetero-Friedel-Crafts Reactions or the like is applicable.

Specific examples of the compound represented by the formula (6) are shown below. It should however be noted that these specific examples are merely exemplary and do not limit the compound represented by the formula (6).

[Formula 221]

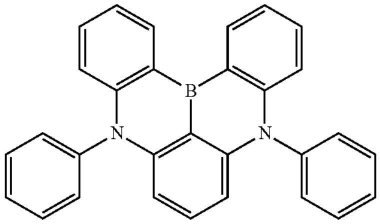

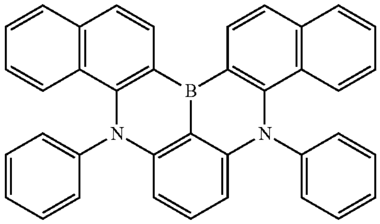

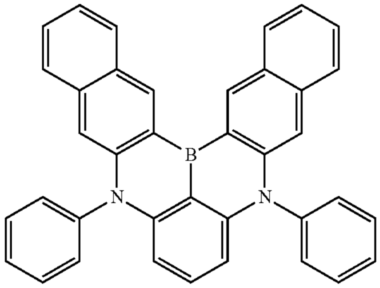

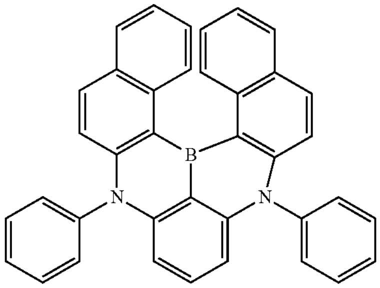

-continued

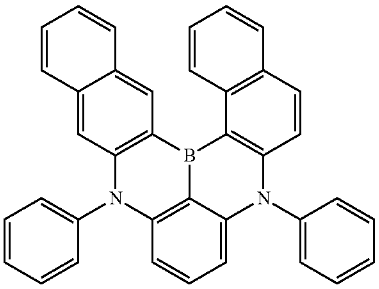

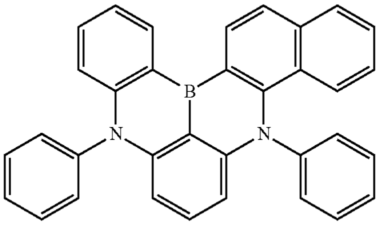

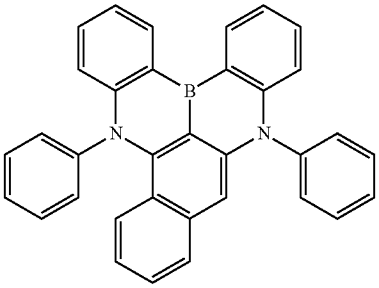

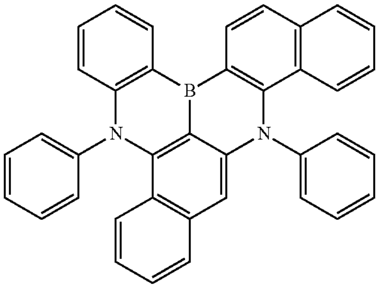

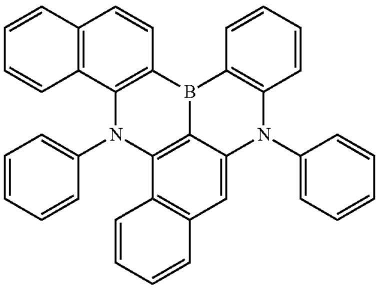

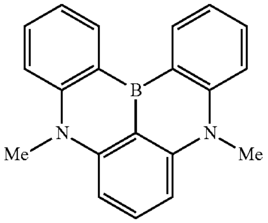

-continued
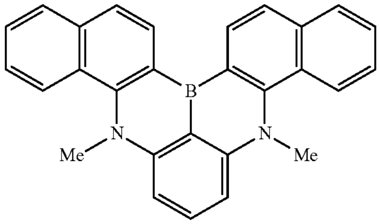
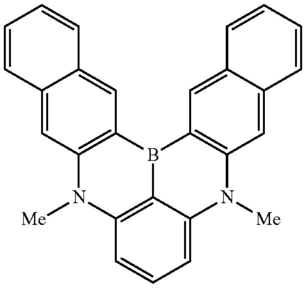
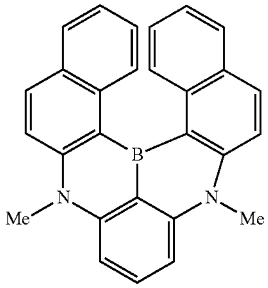
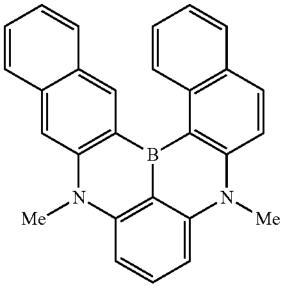
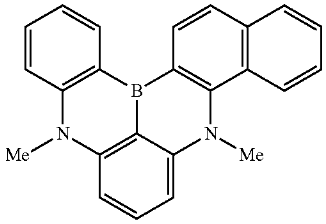
-continued
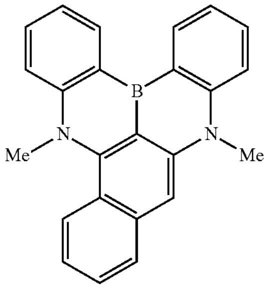
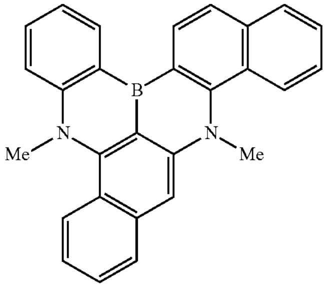
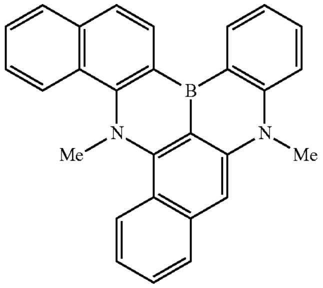
[Formula 222]
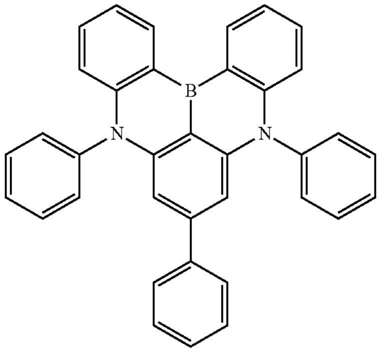
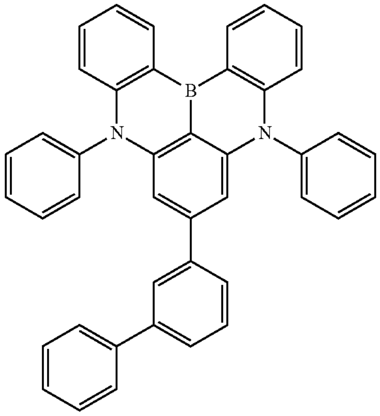

-continued
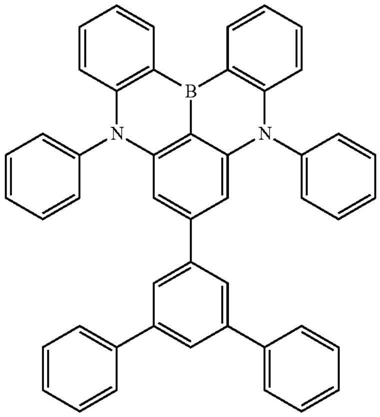
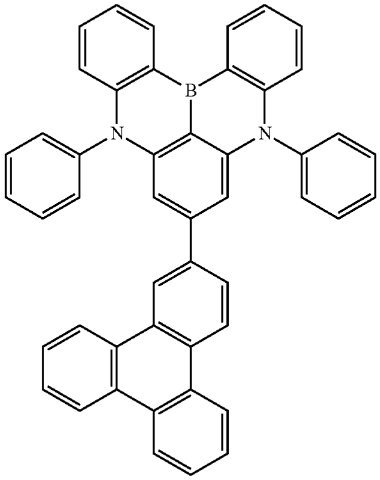
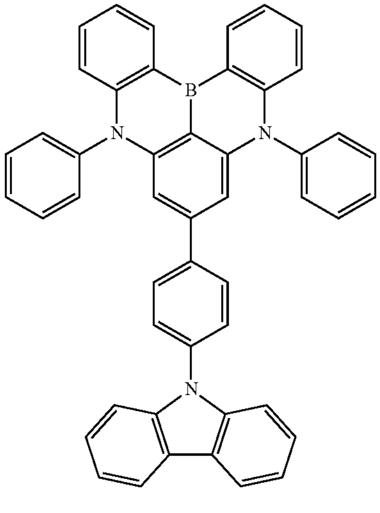
-continued
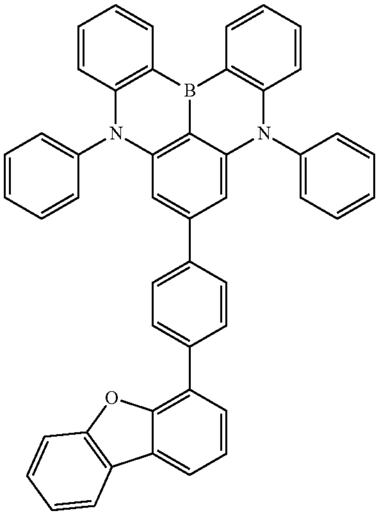
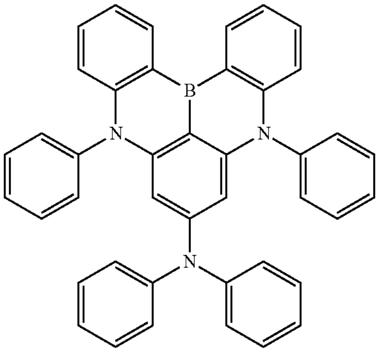
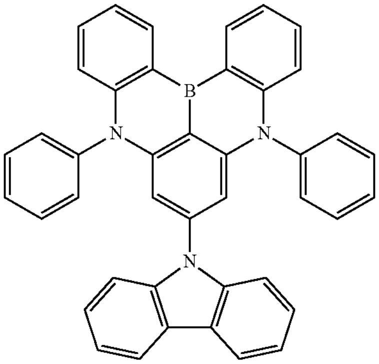
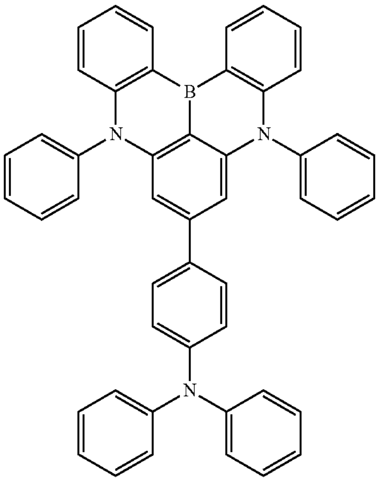

-continued
[Formula 223]
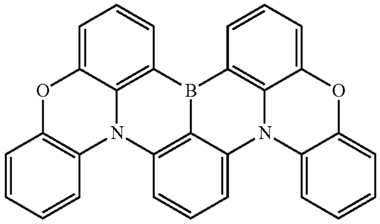
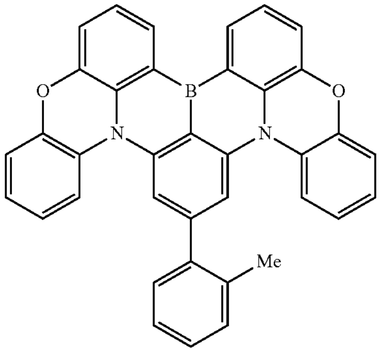
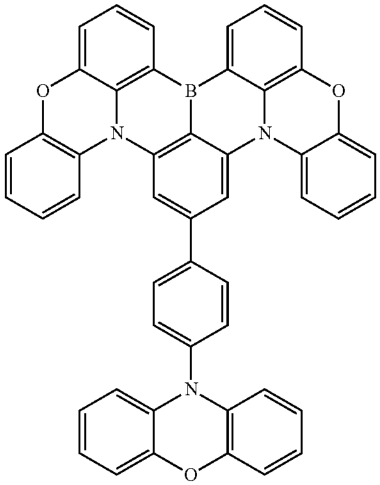
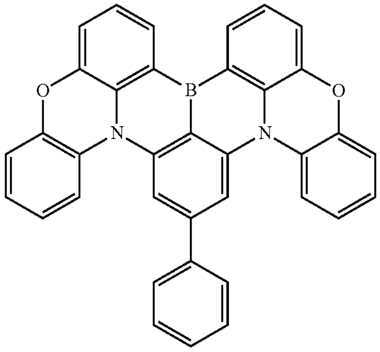
-continued
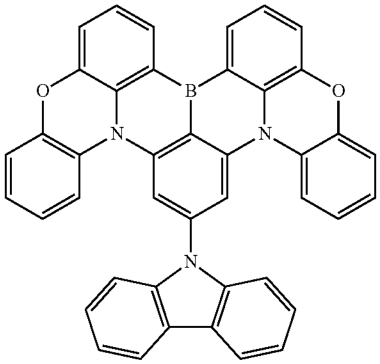
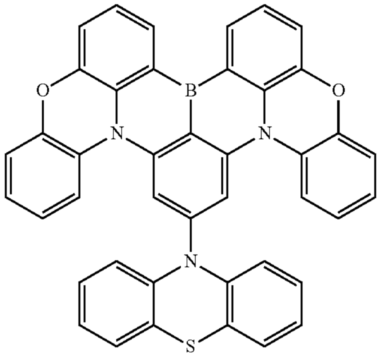
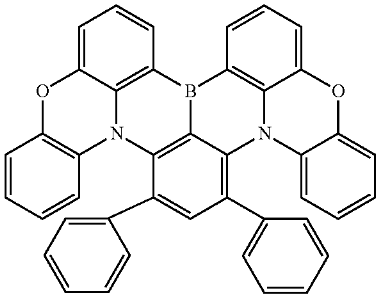
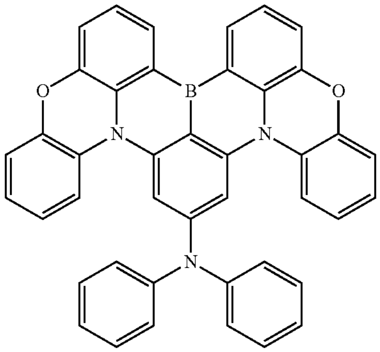

-continued
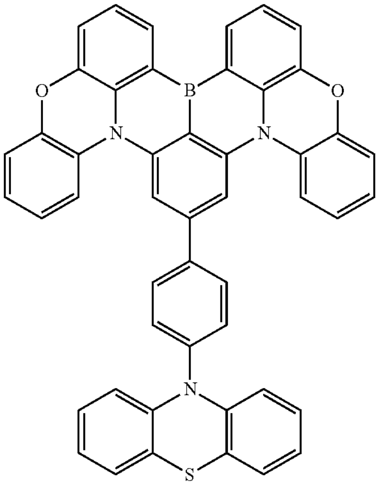
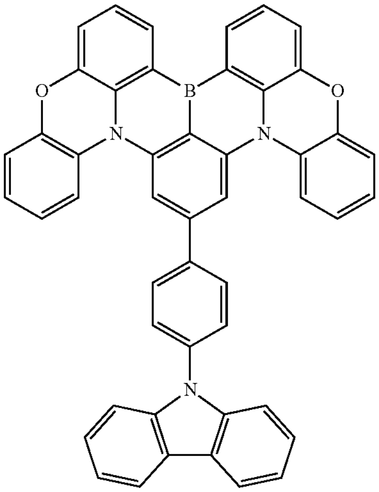
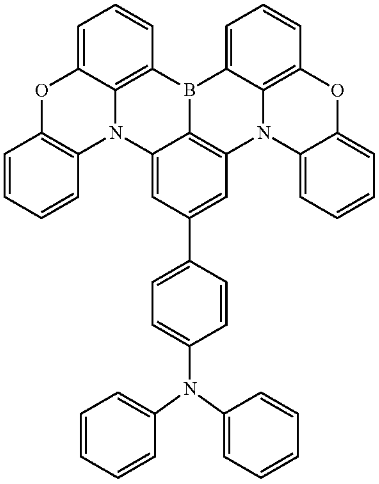
-continued
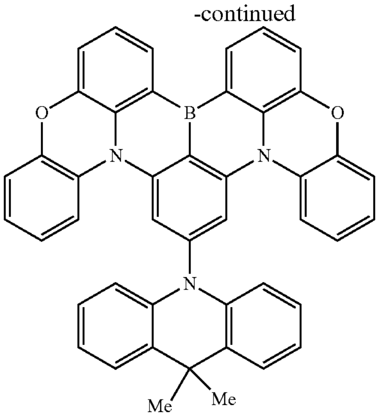
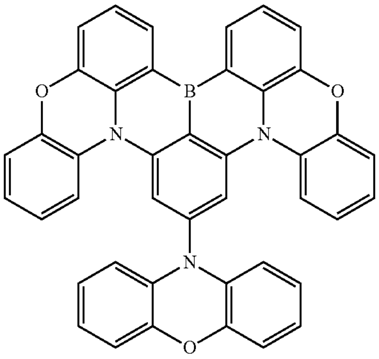
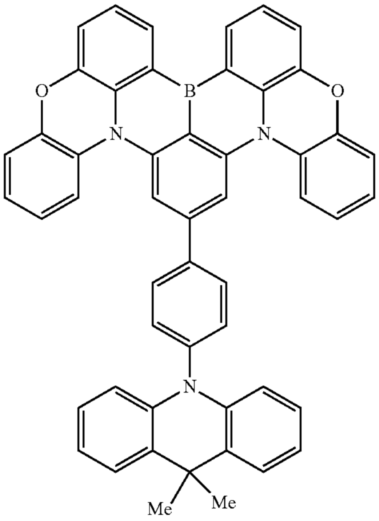
[Formula 224]
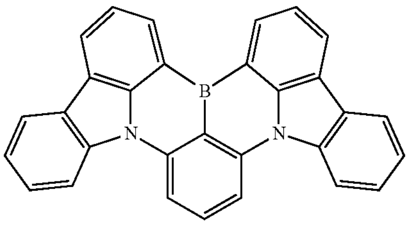

-continued
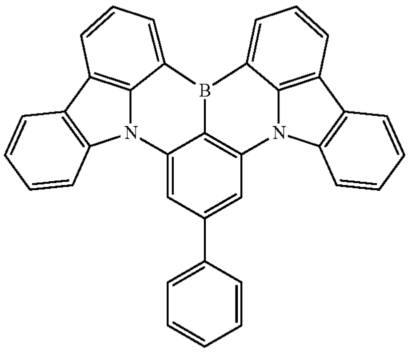
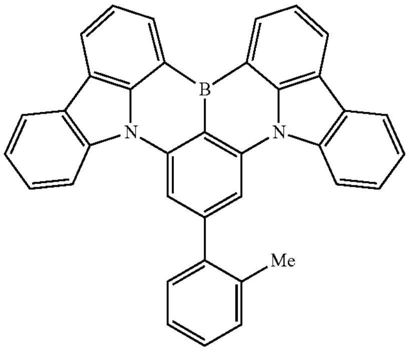
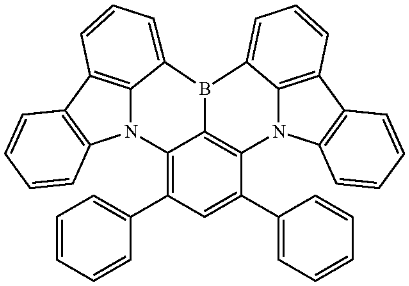
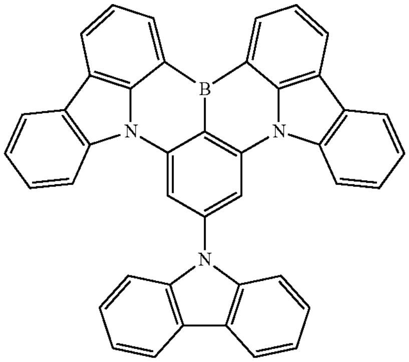
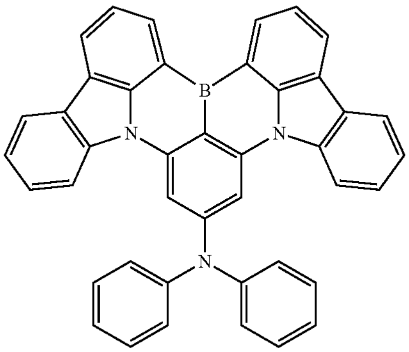
-continued
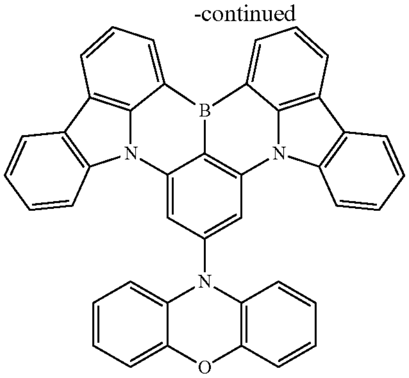
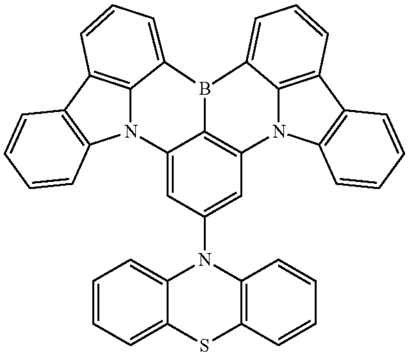
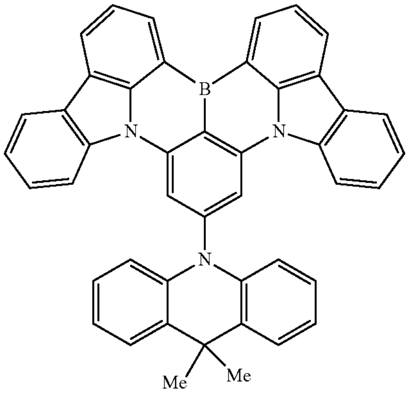
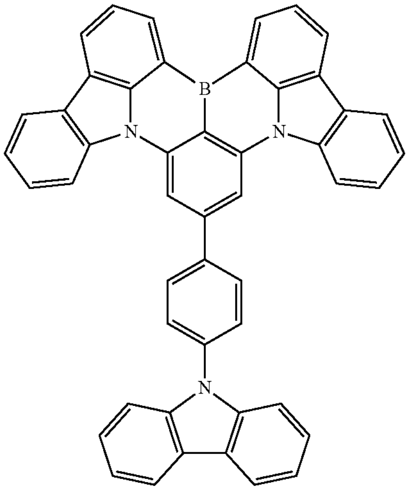

-continued
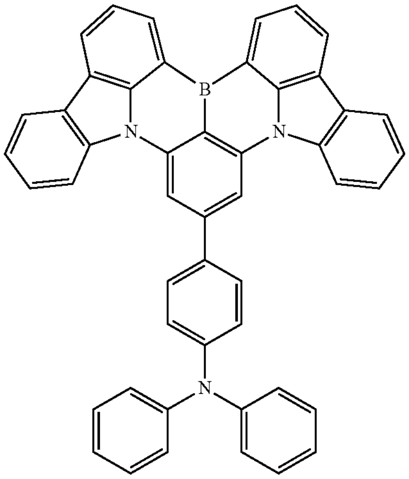
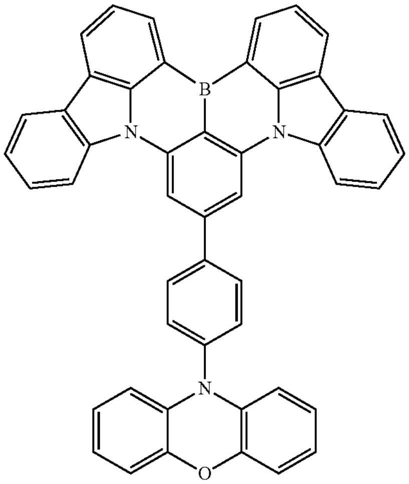
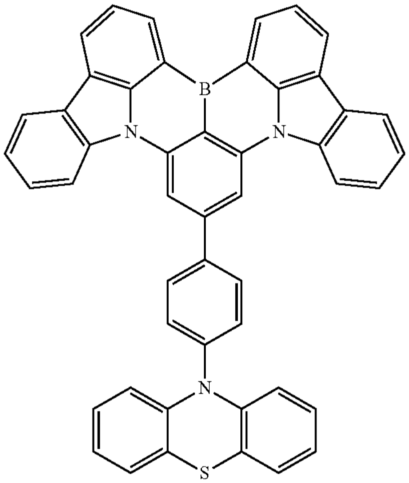
-continued
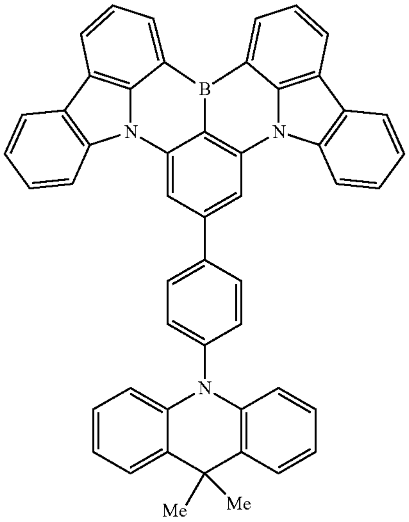
[Formula 225]
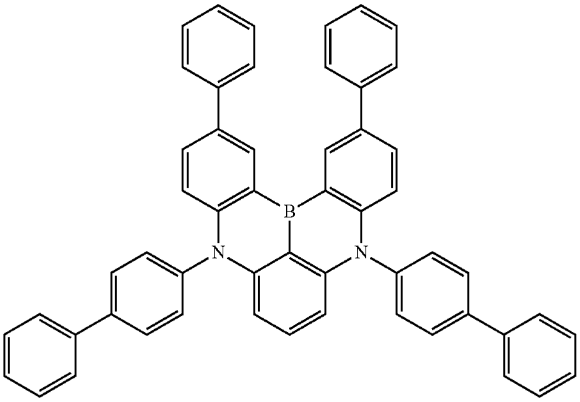
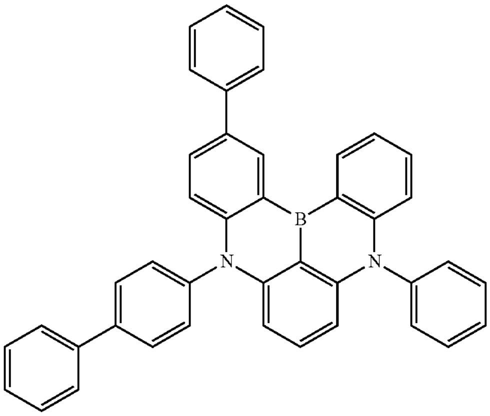
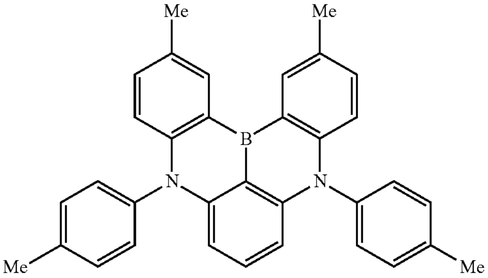

-continued
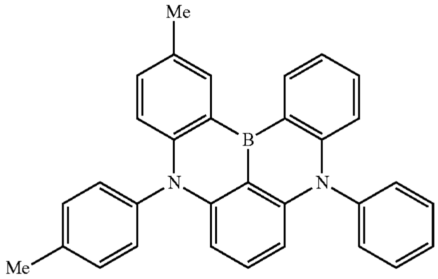
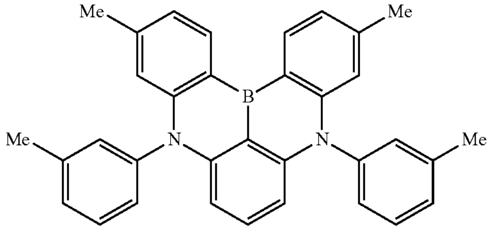
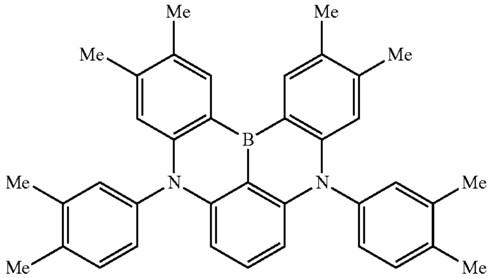
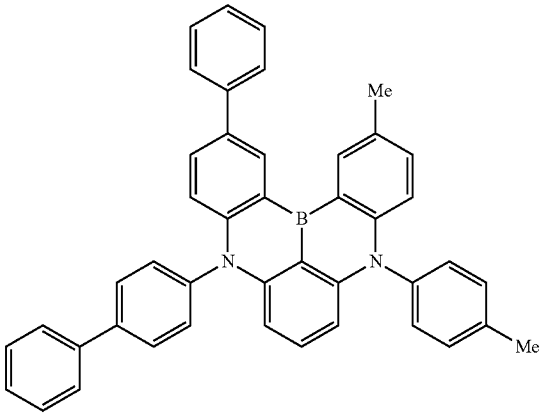
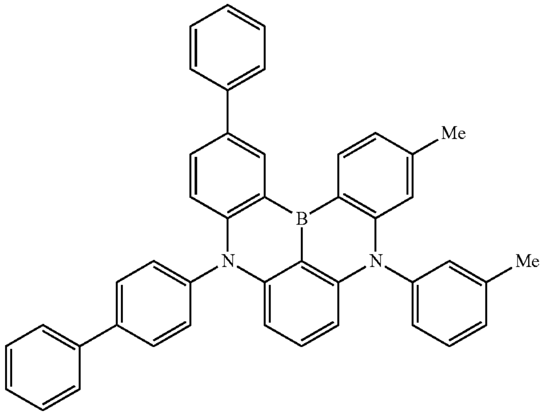
-continued
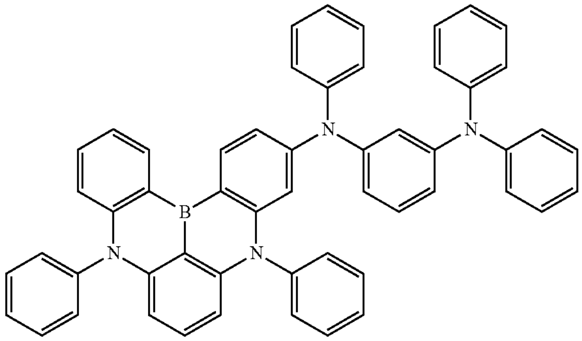
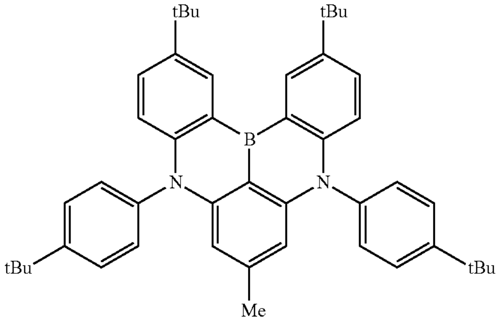
[Formula 226]
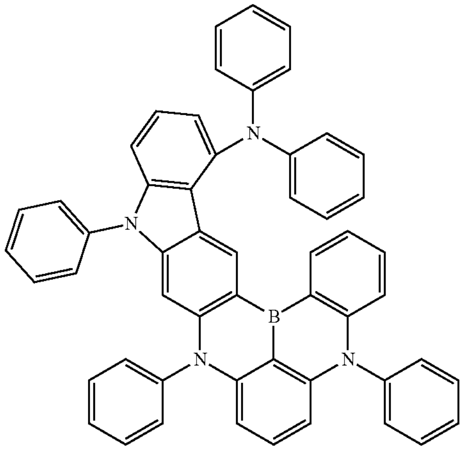
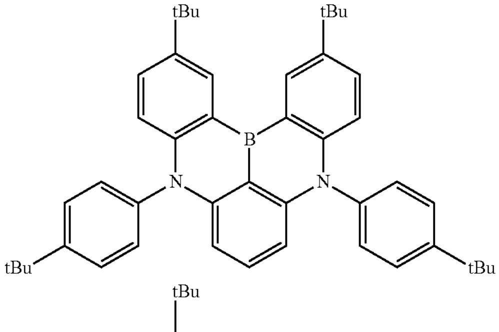
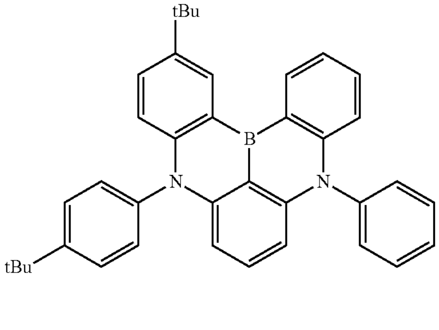

-continued
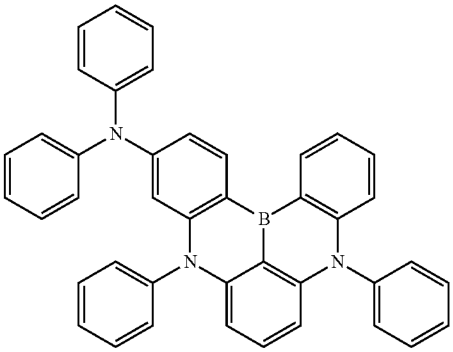
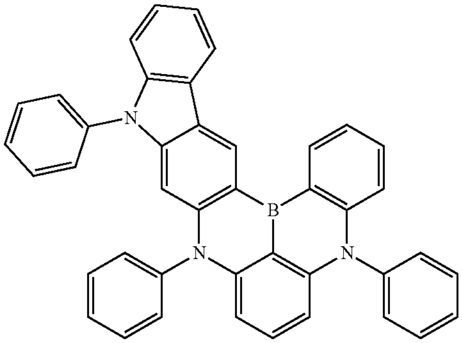
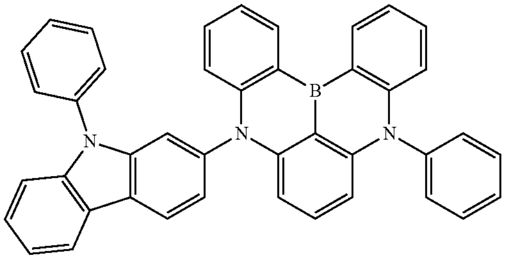
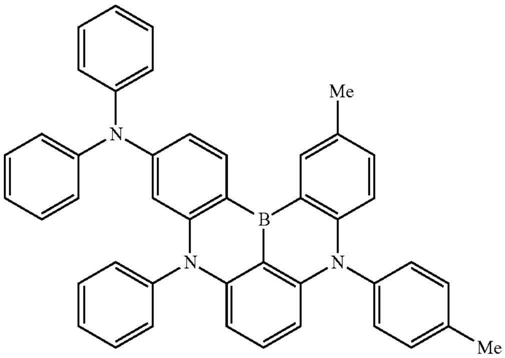
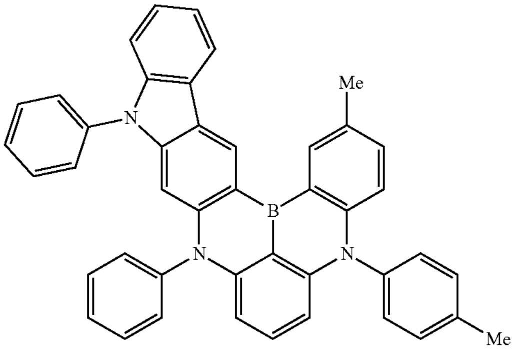
-continued
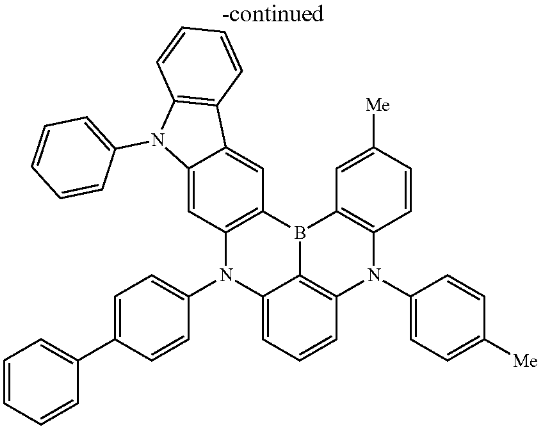
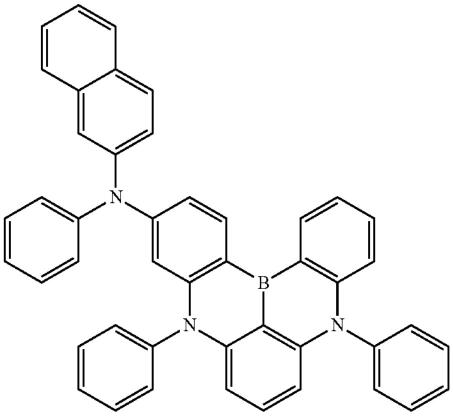 [SMILES: c1ccc(N(c2ccc3c(c2)N(c2ccccc2)c2cccc4c2B3c2ccccc2N4c2ccccc2)c2ccc3ccccc3c2)cc1]
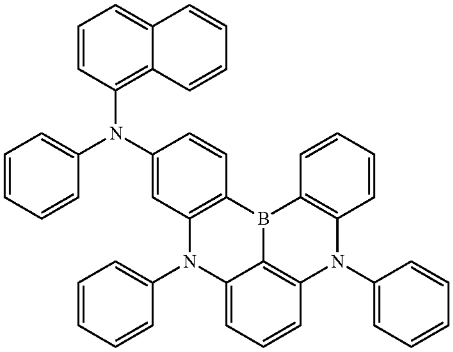
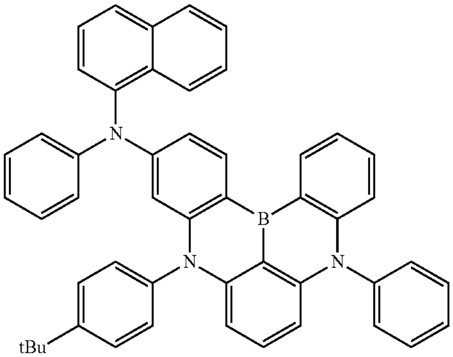

-continued
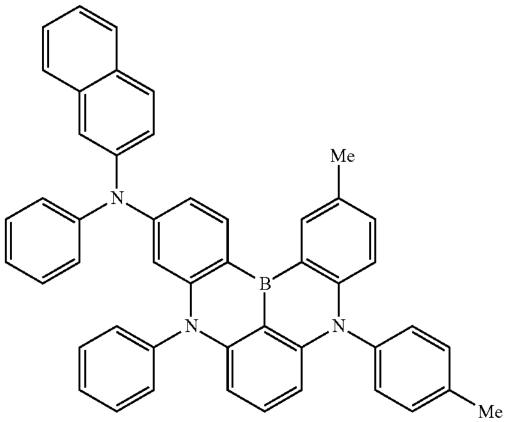
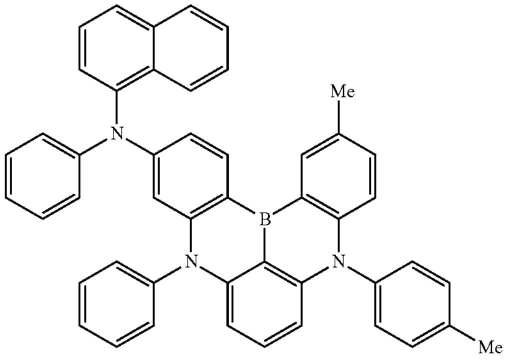
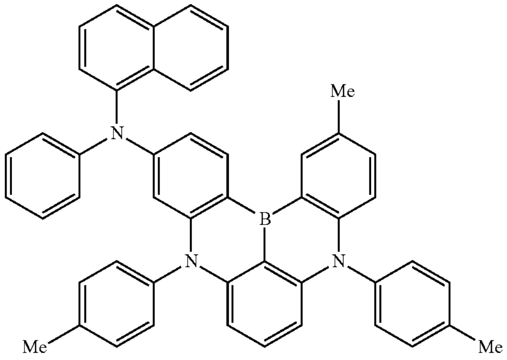
[Formula 227]
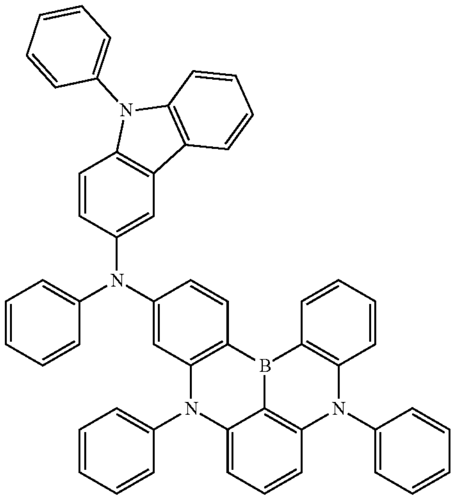
-continued
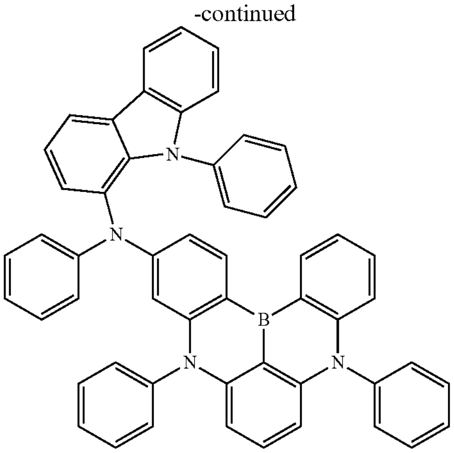
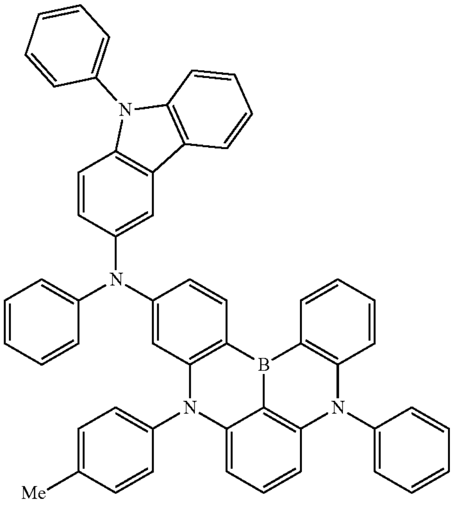
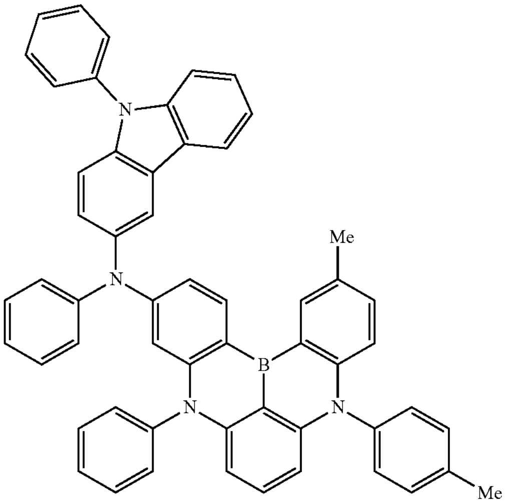

-continued
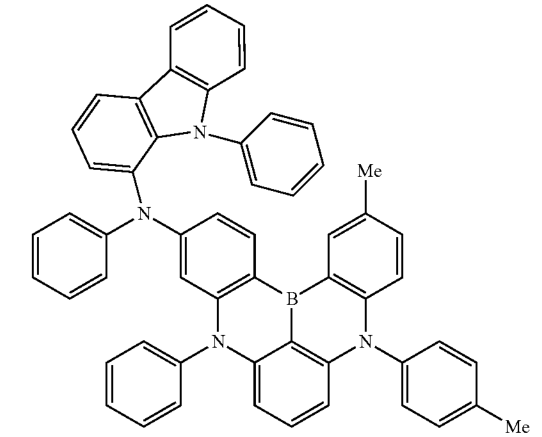
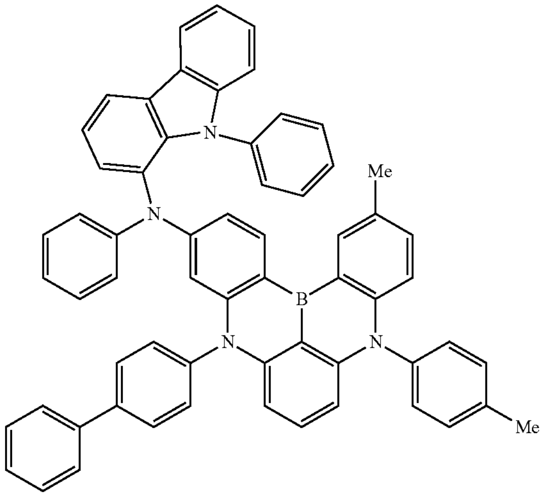
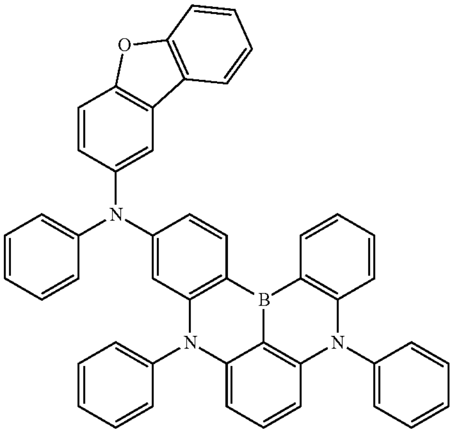
-continued
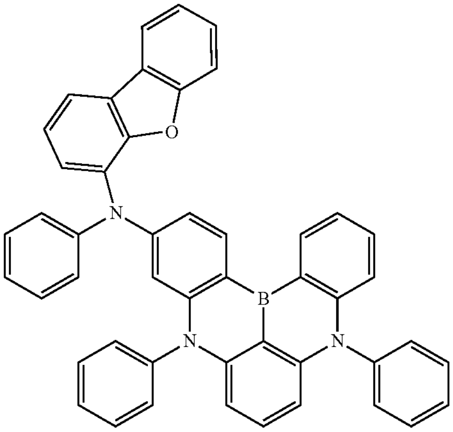
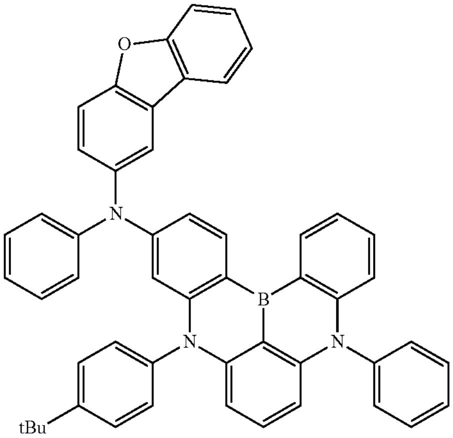
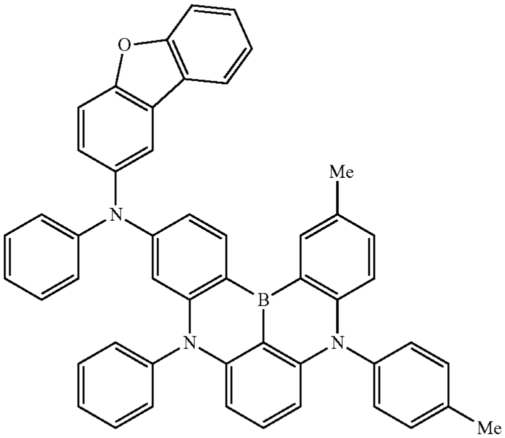

-continued
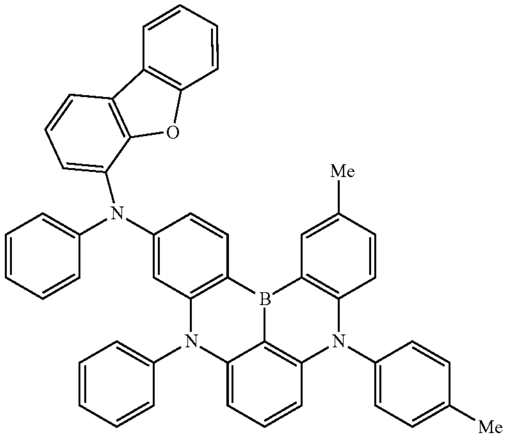
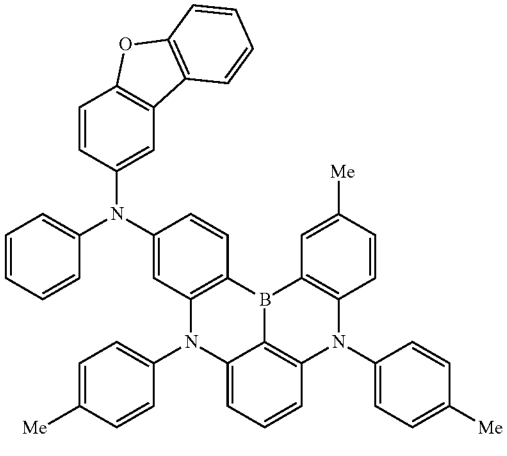
[Formula 228]
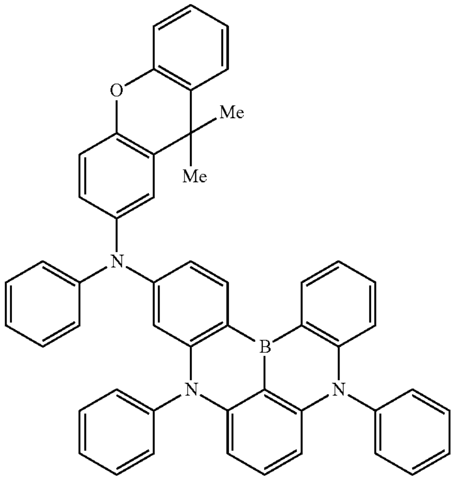
-continued
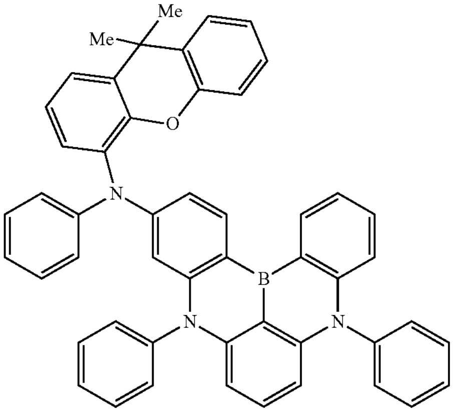
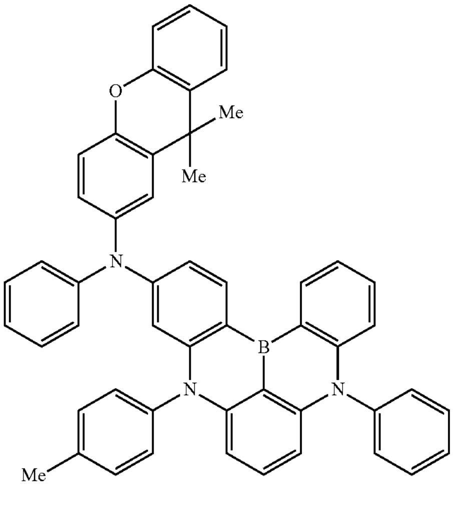
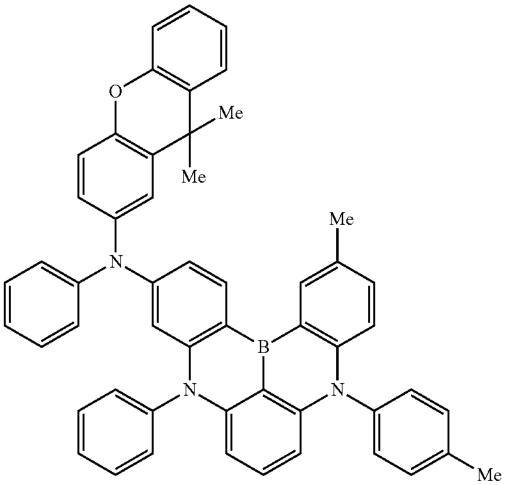

-continued
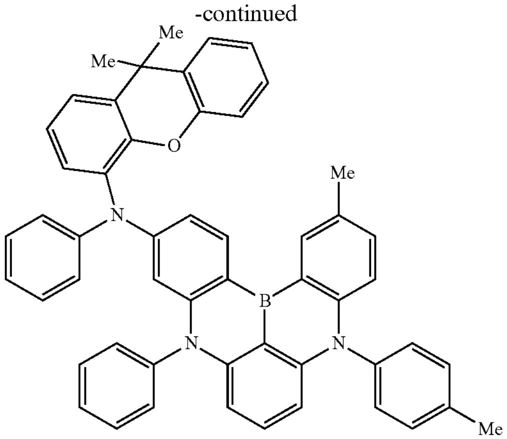
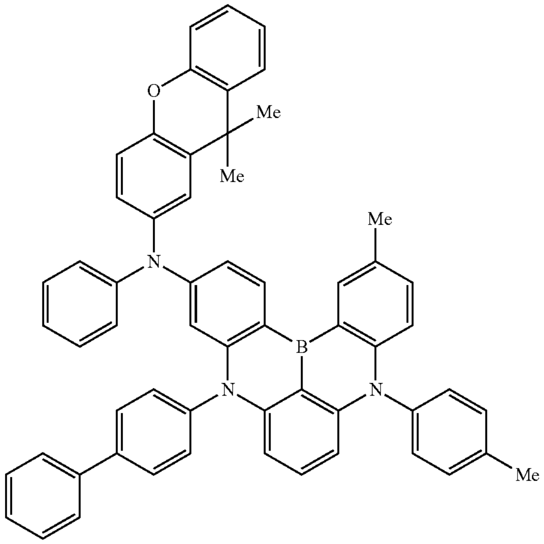
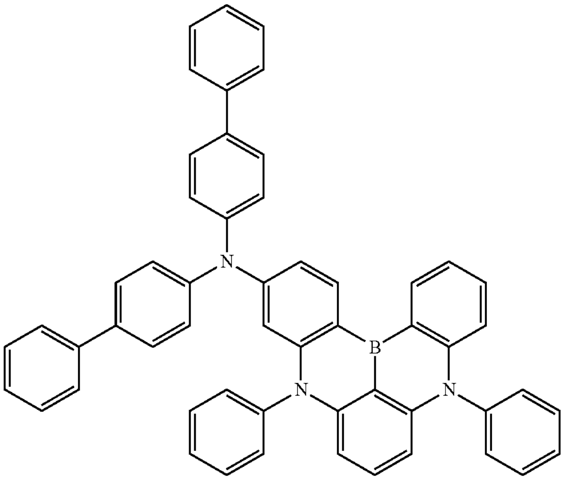
-continued
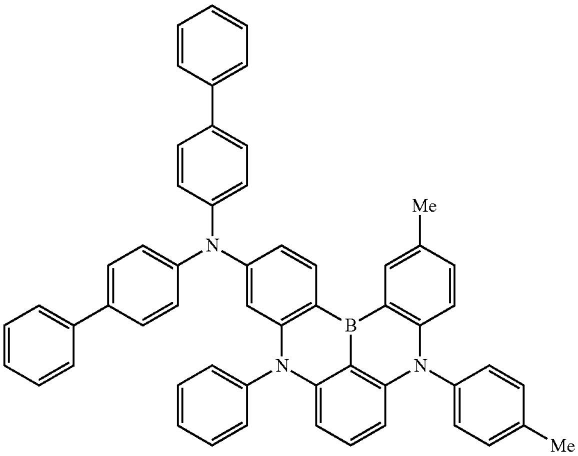
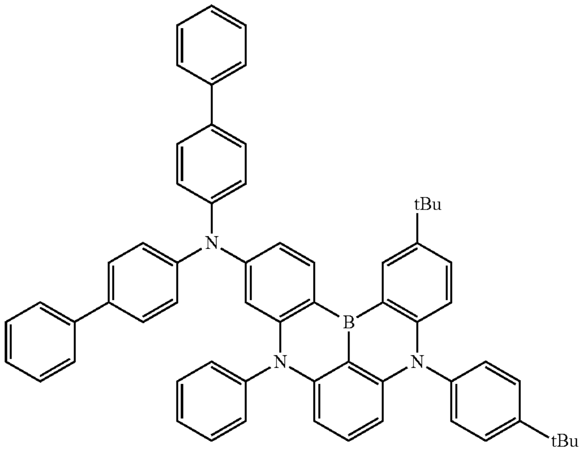
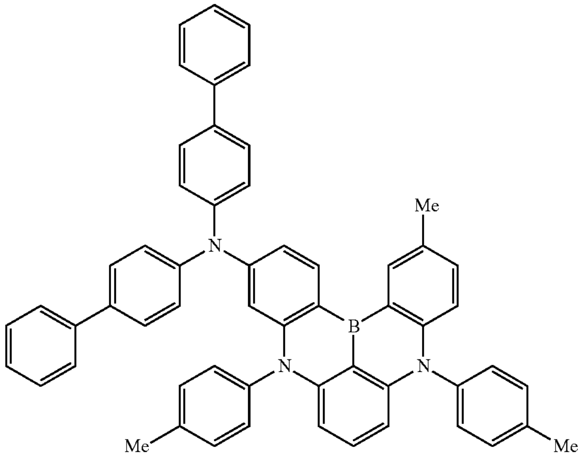
[Formula 229]
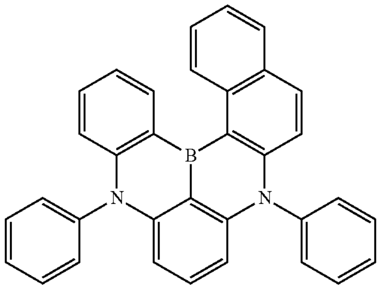

-continued
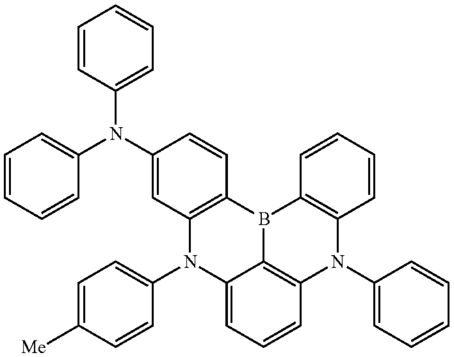
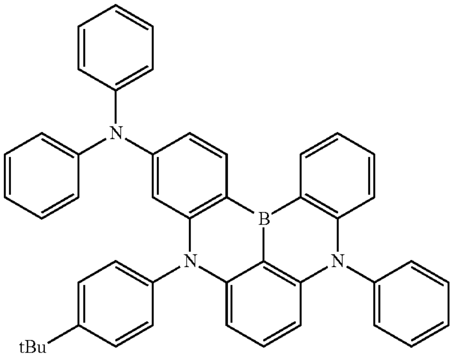
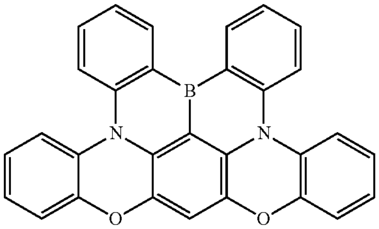
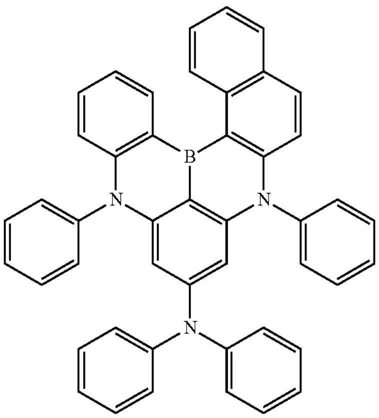
-continued
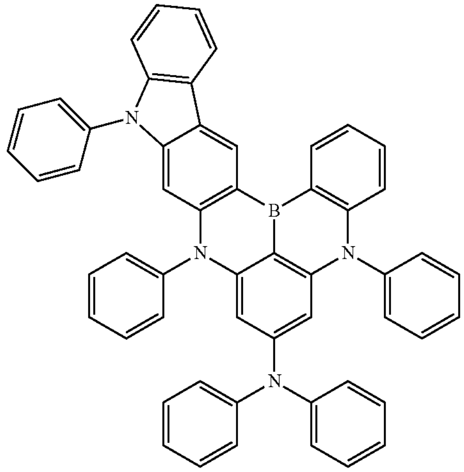
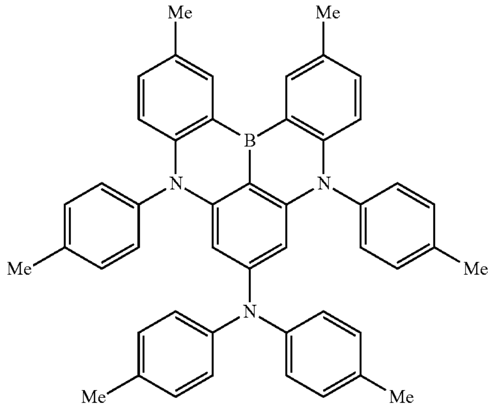
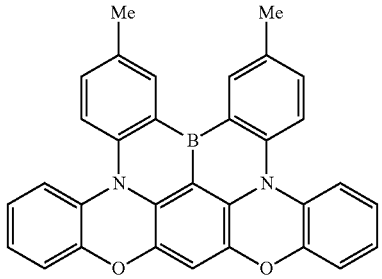
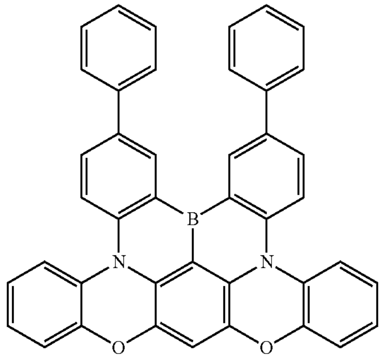

-continued
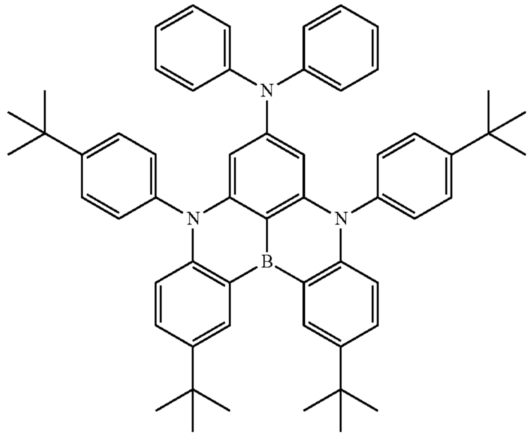
[Formula 230]
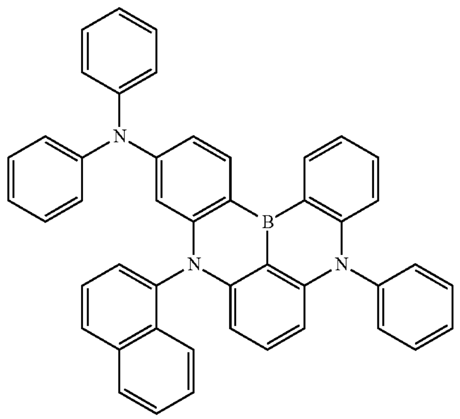
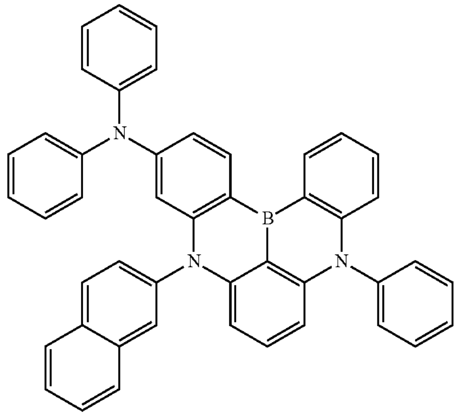
-continued
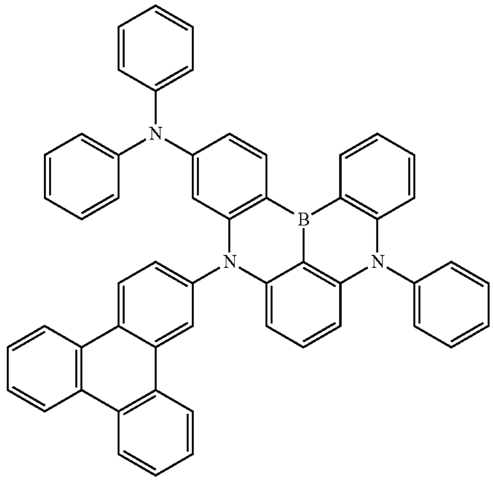
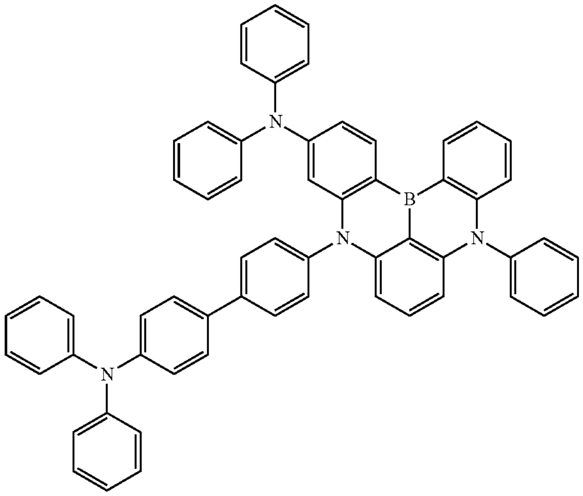
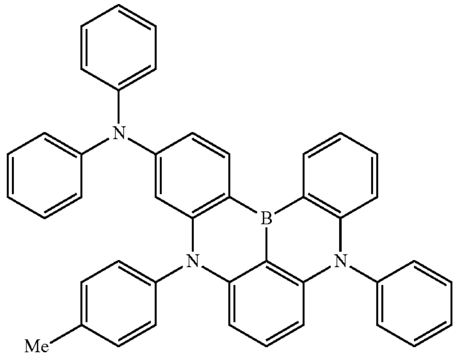
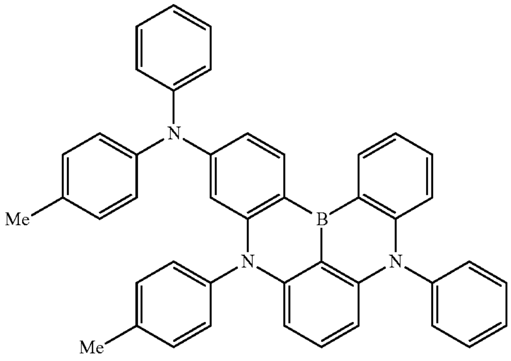

-continued
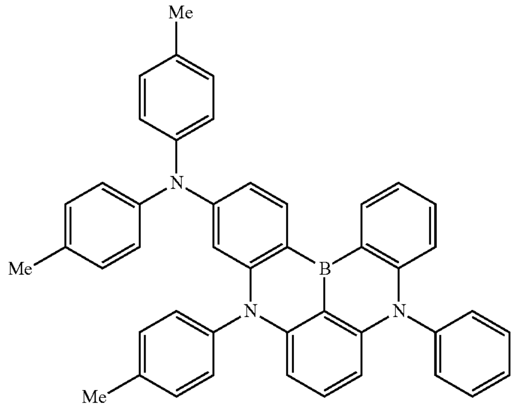
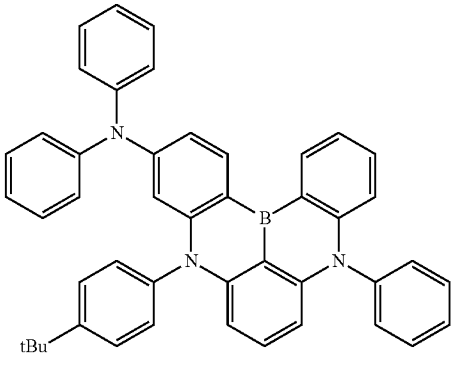
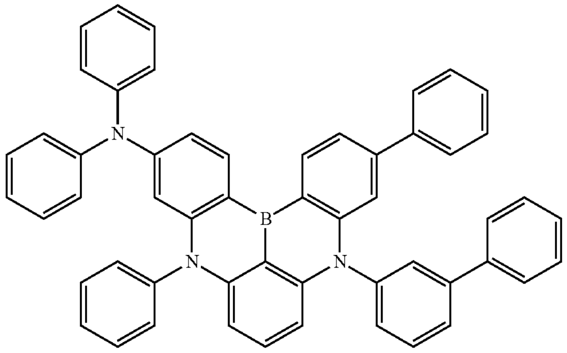
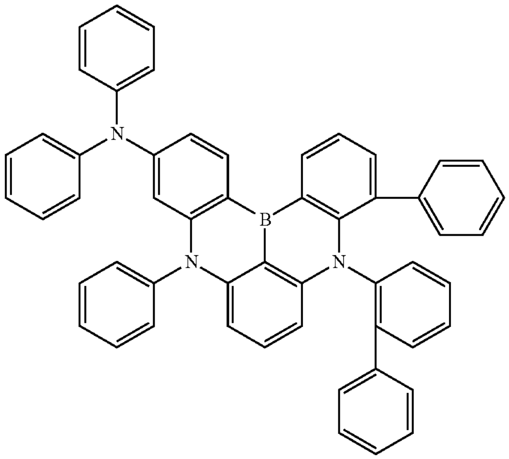
-continued
[Formula 231]
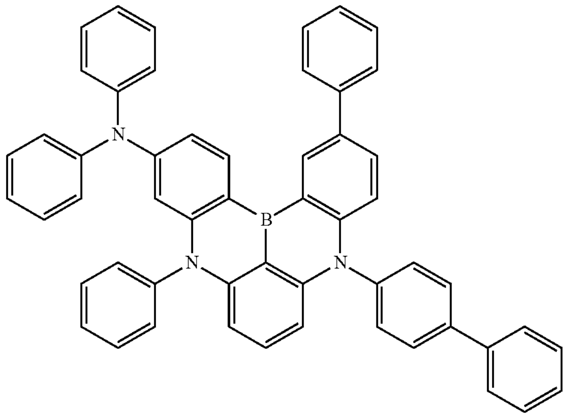
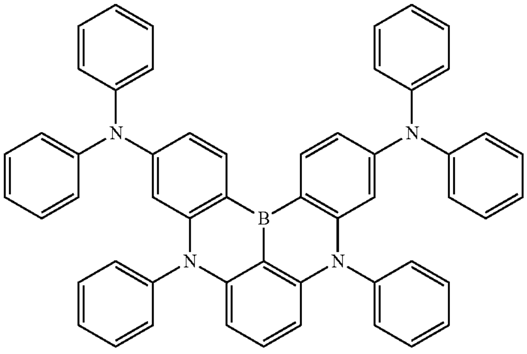
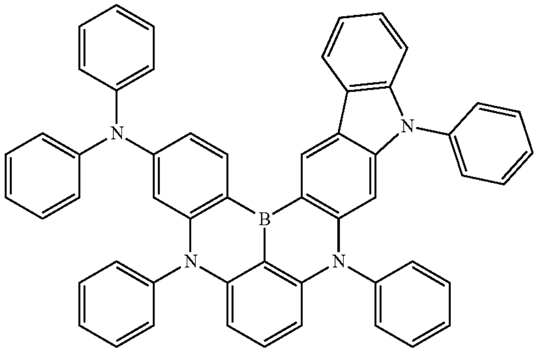
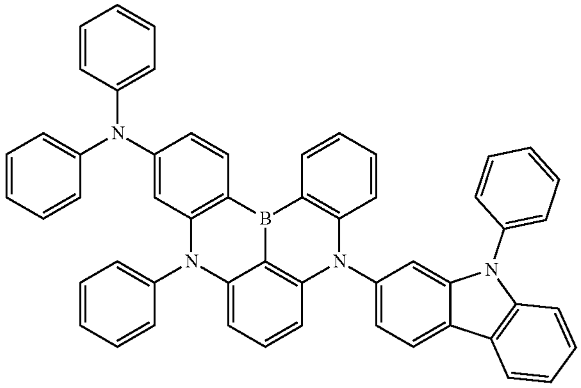

-continued
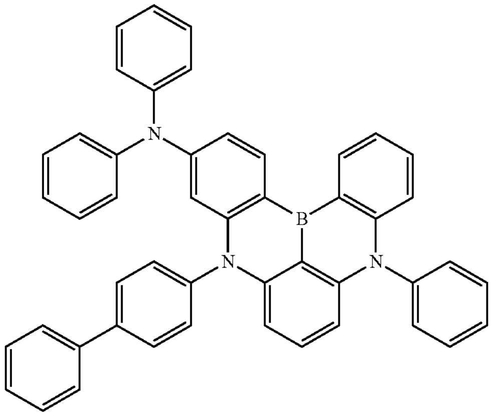
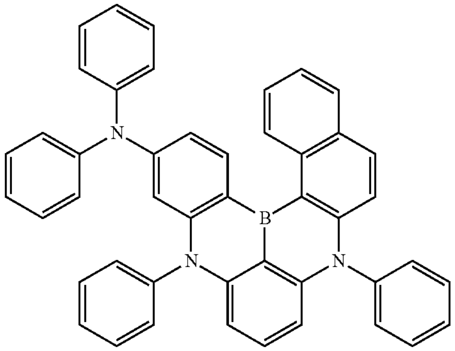
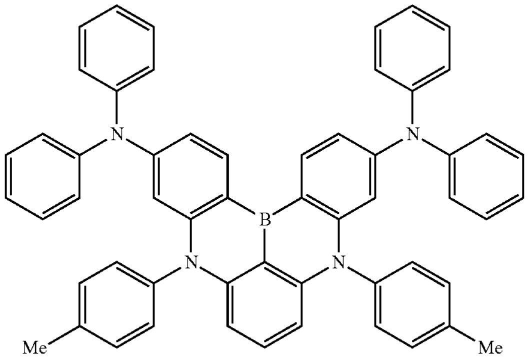
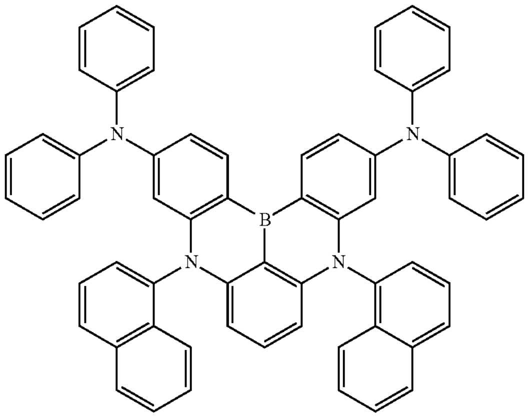
-continued
[Formula 232]
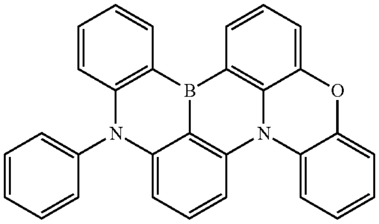
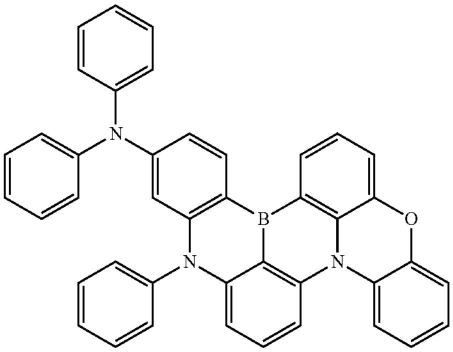
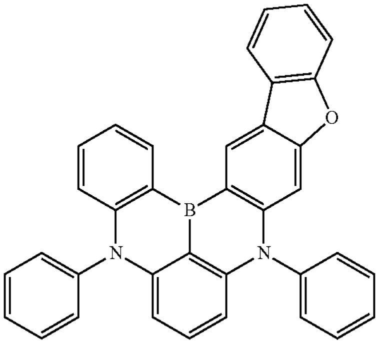
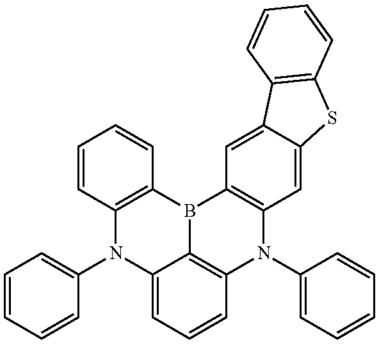
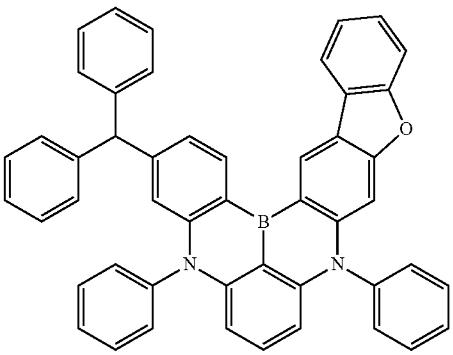

-continued

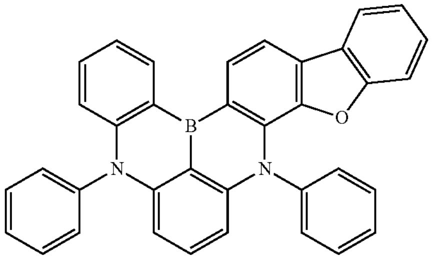

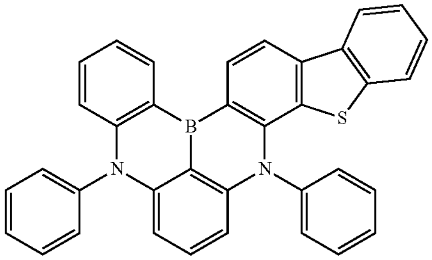

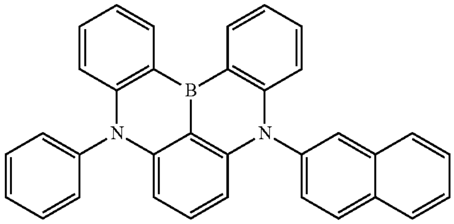

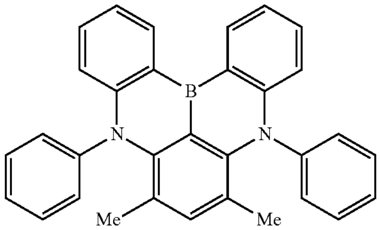

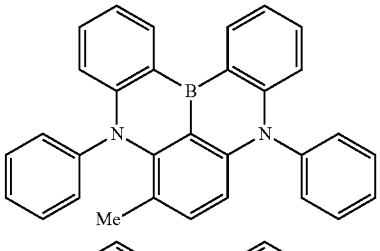

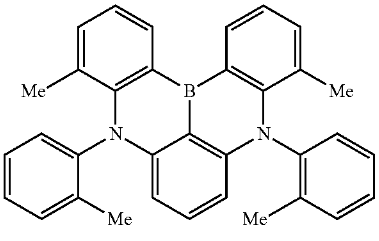

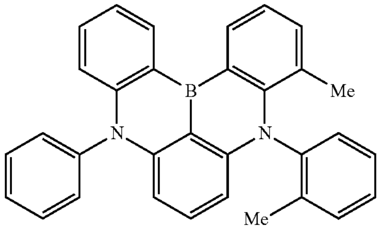

-continued

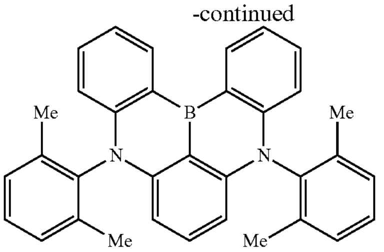

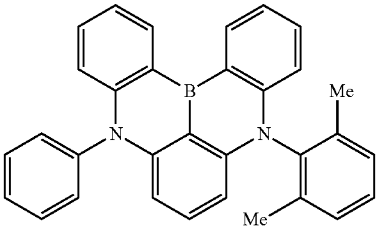

Compound Represented by Formula (7)

The compound represented by the formula (7) will be described.

[Formula 233]

p—q—r—s—t (7)

[Formula 234]

(72)

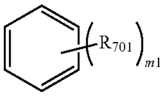

(73)

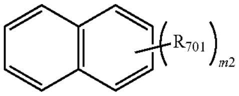

(74)

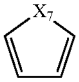

(75)

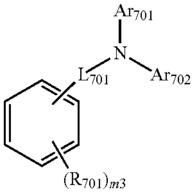

(76)

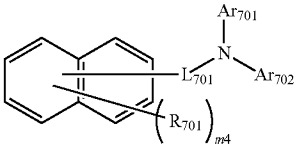

In the formula (7):

r ring is a ring represented by the formula (72) or the formula (73), the r ring being fused with any position(s) of adjacent ring(s);

q ring and s ring are each independently a ring represented by the formula (74) and fused with any position(s) of adjacent ring(s);

p ring and t ring are each independently a structure represented by the formula (75) or the formula (76) and fused with any position(s) of adjacent ring(s);

$X_7$ is an oxygen atom, a sulfur atom, or $NR_{702}$;

when a plurality of $R_{701}$ are present, adjacent ones of the plurality of $R_{701}$ are mutually bonded to form a substituted or unsubstituted monocyclic ring, mutually bonded to form a substituted or unsubstituted fused ring, or not mutually bonded;

$R_{701}$ and $R_{702}$ not forming the monocyclic ring and not forming the fused ring are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

$Ar_{701}$ and $Ar_{702}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

$L_{701}$ is a substituted or unsubstituted alkylene group having 1 to 50 carbon atoms, a substituted or unsubstituted alkenylene group having 2 to 50 carbon atoms, a substituted or unsubstituted alkynylene group having 2 to 50 carbon atoms, a substituted or unsubstituted cycloalkylene group having 3 to 50 ring carbon atoms, a substituted or unsubstituted arylene group having 6 to 50 ring carbon atoms, or a substituted or unsubstituted divalent heterocyclic group having 5 to 50 ring atoms;

m1 is 0, 1, or 2;

m2 is 0, 1, 2, 3, or 4;

m3 is each independently 0, 1, 2, or 3;

m4 is each independently 0, 1, 2, 3, 4, or 5;

when a plurality of $R_{701}$ are present, the plurality of $R_{701}$ are mutually the same or different;

when a plurality of $X_7$ are present, the plurality of $X_7$ are mutually the same or different;

when a plurality of $R_{702}$ are present, the plurality of $R_{702}$ are mutually the same or different;

when a plurality of $Ar_{701}$ are present, the plurality of $Ar_{701}$ are mutually the same or different;

when a plurality of $Ar_{702}$ are present, the plurality of $Ar_{702}$ are mutually the same or different; and when a plurality of $L_{701}$ are present, the plurality of $L_{701}$ are mutually the same or different.

In the formula (7), each of the p ring, q ring, r ring, s ring, and t ring is fused with an adjacent ring(s) sharing two carbon atoms. The fused position and orientation are not limited but may be defined as required.

In an exemplary embodiment, in the formula (72) or the formula (73) representing the r ring, m1=0 or m2=0 is satisfied.

In an exemplary embodiment, the compound represented by the formula (7) is represented by any one of formulae (71-1) to (71-6) below.

[Formula 235]

(71-1)

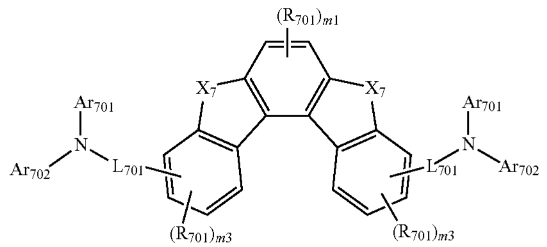

[Formula 236]

(71-2)

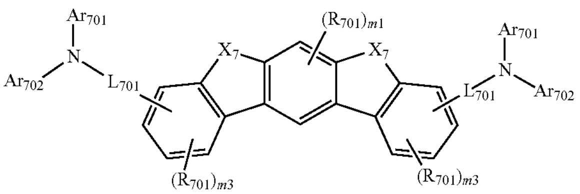

[Formula 237]

(71-3)

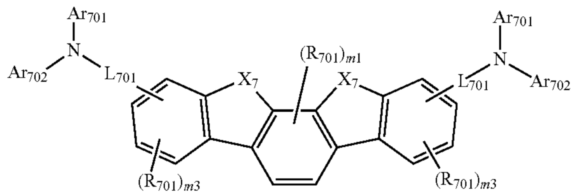

[Formula 238]

(71-4)

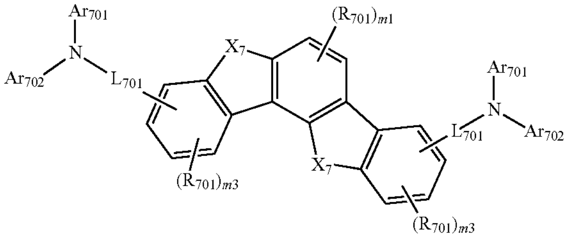

[Formula 239]

(71-5)

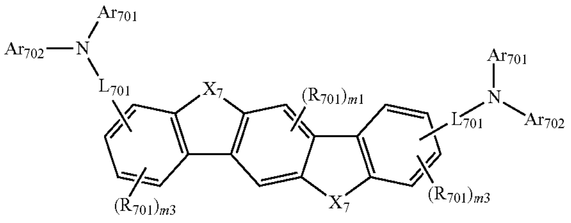

-continued

[Formula 240]

(71-6)

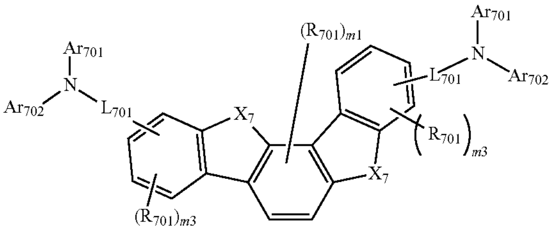

In the formulae (71-1) to (71-6), $R_{701}$, $X_7$, $Ar_{701}$, $Ar_{702}$, $L_{701}$, m1 and m3 respectively represent the same as $R_{701}$, $X_7$, $Ar_{701}$, $Ar_{702}$, $L_{701}$, m1 and m3 in the formula (7).

In an exemplary embodiment, the compound represented by the formula (7) is represented by any one of formulae (71-11) to (71-13) below.

[Formula 241]

(71-11)

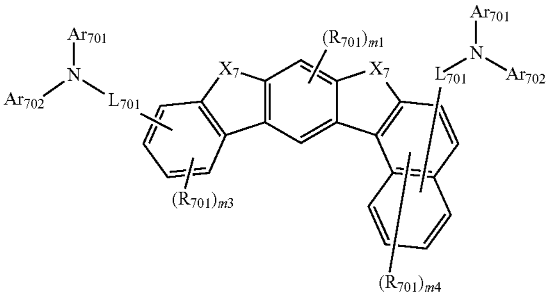

-continued

[Formula 242]

(71-12)

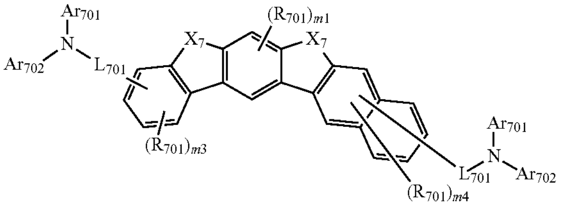

[Formula 243]

(71-13)

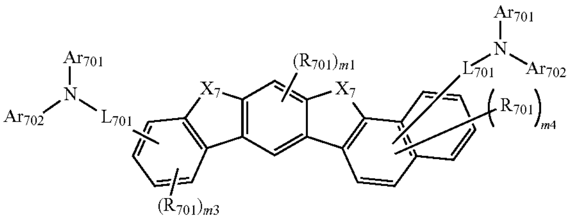

In the formulae (71-11) to (71-13), $R_{701}$, $X_7$, $Ar_{701}$, $Ar_{702}$, $L_{701}$, m1, m3 and m4 respectively represent the same as $R_{701}$, $X_7$, $Ar_{701}$, $Ar_{702}$, $L_{701}$, m1, m3 and m4 in the formula (7).

In an exemplary embodiment, the compound represented by the formula (7) is represented by any one of formulae (71-21) to (71-25) below.

[Formula 244]

(71-21)

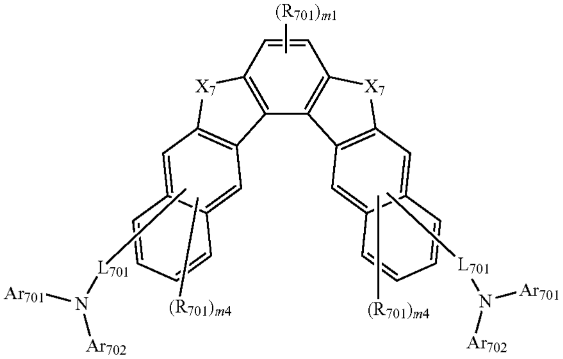

[Formula 245]

(71-22)

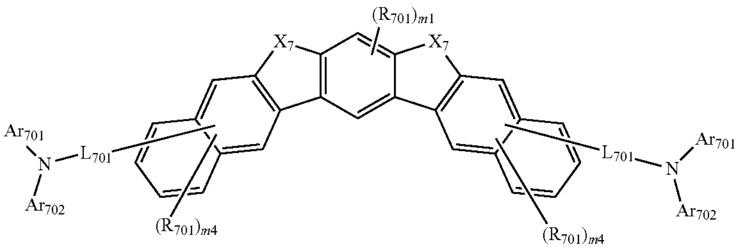

-continued
[Formula 246]
(71-23)
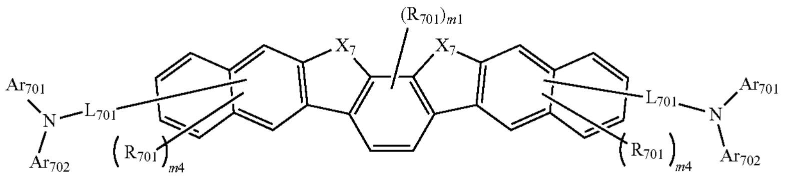
[Formula 247]
(71-24)
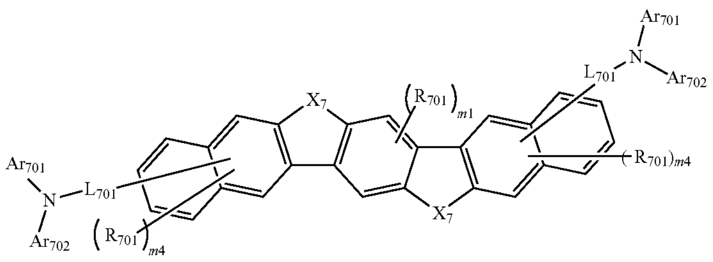
[Formula 248]
(71-25)
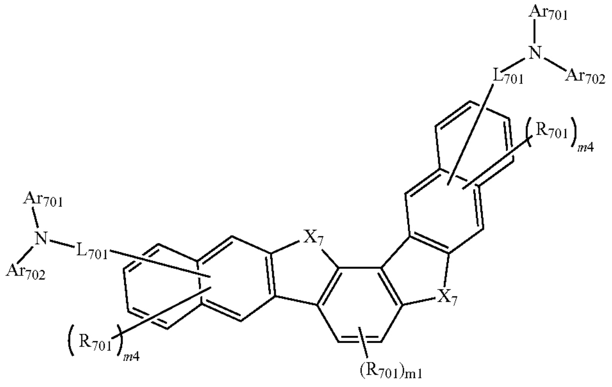
In the formulae (71-21) to (71-25), $R_{701}$, $X_7$, $Ar_{701}$, $Ar_{702}$, $L_{701}$, m1 and m4 respectively represent the same as $R_{701}$, $X_7$, $Ar_{701}$, $Ar_{702}$, $L_{701}$, m1 and m4 in the formula (7).
In an exemplary embodiment, the compound represented by the formula (7) is represented by any one of formulae (71-31) to (71-33) below.
[Formula 249]
(71-31)
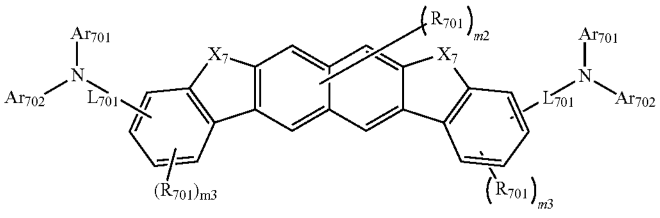

-continued

[Formula 250]

(71-32)

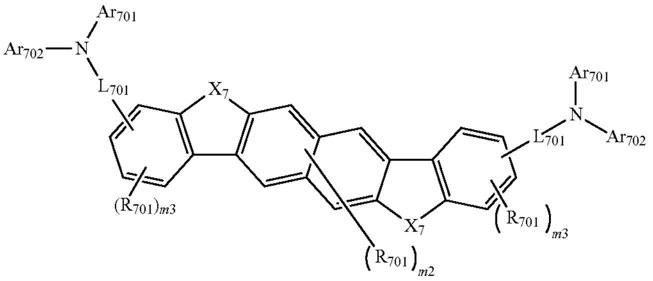

[Formula 251]

(71-33)

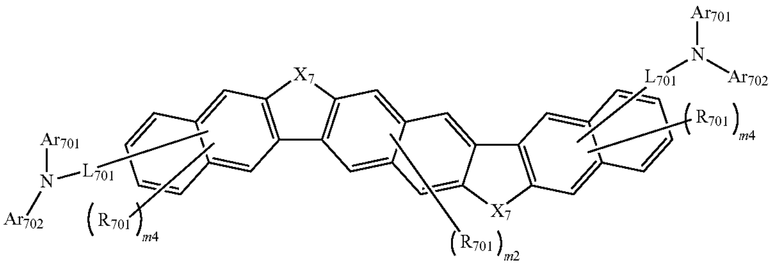

In the formulae (71-31) to (71-33), $R_{701}$, $X_7$, $Ar_{701}$, $Ar_{702}$, $L_{701}$ and m2 to m4 respectively represent the same as $R_{701}$, $X_7$, $Ar_{701}$, $Ar_{702}$, $L_{701}$ and m2 to m4 in the formula (7).

In an exemplary embodiment, $Ar_{701}$ and $Ar_{702}$ are each independently a substituted or unsubstituted aryl group having 6 to 50 ring carbon atoms.

In an exemplary embodiment, one of $Ar_{701}$ and $Ar_{702}$ is a substituted or unsubstituted aryl group having 6 to 50 ring carbon atoms, and the other of $Ar_{701}$ and $Ar_{702}$ is a substituted or unsubstituted heterocyclic group having 5 to 50 ring atoms.

Specific examples of the compound represented by the formula (7) include compounds shown below.

[Formula 252]

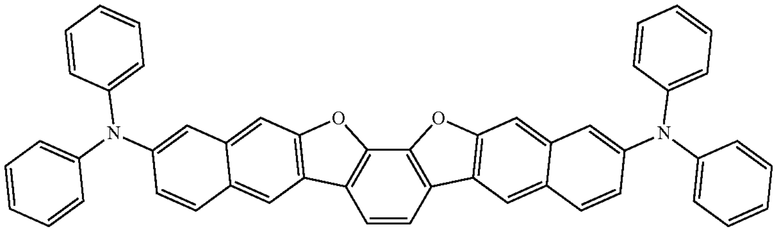

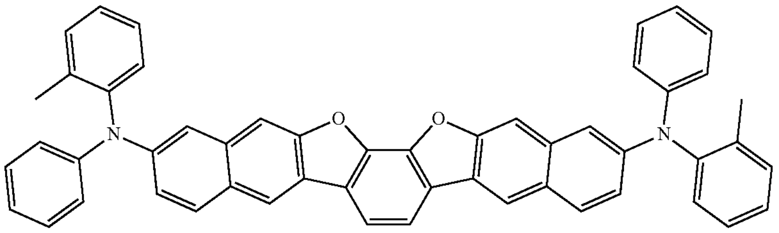

-continued
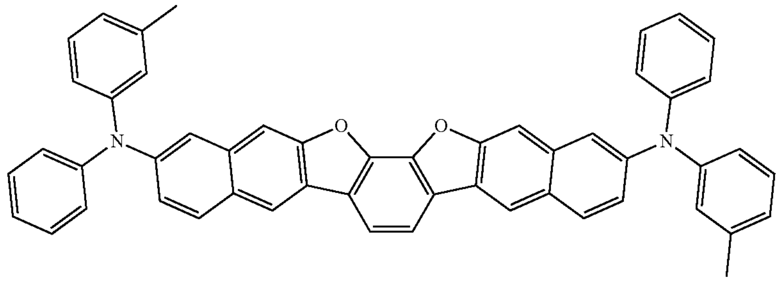
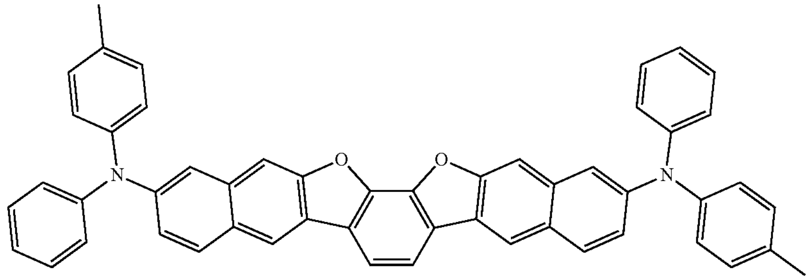
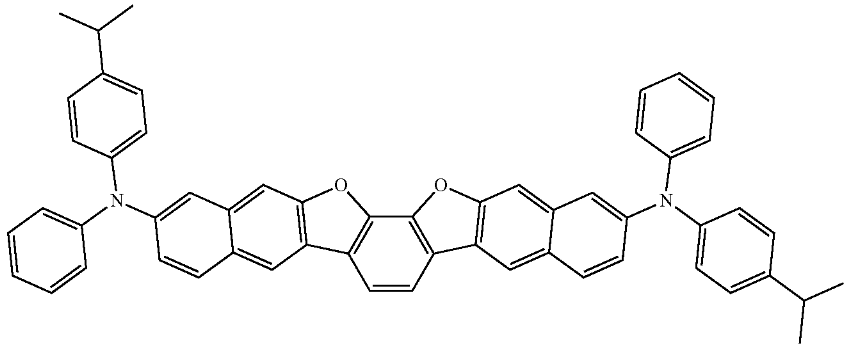
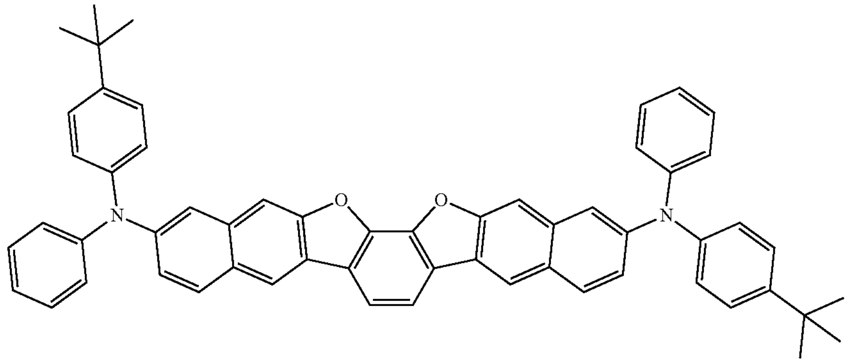
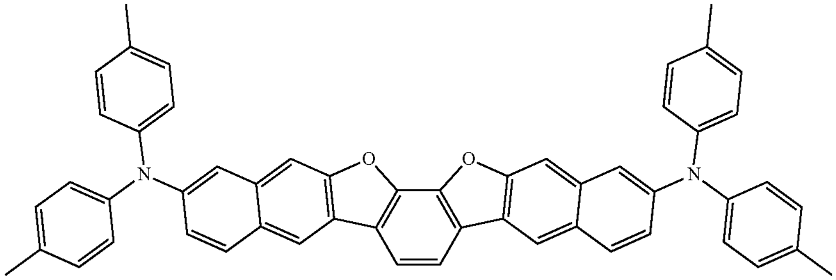

-continued
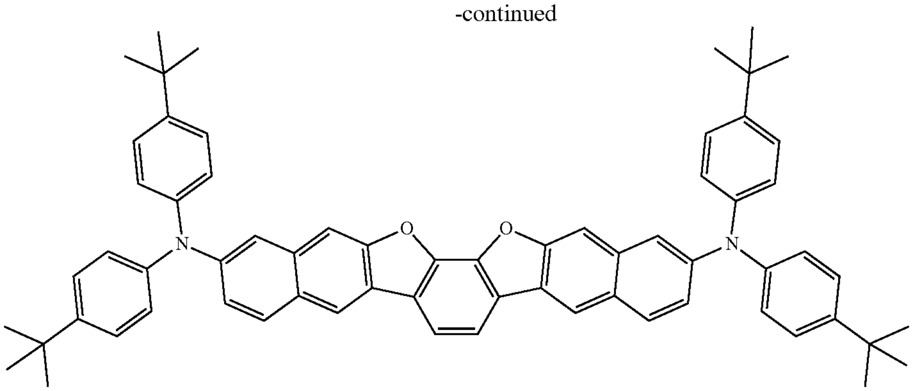
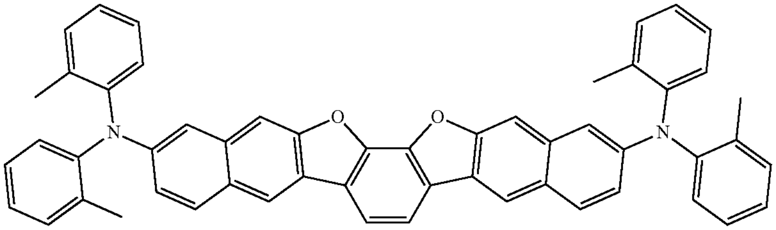
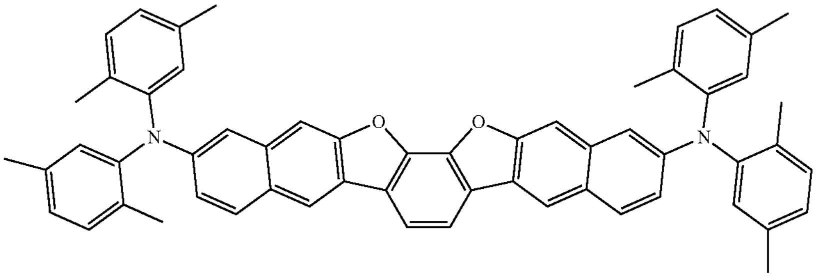
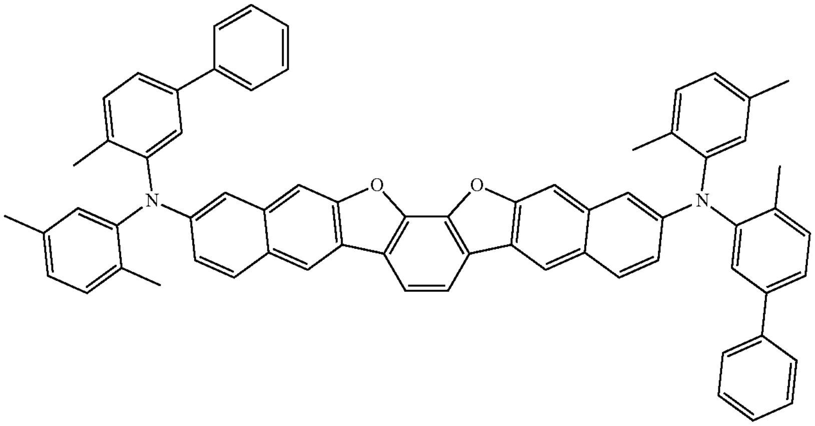
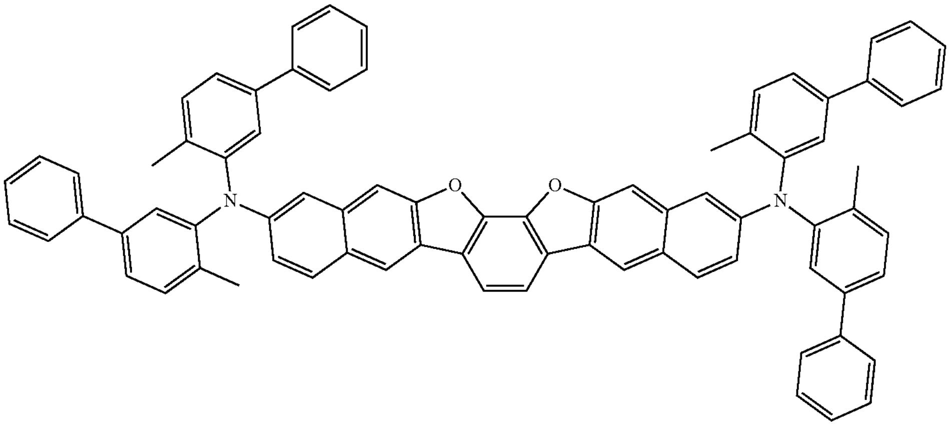

-continued
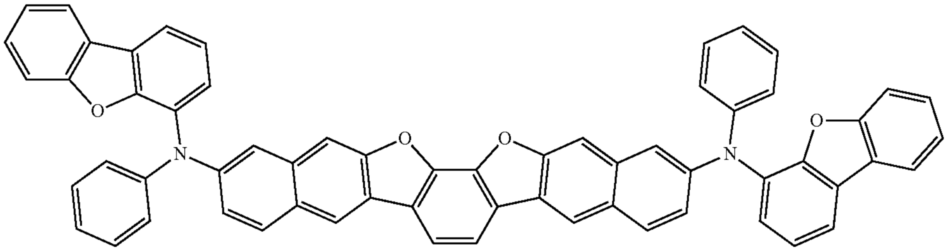
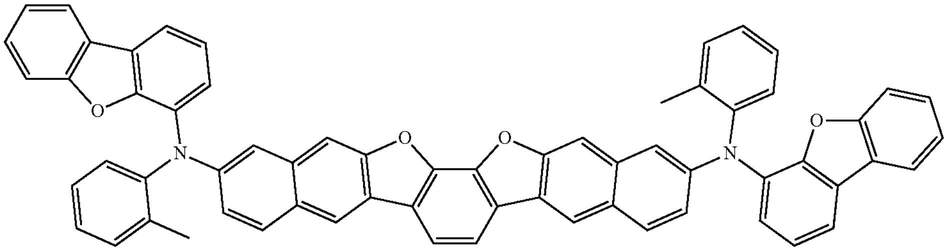
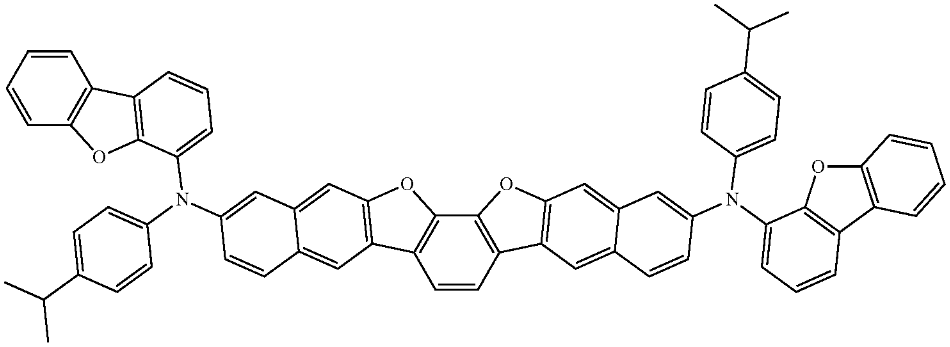
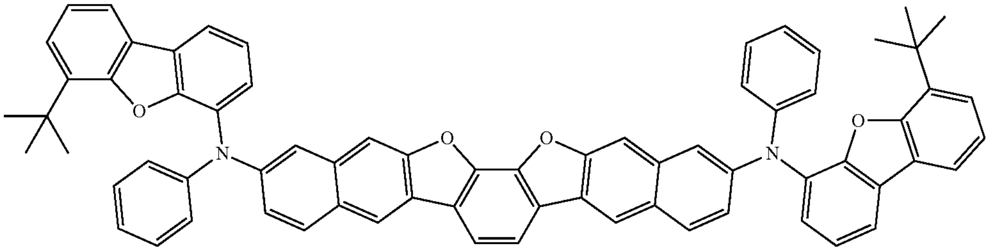
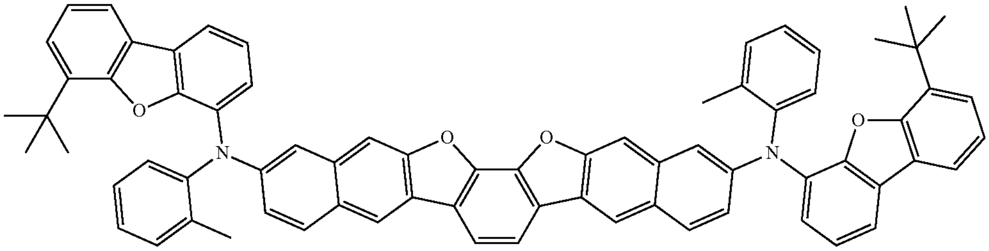
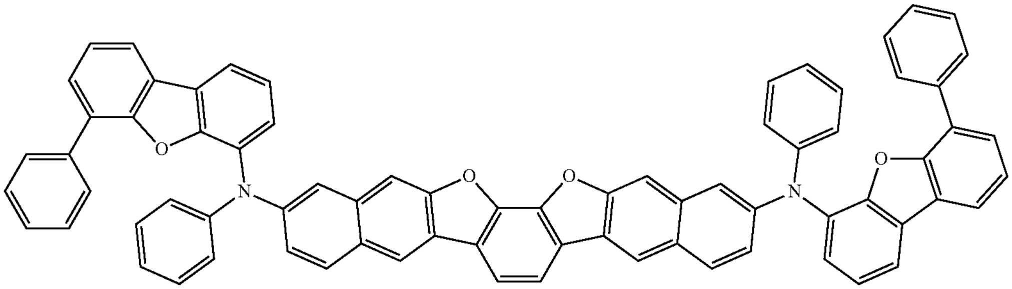

-continued
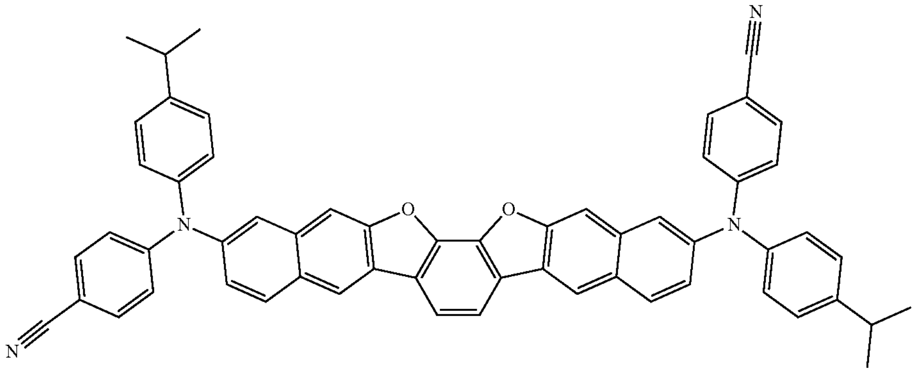
[Formula 253]
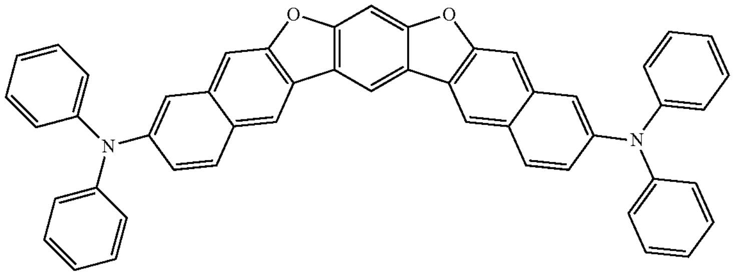
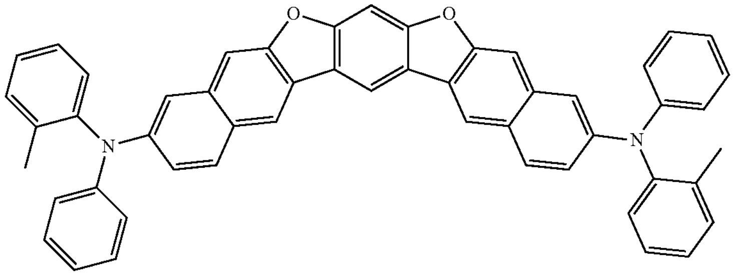
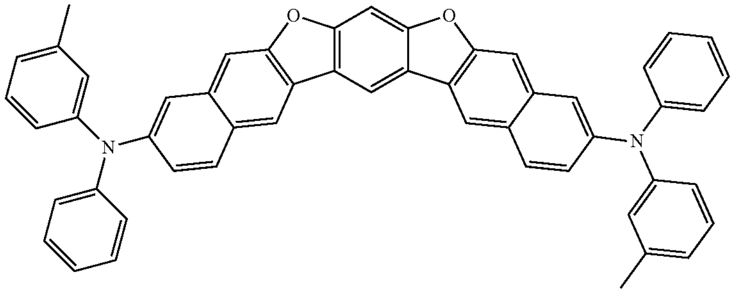
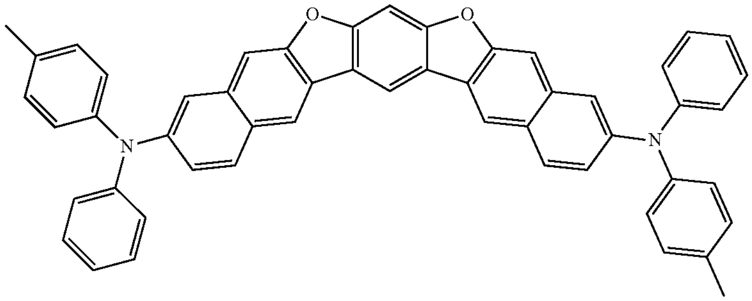

-continued
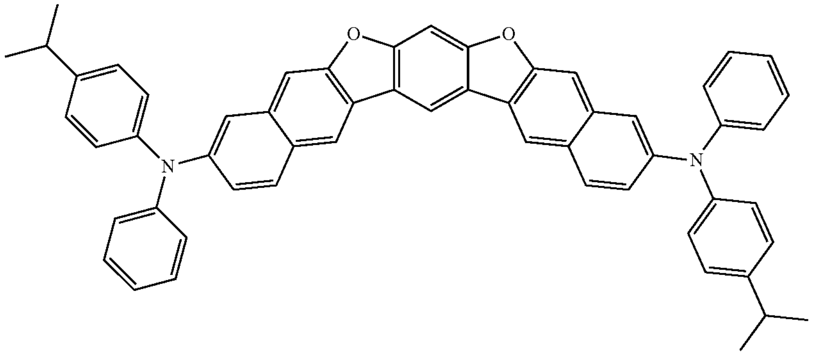
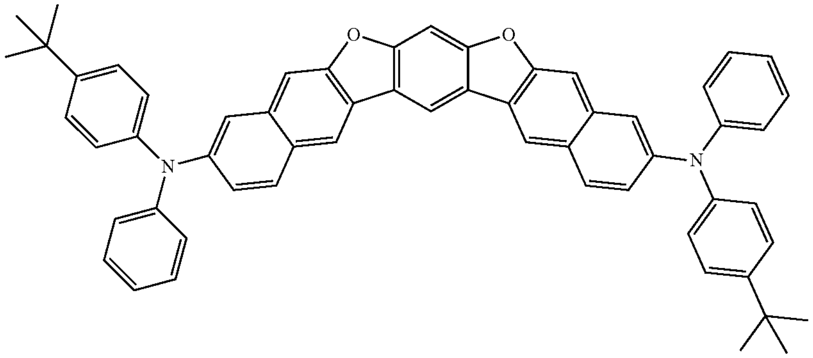
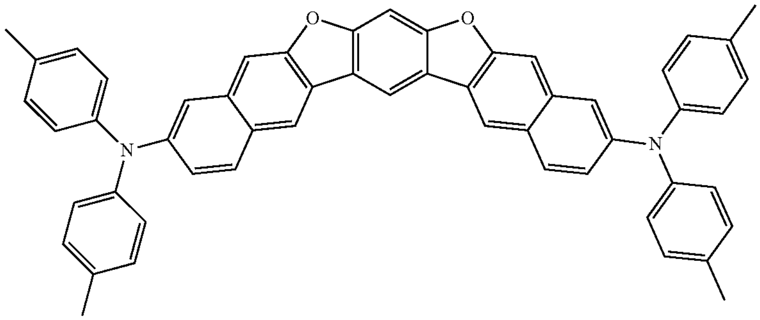
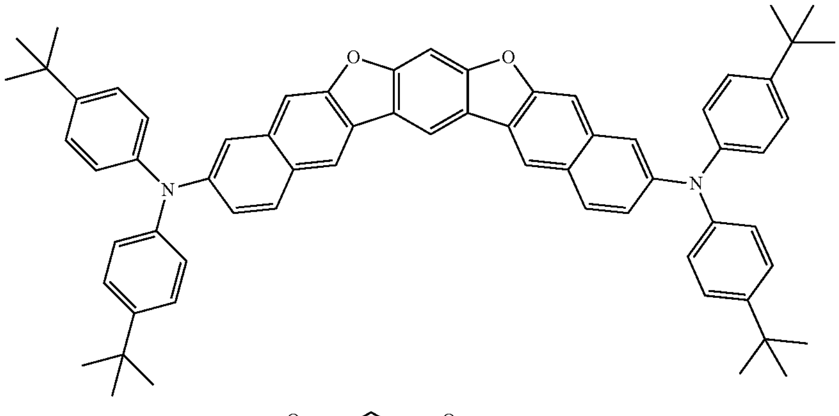
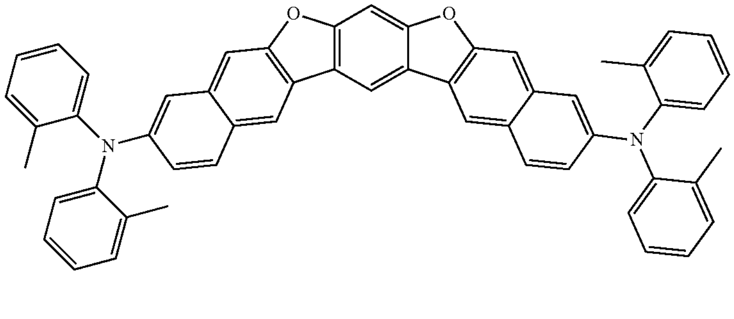

-continued
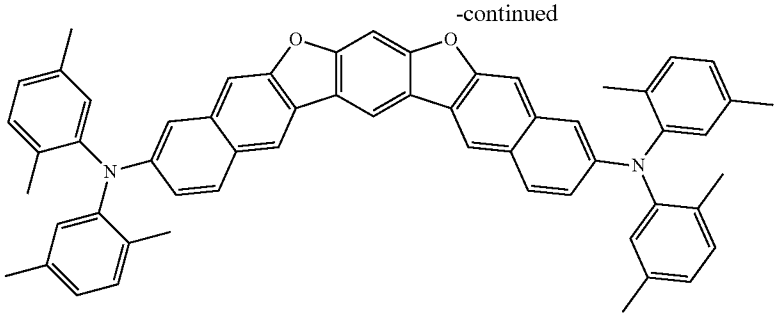
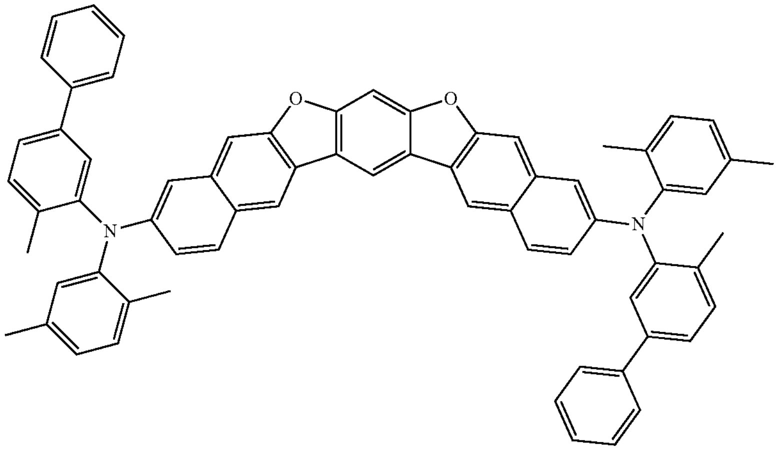
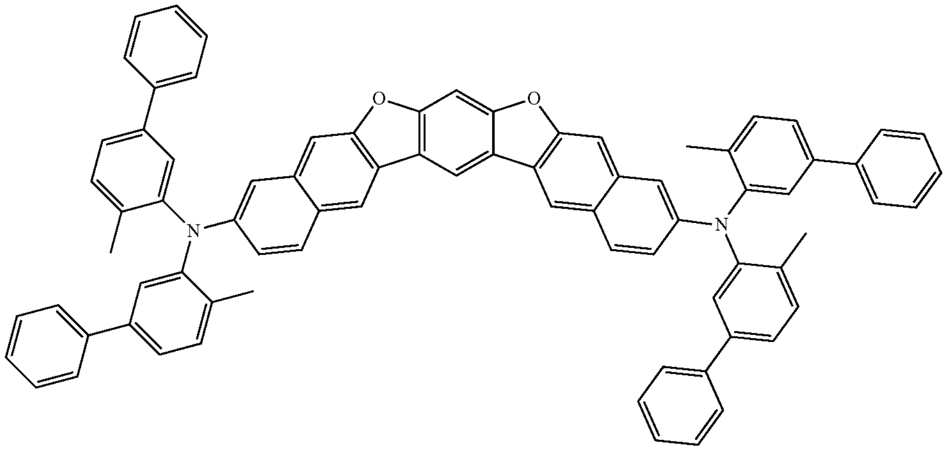
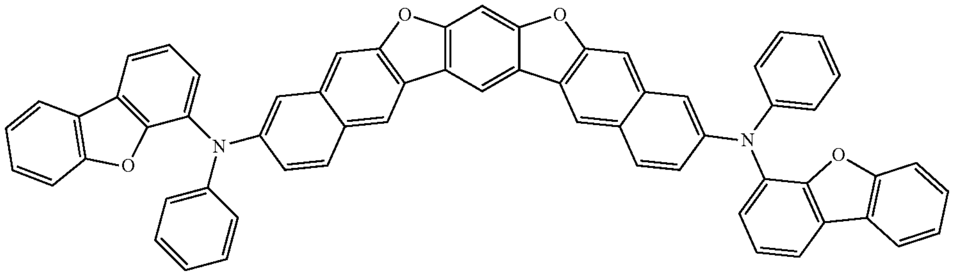

-continued
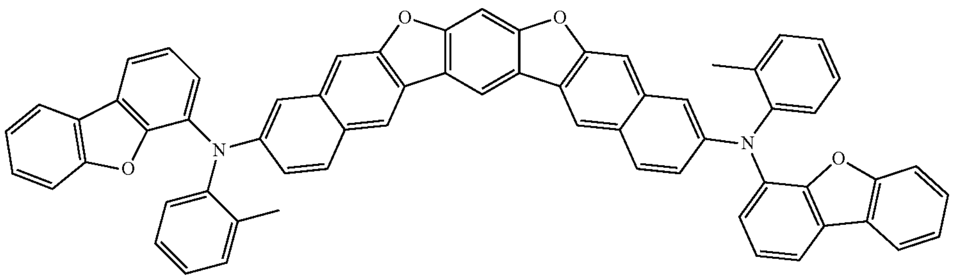
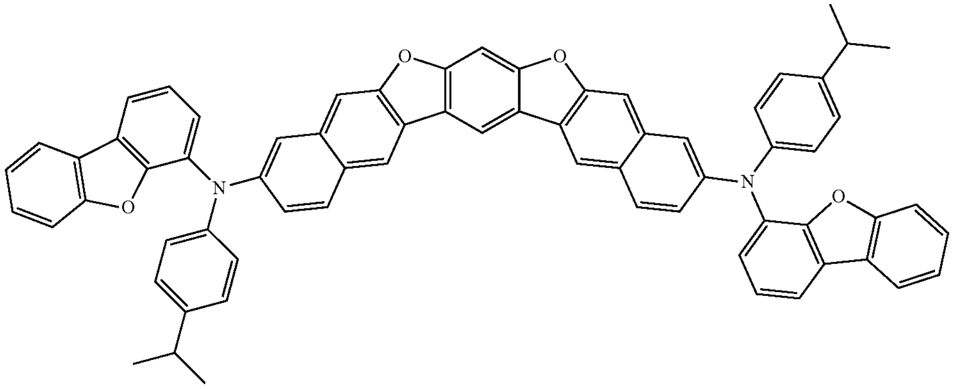
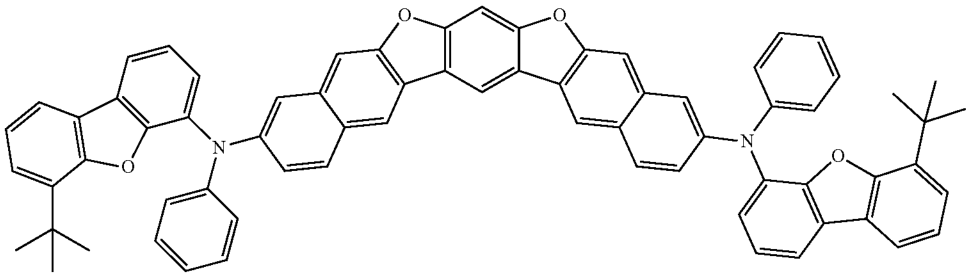
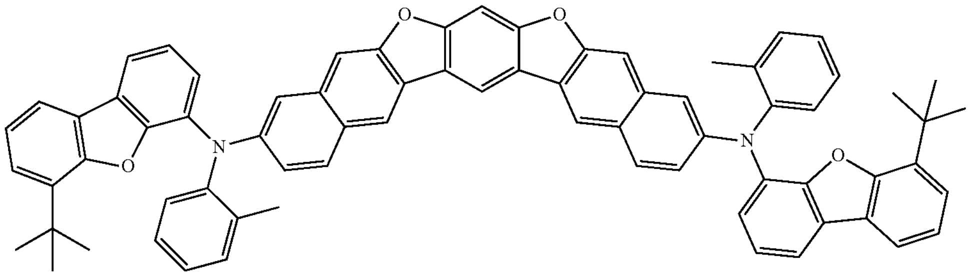
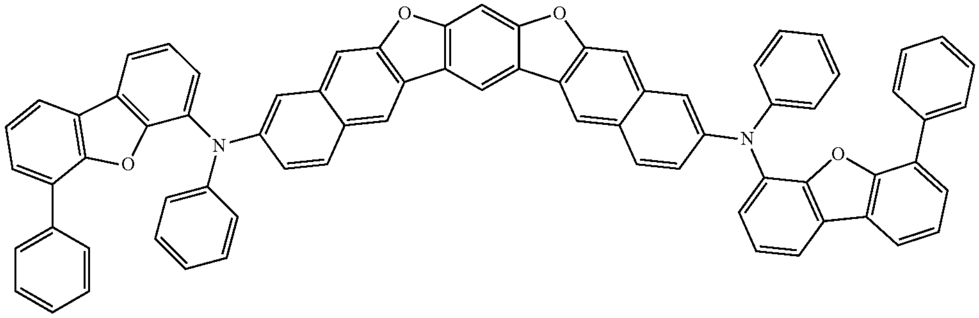

-continued
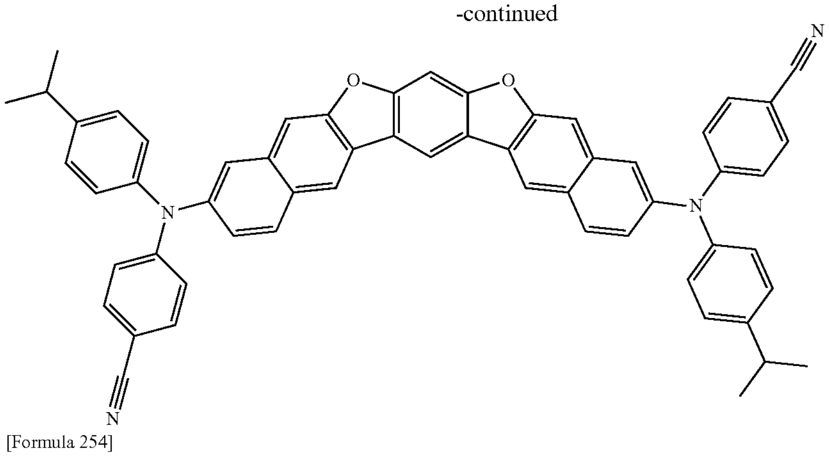
[Formula 254]
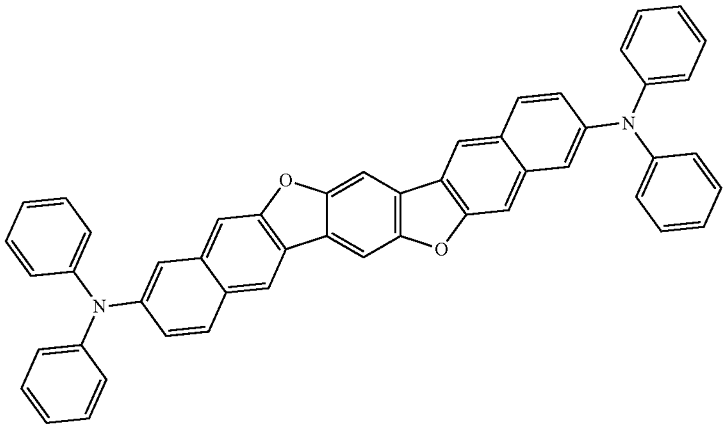
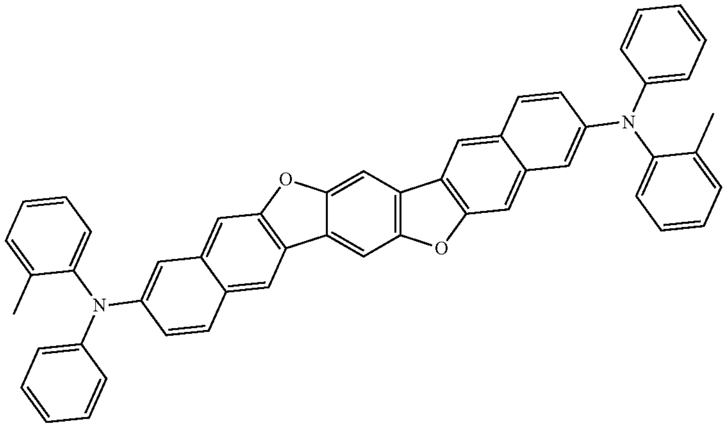
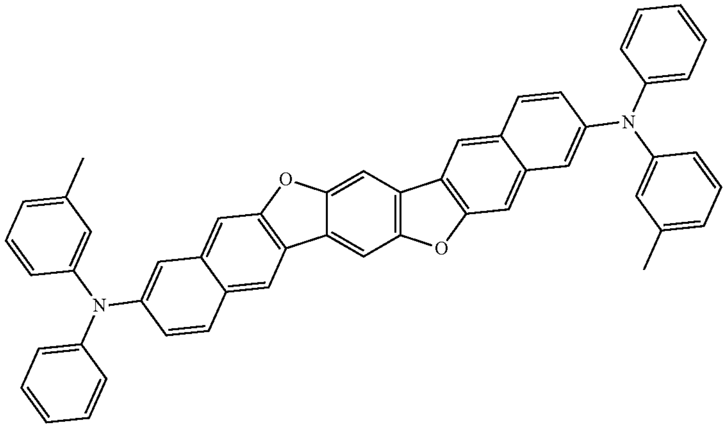

-continued
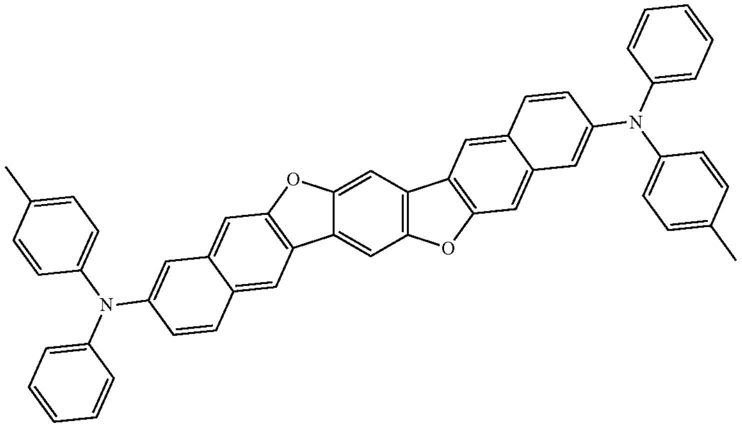
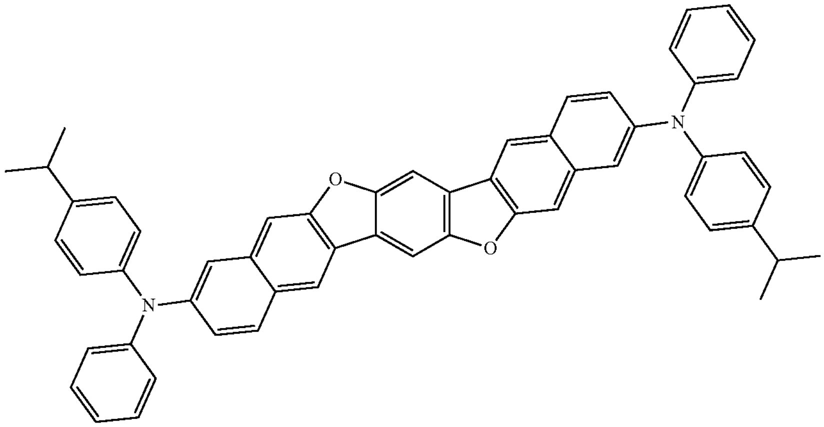
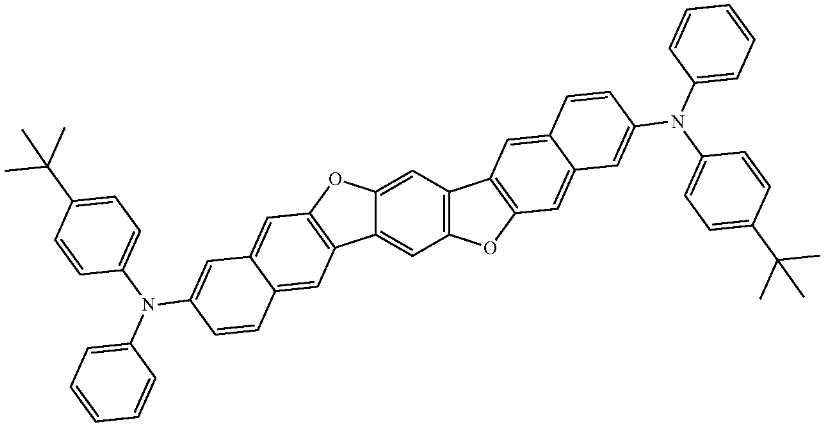
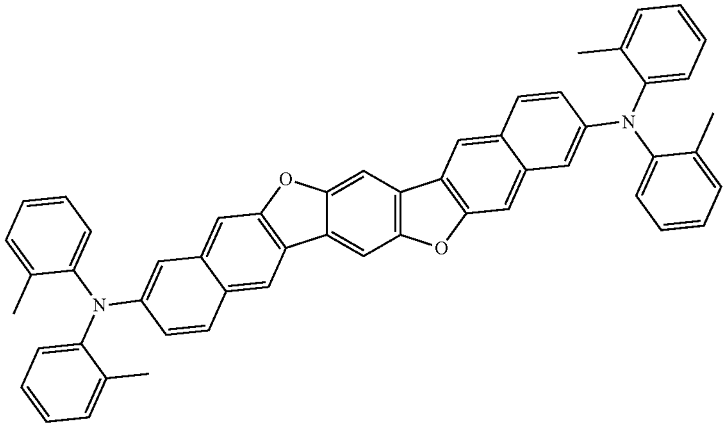

-continued
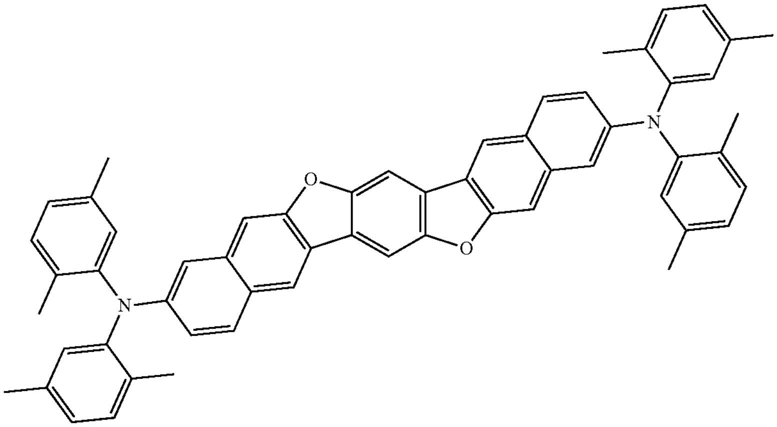
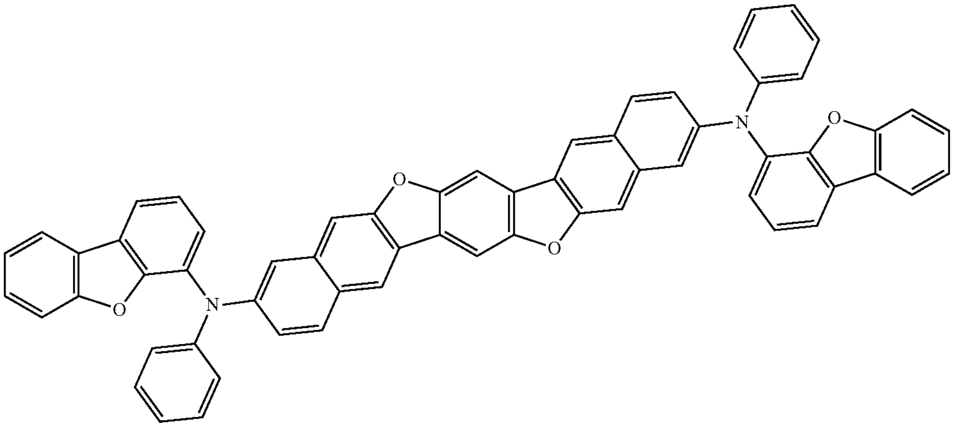
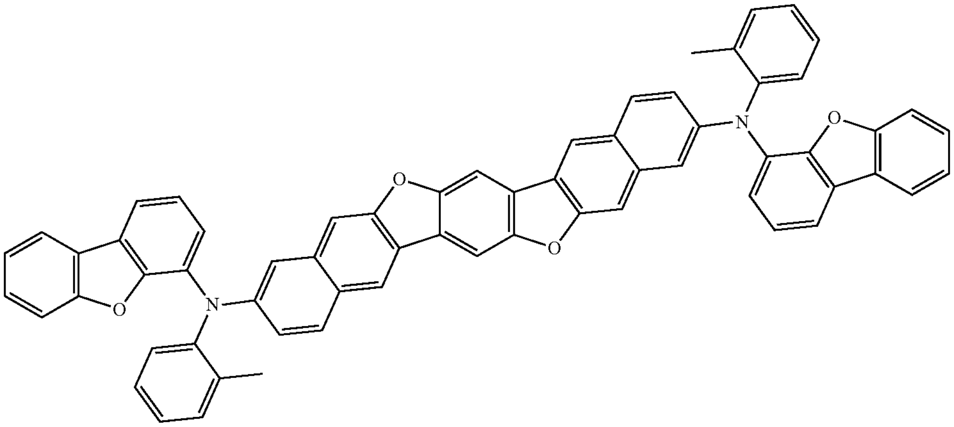
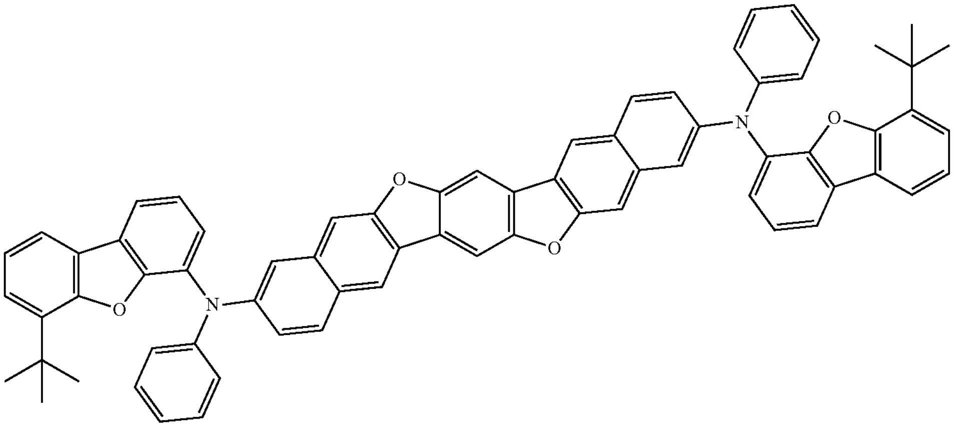

-continued
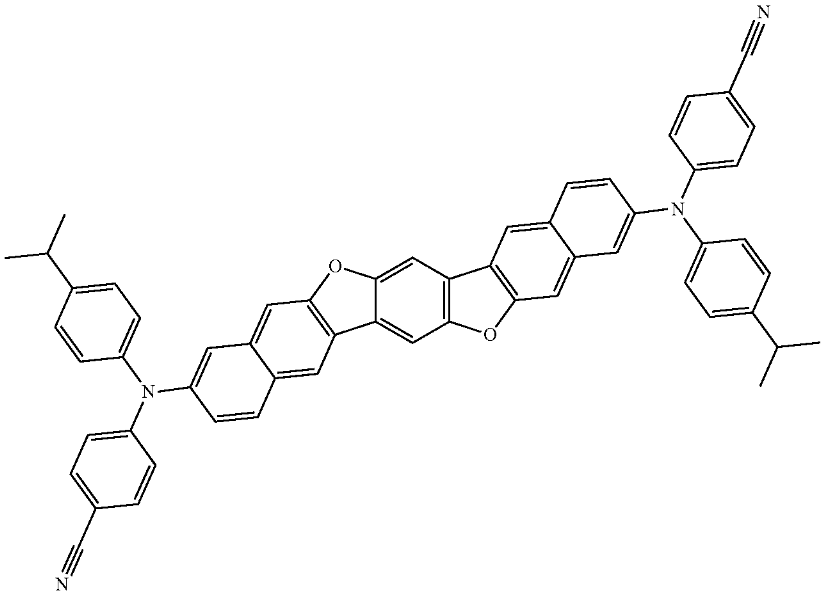
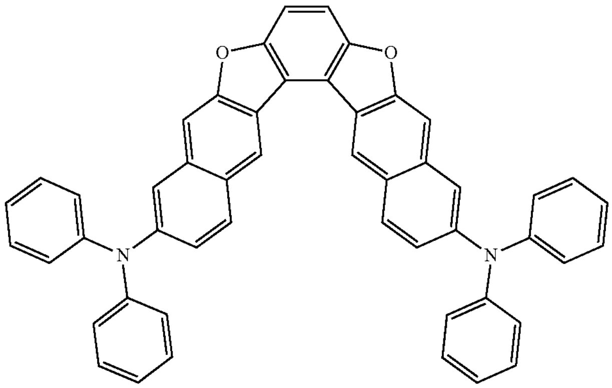
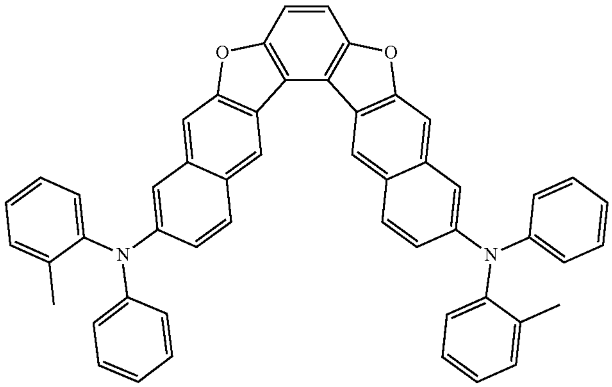

-continued
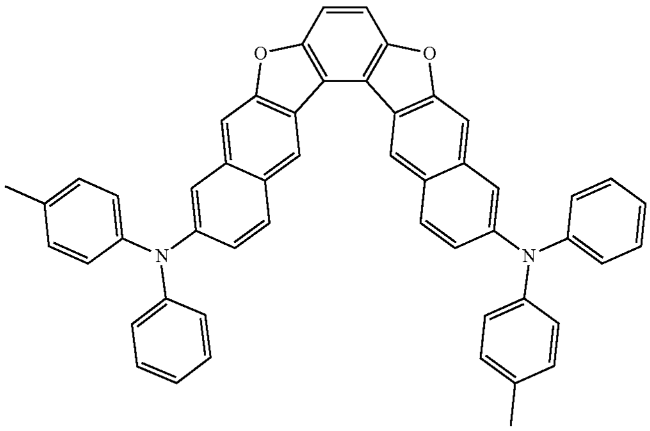
[Formula 255]
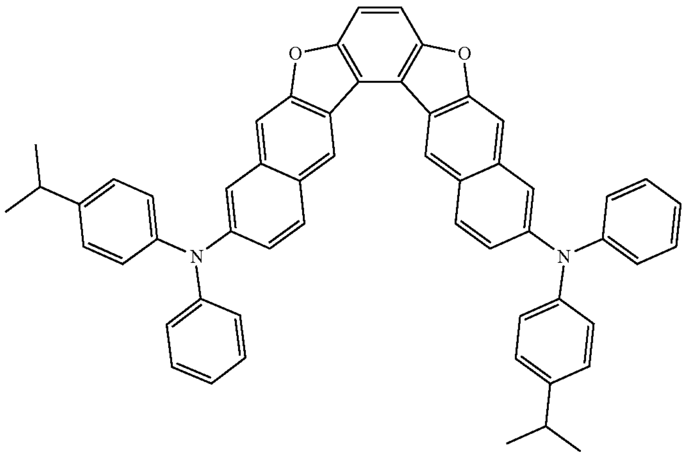
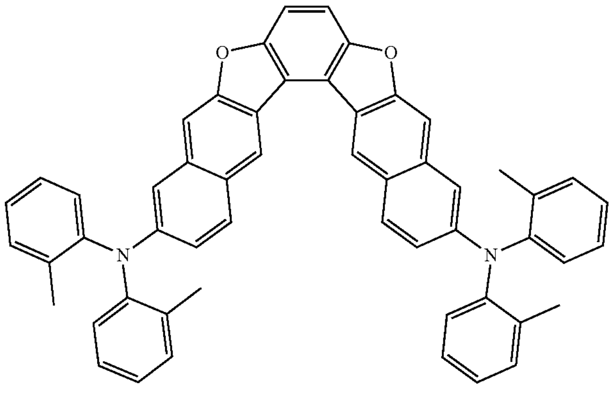

-continued
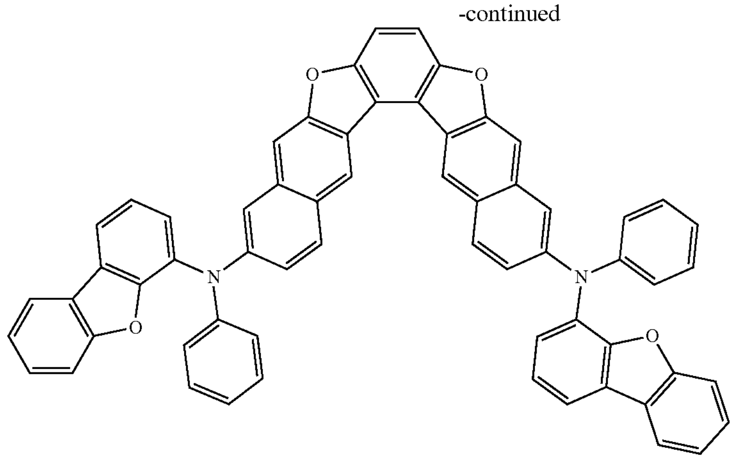
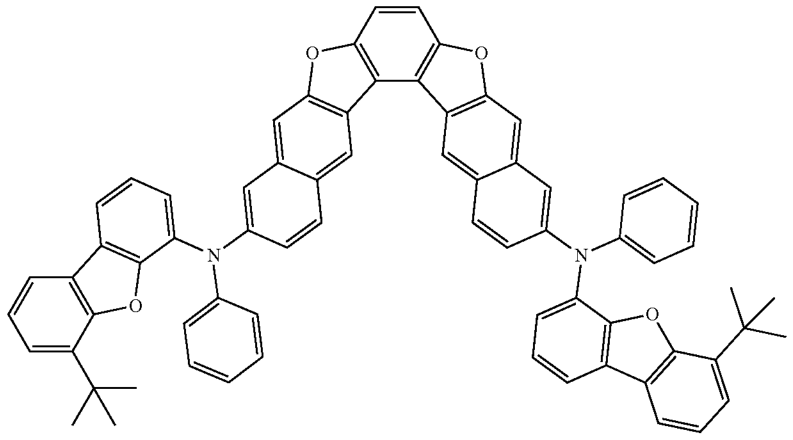
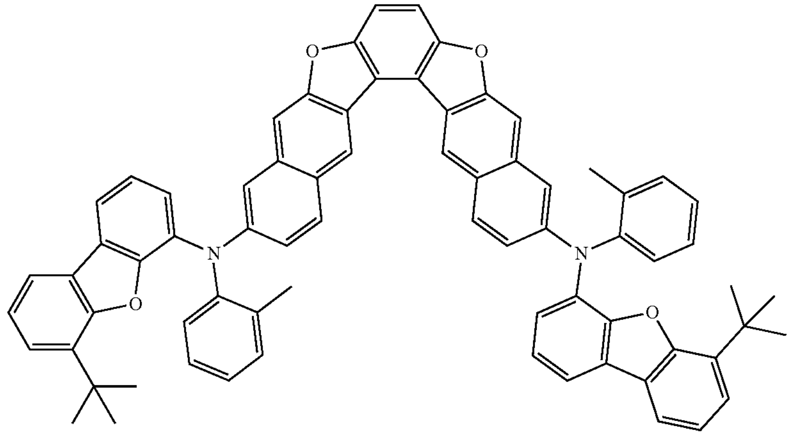

-continued
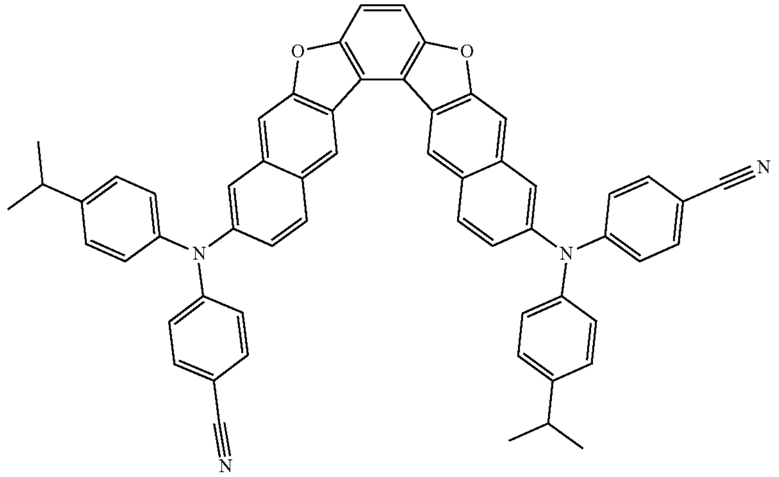
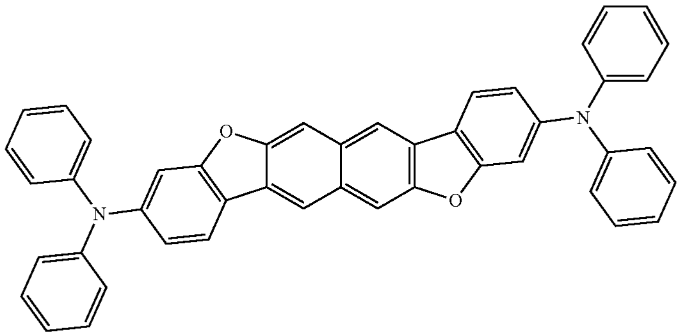
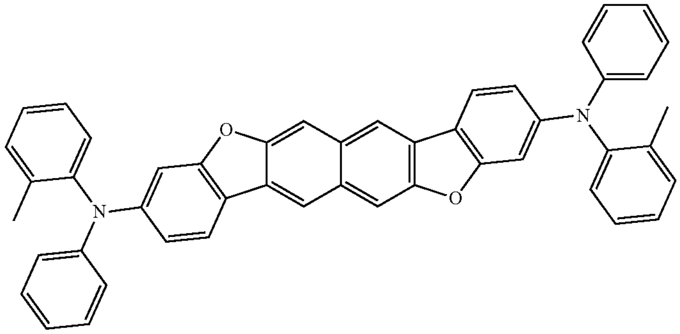
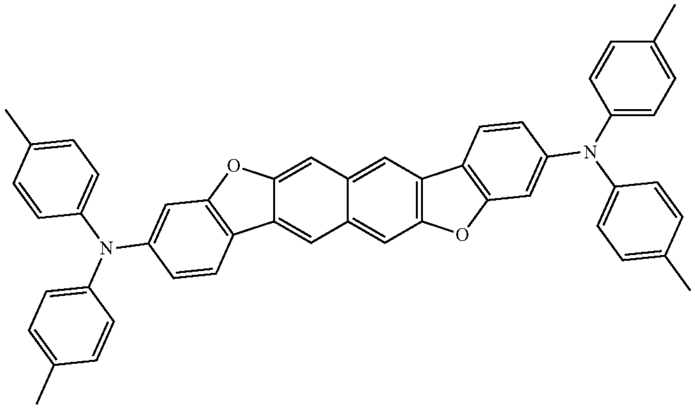

-continued
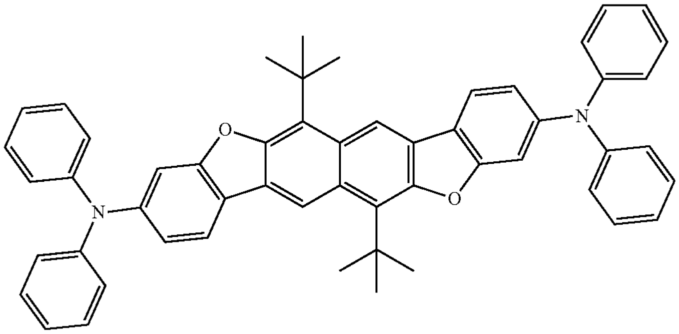
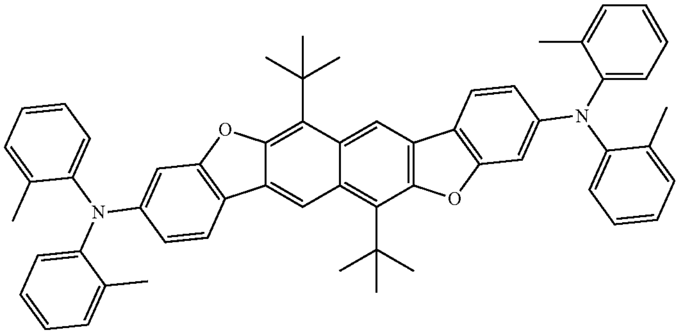
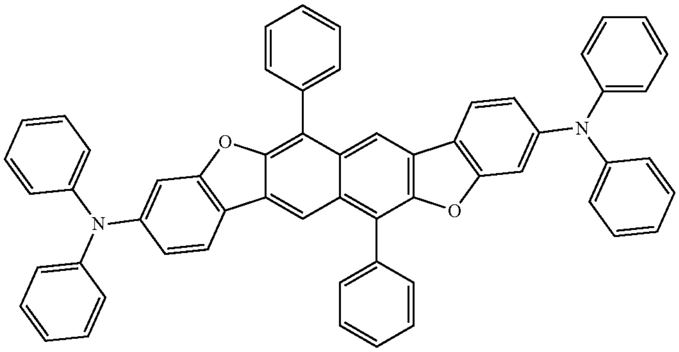
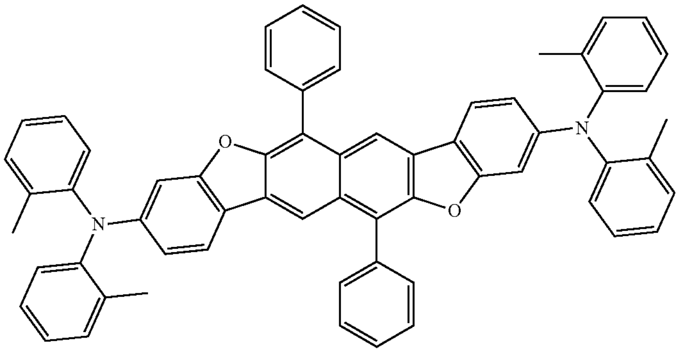
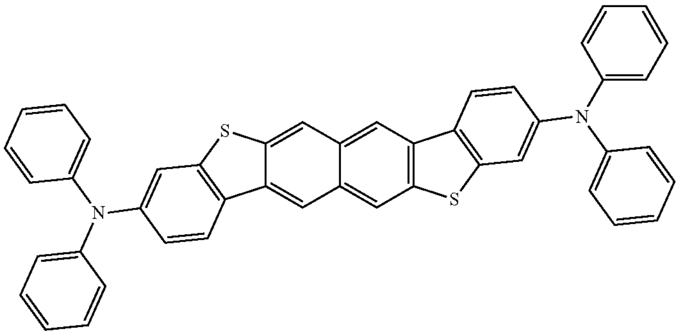

-continued
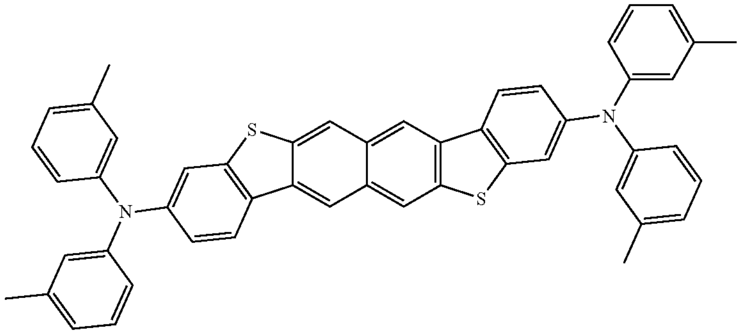
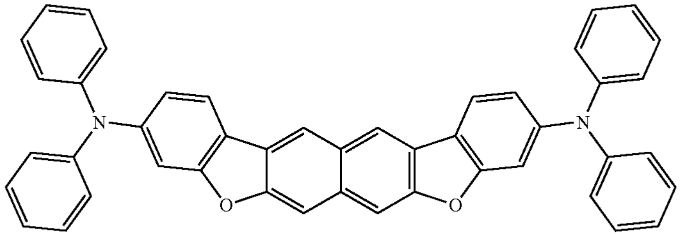
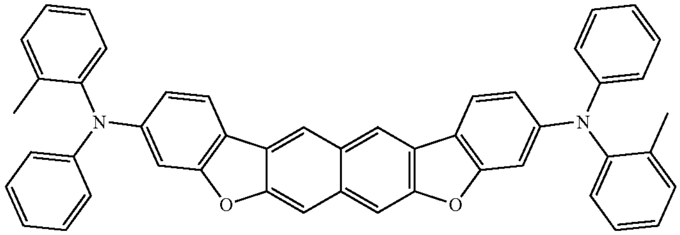
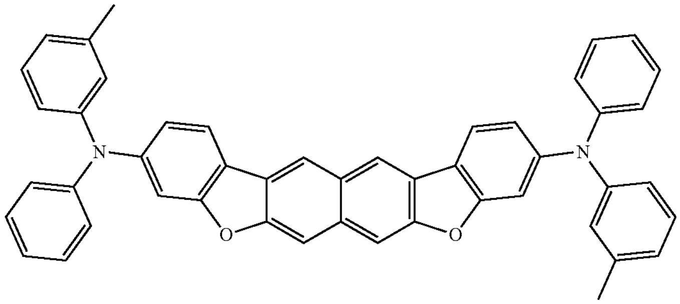
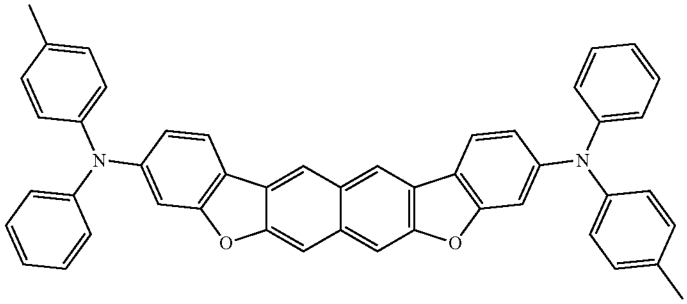

-continued
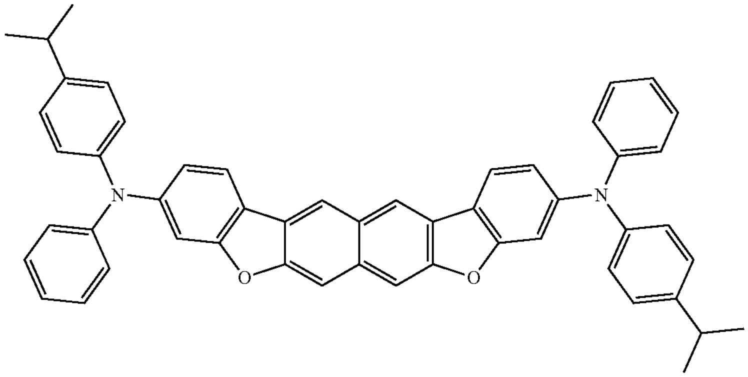
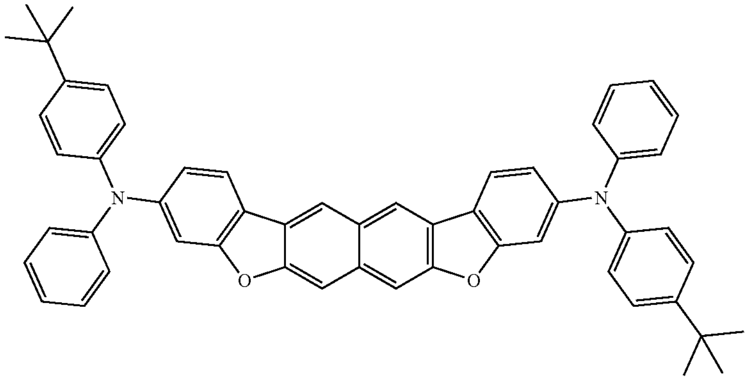
[Formula 256]
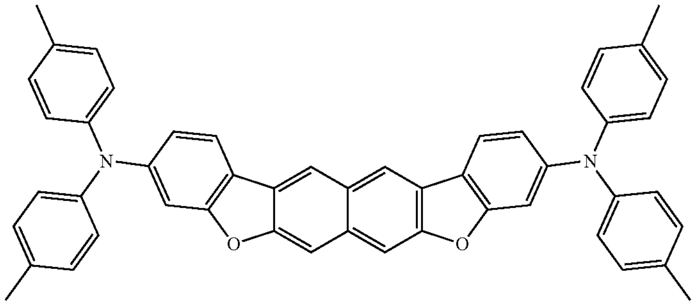
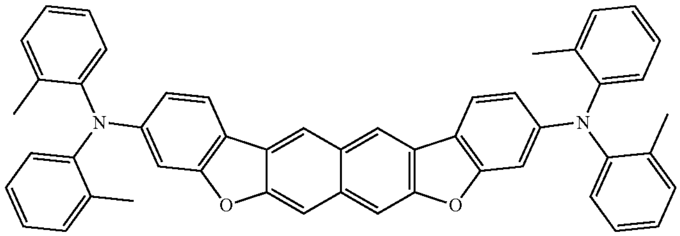
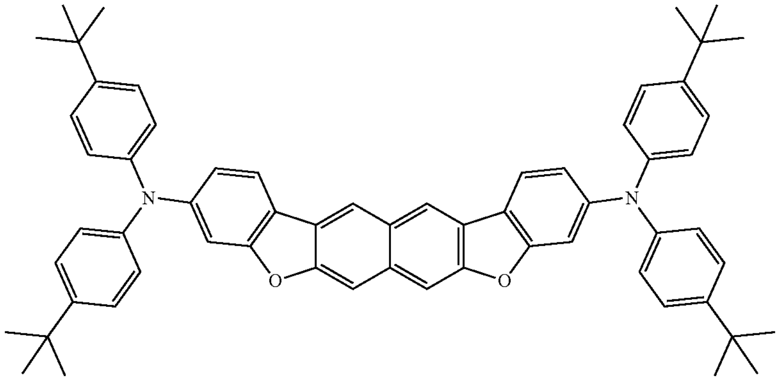

-continued
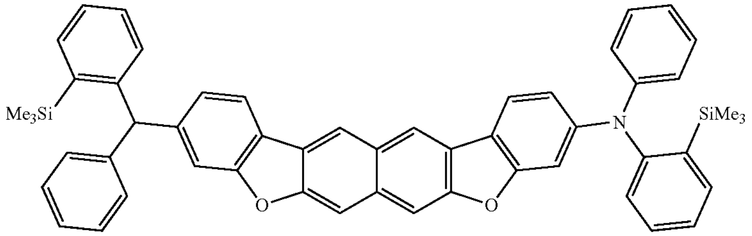
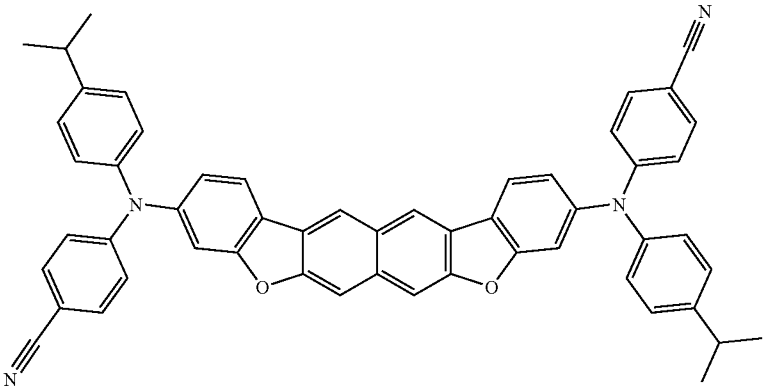
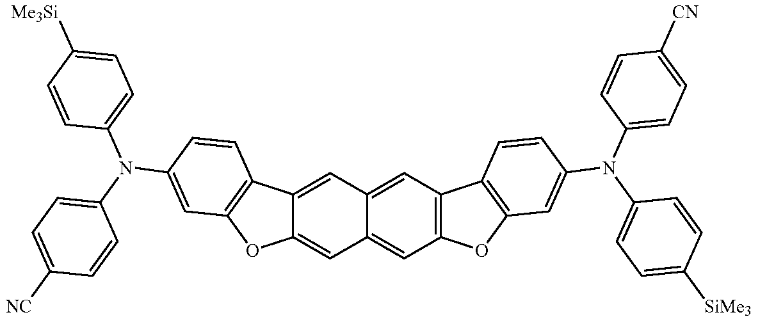
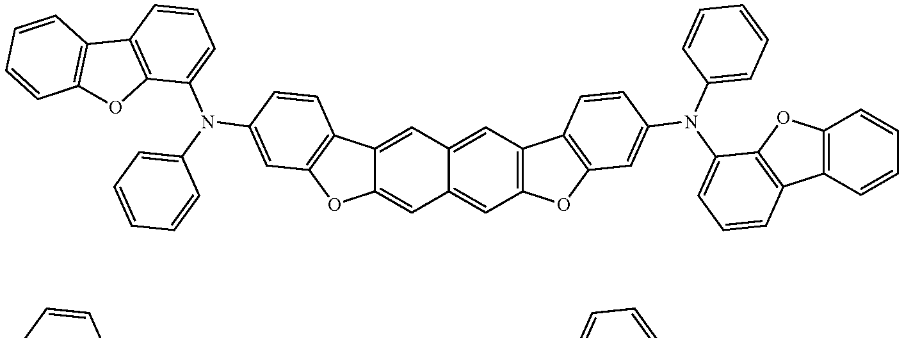
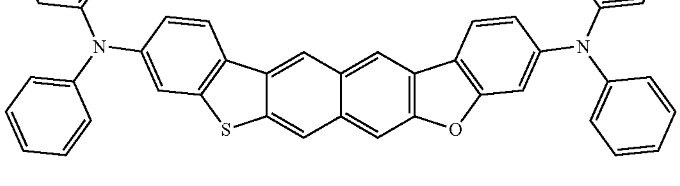

-continued
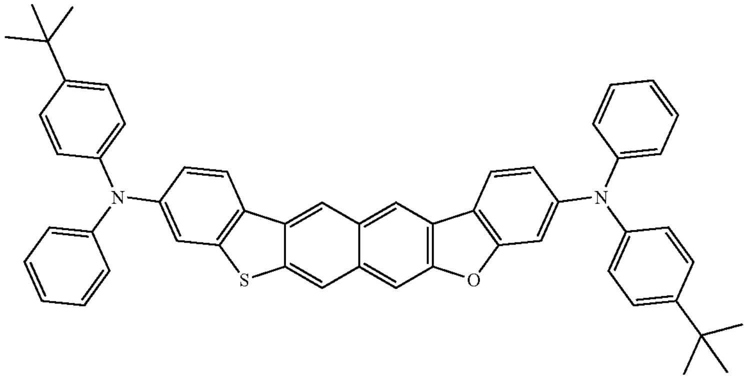
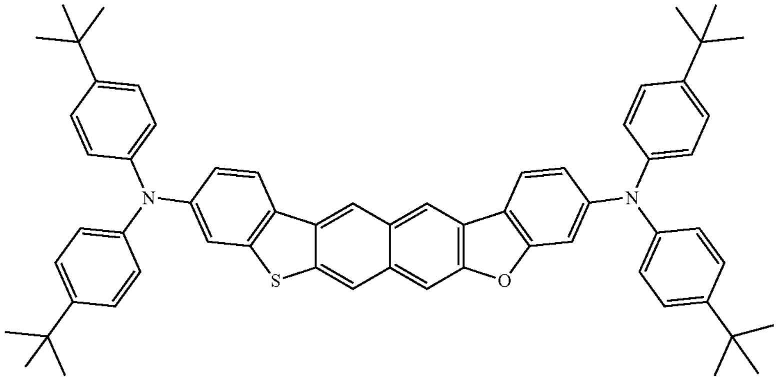
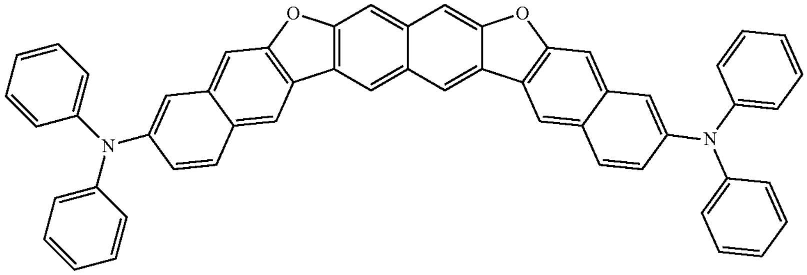
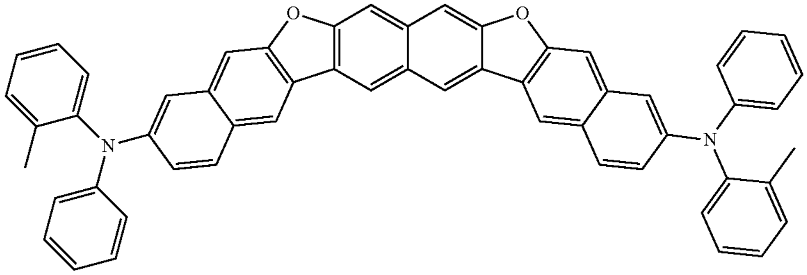
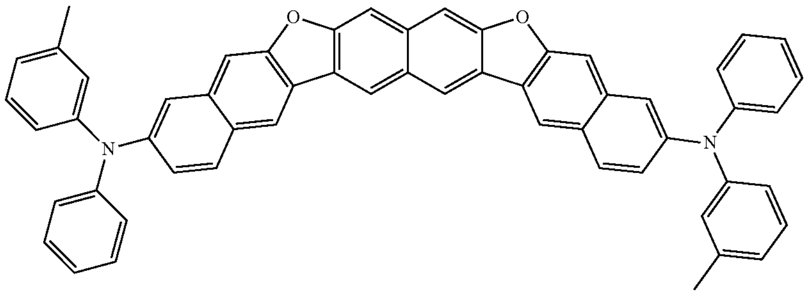

-continued
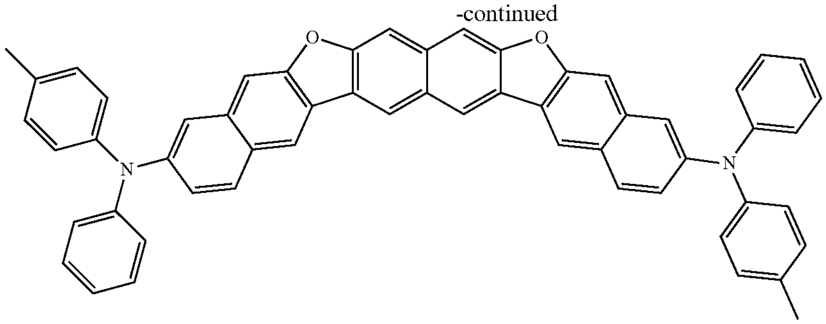
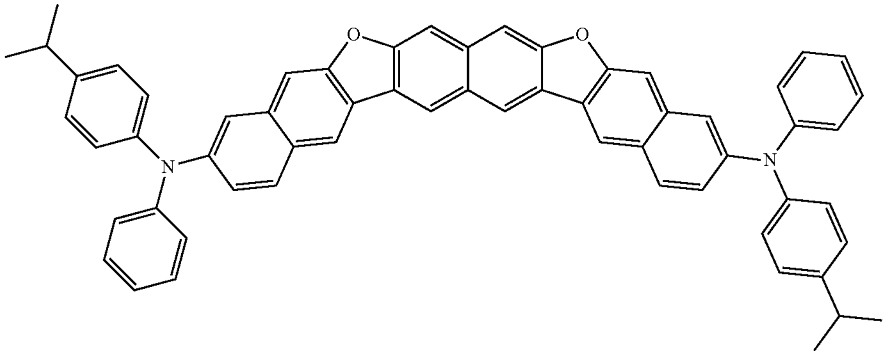
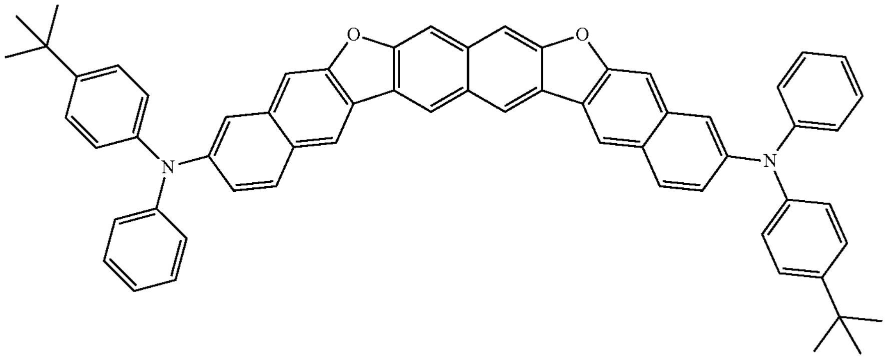
[Formula 257]
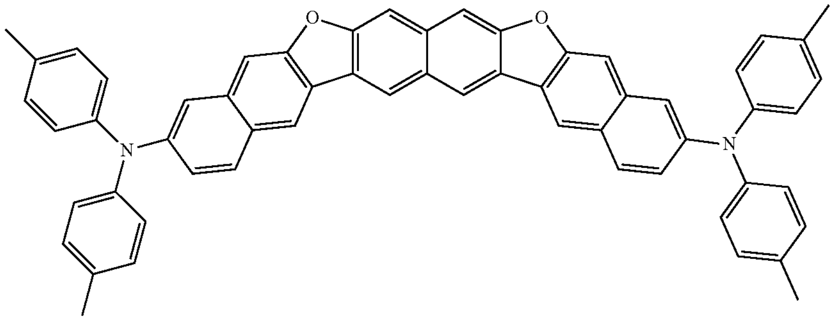
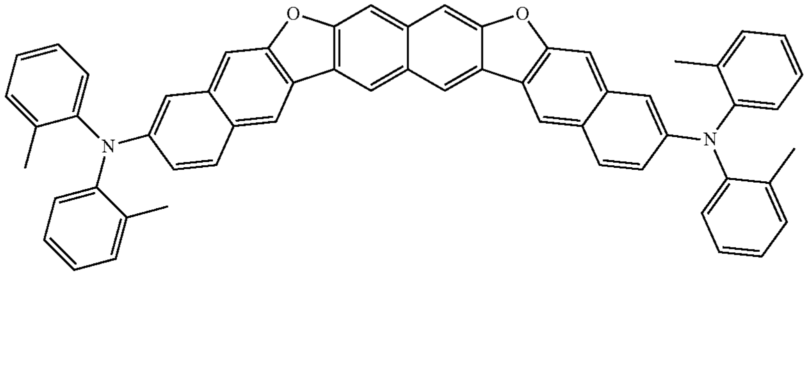

-continued
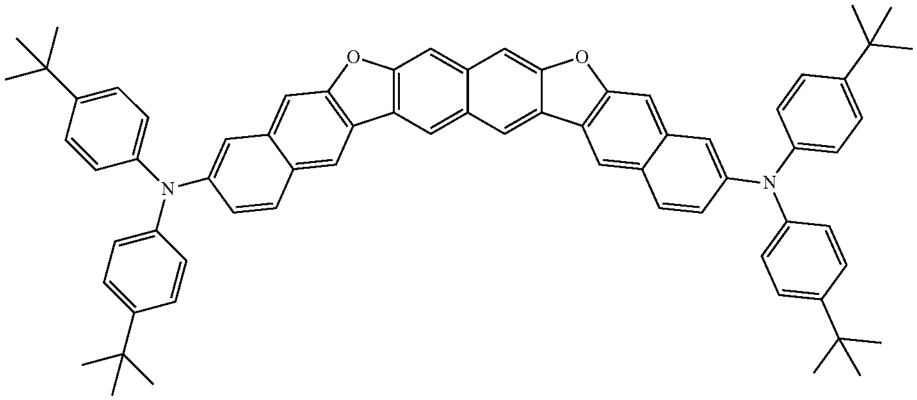
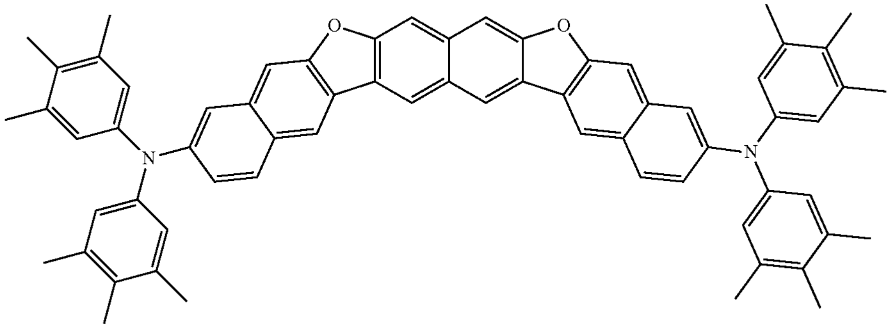
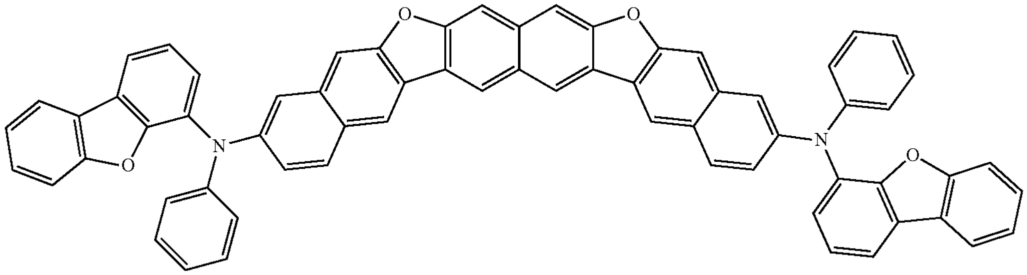
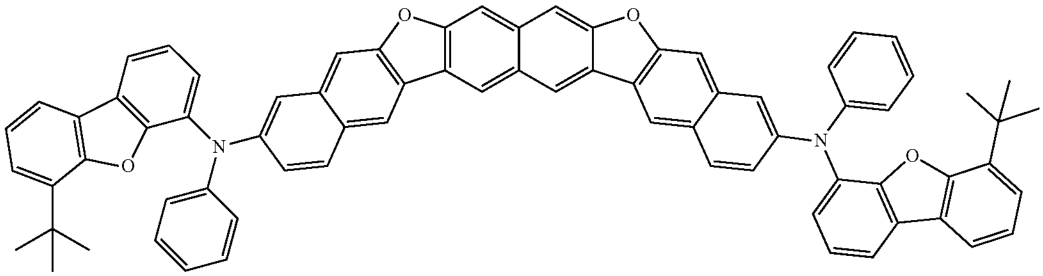

Compound Represented by Formula (8)

The compound represented by the formula (8) will be described.

[Formula 258]

(8)

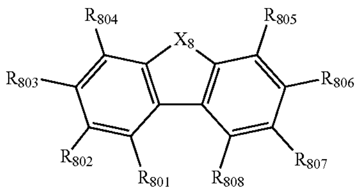

In the formula (8):

at least one combination of $R_{801}$ and $R_{802}$, $R_{802}$ and $R_{803}$, or $R_{803}$ and $R_{804}$ are mutually bonded to form a divalent group represented by a formula (82) below; and at least one combination of $R_{805}$ and $R_{806}$, $R_{806}$ and $R_{807}$, or $R_{807}$ and $R_{808}$ are mutually bonded to form a divalent group represented by a formula (83) below.

[Formula 259]

(82)

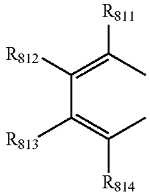

(83)

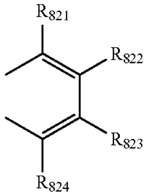

At least one of $R_{801}$ to $R_{804}$ not forming the divalent group represented by the formula (82) or $R_{811}$ to $R_{814}$ is a monovalent group represented by a formula (84) below;

at least one of $R_{805}$ to $R_{808}$ not forming the divalent group represented by the formula (83) or $R_{821}$ to $R_{824}$ is a monovalent group represented by the formula (84);

$X_8$ is an oxygen atom, a sulfur atom, or $NR_{809}$; and $R_{801}$ to $R_{808}$ not forming the divalent group represented by the formula (82) or (83) and not being the monovalent group represented by the formula (84), $R_{811}$ to $R_{814}$ and $R_{821}$ to $R_{824}$ not being the monovalent group represented by the formula (84), and $R_{809}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

[Formula 260]

(84)

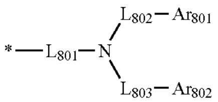

In the formula (84):

$Ar_{201}$ and $Ar_{802}$ are each independently a substituted or unsubstituted aryl group having 6 to 50 ring carbon atoms, or a substituted or unsubstituted heterocyclic group having 5 to 50 ring atoms;

$L_{801}$ to $L_{803}$ are each independently a single bond, a substituted or unsubstituted arylene group having 6 to 30 ring carbon atoms, a substituted or unsubstituted divalent heterocyclic group having 5 to 30 ring atoms, or a divalent linking group formed by bonding two, three or four groups selected from the group consisting of a substituted or unsubstituted arylene group having 6 to 30 ring carbon atoms and a substituted or unsubstituted divalent heterocyclic group having 5 to 30 ring atoms; and

* in the formula (84) represents a bonding position to a cyclic structure represented by the formula (8) or a bonding position to the group represented by the formula (82) or (83).

In the formula (8), the positions for the divalent group represented by the formula (82) and the divalent group represented by the formula (83) to be formed are not specifically limited but the divalent groups may be formed at any possible positions on $R_{801}$ to $R_{808}$.

In an exemplary embodiment, the compound represented by the formula (8) is represented by any one of formulae (81-1) to (81-6) below.

[Formula 261]

(81-1)

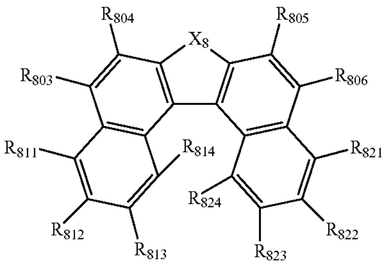

(81-2)

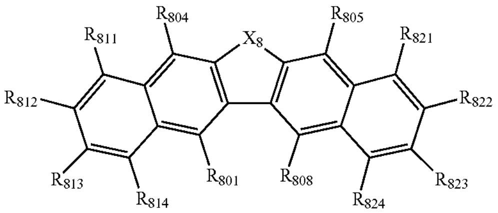

-continued

[Formula 262]

(81-3)

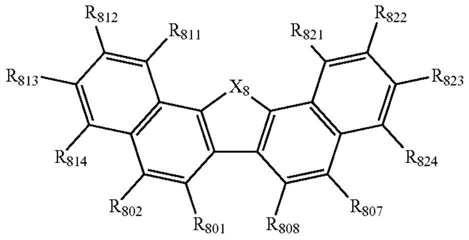

(81-4)

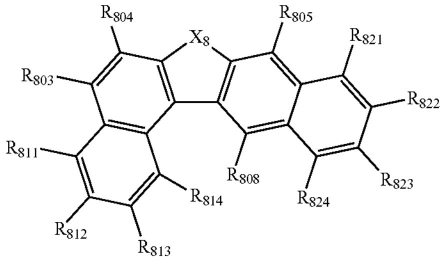

[Formula 263]

(81-5)

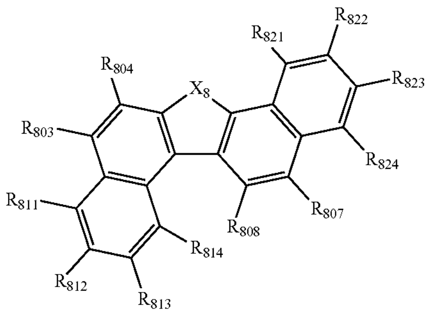

(81-6)

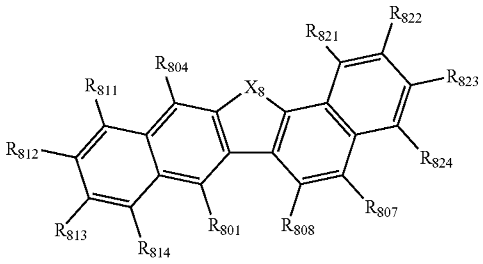

In the formulae (81-1) to (81-6):

$X_8$ represents the same as $X_8$ in the formula (8);

at least two of $R_{801}$ to $R_{824}$ are each a monovalent group represented by the formula (84); and $R_{801}$ to $R_{824}$ not being the monovalent group represented by the formula (84) are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (8) is represented by any one of formulae (81-7) to (81-18) below.

[Formula 264]

(81-7)

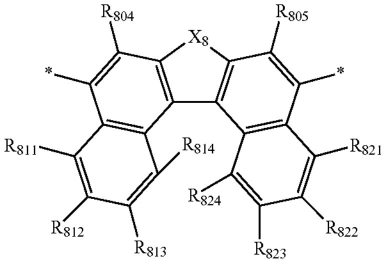

(81-8)

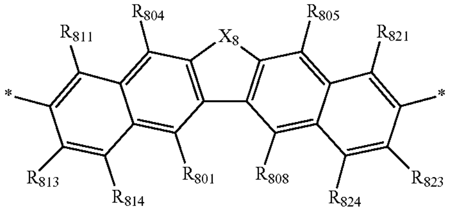

[Formula 265]

(81-9)

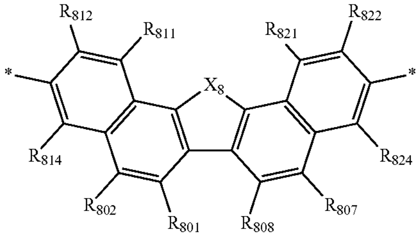

(81-10)

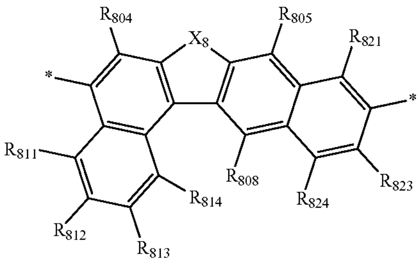

[Formula 266]

(81-11)

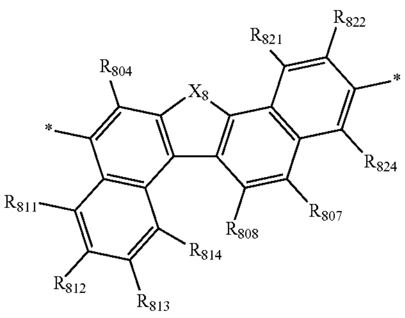

-continued (81-12)

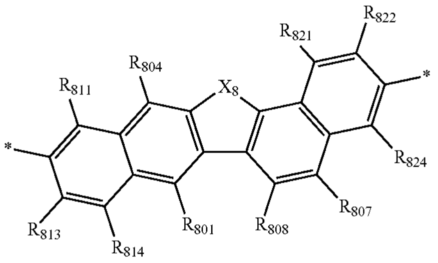

[Formula 267]

(81-13)

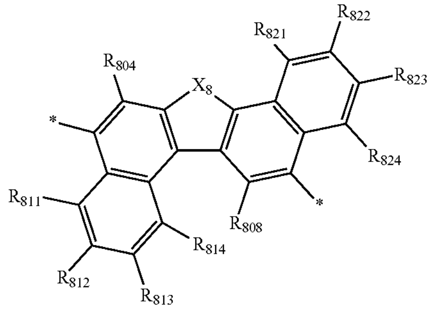

(81-14)

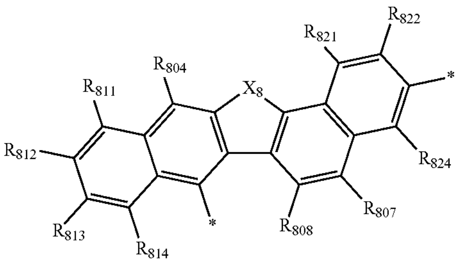

[Formula 268]

(81-15)

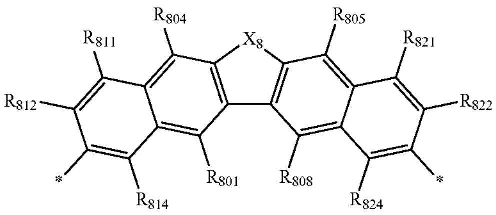

(81-16)

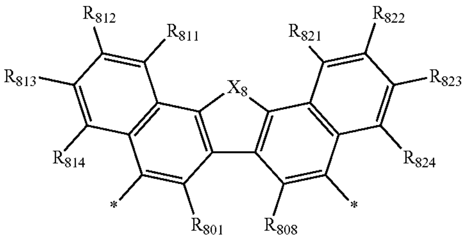

-continued

[Formua 269]

(81-17)

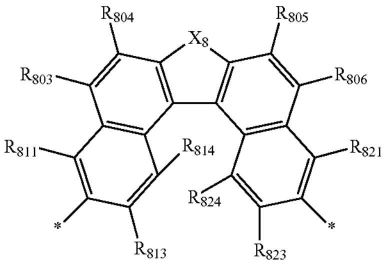

(81-18)

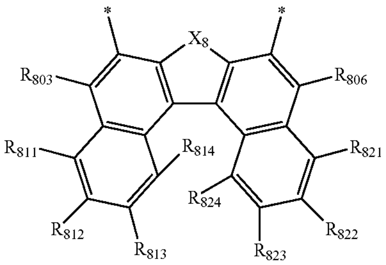

In the formulae (81-7) to (81-18):

$X_8$ represents the same as $X_8$ in the formula (8);

is a single bond to be bonded with the monovalent group represented by the formula (84); and $R_{801}$ to $R_{824}$ each independently represent the same as $R_{801}$ to $R_{824}$ in the formulae (81-1) to (81-6) not being the monovalent group represented by the formula (84).

$R_{801}$ to $R_{808}$ not forming the divalent group represented by the formula (82) or (83) and not being the monovalent group represented by the formula (84), and $R_{811}$ to $R_{814}$ and $R_{821}$ to $R_{824}$ not being the monovalent group represented by the formula (84) are preferably each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The monovalent group represented by the formula (84) is preferably represented by a formula (85) or (86) below.

[Formula 270]

(85)

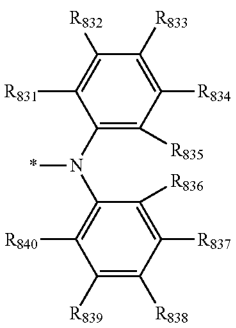

In the formula (85):

$R_{831}$ to $R_{840}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and

* in the formula (85) represents the same as * in the formula (84).

[Formula 271]

(86)

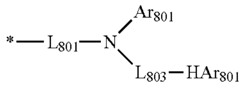

In the formula (86):

$Ar_{801}$, $L_{801}$ and $L_{803}$ represent the same as $Ar_{801}$, $L_{801}$ and $L_{803}$ in the formula (84); and $HAr_{801}$ is a structure represented by a formula (87) below.

[Formula 272]

(87)

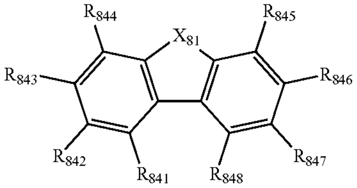

In the formula (87):

$X_{81}$ represents an oxygen atom or a sulfur atom;

one of $R_{841}$ to $R_{848}$ is a single bond with $L_{803}$; and $R_{841}$ to $R_{848}$ not being the single bond are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

Specific examples of the compound represented by the formula (8) include compounds shown below as well as the compounds disclosed in WO 2014/104144.

[Formula 273]

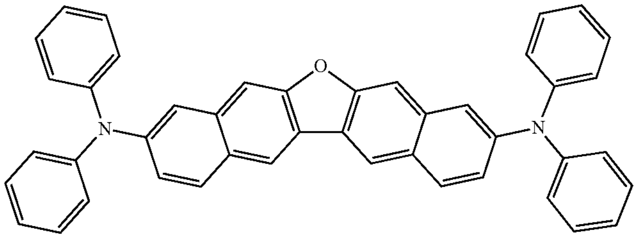

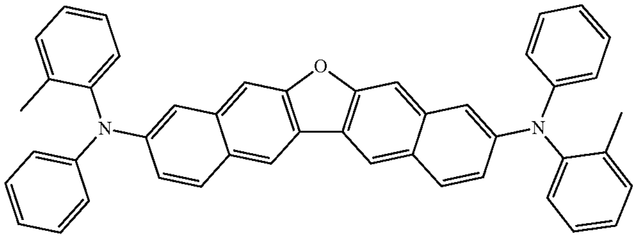

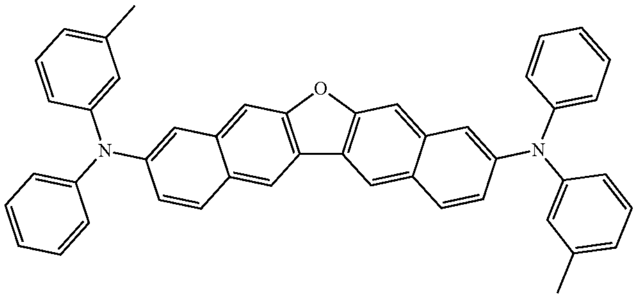

-continued
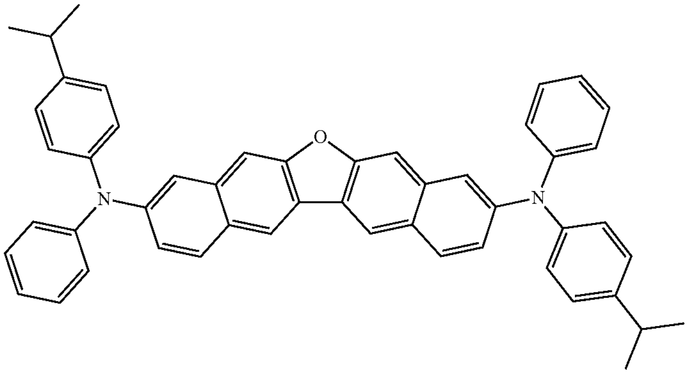
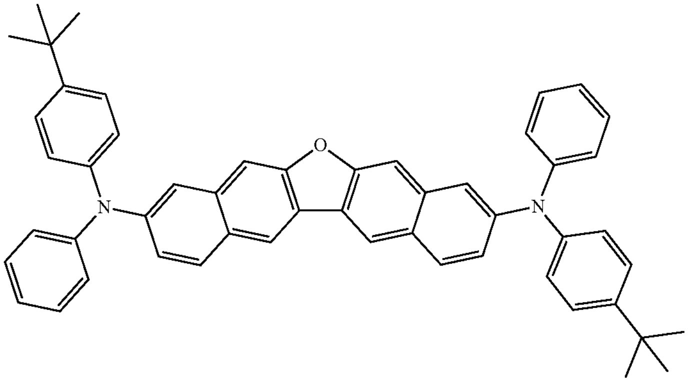
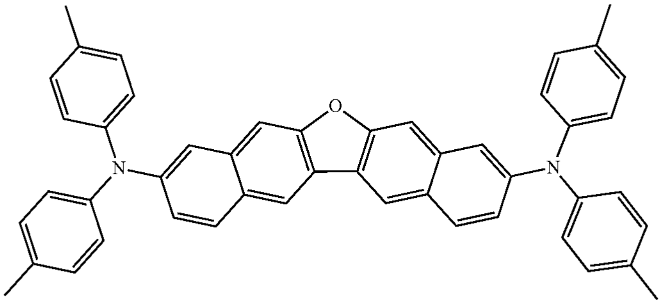
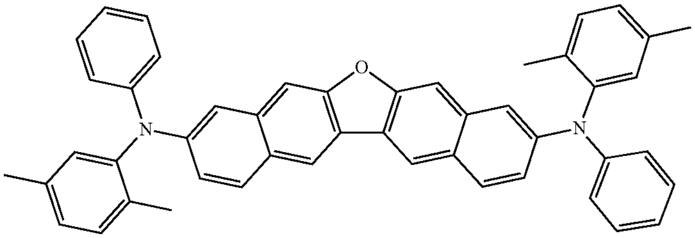
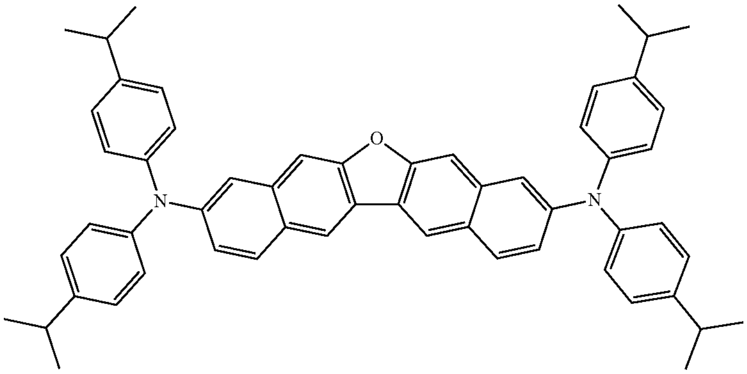

-continued
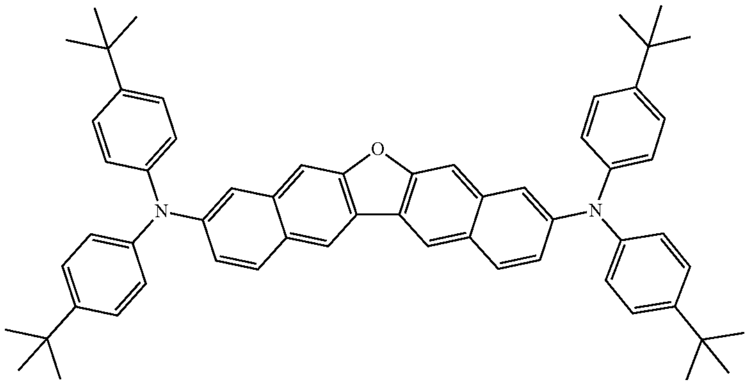
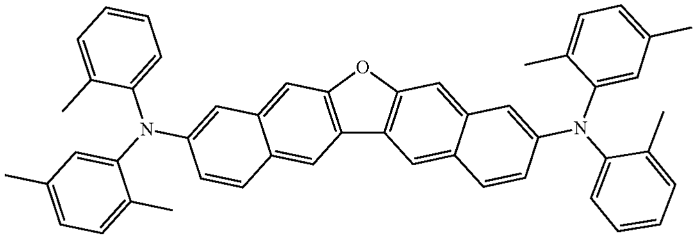
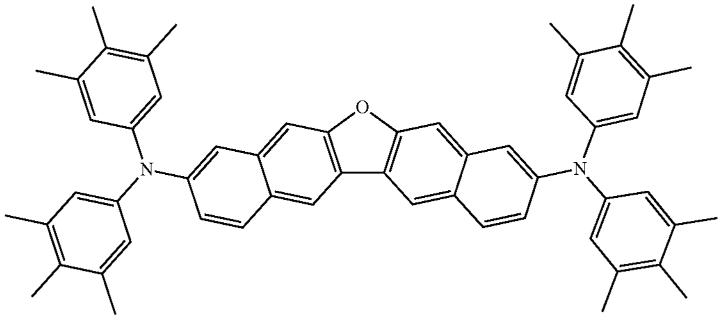
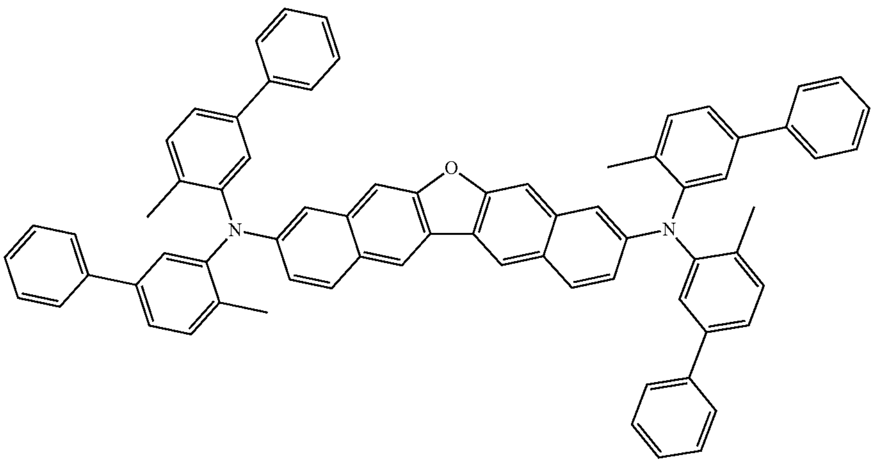

-continued
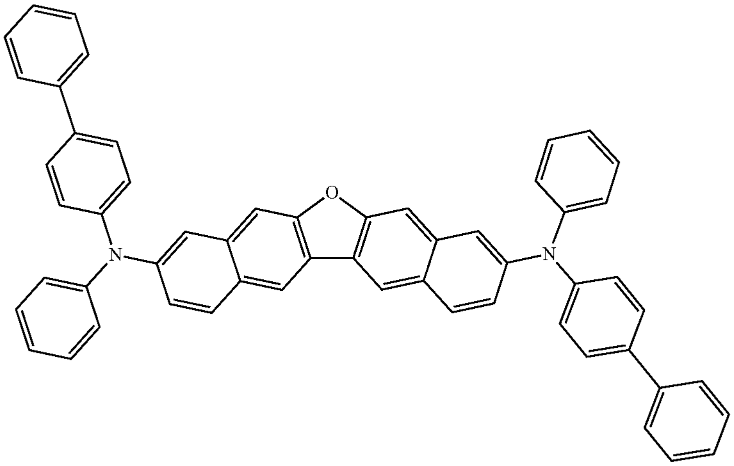
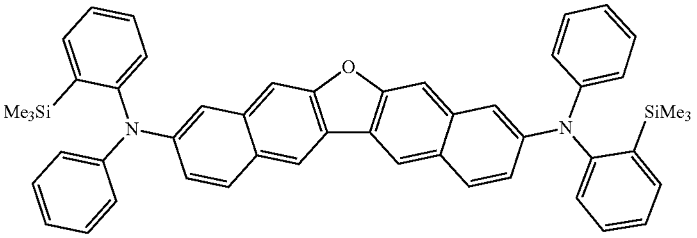
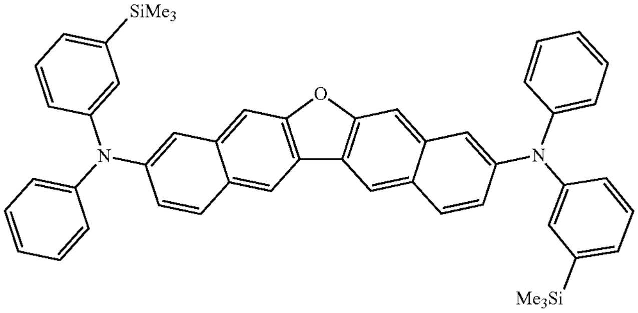
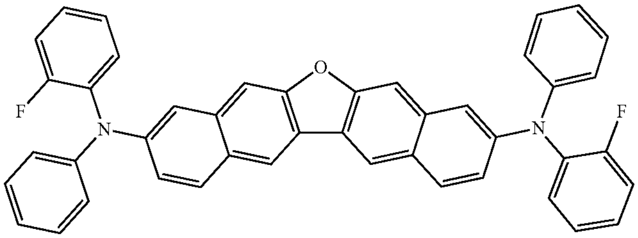
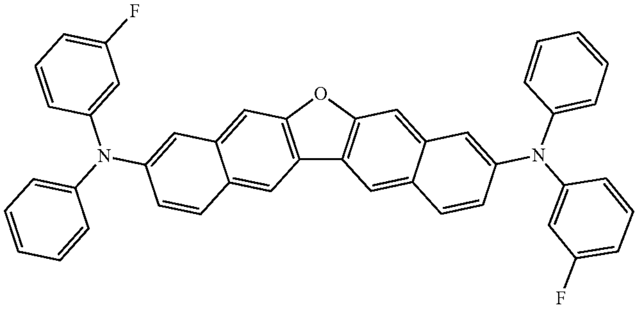

-continued
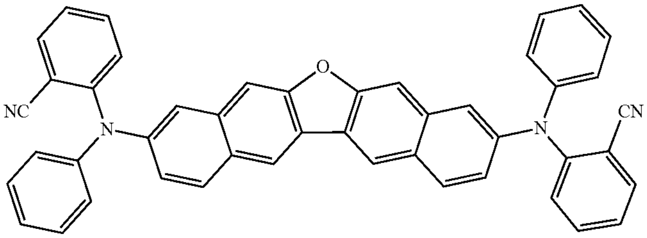
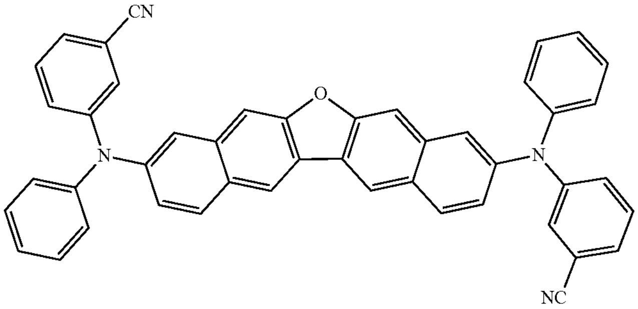
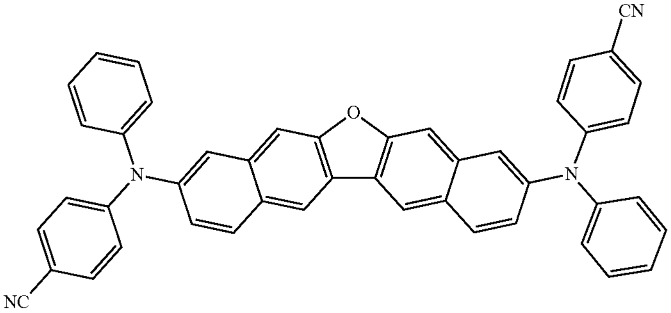
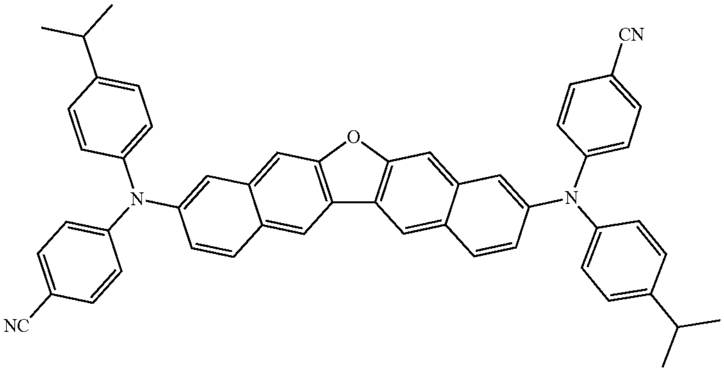
[Formula 274]
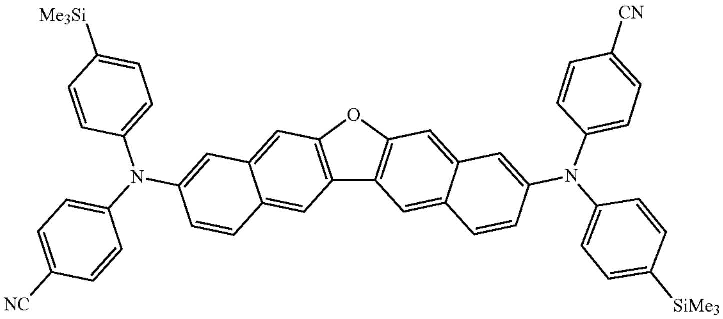

-continued
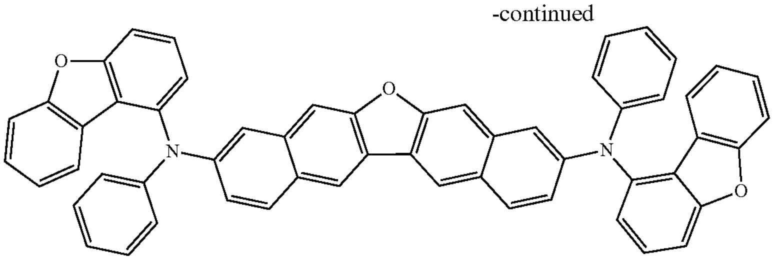
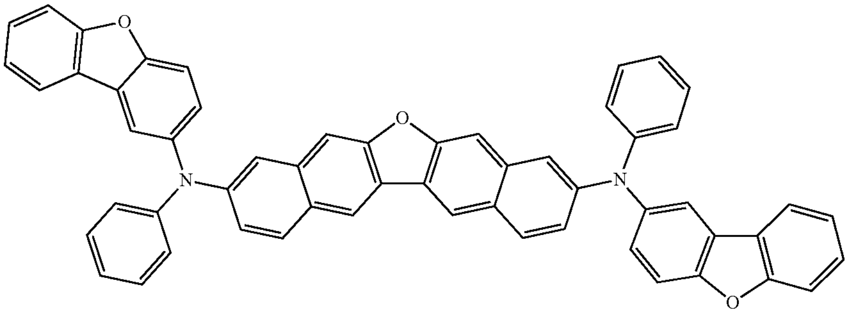
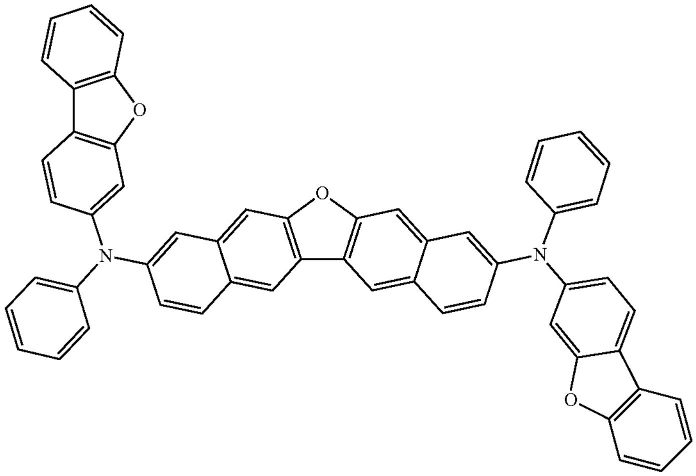
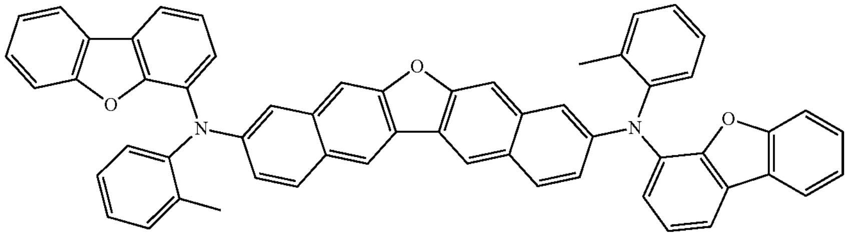
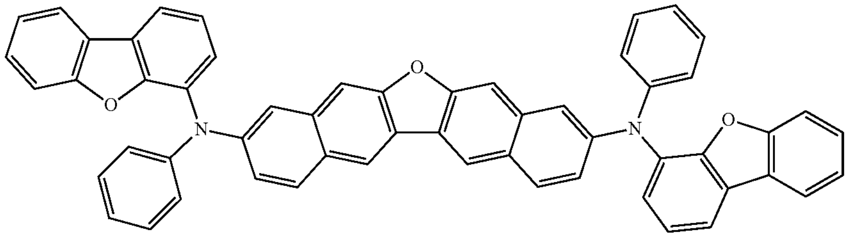
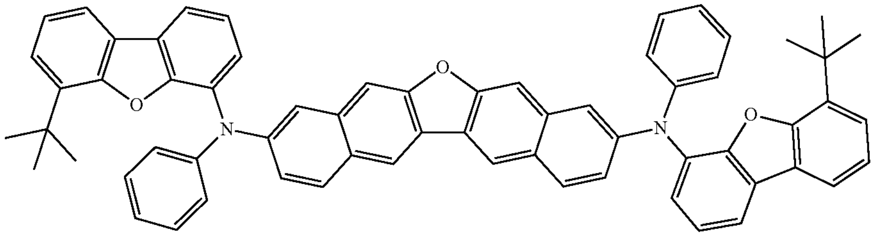

-continued
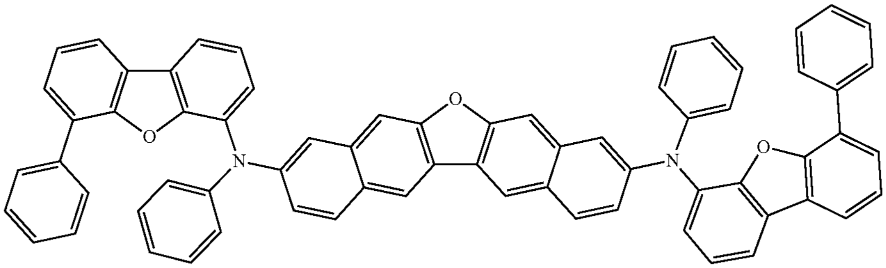
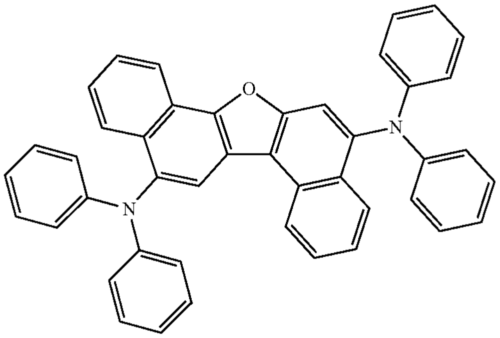
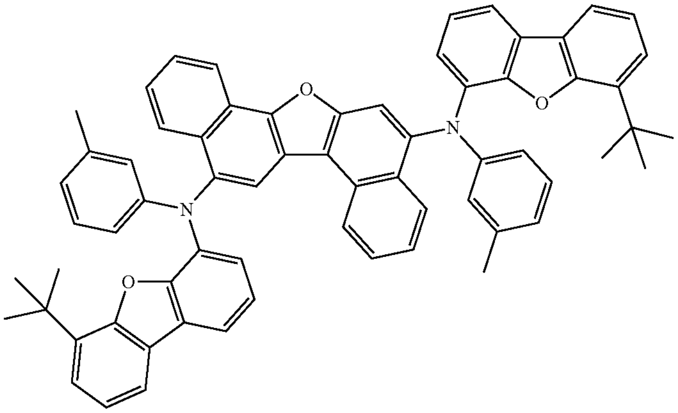
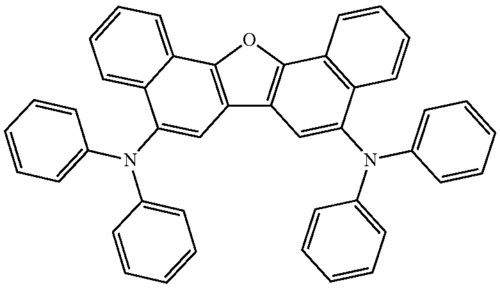
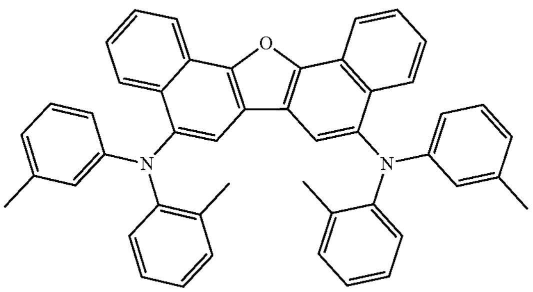
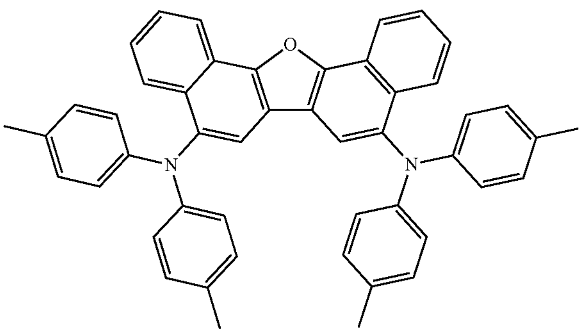

-continued
[Formula 275]
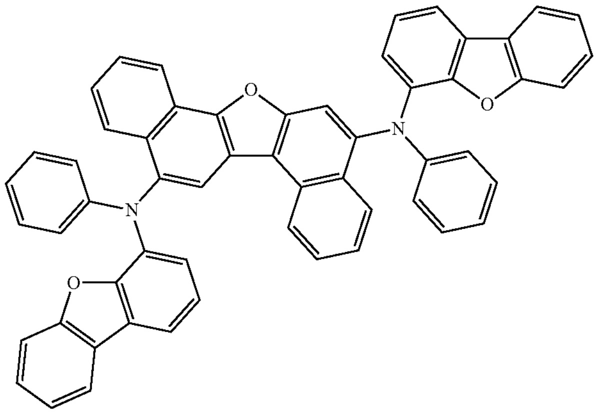
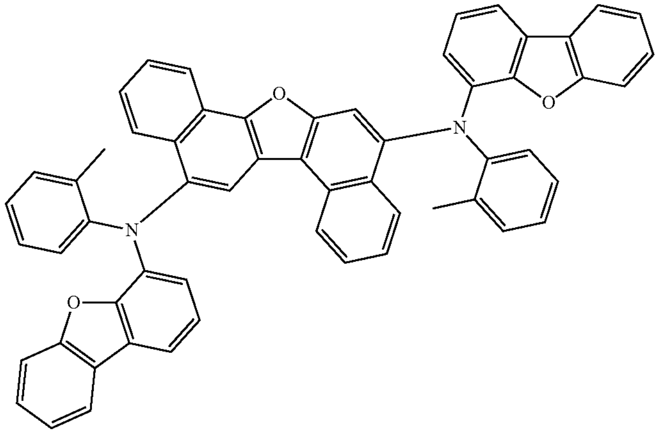
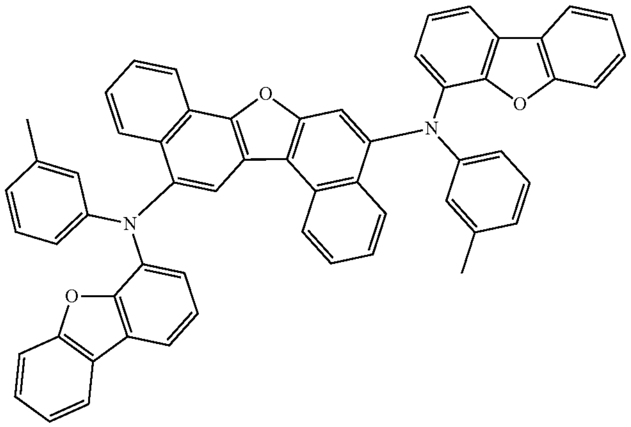
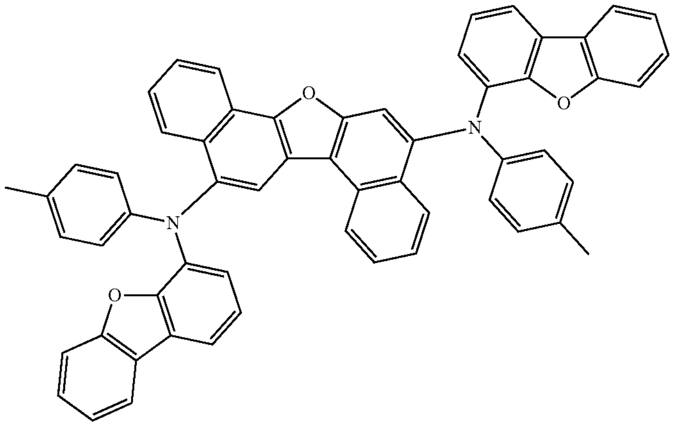

-continued
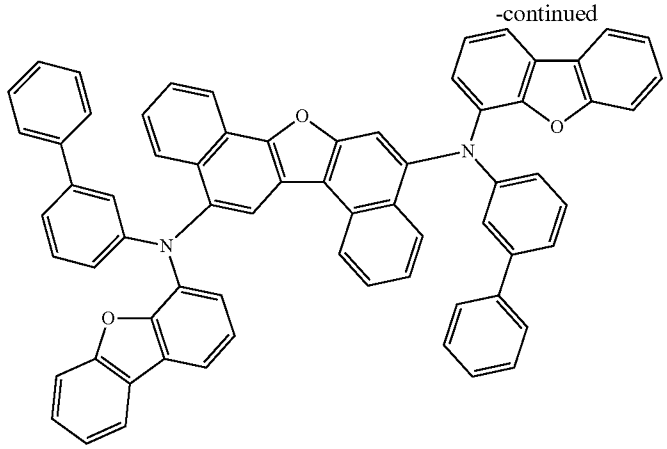
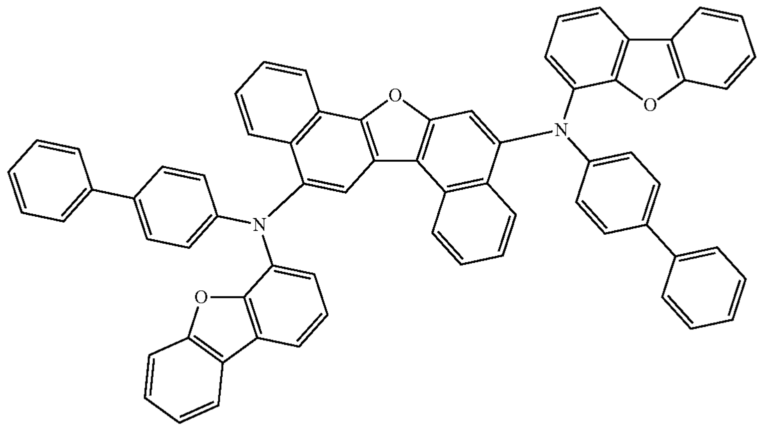
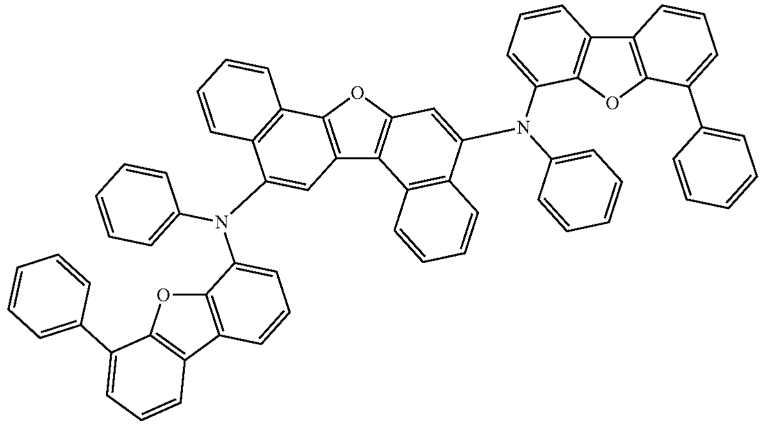

-continued
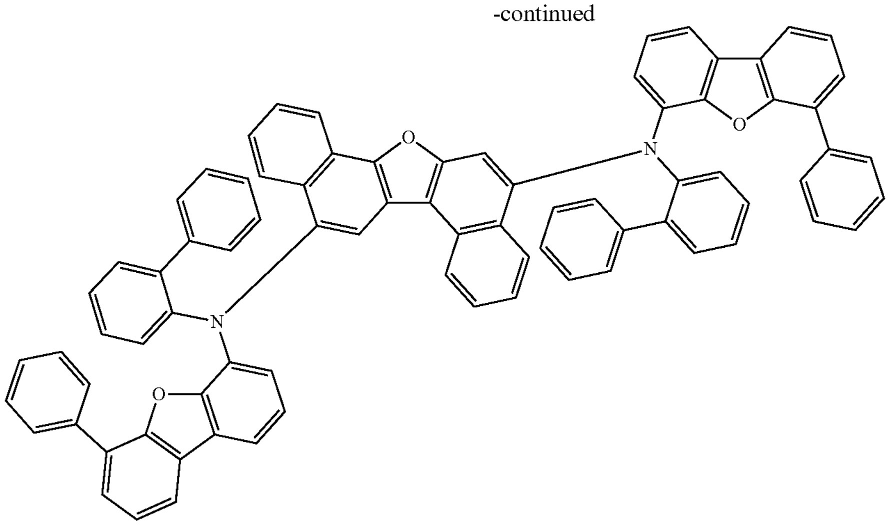
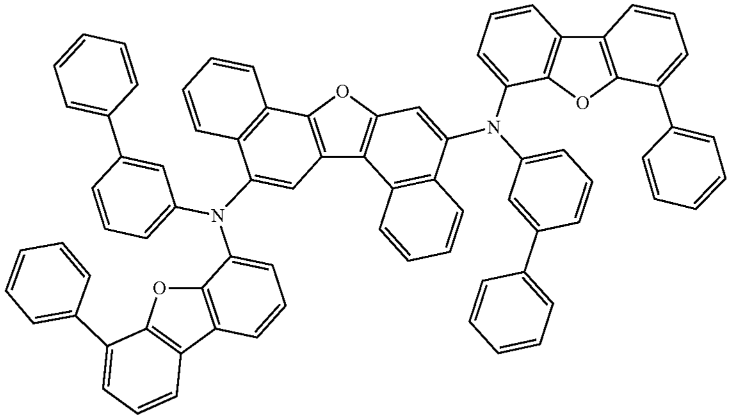
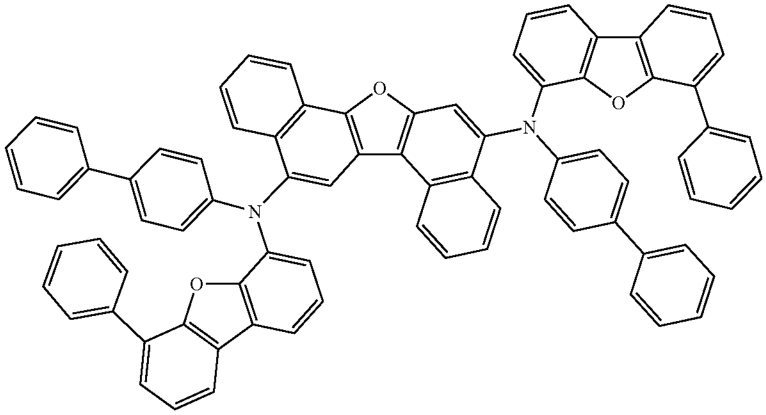

-continued
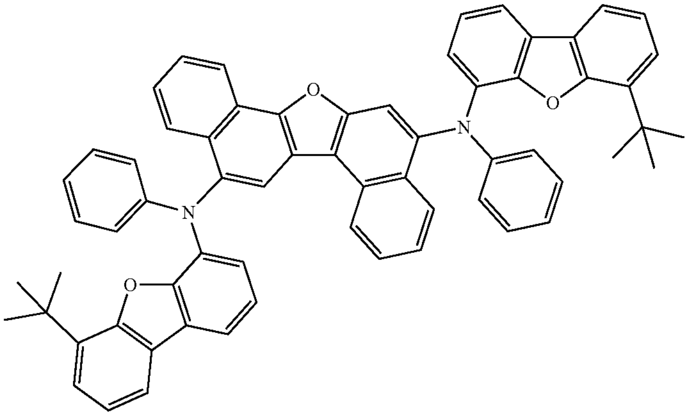
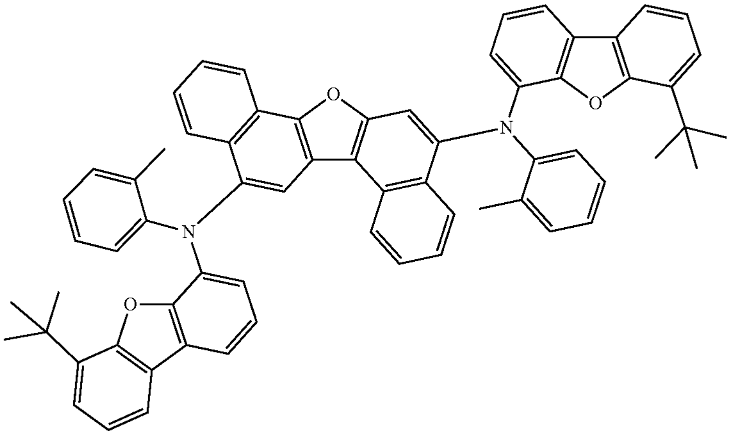
[Formula 276]
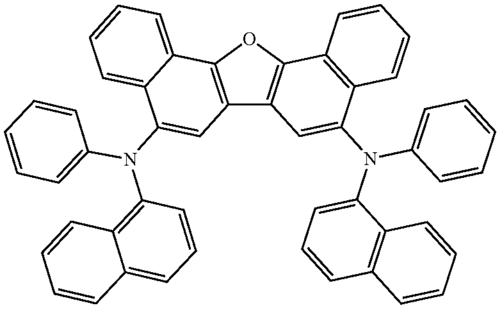
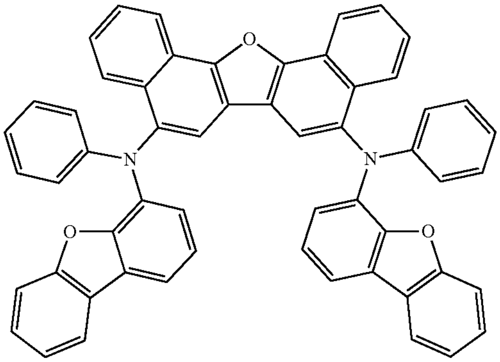
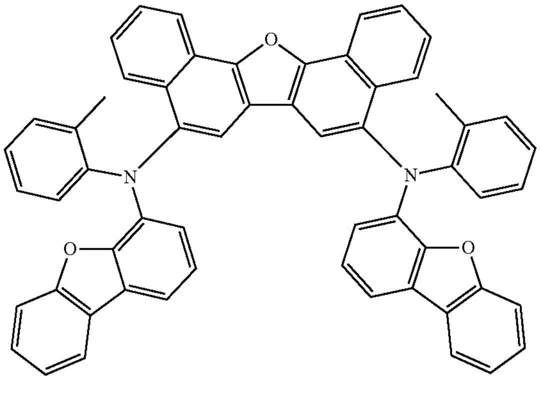
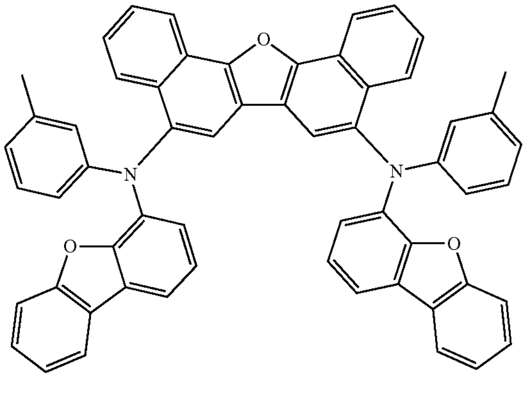

-continued
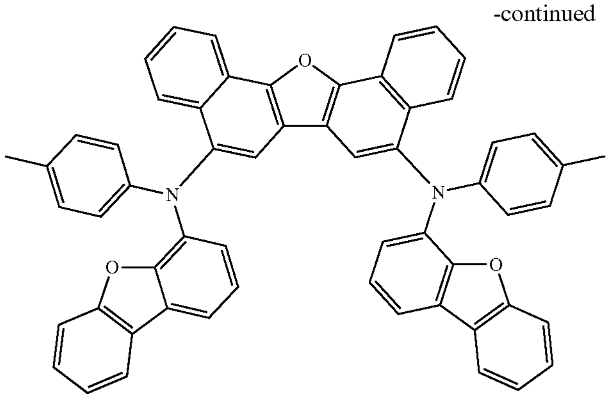
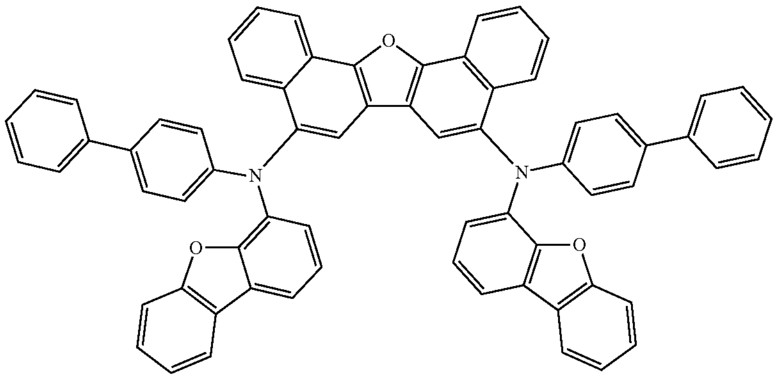
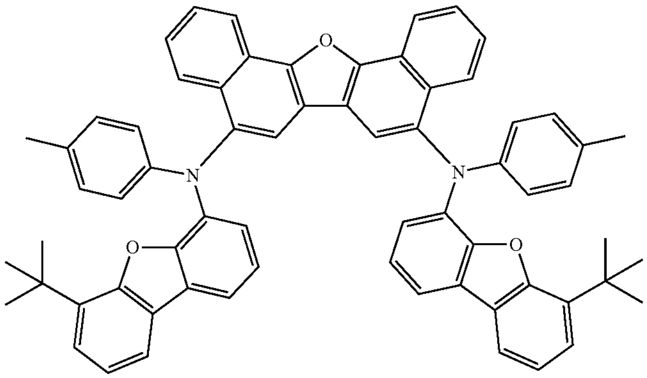
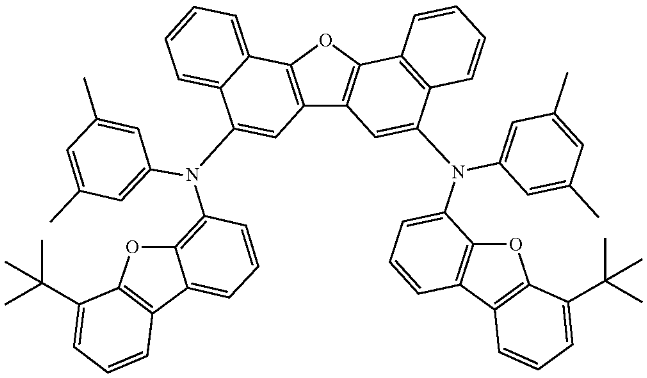

-continued
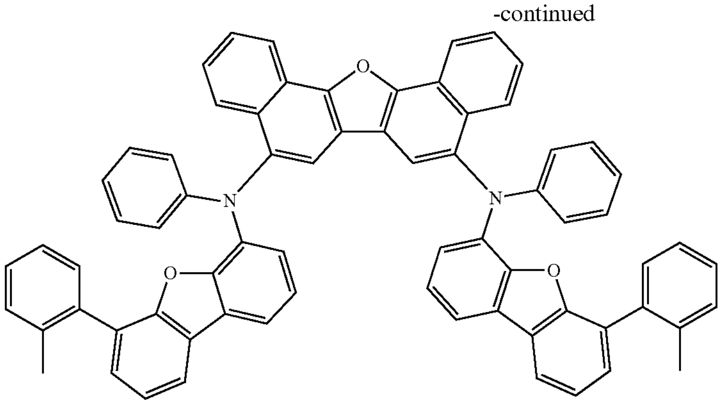
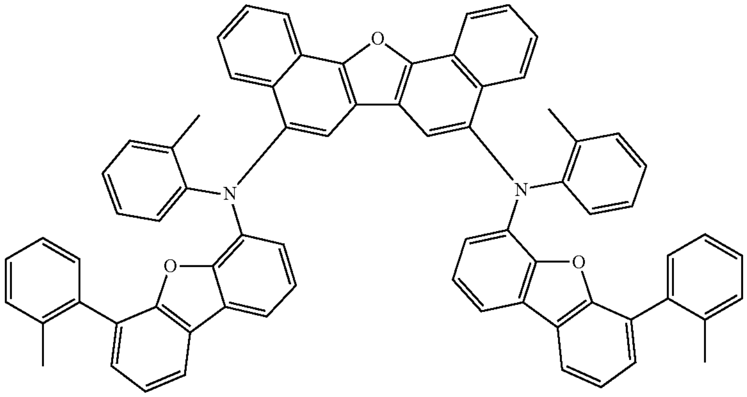
[Formula 277]
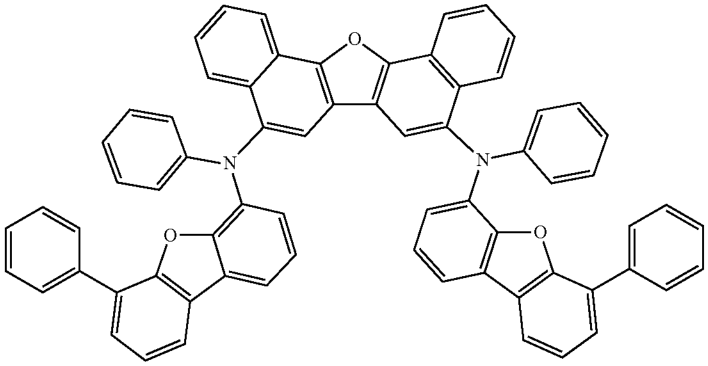
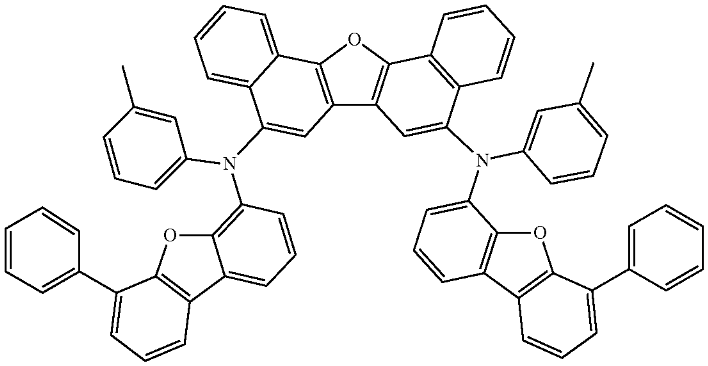

-continued
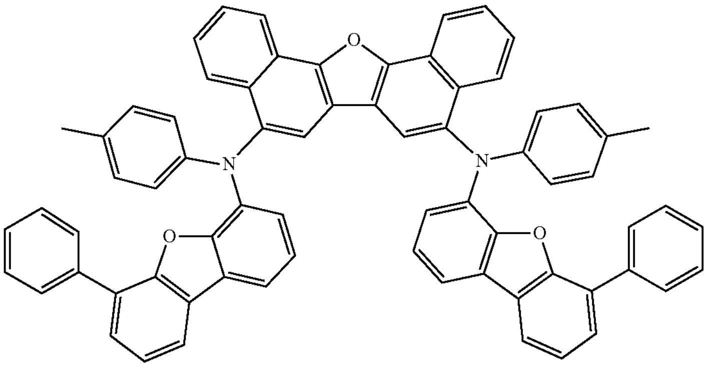
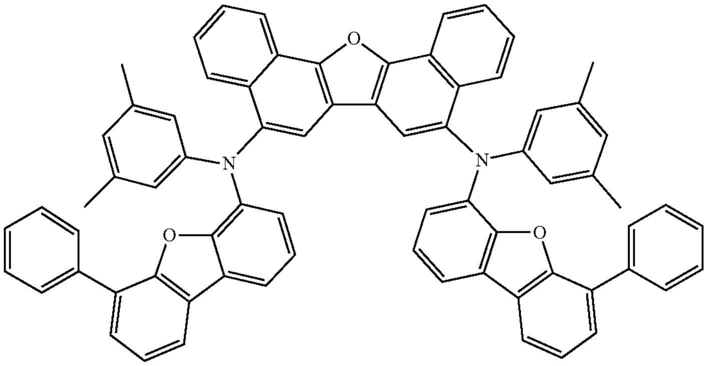
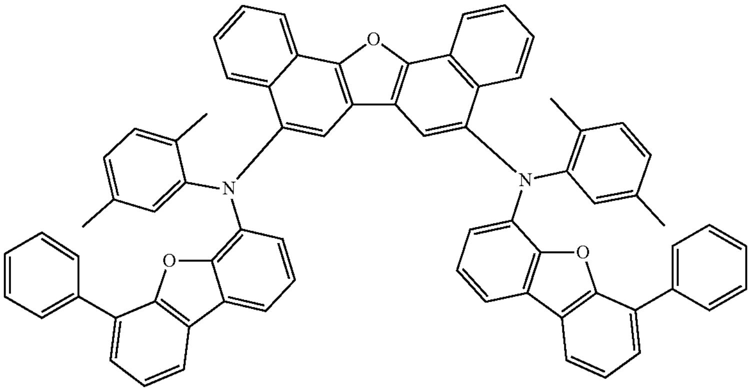
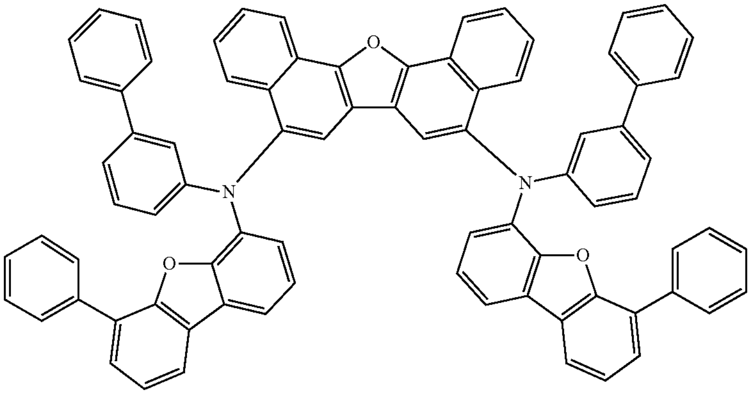

-continued
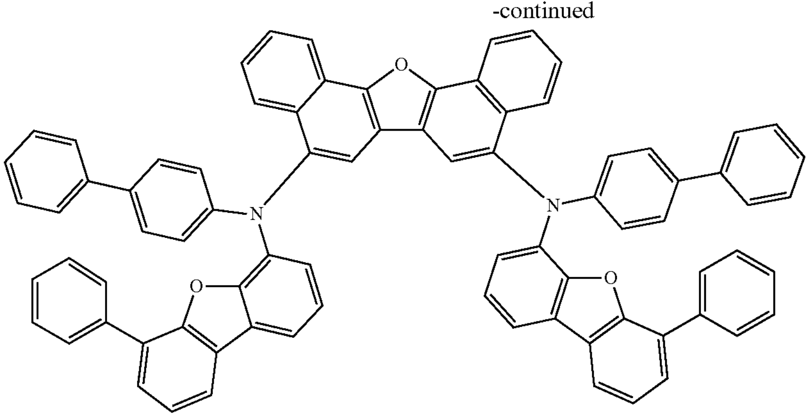
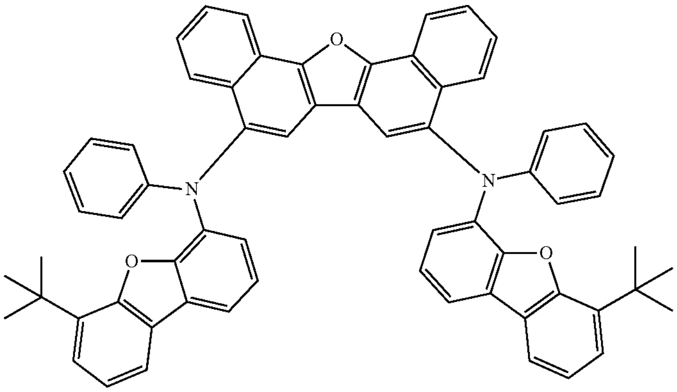
[Formula 278]
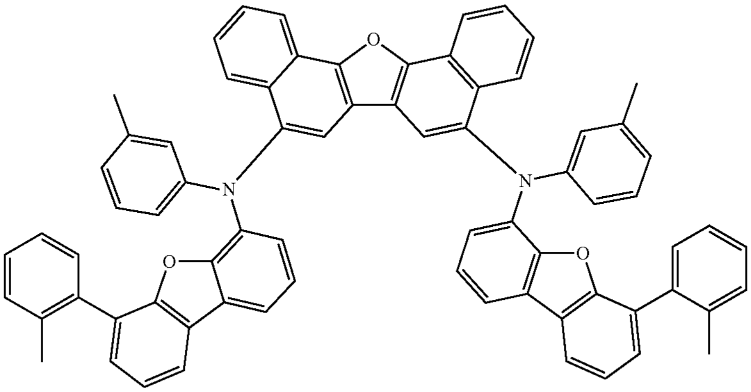
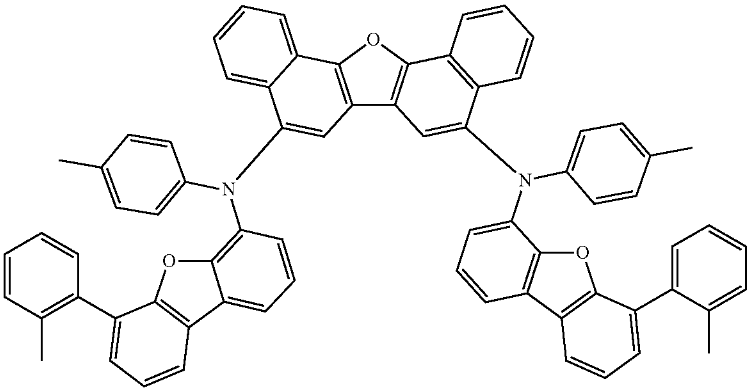

-continued
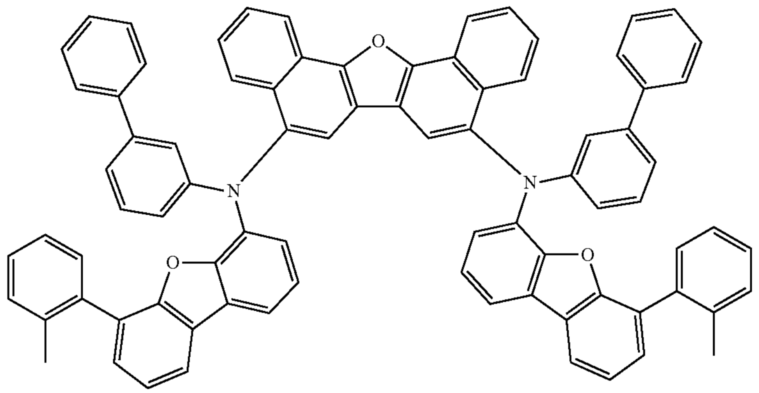
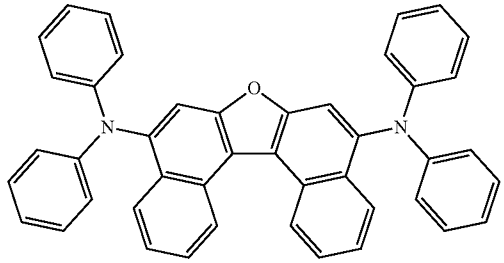
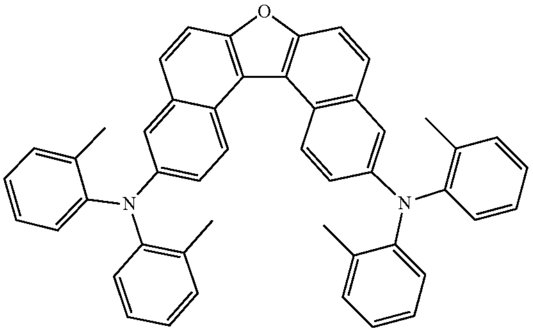
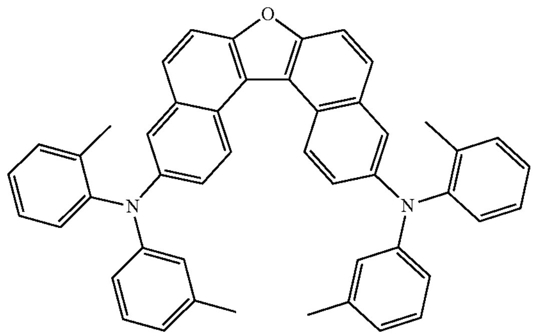
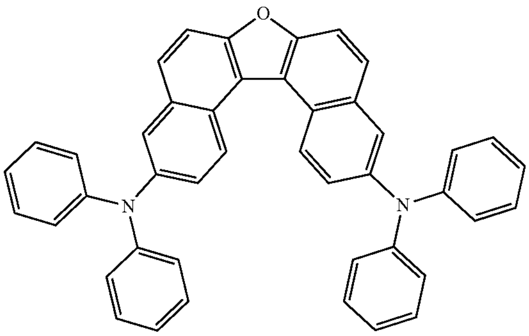
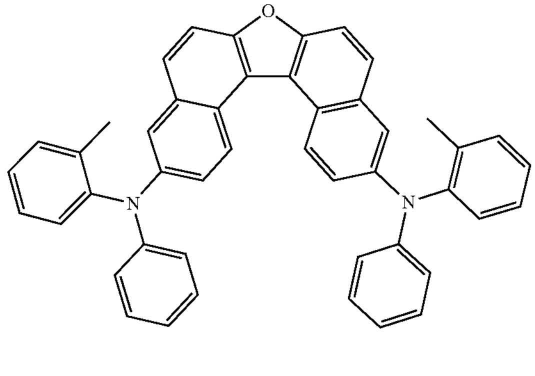
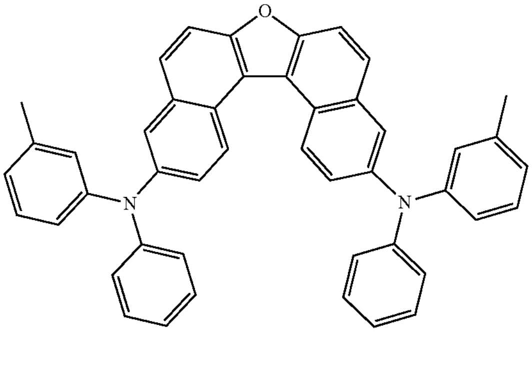

-continued
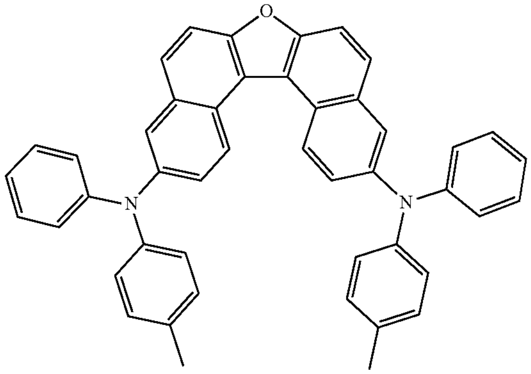
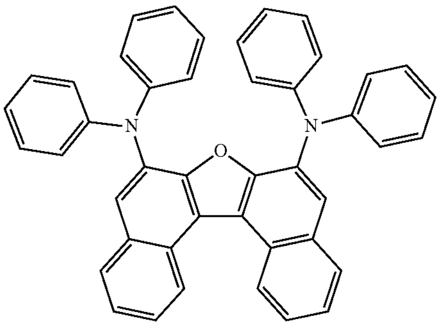
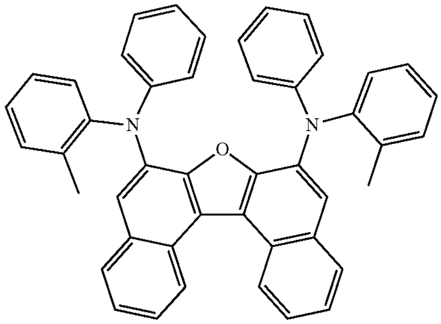
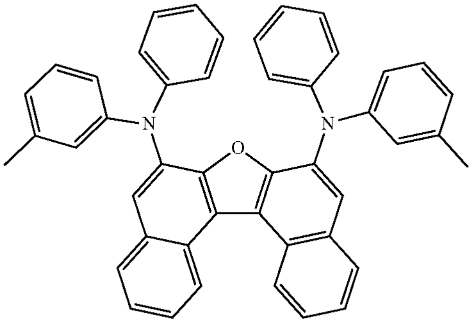
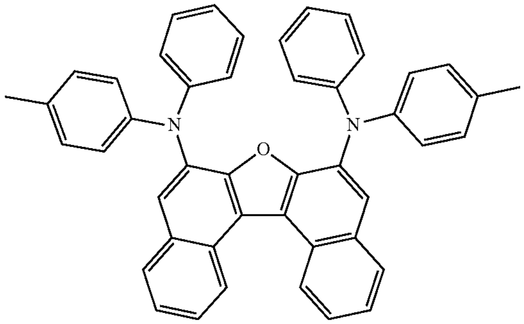
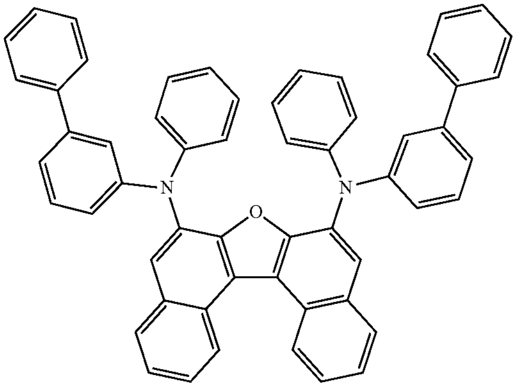
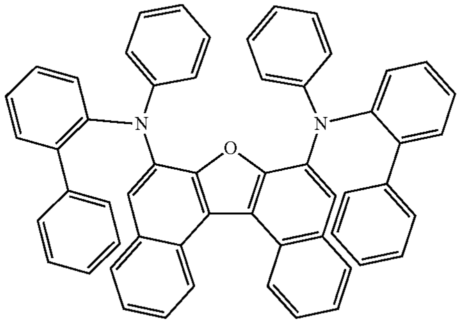

Compound Represented by Formula (9)

The compound represented by the formula (9) will be described.

[Formula 279]

(9)

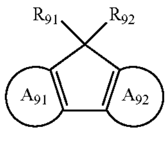

In the formula (9):

$A_{91}$ ring and $A_{92}$ ring are each independently a substituted or unsubstituted aromatic hydrocarbon ring having 6 to 50 ring carbon atoms, or a substituted or unsubstituted heterocycle having 5 to 50 ring atoms;

at least one of $A_{91}$ ring or $A_{92}$ ring is bonded with * in a structure represented by a formula (92) below.

[Formula 280]

(92)

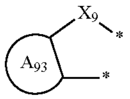

In the formula (92):

$A_{93}$ ring is a substituted or unsubstituted aromatic hydrocarbon ring having 6 to 50 ring carbon atoms, or a substituted or unsubstituted heterocycle having 5 to 50 ring atoms;

$X_9$ is $NR_{93}$, $C(R_{94})(R_{95})$, $Si(R_{96})(R_{97})$, $Ge(R_{98})(R_{99})$, an oxygen atom, a sulfur atom, or a selenium atom;

$R_{91}$ and $R_{92}$ are mutually bonded to form a substituted or unsubstituted monocyclic ring, mutually bonded to form a substituted or unsubstituted fused ring, or not mutually bonded; and $R_{91}$ and $R_{92}$ not forming the monocyclic ring and not forming the fused ring, and $R_{93}$ to $R_{99}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

At least one ring selected from the group consisting of $A_{91}$ ring and $A_{92}$ ring is bonded to a bond * of the structure represented by the formula (92). In other words, the ring-forming carbon atoms of the aromatic hydrocarbon ring or the ring atoms of the heterocycle of the $A_{91}$ ring in an exemplary embodiment are bonded to the bonds * in the structure represented by the formula (92). Further, the ring-forming carbon atoms of the aromatic hydrocarbon ring or the ring atoms of the heterocycle of the $A_{92}$ ring in an exemplary embodiment are bonded to the bonds * in the structure represented by the formula (92).

In an exemplary embodiment, a group represented by a formula (93) below is bonded to one or both of the $A_{91}$ ring and $A_{92}$ ring.

[Formula 281]

(93)

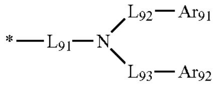

In the formula (93):

$Ar_{91}$ and $Ar_{92}$ are each independently a substituted or unsubstituted aryl group having 6 to 50 ring carbon atoms, or a substituted or unsubstituted heterocyclic group having 5 to 50 ring atoms;

$L_{91}$ to $L_{93}$ are each independently a single bond, a substituted or unsubstituted arylene group having 6 to 30 ring carbon atoms, a substituted or unsubstituted divalent heterocyclic group having 5 to 30 ring atoms, or a divalent linking group formed by bonding two, three or four groups selected from the group consisting of a substituted or unsubstituted arylene group having 6 to 30 ring carbon atoms and a substituted or unsubstituted divalent heterocyclic group having 5 to 30 ring atoms; and

* in the formula (93) represents a bonding position to one of $A_{91}$ ring and $A_{92}$ ring.

In an exemplary embodiment, in addition to the $A_{91}$ ring, the ring-forming carbon atoms of the aromatic hydrocarbon ring or the ring atoms of the heterocycle of the $A_{92}$ ring are bonded to * in the structure represented by the formula (92). In this case, the structures represented by the formula (92) are mutually the same or different.

In an exemplary embodiment, $R_{91}$ and $R_{92}$ are each independently a substituted or unsubstituted aryl group having 6 to 50 ring carbon atoms.

In an exemplary embodiment, $R_{91}$ and $R_{92}$ are mutually bonded to form a fluorene structure.

In an exemplary embodiment, the rings $A_{91}$ and $A_{92}$ are each independently a substituted or unsubstituted aromatic hydrocarbon ring having 6 to 50 ring carbon atoms, example of which is a substituted or unsubstituted benzene ring.

In an exemplary embodiment, the ring $A_{93}$ is a substituted or unsubstituted aromatic hydrocarbon ring having 6 to 50 ring carbon atoms, example of which is a substituted or unsubstituted benzene ring.

In an exemplary embodiment, $X_9$ is an oxygen atom or a sulfur atom.

Specific examples of the compound represented by the formula (9) include compounds shown below.

[Formula 282]

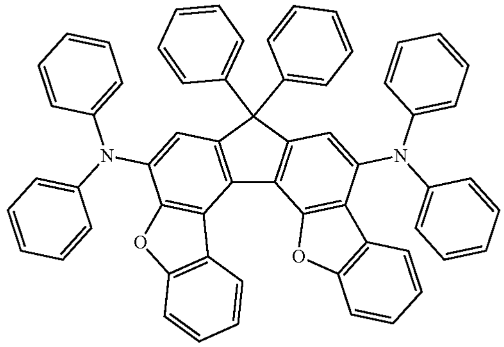

-continued
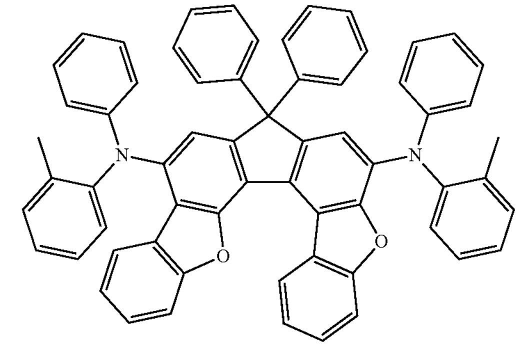
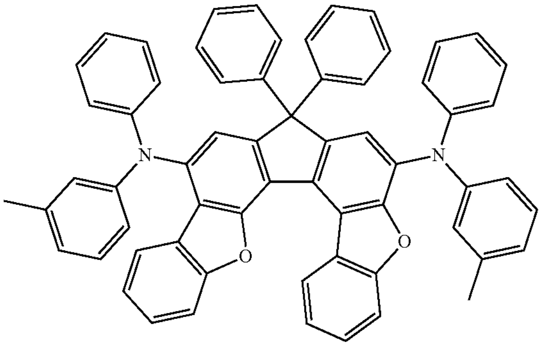
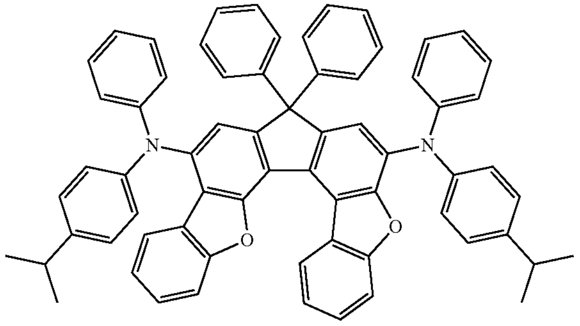
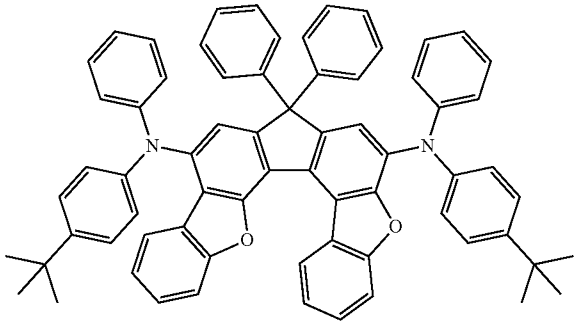
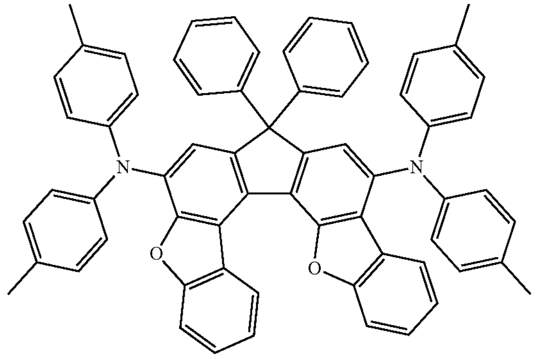
-continued
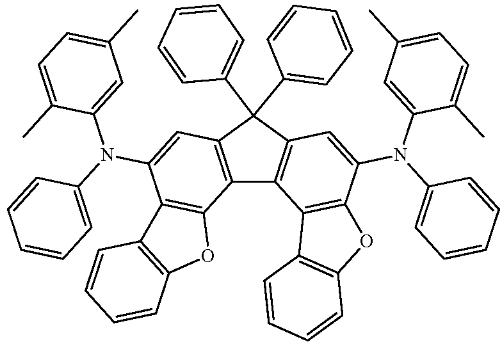
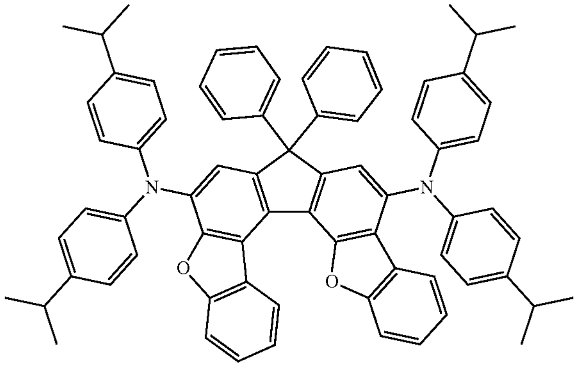
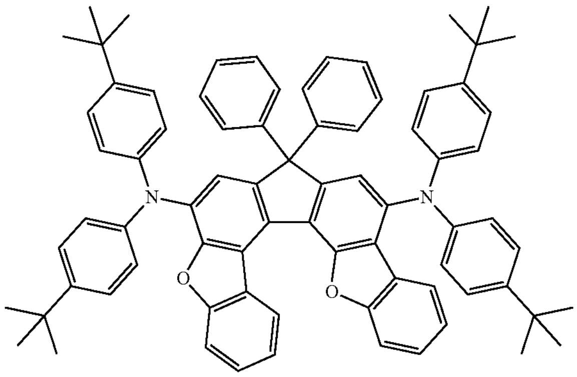
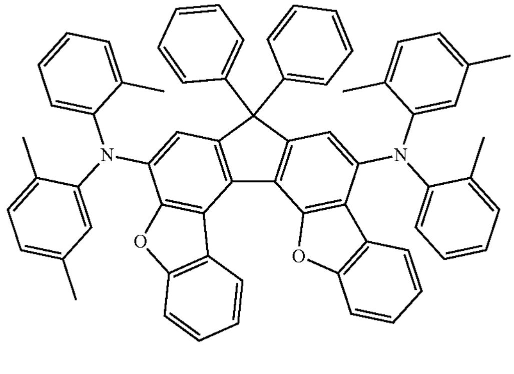

-continued
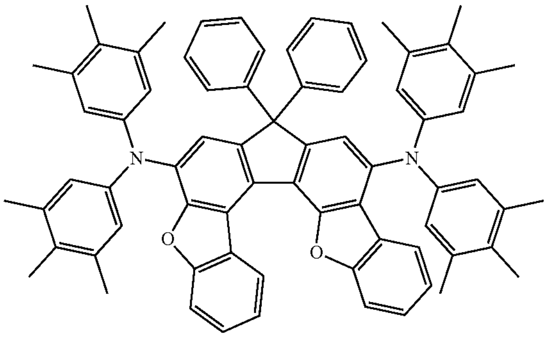
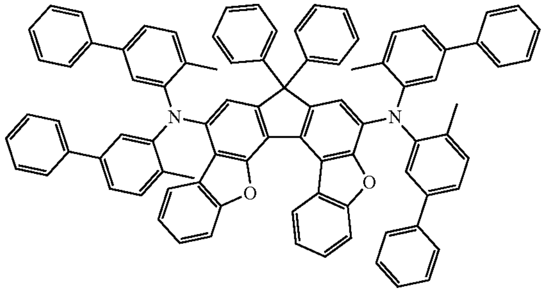
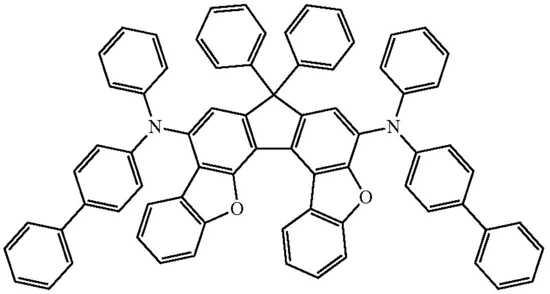
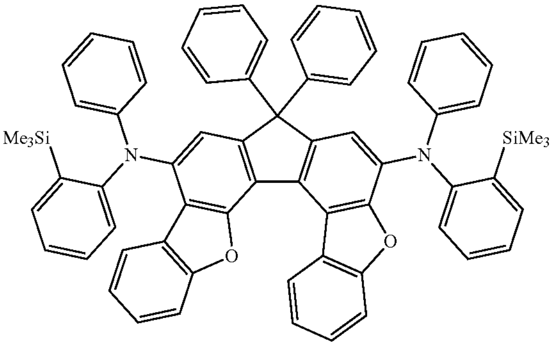
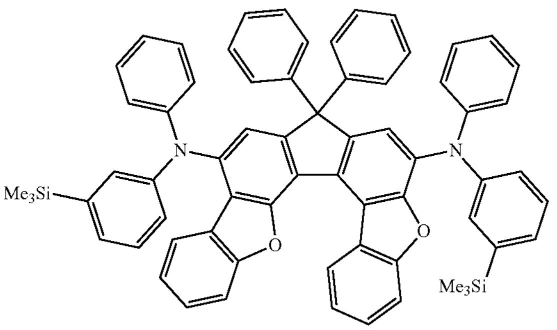
-continued
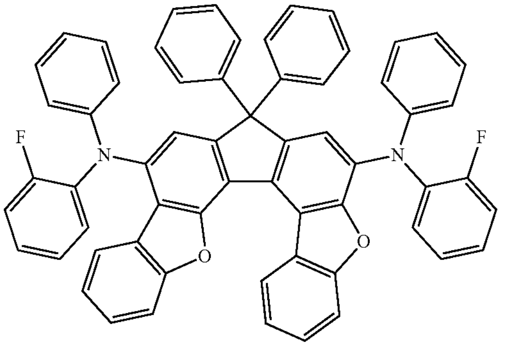
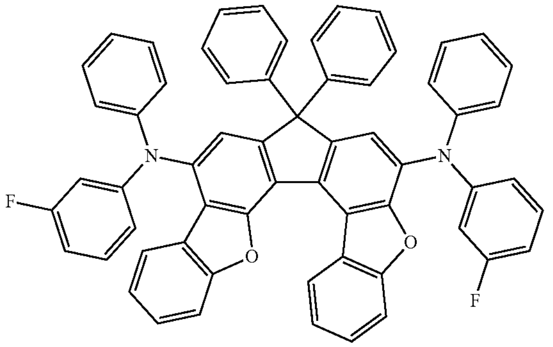
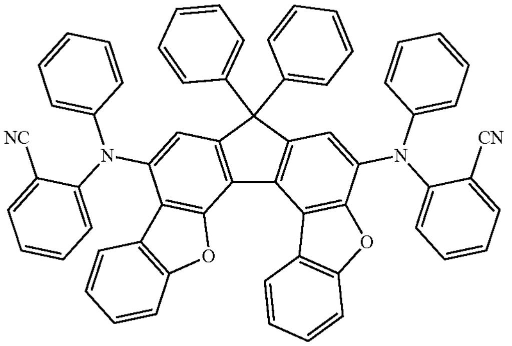
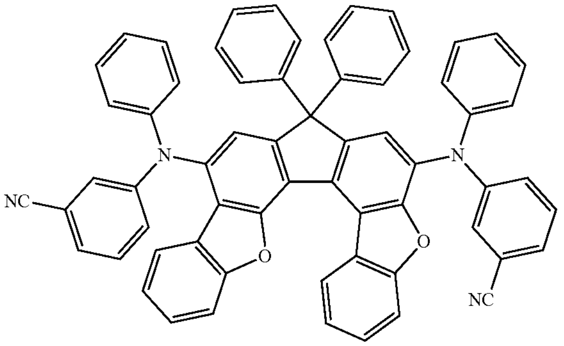

-continued
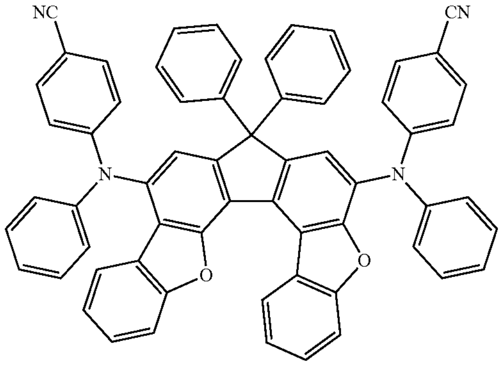
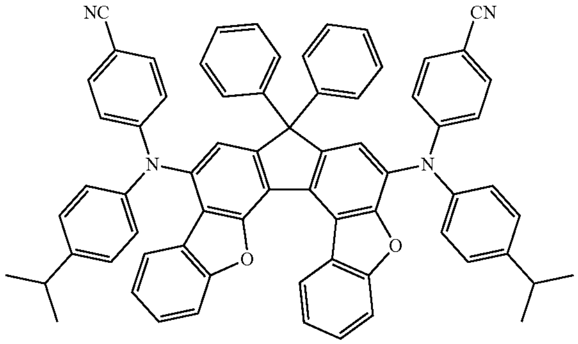
[Formula 283]
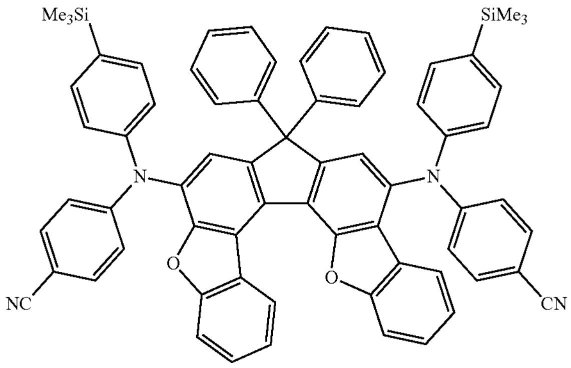
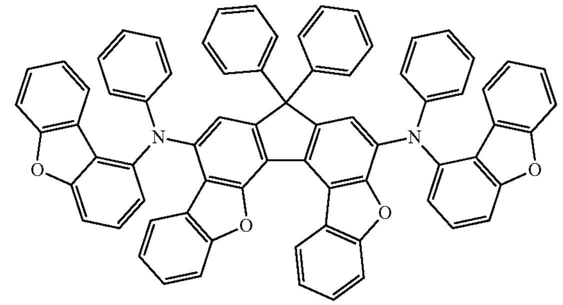
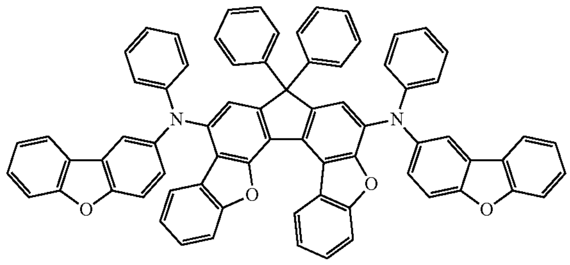
-continued
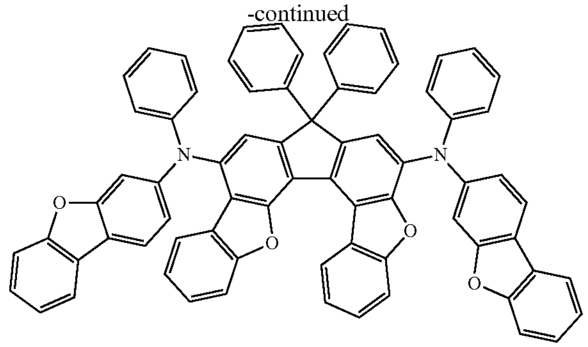
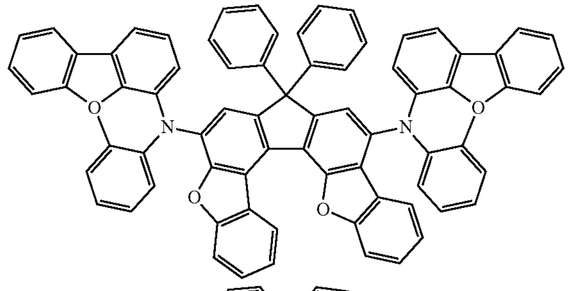
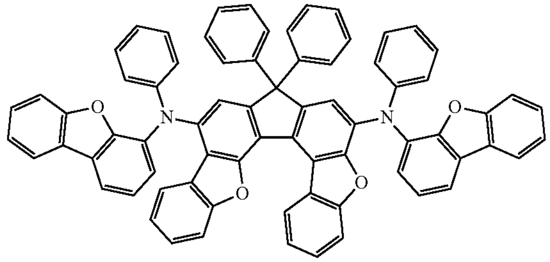
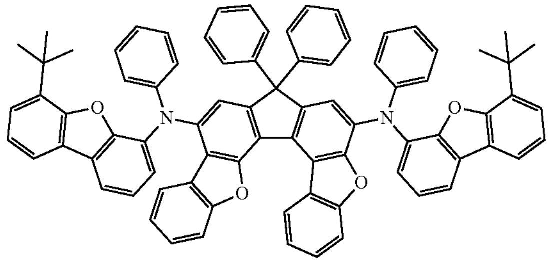
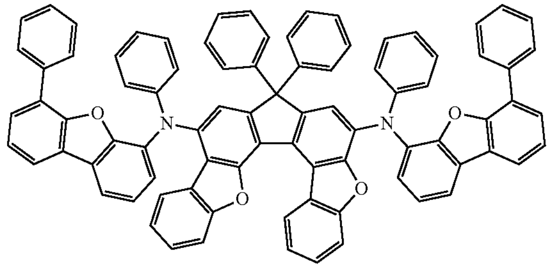
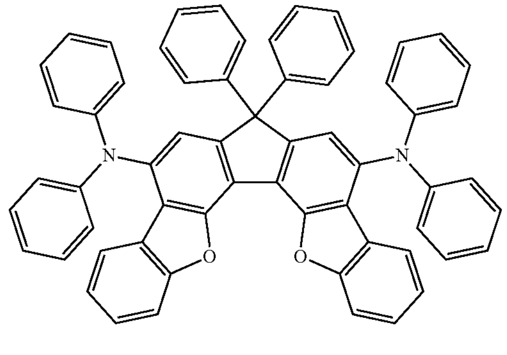

-continued
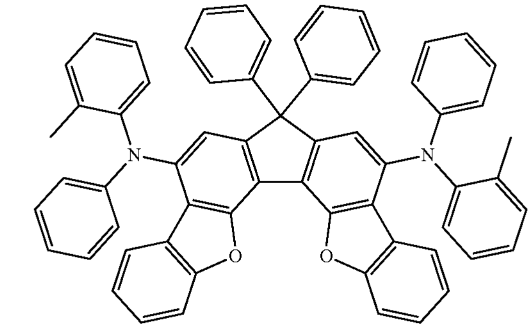
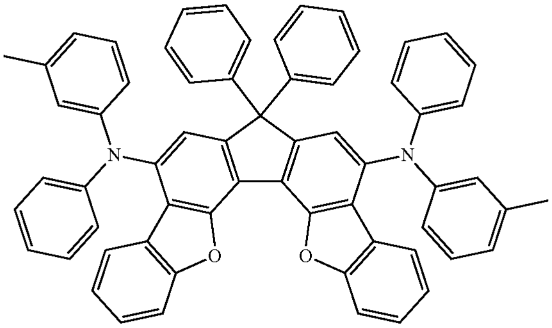
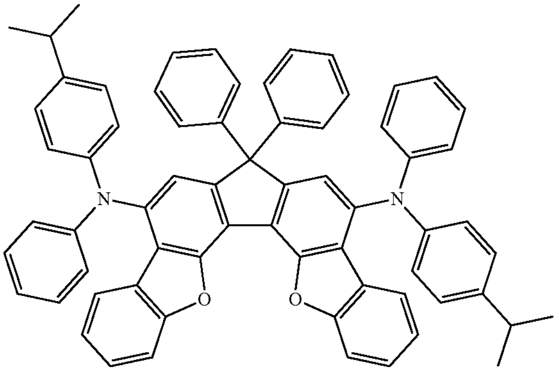
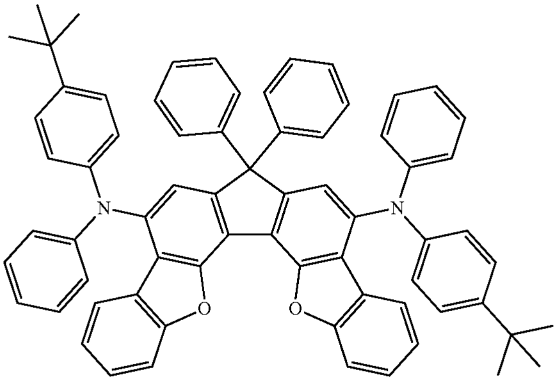
-continued
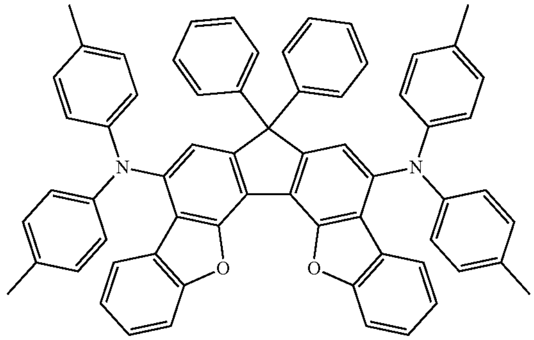
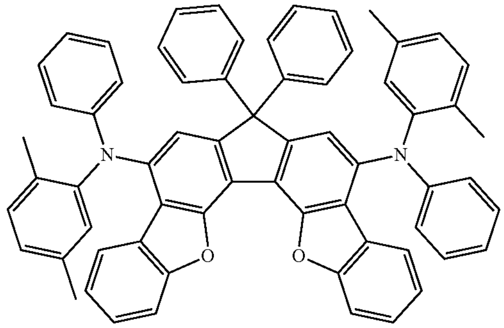
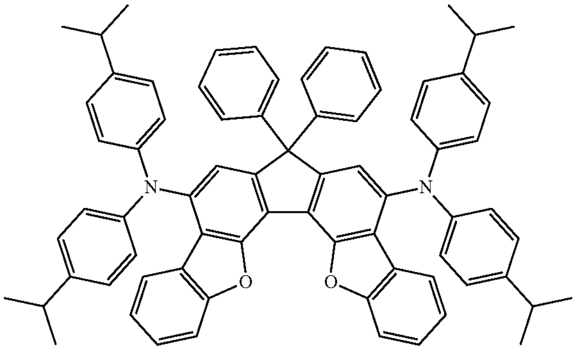
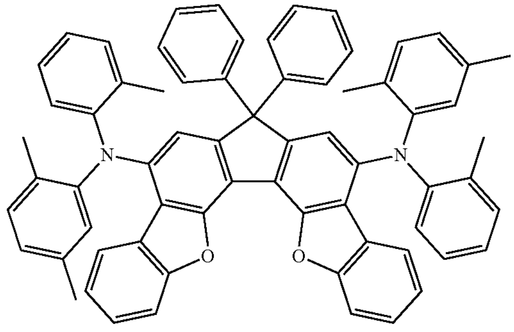
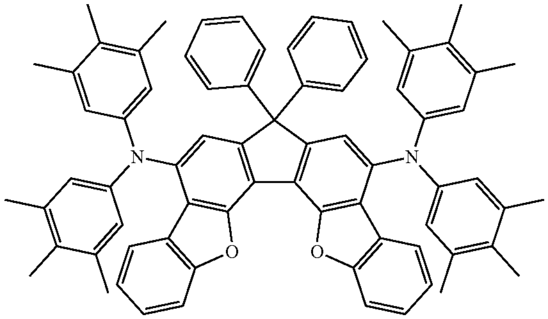

-continued
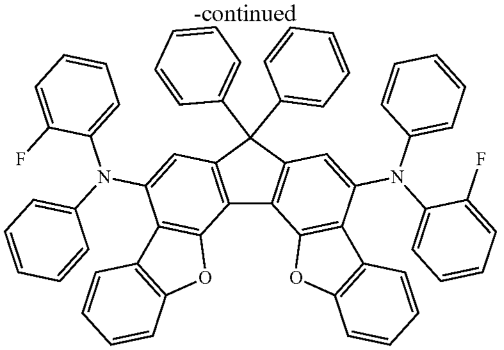
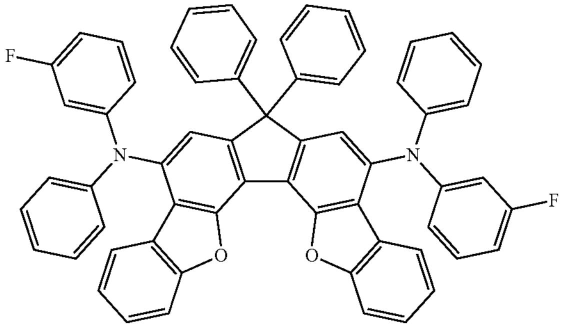
[Formula 284]
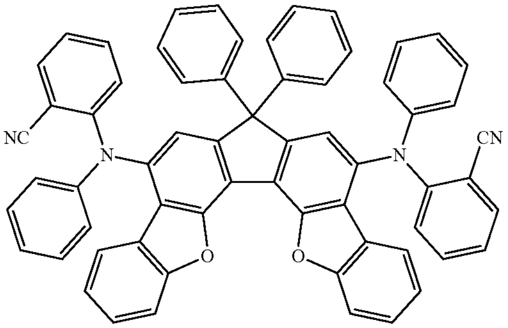
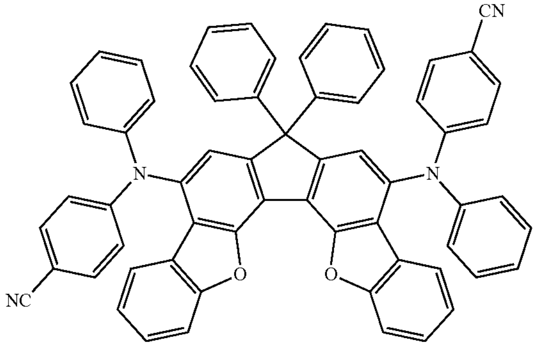
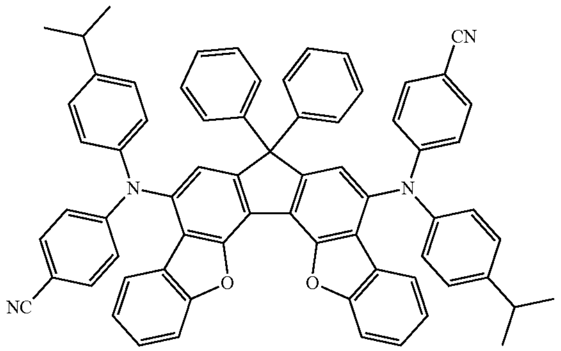
-continued
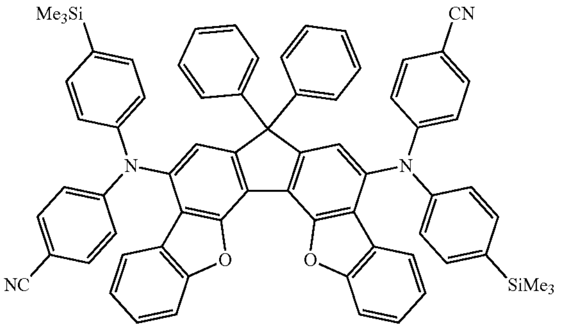
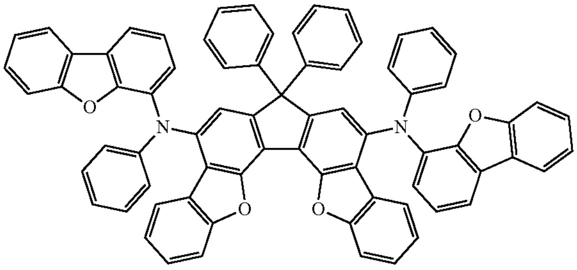
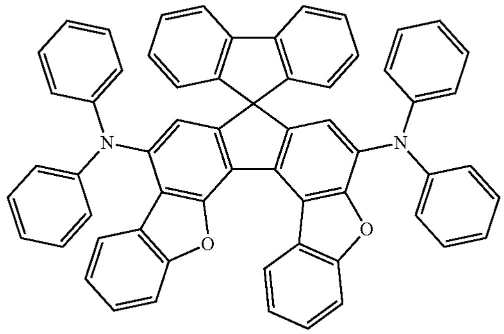
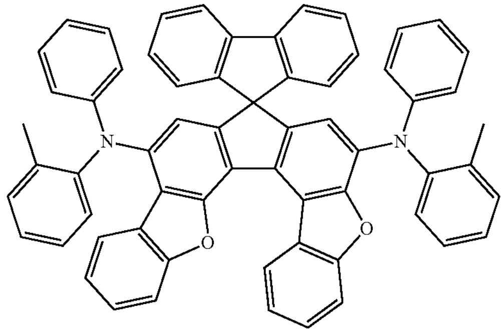
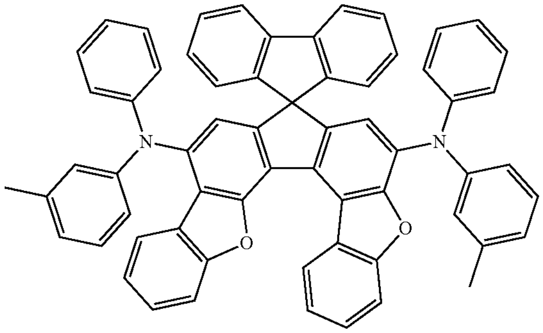

-continued
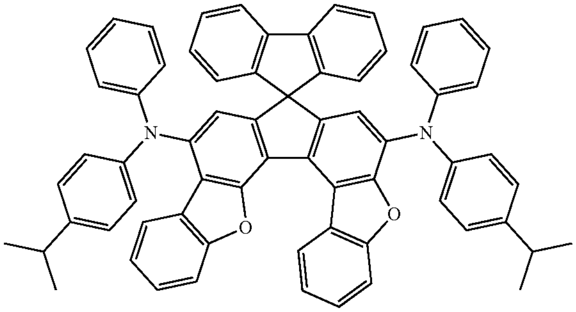
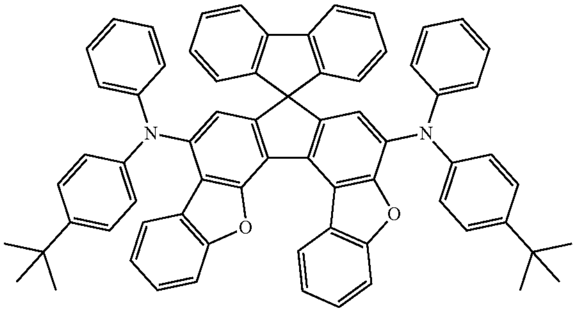
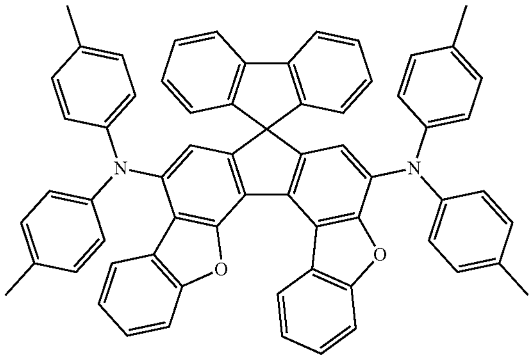
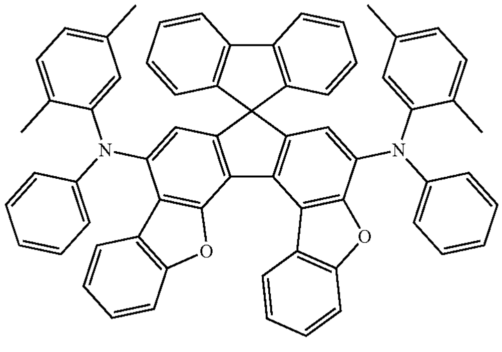
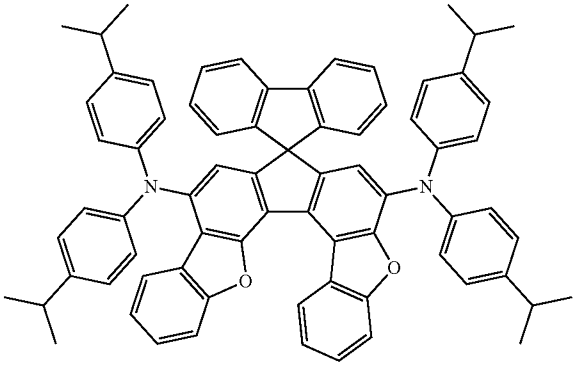
-continued
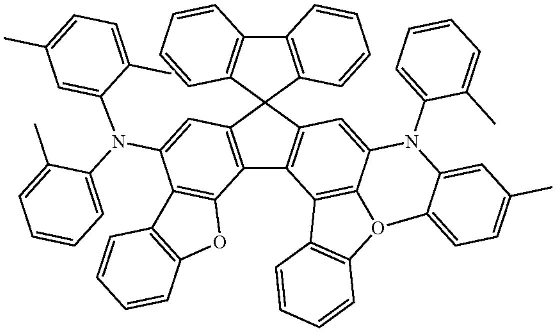
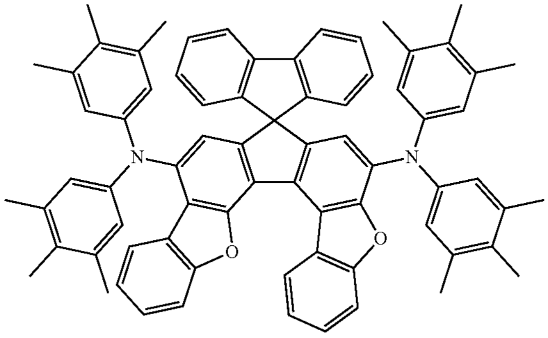
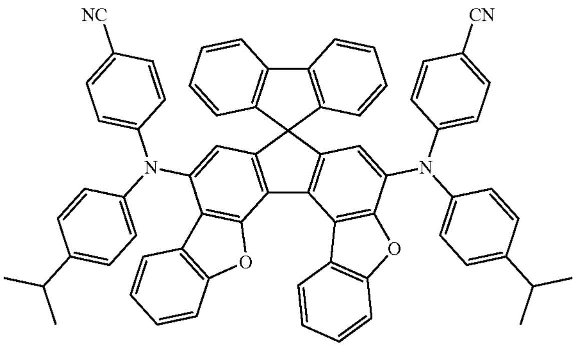
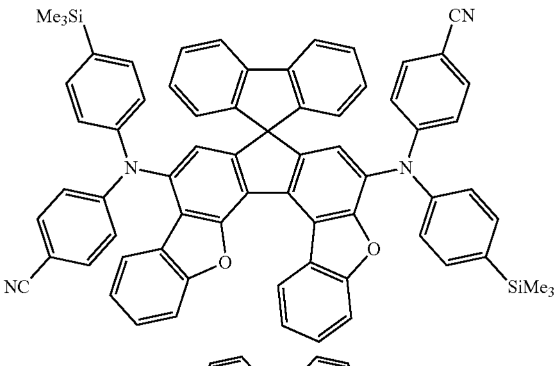
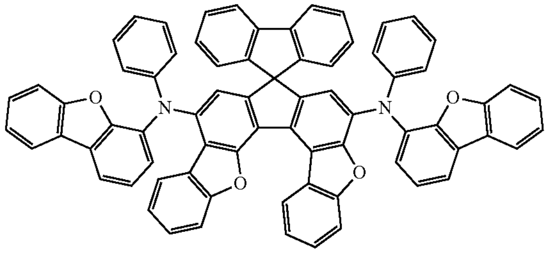

-continued

[Formula 285]

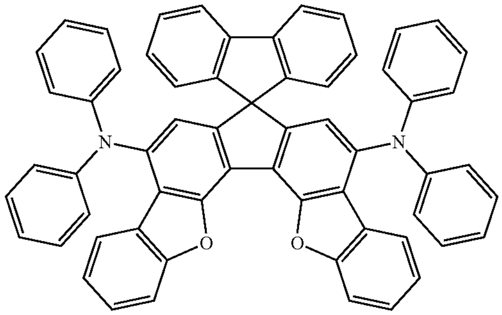

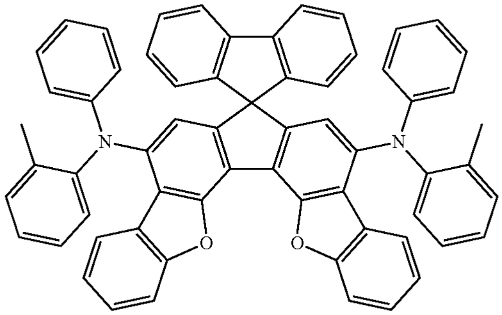

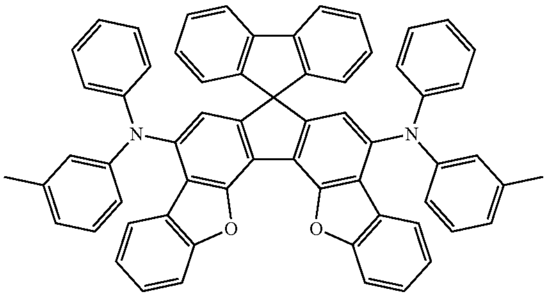

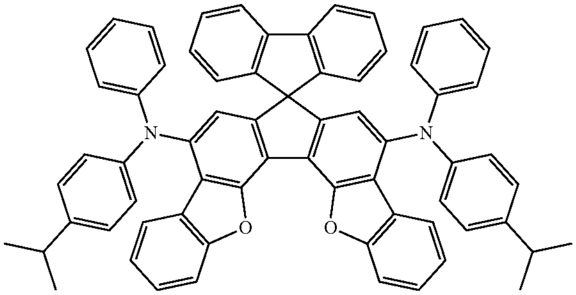

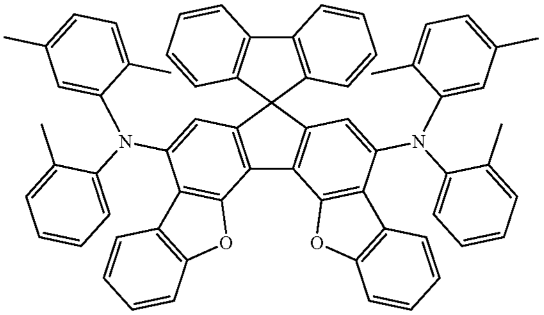

-continued

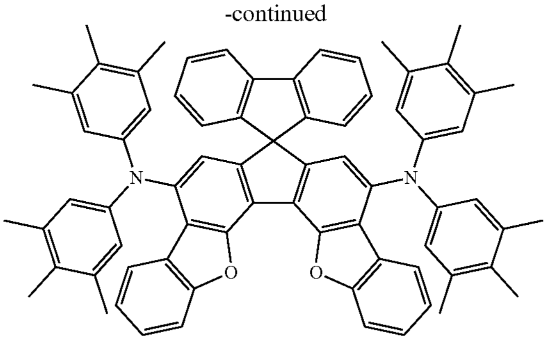

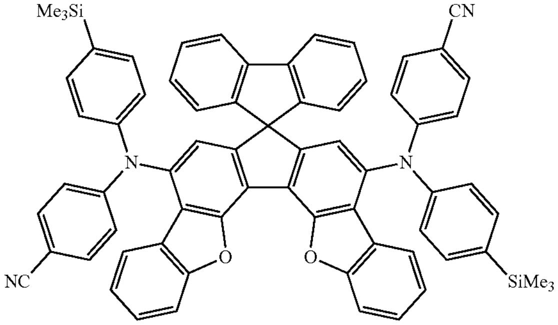

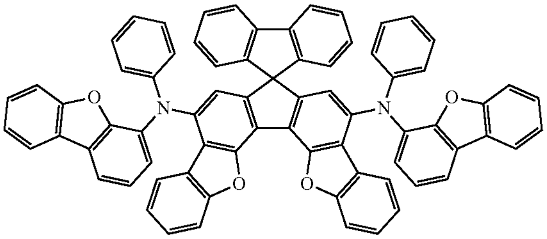 [SMILES: c1ccc(N(c2cccc3c2oc2ccccc23)c2cc3c(c4oc5ccccc5c24)-c2c(cc(N(c4ccccc4)c4cccc5c4oc4ccccc45)c4c2oc2ccccc24)C32c3ccccc3-c3ccccc32)cc1]

Compound Represented by Formula (10)

The compound represented by the formula (10) will be described.

[Formula 286]

(10)

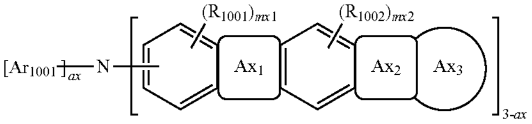

[Formula 287]

(10a)

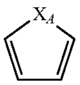

(10b)

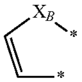

In the formula (10):

$Ax_1$ ring is a ring represented by the formula (10a) and fused with any position(s) of adjacent ring(s);

$Ax_2$ ring is a ring represented by the formula (10b) and fused with any position(s) of adjacent ring(s);

two * in the formula (10b) are bonded to any position of $Ax_3$ ring;

$X_A$ and $X_B$ are each independently $C(R_{1003})(R_{1004})$, $Si(R_{1005})(R_{1006})$, an oxygen atom, or a sulfur atom;

$Ax_3$ ring is a substituted or unsubstituted aromatic hydrocarbon ring having 6 to 50 ring carbon atoms, or a substituted or unsubstituted heterocycle having 5 to 50 ring atoms;

$Ar_{1001}$ is a substituted or unsubstituted aryl group having 6 to 50 ring carbon atoms, or a substituted or unsubstituted heterocyclic group having 5 to 50 ring atoms;

$R_{1001}$ to $R_{1006}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

mx1 is 3, mx2 is 2;

a plurality of $R_{1001}$ are mutually the same or different;

a plurality of $R_{1002}$ are mutually the same or different;

ax is 0, 1, or 2;

when ax is 0 or 1, the structures enclosed by brackets indicated by "3-ax" are mutually the same or different; and when ax is 2, a plurality of $Ar_{1001}$ are mutually the same or different.

In an exemplary embodiment, $Ar_{1001}$ is a substituted or unsubstituted aryl group having 6 to 50 ring carbon atoms.

In an exemplary embodiment, $Ax_3$ ring is a substituted or unsubstituted aromatic hydrocarbon ring having 6 to 50 ring carbon atoms, example of which is a substituted or unsubstituted benzene ring, a substituted or unsubstituted naphthalene ring, or a substituted or unsubstituted anthracene ring.

In an exemplary embodiment, $R_{1003}$ and $R_{1004}$ are each independently a substituted or unsubstituted alkyl group having 1 to 50 carbon atoms.

In an exemplary embodiment, ax is 1.

Specific examples of the compound represented by the formula (10) include compounds shown below.

[Formula 288]

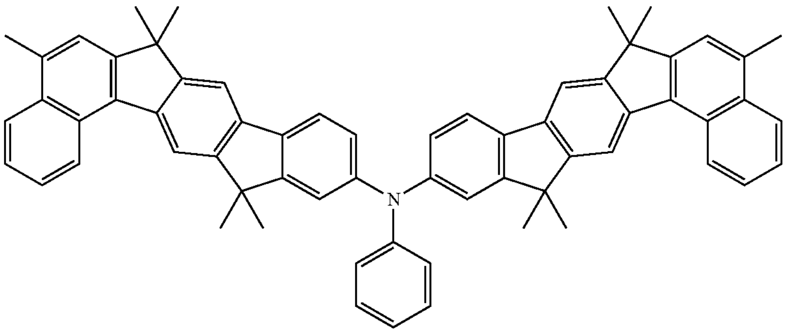

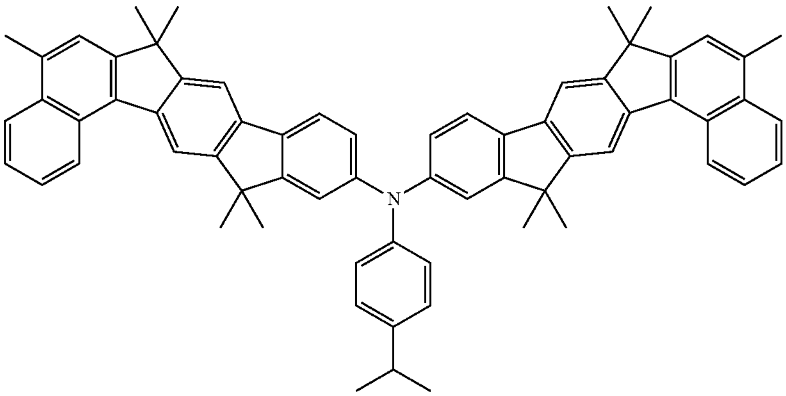

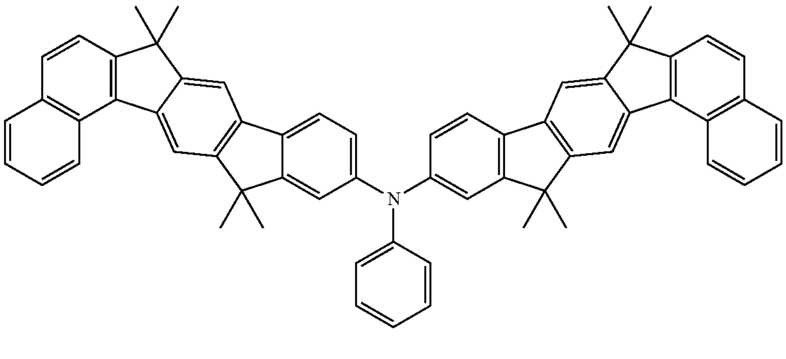

-continued
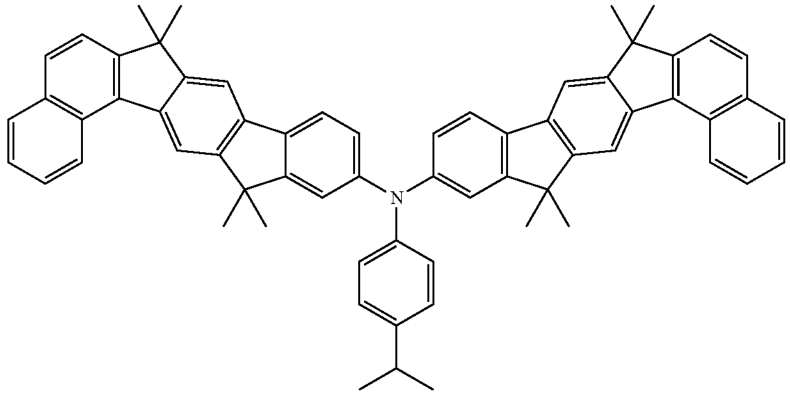
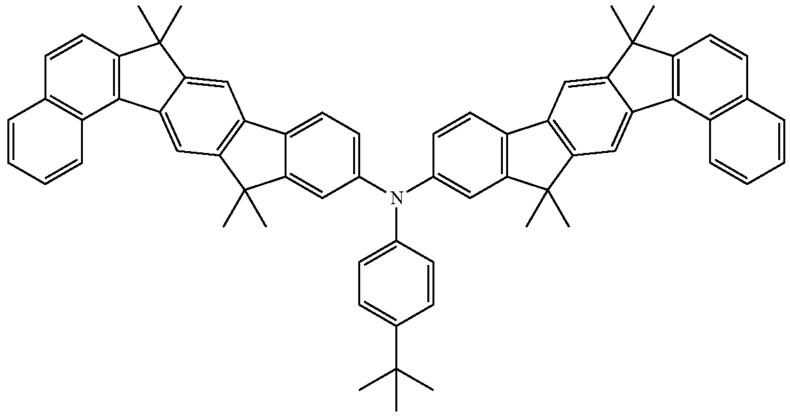
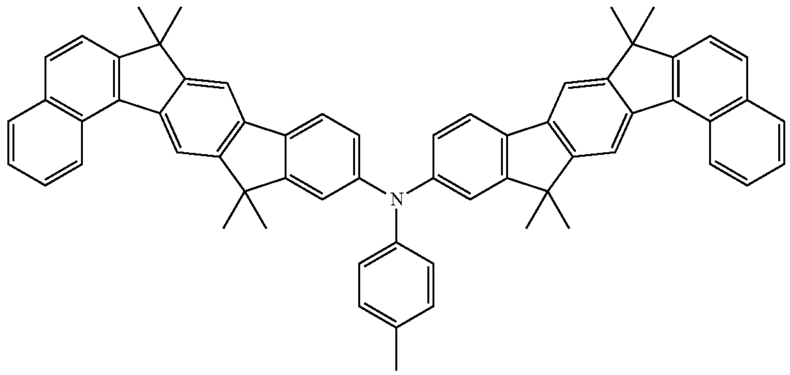
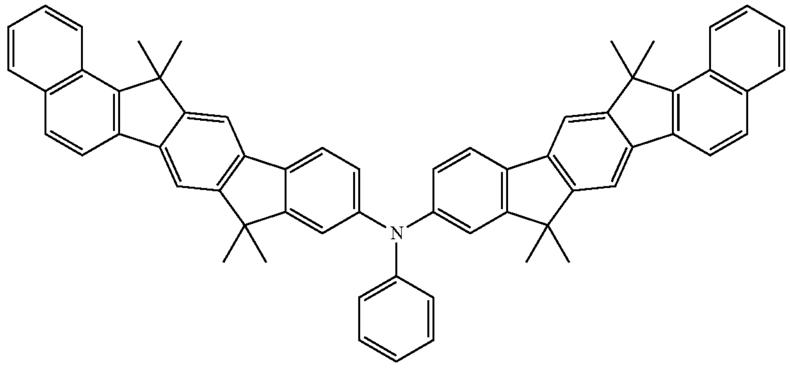

-continued

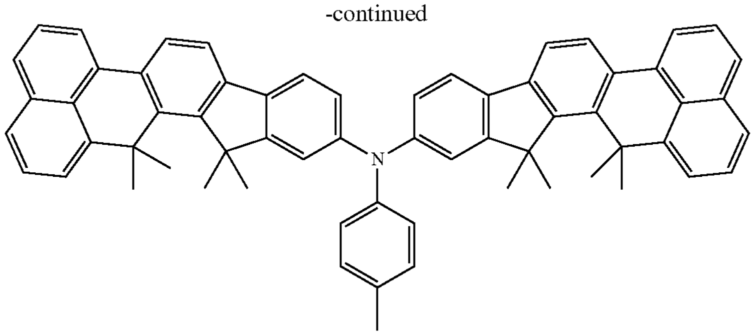

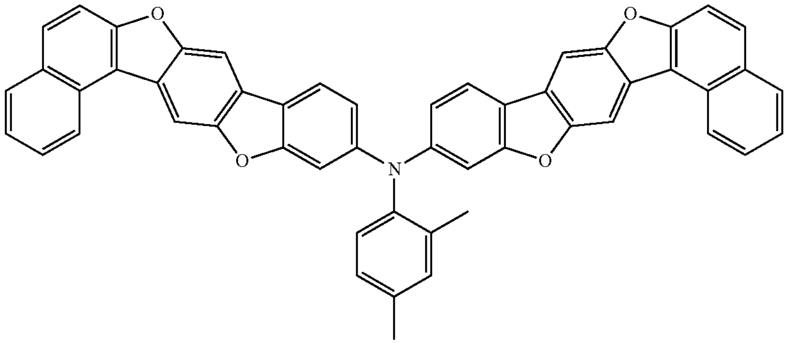

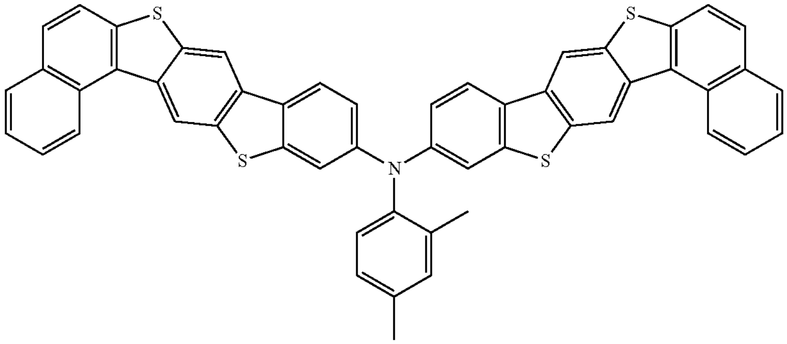

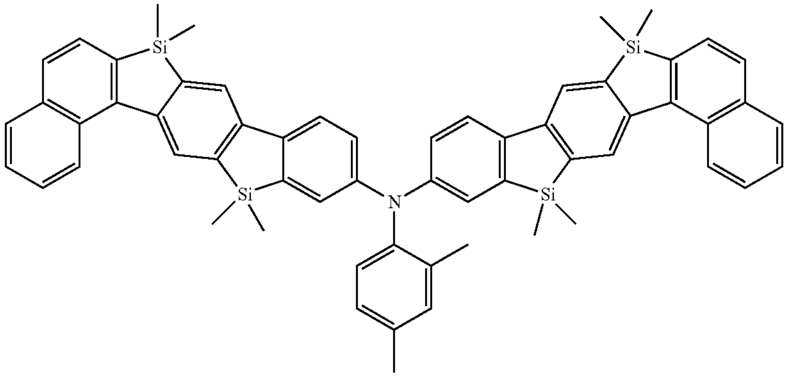

In an exemplary embodiment, the emitting layer contains, as at least one of the third compound or the fourth compound, at least one compound selected from the group consisting of the compound represented by the formula (4), the compound represented by the formula (5), the compound represented by the formula (7), the compound represented by the formula (8), the compound represented by the formula (9), and a compound represented by a formula (63a) below.

[Formula 289]

(63a)

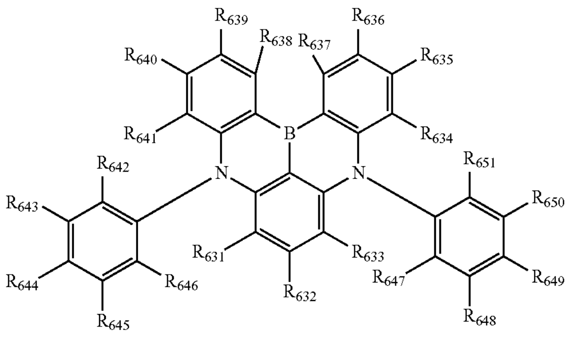

In the formula (63a):

$R_{631}$ is bonded with $R_{646}$ to form a substituted or unsubstituted heterocycle or not bonded to form no substituted or unsubstituted heterocycle;

$R_{633}$ is bonded with $R_{647}$ to form a substituted or unsubstituted heterocycle or not bonded to form no substituted or unsubstituted heterocycle;

$R_{634}$ is bonded with $R_{651}$ to form a substituted or unsubstituted heterocycle or not bonded to form no substituted or unsubstituted heterocycle;

$R_{641}$ is bonded with $R_{642}$ to form a substituted or unsubstituted heterocycle or not bonded to form no substituted or unsubstituted heterocycle;

at least one combination of adjacent two or more of $R_{631}$ to $R_{651}$ are mutually bonded to form a substituted or unsubstituted monocyclic ring, mutually bonded to form a substituted or unsubstituted fused ring, or not mutually bonded;

$R_{631}$ to $R_{651}$ not forming the substituted or unsubstituted heterocycle, not forming the monocyclic ring and not forming the fused ring are each independently a hydrogen atom, a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a substituted or unsubstituted aryl group having 6 to 50 ring carbon atoms, or a substituted or unsubstituted heterocyclic group having 5 to 50 ring atoms; and at least one of $R_{631}$ to $R_{651}$ not forming the substituted or unsubstituted heterocycle, not forming the monocyclic ring and not forming the fused ring are a halogen atom, a cyano group, a nitro group, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms.

In an exemplary embodiment, the compound represented by the formula (4) is a compound represented by the formula (41-3), the formula (41-4) or the formula (41-5), the $A_1$ ring in the formula (41-5) being a substituted or unsubstituted fused aromatic hydrocarbon ring having 10 to 50 ring carbon atoms, or a substituted or unsubstituted fused heterocycle having 8 to 50 ring atoms.

In an exemplary embodiment, the substituted or unsubstituted fused aromatic hydrocarbon ring having 10 to 50 ring carbon atoms in the formulae (41-3), (41-4) and (41-5) is a substituted or unsubstituted naphthalene ring, a substituted or unsubstituted anthracene ring, or a substituted or unsubstituted fluorene ring; and the substituted or unsubstituted fused heterocycle having 8 to 50 ring atoms is a substituted or unsubstituted dibenzofuran ring, a substituted or unsubstituted carbazole ring, or a substituted or unsubstituted dibenzothiophene ring.

In an exemplary embodiment, the substituted or unsubstituted fused aromatic hydrocarbon ring having 10 to 50 ring carbon atoms in the formula (41-3), (41-4) or (41-5) is a substituted or unsubstituted naphthalene ring, or a substituted or unsubstituted fluorene ring; and the substituted or unsubstituted fused heterocycle having 8 to 50 ring atoms is a substituted or unsubstituted dibenzofuran ring, a substituted or unsubstituted carbazole ring, or a substituted or unsubstituted dibenzothiophene ring.

In an exemplary embodiment, the compound represented by the formula (4) is selected from the group consisting of a compound represented by a formula (461) below, a compound represented by a formula (462) below, a compound represented by a formula (463) below, a compound represented by a formula (464) below, a compound represented by a formula (465) below, a compound represented by a formula (466) below, and a compound represented by a formula (467) below.

[Formula 290]

(461)

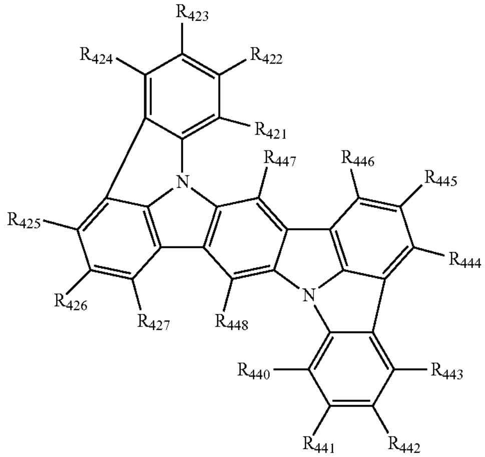

-continued (462)

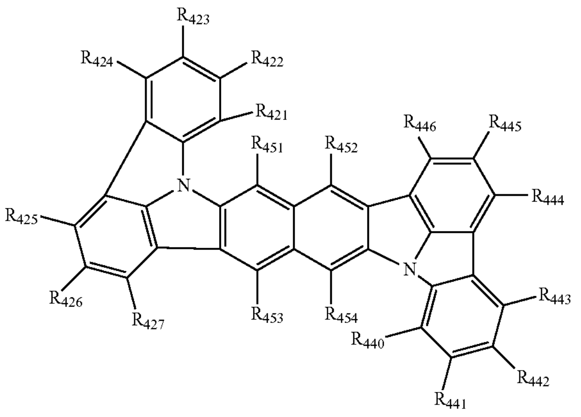

[Formula 291]

(463)

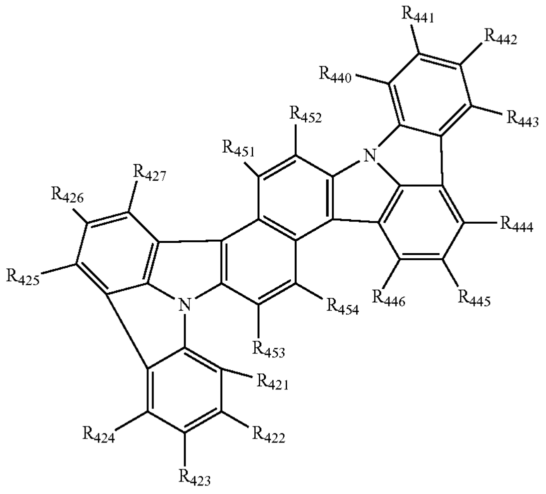

(464)

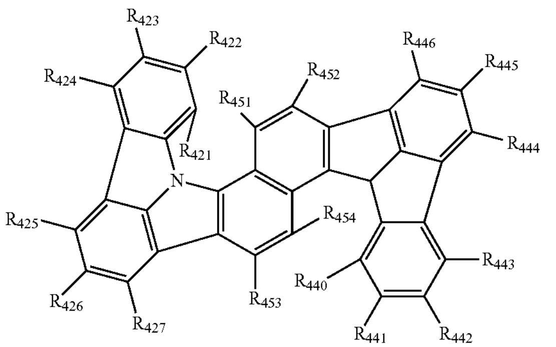

-continued

[Formula 292]

(465)

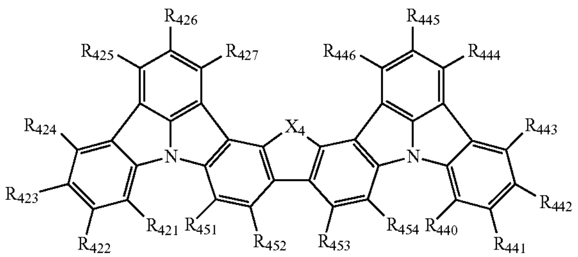

[Formula 293]

(466)

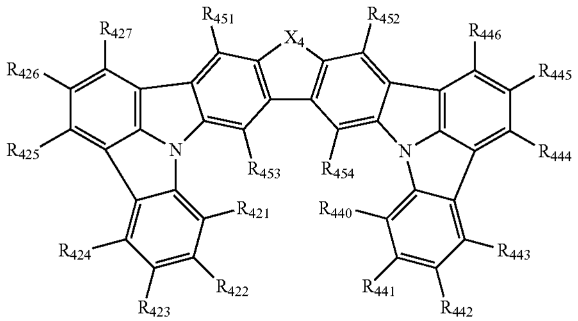

[Formula 294]

(467)

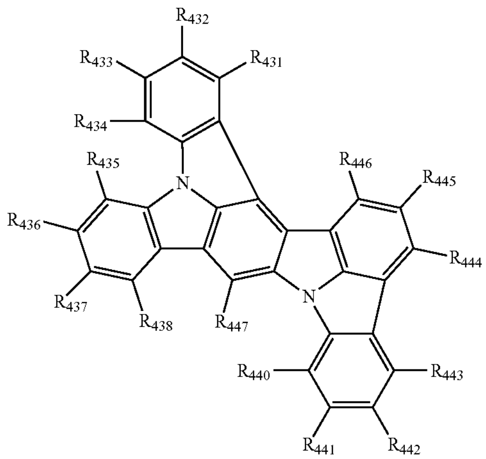

In the formulae (461) to (467):

at least one combination of adjacent two or more of $R_{421}$ to $R_{427}$, $R_{431}$ to $R_{436}$, $R_{440}$ to $R_{448}$, and $R_{451}$ to $R_{454}$ are mutually bonded to form a substituted or unsubstituted monocyclic ring, mutually bonded to form a substituted or unsubstituted fused ring, or not mutually bonded;

$R_{437}$, $R_{438}$, and $R_{421}$ to $R_{427}$, $R_{431}$ to $R_{436}$, $R_{440}$ to $R_{448}$, and $R_{451}$ to $R_{454}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

$X_4$ is an oxygen atom, $NR_{801}$, or $C(R_{802})(R_{803})$;

$R_{801}$, $R_{802}$, and $R_{803}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

a substituted or unsubstituted alkyl group having 1 to 50 carbon atoms, or a substituted or unsubstituted aryl group having 6 to 50 ring carbon atoms;

when a plurality of $R_{801}$ are present, the plurality of $R_{801}$ are mutually the same or different;

when a plurality of $R_{802}$ are present, the plurality of $R_{802}$ are mutually the same or different; and when a plurality of $R_{803}$ are present, the plurality of $R_{803}$ are mutually the same or different.

In an exemplary embodiment, $R_{421}$ to $R_{427}$ and $R_{440}$ to $R_{448}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{421}$ to $R_{427}$ and $R_{440}$ to $R_{447}$ are each independently selected from the group consisting of a hydrogen atom, a substituted or unsubstituted aryl group having 6 to 18 ring carbon atoms, and a substituted or unsubstituted heterocyclic group having 5 to 18 ring atoms.

In an exemplary embodiment, the compound represented by the formula (41-3) is a compound represented by a formula (41-3-1) below.

[Formula 295]

(41-3-1)

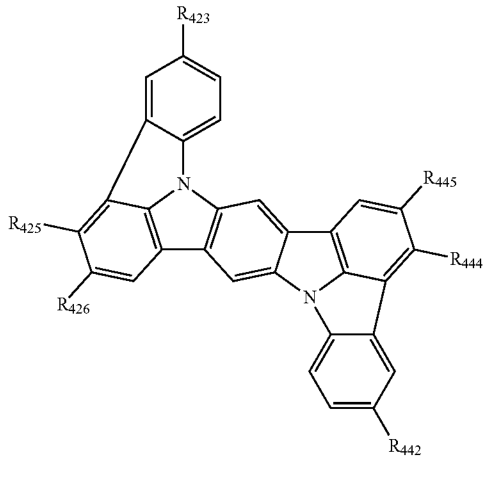

In the formula (41-3-1), $R_{423}$, $R_{425}$, $R_{426}$, $R_{442}$, $R_{444}$ and $R_{445}$ each independently represent the same as $R_{423}$, $R_{425}$, $R_{426}$, $R_{442}$, $R_{444}$ and $R_{445}$ in the formula (41-3).

In an exemplary embodiment, the compound represented by the formula (41-3) is a compound represented by formula (41-3-5) below.

[Formula 296]

(41-3-2)

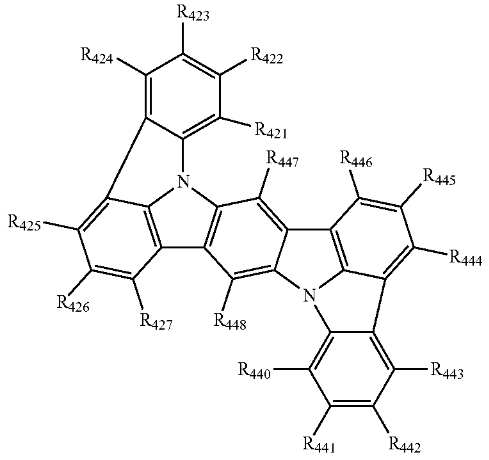

In the formula (41-3-2): $R_{421}$ to $R_{427}$ and $R_{440}$ to $R_{448}$ each independently represent the same as $R_{421}$ to $R_{427}$ and $R_{440}$ to $R_{448}$ in the formula (41-3); and at least one of $R_{421}$ to $R_{427}$ or $R_{440}$ to $R_{446}$ is a group represented by —$N(R_{906})(R_{907})$.

In an exemplary embodiment, two of $R_{421}$ to $R_{427}$ and $R_{440}$ to $R_{446}$ in the formula (41-3-2) are groups represented by —$N(R_{906})(R_{907})$.

In an exemplary embodiment, the compound represented by the formula (41-3-2) is a compound represented by a formula (41-3-3) below.

[Formula 297]

(41-3-3)

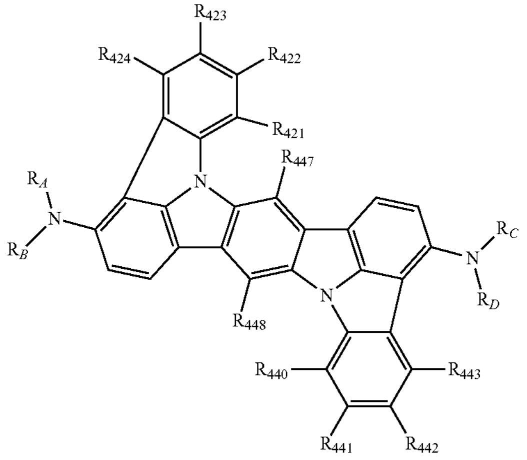

In the formula (41-3-3): $R_{421}$ to $R_{424}$, $R_{440}$ to $R_{443}$, $R_{447}$, and $R_{448}$ each independently represent the same as $R_{421}$ to $R_{424}$, $R_{440}$ to $R_{443}$, $R_{447}$, and $R_{448}$ in the formula (41-3); and $R_A$, $R_B$, $R_C$, and $R_D$ are each independently a substituted or unsubstituted aryl group having 6 to 18 ring carbon atoms, or a substituted or unsubstituted heterocyclic group having 5 to 18 ring atoms.

In an exemplary embodiment, the compound represented by the formula (41-3-3) is a compound represented by a formula (41-3-4) below.

[Formula 298]

(41-3-4)

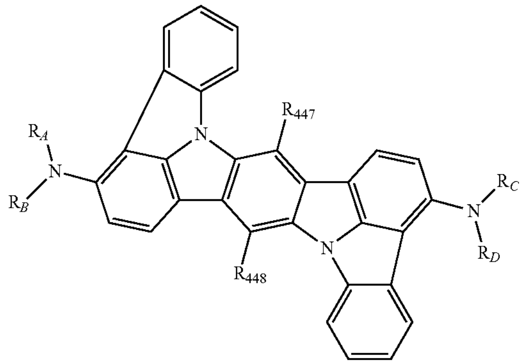

In the formula (41-3-4), $R_{447}$, $R_{448}$, $R_A$, $R_B$, $R_C$ and $R_D$ each independently represent the same as $R_{447}$, $R_{448}$, $R_A$, $R_B$, $R_C$ and $R_D$ in the formula (41-3-3).

In an exemplary embodiment, $R_A$, $R_B$, $R_C$, and $R_D$ are each independently a substituted or unsubstituted aryl group having 6 to 18 ring carbon atoms.

In an exemplary embodiment, $R_A$, $R_B$, $R_C$, and $R_D$ are each independently a substituted or unsubstituted phenyl group.

In an exemplary embodiment, $R_{447}$ and $R_{448}$ are each a hydrogen atom.

In an exemplary embodiment, a substituent for the "substituted or unsubstituted" group in each of the formulae is an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, —Si($R_{901a}$)($R_{902a}$)($R_{903a}$), —O—($R_{904a}$), —S—($R_{905a}$), —N($R_{906a}$)($R_{907a}$), a halogen atom, a cyano group, a nitro group, an unsubstituted aryl group having 6 to 50 ring carbon atoms, or an unsubstituted heterocyclic group having 5 to 50 ring atoms;

$R_{901a}$ to $R_{907a}$ are each independently a hydrogen atom, an unsubstituted alkyl group having 1 to 50 carbon atoms, an unsubstituted aryl group having 6 to 50 ring carbon atoms, or an unsubstituted heterocyclic group having 5 to 50 ring atoms;

when two or more $R_{901a}$ are present, the two or more $R_{901a}$ are mutually the same or different;

when two or more $R_{902a}$ are present, the two or more $R_{902a}$ are mutually the same or different;

when two or more $R_{903a}$ are present, the two or more $R_{903a}$ are mutually the same or different;

when two or more $R_{904a}$ are present, the two or more $R_{904a}$ are mutually the same or different;

when two or more $R_{905a}$ are present, the two or more $R_{905a}$ are mutually the same or different;

when two or more $R_{906a}$ are present, the two or more $R_{906a}$ are mutually the same or different; and when two or more $R_{907a}$ are present, the two or more $R_{907a}$ are mutually the same or different.

In an exemplary embodiment, a substituent for the "substituted or unsubstituted" group in each of the formulae is an unsubstituted alkyl group having 1 to 50 carbon atoms, an unsubstituted aryl group having 6 to 50 ring carbon atoms, or an unsubstituted heterocyclic group having 5 to 50 ring atoms.

In an exemplary embodiment, a substituent for the "substituted or unsubstituted" group in each of the formulae is an unsubstituted alkyl group having 1 to 18 carbon atoms, an unsubstituted aryl group having 6 to 18 ring carbon atoms, or an unsubstituted heterocyclic group having 5 to 18 ring atoms.

In the organic EL device according to the exemplary embodiment, it is preferable that the second emitting layer further contains a fourth compound that fluoresces, and the fourth compound is a compound that emits light having a main peak wavelength in a range from 430 nm to 480 nm.

In the organic EL device according to the exemplary embodiment, it is preferable that the first emitting layer further contains a third compound that fluoresces, and the third compound is a compound that emits light having a main peak wavelength in a range from 430 nm to 480 nm.

A measurement method of a main peak wavelength of the compound is as follows. A toluene solution of a measurement target compound at a concentration ranging from $10^{-6}$ mol/L to $10^{-5}$ mol/L is prepared and put in a quartz cell. An emission spectrum (ordinate axis:luminous intensity, abscissa axis:wavelength) of the thus-obtained sample is measured at a normal temperature (300K). The emission spectrum is measurable using a spectrophotometer (machine name: F-7000) manufactured by Hitachi High-Tech Science Corporation. It should be noted that the machine for measuring the emission spectrum is not limited to the machine used herein.

A peak wavelength of the emission spectrum exhibiting the maximum luminous intensity is defined as an emission main peak wavelength. It should be noted that the main peak wavelength is sometimes referred to as a fluorescence main peak wavelength (FL-peak) herein.

When the first emitting layer of the organic EL device according to the exemplary embodiment contains the first compound and the third compound, the first compound is preferably a host material (sometimes referred to as a matrix material) and the third compound is preferably a dopant material (sometimes referred to as a guest material, emitter, or luminescent material).

When the first emitting layer of the organic EL device according to the exemplary embodiment contains the first compound and the third compound, a singlet energy $S_1$(H1) of the first compound and a singlet energy $S_1$(D3) of the third compound preferably satisfy a relationship of a numerical formula (Numerical Formula 1) below.

$$S_1(H1)>S_1(D3) \quad \text{(Numerical Formula 1)}$$

In the organic EL device according to the exemplary embodiment, when the second emitting layer contains the second compound and the fourth compound, the second compound is preferably a host material (occasionally also referred to as a matrix material) and the fourth compound is preferably a dopant material (occasionally also referred to as a guest material, emitter or luminescent material).

When the second emitting layer of the organic EL device according to the exemplary embodiment contains the second and fourth compounds, a singlet energy $S_1(H_2)$ of the second compound and a singlet energy $S_1$(D4) of the fourth compound preferably satisfy a relationship of a numerical formula (Numerical Formula 2) below.

$$S_1(H_2)>S_1(D4) \quad \text{(Numerical Formula 2)}$$

Singlet Energy $S_1$

A method of measuring the singlet energy Si with use of a solution (occasionally referred to as a solution method) is exemplified by a method below.

A toluene solution of a measurement target compound at a concentration ranging from $10^{-5}$ mol/L to $10^{4}$ mol/L is prepared and put in a quartz cell. An absorption spectrum (ordinate axis:absorption intensity, abscissa axis:wavelength) of the thus-obtained sample is measured at a normal temperature (300K). A tangent is drawn to the fall of the absorption spectrum close to the long-wavelength region, and a wavelength value λedge (nm) at an intersection of the tangent and the abscissa axis is assigned to a conversion equation (F2) below to calculate singlet energy.

$$S_1\ [eV]=1239.85/\lambda edge \qquad \text{Conversion Equation (F2):}$$

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the local maximum value closest to the long-wavelength region, among the local maximum values of the absorption spectrum, in a long-wavelength direction, a tangent at each point on the curve is checked. An inclination of the tangent is decreased and increased in a repeated manner as the curve falls (i.e., a value of the ordinate axis is decreased). A tangent drawn at a point where the inclination of the curve is the local minimum closest to the long-wavelength region (except when absorbance is 0.1 or less) is defined as the tangent to the fall of the absorption spectrum close to the long-wavelength region.

The local maximum absorbance of 0.2 or less is not counted as the above-mentioned local maximum absorbance closest to the long-wavelength region.

In the organic EL device according to the exemplary embodiment, an electron mobility μH1 of the first compound and an electron mobility μH2 of the second compound also preferably satisfy a relationship of a numerical formula (Numerical Formula 3) below.

$$\mu H2>\mu H1 \qquad \text{(Numerical Formula 3)}$$

When the first compound and the second compound satisfy the relationship of the numerical formula (Numerical Formula 3), a recombination ability of holes and electrons in the first emitting layer is improved.

The electron mobility can be measured according to impedance spectroscopy.

A measurement target layer having a thickness in a range from 100 nm to 200 nm is held between the anode and the cathode, and a small alternating voltage of 100 mV or less is applied thereto while a bias DC voltage is applied. The value of an alternating current (the absolute value and the phase) which flows at this time is measured. This measurement is performed while changing a frequency of the alternating voltage, and complex impedance (Z) is calculated from the current value and the voltage value. A frequency dependency of the imaginary part (ImM) of the modulus M=iωZ (i: imaginary unit, ω: angular frequency) is obtained. The reciprocal number of a frequency ω at which the ImM becomes the maximum is defined as a response time of electrons carried in the measurement target layer. The electron mobility is calculated by the following equation.

$$\text{Electron Mobility}=(\text{Film Thickness of Measurement Target Layer})^2/(\text{Response Time}\cdot\text{Voltage})$$

The first emitting layer and the second emitting layer preferably do not contain a phosphorescent material (dopant material).

The first emitting layer and the second emitting layer preferably do not contain a heavy metal complex and a phosphorescent rare earth metal complex. Examples of the heavy-metal complex herein include iridium complex, osmium complex, and platinum complex.

Further, the first emitting layer and the second emitting layer also preferably do not contain a metal complex.

Film Thickness of Emitting Layer

A film thickness of the emitting layer of the organic EL device according to the exemplary embodiment is preferably in a range from 5 nm to 50 nm, more preferably in a range from 7 nm to 50 nm, further preferably in a range from 10 nm to 50 nm. When the film thickness of the emitting layer is 5 nm or more, the emitting layer is easily formable and chromaticity is easily adjustable. When the film thickness of the emitting layer is 50 nm or less, a rise in the drive voltage is easily reducible.

Content Ratios of Compounds in Emitting Layer

When the first emitting layer contains the first compound and the third compound, a content ratio of each of the first compound and the third compound in the first emitting layer preferably falls, for instance, within a range below.

The content ratio of the first compound is preferably in a range from 80 mass % to 99 mass %, more preferably in a range from 90 mass % to 99 mass %, further preferably in a range from 95 mass % to 99 mass %.

The content ratio of the third compound is preferably in a range from 1 mass % to 10 mass %, more preferably in a range from 1 mass % to 7 mass %, further preferably in a range from 1 mass % to 5 mass %.

The upper limit of the total of the content ratios of the first compound and the third compound in the first emitting layer is 100 mass %.

It is not excluded that the first emitting layer of the exemplary embodiment further contains a material(s) other than the first and third compounds.

The first emitting layer may include a single type of the first compound or may include two or more types of the first compound. The first emitting layer may include a single type of the third compound or may include two or more types of the third compound.

When the second emitting layer contains the second compound and the fourth compound, a content ratio of each of the second compound and the fourth compound in the second emitting layer preferably falls, for instance, within a range below.

The content ratio of the second compound is preferably in a range from 80 mass % to 99 mass %, more preferably in a range from 90 mass % to 99 mass %, further preferably in a range from 95 mass % to 99 mass %.

The content ratio of the fourth compound is preferably in a range from 1 mass % to 10 mass %, more preferably in a range from 1 mass % to 7 mass %, further preferably in a range from 1 mass % to 5 mass %.

An upper limit of the total of the content ratios of the second and fourth compounds in the second emitting layer is 100 mass %.

It is not excluded that the second emitting layer of the exemplary embodiment further contains a material(s) other than the second and fourth compounds.

The second emitting layer may include a single type of the second compound or may include two or more types of the second compound. The second emitting layer may include a single type of the fourth compound or may include two or more types of the fourth compound.

An arrangement of the organic EL device 1 will be further described. It should be noted that the reference numerals will be occasionally omitted below.

Substrate

The substrate is used as a support for the organic EL device. For instance, glass, quartz, plastics and the like are usable for the substrate. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal, an alloy, an electrically conductive compound, a mixture thereof, or the like having a large work function (specifically, 4.0 eV or more) is preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since a hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, a mixture thereof, or the like having a small work function (specifically, 3.8 eV or less) for the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule organic compound, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high polymer compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N, N'-bis(4-butylphenyl)-N, N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include an aromatic amine compound such as 4,4'-bis[N-(1-naphthyl)-N-phenylamino]biphenyl (abbreviation: NPB), N, N'-bis(3-methylphenyl)-N, N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino) triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have an electron mobility of $10^{-6}$ $cm^2/(V \cdot s)$ or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: $Almq_3$), bis(10-hydroxybenzo[h]quinolinato)beryllium (abbreviation: $BeBq_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the exemplary embodiment, a benzimidazole compound is preferably usable. The above-described substances mostly have an electron mobility of $10^{-6}$ $cm^2/Vs$ or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Further, a high polymer compound is usable for the electron transporting layer. For instance, poly[(9,9-dihexylfluorene-2,7-diyl)-co-(pyridine-3,5-diyl)](abbreviation: PF-Py), poly[(9,9-dioctylfluorene-2,7-diyl)-co-(2,2'-bipyridine-6,6'-diyl)](abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride ($CaF_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method(s)

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or ink jet are applicable.

Film Thickness

A film thickness of each of the organic layers of the organic EL device in the exemplary embodiment is not limited unless otherwise specified in the above. In general, the thickness preferably ranges from several nanometers to 1 pm because excessively small film thickness is likely to cause defects (e.g. pin holes) and excessively large thickness leads to the necessity of applying high voltage and consequent reduction in efficiency.

According to the exemplary embodiment, an organic electroluminescence device with an improved lifetime can be provided.

In the organic EL device according to the exemplary embodiment, the first emitting layer containing the first host material in a form of the first compound represented by the formula (1) or the like and the second emitting layer containing the second host material in a form of the second compound represented by the formula (2) or the like are in direct contact with each other. By thus layering the first emitting layer and the second emitting layer, the generated singlet excitons and the triplet excitons can be efficiently used and, consequently, the luminous efficiency of the organic EL device can be improved.

Second Exemplary Embodiment

Electronic Device

An electronic device according to a second exemplary embodiment is installed with any one of the organic EL devices according to the above exemplary embodiment.

Examples of the electronic device include a display device and a light-emitting unit. Examples of the display device include a display component (e.g., an organic EL panel module), TV, mobile phone, tablet and personal computer. Examples of the light-emitting unit include an illuminator and a vehicle light.

MODIFICATION OF EXEMPLARY EMBODIMENT(S)

The scope of the invention is not limited to the above-described exemplary embodiments but includes any modification and improvement as long as such modification and improvement are compatible with the invention.

For instance, the number of emitting layers is not limited to two, and more than two emitting layers may be provided and laminated with each other. When the organic EL device includes more than two emitting layers, it is only necessary that at least two of the emitting layers should satisfy the requirements mentioned in the above exemplary embodiments. For instance, the rest of the emitting layers may be a fluorescent emitting layer or a phosphorescent emitting layer with use of emission caused by electron transfer from the triplet excited state directly to the ground state.

When the organic EL device includes a plurality of emitting layers, these emitting layers may be mutually adjacently provided, or may form a so-called tandem organic EL device, in which a plurality of emitting units are layered via an intermediate layer.

For instance, a blocking layer may be provided adjacent to at least one of a side of the emitting layer close to the anode or a side of the emitting layer close to the cathode. The blocking layer is preferably provided in contact with the emitting layer to block at least any of holes, electrons, or excitons.

For instance, when the blocking layer is provided in contact with the side of the emitting layer close to the cathode, the blocking layer permits transport of electrons and blocks holes from reaching a layer provided closer to the cathode (e.g., the electron transporting layer) beyond the blocking layer. When the organic EL device includes the electron transporting layer, the blocking layer is preferably disposed between the emitting layer and the electron transporting layer.

When the blocking layer is provided in contact with the side of the emitting layer close to the anode, the blocking layer permits transport of holes and blocks electrons from reaching a layer provided closer to the anode (e.g., the hole transporting layer) beyond the blocking layer. When the organic EL device includes the hole transporting layer, the blocking layer is preferably interposed between the emitting layer and the hole transporting layer.

Alternatively, the blocking layer may be provided adjacent to the emitting layer so that the excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded with the blocking layer.

Specific structure, shape and the like of the components in the invention may be designed in any manner as long as an object of the invention can be achieved.

EXAMPLES

The invention will be described in further detail with reference to Example(s). It should be noted that the scope of the invention is by no means limited to Examples.

Compounds

Structures of compounds represented by the formula (1) in Examples and Reference Examples are shown below.

[Formula 299]

BH1

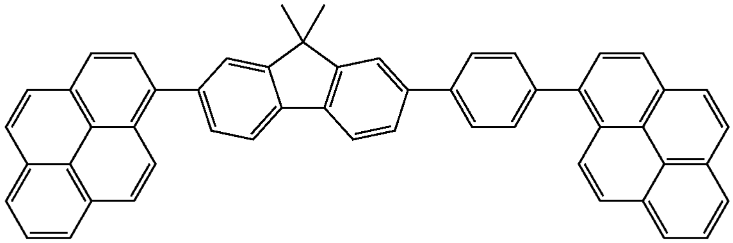

[Formula 300]

BH1-2

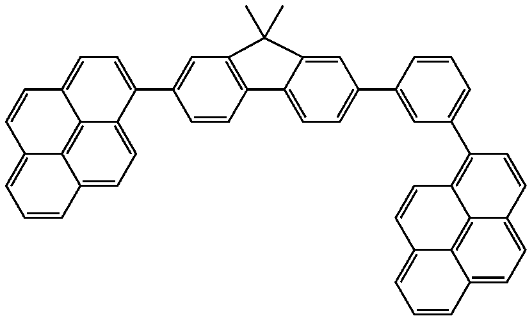

BH1-3

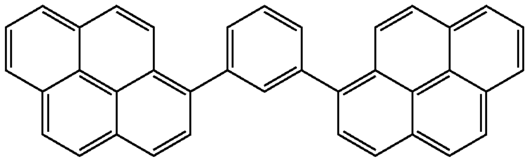

-continued
[Formula 301]
BH1-4
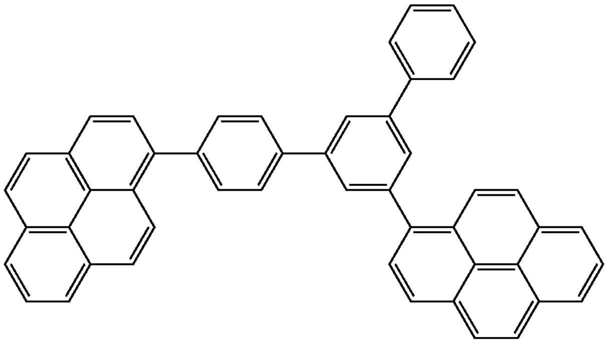
BH1-5
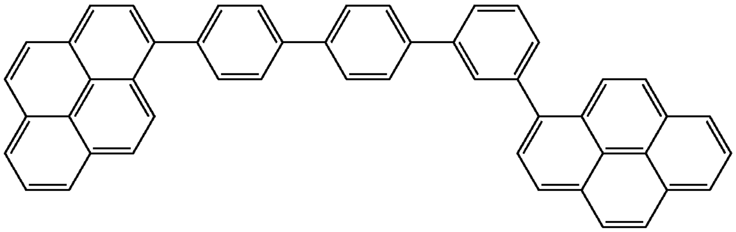
[Formula 302]
BH1-6
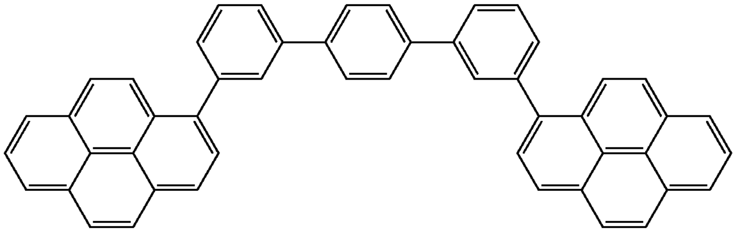
BH1-7
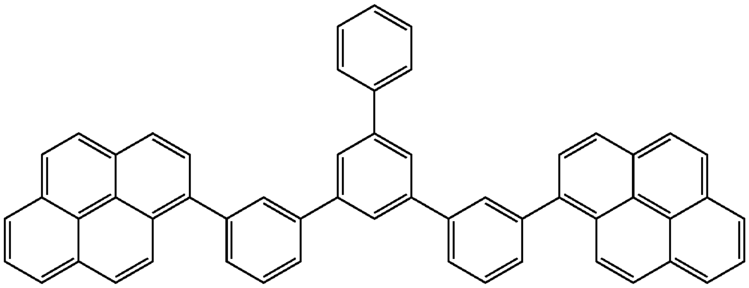
[Formula 303]
BH1-8
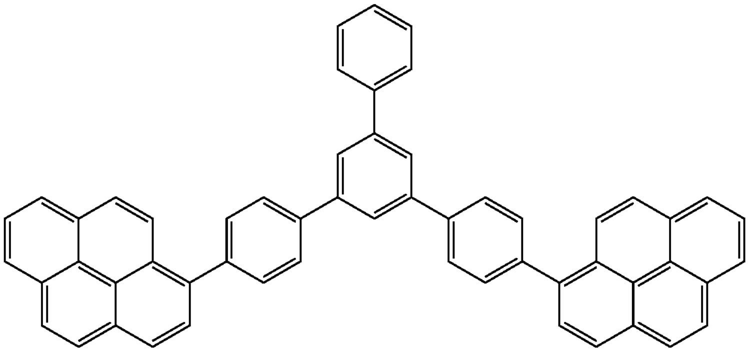

-continued
BH1-9
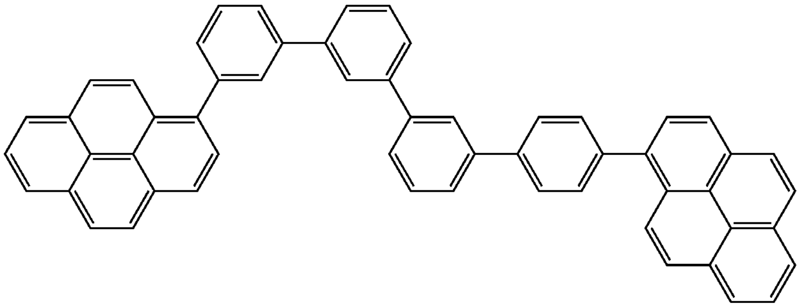
[Formula 304]
BH1-10
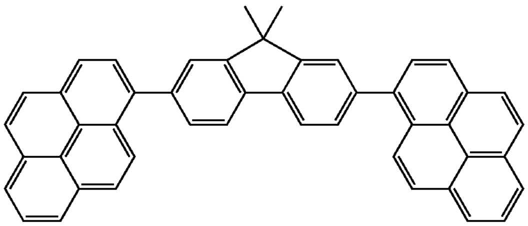
BH1-11
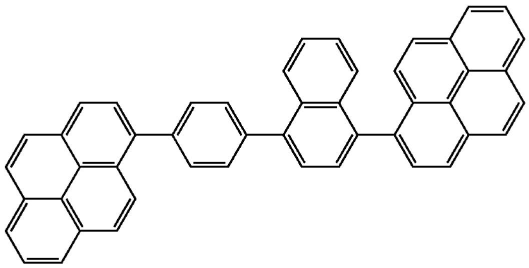
[Formula 305]
BH1-12
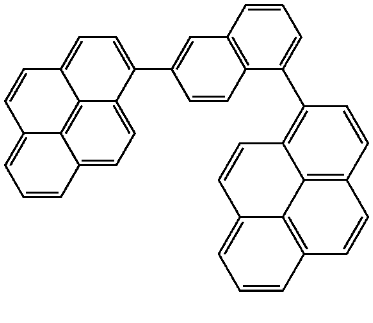
BH1-13
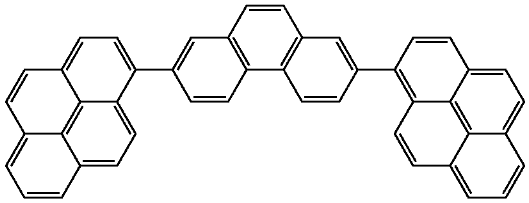
[Formula 306]
BH1-14
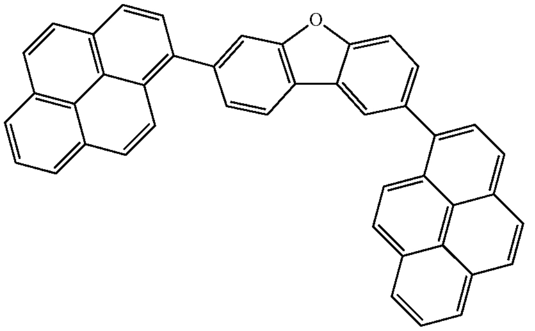
BH1-15
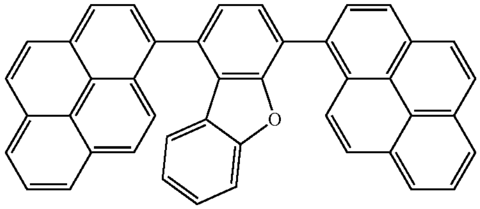

-continued
[Formula 307]
BH1-16
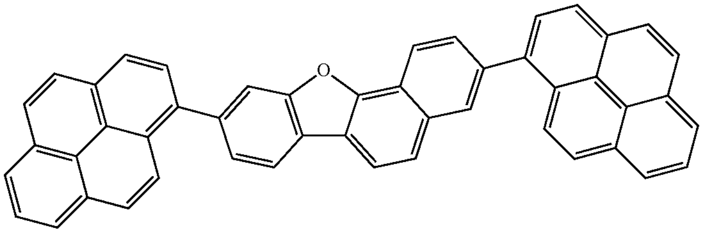
BH1-17
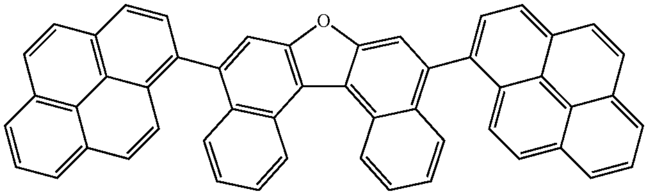
[Formula 308]
BH1-18
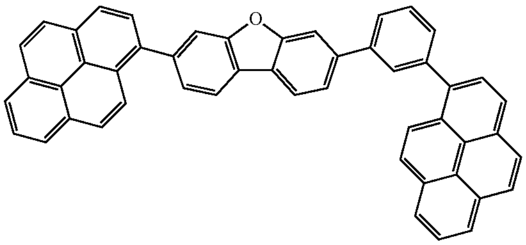
BH1-19
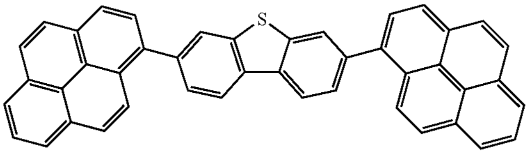
[Formula 309]
BH1-20
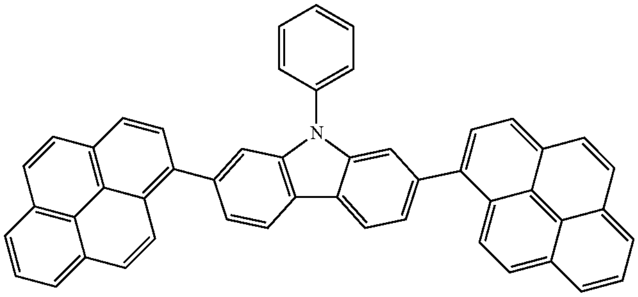
[Formula 310]
BH1-21
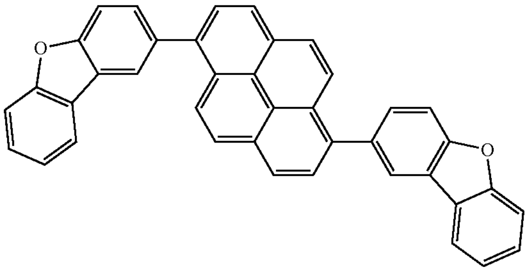
BH1-22
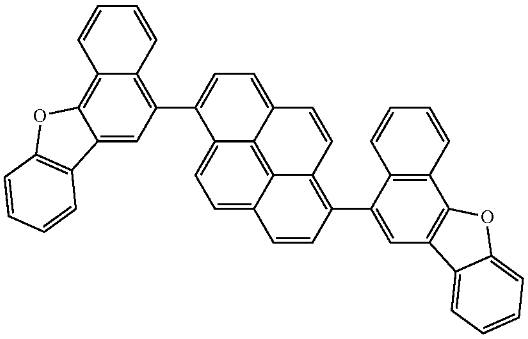

-continued
[Formula 311]
BH1-23
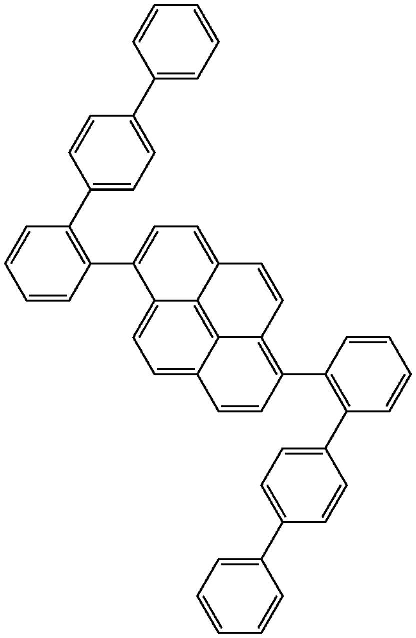
BH1-24
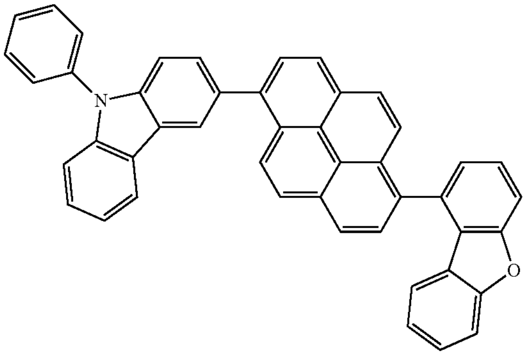
BH1-25
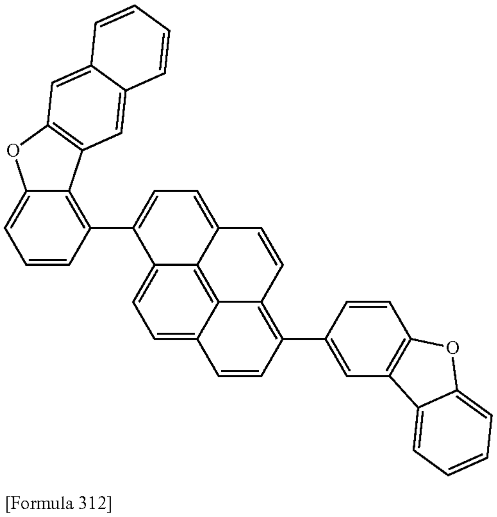
[Formula 312]
BH1-26
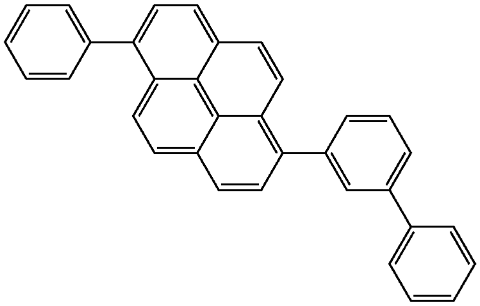
BH1-27
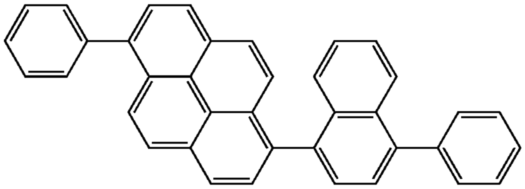

-continued
[Formula 313]
BH1-28
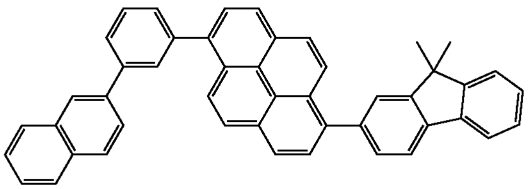
BH1-29
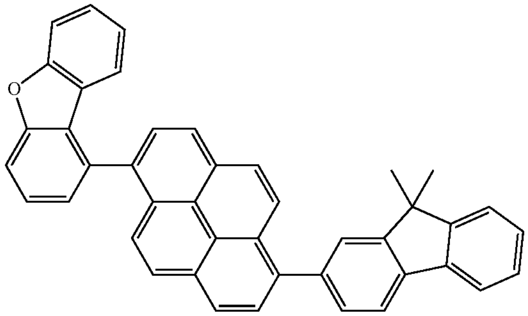
[Formula 314]
BH1-30
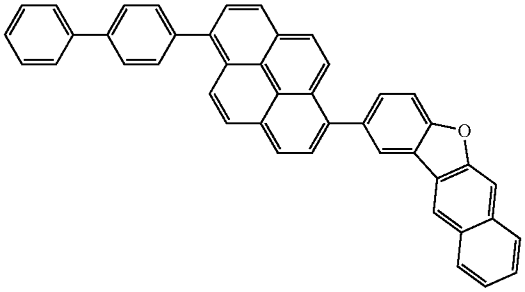
BH1-31
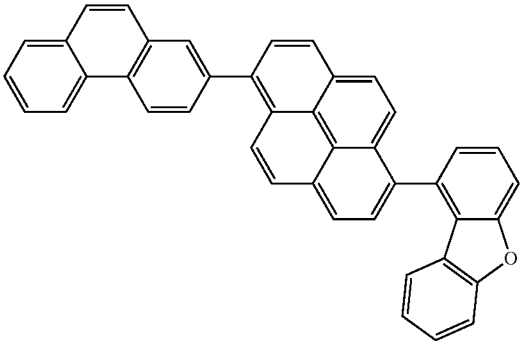
[Formula 315]
BH1-32
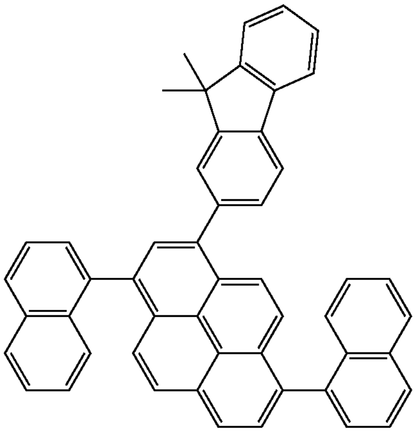
BH1-33
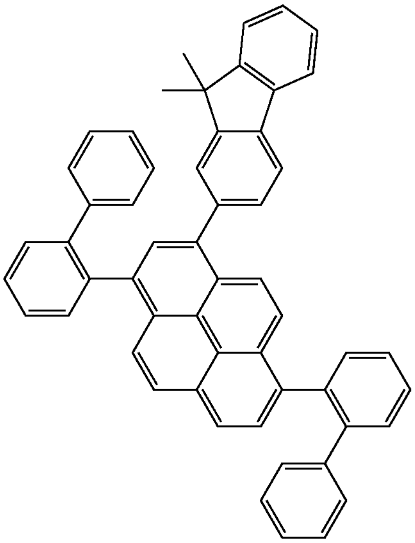

-continued
BH1-34
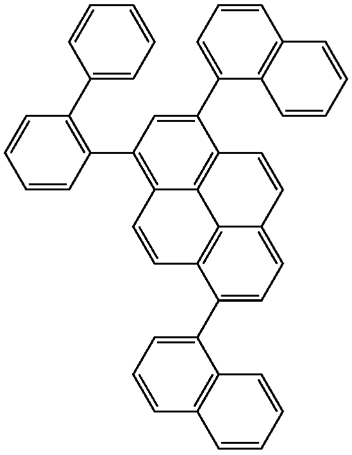
[Formula 316]
BH1-35
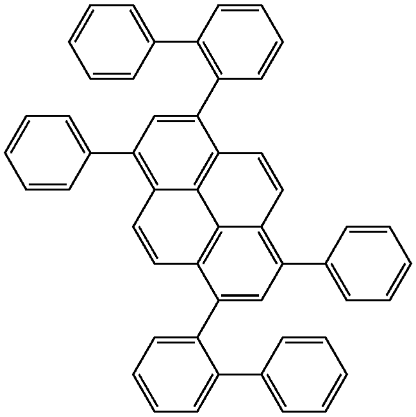
BH1-36
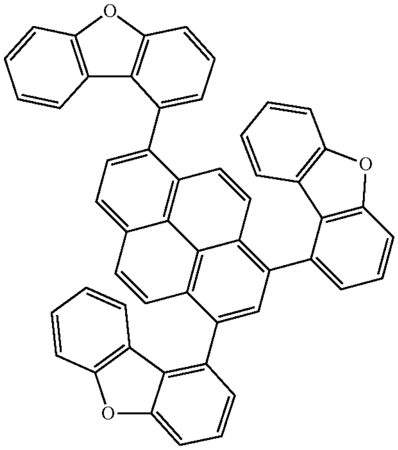
BH1-37
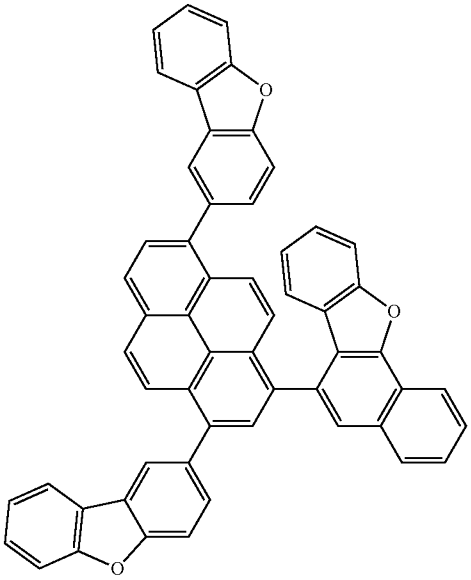

-continued
[Formula 317]
BH1-38
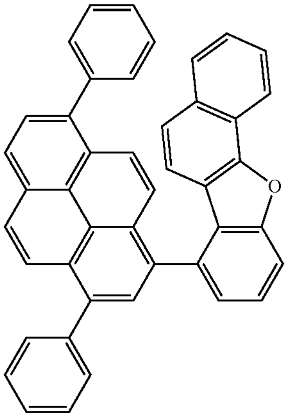
BH1-39
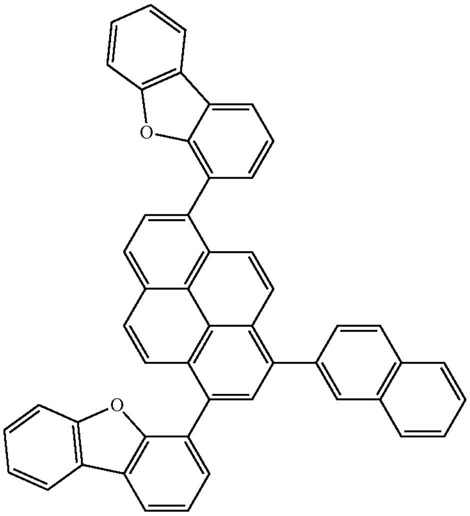
BH1-40
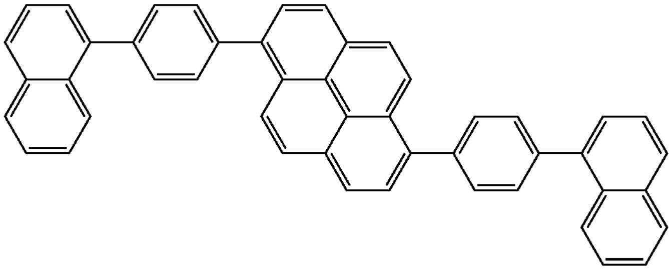
[Formula 318]
BH1-41
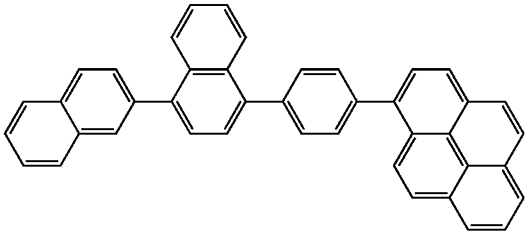
BH1-42
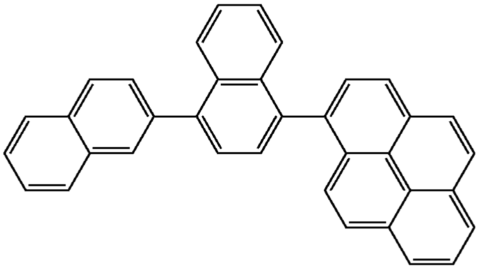
[Formula 319]
BH1-43
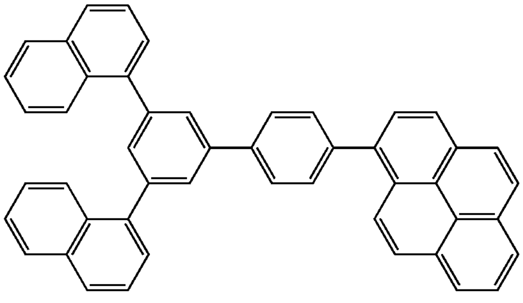
BH1-44
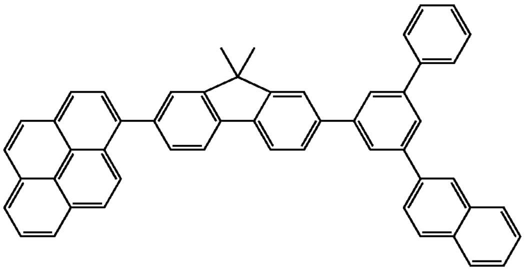

-continued
[Formula 320]
BH1-45
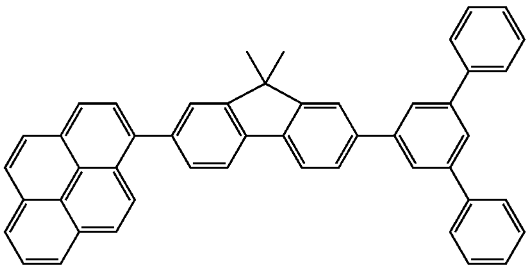
BH1-46
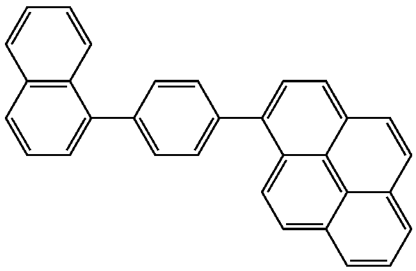
[Formula 321]
BH1-47
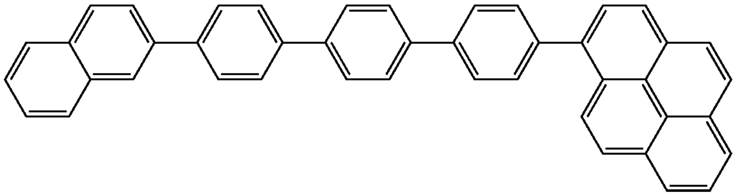
BH1-48
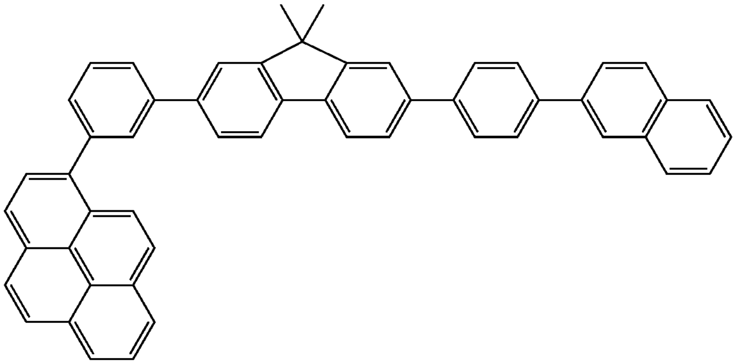
[Formula 322]
BH1-49
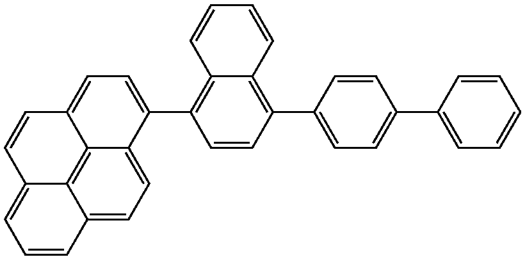
BH1-50
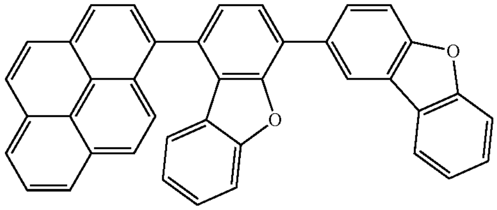

-continued
[Formula 323]
BH1-51
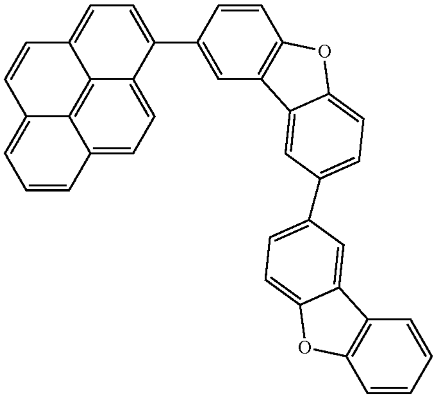
BH1-52
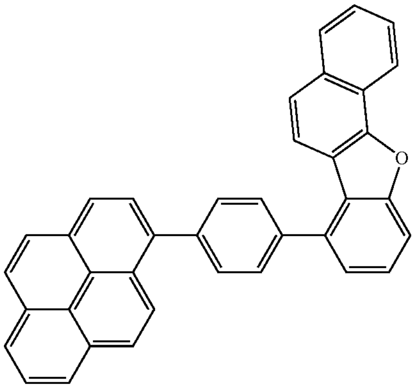
[Formula 324]
BH1-53
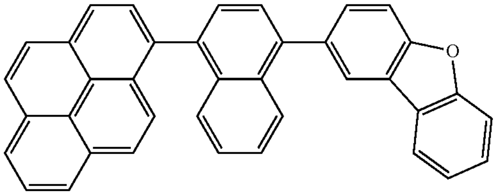
BH1-54
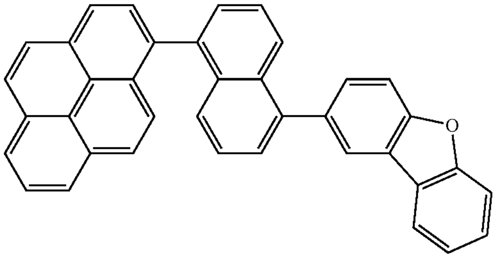
[Formula 325]
BH1-55
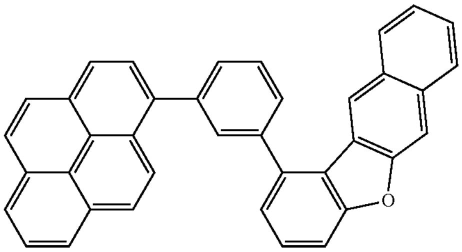
BH1-56
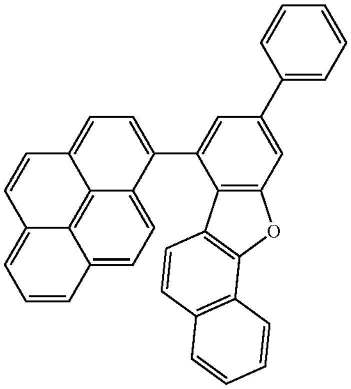
BH1-57
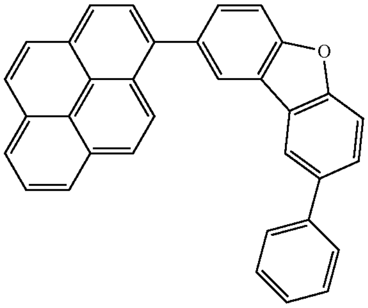

-continued
[Formula 326]
R-BH1
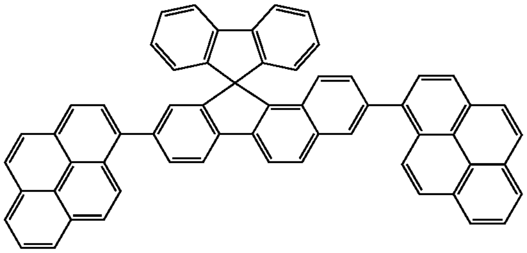
R-BH2
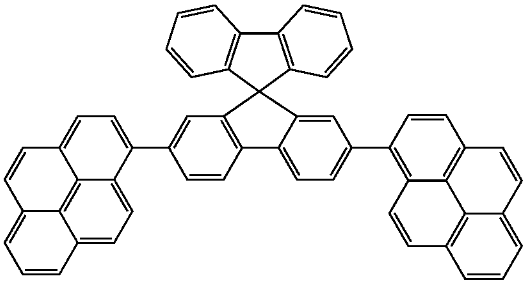
[Formula 327]
R-BH3
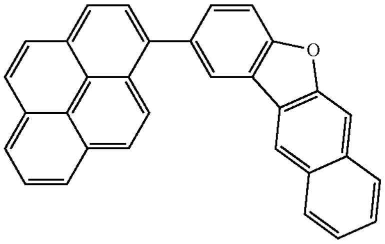
[Formula 328]
BH1-61
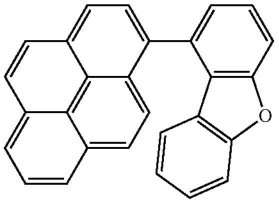
BH1-62
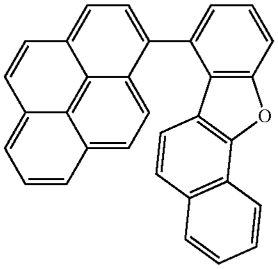
BH1-63
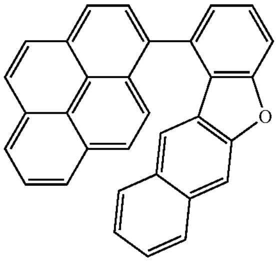
[化 329]
BH1-64
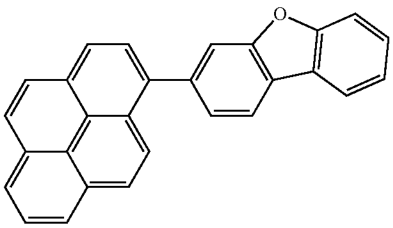
BH1-65
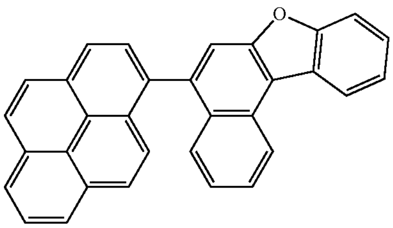

-continued
BH1-66
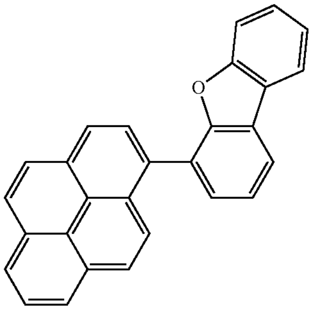
[Formula 330]
BH1-67
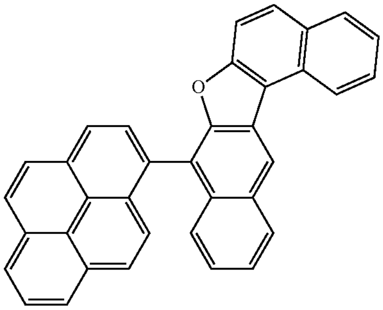
BH1-68
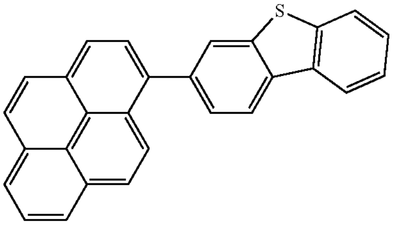
BH1-69
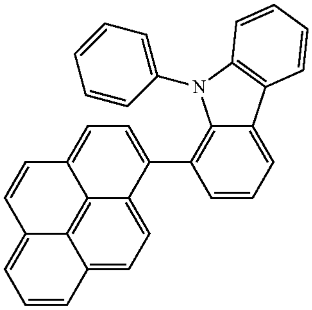
[Formula 331]
BH1-70
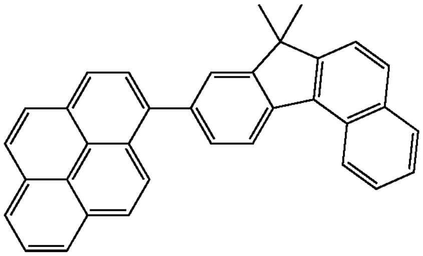
BH1-71
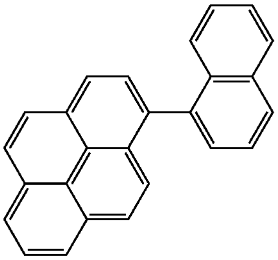
BH1-72
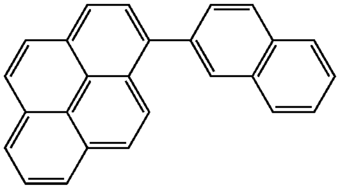

-continued
[Formula 332]
BH1-73
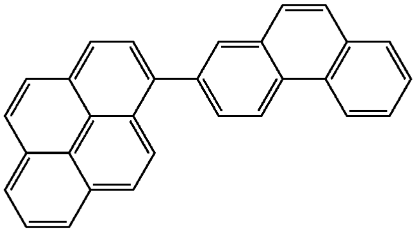
BH1-74
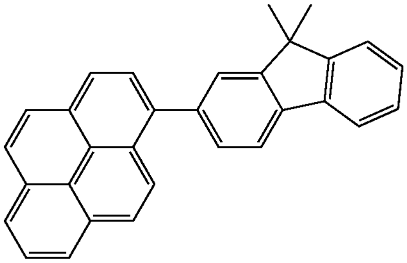
BH1-75
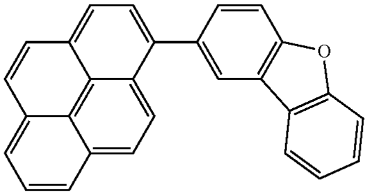
[Formula 333]
BH1-81
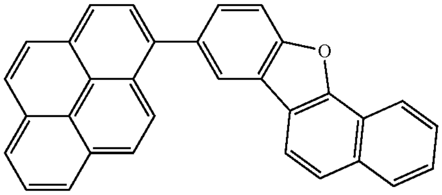
BH1-82
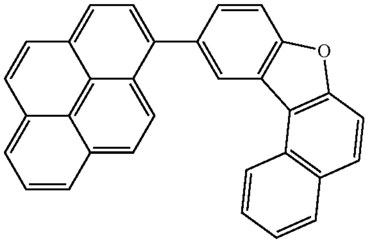
BH1-83
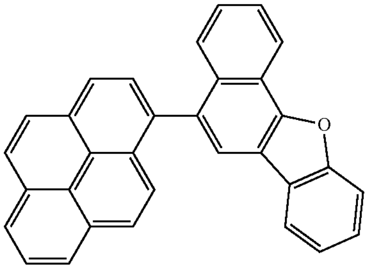
[Formula 334]
BH1-84
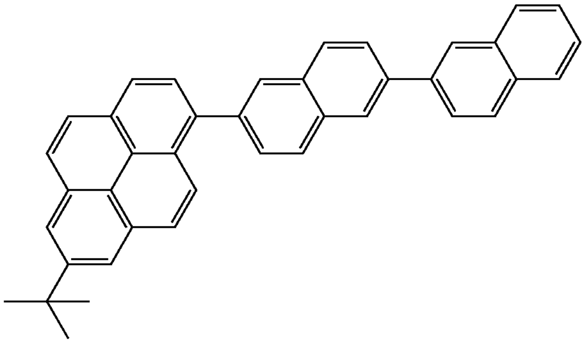

[Formula 335]
BH1-85
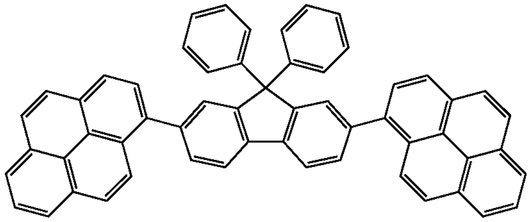
-continued
BH1-86
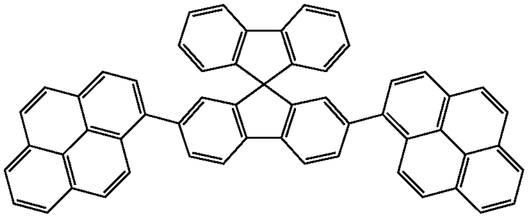
Structures of compounds represented by one of the formulae (2-1 D) to (2-4D), (2-1E) and (2-1F) in Examples and compounds represented by the formula (2) in Reference Examples are shown below.
[Formula 336]
BH2
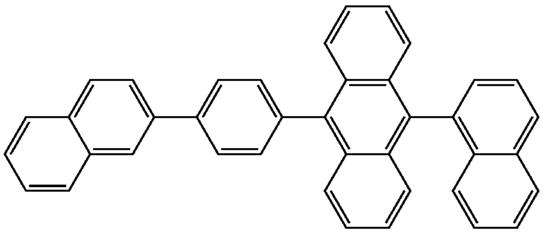
[Formula 337]
BH2-2
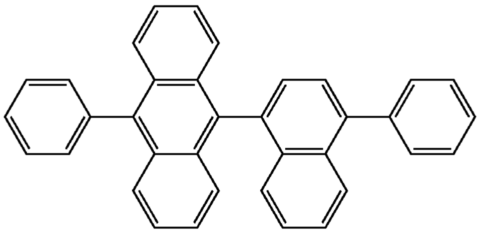
BH2-3
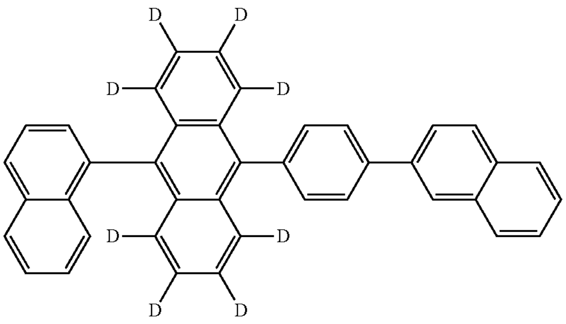
-continued
[Formula 338]
BH2-4
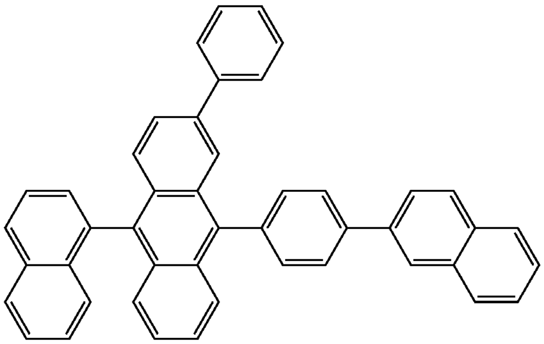
BH2-5
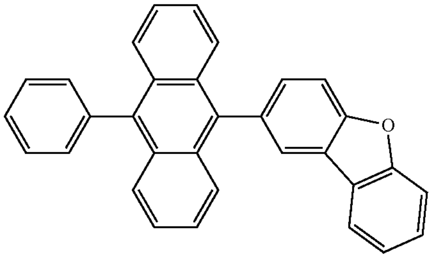
BH2-6
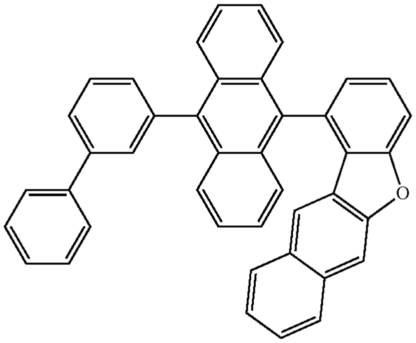

-continued
[Formula 339]
BH2-7
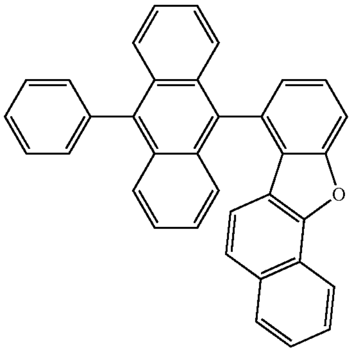
BH2-8
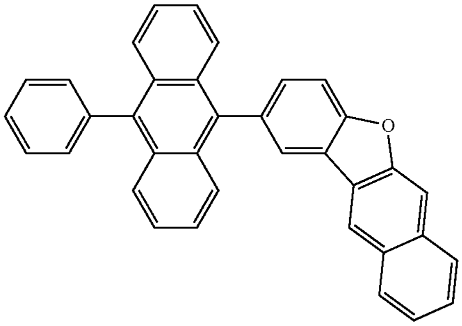
[Formula 340]
BH2-9
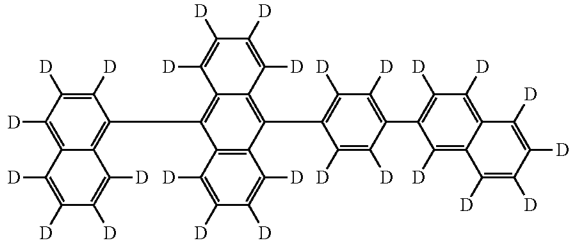
BH2-10
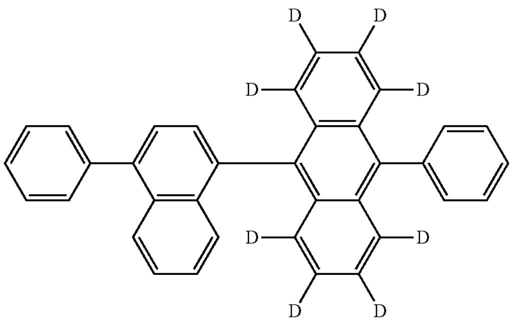
-continued
[Formula 341]
BH2-11
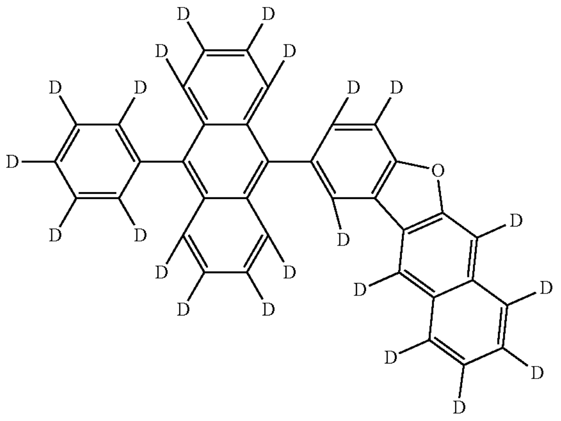
BH2-12
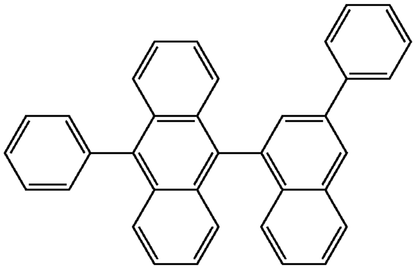
[Formula 342]
BH2-13
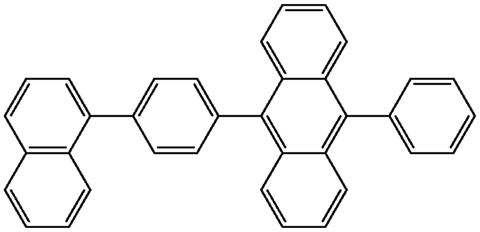
BH2-14
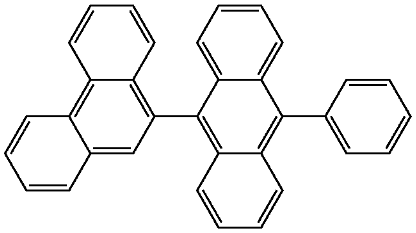
[Formula 343]
BH2-15
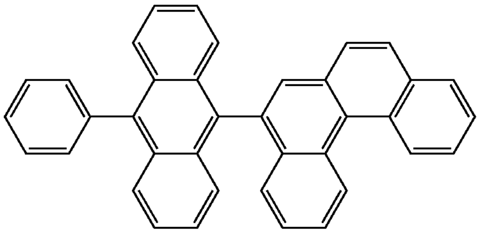

BH2-16
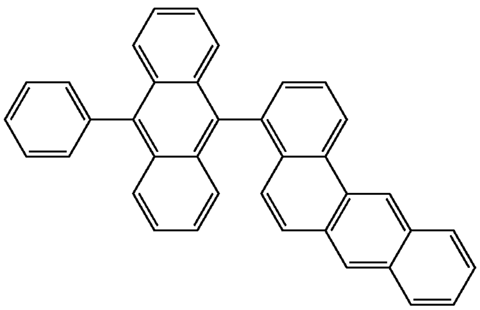
[Formula 344]
BH2-17
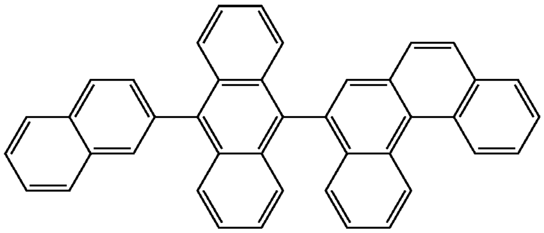
BH2-18
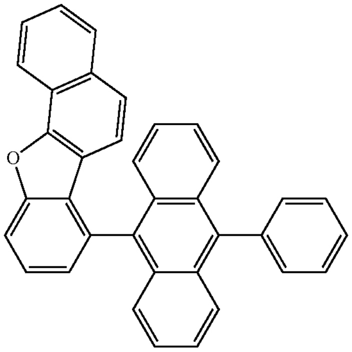
[Formula 345]
BH2-19
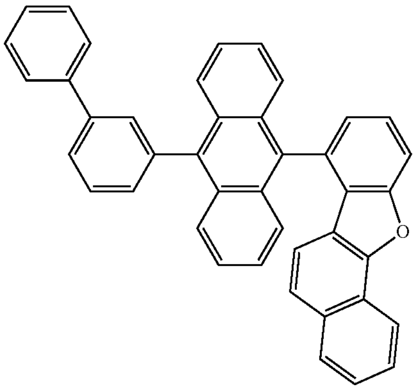
BH2-20
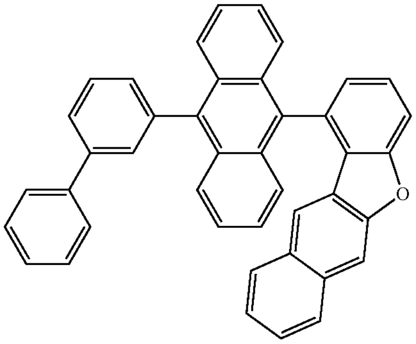
[Formula 346]
BH2-21
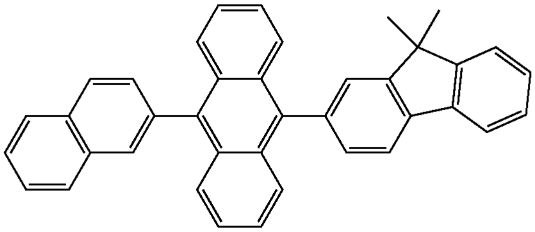
BH2-22
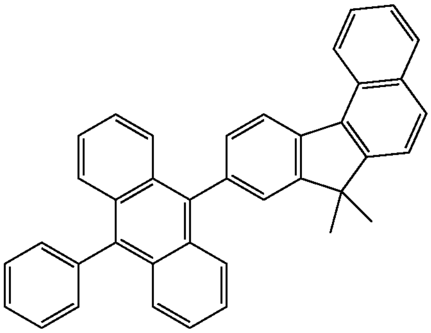
[Formula 347]
BH2-23
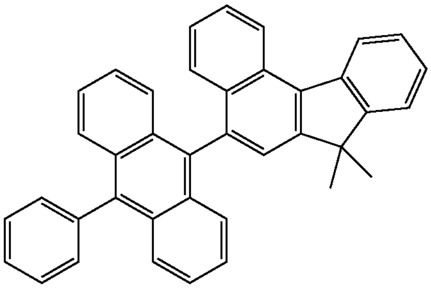
BH2-24
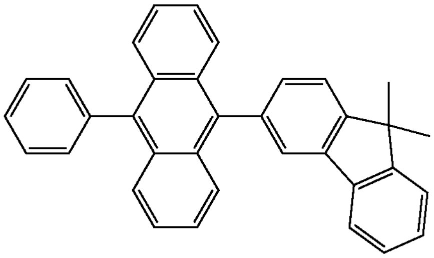

-continued
[Formula 348]
BH2-25
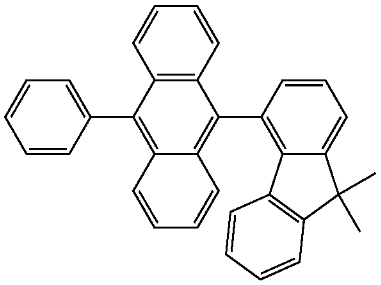
BH2-26
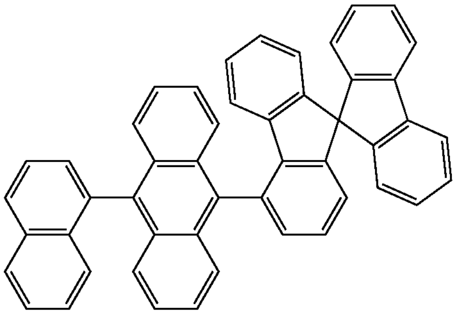
BH2-27
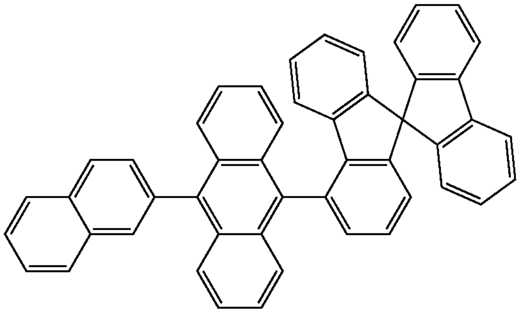
[Formula 349]
BH2-28
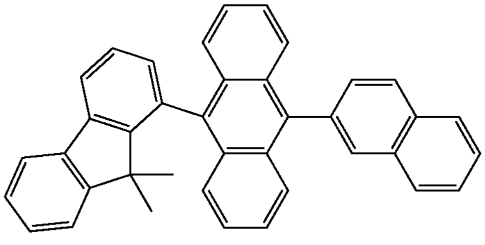
BH2-29
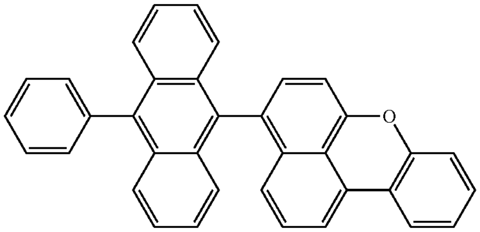
-continued
[Formula 350]
BH2-30
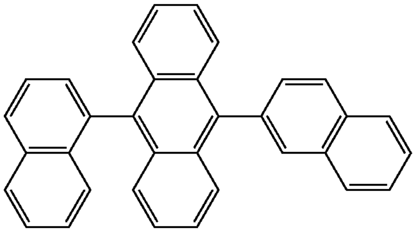
[Formula 351]
BH2-31
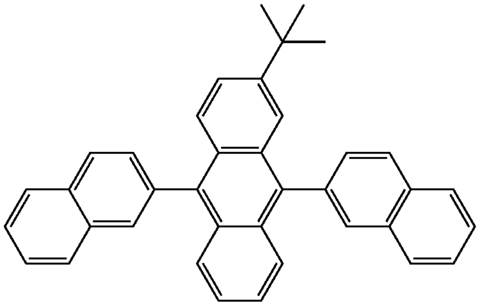
Structures of other compounds used for manufacturing organic EL devices in Examples, Reference Examples and Comparatives are shown below.
[Formula 352]
HA1
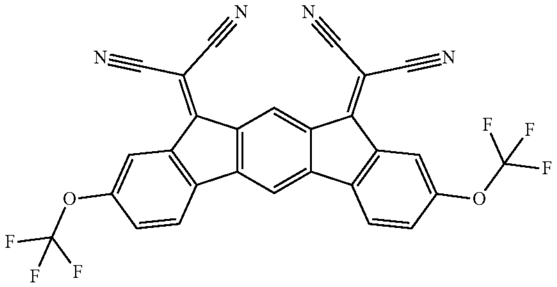
HT1
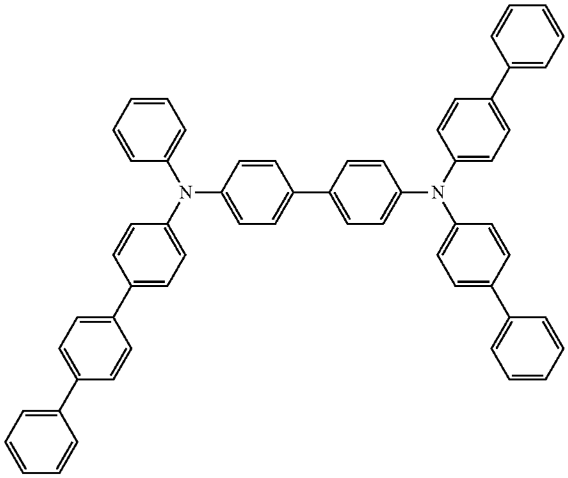

-continued
[Formula 353]
HT2
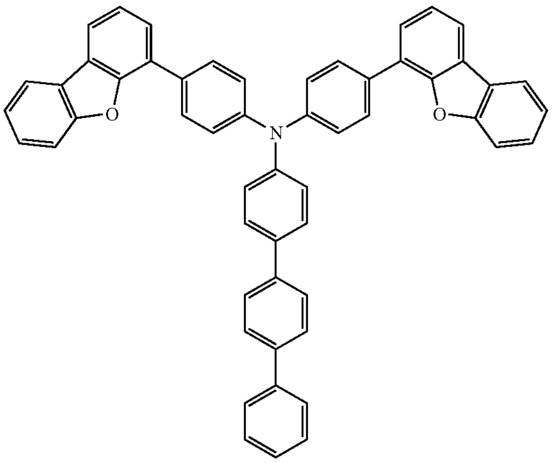
BD1
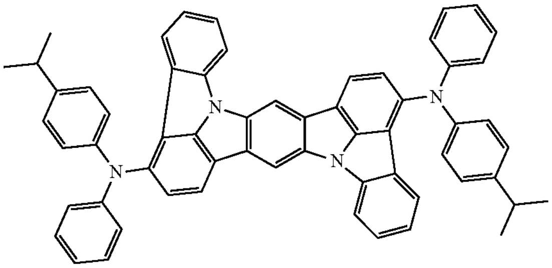
[Formula 354]
HT3
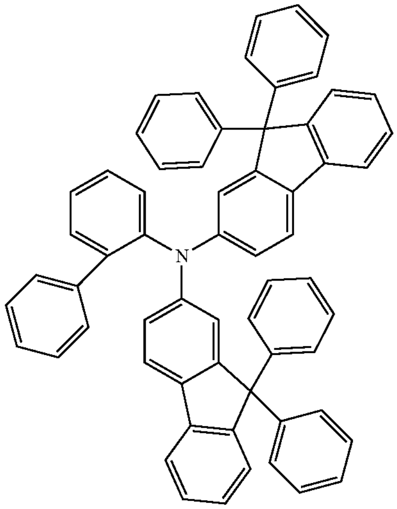
-continued
HT4
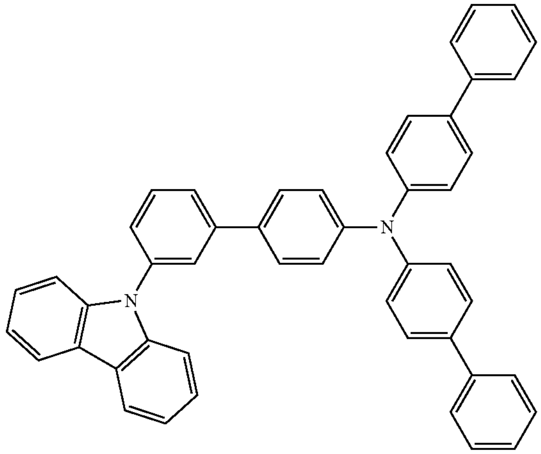
[Formula 355]
HT5
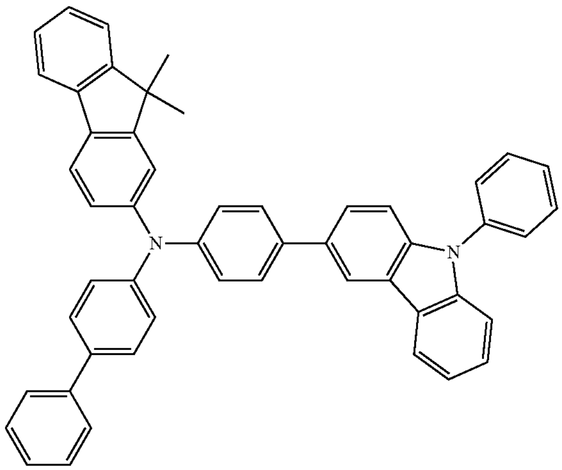
HA2
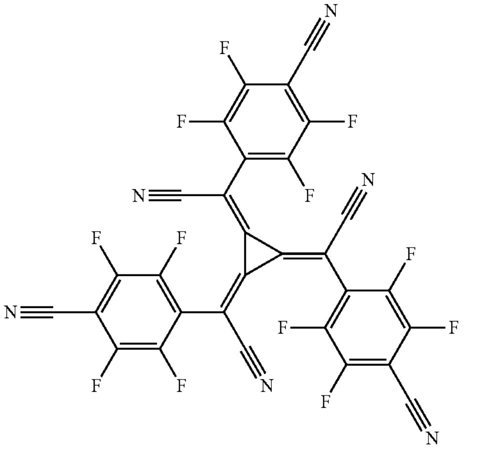

-continued
[Formula 356]
HT6
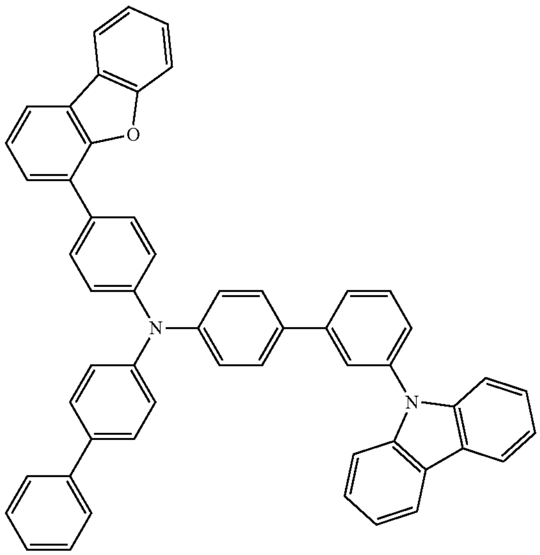
HT7
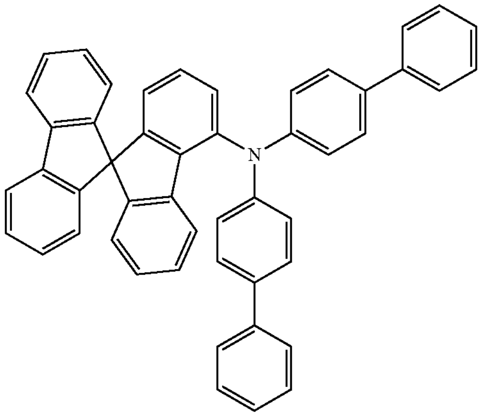
[Formula 357]
HT8
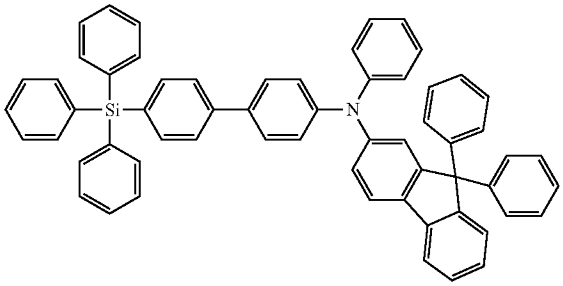
-continued
[Formula 358]
HT9
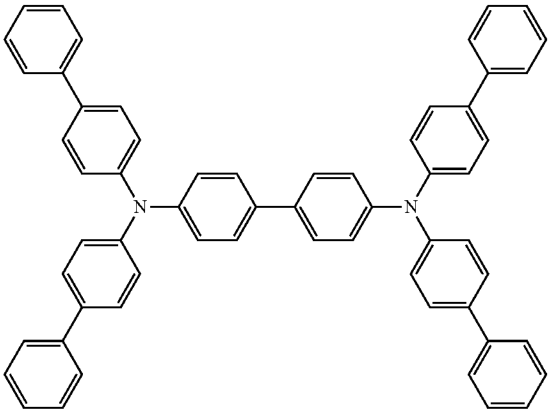
HT10
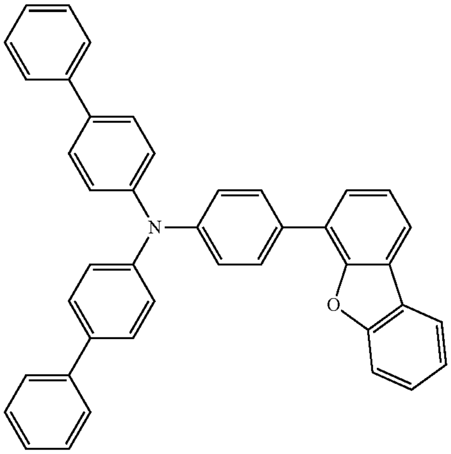
[Formula 359]
HT11
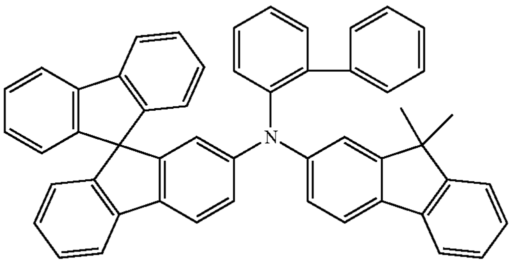

-continued
HT12
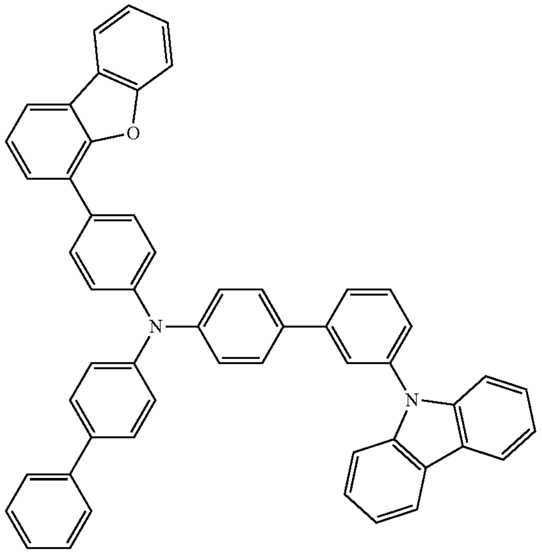
[Formula 360]
BD2
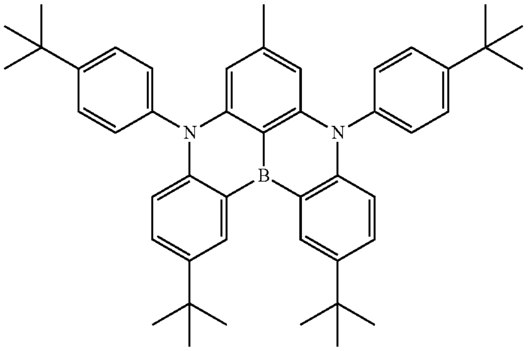
BD3
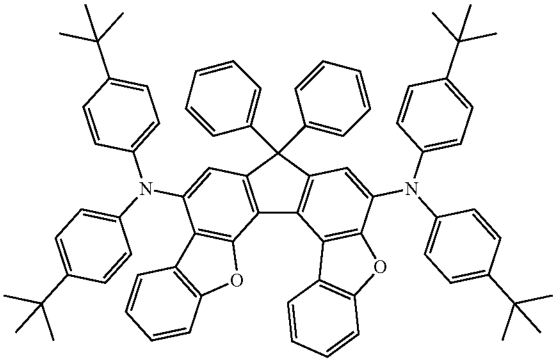
-continued
[Formula 361]
BD4
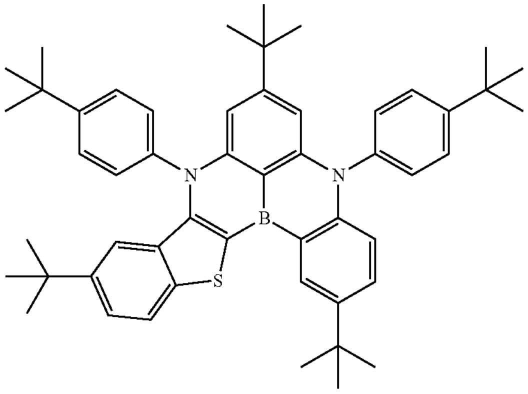
[Formula 362]
ET1
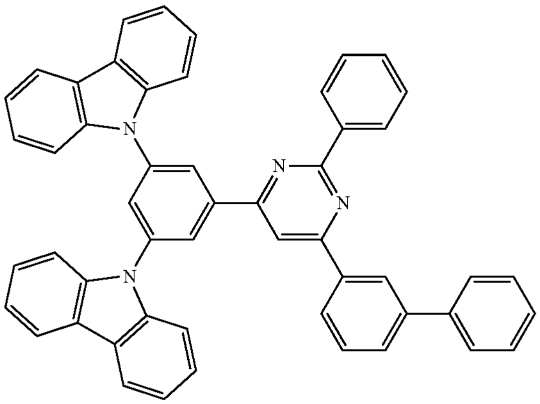
ET2
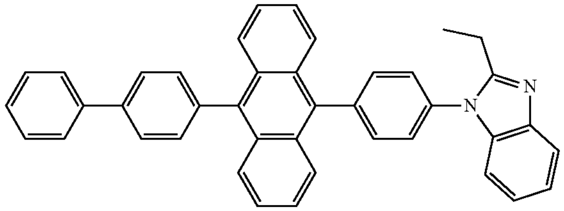
[Formula 363]
ET3
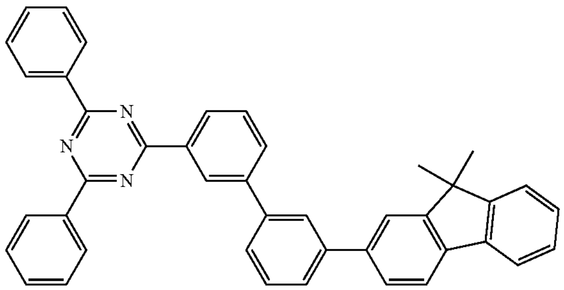

-continued

ET4

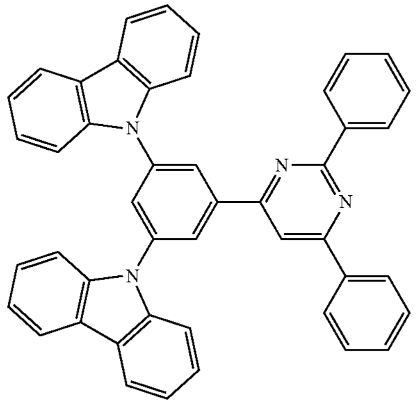

[Formula 364]

ET5

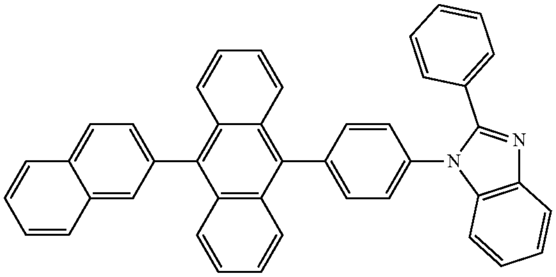

ET6

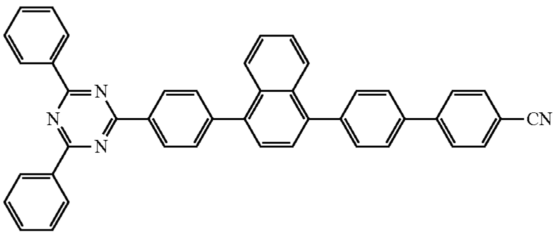

[Formula 365]

ET7

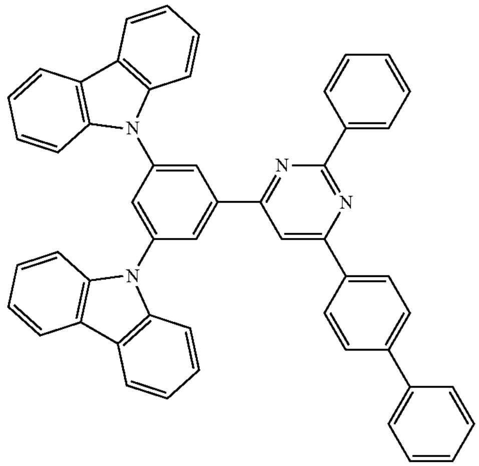

-continued

ET8

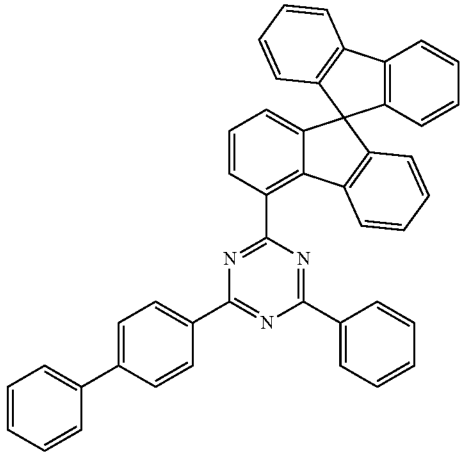

[Formula 366]

ET9

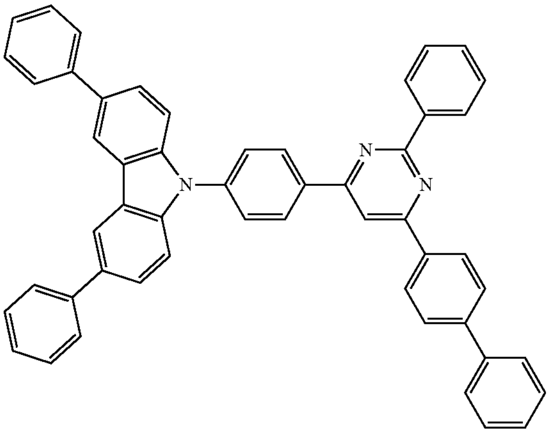

[Formula 367]

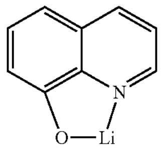

Liq

Manufacture 1 of Organic EL Device

The organic EL devices were manufactured and evaluated as follows.

Reference Example 1

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, a compound HA1 was vapor-deposited on a surface provided with the transparent electrode line to cover the transparent electrode, thereby forming a 5-nm-thick hole injecting layer (HI).

After the formation of the hole injecting layer, a compound HT1 was vapor-deposited to form an 80-nm-thick first hole transporting layer (HT).

After the formation of the first hole transporting layer, a compound HT2 was vapor-deposited to form a 10-nm-thick second hole transporting layer (also referred to as an electron blocking layer (EBL)).

A compound BH1 (first host material (BH)) and a compound BD1 (dopant material (BD)) were co-deposited on the second hole transporting layer such that the ratio of the compound BD1 accounted for 2 mass %, thereby forming a 5-nm-thick first emitting layer.

A compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

A compound ET1 was vapor-deposited on the second emitting layer to form a 10-nm-thick first electron transporting layer (also referred to as a hole blocking layer (HBL)).

A compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 1 is roughly shown as follows.

ITO (130)/HA1(5)/HT1(80)/HT2(10)/BH1:BD1 (5.98%:2%)/BH2:BD1 (20.98%:2%)/ET1(10)/ET2(15)/LiF (1)/Al (80)

The numerals in parentheses represent film thickness (unit: nm).

The numerals (98%:2%) represented by percentage in the same parentheses indicate a ratio (mass %) between the host material (compound BH1 or BH2) and the compound BD1 in the first emitting layer or the second emitting layer. Similar notations apply to the description below.

Comparative 1

The organic EL device according to Comparative 1 was manufactured in the same manner as that of Reference Example 1 except that a 25-nm-thick first emitting layer was formed as the emitting layer and the first electron transporting layer was formed on the first emitting layer without forming the second emitting layer as shown in Table 1.

Comparative 2

The organic EL device according to Comparative 2 was manufactured in the same manner as that of Reference Example 1 except that a 25-nm-thick second emitting layer was formed on the second hole transporting layer as the emitting layer without forming the first emitting layer as shown in Table 1.

Evaluation of Organic EL Devices

The organic EL devices manufactured in Examples, Reference Examples, and Comparatives were evaluated as follows. Tables 1 to 48 show the evaluation results.

Herein, evaluation results of some Examples, some Reference Examples, and some Comparatives are shown in a plurality of Tables.

External Quantum Efficiency EQE

Voltage was applied on the organic EL devices so that a current density was 10 $mA/cm^2$, where spectral radiance spectrum was measured by a spectroradiometer CS-2000 (manufactured by Konica Minolta, Inc.). The external quantum efficiency EQE (unit: %) was calculated based on the obtained spectral-radiance spectra, assuming that the spectra was provided under a Lambertian radiation.

Lifetime LT90

Voltage was applied on the resultant organic EL devices such that a current density was 50 $mA/cm^2$, where a time (LT90 (unit: hr)) elapsed before a luminance intensity was reduced to 90% of the initial luminance intensity was measured. Table 1 shows the results.

Lifetime LT95

Voltage was applied on the resultant organic EL devices such that a current density was 50 $mA/cm^2$, where a time (LT95 (unit: hr)) elapsed before a luminance intensity was reduced to 95% of the initial luminance intensity was measured.

Main Peak Wavelength λp when Device is Driven

Voltage was applied on each of the organic EL devices such that a current density of the organic EL device was 10 $mA/cm^2$, where spectral radiance spectrum was measured by a spectroradiometer CS-2000 (manufactured by Konica Minolta, Inc.). The main peak wavelength $\Delta_p$ (unit: nm) was calculated based on the obtained spectral radiance spectrum.

Drive Voltage

The voltage (unit: V) when electric current was applied between the anode and the cathode so that the current density was 10 $mA/cm^2$ was measured.

TABLE 1

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | EQE [%] | LT90 [hr] | λp [nm] |
| Reference Example 1 | BH1 | BD1 | 5 | BH2 | BD1 | 20 | 10.6 | 600 | 461 |
| Comparative 1 | BH1 | BD1 | 25 | — | — | — | 7.6 | 360 | 462 |
| Comparative 2 | — | — | — | BH2 | BD1 | 25 | 9.9 | 363 | 460 |

As shown in Table 1, the organic EL device according to Reference Example 1, in which the first emitting layer containing the first host material in a form of the first compound was in direct contact with the second emitting layer containing the second host material in a form of the second compound, emitted at a higher luminous efficiency than the organic EL devices according to Comparatives 1 and 2 including only one of the emitting layers. Further, the organic EL device according to Reference Example 1 exhibited a longer lifetime than that of the organic EL devices according to Comparatives 1 and 2.

Reference Examples 2 to 20

The organic EL devices according to Reference Examples 2 to 20 were manufactured in the same manner as that of Reference Example 1 except that the compound BH1 (first host material) in the first emitting layer was replaced with the first compounds listed in Table 2.

Comparatives 3 to 21

The organic EL devices according to Comparatives 3 to 21 were manufactured in the same manner as that of Comparative 1 except that the compound BH1 (first host material) in the first emitting layer was replaced with the first compounds listed in Table 3.

TABLE 2

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 1 | BH1 | BD1 | 5 | BH2 | BD1 | 20 | 3.47 | 10.6 | 255 |
| Reference Example 2 | BH1-2 | BD1 | 5 | BH2 | BD1 | 20 | 3.47 | 10.2 | 205 |
| Reference Example 3 | BH1-3 | BD1 | 5 | BH2 | BD1 | 20 | 3.56 | 10.5 | 268 |
| Reference Example 4 | BH1-4 | BD1 | 5 | BH2 | BD1 | 20 | 3.56 | 10.7 | 222 |
| Reference Example 5 | BH1-5 | BD1 | 5 | BH2 | BD1 | 20 | 3.64 | 10.7 | 251 |
| Reference Example 6 | BH1-6 | BD1 | 5 | BH2 | BD1 | 20 | 3.65 | 10.6 | 224 |
| Reference Example 7 | BH1-7 | BD1 | 5 | BH2 | BD1 | 20 | 3.63 | 10.4 | 239 |
| Reference Example 8 | BH1-8 | BD1 | 5 | BH2 | BD1 | 20 | 3.62 | 10.4 | 224 |
| Reference Example 9 | BH1-9 | BD1 | 5 | BH2 | BD1 | 20 | 3.70 | 10.8 | 249 |
| Reference Example 10 | BH1-10 | BD1 | 5 | BH2 | BD1 | 20 | 3.34 | 10.4 | 216 |
| Reference Example 11 | BH1-11 | BD1 | 5 | BH2 | BD1 | 20 | 3.48 | 10.8 | 275 |
| Reference Example 12 | BH1-12 | BD1 | 5 | BH2 | BD1 | 20 | 3.39 | 10.6 | 212 |
| Reference Example 13 | BH1-13 | BD1 | 5 | BH2 | BD1 | 20 | 3.51 | 10.6 | 231 |
| Reference Example 14 | BH1-14 | BD1 | 5 | BH2 | BD1 | 20 | 3.36 | 10.4 | 198 |
| Reference Example 15 | BH1-15 | BD1 | 5 | BH2 | BD1 | 20 | 3.43 | 10.5 | 190 |
| Reference Example 16 | BH1-16 | BD1 | 5 | BH2 | BD1 | 20 | 3.30 | 10.5 | 192 |
| Reference Example 17 | BH1-17 | BD1 | 5 | BH2 | BD1 | 20 | 3.38 | 10.2 | 185 |
| Reference Example 18 | BH1-18 | BD1 | 5 | BH2 | BD1 | 20 | 3.41 | 10.6 | 204 |
| Reference Example 19 | BH1-19 | BD1 | 5 | BH2 | BD1 | 20 | 3.39 | 10.3 | 191 |
| Reference Example 20 | R-BH1 | BD1 | 5 | BH2 | BD1 | 20 | 3.91 | 10.1 | — |

TABLE 3

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Comparative 1 | BH1 | BD1 | 25 | — | — | — | — | 7.6 | 65 |
| Comparative 2 | — | — | — | BH2 | BD1 | 25 | — | 9.9 | 167 |
| Comparative 3 | BH1-2 | BD1 | 25 | — | — | — | — | 7.2 | 59 |
| Comparative 4 | BH1-3 | BD1 | 25 | — | — | — | — | 7.4 | 71 |
| Comparative 5 | BH1-4 | BD1 | 25 | — | — | — | — | 7.8 | 70 |
| Comparative 6 | BH1-5 | BD1 | 25 | — | — | — | — | 7.5 | 62 |
| Comparative 7 | BH1-6 | BD1 | 25 | — | — | — | — | 7.4 | 60 |
| Comparative 8 | BH1-7 | BD1 | 25 | — | — | — | — | 7.3 | 53 |
| Comparative 9 | BH1-8 | BD1 | 25 | — | — | — | — | 7.4 | 55 |
| Comparative 10 | BH1-9 | BD1 | 25 | — | — | — | — | 7.5 | 67 |
| Comparative 11 | BH1-10 | BD1 | 25 | — | — | — | — | 7.1 | 51 |
| Comparative 12 | BH1-11 | BD1 | 25 | — | — | — | — | 7.8 | 81 |
| Comparative 13 | BH1-12 | BD1 | 25 | — | — | — | — | 7.0 | 48 |
| Comparative 14 | BH1-13 | BD1 | 25 | — | — | — | — | 7.1 | 53 |
| Comparative 15 | BH1-14 | BD1 | 25 | — | — | — | — | 6.9 | 56 |
| Comparative 16 | BH1-15 | BD1 | 25 | — | — | — | — | 7.1 | 59 |
| Comparative 17 | BH1-16 | BD1 | 25 | — | — | — | — | 7.0 | 62 |
| Comparative 18 | BH1-17 | BD1 | 25 | — | — | — | — | 6.7 | 53 |
| Comparative 19 | BH1-18 | BD1 | 25 | — | — | — | — | 7.1 | 62 |
| Comparative 20 | BH1-19 | BD1 | 25 | — | — | — | — | 6.9 | 43 |
| Comparative 21 | BH1-20 | BD1 | 25 | — | — | — | — | 6.5 | 21 |

Reference Example 21

The organic EL device according to Reference Example 21 was manufactured in the same manner as that of Reference Example 1 except that the compound BH2 (second host material) in the second emitting layer was replaced with the compound listed in Table 4.

Reference Examples 22 and 23

The organic EL devices according to Reference Examples 22 and 23 were manufactured in the same manner as that of Reference Example 1 except that the compound BH1 (first host material) in the first emitting layer and the compound BH2 (second host material) in the second emitting layer were replaced with the compounds listed in Table 4.

Comparative 22

The organic EL device according to Comparative 22 was manufactured in the same manner as that of Comparative 2 except that the compound BH2 (second host material) in the second emitting layer was replaced with the compound listed in Table 4.

TABLE 4

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 21 | BH1 | BD1 | 5 | BH2-2 | BD1 | 20 | 3.96 | 9.8 | 192 |
| Reference Example 22 | R-BH1 | BD1 | 5 | BH2-2 | BD1 | 20 | 4.40 | 9.4 | — |
| Reference Example 23 | R-BH2 | BD1 | 5 | BH2-2 | BD1 | 20 | 4.68 | 9.5 | — |
| Comparative 1 | BH1 | BD1 | 25 | — | — | — | — | 7.6 | 65 |
| Comparative 22 | — | — | — | BH2-2 | BD1 | 25 | — | 9.2 | 115 |

Reference Example 24

The organic EL device according to Reference Example 24 was manufactured in the same manner as that of Reference Example 1 except that the compound BH2 (second host material) in the second emitting layer was replaced with the compound listed in Table 5.

Reference Examples 25 and 26

The organic EL devices according to Reference Examples 25 and 26 were manufactured in the same manner as that of Reference Example 1 except that the compound BH1 (first host material) in the first emitting layer and the compound BH2 (second host material) in the second emitting layer were replaced with the compounds listed in Table 5.

Comparative 23

The organic EL device according to Comparative 23 was manufactured in the same manner as that of Comparative 2 except that the compound BH2 (second host material) in the second emitting layer was replaced with the compound listed in Table 5.

TABLE 5

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 24 | BH1 | BD1 | 5 | BH2-3 | BD1 | 20 | 3.54 | 10.6 | 278 |
| Reference Example 25 | R-BH1 | BD1 | 5 | BH2-3 | BD1 | 20 | 3.98 | 10.1 | — |
| Reference Example 26 | R-BH2 | BD1 | 5 | BH2-3 | BD1 | 20 | 4.26 | 10.2 | — |
| Comparative 1 | BH1 | BD1 | 25 | — | — | — | — | 7.6 | 65 |
| Comparative 23 | — | — | — | BH2-3 | BD1 | 25 | — | 9.9 | 182 |

Reference Example 27

The organic EL device according to Reference Example 27 was manufactured in the same manner as that of Reference Example 1 except that the compound BH2 (second host material) in the second emitting layer was replaced with the compound listed in Table 6.

Reference Examples 28 and 29

The organic EL devices according to Reference Examples 28 and 29 were manufactured in the same manner as that of Reference Example 1 except that the compound BH1 (first host material) in the first emitting layer and the compound BH2 (second host material) in the second emitting layer were replaced with the compounds listed in Table 6.

Comparative 24

The organic EL device according to Comparative 24 was manufactured in the same manner as that of Comparative 2 except that the compound BH2 (second host material) in the second emitting layer was replaced with the compound listed in Table 6.

TABLE 6

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 27 | BH1 | BD1 | 5 | BH2-4 | BD1 | 20 | 3.26 | 8.1 | 272 |
| Reference Example 28 | R-BH1 | BD1 | 5 | BH2-4 | BD1 | 20 | 3.70 | 7.9 | — |
| Reference Example 29 | R-BH2 | BD1 | 5 | BH2-4 | BD1 | 20 | 3.98 | 7.9 | — |
| Comparative 1 | BH1 | BD1 | 25 | — | — | — | — | 7.6 | 65 |
| Comparative 24 | — | — | — | BH2-4 | BD1 | 25 | — | 7.7 | 114 |

Reference Example 30

The organic EL device according to Reference Example 30 was manufactured in the same manner as that of Reference Example 1 except that the compound BH2 (second host material) in the second emitting layer was replaced with the compound listed in Table 7.

Reference Examples 31 and 32

The organic EL devices according to Reference Examples 31 and 32 were manufactured in the same manner as that of Reference Example 1 except that the compound BH1 (first host material) in the first emitting layer and the compound BH2 (second host material) in the second emitting layer were replaced with the compounds listed in Table 7.

Comparative 25

The organic EL device according to Comparative 25 was manufactured in the same manner as that of Comparative 2 except that the compound BH2 (second host material) in the second emitting layer was replaced with the compound listed in Table 7.

TABLE 7

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 30 | BH1 | BD1 | 5 | BH2-5 | BD1 | 20 | 3.76 | 8.0 | 196 |
| Reference Example 31 | R-BH1 | BD1 | 5 | BH2-5 | BD1 | 20 | 4.20 | 7.8 | — |
| Reference Example 32 | R-BH2 | BD1 | 5 | BH2-5 | BD1 | 20 | 4.48 | 7.8 | — |
| Comparative 1 | BH1 | BD1 | 25 | — | — | — | — | 7.6 | 65 |
| Comparative 25 | — | — | — | BH2-5 | BD1 | 25 | — | 7.6 | 92 |

Reference Example 33

The organic EL device according to Reference Example 33 was manufactured in the same manner as that of Reference Example 1 except that the compound BH2 (second host material) in the second emitting layer was replaced with the compound listed in Table 8.

Reference Examples 34 and 35

The organic EL devices according to Reference Examples 34 and 35 were manufactured in the same manner as that of Reference Example 1 except that the compound BH1 (first host material) in the first emitting layer and the compound BH2 (second host material) in the second emitting layer were replaced with the compounds listed in Table 8.

Comparative 26

The organic EL device according to Comparative 26 was manufactured in the same manner as that of Comparative 2 except that the compound BH2 (second host material) in the second emitting layer was replaced with the compound listed in Table 8.

TABLE 8

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 33 | BH1 | BD1 | 5 | BH2-6 | BD1 | 20 | 3.14 | 10.5 | 198 |
| Reference Example 34 | R-BH1 | BD1 | 5 | BH2-6 | BD1 | 20 | 3.58 | 8.2 | — |
| Reference Example 35 | R-BH2 | BD1 | 5 | BH2-6 | BD1 | 20 | 3.86 | 8.2 | — |
| Comparative 1 | BH1 | BD1 | 25 | — | — | — | — | 7.6 | 65 |
| Comparative 26 | — | — | — | BH2-6 | BD1 | 25 | — | 8.0 | 71 |

Reference Example 36

The organic EL device according to Reference Example 36 was manufactured in the same manner as that of Reference Example 1 except that the compound BH2 (second host material) in the second emitting layer was replaced with the compound listed in Table 9.

Reference Examples 37 and 38

The organic EL devices according to Reference Examples 37 and 38 were manufactured in the same manner as that of Reference Example 1 except that the compound BH1 (first host material) in the first emitting layer and the compound BH2 (second host material) in the second emitting layer were replaced with the compounds listed in Table 9.

Comparative 27

The organic EL device according to Comparative 27 was manufactured in the same manner as that of Comparative 2 except that the compound BH2 (second host material) in the second emitting layer was replaced with the compound listed in Table 9.

TABLE 9

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 36 | BH1 | BD1 | 5 | BH2-7 | BD1 | 20 | 3.21 | 10.7 | 217 |
| Reference Example 37 | R-BH1 | BD1 | 5 | BH2-7 | BD1 | 20 | 3.65 | 8.0 | — |
| Reference Example 38 | R-BH2 | BD1 | 5 | BH2-7 | BD1 | 20 | 3.93 | 8.0 | — |
| Comparative 1 | BH1 | BD1 | 25 | — | — | — | — | 7.6 | 65 |
| Comparative 27 | — | — | — | BH2-7 | BD1 | 25 | — | 7.8 | 106 |

Reference Example 39

The organic EL device according to Reference Example 39 was manufactured in the same manner as that of Reference Example 1 except that the compound BH2 (second host material) in the second emitting layer was replaced with the compound listed in Table 10.

Reference Examples 40 and 41

The organic EL devices according to Reference Examples 40 and 41 were manufactured in the same manner as that of Reference Example 1 except that the compound BH1 (first host material) in the first emitting layer and the compound BH2 (second host material) in the second emitting layer were replaced with the compounds listed in Table 10.

Comparative 28

The organic EL device according to Comparative 28 was manufactured in the same manner as that of Comparative 2 except that the compound BH2 (second host material) in the second emitting layer was replaced with the compound listed in Table 10.

TABLE 10

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 39 | BH1 | BD1 | 5 | BH2-8 | BD1 | 20 | 3.39 | 9.2 | 192 |
| Reference Example 40 | R-BH1 | BD1 | 5 | BH2-8 | BD1 | 20 | 3.83 | 8.0 | — |
| Reference Example 41 | R-BH2 | BD1 | 5 | BH2-8 | BD1 | 20 | 4.11 | 8.0 | — |
| Comparative 1 | BH1 | BD1 | 25 | — | — | — | — | 7.6 | 65 |
| Comparative 28 | — | — | — | BH2-8 | BD1 | 25 | — | 7.8 | 74 |

Reference Example 42

The organic EL device according to Reference Example 42 was manufactured in the same manner as that of Reference Example 1 except that the compound BH2 (second host material) in the second emitting layer was replaced with the compound listed in Table 11.

Reference Examples 43 and 44

The organic EL devices according to Reference Examples 43 and 44 were manufactured in the same manner as that of Reference Example 1 except that the compound BH1 (first host material) in the first emitting layer and the compound BH2 (second host material) in the second emitting layer were replaced with the compounds listed in Table 11.

Comparative 29

The organic EL device according to Comparative 29 was manufactured in the same manner as that of Comparative 2 except that the compound BH2 (second host material) in the second emitting layer was replaced with the compound listed in Table 11.

TABLE 11

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 42 | BH1 | BD1 | 5 | BH2-9 | BD1 | 20 | 3.56 | 10.5 | 300 |
| Reference Example 43 | R-BH1 | BD1 | 5 | BH2-9 | BD1 | 20 | 4.00 | 10.0 | — |
| Reference Example 44 | R-BH2 | BD1 | 5 | BH2-9 | BD1 | 20 | 4.28 | 10.1 | — |
| Comparative 1 | BH1 | BD1 | 25 | — | — | — | — | 7.6 | 65 |
| Comparative 29 | — | — | — | BH2-9 | BD1 | 25 | — | 9.8 | 195 |

Reference Example 45

The organic EL device according to Reference Example 45 was manufactured in the same manner as that of Reference Example 1 except that the compound BD1 in the first emitting layer and the compound BD1 in the second emitting layer were replaced with the compounds listed in Table 12.

Reference Examples 46 and 47

The organic EL devices according to Reference Examples 46 and 47 were manufactured in the same manner as that of Reference Example 1 except that the compound BH1 (first host material) and the compound BD1 in the first emitting layer and the compound BD1 in the second emitting layer were replaced with the compounds listed in Table 12.

Comparative 30

The organic EL device according to Comparative 30 was manufactured in the same manner as that of Comparative 1 except that the compound BD1 in the first emitting layer was replaced with the compound listed in Table 12.

Comparative 31

The organic EL device according to Comparative 31 was manufactured in the same manner as that of Comparative 2 except that the compound BD1 in the second emitting layer was replaced with the compound listed in Table 12.

TABLE 12

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 45 | BH1 | BD2 | 5 | BH2 | BD2 | 20 | 3.57 | 9.7 | 203 |
| Reference Example 46 | R-BH1 | BD2 | 5 | BH2 | BD2 | 20 | 4.01 | 9.3 | — |
| Reference Example 47 | R-BH2 | BD2 | 5 | BH2 | BD2 | 20 | 4.29 | 9.4 | — |
| Comparative 30 | BH1 | BD2 | 25 | — | — | — | — | 7.0 | 51 |
| Comparative 31 | — | — | — | BH2 | BD2 | 25 | — | 9.1 | 120 |

Reference Example 48

The organic EL device according to Reference Example 48 was manufactured in the same manner as that of Reference Example 1 except that the compound BD1 in the first emitting layer and the compound BD1 in the second emitting layer were replaced with the compounds listed in Table 13.

Reference Examples 49 and 50

The organic EL devices according to Reference Examples 49 and 50 were manufactured in the same manner as that of Reference Example 1 except that the compound BH1 (first host material) and the compound BD1 in the first emitting layer and the compound BD1 in the second emitting layer were replaced with the compounds listed in Table 13.

Comparative 32

The organic EL device according to Comparative 32 was manufactured in the same manner as that of Comparative 1 except that the compound BD1 in the first emitting layer was replaced with the compound listed in Table 13.

Comparative 33

The organic EL device according to Comparative 33 was manufactured in the same manner as that of Comparative 2 except that the compound BD1 in the second emitting layer was replaced with the compound listed in Table 13.

TABLE 13

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 48 | BH1 | BD3 | 5 | BH2 | BD3 | 20 | 3.51 | 10.2 | 167 |
| Reference Example 49 | R-BH1 | BD3 | 5 | BH2 | BD3 | 20 | 3.95 | 9.7 | — |

TABLE 13-continued

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 50 | R-BH2 | BD3 | 5 | BH2 | BD3 | 20 | 4.23 | 9.8 | — |
| Comparative 32 | BH1 | BD3 | 25 | — | — | — | — | 7.4 | 46 |
| Comparative 33 | — | — | — | BH2 | BD3 | 25 | — | 9.5 | 103 |

Reference Examples 51 to 69

The organic EL devices according to Reference Examples 51 to 69 were manufactured in the same manner as that of Reference Example 1 except that the compound BH1 (first host material) in the first emitting layer was replaced with the compounds listed in Table 14.

TABLE 14

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Reference Example 51 | BH1-23 | BD1 | 5 | BH2 | BD1 | 20 | 10.2 | 198 |
| Reference Example 52 | BH1-26 | BD1 | 5 | BH2 | BD1 | 20 | 10.3 | 214 |
| Reference Example 53 | BH1-27 | BD1 | 5 | BH2 | BD1 | 20 | 10.6 | 239 |
| Reference Example 54 | BH1-28 | BD1 | 5 | BH2 | BD1 | 20 | 10.5 | 222 |
| Reference Example 55 | BH1-32 | BD1 | 5 | BH2 | BD1 | 20 | 10.4 | 207 |
| Reference Example 56 | BH1-33 | BD1 | 5 | BH2 | BD1 | 20 | 10.3 | 205 |
| Reference Example 57 | BH1-34 | BD1 | 5 | BH2 | BD1 | 20 | 10.5 | 213 |
| Reference Example 58 | BH1-35 | BD1 | 5 | BH2 | BD1 | 20 | 10.4 | 198 |
| Reference Example 59 | BH1-40 | BD1 | 5 | BH2 | BD1 | 20 | 10.4 | 221 |
| Reference Example 60 | BH1-41 | BD1 | 5 | BH2 | BD1 | 20 | 10.7 | 248 |
| Reference Example 61 | BH1-42 | BD1 | 5 | BH2 | BD1 | 20 | 10.5 | 232 |
| Reference Example 62 | BH1-43 | BD1 | 5 | BH2 | BD1 | 20 | 10.6 | 211 |
| Reference Example 63 | BH1-44 | BD1 | 5 | BH2 | BD1 | 20 | 10.5 | 205 |
| Reference Example 64 | BH1-45 | BD1 | 5 | BH2 | BD1 | 20 | 10.4 | 230 |
| Reference Example 65 | BH1-46 | BD1 | 5 | BH2 | BD1 | 20 | 10.8 | 249 |
| Reference Example 66 | BH1-47 | BD1 | 5 | BH2 | BD1 | 20 | 10.6 | 217 |
| Reference Example 67 | BH1-48 | BD1 | 5 | BH2 | BD1 | 20 | 10.6 | 243 |
| Reference Example 68 | BH1-49 | BD1 | 5 | BH2 | BD1 | 20 | 10.7 | 268 |
| Reference Example 69 | R-BH3 | BD1 | 5 | BH2 | BD1 | 20 | 10.1 | 183 |

Comparatives 34 to 51

The organic EL devices according to Comparatives 34 to 51 were manufactured in the same manner as that of Comparative 1 except that the compound BH1 (first host material) in the first emitting layer was replaced with the compounds listed in Table 15.

TABLE 15

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Comparative 34 | BH1-23 | BD1 | 25 | — | — | — | 6.3 | 50 |
| Comparative 35 | BH1-26 | BD1 | 25 | — | — | — | 6.6 | 78 |
| Comparative 36 | BH1-27 | BD1 | 25 | — | — | — | 6.7 | 81 |
| Comparative 37 | BH1-28 | BD1 | 25 | — | — | — | 6.5 | 72 |
| Comparative 38 | BH1-32 | BD1 | 25 | — | — | — | 6.1 | 49 |
| Comparative 39 | BH1-33 | BD1 | 25 | — | — | — | 6.2 | 55 |
| Comparative 40 | BH1-34 | BD1 | 25 | — | — | — | 6.2 | 57 |
| Comparative 41 | BH1-35 | BD1 | 25 | — | — | — | 6.0 | 49 |
| Comparative 42 | BH1-40 | BD1 | 25 | — | — | — | 6.2 | 68 |
| Comparative 43 | BH1-41 | BD1 | 25 | — | — | — | 6.6 | 91 |
| Comparative 44 | BH1-42 | BD1 | 25 | — | — | — | 6.4 | 85 |

TABLE 15-continued

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Comparative 45 | BH1-43 | BD1 | 25 | — | — | — | 6.4 | 72 |
| Comparative 46 | BH1-44 | BD1 | 25 | — | — | — | 6.4 | 77 |
| Comparative 47 | BH1-45 | BD1 | 25 | — | — | — | 6.2 | 81 |
| Comparative 48 | BH1-46 | BD1 | 25 | — | — | — | 6.3 | 94 |
| Comparative 49 | BH1-47 | BD1 | 25 | — | — | — | 6.2 | 67 |
| Comparative 50 | BH1-48 | BD1 | 25 | — | — | — | 6.1 | 64 |
| Comparative 51 | BH1-49 | BD1 | 25 | — | — | — | 6.8 | 97 |
| Comparative 2 | — | — | — | BH2 | BD1 | 25 | 9.9 | 167 |

Manufacture 2 of Organic EL Device

The organic EL devices were manufactured and evaluated as follows.

Reference Example 70

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, a compound HT3 was vapor-deposited to form an 80-nm-thick first hole transporting layer (HT).

After the formation of the first hole transporting layer, a compound HT4 was vapor-deposited to form a 10-nm-thick second hole transporting layer (also referred to as an electron blocking layer (EBL)).

A compound BH1-21 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

A compound ET4 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 70 is roughly shown as follows.

ITO (130)/HA1(5)/HT3(80)/HT4(10)/BH1-21:BD1 (5.98%:2%)/BH2:BD1 (20.98%:2%)/ET4(10)/ET2(15)/LiF (1)/Al (80)

The numerals in parentheses represent film thickness (unit: nm).

The numerals (98%:2%) represented by percentage in the same parentheses indicate a ratio (mass %) between the host material (compound BH1-21 or BH2) and the compound BD1 in the first emitting layer or the second emitting layer. Similar notations apply to the description below.

Reference Examples 71 to 78

The organic EL devices according to Reference Examples 71 to 78 were manufactured in the same manner as that of Reference Example 70 except that the compound BH1-21 (first host material) in the first emitting layer was replaced with the first compounds listed in Table 16.

Comparatives 52 to 59

The organic EL devices according to Comparatives 52 to 59 were manufactured in the same manner as that of Reference Example 70 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 16.

Comparative 60

The organic EL device according to Comparative 60 was manufactured in the same manner as that of Reference Example 70 except that a 25-nm-thick second emitting layer was formed on the second hole transporting layer without forming the first emitting layer as shown in Table 16.

TABLE 16

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT95 [hr] |
| Reference Example 70 | BH1-21 | BD1 | 5 | BH2 | BD1 | 20 | 3.40 | 8.7 | 160 |
| Reference Example 71 | BH1-22 | BD1 | 5 | BH2 | BD1 | 20 | 3.46 | 9.0 | 225 |
| Reference Example 72 | BH1-24 | BD1 | 5 | BH2 | BD1 | 20 | 3.27 | 8.4 | 79 |
| Reference Example 73 | BH1-25 | BD1 | 5 | BH2 | BD1 | 20 | 3.35 | 8.7 | 174 |
| Reference Example 74 | BH1-36 | BD1 | 5 | BH2 | BD1 | 20 | 3.39 | 8.5 | 125 |
| Reference Example 75 | BH1-37 | BD1 | 5 | BH2 | BD1 | 20 | 3.44 | 8.8 | 135 |
| Reference Example 76 | BH1-50 | BD1 | 5 | BH2 | BD1 | 20 | 3.42 | 8.5 | 111 |
| Reference Example 77 | BH1-51 | BD1 | 5 | BH2 | BD1 | 20 | 3.31 | 8.4 | 105 |
| Reference Example 78 | R-BH3 | BD1 | 5 | BH2 | BD1 | 20 | 3.53 | 7.9 | 36 |
| Comparative 52 | BH1-21 | BD1 | 25 | — | — | — | — | 6.2 | 32 |
| Comparative 53 | BH1-22 | BD1 | 25 | — | — | — | — | 6.4 | 45 |
| Comparative 54 | BH1-24 | BD1 | 25 | — | — | — | — | 6.0 | 13 |
| Comparative 55 | BH1-25 | BD1 | 25 | — | — | — | — | 6.2 | 25 |
| Comparative 56 | BH1-36 | BD1 | 25 | — | — | — | — | 6.1 | 25 |
| Comparative 57 | BH1-37 | BD1 | 25 | — | — | — | — | 6.3 | 27 |
| Comparative 58 | BH1-50 | BD1 | 25 | — | — | — | — | 6.1 | 21 |
| Comparative 59 | BH1-51 | BD1 | 25 | — | — | — | — | 6.0 | 19 |
| Comparative 60 | — | — | — | BH2 | BD1 | 25 | — | 7.7 | 56 |

Manufacture 3 of Organic EL Device

The organic EL devices were manufactured and evaluated as follows.

Reference Example 79

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, the compound HT4 was vapor-deposited to form a 10-nm-thick second hole transporting layer (also referred to as an electron blocking layer (EBL)).

A compound BH1-29 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

A compound ET3 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 79 is roughly shown as follows.

ITO (130)/HA1(5)/HT3(80)/HT4(10)/BH1-29:BD1 (5.98%:2%)/BH2:BD1 (20.98%:2%)/ET3(10)/ET2(15)/LiF (1)/Al (80)

The numerals in parentheses represent film thickness (unit: nm).

The numerals (98%:2%) represented by percentage in the same parentheses indicate a ratio (mass %) between the host material (compound BH1-29 or BH2) and the compound BD1 in the first emitting layer or the second emitting layer. Similar notations apply to the description below.

Reference Examples 80 to 90

The organic EL devices according to Reference Examples 80 to 90 were manufactured in the same manner as that of Reference Example 79 except that the compound BH1-29 (first host material) in the first emitting layer was replaced with the first compounds listed in Table 17.

Comparatives 61 to 71

The organic EL devices according to Comparatives 61 to 71 were manufactured in the same manner as that of Reference Example 79 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 17.

Comparative 72

The organic EL device according to Comparative 72 was manufactured in the same manner as that of Reference Example 79 except that a 25-nm-thick second emitting layer was formed on the second hole transporting layer without forming the first emitting layer as shown in Table 17.

TABLE 17

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Reference Example 79 | BH1-29 | BD1 | 5 | BH2 | BD1 | 20 | 9.3 | 125 |
| Reference Example 80 | BH1-30 | BD1 | 5 | BH2 | BD1 | 20 | 9.3 | 103 |
| Reference Example 81 | BH1-31 | BD1 | 5 | BH2 | BD1 | 20 | 9.6 | 119 |
| Reference Example 82 | BH1-38 | BD1 | 5 | BH2 | BD1 | 20 | 9.8 | 138 |
| Reference Example 83 | BH1-39 | BD1 | 5 | BH2 | BD1 | 20 | 9.7 | 122 |
| Reference Example 84 | BH1-52 | BD1 | 5 | BH2 | BD1 | 20 | 9.5 | 151 |
| Reference Example 85 | BH1-53 | BD1 | 5 | BH2 | BD1 | 20 | 9.3 | 132 |
| Reference Example 86 | BH1-54 | BD1 | 5 | BH2 | BD1 | 20 | 9.1 | 110 |
| Reference Example 87 | BH1-55 | BD1 | 5 | BH2 | BD1 | 20 | 9.4 | 109 |
| Reference Example 88 | BH1-56 | BD1 | 5 | BH2 | BD1 | 20 | 9.2 | 111 |
| Reference Example 89 | BH1-57 | BD1 | 5 | BH2 | BD1 | 20 | 9.2 | 121 |
| Reference Example 90 | R-BH3 | BD1 | 5 | BH2 | BD1 | 20 | 8.3 | 97 |
| Comparative 61 | BH1-29 | BD1 | 25 | — | — | — | 6.7 | 61 |
| Comparative 62 | BH1-30 | BD1 | 25 | — | — | — | 6.9 | 53 |
| Comparative 63 | BH1-31 | BD1 | 25 | — | — | — | 6.4 | 51 |
| Comparative 64 | BH1-38 | BD1 | 25 | — | — | — | 6.1 | 48 |
| Comparative 65 | BH1-39 | BD1 | 25 | — | — | — | 6.1 | 45 |
| Comparative 66 | BH1-52 | BD1 | 25 | — | — | — | 6.8 | 62 |
| Comparative 67 | BH1-53 | BD1 | 25 | — | — | — | 6.8 | 54 |
| Comparative 68 | BH1-54 | BD1 | 25 | — | — | — | 6.7 | 42 |
| Comparative 69 | BH1-55 | BD1 | 25 | — | — | — | 6.7 | 59 |
| Comparative 70 | BH1-56 | BD1 | 25 | — | — | — | 6.5 | 40 |
| Comparative 71 | BH1-57 | BD1 | 25 | — | — | — | 6.2 | 34 |
| Comparative 72 | — | — | — | BH2 | BD1 | 25 | 8.1 | 89 |

Manufacture 4 of Organic EL Device

The organic EL devices were manufactured and evaluated as follows.

Reference Example 91

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, a compound HT5 and a compound HA2 were co-deposited on a surface provided with the transparent electrode line to cover the transparent electrode, thereby forming a 10-nm-thick hole injecting layer (HI). The ratios of the compound HT5 and the compound HA2 in the hole injecting layer were 97 mass % and 3 mass %, respectively.

After the formation of the hole injecting layer, the compound HT5 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

A compound BH1-61 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET3 was vapor-deposited on the second emitting layer to form a 5-nm-thick first electron transporting layer (also referred to as a hole blocking layer (HBL)).

A compound ET6 and the compound Liq were co-deposited on the first electron transporting layer (HBL) to form a 25-nm-thick electron transporting layer (ET). The ratios of the compound ET6 and the compound Liq in the electron transporting layer (ET) were 50 mass % and 50 mass %, respectively. Liq is an abbreviation of (8-quinolinolato) lithium.

Liq was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 91 is roughly shown as follows.

ITO (130)/HT5:HA2 (10.97%:3%)/HT5(85)/HT4(5)/BH1-61:BD1 (5.98%:2%)/BH2:BD1 (20.98%:2%)/ET3(5)/ET6:Liq (25, 50%:50%)/Liq (1)/Al (80)

The numerals in parentheses represent film thickness (unit: nm).

The numerals (97%:3%) represented by percentage in the same parentheses indicate a ratio (mass %) between the compound HT5 and the compound HA2 in the hole injecting layer, the numerals (98%:2%) represented by percentage in the same parentheses indicate a ratio (mass %) between the host material (compound BH1-61 or BH2) and the dopant material (compound BD1) in the first emitting layer or the second emitting layer, and the numerals (50%:50%) represented by percentage in the same parentheses indicate a ratio (mass %) between the compound ET6 and the compound Liq in the electron transporting layer (ET). Similar notations apply to the description below.

Reference Examples 92 to 95

The organic EL devices according to Reference Examples 92 to 95 were manufactured in the same manner as that of Reference Example 91 except that the compound BH1-61 (first host material) in the first emitting layer was replaced with the first compounds listed in Table 18.

Comparatives 73 to 76

The organic EL devices according to Comparatives 73 to 76 were manufactured in the same manner as that of Reference Example 91 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 18.

Comparative 77

The organic EL device according to Comparative 77 was manufactured in the same manner as that of Reference Example 91 except that a 25-nm-thick second emitting layer was formed on the second hole transporting layer without forming the first emitting layer as shown in Table 18.

A compound BH1-75 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET3 was vapor-deposited on the second emitting layer to form a 5-nm-thick first electron transporting layer (also referred to as a hole blocking layer (HBL)).

A compound ET8 and the compound Liq were co-deposited on the first electron transporting layer (HBL) to form a 25-nm-thick electron transporting layer (ET). The ratios of the compound ET5 and the compound Liq in the electron transporting layer (ET) were 50 mass % and 50 mass %, respectively. Liq is an abbreviation of (8-quinolinolato) lithium.

Liq was vapor-deposited on the second electron transporting layer to form a 1-nm-thick electron injecting layer.

TABLE 18

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Reference Example 91 | BH1-61 | BD1 | 5 | BH2 | BD1 | 20 | 9.2 | 128 |
| Reference Example 92 | BH1-62 | BD1 | 5 | BH2 | BD1 | 20 | 9.7 | 153 |
| Reference Example 93 | BH1-63 | BD1 | 5 | BH2 | BD1 | 20 | 9.5 | 144 |
| Reference Example 94 | BH1-69 | BD1 | 5 | BH2 | BD1 | 20 | 9.0 | 110 |
| Reference Example 95 | R-BH3 | BD1 | 5 | BH2 | BD1 | 20 | 8.8 | 101 |
| Comparative 73 | BH1-61 | BD1 | 25 | — | — | — | 6.1 | 47 |
| Comparative 74 | BH1-62 | BD1 | 25 | — | — | — | 6.4 | 64 |
| Comparative 75 | BH1-63 | BD1 | 25 | — | — | — | 6.3 | 60 |
| Comparative 76 | BH1-69 | BD1 | 25 | — | — | — | 5.9 | 19 |
| Comparative 77 | — | — | — | BH2 | BD1 | 25 | 8.4 | 72 |

Manufacture 5 of Organic EL Device

The organic EL devices were manufactured and evaluated as follows.

Reference Example 96

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT3 and the compound HA2 were co-deposited on a surface provided with the transparent electrode line to cover the transparent electrode, thereby forming a 10-nm-thick hole injecting layer (HI). The ratios of the compound HT3 and the compound HA2 in the hole injecting layer were 97 mass % and 3 mass %, respectively.

After the formation of the hole injecting layer, the compound HT3 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

Metal Al was vapor-deposited on the electron injecting layer to form an 80-nm-thick cathode.

A device arrangement of the organic EL device in Reference Example 96 is roughly shown as follows.

ITO (130)/HT3:HA2 (10.97%:3%)/HT3(85)/HT4(5)/BH1-75:BD1 (5.98%:2%)/BH2:BD1 (20.98%:2%)/ET3(5)/ET8:Liq (25, 50%:50%)/Liq (1)/Al (80)

The numerals in parentheses represent film thickness (unit: nm).

The numerals (97%:3%) represented by percentage in the same parentheses indicate a ratio (mass %) between the compound HT3 and the compound HA2 in the hole injecting layer, the numerals (98%:2%) represented by percentage in the same parentheses indicate a ratio (mass %) between the host material (compound BH1-75 or BH2) and the dopant material (compound BD1) in the first emitting layer or the second emitting layer, and the numerals (50%:50%) represented by percentage in the same parentheses indicate a ratio (mass %) between the compound ET8 and the compound Liq in the electron transporting layer (ET). Similar notations apply to the description below.

Reference Example 97

The organic EL device according to Reference Example 97 was manufactured in the same manner as that of Reference Example 96 except that the compound BH1-75 (first host material) in the first emitting layer was replaced with the first compound listed in Table 19.

Comparative 78

The organic EL device according to Comparative 78 was manufactured in the same manner as that of Reference Example 96 except that a 25-nm-thick first emitting layer was formed as the emitting layer, the first electron transporting layer was formed on the first emitting layer without forming the second emitting layer, and the first compound (first host material) in the first emitting layer was replaced with the first compound listed in Table 19.

Comparative 79

The organic EL device according to Comparative 79 was manufactured in the same manner as that of Reference Example 96 except that a 25-nm-thick second emitting layer was formed on the second hole transporting layer without forming the first emitting layer as shown in Table 19.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET3 was vapor-deposited on the second emitting layer to form a 5-nm-thick first electron transporting layer (also referred to as a hole blocking layer (HBL)).

The compound ET8 and the compound Liq were co-deposited on the first electron transporting layer (HBL) to form a 25-nm-thick electron transporting layer (ET). The ratios of the compound ET8 and the compound Liq in the electron transporting layer (ET) were 50 mass % and 50 mass %, respectively.

Liq was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 98 is roughly shown as follows.

TABLE 19

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Reference Example 96 | BH1-75 | BD1 | 5 | BH2 | BD1 | 20 | 9.2 | 169 |
| Reference Example 97 | R-BH3 | BD1 | 5 | BH2 | BD1 | 20 | — | 118 |
| Comparative 78 | BH1-75 | BD1 | 25 | — | — | — | 6.0 | 63 |
| Comparative 79 | — | — | — | BH2 | BD1 | 25 | 8.1 | 91 |

Manufacture 6 of Organic EL Device

The organic EL devices were manufactured and evaluated as follows.

Reference Example 98

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT5 and the compound HA2 were co-deposited on a surface provided with the transparent electrode line to cover the transparent electrode, thereby forming a 10-nm-thick hole injecting layer (HI). The ratios of the compound HT5 and the compound HA2 in the hole injecting layer were 97 mass % and 3 mass %, respectively.

After the formation of the hole injecting layer, the compound HT5 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

A compound BH1-64 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

ITO (130)/HT5:HA2 (10.97%:3%)/HT5(85)/HT4(5)/BH1-64:BD1 (5.98%:2%)/BH2:BD1 (20.98%:2%)/ET3(5)/ET8:Liq (25, 50%:50%)/Liq (1)/Al (80)

The numerals in parentheses represent film thickness (unit: nm).

The numerals (97%:3%) represented by percentage in the same parentheses indicate a ratio (mass %) between the compound HT5 and the compound HA2 in the hole injecting layer, the numerals (98%:2%) represented by percentage in the same parentheses indicate a ratio (mass %) between the host material (compound BH1-64 or BH2) and the dopant material (compound BD1) in the first emitting layer or the second emitting layer, and the numerals (50%:50%) represented by percentage in the same parentheses indicate a ratio (mass %) between the compound ET8 and the compound Liq in the electron transporting layer (ET). Similar notations apply to the description below.

Reference Examples 99 to 103

The organic EL devices according to Reference Examples 99 to 103 were manufactured in the same manner as that of Reference Example 98 except that the compound BH1-64 (first host material) in the first emitting layer was replaced with the first compounds listed in Table 20.

Comparatives 80 to 84

The organic EL devices according to Comparatives 80 to 84 were manufactured in the same manner as that of Reference Example 98 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 20.

Comparative 85

The organic EL device according to Comparative 85 was manufactured in the same manner as that of Reference Example 98 except that a 25-nm-thick second emitting layer was formed on the second hole transporting layer without forming the first emitting layer as shown in Table 20.

TABLE 20

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Reference Example 98 | BH1-64 | BD1 | 5 | BH2 | BD1 | 20 | 9.6 | 106 |
| Reference Example 99 | BH1-65 | BD1 | 5 | BH2 | BD1 | 20 | 9.7 | 112 |
| Reference Example 100 | BH1-66 | BD1 | 5 | BH2 | BD1 | 20 | 9.5 | 83 |
| Reference Example 101 | BH1-67 | BD1 | 5 | BH2 | BD1 | 20 | 9.4 | 93 |
| Reference Example 102 | BH1-68 | BD1 | 5 | BH2 | BD1 | 20 | 9.5 | 101 |
| Reference Example 103 | R-BH3 | BD1 | 5 | BH2 | BD1 | 20 | 9.1 | — |
| Comparative 80 | BH1-64 | BD1 | 25 | — | — | — | 6.1 | 31 |
| Comparative 81 | BH1-65 | BD1 | 25 | — | — | — | 6.3 | 48 |
| Comparative 82 | BH1-66 | BD1 | 25 | — | — | — | 6.1 | 31 |
| Comparative 83 | BH1-67 | BD1 | 25 | — | — | — | 6.3 | 55 |
| Comparative 84 | BH1-68 | BD1 | 25 | — | — | — | 6.0 | 28 |
| Comparative 85 | — | — | — | BH2 | BD1 | 25 | 8.6 | 61 |

Manufacture 7 of Organic EL Device

The organic EL devices were manufactured and evaluated as follows.

Reference Example 104

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HT5 and the compound HA2 were co-deposited on a surface provided with the transparent electrode line to cover the transparent electrode, thereby forming a 10-nm-thick hole injecting layer (HI). The ratios of the compound HT5 and the compound HA2 in the hole injecting layer were 97 mass % and 3 mass %, respectively.

After the formation of the hole injecting layer, the compound HT5 was vapor-deposited to form an 85-nm-thick first hole transporting layer (HT).

After the formation of the first hole transporting layer, the compound HT4 was vapor-deposited to form a 5-nm-thick second hole transporting layer (also referred to as an electron blocking layer (EBL)).

A compound BH1-70 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 5-nm-thick first electron transporting layer (also referred to as a hole blocking layer (HBL)).

The compound ET6 and the compound Liq were co-deposited on the first electron transporting layer (HBL) to form a 25-nm-thick electron transporting layer (ET). The ratios of the compound ET6 and the compound Liq in the electron transporting layer (ET) were 50 mass % and 50 mass %, respectively.

Liq was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 104 is roughly shown as follows.

ITO (130)/HT5:HA2 (10.97%:3%)/HT5(85)/HT4(5)/BH1-70:BD1 (5.98%:2%)/BH2:BD1 (20.98%:2%)/ET1(5)/ET6:Liq (25, 50%:50%)/Liq (1)/Al (80)

The numerals in parentheses represent film thickness (unit: nm).

The numerals (97%:3%) represented by percentage in the same parentheses indicate a ratio (mass %) between the compound HT5 and the compound HA2 in the hole injecting layer, the numerals (98%:2%) represented by percentage in the same parentheses indicate a ratio (mass %) between the host material (compound BH1-70 or BH2) and the dopant material (compound BD1) in the first emitting layer or the second emitting layer, and the numerals (50%:50%) represented by percentage in the same parentheses indicate a ratio (mass %) between the compound ET6 and the compound Liq in the electron transporting layer (ET). Similar notations apply to the description below.

Reference Examples 105 to 109

The organic EL devices according to Reference Examples 105 to 109 were manufactured in the same manner as that of Reference Example 104 except that the compound BH1-70 (first host material) in the first emitting layer was replaced with the first compounds listed in Table 21.

Comparatives 86 to 90

The organic EL devices according to Comparatives 86 to 90 were manufactured in the same manner as that of Reference Example 104 except that a 25-nm-thick first emitting layer was formed as the emitting layer, the first electron transporting layer was formed on the first emitting layer without forming the second emitting layer, and the first compound (first host material) in the first emitting layer was replaced with the first compounds listed in Table 21.

Comparative 91

The organic EL device according to Comparative 91 was manufactured in the same manner as that of Reference Example 104 except that a 25-nm-thick second emitting layer was formed on the second hole transporting layer without forming the first emitting layer as shown in Table 21.

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 110 is roughly shown as follows.

ITO (130)/HA1(5)/HT1(80)/HT8(10)/BH1-81:BD1 (5.98%:2%)/BH2:BD1 (20.98%:2%)/ET1(10)/ET2(15)/LiF (1)/Al (80)

TABLE 21

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Reference Example 104 | BH1-70 | BD1 | 5 | BH2 | BD1 | 20 | 10.2 | 185 |
| Reference Example 105 | BH1-71 | BD1 | 5 | BH2 | BD1 | 20 | 10.7 | 223 |
| Reference Example 106 | BH1-72 | BD1 | 5 | BH2 | BD1 | 20 | 10.4 | 212 |
| Reference Example 107 | BH1-73 | BD1 | 5 | BH2 | BD1 | 20 | 10.6 | 220 |
| Reference Example 108 | BH1-74 | BD1 | 5 | BH2 | BD1 | 20 | 10.3 | 218 |
| Reference Example 109 | R-BH3 | BD1 | 5 | BH2 | BD1 | 20 | 8.7 | 101 |
| Comparative 86 | BH1-70 | BD1 | 25 | — | — | — | 6.2 | 59 |
| Comparative 87 | BH1-71 | BD1 | 25 | — | — | — | 6.6 | 63 |
| Comparative 88 | BH1-72 | BD1 | 25 | — | — | — | 6.5 | 51 |
| Comparative 89 | BH1-73 | BD1 | 25 | — | — | — | 6.5 | 62 |
| Comparative 90 | BH1-74 | BD1 | 25 | — | — | — | 6.4 | 60 |
| Comparative 91 | — | — | — | BH2 | BD1 | 25 | 8.3 | 76 |

Manufacture 8 of Organic EL Device

Reference Example 110

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, a compound HT8 was vapor-deposited to form a 10-nm-thick second hole transporting layer (also referred to as an electron blocking layer (EBL)).

A compound BH1-81 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

The numerals in parentheses represent film thickness (unit: nm).

The numerals (98%:2%) represented by percentage in the same parentheses indicate a ratio (mass %) between the host material (compound BH1-81 or BH2) and the compound BD1 in the first emitting layer or the second emitting layer. Similar notations apply to the description below.

Reference Example 111

The organic EL device according to Reference Example 111 was manufactured in the same manner as that of Reference Example 110 except that the compound BH1-81 (first host material) in the first emitting layer was replaced with the first compound listed in Table 22.

Comparative 92

The organic EL device according to Comparative 92 was manufactured in the same manner as that of Reference Example 110 except that a 25-nm-thick first emitting layer was formed as the emitting layer and the first electron transporting layer was formed on the first emitting layer without forming the second emitting layer.

Comparative 93

The organic EL device according to Comparative 93 was manufactured in the same manner as that of Reference Example 110 except that a 25-nm-thick second emitting layer was formed on the second hole transporting layer without forming the first emitting layer as shown in Table 22.

TABLE 22

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Reference Example 110 | BH1-81 | BD1 | 5 | BH2 | BD1 | 20 | 10.7 | 134 |
| Reference Example 111 | R-BH3 | BD1 | 5 | BH2 | BD1 | 20 | 10.4 | — |
| Comparative 92 | BH1-81 | BD1 | 25 | — | — | — | 6.4 | 35 |
| Comparative 93 | — | — | — | BH2 | BD1 | 25 | 10.2 | 102 |

Manufacture 9 of Organic EL Device

Reference Examples 112 and 113

The organic EL devices according to Reference Examples 112 and 113 were manufactured in the same manner as that of Reference Example 1 except that the compound BH1 (first host material) in the first emitting layer was replaced with the compounds listed in Table 23.

Comparative 94

The organic EL device according to Comparative 94 was manufactured in the same manner as that of Comparative 1 except that the compound BH1 (first host material) in the first emitting layer was replaced with the compound listed in Table 23.

on the second hole transporting layer such that the ratio of the compound BD1 accounted for 2 mass %, thereby forming a 5-nm-thick first emitting layer.

The compound BH2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

A compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 15-nm-thick second electron transporting layer (ET).

LiF was vapor-deposited on the second electron transporting layer to form a 1-nm-thick electron injecting layer.

TABLE 23

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Reference Example 112 | BH1-82 | BD1 | 5 | BH2 | BD1 | 20 | 10.4 | 219 |
| Reference Example 113 | R-BH3 | BD1 | 5 | BH2 | BD1 | 20 | 10.1 | 183 |
| Comparative 94 | BH1-82 | BD1 | 25 | — | — | — | 6.2 | 71 |
| Comparative 2 | — | — | — | BH2 | BD1 | 25 | 9.9 | 167 |

Manufacture 10 of Organic EL Device

Reference Example 114

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

A compound BH1-83 (first host material (BH)) and the compound BD1 (dopant material (BD)) were co-deposited Metal Al was vapor-deposited on the electron injecting layer to form an 80-nm-thick cathode.

A device arrangement of the organic EL device in Reference Example 114 is roughly shown as follows.

ITO (130)/HA1(5)/HT1(80)/HT2(10)/BH1-83:BD1 (5.98%:2%)/BH2:BD1 (20.98%:2%)/ET7(10)/ET2(15)/LiF (1)/Al (80)

The numerals in parentheses represent film thickness (unit: nm).

The numerals (98%:2%) represented by percentage in the same parentheses indicate a ratio (mass %) between the host material (compound BH1-83 or BH2) and the compound BD1 in the first emitting layer or the second emitting layer. Similar notations apply to the description below.

Reference Example 115

The organic EL device according to Reference Example 115 was manufactured in the same manner as that of Reference Example 114 except that the compound BH1-83 (first host material) in the first emitting layer was replaced with the first compound listed in Table 24.

Comparative 95

The organic EL device according to Comparative 95 was manufactured in the same manner as that of Reference Example 114 except that a 25-nm-thick first emitting layer was formed as the emitting layer and the first electron transporting layer was formed on the first emitting layer without forming the second emitting layer.

Comparative 96

The organic EL device according to Comparative 96 was manufactured in the same manner as that of Reference Example 114 except that a 25-nm-thick second emitting layer was formed on the second hole transporting layer without forming the first emitting layer as shown in Table 24.

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 116 is roughly shown as follows.

ITO (130)/HA1(5)/HT1(80)/HT4(10)/BH1:BD1 (5.98%:2%)/BH2-8:BD1 (20.98%:2%)/ET1(10)/ET2(20)/LiF (1)/Al (80)

TABLE 24

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT95 [hr] |
| Reference Example 114 | BH1-83 | BD1 | 5 | BH2 | BD1 | 20 | 9.7 | 247 |
| Reference Example 115 | R-BH3 | BD1 | 5 | BH2 | BD1 | 20 | 8.5 | — |
| Comparative 95 | BH1-83 | BD1 | 25 | — | — | — | 6.0 | 76 |
| Comparative 96 | — | — | — | BH2 | BD1 | 25 | 9.1 | 183 |

Manufacture 11 of Organic EL Device

Reference Example 116

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT4 was vapor-deposited to form a 10-nm-thick second hole transporting layer (also referred to as an electron blocking layer (EBL)).

The compound BH1 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

A compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

The numerals in parentheses represent film thickness (unit: nm).

The numerals (98%:2%) represented by percentage in the same parentheses indicate a ratio (mass %) between the host material (compound BH1) and the compound BD1 in the first emitting layer, and numerals (98%:2%) represented by percentage in the same parentheses indicate a ratio (mass %) between the host material (compound BH2-8) and the compound BD1 in the second emitting layer. Similar notations apply to the description below.

Reference Example 117

The organic EL device according to Reference Example 117 was manufactured in the same manner as that of Reference Example 116 except that the compound BH2-8 (second host material) in the second emitting layer was replaced with the second compound listed in Table 25.

Comparative 97

The organic EL device according to Comparative 97 was manufactured in the same manner as that of Reference Example 116 except that a 25-nm-thick second emitting layer was formed on the second hole transporting layer without forming the first emitting layer, and the second compound (second host material) in the second emitting layer was replaced with the second compound listed in Table 25, as shown in Table 25.

TABLE 25

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 116 | BH1 | BD1 | 5 | BH2-8 | BD1 | 20 | 3.4 | 9.8 | 120 |
| Reference Example 117 | BH1 | BD1 | 5 | BH2-5 | BD1 | 20 | 3.6 | 10.1 | 160 |
| Comparative 97 | — | — | — | BH2-5 | BD1 | 25 | 3.8 | 8.9 | 110 |

Manufacture 12 of Organic EL Device

Reference Examples 118 and 119

The organic EL devices according to Reference Examples 118 and 119 were manufactured in the same manner as that of Reference Example 116 except that the compound BH2-8 (second host material) in the second emitting layer was replaced with the second compounds listed in Table 26.

Comparative 98

The organic EL device according to Comparative 98 was manufactured in the same manner as that of Reference Example 116 except that a 25-nm-thick second emitting layer was formed on the second hole transporting layer without forming the first emitting layer, and the second compound (second host material) in the second emitting layer was replaced with the second compound listed in Table 26, as shown in Table 26.

TABLE 26

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 118 | BH1 | BD1 | 5 | BH2-2 | BD1 | 20 | 3.8 | 10.5 | 200 |
| Reference Example 119 | BH1 | BD1 | 5 | BH2-10 | BD1 | 20 | 3.8 | 10.5 | 240 |
| Comparative 98 | — | — | — | BH2-10 | BD1 | 25 | 4.0 | 9.8 | 140 |

Reference Example 120

The organic EL device according to Reference Example 120 was manufactured in the same manner as that of Reference Example 116 except that the compound BH2-8 (second host material) in the second emitting layer was replaced with the second compound listed in Table 27.

Comparative 99

The organic EL device according to Comparative 99 was manufactured in the same manner as that of Reference Example 116 except that a 25-nm-thick second emitting layer was formed on the second hole transporting layer without forming the first emitting layer, and the second compound (second host material) in the second emitting layer was replaced with the second compound listed in Table 27, as shown in Table 27.

TABLE 27

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 116 | BH1 | BD1 | 5 | BH2-8 | BD1 | 20 | 3.4 | 9.8 | 120 |
| Reference Example 120 | BH1 | BD1 | 5 | BH2-11 | BD1 | 20 | 3.4 | 9.8 | 150 |
| Comparative 99 | — | — | — | BH2-11 | BD1 | 25 | 3.6 | 7.5 | 100 |

Manufacture 13 of Organic EL Device

Reference Example 121

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, the compound HT4 was vapor-deposited to form a 10-nm-thick second hole transporting layer (also referred to as an electron blocking layer (EBL)).

The compound BH1 (first host material (BH)) and a compound BD2 (dopant material (BD)) were co-deposited on the second hole transporting layer such that the ratio of the compound BD2 accounted for 2 mass %, thereby forming a 5-nm-thick first emitting layer.

A compound BH2-2 (second host material (BH)) and the compound BD2 (dopant material (BD)) were co-deposited on the first emitting layer such that the ratio of the compound BD2 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 121 is roughly shown as follows.

ITO (130)/HA1(5)/HT3(80)/HT4(10)/BH1:BD2 (5.98%:2%)/BH2-2:BD2 (20.98%:2%)/ET7(10)/ET2(20)/LiF (1)/Al (80)

The numerals in parentheses represent film thickness (unit: nm).

The numerals (98%:2%) represented by percentage in the same parentheses indicate a ratio (mass %) between the host material (compound BH1) and the compound BD2 in the first emitting layer, and numerals (98%:2%) represented by percentage in the same parentheses indicate a ratio (mass %) between the host material (compound BH2-2) and the compound BD2 in the second emitting layer. Similar notations apply to the description below.

Example 122

The organic EL device according to Example 122 was manufactured in the same manner as that of Reference Example 121 except that the compound BH2-2 (second host material) in the second emitting layer was replaced with the second compound listed in Table 28.

Comparative 100

The organic EL device according to Comparative 100 was manufactured in the same manner as that of Reference Example 121 except that a 25-nm-thick second emitting layer was formed on the second hole transporting layer without forming the first emitting layer, and the second compound (second host material) in the second emitting layer was replaced with the second compound listed in Table 28, as shown in Table 28.

TABLE 28

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 121 | BH1 | BD2 | 5 | BH2-2 | BD2 | 20 | 3.8 | 10.1 | 180 |
| Example 122 | BH1 | BD2 | 5 | BH2-12 | BD2 | 20 | 4.0 | 10.3 | 200 |
| Comparative 100 | — | — | — | BH2-12 | BD2 | 25 | 4.2 | 8.8 | 110 |

Manufacture 14 of Organic EL Device

Reference Example 123

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT5 was vapor-deposited to form an 80-nm-thick first hole transporting layer (HT).

After the formation of the first hole transporting layer, a compound HT6 was vapor-deposited to form a 10-nm-thick second hole transporting layer (also referred to as an electron blocking layer (EBL)).

A compound BH1-10 (first host material (BH)) and the compound BD2 (dopant material (BD)) were co-deposited on the second hole transporting layer such that the ratio of the compound BD2 accounted for 2 mass %, thereby forming a 5-nm-thick first emitting layer.

The compound BH2-2 (second host material (BH)) and the compound BD2 (dopant material (BD)) were co-deposited on the first emitting layer such that the ratio of the compound BD2 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 123 is roughly shown as follows.

ITO (130)/HA1(5)/HT5(80)/HT6(10)/BH1-10:BD2 (5.98%:2%)/BH2-2:BD2 (20.98%:2%)/ET7(10)/ET2(20)/LiF (1)/Al (80)

The numerals in parentheses represent film thickness (unit: nm).

The numerals (98%:2%) represented by percentage in the same parentheses indicate a ratio (mass %) between the host material (compound BH1-10) and the compound BD2 in the first emitting layer, and numerals (98%:2%) represented by percentage in the same parentheses indicate a ratio (mass %) between the host material (compound BH2-2) and the compound BD2 in the second emitting layer. Similar notations apply to the description below.

Reference Example 124

The organic EL device according to Reference Example 124 was manufactured in the same manner as that of Reference Example 123 except that the compound BH2-2 (second host material) in the second emitting layer was replaced with the second compound listed in Table 29.

Comparative 101

The organic EL device according to Comparative 101 was manufactured in the same manner as that of Reference Example 123 except that a 25-nm-thick second emitting layer was formed on the second hole transporting layer without forming the first emitting layer, and the second compound (second host material) in the second emitting layer was replaced with the second compound listed in Table 29, as shown in Table 29.

TABLE 29

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 123 | BH1-10 | BD2 | 5 | BH2-2 | BD2 | 20 | 3.9 | 10.0 | 210 |
| Reference Example 124 | BH1-10 | BD2 | 5 | BH2-13 | BD2 | 20 | 3.8 | 10.3 | 190 |
| Comparative 101 | — | — | — | BH2-13 | BD2 | 25 | 4.1 | 9.2 | 110 |

Manufacture 15 of Organic EL Device

Reference Example 125

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, a compound HT7 was vapor-deposited to form a 10-nm-thick second hole transporting layer (also referred to as an electron blocking layer (EBL)).

The compound BH1-10 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-2 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 125 is roughly shown as follows.

ITO (130)/HA1(5)/HT3(80)/HT7(10)/BH1-10:BD1 (5.98%:2%)/BH2-2:BD1 (20.98%:2%)/ET7(10)/ET2(20)/LiF (1)/Al (80)

The numerals in parentheses represent film thickness (unit: nm).

The numerals (98%:2%) represented by percentage in the same parentheses indicate a ratio (mass %) between the host material (compound BH1-10) and the compound BD1 in the first emitting layer, and numerals (98%:2%) represented by percentage in the same parentheses indicate a ratio (mass %) between the host material (compound BH2-2) and the compound BD1 in the second emitting layer. Similar notations apply to the description below.

Example 126

The organic EL device according to Example 126 was manufactured in the same manner as that of Reference Example 125 except that the compound BH2-2 (second host material) in the second emitting layer was replaced with the second compound listed in Table 30.

Comparative 102

The organic EL device according to Comparative 102 was manufactured in the same manner as that of Reference Example 125 except that a 25-nm-thick second emitting layer was formed on the second hole transporting layer without forming the first emitting layer, and the second compound (second host material) in the second emitting layer was replaced with the second compound listed in Table 30, as shown in Table 30.

TABLE 30

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 125 | BH1-10 | BD1 | 5 | BH2-2 | BD1 | 20 | 4.0 | 10.5 | 150 |
| Example 126 | BH1-10 | BD1 | 5 | BH2-14 | BD1 | 20 | 4.0 | 10.8 | 160 |
| Comparative 102 | — | — | — | BH2-14 | BD1 | 25 | 4.2 | 9.5 | 100 |

Example 127

The organic EL device according to Example 127 was manufactured in the same manner as that of Reference Example 125 except that the compound BH2-2 (second host material) in the second emitting layer was replaced with the second compound listed in Table 31.

Comparative 103

The organic EL device according to Comparative 103 was manufactured in the same manner as that of Reference Example 125 except that a 25-nm-thick second emitting layer was formed on the second hole transporting layer without forming the first emitting layer, and the second compound (second host material) in the second emitting layer was replaced with the second compound listed in Table 31, as shown in Table 31.

TABLE 31

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 125 | BH1-10 | BD1 | 5 | BH2-2 | BD1 | 20 | 4.0 | 10.5 | 150 |
| Example 127 | BH1-10 | BD1 | 5 | BH2-15 | BD1 | 20 | 3.9 | 10.3 | 180 |
| Comparative 103 | — | — | — | BH2-15 | BD1 | 25 | 4.0 | 9.2 | 80 |

Example 128

The organic EL device according to Example 128 was manufactured in the same manner as that of Reference Example 125 except that the compound BH2-2 (second host material) in the second emitting layer was replaced with the second compound listed in Table 32.

Comparative 104

The organic EL device according to Comparative 104 was manufactured in the same manner as that of Reference Example 125 except that a 25-nm-thick second emitting layer was formed on the second hole transporting layer without forming the first emitting layer, and the second compound (second host material) in the second emitting layer was replaced with the second compound listed in Table 32, as shown in Table 32.

TABLE 32

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 125 | BH1-10 | BD1 | 5 | BH2-2 | BD1 | 20 | 4.0 | 10.5 | 150 |
| Example 128 | BH1-10 | BD1 | 5 | BH2-16 | BD1 | 20 | 3.8 | 10.5 | 170 |
| Comparative 104 | — | — | — | BH2-16 | BD1 | 25 | 4.1 | 9.5 | 70 |

Example 129

The organic EL device according to Example 129 was manufactured in the same manner as that of Reference Example 125 except that the compound BH2-2 (second host material) in the second emitting layer was replaced with the second compound listed in Table 33.

Comparative 105

The organic EL device according to Comparative 105 was manufactured in the same manner as that of Reference Example 125 except that a 25-nm-thick second emitting layer was formed on the second hole transporting layer without forming the first emitting layer, and the second compound (second host material) in the second emitting layer was replaced with the second compound listed in Table 33, as shown in Table 33.

TABLE 33

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 125 | BH1-10 | BD1 | 5 | BH2-2 | BD1 | 20 | 4.0 | 10.5 | 150 |
| Example 129 | BH1-10 | BD1 | 5 | BH2-17 | BD1 | 20 | 3.7 | 10.6 | 170 |
| Comparative 105 | — | — | — | BH2-17 | BD1 | 25 | 4.0 | 9.1 | 60 |

Manufacture 16 of Organic EL Device

Reference Example 130

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT3 was vapor-deposited to form an 80-nm-thick first hole transporting layer (HT).

After the formation of the first hole transporting layer, the compound HT7 was vapor-deposited to form a 10-nm-thick second hole transporting layer (also referred to as an electron blocking layer (EBL)).

The compound BH1-10 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET1 was vapor-deposited on the second emitting layer to form a 10-nm-thick first electron transporting layer (also referred to as a hole blocking layer (HBL)).

A compound ET5 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 130 is roughly shown as follows.

ITO (130)/HA1(5)/HT3(80)/HT7(10)/BH1-10:BD1 (5.98%:2%)/BH2-8:BD1 (20.98%:2%)/ET1(10)/ET5(20)/LiF (1)/Al (80)

The numerals in parentheses represent film thickness (unit: nm).

The numerals (98%:2%) represented by percentage in the same parentheses indicate a ratio (mass %) between the host material (compound BH1-10) and the compound BD1 in the first emitting layer, and numerals (98%:2%) represented by percentage in the same parentheses indicate a ratio (mass %) between the host material (compound BH2-8) and the compound BD1 in the second emitting layer. Similar notations apply to the description below.

Reference Example 131

The organic EL device according to Reference Example 131 was manufactured in the same manner as that of Reference Example 130 except that the compound BH2-8 (second host material) in the second emitting layer was replaced with the second compound listed in Table 34.

Comparative 106

The organic EL device according to Comparative 106 was manufactured in the same manner as that of Reference Example 130 except that a 25-nm-thick second emitting layer was formed on the second hole transporting layer without forming the first emitting layer, and the second compound (second host material) in the second emitting layer was replaced with the second compound listed in Table 34, as shown in Table 34.

TABLE 34

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 130 | BH1-10 | BD1 | 5 | BH2-8 | BD1 | 20 | 3.4 | 9.5 | 140 |
| Reference Example 131 | BH1-10 | BD1 | 5 | BH2-18 | BD1 | 20 | 3.4 | 10.0 | 150 |
| Comparative 106 | — | — | — | BH2-18 | BD1 | 25 | 3.6 | 9.0 | 100 |

Reference Example 132

The organic EL device according to Reference Example 132 was manufactured in the same manner as that of Reference Example 130 except that the compound BH2-8 (second host material) in the second emitting layer was replaced with the second compound listed in Table 35.

Comparative 107

The organic EL device according to Comparative 107 was manufactured in the same manner as that of Reference Example 130 except that a 25-nm-thick second emitting layer was formed on the second hole transporting layer without forming the first emitting layer, and the second compound (second host material) in the second emitting layer was replaced with the second compound listed in Table 35, as shown in Table 35.

TABLE 35

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 130 | BH1-10 | BD1 | 5 | BH2-8 | BD1 | 20 | 3.4 | 9.5 | 140 |
| Reference Example 132 | BH1-10 | BD1 | 5 | BH2-19 | BD1 | 20 | 3.5 | 10.3 | 140 |
| Comparative 107 | — | — | — | BH2-19 | BD1 | 25 | 3.6 | 9.2 | 80 |

Reference Example 133

The organic EL device according to Reference Example 133 was manufactured in the same manner as that of Reference Example 130 except that the compound BH2-8 (second host material) in the second emitting layer was replaced with the second compound listed in Table 36.

Comparative 108

The organic EL device according to Comparative 108 was manufactured in the same manner as that of Reference Example 130 except that a 25-nm-thick second emitting layer was formed on the second hole transporting layer without forming the first emitting layer, and the second compound (second host material) in the second emitting layer was replaced with the second compound listed in Table 36, as shown in Table 36.

TABLE 36

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 130 | BH1-10 | BD1 | 5 | BH2-8 | BD1 | 20 | 3.4 | 9.5 | 140 |
| Reference Example 133 | BH1-10 | BD1 | 5 | BH2-20 | BD1 | 20 | 3.4 | 9.9 | 160 |
| Comparative 108 | — | — | — | BH2-20 | BD1 | 25 | 3.7 | 8.8 | 120 |

Manufacture 17 of Organic EL Device

Reference Example 134

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

The compound BH1 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET4 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 134 is roughly shown as follows.

ITO (130)/HA1(5)/HT1(80)/HT2(10)/BH1:BD1 (5.98%: 2%)/BH2-8:BD1 (20.98%:2%)/ET4(10)/ET2(20)/LiF (1)/Al (80)

The numerals in parentheses represent film thickness (unit: nm).

The numerals (98%:2%) represented by percentage in the same parentheses indicate a ratio (mass %) between the host material (compound BH1) and the compound BD1 in the first emitting layer, and numerals (98%:2%) represented by percentage in the same parentheses indicate a ratio (mass %) between the host material (compound BH2-8) and the compound BD1 in the second emitting layer. Similar notations apply to the description below.

Example 135

The organic EL device according to Example 135 was manufactured in the same manner as that of Reference Example 134 except that the compound BH2-8 (second host material) in the second emitting layer was replaced with the second compound listed in Table 37.

Comparative 109

The organic EL device according to Comparative 109 was manufactured in the same manner as that of Reference Example 134 except that a 25-nm-thick second emitting layer was formed on the second hole transporting layer without forming the first emitting layer, and the second compound (second host material) in the second emitting layer was replaced with the second compound listed in Table 37, as shown in Table 37.

TABLE 37

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 134 | BH1 | BD1 | 5 | BH2-8 | BD1 | 20 | 3.3 | 9.8 | 90 |
| Example 135 | BH1 | BD1 | 5 | BH2-21 | BD1 | 20 | 3.3 | 9.6 | 130 |
| Comparative 109 | — | — | — | BH2-21 | BD1 | 25 | 3.5 | 8.5 | 80 |

Example 136

The organic EL device according to Example 136 was manufactured in the same manner as that of Reference Example 134 except that the compound BH2-8 (second host material) in the second emitting layer was replaced with the second compound listed in Table 38.

Comparative 110

The organic EL device according to Comparative 110 was manufactured in the same manner as that of Reference Example 134 except that a 25-nm-thick second emitting layer was formed on the second hole transporting layer without forming the first emitting layer, and the second compound (second host material) in the second emitting layer was replaced with the second compound listed in Table 38, as shown in Table 38.

TABLE 38

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 134 | BH1 | BD1 | 5 | BH2-8 | BD1 | 20 | 3.3 | 9.8 | 90 |
| Example 136 | BH1 | BD1 | 5 | BH2-22 | BD1 | 20 | 3.4 | 8.3 | 140 |
| Comparative 110 | — | — | — | BH2-22 | BD1 | 25 | 3.5 | 7.3 | 80 |

Example 137

The organic EL device according to Example 137 was manufactured in the same manner as that of Reference Example 134 except that the compound BH2-8 (second host material) in the second emitting layer was replaced with the second compound listed in Table 39.

Comparative 111

The organic EL device according to Comparative 111 was manufactured in the same manner as that of Reference Example 134 except that a 25-nm-thick second emitting layer was formed on the second hole transporting layer without forming the first emitting layer, and the second compound (second host material) in the second emitting layer was replaced with the second compound listed in Table 39, as shown in Table 39.

TABLE 39

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 134 | BH1 | BD1 | 5 | BH2-8 | BD1 | 20 | 3.3 | 9.8 | 90 |
| Example 137 | BH1 | BD1 | 5 | BH2-23 | BD1 | 20 | 3.3 | 8.8 | 130 |
| Comparative 111 | — | — | — | BH2-23 | BD1 | 25 | 3.4 | 8.0 | 80 |

Example 138

The organic EL device according to Example 138 was manufactured in the same manner as that of Reference Example 134 except that the compound BH2-8 (second host material) in the second emitting layer was replaced with the second compound listed in Table 40.

Comparative 112

The organic EL device according to Comparative 112 was manufactured in the same manner as that of Reference Example 134 except that a 25-nm-thick second emitting layer was formed on the second hole transporting layer without forming the first emitting layer, and the second compound (second host material) in the second emitting layer was replaced with the second compound listed in Table 40, as shown in Table 40.

TABLE 40

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 134 | BH1 | BD1 | 5 | BH2-8 | BD1 | 20 | 3.3 | 9.8 | 90 |
| Example 138 | BH1 | BD1 | 5 | BH2-24 | BD1 | 20 | 3.5 | 9.1 | 120 |
| Comparative 112 | — | — | — | BH2-24 | BD1 | 25 | 3.7 | 7.8 | 90 |

Example 139

The organic EL device according to Example 139 was manufactured in the same manner as that of Reference Example 134 except that the compound BH2-8 (second host material) in the second emitting layer was replaced with the second compound listed in Table 41.

Comparative 113

The organic EL device according to Comparative 113 was manufactured in the same manner as that of Reference Example 134 except that a 25-nm-thick second emitting layer was formed on the second hole transporting layer without forming the first emitting layer, and the second compound (second host material) in the second emitting layer was replaced with the second compound listed in Table 41, as shown in Table 41.

TABLE 41

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 134 | BH1 | BD1 | 5 | BH2-8 | BD1 | 20 | 3.3 | 9.8 | 90 |
| Example 139 | BH1 | BD1 | 5 | BH2-25 | BD1 | 20 | 3.4 | 9.4 | 130 |
| Comparative 113 | — | — | — | BH2-25 | BD1 | 25 | 3.4 | 7.1 | 70 |

Example 140

The organic EL device according to Example 140 was manufactured in the same manner as that of Reference Example 134 except that the compound BH2-8 (second host material) in the second emitting layer was replaced with the second compound listed in Table 42.

Comparative 114

The organic EL device according to Comparative 114 was manufactured in the same manner as that of Reference Example 134 except that a 25-nm-thick second emitting layer was formed on the second hole transporting layer without forming the first emitting layer, and the second compound (second host material) in the second emitting layer was replaced with the second compound listed in Table 42, as shown in Table 42.

TABLE 42

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 134 | BH1 | BD1 | 5 | BH2-8 | BD1 | 20 | 3.3 | 9.8 | 90 |
| Example 140 | BH1 | BD1 | 5 | BH2-26 | BD1 | 20 | 3.5 | 9.2 | 130 |
| Comparative 114 | — | — | — | BH2-26 | BD1 | 25 | 3.4 | 7.5 | 75 |

Example 141

The organic EL device according to Example 141 was manufactured in the same manner as that of Reference Example 134 except that the compound BH2-8 (second host material) in the second emitting layer was replaced with the second compound listed in Table 43.

Comparative 115

The organic EL device according to Comparative 115 was manufactured in the same manner as that of Reference Example 134 except that a 25-nm-thick second emitting layer was formed on the second hole transporting layer without forming the first emitting layer, and the second compound (second host material) in the second emitting layer was replaced with the second compound listed in Table 43, as shown in Table 43.

TABLE 43

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 134 | BH1 | BD1 | 5 | BH2-8 | BD1 | 20 | 3.3 | 9.8 | 90 |
| Example 141 | BH1 | BD1 | 5 | BH2-27 | BD1 | 20 | 3.2 | 9.1 | 130 |
| Comparative 115 | — | — | — | BH2-27 | BD1 | 25 | 3.5 | 7.2 | 80 |

Example 142

The organic EL device according to Example 142 was manufactured in the same manner as that of Reference Example 134 except that the compound BH2-8 (second host material) in the second emitting layer was replaced with the second compound listed in Table 44.

Comparative 116

The organic EL device according to Comparative 116 was manufactured in the same manner as that of Reference Example 134 except that a 25-nm-thick second emitting layer was formed on the second hole transporting layer without forming the first emitting layer, and the second compound (second host material) in the second emitting layer was replaced with the second compound listed in Table 44, as shown in Table 44.

TABLE 44

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 134 | BH1 | BD1 | 5 | BH2-8 | BD1 | 20 | 3.3 | 9.8 | 90 |
| Example 142 | BH1 | BD1 | 5 | BH2-28 | BD1 | 20 | 3.3 | 9.0 | 140 |
| Comparative 116 | — | — | — | BH2-28 | BD1 | 25 | 3.4 | 7.4 | 65 |

Manufacture 18 of Organic EL Device

Reference Example 143

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, the compound HA1 was vapor-deposited on a surface provided with the transparent electrode line to cover the transparent electrode, thereby forming a 5-nm-thick hole injecting layer (HI).

After the formation of the hole injecting layer, the compound HT1 was vapor-deposited to form an 80-nm-thick first hole transporting layer (HT).

After the formation of the first hole transporting layer, the compound HT2 was vapor-deposited to form a 10-nm-thick second hole transporting layer (also referred to as an electron blocking layer (EBL)).

The compound BH1 (first host material (BH)) and the compound BD1 (dopant material (BD)) were co-deposited on the second hole transporting layer such that the ratio of the compound BD1 accounted for 2 mass %, thereby forming a 5-nm-thick first emitting layer.

The compound BH2-8 (second host material (BH)) and the compound BD1 (dopant material (BD)) were co-deposited on the first emitting layer such that the ratio of the compound BD1 accounted for 2 mass %, thereby forming a 20-nm-thick second emitting layer.

The compound ET7 was vapor-deposited on the second emitting layer to form a 10-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form an 80-nm-thick cathode.

A device arrangement of the organic EL device in Reference Example 143 is roughly shown as follows.

ITO (130)/HA1(5)/HT1(80)/HT2(10)/BH1:BD1 (5.98%: 2%)/BH2-8:BD1 (20.98%:2%)/ET7(10)/ET2(20)/LiF (1)/Al (80)

The numerals in parentheses represent film thickness (unit: nm).

The numerals (98%:2%) represented by percentage in the same parentheses indicate a ratio (mass %) between the host material (compound BH1) and the compound BD1 in the first emitting layer, and numerals (98%:2%) represented by percentage in the same parentheses indicate a ratio (mass %) between the host material (compound BH2-8) and the compound BD1 in the second emitting layer. Similar notations apply to the description below.

Reference Example 144

The organic EL device according to Reference Example 144 was manufactured in the same manner as that of Reference Example 143 except that the compound BH2-8 (second host material) in the second emitting layer was replaced with the second compound listed in Table 45.

Comparative 117

The organic EL device according to Comparative 117 was manufactured in the same manner as that of Reference Example 143 except that a 25-nm-thick second emitting layer was formed on the second hole transporting layer without forming the first emitting layer, and the second compound (second host material) in the second emitting layer was replaced with the second compound listed in Table 45, as shown in Table 45.

TABLE 45

| | First Emitting Layer | | | Second Emitting Layer | | | | | |
|---|---|---|---|---|---|---|---|---|---|
| | First Compound | Third Compound | Film Thickness [nm] | Second Compound | Fourth Compound | Film Thickness [nm] | Voltage [V] | EQE [%] | LT90 [hr] |
| Reference Example 143 | BH1 | BD1 | 5 | BH2-8 | BD1 | 20 | 3.5 | 9.0 | 120 |
| Reference Example 144 | BH1 | BD1 | 5 | BH2-29 | BD1 | 20 | 4.0 | 10.1 | 80 |
| Comparative 117 | — | — | — | BH2-29 | BD1 | 25 | 4.5 | 8.2 | 40 |

Manufacture 19 of Organic EL Device

Example 145

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, a compound HT9 and the compound HA2 were co-deposited on a surface provided with the transparent electrode line to cover the transparent electrode, thereby forming a 10-nm-thick hole injecting layer (HI). The ratios of the compound HT9 and the compound HA2 in the hole injecting layer were 97 mass % and 3 mass %, respectively.

After the formation of the hole injecting layer, the compound HT9 was vapor-deposited to form a 90-nm-thick first hole transporting layer (HT).

After the formation of the first hole transporting layer, a compound HT10 was vapor-deposited to form a 5-nm-thick second hole transporting layer (also referred to as an electron blocking layer (EBL)).

A compound BH1-84 (first host material (BH)) and the compound BD2 (dopant material (BD)) were co-deposited on the second hole transporting layer such that the ratio of the compound BD2 accounted for 2 mass %, thereby forming a 5-nm-thick first emitting layer.

A compound BH2-30 (second host material (BH)) and the compound BD2 (dopant material (BD)) were co-deposited on the first emitting layer such that the ratio of the compound BD2 accounted for 2 mass %, thereby forming a 15-nm-thick second emitting layer.

A compound ET9 was vapor-deposited on the second emitting layer to form a 5-nm-thick first electron transporting layer (also referred to as a hole blocking layer (HBL)).

The compound ET2 and the compound Liq were co-deposited on the first electron transporting layer (HBL) to form a 20-nm-thick electron transporting layer (ET). The ratios of the compound ET2 and the compound Liq in the electron transporting layer (ET) were 50 mass % and 50 mass %, respectively.

Yb was vapor-deposited on the second electron transporting layer to form a 1-nm-thick electron injecting layer.

Metal Al was vapor-deposited on the electron injecting layer to form a 50-nm-thick cathode.

A device arrangement of the organic EL device in Example 145 is roughly shown as follows.

ITO (130)/HT9:HA2 (10.97%:3%)/HT9(90)/HT10(5)/BH1-84:BD2 (5.98%:2%)/BH2-30:BD2 (15.98%:2%)/ET9 (5)/ET2:Liq (20.50%:50%)/Yb (1)/Al (50)

The numerals in parentheses represent film thickness (unit: nm).

The numerals (97%:3%) represented by percentage in the same parentheses indicate a ratio (mass %) between the compound HT9 and the compound HA2 in the hole injecting layer, the numerals (98%:2%) represented by percentage in the same parentheses indicate a ratio (mass %) between the host material (compound BH1-84) and the compound BD2 in the first emitting layer, the numerals (98%:2%) represented by percentage in the same parentheses indicate a ratio (mass %) between the host material (compound BH2-30) and the compound BD2 in the second emitting layer, and the numerals (50%:50%) represented by percentage in the same parentheses indicate a ratio (mass %) between the compound ET2 and the compound Liq in the electron transporting layer (ET).

Comparative 118

The organic EL device according to Comparative 118 was manufactured in the same manner as that of Example 145 except that the compound BH1-84 (first host material) in the first emitting layer was replaced with the compound BH2-30 listed in Table 46, and the compound BH2-30 (second host material) in the second emitting layer was replaced with the compound BH1-84 listed in Table 46.

TABLE 46

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT90 [hr] |
| Example 145 | BH1-84 | BD2 | 5 | BH2-30 | BD2 | 15 | 10.4 | 195 |
| Comparative 118 | BH2-30 | BD2 | 5 | BH1-84 | BD2 | 15 | 8.8 | 180 |

Example 145 in which the first emitting layer containing the first compound represented by the formula (1) and the second emitting layer containing the second compound represented by the formula (2-1E) were laminated in normal order from the anode had a higher luminous efficiency and longer lifetime than Comparative 118 in which the second compound and the first emitting layer were laminated in this order from the anode (in reverse order).

Manufacture 20 of Organic EL Device

Example 146

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, a compound HT11 and the compound HA2 were co-deposited on a surface provided with the transparent electrode line to cover the transparent electrode, thereby forming a 5-nm-thick hole injecting layer (HI). The ratios of the compound HT11 and the compound HA2 in the hole injecting layer were 97 mass % and 3 mass %, respectively.

After the formation of the hole injecting layer, the compound HT11 was vapor-deposited to form a 90-nm-thick first hole transporting layer (HT).

After the formation of the first hole transporting layer, a compound HT12 was vapor-deposited to form a 10-nm-thick second hole transporting layer (also referred to as an electron blocking layer (EBL)).

A compound BH1-85 (first host material (BH)) and a compound BD4 (dopant material (BD)) were co-deposited on the second hole transporting layer such that the ratio of the compound BD4 accounted for 2 mass %, thereby forming a 5-nm-thick first emitting layer.

A compound BH2-15 (second host material (BH)) and the compound BD4 (dopant material (BD)) were co-deposited on the first emitting layer such that the ratio of the compound BD4 accounted for 2 mass %, thereby forming a 20-nm-thick second emitting layer.

The compound ET3 was vapor-deposited on the second emitting layer to form a 5-nm-thick first electron transporting layer (also referred to as a hole blocking layer (HBL)).

The compound ET7 and the compound Liq were co-deposited on the first electron transporting layer (HBL) to form a 20-nm-thick electron transporting layer (ET). The ratios of the compound ET7 and the compound Liq in the electron transporting layer (ET) were 50 mass % and 50 mass %, respectively.

Yb was vapor-deposited on the second electron transporting layer to form a 1-nm-thick electron injecting layer.

Metal Al was vapor-deposited on the electron injecting layer to form a 50-nm-thick cathode.

A device arrangement of the organic EL device in Example 146 is roughly shown as follows.

ITO (130)/HT11:HA2 (5.97%:3%)/HT11(90)/HT12(10)/BH1-85:BD4 (5.98%:2%)/BH2-15:BD4 (20.98%:2%)/ET3 (5)/ET7:Liq (20.50%:50%)/Yb (1)/Al (50)

The numerals in parentheses represent film thickness (unit: nm).

The numerals (97%:3%) represented by percentage in the same parentheses indicate a ratio (mass %) between the compound HT11 and the compound HA2 in the hole injecting layer, the numerals (98%:2%) represented by percentage in the same parentheses indicate a ratio (mass %) between the host material (compound BH1-85) and the compound BD4 in the first emitting layer, the numerals (98%:2%) represented by percentage in the same parentheses indicate a ratio (mass %) between the host material (compound BH2-15) and the compound BD4 in the second emitting layer, and the numerals (50%:50%) represented by percentage in the same parentheses indicate a ratio (mass %) between the compound ET7 and the compound Liq in the electron transporting layer (ET).

Example 147

The organic EL device according to Example 147 was manufactured in the same manner as that of Example 146 except that the compound BH1-85 (first host material) in the first emitting layer was replaced with the first compound listed in Table 47.

TABLE 47

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT90 [hr] |
| Example 146 | BH1-85 | BD4 | 5 | BH2-15 | BD4 | 20 | 10.9 | 244 |
| Example 147 | BH1-86 | BD4 | 5 | BH2-15 | BD4 | 20 | 10.3 | 200 |

Example 146 in which the compound BH1-85 (bispyrene having a diphenylfluorene ring) was used as the first host material had enhanced luminous efficiency and also an improved lifetime as compared with Example 147 in which the compound BH1-86 (bispyrene having a spirofluorene ring) was used as the first host material.

Manufacture 21 of Organic EL Device

Example 148

A glass substrate (size: 25 mm×75 mm×1.1 mm thick, manufactured by Geomatec Co., Ltd.) having an ITO (Indium Tin Oxide) transparent electrode (anode) was ultrasonic-cleaned in isopropyl alcohol for five minutes, and then UV-ozone-cleaned for 30 minutes. The film thickness of the ITO transparent electrode was 130 nm.

The cleaned glass substrate having the transparent electrode line was attached to a substrate holder of a vacuum deposition apparatus. Initially, a compound HA3 was vapor-deposited on a surface provided with the transparent electrode line to cover the transparent electrode, thereby forming a 10-nm-thick hole injecting layer (HI).

After the formation of the hole injecting layer, the compound HT9 was vapor-deposited to form a 90-nm-thick first hole transporting layer (HT).

After the formation of the first hole transporting layer, the compound HT10 was vapor-deposited to form a 5-nm-thick second hole transporting layer (also referred to as an electron blocking layer (EBL)).

The compound BH1-10 (first host material (BH)) and the compound BD2 (dopant material (BD)) were co-deposited on the second hole transporting layer such that the ratio of the compound BD2 accounted for 2 mass %, thereby forming a 5-nm-thick first emitting layer.

A compound BH2-31 (second host material (BH)) and the compound BD2 (dopant material (BD)) were co-deposited on the first emitting layer such that the ratio of the compound BD2 accounted for 2 mass %, thereby forming a 15-nm-thick second emitting layer.

The compound ET9 was vapor-deposited on the second emitting layer to form a 5-nm-thick first electron transporting layer (also referred to as a hole blocking layer (HBL)).

The compound ET2 was vapor-deposited on the first electron transporting layer to form a 20-nm-thick second electron transporting layer (ET).

LiF was vapor-deposited on the second electron transporting layer to form a 1-nm-thick electron injecting layer.

Metal Al was vapor-deposited on the electron injecting layer to form a 50-nm-thick cathode.

A device arrangement of the organic EL device in Example 148 is roughly shown as follows.

ITO (130)/HA3(10)/HT9(90)/HT10(5)/BH1-10:BD2 (5.98%:2%)/BH2-31:BD2 (15.98%:2%)/ET9(5)/ET2(20)/LiF (1)/Al (50)

The numerals in parentheses represent film thickness (unit: nm).

The numerals (98%:2%) represented by percentage in the same parentheses indicate a ratio (mass %) between the host material (compound BH1-10) and the compound BD2 in the first emitting layer, and numerals (98%:2%) represented by percentage in the same parentheses indicate a ratio (mass %) between the host material (compound BH2-31) and the compound BD2 in the second emitting layer.

TABLE 48

| | First Emitting Layer | | | Second Emitting Layer | | | | |
|---|---|---|---|---|---|---|---|---|
| | First Compound | Third Compound | Film Thickness [nm] | Second Compound | Fourth Compound | Film Thickness [nm] | EQE [%] | LT90 [hr] |
| Example 148 | BH1-10 | BD2 | 5 | BH2-31 | BD2 | 15 | 9.5 | 145 |

An organic EL device containing the compound BH2-31 in the second emitting layer, although having the device arrangement of the invention that improves luminous efficiency, may have a limited degree of increase in luminous efficiency because the compound BH2-31 having a bulky tert-butyl group has inhibited intermolecular interaction.

Evaluation of Compounds

Preparation of Toluene Solution

The compound BD1 was dissolved in toluene at a concentration of $4.9\times10^{-6}$ mol/L to prepare a toluene solution of the compound BD1. A toluene solution of the compound BD2 and a toluene solution of the compound BD3 were prepared in the same manner.

Measurement of Fluorescence Main Peak Wavelength (FL-Peak)

Fluorescence main peak wavelength of the toluene solution of the compound BD1 excited at 390 nm was measured using a fluorescence spectrometer (spectrophotofluorometer F-7000 (manufactured by Hitachi High-Tech Science Corporation)). The fluorescence main peak wavelengths of the toluene solutions of the compound BD2 and the compound BD3 were measured in the same manner as the compound BD1.

The fluorescence main peak wavelength of the compound BD1 was 453 nm.

The fluorescence main peak wavelength of the compound BD2 was 455 nm.

The fluorescence main peak wavelength of the compound BD3 was 451 nm.

The invention claimed is:

1. An organic electroluminescence device comprising:
an anode;
a cathode;
a first emitting layer provided between the anode and the cathode; and
a second emitting layer provided between the first emitting layer and the cathode, wherein the first emitting layer comprises a first compound represented by a formula (1) below as a first host material, the first compound comprising a group represented by a formula (11) below, the second emitting layer comprises a second compound represented by one of formulae (21D) to (24D) below as a second host material, the film thicknesses of the first emitting layer and the second emitting layer are each independently in a range from 5 nm to 50 nm, and the first emitting layer is in direct contact with the second emitting layer, (1)

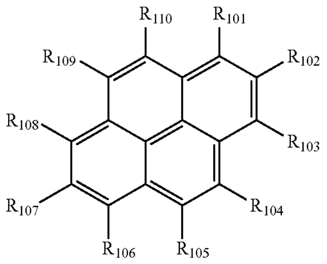

(11)

$*\!-\!(L_{101})_{mx}\!-\!Ar_{101}$ where, in the formula (1):

$R_{101}$ to $R_{110}$ are each independently a hydrogen atom, an unsubstituted alkyl group having 1 to 6 carbon atoms, an unsubstituted cycloalkyl group having 3 to 20 ring carbon atoms, an unsubstituted aryl group having 6 to 18 ring carbon atoms, an unsubstituted heterocyclic group having 5 to 18 ring atoms, or a group represented by the formula (11);

one of $R_{101}$ to $R_{110}$ is a group represented by the formula (11);

$L_{101}$ is a single bond, a substituted or unsubstituted arylene group having 6 to 18 ring carbon atoms, or a substituted or unsubstituted divalent heterocyclic group having 5 to 18 ring atoms;

$Ar_{101}$ is a substituted or unsubstituted aryl group having 6 to 18 ring carbon atoms, or a substituted or unsubstituted heterocyclic group having 5 to 18 ring atoms;

mx is 0 or 1;

in $L_{101}$ and $Ar_{101}$, the substituents referred to as "substituted or unsubstituted" are each independently an unsubstituted alkyl group having 1 to 6 carbon atoms, an unsubstituted cycloalkyl group having 3 to 20 ring carbon atoms, unsubstituted aryl groups having 6 to 18 ring carbon atoms, or unsubstituted heterocyclic groups having 5 to 18 ring atoms, and

* in the formula (11) represents a bonding position to a pyrene ring in the formula (1), (21D)

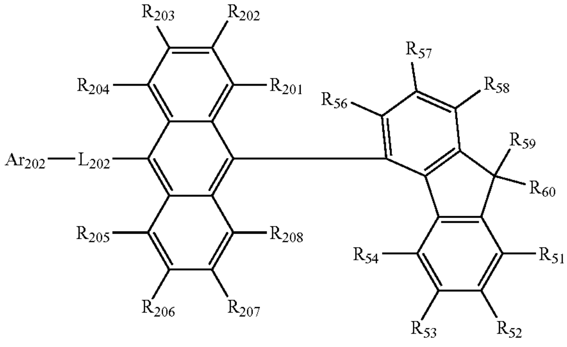

-continued (22D)

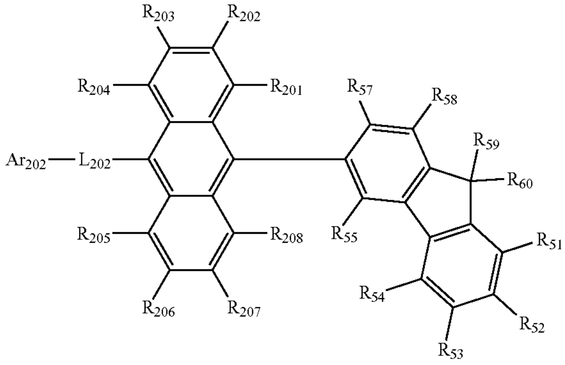

(23D)

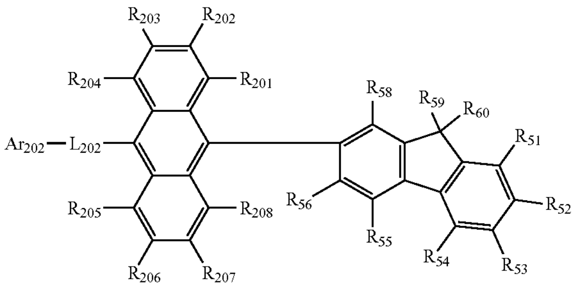

(24D)

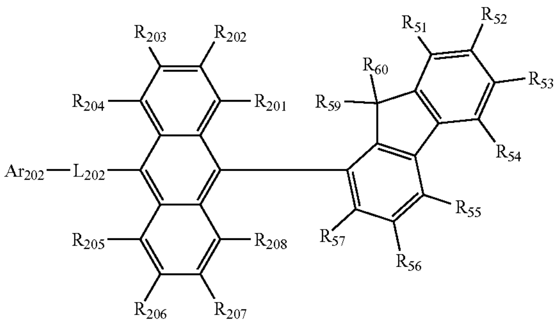

where, in the formulae (21D) to (24D):

$R_{201}$ to $R_{208}$ are each independently a hydrogen atom, or unsubstituted aryl group having 6 to 18 ring carbon atoms;

$R_{51}$ to $R_{60}$ in the formulae (21D), (22D) and (24D) are each independently a hydrogen atom or a substituent;

$R_{51}$ to $R_{60}$ in the formula (23D) are each independently a hydrogen atom or a substituent, or at least one combination of a combination of $R_{53}$ and $R_{54}$, or a combination of $R_{55}$ and $R_{56}$ are mutually bonded to form a monocyclic ring or a fused ring;

$R_{51}$ to $R_{60}$ as a substituent are each independently an unsubstituted alkyl group having 1 to 6 carbon atoms, or an unsubstituted aryl group having 6 to 18 ring carbon atoms;

$L_{202}$ is a single bond, or a substituted or unsubstituted arylene group having 6 to 18 ring carbon atoms;

a substituent, if present, for $L_{202}$ is each independently selected from the group consisting of an unsubstituted alkyl group having 1 to 6 carbon atoms, and an unsubstituted aryl group having 6 to 18 ring carbon atoms;

$Ar_{202}$ is a substituted or unsubstituted phenyl group, a substituted or unsubstituted naphthyl group, a substituted or unsubstituted phenanthryl group, a substituted or unsubstituted biphenyl group, a substituted or unsubstituted terphenyl group; and a substituent, if present, for $Ar_{202}$ is each independently selected from the group consisting of an unsubstituted alkyl group having 1 to 6 carbon atoms, and an unsubstituted aryl group having 6 to 18 ring carbon atoms.

2. The organic electroluminescence device according to claim 1, wherein $L_{202}$ is a single bond, or a group represented by one of formulae (2-1a) to (2-4a) below, (2-1a)

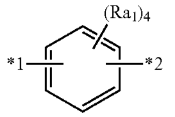

(2-2a)

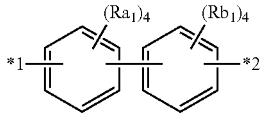

(2-3a)

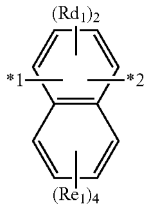

(2-4a)

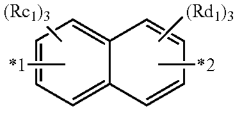

where, in the formulae (2-1a) to (2-4a):

$Ra_1$ to $Re_1$ each independently represent the same as the substituent, if present, for $L_{202}$ in the formulae (21D) to (24D); and

*1 and *2 each represent a bonding position.

3. The organic electroluminescence device according to claim 1, wherein $L_{101}$ is selected from the group consisting of a substituted or unsubstituted phenyl group, a substituted or unsubstituted biphenyl group, a substituted or unsubstituted naphthyl group, a substituted or unsubstituted fluorenyl group, a substituted or unsubstituted dibenzofuran group, a substituted or unsubstituted dibenzothiophenyl group, a substituted or unsubstituted indolyl group, a substituted or unsubstituted benzimidazolyl group, a substituted or unsubstituted benzofuranyl group, and a substituted or unsubstituted benzothiophenyl group, with one hydrogen atom removed.

4. The organic electroluminescence device according to claim 1, wherein the first emitting layer further comprises a third compound that fluoresces;

the second emitting layer further comprises a fourth compound that fluoresces;

the third compound and the fourth compound are each independently a compound represented by a formula (5) below, and the third compound and the fourth compound are mutually the same or different, (5)

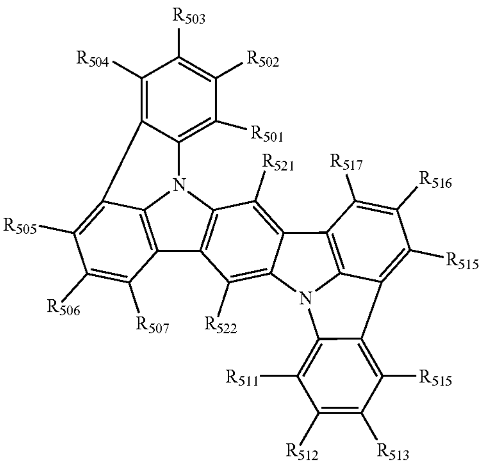

wherein in the formula (5):

at least one combination of adjacent two or more of $R_{501}$ to $R_{507}$ and $R_{511}$ to $R_{517}$ are mutually bonded to form a substituted or unsubstituted monocyclic ring, mutually bonded to form a substituted or unsubstituted fused ring, or not mutually bonded;

$R_{501}$ to $R_{507}$ and $R_{511}$ to $R_{517}$ not forming the monocyclic ring and not forming the fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms; and $R_{521}$ and $R_{522}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a group represented by —$N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms; and $R_{901}$, $R_{902}$, $R_{903}$, $R_{904}$, $R_{905}$, $R_{906}$, and $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different.

* * * * *